United States Patent
Pedersen et al.

(10) Patent No.: US 10,722,562 B2
(45) Date of Patent: Jul. 28, 2020

(54) COMBINATORIAL ANALYSIS AND REPAIR

(75) Inventors: Henrik Pedersen, Lynge (DK);
Liselotte Brix, Bagsværd (DK)

(73) Assignees: Immudex ApS, Virum (DK); Agilent Technologies, Inc., Santa Clara, CA (US)

( * ) Notice: Subject to any disclaimer, the term of this patent is extended or adjusted under 35 U.S.C. 154(b) by 1317 days.

(21) Appl. No.: 13/055,321

(22) PCT Filed: Jul. 22, 2009

(86) PCT No.: PCT/DK2009/050185
§ 371 (c)(1),
(2), (4) Date: May 16, 2011

(87) PCT Pub. No.: WO2010/009735
PCT Pub. Date: Jan. 28, 2010

(65) Prior Publication Data
US 2011/0212090 A1     Sep. 1, 2011

Related U.S. Application Data

(60) Provisional application No. 61/082,980, filed on Jul. 23, 2008.

(30) Foreign Application Priority Data

Jul. 23, 2008  (DK) ................................ 2008 01035

(51) Int. Cl.
*A61K 39/00*     (2006.01)
*A61K 39/02*     (2006.01)

(52) U.S. Cl.
CPC ...... *A61K 39/0011* (2013.01); *A61K 39/0225* (2013.01); *A61K 2039/5158* (2013.01);
(Continued)

(58) Field of Classification Search
CPC ........... A61K 39/0011; A61K 39/0225; A61K 2039/5158; A61K 2039/55505;
(Continued)

(56) References Cited

U.S. PATENT DOCUMENTS

| 4,281,061 A | 7/1981 | Zuk et al. |
| 4,336,173 A | 6/1982 | Ugelstad |

(Continued)

FOREIGN PATENT DOCUMENTS

| DE | 197 40 735 | 3/1999 |
| DE | 102 47 014 | 4/2004 |

(Continued)

OTHER PUBLICATIONS

Speiser et al. (Eur. J. Immunol. 2002, 32:731-741).*
(Continued)

*Primary Examiner* — Jeremy C Flinders
(74) *Attorney, Agent, or Firm* — Verrill Dana, LLP

(57) ABSTRACT

A method for the repair of a unit, by specific diagnosis of the undesired state, and its appropriate repair, using said specific diagnosis as a means to repair in an appropriate way said unit. The diagnosis and repair processes may involve chemical, physical, or mechanical means. The units being diagnosed and repaired include live matter (e.g. human beings, animals, plants) as well as non-live matter (e.g. buildings, electronic equipment, polymer materials).

Figure 7:
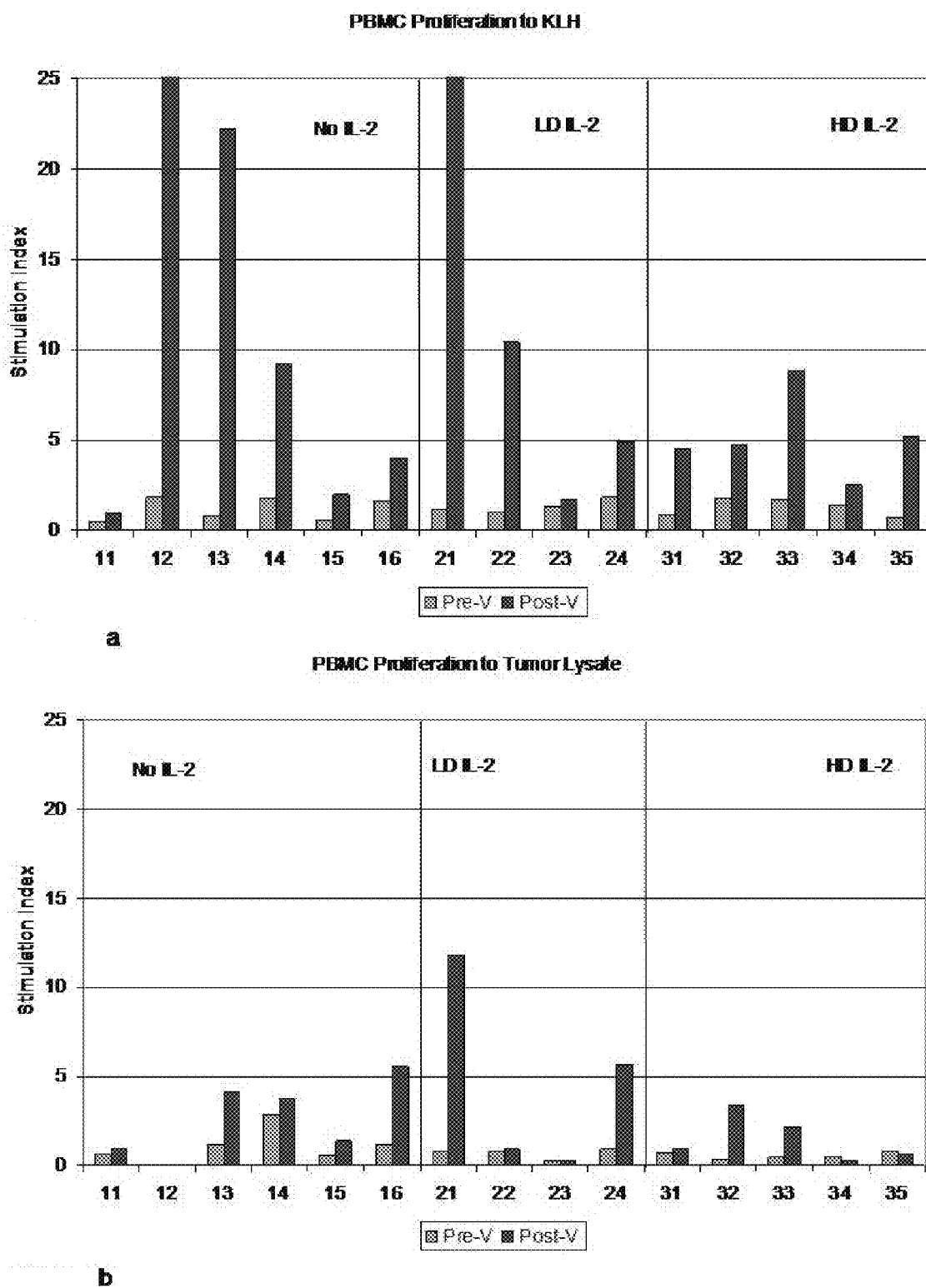

9 Claims, 12 Drawing Sheets
Specification includes a Sequence Listing.

Flow cytometry analysis of MHC multimer constructs

(52) U.S. Cl.
CPC ............... *A61K 2039/55505* (2013.01); *A61K 2039/55566* (2013.01); *A61K 2039/6006* (2013.01); *C12N 2710/16122* (2013.01); *C12N 2710/16222* (2013.01)

(58) Field of Classification Search
CPC .. A61K 2039/55566; A61K 2039/6006; C12N 2710/16122; C12N 2710/16222
See application file for complete search history.

(56) References Cited

U.S. PATENT DOCUMENTS

| | | | |
|---|---|---|---|
| 4,387,164 A | 6/1983 | Hevey et al. |
| 4,459,378 A | 7/1984 | Ugelstad |
| 4,654,267 A | 3/1987 | Ugelstad et al. |
| 4,876,190 A | 10/1989 | Recktenwald |
| 5,039,487 A | 8/1991 | Smith |
| 5,130,297 A | 7/1992 | Sharma et al. |
| 5,194,425 A | 3/1993 | Sharma et al. |
| 5,260,422 A | 11/1993 | Clark et al. |
| 5,284,935 A | 2/1994 | Clark et al. |
| 5,312,744 A | 5/1994 | Shibata |
| 5,468,481 A | 11/1995 | Sharma et al. |
| 5,583,031 A | 12/1996 | Stern |
| 5,627,037 A | 5/1997 | Ward et al. |
| 5,635,363 A | 7/1997 | Altman et al. |
| 5,652,342 A | 7/1997 | Zimmerman et al. |
| 5,807,552 A | 9/1998 | Stanton et al. |
| 5,869,270 A | 2/1999 | Rhode et al. |
| 5,891,741 A | 4/1999 | Siiman et al. |
| 5,955,079 A | 9/1999 | Mond et al. |
| 5,994,089 A | 11/1999 | Siiman et al. |
| 5,998,204 A | 12/1999 | Tsien et al. |
| 6,015,884 A | 1/2000 | Schneck et al. |
| 6,096,315 A | 1/2000 | Zimmerman et al. |
| 6,156,317 A | 5/2000 | Diamond et al. |
| 6,074,645 A | 6/2000 | Diamond et al. |
| 6,090,587 A | 7/2000 | Rhode et al. |
| 6,106,840 A | 8/2000 | Clark et al. |
| 6,129,916 A | 10/2000 | Chang |
| 6,140,113 A | 10/2000 | Schneck et al. |
| 6,156,514 A | 12/2000 | Acevedo et al. |
| 6,197,302 B1 | 3/2001 | Hirsch et al. |
| 6,197,928 B1 | 3/2001 | Tsien et al. |
| 6,211,342 B1 | 4/2001 | Hirsch et al. |
| 6,232,445 B1 | 5/2001 | Rhode et al. |
| 6,248,564 B1 | 6/2001 | Walter et al. |
| 6,251,399 B1 | 6/2001 | Diamond et al. |
| 6,268,411 B1 | 7/2001 | Schneck et al. |
| 6,306,605 B1 | 10/2001 | Acevedo et al. |
| 6,309,645 B1 | 10/2001 | Rhode et al. |
| 6,335,173 B1 | 1/2002 | Kaplan |
| 6,387,622 B1 | 5/2002 | Siiman et al. |
| 6,448,071 B1 | 9/2002 | Schneck et al. |
| 6,451,314 B1 | 9/2002 | Clark et al. |
| 6,451,769 B1 | 9/2002 | Huebner et al. |
| 6,458,354 B1 | 10/2002 | Schneck et al. |
| 6,458,933 B1 | 10/2002 | Hansen |
| 6,486,130 B1 | 11/2002 | Livey et al. |
| 6,517,838 B1 | 2/2003 | Hook et al. |
| 6,534,633 B1 | 3/2003 | Weidanz et al. |
| 6,548,067 B1 | 4/2003 | Seeman et al. |
| 6,605,711 B1 | 8/2003 | Valmori et al. |
| 6,734,013 B2 | 5/2004 | Schneck et al. |
| 7,041,442 B1 | 5/2006 | Kern et al. |
| 7,060,869 B2 | 6/2006 | Tsien et al. |
| 7,064,190 B1 | 6/2006 | Endl et al. |
| 7,074,904 B2 | 6/2006 | Wong et al. |
| 7,094,555 B2 | 8/2006 | Kwok et al. |
| 7,116,407 B2 | 10/2006 | Hansen et al. |
| 7,141,656 B2 | 11/2006 | Rhode et al. |
| 7,202,349 B2 | 4/2007 | Davis et al. |
| 7,364,869 B2 | 4/2008 | Nixon et al. |
| 7,502,580 B2 | 3/2009 | Hays |
| 7,519,318 B2 | 4/2009 | Kurogawa et al. |
| 7,524,503 B2 | 4/2009 | Khanna et al. |
| 7,706,782 B1 | 4/2010 | Hosmer et al. |
| 7,902,121 B2 | 3/2011 | Chen et al. |
| 8,114,669 B2 | 2/2012 | Choo |
| 8,268,964 B2 | 9/2012 | Scholler et al. |
| 8,298,782 B2 | 10/2012 | Busch et al. |
| 2002/0006903 A1 | 1/2002 | Schneck et al. |
| 2002/0034513 A1 | 3/2002 | Rhode et al. |
| 2002/0058787 A1 | 5/2002 | Strominger et al. |
| 2002/0082411 A1 | 6/2002 | Carter et al. |
| 2002/0091079 A1 | 7/2002 | Rhodes et al. |
| 2002/0119149 A1 | 8/2002 | Jakobsen et al. |
| 2002/0127231 A1 | 9/2002 | Schneck et al. |
| 2002/0164340 A1 | 11/2002 | Brumeanu et al. |
| 2002/0165364 A1 | 11/2002 | Tsien et al. |
| 2002/0198144 A1 | 12/2002 | Wong et al. |
| 2003/0017447 A1 | 1/2003 | Bernardo et al. |
| 2003/0027194 A1 | 2/2003 | Kurz et al. |
| 2003/0073102 A1 | 4/2003 | Kwok et al. |
| 2003/0096432 A1 | 5/2003 | Jakobsen |
| 2003/0104635 A1 | 6/2003 | Jakobsen |
| 2003/0118594 A1 | 6/2003 | Nag et al. |
| 2003/0171290 A1 | 9/2003 | Carr et al. |
| 2003/0199438 A1 | 10/2003 | Shaw et al. |
| 2003/0228258 A1 | 12/2003 | Scheinberg et al. |
| 2004/0068100 A1 | 4/2004 | Mach et al. |
| 2004/0072262 A1 | 4/2004 | Montero-Julian et al. |
| 2004/0082012 A1 | 4/2004 | Busch et al. |
| 2004/0086520 A1 | 5/2004 | Diamond |
| 2004/0137642 A1 | 7/2004 | Erfle et al. |
| 2004/0141958 A1 | 7/2004 | Steinaa et al. |
| 2004/0143094 A1 | 7/2004 | Donda et al. |
| 2004/0204565 A1 | 10/2004 | Schneck et al. |
| 2004/0209295 A1 | 10/2004 | Schwabe et al. |
| 2004/0209314 A1 | 10/2004 | Lang et al. |
| 2004/0223977 A1 | 11/2004 | Diamond |
| 2004/0253632 A1 | 12/2004 | Rhode et al. |
| 2005/0003431 A1 | 1/2005 | Wucherpfennig et al. |
| 2005/0074822 A1 | 4/2005 | Nixon et al. |
| 2005/0074848 A1 | 4/2005 | Schwabe |
| 2005/0079152 A1 | 4/2005 | Bot et al. |
| 2005/0095655 A1 | 5/2005 | Montero-Julian et al. |
| 2005/0208529 A1 | 9/2005 | Winther et al. |
| 2005/0214284 A1 | 9/2005 | Price-Schiavi et al. |
| 2005/0214852 A1 | 9/2005 | Gaynor et al. |
| 2005/0239160 A1 | 10/2005 | Shaw et al. |
| 2006/0018878 A1 | 1/2006 | Cooper et al. |
| 2006/0018929 A1 | 1/2006 | Zaia et al. |
| 2006/0073159 A1 | 4/2006 | Vonderheide et al. |
| 2006/0078563 A1 | 4/2006 | Srivastava |
| 2006/0084116 A1 | 4/2006 | Muchhal |
| 2006/0112440 A1 | 5/2006 | Tsien et al. |
| 2006/0141540 A1 | 6/2006 | Miltenyi et al. |
| 2006/0155115 A1 | 7/2006 | Jakobsen et al. |
| 2006/0166214 A1 | 7/2006 | Kato et al. |
| 2006/0166875 A1 | 7/2006 | Jakobsen et al. |
| 2006/0171954 A1 | 8/2006 | Endl et al. |
| 2006/0228758 A1 | 10/2006 | Muchhal et al. |
| 2006/0228759 A1 | 10/2006 | Muchhal et al. |
| 2006/0234309 A1 | 10/2006 | Shankar et al. |
| 2006/0234310 A1 | 10/2006 | Cai et al. |
| 2006/0240482 A1 | 10/2006 | Kwok et al. |
| 2007/0026503 A1 | 2/2007 | Lacey |
| 2007/0134814 A1 | 6/2007 | Kajander et al. |
| 2007/0154953 A1 | 7/2007 | Brunner et al. |
| 2007/0178532 A1 | 8/2007 | Jacobson et al. |
| 2007/0184022 A1 | 8/2007 | Wang et al. |
| 2007/0280957 A1 | 12/2007 | Falk et al. |
| 2008/0219947 A1 | 9/2008 | Linette et al. |
| 2009/0004213 A1 | 1/2009 | Singh et al. |
| 2009/0061478 A1 | 3/2009 | Poulsen et al. |
| 2009/0232766 A1 | 9/2009 | Wang et al. |
| 2009/0324630 A1 | 12/2009 | Jensen |
| 2010/0159594 A1 | 6/2010 | Hansen et al. |

(56) References Cited

U.S. PATENT DOCUMENTS

| | | |
|---|---|---|
| 2011/0236411 A1 | 9/2011 | Scholler et al. |
| 2012/0020998 A1 | 1/2012 | Plumas et al. |

FOREIGN PATENT DOCUMENTS

| | | |
|---|---|---|
| EP | 0 106 873 | 5/1984 |
| EP | 0 352 761 | 1/1990 |
| EP | 0 516 953 | 12/1992 |
| EP | 0 633 028 | 1/1995 |
| EP | 0 636 696 | 2/1995 |
| EP | 0 420 913 | 11/1995 |
| EP | 0 423 201 | 6/1996 |
| EP | 0 742 014 | 11/1996 |
| EP | 0 949 508 | 10/1999 |
| EP | 0946592 | 10/1999 |
| EP | 1023319 | 8/2000 |
| EP | 0 776 339 | 10/2000 |
| EP | 1 051 619 | 11/2000 |
| EP | 1181313 | 2/2002 |
| EP | 0 981 747 | 7/2002 |
| EP | 1 227 321 | 7/2002 |
| EP | 0 630 255 | 12/2002 |
| EP | 0 812 331 | 5/2004 |
| EP | 0 935 607 | 7/2004 |
| EP | 1 437 366 | 7/2004 |
| EP | 0 877 760 | 9/2004 |
| EP | 1 526 141 | 8/2005 |
| EP | 0 997 477 | 3/2006 |
| EP | 1 017 799 | 3/2006 |
| EP | 1 349 569 | 4/2007 |
| EP | 0 665 289 | 5/2007 |
| EP | 1 012 320 | 10/2007 |
| RU | 2 260 047 | 4/2005 |
| WO | WO 89/12458 | 12/1989 |
| WO | WO 89/12459 | 12/1989 |
| WO | WO 90/04411 | 5/1990 |
| WO | WO 91/09870 | 7/1991 |
| WO | WO 91/15766 | 10/1991 |
| WO | WO 92/00055 | 1/1992 |
| WO | WO 92/08983 | 5/1992 |
| WO | WO 92/18150 | 10/1992 |
| WO | WO 92/21972 | 12/1992 |
| WO | WO 93/01498 | 1/1993 |
| WO | WO 93/04175 | 3/1993 |
| WO | WO 93/08306 | 4/1993 |
| WO | WO 93/10220 | 5/1993 |
| WO | WO 94/11078 | 5/1994 |
| WO | WO 94/12196 | 6/1994 |
| WO | WO 95/11998 | 5/1995 |
| WO | WO 95/12676 | 5/1995 |
| WO | WO 95/14781 | 6/1995 |
| WO | WO 96/04314 | 2/1996 |
| WO | WO 96/26962 | 9/1996 |
| WO | WO 97/05239 | 2/1997 |
| WO | WO 97/28191 | 8/1997 |
| WO | WO 97/35991 | 10/1997 |
| WO | WO 97/42221 | 11/1997 |
| WO | WO 97/44667 | 11/1997 |
| WO | WO 98/03552 | 1/1998 |
| WO | WO 98/05965 | 2/1998 |
| WO | WO 98/06749 | 2/1998 |
| WO | WO 98/05684 | 5/1998 |
| WO | WO 1999/002183 | 1/1999 |
| WO | WO 99/11661 | 3/1999 |
| WO | WO 99/11775 | 3/1999 |
| WO | WO 99/14236 | 3/1999 |
| WO | 1999024577 A1 | 5/1999 |
| WO | WO 99/21572 | 5/1999 |
| WO | WO 99/13095 | 7/1999 |
| WO | WO 1999/36568 | 7/1999 |
| WO | WO 99/42597 | 8/1999 |
| WO | WO 99/50637 | 10/1999 |
| WO | WO 99/58557 | 11/1999 |
| WO | WO 99/60119 | 11/1999 |
| WO | WO 2000/006745 | 2/2000 |
| WO | WO 2000/015665 | 3/2000 |
| WO | 200021989 A1 | 4/2000 |
| WO | WO 2000/023053 | 4/2000 |
| WO | WO 2000/075180 | 12/2000 |
| WO | WO 2000/078966 | 12/2000 |
| WO | WO 2003/000720 | 1/2001 |
| WO | WO 2001/63286 | 8/2001 |
| WO | 200173443 A1 | 10/2001 |
| WO | WO 2001/72782 | 10/2001 |
| WO | WO 2001/072782 | 10/2001 |
| WO | WO 2001/070245 | 11/2001 |
| WO | WO 2001/080833 | 11/2001 |
| WO | WO 2001/090198 | 11/2001 |
| WO | WO 2001/090747 | 11/2001 |
| WO | WO 2002/016422 | 2/2002 |
| WO | WO 2002/054065 | 7/2002 |
| WO | WO 2002/072631 | 9/2002 |
| WO | WO 2002/089837 | 11/2002 |
| WO | WO 03/016905 | 2/2003 |
| WO | WO 2002/055992 | 3/2003 |
| WO | WO 2003/073097 | 9/2003 |
| WO | WO 2002/083906 | 10/2003 |
| WO | WO 2003/101473 | 12/2003 |
| WO | WO 2004/000873 | 12/2003 |
| WO | WO 2004/014957 | 2/2004 |
| WO | WO 2004-018520 | 3/2004 |
| WO | WO 2004-033497 | 4/2004 |
| WO | WO 2004/093905 | 11/2004 |
| WO | 2005003394 A2 | 1/2005 |
| WO | WO 2005/002621 | 1/2005 |
| WO | WO 2005/007689 | 1/2005 |
| WO | WO 2005/035567 | 4/2005 |
| WO | WO 2005/049073 | 6/2005 |
| WO | WO 2005/116051 | 12/2005 |
| WO | WO 2006/009838 | 1/2006 |
| WO | WO 2006/014292 | 2/2006 |
| WO | WO 2006/056027 | 6/2006 |
| WO | WO 2006/071990 | 7/2006 |
| WO | WO 2006/081826 | 8/2006 |
| WO | WO 2006/082387 | 8/2006 |
| WO | WO 2006/090283 | 8/2006 |
| WO | WO 2006/113622 | 10/2006 |
| WO | 2007015168 A2 | 2/2007 |
| WO | WO 2007/065098 | 6/2007 |
| WO | WO 2007/085266 | 8/2007 |
| WO | WO 2007/136778 | 11/2007 |
| WO | WO 2008/019366 | 2/2008 |
| WO | WO 2008/031133 | 3/2008 |
| WO | WO 2008/116468 | 10/2008 |
| WO | WO 2009/003492 | 1/2009 |
| WO | WO 2009/003493 | 1/2009 |
| WO | WO 2009/039854 | 4/2009 |
| WO | 2009077173 A2 | 6/2009 |
| WO | WO 2009/106073 | 9/2009 |
| WO | WO 2009/114207 | 9/2009 |
| WO | 2009126828 A2 | 10/2009 |
| WO | WO 2009/125231 | 10/2009 |
| WO | WO 2009/126816 | 10/2009 |
| WO | WO 2009/155535 | 11/2009 |
| WO | WO 2010/009735 | 1/2010 |
| WO | WO 2010/032022 | 3/2010 |
| WO | WO 2010/037395 | 4/2010 |
| WO | WO 2010/037397 | 4/2010 |
| WO | WO 2010/037402 | 4/2010 |
| WO | 2012044999 A2 | 4/2012 |
| WO | 2012094492 A2 | 7/2012 |

OTHER PUBLICATIONS

Oka et al. (PNAS, 2004, 101(38):13885-13890) (Year: 2004).*
Hodi et al. (PNAS,100(8):4712-4717) (Year: 2003).*
June (J. Clin. Invest., 117(6):1466-1476) (Year: 2007).*
Demaria et al. (Int. J. Radiation Oncology Biol. Phys., vol. 63, No. 3, pp. 655-666) (Year: 2005).*
Timmerman et al. (Cancer Research, 2002, 62:5845-5852) (Year: 2002).*

(56) References Cited

OTHER PUBLICATIONS

Akiyama, "Analysis of HLA-A24-restricted CMVpp65 peptide-specific CTL with HLA-A-*2402-CMVpp65 tetramer," Immunology Letters, vol. 95, Issue 2, pp. 199-205 (2004).
Busch, "Detection of Borrelia burgdorferi-Specific CD8+ Cytotoxic T Cells in Patients with Lyme Arthritis," The Journal of Immunology, vol. 157, No. 8, pp. 3534-3541 (1996).
Celis, "Identification of potential CTL Epitopes of Tumor-Associated Antigen Mage-1 for Five Common HLA-A Alleles," Molecular Immunology, vol. 31, No. 18, pp. 1423-1430 (1994).
Chen, "Modulation of CD1d-restricted NKT cell responses by CD4," Journal of Leukocyte Biology, vol. 82, pp. 1455-1465 (2007).
Dibrino, "Endogenous peptides bound to HLA-A3 possess a specific combination of anchor residues that permit identification of potential antigenic peptides," Proc. Natl. Acad. Sci. USA, vol. 90, pp. 1508-1512 (1993).
Denkberg, "Recombinant human single-chain MHC-peptide complexes made from E. coli by in vitro refolding: functional single-chain MHC-peptide complexes and tetramers with tumor associated antigens," Eur. J. Immunol., vol. 30, pp. 3522-3532 (2000).
Drake, "Cutting Edge: Lipid Raft Integrity Affects the Efficiency of MHC Class I Tetramer Binding and Cell Surface TCR Arrangement on CD8+ T Cells," The Journal of Immunology, vol. 166, No. 12, pp. 7009-7013 (2001).
He, "Procedure for preparing peptide-major histocompatibility complex tetramers for direct quantification of antigen-specific cytotoxic T lymphocytes," World J Gastroenterol, vol. 11, No. 27, pp. 4180-4187 (2005).
Kao, "Loss of CD8 and TCR binding to Class I MHC ligands following T cell activation," International Immunology, vol. 17, No. 12, pp. 1607-1617 (2005).
Karin, "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor α Production," J. Exp. Med., vol. 180, pp. 2227-2237 (1994).
Kronenberg, "The Unconventional Lifestyle of NKT Cells," Nature Reviews Immunology, vol. 2, pp. 557-568 (2002).
Nepom, "MHC Multimers: expanding the clinical toolkit," Clinical Immunology, vol. 106, pp. 1-4 (2003).
Parker, "Peptide Binding to HLA-A2 and HLA-B27 Isolated from Escherichia coli," The Journal of Biological Chemistry, vol. 267, pp. 5451-5459 (1992).
Rognan, "Rational design of nonnatural peptides as high-affinity ligands for the HLA-B*2705 human leukocyte antigen," Proc. Natl. Acad. Sci. USA, vol. 92, pp. 753-757 (1995).
Ruan, "Preparation of HLA-A*0201 NLVPMVATV peptide tetramers and application to detect cytomegalovirus specific CTL," Zhonghua Weishengwuxue He Mianyixue Zazhi, vol. 26., No. 9, pp. 855-858 (2006)—English Abstract Only.
Ruan, "Improved preparation of class I HLA tetramers and their use in detecting CMV-specific CTL," Journal of Immunological Methods, vol. 312, pp. 148-156 (2006).
Schueler-Furman, "Structure-based prediction of binding peptides to MHC class I molecules: Application to a broad range of MHC alleles," Protein Science, vol. 9, pp. 1838-1846 (2000).
Theisen, "Evolution of the borrelia burgdorferi outer surface protein OspC," Journal of Bacteriology vol. 177, No. 11, pp. 3036-3044 (1995).
Weinberg, "The Biology of Cancer," Garland Science, pp. 737-747 (2007).
Wulff, "Guide to Flow Cytometry," Dako Educational Guide, www.dako.com, (2006).
U.S. Appl. No. 08/374,468, filed Jan. 18, 1995, Boehringer Mannheim.
Altman et al., "Formation of functional peptide complexes of class II major histocompatibility complex proteins from subunits produced in Escherichia coli," Proc. Natl. Acad. Sci. USA, pp. 10330-10334, Nov. 1993, vol. 90.

Altman et al., "Phenotypic Analysis of Antigen-Specific T Lymphocytes," Science 274:94-97, 1996.
Appel et al., "Anergy induction by dimeric TCR ligands," J. Immunol., pp. 5279-5285, Apr. 15, 2001, vol. 166.
Appel et al., "Kinetics of T-cell receptor binding by bivalent HLA-DR-peptide complexes that activate antigen-specific human T-cells," J. Biol. Chem., pp. 312-321, Jan. 7, 2000, vol. 275.
Andersen et al., "Spontaneous cytotoxic T-cell responses against survivin MHC class I-restricted T-cell epttopes in situ as well as ex vivo in cancer patients," Cancer Res., vol. 61, pp. 5964-5968, Aug. 15, 2001.
Ausubel et al., "Characterization of in vivo expanded OspA-specific human T-cell clones," Clinical Immunology, Academic Press, pp. 313-322, Jun. 1, 2005 (Jun. 1, 2005), vol. 115, No. 3.
Barany et al., "Solid-phase peptide synthesis: a silver anniversary report," Int. J. Peptide Protein Res., 30:705-739, 1987 (Abstract Only).
Batard et al., "Dextramers: New generation of fluorescent MHC class I-peptide multimers for visualization of antigen-specific CD8<+> T cells," Journal of Immunological Methods, Elsevier Science Publishers, pp. 136-148, Mar. 20, 2006 (Mar. 20, 2006), vol. 310, No. 1-2.
Berger et al., "Circulation and hoimg of melanoma-reactive T cells to both cutaneous and visceral metastases after vaccinnation with monocyte-derived dendritic cells," Int. J. Cancer, pp. 229-237, 2004, vol. 111.
Bergmeier et al., "Innate and adoptive mucosal immunity in protection against HIV infection," Advances in Dental Research 2006, pp. 21-28, 2006, vol. 19, No. 1, XP002562924.
Bill et al., "Use of soluble MHC class II-peptide multimers to detect antigen-specific T cells in human disease," Arthritis Res., pp. 261-265, Feb. 28, 2002, vol. 4.
Bjorkman et al., "The foreign antigen binding site and T cell recognition regions of class I histocompatibility antigen," Nature 329:512-518, 1987.
Bogers, "CCR5 targeted SIV vaccination strategy preventing or inhabiting SIV infection," Vaccine, Butterworth Scientific, pp. 2974-2984, Aug. 13, 2004 (Aug. 13, 2004), vol. 22, No. 23-24. Guildford, GB.
Burlingham et al., "Soluble MHC, Immunoregulation, and tolerance: A progress report," Human Immunol., pp. 1316-1319, Dec. 2000, vol. 61.
Callan et al., "Direct Visualizing of Antigen.specific CD8+ T Cells during th ePRimary Immune Response to Epstein-Barr Virus in Vivo," J. Exp. Med., May 1998, pp. 1395-1402, vol. 187, No. 9.
Cameron et al., "Labeling antigen-specific DC4(+) T cells with class II MHC oligomers," J. Immunol. Methods, pp. 51-69, Oct. 1, 2002, vol. 268.
Carena et al., "Major Histocompatibility Complex Class I Molecules Modulate Activation Threshold and Early Signaling of T-Cell Antigen Receptor-γδStimulated by Nonpeptidic Ligands," J. Exp. Med., Nov. 17, 1997, pp. 1769-1774, 186 (10).
Casares et al., "Antigen-specific downregulation of T cells by doxorubicin delivered through a recombinant MHC II-peptide chimera," Nature Biotech., pp. 142-147, Feb. 2001, vol. 19.
Cochran et al., "Receptor clustering and transmembrane signaling T cells," TIBS, pp. 304-310, May 2001, vol. 26 (Abstract Only).
Coles et al., "Memory CD8 T lymphocytes express inhibitory MHC-specific Ly49 receptors," EUR. J. Immunol. 30:236-244, 2000.
Constantin et al., "Major histocompatibility complex (MHC) tetramer technologt: An evaluation," Biol. Res. Nursing, pp. 115-127, Oct. 2002, vol. 4.
Dal Porto et al, "A soluble divalent class I major histocompatibility complex molecule inhibits alloreactive T cells at nanomolar concentrations," Porc. Natl. Acad. Sci. 90.6671-6675, 1993.
Dako: "MHC Dextramers" Internet Article Jul. 6, 2006 URL: pri.dako.com-00207_mhcdex_0406.pdf.
Devito-Haynes et al., "Soluble donor HLA class I and β2-m-free heavy chain in serum of lung transplant recipients: Steady-state levels and increases in patients with recurrent CMV infection, acute rejection episodes, and poor outcome," Human Immunol., pp. 1370-1382, Dec. 2000, vol. 61.

(56) References Cited

OTHER PUBLICATIONS

Drouin et al., "Searching for borrelial T-cell epitopes associated with antibiotic-refractory Lyme arthritis," Molecular Immunology, pp. 2323-2332, Jan. 11, 2008 (Jan. 11, 2008), vol. 45, No. 8, GB.
Ed. Charron, "HLA: Genetic diversity of HLA. Functional and Medical Implication," EDK Press, pp. corresponding to Tables 1A and 1B, 1997.
Erout et al., "Preparation of Conjugates between Oligonucleotide and N-Vinylpyrrolidone-N-Acryoxysuccinimide Coplymers and Applications in Nucleic Acid Assays to Improve Sensitivity," Bioconjugate Chem. 1996, pp. 568-575, vol. 7.
Fields et al., "Solid phase peptide synthesis utilizing 9-fluorenylmethoxycarbonyl amino acids," Int. J. Peptide Res., 353:161-214, 1990 (Abstract Only).
Frayser et al., "Empty and peptide-loaded class II major histocompatibility complex proteins produced by expression in *Escherichia coli* and folding in vitro," Protein Expression and Purification, pp. 105-114, Feb. 1999, vol. 15 (Abstract Only).
Garboczi et al., "HLA-A2.peptide complexes: Refolding and crystallization of molecules expressed in *Escherichia coli* and complexed with single antigenic peptides," Proc. Natl. Acad. Sci., 89:3429-3433, 1992.
Gordon et al., "Applications of Combinatorial Technologies to Drug Discovery. 2. Combinatorial Organic Synthesis, Library Screening Strategies, and Future Directions," Journal of Medicinal Chemistry, 37 (10):1385-1401, 1994 (Abstract Only).
Haanen et al., "In situ detection of virus- and tumor-specific T-cell Immunity," Nature Medicine, Sep. 2000, pp. 1056-1060, vol. 6 (Abstract Only).
Hadrup et al., "Persistence of survivin specific T cells for seven years in a melanoma patient during complete remission," Cancer Biol. Ther., pp. 480-482, May 2006, vol. 5.
Houghten et al., "Generation and use of synthetic peptide combinatorial libraries for basic research and drug discovery," Nature, 354:84-86, 1991 (Abstract Only).
Huges et al., "Generation and use of alternative multimers of peptide-MHC complexes," Journal of Immunological Methods, 268:83-92, 2002.
Jung et al., "Multiple Peptide Synthesis Methods and their Applications," Angewandte Chemie, 31 (4):367-486, 1992 (Abstract Only).
Kalandadze et al., "Expression of Recombinant HLA-DR2 molecules," J. Biol. Chem., pp. 20156-20162, Aug. 16, 1996, vol. 271.
Knabel et al., "Reversible MHC multimer staining for functional isolation of T-cell populations and effective adoptive transfer," Nature Medicine, Nature Publishing Group, pp. 631-637, Jun. 1, 2002 (Jun. 1, 2002), vol. 8, No. 6.
König, "Interactions between MHC molecules and co-receptors of the TCR," Current Opinion in Immunology, pp. 75-83, 2002, vol. 14.
Kozono et al., "Production of soluble MHC class II proteins with covalently bound single peptides," Nature, pp. 151-154, May 12, 1994, vol. 369 (Abstract Only).
Kuroda et al., "Analysis of Gag-specific Cytotoxic T Lymphocytes in Simian Immunodeficiency Virus-intected Rhesus Monkeys by Cell Staining with Tetrameric Major Histocompatibility Complex Class I-Peptide Complex," J.Exp. Med., May 4 1998, 1373-1381, vol. 187, No. 9.
Kuttler et al., "An Algorithm for the Prediction of Proteasomal Cleavages," J. Miol. Biol., 298:417-429, 2000.
Larsson, "Immunocytochemical detection systems," in Immunocytohemistry: Theory and Practice, pp. 77-145, CRC Press, 1988.
Lee et al., "Characterizatio of circulating T cells specific for tumor-associateda ntigens in melanoma patients," Nature Medicine, Jun. 1999, pp. 677-685, vol. 5, No. 6.
Lehner, "Allomicrovac: A combined microbicidal-immunising strategy against SIV and HIV infection," Vaccines for Humans, pp. 64-65, Dec. 5, 2008 (Dec. 5, 2008), XP0025629223, URL: http:--www.biblioteca.porto.ucp.pt-docbweb-MULTIMEDIA-ASSOCIA-PDF-VAC.PDF.
Ljunggren et al., "Empty MHC class I molecules come out in the cold," Nature 346:476-480, 1990.
Mallone et al., "MHC class II tetramers and the pursuit of antigen-specific T cells: Define, deviate, delete," Clin. Immunol., pp. 232-242, 2004, vol. 110.
Marchand et al., "Tumor regression responses in melanoma patients treated with a peptide encoded by gene MAGE-3,"Int. J. Cancer, 63:883-885, 1995.
Matsumura et al., "Emerging Principles for the Recognition of Peptide Antigen by MHC class I Molecules," Science 257:927-934, 1992.
Matsumura et al., "In vitro peptide binding to soluble empty calss I major histocompatibility complex molecules isolated from transfected *Drosophila melanogaster* cells," J. Biol. Chem., pp. 23589-23595, Nov. 25, 1992, vol. 267.
McCluskey et al., "T-cell activation by purified, soluble , class I MHC molecules: Requirement for polyvalency," *J. Immunol.* 141(5): 1451-55, 1988.
McHeyzer-Williams et al., "Tracking antigen-specific helper T cell responses," Current Opinion in Immunology, pp. 278-284, 1996, vol. 8.
Merrifield et al., "Instrument for Automated Synthesis of peptides," Analytical Chemistry, 38 (13):1905-1914, 1966 (Abstract Only).
Merrifield, "Solid Phase Synthesis," Science 232:341-347, 1986 (Abstract Only).
Meyer et al., "Direct enumeration of Borrelia-reactive CD4 T-cell ex vivo by using MHC class II tetramers," Proceedings of the National Academy of Sciences of USA. (PNAS), National Academy of Science, pp. 11433-11438, Oct. 10, 2000 (Oct. 10, 2000), vol. 97, No. 21, Washington D.C., US.
Mutis et al., "Tetrameric HLA class I-minor histocompatability antigen peptide complexes demnstrate minor histocompatibility antigen-specific cytoxic T lymphocytes in patients with graft-visus-host disease," Nature Medicine, Jul. 1999, pp. 839-842, vol. 5, No. 7.
Neudorfer et al., "Reversible HLA multimers (streptamers) for the isolation of human cytotoxic T lymphocytes functionally active against tumor- and virus-derived antigens," Journal of Immunological Methods, 320:119-131, 2007.
O'Herrin et al., "Analysis of the Expression of Peptide-Major Histocaompatibility Complexes using high affinity Soluble Divalent T-Cell Receptors," The Journal of Biological Chemistry, Oct. 20, 1997, pp. 1333-1345, vol. 186, No. 8.
Reich et al., "Stability of empty and peptide-loaded class II major histocompatibility complex molecules at neutral and endosomal pH: Comparison to class I proteins," Proc. Natl. Acad. Sci. USA, pp. 2495-2500, Mar. 1997, vol. 94.
Reijonen et al., "Use of HLA class II tetramers in tracking antigen-specific T cell and mapping T-call epitopes," pp. 282-288, 2003, vol. 29.
Scheirle et al., "Peptide binding to soluble HLA-DR4 molecules produced by insect cells," J. Immunol., pp. 1994-1999, Sep. 15, 1992, vol. 149 (Abstract Only).
Scheffold et al., "Recent Development in Flow Cytometry," Journal of Clinical Immunology, Aug. 2000, vol. 20, No. 6.
Sengupta et al., "Heat shock protein-mediated cross-presentation of exogenous HIV antigen on HLA class I and class II," Journal of Immunology, American Association of Immunologists, pp. 1987-1993, Aug. 1, 2004 (Aug. 1, 2004), vol. 173, No. 3.
Shambrook, Fritsch and Maniatis, "Molecular Cloning," Cold Spring Harbor Press, 1989, Index and Table of Contents pp. xi to xxxviii and I-1 to I-47.
Shields et al., "The Effect of Human β2-Microglobulin on Major Histocompatibility Complex I Peptide Loading and the Engineering of a High Affinity Variant," The Journal of Biological Chemistry, Oct. 23, 1998, pp. 28010-28018, vol. 273, No. 43.
Siiman et al., Bioconjugate Chem. 1999, pp. 1090-1106.
Skinner et al., "In situ tetramer staining," J. Immunol. Meth., pp. 29-34, 2002, vol. 268.

(56) References Cited

OTHER PUBLICATIONS

Sørensen et al., "Efficient tumor cell lysis mediated by a bcl-X(L) specific T cell clone isolated from a breast cancer patient," Cancer Immunology, Immunotherapy, Springer, pp. 527-533, Jul. 19, 2006 (Jul. 19, 2006), vol. 56, No. 4.
Stern et al., "The human class II MHC protein HLA-DR1 assembles as empty alpha beta heterodimers in the absence of antigenic peptide," Cell, pp. 465-477, Feb. 7, 1992, vol. 68 (Abstract Only).
Stratmann et al., "Susceptible MHC Alleles, not background genes, select an autoimmune T cell reactivity," The Journal of Clinical Investigation, pp. 902-914, Sep. 2003, vol. 112, No. 6.
Stöckel et al., "Refolding of human class II major histocompatibility complex molecules isolated from *Escherichia coli*", J. Biol. Chem., pp. 29571-29578, Nov. 25, 1994, vol. 269.
Sun et al., "MHC class I multimers," Arthritis Res., pp. 265-269, Jul. 2001, vol. 3.
Ugolini et al., "Regulation of T cell function by NK cell receptors for classical MHC class I molecules," Current Opinion in Immunology 12:295-300, 2000.
Valmori et al., "Enhanced generation of specific tumor-reactive CTL in vitro by selected Melan-A-MART-1 immunodominant peptide analogues," J. Immunol., pp. 1750-1758, Feb. 15, 1998, vol. 160.
Viola et al., "T-cell activation and the dynamic world of rafts.," APMIS 107:615-623, 1999.
Vyth-Dreese et al., "In situ visualization of antigen specific T cells in cryopreserved human tissues," J. Immunol. Meth., pp. 78-85, 2006, vol. 310.
White et al., "Soluble class I MHC with β2-microglobulin covalently linked peptides: Specific binding to a T cell hybridoma," J. Immunol., pp. 2671-2676, Mar. 1, 1999, vol. 162.
Xu et al., "MHC-peptide tetramer-based studies of T cell function," J. Immunol Meth., pp. 21-28, 2002, vol. 268.
Zhang et al., "Essential role of LAT in T cell development," Immunity 10:323-332, 1999.
U.S. Appl. No. 12/619,039, filed Nov. 16, 2009, Jorgen Scholler.
U.S. Appl. No. 12/644,554, filed Dec. 22, 2009, Liselotte Brix.
U.S. Appl. No. 12/647,747, filed Dec. 18, 2009, Kivin Jacobsen.
U.S. Appl. No. 12/680,248, filed Mar. 26, 2010, Jorgen Scholler.
U.S. Appl. No. 12/919,405, filed Aug. 25, 2010, Jorgen Scholler.
Alp, et al., "Fine specificity of cellular immune responses in humans to human cytomegalovirus immediate-early 1 protein", Journal of Virology, vol. 65, No. 9, 1991 pp. 4812-4820.
Bleesing, et al., "Cell Function-Based Flow Cytometry" Seminars in Hematology, Apr. 2001, pp. 169-178, vol. 38, No. 2.
Bross, et al., "Approval summary: Gemtuzumab ozogamicin in relapsed acute myeloid leukemia", Clin. Cancer Res., 2001, 7:1490-1496.
Cecconi, et al., "Use of MHC Class II Tetramers to Investigate CD4 + T Cell Responses: Problems and Solutions," Cytometry, 2008, Part A 73, No. 11, pp. 1010-10018.
Chattopadhyay, et al.,"Techniques to improve the direct Ex Vivo detection of low frequency antigen-specific CD8+T cells with peptide-major histocompatibility complex class I tetramers," Cytometry, 2008, Part A, vol. 73, pp. 1001-1009.
Drouin, et al., "Molecular Characterization of the OspA161-175 T cell epitope associated with the treatment-resistant Lyme Arthritis: difference among the three pathogenic species of *Borrelia burgdorferu* sensu lato", Journal of Autoimmunology, 2004, vol. 23, No. 3, pp. 281-292.
Ferré, et al., "Purification of correctly oxidized MHC class I heavy-chain molecules under denaturing conditions: A novel strategy exploiting disulfide assisted protein folding", Protein Science, 2003, 12, pp. 551-559.
Fornas, et al., Flow Cytometry Counting of CD34+ cells in whole blood, Nature Medicine, 6 (2000) 7:833-836.
Heijnen, et al., "Enumeration of Antigen-Specific CD8+ T Lymphocytes by Single-Platform, Hla Tetramer-Based Flow Cytometry: A European Multicenter Evaluation", Clinical Cytometry, 2004, pp. 1-13, vol. 62B.

International Search report dated May 6, 2007 in International Application No. PCT/DK2007/000045.
Lissina, et al., "Protein Kinase Inhibitors Substantially Improve the Physical Detection of T-Cells with Peptide-MHC Tetramers," J. Immunol. Methods, 2009, vol. 340, pp. 11-24.
Maloney, et al., "IDEC-C2B8 (Rituximab) anti-CD20 monoclonal antibody therapy in patients with relapsed low-grade non-Hodgkin's lymphoma," Sep. 1997, Blood, 90 (6):21 :88-2195.
Melenhorst, et al.,"Detection of Low Avidity CD8+ T Cell Populations with Coreceptor-Enhanced Peptide-Major Histocompatibility Complex Class I Tetramers," j. Immunol. Methods, 2008, vol. 338, No. 1-2, pp. 31-39.
Vollers, et al., "Class II Major Histocompatibility Complex Tetramer Staining: Progress, Problems, and Prospects," Immunology, 2008, vol. 123, pp. 305-313.
Weichsel, et al. ,"Profound Inhibition of Antigen-Specific T-Cell Effector Functions by Dasatinib," Clin. Cancer Res.2008, vol. 14, pp. 2484-2491.
Wolfl, et al., "Quantitation of MHC Tetramer-Positive Cells From Whole Blood: Evaluation of Single-Platform, Six-parameter Flow Cytometric Method", Cytometry Part A, 2004, pp. 120-130, vol. 57A.
Andersen et al., Parallel detection of antigen-specific T-cell responses by combinatorial encoding of MHC multimers. NatProtoc., vol. 7, No. 5, pp. 891-902 (2012).
Bakker et al., "MHC multimer technology: Current status and future prospects", Current Opinion in Immunology, 17: 428-433, 2005.
Bauer et al., "Maximizing immune responses: the effects of covalent peptide linkage to beta-2-microglobulin"; Oncol Res. 17(5):205-16, (2008).
Cortez-Gonzales et al., Immunogenic HLA-B7-restricted peptides of hTRT. Intl Immunology vol. 18, No. 12 1707-1718 (2006).
Desrosiers, "Prospects for an AIDS vaccine," Nature Medicine, vol. 10, No. 3, 221-223 (2004).
Dibrino et al., "HLA-A1 and HLA-A3 T cell epitopes derived from influenza virus proteins predicted from peptide binding motifs." J Immunol., 151(11):5930-5 (1993).
Greten et al., "Peptide-beta-2-microglubulin-MHC fusion molecules bind antigen-specific T cells and can be used for multivalent MHC-Ig complexes," J. Immunological Methods, 27(1-2):125-135 (2002).
Hackett et al., "Frontiers in peptide-MHC class II multimer technology," Nature Immunology, vol. 3, No. 10, 887-889 (2002).
HLA nomenclature (hia.alleles.org/nomenclature/stats.html, 2010).
Larsen MV (4/07 Prediction of T-cell epitopes for therapeutic and prophylactic vaccines, Ph.D. thesis, Center for Biological Sequence Analysis BioCentrum DTU—Denmark), (2007).
Lauritsen et al., Two distinct pathways exist for down-regulation of the TCR. J Immunology, 161:260-7 (1998).
Maher, 'Liposomes and Micelles', Dynamic Chiropractic. www.dynamicchirpractic.com (2016).
Matthews et al., "Prospects for Development of a Vaccine Against HTLV-III-Related Disorders"; Aids Research and Human Retroviruses, 3: 197-206 (1987).
Hadrup et al., "Parallel detection of antigen-specific T-cell responses by multidimensional encoding of MHC multimers", Nature Methods (Nature Publishing Group), Basinstoke GB, vol. 6, No. 7, doi:10.1038/NMETH.1345, ISSN 1548-7091, pp. 520-528 (2009).
Nikolich-Zugich et al., "The many important facets of t-cell repertoire diversity, Nature Reviews Immunology," vol. 4, 123-132 (2004).
Rammensee et al., "MHC ligands and peptide motifs: first listing. Immunogenetics," 41:178-228 (1995).
Sano et al., "Immuno-PCR: Very sensitive antigen detection by means of specific antibody-DNA conjugates," Science American Association for the Advancement of Science, US, vol. 258, No. 5079, 120-122 (1992).
Schroers et al., Identification of HLA DR7-restricted epitopes from human telomerase reverse transcriptase recognized by CD4+ T-helper cells, Cancer Research 62, 2600-2605 (2002).
Stoeva et al., "Multiplexed Detection of Protein Cancer Markers with Biobarcoded Nanoparticle Probes", Journal of the American

(56) References Cited

OTHER PUBLICATIONS

Chemical Society, American Chemical Society, US, vol. 128, No. 26, doi:10.1021/JA0613106, ISSN 0002-7863, (2006), pp. 8378-8379 (2006).

Xu, "Preparation and Characterization of HLA-A *0201 Tretamer Loaded with IE-1 316-324 Antigenic Peptide of Human Cytomegalovirus," Cullular & Molecular Immunology, vol. 3, No. 5, pp. 367-371 (2006).

Yang et al. "Immunization with recombinant macaque major histocompatibility complex class I and II and human immunodeficiency virus gp140 inhibits simian-human immunodeficiency virus infection in macaques," Journal of General Virology, vol. 93, pp. 1506-1518 (2012).

Busch et al., J. Gen Virol, 88: 1708-1716, (2007) (cited in P1995US01 2016).

Le Doussal et al., "Phage display of peptide/major histocompatibility complex", Journal of Immunological Methods, vol. 241, issues 1-2, 31, pp. 147-158, 2000.

Seneci, Pierfausto, "Encoding Techniques for Pool Libraries of Small Organic Molecules", Journal of Receptors and Signal Transduction, vol. 21, 2001—Issue 4. pp. 409-445. doi.org/10.1081/RRS-100107925.

* cited by examiner

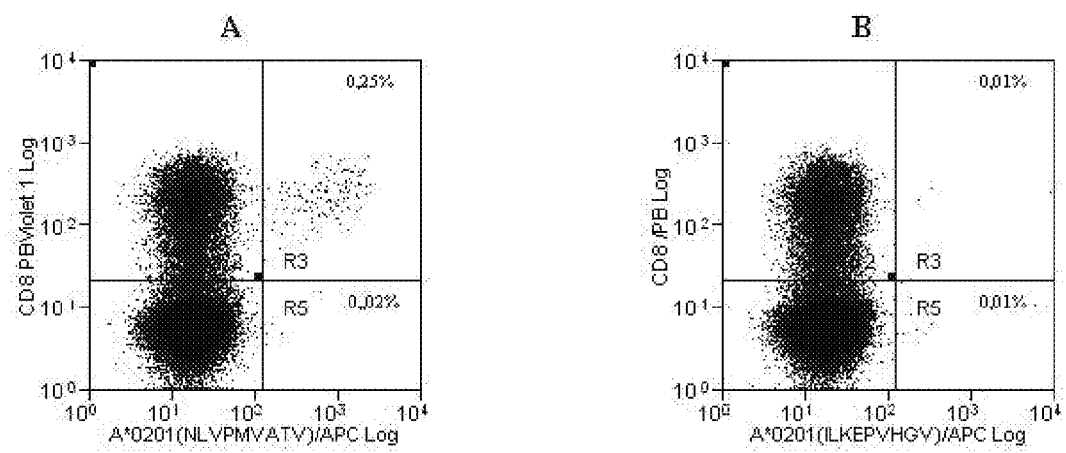
Fig. 1: Flow cytometry analysis of MHC multimer constructs

A
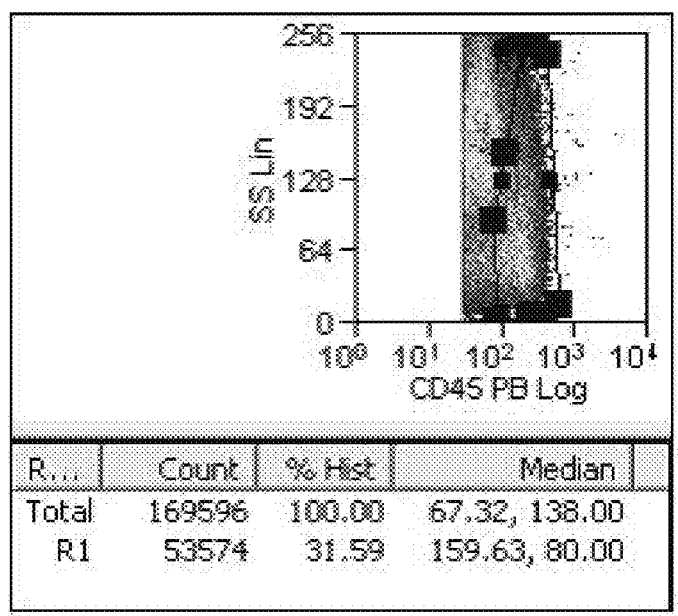
B
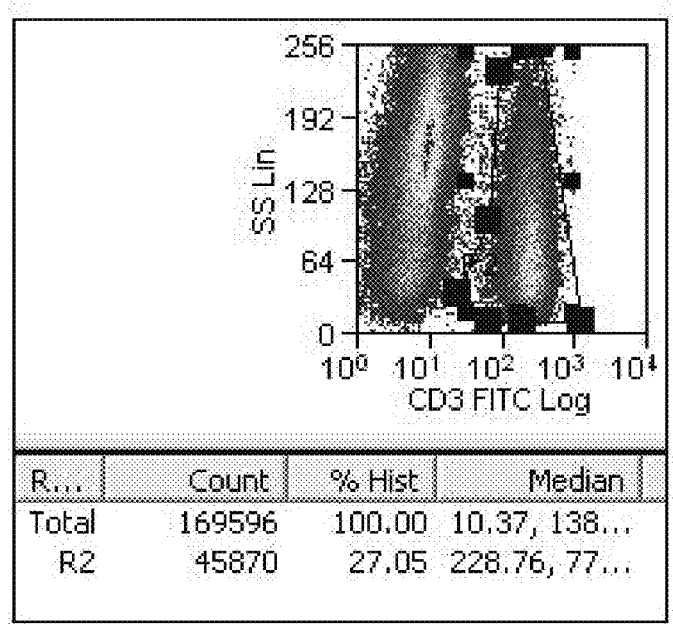
Fig. 2: Gating strategy for no-lyse no-wash procedure

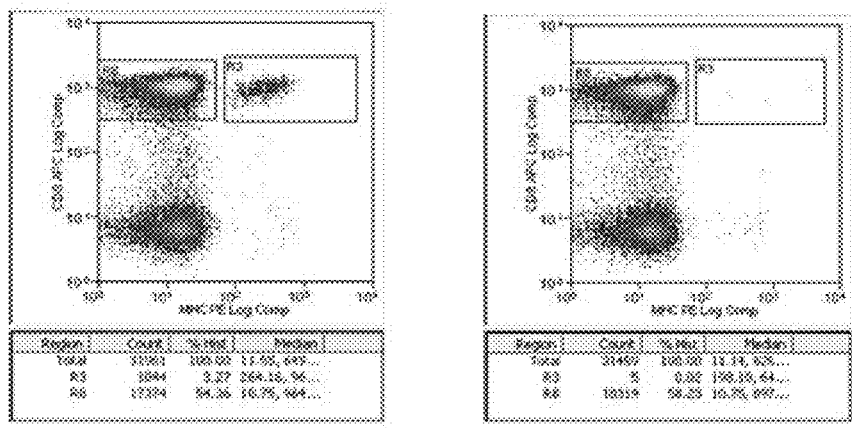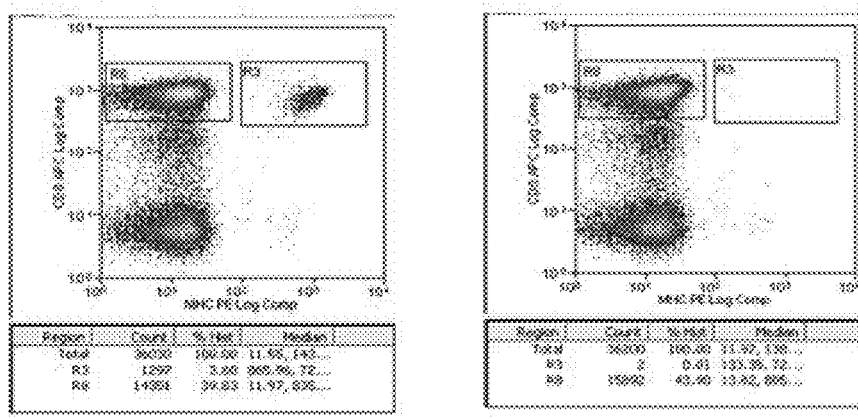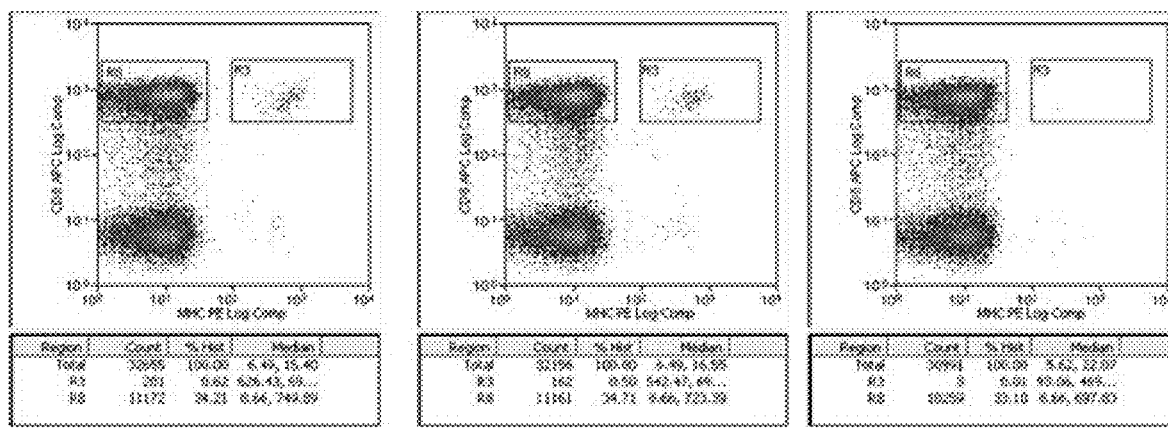
Fig. 3: Identification of CMV-specific T cells in a blood sample using no-lyse no-wash procedure

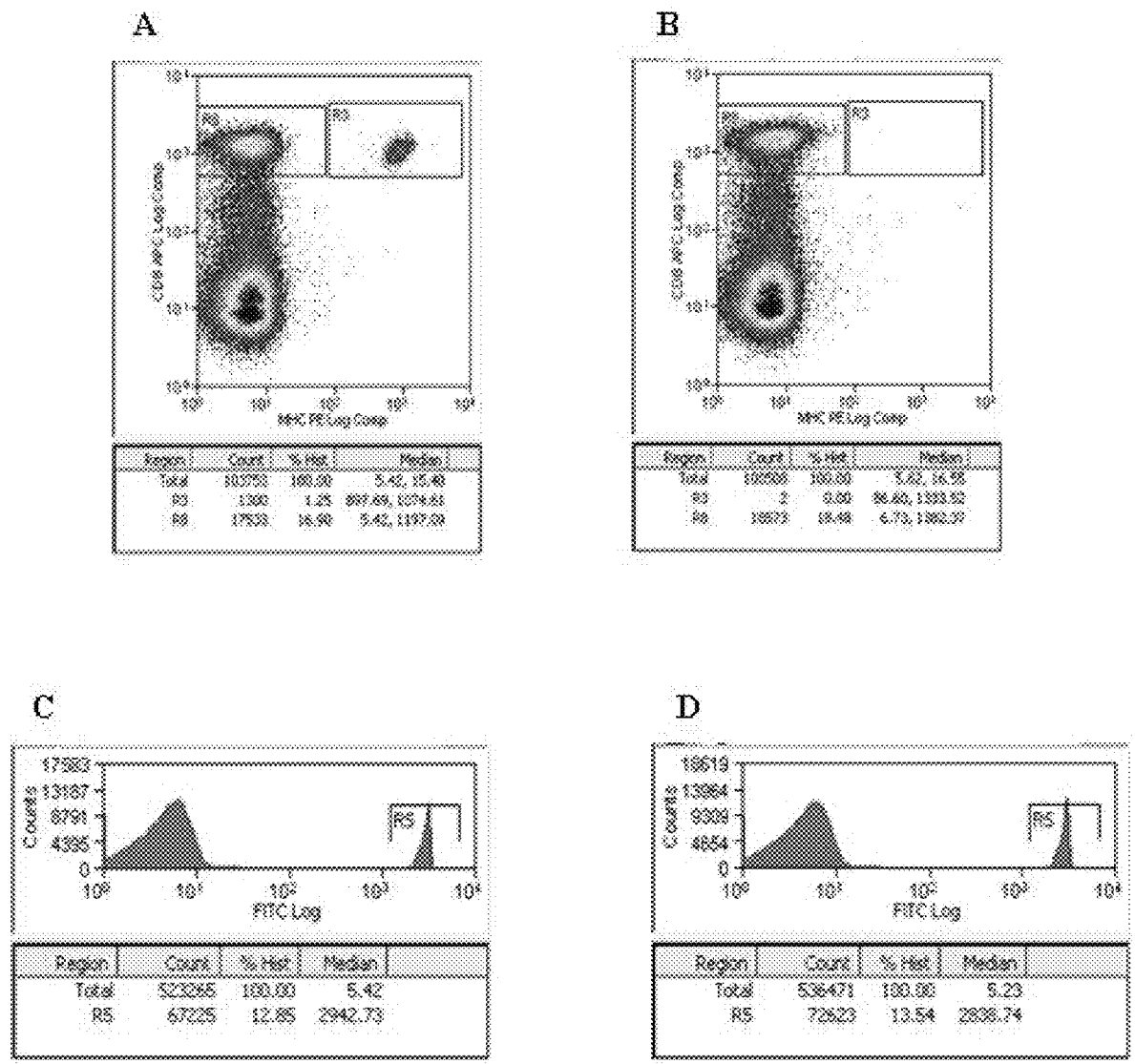
Fig. 4: Enumeration of specific T cells using CytoCountTM beads

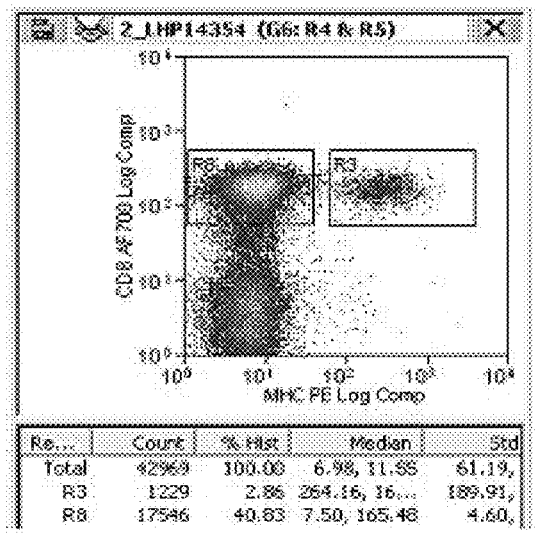
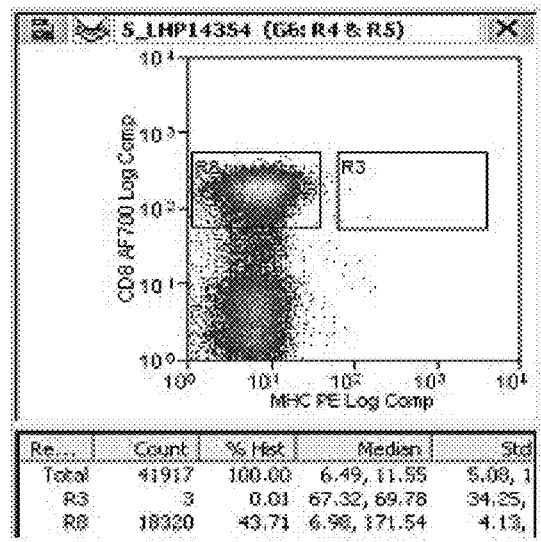
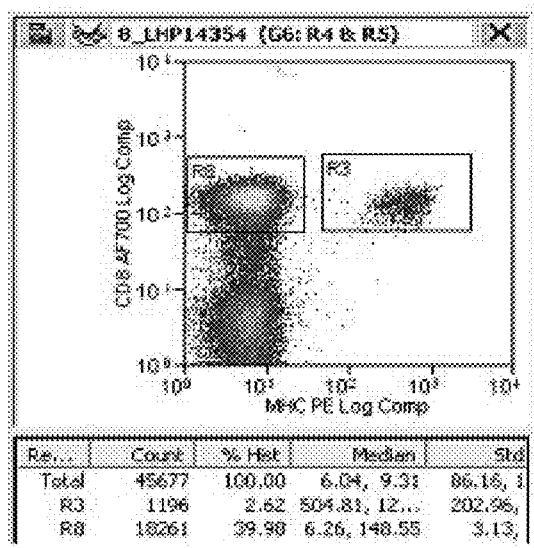
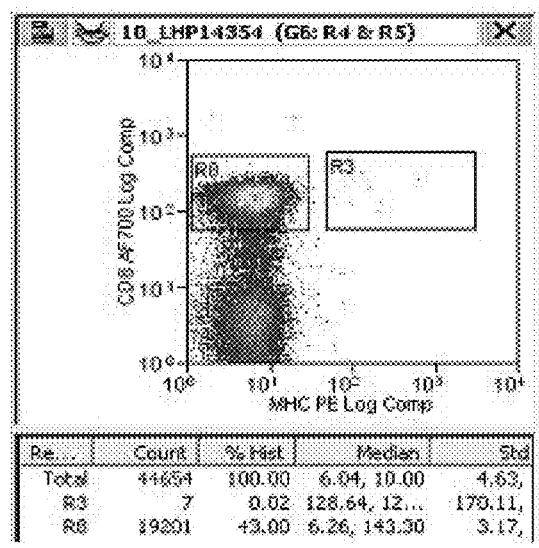
Fig. 5: MHC-peptide complexes embedded in a sugar matrix together with antibodies and used for detection of specific T cells in a blood sample

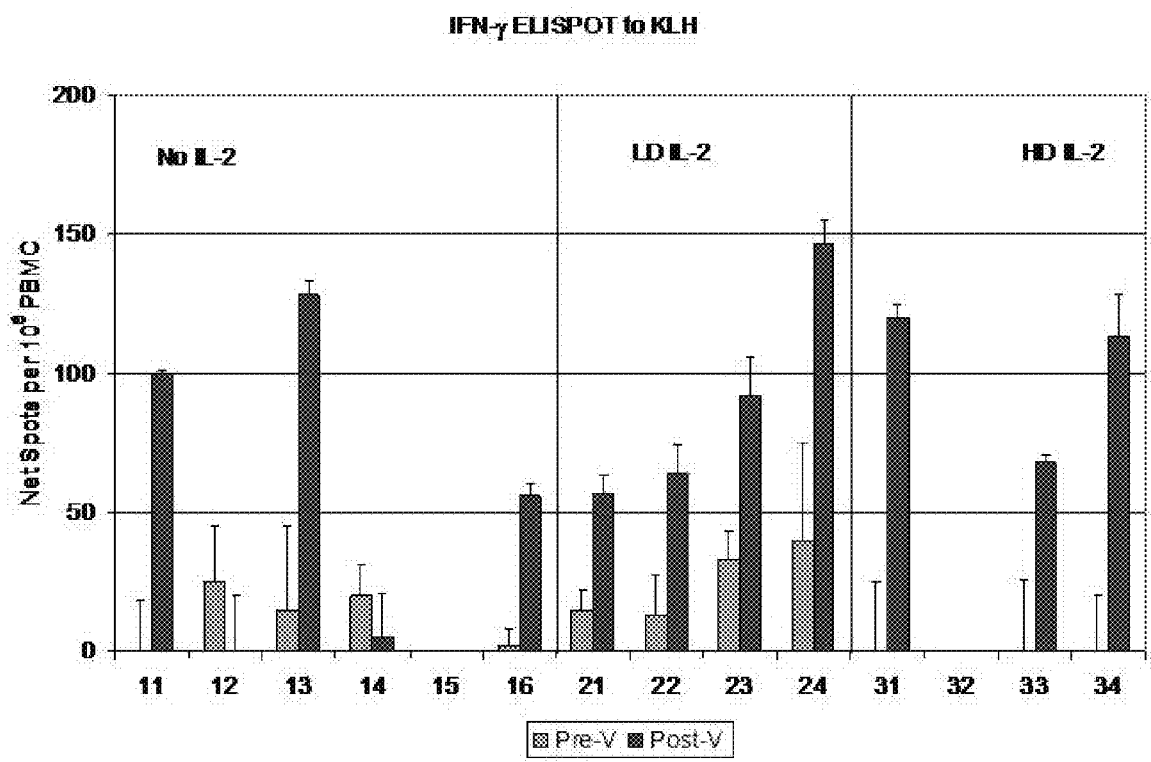
a
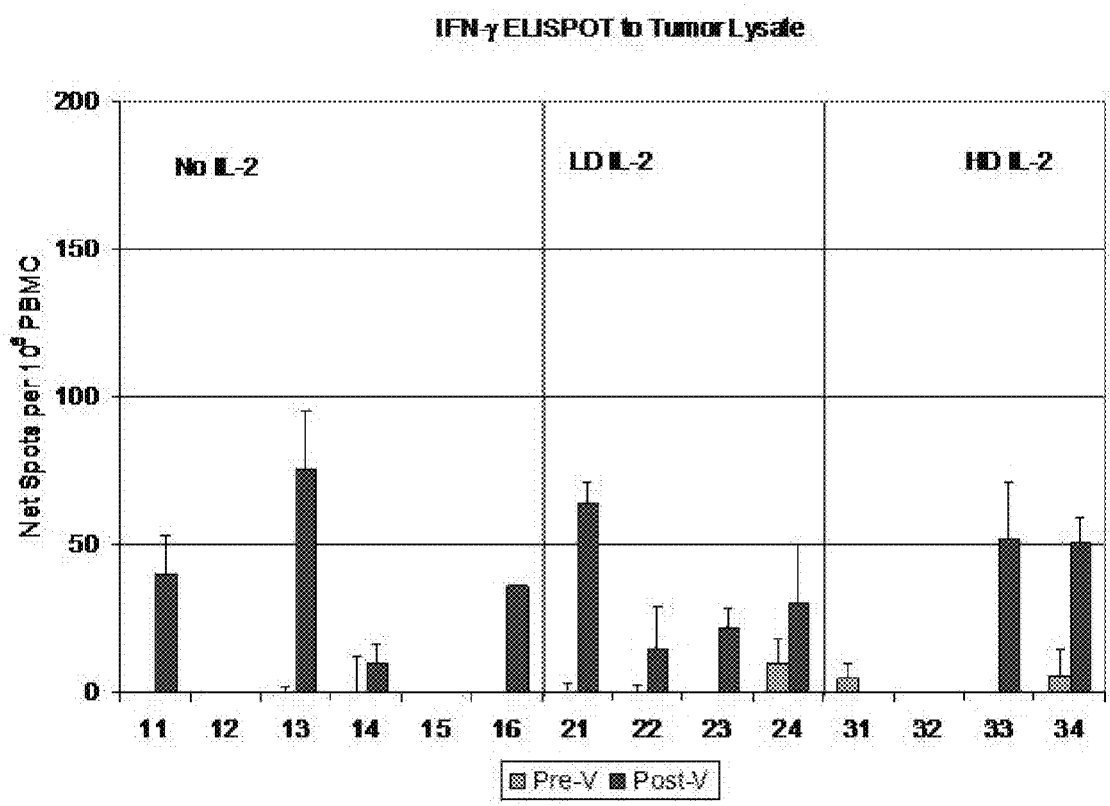
b
Fig. 6

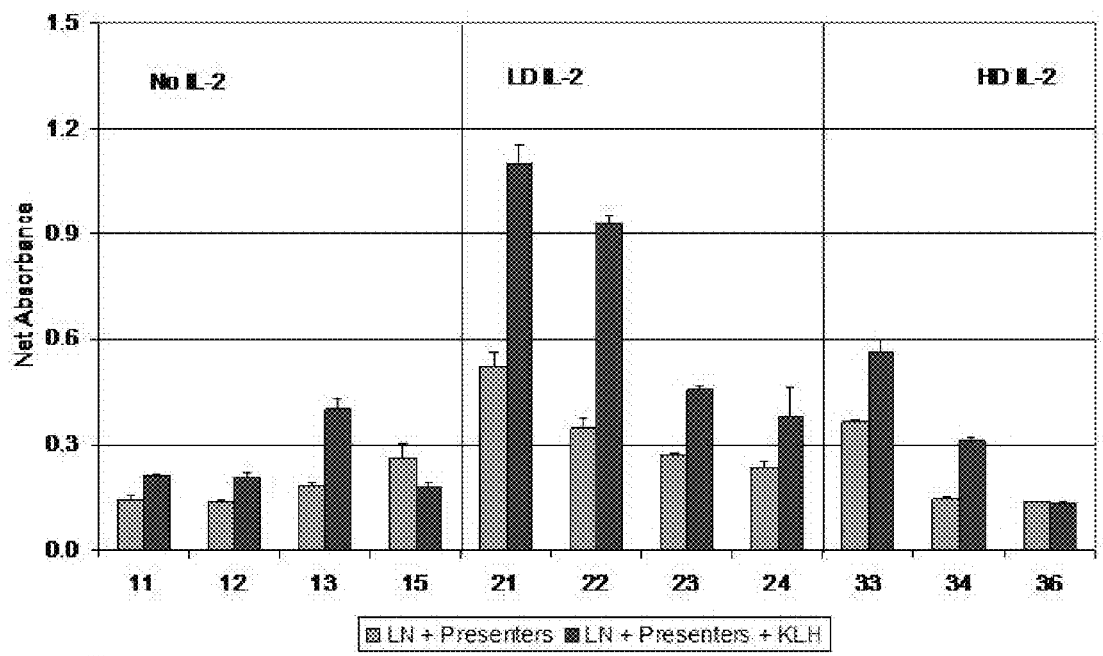
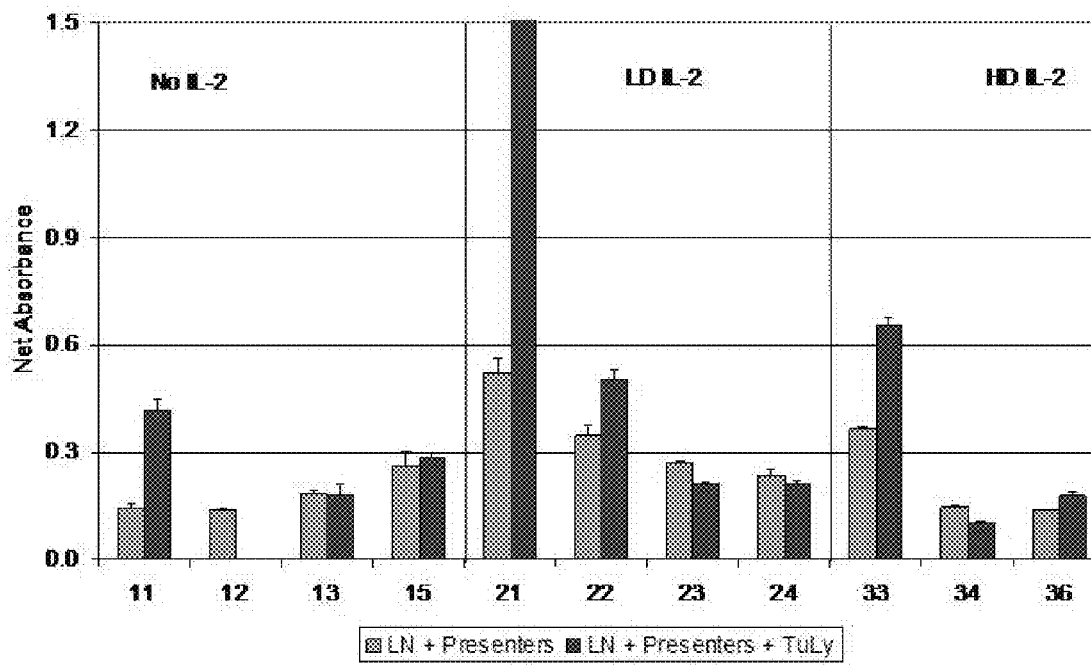
Fig. 8

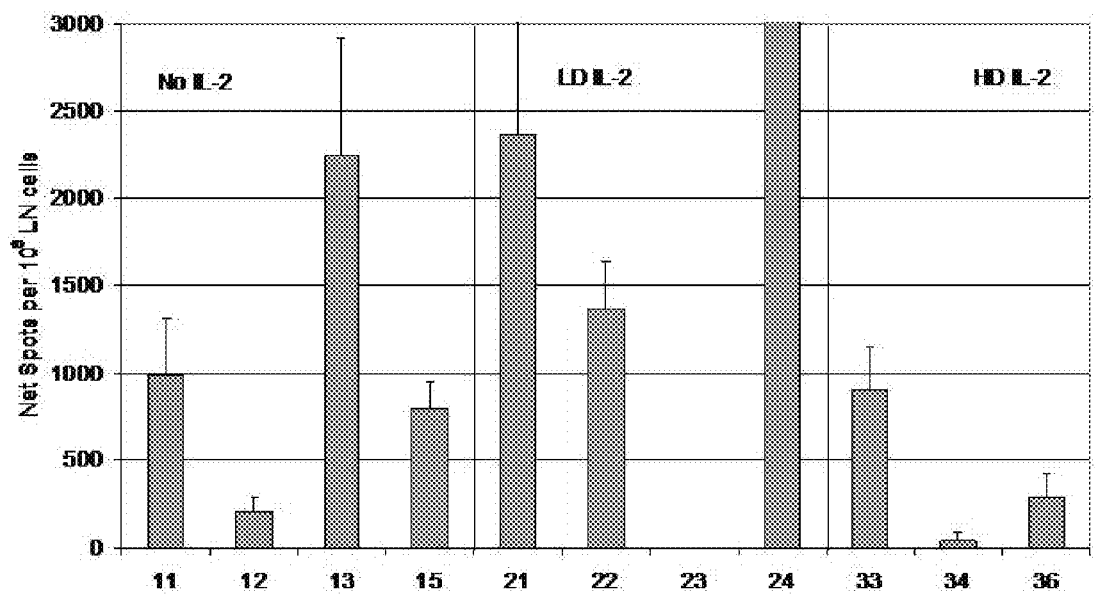
a
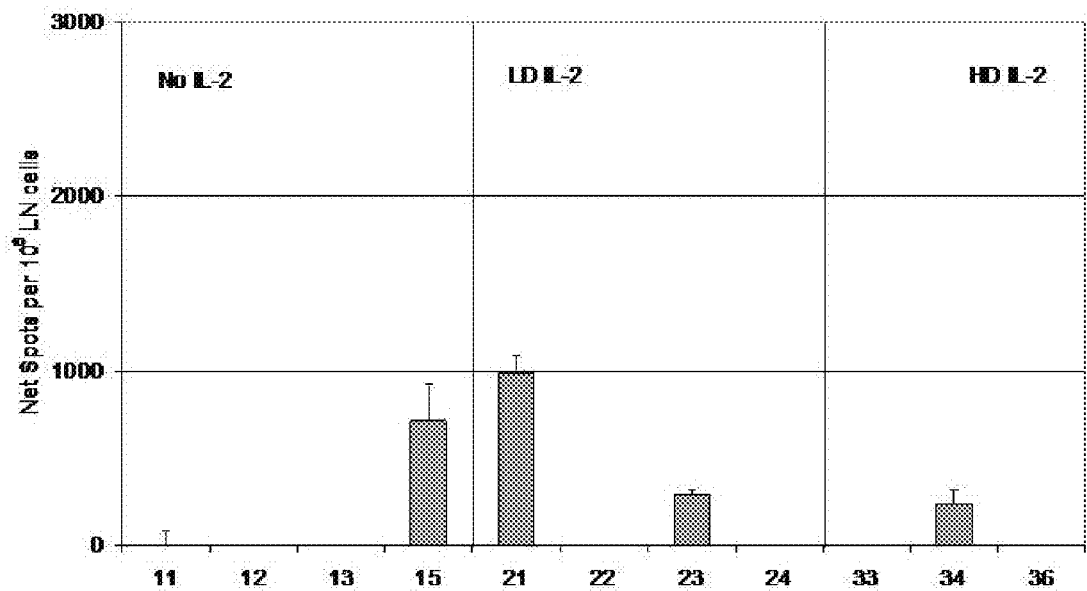
b
Fig. 9

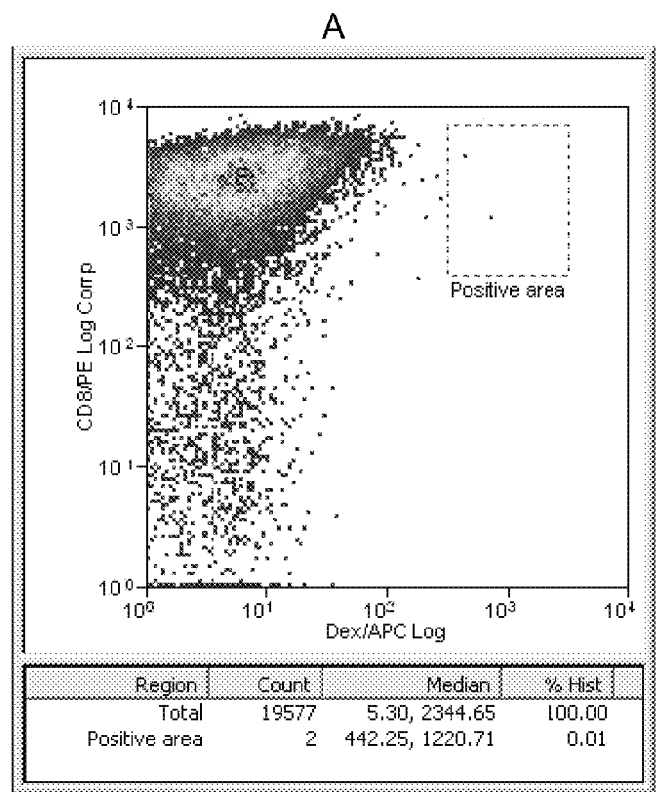
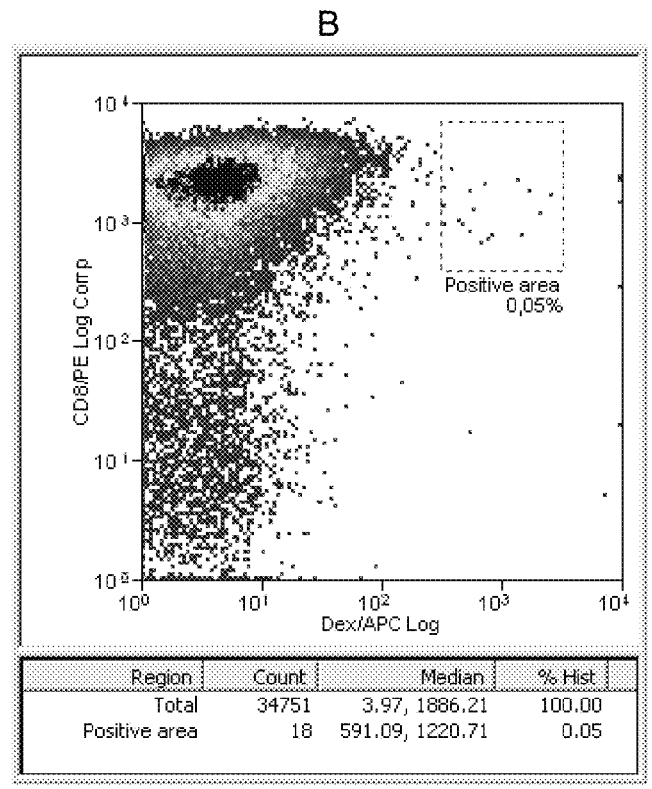
Fig. 11

COMBINATORIAL ANALYSIS AND REPAIR

TECHNICAL FIELD

The present invention relates to a method for combinatorial use of a diagnostics method and a repair process, on an undesired state of a live or non-live unit, in order to repair said unit in an appropriate way. The present invention also relates to a method for combinatorial use of one or more analysis method(s) such as one or more diagnostic method(s) and one or more repair process(es) such as one or more treatment(s), on an undesired state of a live or non-live unit, in order to repair or improve the undesired state of said unit in an appropriate way.

BACKGROUND OF THE INVENTION

In the field of medicine, a large number of new analyses have recently been developed, allowing more precise and earlier diagnosis of disease states. Likewise, improved treatments for a large number of diseases have recently been developed. Many novel treatments are directed at specific molecular targets in the body, giving rise to fewer side effects than with previously available treatments.

These developments would allow a much better treatment of the diseases at an earlier state, if the recently developed diagnostics were combined with the recently developed treatments.

In related fields such as agriculture and animal health, similar technological developments have recently occurred, and therefore, a similar improvement would result from a combination of new diagnostics and therapeutic methods.

In more distant fields, such as in the building industry, a similar development has taken place. Again, combination of the new methods would allow a better and more appropriate repair of structures already produced (e.g. bridges, motor parts, windmills (e.g. propellers), cars, airplanes, glass structures, pipelines, buildings, roads, railway tracks, teeth, electronic equipment (e.g. computers), textiles, electric installations).

In the development of new materials such as e.g. composite materials, it would be advantageous to have at hand analytical methods that allow stringent determination of a number of parameters (e.g. homogeneity, viscosity) during the production, and being able to modify these parameters during the production, to achieve materials of the best possible character. Thus, combinatorial analysis and repair would improve the development of new materials.

Finally, in the computer software industry, the development of new programs including neural networks and programs coordinating computers in interconnected networks has led to a number of novel ways to analyse the behaviour of these new programs, and likewise, novel ways of repairing these programs. Improved software programs and lower costs of software development would result from a more appropriate combination of analytical and repair technologies.

SUMMARY OF THE INVENTION

The problem to be solved by the present invention is to provide an appropriate means of repairing a unit, by measuring parameters or features of the unit that are appropriate for a correct diagnosis of the undesired state of the unit, or that are appropriate for an appropriate repair of the unit, followed by a repair process in which the unit is modified, to change the state of the unit into a more desired condition, compared to the condition of the unit before the repair process was performed.

The diagnosis may involve chemical, physical or mechanical means of analysis, and may measure chemical, physical or mechanical parameters. In the present invention the term diagnosis is used interchangeably with the term diagnosis to describe the detection or measurement of substances or features, characteristics for an undesired state or desired state of a unit. Likewise, the repair may involve chemical, physical or mechanical processes, and may affect chemical, physical or mechanical parameters of the unit.

The solution to the problem is based on an advantageous combination of a diagnosis procedure and a repair process, or advantageous combination of a diagnosis procedure, a repair process and an undesired state, or advantageous combination of a diagnosis procedure, a repair process, an undesired state and a unit.

Accordingly, in a first aspect the invention relates to a method for repairing a unit, by measuring parameters or features of the unit that are appropriate for a correct diagnosis of the undesired state of the unit, or that are appropriate for an appropriate repair of the unit, followed by a repair process in which the unit is modified, to change the state of the unit into a more desired condition, compared to the condition of the unit before the repair process was performed, and wherein said method comprises the following steps, (i) determining the amount or relative amount of a substance or a feature of a unit, by measuring the amount of said substance or said feature of said unit, or by measuring the amount of said substance or said feature in the vicinity of said unit, and (ii) changing the amount or relative amount of a substance or a feature of a unit, by addition or removal of an amount of said substance or said feature from said unit, or by addition of an effector that mediates a decrease or increase in the amount of said substance or said feature in said unit.

DEFINITIONS

Adjuvant: Any substance whose admixture with an administered immunogenic determinant increases or otherwise modifies the immune response to said determinant. Adjuvants are often used to optimise the efficacy of an immunogenic composition. Adjuvants generally consist of agents that are included in the formulation used to provide and/or enhance the ability of the immunogenic composition to induce a desired immune response. Potent, nontoxic adjuvants that will enhance and/or modulate the immunogenicity of immunogenic determinants including antigenic determinants including haptenic determinants represent one group of preferred adjuvants. In addition, such adjuvants preferably also elicit an earlier, more potent, or more prolonged immune response. Such an adjuvant would also be useful in cases where an antigen supply is limited or is costly to produce.

Adjuvants are thus pharmacological or immunological agents that modify the effect of other agents (e.g., drugs, vaccines) while having few if any direct effects when given by themselves. Adjuvants are drugs that have few or no pharmacological effects by themselves, but can increase the efficacy or potency of other drugs when given at the same time. In another embodiment, an adjuvant is an agent which, while not having any specific antigenic effect in itself, can stimulate the immune system, increasing the response to a vaccine.

Amount: The concentration, number, weight, volume, or other measure of the abundance or presence of a given substance or feature.

Analysing: Performing an analysis.

Analysis: Used interchangeably herein with the term "diagnosis", to describe the detection or measurement of substances or features, characteristic for an undesired state or desired state of a unit.

Antigenic peptide: Any peptide molecule that is bound or able to bind into the binding groove of either MHC class 1 or MHC class 2.

Aptamer: the term aptamer as used herein is defined as oligonucleic acid or peptide molecules that bind a specific target molecule. Aptamers are usually created by selecting them from a large random sequence pool, but natural aptamers also exist. Aptamers can be divided into DNA aptamers, RNA aptamers and peptide aptamers Avidin: Avidin as used herein is a glycoprotein found in the egg white and tissues of birds, reptiles and amphibians. It contains four identical subunits having a combined mass of 67,000-68,000 daltons. Each subunit consists of 128 amino acids and binds one molecule of biotin.

Carrier: A carrier as used herein can be any type of molecule that is directly or indirectly associated with the MHC peptide complex. In this invention, a carrier will typically refer to a functionalized polymer (e.g. dextran) that is capable of reacting with MHC-peptide complexes, thus covalently attaching the MHC-peptide complex to the carrier, or that is capable of reacting with scaffold molecules (e.g. streptavidin), thus covalently attaching streptavidin to the carrier; the streptavidin then may bind MHC-peptide complexes. Carrier and scaffold are used interchangeably herein where scaffold typically refers to smaller molecules of a multimerization domain and carrier typically refers to larger molecule and/or cell like structures.

Chromophore: A chromophore, as used herein, is the part of a visibly coloured molecule responsible for light absorption over a range of wavelengths thus giving rise to the colour. By extension the term can be applied to uv or it absorbing parts of molecules.

Counting beads: Beads countable in a flow cytometry experiment.

CSF: Cerebrospinal fluid

Dendritic cell: The term dendritic cell as used herein is a type of immune cells. Their main function is to process antigen material and present it on the surface to other cells of the immune system, thus functioning as antigen-presenting cells.

Detection: In this invention detection means any method capable of measuring one molecule bound to another molecule. The molecules are typically proteins but can be any type of molecule Dextran: the term dextran as used herein is a complex, branched polysaccharide made of many glucose molecules joined into chains of varying lengths. The straight chain consists of _1->6 glycosidic linkages between glucose molecules, while branches begin from _1->3 linkages (and in some cases, _1->2 and _1->4 linkages as well).

Diagnosing: Performing a diagnosis.

Diagnosis: Used interchangeably herein with the term "analysis", to describe the detection or measurement of substances or features, characteristic for an undesired state of a unit.

Diagnostics. Substances used to make a diagnosis.

Diagnostic test: Test used for diagnosing, monitoring or analysing specific substances, features, conditions and/or characteristics for an undesired state of a unit.

Direct detection of T cells: Direct detection of T cells is used herein interchangeably with direct detection of TCR and direct detection of T cell receptor. As used herein direct detection of T cells is detection directly of the binding interaction between a specific T cell receptor and a MHC multimer DNA: The term DNA (Deoxyribonucleic acid) duplex as used herein is a polymer of simple units called nucleotides, with a backbone made of sugars and phosphate atoms joined by ester bonds. Attached to each sugar is one of four types of molecules called bases.

Drug: a chemical substance used in the treatment, cure or prevention of disease or used to otherwise enhance physical or mental well-being.

Effector: An effector is a molecule, structure or condition that has an effect on the amount or relative amount of a substance or a feature. Example effectors and the substance or feature they affect are: Antihypertension drug (effector) that lowers the blood pressure (feature); crosslinking agent such as a radical (effector) that increases the strength (feature) of a polymer network such as a poly acrylamide gel; crosslinking agent (effector) that increases the tensile strength (feature) of a polymer fiber; etc.

Entity: An entity of the present invention is something that has a distinct, separate existence. Example of entities of the present invention includes cells, cell like structures, supramolecular compartments, molecules, supra molecular structures and particles.

Elimination: An elimination process removes entirely or partly a feature or substance.

Fab fragment: The fragment of antibodies with specific antigen binding. Fab fragments consist of antibody light chain and the amino terminal half of the heavy chain held together by disulfide bond.

Feature: A feature is a characteristic of a unit, for example a crack or a hole in a structure, the flexibility or strength of the unit, or its appearance (e.g. color or refractory index)

Flow cytometry: The analysis of single cells using a flow cytometer.

Flow cytometer: Instrument that measures cell size, granularity and fluorescence due to bound fluorescent marker molecules as single cells pass in a stream past photodectors. A flow cytometer carry out the measurements and/or sorting of individual cells.

Fluorescent: the term fluorescent as used herein is to have the ability to emit light of a certain wavelength when activated by light of another wavelength.

Fluorochromes: fluorochrome, as used herein, is any fluorescent compound used as a dye to mark e.g. protein with a fluorescent label.

Fluorophore: A fluorophore, as used herein, is a component of a molecule which causes a molecule to be fluorescent.

Folding: In this invention folding means in vitro or in vivo folding of proteins in a tertiary structure.

IgG: IgG as used herein is a monomeric immunoglobulin, built of two heavy chains and two light chains. Each molecule has two antigen binding sites.

Immune monitoring: Immune monitoring of the present invention refers to testing of immune status in the diagnosis and therapy of diseases like but not limited to cancer, immunoproliferative and immunodeficiency disorders, autoimmune abnormalities, and infectious disease. It also refers to testing of immune status before, during and after vaccination and transplantation procedures and other treatments.

Immune monitoring process: a series of one or more immune monitoring analysis

Label: Label herein is used interchangeable with labeling molecule. Label as described herein is an identifiable substance that is detectable in an assay and that can be attached to a molecule creating a labeled molecule. The behavior of the labeled molecule can then be studied.

Labelling: Labelling herein means attachment of a label to a molecule.

Liposomes: The term liposomes as used herein is defined as a spherical vesicle with a membrane composed of a phospholipid and cholesterol bilayer. Liposomes, usually but not by definition, contain a core of aqueous solution; lipid spheres that contain no aqueous material are called micelles.

Linker molecule: Linker molecule and linker is used interchangeable herein. A linker molecule is a molecule that covalently or non-covalently connects two or more molecules, thereby creating a larger complex consisting of all molecules including the linker molecule.

Marker molecule: Marker molecule is used interchangeably with marker herein. A marker is molecule that specifically associates covalently or non-covalently with a molecule belonging to or associated with an entity.

Medicament: Any composition for use prophylactically, therapeutically, diagnostically, or a cosmetic agent, in connection with treatment of an individual, such as man or any other animal.

MHC: Denotes the major histocompatibility complex.

An "MHC Class I molecule" as used everywhere herein is defined as a molecule which comprises 1-3 subunits, including a heavy chain, a heavy chain combined with a light chain (beta2m), a heavy chain combined with a light chain (beta2m) 5 through a flexible linker, a heavy chain combined with a peptide, a heavy chain combined with a peptide through a flexible linker, a heavy chain/beta2m dimer combined with a peptide, and a heavy chain/beta2m dimer with a peptide through a flexible linker to the heavy or light chain. The MHC molecule chain can be changed by substitution of single or by cohorts 10 of native amino acids or by inserts, or deletions to enhance or impair the functions attributed to said molecule. By example, it has been shown that substitution of XX with YY in position nn of human beta2m enhance the biochemical stability of MHC Class I molecule complexes and thus can lead to more efficient antigen presentation of subdominant peptide epitopes.

A "MHC Class II molecule" as used everywhere herein is defined as a molecule which comprises 2-3 subunits including an alpha-chain and a beta-chain (alpha/beta-dimer), an alpha/beta dimer with a peptide, and an alpha/beta dimer combined with a peptide through a flexible linker to the alpha or beta chain, an alpha/beta dimer combined through an interaction by affinity tags e.g. jun-fos, an alpha/beta dimer combined through an interaction by affinity tags e.g. jun-fos and further combined with a peptide through a flexible linker to the alpha or beta chain. The MHC molecule chains can be 30 changed by substitution of single or by cohorts of native amino acids or by inserts, or deletions to enhance or impair the functions attributed to said molecule. Under circumstances where the alpha-chain and beta-chain have been fused, to form one subunit, the "MHC Class II molecule" can comprise only 1 subunit.

MHC Class II like molecules (including non-classical MHC Class II molecules) include HLA DM, HLA DO, I-A beta2, and I-E beta2.

"MHC complexes" and "MHC constructs" are used interchangeably herein.

MHC complex: MHC complex is herein used interchangeably with MHC-peptide complex, unless it is specified that the MHC complex is empty, i.e. is not complexed with peptide.

"MHC protein" and "MHC molecule" are used interchangeably herein. Accordingly, a functional MHC peptide complex comprises a MHC protein or MHC molecule associated with a peptide to be presented for cells or binding partners having an affinity for said peptide.

By the terms "MHC complexes" and "MHC multimers" as used herein are meant such complexes and multimers thereof, which are capable of performing at least one of the functions attributed to said complex or multimer. The terms include both classical and non-classical MHC complexes. The meaning of "classical" and "non-classical" in connection with MHC complexes is well known to the person skilled in the art.

Nonclassical MHC complexes are subgroups of MHC-like complexes. The term "MHC complex" includes MHC Class I molecules, MHC Class II molecules, as well as MHClike molecules (both Class I and Class II), including the subgroup non-classical MHC Class I and Class II molecules.

The MHC molecule can suitably be a vertebrate MHC molecule such as a human, a mouse, a rat, a porcine, a bovine or an avian MHC molecule. Such MHC complexes from different species have different names. E.g. in humans, MHC complexes are denoted HLA. The person skilled in the art will readily know the name of the MHC complexes from various species.

MHC dextramer: A MHC multimer where MHC molecules are attached to dextran backbone together with or without labeling molecules.

MHC multimer: The terms MHC multimer, MHCmer and MHC'mer herein are used interchangeably, to denote a complex comprising more than one MHC-peptide complexes, held together by covalent or non-covalent bonds.

MHC molecule: Herein denotes the empty MHC protein, i.e. MHC protein not complexed with antigenic peptide.

Monoclonal antibodies: Monoclonal antibodies, as used herein, are antibodies that are identical because they were produced by one type of immune cell and are all clones of a single parent cell.

Multimerization domain: A multimerization domain is a molecule, a complex of molecules, or a solid support, to which one or more MHC or MHC-peptide complexes can be attached. A multimerization domain consist of one or more carriers and/or one or more scaffolds and may also contain one or more linkers connecting carrier to scaffold, carrier to carrier, scaffold to scaffold. The multimerization domain may also contain one or more linkers that can be used for attachment of MHC complexes and/or other molecules to the multimerization domain.

Multimerization domains thus include IgG, streptavidin, streptactin, micelles, cells, polymers, beads and other types of solid support, and small organic molecules carrying reactive groups or carrying chemical motifs that can bind MHC complexes and other molecules.

NMR: NMR (Nuclear magnetic resonance), as used herein, is a physical phenomenon based upon the quantum mechanical magnetic properties of an atom's nucleus. NMR refers to a family of scientific methods that exploit nuclear magnetic resonance to study molecules.

Non-covalent: The term non-covalent bond as used herein is a type of chemical bond, that does not involve the sharing of pairs of electrons, but rather involves more dispersed variations of electromagnetic interactions.

"One or more" as used everywhere herein is intended to include one and a plurality.

Pegylated: pegylated, as used herein, is conjugation of Polyethylene glycol (PEG) to proteins.

Peptide or protein: Any molecule composed of at least two amino acids. Peptide normally refers to smaller molecules of up to around 30 amino acids and protein to larger molecules containing more amino acids.

Phosphorylated: phosphorylated, as used herein, is the addition of a phosphate ($PO_4$) group to a protein molecule or a small molecule.

"A plurality" as used everywhere herein should be interpreted as two or more.

PNA: PNA (Peptide nucleic acid) as used herein is a chemical similar to DNA or RNA. PNA is not known to occur naturally in existing life on Earth but is artificially synthesized and used in some biological research and medical treatments. DNA and RNA have a deoxyribose and ribose sugar backbone, respectively, whereas PNA's backbone is composed of repeating N-(2-aminoethyl)-glycine units linked by peptide bonds. The various purine and pyrimidine bases are linked to the backbone by methylene carbonyl bonds. PNAs are depicted like peptides, with the N-terminus at the first (left) position and the C-terminus at the right.

Polyclonal antibodies: a polyclonal antibody as used herein is an antibody that is derived from different B-cell lines. They are a mixture of immunoglobulin molecules secreted against a specific antigen, each recognising a different epitope.

Polymer: the term polymer as used herein is defined as a compound composed of repeating structural units, or monomers, connected by covalent chemical bonds.

Polypeptide: Peptides are the family of short molecules formed from the linking, in a defined order, of various α-amino acids. The link between one amino acid residue and the next is an amide bond and is sometimes referred to as a peptide bond. Longer peptides are referred to as proteins or polypeptide.

Polysaccharide: The term polysaccharide as used herein is defined as polymers made up of many monosaccharides joined together by glycosidic linkages.

Radicals: radicals, as used herein, are atomic or molecular species with unpaired electrons on an otherwise open shell configuration. These unpaired electrons are usually highly reactive, so radicals are likely to take part in chemical reactions.

Radioactivity: Radioactive decay is the process in which an unstable atomic nucleus loses energy by emitting radiation in the form of particles or electromagnetic waves.

RNA: RNA (Ribonucleic acid) as used herein is a nucleic acid polymer consisting of nucleotide monomers that plays several important roles in the processes that translate genetic information from deoxyribonucleic acid (DNA) into protein products.

Relative amount: The relative amount of a substance or feature is its amount compared to the amount of another feature or substance of the unit or the units surroundings.

Repair: Bringing a unit from an undesired state to a less undesired state.

Scaffold: A scaffold is typically an organic molecule carrying reactive groups, capable of reacting with reactive groups on a MHC-peptide complex. Particularly small organic molecules of cyclic structure (e.g. functionalized cycloalkanes or functionalized aromatic ring structures) are termed scaffolds. Scaffold and carrier are used interchangeably herein where scaffold typically refers to smaller molecules of a multimerization domain and carrier typically refers to larger molecule and/or cell like structures.

scFV: Single chain Fv fragment, comprising a variable region of antibody heavy chain linked by a stretch of synthetic peptide to variable region of antibody light chain.

Staining: In this invention staining means specific or unspecific labelling of cells by binding labeled molecules to defined proteins or other structures on the surface of cells or inside cells. The cells are either in suspension or part of a tissue. The labeled molecules can be MHC multimers, antibodies or similar molecules capable of binding specific structures on the surface of cells.

Streptavidin: Streptavidin as used herein is a tetrameric protein purified from the bacterium *Streptomyces avidinii*. Streptavidin is widely use in molecular biology through its extraordinarily strong affinity for biotin.

Substance: A substance can be a specific type of molecule, or a collection of particular molecules, or molecules comprised within a substructure.

T cells: The term T cell and T lymphocyte is used interchangeable herein and refers to a subset of lymphocytes defined by their development in thymus and by heterodimeric receptors associated with proteins of the CD3 complex. CD3 is exposed on all T cells.

Treatment: Used interchangeably herein with the term repair.

Undesired state of a unit: Example undesired states are a human or animal carrying or displaying a disease, e.g. a human with hypertension, high amount of alcohol in the blood, or low blood sugar; or a cement bridge with cracks or breakages at undesired locations; or an iron plate with rust; or a coating that has started to deteriorate, etc.

Unit: A structure or part of a structure, or a software or a part of a software program. Example units are a human being, or parts of a human being, e.g. blood or an organ; an animal, a plant, a leaf, a cell or a collection of cells; a substructure of a cell, e.g. a mitochondria, Golgi apparatus; a mechanical part, a motor, a bridge or part of a bridge, a propeller from a windmill or airplane; a macrostructure, nanostructure, or supramolecular structure.

Vaccine: A vaccine is an antigenic preparation used to establish immunity to a disease or illness and thereby protect or cure the body from a specific disease or illness. Vaccines are either prophylactic and prevent disease or therapeutic and treat disease. Vaccines may contain more than one type of antigen and is then called a combined vaccine.

Vaccination: The introduction of vaccine into the body of human or animals for the purpose of inducing immunity.

Virulence: refers to the degree of pathogenicity of a microbe, or in other words the relative ability of a microbe to cause disease.

Marker molecule: The terms binding molecules and marker molecules are used interchangeably herein. Binding of molecule, cells or other substances to one or more defined structures in the sample can be used as diagnostic test and in the following the substances are collectively called binding molecules or marker molecules. A marker molecule or binding molecule is a molecule that specifically associates covalently or non-covalently with a structure belonging to or associated with an entity in the sample.

Target structure: A defined structure in a sample bound by a marker molecule is called the target structure or target of the marker molecule.

FIGURE LEGENDS

FIG. 1: Flow Cytometry Analysis of MHC Multimer Constructs.

Human Peripheral Blood Lymphocytes were ficoll purified from blood from a human donor and stained with mouse anti-human CD3/PE antibody and mouse anti-human CD8/PB antibody together with either of the MHC Dextramer molecule constructs A) HLA-A*0201(NLVPMVATV)/APC (SEQ ID NO 1), B) HLA-A*0201(ILKEPVHGV)/APC (SEQ ID NO 2). The staining was analysed on a CyAn ADP flow cytometer. Live-gated and CD3 positive lymphocytes are shown.

FIG. 2: Gating Strategy for No-Lyse No-Wash Procedure.

Whole blood was stained with MHC dextramer, anti-CD8/APC, anti-CD3/PB and CD45/CY antibody in a no-lyse no-wash procedure. For further details see text in example 37. During analysis of data the following gating strategy was used: CD45/PB antibody was used to set a trigger discriminator to allow the flow cytometer to distinguish between red blood cells and stained white blood cells. This was done during data collection by gating on CD45/PB positive cells in a CD45/PB vs. side scatter dot plot as shown in A. After data collection and during data analysis CD3 positive cells were selected by gating CD3/FITC positive cells in a CD3/FITC vs side scatter plot as shown in B. The final data was illustrated in a MHC dextramer/PE vs CD8/APC plot (see FIG. 10).

FIG. 3: Identification of CMV-Specific T Cells in a Blood Sample Using No-Lyse No-Wash Procedure.

Whole blood from three different donors were analysed for the presence of CMV-specific T cells by flow cytometry using a no-lyse no-wash procedure. Donor 1 was stained with a MHC multimer consisting of PE-conjugated 270 kDa dextran coupled with HLA-A*0201 in complex with beta2 microglobulin and the peptide NLVPMVATV (SEQ ID NO 1) derived from Human Cytomegalo Virus (HCMV) (left panel) and with a negative control MHC multimer consisting of PE conjugated 270 kDa dextran coupled with HLA-A*0201 in complex with beta2 microglobulin and the peptide ILKEPVHGV (SEQ ID NO 2) derived from Human Immunodeficiency Virus (HIV) (right panel). Donor 2 was stained with a MHC multimer consisting of PE-conjugated 270 kDa dextran coupled with HLA-A*0101 in complex with beta2 microglobulin and the peptide VTEHDTLLY (SEQ ID NO 3) derived from Human Cytomegalo Virus (HCMV) (left panel) and a negative control MHC multimer consisting of PE-conjugated 270 kDa dextran coupled with HLA-A*0101 in complex with beta2 microglobulin and the peptide IVDCLTEMY (SEQ ID NO 4) derived from ubiquitin specific peptidase 9 (USP9) (right panel). Donor 3 was stained with two MHC multimers consisting of PE conjugated 270 kDa dextran coupled with HLA-B*0207 in complex with beta2 microglobulin and either of the peptides TPRVTGGGAM (SEQ ID NO 5) (left panel) or RPHERNGFTVL (SEQ ID NO 6) (center panel) both derived from Human Cytomegalo Virus (HCMV) and with a negative control MHC multimer consisting of PE-conjugated 270 kDa dextran coupled with HLA-B*0207 in complex with beta2 microglobulin and the peptide TPGPGVRYPL (SEQ ID NO 7) derived from Human Immunodeficiency Virus (HIV) (right panel).

All samples were also added Anti-CD45/PB, anti-CD3/FITC and anti-CD8/APC antibodies. The samples were gated as shown in FIG. 9.

FIG. 4: Enumeration of Specific T Cells Using CytoCount™ Beads.

Whole blood from a human donor were analysed for the presence of CMV-specific T cells with MHC multimers by flow cytometry using a no-lyse no-wash procedure. 2×100 µl donor blood was analysed with two different MHC multimers: A) PE-conjugated 270 kDa dextran coupled with HLA-A*0101 in complex with beta2 microglobulin and the peptide VTEHDTLLY (SEQ ID NO 3) derived from Human Cytomegalo Virus (HCMV) and a negative control construct B) consisting of PE-conjugated 270 kDa dextran coupled with HLA-A*0101 in complex with beta2 microglobulin and the peptide IVDCLTEMY (SEQ ID NO 4) derived from ubiquitin specific peptidase 9 (USP9). To each sample Anti-CD45/CY, anti-CD3/APC and anti-CD8/PB antibody was added together with 50 µl CytoCount beads (1028 beads/µl). Following staining for 15 minutes PBS was added to 1 ml and the samples analysed on a CyAn flow cytometer. During analysis CD45/CY antibody was used to set a trigger discriminator to allow the flow cytometer to distinguish between red blood cells and stained white blood cells and CD3/APC antibody was used to gate for CD3 positive T lymphocytes. Amount of counted beads in sample A are shown in the histogram C and amount of beads counted in the negative control sample B are show in histogram D. Concentration of HLA-A*0101(VTEHDTLLY) (SEQ ID NO 3) specific T cells in the blood sample were determined as follows:

((count of MHC multimer+CD8+ cells in A×concentration of beads×dilution factor of beads)/counted beads C))−((counted MHC multimer+CD8+ cells in B×concentration of beads×dilution factor of beads)/counted beads D)=
((1300 cells×1028 beads/µl×0.05)/67225 beads)−((2 cells×1028 beads/µl×0.05)/72623 beads)=0.9926 cells/µl=992.6 celler/ml FIG. 5: Detection of Specific T Cells in a Blood Sample.

MHC-peptide complexes embedded in a sugar matrix together with antibodies and used for detection of specific T cells in a blood sample. MHC dextramer constructs was embedded in a sugar matrix together with relevant gating reagents (anti-CD3/Pacific Blue, anti-CD8/Alexa700 and anti-CD45/Cascade Yellow antibodies) and the matrix dried. Then EDTA stabilized blood from a human donor were added and the samples analyzed by flow cytometry. Two different MHC construct were used HLA-A*0101(VTEHDTLLY)/PE dextramer (SEQ ID NO 3) (A) and the negative control construct HLA-A*0101(IVDCLTEMY)/PE (SEQ ID NO 4) (B). As a control antibodies and MHC dextramer constructs were used to stain blood from the same donor following a general staining procedure without embedding the antibodies and MHC dextramers in a sugar matrix as described elsewhere herein. (C) Staining with HLA-A*0101 (VTEHDTLLY)/PE dextramer (SEQ ID NO 3) following a normal staining procedure and (D) Staining with HLA-A*0101(IVDCLTEMY)/PE dextramer (SEQ ID NO 4) following a normal staining procedure.

FIG. 6: IFN-γ ELISPOT to KLH and Autologous Tumor Lysate

PBMC response to KLH (a) and autologous tumor lysate (b) was examined pretreatment (Pre-V) and post treatment 4 weeks after last vaccination (Post-V), as described in example 28. The figure is modified from Redman et al. Phase 1b trial assessing autologous, tumor-pulsed dendritic cells as a vaccine administered with or without IL-2 in patients with metastatic melanoma. J. Immunother: 2008; 31 (6): 591-598.

FIG. 7: Proliferation to KLH and Autologous Tumor Lysate

PBMC to KLH (a) and autologous tumor lysate (b) was measured pretreatment (Pre-V) and post treatment 4 weeks after last vaccination (Post-V), as described in example 28. The figure is modified from Redman et al. Phase 1 b trial assessing autologous, tumor-pulsed dendritic cells as a vaccine administered with or without IL-2 in patients with metastatic melanoma. J. Immunother. 2008; 31 (6): 591-598.

FIG. 8: Proliferation of Vaccine Draining Lymph Node Cells.

Vaccine draining lymph node cells response was measured to KLH (a) and autologous tumor lysate (b), as described in example 28. The figure is modified from Redman et al. Phase 1b trial assessing autologous, tumor-pulsed dendritic cells as a vaccine administered with or without IL-2 in patients with metastatic melanoma. J. Immunother. 2008; 31 (6): 591-598.

FIG. 9: IFN-γ ELISPOT of Vaccine Draining Lymph Node Cells

Vaccine draining lymph node cells response was examined to KLH (a) and autologous tumor lysate (b) as described in example 28. The figure is modified from Redman et al. Phase 1 b trial assessing autologous, tumor-pulsed dendritic cells as a vaccine administered with or without IL-2 in patients with metastatic melanoma. J. Immunother. 2008; 31 (6): 591-598.

Figure 10:
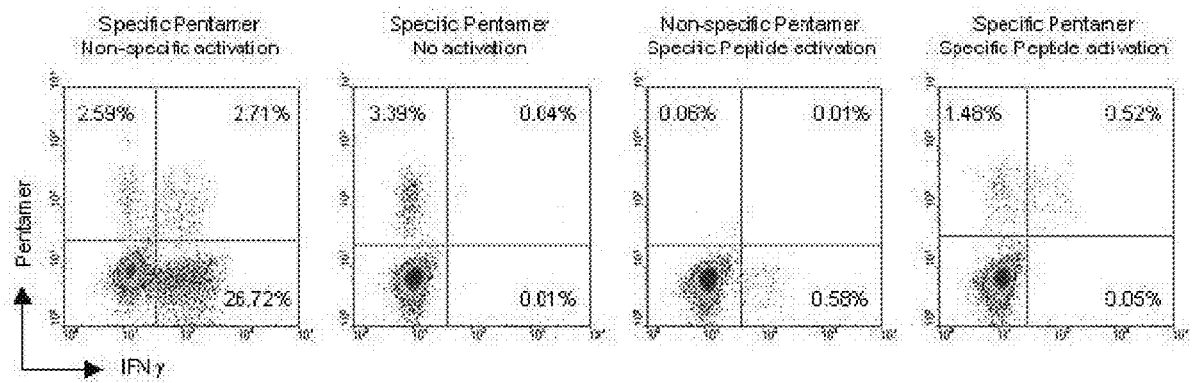

FIG. 10: IFN-γ Versus Pentamer Staining of Live Lymphocytes.

The figure illustrate IFN-γ versus Pentamer staining of live lymphocytes. PBMCs were incubated with either a negative control (non-specific) Pentamer (A*0201/EBV (GLCTLVAML)) (SEQ ID NO 8) or a Pentamer specific for the cells of interest (B*0801/EBV (RAKFKQLL)) (SEQ ID NO 9), then stimulated with LAC (non-specific activation) or B*0801/EBV peptide (specific peptide activation) for 15 hours in the presence of Brefeldin A. Fixation, permeabilization and staining for IFN-γ were carried out exactly as detailed in the protocol in example 37.

FIG. 11: Detection of Borrelia Specific T Cells Using MHC Dextramers.

Dot plots showing live gated CD3$^+$/CD4$^-$ lymphocytes from Borrelia patient stained with (A) Negative Control MHC Dextramer (HLA-A*0201(GLAGDVSAV) (SEQ ID NO 10) or (B) pool of MHC Dextramers containing peptides from Borrelia antigen Osp A and Fla B. pool of MHC Dextramers containing peptides from Borrelia antigen. 0.05% of the live gated CD3$^+$/CD4$^-$ lymphocytes are positive for one or more of the MHC Dextramers in the pool.

Figure 12:
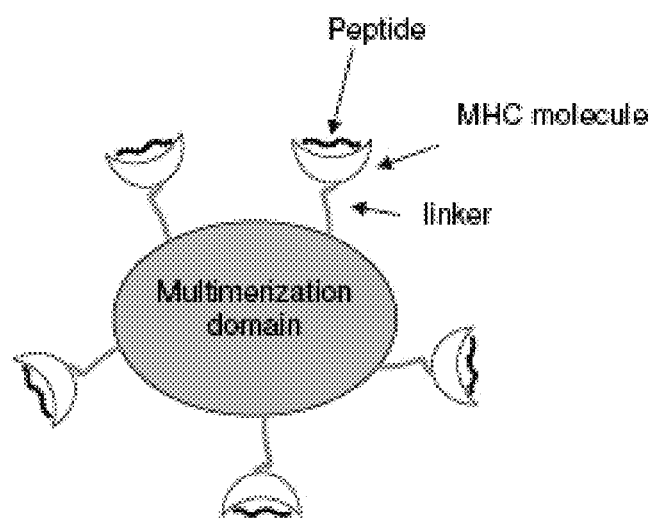

FIG. 12: Schematic Representation of MHC Multimer.

A MHC multimer consist of a multimerization domain whereto one or more MHC-peptide complexes are attached through one or more linkers. The multimerization domain comprise one or more carriers and/or one or more scaffolds. The MHC-peptide complexes comprise a peptide and a MHC molecule

DETAILED DESCRIPTION OF THE INVENTION

The present invention relates to a method involving the combinatorial use of one or more analyses(s), and/or one or more repair(s), for one or more undesired or desired states of a unit.

An embodiment of the invention relates to a method for diagnosing and repairing an undesired state of a unit, by determining the amount or relative amount of a substance or a feature of a unit, by measuring the amount of said substance or said feature of said unit, or by measuring the amount of said substance or said feature in the vicinity of said unit, and changing the amount or relative amount of a substance or a feature of a unit, by addition or removal of an amount of said substance or said feature from said unit, or by addition of an effector that mediates a decrease or increase in the amount of said substance or said feature in said unit.

Live Unit

One embodiment of the invention relates to a method for diagnosis of a specific disease (an undesired state) of an individual human being, an animal or a plant (a unit), followed by a treatment aimed at establishing a more healthy condition (desired state) of that individual human being, animal or plant. Diagnosis here means initial diagnosis of a specific disease and/or monitoring of disease progression/status following or during treatment.

The table below provides examples of combinations of undesired state (disease), analysis (diagnosis) and repair (treatment) of human beings:

| Disease | Diagnosis principle | Treatment |
| --- | --- | --- |
| Bacterial infection | blood analysis - anti-bacteria antibodies | oral antibiotics |
| Cancer tumor in brain | brain scanning | chemotherapy |
| Diabetes | blood sugar analysis | insulin injection |
| Rectal carcinoma | CEA-scan using arcitumomab, a monoclonal antibody | chemotherapy |
| Rectal carcinoma | CEA-scan using arcitumomab, a monoclonal antibody | X-ray treatment |
| Osteomyelitis | imaging for infection/inflammation using Sulesomab, a monoclonal antibody | anti-inflammatory agent |

More examples of combinations of undesired state (disease), analysis (diagnosis) and repair (treatment) of human beings are given elsewhere herein.

In a special embodiment of the invention a method for diagnosis of a specific disease of an individual human being, an animal or a plant followed by a specific treatment may be combined with a method to monitor the effect of the treatment. The method for diagnosis and monitoring may be identical or different from each other.

A number of different types of diseases, as well as different diseases within each type of disease, may be diagnosed and treated, using the methods for diagnosis and treatment described by this invention. In principle, any disease may be diagnosed and treated, including the following classes and types of diseases:

A1: Cardiovascular disease, including heart disease, haemophilia, deep venous thrombosis, acute myocardial infarction, thrombocytopenia,
A2: Degeneration
A3: Dermatological disease
A4: Ear, nose, throat disease
A5: Endocrine disease
A6: Fatigue
A7: Gastrointestinal disease
A8: Genetic disorder
A9: Genitourinary disease
A10: Growth disorder
A11: Andrology
A12: Gynaecology and obstetrics
A13: Haematological disease
A14: Immune disorder A15: Infection, including bacterial infection, fungal infection, cancer, parasitic infection, viral infection; hepatitis C virus infection, hepatitis B virus infection, HIV-1 infection, influenza virus infection, herpes simplex virus infection, *Mycobacterium tuberculosis* infection (tuberculosis, TB), *Borrelia* infection, Human papillomavirus (HPV) infection, Cytomegalovirus (CMV) infection, Epstein-Barr Virus (EBV) infection, BK virus infection
A16: Inflammation
A17: Injury
A18: Metabolic disorder, including diabetes.
A19: Mouth disease
A20: Musculoskeletal disease
A21: Neoplasm, including ovarian carcinoma, colonic and rectal carcinoma, cutaneous melanoma,
A22: Neurological disease
A23: Nutritional disorder
A24: Ocular disease, and other eye-related disorders
A25: Prophylaxis
A26: Psychiatric disorder
A27: Respiratory disease
A28: Temperature disorder
A29: Toxicity & intoxication
A30: Ulcer
A31: Digestive disorders
A32: Infertility
A33: Autoimmune disease
A32: Genetic disorders
A33: Neurologic disorders
A34: Respiratory disease
A35: Skin disorder
A36: Transplantation-related disorders
A37: Multiple sclerosis
A38: Diphtheria
A39: Tetanus
A40: Pertussis
A41: Osteomyelitis
A42: Anemia
A43: Gaucher's disease
A44: Tuberculosis (TB)
A45: Borreliosis/Lyme disease
A46: CMV infection
A47: Cervix cancer Diseases of special interest for the present invention are cancer, infectious disease and transplantation-related disorders.

A comprehensive list of infectious diseases is given in Tables A to G.

A comprehensive list of immunodeficiencies and transplantation-related disorders are given in Table H In one embodiment, the present invention relates to diagnosis, monitoring and/or treatment of Immunodeficiencies and Transplantation-related disorders as listed in table H

TABLE H

A) Classes of primary immunodeficiencies
1) Combined T- and B-cell immunodeficiencies
In these disorders both T lymphocytes and often B lymphocytes, regulators of adaptive immunity, are dysfunctional or decreased in number. The main members are various types of severe combined immunodeficiency (SCID).
    A) T−/B+ SCID (T cells predominantly absent): γc deficiency, JAK3 deficiency,
    interleukin 7 receptor chain α deficiency, CD45 deficiency, CD3δ/CD3Σ deficiency.
    B) T−/B− SCID (both T and B cells absent): RAG ½ deficiency, DCLRE1C
    deficiency, adenosine deaminase (ADA) deficiency, reticular dysgenesis
    C) Omenn syndrome
    D) DNA ligase type IV deficiency
    E) CD40 ligand deficiency
    F) CD40 deficiency
    G) Purine nucleoside phosphorylase (PNP) deficiency
    H) MHC class II deficiency
    I) CD3γ deficiency
    J) CD8 deficiency
    K) ZAP-70 deficiency
    L) TAP-½ deficiency
    M) Winged helix deficiency
    N) X-SCID (X-linked SCID, absence of NK- and T-cells)
2) Antibody deficiencies
In antibody deficiencies, one or more isotypes of immunoglobulin are decreased or don't function properly. These proteins, generated by plasma cells, normally bind to pathogens, targeting them for destruction.
    A) Absent B cells with a resultant severe reduction of all types of antibody: X-
    linked agammaglobulinemia (btk deficiency), μ-Heavy chain deficiency, I 5 deficiency,
    Igα deficiency, BLNK deficiency, thymoma with immunodeficiency
    B) B cells low but present or normal, but with reduction in 2 or more isotypes
    (usually IgG & IgA, sometimes IgM): common variable immunodeficiency (CVID),
    ICOS deficiency, CD19 deficiency, TACI (TNFRSF13B) deficiency, BAFF receptor
    deficiency.
    C) Normal numbers of B cells with decreased IgG and IgA and increased IgM: AID
    deficiency, UNG deficiency
    D) Normal numbers of B cells with isotype or light chain deficiencies: heavy chain
    deletions, kappa chain deficiency, isolated IgG subclass deficiency, IgA with IgG
    subclass deficiency, selective immunoglobulin A deficiency
    E) Specific antibody deficiency to specific antigens with normal B cell and normal
    Ig concentrations
    F) Transient hypogammaglobulinemia of infancy (THI)
3) Well-defined syndromes
A number of syndromes escape formal classification but are otherwise recognisable by particular clinical or immunological features.
    A) Wiskott-Aldrich syndrome
    B) DNA repair defects not causing isolated SCID: ataxia telangiectasia, ataxia-like
    syndrome, Nijmegen breakage syndrome, Bloom syndrome TABLE H-continued C) DiGeorge syndrome (when associated with thymic defects)
  D) Various immuno-osseous dysplasias (abnormal development of the skeleton
  with immune problems): cartilage-hair hypoplasia, Schimke syndrome
  E) Hermansky-Pudlak syndrome type 2
  F) Hyper-IgE syndrome
  G) Chronic mucocutaneous candidiasis
  H) Nezelof syndrome
  I) Bare lymphocyte syndrome
4) Immune dysregulation diseases
In certain conditions, the regulation rather than the intrinsic activity of parts of the immune system
is the predominant problem.
  A) Immunodeficiency with hypopigmentation or albinism: Chediak-Higashi
  syndrome, Griscelli syndrome type 2
  B) familial hemophagocytic lymphohistiocytosis: perforin deficiency, MUNC13D
  deficiency, syntaxin 11 deficiency
  C) X-linked lymphoproliferative syndrome
  D) Syndromes with autoimmunity:
    Autoimmune lymphoproliferative syndrome: type 1a (CD95 defects), type
    1b (Fas ligand defects), type 2a (CASP10 defects), type 2b (CASP8 defects)
    APECED (autoimmune polyendocrinopathy with candidiasis and
    ectodermal dystrophy)
    IPEX (immunodysregulation polyendocrinopathy enteropathy X-linked
    syndrome)
5) Phagocyte disorders
Phagocytes are the cells that engulf and ingest pathogens (phagocytosis), and destroy them with
chemicals. Monocytes/macrophages as well as granulocytes are capable of this process. In certain
conditions, either the number of phagocytes is reduced or their functional capacity is impaired.
  A) Severe congenital neutropenia: due to ELA2 deficiency (with myelodysplasia),
  GFI1 deficiency (with T/B lymphopenia) or G-CSFR deficiency (G-CSF-unresponsive)
  B) Kostmann syndrome
  C) Cyclic neutropenia
  D) X-linked neutropenia/myelodysplasia
  E) Leukocyte adhesion deficiency types 1, 2 and 3
  F) RAC2 deficiency
  G) Beta-actin deficiency
  H) Localized juvenile periodontitis
  I) Papillon-Lefevre syndrome
  J) Specific granule deficiency
  K) Shwachman-Diamond syndrome
  L) Chronic granulomatous disease: X-linked and autosomal forms
  M) Neutrophil glucose-6-phosphate dehydrogenase deficiency
  N) IL-12 and IL-23 β1 chain deficiency
  O) IL-12p40 deficiency
  P) Interferon γ receptor 1 deficiency
  Q) Interferon γ receptor 2 deficiency
  R) STAT1 deficiency (2 forms)
6) Innate immunity deficiencies
Several rare conditions are due to defects in the innate immune system, which is a basic line of
defence that is independent on the more advanced lymphocyte-related systems. Many of these
conditions are associated with skin problems.
  A) Hypohidrotic ectodermal dysplasia
    NEMO deficiency
    IKBA deficiency
  B) IRAK-4 deficiency
  C) WHIM syndrome (warts, hypogammaglobulinaemia, infections, myleokathexis)
  D) Epidermodysplasia verruciformis
7) Autoinflammatory disorders
Rather than predisposing for infections, most of the autoinflammatory disorders lead to excessive
inflammation. Many manifest themselves as periodic fever syndromes. They may involve various
organs directly, as well as predisposing for long-term damage (e.g. by leading to amyloid
deposition).
  A) Familial Mediterranean fever
  B) TNF receptor associated periodic syndrome (TRAPS)
  C) Hyper-IgD syndrome (HIDS)
  D) CIAS1-related diseases:
    Muckle-Wells syndrome
    Familial cold autoinflammatory syndrome
    Neonatal onset multisystem inflammatory disease
  E) PAPA syndrome (pyogenic sterile arthritis, pyoderma gangrenosum, acne)
  F) Blau syndrome
8) Complement deficiencies
The complement system is part of the innate as well as the adaptive immune system; it is a group of
circulating proteins that can bind pathogens and form a membrane attack complex. Complement
deficiencies are the result of a lack of any of these proteins. They may predispose to infections but
also to autoimmune conditions.
  A) C1q deficiency (lupus-like syndrome, rheumatoid disease, infections)
  B) C1r deficiency (idem)
  C) C4 deficiency (idem)
  D) C2 deficiency (lupus-like syndrome, vasculitis, polymyositis, pyogenic
  infections)

TABLE H-continued

E) C3 deficiency (recurrent pyogenic infections)
F) C5 deficiency (Neisserial infections, SLE)
G) C6 deficiency (idem)
H) C7 deficiency (idem, vasculitis)
I) C8a and C8b deficiency (idem)
J) C9 deficiency (Neisserial infections)
K) C1-inhibitor deficiency (hereditary angioedema)
L) Factor I deficiency (pyogenic infections)
M) Factor H deficiency (haemolytic-uraemic syndrome, membranoproliferative glomerulonephritis)
N) Factor D deficiency (Neisserial infections)
O) Properdin deficiency (Neisserial infections)
P) MBP deficiency (pyogenic infections)
Q) MASP2 deficiency B) Classes of secondary immunodeficiencies
Chronic infections
Malnutrition
Ageing
Irradiation
Medications (chemotherapy, immunosuppressiva, disease-modifying antirheumatic drugs)
Cancer C) Transplantation-related disorders
1) Secondary immunodeficiencies
Opportunistic infections caused by medicine-induced immuno-suppression, including
    A) Viral infections (e.g. Epstein-Barr (EBV), Hepatitis C (HCV), Cytomegalovirus (CMV))
    B) Bacterial infections (e.g. *Staphylococcus aureus*, *Streptococcus pyogenes*, *Pseudomonas aeruginosa*, *Acinetobacter baumannii*)
    C) Fungal infections (e.g. *Pneumocystis jirovecii*, *Candida albicans*, *Aspergillus* sp.)
    D) Parasitic infections (e.g. *Toxoplasma gondii*).

2) Disorders related to a transplant-related medicine-induced immunedeficiency
Transplant-related cancers including Immunodeficiency-related B-cell disorders or Post-transplant lymphoproliferative disorders (PTLD), Kaposi's Sarcoma, Solid tumors (e.g. of the skin, mouth and lungs) or any other secondary cancer related to transplantation or its concurrent medicinal treatment; Toxoplasmosis, Pneumocystis pneumonia, Candidiasis or 'thrush', Pneumonia, Meningitis, Osteomyelitis endocarditis, Toxic shock syndrome (TSS), Septicemia, Pharyngitis, Impetigo, Necrotizing fasciitis, Scarlet fever, Skin infections (such as pimples, boils, cellulitis folliculitis, furuncles, carbuncles, erysipelas, scalded skin syndrome and abscesses)

3) Side-effects of medicinal treatment concurrent to transplantation
Serum sickness;
Immune complex glomerulonephritis;
Delayed hypersensitivity (tuberculin skin reaction);
Infertility;
Cataracts (clouding of the lens of the eye, which causes loss of vision);
Hormone changes;
Risk of bleeding (due to destruction of platelets).

4) Directly related to organ transplantation
    Graft-versus-host disease (GVHD)
        Acute
        Chronic
    Host-versus-graft (transplant or graft rejection)
        Hyperacute
        Acute
        Chronic A number of different diagnostics principles may be applied to the diagnosis of the abovementioned types of diseases, including:

B1: Temperature measurement
B2: Heart rate measurement
B3: Blood pressure measurement
B4: Hematological tests, including RBC tests, erythrocyte sedimentation rate (ESR), hematocrit-values, hemoglobin level, WBC tests, white blood number and blood cell types
B5: Urine testing
B6: Imaging, including endoscopy, visual observation, pseudomembraneous ulcerative colitis endoscopy
B7: CT scan (computerized tomography), including abscess of the lung, cysticercosis, brain lesions, taxoplasma gondii, nocardiosis
B8: MRI scan (magnetic resonance imaging), including sinus infection
B9: Nuclear medicine
B10: Ultrasound, including echocardiography
B11: X-ray imaging, including X-ray imaging in relation to disorders related to the chest, congestive heart failure, coronary angiography, diverticulitis, multiple myeloma, mycoplasma pneumonia, nocardiosis, pneumothorax, pyelonephritis, tuberculosis, urology
B12: Histochemical staining of tissue sections
B13: Antibody-specific staining of tissue sections
B14: DNA-based chip technologies (e.g. Affymax DNA arrays)
B15: Nucleic acid analogue-based chip technologies for measuring abundance of RNA transcripts in e.g. blood samples
B16: Arrays of aptamers on chips (e.g. RNA aptamers or antibodies located in array) for measurement of abundance of e.g. specific proteins in samples
B17: Infrared scanning B18: Hybridisation of antibody to antigen
B19: Hybridization of nucleic acid or nucleic acid analogue to nucleic acid or nucleic acid analogue
B20: Visual inspection
B21: Flow cytometry of blood, cerebrospinal fluid or other liquid samples
B22: Stationary cytometry
B23: Cytology
B24: ELISA
B25: Western blotting
B26: ELISPOT
B27: Turbidometry
B28: DELFIA
B29: RIA
B30: Northern blot
B31 Southern blot
B32: Proliferation assays
B33: Other principles allowing a diagnosis to be performed, as described elsewhere herein.

A more detailed description of diagnostic principles are given in the section: "Diagnostic principles of the invention".

A list of examples of diagnostic methods is given in Table T.

TABLE T examples of diagnostic methods

A) Analysis of extracted tissue/blood:
Hematological tests, including RBC tests, erythrocyte sedimentation rate (ESR), hematocrit-values, hemoglobin level, WBC tests, white blood number and blood cell types, Blood sugar, Blood count, maternal serum screening, Erythrocyte sedimentation rate (ESR), Complete blood count (CBC), Comprehensive metabolic panel (CMP), Arterial blood gas (ABG), Urine testing, Histochemical staining of tissue sections, Antibody-specific staining of tissue sections, Papanicolaou test (or Pap smear, cervical smear), DNA-based chip technologies (e.g. Affymax DNA arrays), Nucleic acid analogue-based chip technologies for measuring abundance of RNA transcripts, Arrays of aptamers on chips (e.g. RNA aptamers or antibodies located in array) for measurement of abundance of e.g. specific proteins, Hybridisation of antibody to antigen, Hybridization of nucleic acid or nucleic acid analogue to nucleic acid or nucleic acid analogue, ELISA, DELFIA, RIA, Immune electrophoresis, ELISPOT, Measurement of induced crosslinking by e.g. turbidometry, PCR (polymerase chain reaction), gel electrophoresis, SDS-PAGE, QPNC-PAGE, agarose gel electrophoresis, 2D gel electrophoresis, Chromatography, Western blotting, Northern blotting, Southern blotting, Cytology with DNA-, RNA-, LNA-, PNA-, protein-, antibody-, MHC-probes; Flow cytometry with DNA-, RNA-, LNA-, PNA-, protein-, antibody-, MHC-probes; Stationary cytometry with DNA-, RNA-, LNA-, PNA-, protein-, antibody-, MHC-probes; IHC (immunohistochemistry) with DNA-, RNA-, LNA-, PNA-, protein-, antibody-, MHC-probes; Genetic testing (the analysis of RNA, DNA, proteins, and certain metabolites in order to detect heritable disease-related genotypes, mutations, phenotypes, or karyotypes for clinical purposes), Proliferation assay (mRNA, thymidine or BrdU incorporation, ATP measurement), Measurement of effector function in sample (.g. a chromium release assay), Mass spechtrometry
B) Analysis of intact patient:
Measurement of Temperature, Heart rate, Pulse, Blood pressure, Body weight, Height, Reflexes, Breath, Hearing, Eyesight, muscle tonus and strength, Esophageal motility study, (EMS)/esophageal manometry, Torsional flexibility, Humidity, Emission, Sound, Flow (blood or breath), Volume, Conductivity, Visual observation, Measurement of electric pulses (Electromyography (EMG), Electroencephalography (EEG), Electrocardiography (ECG or EKG), Ballistocardiography or BCG, Electrogastrography (EGG), Electroretinography, Electrocorticography (EcoG), Electrooculography, EEG topography, Electroneuronography Exercise tests, Physical examination (body features, nutritional state, appearance, color, swelling, tumor, posture, odours, palpation, percussion, ascultation), Amniocentesis (also referred to as amniotic fluid test or AFT), Chorionic villus sampling (CVS), Percutaneous umbilical cord blood sampling, Pulse diagnosis or Chinese pulse diagnosis, Auscultation
c) Medical imaging:
Photographing, Microscopy, Electron microscopy, Fluoroscopy, X-ray crystallography, Spectroscophy, Circular dichroism, CEA-scan using arcitumomab, a monoclonal ab, CT scan (computerized tomography, aka. CAT scan: computed axial tomography), Electron beam tomography (EBT), Helical (or spiral) cone beam computed tomography MRI scan (magnetic resonance imaging, alias Nuclear magnetic resonance NMR) Functional MRI or functional Magnetic Resonance Imaging (fMRI), Contrast MR, Arterial spin labeling, Magnetic resonance spectroscopic imaging, Diffusion tensor imaging, In vivo magnetic resonance spectroscopy (MRS), Thermography, Electric impediance tomography, Corneal topography, Nuclear medicine: radioactive-labelled substances or radionuclides are administered to patients by intravenous injection (e.g. Technetium-99m, Iodine-123 and 131, Thallium-201, Gallium-67, Fluorine-18 Fluorodeoxyglucose, Indium-111 Labeled Leukocytes), ingestion, inhalation (e.g. Xenon-133, Krypton-81m, Technetium-99m Technegas, Technetium-99m DTPA), and the radiation emitted is detected by e.g. gamma camera or positron emission tomography;
Gallium imaging, Indium leukocyte imaging, Technetium antigranulocyte antibodies, Scintigraphy, Leukocyte scintigraphy, Red blood cell scintigraphy, Radionuclide cisternogram, PET scan (positron emission tomography), Gamma camera, Single photon emission computed tomography (SPECT), Ultrasound, including echocardiography, Medical sonography (ultrasonography), Nuchal scan (nuchal translucency (NT)), Intravascular ultrasound, Contrastenhanced ultrasound, X-ray imaging (including Chest radiology, Abdominal & Pelvic radiology. Interventional radiology, Vascular radiology, Neuroradiology, Interventional Neuroradiology, Musculoskeletal radiology, Pediatric radiology, Mammography, Emergency radiology, Nuclear Medicine, Barium enema, intravenous pyelography (IVP, intravenous urography or IVU), with or without the use of Radiocontrast agents (contrast agents, based on barium sulphate or iodine), Angiography (arteriography;

TABLE T-continued examples of diagnostic methods may be coronary, retinal or peripheral), Arthrography, Magnetic Resonance Arthrography,
Hysterosalpingography (HSG), Infrared scanning, Visual inspection, Radiography
NMR, Thermographic scanning, Electrophysiologic study (EPS), Endoscopy (including
gastroscopy, esophagogastroduodenoscopy, colonoscopy, sigmoidscopy, endoscopic
retrograde cholangiopancreatography (ERCP), anoscopy, cystoscopy, bronchoscopy,
laryngoscopy, esophagoscopy, proctosigmoidoscopy, rhinoscopy, colposcopy, hysteroscopy,
Falloscopy, laparoscopy, arthroscopy, thoracoscopy, mediastinoscopy, amnioscopy,
fetoscopy, otoscopy, Panendoscopy (or triple endoscopy), architectural endoscopy,
borescope, Ophthalmoscopy, Videoendoscopy, Laparoscopy), Magnetic resonance
cholangiopancreatography (MRCP)
Magnetic resonance neurography, Dual energy x-ray absorptiometry (DXA), Computed
Quantitative Computer Tomography (QCT), Photoacoustic imaging, Projection radiography
Diffuse optical tomography, Elastography (using ultrasound or magnetic resonance
elastography (MRE) or CT), Transient elastography, Electrical impedance tomography,
Optoacoustic imaging
Ophthalmology (A-scan, B-scan, Corneal topography, Optical coherence tomography,
Scanning laser ophthalmoscopy), Embroscopy, Fetoscopy, Video cystometrography or
VCMG, MAG3 scan
MUGA scan (Multiple Uptake Gated Acquisition Scan), Positron emission tomography-
computed tomography (PET-CT), FDG imaging (fluorodeoxyglucose, FDG), Perfusion
scanning, Magnetoencephalography (MEG), Imaging for infection/inflammation using
Sulesomab, A monoclonal antibody Once the disease has been diagnosed, a number of treatment procedures exist. These include the following principles:

C1: Oral uptake of formulation of drug (small molecule drug)
C2: Oral uptake of formulation of drug (peptidic molecule drug)
C3: Injection of peptide, protein, or antibody drug
C4: Uptake through the skin of drug molecule
C5: Inhalation of drug molecule through nose or mouth
C6: Oral uptake or injection of antibiotics
C7: X-ray exposure
C8: Heat exposure
C9: Exposure to light, e.g. UV-light
C10: Transplantation
C11: Removal of diseased organ or part of organ
C12: Cell transplant
C13: Autologous therapy
C14: Gene therapy
C15: Injection of ribozyme or other type of nucleic acid, including siRNA
C16: Treatment with antisense nucleic acid analogues, including LNA (locked nucleic acid) and PNA (peptide nucleic acid)
C17: Immuno-stimulatory agents
C18: Vaccines, including cancer vaccines
C19: Anticoagulation therapy, e.g. using recombinant hirudin
C20: Treatment using organic or inorganic molecule
C21: Removal of infected or otherwise compromised cells from the body
C22: Other disease treatment procedures A more detailed description of treatment principles are given in the section: "Treatment principles of the invention".

A list of examples of treatment methods is given in Table P, and lists of examples of drugs to be used for medical therapy of diseases is given in table Q, table R and table S and in the items.

TABLE P

Examples of treatments

| Type of treatment | Non-limiting examples of the treatment type |
|---|---|
| Chemotherapy | 1) Alkylating agents (L01A)<br>Alkylating agents are so named because of their ability to add alkyl groups to many electronegative groups under conditions present in cells. Cisplatin and carboplatin, as well as oxaliplatin are alkylating agents.<br>Other agents are mechlorethamine, cyclophosphamide, chlorambucil. They work by chemically modifying a cell's DNA.<br>2) Anti-metabolites (L01B)<br>Anti-metabolites masquerade as purine ((azathioprine, mercaptopurine)) or pyrimidine - which become the building blocks of DNA. They prevent these substances becoming incorporated in to DNA during the "S" phase (of the cell cycle), stopping normal development and division. They also affect RNA synthesis. Due to their efficiency, these drugs are the most widely used cytostatics.<br>3) Plant alkaloids and terpenoids (L01C)<br>These alkaloids are derived from plants and block cell division by preventing microtubule function. Microtubules are vital for cell division and without them it can not occur. The main examples are vinca alkaloids and taxanes.<br>4) Vinca alkaloids (L01CA)<br>Vinca alkaloids bind to specific sites on tubulin, inhibiting the assembly of tubulin into microtubules (M phase of the cell cycle). They |

TABLE P-continued

Examples of treatments

| Type of treatment | Non-limiting examples of the treatment type |
|---|---|
| | are derived from the Madagascar periwinkle, *Catharanthus roseus* (formerly known as *Vinca rosea*). The vinca alkaloids include: Vincristine, Vinblastine, Vinorelbine, Vindesine.<br>5) Podophyllotoxin (L01CB)<br>Podophyllotoxin is a plant-derived compound used to produce two other cytostatic drugs, etoposide and teniposide. They prevent the cell from entering the G1 phase (the start of DNA replication) and the replication of DNA (the S phase). The exact mechanism of its action still has to be elucidated.<br>The substance has been primarily obtained from the American Mayapple (*Podophyllum peltatum*). Recently it has been discovered that a rare Himalayan Mayapple (*Podophyllum hexandrum*) contains it in a much greater quantity, but as the plant is endangered, its supply is limited. Studies have been conducted to isolate the genes involved in the substance's production, so that it could be obtained recombinantively.<br>6) Taxanes (L01CD)<br>The prototype taxane is the natural product paclitaxel, originally known as Taxol and first derived from the bark of the Pacific Yew tree. Docetaxel is a semi-synthetic analogue of paclitaxel. Taxanes enhance stability of microtubules, preventing the separation of chromosomes during anaphase.<br>7) Topoisomerase inhibitors (L01CB and L01XX)<br>Topoisomerases are essential enzymes that maintain the topology of DNA. Inhibition of type I or type II topoisomerases interferes with both transcription and replication of DNA by upsetting proper DNA supercoiling.<br>Some type I topoisomerase inhibitors include camptothecins: irinotecan and topotecan.<br>Examples of type II inhibitors include amsacrine, etoposide, etoposide phosphate, and teniposide. These are semisynthetic derivatives of epipodophyllotoxins, alkaloids naturally occurring in the root of American Mayapple (*Podophyllum peltatum*).<br>8) Antitumour antibiotics (L01D)<br>The most important immunosuppressant from this group is dactinomycin, which is used in kidney transplantations.<br>9) Monoclonal antibodies<br>Monoclonal antibodies work by targeting tumour specific antigens, thus enhancing the host's immune response to tumour cells to which the agent attaches itself. Examples are trastuzumab (Herceptin), cetuximab, and rituximab (Rituxan or Mabthera). Bevacizumab (Avastin) is a monoclonal antibody that does not directly attack tumor cells but instead blocks the formation of new tumor vessels.<br>10) Hormonal therapy<br>Several malignancies respond to hormonal therapy. Strictly speaking, this is not chemotherapy. Cancer arising from certain tissues, including the mammary and prostate glands, may be inhibited or stimulated by appropriate changes in hormone balance.<br>Steroids (often dexamethasone) can inhibit tumour growth or the associated edema (tissue swelling), and may cause regression of lymph node malignancies. Dexamethasone is also an antiemetic, so it may be used with cytotoxic chemotherapy even if it has no direct effect on the cancer.<br>Prostate cancer is often sensitive to finasteride, an agent that blocks the peripheral conversion of testosterone to dihydrotestosterone. Breast cancer cells often highly express the estrogen and/or progesterone receptor. Inhibiting the production (with aromatase inhibitors) or action (with tamoxifen) of these hormones can often be used as an adjunct to therapy.<br>Gonadotropin-releasing hormone agonists (GnRH), such as goserelin possess a paradoxical negative feedback effect followed by inhibition of the release of FSH (follicle-stimulating hormone) and LH (luteinizing hormone), when given continuously.<br>Some other tumours are also hormone dependent, although the specific mechanism is still unclear. |
| Counseling | |
| Pharmacotherapy | 1) For the gastrointestinal tract or digestive system<br>Upper digestive tract: antacids, reflux suppressants, antiflatulents, antidopaminergics, proton pump inhibitors, H2-receptor antagonists, cytoprotectants, prostaglandin analogues<br>Lower digestive tract: laxatives, antispasmodics, antidiarrhoeals, bile acid sequestrants, opioids<br>2) For the cardiovascular system<br>General: beta-receptor blocker or beta blocker, calcium channel blockers, diuretics, cardiac glycosides, antiarrhythmics, nitrate, |

TABLE P-continued

Examples of treatments

| Type of treatment | Non-limiting examples of the treatment type |
|---|---|
| | antianginals, vasoconstrictor, vasodilator, peripheral activator |
| | Affecting Blood pressure: ACE inhibitors, angiotensin receptor blockers, alpha blocker |
| | Coagulation: anticoagulant, heparin, antiplatelet drug, fibrinolytic, anti-hemophilic factor, haemostatic drugs |
| | Atherosclerosis/cholesterol agents: hypolipidaemic agents, statins. |
| | 3) For the central nervous system |
| | hypnotic, anaesthetics, antipsychotic, antidepressant (including tricyclic antidepressants, monoamine oxidase inhibitor, lithium salt, selective serotonin reuptake inhibitor), anti-emetic, anticonvulsant and antiepileptic, anxiolytic, barbiturate, movement disorder drug, stimulant (including amphetamines), benzodiazepine, cyclopyrrolone, dopamine antagonist, antihistamine, cholinergic, anticholinergic, emetic, cannabinoids, 5-HT antagonist |
| | 4) For pain & consciousness (analgesic drugs) |
| | The main classes of painkillers are NSAIDs, opioids and various orphans such as paracetamol, tricyclic antidepressants and anticonvulsants. |
| | 5) For musculo-skeletal disorders |
| | NSAIDs (including COX-2 selective inhibitors), muscle relaxant, neuromuscular drug |
| | anticholinesterase |
| | 6) For the eye |
| | General: adrenergic neurone blocker, astringent, ocular lubricant |
| | Diagnostic: topical anesthetics, sympathomimetics, parasympatholytics, mydriatics, cycloplegics |
| | Anti-bacterial: antibiotics, topical antibiotics, sulfa drugs, aminoglycosides, fluoroquinolones |
| | Anti-viral: |
| | Anti-fungal: imidazoles, polyenes |
| | Anti-inflammatory: NSAIDs, corticosteroids |
| | Anti-allergy: mast cell inhibitors |
| | Anti-glaucoma: adrenergic agonists, beta-blockers, carbonic anhydrase inhibitors/hyperosmotics, cholinergics, miotics, parasympathomimetics, prostaglandin agonists/prostaglandin inhibitors. nitroglycerin |
| | 7) For the ear, nose and oropharynx |
| | sympathomimetic, antihistamine, anticholinergic, NSAIDs, steroid, antiseptic, local anesthetic, antifungal, cerumenolyti |
| | 8) For the respiratory system |
| | bronchodilator, NSAIDs, anti-allergic, antitussive, mucolytic, decongestant |
| | corticosteroid, beta-receptor antagonist, anticholinergic, steroid |
| | 9) For endocrine problems |
| | androgen, antiandrogen, gonadotropin, corticosteroid, growth hormone, insulin, antidiabetic (sulfonylurea, biguanide/metformin, thiazolidinedione, insulin), thyroid hormones, antithyroid drugs, calcitonin, diphosponate, vasopressin analogues |
| | 10) For the reproductive system or urinary system |
| | antifungal, alkalising agent, quinolones, antibiotic, cholinergic, anticholinergic, anticholinesterase, antispasmodic, 5-alpha reductase inhibitor, selective alpha-1 blocker, sildenafil, fertility medication |
| | 11) For contraception |
| | Hormonal contraception |
| | Ormeloxifene |
| | Spermicide |
| | 12) For obstetrics and gynecology |
| | NSAIDs, anticholinergic, haemostatic drug, antifibrinolytic, Hormone Replacement Therapy, bone regulator, beta-receptor agonist, follicle stimulating hormone, luteinising hormone, LHRH |
| | gamolenic acid, gonadotropin release inhibitor, progestogen, dopamine agonist, oestrogen, prostaglandin, gonadorelin, clomiphene, tamoxifen, Diethylstilbestrol |
| | 13) For the skin |
| | emollient, anti-pruritic, antifungal, disinfectant, scabicide, pediculicide, tar products, vitamin A derivatives, vitamin D analogue, keratolytic, abrasive, systemic antibiotic, topical antibiotic, hormones, desloughing agent, exudate absorbent, fibrinolytic, proteolytic, sunscreen, antiperspirant, corticosteroid |
| | 14) For infections and infestations |
| | antibiotic, antifungal, antileprotic, antituberculous drug, antimalarial, anthelmintic, amoebicide, antiviral, antiprotozoal |
| | 15) For immunology |
| | vaccine, immunoglobulin, immunosuppressant, interferon, monoclonal antibody |

TABLE P-continued

Examples of treatments

| Type of treatment | Non-limiting examples of the treatment type |
|---|---|
| | 16) For allergic disorders<br>anti-allergic, antihistamine, NSAIDs<br>17) For nutrition<br>tonic, iron preparation, electrolyte, parenteral nutritional supplement, vitamins, anti-obesity drug, anabolic drug, haematopoietic drug, food product drug<br>18) For neoplastic disorders<br>cytotoxic drug, sex hormones, aromatase inhibitor, somatostatin inhibitor, recombinant interleukins, G-CSF, erythropoietin<br>19) For diagnostics<br>contrast media<br>20) For euthanasia<br>An euthanaticum is used for euthanasia and physician-assisted suicide, see also barbiturates.<br>Euthanasia is not permitted by law in many countries, and consequently medicines will not be licenesed for this use in those countries. |
| Psychotherapy | 1) Psychoanalysis - the first practice to be called a psychotherapy. It encourages the verbalization of all the patient's thoughts, including free associations, fantasies, and dreams, from which the analyst formulates the nature of the unconscious conflicts which are causing the patient's symptoms and character problems.<br>2) Cognitive behavioral - is based on cognitions, assumptions, beliefs, and behaviors, with the aim of influencing negative emotions that relate to inaccurate appraisal of events.<br>3) Psychodynamic - is a form of depth psychology, the primary focus of which is to reveal the unconscious content of a client's psyche in an effort to alleviate psychic tension. Although it has its roots in psychoanalysis, psychodynamic therapy tends to be briefer and less intensive than traditional psychoanalysis.<br>4) Existential - is based on the existential belief that human beings are alone in the world. This aloneness leads to feelings of meaninglessness which can be overcome only by creating one's own values and meanings.<br>5) Humanistic - emerged in reaction to both behaviorism and psychoanalysis and is therefore known as the Third Force in the development of psychology. It is explicitly concerned with the human context of the development of the individual with an emphasis on subjective meaning, a rejection of determinism, and a concern for positive growth rather than pathology. It posits an inherent human capacity to maximise potential, 'the self-actualing tendency'. The task of Humanistic therapy is to create a relational environment where this tendency might flourish.<br>6) Brief therapy - is an umbrella term for a variety of approaches to psychotherapy. It differs from other schools of therapy in that it emphasizes (1) a focus on a specific problem and (2) direct intervention. It is solution-based rather than problem-oriented. It is less concerned with how a problem arose than with the current factors sustaining it and preventing change.<br>7) Systemic Therapy - seeks to address people not at an individual level, as is often the focus of other forms of therapy, but as people in relationship, dealing with the interactions of groups, their patterns and dynamics.(includes family therapy & marriage counseling)<br>8) Somatic Psychotherapy - also referred to as body psychotherapy, is a field in which the therapist uses touch in some way as part of therapy process.<br>9) Transpersonal Psychotherapy is a school that studies the transpersonal, the transcendent or spiritual aspects of the human experience.<br>10) Hypno-Psychotherapy - is undertaken with a subject in hypnosis.<br>11) Psychodrama/Dramatherapy - explores, through dramatic action in groups, the problems, issues, concerns, dreams and highest aspirations of people. |
| Surgical Treatment | 1) General surgery<br>2) Trauma surgery<br>3) Cardiovascular surgery<br>4) Neurosurgery<br>5) Maxillofacial surgery<br>6) Orthopedic surgery<br>7) Otolaryngology<br>8) Plastic surgery<br>9) Oncologic surgery<br>10) Vascular surgery<br>11) Pediatric surgery<br>12) Diagnostic Surgery such as incisional biopsy, excisional biopsy, endoscopic biopsy, colposcopic biopsy, bone marrow biopsy, fine |

TABLE P-continued

Examples of treatments

| Type of treatment | Non-limiting examples of the treatment type |
|---|---|
| | needle aspiration biopsy, stereotactic biopsy, and core biopsy |
| | 13) preventive surgery |
| | 14) curative surgery |
| | 15) Palliative Surgery |
| | 16) Reconstructive Surgery |
| | 17) Major surgery |
| | 18) Minor surgery |
| | 19) Elective surgery |
| | 20) Required surgery |
| | 21) Urgent or emergency surgery |
| Medicine | Treatment with one or more drugs |
| Ergotherapy | Muscular exercise |
| Massage | |
| Physiotherapy | 1) Cardiopulmonary |
| | Cardiovascular and pulmonary rehabilitation physical therapists treat a wide variety of individuals with cardiopulmonary disorders or those who have had cardiac or pulmonary surgery. Primary goals of this specialty include increasing endurance and functional independence. Manual therapy is utilized in this field to assist in clearing lung secretions experienced with cystic fibrosis. Disorders, including heart attacks, post coronary bypass surgery, chronic obstructive pulmonary disease, and pulmonary fibrosis, treatments can benefit from cardiovascular and pulmonary specialized physical therapists. |
| | 2) Geriatric |
| | Geriatric physical therapy covers a wide area of issues concerning people as they go through normal adult aging, but is usually focused on the older adult. There are many conditions that affect many people as they grow older and include but are not limited to the following: arthritis, osteoporosis, cancer, Alzheimer's disease, hip and joint replacement, balance disorders, incontinence, etc. Geriatric physical therapy helps those affected by such problems in developing a specialized program to help restore mobility, reduce pain, and increase fitness levels. |
| | 3) Neurological |
| | Neurological physical therapy is a discipline focused on working with individuals who have a neurological disorder or disease. These include Alzheimer's disease, ALS, brain injury, cerebral palsy, multiple sclerosis, Parkinson's disease, spinal cord injury, and stroke. Common symptoms of neurological disorders include paralysis, vision impairment, poor balance, inability to ambulate, and loss of functional independence. Therapists work to improve these areas of dysfunction.[16] |
| | 4) Orthopaedic |
| | Orthopaedic physical therapists diagnose, manage, and treat disorders and injuries of the musculoskeletal system including rehabilitation after orthopedic surgery. This specialty of physical therapy is most often found in the out-patient clinical setting. Orthopedic therapists are trained in the treatment of post-operative orthopaedic procedures, fractures, acute sports injuries, arthritis, sprains, strains, back and neck pain, spinal conditions and amputations. Joint mobilization and manipulation, therapeutic exercise, neuromuscular reeducation, hot/cold packs, and electrical stimulation (e.g., cryotherapy, iontophoresis, electrotherapy) are modalities often used to expedite recovery in the orthopedic setting.[17] Additionally, an emerging treatment in this field is the use of sonography for diagnosis and to guide treatments such as muscle retraining.[18][19][20] Those who have suffered injury or disease affecting the muscles, bones, ligaments, or tendons of the body will benefit from assessment by a physical therapist specialized in orthopaedics. |
| | 5) Pediatric |
| | Pediatric physical therapy assists in early detection of health problems and uses a wide variety of modalities to treat disorders in the pediatric population. These therapists are specialized in the diagnosis, treatment, and management of infants, children, and adolescents with a variety of congenital, developmental, neuromuscular, skeletal, or acquired disorders/diseases. Treatments focus on improving gross and fine motor skills, balance and coordination, strength and endurance as well as cognitive and sensory processing/integration. Children with developmental delays, cerebral palsy, spina bifida, or torticollis, may be treated by pediatric physical therapists.[16] Another PT specialty area is Integumentary (treatment of conditions involving the skin and related organs). |
| Diet adjustment | 1) Gluten-free diet |
| | 2) To obtain weight loss or weight gain |

TABLE P-continued

Examples of treatments

| Type of treatment | Non-limiting examples of the treatment type |
|---|---|
| | 3) Herbs and Nutritional Supplements |
| | 4) Vitamin and/or mineral supplement |
| Exercise | To obtain weight loss |
| | To obtain increased bone strength |
| Radiation therapy | External Beam Radiation Therapy |
| | Internal Radiation Therapy |
| | Internal systemic radiation therapy |
| | Interstitial radiation therapy |
| | Intracavitary radiation therapy |
| | brachytherapy |
| | prophylactic radiation therapy. |
| | Curative radiation therapy. |
| | Intraoperative radiation therapy (IORT) |
| | Prophylactic cranial irradiation |
| | Intracavitary or intraluminal radiation therapy |
| | radiation therapy using radioactive materials such as iodine 131 and/or strontium 89. |
| | Stereotactic (or stereotaxic) radiosurgery |
| | Three-dimensional (3-D) conformal radiation therapy |
| | Radiation therapy using a dose in the range of 5 to 200 Gy, such as from 5 to 10 Gy, for example from 10 to 20 Gy, such as from 20 to 30 Gy, for example from 30 to 40 Gy, such as from 40 to 50 Gy, for example from 50 to 60 Gy, such as from 60 to 70 Gy, for example from 70 to 80 Gy, such as from 80 to 90 Gy, for example from 90 to 100 Gy, such as from 100 to 120 Gy, for example from 120 to 140 Gy, such as from 140 to 160 Gy, for example from 160 to 180 Gy, such as from 180 to 200 Gy. |
| Gene therapy | 1) Germ line gene therapy |
| | In the case of germ line gene therapy, germ cells, i.e., sperm or eggs, are modified by the introduction of functional genes, which are ordinarily integrated into their genomes. Therefore, the change due to therapy would be heritable and would be passed on to later generations. This new approach, theoretically, should be highly effective in counteracting genetic disorders. However, this option is prohibited for application in human beings, at least for the present, for a variety of technical and ethical reasons. |
| | 2) Somatic cell gene therapy |
| | In somatic cell gene therapy, the gene is introduced only in somatic cells, especially of those tissues in which expression of the concerned gene is critical for health. Expression of the introduced gene relieves/eliminates symptoms of the disorder, but this effect is not heritable as it does not involve the germ line. At present, somatic cell therapy is the only feasible option, and clinical trials addressing a variety of conditions have already begun. |
| Immunotherapy | 1) Cancer immunotherapy: Cancer immunotherapy attempts to stimulate the immune system to reject and destroy tumors. BCG immunotherapy for early stage (non-invasive) bladder cancer utilizes instillation of attenuated live bacteria into the bladder, and is effective in preventing recurrence in up to two thirds of cases. Topical immunotherapy utilizes an immune enhancement cream (imiquimod) which is an interferon producer causing the patients own killer T cells to destroy warts, actinic keratoses, basal cell cancer, squamous cell cancer, cutaneous lymphoma, and superficial malignant melanoma. Injection immunotherapy uses mumps, candida or trichophytin antigen injections to treat warts (HPV induced tumors). |
| | 2) Dendritic cell based immunotherapy |
| | This utilizes dendritic cells to activate a cytotoxic response towards an antigen. Dendritic cells, an antigen presenting cell, are harvested from a patient. These cells are then either pulsed with an antigen or transfected with a viral vector. The activated dendritic cells are then placed back into the patient; these cells then present the antigens to effector lymphocytes (CD4+ T cells, CD8+ T cells, and in specialized dendritic cells, B cells also). This initiates a cytotoxic response to occur against these antigens and anything that may present these antigens. One use for this therapy is in cancer immunotherapy. Tumor Antigens are presented to dendritic cells, which cause the immune system to target these antigens, which are often expressed on cancerous cells. |
| | 3) T cell based adoptive immunotherapy |
| | This therapy uses T cell-based cytotoxic responses to attack cancer. In brief, T cells that have a natural or genetically engineered reactivity to a patients' cancer are expanded in vitro using a variety of means and then adoptively transferred into a cancer patient. T cells with a natural occurring reactivity to a patient's cancer can be found infiltrated in the patients' own tumors. The tumor is harvested, and these tumor infiltrating lymphocytes (TIL) are expanded in vitro using |

TABLE P-continued

Examples of treatments

| Type of treatment | Non-limiting examples of the treatment type |
|---|---|
| | high concentrations of interluekin-2 (IL-2), anti-CD3 and allo-reactive feeders. These T cells are then transferred back into the patient along with exogenous administration of IL-2. Thus far, a 51% objective response rate has been observed; in some patients, tumors shrank to indetectable size. In the case of engineered T cells, T cell receptors (TCR) that have been identified to have reactivity against tumor associated antigens are cloned into a replication incompetent virus that is capable of genomic integration. A patients own lymphocytes are exposed to these viruses and then expanded non-specifically or stimulated using the engineered TCR. The cells are then transferred back into the patient. This therapy has been demonstrated to result in objective clinical responses in patients with refractory stage IV cancer. The Surgery Branch of the National Cancer Institute (Bethesda, Maryland) is actively investigating this form of cancer treatment for patients suffering aggressive melanomas.<br>4) Vaccination<br>Anti-microbial immunotherapy, which includes vaccination, involves activating the immune system to respond to an infectious agent.<br>5) monoclonal antibodies (passive immunotherapies)<br>6) non-specific immunotherapies and adjuvants |

For a disease (An) any combination of diagnosis procedure (Bn) and treatment process (Cn) may be used, in order to treat the individual for the disease. Thus, any combinations of disease(s), diagnostic analysis or analyses, and treatment(s) may be applied, in any sequence and combination. The following combinations of disease, diagnosis procedure, and treatment procedure are examples of the present invention, where for each combination the diagnosis and treatment may be performed in any order:

A1C1, A2C1, . . . AnC1, . . . , A1C2, . . . AnCn
and
B1C1, B2C1, . . . , BnC1, . . . , B1C2, . . . , BnCn
and
A1A1C1, A1A2C1, . . . , A1B1C1, A1BnC1, . . . ,
   A2B1C1, . . . , A2BnC1, . . . , AnAnC1, . . . , BnBnC1,
   A1A1C2, A1A2C2, . . . , A1B1C2, A1BnC2, . . . ,
   A2B1C2, . . . , A2BnC2, . . . , AnAnC2, . . . , BnBnC2,
A1A1Cn, A1A2Cn, . . . , A1B1Cn, A1BnCn, . . . ,
   A2B1Cn, . . . , A2BnCn, . . . , AnAnCn, . . . , BnBnCn
and
A1A1A1C1, A1A1A2C1, . . . , . . . , AnAnAnC1, . . . ,
   AnAnBnC1, . . . , BnBnBnC1, A1A1A1C2,
   A1A1A2C2, . . . , . . . , AnAnAnC2, . . . ,
   AnAnBnC2, . . . , BnBnBnC2, A1A1A1Cn,
   A1A1A2Cn, . . . , . . . , AnAnAnCn, . . . ,
   AnAnBnCn, . . . , BnBnBnCn
and
A1A1A1A1C1, . . . , . . . , . . . , BnBnBnBnCn
and
A1A1A1A1A1C1, . . . , . . . , . . . , . . . , BnBnBnBnBnCn
and
A1A1A1A1A1A1C1, . . . , . . . , . . . , . . . , . . . , . . .
, BnBnBnBnBnBnBnBnCn, . . . , . . . , . . . .

In other words, any number and kind of diagnostics test may precede or follow any number and kind of treatments, for any kind of disease(s). This combinatorial diagnosis and treatment campaign thus may involve diagnostic test(s) first, followed by treatment(s); or treatment(s) followed by diagnostic test(s); or diagnostic test(s) followed by treatment(s) followed by diagnostic test(s); or diagnostic test(s) followed by treatment(s) followed by diagnostic test(s) followed by treatment(s), etc.

A preferred embodiment of the present invention relates to treatment, diagnosis and monitoring of cancers, preferably cancers able to be treated with immunotherapy. Cancer immunotherapy is the use of the immune system to reject cancer. The main premise is stimulating the patient's immune system to attack the malignant tumor cells that are responsible for the disease. This can be through immunization of the patient, in which case the patient's own immune system is trained to recognize tumor cells as targets to be destroyed. This can for example be done through the administration of therapeutic antibodies as drugs, in which case the patient's immune system is recruited to destroy tumor cells by the therapeutic antibodies, through administration of interferones or cytokines, through administration of one or more cancer antigens or cancer antigenic peptides, through administration of cells expressing cancer antigens and/or cancer antigenic peptide, through administration of DNA, DNA plasmids or viral vectors encoding one/or more cancer antigens and/or cancer antigenic peptides. One or more different immunization types may be employed for a given cancer immunotherapy of a given individual.

Examples of combinatorial diagnosis and treatment campaigns of cancers are:

Diagnosis of cancer e.g. multiple myeloma, chronic myelogenous leukemia, hairy cell leukemia, or malignant melanoma by flow cytometry/visual inspection/biopsy—treatment with interferons/cytokines e.g. INFα, IL2, IFNβ-follow up diagnosis for residual cancer by flow cytometry/visual inspection/biopsy Diagnosis of cancer e.g. acute myeloid leukaemia, B cell leukemia, non-Hodgkin's lymphoma, breast cancer, testis cancer, liver cancer by flowcytometry, visual inspection, cytometry, biopsy followed by IHC-treatment with monoclonal antibody-follow up diagnosis by flow cytometry, visual inspection, cytometry, biopsy followed by IHC and optional supplemented with analysis for the presences of tumor specific T cells using MHC multimers and flowcytometry Diagnosis of cancer e.g. melanoma, liver, prostate, renal cancer by flow cytometry, visual inspection, cytometry, biopsy followed by IHC-treatment with cancer vaccine e.g. cancer antigen alone, cancer antigen+dendritic cells, cancer antigens+adenoviral vector—follow up diagnosis by flow cytometry, visual inspection, cytometry, biopsy followed by IHC and optional supplemented with analysis for the presences of tumor specific T cells using MHC multimers and flowcytometry Therapeutic vaccination against HPV—pap smear test Another preferred embodiment of the present invention relates to diagnosis, treatment and monitoring of viral infections. Of special interest are diagnosis, prevention and treatment of HIV infection.

Examples of combinatorial diagnosis and treatment campaigns of HIV infection:

Diagnosis of HIV by ELISA or Western blot—treatment with protease inhibitors—follow up diagnosis by measuring number of CD4+ T cells by flow cytometry—treatment with protease inhibitor etc.

Diagnosis of HIV by ELISA or Western blot—treatment with antibody based HIV vaccine—follow up diagnosis by measuring number of CD4+ T cells by flow cytometry—treatment with antibody based HIV vaccine—follow up diagnosis by measuring number of CD4+ T cells by flow cytometry etc.

Preventive HIV vaccine—monitoring/diagnosis of HIV by ELISA or Western blot upon exposure.

Another preferred embodiment of the present inventions relates to diagnosis, monitoring and treatment of bacterial infections, preferably infections caused by intracellular bacteria, preferably *Borrelia* infection. Another preferred embodiment relates to diagnosis, monitoring and treatment of latent and/or active infection with TB (tuberculosis).

Examples of combinatorial diagnosis and treatment campaigns of TB infection:

Diagnosis of active TB infection by tuberculin skin test—treatment with isoniazid, rifampicin, pyrazinamide, and ethambutol Diagnosis of latent TB with ELISPOT assay—treatment with isoniazid—monitoring/diagnosis of TB with ELISPOT Diagnosis of latent TB by ELISA—treatment with isoniazid—monitoring/diagnosis of TB with ELISA Diagnosis of latent TB by MHC multimers and flow cytometry—treatment with isoniazid—monitoring/diagnosis of TB with MHC multimers and flowcytometry Another preferred embodiment of the present invention relates to immune-monitoring following transplantation, especially monitoring of CMV, EBV and BK virus infection, but other virus or bacteria causing opportunistic infection could also be monitored.

Examples of combinatorial diagnosis and treatment campaigns for transplantation related disorders:

Diagnosis of defect organ e.g. kidney—transplantation of kidney+immune suppressive drug(s)—diagnosis of opportunistic infection e.g. BK virus infection—reduce immune suppressive drug—diagnosis of beginning transplant rejection—increase immune suppressive drug(s)—etc.

Diagnosis of defect organ e.g. liver, lung, bone marrow, heart—transplantation of new organ+immune suppressive drug(s)—diagnosis of opportunistic infection e.g. CMV or EBV virus infection—reduce immune suppressive drug-diagnosis of beginning transplant rejection—increase immune suppressive drug(s)—etc.

Patients

The individual to be diagnosed and/or treated can be a human being such as a man or a woman. The individual to be diagnosed and/or treated can be a pregnant woman. The individual to be diagnosed and/or treated can be a lactating woman. The individual to be diagnosed and/or treated can be a human being of any age, such as an infant, a child or an adult.

The individual to be diagnosed and/or treated can be of any age such as from newborn to 120 years old, for example from 0 to 6 months, such as from 6 to 12 months, for example from 1 to 5 years, such as from 5 to 10 years, for example from 10 to 15 years, such as from 15 to 20 years, for example from 20 to 25 years, such as from 25 to 30 years, for example from 30 to 35 years, such as from 35 to 40 years, for example from 40 to 45 years, such as from 45 to 50 years, for example from 50 to 60 years, such as from 60 to 70 years, for example from 70 to 80 years, such as from 80 to 90 years, for example from 90 to 100 years, such as from 100 to 110 years, for example from 110 to 120 years.

The individual to be diagnosed and/or treated can be of any race such as a Caucasian, a black person, an East Asian person, a person of Mongoloid race, a person of Ethiopian race, a person of Negroid race, a person of American Indian race, or a person of Malayan race.

The individual to be diagnosed and/or treated can be healthy, ill, diagnosed with one or more diseases, can have one or more symptoms of one or more diseases, can be asymptomatic or can be genetically disposed to one or more diseases.

Non-live Units

For non-live units such as e.g. buildings and materials, some of the above-mentioned diagnosis- and repair procedures may be used as well. For non-live units additional diagnosis- and repair procedures may be used as well. Examples of the present invention are shown below:

Undesired states (Xn) of units:

X1: Rusty material

X2: Broken or otherwise damaged structure

X3: Non-homogenous state of a material

X4: Low tensile strength of material

X5: Low flexibility of material

X6: Structure's or material's surface corroded, or otherwise unintentionally modified X7: Structure's or material's surface or internal part covered with bacteria or fungi, other biofilm, or otherwise disintegrated or modified X7: Other undesired change to the characteristics of the material or structure Diagnosis (Yn) of undesired state:

Y1: Temperature measurement

Y2: Imaging

Y3: CT scan (computerized tomography)

Y4: MRI scan (magnetic resonance imaging)

Y5: Ultrasound

Y6: X-ray imaging

Y7: Histochemical staining of surface or cut sections

Y8: Antibody-specific staining of surface or cut sections

Y9: Infrared scanning

Y10: Hybridisation of antibody to antigen

Y11: Hybridization of nucleic acid or nucleic acid analogue to nucleic acid or nucleic acid analogue Y12: Visual inspection Y13: Other principles allowing a diagnosis to be performed.

Once the undesired state has been diagnosed, a number of repair procedures (Zn) exist. These include the following principles:

Z1: Injection or passive uptake of agent (chemical or biological) that restores a less undesired state of unit Z2: X-ray exposure Z3: Heat exposure Z4: Exposure to light, e.g. UV-light Z5: Removal of agent causing the undesired state, e.g. removal of bacteria, fungi, or modified surface, by chemical, physical or mechanical means Z6: Injection or passive uptake of a cross-linking agent that restores a polymer network Z7: Filling of cracks in structure, e.g. cracks in cement bridge Z8: Other repair procedures For an undesired state (Xn) any combination of diagnosis procedures) (Yn) and repair processes (Zn) may be used, in order to obtain a less undesired state of the unit. Thus, any combinations of undesired state(s), diagnostic test(s), and repair(s) may be applied. The following combinations of undesired state(s), diagnosis procedure(s), and repair procedure(s) are examples of the present invention:

X1Z1, X2Z1, . . . XnZ1, . . . , X1Z2, . . . XnZn
and
Y1Z1, Y2Z1, . . . , YnZ1, . . . , Y1Z2, . . . , YnZn
and
X1X1Z1, X1X2Z1, . . . , X1Y1Z1, X1YnZ1, . . . , X2Y1Z1, . . . , X2YnZ1, . . . , XnXnZ1, . . . , YnYnZ1, X1X1Z2, X1X2Z2, . . . , X1Y1Z2, X1YnZ2, . . . , X2Y1Z2, . . . , X2YnZ2, . . . , XnXnZ2, . . . , YnYnZ2, X1X1Zn, X1X2Zn, . . . , X1Y1Zn, X1YnZn, . . . , X2Y1Zn, . . . , X2YnZn, . . . , XnXnZn, . . . , YnYnZn
and
X1X1X1Z1, X1X1X2Z1, . . . , . . . , XnXnXnZ1, . . . , XnXnYnZ1, . . . , YnYnYnZ1, X1X1X1Z2, X1X1X2Z2, . . . , . . . , XnXnXnZ2, . . . , XnXnYnZ2, . . . , YnYnYnZ2, X1X1X1Zn, X1X1X2Zn, . . . , . . . , XnXnXnZn, . . . , XnXnYnZn, . . . , YnYnYnZn
and
X1X1X1X1Z1, . . . , . . . , . . . , YnYnYnYnZn
and
X1X1X1X1X1Z1, . . . , . . . , . . . , . . . , YnYnYnYnYnZn
and
X1X1X1X1X1X1Z1, . . . , . . . , . . . , . . . , . . . , YnYnYnYnYnYnYnYnZn, . . . , . . . , . . . .

Diagnostic Principles of the Invention

The diagnostic test(s) of the unit may be categorized depending on a number of characteristics, including how the sample was obtained; what the sample is and how it was prepared; what kind of physical feature or matter is measured; what specific physical feature or matter is measured; how is this feature or matter measured; and what is the undesired or desired state being analyzed.

Diagnostic test of special interest for the present invention are tests used for diagnosis and/or monitoring of specific diseases or disease conditions. Such diagnostic tests may be direct (e.g. measuring of a virus titer in a viral infected individual) or indirect (e.g. clinical symptoms, detection of specific tumor markers, detection of specific cells, detection of hormones in blood or urine etc.).

The present invention relates in one embodiment to diagnosis of one or more diseases and one or more treatments for said disease.

In the following, principles for diagnostic tests and/or analysis for specific diseases/disease conditions are described in further details.

Type of Sample

The sample used for the analysis may be the entire unit, or a part of the unit or the sample may in some way be related to the unit, wherefore the analysis of the sample will be informative about the status of the unit. For example, the sample may be sweat that evaporates from the body, or urine. The sample used in the analysis is either the entire structure or part of it. For example, a blood sample may be treated with hormones and redelivered to the body.

Sample sources include samples obtained from live as well as non-live sources, including but not limited to humans, animals, birds, insects, plants, algae, fungi's, yeast, viruses, bacteria and phages, multi-cellular and mono-cellular organisms, and chemical reactions comprising e.g. supra-molecular structures, transitions state molecules, chemical, and enzymatic reactions. Human and animal samples include blood, semen, cerebrospinal fluid (CSF), sputum, vaginal fluid, faeces, urine, saliva, hair, other bodily fluids, tissue samples, whole organs, sweat, tears or other sub-structures of humans or animals. The sample therefore may be a solid, semi-solid or a fluent. Human samples could also be records of impulses e.g. heart beat, breath, nerve impulses or records of oral, visual or hearing tests.

Sources of pathogens include bacteria, viruses, parasites and other infective organisms. Other sources may be environmental samples such as drinking water, sewage, or soil.

How the Diagnostic Test Sample is Obtained

Sampling is the process by which the sample is collected from the source and optionally kept until the sample can be prepared and analyzed. The sample may be the entire unit, or part thereof, and may be obtained in a number of ways. Sampling may be categorized as invasive or non-invasive. Example invasive sampling include drawing of blood, resection of tissues, organs or part thereof (e.g. by biopsy) and drawing of cerebrospinal fluid (lumbar puncture); Example non-invasive sampling include collection of externally secreted fluids (e.g. sputum, urine), measurement/recording of physical impulses, (e.g. heartbeat, breath, nerve impulses), measurement and recording of muscle tonus, images or sounds.

The sample may be collected into a container that is appropriate for the intended type of analysis, or that protects the sample from the environment or protects the experimenter from the sample. The sampling devise preferably is a sterile, single-use devise, into which the sample passively drips or is actively drawn by e.g. vacuum. For blood transfusion such devises may hold up to one liter or more of blood; for analytical purposes as little as a few milliliters or less may be collected. Even smaller volumes may be obtained through micro-puncture followed by aspiration of e.g. a single drop of blood directly into the analytical devise. For patients that require frequent sample extraction, the sampling devise is preferably designed so as to allow sampling by non-professional health workers or the patient. Alternatively, the sample is drawn directly from patient circulation, e.g. during surgery, which may allow simultaneous analysis in a continuous manner.

Other features of sample containers include mechanical strength to allow centrifugation, transparent walls or opaque walls protecting the sample from light with transparent windows to allow visual sample monitoring. For blood sampling, the sampling needle should be easily extractable preferably directly into disposal containers. A chemical or electronic monitoring devise that integrates time and temperature following sample introduction into the devise may be used as a measure of sample integrity.

Often, additional preparation of sample must be performed in order to run the analysis on the sample. The preparation process include but is not limited to i) addition of anti-oxidants, anti-coagulants, biocides or other reagents that protect the sample from the surroundings, or alternatively, protect the surroundings (e.g. the experimenter) from the sample, ii) physical or chemical removal or destruction of troublesome contaminants, iii) addition of chemicals or processing steps that provide the sample in a form (e.g. solid or fluid) appropriate for the analytical step that follows, iv) enrichment of the desired entities, v) labeling of the entities, vi) addition of internal standard reagents and vii) changing the format of the sample into another format, e.g. changing an electronically collected file into another format suitable for the software used for analysis.

Preparation of the sample for subsequent analysis can be an integrated part of the total analysis, because the way the sample preparation is performed will influence the basic of the subsequent analysis. Sample preparation may remove or add factors, and therefore influences the analytical data acquired.

During sample preparation, the sample may be fractionated to enrich for or remove certain factors or entities. This may be done by physical or chemical separation. Example physical separations are simple centrifugation, density centrifugation in ficoll, glycerol, sucrose or other chemicals that alter the physical density of the sample during centrifugation. Example chemical treatment is induced precipitation or destruction of contaminants or undesired entities by an added chemical, e.g. for blood sample preparation, chemical separation include selective destruction of entities, e.g. lysis of red blood cells in full blood using chemical reagents.

Analysis of Sample

One or more characteristics of the sample may be measured. These include both physical and chemical characteristics. The characteristics may be internal characteristics, such as weight, temperature, flow or may be externally induced, such as fluorescence induced by exposure to UV-light, temperature increase as a result of exposure to microwaves, or a radiography of a certain distribution pattern obtained by the addition of a tracer molecule such as a radioactive antibody, with affinity for a tumor, to a cancer patient.

For a given analysis of an individual the measured characteristics may all be measured in same sample. Alternatively, one or more different characteristics may be measured in different samples obtained from the same individual and the combined results of the different measurements of the different samples then comprise the final analysis. A list of examples of diagnostic methods is found in Table T.

Analysis can be classified as follows:

A) Chemical Assays

Chemical assays of the present invention are procedures measuring one or more properties and/or amount of a sample or part of sample. Chemical assays can be based on different principles:

Measurement of Binding

Binding of molecule, cells or other substances to one or more defined structures in the sample can be used as diagnostic test and in the following the substances are collectively called binding molecules or marker molecules. The terms binding molecules and marker molecules are used interchangeably herein. A marker molecule or binding molecule is a molecule that specifically associates covalently or non-covalently with a structure belonging to or associated with an entity in the sample. The defined structure in sample bound by a marker molecule is also called the target structure or target of the marker molecule. Example binding molecule include but is not limited to proteins, antibodies (monoclonal or polyclonal, derived from any species e.g. man, mouse, rat, rabbit, pig or camel, monkey or may be recombinant antibodies), antibody fragments, MHC multimers (including but not limited to MHC dextramers, MHC tetramers, MHC Pentamers, cells expressing MHC molecules, MHC-peptide molecules covalently or non-covalently attached to beads, streptactin or other molecule structures), scaffold molecules, small organic molecules, nucleic acids (e.g. DNA, RNA, PNA), polysaccharides, other polymers, Aptamers, beads, cells, living cells, dead cells, naturally occurring cells, genetic modified cells, hybridoma cells, gene transfected cells, cell like structures (e.g. liposomes, micelles) or other molecules, cells or substances able to bind defined structure in sample.

A marker molecule is useful for detection of a given defined structure in sample if the marker molecule binds the defined structure with a certain affinity. In one embodiment the affinity of the marker molecule for the defined structure is in the range of from $K_D=10^{-12}$ to $K_D=10^{-2}$ M, such as in the range of from $K_D=10^{-12}$ to $K_D=10^{-11}$ M, for example in the range of from $K_D=10^{-11}$ to $K_D=10^{-10}$ M, such as in the range of from $K_D=10^{-10}$ to $K_D=10^{-9}$ M, for example in the range of from $K_D=10^{-9}$ to $K_D=10^{-8}$ M, such as in the range of from $K_D=10^{-8}$ to $K_D=10^{-7}$ M, for example in the range of from $K_D=10^{-7}$ to $K_D=10^{-6}$ M, such as in the range of from $K_D=10^{-6}$ to $K_D=10^{-5}$ M, for example in the range of from $K_D=10^{-5}$ to $K_D=10^{-4}$ M, such as in the range of from $K_D=10^{-4}$ to $K_D=10^{-3}$ M, for example in the range of from $K_D=10^{-3}$ to $K_D=10^{-2}$ M, or any combination thereof.

In order to be specific the marker molecule has to have a binding affinity that is higher than the marker molecules binding affinity for other structures in sample. The specificity of a marker molecule is given by the ratio:

Marker molecules affinity for defined structure (the target structure)/Marker molecules affinity for other structures in sample In one embodiment this ratio (marker molecules affinity for defined structure: marker molecules affinity for other structures in sample) is in the range from 1:1 to $10^8$:1, such as from 1:1 to $10^1$:1, for example from $10^1$:1 to $10^2$:1, such as from $10^2$:1 to $10^3$:1, for example from $10^3$:1 to $10^4$:1, such as from $10^4$:1 to $10^5$:1, for example from $10^5$:1 to $10^6$:1, such as from $10^6$:1 to $10^7$:1, for example from $10^7$:1 to $10^8$:1, or any combination thereof.

A high ratio indicates a high specificity while a low ratio will result in increased background noise in the measurement.

Marker molecules may be labeled with a labeling molecule. A labeling molecule is used interchangeably herein with label and describes an identifiable substance that is detectable in an assay and that can be attached to a binding molecule creating a labeled binding molecule. Labeling molecules are described in more detail elsewhere herein.

Upon binding to defined structures in sample labelled marker molecules release a measurable signal thereby identifying the defined structure. This signal is often called the specific signal or the specific staining and is optimally much higher than the background signal obtained from the sample itself or from binding of the labelled marker molecules to other irrelevant structures in sample. The background signal is often called background staining.

In one embodiment the difference between the background signal and a specific signal (i.e. the specific staining) is in the range (fold difference; i.e. the ratio specific signal: background signal) from 1:1 to $10^8$:1, such as from 1:1 to $10^1$:1, for example from $10^1$:1 to $10^2$:1, such as from $10^2$:1 to $10^3$:1, for example from $10^3$:1 to $10^4$:1, such as from $10^4$:1 to $10^5$:1, for example from $10^5$:1 to $10^6$:1, such as from $10^6$:1 to $10^7$:1, for example from $10^7$:1 to $10^8$:1, or any combination thereof.

In an analysis, typically one type of defined structure in a sample is measured. Alternatively, more than one type of defined structures in the same sample can be measured. In a preferred embodiment 2 to 50 different defined structures are measured in same sample, such as 2 to 3, for example 3 to 4, such as 4 to 5, for example 5 to 6, such as 6 to 7, for example 7 to 8, such as 8 to 9, for example 9 to 10, such as 10 to 11, for example 11 to 12, such as 12 to 13, for example 13 to 14, such as 14 to 15, for example 15 to 16, such as 16 to 17, for example 17 to 18, such as 18 to 19, for example 19 to 20, such as 20 to 21, for example 21 to 22, such as 22 to 23, for example 23 to 24, such as 24 to 25, for example 25 to 26, such as 26 to 27, for example 27 to 28, such as 28 to 29, for example 29 to 30, such as 30 to 31, for example 31 to 32, such as 32 to 33, for example 33 to 34, such as 34 to 35, for example 35 to 36, such as 36 to 37, for example 37 to 38, such as 38 to 39, for example 39 to 40, such as 40 to 41, for example 41 to 42, such as 42 to 43, for example 43 to 44, such as 44 to 45, for example 45 to 46, such as 46 to 47, for example 47 to 48, such as 48 to 49, for example 49 to 50, or any combination thereof.

In one embodiment of the present invention the expression level of specific defined structures can be graded according to signal intensity upon binding of labelled marker molecule to defined structure and then this grading correlated to a certain diagnosis. An example is Immunohistochemistry (IHC) analysis where the overexpression of certain defined structures is measured by binding of marker molecules to defined structure. The signal intensity obtained from this binding interaction is then graded as 0, 1+, 2+ or 3+ where 0 is signal corresponding to background signal, 1+ is signal intensity a little over background 2+ is signal intensity clearly different from background and 3+ is maximum signal. IHC analysis graded as 0 or 1+ are not defined as having any overexpression of the defined structure while IHC analysis graded 2+ or 3+ do have overexpression of the defined structure and are diagnosed positive. Similar grading some systems may be employed to other chemical assays.

Typical defined structures measured in chemical assays by binding marker molecules/binding molecules to the defined structure include but is not limited to: surface receptors on cells (e.g. TCR, CD molecules, growth receptors, MHC complexes, mannose binding receptor, transporter proteins), other structures on the surface of cells (e.g. lipids, sugars, proteins), intracellular substances in cells (e.g. DNA, RNA, ribosomes, cytokines, transcription factors, cytoskeleton components, intracellular proteins, sugars), components in fluidics (e.g. antibodies, blood plates, serum proteins, sugars), structures in interstitial space in tissues etc.

When measuring a defined structure the amount of the structure in the sample or in a defined part of the sample, are quantified. Of special interest is the measurement of expression of defined structures (e.g. proteins or sugars) on the surface of or inside a cell. In a preferred embodiment 1 to $1\times10^8$ copies of a given defined structure is detected, such as from 1 to 10 defined structures, for example from 10 to $10^2$ defined structures, such as from $10^2$ to $10^3$ defined structures, for example from $10^3$ to $10^4$ defined structures, such as from $10^4$ to $10^5$ defined structures, for example from $10^5$ to $10^6$ defined structures, such as from $10^6$ to $10^7$ defined structures, for example from $10^7$ to $10^8$ defined structures, or any combination thereof.

If more than one defined structure is measured these structures may be localized on the same entity for example on the same cell or in the same compartment of the sample (e.g. in the serum of a blood sample). Alternatively the various measured defined structures are positioned on different entities e.g. on different cell types or in different compartments of the sample. For example in a blood sample one defined structure is on a cell, another defined structure is in serum, a third is on a blood plate etc.

The defined structures may all be measured in same sample or measured in different samples obtained from the individual being analyzed.

In one embodiment the same defined structure may be measured in more than one sample obtained from the individual being analyzed. For example the presence of specific antigenic T cells may be measured in a blood sample and also in a biopsy from a tumor obtained from same individual.

In another embodiment different defined structures are measured in different samples obtained from the individual being analyzed. For example the presence of a given population of T cells specific for a certain tumor antigen is measured in the blood from a patient treated for cancer and the expression level of the same tumor antigen is measured on tumor cells in a biopsy obtained from tumor from the same patient.

Different principles exist for measurement of binding:
Direct measurement of binding is the direct detection of the binding interaction between the marker molecule and the structure in sample and includes:
  Measurement of binding of marker molecule through covalently or non-covalently association with defined structure in sample. Marker molecules can be antibodies aptamers, proteins, peptides, small organic molecules, natural compounds (e.g. steroids), non-peptide polymers, MHC multimers (including MHC-dextramers, MHC-tetramers, MHC-pentamers and other MHC-multimers), or any other molecules that specifically and efficiently bind to other molecules are also marker molecules. Typically, marker molecules bind molecules associated with an entity inhere defined as the target for the marker molecule.
Marker molecules are most often labeled either directly or indirectly by binding another marker molecule that has been labeled.
Examples of marker molecules and corresponding target molecules are given below:
  I. Antibodies binding to membrane components on, or within cells; e.g. Polysaccharides, proteins, or lipid residues.
  II. MHC multimers (e.g. MHC dextramers, MHC tetramers, MHC pentamers), complexed with a specific peptide, binds to the T-cell receptor (TCR) on T-cells.
  III. MHC multimers (e.g. MHC dextramers, MHC tetramers, MHC pentamers), complexed with a so-called nonsense peptide (i.e. a peptide that binds the MHC protein but expectably does not mediate efficient MHC complex-TCR interaction with any T-cell), are used as negative control for the specific binding of a specific MHC multimers to the cell.
  IV. Marker molecules such as Propidium Iodide (PI) that stain DNA in cells, here the marker and the label is the same molecule.
  V. Marker molecules that stain DNA, and that is used to characterize the state of a cell (e.g. state of cell cycle), e.g. Draq 5, PI, or other DNA binding molecules.
  VI. Markers that bind specifically to incorporated molecules. An example is BrdU, which may be added to a cell which will incorporate BrdU into its DNA; by using anti-BrdU antibody, cells that have incorporated BrdU will be detected.
  VII. Marker molecules such as hormones, or growth factors, that specifically interacts with a cellular component, such as the estrogen receptor with estrogen or the EGF receptor with EGF.

VIII. Introduction of modified (and optionally labeled) nucleotides, amino acids, or vitamins into cells which incorporate these into cellular components that subsequently can be detected, by themselves (e.g. if they are radioactive, or fluoresce) or by their association with a detection molecule.

Binding of marker molecules can be detected using various principles:

Fluidic samples are one embodiment of the present invention where binding and detection of marker molecules can be used to make a diagnostic analysis. One or more defined structures may be measured. Often entities like cells or other particles in a sample are detected by binding marker molecules to surface receptors or intracellular structures of the cell or binding structures exposed on the bead One way to analyse fluidic samples is using flow cytometry. In flow cytometry, the sample is a suspension of entities, which are moved to and centered in the flow cell (interrogation point) by co-flow with sheath fluid, or is directly injected into the instrument.

Liquid cell samples can be analyzed using a flow cytometer, able to detect and count individual cells passing in a stream through a laser beam. For identification of specific cells in a sample, cells are tagged with fluorescent labeled marker molecules by incubating cells with labelled marker molecule and then force the cells with a large volume of liquid through a nozzle creating a stream of individually spaced cells. Each cell passes through a laser beam and during the passage the laser light is scattered and any fluorochrome bound to the cell is excited and thereby fluoresce. Sensitive photomultipliers detect emitted fluorescence and thereby gives information of binding marker molecules to the surface of a given cell. By this method labelled marker molecules can be used to identify specific cell populations in cell samples of any individual. In here the term "labeling" of cells with labelled marker molecules is used interchangeably with the term "staining".

Cell samples capable of being analyzed by binding marker molecules and then analysed using flow cytometry include but is not limited to blood, CSF, lymph, cell lines (e.g. hybridomas, transfected cells), semen, suspension of bacteria, suspension of viral particles, suspension of beads or other particles or supra molecular structures, homogenized tissues or any other fluidic sample from a given unit.

Flow cytometry allows detection of a single entity with a specified set of characteristics, within a population of entities with other sets of characteristics. A major advantage of flowcytometry is that it allows rapid analysis of multiple parameters for each individual entity, simultaneously.

In the most widely used flow cytometry instruments, such as the CyAn ADP™ (Dako), FACS-Calibur, and Canto (BD biosciences), or the EPIC and FC 500 (Beckmann Coulter), the sample is transported to the flow cell by applying pressure to the sample tube and focused in the flow cell using sheath fluid. A sheath fluidic system accelerates each entity into the flow-cell resulting in a focused line of entities. As a result, the entities pass through the interrogation point one at a time.

Alternatively, in micro-fluidics-based, flow-on-a-chip system (a "dry" flow cytometer), the sample is passed through the interrogation point by the means of micrometer-scale tubing's, using capillary forces acting on the liquid in a capillary tube.

In flow cytometry, the most commonly used detection parameters are the scatter and fluorescence parameters, but other means of detection, e.g. color (absorption) and radioactivity may be used as well. The scatter parameters are defined as the quantity of light detected in a forward (FSC) and a sideward or 90° scatter (SSC), or in any other defined angle to the light source and the sample stream. These measurements provide information on characteristics such as relative size, transparency and granularity of the entity. The fluorescence parameters describe the fluorescence that is emitted from the marker molecules associated with the entity. One or more lasers of well defined wavelengths are used to generate scatter light from, and to excite the fluorochromes associated with, each entity. A common combination of lasers is the 405 nm-, 488 nm- and 635 nm-lasers, as used in the CyAn ADP™ flowcytometer. However, the number of lasers may be more or less than that. Furthermore, lasers emitting tuneable and multiple wavelengths of light, conventional light sources or diode-based light sources can also be employed. Additionally, one may measure transmitted (absorbed), or reflected light, rather than fluorescence, from the entities.

When an entity or sample comprises two or more different fluorochromes, a number of principles for the detection of the individual fluorochromes may be employed. These include:

I. The photomultipliers are performing intensity measurements of light of discrete wavelength intervals. The light emitted by the fluorochromes of each entity may be split into a number of different channels, each corresponding to discrete wavelength intervals, as the light goes through an optical system comprised of multiple dichroics and optical filters, prisms, diffraction grating, or photonic crystals. Finally the quantity of light within a defined wavelength interval is measured using a PMT (photomultiplier tube)-based detection system, whereby the fluorescence intensity of each fluorochromes may be determined, thus providing a measure of the abundance of each marker molecule bound to the individual entity.

II. Total wavelength spectra intensity measurement. By performing full wavelength spectra analysis on each entity, and combining this with knowledge of the individual fluorochromes emission spectrum, one may calculate the abundance of each of the fluorochromes bound to an entity.

III. Imaging. The emitted light may also be analyzed using a photo-responsive chip, or a multi-channel photomultiplier. In this way a 2-dimensional image of the entity may be obtained. This can provide further informative data about the entity, such as cell morphology, shape and the location of bound marker molecules on the entity.

IV. Fluorescence decay time measurements. Determination of the decay rate of the emitted light over time may be applied to identify the identity and abundance of each of the labeling molecules (and hence identity and abundance of marker molecules) bound to the individual entity. This requires an oscillating excitation light source, and involves first a pulse excitation of the fluorochromes attached to the entity, and then determination of the emitted light over time as the fluorescence decays. By using an appropriate mathematical model and knowledge about each of the fluorochromes' half-life and emission spectra, the abundance of each fluorochrome is determined of the fluorochrome signals. This approach has several advantages compared to traditional fluorescence intensity measurements, including better separation. As a result, more fluorochromes may be employed simultaneously in an experiment.

V. Enzymatic labeling; this principle may involves an enzyme as the labeling molecule, capable of converting a chemical compound from a solvable molecule to a precipitated product or a reactive product that reacts with molecules in the vicinity of the enzyme, the detectable molecule is associated to the entity, or entering the entity, e.g. a cell. The precipitate may be fluorescing, or carrying a hapten for a second layer of detection.

VI. The flow cytometer can be equipped to separate and collect particular types of cells or particles in sample. This is called cell sorting. For example labeled MHC multimers binding specific T cells in sample in combination with sorting on a flow cytometer can be used to isolate specific T cell populations. Isolated specific T cell populations can then be expanded in vitro and used in autologous cancer therapy Another example of a method measuring binding of labeled marker molecule to structure in fluidic samples is detection of cells or particles in the sample by binding labeled marker molecule followed by identification of labeled structures using microscopy include light microscopy, immunofluorescence microscopy, confocal microscopy or other forms of microscopy. Basically the fluidic sample is stained with labeled marker molecule and non-binding marker molecule removed by washing. Then the sample is spread out on a slide or similar in a thin layer and labelled cells identified using a microscope.

Measurement of binding marker molecule can also be used on solid samples. Example solid sample include but is not limited to solid tissue, blocks of solid tissue, slices of solid tissue, cells or particles embedded in a solid matrix or any other solid or semisolid sample.

Solid samples are typically analysed by placing them in instruments as blocks or in the form of thin slide of material on e.g. a glass plate. Solid material can then be labeled by binding marker molecule and the amount of bound marker molecule measured.

An example of a method measuring binding of labeled marker molecule to solid sample is immunohistochemistry. This assay technique involves immobilization of the tissue slice on a glass slice, carrying the sample through the assay steps to the final analysis.

The sample is "stained" or labeled, using principles as described for markers and labeling elsewhere herein, and in the following:

I. Precipitate labeling; this principle typically involves an enzyme as the labeling molecule, capable of converting a chemical compound from a non-detectable molecule to a precipitated detectable molecule. The precipitated molecule may be colored, or carry a hapten recognized by another detectable molecule in a second layer of detection.

The enzyme is attached to the marker molecule. Binding of the marker molecule to its specific target on an entity, leads to the immobilization of the enzyme on the entity. Then, a substrate is added that is turned into a precipitated product by the enzyme, if the product precipitates or reacts with molecules in the vicinity of the enzyme, the signal will accumulate in the vicinity of the immobilized enzyme. This product, may give a signal by itself, e.g. fluoresce or absorb light at a given wavelength and thus be directly detectable. However, the product may additionally, or only, carry a residue, that is recognized by another detection molecule, which may be enzyme labeled, or labeled by any means as described elsewhere within this invention.

The principle of enzyme-catalyzed precipitation of dyes (or molecules carrying a second target molecule for amplification of the signal) is particularly useful in stationary cytometry.

II. "Reaction" labeling; this principle typically involves an enzyme, such as peroxidase, as the labeling molecule. Additions of the substrates generate a reaction at the site of the detection molecule which emits light of a certain wavelength and spectra, which in turn can be detected by photometry.

III. The most commonly used type of labeling in stationary cytometry is based on chromophores, e.g. which by catalytic reaction with the labeling enzyme is precipitated in the vicinity of the detection molecule. However also radioactivity and fluorescence are used.

The means of detection, typically involve photometric methods, micropy and/or digital scanning of the stained sample. It may be simple light or fluorescence microscopy, for determination of chemiluminescence, morphology, shape, and fluorescence. Also, laser scanning techniques may be employed, where confocal microscopy or standard light microscopy is employed to give a 3- and 2-dimensional picture, respectively, of the sample. A digital image may be acquired, whereby the individual features e.g. light intensity at a given area of the sample can be determined.

Another example of a method measuring binding of labeled marker molecule to solid sample is immunoelectron microscopy. In this technique marker molecules labeled with gold particle are applied to thin section of sample which are then examined in a transmission electron microscope. This method is used to detect intracellular location of structures or particular matter in a sample at high resolution.

Samples can also be attached to solid support and then labeled with marker molecule and bound marker molecule measured. Alternatively marker molecule of interest is bound to structure in sample before immobilization of sample to solid support. This principle is especially useful for binding of marker molecule/molecules of interest in solution to its binding partner in fluidic samples but can also be used on solid samples. Below different principles for measurement of binding marker molecule to sample immobilized to solid support is listed.

Molecule of interest is immobilized on solid support and detected using labeled marker. Alternatively the sample is first labeled and then immobilized on solid support. An example is ELISA based and Radioimmuno based assays. In both assays the immobilized sample is incubated with marker molecule (or the sample is incubated with marker molecule and then immobilized on solid support), then non-binding marker molecule is removed by washing. Bound marker molecule is measured. The marker molecule may be labeled directly or through one or more marker molecule(s) binding the first marker molecule. In ELISA the label is most often an enzyme while in radioimmuno assays the label is a radioactive molecule. Other labeling molecules may also be used like fluorochromes, chromophores or other molecules that can be measured. Useful labeling molecules are described elsewhere herein.

Structure of interest in sample is catched by its partner; the specific marker molecule that is immobilized on solid support. Bound sample or part of sample is then detected using a labeled marker specific for the same or a different structure in the bound sample.

Different marker molecules to two or more structures of interest in same sample are immobilized on solid support in a defined pattern. Structures of interest in sample are bound to the defined areas of the support and are detected by a labeled marker. Each individual structure binds to different partners immobilized in different positions on the solid support. Thereby the sample may be phenotyped.

Two or more solid supports (e.g. beads) with different characteristics (e.g. size, fluorescence, fluorescence intensities, labels), where each kind of bead has a specific marker molecule immobilized. Structures of interest in sample are bound to specific populations of beads, where each bead population is defined by the marker molecule they have immobilized. The different populations of beads are detected through their special characteristics.

The sample analysed by the above described methods may first be subjected to another analysis e.g. separation according to size. An example is Blotting techniques were molecular structures of a sample are first separated according to size and then transferred to a solid support followed by detection with labeled marker molecule. Depending on the structure to be analysed different forms of blotting exist, e.g. Western blotting for analysis of proteins, Northern blotting for analysis of RNA and Southern blotting for analysis of DNA.

Binding may also be measured without using labeled marker molecules for detection. A sample may be captured by immobilized binding molecule, then eluted and quantified. Usually the starting point is a sample in solution, such as a cell lysate, growth medium or blood. The molecule or structure of interest will have a well known and defined property which can be exploited during the binding process. The process itself can be thought of as an entrapment, with the target molecule becoming trapped on a solid or stationary phase or medium. The other molecules in solution will not become trapped as they do not possess this property. The solid medium can then be removed from the mixture, washed and the target molecule released from the entrapment in a process known as elution.

Binding to the solid phase may be achieved by column chromatography, whereby the solid medium is packed onto a chromatography column, the initial mixture run through the column to allow binding, a wash buffer run through the column and the elution buffer subsequently applied to the column and collected. These steps are usually done at ambient pressure (as opposed to HPLC or FPLC).

Alternatively binding may be achieved using a batch treatment, by adding the initial mixture to the solid phase in a vessel, mixing, separating the solid phase (by centrifugation for example), removing the liquid phase, washing, re-centrifuging, adding the elution buffer, re-centrifuging and removing the eluate.

Sometimes a hybrid method is employed, the binding is done by the batch method, then the solid phase with the target molecule bound is packed onto a column and washing and elution are done on the column.

A third method, expanded bed adsorption, which combines the advantages of the two methods mentioned above, has also been developed. The solid phase particles are placed in a column where liquid phase is pumped in from the bottom and exits at the top. The gravity of the particles ensures that the solid phase does not exit the column with the liquid phase.

Following elution the purified or enriched molecule or structure can be quantitated, enriched further or used in new analytical processes or treatment processes.

Measurement of alteration of physical state of sample or structure in sample upon binding molecule. For example addition of binding molecule to a fluidic sample may induce cross-linking of structures, clumping and/or aggregation of sample. E.g. antibodies or other binding molecules can bind large particles and make the particle to clump or agglutinate. The antibody or other molecule binds multiple particles and joins them, creating a large complex.

Similar addition of binding molecule to solid sample may make the solid sample becoming semi solid, fluidic or in another way change texture.

Other physical characteristics may be changed as a consequence of addition of binding molecule to sample and if measurable they can be used for analysis of sample.

An example of a specific assay measuring alteration in the physical state of a sample upon addition of binding molecule is turbidimetry. This is a method for determining the concentration of a substance in a solution by the degree of cloudiness or turbidity it causes or by the degree of clarification it induces in a turbid solution.

Indirect measurement of binding is measurement of the result of the interaction between binding molecule and structure in sample in contrast to direct measurement of the binding molecule bound in sample. The result of interaction between binding molecule and structure in sample can be measured in several ways indirect ways.

Measurement of produced substance. Upon binding of binding molecule to structure in sample the sample may release and/or produce a substance that can be measured. Depending on the nature of the sample different principles exists The produced substance may be measured in solution either directly or by detection with a labeled marker molecule. The produced substance may be easily accessible for detection or alternatively need to be extracted from sample before measurement is possible.

One example of measurement of produced substance in solution is Polymerase Chain reaction (PCR). In this method fragments of DNA in solution are amplified by binding DNA primers (binding molecules) to defined areas of the DNA in sample. The amount of amplified DNA is then measured.

Another example is measurement of produced soluble substance inside cells using intracellular flow cytometry. This can be done using block of secretion of soluble substance (e.g. by monensin), permeabilization of cell (by e.g. saponine) followed by immunofluorescent staining. The method involves the following steps: 1) An reagent able to block extracellular secretion of cytokine is added, e.g. monensin that interrupt intracellular transport processes leading to accumulation of produced soluble factor, e.g. cytokine in the Golgi complex. 2) Fixation of cell membrane using mild fixator followed by permeabilization of cell membrane by. e.g. saponine. 3) Addition of labelled marker molecule specific for the produced soluble substance to be determined. 5) Measurement of labelled cells using a flow cytometer. Optionally this analysis can be combined with labeling with marker molecules specific for surface exposed structures. If so these marker molecules are added before step 2.

An alternative to this procedure is to trap secreted soluble factors on the surface of the secreting cells followed by detection with specific marker molecules as described by Manz, R. et al., Proc. Natl. Acad. Sci. USA 92:1921 (1995).

The produced substance may be immobilized to solid support followed by detection using labeled marker. Principles for immobilization and detection are as described elsewhere herein for immobilization of samples and direct detection An example of indirect detection of produced substance immobilized on solid support is measurement of substances secreted from stimulated cells by capture of the secreted substance on solid support followed by detection with labeled marker molecule. Secreted soluble substance in the supernatant is immobilized on solid support either directly or through a linker molecule. The cells may be stimulated by addition of other cells to the sample, addition of antigens (peptides/proteins) to the sample, addition of stimulatory proteins or other molecules or stimulated by other means. The amount of secreted substance can be measured in different ways:

Soluble substances secreted from individual cells can be detected by capturing of the secreted soluble substances locally by marker molecules, e.g. antibody specific for the soluble substance. Soluble substance recognizing marker molecules are then immobilised on a solid support together with cells and soluble substances secreted by individual cells are thereby captured in the proximity of each cell. Bound soluble substance can be measured using labelled marker molecule specific for the captured soluble substance. The number of cells that has given rise to labelled spots on solid support can then be enumerated and these spots indicate the presence of specific cells that have been stimulated with particular stimulator.

Soluble substances secreted from a population of cells are detected by capture and detection of soluble substance secreted from the entire population of specific cells. In this case soluble substance do not have to be captured locally close to each cell but the secreted soluble substances my be captured and detected in the same well as where the cells are or transferred to another solid support with marker molecules for capture and detection e.g. beads or wells of ELISA plate.

The produced substance is measured directly in solid sample using principles as described for solid samples elsewhere herein.

Measurement of effector function in sample. Binding of binding molecule may also result in changes in effector function of sample. Effector function is inhere any function of sample or produced in sample. This type of measurement is only relevant for samples comprising living cells, living organisms or other living material. Examples of effector function of/in a sample include but are not limited to cytolytic activity, catalytic activity, ability to stimulate other cells or samples or ability to induce apoptosis in sample itself or in other samples.

An example is measurement of activation of T cells in a sample by measurement of cytolytic activity of the T cell in a cytolytic assay, e.g. a chromium release assay.

Measurement of growth. Binding of binding molecule may induce or inhibit growth in a sample. This type of measurement is only relevant for samples comprising living cells, living organisms or other living material. In cell samples growth can be measured as proliferation of cells in the sample.

Examples of methods useful for measuring proliferation include but are not limited to:

Detection of mRNA. Proliferation of T cells can be detected by measurement of mRNA inside cell. Cell division and proliferation requires production of new protein in each cell which as an initial step requires production of mRNA encoding the proteins to be synthesized.

Detection of incorporation of thymidine. The proliferative capacity of T cells in response to stimulation by MHC multimer can be determined by a radioactive assay based on incorporation of [3H]thymidine ([3H]TdR) into newly generated DNA followed by measurement of radioactive signal.

Detection of incorporation of BrdU. Cell proliferation can also be detected by of incorporation of bromo-2'-deoxyuridine (BrdU) followed by measurement of incorporated BrdU using a labeled anti-BrdU antibody in an ELISA based analysis.

Viability of cells may be measured by measurement ATP in a cell culture.

Separation According to Size, Structure or Other Physical Characteristics

Properties of a sample can also be determined by measuring size and/or structure of sample. Below different methods based on different principles are listed.

Gel Electrophoresis

Gel electrophoresis is a technique used for the separation of deoxyribonucleic acid, ribonucleic acid, or protein molecules using an electric current applied to a gel matrix. The term "gel" in this instance refers to the matrix used to contain and separate the target molecules. In most cases the gel is a crosslinked polymer whose composition and porosity is chosen based on the specific weight and composition of the target to be analyzed. When separating proteins or small nucleic acids (DNA, RNA, or oligonucleotides) the gel is usually composed of different concentrations of acrylamide and a cross-linker, producing different sized mesh networks of polyacrylamide. When separating larger nucleic acids (greater than a few hundred bases), the preferred matrix is purified agarose. In both cases, the gel forms a solid, yet porous matrix. Acrylamide, in contrast to polyacrylamide, is a neurotoxin and must be handled using appropriate safety precautions to avoid poisoning.

"Electrophoresis" refers to the electromotive force (EMF) that is used to move the molecules through the gel matrix. By placing the molecules in wells in the gel and applying an electric current, the molecules will move through the matrix at different rates, usually determined by mass, toward the positive anode if negatively charged or toward the negative cathode if positively charged.

After the electrophoresis is complete, the molecules in the gel can be stained to make them visible. Ethidium bromide, silver, or coomassie blue dye may be used for this process. Other methods may also be used to visualize the separation of the mixture's components on the gel. If the analyte molecules fluoresce under ultraviolet light, a photograph can be taken of the gel under ultraviolet lighting conditions. If the molecules to be separated contain radioactivity added for visibility, an autoradiogram can be recorded of the gel.

If several mixtures have initially been injected next to each other, they will run parallel in individual lanes. Depending on the number of different molecules, each lane shows separation of the components from the original mixture as one or more distinct bands, one band per component. Incomplete separation of the components can lead to overlapping bands, or to indistinguishable smears representing multiple unresolved components.

Bands in different lanes that end up at the same distance from the top contain molecules that passed through the gel with the same speed, which usually means they are approximately the same size. There are molecular weight size markers available that contain a mixture of molecules of known sizes. If such a marker was run on one lane in the gel parallel to the unknown samples, the bands observed can be compared to those of the unknown in order to determine their size. The distance a band travels is approximately inversely proportional to the logarithm of the size of the molecule.

Gel electrophoresis is usually performed for analytical purposes, but may be used as a preparative technique prior to use of other methods such as mass spectrometry, RFLP, PCR, cloning, DNA sequencing, or Southern blotting for further characterization.

Depending on the type of material to be separated different techniques may be used some of these are listed below:

Polypeptide length can be determined by SDS PAGE. The solution of proteins to be analyzed is first mixed with SDS, an anionic detergent which denatures secondary and non-disulfide-linked tertiary structures, and applies a negative charge to each protein in proportion to its mass. Without SDS, different proteins with similar molecular weights would migrate differently due to differences in mass charge ratio, as each protein has an isoelectric point and molecular weight particular to its primary structure. This is known as Native PAGE. Adding SDS solves this problem, as it binds to and unfolds the protein, giving a near uniform negative charge along the length of the polypeptide.

SDS binds in a ratio of approximately 1.4 g SDS per 1.0 g protein (although binding ratios can vary from 1.1-2.2 g SDS/g protein), giving an approximately uniform mass:charge ratio for most proteins, so that the distance of migration through the gel can be assumed to be directly related to only the size of the protein. A tracking dye may be added to the protein solution to allow the experimenter to track the progress of the protein solution through the gel during the electrophoretic run.

Native Gel Electrophoresis is a technique used mainly in protein electrophoresis where the proteins are not denatured and therefore separated based on their charge-to-mass ratio. The two main types of native gels used in protein electrophoresis are polyacrylamide gels and agarose gels.

Polyacrylamide gel electrophoresis (PAGE) is used for separating proteins ranging in size from 5 to 2,000 kDa due to the uniform pore size provided by the polyacrylamide gel. Pore size is controlled by controlling the concentrations of acrylamide and bis-acrylamide powder used in creating a gel. Care must be used when creating this type of gel, as acrylamide is a potent neurotoxin in its liquid and powdered form. The other type of gel used is agarose gel. Agarose gels can also be used to separate native protein. They do not have a uniform pore size, but are optimal for electrophoresis of proteins that are larger than 200 kDa.

Unlike SDS-PAGE type electrophoreses, Native gel electrophoresis does not use a charged denaturing agent. The molecules being separated (usually proteins) therefore differ in Molecular mass and intrinsic charge and experience different electrophoretic forces dependent on the ration of the two. Since the proteins remain in the native state they may be visualised not only by general protein staining reagents but also by specific enzyme-linked staining.

QPNC-PAGE, or quantitative preparative native continuous polyacrylamide gel electrophoresis, is a high-resolution technique applied in biochemistry and bioinorganic chemistry to separate proteins by isoelectric point. This variant of gel electrophoresis is used by biologists to isolate active or native metalloproteins in biological samples and to resolve properly and improperly folded metal cofactor-containing proteins in complex protein mixtures Determination of size of DNA or RNA fragments, e.g. agarose gel electrophoresis Separation of proteins according to mass and isoelectric point, e.g. 2D gel electrophoresis. Two-dimensional gel electrophoresis, abbreviated as 2-DE or 2-D electrophoresis, is a form of gel electrophoresis where mixtures of proteins are separated by two properties in two dimensions on 2D gels.

2-D electrophoresis begins with 1-D electrophoresis but then separates the molecules by a second property in a direction 90 degree from the first. In 1-D Celectrophoresis, proteins (or other molecules) are separated in one dimension, so that all the proteins/molecules will lie along a lane but be separated from each other by a property (e.g. isoelectric point). The result is that the molecules are spread out across a 2-D gel. Because it is unlikely that two molecules will be similar in two distinct properties, molecules are more effectively separated in 2-D electrophoresis than in 1-D electrophoresis.

The two dimensions that proteins are separated into using this technique can be isoelectric point, protein complex mass in the native state, and protein mass.

Chromatography

Chromatography is another method to separate structures according to size, structure or other physical characteristics. In principle a sample dissolved in a "mobile phase" is passed through a stationary phase, which separates the analyte to be measured from other molecules in the mixture and allows it to be isolated.

Below different types of chromatography is listed
    Column chromatography
        Ion exchange chromatography
        Size exclusion chromatography
        Liquid chromatography (LC, HPLC)
        Gas chromatography
    Planar chromatography
        Paper chromatography
        Thin layer chromatography Separation Based on Chemical Properties Samples can also be analysed be analyzing their chemical composition. The chemical composition of the whole sample med be determined, alternatively the chemical composition of fragments or individual structures of the sample is identified. Often this type of analysis are preceded by one or more other diagnostic or analytical methods e.g. separation according to size.

An example of this type of analysis is mass spectrometry. Mass spectrometry is an analytical technique that identifies the chemical composition of a compound or sample on the basis of the mass-to-charge ratio of charged particles. The method employs chemical fragmentation of a sample into charged particles (ions) and measurements of two properties, charge and mass, of the resulting particles, the ratio of which is deduced by passing the particles through electric and magnetic fields in a mass spectrometer. The design of a mass spectrometer has three essential modules: an ion source, which transforms the molecules in a sample into ionized fragments; a mass analyzer, which sorts the ions by their masses by applying electric and magnetic fields; and a detector, which measures the value of some indicator quantity and thus provides data for calculating the abundances each ion fragment present. The technique has both qualitative and quantitative uses, such as identifying unknown compounds, determining the isotopic composition of elements in a compound, determining the structure of a compound by observing its fragmentation, quantifying the amount of a compound in a sample using carefully designed methods (e.g., by comparison with known quantities of heavy isotopes), studying the fundamentals of gas phase ion chemistry (the chemistry of ions and neutrals in vacuum), and determining other physical, chemical, or biological properties of compounds.

Measurement of Catalysis

Catalysis is the process in which the rate of a chemical reaction is increased by means of a chemical substance known as a catalyst. Unlike other reagents that participate in the chemical reaction, a catalyst is not consumed. Thus, the catalyst may participate in multiple chemical transformations, although in practice catalysts are sometimes consumed in secondary processes. Examples of catalysis include but are not limited to:

Measurement of enzymatic activity
  Measurement of induction of enzymatic activity
  Measurement of inhibition of enzymatic activity
Measurement of substrate for enzyme in a sample Measurement of Growth Growth is another parameter that can be measured in a sample. It can be natural growth in sample, the samples impact of growth on another sample or analysis system and/or the growth in sample after the sample has been added stimulus, inhibitor or other substance influencing growth.

Examples of measurement of growth in sample include but are not limited to
Measurement of proliferation
Measurement of viability
Measurement of volume
Measurement of density The above described chemical assays may be combined with one or more other chemical assays in order to make the final diagnosis of the unit. The chemical assays may be applied to the sample of the unit or to different samples from the same unit.

Labelling Molecules

Labeling molecules are useful in many chemical assays to label binding molecules. Different principles of labeling and detection exist, based on the specific property of the labeling molecule, including molecules that absorb, excite, or modify radiation, such as emission of radioactive radiation (radionuclide, isotopes), absorption of light (e.g. dyes, chromophores), emission of light after excitation (fluorescence from fluorochromes), nuclear magnetic resonance form paramagnetic molecules (NMR), reflection of light (scatter from e.g. such as gold-, plastic- or glass-beads/particles of various sizes and or shapes).

Furthermore, labelling molecules may have an enzymatic activity, by which it catalyze a reaction between chemicals in the near environment of the labeling molecules, producing a signal which include production of light (chemiluminescence) or precipitation of chromophors, dyes, or a precipitate that can be detected by an additional layer of detection molecules. The enzymatic product may deposit at the location of the enzyme, in cell based assays, react with the membrane of the cell, or diffuse into the cell to which the enzymatic marker is attached, in this way labeling the cell.

A single labelling molecule on a marker does not always generate sufficient signal intensity. The signal intensity may be improved by assembling single label molecules into large multi-labelling compounds, containing two or more label molecule residues. Generation of multi-label compounds may be achieved by covalent or non covalent, association of labelling molecules with a major structural molecule. Such structures may be synthetic or natural polymers e.g. dextrans, DNA, PNA, a protein such as streptavidin. The label molecules in a multi-labelling compound may all be of the same type or may be a mix of different labelling molecules. Table 1 (Below): Example Labeling Substances and Example Detection Principle:

The table lists labelling substances that may be used as labeling molecules in any of the described assays. Also is described how the label "gives the signal", and the physical appearance of the signal, as well as the detection principle employed, may any of these labels be used in the herein described methods:

| Labeling substance | Effect | Assay-principle |
| --- | --- | --- |
| Fluorochromes e.g. Table 3a and b | emission of light having a specific spectra | □Photometry, Microscopy, spectroscopy PMT, photographic film, CCD's (Color-Capture Device or Charge-coupled device). |
| Radionuclide | irradiation, α, β or γ-rays | Scintillation counting, GM-tube, photographic film, excitation of phosphor-imager screen |
| Enzyme; HRP, horse raddish peroxidase, peroxidases in general | catalysis of $H_2O_2$ reduction using luminol as Oxygen acceptor, resulting in oxidized luminal + light catalysis of $H_2O_2$ reduction using a soluble dye, or molecule containing a hapten, such as a biotin residue as Oxygen acceptor, resulting in precipitation. | □Photometry, Microscopy, spectroscopy PMT, photographic film, CCD's (Color-Capture Device or Charge-coupled device), Secondary label linked antibody |

-continued

| Labeling substance | Effect | Assay-principle |
|---|---|---|
| | The habten can be recognized by a detection molecule. | |
| Particles; gold, polystyrene beads, pollen and other particles | Change of scatter, reflection and transparency of the associated entity | Microscopy, cytometry, electron microscopy PMT's, light detecting devices, flowcytometry scatter |
| Alkaline Phosphatase | Catalyze a chemical conversion of a non-detectable to a precipitated detectable molecule, such as a dye or a hapten | □Photometry, Microscopy, spectroscopy Secondary label linked antibody |
| Ionophores or chelating chemical compounds binding to specific ions, e.g. $Ca^{2+}$ | Change in absorption and emission spectrums when binding. Change in intensity | □Photometry, Cytometry, spectroscopy |
| Lanthanides | Fluorescence Phosphorescence Paramagnetic | □photometry, cytometry, spectroscopy NMR (Nuclear magnetic resonance) |
| DNA fluorescing stains | Propidium iodide Hoechst stain DAPI AMC DraQ5 ™ Acridine orange 7-AAD | □Photometry, cytometry, spectroscopy |

□Photometry; being any means that can be applied to detect the intensity, analyze the wavelength spectra, and or measure the accumulation of light coming form a source emitting light of one or multiple wavelength or spectra.

TABLE 2a

Example fluorochromes.
Example fluorochromes which may be used to label any of the marker molecules described in this invention, and the maximum excitation and the emission wavelengths for these fluorochromes.

| Fluorofor/Fluorochrome | Excitation nm | Emission nm |
|---|---|---|
| 2-(4'-maleimidylanilino)naphthalene-6-sulfonic acid, sodium salt | 322 | 417 |
| 5-((((2-iodoacetyl)amino)ethyl)amino)naphthalene-1-sulfonic acid | 336 | 490 |
| Pyrene-1-butanoic acid | 340 | 376 |
| AlexaFluor 350 (7-amino-6-sulfonic acid-4-methyl coumarin-3-acetic acid | 346 | 442 |
| AMCA (7-amino-4-methyl coumarin-3-acetic acid | 353 | 442 |
| 7-hydroxy-4-methyl coumarin-3-acetic acid | 360 | 455 |
| Marina Blue (6,8-difluoro-7-hydroxy-4-methyl coumarin-3-acetic acid | 362 | 459 |
| 7-dimethylamino-coumarin-4-acetic acid | 370 | 459 |
| Fluorescamin-N-butyl amine adduct | 380 | 464 |
| 7-hydroxy-coumarine-3-carboxylic acid | 386 | 448 |
| CascadeBlue (pyrene-trisulphonic acid acetyl azide | 396 | 410 |
| Cascade Yellow | 409 | 558 |
| Pacific Blue (6,8 difluoro-7-hydroxy coumarin-3-carboxylic acid | 416 | 451 |
| 7-diethylamino-coumarin-3-carboxylic acid | 420 | 468 |
| N-(((4-azidobenzoyl)amino)ethyl)-4-amino-3,6-disulfo-1,8-naphthalimide, dipotassium salt | 426 | 534 |
| Alexa Fluor 430 | 434 | 539 |
| 3-perylenedodecanoic acid | 440 | 448 |
| 8-hydroxypyrene-1,3,6-trisulfonic acid, trisodium salt | 454 | 511 |
| 12-(N-(7-nitrobenz-2-oxa-1,3-diazol-4-yl)amino)dodecanoic acid | 467 | 536 |
| N,N'-dimethyl-N-(iodoacetyl)-N'-(7-nitrobenz-2-oxa-1,3-diazol-4-yl)ethylenediamine | 478 | 541 |

TABLE 2a-continued

Example fluorochromes.
Example fluorochromes which may be used to label any of the marker molecules described in this invention, and the maximum excitation and the emission wavelengths for these fluorochromes.

| Fluorofor/Fluorochrome | Excitation nm | Emission nm |
|---|---|---|
| Oregon Green 488 (difluoro carboxy fluorescein) | 488 | 518 |
| 5-iodoacetamidofluorescein | 492 | 515 |
| propidium iodide-DNA adduct | 493 | 636 |
| Carboxy fluorescein | 495 | 519 |

TABLE 2b

Example preferable fluorochrome families.
Many fluorochrome families have been generated by alterations of commonly known fluorochromes, and some new principles for fluorescence labeling has been generated by dedicated companies as well, e.g. Qdot ™'s. This table shows examples off preferable fluorochrome families that can be obtained and used directly in the methods described for detection in this invention.

| Fluorochrome family | Example fluorochrome |
|---|---|
| AlexaFluor ® (AF) | AF ®350, AF405, AF430, AF488, AF500, AF514, AF532, AF546, AF555, AF568, AF594, AF610, AF633, AF635, AF647, AF680, AF700, AF710, AF750, AF800 |
| Quantum Dot (Qdot ®) based dyes | Qdot ®525, Qdot ®565, Qdot ®585, Qdot ®605, Qdot ®655, Qdot ®705, Qdot ®800 |
| DyLight ™ Dyes (DL) | DL549, DL649, DL680, DL800 |
| Small fluorescing dyes | FITC, Pacific Blue ™, Pacific Orange ™, Cascade Yellow ™, Marina blue ™, DSred, DSred-2, 7-AAD, TO-Pro-3, |

TABLE 2b-continued

Example preferable fluorochrome families.
Many fluorochrome families have been generated by alterations of commonly known fluorochromes, and some new principles for fluorescence labeling has been generated by dedicated companies as well, e.g. Qdot ™'s. This table shows examples off preferable fluorochrome families that can be obtained and used directly in the methods described for detection in this invention.

| Fluorochrome family | Example fluorochrome |
| --- | --- |
| Cy-Dyes | Cy2, Cy3, Cy3.5, Cy5, Cy5.5, Cy7 |
| Phycobili Proteins: | R-Phycoerythrin (RPE), PerCP, Allophycocyanin (APC), B-Phycoerythrin, C-Phycocyanin |
| Fluorescent Proteins | (E)GFP and GFP ((enhanced) green fluorescent protein) derived mutant proteins; BFP, CFP, YFP, DsRed, T1, Dimer2, mRFP1, MBanana, mOrange, dTomato, tdTomato, mTangerine, mStrawberry, mCherry |
| Tandem dyes with RPE | RPE-Cy5, RPE-Cy5.5, RPE-Cy7, RPE-AlexaFluor ® tandem conjugates; RPE-Alexa610, RPE-TxRed |
| Tandem dyes with APC | APC-Alexa600, APC-Alexa610, APC-Alexa750, APC-Cy5, APC-Cy5.5 |
| Calcium dyes | Indo-1-$Ca^{2+}$ Indo-2-$Ca^{2+}$ |

Different detection principles for detection of labels exist. Examples listed in Table 1, may be applied to flow cytometry, stationary cytometry, and batch-based analysis. Most batch-based approaches can use any of the labelling substances described, depending on the purpose of the assay. Flow cytometry primarily employs fluorescence, whereas stationary cytometry primarily employs light absorption, e.g. dyes or chromophor-deposit formed by enzymatic activity. Therefore, in the following section, principles involving fluorescence detection will be exemplified for flow cytometry, and principles involving chromophore detection will be exemplified in the context of stationary cytometry. However, the labelling molecules may in principle be applied to any of the analyses described in this invention.

The labelling molecules may be associated, linked or covalent bound to the marker molecule and added to the sample. Alternatively, the marker molecule are first allowed to associate with the specific target, then the label molecule is added, binding specifically to the marker molecule. The latter involves that the marker and the label is modified in a way that will allow a specific association between the marker and the label. This may be archived by any means that mediates a specific interaction between the marker and the labelling molecule. Means as described for the association between the maker molecule and the target, may be applied to mediated specific binding pairs of molecules, such as Antigen/Antibodies, streptavidine/biotin, nucleotides base pairing (DNA:DNA, RNA:RNA, RNA:DNA), or PNA with PNA, PNA with DNA or RNA, where the bead is attached to one of the partner molecules (e.g. the antigen) and the label is attached to the other partner molecule (e.g. the antibody).

Preferable Fluorescent Labeling in Flow Cytometry

In flowcytometry the typical label is detected by its fluorescence, examples are given in Table 2. In most cases a positive detection is based on the presents of light from a single fluorochrome, but in other techniques the signal is detected by a shift in wavelength of emitted light; as in FRET based techniques, where the exited fluorochrome transfer its energy to an adjacent bound fluorochrome (and marker) that emits light, or when using $Ca^{2+}$ chelating fluorescent probes, which change the emission (and absorption) spectra when binding to calcium.

Preferable labelling molecules employed in flow cytometry are described in the following and in Table 2a and b.

Simple fluorescing labels:
Fluor dyes, Pacific Blue™, Pacific Orange™, Cascade Yellow™,
AlexaFluor® (AF);
AF405, AF488, AF500, AF514, AF532, AF546, AF555, AF568, AF594, AF610, AF633, AF635, AF647, AF680, AF700, AF710, AF750, AF800
Quantum Dot based dyes, QDot® Nanocrystals (Invitrogen, MolecularProbs)
Qdot®525, Qdot®565, Qdot®585, Qdot®605, Qdot®655, Qdot®705, Qdot®800
DyLight™ Dyes (Pierce) (DL);
DL549, DL649, DL680, DL800
Fluorescein (Flu) or any derivate of that, ex. FITC (fluorescein isothiocyanate)
Cy-Dyes
Cy2, Cy3, Cy3.5, Cy5, Cy5.5, Cy7
Fluorescent Proteins;
RPE (R-phycoerythrin), PerCp, APC (Allophycocyanin); other of phycobillin containing proteins, e.g. phycobiliprotein
Green fluorescent proteins (GFP);
GFP and GFP derivated mutant proteins; BFP, CFP, YFP, DsRed, T1, Dimer2, mRFP1, MBanana, mOrange, dTomato, tdTomato, mTangerine, mStrawberry, mCherry
Tandem dyes:
RPE-Cy5, RPE-Cy5.5, RPE-Cy7, RPE-AlexaFluor® tandem conjugates; RPE-Alexa610, RPE-TxRed
APC-Aleca600, APC-Alexa610, APC-Alexa750, APC-Cy5, APC-Cy5.5
Multi fluorochrome assemblies
Multiple fluorochromes attached to a polymer molecule, such as a peptide/protein, Dex, or poly-sacceride.
Any combination of the fluorescent dyes involving in generation of FRET (Fluorescence resonance energy transfer) based techniques.
Multiple fluorochromes associated or coupled to a polymeric molecule, or consisting of polymeric residues.
Ionophors; ion chelating fluorescent probes
Probs that change wavelength when binding a specific ion, such as Calcium
Probs that change intensity when binding to a specific ion, such as Calcium
Combinations of fluorochromes on the same marker. The marker is not identified by a single fluorochrome but by a code of identification being a specific combination of fluorochromes, as well as inter related ratio's of intensities.
Example: Antibody Ab1 and Ab2, is conjugated to both FL1 (ex. FITC), and Fl2 (ex. PB), but Ab1 have 1 FL1 to 1 FL2, whereas Ab2 have 2 Fl1 to 1 Fl2. Each antibody may then be identified individually by the relative intensity of the two, or more fluorochromes. Any such combinations of n fluorochromes with m different ratios may be generated.

Choosing Fluorochrome in Multicolor Staining Protocols

Although the choice of fluorochrome or fluorochrome combinations on a specific marker molecules, in particular antibodies, or MHC'multimers are more or less unlimited, a few rules may be employed to give better resolution and clearer identification of the specific cell population that are assayed.

Fluorochromes used on specific marker molecules detecting targets that are co-located on the same cell or entity are selected to have a minimum of spectral overlap.

The brightest fluorochrome is used for detection of the weakest expressed molecules on the cell The binding molecules and detection molecules are optimized for the ability to give the best possible separation between the positive and negative population.

The detection molecules are optimized for having the least binding to cell populations that are not specific interacting with the marker molecule, thus, optimized for having as little unspecific binding as possible.

Preferable Labelling Molecules Employed in Stationary Cytometry and IHC

Enzymatic labelling, as exemplified in Table 3:

Horse radish peroxidase; reduces peroxides ($H_2O_2$), in the presence of an oxygen acceptor the signal are generated its oxidation.

Precipitating dyes; Dyes that when reduced is soluble, and precipitate when oxidized, generating a colored deposit at the site of the reaction.

Precipitating agent, carrying a chemical residue, a hapten, this is exposed from the precipitate, and may be used for a second layer binding of detector molecules, resulting in amplification of the primary signal.

Luminol reaction, generating a light signal at the site of reaction.

Other enzymes, such as Alkaline Phosphatase (AP), capable of converting a chemical compound from a non detectable molecule to a precipitated detectable molecule. The detectable molecule may be colored, or carrying a hapten which may be recognizable by an detections molecule, as described above.

Fluorescent labels, as exemplified in Table 2a and b; however, labels described for Flow cytometry may also be used in stationary cytometry, such as in fluorescent microscopy.

TABLE 3

Example preferable labels for stationary cytometry
Examples of labeling principles preferably used and developed for use in stationary cytometry, but may be used in other detection principles as well, such as flcytometry. The grouping describes the labels, name, what the effector molecule is, how it manifest itself in the assay, any secondary binding pair if used in a second layer of detection.

| Mane of label | Effector molecule | Manifestation of the effector molecule | Second layer of detection: |
|---|---|---|---|
| Label | Enzyme substrate, Oxygen acceptor Chromogen¤/ precipitating agent | Precipitate with or without a residue, hapten* for amplification of the signal | Binding partner to hapten |
| HRP | diaminobenzidine (DAB) | Colored precipitate | — |
| HRP | 3-amino-9-ethyl-carbazole (AEC+) | Colored precipitate | — |
| AP | Fast red dye | Red precipitate | — |
| HRP | biotinyl tyramide | Exposed Biotin residue | Streptavidin, avidine |
| HRP | fluorescein tyramide | Exposed Fluorescein residue | Anti-Fluorecein Antibody |

TABLE 3-continued

Example preferable labels for stationary cytometry
Examples of labeling principles preferably used and developed for use in stationary cytometry, but may be used in other detection principles as well, such as flcytometry. The grouping describes the labels, name, what the effector molecule is, how it manifest itself in the assay, any secondary binding pair if used in a second layer of detection.

| "Enzyme" | Substrate that when reacted precipitate | Primary label; being a dye, chemiluminescence's, or exposure of a hapten | Secondary label in case the primary label is a hapten |
|---|---|---|---|

*Hapten; being any residue/molecule that can be recognized as a binding site for another molecule which may be labled for amplification of the primary signal.
¤A chromogen is a molecule that will become a dye molecule/chromophor when e.g. oxidized by the presence of the label, enzyme.

Immune Monitoring of T-cell Responses

One group of analysis of special interest for the present invention is immune monitoring of T-cell responses. Monitoring of cellular immune response like T-cell responses is useful in relation to diagnosing and monitoring a range of disease, in principle any disease were changes in the immune system has an impact on the disease development, progression and/or cure of the disease.

Immune monitoring may also be used in relation to treatment and development of treatment processes including vaccination, transplantation and some treatments with drugs.

In one embodiment of the present invention immune monitoring of T-cell responses are used in relation to development and use of cancer vaccines. Cancer vaccines stimulate cellular immune responses, involving the stimulation of cancer-antigen-specific T-cells. Typically, cancer vaccines comprise peptides derived from cancer-proteins, or viruses or other DNA vectors encoding these peptides but may also be comprised of other substances as described elsewhere herein. The peptides end up in MHC-peptide complexes displayed on e.g. dendritic cells, which in turn activate the corresponding antigen-specific T-cells. The activated T-cells proliferate and together with other components of the immune system start destroying the cancer cells. By monitoring the elicited T-cell response the strength of the generated immune response can be determined and thereby the biological effect of the vaccine.

This can be used to:

Determine whether the vaccine is effective

Fine-tuning a cancer vaccine treatment by determining whether the dose of the administered vaccine, the number of administrations of vaccine doses or the intervals between administrations of doses should be changed. For example if a low specific T-cell response is measured following a few vaccinations the dose of vaccine could be increased, the interval between administration of doses shortened.

Determine if the content of a vaccine should be changed. A low or no T-cell response could be used as a decision-maker that the dose should be increased or the content of the vaccine changed.

Determine whether a vaccination protocol should continue. A vaccination protocol herein refers to a series of repeated vaccinations. Often many vaccinations are needed to generate an immune response strong enough to combat the cancer. However, if the patient have no or limited biological effect, of the first or the first few vaccinations there may be no need to continue with the vaccination protocol. If in contrast the vaccine during the first couple of vaccinations produce a medium or strong T-cell response the vaccination protocol should be continued.

Determine the duration of a given vaccination protocol. It can be difficult to determine how many vaccinations a patient need in order to build up a maximal immune response. Immune monitoring can be used to determine when the repeated vaccinations result in a steady state level of antigen specific T-cells. When steady state is achieved the vaccination protocol can be terminated. After treatment is ended immune monitoring of T-cell responses can be continued at regular intervals to ensure that the immunocompetency of the individual remains at the wanted level. If the immunocompetency of the individual decreases after endend treatment, i.e. the level of antigen-specific T-cells decrease under a certain level, the vaccination protocol can be resumed.

Selection of responsive patients and de-selection of non-responsive patients. Typically only a small fraction of vaccinated individuals respond to a given cancer vaccine. Patients with an existing (although possible weak) cancer-specific immune response may benefit more from a given cancer vaccine than patients with no cancer-specific immune response. Therefore for treatment with some cancer vaccines an initial immune monitoring of cancer-specific T-cell responses can be used to select only those patients that will benefit from the treatment and to de-select those patients that will have no benefit from treatment.

For treatment with other cancer vaccines a selection or de-selection of patients are not made prior to the first vaccination but following the first few vaccinations that be 1-4 vaccinations such as 1-2, for example 2-3, such as 3-4 or any combination thereof. Immune monitoring of specific T-cell responses can then be made following each vaccination or after the first few vaccinations. Patients responding to the cancer vaccine by an increased cancer-specific T-cell response are then selected for further treatment while patients with no response or very limited response are de-selected and taken of the cancer vaccine treatment.

Immune monitoring of antigen-specific T-cell response is defined herein as the identification and/or enumeration and/or isolation of antigen specific T cells. The strength of an antigen-specific T-cell response is often determined by enumerating the antigen-specific T-cells in a sample. In one embodiment of the present invention the amount of antigen-specific T-cells measured by immune monitoring methods in fluidic samples is in the range of $10^4$-$10^6$ antigen-specific T-cells pr. µl sample, such as from of $10^{-4}$ to $10^{-3}$ antigen-specific T-cells pr. µl sample, for example from $10^{-3}$ to $10^{-2}$ antigen-specific T-cells pr. µl sample, such as from of $10^{-2}$ to $10^{-1}$ antigen-specific T-cells pr. µl sample, for example from $10^{-1}$ to 10 antigen-specific T-cells pr. µl sample, such as from of 10 to $10^2$ antigen-specific T-cells pr. µl sample, for example from $10^2$ to $10^3$ antigen-specific T-cells pr. µl sample, such as from of $10^3$ to $10^4$ antigen-specific T-cells pr. µl sample, for example from $10^4$ to $10^5$ antigen-specific T-cells pr. µl sample, such as from of $10^5$ to $10^6$ antigen-specific T-cells pr. µl sample, or any combination thereof.

In another embodiment of the present invention the amount of antigen-specific T-cells measured by immune monitoring methods in solid samples is in the range of $10^{-4}$-$10^6$ antigen-specific T-cells pr. mm² sample analyzed, such as from of $10^{-4}$ to $10^{-3}$ antigen-specific T-cells pr. mm² sample, for example from $10^{-3}$ to $10^{-2}$ antigen-specific T-cells pr. mm² sample, such as from of $10^{-2}$ to $10^{-1}$ antigen-specific T-cells pr. mm² sample, for example from $10^{-1}$ to 10 antigen-specific T-cells pr. mm² sample, such as from of 10 to $10^2$ antigen-specific T-cells pr. mm² sample, for example from $10^2$ to $10^3$ antigen-specific T-cells pr. mm² sample, such as from of $10^3$ to $10^4$ antigen-specific T-cells pr. mm² sample, for example from $10^4$ to $10^5$ antigen-specific T-cells pr. mm² sample, such as from of $10^5$ to $10^6$ antigen-specific T-cells pr. mm² sample, or any combination thereof.

Of special interest for the present invention is immune monitoring of specific T-cell responses using MHC multimers. MHC multimers are complexes comprising more than one MHC-peptide complexes, held together by covalent or non-covalent bonds. MHC multimers of the present invention comprises (a-b-P)$_n$, wherein n>1, wherein a and b together form a functional MHC protein capable of binding the antigenic peptide P, wherein (a-b-P) is the MHC-peptide complex formed when the antigenic peptide P binds to the functional MHC protein, and wherein each MHC peptide complex of a MHC multimer is associated with one or more multimerization domains.

A schematic drawing of a MHC multimer is shown in FIG. 12.

The MHC multimer can generally be formed by association of the 2 or more MHC-peptide complexes with the multimerization domain to which the 2 or more MHC-peptide complexes are capable of associating.

The multimerization domain can be a scaffold associated with one or more MHC-peptide complexes, or a carrier associated with one or more, preferably more than one, MHC-peptide complex(es), or a carrier associated with a plurality of scaffolds each associated with one or more MHC-peptide complexes, such as 2 MHC-peptide complexes, 3 MHC-peptide complexes, 4 MHC-peptide complexes, 5 MHC-peptide complexes or more than 5 MHC-peptide complexes. Accordingly, multimerization domain collectively refers to each and every of the above. It will be clear from the detailed description of the invention provided herein below when the multimerization domain refers to a scaffold or a carrier or a carrier comprising one or more scaffolds.

Generally, when a multimerization domain comprising a carrier and/or a scaffold is present, the MHC complexes can be associated with this domain either directly or via one or more binding entities. The association can be covalent or non-covalent.

Accordingly, there is provided in one embodiment a MHC complex comprising one or more entities (a-b-P)$_n$, wherein a and b together form a functional MHC protein capable of binding a peptide P, and wherein (a-b-P) is the MHC-peptide complex formed when the peptide P binds to the functional MHC protein, said MHC complex optionally further comprising a multimerization domain comprising a carrier molecule and/or a scaffold. "MHC complex" refers to any MHC complex, including MHC monomers in the form of a single MHC-peptide complex and MHC multimers comprising a multimerization domain to which more than one MHC peptide complex is associated.

When the invention is directed to complexes comprising a MHC multimer, i.e. a plurality of MHC peptide complexes of the general composition (a-b-P)$_n$ associated with a multimerization domain, n is by definition more than 1, i.e. at least 2 or more. Accordingly, the term "MHC multimer" is used herein specifically to indicate that more than one MHC-peptide complex is associated with a multimerization domain, such as a scaffold or carrier or carrier comprising one or more scaffolds. Accordingly, a single MHC-peptide complex can be associated with a scaffold or a carrier or a carrier comprising a scaffold and a MHC-multimer comprising 2 or more MHC-peptide complexes can be formed by association of the individual MHC-peptide complexes with a scaffold or a carrier or a carrier comprising one or more scaffolds each associated with one or more MHC-peptide complexes.

When the MHC complex comprises a multimerization domain to which the n MHC-peptide complexes are associated, the association can be a covalent linkage so that each or at least some of the n MHC-peptide complexes is covalently linked to the multimerization domain, or the association can be a non-covalent association so that each or at least some of the n MHC-peptide complexes are non-covalently associated with the multimerization domain.

The MHC complexes of the invention may be provided in non-soluble or soluble form, depending on the intended application.

Example MHC multimer include but is not limited to MHC Dextramers, MHC tetramers, MHC Pentamers, cells expressing MHC-peptide molecules, streptactin with MHC-peptide complexes covalently or non-covalently attached, beads with MHC-peptide complexes covalently or non-covalently attached or any other molecule with two or more MHC-peptide complexes covalently or non-covalently attached.

MHC multimers are marker molecules and may be labeled as described elsewhere herein for other marker molecules.

In the following different methods and principles for detection of antigen-specific T-cells using MHC multimers is described.

Antigen-specific T cells can be measured in samples by detection of their unique T-cell receptor (TCR) using MHC multimers as Marker molecules. In the following methods and principles using MHC multimers for detection of TCR are outlined.

Detection of TCRs with MHC multimers may be direct or indirect.

Direct Detection

Direct detection of TCRs is detection directly of the binding interaction between the specific T cell receptor and the MHC multimer. The MHC multimer may be generated and then added to sample or alternatively MHC multimers are generated in sample by addition of antigenic peptide and MHC molecules attached to multimerization domain to sample.

Direct detection includes detection of TCR when TCR is attached to lipid bilayer (e.g. T cells), when TCR is attached to or in a solid medium or when TCR is in solution.

Direct Detection of TCR Attached to Lipid Bilayer

One type of TCRs to detect and measure are TCRs attached to lipid bilayer including but not limited to naturally occurring T cells (from blood, spleen, lymph node, brain or any other tissue containing T cells), TCR transfected cells, T cell hybridomas, TCRs embedded in liposomes or any other membrane structure. In the following methods for direct detection of entities of TCRs attached to lipid bilayer will be described and any entity consisting of TCR attached to lipid bilayer will be referred to as T cells.

T cells can be directly detected either when in a fluid solution or when immobilized to a solid support.

Direct Detection of T Cells in Fluid Sample.

T cells can be detected in fluid samples using the methods described below including but not limited to detection of T cells in culture media, in buffers, in water or in other liquids and also suspensions of disrupted tissues e.g. homogenized tissue resuspended in the fluids described above. T cells in fluid samples can be detected individually or detected as populations of T cells. In the following different methods for direct detection of T cells in fluid samples are described.

Direct Detection of Individual T Cells

Direct Detection of Individual T Cells Using Flow Cytometry.

An example of direct detection of individual T cells by flow cytometry is measurement of antigen specific T cells using MHC multimers like Tetramers, Pentamers, Dextramers or similar types of reagents.

Briefly, a suspension of T cells are added MHC multimers, the sample washed and then the amount of MHC multimer bound to each cell are measured. Bound MHC multimers may be labelled directly or measured through addition and binding of labelled marker molecules. The sample is analyzed using a flow cytometer, able to detect and count individual cells passing in a stream through a laser beam. For identification of specific T cells using MHC multimers, cells are stained with fluorescently labeled MHC multimer by incubating cells with fluorochrome labelled MHC multimer and then forcing the cells with a large volume of liquid through a nozzle creating a stream of spaced cells. Each cell passes through a laser beam and any fluorochrome bound to the cell is excited and thereby fluoresces. Sensitive photomultipliers detect emitted fluorescence, providing information about the amount of MHC multimer bound to the cell. By this method MHC multimers can be used to identify specific T cell populations in liquid samples such as blood, CSF, synovial fluid, cell cultures or any other liquid sample containing T cells.

When analyzing blood samples whole blood can be used with or without lysis of red blood cells. Alternatively lymphocytes can be purified from blood before flow cytometry analysis e.g. using a standard procedure like a Ficoll-Hypaque gradient. Another possibility is to isolate lymphocytes, subgroups of lymphocytes, T cells or subgroups of T cells from the blood sample for example by affinity purification like binding to antibody coated surfaces, followed by elution of bound cells. This purified lymphocyte or T cell population can then be used for flow cytometry analysis together with MHC multimers.

Instead of actively isolating T cells or subgroups of lymphocytes unwanted cells like B cells, NK cells or any other unwanted cells or substances can be removed prior to the analysis. One way to do this is by affinity purification e.g. using columns or beads or other surfaces coated with antibodies specific for the unwanted cells. Alternatively, specific antibodies recognizing the unwanted cells can be added to the blood sample together with complement proteins, thereby killing cells recognized by the antibodies.

Various gating reagents can be included in the analysis. Gating reagents here means labeled antibodies or other labeled marker molecules identifying subsets of cells by binding to unique surface proteins. Preferred gating reagents when using MHC multimers are antibodies or other marker molecules directed against CD3, CD4, and CD8 identifying major subsets of T cells. Other preferred gating reagents are antibodies or marker molecules specifically binding CD14, CD15, CD19, CD25, CD56, CD27, CD28, CD45, CD45RA, CD45RO, CCR7, CCR5, CD62L, Foxp3, CD95, CD127, CD7, CD57, CD154 or other specific proteins or molecules unique for different lymphocytes of the immune system.

Following labelling with MHC multimers and before analysis on a flow cytometer stained cells can be treated with a fixation reagent e.g. formaldehyde to cross-link bound MHC multimer to the cell surface. Stained cells can also be analyzed directly without fixation.

The number of cells in a sample can vary. When the target cells are rare, it is preferable to analyze large amounts of cells. In contrast, fewer cells are required when looking at T cell lines or samples containing many cells of the target cell type.

The flow cytometer can be equipped to separate and collect particular types of cells. This is called cell sorting. MHC multimers in combination with sorting on a flow cytometer can be used to isolate specific T cell populations. Isolated specific T cell populations can then be further manipulated as described elsewhere herein, e.g. expanded in vitro. This can be useful in autologous cancer therapy.

Amounts of MHC-peptide specific T cells in a blood sample can be determined by flow cytometry by calculating the amount of MHC multimer labeled cells in a given volume of sample with a given cell density and then back calculate. Exact enumeration of specific T cells is better achieved by incubating sample with MHC multimers (and optionally gating reagents) together with an exact amount of counting beads followed by flow cytometry analysis. Counting beads is here to be understood as any fluorescent bead with a size that can be visualized in a sample containing T cells by flow cytometry. The beads could e.g. be made of polystyrene with a size of about 1-10 µm. They could also be made of agarose, polyacrylamide, silica, or any other material, and have any size between 0.1 µm and 100 µm. The counting beads are used as reference population to measure the exact volume of analyzed sample. The sample are analyzed on a flow cytometer and the amount of MHC-specific T cell detected can then be correlated with the amount of counting beads in the same volume of the sample and an exact number of MHC-peptide specific T cells determined using the following equation:

Concentration of MHC-specific T-cell in sample=
(number of MHC-peptide specific T cells counted/number of counting beads counted)× concentration of counting beads in sample Alternatively MHC multimers are added to one tube (below denoted tube 1) together with sample and counting beads are added to a separate tube (below denoted tube 2) containing the same sample but no MHC multimers. To both tubes one or more gating reagents are added able to identify other cell subsets in sample e.g. CD3+, CD4+, CD8+, CD19+, CD56+ cells. The exact amount of one of the cell subsets for which gating reagents are included are then calculated from the tube containing counting beads. For example if CD8+ cells are measured in both tubes the following equation can be used to determine the exact concentration of CD8+ cells in the sample:

(((number of CD8+ cells counted(tube 2))/(number of counting beads counted (tube 2)))×(concentration of counting beads in sample)=exact concentration of CD8+ cells in sample The exact concentration of CD8+ cells in sample are then used to determine the exact concentration of MHC-specific T cells in sample using the equation:

(Calculated exact concentration of CD8+ cells in sample(calculated from tube 2))×(MHC-specific T cells counted as percentage of CD8+ events counted in sample(tube 1))=concentration of MHC-specific T-cell in sample Direct Detection of Individual T Cells in Fluid Sample by Microscopy A suspension of T cells are added MHC multimers, the sample washed and then the amount of MHC multimer bound to each cell are measured. Bound MHC multimers may be labelled directly or labelled through addition of labelled marker molecules. The sample is then spread out on a slide or similar in a thin layer able to distinguish individual cells and labelled cells identified using a microscope. Depending on the type of label different types of microscopes may be used, e.g. if fluorescent labels are used a fluorescent microscope is used for the analysis. For example MHC multimers can be labeled with a fluorochrome or bound MHC multimer detected with a fluorescent antibody. Cells with bound fluorescent MHC multimers can then be visualized using an immunofluorescence microscope or a confocal fluorescence microscope.

Direct Detection of Populations of T Cells

Cell suspensions are added labeled MHC multimer, samples are washed and then total signal from label are measured. The MHC multimers may be labeled themselves or detected through a labeled marker molecule.

Cell suspensions are added labeled MHC multimer, samples are washed and then signal from label are amplified and then total signal from label and/or amplifier are measured.

Direct Detection of Immobilized T Cells.

T cells may be immobilized and then detected directly. Immobilization can be on solid support, in solid tissue or in fixator (e.g. paraffin, a sugar matrix or another medium fixing the T cells).

Direct Detection of T Cells Immobilized on Solid Support.

In a number of applications, it may be advantageous to immobilize the T cell onto a solid or semi-solid support. Such support may be any which is suited for immobilisation, separation etc. Non-limiting examples include particles, beads, biodegradable particles, sheets, gels, filters, membranes (e.g. nylon membranes), fibres, capillaries, needles, microtitre strips, tubes, plates or wells, combs, pipette tips, micro arrays, chips, slides, or indeed any solid surface material. The solid or semi-solid support may be labelled, if this is desired. The support may also have scattering properties or sizes, which enable discrimination among supports of the same nature, e.g. particles of different sizes or scattering properties, colour or intensities.

Conveniently the support may be made of glass, silica, latex, plastic or any polymeric material. The support may also be made from a biodegradable material.

Generally speaking, the nature of the support is not critical and a variety of materials may be used. The surface of support may be hydrophobic or hydrophilic.

Preferred are materials presenting a high surface area for binding of the T cells. Such supports may for example be porous or particulate e.g. particles, beads, fibres, webs, sinters or sieves. Particulate materials like particles and beads are generally preferred due to their greater binding capacity. Particularly polymeric beads and particles may be of interest.

Conveniently, a particulate support (e.g. beads or particles) may be substantially spherical. The size of the particulate support is not critical, but it may for example have a diameter of at least 1 µm and preferably at least 2 µm, and have a maximum diameter of preferably not more than 10 µm and more preferably not more than 6 µm. For example, particulate supports having diameters of 2.8 µm and 4.5 µm will work well.

An example of a particulate support is monodisperse particles, i.e. such which are substantially uniform in size (e.g. size having a diameter standard deviation of less than 5%). Such have the advantage that they provide very uniform reproducibility of reaction. Monodisperse particles, e.g. made of a polymeric material, produced by the technique described in U.S. Pat. No. 4,336,173 (ref. 25) are especially suitable.

Non-magnetic polymer beads may also be applicable. Such are available from a wide range of manufactures, e.g. Dynal Particles AS, Qiagen, Amersham Biosciences, Serotec, Seradyne, Merck, Nippon Paint, Chemagen, Promega, Prolabo, Polysciences, Agowa, and Bangs Laboratories.

Another example of a suitable support is magnetic beads or particles. The term "magnetic" as used everywhere herein is intended to mean that the support is capable of having a magnetic moment imparted to it when placed in a magnetic field, and thus is displaceable under the action of that magnetic field. In other words, a support comprising magnetic beads or particles may readily be removed by magnetic aggregation, which provides a quick, simple and efficient way of separating out the beads or particles from a solution. Magnetic beads and particles may suitably be paramagnetic or superparamagnetic. Superparamagnetic beads and particles are e.g. described in EP 0 106 873 (Sintef, ref. 26). Magnetic beads and particles are available from several manufacturers, e.g. Dynal Biotech ASA (Oslo, Norway, previously Dynal AS, e.g. Dynabeads®).

The support may suitably have a functionalised surface. Different types of functionalisation include making the surface of the support positively or negatively charged, or hydrophilic or hydrophobic. This applies in particular to beads and particles. Various methods therefore are e.g. described in U.S. Pat. No. 4,336,173 (ref. 25), U.S. Pat. No. 4,459,378 (ref. 27) and U.S. Pat. No. 4,654,267 (ref. 28).

Immobilized T cells may be detected in several ways including:

Direct Detection of T Cells Directly Immobilized on Solid Support.
- T cells may be directly immobilized on solid support e.g. by non-specific adhesion. Then MHC multimers are added to the immobilized T cells thereby allowing specific T cells to bind the MHC multimers. Bound MHC multimer may be measured through label directly attached to the multimer or through labeled marker molecules. Individual T cells may be detected if the method for analysis is able to distinguish individual labelled cells, e.g. cells are immobilized in a monolayer on a cell culture well or a glass slide. Following staining with labelled multimer a digital picture is taken and labelled cells identified and counted. Alternatively a population of T cells is detected by measurement of total signal from all labelled T cells, e.g. cells are plated to wells of a microtiter plate, stained with labelled MHC multimer and total signal from each well are measured.

Direct Detection of T Cells Immobilized on Solid Support Through Linker Molecule
- T cells can also be immobilized to solid support through a linker molecule. The linker molecule can be an antibody specific for the T cell, a MHC multimer, or any molecule capable of binding T cells. In any case the linker may be attached directly to the solid support, to the solid support through another linker, or the linker molecule may be embedded in a matrix, e.g. a sugar matrix.
- Then MHC multimers are added to the immobilized T cells thereby allowing specific T cells to bind the MHC multimers. Bound MHC multimer may be measured through label directly attached to the multimer or through labeled marker molecules. Individual T cells may be detected if the method for analysis is able to distinguish individual labelled cells, e.g. a digital picture is taken and labelled cells identified and counted.
- By using a specific MHC multimer both for the immobilization of the T-cells and for the labelling of immobilized cells (e.g. by labelling immobilized cells with chromophore- or fluorophore-labelled MHC multimer), a very high analytical specificity may be achieved because of the low background noise that results.
- Alternatively a population of T cells is detected by measurement of total signal from all labeled T cells.

Immuno Profiling: Phenotyping T Cell Sample Using MHC Multimer Beads or Arrays.
- Different MHC multimers are immobilized to different beads with different characteristics (e.g. different size, different fluorophores or different fluorescence intensities) where each kind of bead has a specific type of MHC multimer molecule immobilized. The immobilization may be direct or through a linker molecule as described above. The amount of bound T cells to a specific population of beads can be analyzed, thereby phenotyping the sample. The TCR on the T cell is defined by the MHC multimer and hence the bead to which it binds.
- Likewise, MHC multimers can be immobilized in an array, e.g. on a glass plate or pin array so that the position in the array specifies the identity of the MHC multimer. Again, the immobilization may be direct or through a linker molecule as described above. After addition of T cells, the amount of bound T cells at a specified position in the array can be determined by addition of a label or labelled marker that binds to cells in general, or that binds specifically to the cells of interest. For example, the cells may be generally labelled by the addition of a labelled molecule that binds to all kinds of cells, or specific cell types, e.g. CD4+ T-cells, may be labelled with anti-CD4 antibodies that are labelled with e.g. a chromophore or fluorophore. Either of these approaches allow a phenotyping of the sample. An example for the use of immuno profiling is given below.
- Profiling of an individual's disease-specific T-cell repertoire.
- Mass profiling of the T-cells of an individual may be done by first immobilizing specific MHC multimers (e.g. $10-10^6$ different MHC multimers, each comprising a specific MHC-peptide combination) in an array (e.g. a glass plate), adding e.g. a blood sample from the individual, and then after washing the unbound cells off, label the immobilized cells. Positions in the array of particularly high staining indicate MHC-peptide combinations that recognize specific T-cells of particularly high abundance or affinity. Thus, an immuno profiling of the individual with regard to the tested MHC-peptide combinations is achieved. A similar profiling of an individuals disease may be made using MHC multimers immobilized to different beads as described above.

Whether the profiling is performed using beads or arrays, the profiling may entail a number of diseases, a specific disease, a set of specific antigens implicated in one or more diseases, or a specific antigen (e.g. implicated in a specific disease or set of diseases).

In a preferred embodiment, an individual's immuno profile for a particular antigen is obtained. Thus, peptides corresponding to all possible 8'-, 9'-10'- and 11'-mer peptide sequences derived from the peptide antigen sequence are generated, for example by standard organic synthesis or combinatorial chemistry, and the corresponding MHC multimers are produced, using one or more of the class I MHC-alleles of the individual in question. Further, peptides of e.g. 13, 14, 15, 16 and up to 25 amino acids length may be generated, for example by organic synthesis or combinatorial chemistry, corresponding to all 13', 14', 15', 16' and up to 25'-mers of the antigen, and the corresponding class II MHC multimers are produced, using one or more of the class II MHC-alleles of the individual in question. For a complete profiling for this particular antigen, all of the HLA-alleles of the individual in question should be used for the generation of the array; i.e., if the HLA class I haplotype of the individual is HLA-A*02, HLA-A*03, HLA-B*08 and HLA-B*07, all these HLA class I alleles should be combined with every tested peptide and similarly for all HLA class II alleles of the given individual.

Based on the profile, a personalized drug, -vaccine or -diagnostic test may be produced.

The principle described above may also be employed to distinguish between the immune response raised against a disease (e.g. an infection with a bacterium or the formation of a tumour), and the immune response raised against a vaccine for the same disease (in the example, a vaccine against the bacterium or the tumour). Most vaccines consists of subcomponents of the pathogen/tumour they are directed against and/or are designed to elicit an immune response different from the natural occurring immune response i.e. the T cell epitopes of the two immune responses differs. Thus, by establishing the immuno profile, using a comprehensive array (i.e. an array that comprises all possible epitopes from one or more antigen(s)) or a subset of these epitopes, it is possible to deduce whether the immune response has been generated against the disease or the vaccine, or against both the disease and the vaccine. If the vaccine raises a response against a particular epitope or a particular set of epitopes, the corresponding positions in the array will give rise to high signals (compared to the remaining positions). Similarly a natural generated immune response will be directed against other and/or more particular epitopes and therefore give rise to high signals in other positions and/or more positions in the array. When an individual is vaccinated the immuno profile will reflect the effect of the vaccination on the immune response, and even if the individual has encountered the disease before and has generated a general immune response towards this disease, it will still be possible to deduce from the profiling whether this individual also has generated a specific response against the vaccine.

In another preferred embodiment, an individual's immuno profile for a set of antigens implicated in a specific disease is obtained. A subset of epitopes from a number of antigens is used. Thus, this is not a comprehensive profiling of this individual with regard to these antigens, but careful selection of the epitopes used may ensure that the profiling data can be used afterwards to choose between e.g. a limited set of vaccines available, or the data can be used to evaluate the immune response of the individual following an infection, where the epitopes used have been selected in order to avoid interference from related infectious diseases.

As above, a personalized drug, -vaccine or -diagnostic test may be produced. based on the information obtained from the immuno profiling.

In yet another preferred embodiment, the array comprising all possible 8'-, 9'-10'- and 11'-mer peptide sequences derived from a given peptide antigen, and all 13, 14, 15 and 16'-mers of the same antigen, are synthesized and assembled in MHC multimers, and immobilized in an array. Then, the ability of the individual peptide to form a complex with MHC is tested. As an example, one may add labelled W6/32 antibody, an antibody that binds correctly folded MHC I heavy chain, when this heavy chain is assembled together with antigenic peptide and beta2 microglobulin, and which therefore can be used to detect formation of MHC-peptide complex, as binding of W6/32 antibody is usually considered a strong indication that the MHC-peptide complex has been formed. The ability of different peptides to enter into a MHC-peptide complex may also be promoted by the addition to the array of T-cells. Specific T-cells will drive the formation of the corresponding specific MHC-peptide complexes. Thus, after addition of T-cells to the array, the MHC-peptide complex integrity can be examined by addition of the labelled W6/32 antibody or other antibodies specific for correct conformation. Positions on the array that have strong signals indicate that the peptide that was added to MHC and immobilized at this position, was capable of forming the MHC-peptide complex in the presence of specific T-cells. Alternatively, the binding of the specific T-cells to the corresponding MHC-peptide complexes may be detected directly through a labelled antibody specific for the T cell.

Direct Detection of Immobilized T Cells Followed by Sorting

Specific T cells or specific T cell subsets can be isolated from a sample containing other T cells, T cell subsets and/or other cells by immobilization of the wanted specific T cells in sample to solid support as described above followed by washing and elution. For example, MHC multimers are immobilized to a support e.g. beads, immunotubes, wells of a microtiterplate, CD, mircrochip or similar as described elsewhere herein, then a suspension of T cells (the sample) are added allowing specific T cells to bind MHC multimer molecules. Following washing bound T cells are recovered/eluted (e.g. using acid or competition with one or more competitor molecules) and counted.

Specific T-cells can e.g. be isolated through the use of bead-based MHC multimers. Bead-based MHC multimers are beads whereto monomer MHC-peptide complexes or MHC multimers are immobilized.

The isolated T cells can following elution optionally be manipulated further before final use. For example the isolated cells can be activated (to differentiate or proliferate), they can undergo induced apoptosis, or undesired cells of the isolated cell population can be removed. Then, the manipulated cell population can be re-introduced into the patient from which the sample originate, or can be introduced into another patient.

A typical cell sorting experiment, based on bead-based MHC multimers, would follow some of the steps of the general procedure outlined in general terms in the following: Acquire the sample, e.g. a cell sample from the blood or bone marrow of a cancer patient.

Block the sample with a protein solution, e.g. BSA or skim milk.

Block the beads coated with MHC complexes or MHC multimers, with BSA or skim milk.

Mix MHC-coated beads and the cell sample, and incubate.

Wash the beads with washing buffer, to remove unbound cells and non-specifically bound cells.

Isolate the immobilized cells, by either cleavage of the linker that connects MHC complex/MHC multimer and bead; or alternatively, release the cells by a change in pH, salt-concentration addition of competitive binding molecule or the like. Preferably, the cells are released under conditions that do not disrupt the integrity of the cells. Manipulate the isolated cells (e.g. induce apoptosis, proliferation or differentiation)

Direct Detection of T Cells in Solid Tissue.

Direct Detection of T Cells in Solid Tissue In Vitro.

Example direct detection of T cells in solid tissue in vitro include but is not limited till Immunohsitochemistry (IHC). IHC is here referred to as the detection of antigens in solid tissue by antibodies or other marker molecules labelled with a labelling molecule as described elsewhere herein.

For in vitro methods of the present invention solid tissue includes tissue, tissue biopsies, frozen tissue or tissue biopsies, paraffin embedded tissue or tissue biopsies and sections of either of the above mentioned. In a preferred method of this invention sections of fixed or frozen tissues are incubated with MHC multimer, allowing MHC multimer to bind to specific T cells in the tissue section. The MHC multimer may be labeled directly or through a labeled marker molecule. As an example, the MHC multimer can be labeled with a tag that can be recognized by e.g. a secondary antibody, optionally labeled with HRP or another label. The bound MHC multimer is then detected by its fluorescence or absorbance (for fluorophore or chromophore), or by addition of an enzyme-labeled antibody directed against this tag, or another component of the MHC multimer (e.g. one of the protein chains, a label on the multimerization domain). The enzyme can be Horse Raddish Peroxidase (HRP) or Alkaline Phosphatase (AP), both of which convert a colorless substrate into a colored reaction product in situ. This colored deposit identifies the binding site of the MHC multimer, and can be visualized under a light microscope. The MHC multimer can also be directly labeled with e.g. HRP or AP, and used in IHC without an additional antibody.

The tissue sections may derive from blocks of tissue or tissue biopsies embedded in paraffin, and tissue sections from this paraffin-tissue block fixed in formalin before staining. This procedure may influence the structure of the TCR in the fixed T cells and thereby influence the ability to recognize specific MHC complexes. In this case, the native structure of TCR needs to be at least partly preserved in the fixed tissue. Fixation of tissue therefore should be gentle. Alternatively, the staining is performed on frozen tissue sections, and the fixation is done after MHC multimer staining.

Direct Detection of T Cells in Solid Tissue In Vivo

For in vivo detection of T cells labeled MHC multimers are injected in to the body of the individual to be investigated. The MHC multimers may be labeled with e.g. a paramagnetic isotope. Using a magnetic resonance imaging (MRI) scanner or electron spin resonance (ESR) scanner MHC multimer binding T cells can then be measured and localized. In general, any conventional method for diagnostic imaging visualization can be utilized. Usually gamma and positron emitting radioisotopes are used for camera and paramagnetic isotopes for MRI.

The methods described above for direct detection of TCR embedded in lipid bilayers collectively called T cells using MHC multimers also applies to detection of TCR in solution and detection of TCR attached to or in a solid medium. Though detection of individual TCRs may not be possible when TCR is in solution.

Indirect Detection of TCR

Indirect detection of TCR is primarily useful for detection of TCRs embedded in lipid bilayer, preferably natural occurring T cells, T cell hybridomas or transfected T cells. MHC multimers used for the indirect detection may be generated and then added to sample. Alternatively MHC multimers are generated in sample by addition of antigenic peptide to sample and optionally also addition of MHC molecules, components of MHC molecules or MHC molecules coupled to carrier. For example when antigenic peptide is added to a sample containing antigen presenting cells, the antigenic peptide is taken up by antigen presenting cells in sample, processed inside cells and displayed on their surface by binding MHC molecules, or the antigenic peptides added are bound directly to MHC molecules displayed on the surface of antigen presenting cells by exchange with peptide already present in the peptide binding cleft of the MHC molecules. In indirect detection, the number or activity of T cells are measured, by detection of events that are the result of TCR-MHC-peptide complex interaction. Interaction between MHC multimer and T cell may stimulate the T cell resulting in activation of T cells, in cell division and proliferation of T cell populations or alternatively result in inactivation of T cells. All these mechanism can be measured using various detection methods.

Indirect Detection of T Cells by Measurement of Activation.

MHC multimers, e.g. antigen presenting cells, can stimulate T cells resulting in activation of the stimulated T cells. Activation of T cell can be detected by measurement of production of specific soluble factor from the stimulated T cell, e.g. production of cytokines like INFγ and IL2. Stimulation of T cells can also be detected by measurement of changes in expression of specific surface receptors, or by measurement of T cell effector functions.

Measurement of activation of T cells involves the following steps:

a) Antigenic peptide is added to a sample of T cells containing antigen presenting cells, preferably a suspension of cells e.g. blood. The antigenic peptide have to be able to bind MHC I or MHC II molecules of one or more antigen presenting cells in the sample thereby generating one or more cell based MHC multimer(s) in sample. Alternatively, protein fragment(s) containing one or more antigenic peptides sequences is added to such sample. The protein fragments is then taken up by antigen presenting cells in sample, processed into antigenic peptides and presented by MHC I or MHC II molecules on the surface of antigen presenting cells thereby creating cell based MHC multimers in the sample. Several different antigenic peptides may be added to the sample. The peptide-loaded antigen presenting cells (the cell based MHC multimers) can then stimulate specific T cells in sample, and thereby induce the production of soluble factor, up- or down-regulation of surface receptors, or mediate other changes in the T cell, e.g. enhancing effector functions.

Alternatively, one or more MHC multimer(s) containing one or more antigenic peptide(s) are added to a sample containing T cells, preferably a suspension of cells, to stimulate MHC multimer specific T cells in sample and thereby induce production of soluble factor, up- or down-regulation of surface receptor and/or other changes in the T cell.

Following addition of antigenic peptide, antigenic protein fragments or MHC multimer to sample, a second soluble factor, e.g. cytokine and/or growth factor(s) may optionally be added to facilitate continued activation and expansion of antigen-specific T cells b) Detection of the presence of produced soluble factor, the presence/absence of surface receptor or detection of effector function.

Correlate the measured result with presence of T cells. The measured signal/response indicates the presence of specific T cells that have been stimulated with particular MHC multimer. The signal/response of a T lymphocyte population is a measure of the overall response in sample.

The frequency of specific T cells able to respond to a given MHC multimer can be determined by including a limiting-dilution culture in the assay also called a Limiting dilution assay.

The limiting-dilution culture method involves the following steps:
  i. Sample of T cells in suspension are plated into culture wells at increasing dilutions.
  ii. Antigen presenting cells are provided into the sample if not already in sample and then antigenic peptide or protein containing one or more antigenic peptide sequence(s) is added to the sample as described above thereby creating cell based MHC multimers in sample able to stimulate antigen-specific T cells in the sample. Alternatively, already generated MHC multimers are added to sample to stimulate specific T cells. Optionally growth factors, cytokines or other factors helping T cells to proliferate are added.
  iii. Cells are allowed to grow and proliferate (½-several days). Each well that initially contained a specific T cell will make a response to the MHC multimer and divide.
  iv. Wells are tested for a specific response e.g. production of soluble factors, cell proliferation, cytotoxicity or other effector functions.

The assay is replicated with different numbers of T cells in the sample, and each well that originally contained a specific T cell will make a response to the MHC multimer. The frequency of specific T cells in the sample equals the reciprocal of the number of cells added to each well when 37% of the wells are negative, because due to Poisson distribution each well then on average contained one specific T cell at the beginning of the culture.

Optionally step i) and ii) from above maybe reversed, e.g. adding sample containing T cells in various dilutions to wells or containers containing MHC multimer, antigenic peptide, antigenic peptide+antigen presenting cells or MHC multimer.

In the following various methods to measure production of specific soluble factor, expression of surface receptors, effector functions or proliferation is described.

Indirect Detection of T Cells by Measurement of Production of Soluble Factors.

Indirect Detection of T Cells by Measurement of Secreted Soluble Factors.

Secreted soluble factors can be measured directly in fluid suspension or the soluble factor captured by immobilization on solid support and then detected or an effect of the secreted soluble factor can be detected.

Examples of such detection methods are interferon gamma release assays (IGRA's) like Quantiferon, enzyme-linked immunospot (ELISPOT) and cytokine flow cytometry (CFC), where INF-γ released from antigen stimulated T cells are measured. Principles of the various and alternative assays are described in more details below.

Indirect Detection of T Cells by Measurement of Secreted Soluble Factor Directly in Fluid Sample.

A sample of T cells are added MHC multimer or antigenic peptide as described above to induce production and secretion of soluble factors from antigen-specific T cells. The secreted soluble factors can be measured directly in the supernatant using e.g. mass spectrometry.

Indirect Detection of T Cells by Capture of Secreted Soluble Factor on Solid Support.

A sample of T cells are added MHC multimer and/or, antigenic peptide as described above to induce production and secretion of soluble factors from antigen-specific T cells. Secreted soluble factors in the supernatant are then immobilized on a solid support either directly or through a linker as described for immobilization of T cells elsewhere herein. Then immobilized soluble factors can be detected using labeled marker molecules.

Soluble factors secreted from individual T cells can be detected using ELISPOT assays or related techniques. The principle is capturing of the secreted soluble factors locally by marker molecules, e.g antibodies specific for the soluble factor. Soluble factor recognised by marker molecules are immobilised on a solid support together with T cells and soluble factors secreted by individual T cells are thereby captured in the proximity of each T cell. Bound soluble factor can then be measured using labelled marker molecules specific for the captured soluble factor. The number of T cells that has given rise to labelled spots on solid support can then be enumerated and these spots indicate the presence of specific T cells that have been stimulated with particular MHC multimer and/or antigenic peptide.

Soluble factors secreted from a population of T cells are detected by capture and detection of soluble factor secreted from the entire population of specific T cells. In this case soluble factor do not have to be captured locally close to each T cell but the secreted soluble factors may be captured and detected in the same well or container as where the T cells are, or supernatant containing secreted soluble factor transferred to another solid support with marker molecules for capture e.g. beads or wells of ELISA plate. An example of such an assay is QuantiFERON or QuantiFERON like assays measuring secretion of INF-γ from antigen stimulated T cells.

Indirect Detection of T Cells Immobilized to Solid Support in a Defined Pattern.

Different MHC multimers, or MHC-peptide complexes are immobilized to a support to form a spatial array in a defined pattern, where the position specifies the identity of the MHC multimer/MHC-peptide complex immobilized at this position. Marker molecules able to bind T cell secreted soluble factors are co-spotted together with MHC multimer/MHC-peptide complex. Such marker molecules can e.g. be antibodies specific for cytokines like INFγ or IL-2. The immobilization may be direct or through a linker molecule as described above. Then a suspension of labeled T cells are added or passed over the array of MHC multimers/MHC-peptide complexes and specific T cells will bind to the immobilized MHC multimers/MHC-peptide complexes and upon binding be stimulated to secrete soluble factors e.g. cytokines like INFγ or IL-2. Soluble factors secreted by individual T cells are then captured in the proximity of each T cell and bound soluble factor can be measured using labelled marker molecule specific for the soluble factor. The number and position of different specific T cells that has given rise to labelled spots on solid support can then be identified and enumerated. In this way T cells bound to defined areas of the support are analyzed, thereby, phenotyping the sample. Each individual T cell is defined by the TCR it expose and depending on these TCRs each entity will bind to different types of MHC multimers/MHC-peptide complexes immobilized at defined positions on the solid support.

Alternatively to MHC multimers or MHC-peptide complexes antigenic peptides can be immobilized to a support to form a spatial array in a defined pattern, where the position specifies the identity of the antigenic peptide immobilized. As described above marker molecules able to bind T cell secreted soluble factors are co-spotted together with antigenic peptide. Before or together with addition of the suspension of T cells, MHC molecules, components of MHC molecules or MHC molecules attached to carrier are added to the array thereby generating MHC multimers. Then antigen specific T cells in sample are detected as described above.

Indirect Detection of T Cells by Measurement of Secreted Soluble Factor on Surface of T Cell An alternative way to detect secretion of soluble factor from individual cells is to use soluble factor capture on the surface of the T cell secreting the soluble factor. This can be done by using a bispecific capture molecule able to bind a component on the surface of the T cell with one part of the capture molecule and bind the secreted soluble factor by another part of the capture molecule. Example useful capture molecules are bispecific antibodies in which two different heavy- and light chain pairs from different antibodies are combined in one antibody resulting in an antibody molecule with the two antigen-binding sites recognizing different ligands.

Activated T cells in a sample can then be detected by adding the bispecific capture molecules to the sample. These molecules will then bind all T cells with on part of the molecule. T cells secreting soluble factor (due to activation) will then capture the secreted soluble factor on their surface by the soluble factor binding part of the capture molecule. Bound soluble factor can then be detected by addition of a labelled marker molecule specific for the soluble factor in question.

Indirect Detection of T Cells by Measurement of Effect of Secreted Soluble Factor.

Secreted soluble factors can be measured and quantified indirectly by measurement of the effect of the soluble factor on other cell systems. Briefly, a sample of T cells are added MHC multimer or antigenic peptideMHC multimer and/or antigenic peptide as described above to induce secretion of soluble factors from antigen-specific T cells. The supernatant containing secreted soluble factor are transferred to another cell system and the effect measured. The soluble factor may induce proliferation, secretion of other soluble factors, expression/downregulation of receptors, or the soluble factor may have cytotoxic effects on these other cells. All effects can be measured as described elsewhere herein.

Indirect Detection of T Cells by Measurement of Produced Soluble Factors Intracellularly Production of soluble factors can be measured intracellularly using flow cytometry. Often cytokines are measured and the method is therefore referred to as cytokine flow cytometry (CFC). The principles are described below.

Soluble factor production by stimulated T cells can also be measured intracellular by e.g. flow cytometry. This can be done using block of secretion of soluble factor (e.g. by monensin), permeabilization of cell (by e.g. saponine) followed by immunofluorescent staining. The method involves the following steps: 1) Stimulation of T cells e.g. by binding specific MHC multimers: The MHC multimers may be generated and added to sample containing T cells or antigenic peptide or protein containing antigenic peptide sequences can be added to sample and MHC multimers generated in sample as described elsewhere herein. An example of useful MHC multimers for stimulation of specific T cells is antigen presenting cells displaying MHC molecules containing antigenic peptide. A reagent able to block extracellular secretion of cytokine is added during stimulation, e.g. monensin that interrupt intracellular transport processes leading to accumulation of produced soluble factor, e.g. cytokine in the Golgi complex. Other soluble factors may be added to the T cell sample during stimulation to enhance activation and/or expansion. This other soluble factor can be cytokine and or growth factors. 2) addition of one or more labelled marker molecules able to detect special surface receptors (e.g. marker molecules able to bind CD8, CD4, CD3, CD27, CD28, CD2). 3) Fixation of cell membrane using mild fixator followed by permeabilization of cell membrane e.g. by saponine. 4) Addition of labelled marker specific for the produced soluble factor to be determined, e.g. INFγ, IL-2, IL-4, IL-10. 5) Measurement of labelled cells using a flow cytometer.

An alternative to this procedure is to trap secreted soluble factors on the surface of the secreting T cell as described elsewhere herein or as described by Manz, R. et al., Proc. Natl. Acad. Sci. USA 92:1921 (1995).

Indirect Detection of T Cells by Measurement of Expression of Receptors

Activation of T cells can be detected by measurement of expression and/or down regulation of specific surface receptors. The method includes the following steps. A sample of T cells are added MHC multimer, antigenic peptide or protein containing antigenic peptide as described elsewhere herein to stimulate T cell and thereby induce expression or downregulation of specific surface receptors on antigen-specific T cells. These receptors include but are not limited to CD28, CD27, CCR7, CD45RO, CD45RA, IL2-receptor, CD62L, CCR5. Their expression level can be detected by addition of labelled marker specific for the desired receptor and then measure the amount of labelled cells using flow cytometry, microscopy, immobilization of activated T cell on solid support or any other method like those described for direct detection of TCR.

Indirect Detection of T Cells by Measurement of Effector Function

Activation of T cells can be detected indirectly by measurement of effector functions. A sample of T cells are added MHC multimer, antigenic peptide or protein containing antigenic peptide as described elsewhere herein to stimulate T cell and thereby induce one or more effector functions of the antigen-specific T cells. The one or more effector function(s) are then measured. For example activation of antigen-specific CD8 positive T cells can be determined by measurement of killing of target cells, i.e. cells displaying specific MHC-peptide complexes recognized by the activated antigen-specific CD8 positive T cell. This method is often referred to as cytotoxicity assays or CTL killing assays and involves the following steps:

1) Sample containing antigen-specific CD8 positive cells are stimulated by addition of MHC multimer, antigenic peptide or protein containing antigenic peptide as described elsewhere herein. 2) Another sample containing live target cells displaying MHC I molecules containing specific antigenic peptide are added labelled molecules that can be taken up by live cells but that are not spontaneously released by the target cells following uptake e.g. radioactive labelled compounds. 3) Stimulated and activated T cells from step 1 are then added to target cells of step 2. target cells displaying the MHC complexes containing specific antigenic peptide(s) are then killed releasing labelled compound from the target cells and the presence of this labelled compound may be detected in the supernatant of mixtures of target and cytoxic cells. Alternatively, amount of labelled compound in cells that are not killed by the CD8 positive T cells are measured, by removing labelled compound released by killed target cells followed by measurement of label inside remaining cells either directly or by release of the labelled compound from these remaining cells.

Indirect Detection of T Cells by Measurement of Proliferation

T cells can be stimulated to proliferate upon binding specific MHC multimers. Proliferation of T cells can be measured several ways including but not limited to:

Detection of mRNA
  Proliferation of T cells can be detected by measurement of mRNA inside cell. Cell division and proliferation requires production of new protein in each cell which as an initial step requires production of mRNA encoding the proteins to be synthesized.
  A sample of T cells are added MHC multimer or antigenic peptide MHC multimer and/or antigenic peptide as described above to induce proliferation of antigen-specific T cells. Detection of levels of mRNA inside the proliferating T cells can be done by quantitative PCR and indirectly measure activation of a T cell population as a result of interaction with MHC multimer. An example is measurement of cytokine mRNA by in situ hybridization.

Detection of Incorporation of Thymidine
  The proliferative capacity of T cells in response to stimulation by MHC multimer can be determined by a radioactive assay based on incorporation of [$^3$H]thymidine ([$^3$H]TdR) into newly generated DNA followed by measurement of radioactive signal.

Detection of Incorporation of BrdU
  T cell proliferation can also be detected by of incorporation of bromo-2'-deoxyuridine (BrdU) followed by measurement of incorporated BrdU using a labeled anti-BrdU antibody in an ELISA based analysis.

Viability of cells may be measured by measurement ATP in a cell culture.

Indirect Detection of T Cells by Measurement of Inactivation

Not all MHC multimers will lead to activation of the T cells they bind. Under certain circumstances some MHC multimers may rather inactivate the T cells they bind to.

Indirect Detection of T Cells by Measurement of Effect of Blockade of TCR

Inactivation of T cells by MHC multimers may be measured be measuring the effect of blocking TCR on antigen-specific T cells. MHC multimers, e.g. MHC-peptide complexes coupled to IgG scaffold can block the TCR of an antigen-specific T cell by binding the TCR, thereby prevent the blocked T cell receptor interacting with e.g. antigen presenting cells. Blockade of TCRs of a T cell can be detected in any of the above described methods for detection of TCR by addition of an unlabeled blocking MHC multimer together with the labelled MHC multimer and then measuring the effect of the blockade on the readout.

Indirect Detection of T Cells by Measurement of Induction of Apoptosis

Inactivation of T cells by MHC multimers may be measured be measuring apoptosis of the antigen-specific T cell. Binding of some MHC multimers to specific T cells may lead to induction of apoptosis. Inactivation of T cells by binding MHC multimer may therefore be detected by measuring apoptosis in the T cell population. Methods to measure apoptosis in T cells include but are not limited to measurement of the following:

DNA fragmentation
Alterations in membrane asymmetry (phosphatidylserine translocation)
Activation of apoptotic caspases
Release of cytochrome C and AIF from mitochondria into the cytoplasm B) Physical Examination Physical examination is the process where the physical condition of the unit is investigated with no or only simple tools. Physical examination may include one or more of the types of analysis listed below.

Inspection of a unit is the process where the examiner analyses a unit using his eyes, ears, nose and/or other senses. No extra devices are used for the analysis. The characteristics may be common to the unit or abnormal for the unit. Inspection includes but is not limited to:
  Visual inspection visualizing one or more characteristics of the unit by the naked eye including but not limited to:
    Body features and symmetry appearance
    Nutritional state and weight
    Size of unit
    Volume of unit
    Skin color
    Skin abnormalities
    Unusual spots on surface
    Discoloration
    Hair-distribution
    Frequency and volume of breath
    Manner of speaking
    Manner of movement
    Scars
    Visible masses Swelling
Tremor
Abnormal contour
Facial expression
Posture
Other signs/characteristics either abnormal or normal for the unit Listening to sounds emanating from the unit e.g. the patient like:
Breath (frequency, regularity, whistling, wheezing or abnormal sounds)
Tone of voice
Speech like explanation of medical history, well-being, pain, feelings etc.
Reaction to speech
Normal/abnormal sounds
Sounds from bowel, joints or other Odors from unit/patient can be odors arising from whole unit or from part of unit including but not limited to
Smell of breath
Odor form clothes
Odor form bandages
Odors from other matter surrounding the unit
General odor when close to the unit
Odors arising from parts of the unit
Odors from wounds Palpation is an analysis where a unit is felt with hands of the examiner to determine e.g. size, shape, firmness, temperature or location of an Object.

Percussion is a method to find out about changes in the unit or part of the unit by tapping on the surface to determine the underlying structure. An example is tapping on skin on abdomen or thorax to determine the underlying structure e.g. determine if there could be fluid or air underneath.

Auscultation, listening to internal sounds of the body using naked ear, a stethoscope or similar. May be used for examination of the circulatory system, respiratory system or gastrointestinal system.

Physical Tests
Measurement of electric pulses
Electroencephalography, method to determine electrical activity produced by the brain
Electrocorticography
Electromyography, technique to detect electrical potential generated by muscle cells
Electrocardiography, measures electrical activity of the heart
Electrooculography, technique for measuring resting potential in retina
Electroretinography, used for measurement of electrical responses of various cells in the retina
EEG topography
Electroneuronography Endoscopy (looking inside the body using an endoscope)
Colonoscopy
Gastroscopy
Cystoscopy
Sigmoidoscopy
Colposcopy
Otoscopy
Ophthalmoscopy
Videoendoscopy
Laparoscopy Measurement of pressure
Blood pressure measurement
Esophageal motility study (EMS)/esophageal manometry
Muscle tonus and strength Measurement of shape
Microscopy
Fotographing
X-ray crystallography
Circular dichroism Medical imaging
Ultrasound
Echocardiography
Medical ultrasonography
Contrastenhanced ultrasound
Intravascular ultrasound
X-ray
Magnetic resonance imaging (MRI)
Computed tomography (CT)
Radiography
Fluoroscopy
Positron emission tomography
Single positron emission computed tomography (SPECT)
Scintillography
Thermography
Electric impediance tomography
Corneal topography Measurement of temperature
Measurement of humidity
Measurement of torsional flexibility
Measurement of emission
Measurement of sound
Measurement of weight
Measurement of flow
Blood flow
Breath
Measurement of volume
Measurement of conductivity (e.g. neuronal activity)

Physical characteristics include physical parameters such as shape; temperature; humidity; strength; pressure, including blood pressure; torsional flexibility; rigidity; emission; absorption of radiation including visible light, X-ray, electromagnetic radiation, microwaves, sound; weight; volume; conductivity, vibration, electric impulses and electric current.

Example methods for measurement of physical features include X-ray, MRI, NMR, computed tomography (CT), thermographic scanning, ultrasound, electrocardiogram, electrophysiologic study (EPS), endoscopy, colonscopy, sigmoidscopy, endoscopic retrograde choliopancreatography (ERCP), anoscopy, cytoscopy, bronchoscopy, imaging, hysteroscopy, electromyography, oral tests, visual test, exercise tests, dual energy x-ray absorption (DXA).

Chemical characteristics include the detection of molecules, molecular structures or supramolecular structures. Measurement of chemical characteristics may be categorized into detection of binding events, catalysis, induction/inhibition of growth or depletion/killing of cells.

Example detection methods of binding include ELISA, DELFIA, RIA, immune electrophoresis, ELISPOT, measurement of induced crosslinking by e.g. turbidometry, PCR, SDS PAGE, western blotting, Northern blotting, Southern blotting, cytology with DNA-, RNA-, LNA-, PNA-, protein-, antibody-, MHC-probes, flow cytometry with DNA-, RNA-, LNA-, PNA-, protein-, antibody-, MHC-probes, stationary cytometry with DNA-, RNA-, LNA-, PNA-, protein-, antibody-, MHC-probes, IHC with DNA-, RNA-, LNA-, PNA-, protein-, antibody-, MHC-probes.

Example molecules and molecular structures to be measured in binding assays include, proteins (e.g. antibodies, antibody fragments, enzymes, peptides, receptors, cytokines, interleukins, interferons, hormones, MHC molecules, growth factors), sugars, DNA, RNA, lipids, chemical bonds, atoms.

Catalysis includes measurement of enzymatic activity of one or more enzymes in the sample or measurement of the amount of a given substrate in the sample by addition of enzyme to the sample or extracts of the sample. The enzyme or substrate may be added directly while the sample is still a part of the unit or added to the sample or part of the sample when the sample is taken out of the unit.

Chemical characteristics may also be measured by a sample's ability to inhibit or induce cell proliferation. Measurement of inhibition may be determined internally in the sample or externally when the sample is transferred to another environment e.g. a cell sample. The inhibition is either exerted by the sample itself or exerted on the sample by an external agent. Example inhibition is a sample containing mycoplasma that when transferred to certain cell lines inhibit their proliferation.

Proliferation may be determined internally in the sample or externally when the sample is transferred to another environment e.g. a cell sample. The proliferation is either exerted by the sample itself or exerted on the sample by an external agent. Example proliferation could be the presence of growth factors in a sample that is capable to induce proliferation of cells.

Treatment Principles of the Invention

Treatments (or repair process(es)) may be categorized depending on several characteristics, including type of treatment; way of administration; times of administration; whether the treatment induce complete recovery from disease; improvement of disease or relief from symptoms of disease; is the treatment prophylactic or therapeutic; what kind of physical feature or matter is administered; what specific physical feature or matter is treated and how is this feature or matter treated.

Treatment may be either therapeutic i.e. treating already existing disease or prophylactic to prevent disease from developing or developing further. Furthermore, treatment may induce complete recovery from and/or elimination of from disease, improvement of disease or relief from symptoms of disease.

The present invention relates in one embodiment to treatment of one or more diseases that have been diagnosed and/or monitored.

Treatments according to the present invention may be categorized into four groups;
A) Vaccine
B) Drugs
C) Physical therapy
D) Psychological therapy Each of these groups may be further subcategorized according to the above described characteristics.

A list of examples of treatments is given in Table P.

In the following, principles for and examples of treatments and/or therapies for specific diseases/disease conditions are described in further details.

A) Vaccine

The present invention relates in one embodiment to treatment of one or more diseases by administering a vaccine to a unit such as an individual in need thereof.

A vaccine is an antigenic preparation used to establish immunity to a disease or illness and thereby protect or cure the body from a specific disease or illness. Vaccines are either prophylactic and prevent disease or therapeutic and treat disease. Vaccines may contain more than one type of antigen and is then called a combined vaccine.

Example prophylactic vaccines are conventional vaccines for infectious diseases, such as measles, mumps, and tetanus. These vaccines are effective because they expose the immune system to weakened versions of the disease. This exposure causes the immune system to respond by producing antibodies. Once the immune system has created antibodies, some of the activated immune cells remember the exposure. Therefore, the next time the same antigen enters the body, the immune system can respond more readily to destroy it.

For cancer treatment, researchers are developing vaccines that can encourage the immune system to recognize cancer cells. These vaccines can help the body reject tumors and prevent cancer from recurring. In contrast to traditional vaccines against infectious diseases, cancer vaccines are designed to be injected after the disease is diagnosed, rather than before it develops and are therefore therapeutic. By example, it has been shown that immunization with dendritic cells (DC) loaded with appropriate peptides from tumor associated antigens (TAAs) stimulate "tumor specific" T-cells, which in some patients prevent further progression of the disease and eventually lead to regression of the disease.

Vaccines can be administered by several routes including but not limited to injection including intravenously, intramuscularly, subcutaneously, inter peritoneal and transmucosally (nasal, rectal, vaginal) injection, by inhalation, perorally or by inoculation.

Vaccines can be administered alone or in combination with one or more adjuvant and/or one or more drugs and/or one or more other vaccines.

Vaccines may be administered only once or may be administered several times. Vaccine administered more than once may have the same composition throughout the vaccination program or alternatively the vaccine change composition from $1^{st}$ administration to $2^{nd}$, $3^{rd}$, etc administration.

Vaccine administered more than once can be administered by same route or by alternating routes. Similarly the individual components of the vaccine can be administered alone or in combinations by the same route or by alternating/mixed routes.

Several different types of vaccines exist based on different types of agents including attenuated vaccine (composed of attenuated or killed microorganisms), living fully virulent organisms, macromolecules, cell-based, nanoclusters or reservoirs. Vaccines based on macromolecules may consist of individual macromolecules in solution including natural occurring proteins, recombinant proteins, nucleic acids, nucleic acid analogs and sugars or the macromolecules may be in complex e.g. attached to polymer backbones, proteins, liposomes, cells or other carriers.

Cell-based vaccines include, naturally occurring cells, transfected cells, chemical or genetic modified cells, hybridoma cells or any of the mentioned cells loaded with or attached to macromolecules.

In the present invention vaccines are subdivided into the following categories:
  Vaccines made of living virulent microorganisms. Virulence refers to the degree of pathogenicity of a microbe, or in other words the relative ability of a microbe to cause disease. Examples of such organisms include but is not limited to bacteria, virus, parasites or other pathogens. Most pathogens will not be useful for vaccines if they are fully virulent but certain natural occurring modest virulent strains can be used. The vaccine may result in protection against the organism used for vaccination but may also induce protections against related virulent organisms The organism may be fully virulent The organism may be partly virulent meaning that the virulence of the organism has been reduced. Such organisms are often called live attenuated microorganisms. Attenuated means reducing the virulence of the microorganism while keeping it viable. Examples of reducing the virulence of an microorganism includes but is not limited to

- Modifying the microorganism by physical means, e.g. by heating
- Modifying the microorganism by chemical means, e.g. by addition of chemicals to the microorganism.
- Genetically modified microorganisms, e.g. recombinant bacteria or virus missing virulence factors
- Cultured under conditions that disable their virulent properties One way to reduce the virulence of an organism is passage through a foreign host e.g. tissue cultures, embryo eggs or live animals.

Killed microorganisms are another type of vaccine. Microorganisms can be killed in several ways including but not limited to Physically killing
- Killing by heating
- Killing by radioactive irradiation Chemically killing, e.g. by treatment with phenol, formaldehyde or other chemicals able to kill microorganism.

Subunit/fragment(s) of microorganism can be used as vaccine. The fragments may be isolated directly from microorganism or produced using recombinant DNA technology. Fragments/subunits of microorganisms useful in vaccines of the present invention includes but is not limited to Macromolecules, e.g. naturally occurring or artificial made. Macromolecules of the present invention includes but is not limited to:

Proteins. The proteins may be full length or truncated and may be modified e.g. by introduction of additional amino acids, mutated, chemically modified (e.g. acetylation, methylation, Pegylation, phosphorylation, glycosylation etc.) or carrying other modifications. The proteins may also be stabilized by covalent or non-covalent attachment of protein linkers or other protein molecules. Proteins of the present invention includes but is not limited to:

Proteins of the immune system
Cytokines
Interleukins (cytokines produces by leukocytes)
Interferon's (cytokines that can induce cells to resist viral replication)
Antibodies (monoclonal, polyclonal,
Full length
Fab fragments
scFv fragments
antibody-like (scaffolds)
MHC molecules.
MHC I molecules
MHC I molecules consisting of full length or truncated heavy chain, full length or truncated β2m and peptide
MHC I molecule consisting of full length or truncated heavy chain and full length and truncated β2m but no peptide (empty MHC I molecule)
MHC I molecule consisting of full length or truncated heavy chain and peptide
MHC I molecule consisting of full length or truncated heavy chain
MHC II molecules
MHC II molecules consisting of full length or truncated alpha chain and full length or truncated beta chain and peptide
MHC II molecules consisting of full length or truncated alpha chain and full length and truncated beta chain but no peptide (empty MHC II molecule)
Cytokines
Interleukins (cytokines produces by leukocytes)
Interferon's (cytokines that can induce cells to resist viral replication)
Chemokines or their receptors
Peptides
Antigenic peptides, meaning any peptide that is bound or able to bind MHC molecules.
With binding motif for MHC I
With binding motif for MHC II
Other peptides
Heat shock proteins e.g. HSP70 and HSP90
T cell receptor (TCR)
Full length
Truncated
Stabilized by e.g. a peptide linker
Proteins from microorganisms
Surface proteins
Intracellular proteins
Secreted proteins (e.g. toxins)
Unmodified
Modified (e.g. toxoid)
Chemically modified
Physically modified
Nucleic acids
DNA
Encoding protein
Structural not encoding protein
RNA
Ribosome's
Antisense
Silencing RNA
LNA
PNA
Carbohydrates
Saccharides and derivatives thereof, e.g. phosphorylated, oxidized, reduced, amino derivatives, acetylated etc. Saccharides may have more than one modification
Monosaccharide's
Disaccharides
Polysaccharides
Homopolysaccharides (e.g. glycans, dextran)
Polymers of repeating disaccharide units in which one of the sugars are is either N-acetylgalactosamine or N-acetylglucosamine (e.g. Glucosaminoglycans)
Polysaccharide-peptide polymer (Peptidoglycan (bacterial cell wall))
Proteins carrying covalent attached oligosaccharides or polysaccharides (Glycoprotein's)

Lipids carrying covalent attached oligo- or polysaccharides (Glycolipids)

All macromolecules may be individual or in complex (e.g. attached to polymer backbone, solid support e.g. beads or other solid support, microspheres, liposome's or other nanoclusters)

Cell based vaccine is another type of vaccine of the present invention. Characteristics of different cell based vaccines are listed below.

Consisting of naturally occurring cells

Cells are isolated and optionally amplified e.g. by proliferation

Cells are isolated and modified to display specific molecules e.g. specific MHC complexes by incubation with antigenic peptide. Following modification the cells may be proliferated.

Consisting of non-naturally occurring cells. Non-naturally occurring cells of the present invention includes but is not limited to:

Chemically modified cells

Genetically modified cells

Cells fused to another cell (e.g. hybridomas)

Cells transfected, transformed or transduced with genes or nucleic acids encoding specific proteins (e.g. with super coiled plasmid DNA linear DNA, RNA, siRNA or other)

Adjuvant

Vaccines may be combined with adjuvants in order to improve the effect of the vaccine. Adjuvants are pharmacological or immunological agents that modify the effect of other agents (e.g., drugs, vaccines) while having few if any direct effects when given by themselves.

Immunological adjuvants are substances that stimulate the immune system and increase the response to a vaccine without having any specific antigenic effect itself.

An immunological adjuvant either potentiates the immune responses to an antigen and/or modulates it towards the desired immune responses.

More than one adjuvant may be present in the final vaccine product. They may be combined together with a single antigen or all antigens present in the vaccine, or each adjuvant may be combined with one particular antigen.

Potent, nontoxic adjuvants that will enhance and/or modulate the immunogenicity of immunogenic determinants including antigenic determinants including haptenic determinants represent one group of preferred adjuvants. In addition, such adjuvants preferably also elicit an earlier, more potent, or more prolonged immune response. Such an adjuvant would also be useful in cases where an antigen supply is limited or is costly to produce.

Examples of immunological adjuvants include oil emulsions and surfactant based formulations e.g. MF59, QS21, AS02, Montanide ISA-51 and ISA-720, mineral salts (e.g. aluminium hydroxide, aluminium or calcium phosphate gels), particulate adjuvants (e.g. virosomes, AS04, immune stimulatory complexes (ISCOMs), polylactide co-glycolide (PLG)), natural and synthetic microbial derivatives (e.g. monophosphoryl lipid A (MPL), Detox (MPL+*M. Phlei* cell wall skeleton), AGP [RC-529] (synthetic acylated monosaccharide), DC_Chol (lipoidal immunostimulators able to self organize into liposome's), OM-174 (lipid A derivative), CpG motifs (synthetic oligonucleotides containing immunostimulatory CpG motifs), modified LT and CT (genetically modified bacterial toxins to provide non-toxic adjuvant effects), endogenous human immunomodulators, (e.g., hGM-CSF or hIL-12 (cytokines that can be administered either as protein or plasmid encoded), Immudaptin (C3d tandem array)), saponins, squalene or phosphate based adjuvants, lipopolysaccharides, Inert vehicles, such as gold particles microbial antigens, copolymers.

Pharmacological adjuvants are drugs that have few or no pharmacological effect by themselves but may increase the efficacy or potency of other drugs when given at the same time. An example is caffeine which has minimal analgesic effect on its own but may have an adjuvant effect when given with paracetamol.

Adjuvants pertaining to the present invention may be grouped according to their origin, be it mineral, bacterial, plant, synthetic, or host product. The first group under this classification is the mineral adjuvants, such as aluminum compounds. Antigens precipitated with aluminum salts or antigens mixed with or adsorbed to performed aluminum compounds have been used extensively to augment immune responses in animals and humans. Aluminum particles have been demonstrated in regional lymph nodes of rabbits seven days following immunization, and it may be that another significant function is to direct antigen to T cell containing areas in the nodes themselves. Adjuvant potency has been shown to correlate with intimation of the draining lymph nodes. While many studies have confirmed that antigens administered with aluminum salts led to increased humoral immunity, cell mediated immunity appears to be only slightly increased, as measured by delayed-type hypersensitivity. Aluminum hydroxide has also been described as activating the complement pathway. This mechanism may play a role in the local inflammatory response as well as immunoglobulin production and B cell memory. Primarily because of their excellent record of safety, aluminum compounds are presently the only adjuvants used in humans.

While aluminum salts have been a sufficient adjuvant for strong immunogens that require only antibody responses to elicit protection, they may not always be effective when used with weak immunogens such as e.g. synthetic peptides of malaria, or for introducing cell-mediated immune responses or IgG isotype of the type required to fight infections. Thus, the immunostimulating fragment of TGF according to the present invention may in one embodiment act as an adjuvant or immunostimulator and may be conjugated or non-conjugated to the immunogenic determinant against which it is desirable to raise an immune response.

Another large group of adjuvants are those of bacterial origin. Adjuvants with bacterial origins can be purified and synthesized (e.g. muramyl dipeptides, lipid A) and host mediators have been cloned (Interleukin 1 and 2). The last decade has brought significant progress in the chemical purification of at least three adjuvants of active components of bacterial origin: *Bordetella pertussis*, lipopolysaccharide and Freund's Complete Adjuvant (FCA). Additionally suitable adjuvants in accordance with the present invention are e.g. Titermax, ISCOMS, Quil A, ALUN, see U.S. Pat. Nos. 58,767 and 5,554,372, Lipid A derivatives, choleratoxin derivatives, HSP derivatives, LPS derivatives, synthetic peptide matrixes, GMDP, and other as well as combined with immunostimulants (U.S. Pat. No. 5,876,735).

*B. pertussis* is of interest as an adjuvant in the context of the present invention due to its ability to modulate cell-mediated immunity through action on T-lymphocyte populations. For lipopolysaccharide and Freund's Complete Adjuvant, adjuvant active moieties have been identified and synthesized which permit study of structure-function relationships. These are also considered for inclusion in immunogenic compositions according to the present invention.

Lipopolysaccharide and its various derivatives, including lipid A, have been found to be powerful adjuvants in combination with liposomes or other lipid emulsions. It is not yet certain whether derivatives with sufficiently low toxicity for general use in humans can be produced. Freund's Complete Adjuvant is the standard in most experimental studies.

Endogenous human immunomodulators are another group of adjuvants of interest for the present invention and among others include cytokines, interleukins, interferons and growth factors. These immunomodulators can be administered either as protein or plasmid encoded.

Many other types of materials can be used as adjuvants in immunogenic compositions according to the present invention. They include plant products such as saponin, animal products such as chitin, inert vehicles, such as gold particles and numerous synthetic chemicals.

Adjuvants according to the present invention can also been categorized by their proposed mechanisms of action. This type of classification is necessarily somewhat arbitrary because most adjuvants appear to function by more than one mechanism. Adjuvants may act through antigen localization and delivery, or by direct effects on cells making up the immune system, such as macrophages and lymphocytes. Another mechanism by which adjuvants according to the invention enhance the immune response is by creation of an antigen depot. This appears to contribute to the adjuvant activity of aluminum compounds, oil emulsions, liposomes, and synthetic polymers. The adjuvant activity of lipopolysaccharides and muramyl dipeptides appears to be mainly mediated through activation of the macrophage, whereas *B. pertussis* affects both macrophages and lymphocytes. Further examples of adjuvants that may be useful when incorporated into immunogenic compositions according to the present invention are described in U.S. Pat. No. 5,554,372.

Adjuvants can be mixed with the vaccine and administered simultaneously with vaccine. The adjuvant can be attached to one or more structures of the vaccine by covalent or non-covalent interaction or be in the vaccine as an individual component. The adjuvant may also be administered before or after the vaccine is administered. More than one type of adjuvant can be used together with a given vaccine likewise one specific type of adjuvant may be used for more than one vaccine.

All the above mentioned adjuvants may also be used together with drugs.

Vaccines of special interest of the present invention are cancer vaccines and vaccines for infectious diseases like HIV vaccines, TB vaccines, HPV vaccines and *Borrelia* vaccines.

B) Drugs

The present invention relates in one embodiment to treatment of one or more diseases by administering a drug to a unit such as an individual in need thereof.

In the present invention a drug is a chemical substance used in the treatment, cure or prevention of disease or used to otherwise enhance physical or mental well-being. Drugs may be divided into prophylactic drugs that prevent disease or therapeutic drugs that treat disease and can in principle have either local effects, or systemic effects. Drugs can be further divided into biologics or small molecules.

Biologic drugs may be any biological substance including proteins e.g. cytokines, growth factors, antibodies, MHC molecules, receptors, hormones or fragments of any of the mentioned; nucleic acids, carbohydrates, lipids and lectins. Small molecules are medicinal drug compounds having a molecular weights less than 1000 Daltons and include natural compounds, as well as synthetic chemical compounds.

Drugs can be administered as described above for vaccines or as described in the following. Drug treatment includes the use of single drugs alone or in any molecular combination mentioned elsewhere in the patent application for the purpose of treating a disease in any state. Drugs may be administered using the following routes of administration and form of drug:

Per-orally intake
    Pills
    Capsules
    Mixtures
    Liquid
    Powder
Injections
    Systemic injections
    Local injections
Jet-infusion (micro-drops, micro-spheres, micro-beads) through skin
Drinking solution, suspension or gel
Inhalation
Nose-drops
Eye-drops
Ear-drops
Skin application as ointment, gel or lotion
Vaginal application as ointment, gel, crème or washing
Gastro-Intestinal flushing
Rectal washings or by use of suppositories
Drug treatment can be performed as
Single intake, injection, application, washing
Multiple intake, injection, application, washing
    On single day basis
    Over prolonged time as days, month, years
Drug dose and regimen can be modified during the course.

The drugs according to the invention may be encapsulated, preferably inside a microcapsule. The microcapsule may be made from any suitable material. It may be a hydrophilic or a hydrophobic material. Likewise the microcapsule may be provided with a coating. This coating may be of a kind that prevents agglomeration or sticking of the microcapsules or prevents evaporation of the drug and/or a solvent comprising the drug inside the microcapsule. The invention also foresees the use of coatings providing the microcapsule with an affinity for specific cells or tissues. Such an affinity-coating may be in the form of specific amino-acid sequences or even anti-bodies or parts of anti-bodies having an affinity for specific proteins. Thereby the drug-delivery can be targeted to exactly those cells (e.g. cancer cells, metastases) to which the drug should be administered. Likewise this makes it possible to use the microcapsules for diagnostic use and the drug could in such cases be substituted by a compound suitable for labelling the targeted cells.

Agents for encapsulation include but are not limited to colloids, hydrocolloids such as gelatine, exudates such as gum arabic, tragacanth, gum karya, gum ghatti; extracts from seaweed such as agar, alginate, carrageenan and furcellaran; extracts from plants such as pectin and arabinogalactan; extracts from marine and terrestrial animals such as gelatines and other proteinaceous hydrocolloids; flours from seeds such as guar, locust bean, soya bean; proteins from seeds such as soya bean proteins; flours from cereals such as starches and microcrystalline cellulose; biosynthetic or fermentation derived hydrocolloids such as dextran, xanthan and curdlan; chemically modified hydrocolloids such as cellulose derivatives, including methyl cellulose and other derivatives, including modified starches and low methoxyl pectin; synthetic hydrocolloids such as polyvinylpyrrolidone, carboxyvinyl polymers etc.

Drugs of the present invention can be divided into the following categories:

Macromolecules, e.g. naturally occurring or artificial made.

Macromolecules of the present invention includes but is not limited to:
  Naturally occurring proteins or recombinant proteins. The proteins may be natural in sequence or artificial in sequence. Furthermore the proteins may be unmodified or modified as described elsewhere herein. The proteins may be full length or truncated. Proteins of the present invention includes but is not limited to any protein described elsewhere herein or listed below
    Antibodies
      Full length
      Fab fragments
      scFv fragments
      antibody-like (scaffolds)
    L-Peptides
    D-peptides
    Antigenic peptides
    Other peptides
    MHC molecules
      MHC I molecules
        MHC I molecules consisting of full length or truncated heavy chain, full length or truncated β2m and peptide
        MHC I molecule consisting of full length or truncated heavy chain and full-length and truncated β2m (empty MHC I molecule)
        MHC I molecule consisting of full length and truncated heavy chain and peptide
        MHC I molecule consisting of full-length and truncated heavy chain
      MHC II molecules
        MHC II molecules consisting of full length or truncated alpha chain and full length and truncated beta chain and peptide
        MHC II molecules consisting of full length or truncated alpha chain and full-length and truncated beta chain (empty MHC II molecule)
    Growth factors (protein capable of stimulating cellular proliferation and differentiation)
    Protein hormones
    T cell receptors
  Nucleic acids or nucleic acid analogs
    DNA
      Encoding protein
      Structural not encoding protein
    RNA
      Ribosome's
      Antisense RNA
      Silencing RNA
    LNA
    PNA
  Carbohydrates
    Saccharides and derivatives thereof, e.g. phosphorylated, oxidized, reduced, amino derivatives, acetylated etc. Saccharides may have more than one modification
      Monosaccharide's
      Disaccharides
      Polysaccharides
        Homopolysaccharides (e.g. glycans, dextran)
        Polymers of repeating disaccharide units in which one of the sugars are is either N-acetylgalactosamine or N-acetylglucosamine (e.g. Glucosaminoglycans)
        Polysaccharide-peptide polymer (Peptidoglycan (bacterial cell wall))
    Proteins carrying covalent attached oligosaccharides or polysaccharides (Glycoproteins)
    Lipids carrying covalent attached oligo- or polysaccharides (Glycolipids)
  Lipids
    Fatty acyls (e.g. prostaglandins, leukotrienes etc.)
    Glycerolipids (e.g. triglycerides)
    Glycerophospholipids
    Sphingolipids
    Sterol lipids (eg. cholesterol, estrogen etc.)
    Prenol lipids (eg vitamin E, K)
    Polyketides (eg. erythromycin)
  Small molecules. Small molecules are medicinal drug compounds having a molecular weights less than 1000 Daltons and include:
    Natural compounds including but not limited to
      Hormones
        Lipid and phospholipid derived hormones
          Steroids
          Eicosanoids
        Amine-derived hormones (derivatives of amino acids tyrosine and tryptophan (e.g. catecholamine, thyroxine)
      Salts, e.g. comprising Ca++, Mg++
    Synthetic chemical compound
      Benzodiazepines
      Short peptides
      Peptidommimetics
      Other chemical compounds Drugs may be combined with adjuvant(s) as described for vaccines elsewhere herein.

A list of examples of drugs is given in item 172.

Examples of drugs include, but are not limited to, antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), anti-inflammatory agents (e.g., naproxyn, diclofenac, indomethacin, ibuprofen, acetaminophen, aspirin, sulindac), gastro-intestinals, and anti-emetics (e.g., metoclopramide), anti-epileptics (e.g., phenyloin, meprobamate and nitrazepam), vasodilators (e.g., nifedipine, papaverine, diltiazem and nicardipine), anti-tussive agents and expectorants (e.g., codeine phosphate), anti-asthmatics (e.g. theophylline), anti-spasmodics (e.g. atropine, scopolamine), hormones (e.g., insulin, heparin), diuretics (e.g., ethacrynic acid, bendroflumethiazide), anti-hypotensives (e.g., propranolol, clonidine), bronchodilators (e.g., albuterol), anti-inflammatory steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, antacids, vitamins, stimulants (including appetite suppressants such as phenylpropanolamine). The above list is not meant to be exclusive.

Other types of drugs include flurazepam, nimetazepam, nitrazepam, perlapine, estazolam, haloxazolam, sodium valproate, sodium cromoglycate, primidone, alclofenac, perisoxal citrate, clidanac, indomethacin, sulpyrine, flufenamic acid, ketoprofen, sulindac, metiazinic acid, tolmetin sodium, fentiazac, naproxen, fenbufen, protizinic acid, pranoprofen, flurbiprofen, diclofenac sodium, mefenamic acid, ibuprofen, aspirin, dextran sulfate, carindacillin sodium, and the like.

The drug may be in the form of a physiologically active polypeptide, which is selected from the group consisting of insulin, somatostatin, somatostatin derivatives, growth hormone, prolactin, adrenocorticotrophic hormone, melanocyte stimulating hormone, thyrotropin releasing hormone, its salts or its derivatives, thyroid stimulating hormone, luteinizing hormone, follicle stimulating hormone, vasopressin, vasopressin derivatives, oxytocin, carcitonin, parathyroid hormone, glucagon, gastrin, secretin, pancreozymin, cholecystokinin, angiotensin, human placental lactogen, human chorionic gonadotropin, enkephalin, enkephalin derivatives, endorphin, interferon (in one or more of the forms alpha, beta, and gamma), urokinase, kallikrein, thymopoietin, thymosin, motilin, dynorphin, bombesin, neurotensin, caerulein, bradykinin, substance P, kyotorophin, nerve growth factor, polymyxin B, colistin, gramicidin, bacitracin, bleomycin and neocarzinostatin. Furthermore, the drug may be a polysaccharide, such as heparin, an antitumor agent such as lentinan, zymosan and PS-K (krestin), an aminoglycoside such as e.g. gentamycin, streptomycin, kanamycin, dibekacin, paromomycin, kanendomycin, lipidomycin, tobramycin, amikacin, fradiomycin and sisomicin, a beta-lactam antibiotic, such as e.g. a penicillin, such as e.g. sulbenicillin, mecillinam, carbenicillin, piperacillin and ticarcillin, thienamycin, and cephalosporins such as cefotiam, cefsulodine, cefmenoxime, cefmetazole, cefazolin, cefotaxime, cefoperazone, ceftizoxime and moxalactam, or a nucleic acid drug such as e.g. citicoline and similar antitumor agents, for example cytarabine and 5-FU (5-fluorouracil).

Drugs suitable for vaginal administration are contraceptives, hormones, antibiotics, anaesthetics, analgesics, contraction-preventers, anti-mycotica, bactericides, bacteriostats, anti-protozoan compounds, anti-viral compounds, and compositions for uterus contraction. Other suitable drugs may be dermatological drugs such as antimycotica, antipruritic compositions, dermoprotective compositions, Drugs for administration in the ear (otogenic administration) are e.g. antibiotics, corticosteroids, local anaesthetics, and analgesics.

Drugs for nasal administration are e.g. haemostatica, anti-allergenic compounds, antihistamines, anticholinergica, adrenergic (detumescent) compounds, and local analgesics.

The drugs according to the invention may be encapsulated, preferably inside a microcapsule. The microcapsule may be made from any suitable material. It may be a hydrophilic or a hydrophobic material. Likewise the microcapsule may be provided with a coating. This coating may be of a kind that prevents agglomeration or sticking of the microcapsules or prevents evaporation of the drug and/or a solvent comprising the drug inside the microcapsule. The invention also foresees the use of coatings providing the microcapsule with an affinity for specific cells or tissues. Such an affinity-coating may be in the form of specific amino-acid sequences or even anti-bodies or parts of antibodies having an affinity for specific proteins. Thereby the drug-delivery can be targeted to exactly those cells (e.g. cancer cells, metastases) to which the drug should be administered. Likewise this makes it possible to use the microcapsules for diagnostic use and the drug could in such cases be substituted by a compound suitable for labelling the targeted cells.

Agents for encapsulation include but are not limited to collloids, hydrocolloids such as gelatine, exudates such as gum arabic, tragacanth, gum karya, gum ghatti; extracts from seaweed such as agar, alginate, carrageenan and furcellaran; extracts from plants such as pectin and arabinogalactan; extracts from marine and terrestrial animals such as gelatines and other proteinaceous hydrocolloids; flours from seeds such as guar, locust bean, soya bean; proteins from seeds such as soya bean proteins; flours from cereals such as starches and microcrystalline cellulose; biosynthetic or fermentation derived hydrocolloids such as dextran, xanthan and curdlan; chemically modified hydrocolloids such as cellulose derivatives, including methyl cellulose and other derivatives, including modified starches and low methoxyl pectin; synthetic hydrocolloids such as polyvinylpyrrolidone, carboxyvinyl polymers etc.

Anticancer Drugs

Drugs of special interest for the present invention are drugs for the treatment of cancer. The anticancer drug may in one preferred embodiment be selected from the group consisting of those listed in the cancer drugs listed in the items.

In a preferred embodiment of the present invention, said anti-cancer drug is Aldesleukin/Proleukin (Chiron Corp).

In another preferred embodiment of the present invention, said anti-cancer drug is Alemtuzumab/Campath (Millennium and ILEX Partners, LP), such as for the treatment or prophylaxis of B-cell chronic lymphocytic leukaemia (B-CLL).

In another preferred embodiment of the present invention, said anti-cancer drug is alitretinoin/Panretin (Ligand Pharmaceuticals), such as for the treatment or prophylaxis of cutaneous lesions in sarcoma patients, such as in patients suffering from AIDS-related Kaposi's sarcoma.

In another preferred embodiment of the present invention, said anti-cancer drug is allopurinol/Zyloprim (GlaxoSmithKline), such as for the treatment of patients with leukaemia and/or lymphoma and/or one or more solid tumor malignancies who are receiving cancer therapy which causes elevations of serum and urinary uric acid levels.

In another preferred embodiment of the present invention, said anti-cancer drug is altretamine/Hexalen (US Bioscience), such as for treatment or prophylaxis of ovarian cancer.

In another preferred embodiment of the present invention, said anti-cancer drug is amifostine/Ethyol (US Bioscience), such as for treatment or prophylaxis of post-radiation xerostomia for e.g. head and neck cancer and/or ovarian cancer (preferably advanced) and/or non-small cell lung cancer.

In another preferred embodiment of the present invention, said anti-cancer drug is anastrozole/Arimidex (AstraZeneca), such as for the treatment of breast cancer, for example hormone receptor positive early breast cancer, advanced breast cancer, locally advanced or metastatic breast cancer.

In another preferred embodiment of the present invention, said anti-cancer drug is trioxide/Trisenox (Cell Therapeutic).

In another preferred embodiment of the present invention, said anti-cancer drug is Asparaginase/Elspar (Merck & Co, Inc), such as for the treatment of pediatric patients.

In another preferred embodiment of the present invention, said anti-cancer drug is Live/TICE BCG (Organon Teknika Corp).

In another preferred embodiment of the present invention, said anti-cancer drug is bexarotene capsules/Targretin (Ligand Pharmaceuticals), such as for treatment of cutaneous manifestations of cutaneous T-cell lymphoma, preferably via oral administration.

In another preferred embodiment of the present invention, said anti-cancer drug is bleomycin/Blenoxane (Bristol-Myers Squibb), such as for treatment of malignant pleural effusion (MPE) and prevention of recurrent pleural effusions.

In another preferred embodiment of the present invention, said anti-cancer drug is busulfan/Busulfex (GlaxoSmithKline), such as prior to hematopoietic progenitor cell transplantation for chronic myelogenous leukemia, preferably via oral administration.

In another preferred embodiment of the present invention, said anti-cancer drug is calusterone/Methosarb (Pharmacia & Upjohn Company).

In another preferred embodiment of the present invention, said anti-cancer drug is capecitabine/Xeloda (Roche), such as for treatment of breast cancer, preferably metastatic breast cancer, or colorectal carcinoma, preferably metastatic colorectal carcinoma.

In another preferred embodiment of the present invention, said anti-cancer drug is Carboplatin/Paraplatin (Bristol-Myers Squibb), such as for treatment of ovarian carcinoma.

In another preferred embodiment of the present invention, said anti-cancer drug is carmustine/BCNU, BiCNU (Bristol-Myers Squibb)

In another preferred embodiment of the present invention, said anti-cancer drug is carmustine with Polifeprosan 20 Implant/Gliadel Wafer (Guilford Pharmaceuticals Inc.), such as to prolong survival in patients with recurrent glioblastoma multiforme who qualify for surgery.

In another preferred embodiment of the present invention, said anti-cancer drug is celecoxib/Celebrex (Searle), such as for treatment of familial adenomatous polyposis.

In another preferred embodiment of the present invention, said anti-cancer drug is chlorambucil/Leukeran (GlaxoSmithKline), such as for treatment of chronic lymphocytic leukaemia.

In another preferred embodiment of the present invention, said anti-cancer drug is cisplatin/Platinol (Bristol-Myers Squibb), such as for treatment of ovarian tumour preferably metastatic ovarian tumour, testicular tumour, preferably testicular tumour, transitional cell bladder cancer.

In another preferred embodiment of the present invention, said anti-cancer drug is cladribine/Leustatin, 2-CdA (R.W. Johnson Pharmaceutical Research Institute), such as for treatment of active hairy cell leukaemia.

In another preferred embodiment of the present invention, said anti-cancer drug is cyclophosphamide Cytoxan/Neosar (Bristol-Myers Squibb)

In another preferred embodiment of the present invention, said anti-cancer drug is cytarabine/Cytosar-U (Pharmacia & Upjohn Company)

In another preferred embodiment of the present invention, said anti-cancer drug is dacarbazine/DTIC-Dome (Bayer).

In another preferred embodiment of the present invention, said anti-cancer drug is dactinomycin/actinomycin D Cosmegen (Merck)

In another preferred embodiment of the present invention, said anti-cancer drug is Darbepoetin alfa/Aranesp (Amgen, Inc), such as for treatment of anemia associated with chemotherapeutic regimes.

In another preferred embodiment of the present invention, said anti-cancer drug is daunorubicin/daunomycin/Daunorubicin (Bedford Labs), such as in liposomal form, for example for the treatment of HIV-related Kaposi's sarcoma.

In another preferred embodiment of the present invention, said anti-cancer drug is daunorubicin/daunomycin/Cerubidine (Wyeth Ayerst), such as for treatment of leukaemia.

In another preferred embodiment of the present invention, said anti-cancer drug is Denileukin/diftitox/Ontak (Seragen, Inc), such as for treatment of T-cell lymphoma, preferably of individuals whose malignant cells express the CDC25 component of the IL-2 receptor.

In another preferred embodiment of the present invention, said anti-cancer drug is dexrazoxane/Zinecard (Pharmacia & Upjohn Company), such as to aid in reducing the severity of cardiomyopathy associated with doxorubicin administration in women with metastatic breast cancer.

In another preferred embodiment of the present invention, said anti-cancer drug is docetaxel/Taxotere (Aventis Pharmaceutical), such as for treatment of breast cancer, preferably locally advanced or metastatic breast cancer, or non-small cell lung cancer, preferably locally advanced or metastatic non-small cell lung cancer.

In another preferred embodiment of the present invention, said anti-cancer drug is doxorubicin/Adriamycin Rubex (Pharmacia & Upjohn Company), such as for treatment of AIDS-related Kaposi's sarcoma or metastatic carcinoma of the ovary.

In another preferred embodiment of the present invention, said anti-cancer drug is Dromostanolone propionate/Masterone injection (SYNTEX).

In another preferred embodiment of the present invention, said anti-cancer drug is Elliott's B Solution (Orphan Medical, Inc), such as for treatment or prophylaxis of miningeal leukaemia or lymphocytic lymphoma.

In another preferred embodiment of the present invention, said anti-cancer drug is Epirubicin/Ellence (Pharmacia & Upjohn Company), such as for treatment or prophylaxis of breast cancer.

In another preferred embodiment of the present invention, said anti-cancer drug is etoposide phosphate (Bristol-Myers Squibb), such as for treatment or prophylaxis of refractory testicular tumours, small cell lung cancer.

In another preferred embodiment of the present invention, said anti-cancer drug is etoposide/VP-16/Vepesid (Bristol-Myers Squibb), such as for treatment or prophylaxis of refractory testicular tumours, small cell lung cancer.

In another preferred embodiment of the present invention, said anti-cancer drug is exemestane/Aromasin (Pharmacia & Upjohn Company), such as for treatment or prophylaxis of breast cancer, preferably for treatment of advanced breast cancer.

In another preferred embodiment of the present invention, said anti-cancer drug is Filgrastim/Neupogen (Amgen, Inc), such as for treatment of nonmyeloid malignancies undergoing myeloablative chemotherapy followed by marrow transplantation.

In another preferred embodiment of the present invention, said anti-cancer drug is floxuridine/FUDR (Roche)

In another preferred embodiment of the present invention, said anti-cancer drug is fludarabine/Fludara (Berlex Laboratories Inc.), such as for treatment or prophylaxis of B-cell lymphocytic leukaemia.

In another preferred embodiment of the present invention, said anti-cancer drug is fluorouracil/5-FU/Adrucil (ICN Puerto Rico), such as to prolong survival.

In another preferred embodiment of the present invention, said anti-cancer drug is fulvestrant/Faslodex (IPR), such as for treatment or prophylaxis of breast cancer, preferably in post-menopausal women.

In another preferred embodiment of the present invention, said anti-cancer drug is gemcitabine/Gemzar (Eli Lilly), such as for treatment or prophylaxis of adenocarcinoma of the pancreas or non-small cell lung cancer, preferably locally advanced or metastatic adenocarcinoma of the pancreas or non-small cell lung cancer.

In another preferred embodiment of the present invention, said anti-cancer drug is gemtuzumab/ozogamicin/Mylotarg (Wyeth Ayerst), such as for treatment or prophylaxis of CD33 positive acute myeloid leukaemia in patients who are preferably 60 years of age or older.

In another preferred embodiment of the present invention, said anti-cancer drug is goserelin acetate/Zoladex Implant (AstraZeneca Pharmaceuticals), such as for treatment or prophylaxis of breast cancer, preferably advanced stage breast cancer.

In another preferred embodiment of the present invention, said anti-cancer drug is hydroxyurea/Hydrea (Bristol-Myers Squibb).

In another preferred embodiment of the present invention, said anti-cancer drug is Ibritumomab Tiuxetan/Zevalin (IDEC Pharmaceuticals Corp), such as for treatment or prophylaxis of non-Hodgkin's lymphoma, for example patients with Rituximab refractory follicular non-Hodgkin's lymphoma.

In another preferred embodiment of the present invention, said anti-cancer drug is idarubicin/Idamycin (Adria Laboratories), such as for treatment or prophylaxis of acute myeloid leukaemia, for example in adults.

In another preferred embodiment of the present invention, said anti-cancer drug is ifosfamide/IFEX (Bristol-Myers Squibb), such as for treatment of germ cell testicular cancer.

In another preferred embodiment of the present invention, said anti-cancer drug is imatinib mesylate/Gleevec (Novartis), such as for treatment of chronic myelogeneous leukaemia or gastrointestinal stromal tumours.

In another preferred embodiment of the present invention, said anti-cancer drug is Interferon alfa-2a/Roferon-A (Hoffmann-La Roche Inc), such as for treatment or prophylaxis of malignant melanoma, Non-Hodgkin's Lymphoma, condylomata acuminate, hairy cell leukaemia or AIDS-related Kaposi's sarcoma.

In another preferred embodiment of the present invention, said anti-cancer drug is Interferon alfa-2b/Intron A (Schering Corp).

In another preferred embodiment of the present invention, said anti-cancer drug is irinotecan/Camptosar (Pharmacia & Upjohn Company), such as for treatment or prophylaxis of carcinoma of the colon or rectum, preferably metastatic carcinoma of the colon or rectum.

In another preferred embodiment of the present invention, said anti-cancer drug is letrozole/Femara (Novartis), carcinoma of the colon or rectum, such as for treatment or prophylaxis of breast cancer, preferably in post-menopausal women.

In another preferred embodiment of the present invention, said anti-cancer drug is Leucovorin/Wellcovorin (Immunex Corporation), such as for treatment or prophylaxis of colorectal cancer, preferably advanced colorectal cancer.

In another preferred embodiment of the present invention, said anti-cancer drug is levamisole/Ergamisol (Janssen Research Foundation), such as for treatment or prophylaxis of colon cancer, preferably after surgical resection.

In another preferred embodiment of the present invention, said anti-cancer drug is lomustine/CCNU/CeeBU (Bristol-Myers Squibb).

In another preferred embodiment of the present invention, said anti-cancer drug is meclorethamine/nitrogen mustard/Mustargen (Merck)

In another preferred embodiment of the present invention, said anti-cancer drug is megestrol acetate/Megace (Bristol-Myers Squibb)

In another preferred embodiment of the present invention, said anti-cancer drug is melphalan/L-PAM/Alkeran (GlaxoSmithKline), such as for treatment or prophylaxis of multiple myeloma.

In another preferred embodiment of the present invention, said anti-cancer drug is mercaptopurine/6-MP Purinethol (GlaxoSmithKline)

In another preferred embodiment of the present invention, said anti-cancer drug is mesna/Mesnex (Asta Medica) such as for treatment or prophylaxis of ifosfamide-induced hemorrhagic cystitis.

In another preferred embodiment of the present invention, said anti-cancer drug is methotrexate (Lederle Laboratories), such as for treatment or prophylaxis of osteosarcoma.

In another preferred embodiment of the present invention, said anti-cancer drug is methoxsalen/Uvadex (Therakos), such as for treatment or prophylaxis of skin manifestations of cutaneous T-cell lymphoma (CTCL).

In another preferred embodiment of the present invention, said anti-cancer drug is mitomycin C/Mutamycin (Bristol-Myers Squibb).

In another preferred embodiment of the present invention, said anti-cancer drug is mitomycin C/Mitozytrex (Supergen), such as for treatment or prophylaxis of disseminated adenocarcinoma of the stomach or pancreas.

In another preferred embodiment of the present invention, said anti-cancer drug is mitotane/Lysodren (Bristol-Myers Squibb)

In another preferred embodiment of the present invention, said anti-cancer drug is mitoxantrone/Novantrone (Lederle Laboratories), such as for treatment or prophylaxis of prostrate cancer or acute nonlymphocytic leukaemia (ANLL) in adults.

In another preferred embodiment of the present invention, said anti-cancer drug is nandrolone phenpropionate/Durabolin-50 (Organon).

In another preferred embodiment of the present invention, said anti-cancer drug is Nofetumomab/Verluma (Boehringer Ingelheim Pharma KG (formerly Dr. Karl Tomae GmbH).

In another preferred embodiment of the present invention, said anti-cancer drug is doxorubicin/Adriamycin PFS.

In another preferred embodiment of the present invention, said anti-cancer drug is Oprelvekin/Neumega (Genetics Institute), preferably administered after myelosuppressive chemotherapy in patients with nonmyeloid malignancies In another preferred embodiment of the present invention, said anti-cancer drug is oxaliplatin/Eloxatin (Sanofi Synthelabo), such as for treatment or prophylaxis of carcinoma of the colon, preferably metastatic carcinoma of the colon.

In another preferred embodiment of the present invention, said anti-cancer drug is paclitaxel/Taxol/Paxene (Bristol-Myers Squibb), such as for treatment or prophylaxis of advanced AIDS-related Kaposi's sarcoma, breast cancer, metastatic breast cancer, carcinoma of the ovary, AIDS-related Kaposi's sarcoma, metastatic carcinoma of the ovary, non-small cell lung cancer or node-positive breast cancer.

In another preferred embodiment of the present invention, said anti-cancer drug is pamidronate/Aredia (Novartis), such as for treatment or prophylaxis of osteolytic bone metastases of breast cancer.

In another preferred embodiment of the present invention, said anti-cancer drug is pegademase/Adagen (Pegademase Bovine) (Enzon).

In another preferred embodiment of the present invention, said anti-cancer drug is Pegaspargase/Oncaspar (Enzon, Inc).

In another preferred embodiment of the present invention, said anti-cancer drug is Pegfilgrastim/Neulasta (Amgen, Inc), such as for treatment or prophylaxis of non-myeloid malignancies.

In another preferred embodiment of the present invention, said anti-cancer drug is pentostatin/Nipent (Parke-Davis Pharmaceutical Co.), such as for treatment or prophylaxis of hairy cell leukaemia, for example alpha interferon refractory hairy cell leukaemia.

In another preferred embodiment of the present invention, said anti-cancer drug is pipobroman/Vercyte (Abbott Labs)

In another preferred embodiment of the present invention, said anti-cancer drug is plicamycin/mithramycin/Mithracin (Pfizer Labs)

In another preferred embodiment of the present invention, said anti-cancer drug is porfimer sodium/Photofrin (QLT Phototherapeutics Inc.), such as for the treatment or prophylaxis of partially obstructing or completely obstructing esophogeal cancer.

In another preferred embodiment of the present invention, said anti-cancer drug is procarbazine/Matulane (Sigma Tau Pharms)

In another preferred embodiment of the present invention, said anti-cancer drug is quinacrine/Atabrine (Abbott Labs)

In another preferred embodiment of the present invention, said anti-cancer drug is Rasburicase/Elitek (Sanofi-Synthelabo, Inc), such as for the treatment or prophylaxis of patients suffering from leukaemia, lymphoma or solid tumor malignancies.

In another preferred embodiment of the present invention, said anti-cancer drug is Rituximab/Rituxan (Genentech, Inc)

In another preferred embodiment of the present invention, said anti-cancer drug is Sargramostim/Prokine (Immunex Corp)

In another preferred embodiment of the present invention, said anti-cancer drug is streptozocin/Zanosar (Pharmacia & Upjohn Company)

In another preferred embodiment of the present invention, said anti-cancer drug is talc/Sclerosol (Bryan), such as for the treatment or prophylaxis of malignant pleural effusion in symptomatic patients.

In another preferred embodiment of the present invention, said anti-cancer drug is tamoxifen/Nolvadex (AstraZeneca Pharmaceuticals), such as for the treatment or prophylaxis of breast cancer, for example following mastectomy and axillary dissection in postmenopausal women, or for metastatic breast cancer, for example in men.

In another preferred embodiment of the present invention, said anti-cancer drug is temozolomide/Temodar (Schering), such as for the treatment or prophylaxis of refractory anaplastic astrocytma.

In another preferred embodiment of the present invention, said anti-cancer drug is teniposide/VM-26/Vumon (Bristol-Myers Squibb), such as for the treatment or prophylaxis of refractory childhood acute lymphoblastic leukaemia.

In another preferred embodiment of the present invention, said anti-cancer drug is testolactone/Teslac (Bristol-Myers Squibb)

In another preferred embodiment of the present invention, said anti-cancer drug is thioguanine/6-TG/Thioguanine (GlaxoSmithKline)

In another preferred embodiment of the present invention, said anti-cancer drug is thiotepa/Thioplex (Lederle Laboratories)

In another preferred embodiment of the present invention, said anti-cancer drug is topotecan/Hycamtin (GlaxoSmithKline), such as for the treatment or prophylaxis of metastatic carcinoma of the ovary, or small cell lung cancer.

In another preferred embodiment of the present invention, said anti-cancer drug is toremifene/Fareston (Orion Corp), such as for the treatment or prophylaxis of advanced breast cancer in postmenopausal women.

In another preferred embodiment of the present invention, said anti-cancer drug is Tositumomab/Bexxar (Corixa Corporation), such as for the treatment or prophylaxis of non-Hodgkin's lymphoma.

In another preferred embodiment of the present invention, said anti-cancer drug is Trastuzumab/Herceptin (Genentech, Inc), such as for the treatment or prophylaxis of metastatic breast cancer.

In another preferred embodiment of the present invention, said anti-cancer drug is tretinoin/ATRA/Vesanoid (Roche), such as for the treatment or prophylaxis of acute promyeocytic leukaemia.

In another preferred embodiment of the present invention, said anti-cancer drug is Uracil Mustard (Roberts Labs)

In another preferred embodiment of the present invention, said anti-cancer drug is valrubicin/Valstar (Medeva), such as for the treatment or prophylaxis of BCG-refractory carcinoma in situ (CIS) of the urinary bladder.

In another preferred embodiment of the present invention, said anti-cancer drug is vinblastine/Velban (Eli Lilly)

In another preferred embodiment of the present invention, said anti-cancer drug is vincristine/Oncovin (Eli Lilly)

In another preferred embodiment of the present invention, said anti-cancer drug is vinorelbine/Navelbine (GlaxoSmithKline), such as for the treatment or prophylaxis of non-small cell lung cancer, such as unresectable, advanced non-small cell lung cancer.

In another preferred embodiment of the present invention, said anti-cancer drug is zoledronate/Zometa (Novartis), such as for the treatment or prophylaxis of multiple myeloma or patients with documented bone metastases from solid tumours.

In another embodiment of the present invention one or more cancer vaccines can be administered to an individual in need thereof. The one or more cancer vaccines can in one embodiment be selected from table S.

TABLE S

| Cancer vaccines |
|---|
| NY-ESO-1 Plasmid DNA (pPJV7611) Cancer Vaccine |

| | |
|---|---|
| Conditions: | Prostate Cancer; Bladder Cancer; Non-Small Cell Lung Cancer; Esophageal Cancer; Sarcoma |
| Intervention: | Biological: NY-ESO-1 plasmid DNA Cancer Vaccine |
| | A Cancer Vaccine (CG8123) Given With and Without Cyclophosphamide for Advanced Stage Non-Small Cell Lung Cancer (NSCLC) |

| | |
|---|---|
| Conditions: | Lung Cancer; Carcinoma, Non-Small-Cell Lung |
| Interventions: | Biological: CG8123; Drug: Cyclophosphamide |

TABLE S-continued

Cancer vaccines

Vaccine Maintenance Treatment for Non-Small Cell Lung Cancer

Condition: Carcinoma, Non-Small-Cell Lung
Intervention: Biological: HyperAcute-Lung Cancer Vaccine
  Trastuzumab, Cyclophosphamide, and an Allogeneic GM-CSF-Secreting Breast Tumor
  Vaccine for the Treatment of HER-2/Neu-Overexpressing Metastatic Breast Cancer Condition: Breast Neoplasms
Interventions: Biological: Allogeneic GM-CSF-secreting breast cancer vaccine;
  Drug: Trastuzumab; Drug: Cyclophoshamide
    Dose Escalation and Efficacy Trial of GVAX ® Prostate Cancer Vaccine Condition: Prostate Cancer
Intervention: Biological: Immunotherapy allogeneic GM-CSF secreting cellular
  vaccine
    Cancer Vaccine Study for Unresectable Stage III Non-Small Cell Lung Cancer Condition: Non-Small Cell Lung Cancer
Interventions: Biological: Stimuvax; Biological: Placebo
    Vaccine Study for Surgically Resected Pancreatic Cancer Condition: Pancreatic Cancer
Intervention: Biological: HyperAcute(R)-Pancreatic Cancer Vaccine
    Low Dose Vaccine Study for Surgically Resected Pancreatic Cancer Condition: Pancreatic Cancer
Intervention: Biological: HyperAcute(R)-Pancreatic Cancer Vaccine
  Prime-Boost Dose Scheduling Trial for Human GM-CSF Gene Transduced Irradiated Prostate
    Allogeneic Cancer Vaccine (Allogeneic Prostate GVAX ®) in Patients With Hormone-
                  Refractory Prostate Cancer Condition: Prostate Cancer
Intervention: Biological: Immunotherapy allogeneic GM-CSF secreting cellular
  vaccine
    Trial of Melaxin Cancer Vaccine Plus Bacillus Calmette-Guerin (BCG) to Treat Malignant
                  Melanoma Condition: Melanoma
Intervention: Biological: Melaxin (autologous dendritoma vaccine) and BCG
    Vaccine Therapy in Treating Patients With Stage IIIB or Stage IV Bronchoalveolar Lung
                  Cancer Condition: Lung Cancer
Intervention: Drug: GVAX lung cancer vaccine
  The Use of Dendritic Cell/Tumor Fusions as a Novel Tumor Vaccine in Patients With Multiple
                  Myeloma Condition: Multiple Myeloma
Intervention: Biological: Dendritic Cell Tumor Fusion Vaccine
  Vaccine Therapy With or Without Cyclophosphamide and Doxorubicin in Women With Stage
                  IV Breast Cancer Condition: Breast Cancer
Interventions: Drug: allogeneic GM-CSF-secreting breast cancer vaccine;
  Drug: cyclophosphamide; Drug: doxorubicin hydrochloride
    Comparison of the Human Papillomavirus (HPV) Type 16 E7-Specific Immune Response
        Between a Normal Population and Patients With Cervical Lesions Condition: Cervical Cancer
Intervention:
  Trastuzumab, Cyclophosphamide, and Vaccine Therapy in Treating Patients With Metastatic
                  Breast Cancer Condition: Breast Cancer
Interventions: Drug: allogeneic GM-CSF-secreting breast cancer vaccine;
  Drug: cyclophosphamide; Drug: trastuzumab; Procedure: biopsy;
  Procedure: flow cytometry; Procedure: gene expression profiling;
  Procedure: immunoenzyme technique;
  Procedure: immunohistochemistry staining method;
  Procedure: immunologic technique TABLE S-continued Cancer vaccines Vaccine Therapy, Interferon Alfa, and Cyclophosphamide in Treating Women With Stage IV Breast Cancer

| | |
|---|---|
| Condition: | Breast Cancer |
| Interventions: | Drug: allogeneic GM-CSF-secreting breast cancer vaccine; Drug: cyclophosphamide; Drug: recombinant interferon alfa |

Safety and Immune Response to a Multi-Component Immune Based Therapy (MKC1106-MT) for Patients With Melanoma.

| | |
|---|---|
| Conditions: | Advanced Melanoma; Stage III and IV Melanoma |
| Interventions: | Biological: Low dose Peptide Cohort; Biological: High Dose Peptide Cohort |

Vaccine Treatment for Advanced Breast Cancer

| | |
|---|---|
| Condition: | Breast Cancer |
| Intervention: | Biological: HyperAcute-Breast cancer vaccine |

Vaccine Treatment for Surgically Resected Pancreatic Cancer

| | |
|---|---|
| Condition: | Pancreatic Cancer |
| Intervention: | Biological: HyperAcute-Pancreatic Cancer Vaccine |

Vaccine Treatment for Hormone Refractory Prostate Cancer

| | |
|---|---|
| Condition: | Prostate Cancer |
| Intervention: | Biological: HyperAcute-Prostate Cancer Vaccine |

GVAX in Advanced Prostate Cancer Patients Made Lymphopenic

| | |
|---|---|
| Condition: | Prostate Cancer |
| Intervention: | Biological: GM-CSF gene transduced allogeneic vaccine GVAX |

Tumor-Pulsed Dendritic Cells Used as a Tumor Vaccine

| | |
|---|---|
| Condition: | Metastatic Colorectal Cancer |
| Intervention: | Drug: Interleukin-2 (IL-2) |

Tumor Vaccine and Interferon Gamma in Treating Patients With Refractory Epithelial Ovarian Cancer

| | |
|---|---|
| Condition: | Ovarian Cancer |
| Interventions: | Drug: ALVAC-hB7.1; Drug: recombinant interferon gamma |

The Use of Dendritic Cell/Tumor Hybridomas as a Novel Tumor Vaccine in Patients With Advance Melanoma

| | |
|---|---|
| Condition: | Metastatic Melanoma |
| Intervention: | Biological: DC/tumor fusion vaccine |

Treating High Risk Leukemia With CD40 Ligand & IL-2 Gene Modified Tumor Vaccine.

| | |
|---|---|
| Condition: | Leukemia |
| Intervention: | Biological: Tumor Vaccine: CD40 LIGAND AND IL-2 GENE MODIFIED AUTOLOGOUS SKIN FIBROBLASTS AND TUMOR CELLS |

A Pilot Study of NY-ESO-1b Peptide Plus CpG 7909 and Montanide ISA-51 in Patients With Cancer.

| | |
|---|---|
| Conditions: | Cancer; Neoplasm |
| Intervention: | Biological: NY-ESO-1b peptide plus CpG 7909 and Montanide ISA-51 |

Allogeneic Cellular Vaccine 1650-G for Non-Small Cell Lung Cancer

| | |
|---|---|
| Condition: | Non-Small Cell Lung Cancer |
| Intervention: | Drug: 1650-G Vaccine |

RNA-Loaded Dendritic Cell Cancer Vaccine

| | |
|---|---|
| Condition: | Renal Cell Carcinoma |
| Intervention: | Biological: Dendritic cell vaccine |

A Phase I Cancer Vaccine Study for Patients With Metastatic Breast Cancer

| | |
|---|---|
| Condition: | Metastatic Breast Cancer |
| Intervention: | Biological: Dendritic Cell Vaccination |

A Dose-Escalation Vaccine Trial In HER2-Overexpressing Patients With High-Risk Breast Cancer

| | |
|---|---|
| Condition: | Breast Cancer |
| Intervention: | Biological: Investigational Cancer Vaccine |

Vaccine Therapy and Biological Therapy in Treating Patients With Advanced Cancer

| | |
|---|---|
| Conditions: | Breast Cancer; Cervical Cancer; Colorectal Cancer; Lung Cancer; Ovarian Cancer; Pancreatic Cancer |
| Interventions: | Drug: aldesleukin; Drug: mutant p53 peptide pulsed dendritic cell vaccine; Drug: ras peptide cancer vaccine; Drug: sargramostim; Drug: therapeutic autologous lymphocytes; |

TABLE S-continued

Cancer vaccines

Drug: therapeutic tumor infiltrating lymphocytes
Vaccine Therapy Plus Biological Therapy in Treating Adults With Metastatic Solid Tumors

| | |
|---|---|
| Conditions: | Colorectal Cancer; Endometrial Cancer; Head and Neck Cancer; Liver Cancer; Lung Cancer; Melanoma (Skin); Pancreatic Cancer; Testicular Germ Cell Tumor; Unspecified Adult Solid Tumor, Protocol Specific |
| Interventions: | Drug: DetoxPC; Drug: aldesleukin; Drug: ras peptide cancer vaccine; Drug: sargramostim |

Vaccine Therapy in Treating Patients With Colon, Pancreatic, or Lung Cancer

| | |
|---|---|
| Conditions: | Recurrent Colon Cancer; Extensive Stage Small Cell Lung Cancer; Stage III Pancreatic Cancer; Stage III Rectal Cancer; Limited Stage Small Cell Lung Cancer; Recurrent Pancreatic Cancer; Recurrent Rectal Cancer; Stage III Non-Small Cell Lung Cancer; Stage I Pancreatic Cancer; Stage II Non-Small Cell Lung Cancer; Stage IVB Pancreatic Cancer; Stage II Pancreatic Cancer; Stage III Colon Cancer; Stage IVA Pancreatic Cancer |
| Interventions: | Drug: Detox-B adjuvant; Drug: ras peptide cancer vaccine |

Vaccine Therapy Plus QS21 in Treating Patients With Advanced Pancreatic or Colorectal Cancer

| | |
|---|---|
| Conditions: | Colorectal Cancer; Pancreatic Cancer |
| Interventions: | Drug: QS21; Drug: ras peptide cancer vaccine |

Vaccine Therapy With or Without Interleukin-2 in Treating Patients With Locally Advanced or Metastatic Colorectal Cancer

| | |
|---|---|
| Condition: | Colorectal Cancer |
| Interventions: | Drug: aldesleukin; Drug: ras peptide cancer vaccine; Procedure: adjuvant therapy |

Vaccine Therapy Plus Interleukin-12 in Treating Patients With Metastatic Prostate Cancer That Has Not Responded to Hormone Therapy

| | |
|---|---|
| Condition: | Prostate Cancer |
| Interventions: | Drug: PSA prostate cancer vaccine; Drug: recombinant interleukin-12 |

Vaccine Therapy Combined With Adjuvant Chemoradiotherapy in Treating Patients With Resected Stage I or Stage II Adenocarcinoma (Cancer) of the Pancreas

| | |
|---|---|
| Condition: | Pancreatic Cancer |
| Interventions: | Drug: GVAX pancreatic cancer vaccine; Drug: fluorouracil; Procedure: adjuvant therapy; Procedure: radiation therapy |

Vaccine Therapy in Treating Patients With Recurrent Prostate Cancer

| | |
|---|---|
| Condition: | Prostate Cancer |
| Interventions: | Drug: PSA prostate cancer vaccine; Drug: incomplete Freund's adjuvant |

Vaccine Therapy and Sargramostim in Treating Patients With Non-Small Cell Lung Cancer

| | |
|---|---|
| Condition: | Lung Cancer |
| Interventions: | Drug: ras peptide cancer vaccine; Drug: sargramostim |

Vaccine Therapy in Treating Patients With Metastatic Prostate Cancer That Has Not Responded to Hormone Therapy

| | |
|---|---|
| Condition: | Prostate Cancer |
| Interventions: | Drug: PSA prostate cancer vaccine; Drug: therapeutic autologous dendritic cells |

The Development of Human Papillomavirus Type 16 E7-Specific Human Immunologic Assays in Non-HLA2 Type Human Being

| | |
|---|---|
| Condition: | Cervical Cancer |
| Intervention: | |

Vaccine Therapy in Treating Patients With Myelodysplastic Syndrome

| | |
|---|---|
| Conditions: | Leukemia; Myelodysplastic Syndromes |
| Interventions: | Drug: ras peptide cancer vaccine; Drug: sargramostim |

Clinical Trial Studying a Personalized Cancer Vaccine in Patients With Non-Metastatic Kidney Cancer

| | |
|---|---|
| Conditions: | Kidney Cancer; Renal Cell Carcinoma |
| Intervention: | Biological: HSPPC-96 |

Vaccine Therapy in Treating Women With Metastatic Breast Cancer

| | |
|---|---|
| Condition: | Breast Cancer |
| Interventions: | Drug: BCG vaccine; Drug: CD80 breast cancer vaccine; Drug: sargramostim |

Provenge ® (Sipuleucel-T) Active Cellular Immunotherapy Treatment of Metastatic Prostate TABLE S-continued Cancer vaccines Cancer After Failing Hormone Therapy Condition: Prostate Cancer
Intervention: Biological: Provenge
  NY-ESO-1 Protein With Montanide and CpG 7909 as Cancer Vaccine in Several Tumors Condition: Tumors
Intervention: Biological: NY-ESO-1 protein with CpG 7909 and Montanide
  Trial of Autologous, Hapten-Modified Vaccine, OVAX, in Patients With Relapsed Stage III or IV Ovarian Cancer Condition: Adenocarcinoma of the Ovary
Intervention: Biological: OVax: Autologous, DNP-Modified Ovarian Cancer Vaccine
  Biological Therapy in Treating Patients With Metastatic Cancer Conditions: Breast Cancer; Colorectal Cancer; Extrahepatic Bile Duct Cancer;
  Gallbladder Cancer; Gastric Cancer; Head and Neck Cancer;
  Liver Cancer; Lung Cancer; Metastatic Cancer; Ovarian Cancer;
  Pancreatic Cancer; Testicular Germ Cell Tumor
Intervention: Drug: carcinoembryonic antigen RNA-pulsed DC cancer vaccine
  Immunotherapy in Treating Patients With Metastatic Breast Cancer Condition: Breast Cancer
Intervention: Drug: carcinoembryonic antigen RNA-pulsed DC cancer vaccine
  Immunotherapy in Treating Patients With Resected Liver Metastases From Colon Cancer Conditions: Colorectal Cancer; Metastatic Cancer
Intervention: Drug: carcinoembryonic antigen RNA-pulsed DC cancer vaccine
  Four Doses of MAGE Vaccine for Patients With Squamous Cell Carcinoma of the Head and Neck Conditions: Squamous Cell Carcinoma; Head and Neck Cancer
Intervention: Biological: MAGE-A3 HPV-16 vaccine
  Trial to Compare the Routes of Administration of an Investigational, Personalized, Therapeutic Cancer Vaccine Oncophage (HSPPC-96) in Patients With Metastatic Renal Cell Carcinoma Condition: Renal Cell Carcinoma
Intervention: Biological: autologous human tumor-derived HSPPC-96
  Vaccine Therapy, Paclitaxel, and Carboplatin in Treating Patients Who Are Undergoing Surgery for Stage III or Stage IV Ovarian Cancer, Primary Peritoneal Cancer, or Fallopian Tube Cancer Conditions: Fallopian Tube Cancer; Ovarian Cancer; Peritoneal Cavity Cancer
Interventions: Drug: MAGE-A1, Her-2/neu, FBP peptides ovarian cancer vaccine;
  Drug: carboplatin; Drug: paclitaxel; Drug: tetanus toxoid helper peptide;
  Procedure: conventional surgery
  Vaccine Therapy in Treating Patients With Stage D0 Prostate Cancer Condition: Prostate Cancer
Interventions: Drug: BCG vaccine; Drug: placebo;
  Drug: prostate cancer vaccine ONY-P1
  Oregovomab With or Without Cyclophosphamide in Treating Patients With Stage III or Stage IV Ovarian Epithelial Cancer, Fallopian Tube Cancer, or Primary Peritoneal Cancer That Responded to Second-Line Chemotherapy Conditions: Fallopian Tube Cancer; Ovarian Cancer; Peritoneal Cavity Cancer
Interventions: Drug: cyclophosphamide; Drug: oregovomab;
  Procedure: adjuvant therapy; Procedure: immunoenzyme technique;
  Procedure: laboratory biomarker analysis
  Vaccination With Dendritic Cell/Tumor Fusions With Autologous Stem Cell Transplants in Patients With Multiple Myeloma Condition: Multiple Myeloma
Intervention: Biological: Dendritic Cell Tumor Fusion
  Vaccine Therapy in Treating Patients With Stage III or Stage IV Ovarian Epithelial Cancer Condition: Ovarian Cancer
Interventions: Drug: BCG vaccine; Drug: autologous tumor cell vaccine;
  Drug: carboplatin; Drug: cisplatin; Drug: cyclophosphamide;
  Drug: dinitrophenyl; Drug: paclitaxel; Procedure: surgical procedure
  Long Term Follow Up Of Patients Who Have Received Gene Therapy Or Gene Marked Products Conditions: Severe Combined Immunodeficiency; Malignancy, Hematologic;
  Neuroblastoma; Neoplasm; Mucopolysaccharidosis I
Intervention: Procedure: Venipuncture TABLE S-continued Cancer vaccines Cytotoxicity Induced by Tumor Lysate Pulsed Dendritic Cells Against Autologous Hepatocellular Carcinoma Cells Condition: Carcinoma, Hepatocellular
Intervention: Biological: DC vaccine Vaccine Therapy in Treating Patients With Non-Small Cell Lung Cancer (NSCLC) Stages IIIB/IV Condition: Non-Small-Cell Lung Cancer (NSCLC) Stage IIIb/IV
Intervention: Biological: Recombinant Human rEGF-P64K/Montanide Vaccine GM-CSF Vaccinations After Allogeneic Blood Stem Cell Transplantation in Patients With Advanced Myeloid Malignancies Conditions: Myelodysplastic Syndrome RAEB-I or RAEB-II; Refractory Acute Myeloid Leukemia; Refractory CML Myeloid Blast Crisis
Intervention: Biological: GM-CSF secreting leukemia vaccine Phase I Study of CDX-1307, hCG-B Vaccine, for Patients With Incurable, Locally Advanced or Metastatic Breast, Colorectal, Pancreatic, Bladder or Ovarian Cancer Conditions: Breast Cancer; Colorectal Cancer; Pancreatic Cancer; Bladder Cancer; Ovarian Cancer
Intervention: Biological: CDX-1307

Study of NY-ESO-1 ISCOMATRIX ® in Patients With Measurable Stage III or IV Melanoma Condition: Melanoma
Interventions: Biological: NY-ESO-1 ISCOMATRIX ® vaccine; Drug: Cyclophosphamide Vaccine Therapy With or Without Donor Lymphocyte Infusion in Treating Patients With Acute Myeloid Leukemia, Acute Lymphoblastic Leukemia, or Multiple Myeloma Undergoing Donor Stem Cell Transplant Conditions: Leukemia; Multiple Myeloma and Plasma Cell Neoplasm
Interventions: Procedure: peripheral blood lymphocyte therapy; Procedure: tumor cell-derivative vaccine therapy Phase II Feasibility Study of Dendritic Cell Vaccination for Newly Diagnosed Glioblastoma Multiforme Condition: Glioblastoma Multiforme
Interventions: Biological: Autologous Dendritic Cell; Drug: Temozolomide; Procedure: Radiotherapy; Biological: Dendritic Cell Vaccine Study of NY-ESO-1 ISCOMATRIX ® in Patients With High-Risk, Resected Melanoma Condition: Melanoma
Interventions: Biological: NY-ESO-1 ISCOMATRIX ®; Biological: ISCOMATRIX ® adjuvant A Study of CDX-1307, in Patients With Incurable Breast, Colorectal, Pancreatic, Ovarian or Bladder Cancer Conditions: Breast Cancer; Colorectal Cancer; Pancreatic Cancer; Bladder Cancer; Ovarian Cancer
Intervention: Biological: CDX1307

Safety Study of NY-ESO-1 Protein Vaccine to Treat Cancer Expressing NY-ESO-1

Condition: Neoplasms
Intervention: Biological: protein vaccination

Immunotherapy With TG4010 in Patients With Advanced Non-Small Cell Lung Cancer

Condition: Carcinoma, Non-Small-Cell Lung
Intervention: Biological: MVA-MUC1-IL2

A Phase I Study of NY-ESO-1 Overlapping Peptides (OLP4) With or Without Montanide Vaccination of Epithelial Ovarian Cancer (EOC), Fallopian Tube, or Primary Peritoneal Cancer Patients in Second or Third Remission Conditions: Epithelial Ovarian Cancer; Fallopian Tube Cancer; Primary Peritoneal Cancer
Interventions: Biological: NY-ESO-1 OLP4; Biological: NY-ESO-1 OLP4 + Montanide A Study of ZYC300 Administered With Cyclophosphamide Pre-Dosing Conditions: Breast Cancer; Ovarian Cancer; Prostate Cancer; Colon Cancer; Renal Cancer; Kidney Cancer
Intervention: Drug: Cyclophosphamide To Evaluate Sipuleucel-T Manufactured With Different Concentrations of PA2024 Antigen Condition: Prostate Cancer
Intervention: Biological: Sipuleucel-T TABLE S-continued Cancer vaccines A Phase II Trial of CG 8020 and CG 2505 in Patients With Nonresectable or Metastatic Pancreatic Cancer

| | |
|---|---|
| Conditions: | Metastatic Pancreatic Cancer; Nonresectable Pancreatic Cancer |
| Intervention: | Biological: CG 8020 and CG 2505 |

Phase II Trial of Allovectin-7 ® for Head and Neck Cancer

| | |
|---|---|
| Conditions: | Head and Neck Cancer; Squamous Cell Carcinoma of the Oral Cavity or Oropharynx; Head and Neck Neoplasms; Carcinoma of the Head and Neck |
| Intervention: | Genetic: Allovectin-7 ® |

Vaccine Therapy Compared With Interferon Alfa in Treating Patients With Stage III Melanoma

| | |
|---|---|
| Condition: | Melanoma (Skin) |
| Interventions: | Drug: BCG vaccine; Drug: autologous tumor cell vaccine; Drug: cyclophosphamide; Drug: recombinant interferon alfa; Procedure: chemotherapy |

Vaccine Therapy in Treating Patients With Stage III, Stage IV, or Relapsed Non-Small Cell Lung Cancer Treated With First-Line Chemotherapy

| | |
|---|---|
| Condition: | Lung Cancer |
| Intervention: | Drug: gp96-Ig fusion protein-expressing non-small cell lung cancer cell vaccine |

Vaccine Therapy Before and After Dose-Intensive Induction Chemotherapy Plus Immune-Depleting Chemotherapy in Treating Patients With Metastatic Breast Cancer

| | |
|---|---|
| Condition: | Breast Cancer |
| Interventions: | Drug: cyclophosphamide; Drug: doxorubicin hydrochloride; Drug: filgrastim; Drug: fludarabine phosphate; Drug: paclitaxel; Drug: recombinant fowlpox-CEA(6D)/TRICOM vaccine; Drug: recombinant vaccinia-CEA(6D)-TRICOM vaccine; Drug: sargramostim; Drug: therapeutic autologous lymphocytes |

Monoclonal Antibody Therapy in Treating Patients With Ovarian Epithelial Cancer, Melanoma, Acute Myeloid Leukemia, Myelodysplastic Syndrome, or Non-Small Cell Lung Cancer

| | |
|---|---|
| Conditions: | Leukemia; Lung Cancer; Melanoma (Skin); Myelodysplastic Syndromes; Myelodysplastic/Myeloproliferative Diseases; Ovarian Cancer |
| Intervention: | Drug: ipilimumab |

Safety and Immunological Response Rate Study of THERATOPE ® Vaccine in Metastatic Breast Cancer Patients

| | |
|---|---|
| Condition: | Breast Neoplasms |
| Intervention: | Drug: THERATOPE ® vaccine |

Immune Response in Patients Who Have Undergone Vaccine Therapy for Stage III or Stage IV Breast Cancer That Overexpresses HER2

| | |
|---|---|
| Condition: | Breast Cancer |
| Interventions: | Drug: HER-2/neu intracellular domain protein; Procedure: biopsy; Procedure: flow cytometry; Procedure: immunohistochemistry staining method; Procedure: immunological diagnostic method; Procedure: laboratory biomarker analysis |

Novel Adjuvants for Peptide-Based Melanoma Vaccines

| | |
|---|---|
| Condition: | Melanoma |
| Intervention: | Biological: MDX-CTLA4 Antibody; Tyrosinase/gp100/MART-1 Peptides Melanoma Vaccine |

An Open Label Study of a Peptide Vaccine in Patients With Stage III Colon Cancer

| | |
|---|---|
| Conditions: | Colonic Neoplasms; Colorectal Neoplasms |
| Intervention: | Biological: EP2101 |

An Open Label Study of a Peptide Vaccine in Patients With Stage IIb or IIIa Non-Small Cell Lung Cancer

| | |
|---|---|
| Conditions: | Carcinoma, Non-Small-Cell Lung; Lung Neoplasm |
| Intervention: | Biological: EP2101 |

Dendritic Cell Vaccine for Head and Neck Cancer

| | |
|---|---|
| Condition: | Squamous Cell Carcinoma of Head and Neck |
| Intervention: | Biological: dendritic cell vaccine |

IMA901 in Advanced Renal Cell Carcinoma Patients With Measurable Disease

| | |
|---|---|
| Condition: | Renal Cell Carcinoma |
| Interventions: | Drug: Endoxana, IMA901, Leukine; Drug: IMA901 and Leukine |

TABLE S-continued

Cancer vaccines

PROSTVAC ®-VF/TRICOM ™ Vaccine for the Treatment of Metastatic Prostate Cancer After Failing Hormone Therapy Condition: Prostate Cancer
Intervention: Biological: PROSTVAC ®-VF/TRICOM ™
NY-ESO-1 Protein Vaccine With Imiquimod in Melanoma (Adjuvant Setting)

Condition: Malignant Melanoma
Interventions: Biological: NY-ESO-1 protein; Drug: Imiquimod
Immunotherapy of Recurrent Cervical Cancers Using Dendritic Cells (DCs)

Condition: Cervical Cancer
Intervention: Biological: HPV16 E7 peptide-pulsed autologous DCs
Administration of Autologous Dendritic Cells (DCs) Infected With an Adenovirus Expressing Her-2

Condition: Breast Neoplasms
Intervention: Biological: CD34+ derived DCs
A Pilot Study of Tumor Cell Vaccine for High-Risk Solid Tumor Patients Following Stem Cell Transplantation Conditions: Sarcoma; Neuroblastoma; Wilm's Tumor
Interventions: Biological: tumor lysate-pulsed dendritic cell vaccine; Other: hematopoietic stem cell transplantation (HSCT)
Dendritic Cells in Lung Cancer Condition: Non Small Cell Lung Cancer
Intervention: Biological: Allogeneic Tumour Lysate (MelCancerVac)
AdV-tk Therapy With Surgery and Chemoradiation for Pancreas Cancer Conditions: Pancreatic Adenocarcinoma; Pancreatic Cancer
Interventions: Biological: AdV-tk; Drug: Valacyclovir
Phase 2a Study of AdV-tk With Standard Radiation Therapy for Malignant Glioma Conditions: Malignant Glioma; Glioblastoma Multiforme; Anaplastic Astrocytoma
Interventions: Biological: AdV-tk; Drug: Valacyclovir
Procurement of Follicular B Cell Lymphoma Cells for the Purpose of Possible Use in Future Clinical Trials Condition: Non-Hodgkin's Lymphoma
Intervention: Procedure: Procurement of Follicular B Cell Lymphoma Cells
Safety and Immunogenicity of CHP-HER2 and CHP-NY-ESO-1 Protein With OK-432 in Antigen-Expressing Cancers Conditions: Esophageal Cancer; Lung Cancer; Stomach Cancer; Breast Cancer; Ovarian Cancer
Intervention: Drug: CHP-HER2, CHP-NY-ESO-1
Autologous PBHCT Followed by Dendritic Cell p53 Vaccination & Adoptive T Cell Transfer Condition: Small Cell Lung Cancer
Intervention: Biological: PBHCT followed by Dendritic Vaccination and T Cell transfer
Vaccination With Tetanus and KLH to Assess Immune Responses.

Condition: Cancer
Intervention: Biological: Tetanus and KLH
Surgical Resection With Gliadel Wafer Followed by Dendritic Cells Vaccination for Malignant Glioma Patients Condition: Malignant Glioma
Intervention: Biological: Dendritic cell Vaccine
Active Immunization of Patients With Carcinoma of Oral Cavity or Oropharynx With Autologous Dendritic Cells Transfected With DNA From Autologous Tumor Conditions: Primary Advanced Carcinoma of the Oral Cavity or Oropharynx; Squamous Cell Carcinoma of the Head and Neck
Intervention: Biological: autologous monocyte-derived dendritic cells (DC) transfected with DNA
Vaccination for the Treatment of Previously Untreated or Relapsed Follicular Lymphoma Condition: Follicular Lymphoma
Intervention: Biological: Lethally Irradiated Lymphoma cells with GM-CSF K562 Cells
Treatment of B-CLL With Human IL-2 and CD40 Ligand and Plasmid Gene Modified Autologous Tumor Cells Conditions: Leukemia; Leukemia, B-Cell, Chronic
Intervention: Biological: IL-2 AND HUMAN CD40 LIGAND PLASMID GENE MODIFIED AUTOLOGOUS TUMOR CELLS

TABLE S-continued

Cancer vaccines

Gene Modified Allogeneic Neuroblastoma Cells For Treatment of Relapsed/Refractory Neuroblastoma

| | |
|---|---|
| Condition: | Neuroblastoma |
| Intervention: | Drug: Interleukin-2 |

Immune Responses To Antigen-Bearing Dendritic Cells in Patients With Malignancy

| | |
|---|---|
| Condition: | Melanoma |
| Intervention: | Biological: dendritic cell vaccine |

Vaccine Therapy in Treating Patients With Stage IIIB or Stage IV Breast Cancer in Remission

| | |
|---|---|
| Condition: | Breast Cancer |
| Interventions: | Drug: recombinant modified vaccinia Ankara-5T4 vaccine; Procedure: adjuvant therapy; Procedure: recombinant viral vaccine therapy |

Denileukin Diftitox in Treating Patients With Advanced Refractory Ovarian Epithelial Cancer, Primary Peritoneal Cavity Cancer, or Fallopian Tube Cancer

| | |
|---|---|
| Conditions: | Fallopian Tube Cancer; Ovarian Cancer; Peritoneal Cavity Cancer |
| Intervention: | Drug: denileukin diftitox |

Vaccination Priming and Vaccine Boosting Trial of Allogeneic Human GM-CSF Gene Transduced Irradiated Prostate Cancer Cell Vaccines (GVAX ® Vaccine for Prostate Cancer)

| | |
|---|---|
| Condition: | Prostate Cancer |
| Intervention: | Biological: Immunotherapy allogeneic GM-CSF secreting cellular vaccine |

Vaccine Therapy With or Without Docetaxel in Treating Patients With Metastatic Prostate Cancer

| | |
|---|---|
| Condition: | Prostate Cancer |
| Interventions: | Drug: docetaxel; Drug: recombinant fowlpox-prostate apecific antigen vaccine; Drug: recombinant vaccinia prostate-specific antigen vaccine; Drug: recombinant vaccinia-B7.1 vaccine; Drug: sargramostim |

Vaccine Therapy and Cyclophosphamide in Treating Patients Who Have Undergone Surgery for Liver Metastases Due to Colorectal Cancer

| | |
|---|---|
| Conditions: | Colorectal Cancer; Metastatic Cancer |
| Interventions: | Drug: GM-K562 cell vaccine; Drug: allogeneic tumor cell vaccine; Drug: cyclophosphamide; Procedure: gene expression analysis; Procedure: immunoenzyme technique; Procedure: immunologic technique; Procedure: laboratory biomarker analysis; Procedure: protein analysis |

Alpha-Type-1 Dendritic Cell-Based Vaccines in Patients With Metastatic Colorectal Cancer

| | |
|---|---|
| Condition: | Metastatic Colorectal Cancer |
| Interventions: | Biological: DC-based vaccine; Biological: DC-based vaccine; Biological: DC-based vaccine |

Vaccine Therapy With or Without Sargramostim in Treating Patients With Metastatic Prostate Cancer

| | |
|---|---|
| Conditions: | Recurrent Prostate Cancer; Stage IV Prostate Cancer |
| Interventions: | Drug: fowlpox-PSA-TRICOM vaccine; Drug: recombinant fowlpox GM-CSF vaccine; Drug: sargramostim; Drug: vaccinia-PSA-TRICOM vaccine; Procedure: biological therapy; Procedure: non-specific immune-modulator therapy; Procedure: recombinant viral vaccine; Procedure: vaccine therapy |

Vaccine Therapy in Treating Patients With Breast Cancer

| | |
|---|---|
| Condition: | Breast Cancer |
| Interventions: | Drug: AE37 peptide/GM-CSF vaccine; Drug: GP2 peptide/GM-CSF vaccine; Drug: sargramostim |

Vaccine Therapy and Radiation Therapy in Treating Patients With Carcinoembryonic Antigen-Positive Solid Tumors That Have Metastasized to the Liver

| | |
|---|---|
| Conditions: | Breast Cancer; Colorectal Cancer; Lung Cancer; Metastatic Cancer; Pancreatic Cancer; Unspecified Adult Solid Tumor, Protocol Specific |
| Interventions: | Drug: recombinant fowlpox GM-CSF vaccine adjuvant; Drug: recombinant fowlpox-CEA(6D)/TRICOM vaccine; Drug: recombinant vaccinia-CEA(6D)-TRICOM vaccine; Procedure: radiation therapy |

Vaccine Therapy in Treating Patients With Kidney Cancer

| | |
|---|---|
| Condition: | Kidney Cancer |
| Interventions: | Drug: autologous tumor cell vaccine; Drug: sargramostim; Drug: therapeutic autologous dendritic cells |

TABLE S-continued

Cancer vaccines

Vaccine Therapy and GM-CSF in Treating Patients With Prostate Cancer That Progressed After Surgery and/or Radiation Therapy

| | |
|---|---|
| Condition: | Prostate Cancer |
| Interventions: | Drug: bicalutamide; Drug: fowlpox-PSA-TRICOM vaccine; Drug: goserelin; Drug: sargramostim; Drug: vaccinia-PSA-TRICOM vaccine |

Radiation Therapy With or Without Vaccine Therapy in Treating Patients With Prostate Cancer

| | |
|---|---|
| Condition: | Prostate Cancer |
| Interventions: | Drug: aldesleukin; Drug: recombinant fowlpox-prostate apecific antigen vaccine; Drug: recombinant vaccinia prostate-specific antigen vaccine; Drug: recombinant vaccinia-B7.1 vaccine; Drug: sargramostim; Procedure: brachytherapy; Procedure: radiation therapy |

Vaccine Therapy, Chemotherapy, and Radiation Therapy in Treating Patients With Stage III Non-Small Cell Lung Cancer That Cannot Be Removed With Surgery

| | |
|---|---|
| Condition: | Lung Cancer |
| Interventions: | Drug: carboplatin; Drug: paclitaxel; Drug: recombinant fowlpox GM-CSF vaccine adjuvant; Drug: recombinant fowlpox-CEA(6D)/TRICOM vaccine; Drug: recombinant vaccinia-CEA(6D)-TRICOM vaccine; Procedure: radiation therapy |

Vaccine Therapy With or Without Sargramostim in Treating Patients With Advanced or Metastatic Cancer

| | |
|---|---|
| Conditions: | Breast Cancer; Colorectal Cancer; Gallbladder Cancer; Gastric Cancer; Head and Neck Cancer; Liver Cancer; Ovarian Cancer; Pancreatic Cancer; Testicular Germ Cell Tumor |
| Interventions: | Drug: recombinant fowlpox GM-CSF vaccine adjuvant; Drug: recombinant fowlpox-CEA(6D)/TRICOM vaccine; Drug: sargramostim |

Vaccine Therapy Combined With Interleukin-2 and Interferon Alfa in Treating Patients With Metastatic Renal Cell Carcinoma (Kidney Cancer)

| | |
|---|---|
| Condition: | Kidney Cancer |
| Interventions: | Drug: aldesleukin; Drug: autologous tumor cell vaccine; Drug: recombinant interferon alfa; Drug: therapeutic autologous dendritic cells |

Samarium Sm 153 Lexidronam Pentasodium With or Without Vaccine Therapy and GM-CSF in Treating Patients With Prostate Cancer and Bone Metastases

| | |
|---|---|
| Conditions: | Metastatic Cancer; Pain; Prostate Cancer |
| Interventions: | Drug: recombinant fowlpox-TRICOM vaccine; Drug: recombinant vaccinia-TRICOM vaccine; Drug: samarium Sm 153 lexidronam pentasodium; Drug: sargramostim |

Vaccine Therapy in Treating Patients With Progressive or Locally Recurrent Prostate Cancer

| | |
|---|---|
| Condition: | Prostate Cancer |
| Interventions: | Drug: fowlpox-PSA-TRICOM vaccine; Drug: recombinant fowlpox GM-CSF vaccine adjuvant; Drug: vaccinia-PSA-TRICOM vaccine |

Vaccine Therapy, MDX-010, and GM-CSF in Treating Patients With Metastatic Prostate Cancer

| | |
|---|---|
| Condition: | Prostate Cancer |
| Interventions: | Drug: fowlpox-PSA-TRICOM vaccine; Drug: ipilimumab; Drug: sargramostim; Drug: vaccinia-PSA-TRICOM vaccine |

Prospective Trial of Vaccine Responses in Childhood Cancer Survivors

| | |
|---|---|
| Conditions: | Childhood Cancer; Multiple Diseases |
| Interventions: | Biological: Immunizations; Biological: Immunizations |

Vaccine Therapy in Treating Patients With Colorectal Cancer Metastatic to the Liver

| | |
|---|---|
| Conditions: | Colorectal Cancer; Metastatic Cancer |
| Interventions: | Drug: monoclonal antibody 11D10 anti-idiotype vaccine; Drug: monoclonal antibody 3H1 anti-idiotype vaccine; Procedure: adjuvant therapy |

Flutamide With or Without Vaccine Therapy in Treating Patients With Nonmetastatic Prostate Cancer

| | |
|---|---|
| Condition: | Prostate Cancer |
| Interventions: | Drug: flutamide; Drug: recombinant fowlpox-prostate apecific antigen vaccine; Drug: recombinant vaccinia prostate-specific antigen vaccine; Drug: sargramostim |

DNP-Modified Autologous Tumor Cell Vaccine for Resectable Non-Small Cell Lung Cancer

| | |
|---|---|
| Condition: | Non-Small Cell Lung Cancer - Completely Resectable |
| Intervention: | Biological: L-Vax: Autologous, DNP-Modified NSCLC Vaccine |

TABLE S-continued

Cancer vaccines

Monoclonal Anybody Therapy and/or Vaccine Therapy in Treating Patients With Locally Advanced or Metastatic Colorectal Cancer Condition: Colorectal Cancer
Interventions: Drug: BCG vaccine; Drug: alum adjuvant; Drug: monoclonal antibody 105AD7 anti-idiotype vaccine Vaccine Therapy With Either Neoadjuvant or Adjuvant Chemotherapy and Adjuvant Radiation Therapy in Treating Women With p53-Overexpressing Stage III Breast Cancer Condition: Breast Cancer
Interventions: Drug: autologous dendritic cell-adenovirus p53 vaccine;
Drug: cyclophosphamide; Drug: doxorubicin hydrochloride;
Drug: paclitaxel; Procedure: adjuvant therapy;
Procedure: conventional surgery; Procedure: neoadjuvant therapy;
Procedure: radiation therapy Vaccine Therapy in Treating Patients With Pancreatic Cancer That Has Been Removed by Surgery Conditions: Anorexia; Fatigue; Pain; Pancreatic Cancer; Psychosocial Effects/Treatment
Intervention: Drug: sargramostim plasmid DNA pancreatic tumor cell vaccine Vaccine Therapy of Prostate Cancer Patients With Recombinant Soluble Prostate-Specific Membrane Antigen (Rs-PSMA) Plus the Immunological Adjuvant Alhydrogel Condition: Prostate Cancer
Intervention: Biological: rsPSMA protein plus Alhydrogel ® vaccine Combination Chemotherapy, Radiation Therapy, and Vaccine Therapy in Treating Patients With Limited-Stage Small Cell Lung Cancer Condition: Lung Cancer
Interventions: Drug: cisplatin; Drug: etoposide; Drug: monoclonal antibody 11D10 anti-idiotype vaccine; Drug: monoclonal antibody GD2 anti-idiotype vaccine; Procedure: radiation therapy Vaccine Therapy in Treating Patients With Previously Treated Stage II or Stage III Breast Cancer Condition: Breast Cancer
Interventions: Drug: CpG oligodeoxynucleotide; Drug: HER-2/neu peptide vaccine;
Drug: MUC-1 peptide vaccine; Drug: incomplete Freund's adjuvant;
Drug: sargramostim; Procedure: immunoenzyme technique;
Procedure: immunologic technique PSA Vaccine Therapy in Treating Patients With Advanced Prostate Cancer Condition: Prostate Cancer
Interventions: Drug: fowlpox virus vaccine vector; Drug: recombinant vaccinia prostate-specific antigen vaccine Phase II Study of a HER2/Neu Vaccine for Stage IV HER2/Neu Positive Breast Cancer Patients on Herceptin Condition: Breast Cancer
Intervention: Biological: HER2 Intracellular Domain Peptide-Based Vaccine Vaccine Therapy in Treating Patients With Metastatic Solid Tumors Condition: Unspecified Adult Solid Tumor, Protocol Specific
Interventions: Drug: recombinant fowlpox-B7.1 vaccine; Drug: recombinant fowlpox-TRICOM vaccine Ovarian Dendritic Cell Vaccine Trial Condition: Ovarian Cancer
Interventions: Biological: Ontak DC; Biological: DC vaccination; Drug: Ontak Vaccine Therapy and Sargramostim With or Without Docetaxel in Treating Patients With Metastatic Lung Cancer or Metastatic Colorectal Cancer Conditions: Colorectal Cancer; Lung Cancer
Interventions: Drug: docetaxel; Drug: recombinant fowlpox-CEA(6D)/TRICOM vaccine;
Drug: recombinant vaccinia-CEA(6D)-TRICOM vaccine;
Drug: sargramostim; Procedure: biological therapy;
Procedure: chemotherapy; Procedure: colony-stimulating factor therapy;
Procedure: cytokine therapy; Procedure: non-specific immune-modulator therapy; Procedure: recombinant viral vaccine;
Procedure: vaccine therapy Phase I Trial of TGFB2-Antisense-GMCSF Gene Modified Autologous Tumor Cell (TAG) Vaccine for Advanced Cancer Condition: Advanced Metastatic Carcinoma
Intervention:

TABLE S-continued

Cancer vaccines

Vaccination of Patients With Breast Cancer With Dendritic Cell/Tumor Fusions and IL-12

| | |
|---|---|
| Condition: | Breast Cancer |
| Interventions: | Biological: Dendritic Cell/Tumor Fusion Vaccine; Drug: Interleukin-12; Drug: Interleukin-12 |

Vaccine Therapy and Interleukin-2 After Combination Chemotherapy in Treating Patients With Relapsed or De Novo Stage II, Stage III, or Stage IV Mantle Cell Lymphoma

| | |
|---|---|
| Condition: | Lymphoma |
| Interventions: | Drug: GM.CD40L cell vaccine; Drug: aldesleukin; Drug: autologous tumor cell vaccine; Drug: cyclophosphamide; Drug: cytarabine; Drug: dexamethasone; Drug: doxorubicin hydrochloride; Drug: methotrexate; Drug: prednisone; Drug: vincristine |

Vaccine Therapy and OPT-821 or OPT-821 Alone in Treating Patients With Ovarian Epithelial Cancer, Fallopian Tube Cancer, or Primary Peritoneal Cancer in Complete Remission

| | |
|---|---|
| Conditions: | Fallopian Tube Cancer; Ovarian Cancer; Peritoneal Cavity Cancer |
| Interventions: | Drug: immunological adjuvant OPT-821; Drug: polyvalent antigen-KLH conjugate vaccine |

Vaccine Therapy Plus Interleukin-2 in Treating Women With Stage IV, Recurrent, or Progressive Breast or Ovarian Cancer

| | |
|---|---|
| Conditions: | Breast Cancer; Ovarian Cancer |
| Interventions: | Drug: aldesleukin; Drug: p53 peptide vaccine; Procedure: in vitro-treated peripheral blood stem cell transplantation |

Vaccine Therapy in Treating Patients With Stage II, Stage III, or Stage IV Ovarian Epithelial, Fallopian Tube, or Peritoneal Cancer

| | |
|---|---|
| Conditions: | Fallopian Tube Cancer; Ovarian Cancer; Peritoneal Cavity Cancer |
| Interventions: | Drug: fowlpox-NY-ESO-1 vaccine; Drug: recombinant vaccinia-NY-ESO-1 vaccine; Procedure: adjuvant therapy |

Vaccine To Prevent Cervical Intraepithelial Neoplasia or Cervical Cancer in Younger Healthy Participants

| | |
|---|---|
| Conditions: | Cervical Cancer; Precancerous/Nonmalignant Condition |
| Intervention: | Drug: human papillomavirus 16/18 L1 virus-like particle/AS04 vaccine |

Vaccine Therapy After Surgery in Treating Patients With Stage IB, Stage II, or Stage IIIA Non-Small Cell Lung Cancer

| | |
|---|---|
| Condition: | Lung Cancer |
| Interventions: | Drug: MAGE-A3 peptide vaccine; Drug: SB-AS15 adjuvant; Drug: placebo |

To Immunize Pts w Extensive Stage SCLC Combined w Chemo w or w/oAll Trans Retinoic Acid

| | |
|---|---|
| Condition: | Small Cell Lung Cancer |
| Interventions: | Other: Observation; Biological: Drug: Ad.p53-DC vaccines; Drug: Ad.p53-DC vaccines + ATRA |

Vaccine Therapy and GM-CSF in Treating Patients With Acute Myeloid Leukemia, Myelodysplastic Syndromes, Non-Small Cell Lung Cancer, or Mesothelioma

| | |
|---|---|
| Conditions: | Leukemia; Lung Cancer; Malignant Mesothelioma; Myelodysplastic Syndromes; Peritoneal Cavity Cancer |
| Interventions: | Drug: WT-1 analog peptide vaccine; Drug: incomplete Freund's adjuvant; Drug: sargramostim; Procedure: flow cytometry; Procedure: immunoenzyme technique; Procedure: polymerase chain reaction |

Vaccine Therapy and Interleukin-2 in Treating Patients With Stage IV Kidney Cancer

| | |
|---|---|
| Condition: | Kidney Cancer |
| Interventions: | Drug: adenovirus B7-1; Drug: aldesleukin; Drug: autologous tumor cell vaccine; Procedure: conventional surgery |

Vaccine Therapy Plus QS21 in Treating Patients With Prostate Cancer

| | |
|---|---|
| Condition: | Prostate Cancer |
| Interventions: | Drug: MUC-2-Globo H-KLH conjugate vaccine; Drug: QS21 |

Vaccine Therapy in Treating Patients With Stage II or Stage III Colon Cancer That Has Been Removed During Surgery

| | |
|---|---|
| Condition: | Colorectal Cancer |
| Interventions: | Drug: BCG vaccine; Drug: autologous tumor cell vaccine; Drug: fluorouracil; Drug: leucovorin calcium; Procedure: adjuvant therapy |

TABLE S-continued

Cancer vaccines

Vaccine Therapy and GM-CSF in Treating Patients With Stage III or Stage IV Breast Cancer or Ovarian Cancer

Conditions: Breast Cancer; Ovarian Cancer
Interventions: Drug: pNGVL3-hICD vaccine; Drug: sargramostim;
Procedure: adjuvant therapy; Procedure: biopsy;
Procedure: flow cytometry; Procedure: immunoenzyme technique;
Procedure: immunologic technique;
Procedure: protein expression analysis

Gemcitabine and Capecitabine With or Without Vaccine Therapy in Treating Patients With Locally Advanced or Metastatic Pancreatic Cancer

Condition: Pancreatic Cancer
Interventions: Drug: capecitabine; Drug: gemcitabine hydrochloride;
Drug: sargramostim; Drug: telomerase peptide vaccine GV1001

Vaccine Therapy in Treating Women With Metastatic Breast Cancer

Condition: Breast Cancer
Interventions: Drug: Detox-B adjuvant; Drug: THERATOPE STn-KLH vaccine;
Drug: cyclophosphamide; Drug: keyhole limpet hemocyanin

Phase II Study of Adenovirus/PSA Vaccine in Men With Hormone - Refractory Prostate Cancer

Condition: Hormone Refractory Prostate Cancer
Intervention: Biological: ADENOVIRUS/PSA VACCINE

Multipeptide Vaccine for Advanced Breast Cancer

Conditions: Breast Neoplasm; Breast Cancer; Cancer of the Breast;
Carcinoma, Ductal
Intervention: Biological: hTERT/Survivin Multi-Peptide Vaccine

Vaccine Therapy Plus Biological Therapy in Treating Patients With Relapsed Prostate Cancer

Condition: Prostate Cancer
Interventions: Drug: Globo H-GM2-Lewis-y-MUC1-32-mer-TF(c)-Tn(c)-KLH conjugate
vaccine; Drug: QS21

Vaccine Therapy Plus Biological Therapy in Treating Patients With Prostate Cancer

Condition: Prostate Cancer
Interventions: Drug: GPI-0100; Drug: MUC-2-Globo H-KLH conjugate vaccine

Vaccine Therapy in Treating Patients With Stage IIIC or Stage IV Malignant Melanoma

Condition: Melanoma (Skin)
Interventions: Drug: GM.CD40L cell vaccine; Drug: autologous tumor cell vaccine

Phase II Study of Adenovirus/PSA Vaccine in Men With Recurrent Prostate Cancer After Local Therapy APP21

Condition: Recurrent Prostate Cancer
Intervention: Biological: Adenovirus/PSA Vaccine

Vaccine Therapy in Treating Patients With Metastatic Kidney Cancer

Condition: Kidney Cancer
Interventions: Drug: aldesleukin; Drug: incomplete Freund's adjuvant;
Drug: sargramostim; Drug: von Hippel-Lindau peptide vaccine

Vaccine Therapy in Treating Patients With Ovarian Epithelial or Primary Peritoneal Cancer

Conditions: Ovarian Cancer; Peritoneal Cavity Cancer
Interventions: Drug: incomplete Freund's adjuvant;
Drug: ovarian cancer peptide vaccine; Drug: sargramostim;
Drug: tetanus toxoid helper peptide; Procedure: adjuvant therapy

Vaccine Therapy in Treating Patients With Metastatic Cancer

Conditions: Lung Cancer; Adult Soft Tissue Sarcoma; Colorectal Cancer;
Bone Cancer; Ovarian Sarcoma; Melanoma; Colon Cancer;
Rectal Cancer; Breast Cancer; Eye Cancer; Uterine Sarcoma
Interventions: Drug: interleukin-2; Drug: MAGE-12 peptide vaccine;
Drug: Montanide ISA-51

A Novel Vaccine for the Treatment of MUC1-Expressing Tumor Malignancies

Conditions: Multiple Myeloma; Tumors
Intervention: Biological: Peptide Vaccine (MUC-1)

Vaccine Therapy in Treating Patients With Transitional Cell Cancer of the Bladder

Condition: Bladder Cancer
Interventions: Drug: BCG vaccine; Drug: NY-ESO-1 peptide vaccine;
Drug: sargramostim TABLE S-continued Cancer vaccines Vaccine Therapy and Chemotherapy With or Without Tetanus Toxoid Compared With
Chemotherapy Alone in Treating Patients With Metastatic Colorectal Cancer

| | |
|---|---|
| Condition: | Colorectal Cancer |
| Interventions: | Drug: ALVAC-CEA-B7.1 vaccine; Drug: fluorouracil; Drug: irinotecan hydrochloride; Drug: leucovorin calcium; Drug: tetanus toxoid |

Vaccine Therapy in Treating Patients Who Are Undergoing Surgery for Stage IB, Stage II, or
Stage IIIA Non-Small Cell Lung Cancer

| | |
|---|---|
| Condition: | Lung Cancer |
| Interventions: | Drug: autologous tumor cell vaccine; Drug: therapeutic autologous dendritic cells; Procedure: adjuvant therapy; Procedure: biological therapy; Procedure: conventional surgery; Procedure: surgery; Procedure: tumor cell derivative vaccine; Procedure: vaccine therapy |

Vaccine Therapy in Treating Patients With Advanced Kidney Cancer

| | |
|---|---|
| Condition: | Kidney Cancer |
| Interventions: | Drug: autologous tumor cell vaccine; Procedure: conventional surgery |

Vaccine Therapy in Treating Women With Previously Treated Metastatic Breast Cancer

| | |
|---|---|
| Condition: | Breast Cancer |
| Intervention: | Drug: Ad-sig-hMUC-1/ecdCD40L vaccine |

Vaccine Therapy Plus QS21 in Treating Patients With Progressive Prostate Cancer

| | |
|---|---|
| Condition: | Prostate Cancer |
| Interventions: | Drug: MUC-2-KLH vaccine; Drug: QS21 |

Vaccine Therapy Plus Sargramostim in Treating Patients With Stage III or Stage IV Cancer

| | |
|---|---|
| Conditions: | Breast Cancer; Lung Cancer; Ovarian Cancer |
| Interventions: | Drug: HER-2/neu peptide vaccine; Drug: sargramostim |

Vaccine Therapy in Treating Patients With Stage IIIB or Stage IV Non-Small Cell Lung Cancer
Who Have Finished First-Line Chemotherapy

| | |
|---|---|
| Condition: | Lung Cancer |
| Interventions: | Drug: allogeneic B7.1/HLA-A1 transfected tumor cell vaccine; Drug: placebo |

Vaccine Therapy and Donor Lymphocyte Infusions in Treating Patients With Progressive or
Relapsed Hematologic Malignancies After Donor Stem Cell Transplantation

| | |
|---|---|
| Conditions: | Leukemia; Lymphoma; Myelodysplastic Syndromes |
| Interventions: | Drug: WT-1 analog peptide vaccine; Drug: WT1 126-134 peptide vaccine; Drug: therapeutic allogeneic lymphocytes; Procedure: flow cytometry; Procedure: immunoenzyme technique; Procedure: immunohistochemistry staining method; Procedure: laboratory biomarker analysis; Procedure: reverse transcriptase-polymerase chain reaction |

A Phase I Clinical Trial of Autologous Dendritic Cell Vaccine for Recurrent Ovarian or Primary
Peritoneal Cancer

| | |
|---|---|
| Conditions: | Ovarian Cancer; Peritoneal Cancer |
| Intervention: | Biological: DCVac-L |

Vaccine Therapy, Tretinoin, and Cyclophosphamide in Treating Patients With Metastatic Lung
Cancer

| | |
|---|---|
| Condition: | Lung Cancer |
| Interventions: | Drug: GM.CD40L cell vaccine; Drug: allogeneic tumor cell vaccine; Drug: cyclophosphamide; Drug: tretinoin; Procedure: flow cytometry; Procedure: immunoenzyme technique; Procedure: immunohistochemistry staining method; Procedure: protein expression analysis |

Vaccine Therapy, Interleukin-2, and Sargramostim in Treating Patients With Advanced
Tumors

| | |
|---|---|
| Conditions: | Breast Cancer; Esophageal Cancer; Gastric Cancer; Lung Cancer; Pancreatic Cancer; Unspecified Adult Solid Tumor, Protocol Specific |
| Interventions: | Drug: ALVAC-CEA vaccine; Drug: aldesleukin; Drug: sargramostim; Drug: vaccinia-CEA vaccine |

Vaccine Therapy in Treating Patients With Stage I, Stage II, or Stage III Non-Small Cell Lung
Cancer

| | |
|---|---|
| Condition: | Lung Cancer |
| Interventions: | Drug: allogeneic tumor cell vaccine; Drug: therapeutic autologous dendritic cells; Procedure: adjuvant therapy |

TABLE S-continued

Cancer vaccines

HER-2/Neu Vaccine Plus GM-CSF in Treating Patients With Stage III or Stage IV Breast,
Ovarian, or Non-Small Cell Lung Cancer Conditions: Breast Cancer; Lung Cancer; Ovarian Cancer
Interventions: Drug: HER-2/neu peptide vaccine; Drug: sargramostim
Vaccine Therapy Plus Sargramostim and Interleukin-2 Compared With Nilutamide Alone in
Treating Patients With Prostate Cancer Condition: Prostate Cancer
Interventions: Drug: aldesleukin; Drug: nilutamide; Drug: recombinant fowlpox-
prostate apecific antigen vaccine; Drug: recombinant vaccinia prostate-
specific antigen vaccine; Drug: recombinant vaccinia-B7.1 vaccine;
Drug: sargramostim
Vaccine Therapy in Treating Patients With Stage III Non-Small Cell Lung Cancer Condition: Lung Cancer
Interventions: Drug: mutant p53 peptide pulsed dendritic cell vaccine;
Procedure: adjuvant therapy
Cyclophosphamide Plus Vaccine Therapy in Treating Patients With Advanced Cancer Conditions: Breast Cancer; Colorectal Cancer; Kidney Cancer; Lung Cancer;
Malignant Mesothelioma; Pancreatic Cancer
Interventions: Drug: allogeneic tumor cell vaccine; Drug: autologous tumor cell vaccine;
Drug: cyclophosphamide; Drug: recombinant interferon alfa;
Drug: recombinant interferon gamma; Drug: sargramostim
Human Papilloma Virus (HPV) Vaccine Efficacy Trial Against Cervical Pre-Cancer in Young
Adults With GSK Biologicals HPV-16/18

Conditions: HPV 16/18 Infections; Cervical Neoplasia
Intervention: Biological: HPV 16/18 VLP AS04
Vaccine Therapy in Treating Patients With Stage II, Stage IIIA, Stage IIIB, or Stage IVA Liver
Cancer Condition: Liver Cancer
Interventions: Drug: alpha fetoprotein adenoviral vector vaccine;
Drug: alpha fetoprotein plasmid DNA vaccine; Drug: sargramostim
plasmid DNA hepatocellular carcinoma vaccine adjuvant
Ovarian Cancer and Immune Response to Flu Vaccine Condition: Ovarian Cancer
Intervention: Biological: The current season's trivalent killed influenza vaccine
Vaccine Therapy Plus Sargramostim and Chemotherapy in Treating Women With Stage II or
Stage III Breast Cancer Condition: Breast Cancer
Interventions: Drug: cyclophosphamide; Drug: doxorubicin hydrochloride;
Drug: paclitaxel; Drug: recombinant fowlpox-CEA(6D)/TRICOM vaccine;
Drug: recombinant vaccinia-CEA(6D)-TRICOM vaccine;
Drug: sargramostim; Procedure: radiation therapy
p53 Vaccine in Treating Patients With Adenocarcinoma of the Ovary Who Have Either No
Evidence of Disease or Elevated Biomarkers Condition: Ovarian Cancer
Interventions: Drug: aldesleukin; Drug: incomplete Freund's adjuvant;
Drug: p53 peptide vaccine; Drug: sargramostim;
Drug: therapeutic autologous dendritic cells; Procedure: in vitro-treated
peripheral blood stem cell transplantation
Prime-Boost Dose Scheduling Trial for Human GM-CSF Gene Transduced Irradiated Prostate
Allogeneic Cancer Cell Vaccines (Allogeneic Prostate GVAX ®)

Condition: Prostate Cancer
Intervention: Biological: Immunotherapy allogeneic GM-CSF secreting cellular vaccine
Lenalidomide and Vaccine Therapy in Treating Patients With Relapsed or Refractory Multiple
Myeloma Condition: Multiple Myeloma and Plasma Cell Neoplasm
Interventions: Drug: lenalidomide; Drug: pneumococcal polyvalent vaccine
Vaccine Therapy in Treating Patients With Metastatic, Progressive Prostate Cancer Condition: Prostate Cancer
Intervention: Drug: NY-ESO-1/LAGE-1 HLA class I/II peptide vaccine
Gene-Modified Lymphocytes, High-Dose Aldesleukin, and Vaccine Therapy in Treating
Patients With Progressive or Recurrent Metastatic Cancer Conditions: Kidney Cancer; Melanoma (Skin);
Unspecified Adult Solid Tumor, Protocol Specific
Interventions: Drug: aldesleukin; Drug: anti-p53 T-cell receptor-transduced peripheral
blood lymphocytes; Drug: autologous dendritic cell-adenovirus p53

TABLE S-continued

Cancer vaccines vaccine; Drug: cyclophosphamide; Drug: filgrastim;
Drug: fludarabine phosphate
Study of the Feasibility to Derive Vaccine From Tumor Tissue in Patients With Non-Small Cell Lung Cancer

| | |
|---|---|
| Conditions: | Non-Small-Cell Lung Carcinoma; Lung Cancer; Pulmonary Cancer |
| Intervention: | Biological: HSPPC-96 |

PSMA and TARP Peptide With Poly IC-LC Adjuvant in HLA-A2 (+) Patients With Elevated PSA After Initial Definitive Treatment

| | |
|---|---|
| Condition: | Prostate Cancer |
| Intervention: | Biological: peptide vaccine |

Safety & Activity of P501-AS15 Vaccine as a First-Line Treatment for Patients With Hormone-Sensitive Prostate Cancer Who Show Rising PSA

| | |
|---|---|
| Condition: | Prostate Cancer |
| Intervention: | Biological: P501-AS15 vaccine |

Study Testing the Biologic Activity and Safety of a Vaccine in Patients With Newly Diagnosed Stage IV Kidney Cancer

| | |
|---|---|
| Condition: | Renal Cell Carcinoma |
| Intervention: | Biological: AGS-003 |

Vaccine Therapy in Treating Patients With Ovarian, Fallopian Tube, or Peritoneal Cancer

| | |
|---|---|
| Conditions: | Fallopian Tube Cancer; Ovarian Cancer; Peritoneal Cavity Cancer |
| Interventions: | Drug: MUC1-KLH conjugate vaccine; Drug: MUC1-KLH vaccine/QS21; Drug: QS21 |

A Clinical Trial That Looks at the Safety and Effectiveness of a Vaccine for Prostate Cancer That Uses Each Patients' Own Immune Cells.

| | |
|---|---|
| Condition: | Prostate Cancer |
| Intervention: | Biological: autologous dendritic cell vaccine (DC/LNCaP) |

Vaccine Therapy in Treating Patients With Metastatic Breast Cancer

| | |
|---|---|
| Condition: | Breast Cancer |
| Interventions: | Drug: recombinant vaccinia-MUC-1 vaccine; Drug: recombinant vaccinia-TRICOM vaccine; Drug: sargramostim |

Vaccine Therapy in Treating HIV and Preventing HPV in HIV-Positive Women in India

| | |
|---|---|
| Conditions: | Cervical Cancer; Precancerous/Nonmalignant Condition |
| Interventions: | Drug: quadrivalent human papillomavirus (types 6, 11, 16, 18) recombinant vaccine; Procedure: DNA analysis; Procedure: colposcopic biopsy; Procedure: cytology specimen collection procedure; Procedure: polymerase chain reaction |

Vaccine Therapy in Treating Patients With Kidney Cancer

| | |
|---|---|
| Condition: | Kidney Cancer |
| Interventions: | Drug: human prostate-specific membrane antigen plasmid DNA vaccine; Drug: mouse prostate-specific membrane antigen plasmid DNA vaccine |

Vaccine Therapy Plus Radiation Therapy in Treating Patients With Non-Small Cell Lung Cancer That Has Been Completely Removed in Surgery

| | |
|---|---|
| Condition: | Lung Cancer |
| Interventions: | Drug: monoclonal antibody 11D10 anti-idiotype vaccine; Drug: monoclonal antibody 3H1 anti-idiotype vaccine; Procedure: radiation therapy |

Vaccine Therapy in Treating Patients With Advanced Adenocarcinoma of the Prostate (Prostate Cancer)

| | |
|---|---|
| Condition: | Prostate Cancer |
| Interventions: | Drug: recombinant fowlpox-prostate apecific antigen vaccine; Drug: recombinant vaccinia prostate-specific antigen vaccine |

Phase IIb Randomized Controlled Study of BLP25 Liposome Vaccine for Immunotherapy of Non-Small Cell Lung Cancer

| | |
|---|---|
| Conditions: | Lung Neoplasms; Carcinoma, Non-Small-Cell Lung |
| Interventions: | Biological: BLP25 Liposome Vaccine plus best supportive care; Other: Best Supportive Care (BSC) |

Impaired Immunity in Patients With Cancer: Influence of Cancer Stage, Chemotherapy, and Cytomegalovirus Infection

| | |
|---|---|
| Condition: | Neoplasms |
| Intervention: | Other: Immune profiling and DC vaccine |

TABLE S-continued

Cancer vaccines

Stem Cell Transplant, Chemotherapy, and Biological Therapy in Treating Patients With High-Risk or Refractory Multiple Myeloma

| | |
|---|---|
| Condition: | Multiple Myeloma and Plasma Cell Neoplasm |
| Interventions: | Drug: CMV N495 peptide; Drug: CMV pp65 peptide; Drug: hTERT I540/R572Y/D988Y multipeptide vaccine; Drug: pneumococcal polyvalent vaccine; Drug: survivin Sur1M2 peptide vaccine |

Neoadjuvant Intravesical Vaccine Therapy in Treating Patients With Bladder Carcinoma Who Are Undergoing Cystectomy

| | |
|---|---|
| Condition: | Bladder Cancer |
| Interventions: | Drug: recombinant fowlpox GM-CSF vaccine adjuvant; Drug: recombinant fowlpox-TRICOM vaccine; Procedure: conventional surgery; Procedure: neoadjuvant therapy |

Vaccine Therapy or Observation in Treating Patients With Nasopharyngeal Cancer at High Risk for Recurrence

| | |
|---|---|
| Condition: | Head and Neck Cancer |
| Interventions: | Drug: LMP-2: 340-349 peptide vaccine; Drug: LMP-2: 419-427 peptide vaccine; Drug: incomplete Freund's adjuvant; Procedure: adjuvant therapy |

Tumor Cell Vaccine in Treating Patients With Advanced Cancer

| | |
|---|---|
| Condition: | Unspecified Adult Solid Tumor, Protocol Specific |
| Interventions: | Drug: filgrastim; Drug: recombinant interferon gamma; Procedure: tumor cell-derivative vaccine therapy |

A Phase 1 Study of Mixed Bacteria Vaccine (MBV) in Patients With Tumors Expressing NY-ESO-1 Antigen

| | |
|---|---|
| Conditions: | Melanoma; Sarcoma; Gastrointestinal Stromal Tumor (GIST); Head and Neck Cancer; Transitional Cell Carcinoma; Prostate Cancer |
| Intervention: | Biological: Mixed Bacterial Vaccine (MBV) |

Vaccination of Patients With Renal Cell Cancer With Dendritic Cell Tumor Fusions and GM-CSF

| | |
|---|---|
| Condition: | Renal Cancer |
| Interventions: | Biological: Dendritic Cell Tumor Fusion Vaccine; Drug: Granulocyte Macrophage Colony Stimulating Factor (GM-CSF) |

NY-ESO Phase I Study for Prostate Cancer

| | |
|---|---|
| Condition: | Prostatic Neoplasms |
| Interventions: | Biological: NY-ESO-1 class I and class II peptide vaccine; Biological: LAGE-1 class I and class II peptide vaccine |

GVAX ® Vaccine for Prostate Cancer vs Docetaxel & Prednisone in Patients With Metastatic Hormone-Refractory Prostate Cancer

| | |
|---|---|
| Condition: | Prostate Cancer |
| Interventions: | Biological: Immunotherapy with allogeneic prostate vaccine; Drug: Chemotherapy (Taxotere and prednisone) |

Vaccine Therapy in Treating Patients With Stage IIIB, Stage IV, or Recurrent Non-Small Cell Lung Cancer

| | |
|---|---|
| Condition: | Lung Cancer |
| Interventions: | Drug: EP-2101; Drug: incomplete Freund's adjuvant |

MUC1 Vaccine in Conjunction With Poly-ICLC in Patients With Recurrent and/or Advanced Prostate Cancer

| | |
|---|---|
| Condition: | Prostate Cancer |
| Intervention: | Drug: MUC_1 |

Vaccine Therapy, GM-CSF, and Interferon Alfa-2b in Treating Patients With Locally Advanced or Metastatic Cancer That Expresses Carcinoembryonic Antigen (CEA)

| | |
|---|---|
| Condition: | Unspecified Adult Solid Tumor, Protocol Specific |
| Interventions: | Drug: recombinant fowlpox-CEA(6D)/TRICOM vaccine; Drug: recombinant interferon alfa-2b; Drug: recombinant vaccinia-CEA(6D)-TRICOM vaccine; Drug: sargramostim |

Vaccine Therapy With or Without Sargramostim in Treating Patients With Cancer

| | |
|---|---|
| Condition: | Unspecified Adult Solid Tumor, Protocol Specific |
| Interventions: | Drug: recombinant fowlpox-CEA(6D)/TRICOM vaccine; Drug: recombinant vaccinia-CEA(6D)-TRICOM vaccine; Drug: sargramostim |

Immunogenicity of GSK Bio's HPV Vaccine (580299) Versus Merck's Gardasil ® in Healthy Females 18-45 Years of Age

| | |
|---|---|
| Conditions: | Cervical Cancer; Papillomavirus Infections |
| Intervention: | Biological: HPV-16/18 L1/AS04 (580299) |

TABLE S-continued

Cancer vaccines

Study of the Biovaxld Tumor Derived Idiotype Vaccine in Patients With Follicular Lymphoma Condition: Non-Hodgkins Lymphoma
Interventions: Biological: tumor specific immune response; Biological: control vaccine Vaccine Therapy in Treating Patients With Stage IV or Recurrent Melanoma Condition: Melanoma (Skin)
Interventions: Drug: autologous tumor cell vaccine; Drug: sargramostim;
Drug: therapeutic autologous dendritic cells Vaccine Therapy in Treating Patients With Recurrent Stage III or Stage IV Melanoma That Cannot Be Removed by Surgery Conditions: Intraocular Melanoma; Malignant Conjunctival Neoplasm;
Melanoma (Skin)
Interventions: Drug: CpG 7909; Drug: MART-1: 27-35 peptide vaccine;
Drug: gp100: 209-217(210M) peptide vaccine;
Drug: incomplete Freund's adjuvant; Drug: sargramostim;
Drug: tyrosinase peptide; Procedure: flow cytometry;
Procedure: immunologic technique;
Procedure: laboratory biomarker analysis Pilot Trial of a WT-1 Analog Peptide Vaccine in Patients With Myeloid Neoplasms Condition: Leukemia
Intervention: Biological: WT-1

Vaccine Therapy in Treating Patients With Newly Diagnosed Glioblastoma Multiforme Condition: Brain and Central Nervous System Tumors
Interventions: Drug: PEP-3-KLH conjugate vaccine; Drug: placebo;
Drug: sargramostim Vaccine Therapy in Treating Patients Who Are Undergoing Surgery for Ductal Carcinoma In Situ of the Breast Condition: Breast Cancer
Interventions: Drug: HER-2/neu peptide vaccine;
Drug: therapeutic autologous dendritic cells;
Procedure: conventional surgery; Procedure: neoadjuvant therapy Vaccine Therapy With or Without Fludarabine in Treating Patients With Stage IV Kidney Cancer Condition: Kidney Cancer
Interventions: Drug: autologous tumor cell vaccine; Drug: fludarabine phosphate;
Drug: keyhole limpet hemocyanin;
Drug: therapeutic autologous dendritic cells;
Procedure: conventional surgery Vaccine Therapy and QS21 in Treating Patients With Metastatic Breast Cancer Condition: Breast Cancer
Interventions: Drug: QS21; Drug: sialyl Lewis$^a$-keyhole limpet hemocyanin conjugate
vaccine; Procedure: immunoenzyme technique;
Procedure: immunologic technique;
Procedure: laboratory biomarker analysis Vaccine Therapy, Cyclophosphamide, and Cetuximab in Treating Patients With Metastatic or Locally Advanced Pancreatic Cancer Condition: Pancreatic Cancer
Interventions: Drug: cetuximab; Drug: cyclophosphamide; Drug: sargramostim
plasmid DNA pancreatic tumor cell vaccine; Procedure: biopsy;
Procedure: laboratory biomarker analysis Vaccine Therapy in Preventing Cervical Cancer in Patients With Cervical Intraepithelial Neoplasia Conditions: Cervical Cancer; Precancerous/Nonmalignant Condition
Intervention: Drug: pNGVL4a-Sig/E7(detox)/HSP70 DNA vaccine GP96 Heat Shock Protein-Peptide Complex Vaccine in Treating Patients With Recurrent or Progressive Glioma Condition: Brain and Central Nervous System Tumors
Interventions: Drug: vitespen; Procedure: conventional surgery Vaccine Therapy and Sargramostim in Treating Patients With Sarcoma or Brain Tumor Conditions: Brain and Central Nervous System Tumors;
Gastrointestinal Stromal Tumor; Sarcoma
Interventions: Drug: sargramostim; Drug: telomerase: 540-548 peptide vaccine Vaccine Plus Montanide ISA-51 and Sargramostim in Treating Patients With Stage IV Breast Cancer Condition: Breast Cancer
Interventions: Drug: incomplete Freund's adjuvant; Drug: sargramostim;

TABLE S-continued

Cancer vaccines

Drug: telomerase: 540-548 peptide vaccine
Vaccine Therapy and Chemotherapy With or Without Tretinoin in Treating Patients With
Extensive-Stage Small Cell Lung Cancer

| | |
|---|---|
| Condition: | Lung Cancer |
| Interventions: | Drug: autologous dendritic cell-adenovirus p53 vaccine; Drug: tretinoin; Procedure: observation |

Denileukin Diftitox Followed by Vaccine Therapy in Treating Patients With Metastatic Cancer

| | |
|---|---|
| Conditions: | Breast Cancer; Colorectal Cancer; Lung Cancer; Pancreatic Cancer; Unspecified Adult Solid Tumor, Protocol Specific |
| Interventions: | Drug: denileukin diftitox; Drug: recombinant fowlpox-CEA(6D)/TRICOM vaccine; Drug: therapeutic autologous dendritic cells |

Vaccine Therapy Plus QS21 in Treating Patients With Prostate Cancer

| | |
|---|---|
| Condition: | Prostate Cancer |
| Intervention: | Drug: MUC1-KLH vaccine/QS21 |

Chemotherapy Followed By Vaccine Therapy in Treating Patients With Extensive-Stage Small
Cell Lung Cancer

| | |
|---|---|
| Condition: | Lung Cancer |
| Interventions: | Drug: autologous dendritic cell-adenovirus p53 vaccine; Drug: carboplatin; Drug: etoposide |

Partially Blind Study to Evaluate Immunogenicity & Safety of GSK Bios' HPV Vaccine 580299
in Healthy Women Aged 9-25 Yrs

| | |
|---|---|
| Conditions: | Papillomavirus Infections; Cervical Cancer |
| Intervention: | Biological: HPV vaccine 580299 |

Immunogenicity and Safety of GSK Biologicals' HPV Vaccine 580299 in Healthy Japanese
Females 10-15 Years of Age

| | |
|---|---|
| Conditions: | Papillomavirus Infections; Cervical Cancer |
| Intervention: | Biological: HPV vaccine 580299 |

Cyclophosphamide and Rituximab Followed By Vaccine Therapy in Treating Patients With
Chronic Lymphocytic Leukemia

| | |
|---|---|
| Condition: | Leukemia |
| Interventions: | Drug: autologous tumor cell vaccine; Drug: cyclophosphamide; Drug: rituximab |

Vaccine Therapy, Trastuzumab, and Vinorelbine in Treating Women With Locally Recurrent or
Metastatic Breast Cancer

| | |
|---|---|
| Condition: | Breast Cancer |
| Interventions: | Drug: therapeutic autologous dendritic cells; Drug: trastuzumab; Drug: vinorelbine ditartrate |

Vaccine Therapy, Trastuzumab, and Vinorelbine in Treating Patients With Locally Recurrent or
Metastatic Breast Cancer

| | |
|---|---|
| Condition: | Breast Cancer |
| Interventions: | Drug: sargramostim; Drug: therapeutic autologous dendritic cells; Drug: trastuzumab; Drug: vinorelbine ditartrate |

Tumor Lysate Pulsed Dendritic Cell Immunotherapy for Patients With Brain Tumors

| | |
|---|---|
| Condition: | Glioblastoma |
| Interventions: | Biological: Dendritic Cell Immunotherapy; Biological: Dendritic Cell Vaccine; Biological: Dendritic Cell Vaccine |

Vaccine Therapy and GM-CSF in Treating Patients With Recurrent or Metastatic Melanoma

| | |
|---|---|
| Condition: | Melanoma (Skin) |
| Interventions: | Drug: autologous tumor cell vaccine; Drug: sargramostim; Drug: therapeutic autologous dendritic cells |

Vaccine Therapy in Treating Young Patients Who Are Undergoing Surgery for Malignant
Glioma

| | |
|---|---|
| Condition: | Brain and Central Nervous System Tumors |
| Interventions: | Drug: autologous tumor cell vaccine; Drug: therapeutic autologous dendritic cells; Procedure: adjuvant therapy; Procedure: therapeutic conventional surgery |

Vaccine Therapy in Treating Patients With Non-Small Cell Lung Cancer

| | |
|---|---|
| Condition: | Lung Cancer |
| Interventions: | Drug: autologous tumor cell vaccine; Drug: therapeutic autologous dendritic cells; Procedure: conventional surgery |

TABLE S-continued

Cancer vaccines

Dendritic Cell Vaccine Study (DC/PC3) for Prostate Cancer

| | |
|---|---|
| Condition: | Prostate Cancer |
| Intervention: | Biological: autologous dendritic cell vaccine (DC/PC3) |

Vaccine Therapy in Treating Patients Who Have Undergone Autologous Stem Cell Transplant for High-Risk Lymphoma or Multiple Myeloma

| | |
|---|---|
| Conditions: | Lymphoma; Multiple Myeloma and Plasma Cell Neoplasm; Small Intestine Cancer |
| Interventions: | Drug: pneumococcal polyvalent vaccine; Procedure: immunologic technique; Procedure: laboratory biomarker analysis; Procedure: quality-of-life assessment |

Vaccine Therapy in Treating Patients With Stage III or Stage IV Melanoma

| | |
|---|---|
| Condition: | Melanoma (Skin) |
| Interventions: | Drug: PADRE 965.10; Drug: alpha-type-1 polarized dendritic cells; Drug: keyhole limpet hemocyanin; Procedure: immunoenzyme technique; Procedure: therapeutic autologous dendritic cells |

Vaccine Therapy in Treating Patients With Metastatic Prostate Cancer

| | |
|---|---|
| Condition: | Prostate Cancer |
| Interventions: | Drug: autologous tumor cell vaccine; Drug: therapeutic autologous dendritic cells |

Vaccine Therapy in Treating Patients With Advanced or Recurrent Cancer

| | |
|---|---|
| Conditions: | Anal Cancer; Cervical Cancer; Esophageal Cancer; Head and Neck Cancer; Penile Cancer; Vulvar Cancer |
| Interventions: | Drug: human papillomavirus 16 E7 peptide; Drug: synthetic human papillomavirus 16 E6 peptide |

Vaccine Therapy in Treating Patients With Metastatic or Recurrent Cancer

| | |
|---|---|
| Conditions: | Breast Cancer; Gastric Cancer; Lung Cancer; Ovarian Cancer; Unspecified Adult Solid Tumor, Protocol Specific |
| Intervention: | Drug: MVF-HER-2(628-647)-CRL 1005 vaccine |

Vaccine Therapy in Treating Patients With Ovarian Epithelial, Primary Peritoneal, or Fallopian Tube Cancer

| | |
|---|---|
| Conditions: | Fallopian Tube Cancer; Ovarian Cancer; Peritoneal Cavity Cancer |
| Interventions: | Drug: NY-ESO-1 peptide vaccine; Drug: incomplete Freund's adjuvant |

Vaccine Therapy in Treating Patients With Chronic Phase Chronic Myelogenous Leukemia

| | |
|---|---|
| Condition: | Leukemia |
| Interventions: | Drug: bcr-abl peptide vaccine; Procedure: reverse transcriptase-polymerase chain reaction |

Vaccine Therapy in Treating Patients With Stage III or Stage IV Kidney Cancer

| | |
|---|---|
| Condition: | Kidney Cancer |
| Interventions: | Drug: autologous tumor cell vaccine; Drug: therapeutic autologous dendritic cells; Procedure: conventional surgery |

Vaccine Therapy Plus QS21 in Treating Patients With Progressive Prostate Cancer

| | |
|---|---|
| Condition: | Prostate Cancer |
| Interventions: | Drug: QS21; Drug: TF(c)-KLH conjugate vaccine; Drug: Thomsen-Friedenreich antigen; Drug: keyhole limpet hemocyanin |

Vaccine Therapy in Treating Patients With Advanced or Metastatic Cancer

| | |
|---|---|
| Conditions: | Breast Cancer; Colorectal Cancer; Gallbladder Cancer; Gastric Cancer; Head and Neck Cancer; Liver Cancer; Ovarian Cancer; Pancreatic Cancer; Testicular Germ Cell Tumor |
| Interventions: | Drug: CMV pp65 peptide; Drug: recombinant fowlpox-CEA(6D)/TRICOM vaccine; Drug: tetanus toxoid; Drug: therapeutic autologous dendritic cells |

Vaccine Therapy in Treating Patients With Head and Neck Cancer

| | |
|---|---|
| Condition: | Head and Neck Cancer |
| Interventions: | Drug: mutant p53 peptide pulsed dendritic cell vaccine; Drug: tetanus toxoid helper peptide; Procedure: adjuvant therapy |

Vaccine Therapy in Treating Patients With Liver Cancer

| | |
|---|---|
| Condition: | Liver Cancer |
| Interventions: | Drug: AFP gene hepatocellular carcinoma vaccine; Drug: incomplete Freund's adjuvant |

TABLE S-continued

Cancer vaccines

Vaccine Therapy in Treating Patients With Liver Cancer

| | |
|---|---|
| Condition: | Liver Cancer |
| Interventions: | Drug: AFP gene hepatocellular carcinoma vaccine; Drug: therapeutic autologous dendritic cells |

Vaccine Therapy in Treating Patients With Recurrent Prostate Cancer

| | |
|---|---|
| Condition: | Prostate Cancer |
| Interventions: | Drug: PSA: 154-163(155L) peptide vaccine; Drug: incomplete Freund's adjuvant |

Vaccine Therapy Plus QS21 in Treating Women With Breast Cancer Who Have No Evidence of Disease

| | |
|---|---|
| Condition: | Breast Cancer |
| Interventions: | Drug: GM2-KLH vaccine; Drug: QS21 |

Vaccine Therapy in Treating Patients With Stage III or Stage IV Breast Cancer

| | |
|---|---|
| Condition: | Breast Cancer |
| Intervention: | Drug: synthetic breast cancer peptides-tetanus toxoid-Montanide ISA-51 vaccine |

Vaccine Therapy in Treating Patients With Newly Diagnosed Stage IV Kidney Cancer

| | |
|---|---|
| Condition: | Kidney Cancer |
| Interventions: | Drug: autologous dendritic cell-autologous tumor mRNA-human CD40L vaccine; Drug: therapeutic autologous dendritic cells |

Chemotherapy, Vaccine Therapy, and Peripheral Stem Cell Transplantation in Treating Patients With Newly Diagnosed Multiple Myeloma

| | |
|---|---|
| Condition: | Multiple Myeloma and Plasma Cell Neoplasm |
| Interventions: | Drug: autologous tumor cell vaccine; Procedure: chemotherapy; Procedure: peripheral blood stem cell transplantation |

HER-2 Protein Vaccine in Treating Women With Breast Cancer

| | |
|---|---|
| Condition: | Breast Cancer |
| Intervention: | Drug: HER-2/neu peptide vaccine |

Vaccine Therapy in Treating Patients With Metastatic Breast Cancer

| | |
|---|---|
| Condition: | Breast Cancer |
| Intervention: | Drug: recombinant vaccinia DF3/MUC1 vaccine |

Vaccine Therapy in Treating Patients With Advanced Refractory or Recurrent Non-Small Cell Lung Cancer

| | |
|---|---|
| Condition: | Lung Cancer |
| Intervention: | Drug: alpha-1,3-galactosyltransferase-expressing allogeneic lung tumor cell vaccine |

Vaccine Therapy in Treating Patients With Breast Cancer

| | |
|---|---|
| Condition: | Breast Cancer |
| Intervention: | Drug: MUC1-KLH vaccine/QS21 |

Docetaxel in Combination With GVAX ® Immunotherapy Versus Docetaxel and Prednisone in Prostate Cancer Patients

| | |
|---|---|
| Condition: | Prostate Cancer |
| Interventions: | Biological: Immunotherapy allogeneic GM-CSF secreting cellular vaccine; Drug: Chemotherapy (docetaxel and prednisone) |

Evaluation of Transgenic Lymphocyte Immunization Vaccine in Subjects With Prostate Adenocarcinoma

| | |
|---|---|
| Condition: | Prostatic Neoplasms |
| Intervention: | Biological: Transgenic Lymphocyte Immunization Vaccine (TLI) |

Vaccine Therapy in Treating Patients With Stage IIIB, Stage IV, or Recurrent Non-Small Cell Lung Cancer

| | |
|---|---|
| Condition: | Lung Cancer |
| Interventions: | Drug: autologous dendritic cell-adenovirus CCL21 vaccine; Procedure: flow cytometry; Procedure: immunoenzyme technique; Procedure: immunohistochemistry staining method; Procedure: polymerase chain reaction; Procedure: reverse transcriptase-polymerase chain reaction |

Safety Study of BLP25 Liposome Vaccine in Non-Small Cell Lung Cancer Patients With Unresectable Stage III Disease

| | |
|---|---|
| Conditions: | Carcinoma, Non-Small-Cell Lung; Lung Neoplasms |
| Intervention: | Biological: BLP25 Liposome Vaccine |

Vaccine Therapy in Treating Patients With Metastatic Prostate Cancer

| | |
|---|---|
| Condition: | Prostate Cancer |
| Interventions: | Drug: sargramostim; Procedure: recombinant viral vaccine therapy |

TABLE S-continued

Cancer vaccines

Vaccine Therapy in Treating Patients With Gastric, Prostate, or Ovarian Cancer

| | |
|---|---|
| Conditions: | Brain and Central Nervous System Tumors; Gastric Cancer; Ovarian Cancer; Prostate Cancer |
| Interventions: | Drug: EGFR antisense DNA; Drug: keyhole limpet hemocyanin; Drug: sargramostim |

Health SMART Stress Management and Relaxation Training) to Improve Vaccine Immune Response

| | |
|---|---|
| Condition: | Psychological Stress |
| Intervention: | Behavioral: Cognitive Behavioral Stress Management (CBSM) group intervention |

Vaccine Therapy in Treating Patients at High Risk for Breast Cancer Recurrence

| | |
|---|---|
| Condition: | Breast Cancer |
| Interventions: | Drug: Globo-H-GM2-Lewis-y-MUC1-32(aa)-sTn(c)-TF(c)-Tn(c)-KLH conjugate vaccine; Drug: QS21 |

Vaccine Therapy in Treating Patients With Stage IIB, Stage III, or Stage IV Colorectal Cancer

| | |
|---|---|
| Condition: | Colorectal Cancer |
| Intervention: | Drug: HER-2-neu, CEA peptides, GM-CSF, Montanide ISA-51 vaccine |

Vaccine Therapy Plus Donor Peripheral Stem Cell Transplantation in Treating Patients With Multiple Myeloma

| | |
|---|---|
| Condition: | Multiple Myeloma and Plasma Cell Neoplasm |
| Interventions: | Drug: autologous tumor cell vaccine; Drug: bortezomib; Drug: cyclophosphamide; Drug: cyclosporine; Drug: doxorubicin hydrochloride; Drug: etoposide; Drug: filgrastim; Drug: fludarabine phosphate; Drug: keyhole limpet hemocyanin; Drug: methotrexate; Drug: prednisone; Drug: sargramostim; Drug: vincristine; Procedure: peripheral blood stem cell transplantation |

Vaccine Therapy, Chemotherapy, and GM-CSF in Treating Patients With Advanced Pancreatic Cancer

| | |
|---|---|
| Condition: | Pancreatic Cancer |
| Interventions: | Drug: cyclophosphamide; Drug: recombinant interferon alfa; Drug: sargramostim; Procedure: tumor cell-derivative vaccine therapy |

Vaccine Therapy in Treating Patients With Stage III or Stage IV Kidney Cancer

| | |
|---|---|
| Condition: | Kidney Cancer |
| Interventions: | Drug: HLA-A2, A3-restricted FGF-5 peptides/Montanide ISA-51 vaccine; Drug: aldesleukin; Procedure: adjuvant therapy |

Chemotherapy and Vaccine Therapy Followed by Bone Marrow or Peripheral Stem Cell Transplantation and Interleukin-2 in Treating Patients With Recurrent or Refractory Brain Cancer

| | |
|---|---|
| Condition: | Brain and Central Nervous System Tumors |
| Interventions: | Drug: aldesleukin; Drug: autologous tumor cell vaccine; Drug: carmustine; Drug: cisplatin; Drug: cyclophosphamide; Drug: filgrastim; Drug: paclitaxel; Drug: sargramostim; Drug: therapeutic autologous lymphocytes; Procedure: autologous bone marrow transplantation; Procedure: conventional surgery; Procedure: peripheral blood stem cell transplantation |

Vaccine Therapy in Treating Patients With Recurrent or Persistent Cervical Cancer

| | |
|---|---|
| Condition: | Cervical Cancer |
| Interventions: | Drug: human papillomavirus 16 E7 peptide; Procedure: in vitro-treated peripheral blood stem cell transplantation |

Peptide Vaccine to Prevent Recurrence of Nasopharyngeal Cancer

| | |
|---|---|
| Condition: | Nasopharyngeal Neoplasms |
| Intervention: | Drug: EBV-LMP-2 |

Vaccine Therapy in Treating Patients With Metastatic Prostate Cancer

| | |
|---|---|
| Condition: | Prostate Cancer |
| Intervention: | Drug: PSA RNA-pulsed dendritic cell vaccine |

Vaccine Therapy in Treating Patients With Multiple Myeloma

| | |
|---|---|
| Conditions: | Stage II Multiple Myeloma; Stage III Multiple Myeloma; Refractory Plasma Cell Neoplasm |
| Interventions: | Drug: autologous tumor cell vaccine; Drug: keyhole limpet hemocyanin; Drug: melphalan; Drug: sargramostim |

Vaccine Therapy in Treating Patients With Metastatic Cancer

| | |
|---|---|
| Conditions: | Melanoma (Skin); Unspecified Adult Solid Tumor, Protocol Specific |
| Interventions: | Drug: aldesleukin; Drug: incomplete Freund's adjuvant; Drug: telomerase: 540-548 peptide vaccine |

TABLE S-continued

Cancer vaccines

Combination Chemotherapy and Monoclonal Antibody Therapy Followed by Vaccine Therapy in Treating Patients With Mantle Cell Lymphoma

| | |
|---|---|
| Conditions: | Noncontiguous Stage II Mantle Cell Lymphoma; Stage IV Mantle Cell Lymphoma; Contiguous Stage II Mantle Cell Lymphoma; Stage I Mantle Cell Lymphoma; Stage III Mantle Cell Lymphoma |
| Interventions: | Drug: autologous tumor cell vaccine; Drug: cyclophosphamide; Drug: doxorubicin; Drug: etoposide; Drug: filgrastim; Drug: keyhole limpet hemocyanin; Drug: prednisone; Drug: rituximab; Drug: sargramostim; Drug: vincristine |

Synthetic Vaccine in Patients With Chronic Myeloid Leukemia and Minimal Residual Disease

| | |
|---|---|
| Conditions: | Chronic Myeloid Leukemia; Minimal Residual Disease |
| Intervention: | Biological: Synthetic Tumor-Specific Breakpoint Peptide Vaccine |

Active Specific Immunotherapy for Follicular Lymphomas With Tumor-Derived Immunoglobulin Idiotype Antigen Vaccines

| | |
|---|---|
| Conditions: | B Cell Lymphoma; Follicular Lymphoma; Lymphoma |
| Interventions: | Drug: Id-KLH Vaccine; Drug: GM-CSF |

Vaccine Therapy in Treating Patients With Stage III or Stage IV Melanoma

| | |
|---|---|
| Condition: | Melanoma (Skin) |
| Interventions: | Drug: autologous dendritic cell-tumor fusion vaccine; Drug: gp100 antigen; Drug: therapeutic autologous dendritic cells |

Allogeneic Tumor Cell Vaccination in Patients With Solid Tumors

| | |
|---|---|
| Condition: | Metastatic Solid Tumors |
| Intervention: | Biological: Tumor Cell Vaccine |

Banking of Chronic Lymphocytic Leukemia Tumor Cells for Vaccine Generation

| | |
|---|---|
| Condition: | Chronic Lymphocytic Leukemia |
| Intervention: | Procedure: Leukemia cell harvest |

Vaccine Therapy in Treating Patients With Stage IV Head and Neck Cancer

| | |
|---|---|
| Conditions: | Head and Neck Cancer; Metastatic Cancer |
| Intervention: | Drug: recombinant fowlpox-TRICOM vaccine |

Vaccine Therapy and GM-CSF in Treating Patients With Myeloid Cancer

| | |
|---|---|
| Conditions: | Leukemia; Myelodysplastic Syndromes |
| Interventions: | Drug: PR1 leukemia peptide vaccine; Drug: WT1 126-134 peptide vaccine; Drug: incomplete Freund's adjuvant; Drug: sargramostim |

Vaccine Therapy in Treating Patients With Chronic Myelogenous Leukemia

| | |
|---|---|
| Condition: | Leukemia |
| Interventions: | Drug: QS21; Drug: bcr-abl peptide vaccine |

Vaccine Therapy in Treating Patients With Malignant Glioma

| | |
|---|---|
| Condition: | Brain and Central Nervous System Tumors |
| Intervention: | Drug: glioma-associated antigen peptide-pulsed autologous dendritic cell vaccine |

Reduced Intensity Stem Cell Transplantation for Chronic Lymphocytic Leukemia Followed by Vaccination

| | |
|---|---|
| Condition: | Chronic Lymphocytic Leukemia |
| Interventions: | Biological: GM-K562 vaccine; Procedure: stem cell transplantation |

Phase III Lucanix ™ Vaccine Therapy in Advanced Non-Small Cell Lung Cancer (NSCLC) Following Front-Line Chemotherapy

| | |
|---|---|
| Conditions: | Lung Neoplasm; Carcinoma, Non-Small-Cell Lung: Stage IIIA (T3, N2 Only); Carcinoma, Non-Small-Cell Lung: Stage IIIB; Carcinoma, Non-Small-Cell Lung: Stage IV |
| Interventions: | Biological: Lucanix ™; Other: Placebo Comparator |

SGN-00101 Vaccine in Treating Human Papillomavirus in Patients Who Have Abnormal Cervical Cells

| | |
|---|---|
| Conditions: | Cervical Cancer; Precancerous/Nonmalignant Condition |
| Intervention: | Drug: HspE7 |

Vaccine Therapy in Treating Patients With Acute Myeloid Leukemia

| | |
|---|---|
| Condition: | Leukemia |
| Interventions: | Drug: autologous tumor cell vaccine; Drug: therapeutic autologous dendritic cells; Procedure: tumor cell-derivative vaccine therapy |

TABLE S-continued

Cancer vaccines

Gemcitabine With Peptide Vaccine Therapy in Treating Patients With Bile Duct Cancer Condition: Bile Duct Cancer
Intervention: Biological: Peptide vaccine for URLC10 and gemcitabine Vaccine Therapy and GM-CSF in Treating Patients With Locally Advanced or Metastatic Pancreatic Cancer That Cannot Be Removed By Surgery Condition: Pancreatic Cancer
Interventions: Drug: falimarev; Drug: inalimarev; Drug: sargramostim A Phase I Study of Ovarian Cancer Peptides Plus GM-CSF and Adjuvant (Montanide ISA-51) as Consolidation Following Optimal Debulking and Systemic Chemotherapy for Women With Advanced Stage Ovarian, Tubal or Peritoneal Cancer Condition: Epithelial Ovarian, Tubal or Peritoneal Cancer
Intervention: Biological: OCPM Immunotherapeutic Vaccine Study of Cancer Peptides Plus GM-CSF and Adjuvant for TXN2-3M0 or Metastatic Breast Cancer With No Evidence of Disease Condition: Breast Cancer
Intervention: Biological: OCPM Immunotherapeutic Vaccine Safety and Immunogenicity Study of the New dHER2 Vaccine to Treat HER2-Positive Metastatic Breast Cancer Condition: Metastatic Breast Cancer
Intervention: Biological: dHer 2 vaccine Vaccination With Autologous Breast Cancer Cells Engineered to Secrete Granulocyte-Macrophage Colony-Stimulating Factor (GM-CSF) in Metastatic Breast Cancer Patients Condition: Breast Cancer
Intervention: Biological: Autologous, Lethally Irradiated Breast Cancer Cells Vaccine Therapy in Treating Patients With Advanced Melanoma Conditions: Intraocular Melanoma; Malignant Conjunctival Neoplasm; Melanoma (Skin)
Interventions: Drug: incomplete Freund's adjuvant; Drug: multi-epitope melanoma peptide vaccine; Drug: tetanus toxoid helper peptide; Procedure: biopsy Vaccine Therapy and Interleukin-2 in Treating Young Patients With Relapsed or Refractory Ewing's Sarcoma or Neuroblastoma Conditions: Neuroblastoma; Sarcoma
Interventions: Drug: aldesleukin; Drug: autologous EBV-transformed B lymphoblastoid-tumor fusion cell vaccine; Drug: therapeutic autologous lymphocytes Vaccine Therapy in Treating Patients With Metastatic Melanoma Condition: Melanoma (Skin)
Intervention: Drug: recombinant fowlpox-TRICOM vaccine DCVax-L Vaccination With CD3/CD28 Costimulated Autologous T-Cells for Recurrent Ovarian or Primary Peritoneal Cancer Conditions: Ovarian Cancer; Primary Peritoneal Cancer
Intervention: Biological: DCVax-L and T Cells Vaccine Therapy in Treating Young Patients With Newly Diagnosed Metastatic or Recurrent Ewing Sarcoma Family of Tumors, Rhabdomyosarcoma, or Neuroblastoma Conditions: Neuroblastoma; Sarcoma
Interventions: Drug: cyclophosphamide; Drug: fludarabine phosphate; Drug: therapeutic autologous dendritic cells; Drug: therapeutic autologous lymphocytes Laboratory-Treated T Cells and Cyclophosphamide With or Without Aldesleukin in Treating Patients With HER2/Neu-Overexpressing Metastatic Breast Cancer, Ovarian Cancer, or Non-Small Cell Lung Cancer Previously Treated With a HER2/Neu Vaccine Conditions: Breast Cancer; Lung Cancer; Ovarian Cancer
Interventions: Drug: aldesleukin; Drug: cyclophosphamide; Drug: ex vivo-expanded HER2-specific T cells; Drug: therapeutic autologous lymphocytes; Procedure: flow cytometry; Procedure: immunoenzyme technique; Procedure: laboratory biomarker analysis A Phase I/II Study With CEA(6D) VRP Vaccine in Patients With Advanced or Metastatic CEA-Expressing Malignancies Conditions: Colorectal Cancer; Breast Cancer; Lung Cancer; Pancreatic Cancer
Interventions: Biological: AVX701; Biological: AVX701; Biological: AVX701; Biological: AVX701

TABLE S-continued

Cancer vaccines

Safety Study of Cancer Specific Peptide Vaccines With Cyclophosphamides to Treat Solid Tumors

| | |
|---|---|
| Condition: | Metastatic Solid Tumors |
| Intervention: | Biological: 5 peptide vaccines of KOC1, TTK, CO16, DEPDC1, MPHOSPH1 |

Pilot Multivalent Conjugate Vaccine Trial for Patients With Biochem. Relapsed Prostate Cancer

| | |
|---|---|
| Conditions: | Prostate; Cancer |
| Intervention: | Biological: QS21 |

Safety Study of Multiple Peptide Vaccine to Esophageal Cancer

| | |
|---|---|
| Condition: | Esophageal Cancer |
| Intervention: | Biological: LY6K, VEGFR1, VEGFR2 |

PAP Vaccine in Patients With Prostate Cancer

| | |
|---|---|
| Condition: | Prostate Cancer |
| Interventions: | Biological: pTVG-HP with rhGM-CSF; Biological: pTVG-HP with rhGM-CSF; Biological: pTVG-HP with rhGM-CSF |

Vaccine Treatment for Advanced Malignant Melanoma

| | |
|---|---|
| Condition: | Malignant Melanoma |
| Interventions: | Biological: HyperAcute-Melanoma Vaccine; Genetic: HyperAcute-Melanoma Vaccine |

Broad Spectrum HPV (Human Papillomavirus) Vaccine (V505) in 16 to 26 Year Old Women

| | |
|---|---|
| Conditions: | Cervical Cancer; Vulvar Cancer; Vaginal Cancer; Genital Warts; Human Papillomavirus Infection |
| Interventions: | Biological: V505; Biological: Quadrivalent Human Papillomavirus (Types 6, 11, 16, 18) Recombinant Vaccine; Biological: Comparator: Placebo (unspecified) |

Study to Test the Efficacy of the Vaccine GSK 249553 in Treating Non-Small-Cell Lung Cancer After Tumour Removal by Surgery

| | |
|---|---|
| Condition: | Non-Small-Cell Lung Cancer (NSCLC) in Stage IB or II Following Complete Surgical Resection. |
| Intervention: | Biological: GSK 249553 vaccine |

Histocompatibility Leukocyte Antigen (HLA)-A*0201 Restricted Peptide Vaccine Therapy in Patients With Colorectal Cancer

| | |
|---|---|
| Conditions: | Colorectal Cancer; Colon Cancer; Rectal Cancer |
| Intervention: | Biological: VEGFR1 and VEGFR2 |

Histocompatibility Leukocyte Antigen (HLA)-A*2402 Restricted Peptide Vaccine Therapy in Patients With Colorectal Cancer

| | |
|---|---|
| Conditions: | Colorectal Cancer; Colon Cancer; Rectal Cancer |
| Intervention: | Biological: RNF43, TOMM34, VEGFR1 and VEGFR2 |

Rituximab, Autologous Vaccine Therapy, and Sargramostim in Treating Patients With Recurrent or Refractory Follicular B-Cell Lymphoma

| | |
|---|---|
| Condition: | Lymphoma |
| Interventions: | Drug: autologous immunoglobulin idiotype-KLH conjugate vaccine; Drug: rituximab; Drug: sargramostim |

Vaccine Therapy in Treating Patients With Unresected Stage III or Stage IV Melanoma

| | |
|---|---|
| Condition: | Melanoma (Skin) |
| Intervention: | Drug: autologous dendritic cell-allogeneic melanoma tumor cell lysate vaccine |

Vaccine Therapy in Treating Patients With Recurrent Soft Tissue Sarcoma

| | |
|---|---|
| Condition: | Sarcoma |
| Interventions: | Drug: autologous tumor cell vaccine; Drug: vitespen |

An Immunotherapy Vaccine Against Grade IV Brain Tumors

| | |
|---|---|
| Condition: | Brain Neoplasms |
| Intervention: | Biological: PEP-3-KLH |

Vaccine Therapy Followed by Biological Therapy in Treating Patients With Stage III or Stage IV Melanoma

| | |
|---|---|
| Condition: | Melanoma (Skin) |
| Interventions: | Drug: Candida albicans skin test reagent; Drug: MART-1 antigen; Drug: aldesleukin; Drug: gp100 antigen; Drug: recombinant CD40-ligand; Drug: recombinant interferon gamma; Drug: recombinant interleukin-4; Drug: sargramostim; Drug: therapeutic autologous dendritic cells; Drug: therapeutic tumor infiltrating lymphocytes; Drug: tyrosinase peptide |

TABLE S-continued

Cancer vaccines

Combination of Chemoradiation Therapy and Epitope Peptide Vaccine Therapy in Treating Patients With Esophageal Cancer Condition: Esophageal Cancer
Intervention: Biological: URLC10, TTK, KOC1, VEGFR1, VEGFR2, cisplatin, fluorouracil Vaccine Therapy Plus Interleukin-2 in Treating Patients With Stage III, Stage IV, or Recurrent Follicular Lymphoma Condition: Lymphoma
Interventions: Drug: aldesleukin; Drug: autologous tumor cell vaccine Chemotherapy, Radiation Therapy, and Vaccine Therapy With or Without Daclizumab in Treating Patients With Glioblastoma Multiforme That Has Been Removed by Surgery Condition: Brain and Central Nervous System Tumors
Interventions: Drug: PEP-3-KLH conjugate vaccine; Drug: daclizumab; Drug: placebo; Drug: temozolomide; Drug: therapeutic autologous lymphocytes Vaccine Trial for Clear Cell Sarcoma, Pediatric Renal Cell Carcinoma, Alveolar Soft Part Sarcoma and Children With Stage IV Melanoma Conditions: Sarcoma, Clear Cell; Sarcoma, Alveolar Soft Part; Renal Cell Carcinoma; Melanoma
Intervention: Biological: GVAX Effectiveness, Safety and Immunogenicity of GSK Biologicals' HPV Vaccine GSK580299 Administered in Healthy Adolescents.

Condition: HPV-16/18 Infections and Cervical Neoplasia
Interventions: Biological: GSK Biologicals' HPV vaccine 580299; Biological: Engerix-B Vaccine Therapy in Treating Patients With Acute Lymphoblastic Leukemia Condition: Leukemia
Intervention: Drug: autologous tumor cell vaccine Histocompatibility Leukocyte Antigen (HLA)-A*0201 Restricted Peptide Vaccine Therapy in Patients With Breast Cancer Condition: Breast Cancer
Intervention: Biological: VEGFR1 and VEGFR2

Vaccination of Follicular Lymphomas With Tumor-Derived Immunoglobulin Idiotype

Conditions: B Cell Lymphoma; Follicular Lymphoma; Neoplasm
Interventions: Drug: Id-KLH Vaccine; Drug: QS-21 (Stimulation-QS-21) Drug GM-CSF With or Without Vaccine Therapy After Combination Chemotherapy and Rituximab as First-Line Therapy in Treating Patients With Stage II, Stage III, or Stage IV Diffuse Large B-Cell Lymphoma Condition: Lymphoma
Interventions: Drug: autologous immunoglobulin idiotype-KLH conjugate vaccine;
Drug: cyclophosphamide; Drug: doxorubicin hydrochloride;
Drug: prednisone; Drug: rituximab; Drug: sargramostim;
Drug: vincristine; Procedure: Intervention/procedure;
Procedure: antibody therapy; Procedure: biological therapy;
Procedure: chemotherapy; Procedure: colony-stimulating factor therapy;
Procedure: cytokine therapy; Procedure: monoclonal antibody therapy;
Procedure: non-specific immune-modulator therapy;
Procedure: therapeutic procedure;
Procedure: tumor cell derivative vaccine; Procedure: vaccine therapy Vaccine Therapy and Autologous Lymphocyte Infusion With or Without Fludarabine in Treating Patients With Metastatic Melanoma Conditions: Intraocular Melanoma; Melanoma (Skin)
Interventions: Drug: MART-1 antigen; Drug: NY-ESO-1 peptide vaccine;
Drug: fludarabine phosphate; Drug: gp100 antigen;
Drug: recombinant MAGE-3.1 antigen;
Drug: therapeutic autologous dendritic cells;
Drug: therapeutic autologous lymphocytes; Drug: tyrosinase peptide Vaccine Therapy and Sargramostim in Treating Patients With Soft Tissue Sarcoma Condition: Sarcoma
Interventions: Drug: NY-ESO-1 peptide vaccine; Drug: sargramostim Tumor RNA Transfected Dendritic Cell Vaccines Condition: Prostate Cancer
Intervention: Biological: Tumor RNA transfected dendritic cells Broad Spectrum HPV (Human Papillomavirus) Vaccine Study in 16-to 26-Year-Old Women Conditions: Cervical Cancer; Vulvar Cancer; Vaginal Cancer; Genital Warts; Human Papillomavirus Infection
Interventions: Biological: V503; Biological: GARDASIL ®

TABLE S-continued

Cancer vaccines

Vaccine Therapy With Immune Adjuvant in Treating Patients With Stage IIB, Stage IIC, Stage III, or Stage IV Melanoma

| | |
|---|---|
| Condition: | Melanoma (Skin) |
| Interventions: | Drug: gp100 antigen; Drug: sargramostim plasmid DNA melanoma vaccine adjuvant; Drug: tyrosinase peptide |

Vaccine Therapy in Treating Patients With Stage IIB, Stage IIC, Stage III, or Stage IV Melanoma

| | |
|---|---|
| Conditions: | Intraocular Melanoma; Melanoma (Skin) |
| Interventions: | Drug: mouse gp100 plasmid DNA vaccine; Procedure: adjuvant therapy |

Vaccine Therapy in Treating Patients Who Have Received First-Line Therapy for Hodgkin's Lymphoma

| | |
|---|---|
| Condition: | Lymphoma |
| Interventions: | Drug: Hodgkin's antigens-GM-CSF-expressing cell vaccine; Procedure: adjuvant therapy |

Antiangiogenic Peptide Vaccine Therapy With Gemcitabine in Treating Patient With Pancreatic Cancer (Phase1/2)

| | |
|---|---|
| Condition: | Pancreatic Cancer |
| Intervention: | Biological: VEGFR1-1084, VEGFR2-169, Gemcitabine |

Vaccine Plus Interleukin-2 in Treating Patients With Advanced Melanoma

| | |
|---|---|
| Condition: | Melanoma (Skin) |
| Interventions: | Drug: aldesleukin; Drug: gp100 antigen; Drug: incomplete Freund's adjuvant |

Multiple-Vaccine Therapy in Treating Patients With Non-Small Cell Lung Cancer

| | |
|---|---|
| Condition: | Non Small Cell Lung Cancer |
| Intervention: | Biological: HLA-A*2402restricted URLC10, TTK, VEGFR1 and VEGFR2 |

Vaccine Therapy in Treating Patients With Stage III or Stage IV Melanoma

| | |
|---|---|
| Condition: | Melanoma (Skin) |
| Interventions: | Drug: autologous tumor cell vaccine; Drug: therapeutic autologous dendritic cells |

Histocompatibility Leukocyte Antigen (HLA)-A*0201 Restricted Peptide Vaccine Therapy in Patients With Esophageal Cancer

| | |
|---|---|
| Condition: | Esophageal Cancer |
| Intervention: | Biological: URLC10, VEGFR1 and VEGFR2 |

Histocompatibility Leukocyte Antigen (HLA)-A*2402 Restricted Peptide Vaccine Therapy in Patients With Esophageal Cancer

| | |
|---|---|
| Condition: | Esophageal Cancer |
| Intervention: | Biological: URC10, TTK, KOC1 |

Histocompatibility Leukocyte Antigen (HLA)-A*0201 Restricted Peptide Vaccine Therapy in Patients With Gastric Cancer

| | |
|---|---|
| Condition: | Gastric Cancer |
| Intervention: | Biological: URLC10, VEGFR1 and VEGFR2 |

Histocompatibility Leukocyte Antigen (HLA)-A*2402 Restricted Peptide Vaccine Therapy in Patients With Gastric Cancer

| | |
|---|---|
| Condition: | Gastric Cancer |
| Intervention: | Biological: URLC10, KOC1, VEGFR1 and VEGFR2 |

Human Papillomavirus (HPV) Vaccine Efficacy, Immunogenicity & Safety Trial in Adult Japanese Women With GSK Biologicals HPV-16/18 Vaccine

| | |
|---|---|
| Conditions: | HPV-16/18 Infections; Cervical Neoplasia |
| Intervention: | Biological: HPV-16/18 L1 VLP AS04 |

Cervical Intraepithelial Neoplasm (CIN)-Warts Efficacy Trial in Women (Gardasil)

| | |
|---|---|
| Conditions: | Cervical Cancer; Genital Warts |
| Intervention: | Biological: V501, Gardasil, human papillomavirus (types 6, 11, 16, 18) recombinant vaccine/Duration of Treatment: 4 years |

Cyclophosphamide and Fludarabine Followed by Vaccine Therapy, Gene-Modified White Blood Cell Infusions, and Aldesleukin in Treating Patients With Metastatic Melanoma

| | |
|---|---|
| Condition: | Melanoma (Skin) |
| Interventions: | Drug: MART-1: 27-35 peptide vaccine; Drug: aldesleukin; Drug: cyclophosphamide; Drug: filgrastim; Drug: fludarabine phosphate; Drug: incomplete Freund's adjuvant; Drug: therapeutic autologous lymphocytes; Drug: therapeutic tumor infiltrating lymphocytes; Procedure: autologous hematopoietic stem cell transplantation; Procedure: in vitro-treated peripheral blood stem cell transplantation; Procedure: total-body irradiation |

TABLE S-continued

Cancer vaccines

M-Vax + Low Dose Interleukin-2 Versus Placebo Vaccine in Metastatic Melanoma in Patients
With Stage IV Melanoma Condition: Melanoma
Intervention: Biological: M-Vax-autologous, hapten-modified melanoma vaccine
Histocompatibility Leukocyte Antigen (HLA)-A*2402 Restricted Peptide Vaccine Therapy in
Patients With Non-Small Cell Lung Cancer Condition: Non Small Cell Lung Cancer
Intervention: Biological: URLC10, TTK and KOC1
Histocompatibility Leukocyte Antigen (HLA)-A*0201 Restricted Peptide Vaccine Therapy in
Patients With Non-Small Cell Lung Cancer Condition: Non Small Cell Lung Cancer
Intervention: Biological: URLC10, VEGFR1 and VEGFR2
Histocompatibility Leukocyte Antigen (HLA)-A*2402 Restricted Peptide Vaccine Therapy in
Patients With Breast Cancer Condition: Breast Cancer
Intervention: Biological: TTK peptide mixed with Montanide ISA 51
Autologous T-Cell Transplantation, Vaccine Therapy, and Indinavir in Treating Patients With
Metastatic Pediatric Sarcomas Condition: Sarcoma
Interventions: Drug: indinavir sulfate; Drug: therapeutic autologous dendritic cells;
Procedure: peripheral blood stem cell transplantation
Vaccine Therapy in Treating Patients With Metastatic Melanoma Conditions: Intraocular Melanoma; Melanoma (Skin)
Interventions: Drug: MART-1 antigen; Drug: gp100: 209-217(210M) peptide vaccine;
Drug: therapeutic autologous dendritic cells; Drug: tyrosinase peptide
Human Papillomavirus Vaccine Immunogenicity and Safety Trial in Young Adult Women With
GSK Biologicals Novel HPV Vaccine Conditions: Cervical Neoplasia; Papillomavirus Infections
Intervention: Biological: Novel HPV vaccine (GSK568893A)
Vaccine Therapy With or Without Sargramostim in Treating Patients With High-Risk or
Metastatic Melanoma Condition: Melanoma (Skin)
Interventions: Drug: MAGE-10.A2; Drug: MART-1 antigen; Drug: NY-ESO-
1 peptide vaccine; Drug: sargramostim; Drug: tyrosinase peptide
Vaccine Therapy and GM-CSF in Treating Patients With CNS Lymphoma Condition: Lymphoma
Interventions: Drug: autologous immunoglobulin idiotype-KLH conjugate vaccine;
Drug: methotrexate; Drug: sargramostim; Drug: thiotepa;
Procedure: radiation therapy
Vaccine Therapy in Treating Patients With Stage IV Melanoma Condition: Melanoma (Skin)
Interventions: Drug: autologous tumor cell vaccine;
Drug: therapeutic autologous dendritic cells
Peptide Vaccinations to Treat Patients With Low-Risk Myeloid Cancers Conditions: Myelodysplastic Syndrome (MDS); Acute Myeloid Leukemia (AML);
Chronic Myeloid Leukemia (CML)
Interventions: Biological: WT1: 126-134 Peptide; Biological: PR1: 169-177 Peptide;
Drug: GM-CSF (Sargramostim); Drug: WT1 and PR1 Peptide Vaccines;
Biological: WT1 and PR1 Peptide Vaccines
Rituximab and Cyclophosphamide Followed by Vaccine Therapy in Treating Patients With
Relapsed Hodgkin's Lymphoma Condition: Lymphoma
Interventions: Drug: Hodgkin's antigens-GM-CSF-expressing cell vaccine;
Drug: cyclophosphamide; Drug: filgrastim; Drug: rituximab
Vaccine Therapy and Ganciclovir in Treating Patients With Mesothelioma Condition: Malignant Mesothelioma
Interventions: Drug: PA-1-STK ovarian carcinoma vaccine; Drug: ganciclovir
Vaccine Therapy and Imatinib Mesylate in Treating Patients With Chronic Phase Chronic
Myelogenous Leukemia Condition: Leukemia
Interventions: Drug: GM-K562 cell vaccine; Drug: imatinib mesylate TABLE S-continued Cancer vaccines Peptide-Pulsed vs. RNA-Transfected Dendritic Cell Vaccines in Melanoma Patients Condition: Melanoma Stage III or IV
Intervention: Biological: Dendritic cell vaccine Vaccine Therapy Plus Immune Adjuvant in Treating Patients With Chronic Myeloid Leukemia, Acute Myeloid Leukemia, or Myelodysplastic Syndrome Conditions: Leukemia; Myelodysplastic Syndromes; Myelodysplastic/Myeloproliferative Diseases
Interventions: Drug: PR1 leukemia peptide vaccine; Drug: incomplete Freund's adjuvant; Drug: sargramostim Evaluation of the Immune and Safety Response of GlaxoSmithKline (GSK) Biologicals' HPV Vaccine in Healthy Indian Women Conditions: Cervical Cancer; Papillomavirus Infections
Intervention: Biological: HPV-16/18 L1/AS04

Vaccine Therapy With or Without Interleukin-12 in Treating Patients With Stage III or Stage IV Melanoma Conditions: Intraocular Melanoma; Melanoma (Skin)
Interventions: Drug: gp100 antigen; Drug: incomplete Freund's adjuvant; Drug: recombinant interleukin-12; Drug: tyrosinase peptide Interferon-Gamma or Aldesleukin and Vaccine Therapy in Treating Patients With Multiple Myeloma Condition: Multiple Myeloma and Plasma Cell Neoplasm
Interventions: Drug: aldesleukin; Drug: idiotype-pulsed autologous dendritic cell vaccine APC8020; Drug: recombinant interferon gamma; Procedure: flow cytometry; Procedure: laboratory biomarker analysis; Procedure: polymerase chain reaction; Procedure: reverse transcriptase-polymerase chain reaction Safety and Immunogenicity of a Melanoma DNA Vaccine Delivered by Electroporation Conditions: Melanoma (Skin); Intraocular Melanoma
Interventions: Biological: Xenogeneic Tyrosinase DNA Vaccine; Device: TriGrid Delivery System for Intramuscular Electroporation A Study to Evaluate Tolerability and Immunogenicity of V504 Administered Concomitantly With GARDASIL Conditions: Cervical Cancer; Vulvar Cancer; Vaginal Cancer; Genital Warts; Human Papillomavirus Infection
Interventions: Biological: V504; Biological: Quadrivalent Human Papillomavirus (Types 6, 11, 16, 18) Recombinant Vaccine; Biological: Comparator: Placebo (unspecified)

A Study to Evaluate the Immunogenicity and Safety of GSK Biologicals' HPV Vaccine in Healthy Women Aged 18-35 Years.

Conditions: HPV-16 Infection; HPV-18 Infection; Associated Cervical Neoplasia
Intervention: Biological: HPV-16/18 L1 VLP AS04

Safety of Co-Administering Human Papillomavirus (HPV) Vaccine With Other Vaccines in Healthy Female Subjects Conditions: Cervical Neoplasms; Papillomavirus Infections
Intervention: Biological: HPV-16/18 L1/AS04

Vaccine Therapy With or Without Cyclophosphamide in Treating Patients Who Have Undergone Surgery for Stage II, Stage III, or Stage IV Melanoma Condition: Melanoma (Skin)
Interventions: Drug: cyclophosphamide; Drug: incomplete Freund's adjuvant; Drug: melanoma helper peptide vaccine; Drug: multi-epitope melanoma peptide vaccine; Drug: tetanus toxoid helper peptide Vaccine Therapy and GM-CSF in Treating Patients With Progressive Non-Hodgkin's Lymphoma Condition: Lymphoma
Interventions: Drug: autologous immunoglobulin idiotype-KLH conjugate vaccine; Drug: sargramostim Trial of Autologous, Hapten-Modified Vaccine in Patients With Stage III or IV Melanoma Condition: Melanoma
Interventions: Biological: Autologous, DNP-modified vaccine (M-Vax); Biological: Autologous, DNP-Modified Melanoma Vaccine; Biological: Autologous, DNP-Modified Vaccine; Biological: Autologous, DNP-Modified Vaccine; Biological: Autologous, DNP-Modified Vaccine TABLE S-continued

| Cancer vaccines |
|---|

Docetaxel With or Without Vaccine Therapy and GM-CSF in Treating Patients With Metastatic Breast Cancer

| | |
|---|---|
| Condition: | Breast Cancer |
| Interventions: | Drug: docetaxel; Drug: falimarev; Drug: inalimarev; Drug: sargramostim |

Vaccine Therapy and Sargramostim in Treating Adults With Metastatic Cancer

| | |
|---|---|
| Conditions: | Breast Cancer; Colorectal Cancer; Ovarian Cancer; Unspecified Adult Solid Tumor, Protocol Specific |
| Interventions: | Drug: falimarev; Drug: inalimarev; Drug: sargramostim |

Peptide Vaccine, Montanide ISA 51 and ISA 51 VG, and CpG 7909 in Treating Patients With Resected Stage IIC, Stage III, or Stage IV Melanoma

| | |
|---|---|
| Conditions: | Intraocular Melanoma; Melanoma (Skin) |
| Interventions: | Drug: CpG 7909; Drug: gp100 antigen; Drug: incomplete Freund's adjuvant; Drug: recombinant MAGE-3.1 antigen; Drug: tyrosinase peptide; Procedure: adjuvant therapy |

3-Dimensional Conformal Radiation Therapy, Arterial Embolization, and Tumor Cell Vaccine in Treating Patients With Unresectable, Recurrent, or Metastatic Primary Liver Cancer or Pancreatic Cancer

| | |
|---|---|
| Conditions: | Liver Cancer; Pancreatic Cancer |
| Interventions: | Drug: poly ICLC; Procedure: 3-dimensional conformal radiation therapy; Procedure: biopsy; Procedure: hepatic artery embolization |

Vaccine Therapy Plus Chemotherapy in Treating Patients With Metastatic or Locally Recurrent Stomach Cancer or Esophageal Cancer

| | |
|---|---|
| Conditions: | Esophageal Cancer; Gastric Cancer |
| Interventions: | Drug: G17DT; Drug: cisplatin; Drug: fluorouracil |

Vaccine Therapy in Treating Patients With Stage I or Stage II Pancreatic Cancer

| | |
|---|---|
| Condition: | Pancreatic Cancer |
| Intervention: | Drug: vitespen |

Vaccine Therapy in Treating Patients With Liver Metastases From Colorectal Cancer

| | |
|---|---|
| Conditions: | Colorectal Cancer; Metastatic Cancer |
| Interventions: | Drug: falimarev; Drug: inalimarev; Drug: sargramostim; Drug: therapeutic autologous dendritic cells |

Vaccine Therapy in Treating Patients With Metastatic Prostate Cancer That Has Not Responded to Hormone Therapy

| | |
|---|---|
| Condition: | Prostate Cancer |
| Interventions: | Drug: prostatic acid phosphatase-sargramostim fusion protein; Drug: sipuleucel-T; Procedure: in vitro-treated peripheral blood stem cell transplantation; Procedure: peripheral blood stem cell transplantation |

Vaccine Therapy in Treating Patients With High-Risk Stage III or Completely Resected Metastatic Melanoma

| | |
|---|---|
| Conditions: | Stage IV Melanoma; Stage III Melanoma; Recurrent Melanoma |
| Interventions: | Drug: dendritic cell-gp100-MART-1 antigen vaccine; Drug: sargramostim |

Vaccine Therapy in Treating Patients With Stage III or Stage IV Non-Small Cell Lung Cancer

| | |
|---|---|
| Condition: | Lung Cancer |
| Interventions: | Drug: belagenpumatucel-L; Drug: placebo |

Lymphocyte-Depleting Nonmyeloablative Preparative Chemotherapy Followed By Autologous Lymphocyte Infusion, Peptide Vaccine Plus Montanide ISA-51, and Interleukin-2 in Treating Patients With Metastatic Melanoma

| | |
|---|---|
| Condition: | Melanoma (Skin) |
| Interventions: | Drug: NY-ESO-1 peptide vaccine; Drug: aldesleukin; Drug: cyclophosphamide; Drug: filgrastim; Drug: fludarabine phosphate; Drug: incomplete Freund's adjuvant; Drug: therapeutic autologous lymphocytes |

Vaccine Therapy in Treating Patients With Melanoma

| | |
|---|---|
| Condition: | Melanoma (Skin) |
| Interventions: | Drug: HPV 16 E7: 12-20 peptide vaccine; Drug: gp100 antigen; Drug: incomplete Freund's adjuvant; Procedure: adjuvant therapy |

Imatinib Mesylate, Interferon Alfa, and GM-CSF Compared With Imatinib Mesylate and Vaccine Therapy in Treating Patients With Chronic Phase Chronic Myelogenous Leukemia

| | |
|---|---|
| Condition: | Leukemia |
| Interventions: | Drug: GM-K562 cell vaccine; Drug: recombinant interferon alfa; Drug: sargramostim |

TABLE S-continued

Cancer vaccines

Vaccine Therapy Following Chemotherapy and Peripheral Stem Cell Transplantation in Treating Patients With Non-Hodgkin's Lymphoma

Condition: Lymphoma
Interventions: Drug: autologous tumor cell vaccine; Drug: keyhole limpet hemocyanin; Drug: sargramostim; Procedure: adjuvant therapy

Surgery and Vaccine Therapy in Treating Patients With Early Cervical Cancer

Condition: Cervical Cancer
Interventions: Drug: human papillomavirus 16 E7 peptide; Drug: synthetic human papillomavirus 16 E6 peptide; Procedure: adjuvant therapy; Procedure: radiation therapy; Procedure: surgical procedure

Vaccine Therapy and Interleukin-2 With or Without White Blood Cell Transplantation in Treating Patients With Recurrent Sarcomas

Conditions: Recurrent Childhood Rhabdomyosarcoma; Extraosseous Ewing's Sarcoma/Primitive Neuroectodermal Tumor; Recurrent Ewing's Sarcoma/Primitive Neuroectodermal Tumor; Adult Rhabdomyosarcoma; Recurrent Childhood Soft Tissue Sarcoma; Alveolar Childhood Rhabdomyosarcoma; Recurrent Tumors of the Ewing's Family; Recurrent Adult Soft Tissue Sarcoma
Intervention: Drug: interleukin-2

Vaccine Therapy in Treating Patients With Stage II Melanoma That Can Be Removed by Surgery

Condition: Melanoma (Skin)
Interventions: Drug: gp100 antigen; Drug: incomplete Freund's adjuvant; Drug: sargramostim; Drug: tyrosinase peptide

Vaccine Therapy and Celecoxib in Treating Patients With Metastatic Nasopharyngeal Cancer

Condition: Head and Neck Cancer
Interventions: Drug: Ad5F35-LMP1/LMP2-transduced autologous dendritic cells; Drug: celecoxib; Procedure: flow cytometry; Procedure: immunoenzyme technique; Procedure: laboratory biomarker analysis

Vaccine Therapy in Treating Patients With Newly Diagnosed Glioblastoma Multiforme

Condition: Brain and Central Nervous System Tumors
Interventions: Drug: tetanus toxoid; Drug: therapeutic autologous dendritic cells; Drug: therapeutic autologous lymphocytes

Gene-Modified White Blood Cells Followed By Interleukin-2 and Vaccine Therapy in Treating Patients With Metastatic Melanoma

Condition: Melanoma (Skin)
Interventions: Drug: aldesleukin; Drug: cyclophosphamide; Drug: filgrastim; Drug: fludarabine phosphate; Drug: gp100-fowlpox vaccine; Drug: therapeutic autologous lymphocytes; Drug: therapeutic tumor infiltrating lymphocytes

Chemotherapy Consisting of Fludarabine and Cyclophosphamide Followed By White Blood Cell Infusion, Vaccine Therapy, and Aldesleukin in Treating Patients With Recurrent or Refractory Metastatic Melanoma

Condition: Melanoma (Skin)
Interventions: Drug: aldesleukin; Drug: cyclophosphamide; Drug: filgrastim; Drug: fludarabine phosphate; Drug: fowlpox virus vaccine vector; Drug: gp100 antigen; Drug: therapeutic autologous lymphocytes; Drug: therapeutic tumor infiltrating lymphocytes

A Study of TroVax Vaccine Given in Conjunction With IL-2 for Treatment of Stage IV Renal Cell Cancer

Condition: Carcinoma, Renal Cell
Intervention: Drug: TroVax in combination with IL-2

Vaccine Therapy in Treating Patients With Melanoma

Condition: Melanoma (Skin)
Interventions: Drug: ALVAC-hB7.1; Drug: canarypox-hIL-12 melanoma vaccine

Melanoma Vaccine With Peptides and Leuprolide

Condition: Melanoma
Interventions: Drug: Leuprolide; Biological: GP100: 209-217(210M) Peptide; Biological: MAGE-3 Peptide

Vaccine Therapy in Treating Patients With Myelodysplastic Syndromes

Condition: Myelodysplastic Syndromes
Interventions: Drug: GM-K562 cell vaccine; Procedure: cytogenetic analysis; Procedure: flow cytometry; Procedure: fluorescence in situ hybridization; Procedure: immunoenzyme technique;

TABLE S-continued

Cancer vaccines

Procedure: laboratory biomarker analysis
Vaccination for Patients With High Risk Cancers of the Blood

| | |
|---|---|
| Conditions: | Myelodysplastic Syndrome; Acute Myeloid Leukemia (AML); Chronic Myeloid Leukemia (CML) |
| Intervention: | Drug: WR 1 and PR 1 Peptide Vaccine |

Immunization Against Tumor Cells in Sezary Syndrome

| | |
|---|---|
| Conditions: | Cutaneous T-Cell Lymphoma; Sezary Syndrome |
| Intervention: | Biological: Autologous Dendritic Cell Vaccine |

Vaccine Therapy in Treating Patients With Metastatic Melanoma

| | |
|---|---|
| Condition: | Melanoma (Skin) |
| Intervention: | Drug: recombinant vaccinia-TRICOM vaccine |

Cervical Intraepithelial Neoplasm (CIN) in Women (Gardasil)

| | |
|---|---|
| Conditions: | Cervical Cancer; Genital Warts |
| Intervention: | Biological: V501, Gardasil, human papillomavirus (type 6, 11, 16, 18) recombinant vaccine/Duration of Treatment: 4 years |

Immunogenicity & Safety of a Commercially Available Vaccine co-Administered With GSK HPV Vaccine (580299)

| | |
|---|---|
| Condition: | Hepatitis B, HPV-16/18 Infections and Cervical Neoplasia |
| Interventions: | Biological: GSK Biologicals' HPV vaccine 580299; Biological: GSK Biologicals' vaccine 103860 |

Vaccine Therapy in Treating Patients With Stage IV Melanoma

| | |
|---|---|
| Condition: | Melanoma (Skin) |
| Interventions: | Drug: dendritic cell-MART-1 peptide vaccine; Drug: gp100 antigen; Drug: therapeutic tumor infiltrating lymphocytes; Drug: tyrosinase peptide |

Vaccine Therapy With or Without Sargramostim in Treating Patients Who Have Undergone Surgery for Melanoma

| | |
|---|---|
| Conditions: | Intraocular Melanoma; Melanoma (Skin) |
| Interventions: | Drug: MART-1 antigen; Drug: gp100 antigen; Drug: incomplete Freund's adjuvant; Drug: sargramostim; Drug: tyrosinase peptide; Procedure: adjuvant therapy |

Vaccine Therapy Using Melanoma Peptides for Cytotoxic T Cells and Helper T Cells in Treating Patients With Metastatic Melanoma

| | |
|---|---|
| Condition: | Melanoma (Skin) |
| Interventions: | Drug: incomplete Freund's adjuvant; Drug: melanoma helper peptide vaccine; Drug: multi-epitope melanoma peptide vaccine; Drug: sargramostim; Drug: tetanus peptide melanoma vaccine |

Vaccine Therapy in Treating Patients With Stage III or Stage IV Melanoma

| | |
|---|---|
| Conditions: | Intraocular Melanoma; Melanoma (Skin) |
| Interventions: | Drug: MART-1 antigen; Drug: gp100 antigen; Drug: incomplete Freund's adjuvant; Drug: progenipoietin; Drug: tyrosinase peptide |

Vaccine Therapy in Treating Patients With Newly Diagnosed Glioblastoma Multiforme Recovering From Lymphopenia Caused by Temozolomide

| | |
|---|---|
| Condition: | Brain and Central Nervous System Tumors |
| Interventions: | Drug: therapeutic autologous dendritic cells; Drug: therapeutic autologous lymphocytes |

Vaccine Therapy and Interleukin-12 With Either Alum or Sargramostim After Surgery in Treating Patients With Melanoma

| | |
|---|---|
| Conditions: | Intraocular Melanoma; Melanoma (Skin) |
| Interventions: | Drug: MART-1 antigen; Drug: alum adjuvant; Drug: gp100 antigen; Drug: incomplete Freund's adjuvant; Drug: recombinant interleukin-12; Drug: sargramostim; Drug: tyrosinase peptide; Procedure: adjuvant therapy |

Vaccine Therapy in Treating Patients With Resected or Locally Advanced Unresectable Pancreatic Cancer

| | |
|---|---|
| Condition: | Pancreatic Cancer |
| Intervention: | Drug: MUC-1 antigen/SB AS-2 |

Vaccine Therapy in Preventing Cervical Cancer in Patients With Cervical Intraepithelial Neoplasia

| | |
|---|---|
| Conditions: | Cervical Cancer; Precancerous/Nonmalignant Condition |
| Intervention: | Drug: HspE7 |

TABLE S-continued

Cancer vaccines

Vaccine Therapy in Treating Patients With Advanced Cancer

| | |
|---|---|
| Condition: | Unspecified Adult Solid Tumor, Protocol Specific |
| Intervention: | Drug: TG4010 |

Adesleukin With or Without Vaccine Therapy in Treating Patients With Locally Advanced or Metastatic Melanoma

| | |
|---|---|
| Condition: | Melanoma (Skin) |
| Interventions: | Drug: aldesleukin; Drug: gp100 antigen; Drug: incomplete Freund's adjuvant |

Vaccine Therapy in Treating Patients With Malignant Glioma

| | |
|---|---|
| Condition: | Brain and Central Nervous System Tumors |
| Intervention: | Drug: therapeutic autologous dendritic cells |

Vaccine Therapy With or Without Biological Therapy in Treating Patients With Metastatic Melanoma

| | |
|---|---|
| Condition: | Melanoma (Skin) |
| Interventions: | Drug: MART-1 antigen; Drug: gp100 antigen; Drug: incomplete Freund's adjuvant; Drug: recombinant interferon alfa; Drug: sargramostim; Drug: tyrosinase peptide |

Cyclophosphamide and Fludarabine Followed By Autologous Gene-Modified Lymphocytes, Vaccine Therapy, and High-Dose Aldesleukin in Treating Patients With Metastatic Melanoma

| | |
|---|---|
| Condition: | Melanoma (Skin) |
| Interventions: | Drug: ALVAC-CEA vaccine; Drug: aldesleukin; Drug: autologous anti-gp 100: 154-162 T-cell receptor gene-engineered peripheral blood lymphocytes; Drug: cyclophosphamide; Drug: fludarabine phosphate |

Vaccine Therapy in Treating Patients With Stage IIB, Stage IIC, Stage III, or Stage IV Melanoma

| | |
|---|---|
| Condition: | Melanoma (Skin) |
| Interventions: | Drug: human gp100 plasmid DNA vaccine; Drug: mouse gp100 plasmid DNA vaccine |

Cyclophosphamide and Fludarabine Followed By Vaccine Therapy, Autologous Gene-Modified Lymphocytes, and High-Dose Aldesleukin in Treating Patients With Metastatic Melanoma

| | |
|---|---|
| Condition: | Melanoma (Skin) |
| Interventions: | Drug: ALVAC-MART-1 vaccine; Drug: aldesleukin; Drug: autologous anti-MART-1 F5 T-cell receptor gene-engineered peripheral blood lymphocytes; Drug: cyclophosphamide; Drug: fludarabine phosphate |

Follow-Up Evaluation of Patients With Solid Tumors Previously Enrolled in a Vaccine Therapy Clinical Trial

| | |
|---|---|
| Conditions: | Breast Cancer; Colorectal Cancer; Long-Term Effects Secondary to Cancer Therapy in Adults; Metastatic Cancer; Ovarian Cancer; Prostate Cancer; Unspecified Adult Solid Tumor, Protocol Specific |
| Interventions: | Procedure: management of therapy complications; Procedure: observation |

Vaccine Therapy Plus QS21 in Treating Patients With Small Cell Lung Cancer That Has Responded to Initial Therapy

| | |
|---|---|
| Condition: | Lung Cancer |
| Interventions: | Drug: QS21; Drug: keyhole limpet hemocyanin; Drug: polysialic acid |

Study of a Multi-Antigen Therapeutic Vaccine in Patients With Metastatic Melanoma

| | |
|---|---|
| Conditions: | Melanoma; Cancer |
| Interventions: | Biological: ALVAC(2) Melanoma multi-antigen therapeutic vaccine; Biological: Intron-A ®: IFN-α2b |

Vaccine Therapy in Treating Patients With Cancer of the Gastrointestinal Tract

| | |
|---|---|
| Conditions: | Colorectal Cancer; Esophageal Cancer; Extrahepatic Bile Duct Cancer; Gallbladder Cancer; Gastric Cancer; Pancreatic Cancer; Small Intestine Cancer |
| Interventions: | Drug: carcinoembryonic antigen peptide 1-6D; Drug: incomplete Freund's adjuvant; Drug: sargramostim |

Vaccine Therapy in Treating Patients With Stage I, Stage II, or Stage IIIA Non-Small Cell Lung Cancer or With Stage I or Stage II Mesothelioma

| | |
|---|---|
| Conditions: | Lung Cancer; Malignant Mesothelioma |
| Interventions: | Drug: DetoxPC; Drug: cyclophosphamide; Drug: lung tumor associated antigen; Procedure: chemotherapy |

Monoclonal Antibody Vaccine Therapy in Treating Patients With Ovarian Epithelial, Fallopian Tube, or Peritoneal Cancer

| | |
|---|---|
| Conditions: | Fallopian Tube Cancer; Ovarian Cancer; Peritoneal Cavity Cancer |
| Intervention: | Drug: abagovomab |

TABLE S-continued

Cancer vaccines

Vaccine Therapy in Treating Patients With Recurrent B-Cell Lymphoma

| | |
|---|---|
| Condition: | Lymphoma |
| Interventions: | Procedure: flow cytometry; Procedure: immunoenzyme technique; Procedure: non-tumor cell-derivative vaccine therapy |

Monoclonal Antibody A1G4 Plus BCG in Treating Patients With Cancer

| | |
|---|---|
| Conditions: | Neuroblastoma; Sarcoma |
| Interventions: | Drug: BCG vaccine; Drug: monoclonal antibody A1G4 anti-idiotype vaccine |

Immunogenicity and Safety of GlaxoSmithKline Biologicals' HPV Vaccine 580299 in Healthy Females 15-25 Years of Age

| | |
|---|---|
| Condition: | HPV-16/18 Infections and Cervical Neoplasia |
| Intervention: | Biological: GSK580299 |

Chemotherapy and Peripheral Stem Cell Transplantation Followed By Immunotherapy in Treating Patients With Multiple Myeloma

| | |
|---|---|
| Conditions: | Infection; Multiple Myeloma and Plasma Cell Neoplasm |
| Interventions: | Drug: carmustine; Drug: cyclophosphamide; Drug: filgrastim; Drug: melphalan; Drug: pneumococcal polyvalent vaccine; Drug: therapeutic autologous lymphocytes; Drug: therapeutic tumor infiltrating lymphocytes; Procedure: bone marrow ablation with stem cell support; Procedure: peripheral blood stem cell transplantation |

Safety and Immunogenicity of GlaxoSmithKline Biologicals' HPV Vaccine 580299 in HIV Infected Females

| | |
|---|---|
| Conditions: | HPV-16/18 Infections; Cervical Neoplasia |
| Intervention: | Biological: GSK Biologicals' HPV vaccine 580299 | flt3L With or Without Vaccine Therapy in Treating Patients With Metastatic Melanoma or Renal Cell Cancer

| | |
|---|---|
| Conditions: | Stage IV Melanoma; Stage IV Renal Cell Cancer; Recurrent Renal Cell Cancer; Recurrent Melanoma |
| Interventions: | Drug: flt3 ligand; Drug: gp100 antigen; Drug: MART-1 antigen; Drug: Montanide ISA-51; Drug: tyrosinase peptide |

Vaccine Therapy in Treating Patients With Refractory Stage IV Cancer

| | |
|---|---|
| Condition: | Unspecified Adult Solid Tumor, Protocol Specific |
| Interventions: | Drug: CMV pp65 peptide; Drug: carcinoembryonic antigen peptide 1-6D; Drug: therapeutic autologous dendritic cells |

A Study to Evaluate the Safety, Immune Response, and Efficacy of Gardasil (V501) in Women

| | |
|---|---|
| Conditions: | Healthy; Papillomavirus Infection |
| Interventions: | Biological: V501, Gardasil, human papillomavirus (types 6, 11, 16, 18) recombinant vaccine; Biological: Comparator: placebo |

LMB-2 Immunotoxin and Vaccine Therapy in Treating Patients With Metastatic Melanoma That Cannot Be Removed By Surgery

| | |
|---|---|
| Conditions: | Melanoma (Skin); Non-Melanomatous Skin Cancer |
| Interventions: | Drug: LMB-2 immunotoxin; Drug: MART-1 antigen; Drug: gp100 antigen; Drug: incomplete Freund's adjuvant |

Feasibility Study of Acute Myelogenous Leukemia mRNA Plus Lysate Loaded Dendritic Cell Vaccines

| | |
|---|---|
| Condition: | Leukemia |
| Intervention: | Biological: Autologous Dendritic Cells |

Vaccination Therapy in Treating Patients With Limited-Stage Small Cell Lung Cancer

| | |
|---|---|
| Condition: | Lung Cancer |
| Interventions: | Drug: BCG vaccine; Drug: monoclonal antibody BEC2 |

Efficacy Study of HPV-16/18 Vaccine (GSK 580299) to Prevent HPV-16 and/or -18 Cervical Infection in Young Healthy Women

| | |
|---|---|
| Condition: | Papillomavirus Infections |
| Interventions: | Biological: Cervarix; Biological: placebo |

Vaccine Therapy With or Without Sargramostim in Treating Patients With Stage IIB, Stage IIC, Stage III, or Stage IV Melanoma

| | |
|---|---|
| Condition: | Melanoma (Skin) |
| Interventions: | Drug: incomplete Freund's adjuvant; Drug: multi-epitope melanoma peptide vaccine; Drug: sargramostim |

TABLE S-continued

Cancer vaccines

Autologous T-Cell Transplantation and the Immunotherapy of Residual Disease in Breast
Cancer: Pilot Study of Vaccine-Driven T-Cell Expansion in Patients Treated With Dose-
Intensive Chemotherapy Conditions: Breast Neoplasm; Neoplasm Metastasis
Interventions: Procedure: Autologous T cells; Drug: Interleukin-2

Study to Evaluate the Immune Response and Safety of GSK Biologicals' HPV Vaccine in
Healthy Women Aged 18-35 Years Conditions: HPV-16 Infection; HPV-18 Infection; Associated Cervical Neoplasia
Intervention: Biological: HPV-16/18 L1 VLP AS04

A Study to Evaluate the Immune Response and Safety of GSK Biologicals' HPV Vaccine in
Healthy Females Aged 15-25 Years.

Conditions: HPV-16 Infection; HPV-18 Infection; Associated Cervical Neoplasia
Intervention: Biological: HPV-16/18 L1 VLP AS04

Vaccine Therapy With or Without Cyclophosphamide in Treating Patients With Recurrent or
Refractory Multiple Myeloma Condition: Multiple Myeloma and Plasma Cell Neoplasm
Interventions: Drug: cyclophosphamide; Drug: oncolytic measles virus encoding
thyroidal sodium iodide symporter; Procedure: biopsy;
Procedure: flow cytometry; Procedure: immunologic technique;
Procedure: laboratory biomarker analysis; Procedure: reverse
transcriptase-polymerase chain reaction Study of Combination Immunotherapy for the Generation of HER-2/Neu Specific Cytotoxic T
Cells Condition: Breast Cancer
Intervention: Biological: HER2 CTL vaccine (plus trastuzumab)

Dendritic Cell Vaccine for High Risk Ovarian Cancer Patients

Condition: Ovarian Cancer
Intervention: Biological: DC-Ova

Vaccine Therapy With or Without Imiquimod in Treating Patients Who Have Undergone
Surgery for Stage II, Stage III, or Stage IV Melanoma Condition: Melanoma (Skin)
Interventions: Drug: dimethyl sulfoxide; Drug: imiquimod;
Drug: incomplete Freund's adjuvant; Drug: multi-
epitope melanoma peptide vaccine; Drug: sargramostim;
Drug: tetanus toxoid helper peptide; Procedure: adjuvant therapy A Phase I Study of gp100 Human Melanoma Peptide Vaccine With Incomplete Freund's
Adjuvant Condition: Melanoma
Intervention: Biological: gp100 human melanoma peptide MDX-010 Antibody, MDX-1379 Melanoma Vaccine, or MDX-010/MDX-1379 Combination
Treatment for Patients With Melanoma Conditions: Melanoma; Metastases
Interventions: Drug: MDX-010 (anti-CTLA4) monoclonal antibody; Biological: MDX-
1379 Melanoma Peptide Vaccine Evaluation of Safety and Immunogenicity of Co-Administering HPV Vaccine With Other
Vaccines in Healthy Female Subjects Conditions: Papillomavirus Infections; Cervical Neoplasia
Interventions: Biological: HPV-16/18 L1 AS04 (580299);
Biological: Boostrix Polio (dTpa-IPV)

Safety of Peptide Vaccination for Patients With Myelodysplastic Syndrome

Condition: Myelodysplastic Syndrome (MDS)
Intervention: Drug: WT1 and PR1 Peptide Vaccine Vaccine Therapy in Treating Patients With Primary Stage II Melanoma Condition: Melanoma (Skin)
Interventions: Drug: GM2-KLH vaccine; Drug: QS21; Procedure: adjuvant therapy Evaluation of Immunogenicity and Safety of Human Papillomavirus (HPV) Vaccine co-
Administered With Another Vaccine in Healthy Female Subjects Condition: Human Papillomavirus Infection
Interventions: Biological: HPV Vaccine (GSK580299); Biological: Engerix B Vaccine Therapy Plus Interleukin-2 With or Without Interferon Alfa-2b in Treating Patients With
Stage III Melanoma Condition: Melanoma (Skin)
Interventions: Drug: interleukin-2 liposome; Drug: polyvalent melanoma vaccine;
Drug: recombinant interferon alfa TABLE S-continued Cancer vaccines Human Papilloma Virus (HPV) Vaccine Trial in Young Adolescent Women With GSK Biologicals' (GSK Bio) HPV-16/18 Vaccine Conditions: Papillomavirus Infections; Cervical Intraepithelial Neoplasia
Intervention: Biological: HPV-16/18 L1/AS04

Antiangiogenic Peptide Vaccine Therapy With Gemcitabine in Treating Patient With Pancreatic Cancer Condition: Pancreatic Cancer
Intervention: Biological: VEGFR1-1084, VEGFR2-169, and gemcitabine Evaluation of Safety and Immunogenicity of co-Administering HPV Vaccine With Another Vaccine in Heal by Female Subjects.

Condition: Human Papillomavirus Infection
Intervention: Biological: HPV vaccine (GSK-580299)

Peptide Vaccine and S-1/CPT-11 Therapy for Patients With Unresectable Advanced Colorectal Cancer Condition: Colorectal Cancer
Intervention: Biological: RNF43-721

Gemcitabine With Antiangiogenic Peptide Vaccine Therapy in Patients With Pancreatic Cancer Condition: Pancreatic Cancer
Intervention: Biological: VEGFR2-169 and gemcitabine Monoclonal Antibody Therapy and Vaccine Therapy in Treating Patients With Resected Stage III or Stage IV Melanoma Conditions: Intraocular Melanoma; Melanoma (Skin)
Interventions: Drug: MART-1 antigen; Drug: gp100 antigen;
Drug: incomplete Freund's adjuvant; Drug: ipilimumab;
Drug: tyrosinase peptide Vaccine Therapy in Treating Patients With Stage IV or Relapsed Malignant Melanoma Condition: Melanoma (Skin)
Interventions: Drug: dendritic cell-MART-1 peptide vaccine; Procedure: in vitro-treated peripheral blood stem cell transplantation Vaccine Therapy in Treating Patients With Stage IV or Recurrent Malignant Melanoma Condition: Melanoma (Skin)
Intervention: Drug: dendritic cell-MART-1 peptide vaccine Fludarabine Followed by Vaccine Therapy and White Blood Cell Infusions in Treating Patients With Unresectable or Metastatic Melanoma Condition: Melanoma (Skin)
Interventions: Drug: fludarabine phosphate; Drug: gp100 antigen;
Drug: incomplete Freund's adjuvant; Drug: keyhole limpet hemocyanin;
Procedure: peripheral blood stem cell transplantation Vaccine Therapy With or Without Interleukin-2 in Treating Patients With Metastatic Melanoma Conditions: Stage IV Melanoma; Recurrent Melanoma
Interventions: Drug: gp100 antigen; Drug: interleukin-2

Vaccine Therapy in Treating Patients With Metastatic Melanoma of the Eye

Conditions: Extraocular Extension Melanoma; Recurrent Intraocular Melanoma
Interventions: Drug: gp100 antigen; Drug: interleukin-2; Drug: MART-1 antigen;
Drug: Montanide ISA-51

Ipilimumab With or Without Vaccine Therapy in Treating Patients With Previously Treated Stage IV Melanoma Condition: Melanoma (Skin)
Interventions: Drug: gp100: 209-217(210M) peptide vaccine; Drug: gp100: 280-288 (288V) peptide vaccine; Drug: incomplete Freund's adjuvant;
Drug: ipilimumab Vaccine Therapy and Interleukin-12 With or Without Interleukin-2 in Treating Patients With Metastatic Melanoma Condition: Melanoma (Skin)
Interventions: Drug: MART-1 antigen; Drug: NA17-A antigen; Drug: aldesleukin;
Drug: gp100 antigen; Drug: recombinant MAGE-3.1 antigen;
Drug: recombinant interleukin-12;
Drug: therapeutic autologous lymphocytes Vaccine Therapy and Sargramostim Compared With Placebo and Sargramostim Following Rituximab in Treating Patients With Non-Hodgkin's Lymphoma Condition: Lymphoma
Interventions: Drug: autologous immunoglobulin idiotype-KLH conjugate vaccine;
Drug: rituximab; Drug: sargramostim

TABLE S-continued

Cancer vaccines

Vaccine Therapy and GM-CSF With or Without Low-Dose Aldesleukin in Treating Patients With Stage II, Stage III, or Stage IV Melanoma

| | |
|---|---|
| Condition: | Melanoma (Skin) |
| Interventions: | Drug: MART-1 antigen; Drug: aldesleukin; Drug: gp100 antigen; Drug: incomplete Freund's adjuvant; Drug: sargramostim; Drug: survivin antigen |

Vaccination With Lethally Irradiated Glioma Cells Mixed With GM-K562 Cells in Patients Undergoing Craniotomy For Recurrent Tumor

| | |
|---|---|
| Condition: | Glioma |
| Intervention: | Biological: GM-K562 Vaccination |

Immunogenicity and Safety of GlaxoSmithKline Biologicals' HPV Vaccine 580299 in Healthy Females 10-25 Years of Age.

| | |
|---|---|
| Conditions: | HPV-16/18 Infections; Cervical Neoplasia |
| Intervention: | Biological: HPV-16/18 L1 VLP AS04 (580299) |

A Safety and Immunology Study of a Modified Vaccinia Vaccine for HER-2(+) Metastatic Breast Cancer

| | |
|---|---|
| Condition: | Breast Cancer |
| Intervention: | Biological: MVA-BN-HER2 |

Vaccine Therapy in Treating Patients With Metastatic Melanoma Who Are Undergoing Surgery for Lymph Node and Tumor Removal

| | |
|---|---|
| Condition: | Melanoma (Skin) |
| Interventions: | Drug: aldesleukin; Drug: gp100 antigen; Drug: tyrosinase peptide |

Carcinoembryonic Antigen-Loaded Dendritic Cells in Advanced Colorectal Cancer Patients

| | |
|---|---|
| Conditions: | Colorectal Cancer; Liver Metastases |
| Intervention: | Biological: CEA-loaded dendritic cell vaccine |

Injection Of AJCC Stage IIB, IIC, III And IV Melanoma Patients With A Multi-Epitope Peptide Vaccine Using GM-CSF DNA As An Adjuvant: A Pilot Trial To Assess Safety And Immunity

| | |
|---|---|
| Condition: | Melanoma |
| Intervention: | Biological: GM-CSF DNA, NSC 683472 gp100: 209-217(210M), NSC 699048 Tyrosinase: 368-376(370D) |

Vaccine Therapy and Sargramostim After Rituximab in Treating Patients With Refractory or Progressive Non-Hodgkin's Lymphoma

| | |
|---|---|
| Condition: | Lymphoma |
| Interventions: | Drug: autologous immunoglobulin idiotype-KLH conjugate vaccine; Drug: sargramostim |

Safety and Immunogenicity of Chiron's Investigational *H. Pylori* Vaccine in Healthy Adults

| | |
|---|---|
| Conditions: | *Helicobacter Pylori*; Gastritis; Gastric Cancer; Gastroduodenal Ulcers; Lymphoma |
| Interventions: | Biological: helicobacter pylori vaccine; Biological: helicobacter pylori vaccine; Biological: helicobacter pylori vaccine; Biological: helicobacter pylori vaccine; Biological: Placebo; Biological: helicobacter pylori vaccine; Biological: helicobacter pylori vaccine |

Rituximab, Vaccine Therapy, and GM-CSF in Treating Patients With Non-Hodgkin's Lymphoma

| | |
|---|---|
| Condition: | Lymphoma |
| Interventions: | Drug: autologous immunoglobulin idiotype-KLH conjugate vaccine; Drug: rituximab; Drug: sargramostim |

Study to Test the Safety of HPV Vaccine in Women

| | |
|---|---|
| Conditions: | Cervical Cancer; Genital Warts |
| Interventions: | Biological: V501, Gardasil, Quadrivalent Human Papillomavirus (Types 6, 11, 16, 18) Recombinant Vaccine/Duration of Treatment: 4 Years; Biological: Comparator: placebo (concomitant-vaccine matched)/ Duration of Treatment: 4 Years |

Immunogenicity Bridge Between an Investigational Monovalent Vaccine and the Equivalent Component of Gardasil (V501) a Quadrivalent Vaccine

| | |
|---|---|
| Conditions: | Cervical Cancer; Genital Warts |
| Intervention: | Biological: V501, Gardasil, human papillomavirus (type 6, 11, 16, 18) recombinant vaccine/Duration of Treatment: 4 years |

Vaccine Therapy Plus GM-CSF in Treating Patients With Multiple Myeloma Undergoing Bone Marrow or Peripheral Stem Cell Transplantation

| | |
|---|---|
| Condition: | Multiple Myeloma and Plasma Cell Neoplasm |
| Interventions: | Drug: keyhole limpet hemocyanin; Drug: sargramostim |

TABLE S-continued

Cancer vaccines

Survival in a Randomized Phase III Trial in Patients With Limited Disease (LD) Small Cell Lung Cancer Vaccinated With Adjuvant BEC2 and BCG Condition: Carcinoma, Small Cell Lung
Intervention: Biological: BEC2 Vaccine Survivin Peptide Vaccination for Patients With Advanced Melanoma, Pancreatic, Colon and Cervical Cancer Conditions: Malignant Melanoma; Pancreatic Cancer; Colon Cancer; Cervical Cancer
Intervention: Biological: Survivin peptide vaccine Vaccine Therapy in Treating Patients Who Have Undergone a Donor Stem Cell Transplant and Have Cytomegalovirus Infection That Has Not Responded to Therapy Condition: Cancer
Interventions: Drug: cytomegalovirus pp65-specific cytotoxic T lymphocytes;
Procedure: flow cytometry; Procedure: immunologic technique;
Procedure: laboratory biomarker analysis;
Procedure: polymerase chain reaction A Controlled Trial to Assess the Immunogenicity of a Proposed Paediatric Dosing Schedule of Human Papillomavirus Vaccine Conditions: Cervical Cancer; Genital Warts
Intervention: Biological: HPV (Human Papillomavirus) Vaccine Vaccine Therapy in Treating Patients With Stage IV Melanoma Condition: Melanoma (Skin)
Intervention: Drug: Synchrovax SEM plasmid DNA vaccine Vaccine Therapy Plus Sargramostim Following Chemotherapy in Treating Patients With Stage III or Stage IV Non-Hodgkin's Lymphoma Condition: Lymphoma
Interventions: Drug: autologous tumor cell vaccine; Drug: keyhole limpet hemocyanin;
Drug: sargramostim Phase II/III Study of CDX-110 in Patients With Glioblastoma Multiforme (GBM)

Condition: Glioblastoma
Interventions: Drug: Temozolomide; Biological: CDX-110 EGFRvIII Vaccine/GM-CSF Monoclonal Anybody and Vaccine Therapy in Treating Patients With Stage III or Stage IV Melanoma That Has Been Removed During Surgery Conditions: Intraocular Melanoma; Melanoma (Skin)
Interventions: Drug: MART-1 antigen; Drug: gp100 antigen;
Drug: incomplete Freund's adjuvant; Drug: ipilimumab;
Drug: tyrosinase peptide; Procedure: adjuvant therapy Vaccine Therapy Plus Sargramostim Following Chemotherapy in Treating Patients With Previously Untreated Aggressive Non-Hodgkin's Lymphoma Condition: Lymphoma
Interventions: Drug: autologous tumor cell vaccine; Drug: cyclophosphamide;
Drug: doxorubicin hydrochloride; Drug: keyhole limpet hemocyanin;
Drug: mitoxantrone hydrochloride; Drug: prednisone;
Drug: sargramostim; Drug: vincristine Vaccination Against High Risk Breast Cancer Using Tumor Derived Heat Shock Protein 70

Condition: Breast Neoplasms
Intervention: Biological: Heat Shock Protein 70-peptide complexes (HSP70)

Human Papilloma Virus Vaccine Consistency and Non-Inferiority Trial in Young Adult Women With GSK Bio HPV-16/18

Conditions: HPV-16/18 Infections; Cervical Neoplasia
Intervention: Biological: HPV-16/18 L1/AS04

Vaccine Therapy and GM-CSF in Treating Patients With Acute Myeloid Leukemia in Remission Condition: Leukemia
Interventions: Drug: PR1 leukemia peptide vaccine; Drug: placebo;
Drug: sargramostim Vaccine Therapy and Resiquimod in Treating Patients With Stage II, Stage III, or Stage IV Melanoma That Has Been Completely Removed by Surgery Condition: Melanoma (Skin)
Interventions: Drug: NY-ESO-1b peptide vaccine; Drug: resiquimod;
Procedure: adjuvant therapy

TABLE S-continued

Cancer vaccines

Human Papillomavirus Vaccine Safety & Immunogenicity Trial in Healthy Young Adult Women With HPV Vaccine (GSK1674330A)

| | |
|---|---|
| Conditions: | HPV Infections; Cervical Neoplasia |
| Intervention: | Biological: HPV vaccine (GSK1674330A) |

Study of an Investigational Vaccine in Pre-Adolescents and Adolescents (Gardasil)

| | |
|---|---|
| Conditions: | Cervical Cancer; Genital Warts |
| Intervention: | Biological: V501, Gardasil, human papillomavirus (type 6, 11, 16, 18) recombinant vaccine/Duration of Treatment: 7 months |

Safety and Efficacy of the Therapeutic Vaccine GI-4000 in Combination With Gemcitabine Versus Placebo for the Treatment of Non-Metastatic, Post-Resection Pancreas Cancer

| | |
|---|---|
| Condition: | Pancreas Cancer |
| Intervention: | Biological: GI-4000 |

Vaccine Therapy and GM-CSF in Treating Patients With Low-Risk or Intermediate-Risk Myelodysplastic Syndrome

| | |
|---|---|
| Condition: | Myelodysplastic Syndromes |
| Interventions: | Drug: PR1 leukemia peptide vaccine; Drug: incomplete Freund's adjuvant; Drug: sargramostim |

Vaccine Therapy in Treating Patients With Stage III or Stage IV Melanoma

| | |
|---|---|
| Condition: | Melanoma (Skin) |
| Interventions: | Drug: recombinant CD40-ligand; Drug: therapeutic autologous dendritic cells |

Human Papilloma Virus Vaccine Safety and Immunogenicity Trial in Young Adolescent Women With GSK Bio HPV-16/18.

| | |
|---|---|
| Conditions: | HPV-16/18 Infections; Cervical Neoplasia |
| Intervention: | Biological: HPV-16/18 L1/AS04 |

Human Papillomavirus Vaccine Therapy in Treating Men With HIV-1 Infection

| | |
|---|---|
| Conditions: | Infection; Precancerous/Nonmalignant Condition |
| Intervention: | Drug: quadrivalent human papillomavirus (types 6, 11, 16, 18) recombinant vaccine |

Combination Chemotherapy Followed By Vaccine Therapy Plus Sargramostim in Treating Patients With Stage III or Stage IV Non-Hodgkin's Lymphoma

| | |
|---|---|
| Condition: | Lymphoma |
| Interventions: | Drug: autologous immunoglobulin idiotype-KLH conjugate vaccine; Drug: cyclophosphamide; Drug: keyhole limpet hemocyanin; Drug: prednisone; Drug: sargramostim; Drug: vincristine |

Vaccine Therapy in Preventing Flu in Children With Acute Lymphoblastic Leukemia

| | |
|---|---|
| Conditions: | Infection; Leukemia |
| Intervention: | Drug: trivalent influenza vaccine |

Vaccine Therapy in Treating Patients With Melanoma

| | |
|---|---|
| Condition: | Melanoma (Skin) |
| Interventions: | Drug: HPV 16 E7: 12-20 peptide vaccine; Drug: gp100 antigen; Drug: incomplete Freund's adjuvant; Procedure: conventional surgery |

Vaccine Therapy in Treating Patients Who Are Being Considered For a Solid Organ Transplant and Are at Risk For Post-Transplant Lymphoproliferative Disorder

| | |
|---|---|
| Condition: | Lymphoma |
| Intervention: | Drug: autologous Epstein-Barr virus-transformed B-lymphoblastoid cell vaccine |

Activated White Blood Cells in Treating Patients Undergoing an Autologous Stem Cell Transplant for Newly Diagnosed Stage II or Stage III Multiple Myeloma

| | |
|---|---|
| Condition: | Multiple Myeloma and Plasma Cell Neoplasm |
| Interventions: | Drug: melphalan; Drug: pneumococcal polyvalent vaccine; Drug: therapeutic autologous lymphocytes; Drug: therapeutic tumor infiltrating lymphocytes; Procedure: autologous hematopoietic stem cell transplantation |

Vaccine Therapy Plus Interleukin-2 in Treating Patients With Stage III or Stage IV Melanoma

| | |
|---|---|
| Condition: | Melanoma (Skin) |
| Interventions: | Drug: aldesleukin; Drug: gp100 antigen; Drug: incomplete Freund's adjuvant; Drug: sargramostim; Drug: tetanus peptide melanoma vaccine; Drug: tyrosinase peptide |

Immunotherapy for Patients With Brain Stem Glioma and Glioblastoma

| | |
|---|---|
| Conditions: | Brain Stem Glioma; Glioblastoma |
| Intervention: | Biological: Dendritic cell Vaccine |

TABLE S-continued

Cancer vaccines

CP-675,206 (CTLA4-Blocking Monoclonal Antibody) Combined With Dendritic Cell Vaccine Therapy in Treating Patients With Stage III or Stage IV Melanoma That Cannot Be Removed With Surgery

| | |
|---|---|
| Condition: | Melanoma (Skin) |
| Interventions: | Drug: MART-1 antigen; Drug: ipilimumab; Drug: therapeutic autologous dendritic cells |

Vaccine Therapy for Patients With Stage III Melanoma

| | |
|---|---|
| Condition: | Malignant Melanoma |
| Intervention: | Biological: CancerVax vaccine (CANVAXIN) |

Vaccine Therapy for Patients With Stage IV Melanoma

| | |
|---|---|
| Condition: | Malignant Melanoma |
| Intervention: | Biological: CancerVax vaccine (CANVAXIN) |

Gene-Modified T Lymphocytes With or Without Vaccine Therapy and/or Aldesleukin in Treating Patients With High-Risk Melanoma

| | |
|---|---|
| Condition: | Melanoma (Skin) |
| Interventions: | Drug: MART-1: 26-35(27L) peptide vaccine; Drug: aldesleukin; Drug: autologous anti-MART-1 F5 T-cell receptor gene-engineered peripheral blood lymphocytes; Drug: incomplete Freund's adjuvant |

Study to Evaluate Safety and Biological Activity of TroVax ® Vaccine Given in Conjunction With IL-2 to Treat Locally Advanced or Metastatic Renal Cell Carcinoma

| | |
|---|---|
| Condition: | Carcinoma, Renal Cell |
| Intervention: | Biological: TroVax ® |

Vaccine Therapy in Treating Patients With Malignant Melanoma

| | |
|---|---|
| Condition: | Melanoma (Skin) |
| Intervention: | Drug: polyvalent melanoma vaccine |

Human Papillomavirus (HPV) Vaccine Consistency and Non-Inferiority Trial in Young Adult Women.

| | |
|---|---|
| Condition: | HPV-16/18 Infections and Cervical Neoplasia |
| Intervention: | Biological: HPV-16/18 L1/AS04 |

Vaccine Therapy in Treating Patients With Stage III or Stage IV Melanoma That Cannot Be Removed With Surgery

| | |
|---|---|
| Condition: | Melanoma (Skin) |
| Interventions: | Drug: D1/3-MAGE-3-His fusion protein; Drug: SB-AS02B adjuvant; Drug: SB-AS15 adjuvant |

Vaccine Therapy Plus Immune Adjuvants in Treating Patients With Advanced Melanoma

| | |
|---|---|
| Condition: | Melanoma (Skin) |
| Interventions: | Drug: QS21; Drug: gp100 antigen; Drug: incomplete Freund's adjuvant; Drug: sargramostim; Drug: tyrosinase peptide |

Vaccine Therapy In Treating Patients At High Risk For Recurrence Of Melanoma

| | |
|---|---|
| Conditions: | Recurrent Melanoma; Stage III Melanoma; Stage IV Melanoma |
| Interventions: | Drug: MART-1 antigen; Drug: Montanide ISA-51; Drug: gp100 antigen; Drug: interleukin-2; Procedure: adjuvant therapy; Procedure: biological response modifier therapy; Procedure: cytokine therapy; Procedure: interleukin therapy; Procedure: non-specific immune-modulator therapy; Procedure: non-tumor cell derivative vaccine; Procedure: vaccine therapy |

Broad Spectrum HPV Vaccine Tolerability, Immunogenicity, and Efficacy Study

| | |
|---|---|
| Conditions: | Cervical Cancer; Condylomata Acuminate |
| Intervention: | Biological: V502 |

Human Papilloma Virus Vaccine Immunogenicity and Safety Trial in Young and Adult Women With GSK Bio HPV-16/18.

| | |
|---|---|
| Condition: | Prophylaxis HPV-16/18 Infections and Cervical Neoplasia |
| Intervention: | Biological: HPV-16/18 L1/AS04 |

Vaccine Therapy in Treating Patients With Stage II or Stage III Melanoma That Has Been Surgically Removed

| | |
|---|---|
| Condition: | Melanoma (Skin) |
| Interventions: | Drug: MART-1 antigen; Drug: NY-ESO-B; Drug: QS21; Drug: flu matrix peptide p58-66; Drug: gp100 antigen; Drug: keyhole limpet hemocyanin; Drug: recombinant MAGE-3.1 antigen; Drug: therapeutic autologous dendritic cells; Drug: tyrosinase peptide; Procedure: adjuvant therapy |

Idiotype Vaccine for Low-Grade Non-Hodgkin's Lymphoma

| | |
|---|---|
| Condition: | Lymphoma, Low-Grade |
| Intervention: | Biological: Favid (Id-KLH) active immunotherapy |

TABLE S-continued

Cancer vaccines

Vaccine Therapy With or Without Interleukin-2 After Chemotherapy and an Autologous White Blood Cell Infusion in Treating Patients With Metastatic Melanoma Condition: Melanoma (Skin)
Interventions: Drug: MART-1 antigen; Drug: aldesleukin; Drug: cyclophosphamide; Drug: filgrastim; Drug: fludarabine phosphate; Drug: gp100 antigen; Drug: incomplete Freund's adjuvant; Drug: therapeutic autologous lymphocytes; Procedure: in vitro-treated peripheral blood stem cell transplantation Gene-Modified Cancer Cells in Treating Patients With B-Cell Chronic Lymphocytic Leukemia Condition: Leukemia
Interventions: Drug: autologous tumor cell vaccine; Procedure: biopsy; Procedure: immunoenzyme technique; Procedure: laboratory biomarker analysis Vaccine Therapy in Treating Patients With Metastatic Melanoma Condition: Melanoma (Skin)
Interventions: Drug: sargramostim; Drug: vaccinia-GM-CSF vaccine Pilot Study to Determine the Safety and Efficacy of Gardasil Against the Human Papilloma Virus (HPV) in HIV-Infected Men Conditions: Anal Cancer; HIV Infections
Intervention: Biological: Gardasil Vaccine Therapy in Treating Patients With Stage III or Stage IV Melanoma That Cannot Be Removed By Surgery Conditions: Intraocular Melanoma; Melanoma (Skin)
Interventions: Drug: incomplete Freund's adjuvant; Drug: multi-epitope melanoma peptide vaccine; Drug: sargramostim Vaccine Therapy in Treating Patients With Stage IIIB, Stage IIIC, or Stage IV Melanoma Conditions: Intraocular Melanoma; Melanoma (Skin)
Interventions: Drug: incomplete Freund's adjuvant; Drug: multi-epitope melanoma peptide vaccine; Drug: sargramostim Vaccine Therapy in Treating Patients With Stage III or Stage IV Melanoma Condition: Melanoma (Skin)
Interventions: Drug: denileukin diftitox; Drug: recombinant CD40-ligand; Drug: therapeutic autologous dendritic cells Evaluate the Immunogenicity & Safety of GSK Biologicals' HPV Vaccine in Female Subjects Aged 10-14 Years Conditions: HPV; Cervical Neoplasia
Intervention: Biological: HPV-16/18 L1/AS04

Immunization of HLA-A201 Patients With Metastatic Melanoma Using a Combination of Immunodominant Peptides From Three Melanoma Antigens, MART-1, GP100 and Tyrosinase Conditions: Melanoma; Neoplasm Metastasis
Intervention: Biological: Immunodominant peptides from three melanoma antigens, MART-1, GP100 and tyrosinase Evaluation of the Immune Responses of GSK Biologicals' HPV Vaccine Following Manufacturing Process Adaptation.

Conditions: HPV-16/18 Infections; Cervical Neoplasia
Intervention: Biological: HPV-16/18 L1/AS04

A Phase I/li Study Of Immunization With Lymphotactin And Interleukin 2 Gene Modified Neuroblastoma Tumor Cells After High-Dose Chemotherapy And Autologous Stem Cell Rescue In Patients With High Risk Neuroblastoma Condition: Neuroblastoma
Intervention: Biological: SJNB-JF-IL2 and SJNB-JF-Lptn cells and SKNLP Unmodified Neuroblastoma Cell Lines Vaccine Therapy in Treating Patients With Metastatic Melanoma Condition: Melanoma (Skin)
Interventions: Drug: aldesleukin; Drug: fowlpox virus vaccine vector; Drug: vaccinia-tyrosinase vaccine Vaccine Therapy and Monoclonal Antibody Therapy in Treating Patients With Stage IV Melanoma Conditions: Intraocular Melanoma; Melanoma (Skin)
Interventions: Drug: gp100 antigen; Drug: incomplete Freund's adjuvant; Drug: ipilimumab Gene-Modified Tumor Cells in Treating Patients With B-Cell Chronic Lymphocytic Leukemia Condition: Leukemia
Interventions: Drug: autologous tumor cell vaccine;

TABLE S-continued

Cancer vaccines

Procedure: immunoenzyme technique;
Procedure: laboratory biomarker analysis

Monoclonal Antibody Therapy in Treating Patients With Stage III or Stage IV Melanoma

| | |
|---|---|
| Condition: | Melanoma (Skin) |
| Interventions: | Drug: alum adjuvant; Drug: monoclonal antibody 4B5 anti-idiotype vaccine; Drug: sargramostim |

Follow-up Study to Evaluate the Safety and Immunogenicity of a HPV Vaccine (580299) in North America

| | |
|---|---|
| Condition: | Human Papillomavirus Infection |
| Intervention: | Biological: HPV (580299) vaccine |

Vaccine Therapy and Interleukin-12 in Treating Patients With Metastatic Melanoma

| | |
|---|---|
| Condition: | Melanoma (Skin) |
| Interventions: | Drug: MART-1 antigen; Drug: recombinant MAGE-3.1 antigen; Drug: recombinant interleukin-12 |

Determine Toxicity and Antibody Responses With a KLH Conjugated Bivalent Vaccine Containing GD2 Lactone, GD3 Lactone With Immunological Adjuvant QS-DG or OPT-821 in Patients With Disease Free AJCC Stage III or IV Cutaneous Melanoma

| | |
|---|---|
| Condition: | Melanoma |
| Intervention: | Biological: KLH conjugates with GD2L and GD3L |

Immunotherapy of Melanoma Patients

| | |
|---|---|
| Condition: | Melanoma |
| Interventions: | Biological: Melan-A analog peptide; Biological: FluMa peptide; Biological: Mage-A10 peptide; Biological: SB AS-2 adjuvant; Biological: Montanide adjuvant |

Vaccine Therapy in Treating Patients With Metastatic Melanoma

| | |
|---|---|
| Condition: | Melanoma (Skin) |
| Interventions: | Drug: QS21; Drug: incomplete Freund's adjuvant; Drug: peptide 946 melanoma vaccine; Drug: peptide 946-tetanus peptide conjugate melanoma vaccine; Drug: tetanus peptide melanoma vaccine |

Complementary Testing to Evaluate Immunogenicity of HPV Vaccine (580299) in Healthy Female Subjects Aged >/= 26 Years

| | |
|---|---|
| Conditions: | HPV-16/18 Infections; Cervical Neoplasia |
| Intervention: | Biological: HPV-16/18 L1 AS04 (580299) |

Vaccine Therapy in Treating Patients With Unresectable Metastatic Melanoma

| | |
|---|---|
| Condition: | Melanoma (Skin) |
| Intervention: | Drug: recombinant vaccinia-B7.1 vaccine |

Vaccine Therapy in Treating Patients With Stage III or Stage IV Melanoma

| | |
|---|---|
| Condition: | Melanoma (Skin) |
| Interventions: | Drug: OVA BiP peptide; Drug: gp209-2M antigen; Drug: recombinant 70-kD heat-shock protein; Drug: tyrosinase peptide |

Vaccine Therapy in Treating Patients With Stage IV Melanoma

| | |
|---|---|
| Condition: | Melanoma (Skin) |
| Interventions: | Drug: D1/3-MAGE-3-His fusion protein; Drug: SB-AS02B adjuvant |

Immunization With 8 Peptides Mixed With Adjuvant Montanide ISA 51 in HLA-A2 Patients With Metastatic Cutaneous Melanoma

| | |
|---|---|
| Condition: | Malignant Melanoma |
| Intervention: | Biological: 8 HLA-A2 restricted peptides and Montanide ISA-51 |

Fludarabine, Cyclophosphamide, and Vaccine Therapy in Treating Patients With Metastatic Melanoma

| | |
|---|---|
| Condition: | Melanoma (Skin) |
| Interventions: | Drug: aldesleukin; Drug: autologous anti-gp 100: 154-162 T-cell receptor gene-engineered peripheral blood lymphocytes; Drug: cyclophosphamide; Drug: fludarabine phosphate; Drug: therapeutic autologous lymphocytes; Procedure: immunologic technique; Procedure: laboratory biomarker analysis; Procedure: polymerase chain reaction |

Vaccine Therapy With or Without Interleukin-2 in Treating Patients With Recurrent Metastatic Melanoma

| | |
|---|---|
| Condition: | Melanoma (Skin) |
| Interventions: | Drug: aldesleukin; Drug: fowlpox virus vaccine vector; Drug: gp100 antigen |

TABLE S-continued

Cancer vaccines

Immuno-Augmentation With GM-CSF of Pneumococcal Vaccine in Chronic Lymphocytic Leukemia Patients Condition: Leukemia
Interventions: Drug: Sargramostim; Biological: Pneumococcal Vaccine Allogeneic Tumor Cell Vaccination in Patients With Chronic Myeloid Leukemia Condition: Chronic Myeloid Leukemia
Intervention: Biological: Allogeneic tumor cell vaccine Vaccination of Melanoma Patients With Dendritic Cells Loaded With Allogeneic Apoptotic-Necrotic Melanoma Cells Condition: Melanoma
Intervention: Biological: DC/Apo-Nec Daclizumab in Treating Patients With Newly Diagnosed Glioblastoma Multiforme Undergoing Targeted Immunotherapy and Temozolomide-Caused Lymphopenia Condition: Brain and Central Nervous System Tumors
Interventions: Drug: RNA-loaded dendritic cell vaccine; Drug: cytomegalovirus pp65-specific cytotoxic T lymphocytes; Drug: daclizumab; Drug: imiquimod; Drug: temozolomide; Drug: therapeutic autologous dendritic cells; Drug: therapeutic autologous lymphocytes; Procedure: radionuclide imaging; Procedure: single photon emission computed tomography; Procedure: stereotactic radiation therapy AD 32 With or Without BCG After Surgery in Treating Patients With Newly Diagnosed or Recurrent Superficial Bladder Cancer Condition: Bladder Cancer
Interventions: Drug: BCG vaccine; Drug: valrubicin; Procedure: conventional surgery Monoclonal Antibody Therapy in Treating Patients With Lymphoma or Colon Cancer That Has Not Responded to Vaccine Therapy Condition: Lymphoma
Intervention: Drug: ipilimumab BCG Plus Interferon Alfa 2b in Treating Patients With Bladder Cancer Condition: Bladder Cancer
Interventions: Drug: BCG vaccine; Drug: recombinant interferon alfa Fluorouracil, Semustine, and Vincristine Compared With BCG in Treating Patients With Dukes' B or Dukes' C Colon Cancer That Has Been Removed By Surgery Condition: Colorectal Cancer
Interventions: Drug: BCG vaccine; Drug: fluorouracil; Drug: semustine; Drug: vincristine; Procedure: biological therapy Monoclonal Antibody Therapy Plus BCG in Treating Patients With Limited-Stage Small Cell Lung Cancer Condition: Lung Cancer
Interventions: Drug: BCG vaccine; Drug: monoclonal antibody BEC2

Biological Therapy in Treating Patients With Bladder Cancer

Condition: Bladder Cancer
Intervention: Drug: BCG vaccine

BCG With or Without Gefitinib in Treating Patients With High-Risk Bladder Cancer Condition: Bladder Cancer
Interventions: Drug: BCG vaccine; Drug: gefitinib; Procedure: quality-of-life assessment Vaccine Therapy in Treating Patients With Stage IV Melanoma Condition: Melanoma (Skin)
Interventions: Drug: Synchrotope TA2M plasmid DNA vaccine; Drug: tyrosinase peptide Radiation Therapy, Chemotherapy, or Observation in Treating Patients With Bladder Cancer Condition: Bladder Cancer
Interventions: Drug: BCG vaccine; Drug: mitomycin C; Procedure: radiation therapy BCG With or Without Mitomycin in Treating Patients With Bladder Cancer Condition: Bladder Cancer
Interventions: Drug: BCG vaccine; Drug: mitomycin C; Procedure: adjuvant therapy; Procedure: conventional surgery Surgery and BCG in Treating Patients With Bladder Cancer Condition: Bladder Cancer
Intervention: Drug: BCG vaccine TABLE S-continued

Cancer vaccines

Influenza Vaccination in Patients Receiving Antineoplastic Therapy for Non-Hodgkin's Lymphoma Condition: Lymphoma
Intervention: Biological: Trivalent Baculovirus-expressed Influenza HA vaccine Human Papilloma Virus Vaccine Immunogenicity and Safety Trial in Young Adult Women With GSK Bio's Novel HPV Vaccine.

Conditions: HPV Infections; Cervical Neoplasia
Intervention: Biological: Novel HPV vaccine Continuation Booster Trial After a Vaccine Combining Tyrosinase/GP100/MART-1 Peptides Emulsified With Montanide ISA 51 With or Without GM-CSF for Patients With Melanoma Condition: Melanoma
Intervention: Biological: Montanide ISA 51

Tumor Lysate Pulsed-Dendritic Cell Vaccines After High-Dose Chemotherapy for Non-Hodgkin's Lymphoma Condition: Lymphoma, Non-Hodgkin
Intervention: Biological: tumor-pulsed dendritic cells Interferon Alfa With or Without Vaccine Therapy in Treating Patients With Metastatic Melanoma Condition: Melanoma (Skin)
Interventions: Drug: Detox-B adjuvant; Drug: recombinant interferon alfa Melanoma Vaccine With or Without Sargramostim in Treating Patients With Stage IV Malignant Melanoma Condition: Melanoma (Skin)
Interventions: Drug: MART-1 antigen; Drug: gp100 antigen;
Drug: incomplete Freund's adjuvant; Drug: sargramostim;
Drug: tyrosinase peptide Neuroblastoma Vaccine for Treatment of High-Risk Neuroblastoma After Chemotherapy Condition: Neuroblastoma
Intervention: Biological: autologous neuroblastoma vaccine Concomitant Use of Gardasil (V501, Human Papillomavirus [Types 6, 11, 16, 18] Recombinant Vaccine) With Combined Diphtheria, Tetanus, Pertussis Vaccine and Meningococcal Conjugate Vaccine in Adolescents Conditions: Neoplasms, Glandular and Epithelial; Diphtheria; Tetanus;
Whooping Cough; Meningitis
Intervention: Biological: V501, Gardasil, HPV rL1 6 11 16 18 VLP vaccine (yeast)/
Duration of Treatment: 7 months Effect of TroVax in Patients Having Colorectal Cancer With Liver Metastases Removed Condition: Colorectal Neoplasms
Intervention: Biological: TroVax Comparison of Dendritic Cells Versus Montanide as Adjuvants in a Melanoma Vaccine Condition: Melanoma
Interventions: Biological: Peptide-loaded dendritic cells;
Biological: Montanide with peptides Interleukin-7 and Vaccine Therapy in Treating Patients With Metastatic Melanoma Condition: Melanoma (Skin)
Interventions: Drug: MART-1 antigen; Drug: gp100 antigen;
Drug: incomplete Freund's adjuvant; Drug: recombinant interleukin-7

Vaccination in the Peripheral Stem Cell Transplant Setting for Acute Myelogenous Leukemia Condition: Acute Myelogenous Leukemia
Intervention: Biological: GVAX leukemia vaccine (therapeutic cellular vaccine, GM-CSF producing)

Concomitant Use of Gardasil (V501, Human Papillomavirus [Types 6, 11, 16, 18] Recombinant Vaccine) With Combined Diphtheria, Tetanus, Pertussis and Poliomyelitis Vaccine in Adolescents Conditions: Neoplasms, Glandular and Epithelial; Diphtheria; Tetanus;
Whooping Cough; Poliomyelitis
Intervention: Biological: V501, Gardasil, human papillomavirus (types 6, 11, 16, 18) recombinant vaccine/Duration of Treatment 7 Months Proteinase 3 PR1 Peptide Mixed With Montanide ISA-51 VG Adjuvant and Administered With GM-CSF and Peginterferon Alfa-2b [PEG-INTRON(R)]

Condition: Leukemia
Interventions: Biological: Peptide Vaccine (PR1 Peptide); Drug: GM-CSF (Sargramostim, Leukine); Drug: Peginterferon alfa-2b (Peg-Intron);
Drug: Imatinib (Gleevec)

TABLE S-continued

Cancer vaccines

Immunotherapy of Melanoma With Tumor Antigen RNA and Small Inhibitory RNA Transfected Autologous Dendritic Cells

| | |
|---|---|
| Conditions: | Metastatic Melanoma; Absence of CNS Metastases |
| Intervention: | Biological: Proteasome siRNA and tumor antigen RNA-transfected dendritic cells |

A Phase I/II Trial of Idiotypic Vaccination for Chronic Lymphocytic Leukemia Using a Genetic Approach

| | |
|---|---|
| Condition: | Leukemia, Lymphocytic, Chronic |
| Intervention: | Biological: CLL vaccine using DNA plasmid vector |

Vaccine Therapy and Interleukin-2 in Treating Patients With Metastatic Melanoma

| | |
|---|---|
| Condition: | Melanoma (Skin) |
| Interventions: | Drug: aldesleukin; Drug: recombinant fowlpox-tyrosinase vaccine; Drug: vaccinia-tyrosinase vaccine |

Cyclophosphamide and Fludarabine Followed by Cellular Adoptive Immunotherapy, and Vaccine Therapy, and G-CSF or GM-CSF in Treating Patients With Metastatic Melanoma

| | |
|---|---|
| Condition: | Melanoma (Skin) |
| Interventions: | Drug: CpG 7909; Drug: MART-1 antigen; Drug: cyclophosphamide; Drug: fludarabine phosphate; Drug: incomplete Freund's adjuvant; Drug: therapeutic autologous lymphocytes |

Vaccine Therapy in Treating Patients With Philadelphia Chromosome-Positive Chronic Myelogenous Leukemia

| | |
|---|---|
| Condition: | Leukemia |
| Interventions: | Drug: bcr-abl p210-b3a2 breakpoint-derived multipeptide vaccine; Drug: sargramostim |

Immunization With the MAGE-3.A1 Peptide Mixed With the Adjuvant CpG 7909 in Patients With Metastatic Melanoma

| | |
|---|---|
| Condition: | Malignant Melanoma |
| Intervention: | Biological: MAGE-3.A1 peptide and CpG 7909 |

Vaccination Plus Ontak in Patients With Metastatic Melanoma

| | |
|---|---|
| Condition: | Melanoma |
| Interventions: | Drug: 4-peptide melanoma vaccine; Drug: 4-peptide melanoma vaccine plus Ontak; Drug: ontak |

Vaccination of Prostate Cancer Patients With MUC-2-KLH Conjugate Plus the Immunological Adjuvant QS21

| | |
|---|---|
| Condition: | Prostate Cancer |
| Intervention: | Biological: MUC-2-KLH |

Vaccine Therapy With or Without Interleukin-2 in Treating Patients With Metastatic Melanoma That Has Not Responded to Previous Treatment

| | |
|---|---|
| Condition: | Melanoma (Skin) |
| Interventions: | Drug: aldesleukin; Drug: incomplete Freund's adjuvant; Drug: recombinant tyrosinase-related protein-2 |

Vaccine Therapy in Treating Patients With Recurrent or Refractory Metastatic Melanoma

| | |
|---|---|
| Condition: | Melanoma (Skin) |
| Interventions: | Drug: aldesleukin; Drug: incomplete Freund's adjuvant; Drug: sargramostim; Drug: tyrosinase peptide; Drug: tyrosinase-related protein-1 |

Vaccine Therapy With High-Dose Interleukin-2 in Treating Patients With Metastatic Melanoma

| | |
|---|---|
| Condition: | Melanoma (Skin) |
| Interventions: | Drug: aldesleukin; Drug: gp100 antigen; Drug: incomplete Freund's adjuvant |

Vaccine Therapy With or Without Interleukin-2 in Treating Patients With Metastatic Melanoma

| | |
|---|---|
| Condition: | Melanoma (Skin) |
| Interventions: | Drug: MART-1 antigen; Drug: aldesleukin; Drug: gp100 antigen; Drug: incomplete Freund's adjuvant |

Vaccination of AJCC Stage IIB, IIC, III and IV Melanoma Patients With Human and Mouse Tyrosinase DNA Vaccines

| | |
|---|---|
| Conditions: | Melanoma; Skin |
| Interventions: | Biological: human tyrosinase; Biological: mouse tyrosinase |

Active Immunization of Sibling Bone Marrow Transplant Donors Against Purified Myeloma Protein of the Recipient Undergoing Allogeneic Bone Marrow Transplantation

| | |
|---|---|
| Conditions: | Graft vs Host Disease; Multiple Myeloma |
| Interventions: | Drug: Myeloma Immunoglobulin Idiotype Vaccine-KLH; Drug: GM-CSF |

TABLE S-continued

Cancer vaccines

Personalized Active Immunotherapy (Vaccine Therapy) and Sargramostim Given After Standard of Care Treatment With Rituximab and Chemotherapy for Initial Treatment With Lymphoma Condition: Non-Hodgkin's Lymphoma
Intervention: Drug: autologous immunoglobulin idiotype-KLH conjugate vaccine Vaccine Therapy With or Without Interleukin-2 in Treating Patients With Metastatic Melanoma Condition: Melanoma (Skin)
Interventions: Drug: aldesleukin; Drug: fowlpox virus vaccine vector;
Drug: gp100 antigen Vaccine Therapy With or Without Montanide ISA-51 and/or Imiquimod in Treating Patients With Melanoma That Has Been Removed By Surgery Condition: Melanoma (Skin)
Interventions: Drug: gp100 antigen; Drug: imiquimod;
Drug: incomplete Freund's adjuvant Vaccine Therapy in Treating Patients With Refractory Metastatic Melanoma Condition: Melanoma (Skin)
Interventions: Drug: NY-ESO-1 peptide vaccine; Drug: aldesleukin Broad Spectrum HPV Vaccine Dose Ranging Study Condition: HPV; Cervical Cancer and Premalignancy; Anogenital Warts
Intervention: Biological: V502

Phase I/II Study of Chemo-Immunotherapy Combination in Melanoma Patients

Condition: Melanoma
Interventions: Biological: Melan-A; Other: Melan-A plus Dacarbazine Dendritic Cell Based Therapy of Renal Cell Carcinoma Condition: Advanced Renal Cell Carcinoma
Intervention: Biological: tumor antigen loaded autologous dendritic cells MAGE-A3/HPV 16 Vaccine for Squamous Cell Carcinoma of the Head and Neck Condition: Squamous Cell Carcinoma of the Head and Neck
Intervention: Biological: MAGE-A3 and HPV 16 Trojan peptides Immunization With gp100 Protein Vaccine in Treating Patients With Metastatic Melanoma Condition: Melanoma (Skin)
Interventions: Drug: aldesleukin; Drug: gp100 antigen;
Drug: incomplete Freund's adjuvant Follow-up Study to Evaluate the Long-Term Efficacy of the HPV Vaccine (580299) in Healthy Young Adult Women in Brazil Conditions: HPV-16/18 Infections; Cervical Neoplasia
Intervention: Biological: HPV-16/18 L1 AS04 (580299)

Vaccine Therapy in Treating Patients With Melanoma of the Eye

Condition: Intraocular Melanoma
Interventions: Drug: MART-1 antigen; Drug: NA17-A antigen; Drug: gp100 antigen;
Drug: tyrosinase peptide Vaccine Therapy With or Without Interleukin-2 in Treating Patients With Stage III or Stage IV Melanoma Condition: Melanoma (Skin)
Interventions: Drug: aldesleukin; Drug: dendritic cell-gp100-MART-1 antigen vaccine A Safety and Effectiveness Study of Vaccine Therapy in Patients With Indolent Lymphoma Conditions: Lymphoma, Follicular; Lymphoma, Small Lymphocytic
Intervention: Drug: autologous human tumor-derived HSPPC-96

Safety and Immunogenicity of Human Papillomavirus (HPV) Vaccine in Solid Organ Transplant Recipients Condition: Transplant
Intervention: Biological: Human papillomavirus quadrivalent vaccine Follow-up Study of GSK Biologicals' Human Papilloma Virus (HPV) Vaccine to Prevent Cervical Infection in Young Adults Condition: Papillomavirus Infections
Intervention: Biological: HPV 16/18 VLP AS04

Vaccine Therapy With gp100 and/or Sargramostim in Treating Patients With Malignant Melanoma Condition: Melanoma (Skin)
Interventions: Drug: gp100 antigen; Drug: sargramostim TABLE S-continued Cancer vaccines Peptide Vaccine Focusing on Prevention of the Recurrence for Bladder Cancer Condition: Bladder Cancer
Intervention: Biological: MPHOSPH1 and DEPDC1

Papilloma Virus Vaccine Therapy in Treating Young Patients With Recurrent Papilloma of the Larynx Condition: Precancerous/Nonmalignant Condition
Intervention: Drug: autologous tumor cell vaccine Biological Therapy Following Surgery and Chemotherapy in Treating Patients With Stage III or Stage IV Colon Cancer Condition: Colorectal Cancer
Interventions: Drug: aldesleukin; Drug: autologous tumor cell vaccine;
Drug: muromonab-CD3; Drug: sargramostim;
Drug: therapeutic autologous lymphocytes; Procedure: chemotherapy;
Procedure: surgical procedure Biological Therapy Following Surgery and Chemotherapy in Treating Patients With Stage III or Stage IV Ovarian Cancer Condition: Ovarian Cancer
Interventions: Drug: aldesleukin; Drug: autologous tumor cell vaccine;
Drug: muromonab-CD3; Drug: sargramostim;
Drug: therapeutic autologous lymphocytes; Procedure: chemotherapy;
Procedure: surgical procedure Biological Therapy Following Surgery and Chemotherapy in Treating Patients With Stage II, Stage III, or Stage IV Lung Cancer Condition: Lung Cancer
Interventions: Drug: aldesleukin; Drug: autologous tumor cell vaccine;
Drug: muromonab-CD3; Drug: sargramostim;
Drug: therapeutic autologous lymphocytes; Procedure: chemotherapy;
Procedure: surgical procedure Biological Therapy Following Surgery in Treating Patients With Stage III or Stage IV Kidney Cancer Condition: Kidney Cancer
Interventions: Drug: aldesleukin; Drug: autologous tumor cell vaccine;
Drug: muromonab-CD3; Drug: sargramostim;
Drug: therapeutic autologous lymphocytes;
Procedure: surgical procedure Biological Therapy Following Surgery and Chemotherapy in Treating Patients With Stage III or Stage IV Breast Cancer Condition: Breast Cancer
Interventions: Drug: aldesleukin; Drug: autologous tumor cell vaccine;
Drug: muromonab-CD3; Drug: sargramostim;
Drug: therapeutic autologous lymphocytes; Procedure: chemotherapy;
Procedure: surgical procedure Vaccine Therapy in Treating Patients With Metastatic Melanoma Condition: Melanoma (Skin)
Interventions: Drug: filgrastim; Drug: therapeutic autologous dendritic cells Biological Therapy Following Surgery and Radiation Therapy in Treating Patients With Primary or Recurrent Astrocytoma or Oligodendroglioma Condition: Brain and Central Nervous System Tumors
Interventions: Drug: aldesleukin; Drug: autologous tumor cell vaccine;
Drug: muromonab-CD3; Drug: sargramostim;
Drug: therapeutic autologous lymphocytes; Procedure: radiation therapy;
Procedure: surgical procedure Rituxan Plus Favld (Idiotype Vaccine) for Low-Grade Non-Hodgkin's Lymphoma Condition: Non-Hodgkin's Lymphoma
Intervention: Biological: Id-KLH Safety/Efficacy of a Vaccine Prepared From Dendritic Cells Combined With Tumor Cells to Treat Advanced Kidney Cancer Condition: Carcinoma, Renal Cell
Intervention: Drug: Allogeneic DCs and Autologous RCC Tumor Derived Cells Biological Therapy in Treating Patients With Glioblastoma Multiforme Condition: Brain and Central Nervous System Tumors
Interventions: Drug: autologous tumor cell vaccine; Drug: cyclophosphamide;
Drug: sargramostim; Procedure: conventional surgery; Procedure:
tumor-draining lymph node lymphocyte therapy TABLE S-continued Cancer vaccines Phase☐/☐ Study of URLC10-177 and TTK-567 Peptide Vaccine Combined With CpG7909 in Patients With Esophageal Cancer Condition: Esophageal Cancer
Intervention: Biological: URLC10-177, TTK-567, CpG-7909
   Study of Vaccination With Autologous Acute Myeloblastic Leukemia Cells in Patients With Advanced Myelodysplasia or Acute Myelogenous Leukemia Conditions: Acute Myelogenous Leukemia; Myelodysplasia
Intervention: Biological: autologous tumor cells
   Biological Therapy Following Surgery in Treating Patients With Stage III or Stage IV Melanoma Condition: Melanoma (Skin)
Interventions: Drug: aldesleukin; Drug: autologous tumor cell vaccine;
   Drug: muromonab-CD3; Drug: sargramostim;
   Drug: therapeutic autologous lymphocytes;
   Procedure: surgical procedure
   Vaccine Study of MVA-MUC1-IL2 in Patients With Prostate Cancer Condition: Prostatic Neoplasms
Intervention: Biological: MVA-MUC1-IL2
   Viral Therapy in Treating Patients With Recurrent Glioblastoma Multiforme Condition: Brain and Central Nervous System Tumors
Interventions: Drug: carcinoembryonic antigen-expressing measles virus;
   Procedure: adjuvant therapy; Procedure: conventional surgery;
   Procedure: fluorescence in situ hybridization;
   Procedure: immunohistochemistry staining method;
   Procedure: immunologic technique;
   Procedure: laboratory biomarker analysis; Procedure: needle biopsy;
   Procedure: neoadjuvant therapy; Procedure: reverse transcriptase-
   polymerase chain reaction
   A Phase I/II Study to Assess the Safety and Efficacy of Vaccinations With Allogeneic Dendritic Cells: Autologous Tumor-Derived Cells Subjected to Electrofusions in Patients With AJCC Stage IV Renal Cell Carcinoma Condition: Renal Cell Carcinoma
Intervention: Biological: Electrofusion DC vaccine
   Dose-Escalation Study of CG0070 for Bladder Cancer After BCG (Bacillus Calmette-Guerin) Failure Conditions: Carcinoma, Transitional Cell; Bladder Neoplasms
Intervention: Biological: Oncolytic adenovirus (serotype 5) - CG0070
   Vaccine Therapy in Treating Patients With Melanoma Condition: Melanoma (Skin)
Interventions: Drug: aldesleukin; Drug: gp100 antigen;
   Drug: incomplete Freund's adjuvant; Drug: tyrosinase peptide
   Vaccine Therapy With or Without Interleukin-2 in Treating Patients With Metastatic Melanoma Condition: Melanoma (Skin)
Interventions: Drug: MART-1 antigen; Drug: aldesleukin; Drug: gp100 antigen
   Phase I of Human Papillomavirus (HPV) DNA Plasmid (VGX-3100) + Electroporation for CIN 2 or 3

Condition: Papillomavirus Infections
Intervention: Biological: VGX-3100
   Vaccine Therapy and/or Sargramostim in Treating Patients With Locally Advanced or Metastatic Melanoma Conditions: Intraocular Melanoma; Melanoma (Skin)
Interventions: Drug: MART-1 antigen; Drug: gp100 antigen;
   Drug: incomplete Freund's adjuvant; Drug: sargramostim;
   Drug: tyrosinase peptide; Procedure: adjuvant therapy
   Biological Therapy in Treating Patients With Prostate Cancer Condition: Prostate Cancer
Interventions: Drug: aldesleukin; Drug: recombinant interferon gamma;
   Procedure: tumor cell-derivative vaccine therapy
   Study Using Vaccination With Heat Shock Protein 70 (HSP70) for the Treatment of CML in Chronic Phase Conditions: Leukemia, Myeloid, Chronic; Leukemia, Myeloid, Philadelphia-Positive
Intervention: Biological: Heat Shock Protein 70 HSP70

TABLE S-continued

Cancer vaccines

Studying Stored Samples From Patients With Localized Prostate Cancer Treated on Clinical Trial NCl-00-C-0154

| | |
|---|---|
| Condition: | Prostate Cancer |
| Interventions: | Procedure: diagnostic procedure; Procedure: molecular diagnostic method; Procedure: protein expression analysis |

Safety Study of TroVax Alone vs. TroVax Plus Interferon Alpha in Patients With Renal Cancer

| | |
|---|---|
| Condition: | Carcinoma, Renal Cell |
| Interventions: | Biological: TroVax ® (Immunological Vaccine Therapy); Drug: Interferon-alpha |

Vaccine Therapy in Treating Patients With Stage IV Cutaneous Melanoma

| | |
|---|---|
| Condition: | Melanoma (Skin) |
| Interventions: | Drug: MART-1 antigen; Drug: keyhole limpet hemocyanin; Drug: recombinant MAGE-3.1 antigen; Drug: survivin antigen; Drug: therapeutic autologous dendritic cells |

PANVAC ™-VF Vaccine for the Treatment of Metastatic Pancreatic Cancer After Failing a Gemcitabine-Containing Regimen

| | |
|---|---|
| Condition: | Pancreatic Cancer |
| Intervention: | Biological: PANVAC ™-VF |

Vaccine Therapy in Treating Patients With Metastatic Melanoma

| | |
|---|---|
| Condition: | Melanoma (Skin) |
| Interventions: | Drug: MART-1 antigen; Drug: aldesleukin; Drug: gp100 antigen; Drug: incomplete Freund's adjuvant |

Study of Immune Responses to Influenza Vaccination With or Without Imiquimod Application in Untreated CLL Patients

| | |
|---|---|
| Condition: | Chronic Lymphocytic Leukemia |
| Interventions: | Drug: Imiquimod cream; Drug: influenza vaccine |

Vaccine Therapy With or Without Interleukin-2 in Treating Patients With Metastatic Melanoma

| | |
|---|---|
| Condition: | Melanoma (Skin) |
| Interventions: | Drug: aldesleukin; Drug: gp209-2M antigen; Drug: incomplete Freund's adjuvant |

Study of gp75 Vaccine in Patients With Stage III and IV Melanoma

| | |
|---|---|
| Condition: | Malignant Melanoma |
| Intervention: | Biological: gp75 DNA vaccine |

Safety and Immunogenicity of Recombinant DNA and Adenovirus Expressing L523S Protein in Early Stage Non-Small Cell Lung Cancer

| | |
|---|---|
| Condition: | Non-Small Cell Lung Cancer |
| Interventions: | Biological: Recombinant DNA-pVAX/L523S; Biological: Recombinant adenovirus-Ad/L523S |

Cytomegalovirus Vaccine in Healthy Participants

| | |
|---|---|
| Condition: | Precancerous/Nonmalignant Condition |
| Interventions: | Drug: CMVpp65-A*0201 peptide vaccine; Procedure: flow cytometry; Procedure: laboratory biomarker analysis |

Safety Study to Evaluate FluMist in Immunocompromised Children

| | |
|---|---|
| Condition: | Cancer |
| Interventions: | Biological: FluMist; Biological: Placebo |

Imiquimod and Laser Therapy With or Without a Green Dye in Treating Patients With Stage III or Stage IV Melanoma That Has Spread to Other Parts of the Skin

| | |
|---|---|
| Conditions: | Melanoma (Skin); Metastatic Cancer |
| Interventions: | Drug: imiquimod; Drug: indocyanine green solution; Procedure: flow cytometry; Procedure: immunologic technique; Procedure: laboratory biomarker analysis |

Vaccine Therapy in Treating Patients Who Have Stage II, Stage III, or Stage IV Melanoma

| | |
|---|---|
| Condition: | Melanoma (Skin) |
| Interventions: | Drug: MART-1 antigen; Drug: gp100 antigen |

A Single Centre Study to Evaluate the Safety and Immunogenicity of the HPV Vaccine (GSK-580299) in Chinese Females

| | |
|---|---|
| Condition: | Human Papillomavirus Infection |
| Intervention: | Biological: HPV vaccine (GSK-580299) |

A Study of OncoVEXGM-CSF in Stage IIIc and Stage IV Malignant Melanoma

| | |
|---|---|
| Condition: | Melanoma |
| Interventions: | Genetic: Oncolytic viral vector; Procedure: Vaccine Therapy; Procedure: Immune-modulator therapy |

TABLE S-continued

Cancer vaccines

Cytomegalovirus (CMV) Vaccine in Donors and Recipients Undergoing Allogeneic Hematopoietic Cell Transplant (HCT)

| | |
|---|---|
| Conditions: | Acute Lymphoblastic Leukemia; Chronic Myelogenous Leukemia; Acute Myelogenous Leukemia; Hodgkin's Lymphoma; Non-Hodgkin's Lymphoma; Myelodysplastic Syndrome |
| Interventions: | Biological: VCL-CB01; Other: PBS |

Perceptions of Cervical Cancer Among Asian Americans

| | |
|---|---|
| Condition: | Epidemiology |
| Interventions: | Behavioral: Focus Group; Behavioral: Questionnaire |

Vaccine Therapy, Incomplete Freund's Adjuvant, and GM-CSF in Treating Patients With HIV

| | |
|---|---|
| Condition: | Precancerous/Nonmalignant Condition |
| Interventions: | Drug: E1M184V peptide vaccine; Drug: incomplete Freund's adjuvant; Drug: sargramostim; Procedure: immunoenzyme technique |

Vaccine Therapy in Treating Patients With Metastatic Melanoma

| | |
|---|---|
| Condition: | Melanoma (Skin) |
| Interventions: | Drug: MART-1 antigen; Drug: filgrastim; Drug: flu matrix peptide p58-66; Drug: gp100 antigen; Drug: recombinant MAGE-3.1 antigen; Drug: tyrosinase peptide; Procedure: in vitro-treated peripheral blood stem cell transplantation |

Dendritic Cells (White Blood Cells) Vaccination for Advanced Melanoma

| | |
|---|---|
| Condition: | Melanoma |
| Interventions: | Drug: cyclophosphamide; Biological: Mature dendritic cell vaccine; Biological: Mature dendritic cell vaccine |

Vaccination of Patients With Stage IV Melanoma With Dendritic Cells

| | |
|---|---|
| Conditions: | Melanoma; Neoplasm Metastasis |
| Intervention: | Biological: Dendritic cell vaccination |

Gene Therapy in Treating Children With Relapsed or Refractory Neuroblastoma

| | |
|---|---|
| Condition: | Neuroblastoma |
| Interventions: | Drug: aldesleukin; Procedure: tumor cell-derivative vaccine therapy |

Patients With Mouse Tyrp2 DNA: A Phase I Trial to Assess Safety and Immune Response

| | |
|---|---|
| Condition: | Melanoma |
| Intervention: | Biological: injection of mouse TYRP2 DNA |

Radiofrequency Therapy-Induced Endogenous Heat-Shock Proteins With or Without Radiofrequency Ablation or Cryotherapy in Treating Patients With Stage IV Melanoma

| | |
|---|---|
| Condition: | Melanoma (Skin) |
| Interventions: | Drug: sargramostim; Procedure: biopsy; Procedure: cryosurgery; Procedure: immunoenzyme technique; Procedure: immunohistochemistry staining method; Procedure: immunologic technique; Procedure: laboratory biomarker analysis; Procedure: radiofrequency ablation |

Monoclonal Antibody With or Without gp100 Peptides Plus Montanide ISA-51 in Treating Patients With Stage IV Melanoma

| | |
|---|---|
| Condition: | Melanoma (Skin) |
| Interventions: | Drug: gp100 antigen; Drug: incomplete Freund's adjuvant; Drug: ipilimumab |

Vaccination in the Peripheral Stem Cell Transplant Setting for Multiple Myeloma

| | |
|---|---|
| Condition: | Multiple Myeloma |
| Intervention: | Biological: Therapeutic Cellular Vaccine, GM-CSF Producing |

Safety and Tolerability Study of FolateImmune in Combination With Cytokines in Patients With Refractory or Metastatic Cancer

| | |
|---|---|
| Condition: | Cancer |
| Interventions: | Biological: EC90 (KLH-FITC); Biological: GPI-0100; Drug: EC17 (Folate-FITC); Drug: Interleukin-2; Drug: Interferon-alpha |

Immunogenicity and Reactogenicity of Alternative Schedules of Gardasil

| | |
|---|---|
| Condition: | Papillomavirus Infections |
| Intervention: | Biological: Gardasil |

Safety and Pharmacodynamic Study of a New Formulation, AGI-101H Vaccine in the Treatment of Advanced Melanoma

| | |
|---|---|
| Condition: | Melanoma |
| Intervention: | Biological: AGI-101H Vaccine |

TABLE S-continued

Cancer vaccines

An Investigational Study of Gardasil (V501) in Reducing the Incidence of Anogenital Warts in Young Men

| | |
|---|---|
| Condition: | Condylomata Acuminate |
| Interventions: | Biological: V501, Gardasil, human papillomavirus (types 6, 11, 16, 18) recombinant vaccine; Biological: Comparator: placebo (unspecified) |

Dendritic Cell Based Therapy of Metastatic Breast Cancer

| | |
|---|---|
| Condition: | Metastatic Breast Cancer |
| Intervention: | Biological: Onco-peptide loaded autologous dendritic cells |

The Role of Peptide-Loaded Dendritic Cells to Augment the Therapeutic Effect of Interleukin-2

| | |
|---|---|
| Condition: | Metastatic Melanoma |
| Intervention: | Procedure: Immunotherapy treatment for melanoma |

Vaccine Therapy in Treating Patients With Chronic Myelogenous Leukemia

| | |
|---|---|
| Condition: | Leukemia |
| Intervention: | Drug: recombinant 70-kD heat-shock protein |

Gene Therapy in Treating Children With Refractory or Recurrent Neuroblastoma

| | |
|---|---|
| Condition: | Neuroblastoma |
| Interventions: | Procedure: gene therapy; Procedure: tumor cell-derivative vaccine therapy |

Safety and Immunogenicity Study of MEDI-517 (GSK 580299) With or Without Adjuvant in Healthy Adult Females

| | |
|---|---|
| Condition: | Prophylaxis HPV-16/18 Infections and Cervical Neoplasia |
| Interventions: | Biological: MEDI-517 HPV-16/18 VLP AS04 vaccine; Biological: MEDI-517 HPV-16/18 VLP vaccine with Al(OH)3; Biological: MEDI-517 HPV-16/18 VLP vaccine without adjuvant |

Dissemination of Cervical Cancer Screening to Primary Care Physicians in Underserved Communities

| | |
|---|---|
| Condition: | Cervical Cancer |
| Intervention: | Behavioral: Academic detailing |

Dose-Comparison Study to Evaluate the Safety and Immunogenicity of MEDI-517 (GSK 580299) in Healthy Adult Females

| | |
|---|---|
| Condition: | Prophylaxis HPV-16/18 Infections and Cervical Neoplasia |
| Interventions: | Biological: MEDI-517 HPV-16/18 VLP AS04 vaccine (Formulation 1); Biological: MEDI-517 HPV-16/18 VLP AS04 vaccine (Formulation 2); Biological: MEDI-517 HPV-16/18 VLP AS04 vaccine (Formulation 3); Biological: MEDI-517 HPV-16/18 VLP with Al(OH)3 (Formulation 4) |

Lymphodepletion Plus Adoptive Cell Transfer With or Without Dendritic Cell Immunization

| | |
|---|---|
| Condition: | Melanoma |
| Interventions: | Biological: Dendritic Cell Immunization; Drug: Cyclophosphamide; Drug: 60 mg/kg/d I.V. in 250 ml NS over 2 hrs; Biological: T Cells; Biological: Interleukin-2 |

Phase II Trial of Allovectin-7 ® for Metastatic Melanoma

| | |
|---|---|
| Conditions: | Melanoma; Metastatic Melanoma; Malignant Melanoma; Skin Cancer |
| Intervention: | Genetic: Allovectin-7 ® |

Docetaxel and Immunotherapy Prior to Prostatectomy for High-Risk Prostate Cancer

| | |
|---|---|
| Condition: | Prostate Cancer |
| Interventions: | Drug: Docetaxel; Biological: CG1940/CG8711 |

Safety and Immunogenicity of CYT004-MelQbG10 Vaccine With and Without Adjuvant in Advanced Stage Melanoma Patients

| | |
|---|---|
| Condition: | Malignant Melanoma |
| Interventions: | Biological: CYT004-MelQbG10 + Montanide; Biological: CYT004-MelQbG10 + Montanide + Imiquimod; Biological: CYT004-MelQbG10 + Imiquimod; Biological: CYT004-MelQbG10 intra nodal injection |

Vaccine Therapy for Multiple Myeloma Utilizing Idiotype-Pulsed Allogeneic Dendritic Cells

| | |
|---|---|
| Condition: | Multiple Myeloma |
| Intervention: | Biological: Idiotype-pulsed allogeneic dendritic cells |

A Phase I Study of Recombinant Vaccinia Virus That Expresses Prostate Specific Antigen in Adult Patients With Adenocarcinoma of the Prostate

| | |
|---|---|
| Condition: | Prostatic Neoplasms |
| Intervention: | Biological: PROSTVAC |

Modified Process Hepatitis B Vaccine in Healthy Neonates

| | |
|---|---|
| Conditions: | Hepatitis B; Hepatocellular Carcinoma |
| Interventions: | Biological: V232/Duration of Treatment 7 Months; Biological: |

TABLE S-continued

Cancer vaccines

Comparator: hepatitis B vaccine (recombinant)/Duration of Treatment 7 Months
Study to Evaluate the Efficacy of the Human Papillomavirus Vaccine in Healthy Adult Women of 26 Years of Age and Older.

Condition: Prophylaxis for HPV Infections & Assoc. Cervical Neoplasia
Intervention: Biological: HPV-16/18 L1/AS04
Phase I Protocol for the Evaluation of the Safety and Immunogenicity of Vaccination With Synthetic HIV Envelope Peptides in Patients With Early Human Immunodeficiency Virus Infection Conditions: Acquired Immunodeficiency Syndrome; HIV Infection
Interventions: Drug: PCLUS 3-18 MN; Drug: PCLUS 6.1 MN
Adenovirus Encoding Rat HER-2 in Patients With Metastatic Breast Cancer (AdHER2.1)

Conditions: Metastatic Breast Cancer; Recurrent Breast Cancer
Intervention: Biological: adenoviral vector encoding rat Her-2/neu
Her-2/Neu in Patients With Metastatic Breast Cancer (AdHERe)

Condition: Metastatic Breast Cancer
Intervention: Biological: AdHer-2/neu transduced dendritic cells
Dose-Ranging Study of Quadrivalent HPV (Types 6, 11, 16, 18) L1 VLP Vaccine Conditions: Papillomavirus Infections; Genital Diseases, Female
Interventions: Biological: V501, /Duration of Treatment: 6 Months; Biological:
Comparator: placebo with adjuvant (unspecified)/Duration of Treatment: 6 Months
Study Testing the Biologic Activity and Safety of a Immunotherapeutic in Patients With Newly Diagnosed Advanced Stage Kidney Cancer in Combination With a Marketed Renal Cell Carcinoma Treatment Condition: Renal Cell Carcinoma
Intervention: Biological: AGS-003+sunitinib
Interleukin-2 Plus Activated White Blood Cells in Treating Patients With Cancer That Has Not Responded to Chemotherapy or Radiation Therapy Condition: Unspecified Adult Solid Tumor, Protocol Specific
Interventions: Drug: aldesleukin; Drug: therapeutic autologous lymphocytes;
Drug: therapeutic tumor infiltrating lymphocytes
Evaluation of the Immunogenicity and Safety of GlaxoSmithKline Biologicals' HPV Vaccine in Young Males.

Condition: Prophylaxis Against HPV Infections
Intervention: Biological: HPV vaccine
Safety of and Immune Response to the Human Papillomavirus (HPV) Vaccine in HIV Infected Women Conditions: HIV Infections; Sexually Transmitted Diseases
Intervention: Biological: Quadrivalent human papillomavirus vaccine
PSC/Lymphoma Study Condition: Influenza
Intervention: Biological: Recombinant rHA0
A Safety Trial of MVA-BN ®-PRO in Men With Androgen-Insensitive Prostate Cancer Condition: Androgen-Insensitive Prostate Cancer
Interventions: Biological: MVA-BN-PRO; Biological: MVA-BN-PRO; Biological: MVA-BN-PRO
A Phase I Study of WT1 Peptides to Induce Anti-Leukemia Immune Responses Following Autologous or Allogeneic Transplantation for AML, CML, ALL, MDS, and B Cell Malignancies Conditions: Acute Myelogenous Leukemia (AML);
Chronic Myelogenous Leukemia (CML);
Acute Lymphoblastic Leukemia (ALL);
Myelodysplastic Syndrome (MDS); B Cell Malignancies
Intervention: Biological: WT1 derived peptides
Prediction and Testing of Antigenic Sites of the AIDS Virus, HTLV-III Recognized by T Lymphocytes for the Development of Synthetic Vaccines Conditions: HIV Infections; Healthy
Intervention:
Dendritic Cell Based Therapy of Malignant Melanoma Condition: Advanced Melanoma
Intervention: Biological: tumor antigen loaded autologous dendritic cells TABLE S-continued Cancer vaccines A Study to Evaluate Pertuzumab + Trastuzumab + Docetaxel vs. Placebo + Trastuzumab + Docetaxel in Previously Untreated Her2-Positive Metastatic Breast Cancer (CLEOPATRA)

Condition: Metastatic Breast Cancer
Interventions: Drug: pertuzumab; Drug: placebo; Drug: trastuzumab; Drug: docetaxel
Lymphocytic B-Leukemia (B-CLL) w/Human IL-2 Gene Modified & Human CD40 Ligand-Expressing Autologous Tumor Cells Conditions: Chronic Lymphocytic B-Leukemia; B-CLL
Interventions: Biological: IL-2 secreting and hCL4OL-expressing autologous B-CLL cells; Biological: IL-2; Biological: CD40L; Drug: ONTAK; Biological: immunotoxin dose
Intratumoral PV701 in Treating Patients With Advanced or Recurrent Unresectable Squamous Cell Carcinoma of the Head and Neck Condition: Head and Neck Cancer
Intervention: Drug: PV701
Study of MAGE-A3 and NY-ESO-1 Immunotherapy in Combo With DTPACE Chemo and Auto Transplantation in Multiple Myeloma Condition: Multiple Myeloma
Intervention: Biological: MAGE-A3
A Phase II Study of EC17 (Folate-Hapten Conjugate) in Patients With Progressive Metastatic Renal Cell Carcinoma Condition: Renal Cell Carcinoma
Interventions: Biological: EC90 (KLH-FITC); Biological: GPI-0100; Drug: EC17 (Folate-FITC); Drug: Interleukin-2; Drug: Interferon-alpha
Study of TA-NIC to Assess the Efficacy and Safety of the Vaccine as an Aid to Smoking Cessation Condition: Smoking
Interventions: Biological: TA-NIC; Biological: Placebo
Phase II Dendritic Cell - Idiotype Vaccination After Autologous Stem Cell Transplant for Mantle Cell Lymphoma Condition: Mantle-Cell Lymphoma
Interventions: Biological: DC-Id-KLH; Procedure: Autologous peripheral blood stem cell transplantation
Effect of Tai Chi Vs. Structured Exercise on Physical Fitness and Stress in Cancer Survivors Conditions: Cancer; Cancer Survivor
Intervention: Procedure: Tai Chi Chuan
Dose Escalation Study of Revlimid With Fludarabine-Rituximab for CLL/SLL Conditions: Chronic Lymphocytic Leukemia; Small Lymphocytic Leukemia
Interventions: Drug: Lenalidomide; Drug: Fludarabine; Drug: Rituximab
Collection and Distribution of Blood Samples From Healthy Donors for In Vitro Research at the NCI Frederick Cancer Research and Development Center Condition: Samples
Intervention:
A Study of Active Immunotherapy With GRNVAC1 in Patients With Acute Myelogenous Leukemia (AML)

Condition: Acute Myelogenous Leukemia
Intervention: Biological: GRNVAC1
A Pilot Study of the Patterns of Cellular Gene Expression in HIV-1 Patients Following Clinical Events Which Increase Plasma Virus Concentrations Condition: HIV Infections
Intervention:
Evaluation of Recovery From Drug-Induced Lymphopenia Using Cytomegalovirus-Specific T-Cell Adoptive Transfer Conditions: Glioblastoma; Cytomegalovirus
Interventions: Biological: CMV-ALT + CMV-DCs; Biological: CMV-ALT + Saline
V930 First in Man (FIM) Study Condition: Cancers Expressing HER-2 and/or CEA
Intervention: Biological: V930
Reduced Intensity Total Body Irradiation + Thymoglobulin Followed by Allogeneic Peripheral Blood Stem Cell Transplantation (PBSCT)

Conditions: Non-Hodgkin's Lymphoma; Leukemia; Multiple Myeloma
Interventions: Biological: thymoglobulin; Biological: thymoglobulin TABLE S-continued Cancer vaccines Intratumoral Dendritic Cell Vaccination Combined With Local Radiotherapy in Patients With Recurrent Lymphoma.

| | |
|---|---|
| Condition: | Lymphoma |
| Intervention: | Biological: Autologous dendritic cells generated using GM-CSF, interferon alpha and LPS |

Active Immunotherapy Of Metastatic Renal Cell Carcinoma Using Autologous Dendritic Cells Transfected With Autologous Total Tumor RNA

| | |
|---|---|
| Condition: | Renal Cell Carcinoma |
| Intervention: | Biological: DC RCC-RNA |

Immunological Consequences of Obstructive Sleep Apnea

| | |
|---|---|
| Condition: | Obstructive Sleep Apnea |
| Intervention: | Biological: Influenza vaccine |

Combined Modality Treatment for Patients With Stage IV Melanoma

| | |
|---|---|
| Condition: | Stage IV Metastatic Melanoma |
| Intervention: | Biological: Dendritic cell vaccination |

A Study of Patients Who Develop HIV Infection After Enrolling in HIV Vaccine Trials or HIV Vaccine Preparedness Trials

| | |
|---|---|
| Condition: | HIV Infections |
| Intervention: | Other: Observation |

An Investigational Combination Vaccine Given to People Who Are Not Infected With HIV

| | |
|---|---|
| Condition: | HIV Infections |
| Interventions: | Biological: Combination Vaccine (NefTat and gp120W61D) Formulated with AS02A; Biological: NefTat; Drug: AS02A Adjuvant; Biological: gp120W61D |

Safety and Immunogenicity of a Melan-A VLP Vaccine in Early Stage Melanoma Patients

| | |
|---|---|
| Condition: | Malignant Melanoma |
| Intervention: | Biological: CYT004-MeIQbG10 |

Safety and Immunogenicity of a Melan-A VLP Vaccine in Advanced Stage Melanoma Patients

| | |
|---|---|
| Condition: | Melanoma |
| Intervention: | Biological: CYT004-MeIQbG10 |

A Study to Test the Safety of Three Experimental HIV Vaccines

| | |
|---|---|
| Conditions: | HIV Infections; HIV Seronegativity |
| Interventions: | Biological: HIV p24/MF59 Vaccine; Biological: ALVAC-HIV MN120TMG (vCP205); Biological: ALVAC-RG Rabies Glycoprotein (vCP65); Biological: rgp120/HIV-1 SF-2 |

A Study of the Effectiveness of an HIV Vaccine (ALVAC vCP205) to Boost Immune Functions in HIV-Negative Volunteers Who Have Already Received an HIV Vaccine

| | |
|---|---|
| Conditions: | HIV Infections; HIV Seronegativity |
| Intervention: | Biological: ALVAC-HIV MN120TMG (vCP205) |

Safety and Immune Response Study of High-Dose Canarypox ALVAC-HIV Vaccine in Healthy, HIV Uninfected Adults

| | |
|---|---|
| Conditions: | HIV Infections; HIV Seronegativity |
| Intervention: | Biological: ALVAC(2)120(B, MN)GNP (vCP1452) |

Trial of rPA-102 Vaccine in Healthy Adult Volunteers

| | |
|---|---|
| Condition: | Anthrax |
| Intervention: | Biological: rPA102 |

Safety of and Immune Response to a DNA HIV Vaccine Followed By Boosting With One of Two Serotypes of Adenoviral Vector HIV Vaccine in Healthy Adults

| | |
|---|---|
| Condition: | HIV Infections |
| Interventions: | Biological: VRC-HIVADV027-00-VP; Biological: VRC-HIVADV038-00-VP; Biological: VRC-HIVDNA044-00-VP |

Safety and Effectiveness of Anti-HIV Vaccines in HIV-Negative Adults

| | |
|---|---|
| Condition: | HIV Infections |
| Interventions: | Biological: ALVAC(2)120(B, MN)GNP (vCP1452); Biological: gp160 MN/LAI-2; Biological: ALVAC(1)120(B, MN)GNP (vCP1433); Biological: ALVAC-HIV MN120TMG (vCP205); Biological: ALVAC-RG Rabies Glycoprotein (vCP65) |

Study of MAGE-3/Melan-A/gp 100/NA17 and rhIL-12 With/Out Low Dose IL-2 in Metastatic Melanoma

| | |
|---|---|
| Condition: | Metastatic Melanoma |
| Interventions: | Drug: MAGE-3/Melan-A/gp100/NA PBMC, rhIL-12 (drug); Drug: MAGE-3/Melan-A/gp100/NA17 Peptide-pulsed autologous PBMC, rhIL-12 with IL-2 |

TABLE S-continued

Cancer vaccines

Safety and Immune Response Study of the Vaccine ALVAC vCP1452 Alone or in Combination With AIDSVAX B/B Condition: HIV Infections
Interventions: Biological: ALVAC(2)120(B, MN)GNP (vCP1452);
Biological: MN rgp120/HIV-1 and GNE8 rgp120/HIV-1

Trial of G250 Peptide and IL-2 Following Surgical Resection of Locally Advanced/Metastatic Renal Cell Carcinoma Condition: Metastatic Renal Cell Carcinoma
Interventions: Drug: G250 peptide; Drug: IL-2

Combined Use of BCG and Interferon Alpha in Bladder Cancer

Condition: Superficial Bladder Cancer
Intervention: Drug: Bacillus Calmette Guerin and interferon alpha Effects on the Immune System of Anti-HIV Drugs in Patients Recently Infected With HIV Condition: HIV Infections
Interventions: Biological: Tetanus Toxoid Vaccine; Drug: Indinavir sulfate;
Drug: Lamivudine/Zidovudine; Drug: Ritonavir; Drug: Abacavir sulfate;
Drug: Amprenavir; Drug: Efavirenz;
Biological: Hepatitis B Vaccine (Recombinant); Drug: Lamivudine;
Drug: Zidovudine Study of CAP1-6D in Patients With Locally Advanced or Surgically Resected Pancreatic Adenocarcinoma Condition: Pancreatic Adenocarcinoma
Interventions: Drug: Modified CEA (CAP1-6D) Peptide (drug); Drug: CEA Peptide;
Drug: Modified CEA (CAP1-6D) Peptide (drug)

P210-B3A2 Derived Peptide Vaccine in CML

Condition: Chronic Myeloid Leukemia
Intervention: Biological: p210-B3A2 derived peptide vaccine Idiotype Vaccine Following High-Dose Chemotherapy and Hematopoietic Stem Cell Transplantation for Patients With Lymphoma Who Had Failed Induction Chemotherapy Condition: Lymphoma
Intervention: Biological: Id-KLH Safety Assessment of a Multipeptide-Gene Vaccine in CML Condition: Leukemia, Myeloid, Chronic
Interventions: Biological: Bcr-abl multipeptide vaccine; Genetic: Cytokine gene adjuvant Safety of and Immune Response to Two Different HIV Vaccines, Each Followed by a Adenoviral Vaccine Boost, in HIV Uninfected Adults Condition: HIV Infections
Interventions: Biological: VRC-HIVADV014-00-VP; Biological: VRC-HIVDNA009-00-VP; Biological: FFB; Biological: PBS Dendritic Cell Vaccination in Melanoma Patients Scheduled for Regional Lymph Node Dissection Condition: Melanoma Stage III or IV
Intervention: Biological: Peptide-pulsed dendritic cells Safety and Efficacy of a Three-Dose Regimen of an Adenoviral HIV Vaccine (MRKAd5 HIV-1 Gag/Pol/Nef) in HIV Uninfected South African Adults Condition: HIV Infections
Interventions: Biological: MRKAd5 HIV-1 gag/pol/nef; Other: Placebo A Phase I, Multicenter, Randomized, Double-Blind, Placebo-Controlled Trial to Evaluate the Safety and Immunogenicity of HIV-1 MN rsgp120 and Bivalent AIDSVAX B/E (HIV-1 MN rgp120/A244 rgp120) in Combination With QS-21 With or Without Alum in Healthy HIV-1 Uninfected Adults Condition: HIV Infections
Interventions: Biological: MN rgp120/HIV-1 and A244 rgp120/HIV-1; Biological: QS-21;
Biological: rgp120/HIV-1MN Expanded Characterization of Immune Response to Merck Adenovirus 5 Gag/Pol/Nef Vaccine to HIV Uninfected Adults Condition: HIV Infections
Intervention: Biological: MRKAd5 HIV-1 gag/pol/nef Safety of and Immune Response to an HIV-1 Vaccine Boost (VRC-HIVADV014-00-VP) in HIV Uninfected Adults Who Participated in HVTN 052

Condition: HIV Infections
Intervention: Biological: VRC-HIVADV014-00-VP

TABLE S-continued

Cancer vaccines

Safety and Immunogenicity of a Melan-A VLP Vaccine in Advanced Stage Melanoma Patients Condition: Malignant Melanoma
Intervention: Biological: CYT004-MelQbG10

Phase I Study to Evaluate the Safety and Immunogenicity of HIV-1 Immunogen in Children With HIV-1 Infection Condition: HIV Infection
Intervention: Biological: HIV-1 Immunogen Safety of and Immune Response to an HIV-1 DNA Vaccine (VRC HIVDNA009-00-VP) in HIV Uninfected Adults Condition: HIV Infections
Intervention: Biological: VRC-HIVDNA009-00-VP A Phase II Safety and Immunogenicity Trial of Live Recombinant Canarypox ALVAC-HIV vCP205 With or Without HIV-1 SF-2 RGP120 in HIV-1 Uninfected Adult Volunteers Condition: HIV Infections
Interventions: Biological: MN rgp120/HIV-1 and GNE8 rgp120/HIV-1;
Biological: MN rgp120/HIV-1 and A244 rgp120/HIV-1;
Biological: ALVAC-HIV MN120TMG (vCP205); Biological: rgp120/HIV-1 SF-2

Effectiveness of Early or Delayed Addition of Hydroxyurea to a Three-Drug Anti-HIV Drug Combination Including Didanosine, in Advanced HIV Patients Who Failed a First or Second Anti-HIV Triple-Drug Therapy Condition: HIV Infections
Interventions: Biological: Tetanus Toxoid Vaccine; Drug: Hydroxyurea;
Drug: Didanosine Idiotypic Vaccination for Follicular Lymphoma Patients Conditions: Follicular Lymphoma; First Relapse/Progression
Intervention: Biological: Follicular lymphoma, patient-specific, soluble protein idiotype vaccine Immunization of Disease-Free Melanoma Patients With Different HLA-A2 Peptides Condition: Melanoma
Intervention: Biological: Immunological peptides and immunological adjuvants Study of Mycobacterium w in Superficial Transitional Cell Carcinoma of Bladder Condition: Superficial Transitional Cell Carcinoma of Bladder
Interventions: Biological: Mycobacterium w; Biological: BCG (bacillus Calmette-Guerin)

Rituximab Post Autografting for Relapsed B-Cell Non-Hodgkin's Lymphoma

Condition: Non-Hodgkin's Lymphoma
Intervention: Drug: rituximab

Effect of Rituximab on Immunological Recall Response to Specific Antigens in the Treatment of Non-Hodgkin's Lymphoma Condition: Non-Hodgkin's Lymphoma
Intervention: Drug: rituximab Randomized Trial of Alternative HPV Vaccination Schedules in a University Setting Condition: Human Papillomavirus Infection
Interventions: Biological: Quadrivalent human papillomavirus vaccine; Biological: Quadrivalent human papillomavirus vaccine Safety, Tolerability and Immunogenicity of Quadrivalent Human Papillomavirus (HPV) Vaccine in Healthy Females 9 to 15 Years of Age in India Condition: Papillomavirus Infections
Intervention: Biological: Quadrivalent Human Papillomavirus (Types 6, 11, 16, 18) Recombinant Vaccine Immune Response to Mycobacterium Tuberculosis Infection Condition: Latent Tuberculosis
Intervention:

Trial Comparing Three Strategies of Vaccination Against the Virus of Hepatitis B in HIV Infected Patients Condition: HIV Infections
Interventions: Biological: GenHevac B Pasteur; Biological: GenHevac B Pasteur;
Biological: GenHevac B Pasteur Trial Comparing Two Strategies of Vaccination Against Hepatitis B in HIV-Infected Patients Non Responding to Primary Immunization (B-BOOST)

Conditions: Hepatitis B; HIV Infection
Interventions: Biological: GenHevac-B; Biological: GenHevac-B

TABLE S-continued

Cancer vaccines

An Immunogenicity and Safety Study of Gardasil ® in Chinese Subjects

| | |
|---|---|
| Condition: | Papillomavirus Infections |
| Interventions: | Biological: Quadrivalent Human Papillomavirus (Types 6, 11, 16, 18) Recombinant Vaccine; Biological: Comparator: Placebo (unspecified) |

Study of HPV 16 Vaccine in the Prevention of HPV 16 Infection in 16- to 23-Year-Old Females

| | |
|---|---|
| Condition: | Papillomavirus Infections |
| Interventions: | Biological: V501, /Duration of Treatment: 6 Months; Biological: Comparator: placebo with adjuvant (unspecified)/Duration of Treatment: 6 Months |

A Study of Gardasil (V501) in Preadolescents and Adolescents

| | |
|---|---|
| Conditions: | Healthy; Papillomavirus Infections |
| Intervention: | Biological: V501, Gardasil, human papillomavirus (types 6, 11, 16, 18) recombinant vaccine/Duration of Treatment: 1.5 years |

Phase 2 Study of Intralesional PV-10 for Metastatic Melanoma

| | |
|---|---|
| Condition: | Melanoma |
| Intervention: | Drug: PV-10 (10% rose bengal disodium) |

Parental Permission and Adolescent Assent and Decision-Making in Clinical Research

| | |
|---|---|
| Condition: | Adolescents |
| Intervention: | |

Human Papillomavirus (HPV) Registration Study (Gardasil)

| | |
|---|---|
| Condition: | Papillomavirus Infections |
| Intervention: | Biological: V501, Gardasil, human papillomavirus (types 6, 11, 16, 18) recombinant vaccine/Duration of treatment: 7 months |

Gardasil Vaccination as Therapy in Low Grade Cervical Abnormalities

| | |
|---|---|
| Condition: | Papillomavirus Infections |
| Intervention: | Biological: human papillomavirus vaccine L1, type 6, 11, 16, 18 |

Multiepitope Peptide Vaccination in Melanoma

| | |
|---|---|
| Condition: | Metastatic Melanoma |
| Intervention: | Biological: Tyrosinase, MAGE-3, GnTV |

Safety Study of CADI-05 in Patients With Advanced Stage Melanoma

| | |
|---|---|
| Condition: | Stage III or Stage IV Melanoma |
| Intervention: | Biological: CADI-05 |

Gardasil (V501) Study in Adult Women

| | |
|---|---|
| Condition: | Papillomavirus Infections |
| Interventions: | Biological: V501, Gardasil, human papillomavirus (types 6, 11, 16, 18) recombinant vaccine/Duration of Treatment: 7 Months; Biological: Placebo (unspecified)/Duration of Treatment: 7 Months |

HLA-B35 Alleles and AIDS

| | |
|---|---|
| Conditions: | HIV-1; AIDS |
| Intervention: | |

V501 (Gardasil) Study in Preadolescent Females

| | |
|---|---|
| Condition: | Papillomavirus Infections |
| Interventions: | Biological: V501, Gardasil, human papillomavirus (types 6, 11, 16, 18) recombinant vaccine/Duration of Treatment: 7 Months; Biological: Comparator: placebo (unspecified)/Duration of Treatment: 7 Months |

Antimicrobial Drugs

Another class of drugs of special interest for the present invention is drugs for the treatment of viral and bacterial disease such as viral or bacterial infections. For a list of examples of antimicrobial drugs, please refer to Table Q (antimicrobials) and the items.

TABLE Q

Antimicrobial drugs

| Generic Name | Brand Names | Common Uses | Mechanism of action |
|---|---|---|---|
| *Aminoglycosides* | | | |
| Amikacin | Amikin | Infections caused by Gram-negative bacteria, such as *Escherichia coli* and *Klebsiella* particularly *Pseudomonas aeruginosa*. Effective against | Binding to the bacterial 30S ribosomal subunit (some work by binding to the 50S subunit), inhibiting the translocation of the peptidyl- |
| Gentamicin | Garamycin | | |
| Kanamycin | Kantrex | | |
| Neomycin | | | |
| Netilmicin | Netromycin | | |

TABLE Q-continued

Antimicrobial drugs

| Generic Name | Brand Names | Common Uses | Mechanism of action |
| --- | --- | --- | --- |
| Streptomycin Tobramycin Paromomycin | Nebcin Humatin | Aerobic bacteria (not obligate/facultative anaerobes). | tRNA from the A-site to the P-site and also causing misreading of mRNA, leaving the bacterium unable to synthesize proteins vital to its growth. |
| Ansamycins | | | |
| Geldanamycin Herbimycin | | Experimental, as antitumor antibiotics | |
| Carbacephem | | | |
| Loracarbef | Lorabid | | Prevents bacterial cell division by inhibiting cell wall synthesis. |
| Carbapenems | | | |
| Ertapenem Doripenem Imipenem/ Cilastatin Meropenem | Invanz Finibax Primaxin Merrem | Bactericidal for both Gram-positive and Gram-negative organisms and therefore useful for empiric broad-spectrum antibacterial coverage. (Note MRSA resistance to this class.) | Inhibition of cell wall synthesis |
| Cephalosporins | | | |
| Cefadroxil Cefazolin Cefalotin or Cefalothin Cefalexin Cefaclor Cefamandole Cefoxitin Cefprozil Cefuroxime Cefixime Cefdinir Cefditoren Cefoperazone Cefotaxime Cefpodoxime Ceftazidime Ceftibuten Ceftizoxime Ceftriaxone Cefepime Ceftobiprole | Duricef Ancef Keflin Keflex Ceclor Mandole Mefoxin Cefzil Ceftin, Zinnat Suprax Omnicef Spectracef Cefobid Claforan Fortaz Cedax Rocephin Maxipime | | Same mode of action as other beta-lactam antibiotics: disrupt the synthesis of the peptidoglycan layer of bacterial cell walls. |
| Glycopeptides | | | |
| Teicoplanin Vancomycin | Vancocin | | Inhibition of peptidoglycan synthesis |
| Macrolides | | | |
| Azithromycin Clarithromycin Dirithromycin Erythromycin Roxithromycin Troleandomycin Telithromycin Spectinomycin | Zithromax, Sumamed, Zitrocin Biaxin Erythocin, Erythroped Ketek | Streptococcal infections, syphilis, respiratory infections, mycoplasmal infections, Lyme disease Pneumonia Antimetabolite, Anticancer | Inhibition of bacterial protein biosynthesis by binding irreversibly to the subunit 50S of the bacterial ribosome, thereby inhibiting translocation of peptidyl tRNA. |
| Monobactams | | | |
| Aztreonam | | | Same mode of action as other beta-lactam antibiotics: disrupt the synthesis of the peptidoglycan layer of bacterial cell walls. |
| Penicillins | | | |
| Amoxicillin Azlocillin Carbenicillin | Novamox, Amoxil | Wide range of infections; penicillin used for streptococcal infections, syphilis, and Lyme disease | Same mode of action as other beta-lactam antibiotics: disrupt the synthesis of the peptidoglycan layer of bacterial cell walls. |

TABLE Q-continued

Antimicrobial drugs

| Generic Name | Brand Names | Common Uses | Mechanism of action |
| --- | --- | --- | --- |
| Cloxacillin<br>Dicloxacillin<br>Flucloxacillin<br>Mezlocillin<br>Meticillin<br>Nafcillin<br>Oxacillin<br>Penicillin<br>Piperacillin<br>Ticarcillin | Floxapen | | |
| Polypeptides | | | |
| Bacitracin | | Eye, ear or bladder infections; usually applied directly to the eye or inhaled into the lungs; rarely given by injection | Inhibits isoprenyl pyrophosphate, a molecule which carries the building blocks of the peptidoglycan bacterial cell wall outside of the inner membrane |
| Colistin<br>Polymyxin B | | | Interact with the bacterial cytoplasmic membrane, changing its permeability. |
| Quinolones | | | |
| Ciprofloxacin | Cipro,<br>Ciproxin,<br>Ciprobay | Urinary tract infections, bacterial prostatitis, community-acquired pneumonia, bacterial diarrhea, mycoplasmal infections, gonorrhea | Inhibits the bacterial DNA gyrase or the topoisomerase IV enzyme, thereby inhibiting DNA replication and transcription. |
| Enoxacin | | | |
| Gatifloxacin | Tequin | | |
| Levofloxacin | Levaquin | | |
| Lomefloxacin | | | |
| Moxifloxacin | Avelox | | |
| Norfloxacin | Noroxin | | |
| Ofloxacin | Ocuflox | | |
| Trovafloxacin | Trovan | | |
| Sulfonamides | | | |
| Mafenide<br>Sulfasalazine<br>Sulfisoxazole<br>Trimethoprim<br>Trimethoprim-<br>Sulfamethoxazole<br>(Co-trimoxazole)<br>(TMP-SMX) | Bactrim | Urinary tract infections | PABA (para-aminobenzoate) to dihydropteroate, a key step in folate synthesis. Folate is necessary for the cell to synthesize nucleic acids (nucleic acids are essential building blocks of DNA and RNA), and in its absence cells will be unable to divide. |
| Tetracyclines | | | |
| Demeclocycline | | Syphilis, chlamydial infections, Lyme disease, mycoplasmal infections, acne rickettsial infections | Inhibiting the binding of aminoacyl-tRNA to the mRNA-ribosome complex. They do so mainly by binding to the 30S ribosomal subunit in the mRNA translation complex. |
| Doxycycline | Vibramycin | | |
| Minocycline | Minocin | | |
| Oxytetracycline | Terracin | | |
| Tetracycline | Sumycin | | |
| Others | | | |
| Arsphenamine | Salvarsan | Spirochaetal infections (obsolete) | |
| Chloramphenicol | Chloromycetin | | |
| Clindamycin | Cleocin | acne infections, prophylaxis before surgery | |
| Lincomycin | | acne infections, prophylaxis before surgery | |
| Ethambutol | | Antituberculosis | |
| Fosfomycin | | | |
| Fusidic acid | Fucidin | | |
| Furazolidone | | | |
| Isoniazid | | Antituberculosis | |
| Linezolid | Zyvox | | |
| Metronidazole | Flagyl | Giardia | |
| Mupirocin | Bactroban | | |
| Nitrofurantoin | Macrodantin,<br>Macrobid | | |

TABLE Q-continued

Antimicrobial drugs

| Generic Name | Brand Names | Common Uses | Mechanism of action |
|---|---|---|---|
| Platensimycin | | | |
| Pyrazinamide | | Antituberculosis | |
| Quinupristin/Dalfopristin | Syncercid | | |
| Rifampin or Rifampicin | | mostly Gram-positive and mycobacteria | Binds to the β subunit of RNA polymerase to inhibit transcription |
| Tinidazole | | | |

An antimicrobial is a substance that kills or inhibits the growth of microbes such as bacteria (antibacterial activity, often antibiotics), viruses (antiviral activity), fungi (antifungal activity) or parasites (antiparasitic activity). Antimicrobial drugs either kill microbes (microbicidal) or prevent the growth of microbes (microbistatic).

Antibiotics/antibacterial (see FIG. 12 A):

Many antibiotic compounds used in modern medicine are produced and isolated from living organisms, such as the penicillin class produced by fungi in the genus *Penicillium*, or streptomycin from bacteria of the genus *Streptomyces*. With advances in medicinal chemistry many antibiotics are now modified chemically from their original form found in nature. In addition, some modern antibiotics have been created through purely synthetic means. Many antibiotics are relatively small molecules with a molecular weight less than 2000 Da.

Aminoglycosides
Ansamycins
Carbacephem
Carbapenems
Cephalosporins
Glycopeptides
Macrolides
Monobactams
Penicillins
Polypeptides
Quinolones
Quinolones
Tetracyclines
Others Antivirals (see FIG. 12 B): Antiviral drugs may act at different stages of the viral life cycle in the host cell. These include drugs that act Before cell entry (entry blockers, examples include amantadine, rimantadine, pleconaril, maraviroc and enfuvirtide);
  agents which mimic the virus-associated protein (VAP) and bind to the cellular receptors
  agents which mimic the cellular receptor and bind to the VAP
On the processes that synthesize virus components
  reverse transcriptase inhibitor
    Nucleoside & nucleotide reverse transcriptase inhibitors (NRTI) (ie. nucleoside analogues, e.g. abacavir)
    Non-nucleoside reverse transcriptase inhibitors (nNRTI) (direct enzyme binding, e.g. lodenosine)
  protease inhibitors (e.g. lopinavir, ritonavir)
  integrase inhibitors (e.g. raltegravir, GS-9137)
  Rnase H inhibitors
  block the attachment of transcription factors to viral DNA (zidovudine (AZT), lamivudine and acyclovir or antisense drug fomivirsen)
  ribozyme antivirals
On the release phase
  Neuraminidase or Sialidase 1 blockers such as zanamivir (Relenza) and oseltamivir (Tamiflu).
  Maturation inhibitors inhibit the last step in 'gag' processing in which the viral capsid polyprotein is cleaved (e.g. bevirimat and vivecon).
Experimental drugs Fixed dose combinations of antiretrovirals are multiple antiretroviral drugs combined into a single pill, which helps reduce pill burden. They may combine different classes of antiretrovirals or contain only a single class. These include: Combivir, Atripla, Trizivir, Truvada, Kaletra, Epzicom Synergistic enhancers either do not possess antiretroviral properties alone or are inadequate or impractical for monotherapy, but when they are taken concurrently with antiretroviral drugs they enhance the effect of one or more of those drugs (often by altering the metabolism of antiretrovirals). These include:

Chloroquine/quinoline antimalarials: Chloroquine is being investigated as a synergistic enhancer of protease inhibitors. The mechanism underlying the effects of chloroquine on response to protease inhibitors is inhibition of cellular drug efflux pumps. The effects of the antimalarial drugs, however, will require further evaluation before being clinically exploited.

Grapefruit juice: Grapefruit juice is a common natural plant extract. The enzyme CYP3A4, a member of the Cytochrome P450 enzyme family, is present in the liver and the lining of the gastrointestinal (GI) tract. One of the functions of CYP3A4 is to metabolise foreign chemicals including many drugs used to treat HIV. Grapefruit juice can neutralize CYP3A4 in the GI tract but not significantly in the liver, and pre-treating with grapefruit juice prior to taking protease inhibitors increase the bioavailabity of the drug. The effect, however, is unreliable and results may vary greatly, therefore it is not a standard recommended practice.

Hydroxyurea: Hydroxyurea (HU) is an older medication (an antimetabolite) used for sickle-cell anemia and some other hematologic disorders. It enhances ddI, and to a lesser extent AZT and ddC. One possible explanation is that HU causes cells to spend more time in the "S" phase checkpoint of cellular growth which allows ddI, AZT and ddC into the cell more. In addition HU inhibits ribonucleotide reductase, an enzyme used to break down certain proteins to form the building blocks of DNA called dNTPs. When dNTPs are depleted the cell tries to absorb more but if ddI, AZT or ddC is present it absorbs that due to the similarity, the net effect is more ddI, AZT or ddC enters the cell. HU can result in bone marrow suppression, and there are warnings that using HU with ddI can increase the risk of pancreatitis.

Leflunomide: Leflunomide has the trade name Arava. It enhances AZT through depleting a dNTP analogous to HU, RV and mycophenolic acid.

Mycophenolic acid: Mycophenolic acid is an inosine-5'-monophosphate dehydrogenase (IMPDH)-inhibitor. It enhances abacavir but reduces the effect of AZT and d4T. Works analogous to HU and RV only the enzyme inhibited is IMPDH which leads to depletion of the dNTP named dGTP which causes cells to take up more abacavir.

Resveratrol: Resveratrol (RV) is a natural product extracted from certain plants. It enhances ddI, and to a lesser extent AZT and ddC in vitro. Like HU, RV also causes cells to spend more time in the "S" phase checkpoint of cellular growth and also inhibits ribonucleotide reductase. RV is generally better tolerated than HU and has fewer side-effects.

Ritonavir: Ritonavir has the trade name Norvir. It enhances other protease inhibitors through the inhibition of CYP3A4, a liver enzyme. While ritonavir is a protease inhibitor, it cannot be used to inhibit HIV significantly by itself at the low doses required to enhance other protease inhibitors. It is the only antiretroviral synergistic enhancer to be FDA-approved specifically for this use.

Antifungal drugs (see FIG. 12 C)
    Medication used to treat fungal infections such as athlete's foot, ringworm, candidiasis (thrush), serious systemic infections such as cryptococcal meningitis, and others.
    Polyene antifungals
    Imidazole and triazole antifungals
    Allylamines
    Echinocandins
    Others Antiparasitics (see FIG. 12 D)
    A class of medications which are indicated for the treatment of infection by parasites such as nematodes, cestodes, trematodes, infectious protozoa, and amoebas.

Parasitic diseases includes: Coccidia (Cryptosporidiosis, Isosporiasis, Cyclosporiasis, Toxoplasmosis), Malaria (Blackwater fever), Babesiosis Giardiasis, Trypanosomiasis (Sleeping sickness, Chagas disease), Leishmaniasis (Cutaneous leishmaniasis, Visceral leishmaniasis), Trichomoniasis Amoebiasis, Blastocystosis, Dientamoebiasis, Microsporidiosis, Primary amoebic meningoencephalitis, Toxoplasmosis.

Immunostimulants

Immunostimulators are substances (drugs and nutrients) that stimulate the immune system by inducing activation or increasing activity of any of its components. One notable example include granulocyte macrophage colony-stimulating factor, commercially available under Leukine name.

There are two main categories of immunostimulators:
1) Specific immunostimulators are those which provide antigenic specificity in immune response, such as vaccines or any antigen.
2) Non-specific immunostimulators are those which act irrespective of antigenic specificity to augment immune response of other antigen or stimulate components of the immune system without antigenic specificity, such as adjuvants and non-specific immunostimulators.

Many endogenous substances are non-specific immunostimulators. For example, female sex hormones are known to stimulate both adaptive and innate immune responses. Some autoimmune diseases such as lupus erythematosus strike women preferentially, and their onset often coincides with puberty. Other hormones appear to regulate the immune system as well, most notably prolactin, growth hormone and vitamin D.

Examples of Immunostimulator drugs are Leukine and Levamisole.

Immunostimulants include, Ampligen, Lentinan, Low dose naltrexone, Roquinimex, Thymopentin.

Immunologic Adjuvant

In immunology, an adjuvant is an agent that may stimulate the immune system and increase the response to a vaccine, without having any specific antigenic effect in itself. An immunologic adjuvant is defined as any substance that acts to accelerate, prolong, or enhance antigen-specific immune responses when used in combination with specific vaccine antigens.

Known adjuvants include oils, aluminum salts and virosomes.

Adjuvants in immunology are often used to modify or augment the effects of a vaccine by stimulating the immune system to respond to the vaccine more vigorously, and thus providing increased immunity to a particular disease. Adjuvants accomplish this task by mimicking specific sets of evolutionarily conserved molecules which include liposomes, lipopolysaccharide (LPS), molecular cages for antigen, components of bacterial cell walls, and endocytosed nucleic acids such as double-stranded RNA (dsRNA), single-stranded DNA (ssDNA), and unmethylated CpG dinucleotide-containing DNA. Because immune systems have evolved to recognize these specific antigenic moieties, the presence of adjuvant in conjunction with the vaccine can greatly increase the innate immune response to the antigen by augmenting the activities of dendritic cells (DCs), lymphocytes and macrophages by mimicking a natural infection. Furthermore, because adjuvants are attenuated beyond any function of virulence, they pose little or no independent threat to a host organism.

Inorganic adjuvants: There are many adjuvants, some of which are inorganic (such as alum), that also carry the potential to augment immunogenicity. Two common salts include Aluminium salts such as aluminum phosphate and aluminum hydroxide. These are the most common adjuvants in human vaccines.

Organic adjuvants: While aluminium salts are popularly used in human vaccines, the organic compound Squalene is also used. However, organic adjuvants are more commonly used in animal vaccines.

Oil-based adjuvants are commonly used in some veterinary vaccines.

Another market-approved adjuvant and carrier system are virosomes. During the last two decades, a variety of technologies have been investigated to improve the widely-used adjuvants based on aluminum salts. These salts are unfavorable, since they develop their effect by inducing local inflammation, which is also the basis for the extended side-effect pattern of this adjuvant. In contrast, the adjuvant capabilities of virosomes are independent of any inflammatory reaction. Virosomes contain a membrane-bound hemagglutinin and neuraminidase derived from the influenza virus, and serve to amplify fusogenic activity and therefore facilitate the uptake into antigen presenting cells (APC) and induce a natural antigen-processing pathway. The delivery of the antigen by virosomes to the immune system in a way that mimics a natural path may be a reason why virosome-based vaccines stand out due to their excellent safety profile.

An increasing number of vaccines with squalene and phosphate adjuvants are being tested on humans. The compound QS21 is under investigation as a possible immunological adjuvant as is Novartis' (formerly Chiron) MF59.

Adjuvants and the Adaptive Immune Response

One misconception concerning adjuvant function is that an adjuvant-enhanced innate immune response should affect only the transitory reaction of the innate immune response and not the more long-lived effects of the adaptive immune response. Although it may appear fitting to separate the two systems, it is however important to realize the interconnected nature of the two systems. When the amount of communication that takes place between the innate immune response and the adaptive immune response with the onset of infection is considered it becomes difficult to separate the two systems.

In order to understand the links between the innate immune response and the adaptive immune response to help substantiate an adjuvant function in enhancing adaptive immune responses to the specific antigen of a vaccine, the following points should be considered:

Innate immune response cells such as DCs engulf pathogens through a process called phagocytosis.

DCs then migrate to the lymph nodes where T cells (adaptive immune cells) wait for signals to trigger their activation.

In the lymph nodes, DCs mince the engulfed pathogen and then express the pathogen clippings as antigen on their cell surface by coupling them to a special receptor known as a major histocompatibility complex (MHC).

T cells can then recognize these clippings and undergo a cellular transformation resulting in its own activation.

γδ T cells possess characteristics of both the innate and adaptive immune responses. Macrophages can also activate T cells in a similar approach.

This process carried out by both DCs and macrophages is termed antigen presentation and represents a physical link between the innate and adaptive immune responses. Upon activation, mast cells release heparin and histamine to effectively increase trafficking to and seal off the site of infection to allow immune cells of both systems to clear the area of pathogens. In addition, mast cells also release chemokines which result in the positive chemotaxis of other immune cells of both the innate and adaptive immune responses to the infected area.

Due to the variety of mechanisms and links between the innate and adaptive immune response, an adjuvant-enhanced innate immune response results in an enhanced adaptive immune response. Specifically, a recent study has observed that adjuvants may exert their immune-enhancing effects according to five immune-functional activities.

First, it was found that adjuvants all help in the translocation of antigens to the lymph nodes where they can be recognized by T cells. This will ultimately lead to greater T cell activity resulting in a heightened clearance of pathogen throughout the organism. Second, adjuvants provide physical protection to antigens which grants the antigen a prolonged delivery. This means that the organism will be exposed to the antigen for a longer duration, making the immune system more robust as it makes use of the additional time by upregulating the production of B and T cells needed for greater immunological memory in the adaptive immune response.

Third, adjuvants help to increase the capacity to cause local reactions at the injection site (during vaccination), inducing greater release of danger signals by chemokine releasing cells such as helper T cells and mast cells.

Fourth, they induce the release of inflammatory cytokines which helps to not only recruit B and T cells at sites of infection but also to increase transcriptional events leading to a net increase of immune cells as a whole.

Finally, adjuvants are believed to increase the innate immune response to antigen by interacting with pattern recognition receptors (PRRs), specifically Toll-like receptors (TLRs), on accessory cells.

Adjuvants and Toll-like Receptors

The ability of immune system to recognize molecules that are broadly shared by pathogens is, in part, due to the presence of special Immune receptors called TLRs that are expressed on leukocyte membranes. TLRs were first discovered in *drosophila*, and are membrane bound pattern recognition receptors (PRRs) responsible for detecting most (although certainly not all) antigen-mediated infections. In fact, some studies have shown that in the absence of TLR, leukocytes become unresponsive (no inflammatory responses) to some microbial components such as LPS. There are at least thirteen different forms of TLR, each with its own characteristic ligand. Prevailing TLR ligands described to date (all of which elicit adjuvant effects) include many evolutionarily conserved molecules such as LPS, lipoproteins, lipopeptides, flagellin, double-stranded RNA, unmethylated CpG islands and various other forms of DNA and RNA classically released by bacteria and viruses.

The binding of ligand—either in the form of adjuvant used in vaccinations or in the form of invasive moieties during times of natural infection—to the TLR marks the key molecular events that ultimately lead to innate immune responses and the development of antigen-specific acquired immunity. The very fact that TLR activation leads to adaptive immune responses to foreign entities explains why so many adjuvants used today in vaccinations are developed to mimic TLR ligands.

It is believed that upon activation, TLRs recruit adapter proteins (proteins that mediate other protein-protein interactions) within the cytosol of the immune cell in order to propagate the antigen-induced signal transduction pathway. To date, four adapter proteins have been well-characterized. These proteins are known as MyD88, Trif, Tram and Tirap (also called Mal). These recruited proteins are then responsible for the subsequent activation of other downstream proteins, including protein kinases (IKKi, IRAK1, IRAK4, and TBK1) that further amplify the signal and ultimately lead to the upregulation or suppression of genes that orchestrate inflammatory responses and other transcriptional events. Some of these events lead to cytokine production, proliferation, and survival, while others lead to greater adaptive immunity. The high sensitivity of TLR for microbial ligands is what makes adjuvants that mimic TLR ligands such a prime candidate for enhancing the overall effects of antigen specific vaccinations on immunological memory.

Finally, the expression of TLRs is vast as they are found on the cell membranes of innate immune cells (DCs, macrophages, natural killer cells), cells of the adaptive immunity (T and B lymphocytes) and non immune cells (epithelial and endothelial cells, fibroblasts).

This further substantiates the importance of administering vaccines with adjuvants in the form of TLR ligands as they will be capable of eliciting their positive effects across the entire spectrum of innate and adaptive immunity. Nevertheless, there are certainly adjuvants whose immune-stimulatory function completely bypasses the putative requisite for TLR signaling. In short, all TLR ligands are adjuvants but not all adjuvants are TLR ligands.

Cancer Vaccines

The term cancer vaccine refers to a vaccine that either prevents infections with cancer-causing viruses, or treats existing cancer.

Some cancers, such as cervical cancer and some liver cancers, are caused by viruses, and traditional vaccines against those viruses, such as HPV vaccine and Hepatitis B vaccine, will prevent those cancers.

Scientists have also been trying to develop vaccines against existing cancers. Some researchers believe that cancer cells routinely arise and are destroyed by the healthy immune system; cancer forms when the immune system fails to destroy them. They are separating proteins from cancer cells and immunizing cancer patients against those proteins, in the hope of stimulating an immune reaction that would kill the cancer cells. Therapeutic cancer vaccines are being developed for the treatment of breast, lung, colon, skin, kidney, prostate, and other cancers but they have not yet been proven to work in phase 3 human trials, and have not been approved by the U.S. Food and Drug Administration or by European Union regulatory agencies.

A list of examples of cancer vaccines are given in Table S.

C) Physical Treatment

The present invention relates in one embodiment to treatment of one or more diseases by physical treatment of a unit such as an individual in need thereof.

Physical treatment of the present invention includes treatment through physical manipulation and/or changes in the unit. The treatment may be through "hand-on" physical intervention or through help of devices.

Physical treatment of the present invention includes but is not limited to:
Surgery
Radiotherapy
Massage
Physiotherapy
Chiropractic
Electric stimulation
Acupuncture In the present invention physical treatment is defined as any treatment that directly affects the physics of the unit by removal, addition, manipulation, blocking, enhancing specific parts of the unit. Of special interest is physical treatment of humans. Physical treatment may be prophylactic or therapeutic. Examples of physical treatments of humans are surgery, radiotherapy, massage, physiotherapy, chiropractic, transplantation, electric stimulation and acupuncture.

In a preferred embodiment of the present invention surgery means a medical specialty that uses operative manual and instrumental techniques on a human being to investigate and/or treat a pathological condition such as disease or injury, to help improve bodily function or appearance.

A physical treatment of special interest is transplantation that in a preferred embodiment of the present invention refers to the replacement of a defective organ or tissue in a body with one from another body, another part of the same body or an artificial made organ or tissue. Examples of organs or tissues that may be transplanted include heart, bone marrow, skin, joints, liver, kidney, lungs, pancreas, bones, tendons, cornea, heart valves, blood vessels, intestine, blood cells, spleen and lymph nodes.

D) Psychological Therapy

The present invention relates in one embodiment to treatment of one or more diseases by psychological therapy to a unit such as an individual in need thereof.

In the present invention psychological therapy is to be understood as manipulation and/or altering of mental processes and behaviour in order to cure or improve mental illness or disease in humans or animals. Psychological therapy is mainly therapeutic but may be also be prophylactic. Methods used for psychological therapy includes but is not limited to:
Psychology
Psychotherapy
Meditation
Hypnosis Intervals of Diagnosis (Analysis) and Treatment (Repair)

Alternating Diagnosis and Treatment

According to the present invention, a method for combinatorial use of one or more analysis method(s) such as one or more diagnostic method(s), and one or more repair process(es) such as one or more treatment(s), are employed on an undesired state of a live (e.g. human being) or non-live unit, in order to repair or improve the undesired state of said unit in an appropriate way.

In one embodiment of the present invention, the unit is diagnosed (analysed) and treated (repaired) once, whereas in another embodiment, the unit is diagnosed and treated multiple times. Therefore, the number of diagnoses carried out on a unit may be 1, such as 2, for example 3, such as 4, for example 5, such as 6, for example 7, such as 8, for example 9, such as 10, for example 11, such as 12, for example 13, such as 14, for example 15, such as 16, for example 17, such as 18, for example 19, such as 20, for example 25, such as 30, for example 40, such as 50, for example 100, such as 200, for example 300, such as 400, for example 500, such as 750, for example 1,000, for example 5,000, such as 10,000, for example 10,000, such as 50,000, for example 50,000, such as 100,000, for example 100,000, such as 1,000,000, such as ∞ (infinity). Therefore, the number of diagnoses may be 1 to 2, such as 2 to 4, for example 4 to 6, such as 6 to 8, for example 8 to 10, such as 10 to 15, for example 15 to 20, such as 20 to 30, for example 30 to 40, such as 40 to 50, for example 50 to 75, such as 75 to 100, for example 100 to 200, such as 200 to 300, for example 300 to 400, such as 400 to 500, for example 500 to 750, such as 750 to 1,000, for example 1,000 to 5,000, such as 5,000 to 10,000, for example 10,000 to 50,000, such as 50,000 to 100,000, for example 100,000 to 1,000,000, such as 1,000,000 to ∞ (infinity).

Accordingly, the number of treatments carried out on a unit may be 1, such as 2, for example 3, such as 4, for example 5, such as 6, for example 7, such as 8, for example 9, such as 10, for example 11, such as 12, for example 13, such as 14, for example 15, such as 16, for example 17, such as 18, for example 19, such as 20, for example 25, such as 30, for example 40, such as 50, for example 100, such as 200, for example 300, such as 400, for example 500, such as 750, for example 1,000, for example 5,000, such as 10,000, for example 10,000, such as 50,000, for example 50,000, such as 100,000, for example 100,000, such as 1,000,000, such as ∞ (infinity).

Therefore, the number of treatments may be 1 to 2, such as 2 to 4, for example 4 to 6, such as 6 to 8, for example 8 to 10, such as 10 to 15, for example 15 to 20, such as 20 to 30, for example 30 to 40, such as 40 to 50, for example 50 to 75, such as 75 to 100, for example 100 to 200, such as 200 to 300, for example 300 to 400, such as 400 to 500, for example 500 to 750, such as 750 to 1,000, for example 1,000 to 5,000, such as 5,000 to 10,000, for example 10,000 to 50,000, such as 50,000 to 100,000, for example 100,000 to 1,000,000, such as 1,000,000 to ∞ (infinity).

The combination of diagnosis and treatment may be 1:1 i.e. the unit is diagnosed as many times as it is treated. Alternatively the unit is diagnosed more times than it is treated, i.e. the ratio of diagnosis to treatment (diagnosis:treatment) may be equal to or more than 2:1, 3:1, 4:1, 5:1, 6:1, 7:1, 8:1, 9:1, 10:1, 11:1, 12:1, 13:1, 14:1, 15:1, 20:1, 25:1, 50:1, 100:1, 250:1, 500:1, 750:1, 1,000:1, 5,000:1, 10,000:1, 50,000:1, 100,000:1, 500,000:1 or 1,000,000:1. Alternatively the unit is treated more times than it is diagnosed, i.e. the ratio of treatment to diagnosis (treatment: diagnosis) may be equal to or more than 2:1, 3:1, 4:1, 5:1, 6:1, 7:1, 8:1, 9:1, 10:1, 11:1, 12:1, 13:1, 14:1, 15:1, 20:1, 25:1, 50:1, 100:1, 250:1, 500:1, 750:1, 1,000:1, 5,000:1, 10,000:1, 50,000:1, 100,000:1, 500,000:1 or 1,000,000:1.

When a unit is diagnosed, it may be treated multiple times to repair the diseased state. In one embodiment, the unit may therefore undergo treatment once daily or multiple times daily, weekly, monthly or yearly for the entire lifespan of the unit or until the unit is disease-free, symptom-free or a new and improved medicament is available.

Treatment

In one embodiment, the medicament, composition or drug to be used for treatment of an undesirable state according to the present invention is administered at a total daily dosage of from about 0.01 milligram to about 1000 milligram per kilogram of animal body weight. The dosage regimen may be adjusted within this range or even outside of this range to provide the optimal therapeutic response.

The drugs used according to the present invention is given in an effective amount to an individual in need there of. The amount of drug according to the present invention in one preferred embodiment is in the range of from about 0.01 milligram per kg body weight per dose to about 1000 milligram per kg body weight per dose, such as from about 0.01 milligram per kg body weight per dose to about 0.025 milligram per kg body weight per dose, for example from about 0.025 milligram per kg body weight per dose to about 0.05 milligram per kg body weight per dose, such as from about 0.05 milligram per kg body weight per dose to about 0.075 milligram per kg body weight per dose, for example from about 0.075 milligram per kg body weight per dose to about 0.1 milligram per kg body weight per dose, such as from about 0.1 milligram per kg body weight per dose to about 0.25 milligram per kg body weight per dose, such as from about 0.25 milligram per kg body weight per dose to about 0.5 milligram per kg body weight per dose, for example from about 0.5 milligram per kg body weight per dose to about 0.75 milligram per kg body weight per dose, such as from about 0.75 milligram per kg body weight per dose to about 1.0 milligram per kg body weight per dose, for example from about 1.0 milligram per kg body weight per dose to about 2.5 milligram per kg body weight per dose, such as from about 2.5 milligram per kg body weight per dose to about 5 milligram per kg body weight per dose, for example from about 5 milligram per kg body weight per dose to about 7.5 milligram per kg body weight per dose, such as from about 7.5 milligram per kg body weight per dose to about 10 milligram per kg body weight per dose, for example from about 10 milligram per kg body weight per dose to about 25 milligram per kg body weight per dose, such as from about 25 milligram per kg body weight per dose to about 50 milligram per kg body weight per dose, such as from about 50 milligram per kg body weight per dose to about 75 milligram per kg body weight per dose, for example from about 75 milligram per kg body weight per dose to about 100 milligram per kg body weight per dose, such as from about 100 milligram per kg body weight per dose to about 250 milligram per kg body weight per dose, for example from about 250 milligram per kg body weight per dose to about 500 milligram per kg body weight per dose, such as from about 500 milligram per kg body weight per dose to about 750 milligram per kg body weight per dose, for example from about 750 milligram per kg body weight per dose to about 1000 milligram per kg body weight per dose.

The amount of drug according to the present invention in another preferred embodiment is in the range of from about 0.01 milligram per kg body weight per dose to about 20 milligram per kg body weight per dose, such as from about 0.02 milligram per kg body weight per dose to about 18 milligram per kg body weight per dose, for example from about 0.04 milligram per kg body weight per dose to about 16 milligram per kg body weight per dose, such as from about 0.06 milligram per kg body weight per dose to about 14 milligram per kg body weight per dose, for example from about 0.08 milligram per kg body weight per dose to about 12 milligram per kg body weight per dose, such as from about 0.1 milligram per kg body weight per dose to about 10 milligram per kg body weight per dose, such as from about 0.2 milligram per kg body weight per dose to about 10 milligram per kg body weight per dose, for example from about 0.3 milligram per kg body weight per dose to about 10 milligram per kg body weight per dose, such as from about 0.4 milligram per kg body weight per dose to about 10 milligram per kg body weight per dose, for example from about 0.5 milligram per kg body weight per dose to about 10 milligram per kg body weight per dose, such as from about 0.6 milligram per kg body weight per dose to about 10 milligram per kg body weight per dose, for example from about 0.7 milligram per kg body weight per dose to about 10 milligram per kg body weight per dose, such as from about 0.8 milligram per kg body weight per dose to about 10 milligram per kg body weight per dose, for example from about 0.9 milligram per kg body weight per dose to about 10 milligram per kg body weight per dose, such as from about 1.0 milligram per kg body weight per dose to about 10 milligram per kg body weight per dose, for example from about 1.2 milligram per kg body weight per dose to about 10 milligram per kg body weight per dose, such as from about 1.4 milligram per kg body weight per dose to about 10 milligram per kg body weight per dose, for example from about 1.6 milligram per kg body weight per dose to about 10 milligram per kg body weight per dose, such as from about 1.8 milligram per kg body weight per dose to about 10 milligram per kg body weight per dose, for example from about 2.0 milligram per kg body weight per dose to about 10 milligram per kg body weight per dose, such as from about 2.2 milligram per kg body weight per dose to about 10 milligram per kg body weight per dose, for example from about 2.4 milligram per kg body weight per dose to about 10 milligram per kg body weight per dose, such as from about 2.6 milligram per kg body weight per dose to about 10 milligram per kg body weight per dose, for example from about 2.8 milligram per kg body weight per dose to about 10 milligram per kg body weight per dose, such as from about 3.0 milligram per kg body weight per dose to about 10 milligram per kg body weight per dose, for example from about 3.2 milligram per kg body weight per dose to about 10 milligram per kg body weight per dose, such as from about 3.4 milligram per kg body weight per dose to about 10 milligram per kg body weight per dose, for example from about 3.6 milligram per kg body weight per dose to about 10 milligram per kg body weight per dose, such as from about 3.8 milligram per kg body weight per dose to about 10 milligram per kg body weight per dose, for example from about 4.0 milligram per kg body weight per dose to about 10 milligram per kg body weight per dose, such as from about 4.2 milligram per kg body weight per dose to about 10 milligram per kg body weight per dose, for example from about 4.4 milligram per kg body weight per dose to about 10 milligram per kg body weight per dose, such as from about 4.6 milligram per kg body weight per dose to about 10 milligram per kg body weight per dose, for example from about 4.8 milligram per kg body weight per dose to about 10 milligram per kg body weight per dose, such as from about 5.0 milligram per kg body weight per dose to about 10 milligram per kg body weight per dose, for example from about 5.2 milligram per kg body weight per dose to about 10 milligram per kg body weight per dose, such as from about 5.4 milligram per kg body weight per dose to about 10 milligram per kg body weight per dose, for example from about 5.6 milligram per kg body weight per dose to about 10 milligram per kg body weight per dose, such as from about 5.8 milligram per kg body weight per dose to about 10 milligram per kg body weight per dose, for example from about 6.0 milligram per kg body weight per dose to about 10 milligram per kg body weight per dose, such as from about 6.2 milligram per kg body weight per dose to about 10 milligram per kg body weight per dose, for example from about 6.4 milligram per kg body weight per dose to about 10 milligram per kg body weight per dose, such as from about 6.6 milligram per kg body weight per dose to about 10 milligram per kg body weight per dose, for example from about 6.8 milligram per kg body weight per dose to about 10 milligram per kg body weight per dose, such as from about 7.0 milligram per kg body weight per dose to about 10 milligram per kg body weight per dose, for example from about 7.2 milligram per kg body weight per dose to about 10 milligram per kg body weight per dose, such as from about 7.4 milligram per kg body weight per dose to about 10 milligram per kg body weight per dose, for example from about 7.6 milligram per kg body weight per dose to about 10 milligram per kg body weight per dose, such as from about 7.8 milligram per kg body weight per dose to about 10 milligram per kg body weight per dose, for example from about 8.0 milligram per kg body weight per dose to about 10 milligram per kg body weight per dose, such as from about 0.2 milligram per kg body weight per dose to about 8 milligram per kg body weight per dose, for example from about 0.3 milligram per kg body weight per dose to about 8 milligram per kg body weight per dose, such as from about 0.4 milligram per kg body weight per dose to about 8 milligram per kg body weight per dose, for example from about 0.5 milligram per kg body weight per dose to about 8 milligram per kg body weight per dose, such as from about 0.6 milligram per kg body weight per dose to about 8 milligram per kg body weight per dose, for example from about 0.7 milligram per kg body weight per dose to about 8 milligram per kg body weight per dose, such as from about 0.8 milligram per kg body weight per dose to about 8 milligram per kg body weight per dose, for example from about 0.9 milligram per kg body weight per dose to about 8 milligram per kg body weight per dose, such as from about 1.0 milligram per kg body weight per dose to about 8 milligram per kg body weight per dose, for example from about 1.2 milligram per kg body weight per dose to about 8 milligram per kg body weight per dose, such as from about 1.4 milligram per kg body weight per dose to about 8 milligram per kg body weight per dose, for example from about 1.6 milligram per kg body weight per dose to about 8 milligram per kg body weight per dose, such as from about 1.8 milligram per kg body weight per dose to about 8 milligram per kg body weight per dose, for example from about 2.0 milligram per kg body weight per dose to about 8 milligram per kg body weight per dose, such as from about 2.2 milligram per kg body weight per dose to about 8 milligram per kg body weight per dose, for example from about 2.4 milligram per kg body weight per dose to about 8 milligram per kg body weight per dose, such as from about 2.6 milligram per kg body weight per dose to about 8 milligram per kg body weight per dose, for example from about 2.8 milligram per kg body weight per dose to about 8 milligram per kg body weight per dose, such as from about 3.0 milligram per kg body weight per dose to about 8 milligram per kg body weight per dose, for example from about 3.2 milligram per kg body weight per dose to about 8 milligram per kg body weight per dose, such as from about 3.4 milligram per kg body weight per dose to about 8 milligram per kg body weight per dose, for example from about 3.6 milligram per kg body weight per dose to about 8 milligram per kg body weight per dose, such as from about 3.8 milligram per kg body weight per dose to about 8 milligram per kg body weight per dose, for example from about 4.0 milligram per kg body weight per dose to about 8 milligram per kg body weight per dose, such as from about 4.2 milligram per kg body weight per dose to about 8 milligram per kg body weight per dose, for example from about 4.4 milligram per kg body weight per dose to about 8 milligram per kg body weight per dose, such as from about 4.6 milligram per kg body weight per dose to about 8 milligram per kg body weight per dose, for example from about 4.8 milligram per kg body weight per dose to about 8 milligram per kg body weight per dose, such as from about 5.0 milligram per kg body weight per dose to about 8 milligram per kg body weight per dose, for example from about 5.2 milligram per kg body weight per dose to about 8 milligram per kg body weight per dose, such as from about 5.4 milligram per kg body weight per dose to about 8 milligram per kg body weight per dose, for example from about 5.6 milligram per kg body weight per dose to about 8 milligram per kg body weight per dose, such as from about 5.8 milligram per kg body weight per dose to about 8 milligram per kg body weight per dose, for example from about 6.0 milligram per kg body weight per dose to about 8 milligram per kg body weight per dose, such as from about 0.2 milligram per kg body weight per dose to about 6 milligram per kg body weight per dose, for example from about 0.3 milligram per kg body weight per dose to about 6 milligram per kg body weight per dose, such as from about 0.4 milligram per kg body weight per dose to about 6 milligram per kg body weight per dose, for example from about 0.5 milligram per kg body weight per dose to about 6 milligram per kg body weight per dose, such as from about 0.6 milligram per kg body weight per dose to about 6 milligram per kg body weight per dose, for example from about 0.7 milligram per kg body weight per dose to about 6 milligram per kg body weight per dose, such as from about 0.8 milligram per kg body weight per dose to about 6 milligram per kg body weight per dose, for example from about 0.9 milligram per kg body weight per dose to about 6 milligram per kg body weight per dose, such as from about 1.0 milligram per kg body weight per dose to about 6 milligram per kg body weight per dose, for example from about 1.2 milligram per kg body weight per dose to about 6 milligram per kg body weight per dose, such as from about 1.4 milligram per kg body weight per dose to about 6 milligram per kg body weight per dose, for example from about 1.6 milligram per kg body weight per dose to about 6 milligram per kg body weight per dose, such as from about 1.8 milligram per kg body weight per dose to about 6 milligram per kg body weight per dose, for example from about 2.0 milligram per kg body weight per dose to about 6 milligram per kg body weight per dose, such as from about 2.2 milligram per kg body weight per dose to about 6 milligram per kg body weight per dose, for example from about 2.4 milligram per kg body weight per dose to about 6 milligram per kg body weight per dose, such as from about 2.6 milligram per kg body weight per dose to about 6 milligram per kg body weight per dose, for example from about 2.8 milligram per kg body weight per dose to about 6 milligram per kg body weight per dose, such as from about 3.0 milligram per kg body weight per dose to about 6 milligram per kg body weight per dose, for example from about 3.2 milligram per kg body weight per dose to about 6 milligram per kg body weight per dose, such as from about 3.4 milligram per kg body weight per dose to about 6 milligram per kg body weight per dose, for example from about 3.6 milligram per kg body weight per dose to about 6 milligram per kg body weight per dose, such as from about 3.8 milligram per kg body weight per dose to about 6 milligram per kg body weight per dose, for example from about 4.0 milligram per kg body weight per dose to about 6 milligram per kg body weight per dose, such as from about 4.2 milligram per kg body weight per dose to about 6 milligram per kg body weight per dose, for example from about 4.4 milligram per kg body weight per dose to about 6 milligram per kg body weight per dose, such as from about 4.6 milligram per kg body weight per dose to about 6 milligram per kg body weight per dose, for example from about 4.8 milligram per kg body weight per dose to about 6 milligram per kg body weight per dose, such as from about 5.0 milligram per kg body weight per dose to about 6 milligram per kg body weight per dose.

A dose or dosage may be given as a single dose or in divided doses. A single dose occurs only once, with the drug administered either as a bolus or by continuous infusion. Alternatively, the dose may be divided into multiple doses and given recurrently, such as twice (two times), for example three times, such as four times, for example five times, such as six times, for example seven times, such as eight times, for example nine times, such as ten divided doses. Furthermore, the dose may be given repeatedly, i.e. more than once, such as twice (two times), for example three times, such as four times, for example five times, such as six times, for example seven times, such as eight times, for example nine times, such as ten times a day. Alternatively, the dose may be in sustained release form. A bolus is in theory regarded as given immediately, and should be administered in less than 5 minutes.

It follows that the drug may be given once or more daily, or alternatively may be given with intervals of 1 day, such as 2 days, for example 3 days, such as 4 days, such as 5 days, for example 6 days, such as 7 days (1 week), for example 8 days, such as 9 days, such as 10 days, for example 11 days, such as 12 days, for example 13 days, such as 14 days (2 weeks), such as 3 weeks, for example 4 weeks, such as 5 weeks, for example 6 weeks, such as 7 weeks, such as 8 weeks, for example 12 weeks.

When the dose is given as a continuous infusion, the dose may be expressed as milligram per kilo body weight per dosage, wherein the dosage is given over a prolonged period, such as an hour (expressed as mg/kg/hr). The doses according to the present invention may be infused over 15 minutes to 24 hours, such as 15 to 30 minutes, for example 30 to 60 minutes, such as 60 to 90 minutes, for example 90 to 120 minutes, such as 2 hour to 3 hours, for example 3 hour to 4 hours, such as 4 hour to 5 hours, for example 5 hours to 6 hours, such as 6 hours to 7 hours, for example 7 hours to 8 hours, such as 8 hours to 9 hours, for example 9 hours to 10 hours, such as 10 hours to 11 hours, for example 11 hours to 12 hours, such as 12 hours to 14 hours, for example 14 hours to 16 hours, such as 16 hours to 18 hours, for example 18 hours to 20 hours, such as 20 hours to 22 hours, for example 22 hours to 24 hours.

Drugs may also be given in combination at the doses and intervals cited above. Therefore, the diseased unit may receive at least 2 drugs each at the cited doses and intervals cited above, such as 3 drugs, for example 4 drugs, such as 5 drugs, for example 6 drugs, such as 7 drugs, for example 8 drugs, such as 9 drugs, for example 10 drugs, such as 11 drugs, for example 12 drugs, such as 13 drugs, for example 14 drugs, such as 15 drugs, for example 16 drugs, such as 17 drugs, for example 18 drugs, such as 19 drugs, for example 20 drugs, such as 25 drugs, for example 30 drugs each at the cited doses and intervals cited above.

The unit being treated with the drugs may continue using a subset of the combination of drugs according to the progression of the disease state.

Examples of Diseases According to the Present Invention

The one or more diseases that may be diagnosed and/or treated according to the present invention comprises the following:

A. Cancer
B. Infection
C. Immunodeficiencies
D. Transplantation and related diseases These are described in detail herein below.

A) Cancer

In one embodiment the present invention relates to diagnosis and/or treatment of a cancer associated with one or more tumor suppressor genes and/or cancer antigens, such as the tumor suppressor genes and the cancer antigens listed in Table I to Table O.

TABLE I

Tumor suppressor genes and related cancers

| Tumor Suppressor | Function | Cancer |
| --- | --- | --- |
| APC | Controls the function of specific transcription factors | Familial adenomatous and noninherited colorectal carcinomas |
| BRCA1, 2 | DNA damage repair | Inherited breast cancers; ovarian cancers |
| CDKN2A | Gene locus that encodes p16 and p14ARF | Brain tumors |
| DCC | Function is still unknown | Colorectal carcinomas |
| DPC4 (SMAD4) | Mediates signaling from growth factor receptors | Colorectal tumors, pancreatic neoplasia |

TABLE I-continued

Tumor suppressor genes and related cancers

| Tumor Suppressor | Function | Cancer |
|---|---|---|
| MADR2/JV18 (SMAD2) | Mediates signaling from growth factor receptors | Colorectal cancer |
| MEN1 | Codes for the menin protein that interacts with trascription factors and prevents transcription of certain genes | Multiple endocrine neoplasia type 1 |
| MTS1 | Inhibitor of cyclin-dependent kinases | Melanomas |
| NF1 | RAS GTPase activating protein | Neurofibromatosis type 1 |
| NF2 | RAS GTPase activating protein | Neurofibromatosis type 2 |
| p53 | Encodes a transcription factor for p21 that arrests the cell cycle in G1 phase | Bladder, breast, colorectal, esophageal, liver, lung, prostate, and ovarian carcinomas; brain tumors, sarcomas, lymphomas, and leukemias |
| PTEN | Lipid phosphatase that regulates cell survival | Cowden syndrome; increased risk of breast and thyroid cancer |
| Rb | Alters activity of certain transcription factors that play a role in the control cell division | Retinoblastoma, sarcomas; bladder, breast, esophageal, prostate, and lung carcinomas |
| VHL | May target proteins for degradation | Renal cell carcinomas |
| WRN | Involved in DNA repair | Werner syndrome |
| WT1 | Transcriptional repressor | Wilms tumors (pediatric kidney cancer) |

TABLE J

Cancer related genes

| Inherited cancer | Abnormal gene | Other non-inherited cancers seen with this gene |
|---|---|---|
| Retinoblastoma | RBI | Many different cancers |
| Li-Fraumeni Syndrome sarcomas, | P53 | Many different cancers |
| Melanoma | INK4a | Many different cancers |
| Colorectal cancer (due to familial polyposis) | APC | Most colorectal cancers |
| Colorectal cancer (without polyposis) | MLH1, MSH2, or MSH6 | Colorectal, gastric, endometrial cancers |
| Breast and/or ovarian | BRCA1, BRCA2 | Only rare ovarian cancers |
| Wilms Tumor | WTI | Wilms tumors |
| Nerve tumors, including brain | NF1, NF2 | Small numbers of colon cancers, melanomas, neuroblastoma |
| Kidney cancer | VHL | Certain types of kidney cancers |

TABLE K

Tumor suppressor genes
Tumor suppressor genes

101F6, ABR, ADPRTL3, ANP32C, ANP32D, APC2, APC, ARF, ARHGAP8, ARHI, AT1G14320, ATM, ATP8A2, AXUD1, BAP1, BECN1, BIN1, BRCA1, BRCA2, BTG1, BTG2, C1orf11, C5orf4, C5orf7, Cables, CACNA2D2, CAP-1, CARS, CAV1, CD81, CDC23, CDK2AP1, CDKN1A, CDKN1C, CDKN2A, CDKN2B, CDKN2X, Ciao1-pending, CLCA2, CREBL2, CTNNA1, CUL2, CW17R, DAB2, DAF-18, D-APC, DBC2, DCC, DDX26, DEC1, DLC1, DLEC1, DLEU1, DLEU2, DLG1, DLGH1, DLGH3, DMBT1, DNAJA3, DOC-1, DPC4, DPH2L, EGR1, FABP3, FAT, FGL1, FHIT, FLJ10506, FOXD1, FOXP1, FT, FUS1, FUS2, GAK, GAS1, GAS11, GLD-1, GLTSCR1, GLTSCR2, GRC5, GRLF1, HDAC3, HEMK, HIC1, HRG22, HSAL2, HTS1, HYAL1, HYAL2, IFGBP7, IGSF4, ING1, ING1L, ING4, I(2)tid, I(3)mbn, I(3)mbt, LAPSER1, LATS1, LATS2, LDOC1, LOH11CR2A, LRP1B, LUCA3, MAD, MAP2K4, MAPKAPK3, MCC, MDC, MEN1, ML-1, MLH1, MRVI1, MTAP, MXI1, NAP1L4, NBR2, NF1, NF2, NORE1, NPR2L, NtRb1, OVCA2, PDGFRL, PHEMX, pHyde, PIG8, PIK3CG, PINX1, PLAGL1, PRDM2, PTCH, PTEN, PTPNI3, PTPRG, RASSF1, RB1, RBBP7, RBX1, RBM6, RECK, RFP2, RIS1, TABLE K-continued Tumor suppressor genes
Tumor suppressor genes RPL10, RPS29, RRM1, S100A2, SEMA3B, SF1, SFRP1, SLC22A1L, SLC26A3,
SMARCA4, ST7, ST7L, ST13, ST14, STIM1, TCEB2, THW, TIMP3, TP53, TP63, TRIM8,
TSC2, TSG101, TSSC1, TSSC3, TSSC4, VHL, Vhlh, WFDC1, WIT-1, WT1, WWOX

TABLE L

DNA-Tumor Suppressor and Oncogene

| Symbol | Description |
|---|---|
| ABL1 | v-abl Abelson murine leukemia viral oncogene homolog 1 |
| ABL2 | v-abl Abelson murine leukemia viral oncogene homolog 2 (arg, Abelson-related gene) |
| AKT1 | v-akt murine thymoma viral oncogene homolog 1 |
| AKT2 | v-akt murine thymoma viral oncogene homolog 2 |
| APC | adenomatosis polyposis coli |
| ARAF1 | v-raf murine sarcoma 3611 viral oncogene homolog 1 |
| ARHA | ras homolog gene family, member A |
| ARHB | ras homolog gene family, member B |
| ARHC | ras homolog gene family, member C |
| AXL | AXL receptor tyrosine kinase |
| BCL2 | B-cell CLL/lymphoma 2 |
| BCL3 | B-cell CLL/lymphoma 3 |
| BCR | breakpoint cluster region |
| BLYM | avian lymphoma virus-derived transforming sequence |
| BMI1 | murine leukemia viral (bmi-1) oncogene homolog |
| BRAF | v-raf murine sarcoma viral oncogene homolog B1 |
| BRCA1 | breast cancer 1, early onset |
| BRCA2 | breast cancer 2, early onset |
| CBL | Cas-Br-M (murine) ecotropic retroviral transforming sequence |
| CCND1 | cyclin D1 (PRAD1: parathyroid adenomatosis 1) |
| CDH1 | cadherin 1, E-cadherin (epithelial) |
| CDK4 | cyclin-dependent kinase 4 |
| CDKN1A | cyclin-dependent kinase inhibitor 1A (p21, Cip1) |
| CDKN1C | cyclin-dependent kinase inhibitor 1C (p57, Kip2) |
| CDKN2A | cyclin-dependent kinase inhibitor 2A (melanoma, p16, inhibits CDK4) |
| CDKN2B | cyclin-dependent kinase inhibitor 2B (p15, inhibits CDK4) |
| CHES1 | checkpoint suppressor 1 |
| COT | cot (cancer Osaka thyroid) oncogene |
| CRK | v-crk avian sarcoma virus CT10 oncogene homolog |
| CRKL | v-crk avian sarcoma virus CT10 oncogene homolog-like |
| CSF1R | colony stimulating factor 1 receptor, formerly McDonough feline sarcoma viral (v-fms) oncogene homolog |
| D10S170 | DNA segment, single copy, probe pH 4 (transforming sequence, thyroid-1, |
| DCC | deleted in colorectal carcinoma |
| DDX6 | DEAD/H (Asp-Glu-Ala-Asp/His) box polypeptide 6 (RNA helicase, 54 kD) |
| E2F1 | E2F transcription factor 1 |
| EGFR | epidermal growth factor receptor (avian erythroblastic leukemia viral (v-erb-b) oncogene homolog) |
| EIF3S6 | eukaryotic translation initiation factor 3, subunit 6 (48 kD) |
| ELE1 | RET-activating gene ELE1 |
| ELK1 | ELK1, member of ETS oncogene family |
| ELK3 | ELK3, ETS-domain protein (SRF accessory protein 2) NOTE: Symbol and name provisional. |
| EMP1 | epithelial membrane protein 1 |
| EMS1 | ems1 sequence (mammary tumor and squamous cell carcinoma-associated (p80/85 src substrate) |
| EPHA1 | EphA1 |
| EPHA3 | EphA3 |
| ERBAL2 | v-erb-a avian erythroblastic leukemia viral oncogene homolog-like 2 |
| ERBB2 | v-erb-b2 avian erythroblastic leukemia viral oncogene homolog 2 (neuro/glioblastoma derived oncogene homolog) |
| ERBB3 | v-erb-b2 avian erythroblastic leukemia viral oncogene homolog 3 |
| ERBB4 | v-erb-a avian erythroblastic leukemia viral oncogene homolog-like 4 |
| ERG | v-ets avian erythroblastosis virus E26 oncogene related |
| ETS1 | v-ets avian erythroblastosis virus E26 oncogene homolog 1 |
| ETS2 | v-ets avian erythroblastosis virus E26 oncogene homolog 2 |
| ETV3 | ets variant gene 3 |
| ETV6 | ets variant gene 6 (TEL oncogene) |
| EVI1 | ecotropic viral integration site 1 |
| EWSR1 | Ewing sarcoma breakpoint region 1 |
| FAT | FAT tumor suppressor (*Drosophila*) homolog |
| FER | fer (fps/fes related) tyrosine kinase (phosphoprotein NCP94) |

TABLE L-continued

DNA-Tumor Suppressor and Oncogene

| Symbol | Description |
|---|---|
| FES | feline sarcoma (Snyder-Theilen) viral (v-fes)/Fujinami avian sarcoma (PRCII) viral (v-fps) oncogene homolog |
| FGF3 | fibroblast growth factor 3 (murine mammary tumor virus integration site (v-int-2) oncogene homolog) |
| FGF4 | fibroblast growth factor 4 (heparin secretory transforming protein 1, Kaposi sarcoma oncogene) |
| FGF6 | fibroblast growth factor 6 |
| FGR | Gardner-Rasheed feline sarcoma viral (v-fgr) oncogene homolog |
| FKHL1 | forkhead (*Drosophila*)-like 1 |
| FLI1 | Friend leukemia virus integration 1 |
| FLT1 | fms-related tyrosine kinase 1 (vascular endothelial growth factor/vascular permeability factor receptor) |
| FOS | v-fos FBJ murine osteosarcoma viral oncogene homolog |
| FOSL1 | FOS-like antigen-1 |
| FOSL2 | FOS-like antigen 2 |
| FYN | FYN oncogene related to SRC, FGR, YES |
| GLI | glioma-associated oncogene homolog (zinc finger protein) |
| GLI2 | GLI-Kruppel family member GLI2 |
| GLI3 | GLI-Kruppel family member GLI3 (Greig cephalopolysyndactyly syndrome) |
| GRO1 | GRO1 oncogene (melanoma growth stimulating activity, alpha) |
| GRO2 | GRO2 oncogene |
| GRO3 | GRO3 oncogene |
| HCK | Hemopoietic cell kinase |
| HKR3 | GLI-Kruppel family member HKR3 |
| HRAS | v-Ha-ras Harvey rat sarcoma viral oncogene homolog |
| IRF4 | interferon regulatory factor 4 |
| JUN | v-jun avian sarcoma virus 17 oncogene homolog |
| JUNB | jun B proto-oncogene |
| JUND | jun D proto-oncogene |
| KAI1 | kangai 1 (suppression of tumorigenicity 6, prostate; CD82 antigen (R2 leukocyte antigen, antigen detected by monoclonal and antibody IA4)) |
| KIT | v-kit Hardy-Zuckerman 4 feline sarcoma viral oncogene homolog |
| KRAS2 | v-Ki-ras2 Kirsten rat sarcoma 2 viral oncogene homolog |
| LCK | lymphocyte-specific protein tyrosine kinase |
| LTA | Lymphotoxin alpha (TNF superfamily, member 1) |
| LTB | Lymphotoxin beta (TNF superfamily, member 3) |
| LYN | v-yes-1 Yamaguchi sarcoma viral related oncogene homolog |
| M1S1 | membrane component, chromosome 1, surface marker 1 (40 kD glycoprotein, identified by monoclonal antibody GA733) |
| M4S1 | membrane component, chromosomal 4, surface marker (35 kD glycoprotein) |
| MADH4 | MAD (mothers against decapentaplegic, *Drosophila*) homolog 4 |
| MAF | v-maf musculoaponeurotic fibrosarcoma (avian) oncogene homolog |
| MAFG | v-maf musculoaponeurotic fibrosarcoma (avian) oncogene family, protein G |
| MAS1 | MAS1 oncogene |
| MAX | MAX protein |
| MCC | mutated in colorectal cancers |
| MCF2 | MCF.2 cell line derived transforming sequence |
| MDM2 | mouse double minute 2, human homolog of; p53-binding protein |
| MEL | mel transforming oncogene (derived from cell line NK14)-RAB8 homolog |
| MEN1 | multiple endocrine neoplasia I |
| MET | met proto-oncogene (hepatocyte growth factor receptor) |
| MLH1 | mutL (*E. coli*) homolog 1 (colon cancer, nonpolyposis type 2) |
| MOS | v-mos Moloney murine sarcoma viral oncogene homolog |
| MPL | myeloproliferative leukemia virus oncogene |
| MSH2 | mutS (*E. coli*) homolog 2 (colon cancer, nonpolyposis type 1) |
| MYB | v-myb avian myeloblastosis viral oncogene homolog |
| MYBL1 | v-myb avian myeloblastosis viral oncogene homolog-like 1 |
| MYBL2 | v-myb avian myeloblastosis viral oncogene homolog-like 2 |
| MYC | v-myc avian myelocytomatosis viral oncogene homolog |
| MYCL1 | v-myc avian myelocytomatosis viral oncogene homolog 1, lung carcinoma derived |
| MYCN | v-myc avian myelocytomatosis viral related oncogene, neuroblastoma derived |
| NBL1 | neuroblastoma, suppression of tumorigenicity 1 |
| NF1 | neurofibromin 1 (neurofibromatosis, von Recklinghausen disease, Watson disease) |
| NF2 | neurofibromin 2 (bilateral acoustic neuroma) |
| NFKB2 | nuclear factor of kappa light polypeptide gene enhancer in B-cells 2 (p49/p100) |
| NKTR | natural killer-tumor recognition sequence |
| NOV | nephroblastoma overexpressed gene |
| NRAS | neuroblastoma RAS viral (v-ras) oncogene homolog |
| NTRK1 | Neurotrophic tyrosine kinase, receptor, type 1 |
| PACE | paired basic amino acid cleaving enzyme (furin, membrane associated receptor protein) |

TABLE L-continued

DNA-Tumor Suppressor and Oncogene

| Symbol | Description |
|---|---|
| PDGFB | platelet-derived growth factor beta polypeptide (simian sarcoma viral (v-sis) oncogene homolog) |
| PIM1 | pim-1 oncogene |
| PTCH | patched (*Drosophila*) homolog |
| PVT1 | pvt-1 (murine) oncogene homolog, MYC activator |
| RAF1 | v-raf-1 murine leukemia viral oncogene homolog 1 |
| RALA | v-ral simian leukemia viral oncogene homolog A (ras related) |
| RALB | v-ral simian leukemia viral oncogene homolog B (ras related; GTP binding protein) |
| RB1 | retinoblastoma 1 (including osteosarcoma) |
| REL | v-rel avian reticuloendotheliosis viral oncogene homolog |
| RET | ret proto-oncogene (multiple endocrine neoplasia MEN2A, MEN2B and medullary thyroid carcinoma 1, Hirschsprung disease) |
| ROS1 | v-ros avian UR2 sarcoma virus oncogene homolog 1 |
| SKI | v-ski avian sarcoma viral oncogene homolog |
| SMARCB1 | SWI/SNF related, matrix associated, actin dependent regulator of chromatin, subfamily b, member 1 |
| SPI1 | spleen focus forming virus (SFFV) proviral integration oncogene spi1 |
| SPINK1 | serine protease inhibitor, Kazal type 1 |
| SRC | v-src avian sarcoma (Schmidt-Ruppin A-2) viral oncogene homolog |
| ST5 | Suppression of tumorigenicity 5 |
| SUPT3H | suppressor of Ty (*S. cerevisiae*) 3 homolog |
| SUPT5H | suppressor of Ty (*S. cerevisiae*) 5 homolog |
| SUPT6H | suppressor of Ty (*S. cerevisiae*) 6 homolog |
| TAL1 | T-cell acute lymphocytic leukemia 1 |
| TGFBR2 | Transforming growth factor, beta receptor II (70-80 kD) |
| THPO | thrombopoietin (myeloproliferative leukemia virus oncogene ligand, megakaryocyte growth and development factor) |
| THRA | thyroid hormone receptor, alpha (avian erythroblastic leukemia viral (v-erb-a) oncogene homolog) |
| THRB | thyroid hormone receptor, beta (avian erythroblastic leukemia viral (v-erb-a) oncogene homolog 2) |
| TIAM1 | T-cell lymphoma invasion and metastasis 1 |
| TIM | Oncogene TIM |
| TM4SF1 | transmembrane 4 superfamily member 1 |
| TNF | tumor necrosis factor (TNF superfamily, member 2) |
| TP53 | tumor protein p53 (Li-Fraumeni syndrome) |
| TP53BP2 | tumor protein p53-binding protein, 2 |
| TP73 | tumor protein p73 |
| VAV1 | vav 1 oncogene |
| VAV2 | vav 2 oncogene |
| VHL | von Hippel-Lindau syndrome |
| WNT1 | wingless-type MMTV integration site family, member 1 |
| WNT2 | wingless-type MMTV integration site family member 2 |
| WNT5A | wingless-type MMTV integration site family, member 5A |
| WT1 | Wilms tumor 1 |
| YES1 | v-yes-1 Yamaguchi sarcoma viral oncogene homolog 1 |

TABLE M

Breast cancer oncogenes
Locus

MEL, merlin, met, MOS, myb, MYC, BMYC, LMYC, NMYC, ERBB2, NM23, NRAS, TP53, p73, pbx1, PDGFR, pdgfra, pdgfrb, pim1, pinF1, pinF2, pkC gamma, PML, PRL, Polyoma Middle, T rab4, RAF, rar, Ras family; H-, K-, & N-, RB1, RD, rebB, REL, RET, RIG, ROS, Rsr1, SEA, SIS, SKI, spi1, SRC, TAL, tcl1, TCL2, tcl5, TCRA, TCRB, TGFbeta, thy1, Tlim, Tpl1, tpl2, tpr, TRK, TSG101, TTG1, Urokinase, VHL, WNT, WNT-1, wt1, YES

TABLE N

Tumor antigens resulting from mutations

| Gene/ protein | Tumor | HLA[a] | HLA Frequency[b] (%) | Peptide[c] | Position | Lymphocyte Stimulation Method |
|---|---|---|---|---|---|---|
| Alpha-actinin-4 | lung carcinoma | A2 | 44 | FIASNGVKLV (SEQ ID NO 11) | 118-127 | autologous tumor cells |

TABLE N-continued

Tumor antigens resulting from mutations

| Gene/ protein | Tumor | HLA[a] | HLA Frequency[b] (%) | Peptide[c] | Position | Lymphocyte Stimulation Method |
|---|---|---|---|---|---|---|
| ARTC1 | melanoma | DR1 | 18 | YSVYFNLPADT IYTN[h] (SEQ ID NO 12) | | autologous tumor cells |
| BCR-ABL fusion protein (b3a2) | chronic myeloid leukemia | A2 | 44 | SSKALQRPV (SEQ ID NO 13) | 926-934 | Peptide |
| | | B8 | 14 | GFKQSSKAL (SEQ ID NO 14) | 922-930 | Peptide |
| | | DR4 | 24 | ATGFKQSSKAL QRPVAS (SEQ ID NO 15) | 920-936 | Peptide |
| | | DR9 | 3 | ATGFKQSSKAL QRPVAS (SEQ ID NO 16) | 920-936 | Peptide |
| B-RAF | melanoma | DR4 | 24 | EDLTVKIGDFG LATEKSRWSG SHQFEQLS (SEQ ID NO 17) | 586-614 | Peptide |
| CASP-5 | colorectal, gastric, and endometrial carcinoma | A2 | 44 | FLIIWQNTM[g] (SEQ ID NO 18) | 67-75 | Peptide |
| CASP-8 | head and neck squamous cell carcinoma | B35 | 20 | FPSDSWCYF (SEQ ID NO 19) | 476-484 | autologous tumor cells |
| beta-catenin | melanoma | A24 | 20 | SYLDSGIHF (SEQ ID NO 20) | 29-37 | autologous tumor cells |
| Cdc27 | melanoma | DR4 | 24 | FSWAMDLDPK GA[e] (SEQ ID NO 21) | 760-771 | autologous tumor cells |
| CDK4 | melanoma | A2 | 44 | ACDPHSGHFV (SEQ ID NO 22) | 23-32 | autologous tumor cells |
| CDKN2A | melanoma | A11 | 13 | AVCPWTWLR[g] (SEQ ID NO 23) | 125-133 (p14ARF-ORF3) 111-119 (p16INK4a-ORF3) | autologous tumor cells |
| COA-1 | colorectal carcinoma | DR4 | 24 | TLYQDDTLTL QAAG[e] (SEQ ID NO 24) | 371-384 | autologous tumor cells |
| | | DR13 | 19 | TLYQDDTLTL QAAG[e] (SEQ ID NO 25) | 371-384 | autologous tumor cells |
| dek-can fusion protein | myeloid leukemia | DR53 | 49 | TMKQICKKEIR RLHQY (SEQ ID NO 26) | 342-357 | Peptide |
| EFTUD2 | melanoma | A3 | 22 | KILDAVVAQK (SEQ ID NO 27) | 668-677 | autologous tumor cells |
| Elongation factor 2 | lung squamous CC | A68 | 8 | ETVSEQSNV (SEQ ID NO 28) | 581-589 | autologous tumor cells |

TABLE N-continued

Tumor antigens resulting from mutations

| Gene/protein | Tumor | HLA[a] | HLA Frequency[b] (%) | Peptide[c] | Position | Lymphocyte Stimulation Method |
|---|---|---|---|---|---|---|
| ETV6-AML1 fusion protein | acute lymphoblastic leukemia | A2 | 44 | RIAECILGM (SEQ ID NO 29) | 334-342 | Peptide |
| | | DP5 | 3 | IGRIAECILGMNPSR (SEQ ID NO 30) | 332-346 | Peptide |
| | | DP17 | 1 | IGRIAECILGMNPSR (SEQ ID NO 31) | 332-346 | Peptide |
| FLT3-ITD | acute myelogenous leukemia | A1 | 26 | YVDFREYEYY (SEQ ID NO 32) | 591-600 | Peptide |
| FN1 | melanoma | DR2 | 25 | MIFEKHGFRRTTPP (SEQ ID NO 33) | 2050-2063 | autologous tumor cells |
| GPNMB | melanoma | A3 | 22 | TLDWLLQTPK (SEQ ID NO 34) | 179-188 | autologous tumor cells |
| LDLR-fucosyltransferaseAS fusion protein | melanoma | DR1 | 18 | WRRAPAPGA (SEQ ID NO 35) | 315-323 | autologous tumor cells |
| | | DR1 | 18 | PVTWRRAPA (SEQ ID NO 36) | 312-320 | autologous tumor cells |
| HLA-A2[d] | renal cell carcinoma | | | | | autologous tumor cells |
| HLA-A11[d] | melanoma | | | | | autologous tumor cells |
| hsp70-2 | renal cell carcinoma | A2 | 44 | SLFEGIDIYT (SEQ ID NO 37) | 286-295 | autologous tumor cells |
| KIAA0205 | bladder tumor | B44 | 21 | AEPINIQTW (SEQ ID NO 38) | 262-270 | autologous tumor cells |
| MART2 | melanoma | A1 | 26 | FLEGNEVGKTY (SEQ ID NO 39) | 446-455 | autologous tumor cells |
| ME1 | non-small cell lung carcinoma | A2 | 44 | FLDEFMEGV (SEQ ID NO 40) | 224-232 | autologous tumor cells |
| MUM-1[f] | melanoma | B44 | 21 | EEKLIVVLF (SEQ ID NO 41) | 30-38 | autologous tumor cells |
| MUM-2 | melanoma | B44 | 21 | SELFRSGLDSY (SEQ ID NO 42) | 123-133 | autologous tumor cells |
| | | Cw6 | 18 | FRSGLDSYV (SEQ ID NO 43) | 126-134 | autologous tumor cells |
| MUM-3 | melanoma | A68 | 8 | EAFIQPITR (SEQ ID NO 44) | 322-330 | autologous tumor cells |
| neo-PAP | melanoma | DR7 | 25 | RVIKNSIRLTL[e] (SEQ ID NO 45) | 724-734 | autologous tumor cells |
| Myosin class I | melanoma | A3 | 22 | KINKNPKYK (SEQ ID NO 46) | 911-919 | expansion of TIL with IL-2 |
| NFYC | lung squamous cell carcinoma | B52 | 5 | QQITKTEV (SEQ ID NO 47) | 275-282 | autologous tumor cells |
| OGT | colorectal carcinoma | A2 | 44 | SLYKFSPFPL[g] (SEQ ID NO 48) | 28-37 | Peptide |

TABLE N-continued

Tumor antigens resulting from mutations

| Gene/protein | Tumor | HLA[a] | HLA Frequency[b] (%) | Peptide[c] | Position | Lymphocyte Stimulation Method |
|---|---|---|---|---|---|---|
| OS-9 | melanoma | B44 | 21 | KELEGILLL (SEQ ID NO 49) | 438-446 | autologous tumor cells |
| P53 | head and neck squamous cell carcinoma | A2 | 44 | VVPCEPPEV (SEQ ID NO 50) | 217-225 | Peptide |
| pml-RARalpha fusion protein | promyelocytic leukemia | DR11 | 25 | NSNHVASGAG EAAIETQSSSSE EIV (SEQ ID NO 51) |  | Peptide |
| PRDX5 | melanoma | A2 | 44 | LLLDDLLVSI (SEQ ID NO 52) | 163-172 | Peptide |
| PTPRK | melanoma | DR10 | 3 | PYYFAAELPPR NLPEP (SEQ ID NO 53) | 667-682 | autologous tumor cells |
| K-ras | pancreatic adenocarcinoma | B35 | 20 | VVVGAVGVG (SEQ ID NO 54) | 7-15 | Peptide |
| N-ras | melanoma | A1 | 26 | ILDTAGREEY (SEQ ID NO 55) | 55-64 | autologous tumor cells |
| RBAF600 | melanoma | B7 | 17 | RPHVPESAF (SEQ ID NO 56) | 329-337 | autologous tumor cells |
| SIRT2 | melanoma | A3 | 22 | KIFSEVTLK (SEQ ID NO 57) | 192-200 | autologous tumor cells |
| SNRPD1 | melanoma | B38 | 5 | SHETVIIEL (SEQ ID NO 58) | 11-19 | autologous tumor cells |
| SYT-SSX1 or -SSX2 fusion protein | sarcoma | B7 | 17 | QRPYGYDQIM (SEQ ID NO 59) | 402-410 (SYT) 111-112 (SSX2) | Peptide |
| Triosephosphate Isomerase | melanoma | DR1 | 18 | GELIGILNAAK VPAD (SEQ ID NO 60) | 23-37 | autologous tumor cells |

TABLE O

Shared tumor-specific antigens

| Gene | HLA[a] | HLA Frequency[b] (%) | Peptide | Position | Lymphocyte Stimulation Method |
|---|---|---|---|---|---|
| BAGE-1 | Cw16 | 7 | AARAVFLAL (SEQ ID NO 61) | 2-10 | autologous tumor cells |
| GAGE-1, 2, 8 | Cw6 | 18 | YRPRPRRY (SEQ ID NO 62) | 9-16 | autologous tumor cells |
| GAGE-3, 4, 5, 6, 7 | A29 | 6 | YYWPRPRRY (SEQ ID NO 63) | 10-18 | autologous tumor cells |
| GnTV[f] | A2 | 44 | VLPDVFIRC(V) (SEQ ID NO 64) | intron | autologous tumor cells |
| HERV-K-MEL | A2 | 44 | MLAVISCAV (SEQ ID NO 65) | 1-9 | autologous tumor cells |
| KK-LC-1 | B15 | 13 | RQKRILVNL (SEQ ID NO 66) | 76-84 | autologous tumor cells |

TABLE O-continued

Shared tumor-specific antigens

| Gene | HLA[a] | HLA Frequency[b] (%) | Peptide | Position | Lymphocyte Stimulation Method |
|---|---|---|---|---|---|
| KM-HN-1 | A24 | 20 | NYNNFYRFL (SEQ ID NO 67) | 196-204 | Peptide |
|  | A24 | 20 | EYSKECLKEF (SEQ ID NO 68) | 499-508 | Peptide |
|  | A24 | 20 | EYLSLSDKI (SEQ ID NO 69) | 770-778 | Peptide |
| LAGE-1 | A2 | 44 | MLMAQEALAFL (SEQ ID NO 70) | ORF2 (1-11) | autologous tumor cells |
|  | A2 | 44 | SLLMWITQC (SEQ ID NO 71) | 157-165 | Peptide |
|  | A31 | 5 | LAAQERRVPR (SEQ ID NO 72) | ORF2 (18-27) | autologous tumor cells |
|  | A68 | 8 | ELVRRILSR (SEQ ID NO 73) | 103-111 | adenovirus-dendritic cells |
|  | B7 | 17 | APRGVRMAV (SEQ ID NO 74) | ORF2 (46-54) | adenovirus-APC |
|  | DP4 | 75 | SLLMWITQCFLPVF (SEQ ID NO 75) | 157-170 | Peptide |
|  | DR3 | 21 | QGAMLAAQERRVPRAAEVPR (SEQ ID NO 76) | ORF2 (14-33) | Protein |
|  | DR4 | 24 | AADHRQLQLSISSCLQQL (SEQ ID NO 77) | 139-156 | Protein |
|  | DR11 | 25 | CLSRRPWKRSWSAGSCPGMPHL (SEQ ID NO 78) | ORF2 (81-102) | Peptide |
|  | DR12 | 5 | CLSRRPWKRSWSAGSCPGMPHL (SEQ ID NO 79) | ORF2 (81-102) | Peptide |
|  | DR13 | 19 | ILSRDAAPLPRPG (SEQ ID NO 80) | 108-120 | autologous tumor cells |
|  | DR15 | 20 | AGATGGRGPRGAGA (SEQ ID NO 81) | 37-50 | Protein |
| MAGE-A1 | A1 | 26 | EADPTGHSY (SEQ ID NO 82) | 161-169 | autologous tumor cells |
|  | A2 | 44 | KVLEYVIKV (SEQ ID NO 83) | 278-286 | Peptide |
|  | A3 | 22 | SLFRAVITK (SEQ ID NO 84) | 96-104 | poxvirus-dendritic cells[c] |
|  | A68 | 8 | EVYDGREHSA (SEQ ID NO 85) | 222-231 | poxvirus-dendritic cells |
|  | B7 | 17 | RVRFFFPSL (SEQ ID NO 86) | 289-298 | poxvirus-dendritic cells |
|  | B35 | 20 | EADPTGHSY (SEQ ID NO 87) | 161-169 | poxvirus-dendritic cells |
|  | B37 | 3 | REPVTKAEML (SEQ ID NO 88) | 127-136 | autologous tumor cells |

TABLE O-continued

Shared tumor-specific antigens

| Gene | HLA[a] | HLA Frequency[b] (%) | Peptide | Position | Lymphocyte Stimulation Method |
|---|---|---|---|---|---|
| | B53 | 2 | DPARYEFLW (SEQ ID NO 89) | 258-266 | poxvirus-dendritic cells |
| | B57 | 8 | ITKKVADLVGF (SEQ ID NO 90) | 102-112 | ALVAC-dendritic cells |
| | Cw2 | 10 | SAFPTTINF (SEQ ID NO 91) | 62-70 | poxvirus-dendritic cells |
| | Cw3 | 17 | SAYGEPRKL (SEQ ID NO 92) | 230-238 | poxvirus-dendritic cells |
| | Cw16 | 7 | SAYGEPRKL (SEQ ID NO 93) | 230-238 | autologous tumor cells |
| | DP4 | 75 | TSCILESLFRAVITK (SEQ ID NO 94) | 90-104 | Peptide |
| | DP4 | 75 | PRALAETSYVKVLEY (SEQ ID NO 95) | 268-282 | Peptide |
| | DR13 | 19 | LLKYRAREPVTKAE (SEQ ID NO 96) | 114-127 | Protein |
| | DR15 | 20 | EYVIKVSARVRF (SEQ ID NO 97) | 281-292 | Protein |
| MAGE-A2 | A2 | 44 | YLQLVFGIEV (SEQ ID NO 98) | 157-166 | Peptide |
| | A24 | 20 | EYLQLVFGI (SEQ ID NO 99) | 156-164 | Peptide |
| | B37 | 3 | REPVTKAEML (SEQ ID NO 100) | 127-136 | autologous tumor cells |
| | Cw7 | 41 | EGDCAPEEK (SEQ ID NO 101) | 212-220 | lentivirus-dendritic cells |
| | DR13 | 19 | LLKYRAREPVTKAE (SEQ ID NO 102) | 121-134 | Protein |
| MAGE-A3 | A1 | 26 | EVDPIGHLY (SEQ ID NO 103) | 168-176 | autologous tumor cells |
| | A2 | 44 | FLWGPRALV[d] (SEQ ID NO 104) | 271-279 | Peptide |
| | A2 | 44 | KVAELVHFL (SEQ ID NO 105) | 112-120 | Peptide |
| | A24 | 20 | TFPDLESEF (SEQ ID NO 106) | 97-105 | Peptide |
| | A24 | 20 | VAELVHFLL (SEQ ID NO 107) | 113-121 | Peptide |
| | B18 | 6 | MEVDPIGHLY (SEQ ID NO 108) | 167-176 | adeno-dendritic cells |
| | B35 | 20 | EVDPIGHLY (SEQ ID NO 109) | 168-176 | poxvirus-dendritic cells |
| | B37 | 3 | REPVTKAEML (SEQ ID NO 110) | 127-136 | autologous tumor cells |
| | B40 | 6 | AELVHFLLL[i] (SEQ ID NO 111) | 114-122 | adeno-dendritic cells |
| | B44 | 21 | MEVDPIGHLY (SEQ ID NO 112) | 167-176 | Peptide |

TABLE O-continued

Shared tumor-specific antigens

| Gene | HLA[a] | HLA Frequency[b] (%) | Peptide | Position | Lymphocyte Stimulation Method |
|---|---|---|---|---|---|
| | B52 | 5 | WQYFFPVIF (SEQ ID NO 113) | 143-151 | retrovirus-dendritic cells[h] |
| | Cw7 | 41 | EGDCAPEEK (SEQ ID NO 114) | 212-220 | lentivirus-dendritic cells |
| | DP4 | 75 | KKLLTQHFVQENYLEY (SEQ ID NO 115) | 243-258 | Protein |
| | DQ6 | 63 | KKLLTQHFVQENYLEY (SEQ ID NO 116) | 243-258 | Peptide |
| | DR1 | 18 | ACYEFLWGPRALVETS (SEQ ID NO 117) | 267-282 | Protein |
| | DR4 | 24 | VIFSKASSSLQL (SEQ ID NO 118) | 149-160 | Peptide |
| | DR7 | 25 | VIFSKASSSLQL (SEQ ID NO 119) | 149-160 | Peptide |
| | DR11 | 25 | GDNQIMPKAGLLIIV (SEQ ID NO 120) | 191-205 | Peptide |
| | DR11 | 25 | TSYVKVLHHMVKISG (SEQ ID NO 121) | 281-295 | Protein |
| | DR13 | 19 | AELVHFLLLKYRAR (SEQ ID NO 122) | 114-127 | Protein |
| | DR13 | 19 | LLKYRAREPVTKAE (SEQ ID NO 123) | 121-134 | Protein |
| MAGE-A4 | A1 | 26 | EVDPASNTY[j] (SEQ ID NO 124) | 169-177 | peptide after tetramer sorting |
| | A2 | 44 | GVYDGREHTV (SEQ ID NO 125) | 230-239 | adeno-dendritic cells |
| | A24 | 20 | NYKRCFPVI (SEQ ID NO 126) | 143-151 | Peptide |
| | B37 | 3 | SESLKMIF (SEQ ID NO 127) | 156-163 | poxvirus-dendritic cells |
| MAGE-A6 | A34 | 1 | MVKISGGPR (SEQ ID NO 128) | 290-298 | autologous tumor cells |
| | B35 | 20 | EVDPIGHVY (SEQ ID NO 129) | 168-176 | autologous tumor cells |
| | B37 | 3 | REPVTKAEML (SEQ ID NO 130) | 127-136 | autologous tumor cells |
| | Cw7 | 41 | EGDCAPEEK (SEQ ID NO 131) | 212-220 | lentivirus-dendritic cells |
| | Cw16 | 7 | ISGGPRISY (SEQ ID NO 132) | 293-301 | autologous tumor cells |
| | DR13 | 19 | LLKYRAREPVTKAE (SEQ ID NO 133) | 121-134 | Protein |
| MAGE-A9 | A2 | 44 | ALSVMGVYV (SEQ ID NO 134) | 223-231 | Peptide |
| MAGE-A10 | A2 | 44 | GLYDGMEHL (SEQ ID NO 135) | 254-262 | autologous tumor cells |

TABLE O-continued

Shared tumor-specific antigens

| Gene | HLA[a] | HLA Frequency[b] (%) | Peptide | Position | Lymphocyte Stimulation Method |
|---|---|---|---|---|---|
| | B53 | 2 | DPARYEFLW (SEQ ID NO 136) | 290-298 | poxvirus-dendritic cells |
| MAGE-A12 | A2[g] | 44 | FLWGPRALV[e] (SEQ ID NO 137) | 271-279 | Peptide |
| | Cw7 | 41 | VRIGHLYIL (SEQ ID NO 138) | 170-178 | autologous tumor cells |
| | Cw7 | 41 | EGDCAPEEK (SEQ ID NO 139) | 212-220 | lentivirus-dendritic cells |
| | DP4 | 75 | REPFTKAEMLGSVIR (SEQ ID NO 140) | 127-141 | Peptide |
| | DR13 | 19 | AELVHFLLLKYRAR (SEQ ID NO 141) | 114-127 | Protein |
| MAGE-C2 | A2 | 44 | LLFGLALIEV (SEQ ID NO 142) | 191-200 | autologous tumor cells |
| | A2 | 44 | ALKDVEERV (SEQ ID NO 143) | 336-344 | autologous tumor cells |
| | B44 | 21 | SESIKKKVL (SEQ ID NO 144) | 307-315 | autologous tumor cells |
| mucin[k] | | | PDTRPAPGSTAPPAHGVTSA (SEQ ID NO 145) | | transfected B cells |
| NA-88 | B13 | 6 | QGQHFLQKV (SEQ ID NO 146) | | autologous tumor cells |
| NY-ESO-1/ LAGE-2 | A2 | 44 | SLLMWITQC (SEQ ID NO 147) | 157-165 | autologous tumor cells |
| | A2 | 44 | MLMAQEALAFL (SEQ ID NO 148) | ORF2 (1-11) | autologous tumor cells |
| | A31 | 5 | ASGPGGGAPR (SEQ ID NO 149) | 53-62 | autologous tumor cells |
| | A31 | 5 | LAAQERRVPR (SEQ ID NO 150) | ORF2 (18-27) | autologous tumor cells |
| | B35 | 20 | MPFATPMEA (SEQ ID NO 151) | 94-102 | autologous tumor cells |
| | B51 | 12 | MPFATPMEA (SEQ ID NO 152) | 94-102 | adenovirus-APC |
| | Cw3 | 17 | LAMPFATPM (SEQ ID NO 153) | 92-100 | adenovirus-PBMC |
| | Cw6 | 18 | ARGPESRLL (SEQ ID NO 154) | 80-88 | adenovirus-PBMC[d] |
| | DP4 | 75 | SLLMWITQCFLPVF (SEQ ID NO 155) | 157-170 | Peptide |
| | DP4 | 75 | LLEFYLAMPFATPMEAELARRSLAQ (SEQ ID NO 156) | 87-111 | Peptide |
| | DR1 | 18 | LLEFYLAMPFATPMEAELARRSLAQ (SEQ ID NO 157) | 87-111 | Peptide |
| | DR1 | 18 | EFYLAMPFATPM (SEQ ID NO 158) | 89-100 | Protein |

TABLE O-continued

Shared tumor-specific antigens

| Gene | HLA[a] | HLA Frequency[b] (%) | Peptide | Position | Lymphocyte Stimulation Method |
|---|---|---|---|---|---|
| | DR2 | 25 | RLLEFYLAMPFA (SEQ ID NO 159) | 86-97 | Protein |
| | DR3 | 21 | QGAMLAAQERRVPRAAEVPR (SEQ ID NO 160) | ORF2 (14-33) | Protein |
| | DR4 | 24 | PGVLLKEFTVSGNILTIRLT (SEQ ID NO 161) | 119-138 | peptide and protein |
| | DR4 | 24 | VLLKEFTVSG (SEQ ID NO 162) | 121-130 | Peptide |
| | DR4 | 24 | AADHRQLQLSISSCLQQL (SEQ ID NO 163) | 139-156 | Protein |
| | DR4 | 24 | LLEFYLAMPFATPMEAELARRSLAQ (SEQ ID NO 164) | 87-111 | Peptide |
| | DR7 | 25 | PGVLLKEFTVSGNILTIRLTAADHR (SEQ ID NO 165) | 119-143 | Peptide |
| | DR7 | 25 | LLEFYLAMPFATPMEAELARRSLAQ (SEQ ID NO 166) | 87-111 | Peptide |
| | DR15 | 20 | AGATGGRGPRGAGA (SEQ ID NO 167) | 37-50 | protein |
| SAGE | A24 | 20 | LYATVIHDI (SEQ ID NO 168) | 715-723 | Peptide |
| Sp17 | A1 | 26 | ILDSSEEDK (SEQ ID NO 169) | 103-111 | Protein |
| SSX-2 | A2 | 44 | KASEKIFYV (SEQ ID NO 170) | 41-49 | autologous tumor cells |
| | DP1 | 14 | EKIQKAFDDIAKYFSK (SEQ ID NO 171) | 19-34 | Peptide |
| | DR3 | 21 | WEKMKASEKIFYVYMKRK (SEQ ID NO 172) | 37-54 | Peptide |
| | DR4 | 24 | KIFYVYMKRKYEAMT (SEQ ID NO 173) | 45-59 | Peptide |
| | DR11 | 25 | KIFYVYMKRKYEAM (SEQ ID NO 174) | 45-58 | Protein |
| SSX-4 | DP10 | 2 | INKTSGPKRGKHAWTHRLRE (SEQ ID NO 175) | 151-170 | Peptide |
| | DR3 | 21 | YFSKKEWEKMKSSEKIVYVY (SEQ ID NO 176) | 31-50 | Peptide |
| | DR8 | 4 | MKLNYEVMTKLGFKVTLPPF (SEQ ID NO 177) | 51-70 | Peptide |
| | DR8 | 4 | KHAWTHRLRERKQLVVYEEI (SEQ ID NO 178) | 161-180 | Peptide |

TABLE O-continued

Shared tumor-specific antigens

| Gene | HLA[a] | HLA Frequency[b] (%) | Peptide | Position | Lymphocyte Stimulation Method |
|---|---|---|---|---|---|
| | DR11 | 25 | LGFKVTLPPFMRSKRAADFH (179) | 61-80 | Peptide |
| | DR15 | 20 | KSSEKIVYVYMKLNYEVMTK (SEQ ID NO 180) | 41-60 | Peptide |
| | DR52 | 41 | KHAWTHRLRERKQLVVYEEI (SEQ ID NO 181) | 161-180 | Peptide |
| TRAG-3 | DR1 | 18 | CEFHACWPAFTVLGE (SEQ ID NO 182) | 34-48 | Peptide |
| | DR4 | 24 | CEFHACWPAFTVLGE (SEQ ID NO 183) | 34-48 | Peptide |
| | DR7 | 25 | CEFHACWPAFTVLGE (SEQ ID NO 184) | 34-48 | Peptide |
| TRP2-INT2[g] | A68 | 8 | EVISCKLIKR (SEQ ID NO 185) | intron 2 | autologous tumor cells |

In one preferred embodiment the present invention relates to diagnosis and/or treatment of cancer. The cancer can be any type of cancer including the types of cancer mentioned herein below and in the items. The treatment can be any kind of treatment including the treatments mentioned elsewhere herein or in the items or any combination thereof. The treatment can be ameliorating, symptomatic, curative or prophylactic. The treatment can result in relief one or more symptoms of the cancer including one or more of the cancer symptoms mentioned herein below. The cancer can be diagnosed by any method including the methods mentioned herein below.

Anal Cancer

Anal cancer is usually curable. The three major prognostic factors are site (anal canal vs. perianal skin), size (primary tumors <2 cm in size have better prognoses), and nodal status.

Anal cancer is an uncommon malignancy and accounts for only a small percentage (4%) of all cancers of the lower alimentary tract.

Overall, the risk of anal cancer is rising, with data suggesting that persons engaging in certain sexual practices, such as receptive anal intercourse, or persons with a high lifetime number of sexual partners are at increased risk of anal cancer. These practices may have led to an increase in the number of individuals at risk for infection with human papillomavirus (HPV); HPV infection is strongly associated with anal cancer development and may be a necessary step in its carcinogenesis.

Cellular Classification

Squamous cell (epidermoid) carcinomas make up the majority of all primary cancers of the anus. The important subset of cloacogenic (basaloid transitional cell) tumors constitutes the remainder. These two histologic variants are associated with human papillomavirus infection. Adenocarcinomas from anal glands or fistulae formation and melanomas are rare.

Stage Information

The anal canal extends from the rectum to the perianal skin and is lined by a mucous membrane that covers the internal sphincter. The following is a staging system for anal canal cancer that has been described by the American Joint Committee on Cancer (AJCC) and the International Union Against Cancer. Tumors of the anal margin (below the anal verge and involving the perianal hair-bearing skin) are classified with skin tumors.

TNM Definitions:
1) Primary Tumor (T)
   TX: Primary tumor cannot be assessed
   T0: No evidence of primary tumor
   Tis: Carcinoma in situ
   T1: Tumor 2 cm or less in greatest dimension
   T2: Tumor more than 2 cm but not more than 5 cm in greatest dimension
   T3: Tumor more than 5 cm in greatest dimension
   T4: Tumor of any size that invades adjacent organ(s), e.g., vagina, urethra, bladder*

[Note: *Direct invasion of the rectal wall, perirectal skin, subcutaneous tissue, or the sphincter muscle(s) is not classified as T4.]

2) Regional Lymph Nodes (N)
   NX: Regional lymph nodes cannot be assessed
   N0: No regional lymph node metastasis
   N1: Metastasis in perirectal lymph node(s)
   N2: Metastasis in unilateral internal iliac and/or inguinal lymph node(s)
   N3: Metastasis in perirectal and inguinal lymph nodes and/or bilateral internal iliac and/or inguinal lymph nodes 3) Distant Metastasis (M)
   MX: Distant metastasis cannot be assessed
   M0: No distant metastasis
   M1: Distant metastasis AJCC Stage Groupings:
Stage 0: Tis, N0, M0.
Stage I: T1, N0, M0.
Stage II: T2, N0, M0 and T3, N0, M0.
Stage IIIA: T1, N1, M0, T2, N1, M0, T3, N1, M0 and T4, N0, M0.
Stage IIIB: T4, N1, M0, Any T, N2, M0 and Any T, N3, M0.
Stage IV: Any T, any N, M1.

Treatment of Anal Cancer

Abdominoperineal resection leading to permanent colostomy was previously thought to be required for all but small anal cancers below the dentate line, with approximately 70% of patients surviving 5 or more years in single institutions, but such surgery is no longer the treatment of choice. Radiation therapy alone may lead to a 5-year survival rate in excess of 70%, though high doses ($\geq 60$ Gy) may yield necrosis or fibrosis. Chemotherapy concurrent with lower-dose radiation therapy as evidenced in the RTOG-8314 trial, for example, has a 5-year survival rate in excess of 70% with low levels of acute and chronic morbidity, and few patients require surgery for dermal or sphincter toxic effects. The optimal dose of radiation with concurrent chemotherapy to optimize local control and minimize sphincter toxic effects is under evaluation as evidenced in the RTOG-9208 trial, for example, but appears to be in the 45 Gy to 60 Gy range. Analysis of an intergroup trial that compared radiation therapy plus fluorouracil/mitomycin with radiation therapy plus fluorouracil alone in patients with anal cancer has shown improved results (lower colostomy rates and higher colostomy-free and disease-free survival) with the addition of mitomycin. Radiation with continuous infusion of fluorouracil plus cisplatin is also under evaluation as seen in the RTOG 9811 trial. Standard salvage therapy for those patients with either gross or microscopic residual disease following chemoradiation therapy has been abdominoperineal resection. Alternately, patients may be treated with additional salvage chemoradiation therapy in the form of fluorouracil, cisplatin, and a radiation boost to potentially avoid permanent colostomy.

Angiocentric Immunoproliferative Lesion

Angiocentric immunoproliferative lesion is an aggressive Non-Hodgkin's adult lymphoma, comprised of two clinical syndromes: nasal T-cell lymphoma (previously called lethal midline granuloma) and pulmonary angiocentric B-cell lymphoma (previously called lymphomatoid granulomatosis).

Angioimmunoblastic Lymphadenopathy with Dysproteinaemia (AILD)

AILD is a type of peripheral T-cell lymphoma that is clinically characterized by high fever and generalized lymphadenopathy that sometimes has cutaneous involvement. As AILD progresses, hepatosplenomegaly, hemolytic anemia, and polyclonal hypergammaglobulinemia may develop. The skin is involved in approximately 40-50% of patients. Patients are usually aged 40-90 years. In one series, other symptoms included weight loss (58%), hepatomegaly (60%), polyclonal hyperglobulinemia (65%), and generalized adenopathy (87%).

AILD may represent a spectrum of disease ranging from a hyperplastic but still benign immune reaction to frank malignant lymphoma. Because clonal expansion of T cells has been demonstrated in most but not all cases of AILD, subclassification has been introduced and comprises 3 subsets of the disease: AILD with no evidence of clonal lymphoid proliferation; AILD-type dysplasia with inconsistent findings regarding the clonality of the proliferating cells; and AILD-type lymphoma with strong evidence of clonality by immunohistochemical tests, rearrangement analysis, and cytogenetic studies. However, AILD-type dysplasia with an oligoclonal T-cell pattern has frequently been shown to progress into AILD-type lymphoma. Thus, subclassification may reflect the existence of stages in the development of the disease rather than independent disease entities.

Treatment of AILD

Polychemotherapy is often used. Prednisone is a first-line agent in the treatment of AILD. Regimens include prednisone alone or cyclophosphamide and prednisone, cyclophosphamide with vincristine, and prednisone. Cyclophosphamide, hydroxydaunorubicin, Oncovin (vincristine), and prednisone (CHOP)-like regimens used as first-line therapy before or after steroids administration, with or without interferon alfa as consolidation, in retrospective analyses have produced complete remission rates of about 60%.

Two thirds of patients treated with low doses of recombinant interferon alfa-2a (used as a single agent) achieved an objective remission, while, in the remaining one third of patients, no change or progressive disease was observed. The median remission duration was 3.5 months. Thus, interferon seems a promising agent in the treatment of AILD, but its role must be further defined.

Radiation therapy has been used as well. Cyclosporine and 2-chlorodeoxyadenosine and cyclophosphamide have also been used. The treatment regimen of cyclophosphamide, Oncovin (vincristine), prednisone, bleomycin, Adriamycin (doxorubicin), and Matulane (procarbazine) (COP-BLAM) and ifosfamide, mesna uroprotection, methotrexate, and etoposide (IMVP-16) has been used. Methotrexate has not been found to be effective.

High-dose chemotherapy (HDCT) followed by autologous bone marrow transplantation (ABMT) represents a promising new treatment modality for patients with advanced lymphoma, conceivably including AILD.

One treatment of AILD comprises interferon alfa, cyclosporine A, deoxyspagarine, and azathioprine, alternating regimens of low-dose 6-mercaptopurine, cyclophosphamide, and methotrexate. Later, a splenectomy can be performed, to induce a prolonged complete remission of the AILD, without any medication.

Sustained remission from angioimmunoblastic T-cell lymphoma induced by alemtuzumab has been reported.

Prolonged survival for patients with angioimmunoblastic T-cell lymphoma after high-dose chemotherapy and autologous stem cell transplantation has been reported. Therapeutic strategies including immunomodulation with agents such as cyclosporine and angiogenesis inhibition with drugs such as bevacizumab might be helpful. Durable remission after the administration of rituximab for EBV-negative, diffuse large B-cell lymphoma following autologous peripheral blood stem cell transplantation for angioimmunoblastic T-cell lymphoma has been reported.

In a few cases, the removal of the spleen has improved the symptoms of AILD or induced remission. In addition, successful coil embolization of a ruptured hepatic aneurysm in a patient with polyarteritis nodosa accompanied by angioimmunoblastic T cell lymphoma has been reported.

This disease requires consultations from all specialists who can deal with specific manifestations of AILD. The primary doctor that should supervise care is an oncologist/hematologist. Because most patients die from infectious complications, an infectious disease specialist should also be involved.

Basal Cell Carcinoma of Skin

Basal cell carcinoma (BCC) is the most common form of skin cancer. It can be destructive and disfiguring. The risk of developing BCC is increased for individuals with a family history of the disease and with a high cumulative exposure to UV light via sunlight. Treatment is with surgery, mohs surgery, topical chemotherapy, X-ray, cryosurgery, or photodynamic therapy. It is rarely life-threatening but, if left untreated, can be disfiguring, cause bleeding, and produce local destruction (e.g., eye, ear, nose, lip). As with squamous cell carcinoma, the incidence of basal cell carcinoma rises sharply with immunosuppression and in patients with inherited defects in DNA repair. Basal cell skin cancer almost never spreads; however, large and longstanding tumours may metastasize into regional lymph nodes and surrounding areas such as nearby tissues and bone.

Types of Basal Cell Carcinoma of Skin
1) Nodular: flesh-colored papule with telangiectasis; if it ulcerates, it becomes a "rodent ulcer" (ulcus rodens), an ulcerating nodule with (often) a pearly border
2) Cystic: rarer and difficult to distinguish from the nodular form, which has a central cavity with fluid
3) Pigmented: a variant of the nodular form that may be confused with melanoma
4) Sclerosing/cicratising: a scar-like lesion
5) Superficial: a red scaling patch.

About two-thirds of basal cell carcinomas occur on sun-exposed areas of the body. One-third occur on areas of the body that are not exposed to sunlight, emphasizing the genetic susceptibility of the basal cell cancer patients.

Diagnosis of Basal Cell Carcinoma of Skin
To diagnose basal cell carcinomas, a biopsy (where tissue is taken for pathological study) is done using local anesthesia. In small lesions, the tumor is, in general, removed in its entirety, whereas larger ones are biopsied first and surgically removed later if it is confirmed that it is malignant.

Histopathology: Basal cell carcinoma is a malignant epithelial tumor arising only in skin, from the basal layer of the epidermis or of the pilosebaceous adnexa. Tumor is represented by compact areas, well delineated and invading the dermis, apparent with no connection with the epidermis. Tumor cells resemble normal basal cells (small, monomorphous) and are disposed in palisade at the periphery of the tumor nests, but are spindle-shaped and irregular in the middle. Tumor clusters are separated by a reduced stroma with inflammatory infiltrate. 1

Treatment of Basal Cell Carcinoma of Skin
The following methods are employed in the treatment of basal cell carcinoma (BCC):
1) Surgery: Most basal cell carcinomas are removed by surgery. A common method is electrodessication and curettage (ED&C). This is done by scraping the tumor out with a curette and cauterizing the base and margins. The wound is left to heal by itself (secondary intention healing). While it is considered cost-effective, recurrences and the requirement for more extensive surgery make this procedure unacceptable for younger patients as well as cancers of the face, hands, or fingers. The cure rate can be very poor, as the margins are undefined and no histological proof of "cure" is allowed. The dermis is often thinned with this procedure, causing bulging of tissue, and unsightly white scalloped scar. Surgical excision is another option with the margins of excised tissue examined under the microscope. Cure rate can be excellent with wide excisional margins (4-6 mm), or very poor with narrow surgical margins (1-2 mm). Certain types, like the sclerosing basal cell cancers, may need a wider margin, as they develop subtle processes that project outside the visible part of the tumor. Although BCCs are carcinomas, they very rarely metastasize. They are invasive cancers; they can cause significant local tissue loss and even death. Despite this, basal cell carcinomas are not formally included in national cancer statistics, probably due to the extreme rarity of metastasis.
2) Chemotherapy: Some superficial cancers respond to local therapy with 5-fluorouracil, a chemotherapy agent. Topical treatment with 5% Imiquimod cream, with five applications per week for six weeks has a reported 70-90% success rate at reducing, even removing, the BCC (basal cell carcinoma). Imiquimod may be used prior to surgery in order to reduce the size of the carcinoma. One can expect a great deal of inflammation with this treatment.
3) Radiation: Radiation therapy is still appropriate in older patients that are not candidates for surgery.
4) Cryosurgery: Cryosurgery is another option, particularly for basal cell cancer that invades cartilage, as the healthy cartilage is cryo-resistant.
5) Mohs surgery: Mohs surgery (or Mohns micrographic surgery) is an outpatient procedure in which the tumor is surgically excised and then immediately examined under a microscope. The base and edges are microscopically examined to verify sufficient margins before the surgical repair of the site. If the margins are insufficient, more is removed from the patient until the margins are sufficient. It is also used for squamous cell carcinoma; however, the cure rate is not as high as Mohs surgery for basal cell carcinoma.
6) Immunotherapy: Immunotherapy research suggests that treatment using *Euphorbia peplus*, a common garden weed, may be effective. Australian biopharmaceutical company Peplin is developing this as topical treatment for BCC.

Treating surgeons will recommend one of these modalities as appropriate treatment depending on the tumor size, location, patient age, and other variables.

Bladder Cancer
Symptoms of Bladder Cancer
Symptoms of bladder cancer include Blood in the urine, change of Urinary frequency, Painful urination, Urinary urgency, Urinary incontinence, Bone pain or tenderness, Abdominal pain, Anemia, Weight loss and/or Lethargy (tiredness).

Diagnosis of Bladder Cancer
A physical examination will be performed, including a rectal and pelvic exam. Diagnostic tests that may be performed include:
Urinalysis
Urine cytology (microscopic exam of urine to look for cancerous cells)
Cystoscopy (use of lighted instrument to view inside of bladder)
Bladder biopsy (usually performed during cystoscopy)
Intravenous pyelogram—IVP (to evaluate upper urinary tract for tumors or blockage)

Treatment of Bladder Cancer
The choice of an appropriate treatment is based on the stage of the tumor, the severity of the symptoms, and the presence of other medical conditions.

Generally, stage 0 and I tumors are treated by removing the tumor without removing the rest of the bladder. They sometimes may also be treated by administering chemotherapy or immunotherapy (see below) directly into the bladder. Because the risk of the cancer returning is so high, people with bladder cancer require constant follow-up for the rest of their lives.

The treatment for patients with stage II and stage III disease is changing. While the accepted treatment has been removing the entire bladder (in a surgery called radical cystectomy), there is growing interest in keeping as much of the bladder as possible. Some patients may be treated by removing only part of the bladder, and that procedure is followed by radiation and chemotherapy. Some patients may be treated with chemotherapy before surgery, to try and shrink their tumor down, so that they might be able to avoid having the entire bladder removed. However, many people with stage II and stage III tumors still require bladder removal. In some patients with stage III tumors who choose not to have surgery, or who cannot tolerate surgery, a combination of chemotherapy and radiation may be used.

Most patients with stage IV tumors cannot be cured and surgery is not indicated. In these patients, chemotherapy is often considered.

Chemotherapy for bladder cancer can be administered through a vein or into the bladder. For early disease (stages 0 and I), it is usually given directly into the bladder. For more advanced stages (II-IV), treatment is usually given by vein.

Chemotherapy may be given to patients with stage II and III disease either before or after surgery in an attempt to prevent the tumor from returning.

Chemotherapy may be given as a single drug or in different combinations of drugs. These drugs include: Methotrexate, Vinblastine, Doxorubicin, Cyclophosphamide, Paclitaxel, Docetaxel, Carboplatin, Cisplatin, Ifosfamide, Gemcitabine.

The combination of two of these drugs, gemcitabine and cisplatin, has been shown to be as effective with less side effects as an older regimen known as MVAC (methotrexate, vinblastine, doxorubicin, and cisplatin). Many centers have replaced MVAC with this new combination. Paclitaxel and carboplatin is another effective combination that is frequently used.

A Foley catheter can be used to instill the medication directly into the bladder of patients with stage I disease. The catheter is removed immediately after the medication has been instilled. You are instructed to try to hold the medication in your bladder for at least two hours after treatment. Additionally, you may be asked to rotate from side to side every 15-30 minutes to completely expose the entire bladder wall to the medication.

Several different types of chemotherapy medications may be delivered directly into the bladder. They include: Thiotepa (Thioplex), Mitomycin-C (Mutamycin) and Doxorubicin (Adriamycin).

Bladder cancers are often treated by immunotherapy, in which a medication causes your own immune system to attack and kill the tumor cells. Immunotherapy for bladder cancer is usually performed using Bacille Calmette-Guerin (commonly known as BCG), which is a solution of genetically changed tuberculosis bacteria. Because they were genetically modified, these bacteria are not able to produce infection. BCG is administered through a Foley catheter directly into the bladder. Since BCG is a biological agent, special precautions must be taken during its handling and administration.

Potential side effects include bladder irritability, urinary frequency, urinary urgency, and painful urination. These are reported by 90% of the people treated with BCG. However, the symptoms usually resolve within a few days after treatment. Rare side effects include blood in the urine, malaise, nausea, chills, joint pain, and itching. Rarely, a systemic tuberculosis (TB) infection can develop, requiring treatment with anti-tuberculosis medication. Systemic infection is suspected if you develop an elevated temperature that lasts for more than one day.

People with stage 0 or I bladder cancer are usually treated with transurethral resection of the bladder (TURB). This surgical procedure is performed under general or spinal anesthesia. A cutting instrument is then inserted through the urethra to remove the bladder tumor.

Many people with stage II or III bladder cancer may require bladder removal (radical cystectomy). Partial bladder removal may be performed in some patients. Removal of part of the bladder is usually followed by radiation therapy and chemotherapy to help decrease the chances of the cancer returning. For those patients who undergo complete bladder removal, chemotherapy is also given after surgery to decrease the risk of a recurrence.

Radical cystectomy in men usually involves removal of the bladder, prostate, and seminal vesicles. In women, the urethra, uterus, and the front wall of the vagina are removed along with the bladder. Often, the pelvic lymph nodes are also removed during the surgery for examination in the laboratory. About half of the people treated with radical cystectomy will be completely cured; the other half shows signs of metastasis at the time of the surgery. A urinary diversion surgery (a surgical procedure to create an alternate method for urine storage) is usually performed with the radical cystectomy procedure. Two common types of urinary diversion are an ileal conduit and a continent urinary reservoir.

An ileal conduit is a small urine reservoir that is surgically created from a small segment of bowel. The ureters that drain urine from the kidneys are attached to one end of the bowel segment and the other end is brought out through an opening in the skin (a stoma). The stoma allows the patient to drain the collected urine out of the reservoir.

A continent urinary reservoir is another method of creating a urinary diversion. In this method, a segment of colon is removed and used to create an internal pouch to store urine. This segment of bowel is specially prepared to prevent reflux of urine back up into the ureters and kidneys, and also to reduce the risk of involuntary loss of urine. Patients are able to insert a catheter periodically to drain the urine. A small stoma is placed flush to the skin. Possible complications include: bowel obstruction, blood clots, pneumonia, urinary tract infection, skin breakdown around the stoma, ureteral reflux, and ureteral obstruction.

Orthotopic neobladder might be relevant for patients with bladder cancer. This surgery is becoming more common in patients undergoing cystectomy. A segment of bowel is folded over to make a pouch (a neobladder or "new bladder"), then attached to the urethral stump, which is the beginning of where the urine normally empties from the bladder.

Prognosis for Patients with Bladder Cancer

Patients will be closely monitored for progression of the disease regardless of the type of bladder cancer treatment received. Monitoring may include:

Cystoscope evaluations every 3 to 6 months after initial treatment for people with stage I disease.

Periodic urine cytology evaluations for people whose bladders have not been removed.

Bone scan and/or CT scan to check for metastasis.

Complete blood count (CBC) to monitor for signs and symptoms of anemia, which would indicate the disease has progressed.

Monitor for other signs of disease progression, such as fatigue, weight loss, increased pain, decreased bowel and bladder function, and weakness.

How well a patient does depends on the specific stage of bladder cancer and the type of treatment chosen. The prognosis for stage 0 or I cancers is fairly good, although the risk of the cancer returning is high. However, most bladder cancers that return can be surgically removed and cured. The cure rates for patients with stage III tumors are less than 50%. Patients with stage IV are rarely cured (although patients with only a few metastatic lesions can be cured in some circumstances).

Genes Associated with Bladder Cancer

Bladder cancer is related to chromosome 9. The FGFR3, HRAS, RB1, TP53, and TSC1 genes are associated with bladder cancer.

Bone Cancer and Bone Metastases

Bone cancer is caused by a problem with the cells that make bone. Bone tumors occur most commonly in children and adolescents and are less common in older adults. Cancer involving the bone in older adults is most commonly the result of metastatic spread from another tumor.

There are many different types of bone cancer. The most common bone tumors include osteosarcoma, Ewing's sarcoma, chondrosarcoma, malignant fibrous histiocytoma, fibrosarcoma, and chordoma.

Osteosarcoma is the most common primary malignant bone cancer. It most commonly affects males between 10 and 25 years old, but can less commonly affect older adults. It often occurs in the long bones of the arms and legs at areas of rapid growth around the knees and shoulders of children. This type of cancer is often very aggressive with risk of spread to the lungs. The five-year survival rate is about 65%.

Ewing's sarcoma is the most aggressive bone tumor and affects younger people between 4-15 years of age. It is more common in males and is very rare in people over 30 years old. It most commonly occurs in the middle of the long bones of the arms and legs. The three-year survival rate is about 65%, but this rate is much lower if there has been spread to the lungs or other tissues of the body.

Chondrosarcoma is the second most common bone tumor and accounts for about 25% of all malignant bone tumors. These tumors arise from the cartilage cells and can either be very aggressive or relatively slow-growing. Unlike many other bone tumors, chondrosarcoma is most common in people over 40 years old. It is slightly more common in males and can potentially spread to the lungs and lymph nodes. Chondrosracoma most commonly affects the bones of the pelvis and hips. The five-year survival for the aggressive form is about 30%, but the survival rate for slow-growing tumors is 90%.

Malignant fibrous histiocytoma (MFH) affects the soft tissues including muscle, ligaments, tendons, and fat. It is the most common soft-tissue malignancy in later adult life, usually occurring in people 50-60 years of age. It most commonly affects the extremities and is about twice as common in males as females. MFH also has a wide range of severity. The overall five-year survival rate is about 35%-60%.

Fibrosarcoma is much more rare than the other bone tumors. It is most common in people 35-55 years of age. It most commonly affects the soft tissues of the leg behind the knee. It is slightly more common in males than females.

Chordoma is a very rare tumor with an average survival of about six years after diagnosis. It occurs in adults over 30 years of age and is about twice as common in males as females. It most commonly affects either the lower or upper end of the spinal column.

In addition to bone cancer, there are various types of benign bone tumors. These include osteoid osteoma, osteoblastoma, osteochondroma, enchondroma, chondromyxoid fibroma, and giant cell tumor (which has the potential to become malignant). As with other types of benign tumors, these are not cancerous.

There are two other relatively common types of cancer than develop in the bones: lymphoma and multiple myeloma. Lymphoma, a cancer arising from the cells of the immune system, usually begins in the lymph nodes but can begin in the bone. Multiple myeloma begins in the bones, but it is not usually considered a bone tumor because it is a tumor of the bone marrow cells and not of the bone cells.

Symptoms of Bone Cancer

The most common symptom of bone tumors is pain. In most cases, the symptoms become gradually more severe with time. Initially, the pain may only be present either at night or with activity. Depending on the growth of the tumor, those affected may have symptoms for weeks, months, or years before seeking medical advice. In some cases, a mass or lump may be felt either on the bone or in the tissues surrounding the bone. This is most common with MFH or fibrosarcoma but can occur with other bone tumors. The bones can become weakened by the tumor and lead to a fracture after little or no trauma or just from standing on the affected bone. Fever, chills, night sweats, and weight loss can occur but are less common. These symptoms are more common after spread of the tumor to other tissues in the body.

Diagnosis of Bone Cancer

The first thing the doctor will do is to take a complete medical history. Some types of cancer are more common in people if they have close family members that have had that type of cancer. A description of your symptoms can help the doctor identify the possibility of bone cancer from other possible causes. Next, a complete physical examination can help find the cause of your symptoms. This may include testing your muscle strength, sensation to touch, and reflexes. Certain blood tests can be ordered that can help to identify a possible cancer.

Next, the doctor will likely order some imaging studies. Plain x-rays are often ordered first. In some cases, if the cancer is identified very early it may not show up on plain x-rays. The appearance of a tumor on the x-ray can help determine the type of cancer and whether or not it is benign or malignant. Benign tumors are more likely to have a smooth border while malignant tumors are more likely to have a ragged border. This is because the benign tumors typically grow more slowly and the bone has time to try to surround the tumor with normal bone. Malignant tumors are more likely to grow more quickly, not giving the normal bone a chance to surround the tumor.

A CT scan (CAT scan or computed tomography) is a more advanced test that can give a cross sectional picture of your bones. This test gives very good detail of your bones and is better able to identify a possible tumor. It also gives additional information on the size and location of the tumor.

An MRI (magnetic resonance imaging) is another advanced test that can also provide cross sectional imaging of your body. The MRI provides better detail of the soft tissues including muscles, tendons, ligaments, nerves, and blood vessels than a CT scan. This test can give better detail on whether or not the bone tumor has broken through the bone and involved the surrounding soft tissues.

A bone scan is a test that identifies areas of rapidly growing or remodeling bone. The bone scan is often taken of the entire body. This test may be ordered to see if there are any other areas of bone involvement throughout the body.

If a tumor is identified, your doctor will use all of the information from the history and physical examination along with the laboratory and imaging studies to put together a list of possible causes (differential diagnosis).

The doctor may then obtain a biopsy sample of the tumor. This involves taking a small sample of the tumor that can be examined in the laboratory to determine what kind of tumor it is. The biopsy can be obtained either through a small needle (needle biopsy) or through a small incision (incisional biopsy).

Treatment of Bone Cancer

There are many different methods available for treatment of bone cancer. The best treatment is based on the type of bone cancer, the location of the cancer, how aggressive the cancer is, and whether or not the cancer has invaded surrounding or distant tissues (metastasized). There are three main types of treatment for bone cancer: surgery, chemotherapy, and radiation therapy. These can be used either individually or combined with each other.

Surgery is often used to treat bone cancer. The goal of surgery is usually to remove the entire tumor and a surrounding area of normal bone. After the tumor has been removed, a pathologist examines it to determine if there is normal bone completely surrounding the tumor. If a portion of the cancer is left behind, it can continue to grow and spread, requiring further treatment. Historically, amputations were frequently used to remove bone cancer. Newer techniques have decreased the need for amputation. In many cases, the tumor can be removed with a rim of normal bone without the need for an amputation. Depending on the amount of bone removed, the surgeon will replace something in its location. For smaller areas, this may be either bone cement or a bone graft from another place in your body or from the bone bank. For larger areas, the surgeon may place larger grafts from the bone bank or metal implants. Some of these metal implants have the ability to lengthen when used in growing children.

The patient may be referred to a medical oncologist for chemotherapy. This is the use of various medications used to try to stop the growth of the cancer cells. Chemotherapy can be used prior to surgery to try to shrink the bone tumor to make surgery easier. It can also be used after surgery to try to kill any remaining cancer cells left following surgery.

The patient could also be referred to a radiation oncologist for radiation therapy. The radiation therapy uses high-energy x-ray aimed at the site of the cancer to try to kill the cancer cells. This treatment is given in small doses daily over a period of days to months.

Bone Metastasis

Cancer cells that break off from a primary tumor and enter the bloodstream can reach nearly all tissues of the body. Bones are one of the most common sites for these circulating cells to settle and start growing. Metastases can occur in bones anywhere in the body, but they are mostly found in bones near the centre of the body.

Bone metastasis is not the same as cancer that starts in the bone, which is called primary bone cancer. Bone metastasis and primary bone cancers are very different. Primary bone cancer is much less common than bone metastasis.

Bone metastasis is one of the most frequent causes of pain in people with cancer. It can also cause bones to break and high calcium levels in the blood (calcium is released from damaged bones). Bone metastasis also causes other symptoms and complications.

Bone metastases develop in many people with cancer (except for those with skin cancers such as basal cell and squamous cell cancer) at some point in the course of the disease. The bone is the third most common site for metastases after lung and liver.

The spine is the part of the skeleton most commonly affected by bone metastasis. The next most common parts are the pelvis, hip, upper leg bones (femurs), and the skull.

Treatment of Bone Metastasis

Treatment options for people with bone metastases depend on where the primary cancer developed, which bones it has spread to, and whether any bones are severely weakened or broken. Other factors will also be considered, such as specific features of the cancer cells (in the case of breast cancer, for instance, whether they contain estrogen receptors), the general state of health, and which treatments the patient has already received.

Most doctors believe the most important treatment for bone metastases is treatment directed against the cancer. This is usually done with systemic therapies. Systemic therapies enter the bloodstream and can therefore reach cancer cells that have spread throughout the body. This is different from local therapies, which are directed at a single area. Systemic therapies include chemotherapy or hormone therapies, which are taken by mouth or injected.

There are also drugs called bisphosphonates that can help make diseased bones stronger and help prevent fractures. These drugs are used to supplement the chemotherapy or hormonal therapy for bone metastasis. If systemic therapy is successful, then the symptoms of the bone metastases will go away and new symptoms are not likely to develop soon.

It may also be important to treat the bone problems. Local treatments such as radiation therapy can relieve the pain in a bone by destroying the cancer. Sometimes a bone such as your femur (thigh bone) might look as if it is close to breaking. To prevent this, your doctor will recommend surgery that involves placing a thin steel rod in the bone. It is much easier to prevent a damaged femur from breaking than to repair it after it has broken.

Systemic Therapy for Treatment of Bone Metastases

This section begins with a summary of the types of systemic treatments used for patients with metastatic cancers.

Chemotherapy: Chemotherapy uses anti-cancer drugs that are usually injected into a vein or taken by mouth. These drugs enter the bloodstream and can reach cancer that has spread. Chemotherapy is used as the main treatment for some metastatic cancers such as lymphomas and germ cell tumors of the ovaries, testicles, or placenta. In many cancers, chemotherapy can shrink tumors. This generally makes the patient feel better and reduces any pain the patient might have.

Chemotherapy drugs kill cancer cells but also damage some normal cells. Therefore, careful attention must be given to avoiding or reducing side effects. These depend on the type of drugs, the amount taken, and the length of treatment. Temporary side effects might include nausea and vomiting, loss of appetite, loss of hair, and mouth sores. Because chemotherapy can damage the blood-producing cells of your bone marrow, you may have low blood cell counts. Low blood cell counts can result in:

an increased chance of infection (caused by a shortage of white blood cells);

increased bleeding or bruising after minor cuts or injuries (caused by a shortage of blood platelets); and fatigue (caused by low red blood cell counts).

Most side effects go away once treatment is stopped. There are remedies to prevent or control many of the temporary side effects of chemotherapy. For example, drugs can prevent or reduce nausea and vomiting (these are called anti-emetic drugs).

Hormone therapy: Estrogen, a hormone produced by the ovaries, promotes growth of some breast cancers, particularly those cancers where tests can detect estrogen receptors. Likewise, androgens, such as testosterone (produced by the testicles) promote growth of most prostate cancers. One of the main ways to treat breast and prostate cancer is to block these hormones. There are several types of hormone-blocking therapies.

One strategy is to remove the organs that produce hormones. Removing the ovaries in women with breast cancer or removing the testicles in men with prostate cancer are hormone therapy options. Drugs are another option. Postmenopausal women can be given aromatase inhibitors, which block the small amount of estrogen they normally produce.

More often, drugs can be given to keep hormones from being produced. This is a common approach to hormone therapy for prostate cancer. Other drugs can be given to prevent the hormones from affecting the cancer cells. For example, drugs such as tamoxifen block estrogen's effects on breast cancers. Men can be given drugs such as luteinizing hormone-releasing hormone (LHRH), which block testosterone production and anti-androgens, which block the male hormone effects on prostate cancer. Side effects depend on the type of hormone treatments used. Use of tamoxifen, for example, may result in hot flashes, blood clots, loss of sex drive, and increased risk of uterine cancer.

Immunotherapy: Immunotherapy is a systemic therapy that helps a patient's immune system recognize and destroy cancer cells more effectively. Several types of immunotherapy are used to treat patients with metastatic cancer, including cytokines, monoclonal antibodies, and tumor vaccines. Most of these are still experimental. These treatments are discussed in detail in American Cancer Society documents on immunotherapy and the specific types of cancer for which this approach is useful.

Radiopharmaceuticals: Radiopharmaceuticals are a group of drugs that have radioactive elements. They are injected into a vein and settle in areas of bone that contain cancer. The radiation they give off kills the cancer cells and relieves some of the pain caused by bone metastases. Some of the radiopharmaceuticals that are most often used are strontium-89 (Metastron) and samarium-153 (Quadramet). Other radiopharmaceuticals, such as rhenium-186, rhenium-188, and tin-17, are also being studied.

Radiopharmaceuticals are not used to treat early stage, localized cancer (cancer that has not spread) or for metastases to other organs of the body. They are only used for cancer that has spread from another site to the bone.

If cancer has spread to many bones, radiopharmaceuticals are much better than trying to aim external beam radiation at each affected bone. In some cases, radiopharmaceuticals may be combined with external beam radiation aimed at the most painful bone metastases. Radiopharmaceuticals have the advantage over external beam radiation of being given in a single dose. This single treatment can reduce the pain for as long as 1 year. Re-treatment is possible when the pain returns, although usually the pain is not reduced for as long as it was with the first treatment. These drugs work best when the metastases are osteoblastic. Osteoblastic means the cancer has stimulated the bone cells (osteoblasts) to form new areas of bone. These areas appear dense (white) on x-rays (as opposed to osteolytic lesions, which appear as dark areas or holes in the bones). Osteoblastic metastases occur most frequently in prostate cancer that has spread to bone. They are found less often in breast cancer that has spread to bone and even less often in most other cancers.

Local Therapy for Treatment of Bone Metastases

Radiation therapy: Radiation therapy uses high-energy rays or particles to destroy cancer cells or slow their rate of growth. Radiation therapy can be used to cure primary cancers that have not spread too far from their original site. When a cancer has metastasized to bones, radiation is used to relieve (palliate) symptoms. Radiation may prevent fractures once the bone has healed. If there is an impending risk of a bone fracture, radiation will not prevent it. Instead the bone must be stabilized with surgery. If the bone is treated before it gets too weak, radiation therapy may help prevent later fractures.

The most common way to deliver radiation to a bone metastasis is to carefully focus a beam of radiation from a machine outside the body. This is known as external beam radiation. To reduce the risk of side effects, doctors carefully figure out the exact dose and aim the beam as accurately as they can to hit the target.

External beam radiation therapy: External beam radiation therapy for bone metastasis can be given as a large dose at one time, or in smaller amounts over e.g. 5 to 10 treatments. Most radiation oncologists prefer to give the radiation over several treatments. Both provide the same benefit in pain reduction and, when asked, most patients prefer the single-dose treatment.

Each external beam radiation treatment lasts only a few minutes. External beam radiation is an excellent option if you have 1 or 2 metastases that are causing symptoms. But if there are many metastases scattered throughout the body, treatment is more difficult. In rare cases, some patients can benefit from radiation therapy to either the entire upper or lower half of the body. A few weeks later, the other half of the body can be treated.

Although it is rarely used to treat bone metastases, another method of delivering radiation is to place (implant) metal rods or tiny pellets (sometimes called seeds) that contain radioactive materials in or near the cancer. This method is called internal radiation, interstitial radiation, or brachytherapy.

Radiofrequency ablation: Radiofrequency ablation involves use of a needle that carries electric current. The needle is placed into a particularly painful tumor that hasn't improved with radiation therapy. The electric current that destroys the tumor and relieves pain is delivered through the needle. This is usually done while the patient is under anesthesia.

Surgery for Treatment of Bone Metastases

Although surgery to remove a primary bone tumor (one that started in the bone) is often done with the intent to cure, the purpose of surgically treating bone metastasis is to relieve symptoms. Bone metastases can weaken bones, leading to breaks that tend to heal very poorly. An operation using a metal rod or external device to stabilize the bone can prevent some fractures and, if the bone is already broken, can rapidly relieve pain and help the patient return to usual activities.

If you can't have surgery to reinforce a bone affected by metastasis (because of poor general state of health, other complications of the cancers, or side effects of other treatments), a cast may help stabilize leg bones to reduce pain and avoid the need to stay in bed.

Sometimes the cancer will spread to a bone in the spine. The cancer can grow enough to press against the spinal cord, causing spinal cord compression. If not treated immediately, this can lead to paralysis. Surgery can relieve the pressure on the spinal cord and prevent paralysis as well as help relieve the pain. Radiation therapy is another option. A recent study has found that surgery followed by radiation may be the best treatment.

Pain Medications for Bone Metastasis

There are effective and safe ways to treat pain caused by bone metastasis. In some cases, this may include treatments that kill the cancer cells (chemotherapy or radiation therapy), slow their growth (hormonal therapy), or reduce bone damage (bisphosphonates). If the treatment does not relieve your pain, you should not hesitate to ask for pain medicines.

You may not want to ask for or accept pain medicines such as opioids (morphine-like pain medicines) because you think you will become addicted or that the medicines will make you too sleepy to continue your usual activities.

Bisphosphonates: Bisphosphonates are a group of drugs routinely used to treat osteoporosis, a condition that weakens the bones. They have also proven useful in treating patients with cancer that has spread to the bones. Drugs in this category include alendronate, clodronate, etidronate, ibandronate, zoledronate, and pamidronate. Bisphosphonates are also used to treat patients with multiple myeloma, a cancer that starts in the bone marrow.

Bisphosphonates help reduce bone pain, slow down bone damage caused by the cancer, reduce high blood calcium levels (hypercalcemia), and lower the risk of broken bones. They are more effective when x-rays show the metastatic cancer is causing the bone to become thinner and weaker (osteolytic metastases). They are less effective in treating osteoblastic metastases (sclerosis).

Bisphosphonates may be taken by mouth or given through a vein. Because the digestive system does not absorb these drugs very well, and because they can cause irritation and ulcers in the esophagus, bisphosphonate treatment for bone metastasis usually is given intravenously, every 3 to 4 weeks. The most commonly used drug is zoledronate (Zometa®). However ibandronate, which can also be given intravenously, may be as effective. Pamidronate is also commonly used to treat bone metastases. Zoledronate has an advantage over pamidronate because it takes less time to inject. Studies have also suggested that zoledronate may reduce the risk of fracture somewhat better than pamidronate.

Clinical studies have reported the most common side effects of bisphosphonates to be fatigue, fever, nausea, vomiting, anemia (low red blood cell counts), and bone or joint pain. But the cancer or other drugs that the patients were taking may have caused many of these effects. Bisphosphonates may also cause arthritis-like joint pain and muscle pain. These can often be relieved or prevented with a mild pain reliever. Recently, doctors have been reporting a very distressing side effect of damage to the jaw bones in patients receiving bisphosphonates. This side effect is called osteonecrosis. Patients complain of pain in the jaw, and examining doctors find that part of the bone of the upper or lower jaw has died. This can lead to loss of teeth in that area. Infections of the jaw bone may also develop. Doctors don't know why this happens or how to prevent it. So far, the only treatment has been to stop the bisphosphonate treatment and try to surgically remove the damaged bone.

Breast Cancer

Breast cancer is a cancer that starts in the tissues of the breast.

There are two main types of breast cancer:
Ductal carcinoma starts in the tubes (ducts) that move milk from the breast to the nipple. Most breast cancers are of this type.
Lobular carcinoma starts in parts of the breast, called lobules, that produce milk.

In rare cases, breast cancer can start in other areas of the breast.

Many breast cancers are sensitive to the hormone estrogen. This means that estrogen causes the breast cancer tumor to grow. Such cancer is called estrogen receptor positive cancer or ER positive cancer.

Some women have what's called HER2-positive breast cancer. HER2 refers to a gene that helps cells grow, divide, and repair themselves. Women with HER2-positive breast cancer have a more aggressive disease and a higher risk of recurrence than those who do not have this type.

Symptoms of Breast Cancer

Early breast cancer usually does not cause symptoms. This is why regular breast exams are important. As the cancer grows, symptoms may include:
Breast lump or lump in the armpit that is hard, has uneven edges, and usually does not hurt
Change in the size, shape, or feel of the breast or nipple—for example, you may have redness, dimpling, or puckering that looks like the skin of an orange
Fluid coming from the nipple—may be bloody, clear-to-yellow, or green, and look like pus Men get breast cancer, too. Symptoms include breast lump and breast pain and tenderness.

Symptoms of advanced breast cancer may include: Bone pain, Breast pain or discomfort, Skin ulcers, Swelling of one arm (next to breast with cancer) and/or Weight loss.

Diagnosis of Breast Cancer

The doctor will ask about symptoms and risk factors, and then perform a physical exam, which includes both breasts, armpits, and the neck and chest area. Additional tests may include:
Mammography to help identify the breast lump
Breast MRI to help better identify the breast lump
Breast ultrasound to show whether the lump is solid or fluid-filled
Breast biopsy, needle aspiration, or breast lump removal to remove all or part of the breast lump for closer examination by a laboratory specialist If the doctor learns that the patient has breast cancer, additional tests will be done to see if the cancer has spread. This is called staging. Staging helps guide future treatment and follow-up and gives some idea of what to expect in the future.

Breast cancer stages range from 0 to IV. In general, breast cancer that stays where it has started is called in situ or noninvasive breast cancer. If it spreads, it is called invasive breast cancer. The higher the number, the more advanced the cancer.

Treatment of Breast Cancer

Treatment is based on many factors, including type and stage of the cancer, whether the cancer is sensitive to certain hormones, and whether or not the cancer overproduces (overexpresses) HER2/neu.

In general, breast cancer treatments may include:
Chemotherapy medicines to kill cancer cells
Radiation therapy to destroy cancerous tissue Surgery to remove cancerous tissue—a lumpectomy removes the breast lump; mastectomy removes all or part of the breast and possible nearby structures Other treatments of breast cancer may include:

Hormonal therapy to block certain hormones that fuel cancer growth

Targeted therapy to interfere with cancer cell grow and function

An example of hormonal therapy is the drug tamoxifen. This drug blocks the effects of estrogen, which can help breast cancer cells survive and grow. Most women with estrogen sensitive breast cancer benefit from this drug. A newer class of medicines called aromatase inhibitors, such as exemestane (Aromasin), has been shown to work just as well or even better than tamoxifen in post-menopausal women with breast cancer.

Targeted therapy, also called biologic therapy, is a newer type of cancer treatment. This therapy uses special anti-cancer drugs that identify certain changes in a cell that can lead to cancer. One such drug is trastuzumab (Herceptin). For women with stage IV HER2-positive breast cancer, Herceptin plus chemotherapy has been shown to be work better than chemotherapy alone. Studies have also shown that in women with early stage HER2-positive breast cancer, this medicine plus chemotherapy cuts the risk of the cancer coming back by 50%.

Breast cancer treatment may be local or systemic.

Local treatments involve only the area of disease. Radiation and surgery are forms of local treatment.

Systemic treatments affect the entire body. Chemotherapy is a type of systemic treatment.

Most women receive a combination of treatments. For women with stage I, II, or III breast cancer, the main goal is to treat the cancer and prevent it from returning. For women with stage IV cancer, the goal is to improve symptoms and help them live longer. In most cases, stage IV breast cancer cannot be cured.

Stage 0—Lumpectomy plus radiation or mastectomy is the standard treatment. There is some controversy on how best to treat DCIS.

Stage I and II—Lumpectomy plus radiation or mastectomy with some sort of lymph node removal is standard treatment. Hormone therapy, chemotherapy, and biologic therapy may also be recommended following surgery.

Stage III—Treatment involves surgery possibly followed by chemotherapy, hormone therapy, and biologic therapy.

Stage IV—Treatment may involve surgery, radiation, chemotherapy, hormonal therapy, or a combination of such treatments.

Genes Associated with Breast Cancer

Variations of the BRCA1, BRCA2, CDH1, PTEN, STK11, and/or TP53 genes increase the risk of developing breast cancer.

The AR, ATM, BARD1, BRIP1, CHEK2, DIRAS3, ERBB2, NBN, PALB2, RAD50, and/or RAD51 genes are associated with breast cancer.

Bronchogenic Carcinoma/Lung Cancer

Lung cancer is a disease of uncontrolled cell growth in tissues of the lung. This growth may lead to metastasis, invasion of adjacent tissue and infiltration beyond the lungs. The vast majority of primary lung cancers are carcinomas of the lung, derived from epithelial cells. Lung cancer, the most common cause of cancer-related death in men and the second most common in women, is responsible for 1.3 million deaths worldwide annually. The most common symptoms are shortness of breath, coughing (including coughing up blood), and weight loss.

The main types of lung cancer are small cell lung carcinoma and non-small cell lung carcinoma. This distinction is important because the treatment varies; non-small cell lung carcinoma (NSCLC) is sometimes treated with surgery, while small cell lung carcinoma (SCLC) usually responds better to chemotherapy and radiation. The most common cause of lung cancer is long term exposure to tobacco smoke. The occurrence of lung cancer in non-smokers, who account for as many as 20% of cases, often attributed to a combination of genetic factors, radon gas, asbestos, and air pollution, including second-hand smoke.

Lung cancer may be seen on chest x-ray and computed tomography (CT scan). The diagnosis is confirmed with a biopsy. This is usually performed via bronchoscopy or CT-guided biopsy. Treatment and prognosis depend upon the histological type of cancer, the stage (degree of spread), and the patient's performance status. Possible treatments include surgery, chemotherapy, and radiotherapy. With treatment, the five-year survival rate is 14%.

Classification of Lung Cancer

The vast majority of lung cancers are carcinomas. There are two main types of lung carcinoma, categorized by the size and appearance of the malignant cells seen by a histo-pathologist under a microscope: non-small cell (80.4%) and small-cell (16.8%) lung carcinoma. This classification, based on histological criteria, has important implications for clinical management and prognosis of the disease.

1) Non-small Cell Lung Carcinoma (NSCLC)

The non-small cell lung carcinomas are grouped together because their prognosis and management are similar. There are three main sub-types: squamous cell lung carcinoma, adenocarcinoma and large cell lung carcinoma.

| Sub-types of non-small cell lung cancer | | Frequency of all lung cancers (%) |
|---|---|---|
| Histological sub-type | | |
| Squamous cell lung carcinoma | | 31.1 |
| Adenocarcinoma | Adenocarcinoma (not otherwise specified) | 23.2 |
| | Bronchioloalveolar carcinoma | 3.0 |
| | Adenosquamous carcinoma | 1.2 |
| | Papillary adenocarcinoma | 0.7 |
| | Mucoepidermoid carcinoma] | 0.1 |
| | Adenoid cystic carcinoma | 0.04 |
| | Other specified adenocarcinoma | 1.1 |
| Large cell carcinoma | | 10.7 |
| Giant cell and spindle cell carcinoma | | 0.4 |
| Other/unspecified non-small cell lung carcinoma | | 8.9 |

Accounting for 31.1% of lung cancers, squamous cell lung carcinoma usually starts near a central bronchus. Cavitation and necrosis within the center of the cancer is a common finding. Well-differentiated squamous cell lung cancers often grow more slowly than other cancer types.

Adenocarcinoma accounts for 29.4% of lung cancers. It usually originates in peripheral lung tissue. Most cases of adenocarcinoma are associated with smoking. However, among people who have never smoked ("never-smokers"), adenocarcinoma is the most common form of lung cancer. A subtype of adenocarcinoma, the bronchioloalveolar carcinoma, is more common in female never-smokers, and may have different responses to treatment.

Accounting for 10.7% of lung cancers, large cell lung carcinoma is a fast-growing form that develops near the surface of the lung. It is often poorly differentiated and tends to metastasize early.

2) Small Cell Lung Carcinoma (SCLC)

Small cell lung carcinoma (SCLC, also called "oat cell carcinoma") is less common. It tends to arise in the larger airways (primary and secondary bronchi) and grows rapidly, becoming quite large. The "oat" cell contains dense neurosecretory granules (vesicles containing neuroendocrine hormones) which give this an endocrine/paraneoplastic syndrome association. While initially more sensitive to chemotherapy, it ultimately carries a worse prognosis and is often metastatic at presentation. Small cell lung cancers are divided into Limited stage and Extensive stage disease. This type of lung cancer is strongly associated with smoking.

3) Metastatic Cancers

The lung is a common place for metastasis from tumors in other parts of the body. These cancers are identified by the site of origin, thus a breast cancer metastasis to the lung is still known as breast cancer. They often have a characteristic round appearance on chest x-ray. Primary lung cancers themselves most commonly metastasize to the adrenal glands, liver, brain, and bone.

4) Lung Cancer Staging

Lung cancer staging is an assessment of the degree of spread of the cancer from its original source. It is an important factor affecting the prognosis and potential treatment of lung cancer. Non-small cell lung carcinoma is staged from IA ("one A", best prognosis) to IV ("four", worst prognosis). Small cell lung carcinoma is classified as limited stage if it is confined to one half of the chest and within the scope of a single radiotherapy field. Otherwise it is extensive stage.

Symptoms of Lung Cancer

Symptoms that suggest lung cancer include: dyspnea (shortness of breath), hemoptysis (coughing up blood), chronic coughing or change in regular coughing pattern, wheezing, chest pain or pain in the abdomen, cachexia (weight loss), fatigue and loss of appetite, dysphonia (hoarse voice), clubbing of the fingernails (uncommon) and dysphagia (difficulty swallowing).

If the cancer grows in the airway, it may obstruct airflow, causing breathing difficulties. This can lead to accumulation of secretions behind the blockage, predisposing the patient to pneumonia. Many lung cancers have a rich blood supply. The surface of the cancer may be fragile, leading to bleeding from the cancer into the airway. This blood may subsequently be coughed up.

Depending on the type of tumor, so-called paraneoplastic phenomena may initially attract attention to the disease. In lung cancer, these phenomena may include Lambert-Eaton myasthenic syndrome (muscle weakness due to auto-antibodies), hypercalcemia or syndrome of inappropriate antidiuretic hormone (SIADH). Tumors in the top (apex) of the lung, known as Pancoast tumors, may invade the local part of the sympathetic nervous system, leading to changed sweating patterns and eye muscle problems (a combination known as Horner's syndrome), as well as muscle weakness in the hands due to invasion of the brachial plexus.

Many of the symptoms of lung cancer (bone pain, fever, weight loss) are nonspecific; in the elderly, these may be attributed to comorbid illness. In many patients, the cancer has already spread beyond the original site by the time they have symptoms and seek medical attention. Common sites of metastasis include the bone, such as the spine (causing back pain and occasionally spinal cord compression), the liver and the brain. About 10% of people with lung cancer do not have symptoms at diagnosis; these cancers are incidentally found on routine chest x-rays.

Diagnosis of Lung Cancer

Performing a chest x-ray is the first step if a patient reports symptoms that may be suggestive of lung cancer. This may reveal an obvious mass, widening of the mediastinum (suggestive of spread to lymph nodes there), atelectasis (collapse), consolidation (pneumonia), or pleural effusion. If there are no x-ray findings but the suspicion is high (such as a heavy smoker with blood-stained sputum), bronchoscopy and/or a CT scan may provide the necessary information. Bronchoscopy or CT-guided biopsy is often used to identify the tumor type.

The differential diagnosis for patients who present with abnormalities on chest x-ray includes lung cancer, as well as nonmalignant diseases. These include infectious causes such as tuberculosis or pneumonia, or inflammatory conditions such as sarcoidosis. These diseases can result in mediastinal lymphadenopathy or lung nodules, and sometimes mimic lung cancers. Lung cancer can also be an incidental finding under the form of a solitary pulmonary nodule (also called a coin lesion) on a chest X-ray or CT scan taken for an unrelated reason.

Screening refers to the use of medical tests to detect disease in asymptomatic people. Possible screening tests for lung cancer include chest x-ray or computed tomography (CT) of the chest.

Treatment of Lung Cancer

Treatment for lung cancer depends on the cancer's specific cell type, how far it has spread, and the patient's performance status. Common treatments include surgery, chemotherapy, and radiation therapy.

1) Surgery

If investigations confirm lung cancer, CT scan and often positron emission tomography (PET) are used to determine whether the disease is localised and amenable to surgery or whether it has spread to the point where it cannot be cured surgically.

Blood tests and spirometry (lung function testing) are also necessary to assess whether the patient is well enough to be operated on. If spirometry reveals poor respiratory reserve (often due to chronic obstructive pulmonary disease), surgery may be contraindicated.

Surgery itself has an operative death rate of about 4.4%, depending on the patient's lung function and other risk factors. Surgery is usually only an option in non-small cell lung carcinoma limited to one lung, up to stage IIIA. This is assessed with medical imaging (computed tomography, positron emission tomography). A sufficient pre-operative respiratory reserve must be present to allow adequate lung function after the tissue is removed.

Procedures include wedge resection (removal of part of a lobe), segmentectomy (removal of an anatomic division of a particular lobe of the lung), lobectomy (one lobe), bilobectomy (two lobes) or pneumonectomy (whole lung). In patients with adequate respiratory reserve, lobectomy is the preferred option, as this minimizes the chance of local recurrence. If the patient does not have enough functional lung for this, wedge resection may be performed. Radioactive iodine brachytherapy at the margins of wedge excision may reduce recurrence to that of lobectomy.

2) Chemotherapy

Small cell lung carcinoma is treated primarily with chemotherapy and radiation, as surgery has no demonstrable influence on survival. Primary chemotherapy is also given in metastatic non-small cell lung carcinoma.

The combination regimen depends on the tumor type. Non-small cell lung carcinoma is often treated with cisplatin or carboplatin, in combination with gemcitabine, paclitaxel, docetaxel, etoposide or vinorelbine. In small cell lung carcinoma, cisplatin and etoposide are most commonly used. Combinations with carboplatin, gemcitabine, paclitaxel, vinorelbine, topotecan and irinotecan are also used.

3) Adjuvant Chemotherapy for NSCLC:

Adjuvant chemotherapy refers to the use of chemotherapy after surgery to improve the outcome. During surgery, samples are taken from the lymph nodes. If these samples contain cancer, then the patient has stage II or III disease. In this situation, adjuvant chemotherapy may improve survival by up to 15%. Standard practice is to offer platinum-based chemotherapy (including either cisplatin or carboplatin).

Adjuvant chemotherapy for patients with stage IB cancer is controversial as clinical trials have not clearly demonstrated a survival benefit. Trials of preoperative chemotherapy (neoadjuvant chemotherapy) in resectable non-small cell lung carcinoma have been inconclusive.

4) Radiotherapy

Radiotherapy is often given together with chemotherapy, and may be used with curative intent in patients with non-small cell lung carcinoma who are not eligible for surgery. This form of high intensity radiotherapy is called radical radiotherapy. A refinement of this technique is continuous hyperfractionated accelerated radiotherapy (CHART), where a high dose of radiotherapy is given in a short time period. For small cell lung carcinoma cases that are potentially curable, in addition to chemotherapy, chest radiation is often recommended. The use of adjuvant thoracic radiotherapy following curative intent surgery for non-small cell lung carcinoma is not well established and controversial. Benefits, if any, may only be limited to those in whom the tumor has spread to the mediastinal lymph nodes.

For both non-small cell lung carcinoma and small cell lung carcinoma patients, smaller doses of radiation to the chest may be used for symptom control (palliative radiotherapy). Unlike other treatments, it is possible to deliver palliative radiotherapy without confirming the histological diagnosis of lung cancer.

Brachytherapy (localized radiotherapy) may be given directly inside the airway when cancer affects a short section of bronchus. It is used when inoperable lung cancer causes blockage of a large airway.

Patients with limited stage small cell lung carcinoma are usually given prophylactic cranial irradiation (PCI). This is a type of radiotherapy to the brain, used to reduce the risk of metastasis. More recently, PCI has also been shown to be beneficial in those with extensive small cell lung cancer. In patients whose cancer has improved following a course of chemotherapy, PCI has been shown to reduce the cumulative risk of brain metastases within one year from 40.4% to 14.6%.

Recent improvements in targeting and imaging have led to the development of extracranial stereotactic radiation in the treatment of early-stage lung cancer. In this form of radiation therapy, very high doses are delivered in a small number of sessions using stereotactic targeting techniques. Its use is primarily in patients who are not surgical candidates due to medical comorbidities.

5) Interventional Radiology

Radiofrequency ablation should currently be considered an investigational technique in the treatment of bronchogenic carcinoma. It is done by inserting a small heat probe into the tumor to kill the tumor cells.

6) Targeted Therapy

In recent years, various molecular targeted therapies have been developed for the treatment of advanced lung cancer. Gefitinib (Iressa) is one such drug, which targets the tyrosine kinase domain of the epidermal growth factor receptor (EGF-R) which is expressed in many cases of non-small cell lung carcinoma. It was not shown to increase survival, although females, Asians, non-smokers and those with bronchioloalveolar carcinoma appear to derive the most benefit from gefitinib. Erlotinib (Tarceva), another tyrosine kinase inhibitor, has been shown to increase survival in lung cancer patients and has recently been approved by the FDA for second-line treatment of advanced non-small cell lung carcinoma. Similar to gefitinib, it appeared to work best in females, Asians, non-smokers and those with bronchioloalveolar carcinoma.

The angiogenesis inhibitor bevacizumab (in combination with paclitaxel and carboplatin) improves the survival of patients with advanced non-small cell lung carcinoma. However this increases the risk of lung bleeding, particularly in patients with squamous cell carcinoma.

Advances in cytotoxic drugs, pharmacogenetics and targeted drug design show promise. A number of targeted agents are at the early stages of clinical research, such as cyclo-oxygenase-2 inhibitors, the apoptosis promoter exisulind, proteasome inhibitors, bexarotene and vaccines. Future areas of research include ras proto-oncogene inhibition, phosphoinositide 3-kinase inhibition, histone deacetylase inhibition, and tumor suppressor gene replacement.

The first successful pneumonectomy for lung cancer was carried out in 1933 and initially, pneumonectomy was the surgical treatment of choice. However, with improvements in cancer staging and surgical techniques, lobectomy with lymph node dissection has now become the treatment of choice.

Palliative radiotherapy has been used since the 1940s. Radical radiotherapy, initially used in the 1950s, was an attempt to use larger radiation doses in patients with relatively early stage lung cancer, but who were otherwise unfit for surgery. In 1997, continuous hyperfractionated accelerated radiotherapy (CHART) was seen as an improvement over conventional radical radiotherapy.

With small cell lung carcinoma, initial attempts in the 1960s at surgical resection and radical radiotherapy were unsuccessful. In the 1970s, successful chemotherapy regimens were developed.

Genes Associated with Lung Cancer

Variations in a region on chromosome 15 containing genes for subunits of the nicotine receptor are associated with an increased risk of lung cancer.

The three genes—TTF1, NKX2-8 and PAX9—work together to promote tumor growth in lung cancer. The genes are located next to each other on chromosome 14.

Case-control studies indicated that homozygotes for the OGG1-Cys326 allele have a higher risk for lung cancer than others.

MYCL1, FHIT, SPARC, p16(INK4) and TP53 genes associated to lung cancer in idiopathic pulmonary fibrosis.

Burkitt Lymphoma

Burkitt lymphoma (or "Burkitt's tumor", or "Malignant lymphoma, Burkitt's type") is a cancer of the lymphatic system (in particular, B lymphocytes). Burkitt lymphoma is curable.

Almost by definition, Burkitt lymphoma are associated with c-myc gene translocation. The most common variant is t(8;14)(q24;q32) while rarer variants include t(2;8)(p12; q24) and t(8;22)(q24;q11). A three-way translocation, t(8; 14;18), has also been identified.

Classification of Burkitt Lymphoma

Currently Burkitt's lymphoma can be divided into three main clinical variants: the endemic, the sporadic and the immunodeficiency-associated variants.

The endemic variant occurs in equatorial Africa. It is the most common malignancy of children in this area. Children affected with the disease often also had chronic malaria which is believed to have reduced resistance to the Epstein-Barr virus and allowed it to take hold. Disease characteristically involves the jaw or other facial bone, distal ileum, cecum, ovaries, kidney or the breast.

The sporadic type of Burkitt lymphoma (also known as "non-African") is another form of non-Hodgkin lymphoma found outside of Africa. The tumor cells have a similar appearance to the cancer cells of classical African or endemic Burkitt lymphoma. Again it is believed that impaired immunity provides an opening for development of the Epstein-Barr virus. Non-Hodgkins, which includes Burkitt's, accounts for 30-50% of childhood lymphoma. Jaw is less commonly involved, comparing with the endemic variant. Ileo-cecal region is the common site of involvement.

Immunodeficiency-associated Burkitt lymphoma is usually associated with HIV infection or occurs in the setting of post-transplant patients who are taking immunosuppressive drugs. Actually, Burkitt lymphoma can be the initial manifestation of AIDS.

By morphology (i.e. microscopic appearance) or immunophenotype, it is almost impossible to differentiate these three clinical variants. Immunodeficiency-associated Burkitt lymphoma may demonstrate more plasmacytic appearance or more pleomorphism, but these features are not specific.

Symptoms of Burkitt Lymphoma

Unexplained swollen lymph nodes
Non-tender nodes
Rapid growth of the lymph nodes
Nodes that grow together to form a lump Diagnosis of Burkitt Lymphoma Lymph node biopsy
Chest x-ray
Bone marrow biopsy
CT scan of the chest, abdomen, and pelvis
Cerebral spinal fluid analysis
PET or gallium scan Treatment of Burkitt Lymphoma Effect of the chemotherapy, as with all cancers, depends on the time of diagnosis. With faster growing cancers, such as this one, the cancer actually responds faster than with slower growing cancers. This rapid response to chemotherapy can be hazardous to patient as a phenomenon called "tumor lysis syndrome" could occur. Close monitoring of patient and adequate hydration is essential during the process.

Chemotherapy comprises one or more compounds selected from the group consisting of cyclophosphamide, doxorubicin, vincristine, methotrexate, cytarabine, ifosfamide, etoposide and rituximab.

Other treatments are immunotherapy, bone marrow transplants, surgery to remove the tumor, and radiotherapy.

Carcinoma of Ampulla of Vater

Carcinoma of the ampulla of Vater is a malignant tumor arising within 2 cm of the distal end of the common bile duct, where it passes through the wall of the duodenum and ampullary papilla. The common bile duct merges with the pancreatic duct of Wirsung at this point and exits through the ampulla into the duodenum. The most distal portion of the common bile duct is dilated (ie, forms the ampulla of Vater) and is surrounded by the sphincter of Oddi, which spirals upward around the terminal portion of the duct. Because of biliary outflow obstruction, carcinoma of the ampulla of Vater tends to manifest early, as opposed to other pancreatic neoplasms that often are advanced at the time of diagnosis.

Curative surgical resection is the only option for long-term survival. Surgical or radiologic biliary decompression, relief of gastric outlet obstruction, and adequate pain control may improve the quality of life but do not affect overall survival rate.

Carcinomatosis

Carcinomatosis is a word that is sometimes used to describe a cancer that has spread widely to affect a number of different parts of the body.

Cerebral Metastases

Cerebral metastasis is the most common malignancy affecting the brain. The 3 most common sites of the primary tumor are the lung, breast and gastrointestinal tract. Seventy percent of the patients with cerebral metastasis have 1 or 2 lesions and 80% are located in the cerebral hemispheres.

Patients with good a neurologic function, a long disease free interval between the diagnosis of the primary tumor and development of the metastases, and lack of progressive systemic disease, tend to have the best prognosis. Therefore, the management of patients with cerebral metastases depends on following factors: the performance status of the patient, the status of the systemic disease, and the number of cerebral lesions.

For patients with progressive systemic disease and/or poor performance status, palliative WBRT or supportive management with dexamethasone alone is considered the most appropriate treatment. On the other hand, patients with solitary brain metastasis, who otherwise have no or stable systemic disease and a good performance status, should be considered for palliative surgical resection prior to whole brain radiotherapy (WBRT). Surgery followed by WBRT has shown to significantly improve both the survival time and the quality of life of patients in this category, when compared to treatment with WBRT alone.

The role of single fraction SRT/radiosurgery in the primary treatment of cerebral metastases is an area of ongoing investigation. Retrospective studies have shown that it benefits patients with good performance status, absence of systemic disease and up to 3 cerebral lesions. Moreover, it seems to produce similar results to those reported in surgical series when the criteria used for patient selection are similar. It is reasonable to consider using a radiosurgery boost in addition to WBRT as initial treatment for patients with the following circumstances: 1) inoperable solitary brain metastasis, 2) up to 3 cerebral lesions, provided that the performance status is good and there is no progressive systemic disease. It may also be useful in the palliation of recurrent cerebral metastases following WBRT in carefully selected cases which there are no more than 3 lesions, performance status is good and there is no progressive systemic disease.

Cervical Cancer

Cervical cancer is malignant cancer of the cervix uteri or cervical area. It may present with vaginal bleeding but symptoms may be absent until the cancer is in its advanced stages. Treatment consists of surgery (including local excision) in early stages and chemotherapy and radiotherapy in advanced stages of the disease.

Pap smear screening can identify potentially precancerous changes. Treatment of high grade changes can prevent the development of cancer. In developed countries, the widespread use of cervical screening programs has reduced the incidence of invasive cervical cancer by 50% or more.

Human papillomavirus (HPV) infection is a necessary factor in the development of nearly all cases of cervical cancer. HPV vaccine effective against the two most common cancer-causing strains of HPV has been licensed in the U.S. and the EU. These two HPV strains together are currently responsible for approximately 70% of all cervical cancers. Experts recommend that women combine the benefits of both programs by seeking regular Pap smear screening, even after vaccination.

Classification of Cervical Cancer

Cervical cancer is a carcinoma, typically composed of squamous cells, and is similar in some respects to squamous cell cancers of the head and neck and anus. All three of these diseases may be associated with human papillomavirus infection.

Symptoms of Cervical Cancer

The early stages of cervical cancer may be completely asymptomatic. Vaginal bleeding, contact bleeding or (rarely) a vaginal mass may indicate the presence of malignancy. Also, moderate pain during sexual intercourse and vaginal discharge are symptoms of cervical cancer. In advanced disease, metastases may be present in the abdomen, lungs or elsewhere.

Symptoms of advanced cervical cancer may include: loss of appetite, weight loss, fatigue, pelvic pain, back pain, leg pain, single swollen leg, heavy bleeding from the vagina, leaking of urine or feces from the vagina, and bone fractures.

Diagnosis of Cervical Cancer

1) Biopsy Procedures

While the pap smear is an effective screening test, confirmation of the diagnosis of cervical cancer or pre-cancer requires a biopsy of the cervix. This is often done through colposcopy, a magnified visual inspection of the cervix aided by using an acetic acid (e.g. vinegar) solution to highlight abnormal cells on the surface of the cervix. Further diagnostic procedures are loop electrical excision procedure (LEEP) and conization, in which the inner lining of the cervix is removed to be examined pathologically. These are carried out if the biopsy confirms severe cervical intraepithelial neoplasia.

2) Pathologic Types

Cervical intraepithelial neoplasia, the precursor to cervical cancer, is often diagnosed on examination of cervical biopsies by a pathologist. Histologic subtypes of invasive cervical carcinoma include the following:
squamous cell carcinoma (about 80-85%)
adenocarcinoma
adenosquamous carcinoma
small cell carcinoma
neuroendocrine carcinoma Non-carcinoma malignancies which can rarely occur in the cervix include
melanoma
lymphoma Note that the FIGO stage does not incorporate lymph node involvement in contrast to the TNM staging for most other cancers.

For cases treated surgically, information obtained from the pathologist can be used in assigning a separate pathologic stage but is not to replace the original clinical stage. For premalignant dysplastic changes, the CIN (cervical intraepithelial neoplasia) grading is used.

3) Staging

Cervical cancer is staged by the International Federation of Gynecology and Obstetrics (FIGO) staging system, which is based on clinical examination, rather than surgical findings. It allows only the following diagnostic tests to be used in determining the stage: palpation, inspection, colposcopy, endocervical curettage, hysteroscopy, cystoscopy, proctoscopy, intravenous urography, and X-ray examination of the lungs and skeleton, and cervical conization.

The TNM staging system for cervical cancer is analogous to the FIGO stage.

Stage 0—full-thickness involvement of the epithelium without invasion into the stroma (carcinoma in situ)
Stage 1—limited to the cervix
—IA—diagnosed only by microscopy; no visible lesions
—IA1—stromal invasion less than 3 mm in depth and 7 mm or less in horizontal spread
—IA2—stromal invasion between 3 and 5 mm with horizontal spread of 7 mm or less
—IB—visible lesion or a microscopic lesion with more than 5 mm of depth or horizontal spread of more than 7 mm
—IB1—visible lesion 4 cm or less in greatest dimension
—IB2—visible lesion more than 4 cm
Stage II—invades beyond cervix
—IIA—without parametrial invasion, but involve upper ⅔ of vagina
—IIB—with parametrial invasion
Stage III—extends to pelvic wall or lower third of the vagina
—IIIA—involves lower third of vagina
—IIIB—extends to pelvic wall and/or causes hydronephrosis or non-functioning kidney
IVA—invades mucosa of bladder or rectum and/or extends beyond true pelvis
IVB—distant metastasis Treatment of Cervical Cancer Microinvasive cancer (stage IA) is usually treated by hysterectomy (removal of the whole uterus including part of the vagina). For stage IA2, the lymph nodes are removed as well. An alternative for patients who desire to remain fertile is a local surgical procedure such as a loop electrical excision procedure (LEEP) or cone biopsy.

If a cone biopsy does not produce clear margins, one more possible treatment option for patients who want to preserve their fertility is a trachelectomy. This attempts to surgically remove the cancer while preserving the ovaries and uterus, providing for a more conservative operation than a hysterectomy. It is a viable option for those in stage I cervical cancer which has not spread; however, it is not yet considered a standard of care, as few doctors are skilled in this procedure. Even the most experienced surgeon cannot promise that a trachelectomy can be performed until after surgical microscopic examination, as the extent of the spread of cancer is unknown. If the surgeon is not able to microscopically confirm clear margins of cervical tissue once the patient is under general anesthesia in the operating room, a hysterectomy may still be needed. This can only be done during the same operation if the patient has given prior consent. Due to the possible risk of cancer spread to the lymph nodes in stage 1b cancers and some stage 1a cancers, the surgeon may also need to remove some lymph nodes from around the uterus for pathologic evaluation.

A radical trachelectomy can be performed abdominally or vaginally and there are conflicting opinions as to which is better. A radical abdominal trachelectomy with lymphadenectomy usually only requires a two to three day hospital stay, and most women recover very quickly (approximately six weeks). Complications are uncommon, although women who are able to conceive after surgery are susceptible to preterm labor and possible late miscarriage. It is generally recommended to wait at least one year before attempting to become pregnant after surgery. Recurrence in the residual cervix is very rare if the cancer has been cleared with the trachelectomy. Yet, it is recommended for patients to practice vigilant prevention and follow up care including pap screenings/colposcopy, with biopsies of the remaining lower uterine segment as needed (every 3-4 months for at least 5 years) to monitor for any recurrence in addition to minimizing any new exposures to HPV through safe sex practices until one is actively trying to conceive.

Early stages (IB1 and IIA less than 4 cm) can be treated with radical hysterectomy with removal of the lymph nodes or radiation therapy. Radiation therapy is given as external beam radiotherapy to the pelvis and brachytherapy (internal radiation). Patients treated with surgery who have high risk features found on pathologic examination are given radiation therapy with or without chemotherapy in order to reduce the risk of relapse. Larger early stage tumors (IB2 and IIA more than 4 cm) may be treated with radiation therapy and cisplatin-based chemotherapy, hysterectomy (which then usually requires adjuvant radiation therapy), or cisplatin chemotherapy followed by hysterectomy. Advanced stage tumors (IIB-IVA) are treated with radiation therapy and cisplatin-based chemotherapy.

On Jun. 15, 2006, the US Food and Drug Administration approved the use of a combination of two chemotherapy drugs, hycamtin and cisplatin for women with late-stage (IVB) cervical cancer treatment. Combination treatment has significant risk of neutropenia, anemia, and thrombocytopenia side effects. Hycamtin is manufactured by GlaxoSmithKline.

Cholangiocarcinoma

Cholangiocarcinoma is a cancer of the bile ducts, which drain bile from the liver into the small intestine. Other biliary tract cancers include pancreatic cancer, gall bladder cancer, and cancer of the ampulla of Vater. Cholangiocarcinoma is a relatively rare adenocarcinoma, with an annual incidence of 1-2 cases per 100,000 in the Western world, but rates of cholangiocarcinoma have been rising worldwide over the past several decades.

Prominent symptoms of cholangiocarcinoma include abnormal liver function tests, abdominal pain, jaundice, weight loss, and sometimes generalized itching, fever, or changes in stool or urine color. The disease is diagnosed through a combination of blood tests, imaging, endoscopy, and sometimes surgical exploration, though it commonly presents at Stage III or IV: too late to be resected surgically. Though most patients present without any risk factors evident, known risk factors for cholangiocarcinoma include primary sclerosing cholangitis (an inflammatory disease of the bile ducts), congenital liver malformations, infection with the parasitic liver flukes *Opisthorchis viverrini* or *Clonorchis sinensis*, and exposure to Thorotrast (thorium dioxide), a chemical formerly used in medical imaging.

Cholangiocarcinoma is considered to be an incurable and rapidly lethal disease unless all of its tumors can be fully resected (that is, cut out surgically). There is no potentially curative treatment except surgery, but unfortunately most patients have advanced and inoperable disease at the time of diagnosis. Patients with cholangiocarcinoma are generally managed, though never cured, with chemotherapy or radiation therapy as well as palliative care measures, and these are also used as adjuvant therapies post-surgically in cases where resection has been successful. Some areas of ongoing medical research in cholangiocarcinoma include the use of newer targeted therapies (such as erlotinib) or photodynamic therapy for treatment, and the concentration of byproducts of cancer stromal cell formation in the blood for diagnosis.

Symptoms of Cholangiocarcinoma
  Stools, clay colored
  Progressive jaundice
  Itching
  Right upper abdominal pain that may radiate to the back
  Loss of appetite
  Weight loss
  Fever
  Chills The most common physical indications of cholangiocarcinoma are abnormal liver function tests, jaundice (yellowing of the eyes and skin), which occurs only when bile ducts are blocked by the tumor, abdominal pain (30%-50%), generalized itching (66%), weight loss (30%-50%), fever (up to 20%), or changes in stool or urine color. To some extent, the symptoms depend upon the location of the tumor: Patients with cholangiocarcinoma in the extrahepatic bile ducts (outside the liver) are more likely to have jaundice, while those with tumors of the bile ducts within the liver often have pain without jaundice.

Blood tests of liver function in patients with cholangiocarcinoma often reveal a so-called "obstructive picture," with elevated bilirubin, alkaline phosphatase, and gamma glutamyl transferase levels, and relatively normal transaminase levels. Such laboratory findings suggest obstruction of the bile ducts, rather than inflammation or infection of the liver, as the primary cause of the jaundice. CA19-9 is elevated in most cases. The most common physical indications of cholangiocarcinoma are abnormal liver function tests, jaundice (yellowing of the eyes and skin), which occurs only when bile ducts are blocked by the tumor, abdominal pain (30%-50%), generalized itching (66%), weight loss (30%-50%), fever (up to 20%), or changes in stool or urine color. To some extent, the symptoms depend upon the location of the tumor: Patients with cholangiocarcinoma in the extrahepatic bile ducts (outside the liver) are more likely to have jaundice, while those with tumors of the bile ducts within the liver often have pain without jaundice.

Blood tests of liver function in patients with cholangiocarcinoma often reveal a so-called "obstructive picture," with elevated bilirubin, alkaline phosphatase, and gamma glutamyl transferase levels, and relatively normal transaminase levels. Such laboratory findings suggest obstruction of the bile ducts, rather than inflammation or infection of the liver, as the primary cause of the jaundice. CA19-9 is elevated in most cases.

Staging of Cholangiocarcinoma

Although there are at least 3 staging systems for cholangiocarcinoma (e.g. Bismuth, Blumgart, American Joint Committee on Cancer) none have been shown to be useful in predicting survival. The most important staging issue is whether the tumor can be surgically removed, or whether it is too advanced or invasive for surgical treatment. Often, this determination can only be made at the time of surgery.
  General guidelines for operability include:
  Absence of lymph node or liver metastases
  Absence of involvement of the portal vein
  Absence of direct invasion of adjacent organs
  Absence of widespread metastatic disease Diagnosis of Cholangiocarcinoma
  Tests that show tumor or obstruction in the bile duct:
  ERCP (endoscopic retrograde cholangiopancreatography)
  PTCA (percutaneous transhepatic cholangiogram)
  Abdominal CT scan
  Abdominal ultrasound CT scan-directed biopsy
Cytology
Blood tests that reveal abnormal function:
Liver function tests
Bilirubin Treatment of Cholangiocarcinoma Cholangiocarcinoma is considered to be an incurable and rapidly lethal disease unless all the tumors can be fully resected (that is, cut out surgically). Since the operability of the tumor can only be assessed during surgery in most cases, a majority of patients undergo exploratory surgery unless there is already a clear-cut indication that the tumor is inoperable.

Adjuvant therapy followed by liver transplantation may have a role in treatment of certain unresectable cases.

1) Adjuvant Chemotherapy and Radiation Therapy

If the tumor can be removed surgically, patients may receive adjuvant chemotherapy or radiation therapy after the operation to improve the chances of cure. If the tissue margins are negative (i.e. the tumor has been totally excised), adjuvant therapy is of uncertain benefit. Both positive and negative results have been reported with adjuvant radiation therapy in this setting, and no prospective randomized controlled trials have been conducted as of March 2007. Adjuvant chemotherapy appears to be ineffective in patients with completely resected tumors. The role of combined chemoradiotherapy in this setting is unclear. However, if the tumor tissue margins are positive, indicating that the tumor was not completely removed via surgery, then adjuvant therapy with radiation and possibly chemotherapy is generally recommended based on the available data.

2) Treatment of Advanced Disease

The majority of cases of cholangiocarcinoma present as inoperable (unresectable) disease in which case patients are generally treated with palliative chemotherapy, with or without radiotherapy. Chemotherapy has been shown in a randomized controlled trial to improve quality of life and extend survival in patients with inoperable cholangiocarcinoma. There is no single chemotherapy regimen which is universally used, and enrollment in clinical trials is often recommended when possible. Chemotherapy agents used to treat cholangiocarcinoma include 5-fluorouracil with leucovorin, gemcitabine as a single agent, or gemcitabine plus cisplatin, irinotecan, or capecitabine. A small pilot study suggested possible benefit from the tyrosine kinase inhibitor erlotinib in patients with advanced cholangiocarcinoma.

Photodynamic therapy, an experimental approach in which patients are injected with a light-sensitizing agent and light is then applied endoscopically directly to the tumor, has shown promising results compared to supportive care in two small randomized controlled trials. However, its ultimate role in the management of cholangiocarcinoma is unclear at present.

Chondrosarcoma

A chondrosarcoma is a type of cancer of the bone. Chondrosarcoma is a cartilage-based tumor and is in a category of cancers called sarcomas. About 25% of primary bone cancers (meaning those which start in the bone) are chondrosarcomas. This disease can affect people or animals of any age, although it is more common among older people than among children.

Classification of Chondrosarcoma

Physicians grade chondrosarcomas based chiefly on how fast they grow and the likelihood of metastasis. Grade 1 is the slowest growing form. Grades 2 and 3 are faster-growing cancers, and some medical facilities also assign grade 4 to the fastest growing and usually metastasized occurrences.

The most common sites for chondrosarcoma to grow are the pelvic and shoulder bones along with the superior metaphysial and diaphysial regions of the arms and legs. But chondrosarcoma may occur in any bone, even the base of the skull.

Diagnosis of Chondrosarcoma

Like all other bone tumors and disease processes, diagnosis is made primarily by imaging. There are no blood tests to determine a diagnosis of chondrosarcoma. The most characteristic imaging findings are on CT, where detection of a chondroid matrix is present.

Nearly all chondrosarcoma patients appear to be in good health. This form of cancer generally doesn't affect the whole body. Often, patients are not aware of the growing tumor until there is a noticeable lump or pain. Earlier diagnosis is generally accidental, when a patient undergoes testing for another problem and physicians discover the cancer. Occasionally the first symptom will be a broken bone at the cancerous site. Any broken bone that occurs from mild trauma warrants further investigation, although there are many conditions that can lead to weak bones, and this form of cancer is not a common cause of such breaks.

Treatment of Chondrosarcoma

Treatment depends on the location of the disease and the aggressiveness of the tumors.

Surgery is the main form of treatment for chondrosarcoma. Musculoskeletal tumor specialists or orthopedic oncologists are usually chosen to treat chondrosarcoma, unless it is located in the skull, spine, or chest cavity, in which case, a neurosurgeon or thoracic surgeon experienced with sarcomas is chosen. Often, a limb-sparing operation can be performed, however in some cases amputation is unavoidable. Amputation of the arm, leg, jaw, or half of the pelvis (called a hemipelvectomy) may be necessary in some cases.

Chemotherapy or traditional radiotherapy are not very effective for most chondrosarcomas, although proton therapy is showing promise with local tumor control at over 80%.

Complete surgical ablation is the most effective treatment, but sometimes this is difficult. Proton therapy Radiation can be useful in awkward locations to make surgery more effective.

Chordoma

Chordoma is a rare slow-growing malignant neoplasm thought to arise from cellular remnants of the notochord. The evidence for this is the location of the tumors (along the neuraxis), the similar immunohistochemical staining patterns, and the demonstration that notochordal cells are preferentially left behind in the clivus and sacrococcygeal regions when the remainder of the notochord regresses during fetal life.

Chordomas can arise from bone in the skull base and anywhere along the spine. The two most common locations are cranially at the clivus and in the sacrum at the bottom of the spine.

There are three histological variants of chordoma: classical, chondroid and dedifferentiated. The histological appearance of classical chordoma is of a lobulated tumor composed of groups of cells separated by fibrous septa. The cells have small round nuclei and abundant vacuolated cytoplasm, sometimes described as physaliferous (having bubbles or vacuoles). Chondroid chordomas histologically show features of both chordoma and chondrosarcoma.

Prognosis and Treatment

In most cases, aggressive surgical resection followed by radiation therapy offers the best chance of long-term control.

Chordomas are relatively radioresistant, requiring high doses of radiation to be controlled. The proximity of chordomas to vital neurological structures such as the brain stem and nerves limits the dose of radiation that can safely be delivered. Therefore, highly focused radiation such as proton therapy and carbon ion therapy are more effective than conventional x-ray radiation.

There are no drugs currently approved to treat chordoma, however a clinical trial conducted in Italy using the PDGFR inhibitor Imatinib demonstrated a modest response in some chordoma patients. The same group in Italy found that the combination of imatinib and sirolimus caused a response in several patients whose tumors progressed on imatinib alone.

Choriocarcinoma

Choriocarcinoma is a malignant and aggressive cancer, usually of the placenta. It is characterized by early hematogenous spread to the lungs. It belongs to the far end of the spectrum of gestational trophoblastic disease (GTD), a subset of germ cell tumors.

Diagnosis

Choriocarcinoma can be diagnosed by observation of one or more of the signs/symptoms: 1) increased quantitative β-hCG levels, 2) vaginal bleeding, 3) shortness of breath, 4) hemoptysis (coughing up blood). 5) chest pain, 6) chest X-ray shows multiple infiltrates of various shapes in both lungs and/or 7) presents in males as a testicular neoplasm.

Treatment

Choriocarcinoma is one of the tumors that is most sensitive to chemotherapy. The cure rate, even for metastatic choriocarcinoma, is around 90-95%. Virtually everyone without metastases can be cured however metastatic disease to the kidneys and/or brain is usually fatal. Chemotherapy regimen include EMACO (etoposide, methotrexate, actinomycin D, cyclosphosphamide and oncovin).

Hysterectomy (surgical removal of the uterus) can also be offered to patients >40 years of age or those desiring sterilization. It may be required for those with severe infection and uncontrolled bleeding.

Choroidal Melanoma

Choroidal melanoma is a primary cancer of the eye. It arises from the pigmented cells of the choroid of the eye and is not a tumor that started somewhere else and spread to the eye. Malignant means that the tumor is a cancer which may metastasize, that is, spread to other parts of the body. Although some choroidal melanomas are more life-threatening than others, almost all should be treated as if they were malignant.

Some choroidal melanomas appear to remain dormant and do not grow. Most enlarge slowly over time and lead to loss of vision. These tumors can spread to other parts of the body and lead eventually to death.

Diagnosis of Choroidal Melanoma

Choroidal melanoma is diagnosed during an examination of the eye by an ophthalmologist. Your eye doctors are able to recognize a choroidal melanoma by the degree of pigmentation of the tumor, by its shape and location, and by other features observed in an eye examination. Unlike tumors in other parts of the body, choroidal melanoma is directly visible through the "window" provided by the pupil. Most of the time, the ophthalmologist can be nearly certain of the diagnosis from clinical appearance, photographs, and ultrasound pictures. Therefore, biopsy, which is often indicated to diagnose tumors in other parts of the body, is avoided.

Some specialized tests which use sound waves (echography or ultrasound) and fluorescent dye (fluorescein angiography) may help your doctor to make the diagnosis of choroidal melanoma more certain. In the echography test, soundwaves are directed towards the tumor by a small probe placed on the eye. The pattern made by reflection of the sound waves helps your doctor to diagnose the tumor.

A test called fluorescein angiography also may be useful. In this test, a fluorescent dye is injected into a vein in the arm. As the dye passes through the blood vessels in the back of the eye, a rapid sequence of photographs is taken through your pupil. The appearance of the eye on these photographs may help your doctor to diagnose choroidal melanoma. Using the information provided by these tests, your doctor has been able to determine that your tumor is a "medium"-sized choroidal melanoma. Although it is classified as "medium," the melanoma is only about the size of a pea.

Treatment

For 100 years or longer, the usual treatment for choroidal melanoma has been removal of the eye, or enucleation. If the tumor has not spread to other parts of the body, then removal of the eye rids the patient of the tumor.

Since World War II, radiation treatment has been used for choroidal melanoma. During the past 20 years, this method of treatment has been refined. Radiation, at the appropriate dose rates and in the proper physical forms, is intended to eliminate growing tumor cells without causing damage to normal tissue sufficient to require removal of the eye. As the cells die, the tumor shrinks, but it usually does not disappear entirely. The most promising widely available method for irradiating medium choroidal melanoma involves constructing a small plaque with radioactive pellets glued to one side. Doctors who take care of patients who have choroidal melanoma are enthusiastic about the possibilities for this treatment, but satisfactory information about long-term results is not available. Your doctors recognize that they have a responsibility to current and future patients with choroidal melanoma to test radiation in a clinical trial. High energy particles (helium ion or proton beam radiation) from a cyclotron also can be used to irradiate tumors. Surgery is performed first to sew small metal clips to the sclera so that the particle beam can be aimed accurately. Treatment is given over several successive days. The equipment needed for these treatments is available only in a few centers in the world. Good results have been reported in some patients, but many patients treated in this way have been followed for only a few years. Therefore, the long-term results of these forms of radiation therapy compared with the more commonly used plaque are unknown.

Over the years, other treatments have been used for a small number of patients. Photocoagulation using white light or laser light has been used to burn small tumors, and cryo-therapy has been used to kill the tumors by freezing them. These techniques are believed to work only for very small tumors. Some doctors have combined laser or cryo-therapy with radiation, but such treatments are experimental. A few patients have had eye wall resection or a related procedure to remove tumors from their eyes. These methods of treatment are considered experimental by most doctors and have been used only for a small number of tumors. No treatment is available that can guarantee to destroy the tumor, to preserve vision, or to assure a normal lifespan.

For enucleation surgery, the patient is admitted to the hospital and the eye is removed under either local or general anesthesia. The enucleated eye cannot be treated or repaired and replaced in the eye socket. Instead, it is replaced with a ball implant that may be made of plastic or other materials. The implant is sewn into position and the eye is allowed to heal. Three to six weeks later, a specialist who makes artificial eyes (called an ocularist) fits the patient with a prosthesis. The prosthesis is a plastic shell painted to resemble the other eye and inserted between the eyelids.

When using radiation to treat medium choroidal melanoma, the goal is to destroy the tumor and save the eye. If the eye is to be saved, it is important to give high doses of radiation to the tumor and very little to the rest of the eye. This goal often can be accomplished with a small radioactive plaque sewn or sutured to the outside of the eye over the base of the tumor. This type of radiation procedure is sometimes called brachytherapy. The plaque is constructed with radioactive iodine seeds or pellets (A) glued to one side (B) and a thin gold sheet (C) attached to the other. Since gold stops this particular type of radiation, it acts as a shield to protect the parts of the head around the eye from radiation damage, especially those tissues beyond the shield. For placement of a radioactive plaque, the patient usually is admitted to the hospital. Surgery under local or general anesthesia is required and usually takes one to two hours. An incision is made in the conjunctiva, a thin membrane which covers the outside of the eye, and the radioactive plaque is stitched to the outside of the eye over the tumor. The conjunctiva is then sewn back over the plaque. After approximately three to seven days, surgery is performed again to remove the plaque.

Clear Cell Adenocarcinoma

A histologic type of adenocarcinoma occurring chiefly in the male and female genitourinary tracts which is characterised by distinctive hobnail cell growth of neoplastic cells in sheets, papillae, and coalescing glands.

Colorectal Cancer

Colorectal cancer, also called colon cancer or large bowel cancer, includes cancerous growths in the colon, rectum and appendix. It is the third most common form of cancer and the second leading cause of cancer-related death in the Western world. Colorectal cancer causes 655,000 deaths worldwide per year. Many colorectal cancers are thought to arise from adenomatous polyps in the colon. These mushroom-like growths are usually benign, but some may develop into cancer over time. The majority of the time, the diagnosis of localized colon cancer is through colonoscopy. Therapy is usually through surgery, which in many cases is followed by chemotherapy.

Symptoms of Colorectal Cancer

The first symptoms of colon cancer are usually vague, like weight loss and fatigue (tiredness). Local (bowel) symptoms are rare until the tumor has grown to a large size. Generally, the nearer the tumor is to the anus, the more bowel symptoms there will be. Symptoms and signs are divided into local, constitutional and metastatic.

1) Local Symptoms
   Change in bowel habits
      Change in frequency (constipation and/or diarrhea),
      Feeling of incomplete defecation (tenesmus) and reduction in diameter of stool, both characteristic of rectal cancer,
      Change in the appearance of stools:
         Bloody stools or rectal bleeding
         Stools with mucus
         Black, tar-like stool (melena), more likely related to upper gastrointestinal eg stomach or duodenal disease
   Bowel obstruction causing bowel pain, bloating and vomiting of stool-like material.
   A tumor in the abdomen, felt by patients or their doctors.
   Symptoms related to invasion by the cancer of the bladder causing hematuria (blood in the urine) or pneumaturia (air in the urine), or invasion of the vagina causing smelly vaginal discharge. These are late events, indicative of a large tumor.

2) Constitutional (Systemic) Symptoms
   Unexplained weight loss, probably the most common symptom, caused by lack of appetite
   Anemia, causing dizziness, fatigue and palpitations. Clinically, there will be pallor and blood tests will confirm the low hemoglobin level.

3) Metastatic Symptoms
   Liver metastases, causing:
      Jaundice.
      Pain in the abdomen, more often the upper part of epigastrium or right side of the abdomen
      Liver enlargement, usually felt by a doctor.
   Blood clots in the veins and arteries, a paraneoplastic syndrome related to hypercoagulability of the blood (the blood is "thickened")

Diagnosing, Screening and Monitoring of Colorectal Cancer

Colorectal cancer can take many years to develop and early detection of colorectal cancer greatly improves the chances of a cure. Therefore, screening for the disease is recommended in individuals who are at increased risk. There are several different tests available for this purpose.

Digital rectal exam (DRE): The doctor inserts a lubricated, gloved finger into the rectum to feel for abnormal areas. It only detects tumors large enough to be felt in the distal part of the rectum but is useful as an initial screening test.

Fecal occult blood test (FOBT): a test for blood in the stool. Two types of tests can be used for detecting occult blood in stools i.e. guaiac based (chemical test) and immunochemical. The sensitivity of immunochemical testing is superior to that of chemical testing without an unacceptable reduction in specifity.

Endoscopy:
   Sigmoidoscopy: A lighted probe (sigmoidoscope) is inserted into the rectum and lower colon to check for polyps and other abnormalities.
   Colonoscopy: A lighted probe called a colonoscope is inserted into the rectum and the entire colon to look for polyps and other abnormalities that may be caused by cancer. A colonoscopy has the advantage that if polyps are found during the procedure they can be immediately removed. Tissue can also be taken for biopsy.

In the United States, colonoscopy or FOBT plus sigmoidoscopy are the preferred screening options.

Other Screening Methods Include:

Double contrast barium enema (DCBE): First, an overnight preparation is taken to cleanse the colon. An enema containing barium sulfate is administered, then air is insufflated into the colon, distending it. The result is a thin layer of barium over the inner lining of the colon which is visible on X-ray films. A cancer or a precancerous polyp can be detected this way. This technique can miss the (less common) flat polyp. Virtual colonoscopy replaces X-ray films in the double contrast barium enema (above) with a special computed tomography scan and requires special workstation software in order for the radiologist to interpret. This technique is approaching colonoscopy in sensitivity for polyps. However, any polyps found must still be removed by standard colonoscopy.

Standard computed axial tomography is an x-ray method that can be used to determine the degree of spread of cancer, but is not sensitive enough to use for screening. Some cancers are found in CAT scans performed for other reasons.

Blood tests: Measurement of the patient's blood for elevated levels of certain proteins can give an indication of tumor load. In particular, high levels of carcinoembryonic antigen (CEA) in the blood can indicate metastasis of adenocarcinoma. These tests are frequently false positive or false negative, and are not recommended for screening, it can be useful to assess disease recurrence.

Genetic counseling and genetic testing for families who may have a hereditary form of colon cancer, such as hereditary nonpolyposis colorectal cancer (HNPCC) or familial adenomatous polyposis (FAP).

Positron emission tomography (PET) is a 3-dimensional scanning technology where a radioactive sugar is injected into the patient, the sugar collects in tissues with high metabolic activity, and an image is formed by measuring the emission of radiation from the sugar. Because cancer cells often have very high metabolic rate, this can be used to differentiate benign and malignant tumors. PET is not used for screening and does not (yet) have a place in routine workup of colorectal cancer cases.

Whole-Body PET imaging is the most accurate diagnostic test for detection of recurrent colorectal cancer, and is a cost-effective way to differentiate resectable from non-resectable disease. A PET scan is indicated whenever a major management decision depends upon accurate evaluation of tumour presence and extent.

Stool DNA testing is an emerging technology in screening for colorectal cancer. Pre-malignant adenomas and cancers shed DNA markers from their cells which are not degraded during the digestive process and remain stable in the stool. Capture, followed by PCR amplifies the DNA to detectable levels for assay. Clinical studies have shown a cancer detection sensitivity of 71%-91%.

Staging of Colon Cancer

Colon cancer staging is an estimate of the amount of penetration of a particular cancer. It is performed for diagnostic and research purposes, and to determine the best method of treatment. The systems for staging colorectal cancers largely depend on the extent of local invasion, the degree of lymph node involvement and whether there is distant metastasis.

Definitive staging can only be done after surgery has been performed and pathology reports reviewed. An exception to this principle would be after a colonoscopic polypectomy of a malignant pedunculated polyp with minimal invasion. Preoperative staging of rectal cancers may be done with endoscopic ultrasound. Adjuncts to staging of metastasis include Abdominal Ultrasound, CT, PET Scanning, and other imaging studies.

Dukes system: Dukes classification, first proposed by Dr Cuthbert E. Dukes in 1932, identifies the stages as:
 A—Tumour confined to the intestinal wall
 B—Tumour invading through the intestinal wall
 C—With lymph node(s) involvement
 D—With distant metastasis TNM system: The most common current staging system is the TNM (for tumors/nodes/metastases) system, though many doctors still use the older Dukes system. The TNM system assigns a number:
 T—The degree of invasion of the intestinal wall
  T0—no evidence of tumor
  Tis—cancer in situ (tumor present, but no invasion)
  T1—invasion through submucosa into lamina propria (basement membrane invaded)
  T2—invasion into the muscularis propria (i.e. proper muscle of the bowel wall)
  T3—invasion through the subserosa
  T4—invasion of surrounding structures (e.g. bladder) or with tumour cells on the free external surface of the bowel
 N—the degree of lymphatic node involvement
  N0—no lymph nodes involved
  N1—one to three nodes involved
  N2—four or more nodes involved
 M—the degree of metastasis
  M0—no metastasis
  M1—metastasis present AJCC stage groupings: The stage of a cancer is usually quoted as a number I, II, III, IV derived from the TNM value grouped by prognosis; a higher number indicates a more advanced cancer and likely a worse outcome.
 Stage 0
  Tis, N0, M0
 Stage I
  T1, N0, M0
  T2, N0, M0
 Stage IIA
  T3, N0, M0
 Stage IIB
  T4, N0, M0
 Stage IIIA
  T1, N1, M0
  T2, N1, M0
 Stage IIIB
  T3, N1, M0
  T4, N1, M0
 Stage IIIC
  Any T, N2, M0
 Stage IV
  Any T, Any N, M1

Treatment of Colon Cancer

The treatment depends on the staging of the cancer. When colorectal cancer is caught at early stages (with little spread) it can be curable. However when it is detected at later stages (when distant metastases are present) it is less likely to be curable.

Surgery remains the primary treatment while chemotherapy and/or radiotherapy may be recommended depending on the individual patient's staging and other medical factors.

1) Surgery

Surgeries can be categorised into curative, palliative, bypass, fecal diversion, or open-and-close.

Curative Surgical treatment can be offered if the tumor is localized.

Very early cancer that develops within a polyp can often be cured by removing the polyp (i.e., polypectomy) at the time of colonoscopy.

In colon cancer, a more advanced tumor typically requires surgical removal of the section of colon containing the tumor with sufficient margins, and radical en-bloc resection of mesentery and lymph nodes to reduce local recurrence (i.e., colectomy). If possible, the remaining parts of colon are anastomosed together to create a functioning colon. In cases when anastomosis is not possible, a stoma (artificial orifice) is created. Curative surgery on rectal cancer includes total mesorectal excision (lower anterior resection) or abdominoperineal excision.

In case of multiple metastases, palliative (non curative) resection of the primary tumor is still offered in order to reduce further morbidity caused by tumor bleeding, invasion, and its catabolic effect. Surgical removal of isolated liver metastases is, however, common and may be curative in selected patients; improved chemotherapy has increased the number of patients who are offered surgical removal of isolated liver metastases.

If the tumor invaded into adjacent vital structures which makes excision technically difficult, the surgeons may prefer to bypass the tumor (ileotransverse bypass) or to do a proximal fecal diversion through a stoma.

The worst case would be an open-and-close surgery, when surgeons find the tumor unresectable and the small bowel involved; any more procedures would do more harm than good to the patient. This is uncommon with the advent of laparoscopy and better radiological imaging. Most of these cases formerly subjected to "open and close" procedures are now diagnosed in advance and surgery avoided.

Laparoscopic-assisted colectomy is a minimally-invasive technique that can reduce the size of the incision and may reduce post-operative pain.

2) Chemotherapy

Chemotherapy is used to reduce the likelihood of metastasis developing, shrink tumor size, or slow tumor growth. Chemotherapy is often applied after surgery (adjuvant), before surgery (neo-adjuvant), or as the primary therapy (palliative). The treatments listed here have been shown in clinical trials to improve survival and/or reduce mortality rate and have been approved for use by the US Food and Drug Administration. In colon cancer, chemotherapy after surgery is usually only given if the cancer has spread to the lymph nodes (Stage III).

A) Adjuvant (after surgery) chemotherapy. One regimen involves the combination of infusional 5-fluorouracil, leucovorin, and oxaliplatin (FOLFOX)
        5-fluorouracil (5-FU) or Capecitabine (Xeloda)
        Leucovorin (LV, Folinic Acid)
        Oxaliplatin (Eloxatin)
    B) Chemotherapy for metastatic disease. Commonly used first line chemotherapy regimens involve the combination of infusional 5-fluorouracil, leucovorin, and oxaliplatin (FOLFOX) with bevacizumab or infusional 5-fluorouracil, leucovorin, and irinotecan (FOLFIRI) with bevacizumab
        5-fluorouracil (5-FU) or Capecitabine
        UFT or Tegafur-uracil
        Leucovorin (LV, Folinic Acid)
        Irinotecan (Camptosar)
        Oxaliplatin (Eloxatin)
        Bevacizumab (Avastin)
        Cetuximab (Erbitux)
        Panitumumab (Vectibix)
    C) In clinical trials for treated/untreated metastatic disease.
        Bortezomib (Velcade)
        Oblimersen (Genasense, G3139)
        Gefitinib and Erlotinib (Tarceva)
        Topotecan (Hycamtin)

3) Radiation Therapy

Radiotherapy is not used routinely in colon cancer, as it could lead to radiation enteritis, and it is difficult to target specific portions of the colon. It is more common for radiation to be used in rectal cancer, since the rectum does not move as much as the colon and is thus easier to target. Indications include:

A) Colon cancer
        pain relief and palliation—targeted at metastatic tumor deposits if they compress vital structures and/or cause pain
    B) Rectal cancer
        neoadjuvant—given before surgery in patients with tumors that extend outside the rectum or have spread to regional lymph nodes, in order to decrease the risk of recurrence following surgery or to allow for less invasive surgical approaches (such as a low anterior resection instead of an abdomino-perineal resection)
        adjuvant—where a tumor perforates the rectum or involves regional lymph nodes (AJCC T3 or T4 tumors or Duke's B or C tumors)
        palliative—to decrease the tumor burden in order to relieve or prevent symptoms Sometimes chemotherapy agents are used to increase the effectiveness of radiation by sensitizing tumor cells if present.

4) Immunotherapy

*Bacillus* Calmette-Guérin (BCG) is being investigated as an adjuvant mixed with autologous tumor cells in immunotherapy for colorectal cancer.

5) Vaccine

In November 2006, it was announced that a vaccine had been developed and tested with very promising results. The new vaccine, called TroVax, works in a totally different way to existing treatments by harnessing the patient's own immune system to fight the disease. Experts say this suggests that gene therapy vaccines could prove an effective treatment for a whole range of cancers. Oxford BioMedica is a British spin-out from Oxford University specialising in the development of gene-based treatments. Phase III trials are underway for renal cancers and planned for colon cancers.

6) Treatment of Liver Metastases

According to the American Cancer Society statistics in 2006, over 20% of patients present with metastatic (stage IV) colorectal cancer at the time of diagnosis, and up to 25% of this group will have isolated liver metastasis that is potentially resectable. Lesions which undergo curative resection have demonstrated 5-year survival outcomes now exceeding 50%.

Resectability of a liver metastasis is determined using preoperative imaging studies (CT or MRI), intraoperative ultrasound, and by direct palpation and visualization during resection. Lesions confined to the right lobe are amenable to en bloc removal with a right hepatectomy (liver resection) surgery. Smaller lesions of the central or left liver lobe may sometimes be resected in anatomic "segments", while large lesions of left hepatic lobe are resected by a procedure called hepatic trisegmentectomy. Treatment of lesions by smaller, non-anatomic "wedge" resections is associated with higher recurrence rates. Some lesions which are not initially amenable to surgical resection may become candidates if they have significant responses to preoperative chemotherapy or immunotherapy regimens. Lesions which are not amenable to surgical resection for cure can be treated with modalities including radio-frequency ablation (RFA), cryoablation, and chemoembolization.

Patients with colon cancer and metastatic disease to the liver may be treated in either a single surgery or in staged surgeries (with the colon tumor traditionally removed first) depending upon the fitness of the patient for prolonged surgery, the difficulty expected with the procedure with either the colon or liver resection, and the comfort of the surgery performing potentially complex hepatic surgery.

Poor prognostic factors of patients with liver metastasis include:
    Synchronous (diagnosed simultaneously) liver and primary colorectal tumors A short time between detecting the primary cancer and subsequent development of liver mets Multiple metastatic lesions High blood levels of the tumor marker, carcino-embryonic antigen (CEA), in the patient prior to resection Larger size metastatic lesions 7) Support Therapies Cancer diagnosis very often results in an enormous change in the patient's psychological wellbeing. Various support resources are available from hospitals and other agencies which provide counseling, social service support, cancer support groups, and other services. These services help to mitigate some of the difficulties of integrating a patient's medical complications into other parts of their life.

Conjunctival Squamous Cell Carcinoma

Squamous cell carcinoma of the conjunctiva is a malignant epithelial neoplasm characterized by basement membrane invasion or distant metastasis. Epithelial tumors of the conjunctiva are similar to conjunctival intraepithelial neoplasia (CIN). Squamous cell carcinoma of the conjunctiva represents a form of CIN that has either broken through the basement membrane to involve the subepithelial tissue or has metastasized. Morbidity is related primarily to local involvement of the conjunctiva and cornea, although regional spread and distant metastasis are possible. Rarely ocular penetration can occur, particularly with the mucoepidermoid type.

Squamous cell carcinoma is believed to arise from limbal stem cells and presents as a mass in the interpalpebral fissure at the nasal or temporal limbus. It may have a gelatinous and velvety, papilliform, or leukoplakic appearance. Given its variable appearance, it may pose a diagnostic challenge as a masquerade syndrome.

Treatment

Excisional biopsy is the treatment of choice. Topical cytotoxic therapy (ie, 5-fluorouracil [5-FU], mitomycin C [MMC]) has been used to treat CIN and to debulk large carcinomas prior to surgical excision.

Surgical Care include one or more of the steps disclosed herein below:
  Surgical excision is best performed under the operating microscope.
  Removal of a cuff of normal conjunctival tissue surrounding the lesion is prudent, and an episclerectomy at the base of the lesion is also advisable if it is adherent to the sclera in order to remove any superficial cells infiltrating the sclera.
  Involved corneal tissues may be best removed following treatment with 100% ethanol. The tissues superficial to the Bowman layer are removed easily in a single sheet and sent to the laboratory for analysis. Care should be taken not to incise into the Bowman membrane.
  Cryotherapy is performed, in a double freeze-thaw manner, to the edges of the uninvolved conjunctiva and Tenon capsule. It also can be applied to the involved limbal area.
  The exposed sclera occasionally is treated with 100% ethanol to devitalize any remaining tumor cells.
  All excised tissues are submitted for histopathologic analysis.
  Reconstruction is performed with direct closure, local flaps, or free conjunctival grafts.
  Extensive lesions with orbital involvement require exenteration.
Radiation therapy may be used as adjunctive therapy in cases of extensive lesions with poorly defined margins and as palliative therapy in cases where the patient cannot tolerate extensive surgery.

Cutaneous Metastasis

Skin, or cutaneous, metastasis refers to growth of cancer cells in the skin originating from an internal cancer. In most cases, cutaneous metastasis develops after the initial diagnosis of the primary internal malignancy (e.g. breast cancer, lung cancer) and late in the course of the disease. In very rare cases, skin metastasis may occur at the same time or before the primary cancer has been discovered and may be the prompt for further thorough investigation.

Skin metastasis may also occur from a skin cancer, usually melanoma. The original or 'primary' melanoma produces metastases or 'secondary' growths in surrounding or distant skin sites and other tissues such as the lungs or brain.

Skin metastasis occurs when cancerous cells break away from the primary tumour and make their way to the skin through the blood circulation or lymphatic system. Most malignant tumours can produce skin metastasis, but some are more likely to do so than others. When the following cancers have metastasised, they have quite a high chance of affecting the skin.

Melanoma—45% chance of developing skin metastasis (but only 15 to 20% of melanomas metastasise, so the overall chance of a skin metastasis is about 7-10%)

Breast cancer—30%

Nasal sinus cancers—20%

Cancer of the larynx—16%

Cancer of the oral cavity—12%

The incidence of skin metastasis varies but is somewhere between 3-10% in patients with a primary malignant tumour.

Signs and Symptoms of Skin Metastasis

Most skin metastasis occurs in a body region near the primary tumour. The first sign of skin metastasis is often the development of a firm, round or oval, mobile, non-painful nodule. The nodules are rubbery, firm or hard in texture and vary in size from barely noticeable lesions to large tumours. These may be skin coloured, red, or in the case of melanoma, blue or black. Sometimes multiple nodules appear rapidly. Sometimes cutaneous metastases present as ill-defined areas of thickened, skin-coloured or red scar-like plaques. The skin metastases may break down and ulcerate through the skin. Depending on the location of the primary tumour, skin metastasis display certain characteristic features.

| Organ of cancer origin | Features of skin metastasis |
|---|---|
| Breast | Most common sites of skin metastasis are the chest and abdomen<br>Less common sites include scalp, neck, upper extremities and back<br>Some patients may develop a firm scar-like area in the skin. If this occurs on the scalp, hair may be lost (alopecia neoplastica)<br>Lesions may appear as inflammatory plaques with a clear cut raised margin (carcinoma erysipeloides) |
| Lung | Most common sites are the chest, abdomen and back<br>Reddish firm nodules suddenly appear in the skin<br>Nodules tend to follow the intercostal vessels when they appear on the chest |
| Melanoma | In men, skin metastasis occurs on the chest, extremities and back<br>In women, metastasis to the lower extremities is common |

-continued

| Organ of cancer origin | Features of skin metastasis |
|---|---|
| Colon and stomach | Common sites are the abdomen and the pelvis<br>A nodule appearing at the umbilicus is called a Sister Mary Joseph nodule and is a sign of extensive colorectal cancer |

Treatment of Skin Metastasis

The underlying primary tumour needs to be treated. However, in most cases where skin metastasis has occurred, the primary cancer is widespread and may be untreatable. In this case, palliative care is given and includes keeping lesions clean and dry. Debridement can be done if lesions bleed or crust. Other therapies that may be helpful include:
  Imiquimod cream—may lead to regression of metastasis in some cases of melanoma
  Liquid nitrogen cryotherapy
  Photodynamic therapy
  Excision
  Carbon dioxide laser therapy
  Pulsed dye laser therapy
  Intralesional chemotherapy and cytokines In many cases, skin metastasis causes disfigurement and discomfort. Removal of skin lesions by simple excision may enhance the patient's quality of life but has little effect on the final outcome that is dictated by the primary cancer.

Dermatofibrosarcoma Protuberans

Dermatofibrosarcoma protuberans (DFSP) is a rare neoplasm of the dermis layer of the skin, and is classified as a sarcoma. In many respects, the disease behaves as a benign tumor, but in 2-5% of cases it can metastasize, so it should be considered to have malignant potential.

Over 95% of DFSP tumors have the chromosomal translocation t(17;22). The translocation fuses the collagen gene (COL1A1) with the platelet-derived growth factor gene. The fibroblast, the cell of origin of this tumor, expresses the fusion gene in the belief that it codes for collagen. However the resulting fusion protein is processed into mature platelet-derived growth factor which is a potent growth factor. Fibroblasts contain the receptor for this growth factor. Thus the cell "thinks" it is producing a structural protein, but in fact produces a self-stimulatory growth signal. The cell divides rapidly and a tumor forms.

Treatment

Treatment is primarily surgical, with chemotherapy and radiation therapy sometimes being used.

There is clinical evidence that imatinib, which inhibits PDGFB, may be effective for tumors positive for the t(17;22) translocation.

Eccrine Porocarcinoma

Carcinomas of the eccrine sweat gland represent a rare group of tumors with potential for local destruction and metastasis. High recurrence rates have been reported following conventional surgical excision. The specific classification of these neoplasms is both complex and nebulous, in large part because of the paucity of reported cases but also because many of these tumors show little histologic resemblance to mature eccrine glands; the histogenetic association is based primarily on histochemical, immunochemical, or ultrastructural features. Nevertheless, these tumors may be taxonomically segregated into 2 main groups, as follows: those that are histologically similar to certain benign appendage tumors (eg, sclerosing sweat duct carcinoma, porocarcinoma, malignant chondroid syringoma, malignant nodular hidradenoma, malignant eccrine spiradenoma) and those that show a diverse array of histologic features, not recapitulating to any degree aspects of a benign counterpart.

A slightly different method of classification has been suggested, which divide these tumors into those that arise de novo in normal skin and those that originate within preexisting benign sweat gland tumors. Precise identification based on histology is of significant importance because therapy and prognosis vary according to microscopic appearance.

Treatment

1) Medical Care

Experience and published data are very sparse. Radiation therapy has been used in select cases; chemotherapy has not been used extensively and presumably is lacking in efficacy.

2) Surgical Care

Mohs micrographic surgery is becoming the mainstay of therapy. Specific surgical treatments administered (as described in isolated case reports) for a few of these subtypes are detailed below.

MAC: A review of the world literature, which included 13 previously unpublished cases, reported 73 cases of MAC treated with Mohs; 39 of these were followed for more than 2 years with only 4 recurrences (89.7% success rate). A more recent review of 10 cases of MAC treated with Mohs reported disease free periods of 23.3 months, compared to one recurrence with standard surgical excision.
  Eccrine porocarcinoma: In a review of 9 cases from 1986-1996, 8 were treated with wide excision and 1 was treated with radiotherapy (RT); only 1 of the excisional cases and the RT case recurred.
  Malignant eccrine spiradenoma: A few case reports exist of this tumor treated with wide excision with or without radiation therapy. However, long-term data are scant.
  Aggressive digital papillary adenocarcinoma: Wide excision or amputation of the affected digit was advised by a recent publication.
  Primary cutaneous adenoid cystic carcinoma: A report on 8 patients treated with wide excision noted 3 recurrences (time period unspecified) with 1 patient lost to follow-up.

Endodermal Sinus Tumor

Endodermal sinus tumor (EST), also known as yolk sac tumor (YST), is a member of the germ cell tumor group of cancers. It is the most common testicular tumor in children under 3, and is also known as infantile embryonal carcinoma. This age group has a very good prognosis. In contrast to the pure form typical of infants, adult endodermal sinus tumors are often found in combination with other kinds of germ cell tumor, particularly teratoma and embryonal carcinoma. While pure teratoma is usually benign, endodermal sinus tumor is malignant.

Diagnosis

The histology of EST is variable, but usually includes malignant endodermal cells. These cells express alpha-fetoprotein (AFP), which can be detected in tumor tissue or serum. When there is incongruence between biopsy and AFP test results for EST, the result indicating presence of EST should guide treatment. This is because EST often occurs as small "malignant foci" within a larger tumor, usually teratoma; biopsy of the tumor may reveal only teratoma, whereas elevated AFP in serum or cerebrospinal fluid reveals that EST is also present. GATA-4, a transcription factor, also may be useful in the diagnosis of EST. Schiller-Duval bodies on histology are pathognomonic.

Treatment

Most treatments involve some combination of surgery and chemotherapy.

Before modern chemotherapy, this type of neoplasm was highly lethal, but the prognosis has significantly improved since.

90% survival rate when treated effectively.

Endometrial Cancer

Endometrial cancer refers to several types of malignancy which arise from the endometrium, or lining of the uterus. Endometrial cancers are the most common gynecologic cancers in the United States, with over 35,000 women diagnosed each year in the U.S. The most common subtype, endometrioid adenocarcinoma, typically occurs within a few decades of menopause, is associated with excessive estrogen exposure, often develops in the setting of endometrial hyperplasia, and presents most often with vaginal bleeding. Endometrial carcinoma is the third most common cause of gynecologic cancer death (behind ovarian and cervical cancer). A total abdominal hysterectomy (surgical removal of the uterus) with bilateral salpingo-oophorectomy is the most common therapeutic approach.

Endometrial cancer may sometimes be referred to as uterine cancer. However, different cancers may develop not only from the endometrium itself but also from other tissues of the uterus, including cervical cancer, sarcoma of the myometrium, and trophoblastic disease.

Classification

Most endometrial cancers are carcinomas (usually adenocarcinomas), meaning that they originate from the single layer of epithelial cells which line the endometrium and form the endometrial glands. There are many microscopic subtypes of endometrial carcinoma, including the common endometrioid type, in which the cancer cells grow in patterns reminiscent of normal endometrium, and the far more aggressive papillary serous and clear cell endometrial carcinomas. Some authorities have proposed that endometrial carcinomas be classified into two pathogenetic groups:

Type I: These cancers occur most commonly in pre- and pen-menopausal women, often with a history of unopposed estrogen exposure and/or endometrial hyperplasia. They are often minimally invasive into the underlying uterine wall, are of the low-grade endometrioid type, and carry a good prognosis.

Type II: These cancers occur in older, post-menopausal women, are more common in African-Americans, and are not associated with increased exposure to estrogen. They are typically of the high-grade endometrioid, papillary serous or clear cell types, and carry a generally poor prognosis In contrast to endometrial carcinomas, the uncommon endometrial stromal sarcomas are cancers which originate in the non-glandular connective tissue of the endometrium. Uterine carcinosarcoma, formerly called Malignant mixed müllerian tumor, is a rare uterine cancer which contains cancerous cells of both glandular and sarcomatous appearance—in this case, the cell of origin is unknown.

Signs and Symptoms

Abnormal uterine bleeding, abnormal menstrual periods
  Bleeding between normal periods in premenopausal women
  Vaginal bleeding and/or spotting in postmenopausal women
in women older than 40: extremely long, heavy, or frequent episodes of bleeding (may indicate premalignant changes)

Anemia, caused by chronic loss of blood. (This may occur if the woman has ignored symptoms of prolonged or frequent abnormal menstrual bleeding.)
Lower abdominal pain or pelvic cramping
Thin white or clear vaginal discharge in postmenopausal women.

Diagnosis

1) Clinical Evaluation

Routine screening of asymptomatic women is not indicated, since the disease is highly curable in its early stages. Results from a pelvic examination are frequently normal, especially in the early stages of disease. Changes in the size, shape or consistency of the uterus and/or its surrounding, supporting structures may exist when the disease is more advanced.

A Pap smear may be either normal or show abnormal cellular changes.

Endometrial curettage is the traditional diagnostic method. Both endometrial and endocervical material should be sampled.

If endometrial curettage does not yield sufficient diagnostic material, a dilation and curettage (D&C) is necessary for diagnosing the cancer.

Endometrial biopsy or aspiration may assist the diagnosis.

Transvaginal ultrasound to evaluate the endometrial thickness in women with postmenopausal bleeding is increasingly being used to evaluate for endometrial cancer.

Recently, a new method of testing has been introduced called the TruTest, offered through Gynecor. It uses the small flexible Tao Brush to brush the entire lining of the uterus. This method is less painful than a pipelle biopsy and has a larger likelihood of procuring enough tissue for testing. Since it is simpler and less invasive, the TruTest can be performed as often, and at the same time as, a routine Pap smear, thus allowing for early detection and treatment.

Ongoing research suggests that serum p53 antibody may hold value in identifying high-risk endometrial cancer.

Diagnostic test study of S-p53 Ab and agreement study for high-risk endometrial cancer Kappa: 0.70 Sensitivity (%): 64 Specificity (%): 96 PPV: 78 NPV: 92

2) Pathology

The histopathology of endometrial cancers is highly diverse. The most common finding is a well-differentiated endometrioid adenocarcinoma, which is composed of numerous, small, crowded glands with varying degrees of nuclear atypia, mitotic activity, and stratification. This often appears on a background of endometrial hyperplasia. Frank adenocarcinoma may be distinguished from atypical hyperplasia by the finding of clear stromal invasion, or "back-to-back" glands which represent nondestructive replacement of the endometrial stroma by the cancer. With progression of the disease, the myometrium is infiltrated.

3) Further Evaluation

Patients with newly-diagnosed endometrial cancer do not routinely undergo imaging studies, such as CT scans to evaluate for extent of disease, since this is of low yield. Preoperative evaluation should include a complete medical history and physical examination, pelvic examination and rectal examination with stool guaiac test, chest X-ray, complete blood count, and blood chemistry tests, including liver function tests. Colonoscopy is recommended if the stool is guaiac positive or the woman has symptoms, due to the etiologic factors common to both endometrial cancer and colon cancer. The tumor marker CA-125 is sometimes checked, since this can predict advanced stage disease.

4) Staging

Endometrial carcinoma is surgically staged using the FIGO cancer staging system.

Stage IA: tumor is limited to the endometrium
Stage IB: invasion of less than half the myometrium
Stage IC: invasion of more than half the myometrium
Stage IIA: endocervical glandular involvement only
Stage IIB: cervical stromal invasion
Stage IIIA: tumor invades serosa or adnexa, or malignant peritoneal cytology
Stage IIIB: vaginal metastasis
Stage IIIC: metastasis to pelvic or para-aortic lymph nodes
Stage IVA: invasion of the bladder or bowel
Stage IVB: distant metastasis, including intraabdominal or inguinal lymph nodes Treatment The primary treatment is surgical. Surgical treatment should consist of, at least, cytologic sampling of the peritoneal fluid, abdominal exploration, palpation and biopsy of suspicious lymph nodes, abdominal hysterectomy, and removal of both ovaries (bilateral salpingo-oophorectomy). Lymphadenectomy, or removal of pelvic and para-aortic lymph nodes, is sometimes performed for tumors that have high risk features, such as pathologic grade 3 serous or clear-cell tumors, invasion of more than ½ the myometrium, or extension to the cervix or adnexa. Sometimes, removal of the omentum is also performed.

Abdominal hysterectomy is recommended over vaginal hysterectomy because it affords the opportunity to examine and obtain washings of the abdominal cavity to detect any further evidence of cancer.

Women with stage 1 disease who are at increased risk for recurrence and those with stage 2 disease are often offered surgery in combination with radiation therapy. Chemotherapy may be considered in some cases, especially for those with stage 3 and 4 disease. hormonal therapy with progestins and antiestrogens has been used for the treatment of endometrial stromal sarcomas.

Enteropathy Associated T-cell Lymphoma

The presence of a monoclonal T-cell population in non-lymphomatous enteropathic small intestinal mucosa has been described in Enteropathy associated T-cell lymphoma, ulcerative jejunitis, and nonresponsive coeliac disease.

This aggressive lymphoma almost always arises in the setting of celiac disease. Rarely the lymphoma may arise in extraintestinal sites. The most common location is the jejunum and presents as single or multiple tumors.

Esthesioneuroblastomas, Olfactory/Esthesioneuroblastoma (ENB)

Olfactory Neuroblastomas are rare neuroectodermal tumors. They are assumed to originate from olfactory receptor cells high in the nasal cavity. Unless resected at an early stage, they carry a poor prognosis. Microscopically, their typical pattern is neuroblastic with occasional formation of rosettes, but some lesions show neuroendocrine differentiation. When this pattern dominates the histology, the diagnosis of a neuro-endocrine carcinoma may occur.

Esthesioneuroblastoma (ENB) is an uncommon malignant neoplasm of the nasal vault, believed to arise from the olfactory epithelium. Because of the uncertainty surrounding its precise histological origin, various names have been ascribed to this tumor, but the only 2 terms used in recent publications are esthesioneuroblastoma and olfactory neuroblastoma.

Diagnosis

1) Lab Studies

No specific lab studies confirm the diagnosis of esthesioneuroblastoma (ENB). Because surgery often is contemplated and because open nasal procedures are associated with significant bleeding and may involve blood transfusions, a CBC count could be obtained, and the patient should be advised about preoperative blood donation.

2) Imaging Studies

CT scan

Standard radiographs do not have a role in the evaluation of ENB. A direct coronal fine-cut CT scan (ie, 3 mm) is the initial radiological study of choice.

ENB lacks a specific radiological appearance and appears as a homogeneous soft tissue mass with uniform and moderate contrast enhancement.

CT images are essential for correct staging and should be evaluated carefully for erosion of the lamina papyracea, cribriform plate, and fovea ethmoidalis.

Obstruction of the sinus-draining ostia results in an accumulation of nasal secretions, which tend to be difficult to differentiate from tumor tissue when viewed by a CT scan.

MRI

MRI often is necessary to better delineate sinonasal and intraorbital extension or an intracerebral extension.

Using MRI, ENB appears as hypointense to gray matter on T1-weighted images and isointense or hyperintense to gray matter on T2-weighted images.

Because details of bony erosion are better demonstrated by CT images, both studies usually are required in the majority of patients.

Octreoscan

Imaging with an Octreoscan is based on the binding of the radiolabeled somatostatin analog, 111In-pentoctreotide (111In-DTPA-D-Pheoctreotide), to a subset of somatostatin receptors.

In few reported cases, this imaging modality was found useful, although its sensitivity and specificity remain unclear.

Since most ENB express somatostatin receptors, Octreoscan is promising.

3) Procedures

Biopsy

Grossly, ENB appears as a gray-to-red mass in the nasal vault. The color usually is related to the extent of tumor vascularization, raising the possibility of profuse nasal bleeding following the biopsy procedure.

Taking a biopsy specimen should be deferred until completion of the radiologic studies to avoid swelling effects and the inadvertent biopsy of other nasal tumors of neurogenic origin.

Biopsy is performed after topical anesthesia under direct vision through a rigid endoscope. The specimen should be sent for regular staining as well as for immunohistochemistry and possibly electron microscopy.

4) Histologic Findings

Well-differentiated ENBs exhibit homogenous small cells with uniform round-to-oval nuclei with rosette or pseudorosette formation and eosinophilic fibrillary intercellular background material. True rosettes (ie, Flexner-Wintersteiner [FW]) refer to a ring of columnar cells circumscribing a central oval-to-round space, which appears clear on traditional pathological sections. Pseudorosettes or Horner Wright (HW) rosettes are characterized by a looser arrangement and the presence of fibrillary material within the lumen. Fibrils have been shown by electron microscopy to represent cellular cytoplasmic processes.

In undifferentiated ENB characterized by anaplastic hyperchromatic small cells with numerous mitoses and scant cytoplasm, differentiation from other small-cell nasal neoplasms via light microscopy becomes difficult. Immunohistochemical staining and electron microscopy are essential for establishing the pathological diagnosis of sinonasal small cell neoplasms, which include malignant melanoma, embryonal rhabdomyosarcoma, malignant lymphoma, extramedullary plasmocytoma, and, especially, sinonasal undifferentiated carcinoma and sinonasal neuroendocrine carcinoma. No specific immunocytologic stain identifies ENB, but a typical staining profile can be very helpful. With ENB, the stain is positive for S-100 protein and/or neuron-specific enolase, while the stain usually is negative for cytokeratin, desmin, vimentin, actin, glial fibrillary acidic protein, UMB 45, and the common leukocytic antigen. For difficult cases, electron microscopy can be useful.

ENB can be distinguished from melanoma by the lack of UMB 45 immunopositivity and the pattern of S-100 staining, which is scattered and peripheral in ENB, but, in melanoma, the staining is diffuse and strong. ENB can be distinguished from rhabdomyosarcoma by the lack of cross-striated cells (ie, rhabdomyoblasts) and an absence of immunostaining with desmin, vimentin, and actin. ENB can be distinguished from lymphoma by the lack of common leukocyte antigen immunostaining.

ENB can be distinguished from sinonasal undifferentiated carcinoma through histology (ie, absence of numerous mitotic figures, areas of necrosis, vascular invasion, glandular differentiation) and immunohistochemistry (ie, lack of staining with cytokeratin antibodies). ENB can be distinguished from neuroendocrine sinonasal carcinoma by the lack of cytokeratin immunopositivity, which, in neuroendocrine carcinoma, tends to assume a punctate paranuclear distribution upon electron microscopy. ENB can be distinguished from Ewing sarcoma (rare within the paranasal sinuses) by the lack of myc-2 protein immunostaining.

In summary, the pathological distinction of poorly differentiated small neoplasms of the nasal cavity is difficult and is based on a panel of immunohistochemical stains and, if necessary, electron microscopy. The reactions used should include S-100 protein, neuron-specific enolase, chromogranin and/or synaptophysin, cytokeratin, desmin, actin, UMB 45, common leukocytic antigen, and myc-2 protein.

The demonstration of HASH gene expression, although still investigational, could become the diagnostic procedure of choice. Mhawech et al were able to distinguish ENB from other sinonasal, poorly differentiated tumors by real-time PCR assay of hASH1 mRNA levels. In addition, as an inverse association was noted between the grade of ENBs and hASH1 mRNA levels.

Histopathologic Grading According to Hyams (1988):

From a limited series of 17 patients, Kadish et al were the first to propose a staging classification for ENB. Patients were divided into 3 categories: groups A, B, and C. Group A is limited to tumors of the nasal fossa; in group B, extension is to the paranasal sinuses; group C is defined as extension beyond the paranasal sinuses.

The Kadish classification has several shortcomings. Recognizing these inadequacies, a proposed classification is based on the Tumor Node Metastasis (TNM) system, which is predicated on CT scan and MRI findings that can be elucidated before treatment. Thus, patients treated by primary or preoperative radiation can be staged as reliably as surgical candidates. Although this classification system has gained popularity, attempts have been made to modify the Kadish system for ENB.

TNM system where T=tumor, N=node, and M=metastasis
- T1—Tumor involving the nasal cavity and/or paranasal sinuses (excluding sphenoid), sparing the most superior ethmoidal cells
- T2—Tumor involving the nasal cavity and/or paranasal sinuses (including the sphenoid), with extension to or erosion of the cribriform plate
- T3—Tumor extending into the orbit or protruding into the anterior cranial fossa, without dural invasion.
- T4—Tumor involving the brain
- N0—No cervical lymph node metastasis
- N1—Any form of cervical lymph node metastasis
- M0—No metastasis
- M1—Distant metastasis Treatment 1) Medical Care The role of an accurate histopathological diagnosis before initiating treatment for ENB cannot be overemphasized. Classic treatment strategies of ENB are based on surgery or radiotherapy as unique modalities or a combination of surgery and radiation therapy. More recently, chemotherapy has been introduced in the therapeutic armamentarium. The optimal treatment sequence varies in different institutions. Because of the lack of any randomized trial comparing these treatment protocols, the available data can be summarized as follows:

Surgery or radiation versus combined therapy
The literature gives little support to single-regimen treatments because few studies advocate either surgery or radiation alone. The authors' meta-analysis clearly provided lower recurrence rates for combined treatment.

The only conceivable indication for single-modality treatment would be a patient with a small tumor located well below the cribriform plate (eg, Dulguerov T1 stage).

Unlike most surgical specimens from the head and neck, specimens from the nasal cavity and paranasal sinuses, even en bloc, are difficult to orient and surgical margins are difficult to analyze. Because one can rarely be completely confident of the adequacy

| Grade | Lobular Architecture Preservation | Mitotic Index | Nuclear Polymorphism | Fibrillary Matrix | Rosettes | Necrosis |
|---|---|---|---|---|---|---|
| I | + | Zero | None | Prominent | HW rosettes | None |
| II | + | Low | Low | Present | HW rosettes | None |
| III | +/− | Moderate | Moderate | Low | FW rosettes | Rare |
| IV | +/− | High | High | Absent | None | Frequent | of surgical margins, postoperative radiation to minimize the risk of local recurrence seems justified in almost all patients.

Timing of surgery and radiation
  Most institutions favor surgery as the first treatment modality, followed by postoperative irradiation. The authors have found that preoperative radiation results in the usual loss of definable tumor borders, which makes an en-bloc resection problematic.
  The theoretical advantage that preoperative radiation will convert an unresectable tumor to resectable status is not supported by most head and neck oncologic surgeons.
  Preoperative radiotherapy as a standard protocol for all patients has been promoted by some institutions.

Radiation technique
  Standard techniques include external megavoltage beam and a 3-field technique; an anterior port is combined with wedged lateral fields to provide a homogeneous dose distribution. The radiation portals are nowadays planned by integrating pretreatment CT or MRI imaging within the radiotherapy software.
  The dose varies from 5500-6500 cGy and, in most cases, is more than 6000 cGy. These doses are close or exceed the radiation dose admitted to sensitive structures such as the optic nerve, optic chiasma, brainstem, retina, and lens.
  A possible role of proton beam radiotherapy, intensity-modulated radiotherapy, and stereotactic radiation has been suggested recently, but it remains to be convincingly demonstrated.

Role of chemotherapy
  The use of chemotherapy has been advocated by publications from the University of Virginia. In their protocol, patients with advanced disease (eg, Kadish stage C) are treated first with 2 cycles of cyclophosphamide (300-650 mg/m$^2$) and vincristine (1-2 mg) with or without doxorubicin, followed by 50 Gy of radiotherapy, which then is followed by a craniofacial resection. With this regimen, the 5-year and 10-year actuarial survival rates are 72% and 60%, respectively. Similar results have been obtained without chemotherapy, and how much chemotherapy contributed to the cure rates is unclear.
  Cisplatin-based regimens are preferred at the Mayo Clinic and at the Gustave-Roussy Institute in France, but, if ENBs are responsive to cisplatin, chemotherapy for high-grade tumors in the advanced setting is not curative.
  At Harvard, the selected regimen is cisplatin (33 mg/m$^2$/d) and etoposide (100 mg/m$^2$/d) for 3 days. This has been followed by proton radiation in 9 patients, with excellent results. This is probably the only study that demonstrates convincingly the possibility of a nonsurgical treatment of ENB, although the patient population is small.
  A more aggressive chemotherapy regimen was reported by Mishima et al. Eight of 12 patients receiving a combination of cyclophosphamide, doxorubicin, and vincristine with continuous-infusion cisplatin and etoposide, with radiation achieved complete response. Toxicity was acceptable according to the authors.
  Isolated case reports exist of survival after chemotherapy treatment of metastatic disease.

Conclusion
  Low-grade and low-stage tumors should be treated by surgery followed, in most cases, by radiation therapy.
  This treatment regimen should be applied to the majority of ENB, with the possible exception of T4 and the highest Hyams grade cases. In these advanced and poorly differentiated cases, the role of preoperative chemotherapy and radiation should be decided on an individual basis.
  The authors do not see a role for chemotherapy in the routine treatment of ENB. However, for patients with advanced or metastatic disease, systemic chemotherapy as part of multimodality therapy could be an option.

2) Surgical Care
  Endocranial extension and the close relationship to the ethmoidal roof and cribriform plate require a combined transfacial and neurosurgical approach. A craniotomy probably is not justified for T1 tumors, where clear radiological evidence of a normal cribriform plate and upper ethmoid cells exist. All other patients should be treated by a transfacial approach combined with a bifrontal craniotomy. In the authors' data, craniofacial resection resulted in much better local control than other surgical resections (ie, 100% vs 40%), and other series tend to support these findings.
  Craniofacial resection permits en-bloc resection of the tumor, with better assessment of any intracranial extension and protection of the brain and optic nerves.
    The en-bloc resection should include the entire ipsilateral cribriform plate and crista-galli.
    The olfactory bulb and overlaying dura should be removed with the specimen.
    Preservation of the contralateral olfactory system, when possible, results in a preserved sense of smell in a few cases.
    A tumor that does not penetrate the orbit can be encompassed by resecting the lamina papyracea or even small segments of orbital periosteum.
    To avoid late frontal sinus mucocele formation, the posterior table of the frontal sinus should be taken down, the mucosa removed, and the cranial contents allowed to fill the defect.
    Repair of the dura is facilitated by the added exposure afforded by craniotomy. Although cranial floor defects as large as 4 cm may be present, bone grafts have not been necessary. The cranial floor is repaired by various techniques, including a pericranium flap, temporalis muscle and fascia transposition, or a layer of fascia lata held with thrombin glue. This has prevented the herniation of cranial contents into the nasal cavity and the occurrence of cerebrospinal fluid leaks.
    Pneumocephalus has been prevented in the immediate postoperative period by the placement of a nasal trumpet in the operated nasal fossa, along with necessary packing, to vent any coughed or pressurized air away from the cranial cavity.
  Neck metastasis at presentation occurs in 5±7% of patients. When neck disease is diagnosed at the initial presentation, it should be treated surgically.
  In their literature review, Beitler et al found an incidence of delayed neck metastasis of 19%, but half of these patients also presented a local recurrence. Salvage treatment was successful in 70% of these patients. Contrary to the conclusion of Beitler et al, the authors do not consider that a 10% incidence rate of a delayed neck recurrence represents justification for elective neck dissection in all cases of ENB.

3) Consultations

Usually, patients with head and neck tumors are discussed in university centers, within multidisciplinary tumor boards. Head and neck tumor boards usually include a head and neck surgeon and radiation and medical oncologists. The treatment protocol is decided in common, and each specialist performs his or her own specific task as described above.

A craniofacial team, in which neurosurgeons form an essential part, usually manages ENB surgically. Most of the important complications after surgery concern the brain and calvarium; thus, close neurosurgical follow-up is necessary.

For ENB, a preoperative ophthalmology evaluation is mandatory because the optic nerves are at risk during either radical surgery or radiation. In addition, ophthalmologists could be helpful if contemplating partial intraorbital resection. Dacryocystorhinostomy usually is performed during surgery, and ophthalmologists could help in this procedure and/or the postoperative evaluation of the lacrimal system.

If contemplating an associated palate resection, the upper dental prosthesis should be made before surgery and placed at the end of the procedure. This usually achieves a separation of the oral cavity from the nasal cavity and allows adequate oral nutrition. Adjustments of this prosthesis are required after ablation of the nasal packing and following tissue scarring and/or retraction that take place within 6 months after completion of treatment.

4) Diet

No specific postoperative dietary restrictions are required for patients with ENB.

Following major surgery, patients only tolerate light meals during the first postoperative days.

Patients with a history of constipation should be given stool softeners for the first postoperative week to prevent undue straining and allow the base of skull repair to heal.

5) Activity

Some surgeons routinely place a lumbar drain to decrease pressure on the dural repair. The authors' tend to restrict CSF decompression to cases with important dural sacrifice and when the base of skull repair is deemed fragile. As long as the drain remains in place, patients require strict bed rest.

Otherwise, patients usually are out of bed on the first postoperative day.

Patients should be advised to not blow their noses for several days and to let the air out during sneezing to avoid the creation of pneumocephalus.

Ewing Sarcoma

Ewing's sarcoma is a malignant round-cell tumor. It is a rare disease in which cancer cells are found in the bone or in soft tissue. The most common areas in which it occurs are the pelvis, the femur, the humerus, and the ribs.

Because a common genetic locus is responsible for a large percentage of Ewing's sarcoma and primitive neuroectodermal tumors, these are sometimes grouped together in a category known as the Ewing family of tumors. The diseases are, however, considered to be different: peripheral primitive neuroectodermal tumors are generally not associated with bones, while Ewing's sarcomas are most commonly related to bone.

Ewing's sarcoma occurs most frequently in male teenagers, with a male/female ratio of 1.6:1.

Although usually classified as a bone tumor, Ewing's sarcoma can have characteristics of both mesodermal and ectodermal origin, making it difficult to classify.

Clinical Findings

Ewing's sarcoma is more common in males and usually presents in childhood or early adulthood, with a peak between 10 and 20 years of age. It can occur anywhere in the body, but most commonly in the pelvis and proximal long tubular bones. The diaphyses of the femur are the most common sites, followed by the tibia and the humerus. Thirty percent are overtly metastatic at presentation. It is positive for CD99 and negative for CD45.

Imaging Findings

On conventional radiographs, the most common osseous presentation is a permeative lytic lesion with periosteal reaction. The classic description of lamellated or "onion skin" type periosteal reaction is often associated with this lesion. Plain films add valuable information in the initial evaluation or screening. The wide zone of transition (e.g. permeative) is the most useful plain film characteristic in differention of benign versus aggressive or malignant lytic lesions.

MRI should be routinely used in the work-up of malignant tumors. MRI will show the full bony and soft tissue extent and relate the tumor to other nearby anatomic structures (e.g. vessels). Gadolinium contrast is not necessary as it does not give additional information over noncontrast studies, though some current researchers argue that dynamic, contrast enhanced MRI may help determine the amount of necrosis within the tumor, thus help in determining response to treatment prior to surgery.

CT can also be used to define the extraosseous extent of the tumor, especially in the skull, spine, ribs and pelvis. Both CT and MRI can be used to follow response to radiation and/or chemotherapy.

Bone scintigraphy can also be used to follow tumor response to therapy.

Differential Diagnosis

Other entities that may have a similar clinical presentation include osteomyelitis, osteosarcoma (especially telangiectatic osteosarcoma) and eosinophilic granuloma. Soft tissue neoplasms such as malignant fibrous histiocytoma that erode into adjacent bone may also have a similar appearance.

Treatment

Because almost all patients with apparently localized disease at diagnosis have occult metastatic disease, multidrug chemotherapy (often including ifosfamide and etoposide) as well as local disease control with surgery and/or radiation is indicated in the treatment of all patients.

Treatment often consists of neo-adjuvant chemotherapy generally followed by wide or radical excision, and may also include radiotherapy. Complete excision at the time of biopsy may be performed if malignancy is confirmed at that time. Treatment lengths vary depending on location and stage of the disease at diagnosis. Radical chemotherapy may be as short as 6 treatments at 3 week cycles, however most patients will undergo chemotherapy for 6-12 months and radiation therapy for 5-8 weeks.

Antisense oligodeoxynucleotides have been proposed as possible treatments.

Fibrolamellar Hepatocellular Carcinoma

Fibrolamellar hepatocellular carcinoma, or fibrolamellar carcinoma, is an uncommon malignant neoplasm of the liver. Fibrolamellar carcinoma has distinctive clinical, histologic, and radiographic features that distinguish it from the relatively more common hepatocellular carcinoma (HCC). Fibrolamellar carcinoma occurs in a younger population than does HCC, and it is typically not associated with underlying liver disease or elevated serum levels of alpha-fetoprotein tumor markers. Also, fibrolamellar carcinoma may have a slightly better prognosis than HCC. Perhaps because of the younger ages of the patients and the lack of coexisting cirrhosis, patients with fibrolamellar carcinoma are often treated aggressively. Resection of large tumor masses, of metastatic disease, and even of recurrent disease can extend patient survival. Radiographic evaluation of patients with fibrolamellar carcinoma may be used for the initial diagnosis of the tumor, for the preoperative staging of the disease, and for follow-up surveillance to detect recurrent or metastatic disease.

Pathophysiology

1) Gross Findings

Fibrolamellar carcinoma most commonly presents as a large, solitary intrahepatic mass with well-defined margins and a lobulated contour. The tumors are typically large at the time of diagnosis, with a mean diameter of 10-20 cm. Regional lymph node metastases are found in 50-70% of patients at the time of initial diagnosis. Portal or hepatic venous invasion is not typical. Grossly, the primary tumor appears as a well-demarcated, lobular, bile-stained, white or tan mass with a central stellate scar or fibrotic bands. Hemorrhage and necrosis are uncommon.

Central calcification is present in 35-60% of tumors and thus can be a useful diagnostic feature. However, fibrolamellar carcinomas are not the only liver tumors in which calcifications appear; calcifications may also be found in a minority of HCCs, as well as in some metastatic tumors, such as those arising from mucinous colon or ovarian carcinomas.

2) Microscopic Findings

Microscopically, fibrolamellar carcinomas have a characteristic pattern of nests, sheets, or cords of malignant cells, which are separated by lamellar bands of dense, hypocellular collagen connective tissue. The fibrotic connective tissue coalesces into the central scar. The malignant cells are usually well-differentiated polygonal cells containing granular cytoplasm, large nuclei, and prominent nucleoli.

Metastatic lesions appear to be histopathologically similar to the primary tumors. The internal architecture of fibrolamellar carcinomas may be heterogeneous, and foci of focal nodular hyperplasia (FNH) may occur in the liver, adjacent to the tumors. For accurate diagnosis at percutaneous biopsy, the acquisition of multiple core specimens is recommended to avoid misdiagnosis resulting from sampling error.

3) Staging

Tumors may be graded histologically according to the Broders method, as follows[2]:

In grade 1 tumors, 75-100% of the tumor cells are well differentiated.
In grade 2 tumors, 50-75% of the tumor cells are well differentiated.
In grade 3 tumors, 25-50% of the tumor cells are well differentiated.
In grade 4 tumors, 0-25% of the tumor cells are well differentiated.

Clinical Details

1) Presentation

Patients with fibrolamellar carcinoma may present with abdominal pain, a palpable abdominal mass, hepatomegaly, or cachexia. Jaundice is not common. Serum alpha-fetoprotein levels are within the reference range or mildly elevated. Liver function test results may be elevated. Patients typically do not have hepatitis or cirrhosis. Computed tomography (CT) scan findings usually suggest the diagnosis.

2) Staging

Fibrolamellar carcinoma is usually advanced at the time of initial diagnosis. Primary tumors are large, with a reported mean diameter of 10-20 cm. Extrahepatic disease, most often in regional lymph nodes, is present in as many as 80% of patients at the time of initial diagnosis. Portal or hepatic venous invasion may occur, but it is not common. Diffuse intraperitoneal carcinomatosis has been reported. Distant metastases are typically not found at the time of presentation.

3) Recurrence and Follow-up

Fibrolamellar carcinoma is an aggressive tumor that in most patients progresses to recurrent liver masses and metastatic lymph node metastases. Recurrent lesions often develop 6-18 months after attempted curative resection and may progress rapidly; therefore, follow-up imaging is recommended at 2- to 4-month intervals for at least 12-18 months after resection of the primary tumor. The early detection of metastatic disease is important because surgical resection of metastases improves patient survival rates.

Diagnosis

Abdominal CT scanning is the preferred examination for the detection, diagnosis, staging, and postoperative follow-up evaluation of fibrolamellar carcinoma. Magnetic resonance imaging (MRI) of the liver can be useful in detecting and characterizing primary tumors, and MRI may be slightly more sensitive than CT scanning in detecting multiple intrahepatic recurrent lesions. However, MRI is less sensitive than CT scanning in the detection of extrahepatic disease.

Ultrasonography has been used in the surveillance of the progression of known intrahepatic lesions. Radionuclide sulfur-colloid scans or scans obtained with labeled red blood cells are occasionally useful in the differentiation of fibrolamellar carcinomas from other types of hepatic tumors. Percutaneous biopsy with CT scanning or ultrasonographic guidance may be necessary for a definitive preoperative diagnosis of fibrolamellar carcinoma.

For the best evaluation of the liver and liver tumors with CT scanning, the intravenous administration of iodinated contrast material is necessary. Therefore, the use of CT scanning is limited in patients who cannot have iodinated contrast material because of an allergy or renal insufficiency. In these patients, MRI is preferred. In addition, CT scanning uses ionizing radiation; therefore, it can be relatively contraindicated in children or in women of childbearing age, in whom radiation doses should be limited as much as possible.

The imaging time with MRI examinations tends to be longer than with CT scanning or ultrasonography. In patients who are unwilling or unable to remain still during the imaging period, poor-quality images can result because of motion artifact; these artifacts can limit the usefulness of the MRI examination. Some patients may become claustrophobic while they are in the MRI machine; patients may require sedation, or they may not be able to complete the examination. Because of the high magnetic field strength, MRI is contraindicated in patients with a cardiac pacemaker or some internal metallic object, such as an aneurysm clip or metal shrapnel or filings in a critical location.

Ultrasonography is more operator dependent than is CT scanning or MRI, and poor technique in scanning can limit its diagnostic usefulness. Ultrasonography may be limited by the patient's anatomy. Hepatic imaging may be difficult in obese patients or in patients whose liver is located high under the ribs. Overlying bowel gas may obscure portions of the liver in some patients.

Treatment

The treatment of choice for fibrolamellar hepatocellular carcinoma is surgical resection. The tumor is usually a large, solitary, circumscribed mass, but it may have separate satellite nodules. Following resection, the five-year survival rate is 63 percent, but survivals of more than 20 years have been reported. Pulmonary metastases often follow the same indolent course as the hepatic tumor, and they also should be resected when possible.

Radiation and chemotherapy should be reserved for patients with unresectable tumors. Chemotherapy may convert a nonresectable lesion into a resectable lesion.

Gallbladder Cancer

Gallbladder cancer is a relatively uncommon cancer. If it is diagnosed early enough, it can be cured by removing the gallbladder. Most often it is found after symptoms such as abdominal pain and jaundice occur, and it has spread to other organs such as the liver.

It is a rare cancer that is still being studied and thought to be related to gallstones building up, which also can lead to calcification of the gallbladder, a condition known as Porcelain gallbladder. Porcelain gallbladder is also rare. Some studies indicate that people with porcelain gallbladder have a high risk of developing gallbladder cancer, but other studies question this. The outlook is poor for recovery if the cancer is found after symptoms have started to occur.

Signs and Symptoms

Signs and symptoms of gallbladder cancer include Steady pain in the upper right abdomen e.g. for around 2 months, Diarrhea, Burping, Weakness, Loss of appetite, Weight loss, Vomiting; Infection, leading to peritonitis, gangrene, perforation, and or liver abscess; and Jaundice, due to obstruction.

Early symptoms mimic gallbladder inflammation and gallstones, which must be excluded as the cause. Later, the symptoms may be that of biliary obstruction.

Diagnosis

Early diagnosis is not generally possible. People at high risk, such as women or Native Americans with frequent gallstones, are evaluated closely. Endoscopic ultrasound, transabdominal ultrasound, CT scan, MRI, and MR cholangiopancreatography can be used to diagnose.

Treatment

The most common and most effective treatment is surgical removal of the gallbladder (cholecystectomy) with lymph node dissection. However, with gallbladder cancer's extremely poor prognosis, most will die by one year following the surgery. If surgery is not possible, endoscopic stenting of the biliary tree can reduce jaundice. Chemotherapy and radiation may also be used with surgery.

Hepatoblastoma

Hepatoblastoma is the most common liver cancer in children, although it is relatively uncommon compared with other solid tumors in the pediatric age group. During the past several years, pathologic variations of hepatoblastoma have been identified, and techniques for establishing the diagnosis of childhood hepatic tumors have improved. Surgical techniques and adjuvant chemotherapy have markedly improved the prognosis of children with hepatoblastoma. Complete surgical resection of the tumor at diagnosis, followed by adjuvant chemotherapy, is associated with 100% survival rates, but the outlook remains poor in children with residual disease after initial resection, even if they receive aggressive adjuvant therapy.

Considerable controversy has surrounded the discrepancy between US and international hepatoblastoma therapeutic protocols; surgery and staging are initially advised in the United States, whereas adjuvant therapy is strongly considered internationally. Significant data now support a role for preoperative neoadjuvant chemotherapy if the tumor is inoperable or if the tumor is unlikely to achieve gross total resection at initial diagnosis. Early involvement of hepatologists and liver transplant teams is recommended if the tumor may not be completely resectable even with preoperative adjuvant chemotherapy. Liver transplantation is playing an increasing role in cases in which the tumor is deemed nonresectable after chemotherapy is administered or in "rescue" transplantation when initial surgery and chemotherapy are not successful.

Finally, reports state that aggressive surgical intervention may be warranted for isolated pulmonary metastases.

Diagnosis

1) Lab Studies

Diagnostic evaluation of a child in whom a liver tumor is suggested should include the following:

CBC count with differential should be obtained.
  Normochromic normocytic anemia is often present.
  Thrombocytosis may be present. In a study by Ortega et al, 60% of patients had platelet counts greater than $500 \times 10^9$/L, and 12% had platelet counts greater than $1000 \times 10^9$/L.

Liver enzyme levels are moderately elevated in 15-30% of patients.

AFP is a major serum protein synthesized by fetal liver cells, yolk sacs, and the GI tract. AFP is found in high concentrations in fetal serum and in children with hepatoblastoma, hepatocellular carcinoma, germ cell tumors, or teratocarcinoma. The tumor's ability to synthesize AFP reflects its fetal origin. Embryonal tumors produce less AFP than fetal tumors.

Levels of AFP in hepatoblastoma are often as high as 100,000-300,000 mcg/mL. Ortega et al found AFP levels elevated for age in 97% of patients.

The half-life of AFP is 4-9 days, and levels usually fall to within reference range within 4-6 weeks following resection.

Other causes of elevated AFP levels include viral hepatitis, cirrhosis, inflammatory bowel disease, and yolk sac tumors.

Although elevated AFP levels are not specific for hepatoblastoma, they provide an excellent marker for response to therapy, disease progression, and detection of recurrent disease.

Rarely, a hepatoblastoma can recur as a non-AFP-secreting tumor with metastases, even if the initial tumor was AFP secreting.

Interpretation of AFP levels can be difficult because hepatoblastoma tends to occur within the first 2 years of life. Reference range AFP levels are comparatively high at birth and even higher in premature infants, which can complicate interpretation of this value. By age 1 year, adult levels of 3-15 mcg/mL have been reached.

Data from the German Cooperative Pediatric Liver Tumor Study showed that both very low (<100 ng/L) and very high (>1,000,000 ng/L) AFP levels are associated with poorer prognosis than intermediate AFP levels.

Laboratory- and age-specific AFP values should be used.

Baseline testing of glomerular filtration rate (GFR) or creatinine clearance should be performed before cisplatin administration; follow-up studies are needed periodically to assess nephrotoxicity.

2) Imaging Studies
   Abdominal radiography
      Plain abdominal films reveal a right upper quadrant abdominal mass.
      Calcification is seen in approximately 6% of hepatic masses and 12% of hemangiomas.
   Ultrasonography
      Abdominal ultrasonography allows assessment of tumor size and anatomy, which helps in surgical planning.
      The mass usually appears hyperechoic on abdominal ultrasound images, which is particularly useful in determining vascular involvement (vessels have lower attenuation than surrounding parenchyma).
      Baseline echocardiography is needed before anthracycline (doxorubicin) administration; follow-up studies are needed to assess cardiotoxicity.
   CT scanning
      CT scanning of the abdomen using contrast reveals patchy enhancement.
      CT scanning reveals involvement of nearby structures. Regional lymph nodes are almost never involved.
      CT scanning of the chest is warranted to assess for pulmonary metastases.
   MRI: This is believed to be superior to CT scanning but does not necessarily add to the anatomic detail seen on CT scans.
   Radionuclide bone scanning: This is recommended to evaluate for bone metastases when a patient is symptomatic.
   Positron emission tomography (PET) scanning: Studies support a potential role for PET scanning at diagnosis and for follow-up evaluation in hepatoblastoma.
3) Other Tests
   A baseline audiology evaluation is needed before cisplatin or carboplatin administration; follow-up studies are needed to assess ototoxicity.
4) Procedures
   Pathologic diagnosis: Before commencing therapy, surgical diagnosis must be made. Surgical resection is the usual manner in which material for pathologic assessment is obtained. Open biopsy is performed when complete surgical resection is not possible. Needle biopsy is not recommended because these lesions usually are highly vascular.
5) Histologic Findings
   Standardizing criteria for histologic classification of hepatoblastoma has been suggested because of the significant variation in the current medical literature. Particular attention to the subtypes of this tumor and direct correlation with clinical outcomes is increasingly being incorporated into all major protocols internationally. Six histologic variants of hepatoblastoma have been described, as follows:
      Epithelial type
         Fetal pattern
         Embryonal and fetal pattern
         Macrotrabecular pattern
         Small cell undifferentiated pattern
      Mixed epithelial and mesenchymal type
         With teratoid features
         Without teratoid features
   Pure epithelial tumors account for approximately 56% of cases; they contain varying amounts of fetal cells, embryonal cells, or both. Within this group, purely fetal tumors account for 31% of hepatoblastomas; embryonal tumors account for 19% of hepatoblastomas; and macrotrabecular tumors and small cell undifferentiated types each account for 3% of hepatoblastomas. The remaining 44% of hepatoblastomas are mixed tumors containing primitive mesenchymal tissue and specialized derived components, such as myofibroblastic, chondroid, and osteoid tissues in addition to epithelial elements. Mixed tumors may express teratoid features. Teratoid hepatoblastomas are admixed with various heterologous structures of epithelial or mesenchymal origin.

Fetal cells are smaller than normal hepatocytes and have low nuclear-to-cytoplasmic (N/C) ratios and infrequent mitoses; cells form slender cords. Embryonal cells have a higher N/C ratio and more mitoses; they resemble early ducts of embryonal liver. Extramedullary hematopoiesis can be associated with mixed tumors. In tumors that have been completely resected, pure fetal histologic (PFH) results (with a 92% rate of disease-free survival) are associated with better prognosis than other histologic types, which have an overall disease-free survival rate of 57%. The absence of mitoses is a good prognostic sign. In advanced disease in which tumors cannot be completely resected, PFH results do not predict a better outcome.
6) Staging
   Staging of hepatoblastoma is based on degree of surgical resection, histologic evaluation, and presence of metastatic disease. The system cited here is based on the work of von Schweinitz et al.[25]
      Stage I
         The tumor is completely resectable via wedge resection or lobectomy.
         The tumor has PFH results.
         The AFP level is within reference range within 4 weeks of surgery.
      Stage IIA
         The tumor is completely resectable.
         The tumor has histologic results other than PFH (UH).
      Stage IIB
         The tumor is completely resectable.
         AFP findings are negative at time of diagnosis (ie, no marker to follow).
      Stage IIC
         The tumor is completely resected or rendered completely resectable by initial radiotherapy or chemotherapy or microscopic residual disease is present.
         The AFP level is elevated 4 weeks after resection.
      Stage III (any of the following)
         The tumor is initially unresectable but is confined to one lobe of liver.
         Gross residual disease is present after surgery.
         Tumor ruptures or spills preoperatively or intraoperatively.
         Regional lymph nodes are involved.
      Stage IV: Distant bone or lung metastasis is present.
   European groups have also developed a staging system through SIOPEL-1; the system uses the predictive value of pretreatment extent of disease (PRETEXT) in order to stage patients and determine which therapy is most appropriate. Using this system, physicians are able to refer higher risk patients for evaluation by liver transplant teams earlier with improved outcomes. These groups also advocate for chemotherapy treatment of lung metastases followed by surgical resection, with attempts for negative surgical margins providing optimal outcomes.
   Which staging regimen is preferred among the Children's Cancer Group (CCG) staging, Pediatric Oncology Group (POG) staging, and the European group staging is still actively discussed. However, for comparability reasons, following one staging regimen has been suggested, and international collaboration with consistency is ideal for this rare tumor.

Treatment

1) Medical Care

European groups, such as the International Society for Paediatric Oncology (SIOP), and groups in the United Kingdom and Australia, have been instrumental in demonstrating a role for preoperative adjuvant chemotherapy in improving surgical and overall outcomes. The European cooperative groups have also been very influential in encouraging a role for liver transplantation in patients with tumors deemed nonresectable. They have also developed criteria that can be used to determine which patients will benefit most from preoperative adjuvant chemotherapy as well as which patients should be referred early on for consideration for liver transplantation.

Chemotherapy

The most important advance in the care of children with hepatoblastoma has been the discovery of effective chemotherapy. Initial reports showed the efficacy of vincristine (VCR), cyclophosphamide (CPM), and doxorubicin with 5-fluorouracil (5-FU). This regimen was based on reports that suggested the efficacy of these agents in children and adults with liver tumors.

Cisplatin is the most active single agent used to treat hepatoblastoma. Doxorubicin is active as well. These agents are currently being combined in clinical trials. Attempts to reduce the ototoxic effects of cisplatin have led to the use of carboplatin; however, whether this agent will be as effective as cisplatin against hepatoblastoma remains to be seen. No direct randomized control trial has addressed this question to date.

The Intergroup Liver Tumor study showed similar efficacy of the cisplatin/5-FU/VCR regimen and the cisplatin plus doxorubicin regimen. Because the latter regimen was more toxic, the cisplatin/5-FU/VCR combination is regarded as standard in hepatoblastoma. The Intergroup Liver Tumor study demonstrated that intensification of therapy by alternating platinum analogs increased the risk of adverse outcome in children with unresectable or metastatic hepatoblastoma. The cisplatin/5-FU/VCR regimen was shown to be superior in this trial. Early referral for evaluation for liver transplantation is encouraged in these patients.

Preoperative chemotherapy can completely eradicate metastatic pulmonary disease and multinodular liver disease. Some authors recommend that all patients undergo preoperative chemotherapy, although patients may present in a setting in which resection occurs first.

Chemotherapy is usually started approximately 4 weeks after surgery to allow liver regeneration. A minimum of 2 weeks should pass after surgery before administration of cytotoxic agents.

Recent international data continue to support the role of neoadjuvant preoperative chemotherapy with improvements in survival. Data from Italy in a cohort of 13 children with hepatoblastoma also support a role for etoposide and epirubicin when combined with cisplatin, with EFS and overall survival rates at 5 years of 84% and 88%, respectively.

Treatment usually consists of 6 cycles of chemotherapy administered every 2-4 weeks; AFP levels are used as a guide to determine response to therapy.

In addition to the drugs discussed above, carboplatin and etoposide have been used along with liver transplantation for advanced or recurrent disease with some success. Paclitaxel is also used in patients with extremely high-risk disease.

Use of neoadjuvant (preoperative) chemotherapy can often render a previously inoperable tumor more easily resectable. Some data from tumor xenografts suggest that these tumors may respond to irinotecan. Irinotecan has indeed shown activity in relapsed or refractory hepatoblastoma but has not yet been used for front-line therapy.

Gemcitabine has been used with some partial responses in phase II trials. Combination therapy with other agents may improve outcomes in patients with relapsed/recurrent disease, perhaps providing decreased time to progression.

An approach with limited pediatric application is hepatic artery chemoembolization (HACE), which has been used successfully in some liver tumors in adults.

Promising studies performed in mice suggest a role for antiangiogenic agents, such as vascular endothelial growth factor (VEGF), in suppressing tumor growth in hepatoblastoma. A considerable amount of preclinical data have also demonstrated a role for multidrug resistance 1 (MDR1) inhibition as potentially leading to an improved response to chemotherapy in tumors that have otherwise become refractory to treatment because of a drug resistance mechanism.

A few isolated studies have reported patients receiving only chemotherapy with survival at greater than 5 years.

Radiotherapy

Doses used for treatment of hepatoblastoma are usually 1200-2000 centigray (cGy). These dose limits are based on the liver's limited ability to regenerate after radiation.

Radiotherapy may be used when microscopic disease is seen at the resection margins; in general, preoperative chemotherapy should minimize this.

Adjuvant radiotherapy may have a role in the treatment of chemoresistant pulmonary metastases.

2) Surgical Care

Because of the rarity of this disease and to optimize results, children with extensive hepatoblastoma should be managed and treated in centers affiliated with experienced liver transplant teams and with surgeons familiar with this diagnosis and familiar with complex decisions regarding planning for resection. These surgical and liver transplant teams work closely with oncologists, pathologists, and radiologists to provide optimal outcomes.

The hepatoblastoma can be completely resected at diagnosis in approximately one third of patients, those who have stage I or II disease. In 60% of patients, hepatoblastomas are localized but are unresectable at diagnosis. Approximately 10% of patients have metastases at diagnosis, most commonly to the lungs. These figures vary depending on the age of the patient at diagnosis, the size of the tumor, and the expertise of the surgical staff available for the procedure. Heroic efforts to resect tumors "up front" should be avoided, and adjuvant chemotherapy should be strongly considered when subtotal resection with microscopic margins is possible or when surgical morbidity is expected to be high.

Initial resection of operable primary tumors by lobectomy is the standard of care. Occasionally, pulmonary lesions are resected. This can occur after chemotherapy as well, with the ultimate goal for negative surgical margins for all disease.

The following cases warrant early referral to a transplant surgeon:
Multifocal or large solitary lesions
Tumors involving all 4 sectors of the liver
Unifocal, centrally located tumors that involve the main hilar structures or main hepatic veins
Second-look laparotomy is warranted if AFP levels remain elevated following resection. Local porta hepatis nodal sampling is performed rather than true nodal dissection because nodal involvement is rare.

The most frequent complication of surgery is intraoperative hemorrhage; loss of the entire blood volume is not uncommon.

In cases involving a substantial portion of the liver, particularly when diaphragmatic extension precludes complete surgical resection, liver transplantation has been advocated. Liver transplantation has also been considered in the presence of unresectable disease following neoadjuvant (preoperative) or adjuvant (postoperative) chemotherapy. Living related-donor transplantation may be considered in some situations as well. Early involvement of the liver transplant team and the hepatology team is essential because delays can adversely affect outcomes.

Results from numerous cooperative international large group studies on hepatoblastoma continue to support a role for preoperative adjuvant chemotherapy in those tumors not easily respectable up front. Some authors advocate using adjuvant chemotherapy preoperatively, even when resection may be successful up front. The controversy over this is considerable, but all are in agreement that complete resection with no residual disease is ultimately the most important prognostic factor for improved survival results in hepatoblastoma. Hence, any treatment, medical or surgical, that leads to an improvement in gross total resection is the goal.

Increasing evidence suggests that arterial chemoembolization is feasible in patients with unresectable hepatoblastoma, patients who are not candidates for liver transplant, or both.

Liver transplantation has an increasing role in children with nonresectable tumors or in those who show chemotherapy resistance. Overall 5-year survival is as high as 70-89% in some series. Early referral and collaboration with liver transplant centers is encouraged. Whether posttransplant chemotherapy is indicated is controversial.

Thoracotomy and resection of pulmonary metastases also have a role, with some patients having long-term disease-free survival when aggressive attempts are made to surgically eradicate all areas of disease.

3) Consultations

A multidisciplinary approach in children with malignancy is necessary to ensure that appropriate care is safely administered with minimal toxicity. The team usually consists of specialized pediatric nurses, pediatric surgeons, pharmacologists with expertise in dealing with chemotherapy in children, nutritionists, social workers, child life specialists, and subspecialists in areas such as pediatric gastroenterology, neurology, cardiology, and infectious diseases. Early referral to liver transplant centers is encouraged for nonresectable tumors or those that show chemotherapy resistance. Referral to a radiation oncologist with pediatric experience may also be indicated.

4) Diet

Adequate nutrition is necessary for childhood growth and development. Maintaining adequate nutritional status is also important to maximize response to therapy. Many of the treatments may result in compromised nutritional status. Children undergoing radiotherapy or chemotherapy, particularly children younger than 5 years, typically require enteral or parenteral supplementation, often with electrolyte supplementation as well. Occupational therapists and child life specialists may be consulted to help with behavioral issues related to feeding, particularly in infants and toddlers.

5) Activity

Specific postoperative limitations on activity may be necessary, and, occasionally, some activities are limited because of central line placement or severe immunosuppression and myelosuppression associated with therapy; otherwise, no specific limitations are placed on activity. Most children are encouraged to attend daycare or school and participate in normal play essential to childhood development. Contact sports should be avoided during therapy, especially during periods of thrombocytopenia.

Hodgkin Lymphoma

Hodgkin's lymphoma is also known as Hodgkin's disease. Hodgkin's lymphoma is characterized clinically by the orderly spread of disease from one lymph node group to another and by the development of systemic symptoms with advanced disease. Pathologically, the disease is characterized by the presence of Reed-Sternberg cells (RS cells). Hodgkin's lymphoma was one of the first cancers to be cured by radiation. Later it was one of the first to be cured by combination chemotherapy. The survival rate is generally around 90% when the disease is detected relatively early, making it one of the most curable forms of cancer. Later-stage cancers show a significantly worse prognosis.

Symptoms

Patients with Hodgkin's lymphoma may present with the following symptoms:

Lymph nodes: the most common symptom of Hodgkin's is the painless enlargement of one or more lymph nodes. The nodes may also feel rubbery and swollen when examined by a physician. The nodes of the neck and shoulders (cervical and supraclavicular) are most frequently involved (80-90% of the time, on average). The lymph nodes of the chest are often affected and these may be noticed on a chest radiograph.

Splenomegaly: enlargement of the spleen occurs in about 30% of people with Hodgkin's lymphoma. The enlargement, however, is seldom massive and the size of the spleen may fluctuate during the course of treatment.

Hepatomegaly: enlargement of the liver, due to liver involvement, is present in about five percent of cases.

Hepatosplenomegaly: the enlargement of both the liver and spleen caused by the same disease.

Pain:
Pain following alcohol consumption: classically, involved nodes are painful after alcohol consumption, though this phenomenon is rare.
Back pain: nonspecific back pain (pain that cannot be localized or its cause determined by examination or scanning techniques) has been reported in some cases of Hodgkin's lymphoma.

Systemic symptoms: about one-third of patients with Hodgkin's disease may also present with systemic symptoms, including low-grade fever; night sweats; unexplained weight loss of at least 10% of the patient's total body mass in six months or less, itchy skin (pruritus) due to increased levels of eosinophils in the bloodstream; or fatigue (lassitude). Systemic symptoms such as fever, night sweats, and weight loss are known as B symptoms; thus, presence of fever, weight loss, and night sweats indicate that the patient's stage is, for example, 2B instead of 2A.

Cyclical fever: patients may also present with a cyclical high-grade fever known as the Pel-Ebstein fever, or more simply "P-E fever". However, there is debate as to whether or not the P-E fever truly exists.

Diagnosis

Hodgkin's lymphoma must be distinguished from non-cancerous causes of lymph node swelling (such as various infections) and from other types of cancer. Definitive diagnosis is by lymph node biopsy (Usually excisional biopsy with microscopic examination). Blood tests are also performed to assess function of major organs and to assess safety for chemotherapy. Positron emission tomography (PET) is used to detect small deposits that do not show on CT scanning. In some cases a Gallium Scan may be used instead of a PET scan.

Pathology

1) Macroscopy

Affected lymph nodes (most often, laterocervical lymph nodes) are enlarged, but their shape is preserved because the capsule is not invaded. Usually, the cut surface is white-grey and uniform; in some histological subtypes (e.g. nodular sclerosis) a nodular aspect may appear.

2) Microscopy

Microscopic examination of the lymph node biopsy reveals complete or partial effacement of the lymph node architecture by scattered large malignant cells known as Reed-Sternberg cells (typical and variants) admixed within a reactive cell infiltrate composed of variable proportions of lymphocytes, histiocytes, eosinophils, and plasma cells. The Reed-Sternberg cells are identified as large often bi-nucleated cells with prominent nucleoli and an unusual CD45−, CD30+, CD15+/− immunophenotype. In approximately 50% of cases, the Reed-Sternberg cells are infected by the Epstein-Barr virus.

Characteristics of classic Reed-Sternberg cells include large size (20-50 micrometres), abundant, amphophilic, finely granular/homogeneous cytoplasm; two mirror-image nuclei (owl eyes) each with an eosinophilic nucleolus and a thick nuclear membrane (chromatin is distributed at the cell periphery).

Variants:

Hodgkin's cell (atypical mononuclear RSC) is a variant of RS cell, which has the same characteristics, but is mononucleated.

Lacunar RSC is large, with a single hyperlobated nucleus, multiple, small nucleoli and eosinophilic cytoplasm which is retracted around the nucleus, creating an empty space ("lacunae").

Pleomorphic RSC has multiple irregular nuclei.

"Popcorn" RSC (lympho-histiocytic variant) is a small cell, with a very lobulated nucleus, small nucleoli.

"Mummy" RSC has a compact nucleus, no nucleolus and basophilic cytoplasm.

Hodgkin's lymphoma can be sub-classified by histological type. The cell histology in Hodgkin's lymphoma is not as important as it is in non-Hodgkin's lymphoma: the treatment and prognosis in Hodgkin's lymphoma depend on the stage of disease rather than the histotype.

Types

Classical Hodgkin's lymphoma (excluding nodular lymphocyte predominant Hodgkin's) can be subclassified into 4 pathologic subtypes based upon Reed-Sternberg cell morphology and the composition of the reactive cell infiltrate seen in the lymph node biopsy specimen.

| Family | Name | Description |
| --- | --- | --- |
| Classical | Nodular sclerosing CHL | Is the most common subtype and is composed of large tumor nodules with lacunar RS cells subtype composed of numerous classic often pleomorphic RS cells with only few reactive lymphocytes which may easily be confused with diffuse large cell lymphoma. |
| Classical | Mixed-cellularity subtype | Is a common subtype and is composed of numerous classic RS cells admixed with numerous inflammatory cells including lymphocytes, histiocytes, eosinophils, and plasma cells. |
| Classical | Lymphocyte-rich | Is a rare subtype. |
| Classical | Lymphocyte depleted | Is a rare subtype. |
| Non-classical | Nodular lymphocyte predominant Hodgkin's lymphoma (NLPHL) | Is no longer classified as a form of classic Hodgkin's lymphoma. This is due to the fact that the RSC variants (popcorn cells) that characterize this form of the disease invariably express B lymphocyte markers such as CD20 (thus making NLPHL an unusual form of B cell lymphoma), and that (unlike classic HL) NLPHL may progress to diffuse large B cell lymphoma. There are small but clear differences in prognosis between the various forms. Lymphocyte predominant HL is an uncommon subtype composed of vague nodules of numerous reactive lymphocytes admixed with large popcorn-shaped RSC. Unlike classic RSC, the non-classic popcorn-shaped RS cells of NLPHL are CD15 and CD30 negative while positive for the B cell marker CD20. |

Staging

After Hodgkin's lymphoma is diagnosed, a patient will be staged: that is, they will undergo a series of tests and procedures which will determine what areas of the body are affected. These procedures will include documentation of their histology, a physical examination, blood tests, chest X-ray radiographs, computed tomography (CT) scans or magnetic resonance imaging (MRI) scans of the chest, abdomen and pelvis, and a bone marrow biopsy. Positron emission tomography (PET) scan is now used instead of the gallium scan for staging. In the past, a lymphangiogram or surgical laparotomy (which involves opening the abdominal cavity and visually inspecting for tumors) were performed. Lymphangiograms or laparotomies are very rarely performed, having been supplanted by improvements in imaging with the CT scan and PET scan On the basis of this staging, the patient will be classified according to a staging classification (the Ann Arbor staging classification scheme is a common one):

Stage I is involvement of a single lymph node region (I) or single extralymphatic site (Ie);

Stage II is involvement of two or more lymph node regions on the same side of the diaphragm (II) or of one lymph node region and a contiguous extralymphatic site (IIe);

Stage III is involvement of lymph node regions on both sides of the diaphragm, which may include the spleen (IIIs) and/or limited contiguous extralymphatic organ or site (IIIe, IIIes);

Stage IV is disseminated involvement of one or more extralymphatic organs.

The absence of systemic symptoms is signified by adding 'A' to the stage; the presence of systemic symptoms is signified by adding 'B' to the stage.

Treatment

Patients with early stage disease (IA or IIA) are effectively treated with radiation therapy or chemotherapy. The choice of treatment depends on the age, sex, bulk and the histological subtype of the disease. Patients with later disease (III, IVA, or IVB) are treated with combination chemotherapy alone. Patients of any stage with a large mass in the chest are usually treated with combined chemotherapy and radiation therapy. Currently, the ABVD chemotherapy regimen is the gold standard for treatment of Hodgkin's disease. The abbreviation stands for the four drugs Adriamycin, bleomycin, vinblastine, and dacarbazine. Developed in Italy in the 1970s, the ABVD treatment typically takes between six and eight months, although longer treatments may be required. Another form of treatment is the newer Stanford V regimen, which is typically only half as long as the ABVD but which involves a more intensive chemotherapy schedule and incorporates radiation therapy. However, in a randomized controlled study, Stanford V was inferior.

Another form of treatment, mainly in Europe for stages >II is BEACOPP. The cure rate with the BEACOPP esc. regimen is approximately 10-15% higher than with standard ABVD in advanced stages. Probably because some physicians think that BEACOPP induces more secondary leukemia. However, this seems negligible compared to the higher cure rates. Also, BEACOPP is more expensive because of the requirement for concurrent treatment with GCSF to increase production of white blood cells. Currently, the German Hodgkin Study group tests 8 cycles (8x) BEACOPP esc vs. 6×BEACOPP esc vs. 8×BEACOPP-14 baseline (HD15-trial).

The high cure rates and long survival of many patients with Hodgkin's lymphoma has led to a high concern with late adverse effects of treatment, including cardiovascular disease and second malignancies such as acute leukemias, lymphomas, and solid tumors within the radiation therapy field. Most patients with early stage disease are now treated with abbreviated chemotherapy and involved-field radiation therapy rather than with radiation therapy alone. Clinical research strategies are exploring reduction of the duration of chemotherapy and dose and volume of radiation therapy in an attempt to reduce late morbidity and mortality of treatment while maintaining high cure rates. Hospitals are also treating those who respond quickly to chemotherapy with no radiation.

Immunocytomal/Lymphoplasmacytic Lymphoma

Lymphoplasmacytic lymphoma (LPL), sometimes called Waldenstrom's Macroglobulinemia, is an indolent (slow growing) lymphoma. It starts in plasma cells which develop from B lymphocytes. It is a rare disease representing only 1.5% of all NHLs diagnosed by lymph node biopsy in one study. Men are slightly more likely to get this lymphoma (53% vs. 47%) and the average patient age at diagnosis is 63 years old. The disease is more common among whites than blacks.

Symptoms

This lymphoma is usually associated with Waldenstrom's macroglobulinemia—a condition of increased monoclonal immunoglobulin paraprotein (IgM) greater than 3 grams per deciliter. Most patients have bone marrow, lymph node, and splenic involvement. Some patients may develop hyperviscosity syndrome. Typically when LPL is found, the patient is in later stages with lymph node, bone marrow, and spleen involvement. If it spreads outside the lymph system the lung and gastrointestinal tract are most likely to be involved.

Causes

The etiology (root cause) of LPL is unknown but it has been suggested that occupational exposure to paints, rubber dyes and leather may be a cause but this has not been confirmed. The disease has been reported in families suggesting a genetic link—gene translocation t(9;14)(p13;q32) and rearrangement of the PAX-5 gene are reported in some cases. An association with hepatitis C was also reported.

Diagnosis & Staging

The following tests may be performed by your medical team during the diagnosis and staging of the disease: Full blood count, renal and liver function, serum uric acid, serum viscosity, cold agglutinins/cryoglobulins, beta two microglobulin, bone marrow aspiration and trephine biopsy, and CT scans.

Treatment

Treatment of lymphoplasmacytic lymphoma is broken into two illnesses:

1) Treatment for hyperviscosity. This can be accomplished by plasmapheresis if treatment of the lymphoma is not reducing the IgM but it is not a cure.
2) Treating the lymphoma (see below)

Chemotherapy with chlorambicil has been used and is the treatment of choice in Europe with about a 70% response rate and a mean survival time of 5.4 years. CHOP chemotherapy has also been used with a response rate of 60% and median survival of 5 years. Fludarabine and 2-CDA have also been used.

High dose treatment with a stem cell transplant has been used in smaller numbers of patients—patient age should be considered when contemplating a stem cell transplant. Rituxan has been tried in studies, especially with Waldenstrom's macroglobulinemia—it appears to decrease IgM but the results were rarely permanent, lasting a mean time of 8 months. Studies are being done combining Rituxan and fluarabine. Since Rituxan has an effect, other immunotherapies like bexxar may also be studied. Zevalin has entered into at least preliminary studies. Several studies have combined CHOP with rituxan for various lymphomas with positive results.

Kaposi Sarcoma

Kaposi's sarcoma (KS) is a tumor caused by Human herpesvirus 8 (HHV8), also known as Kaposi's sarcoma-associated herpesvirus (KSHV).

Clinical Features

KS lesions are nodules or blotches that may be red, purple, brown, or black, and are usually papular (ie palpable or raised).

They are typically found on the skin, but spread elsewhere is common, especially the mouth, gastrointestinal tract and respiratory tract. Growth can range from very slow to explosively fast, and is associated with significant mortality and morbidity.

Skin: Commonly affected areas include the lower limbs, face, mouth and genitalia. The lesions are usually as described above, but may occasionally be plaque-like (often on the soles of the feet) or even involved in skin breakdown with resulting fungating lesions. Associated swelling may be from either local inflammation or lymphoedema (obstruction of local lymphatic vessels by the lesion). Skin lesions may be quite disfiguring for the sufferer, and a cause of much psychosocial pathology.

Mouth: Is involved in about 30%, and is the initial site in 15% of AIDS related KS. In the mouth, the hard palate is most frequently affected, followed by the gums. Lesions in the mouth may be easily damaged by chewing and bleed or suffer secondary infection, and even interfere with eating or speaking.

Gastrointestinal tract: Involvement can be common in those with transplant related or AIDS related KS, and it may occur in the absence of skin involvement. The gastrointestinal lesions may be silent or cause weight loss, pain, nausea/vomiting, diarrhea, bleeding (either vomiting blood or passing it with bowel motions), malabsorption, or intestinal obstruction.

Respiratory tract: Involvement of the airway can present with shortness of breath, fever, cough, hemoptysis (coughing up blood), or chest pain, or as an incidental finding on chest x-ray. The diagnosis is usually confirmed by bronchoscopy when the lesions are directly seen, and often biopsied.

Pathophysiology and Diagnosis

Despite its name, it is generally not considered a true sarcoma, which is a tumor arising from mesenchymal tissue. KS actually arises as a cancer of lymphatic endothelium and forms vascular channels that fill with blood cells, giving the tumor its characteristic bruise-like appearance.

KS lesions contain tumor cells with a characteristic abnormal elongated shape, called spindle cells. The tumor is highly vascular, containing abnormally dense and irregular blood vessels, which leak red blood cells into the surrounding tissue and give the tumor its dark color. Inflammation around the tumor may produce swelling and pain.

Although KS may be suspected from the appearance of lesions and the patient's risk factors, a definite diagnosis can only be made by biopsy and microscopic examination, which will show the presence of spindle cells. Detection of the viral protein LANA in tumor cells confirms the diagnosis.

Treatment and Prevention

Kaposi's sarcoma is not curable, in the usual sense of the word, but it can often be effectively palliated for many years and this is the aim of treatment. In KS associated with immunodeficiency or immunosuppression, treating the cause of the immune system dysfunction can slow or stop the progression of KS. In 40% or more of patients with AIDS-associated Kaposi's sarcoma, the Kaposi lesions will shrink upon first starting highly active antiretroviral therapy (HAART). However, in a certain percentage of such patients, Kaposi's sarcoma may again grow after a number of years on HAART, especially if HIV is not completely suppressed. Patients with a few local lesions can often be treated with local measures such as radiation therapy or cryosurgery. Surgery is generally not recommended as Kaposi's sarcoma can appear in wound edges. More widespread disease, or disease affecting internal organs, is generally treated with systemic therapy with interferon alpha, liposomal anthracyclines (such as Doxil) or paclitaxel.

With the decrease in the death rate among AIDS patients receiving new treatments in the 1990s, the incidence and severity of epidemic KS also decreased. However, the number of patients living with AIDS is increasing substantially in the United States, and it is possible that the number of patients with AIDS-associated Kaposi's sarcoma will again rise as these patients live longer with HIV infection.

Blood tests to detect antibodies against KSHV have been developed and can be used to determine if a patient is at risk for transmitting infection to his or her sexual partner, or if an organ is infected prior to transplantation.

Krukenberg Tumor

A Krukenberg tumor, also Krukenberg tumour, classically refers to a secondary ovarian malignancy whose primary site arose in the gastrointestinal tract. Krukenberg tumors are often found in both ovaries. Microscopically, they are characterized by appearance of mucin-secreting signet-ring cells in the tissue of the ovary; when the primary tumor is discovered, the same signet-ring cells will be found.

Symptoms

Patients with Krukenberg tumor often come to the attention of their doctor when they present complaining of abdominal or pelvic pain, bloatedness, vaginal bleeding, a change in their menstrual habit or pain during intercourse. These symptoms are non-specific (i.e. they point to a range of problems other than cancer) and a diagnosis can only be made following Computed Tomography (CT) scans, laparotomy and/or a biopsy of the ovary.

Pathogenesis

There is some debate over the exact mechanism of metastasis of the tumour cells from the stomach, appendix or colon to the ovaries; classically it was thought that direct seeding across the abdominal cavity accounted for the spread of this tumor, but recently some researchers have suggested that lymphatic (i.e. through the lymph nodes), or haematogenous (i.e. through the blood) spread is more likely, as most of these tumours are found on the inside of the ovaries. Proponents of this theory cite the fact that metastases are never found in the omentum (the fatty apron which envelops the organs of the abdomen and lies between the stomach and ovaries), and that the tumor cells are found within the ovary and not growing inwards. However, this remains a controversy, as cases in Hong Kong always showed omental spread and peritoneal seedlings in patients with Krukenberg tumours.

Although a Krukenberg tumor is most commonly a metastasis from a gastric cancer (usually an adenocarcinoma), this is not always the case. Other tumours of the gastrointestinal tract (including, significantly, colon cancer) have been known to cause Krukenberg tumours, and recent case-reports of Krukenberg tumors originating from tumors of the tip of the appendix have appeared in the medical literature.

Treatment and Prognosis

Since the Krukenberg tumor is a secondary (metastatic) tumor, management of the tumor must involve finding and treating the primary cancer. In general, most cases of Krukenberg tumor have a poor prognosis and radical operation such as removal of the ovaries (and the colon or appendix if involved) can improve survival only in cases of solitary ovarian metastasis or local extended disease (i.e. the lesion is located only in the pelvis). Cancer chemotherapy and radiotherapy before surgery may be used to shrink the tumor and facilitate its removal.

Laryngeal Carcinoma

Laryngeal cancer may also be called cancer of the larynx or laryngeal carcinoma. Most laryngeal cancers are squamous cell carcinomas, reflecting their origin from the squamous cells which form the majority of the laryngeal epithelium. Cancer can develop in any part of the larynx, but the cure rate is affected by the location of the tumor. For the purposes of tumour staging, the larynx is divided into three anatomical regions: the glottis (true vocal cords, anterior and posterior commissures); the supraglottis (epiglottis, arytenoids and aryepiglottic folds, and false cords); and the subglottis.

Most laryngeal cancers originate in the glottis. Supraglottic cancers are less common, and subglottic tumours are least frequent.

Laryngeal cancer may spread by direct extension to adjacent structures, by metastasis to regional cervical lymph nodes, or more distantly, through the blood stream. Distant metastates to the lung are most common.

Symptoms

The symptoms of laryngeal cancer depend on the size and location of the tumor. Symptoms may include the following: Hoarseness or other voice changes, a lump in the neck, a sore throat or feeling that something is stuck in the throat, persistent cough, Stridor, Bad breath and Earache.

Diagnosis

Diagnosis is made by the doctor on the basis of a careful medical history, physical examination, and special investigations which may include a chest x-ray, CT or MRI scans, and tissue biopsy. The examination of the larynx requires some expertise, which may require specialist referral.

The physical exam includes a systematic examination of the whole patient to assess general health and to look for signs of associated conditions and metastatic disease. The neck and supraclavicular fossa are palpated to feel for cervical adenopathy, other masses, and laryngeal crepitus. The oral cavity and oropharynx are examined under direct vision. The larynx may be examined by indirect laryngoscopy using a small angled mirror with a long handle (akin to a dentist's mirror) and a strong light. Indirect laryngoscopy can be highly effective, but requires skill and practice for consistent results. For this reason, many specialist clinics now use fibre-optic nasal endoscopy where a thin and flexible endoscope, inserted through the nostril, is used to clearly visualise the entire pharynx and larynx. Nasal endoscopy is a quick and easy procedure performed in clinic. Local anaesthetic spray may be used.

If there is a suspicion of cancer, biopsy is performed, usually under general anaesthetic. This provides definitive histological proof of cancer type and grade. If the lesion appears to be small and well localised, the surgeon may undertake excision biopsy, where an attempt is made to completely remove the tumour at the time of first biopsy. In this situation, the pathologist will not only be able to confirm the diagnosis, but can also comment on the completeness of excision, i.e., whether the tumour has been completely removed. A full endoscopic examination of the larynx, trachea, and esophagus is often performed at the time of biopsy.

For small glottic tumours further imaging may be unnecessary. In most cases, tumour staging is completed by scanning the head and neck region to accurately assess the local extent of the tumour and any pathologically enlarged cervical lymph nodes. The final management plan will depend on the specific site, stage (tumour size, nodal spread, distant metastasis), and histological type. The overall health and wishes of the patient must also be taken into account.

Staging System

The AJCC has designated staging by using the tumors, nodes, and metastases (TNM) classification. Definitions for the stages are described below.

1) Primary Tumor, T Stage

TX indicates that the primary tumor cannot be assessed; T0 means no evidence of primary tumor; and Tis indicates carcinoma in situ.

In the supraglottis, the T stages are as follows: T1, tumor limited to 1 subsite of the supraglottis with normal vocal cord mobility; T2, tumor invasion of the mucosa of more than 1 adjacent subsite of the supraglottis or glottis or of a region outside the supraglottis (eg, mucosa of base of tongue, vallecula, medial wall of pyriform sinus), without fixation of the larynx; T3, tumor limited to the larynx with vocal cord fixation and/or invasion of any of the postcricoid area or pre-epiglottic tissues; T4, tumor invasion through the thyroid cartilage and/or extension into soft tissues of the neck, thyroid, and/or esophagus.

Subsites include the following: false cords, arytenoids, suprahyoid epiglottis, infrahyoid epiglottis, and aryepiglottic folds (laryngeal aspect).

In the glottis, the T stages are as follows: T1, tumor limited to the vocal cord (may involve anterior or posterior commissure) with normal mobility; T2, tumor extension to the supraglottis and/or subglottis and/or impaired vocal cord mobility; T3, tumor limited to the larynx with vocal cord fixation; and T4, tumor invasion through the thyroid cartilage and/or other tissues beyond the larynx (eg, trachea or soft tissues of the neck, including the thyroid and pharynx).

Stage T1 can be subdivided into T1a, in which the tumor limited to 1 vocal cord and T1 b, in which the tumor involves both vocal cords.

In the subglottis, the T stages are as follows: T1, tumor limited to the subglottis; T2, tumor extension to a vocal cord with normal or impaired mobility; T3, tumor limited to the larynx with vocal cord fixation; T4, tumor invasion through cricoid or thyroid cartilage and/or extension to other tissues beyond the larynx (eg, trachea or soft tissues of neck, including the thyroid and esophagus).

2) Regional Lymph Nodes, N Stage

The N stages are as follows NX, regional lymph nodes cannot be assessed; N0, no regional lymph node metastasis; N1, metastasis in a single ipsilateral lymph node, 3 cm or less in greatest dimension; N2, metastasis in a single ipsilateral lymph node more than 3 cm but not more than 6 cm in greatest dimension, metastases in multiple ipsilateral lymph nodes with none more than 6 cm in greatest dimension, or metastases in bilateral or contralateral lymph nodes none more than 6 cm in greatest dimension; and N3, metastasis in a lymph node more than 6 cm in greatest dimension.

Stage N2 may be further subdivided as follows: N2a, metastasis in a single ipsilateral lymph node more than 3 cm but not more than 6 cm in greatest dimension; N2b, metastasis in multiple ipsilateral lymph nodes, none more than 6 cm in greatest dimension; and N2c, metastasis in bilateral or contralateral lymph nodes, none more than 6 cm in greatest dimension.

3) Distant Metastasis, M Stage

MX indicates that distant metastasis cannot be assessed; M0, no distant metastasis; and M1, distant metastasis.

Treatment

Specific treatment depends on the location, type, and stage of the tumour. Treatment may involve surgery, radiotherapy, or chemotherapy, alone or in combination. This is a specialised area which requires the coordinated expertise of dedicated ear, nose and throat (ENT) surgeons (otolaryngologists) and oncologists.

Leiomyosarcoma

Leiomyosarcoma is a type of sarcoma which is a neoplasm of smooth muscle. (When benign, it is called a leiomyoma.) Smooth muscle cells make up the involuntary muscles, which are found in most parts of the body: in uterus, stomach and intestines, walls of all blood vessels, and skin. It is therefore possible for leiomyosarcomas to appear at any site in the body. It is however most commonly found in the stomach, small intestine and retroperitoneum.

Leiomyosarcoma is a very rare cancer. It makes up 7% of soft tissue sarcomas, which are themselves rare cancers Causes and Symptoms The exact causes of leiomyosarcoma are not known, but there are genetic and environmental risk factors associated with it. Certain inherited conditions that run in families may increase the risk of developing leiomyosarcoma. High-dose radiation exposure, such as radiotherapy used to treat other types of cancer, has also been linked to leiomyosarcoma. It is possible that exposure to certain chemical herbicides may increase the risk of developing sarcomas, but this association has not been proven.

Since leiomyosarcoma can occur in any location, the symptoms are different and depend on the site of the tumor. When leiomyosarcoma begins in an organ in the abdomen, such as the stomach or small bowel, the physician may be able to feel a large lump or mass when he examines the abdomen. When leiomyosarcoma affects a blood vessel, it may block the flow of blood to the body part supplied by the artery. Commonly occurring symptoms include painless lump or mass, painful swelling, abdominal pain, weight loss, nausea and vomiting.

Diagnosis

Some patients who have leiomyosarcomas may be visiting the doctor because they have discovered a lump or mass or swelling on a body part. Others have symptoms related to the internal organ that is affected by the leiomyosarcoma. For example, a tumor in the stomach may cause nausea, feelings of fullness, internal bleeding, and weight loss. The patient's doctor will take a detailed medical history to find out about the symptoms. The history is followed by a complete physical examination with special attention to the suspicious symptom or body part.

Depending on the location of the tumor, the doctor may order imaging studies such as x ray, computed tomography (CT) scan, and magnetic resonance imaging (MRI) to help determine the size, shape, and exact location of the tumor. A biopsy of the tumor is necessary to make the definitive diagnosis of leiomyosarcoma. The tissue sample is examined by a pathologist (specialist in the study of diseased tissue).

Types of Biopsy

The type of biopsy done depends on the location of the tumor. For some small tumors, the doctor may perform an excisional biopsy, removing the entire tumor and a margin of surrounding normal tissue. Most often, the doctor will perform an incisional biopsy, a procedure that involves cutting out only a piece of the tumor that is used to determine its type and grade.

Treatment

Treatment for leiomyosarcoma varies depending on the location of the tumor, its size and grade, and the extent of its spread. Treatment planning also takes into account the patient's age, medical history, and general health.

Leiomyosarcomas on the arms and legs may be treated by amputation (removal of the affected limb) or by limb-sparing surgery to remove the tumor. These tumors may also be treated with radiation therapy, chemotherapy, or a combination of both.

Generally, tumors inside the abdomen are surgically removed. The site, size, and extent of the tumor determine the type of surgery performed. Leiomyosarcomas of organs in the abdomen may also be treated with radiation and chemotherapy.

Alternative and Complementary Therapies

Many patients explore alternative and complementary therapies to help to reduce the stress associated with illness, improve immune function, and feel better. While there is no evidence that these therapies specifically combat disease, activities such as biofeedback, relaxation, therapeutic touch, massage therapy, and guided imagery have been reported to enhance well-being.

Leukemia

Leukemia includes Mast cell leukemia, Hairy cell leukaemia, Chronic lymphocytic leukaemia, Chronic myeloid leukaemia, Acute erythroblastic leukemia, Acute lymphoblastic leukemia (ALL), Acute myeloid leukemia AML and Adult T cell leukemia.

Classification of Leukemia

Leukemia is clinically and pathologically subdivided into several large groups. The first division is between its acute and chronic forms:

Acute leukemia is characterized by the rapid increase of immature blood cells. This crowding makes the bone marrow unable to produce healthy blood cells. Acute forms of leukemia can occur in children and young adults. (In fact, it is a more common cause of death for children in the US than any other type of malignant disease). Immediate treatment is required in acute leukemias due to the rapid progression and accumulation of the malignant cells, which then spill over into the bloodstream and spread to other organs of the body. Central nervous system (CNS) involvement is uncommon, although the disease can occasionally cause cranial nerve palsies.

Chronic leukemia is distinguished by the excessive build up of relatively mature, but still abnormal, blood cells. Typically taking months or years to progress, the cells are produced at a much higher rate than normal cells, resulting in many abnormal white blood cells in the blood. Chronic leukemia mostly occurs in older people, but can theoretically occur in any age group. Whereas acute leukemia must be treated immediately, chronic forms are sometimes monitored for some time before treatment to ensure maximum effectiveness of therapy.

Additionally, the diseases are subdivided according to which kind of blood cell is affected. This split divides leukemias into lymphoblastic or lymphocytic leukemias and myeloid or myelogenous leukemias:

In lymphoblastic or lymphocytic leukemias, the cancerous change took place in a type of marrow cell that normally goes on to form lymphocytes.

In myeloid or myelogenous leukemias, the cancerous change took place in a type of marrow cell that normally goes on to form red cells, some types of white cells, and platelets.

Combining these two classifications provides a total of four main categories:

| Cell type | Acute | Chronic |
|---|---|---|
| Lymphocytic leukemia (or "lymphoblastic") | Acute lymphocytic leukemia (ALL) | Chronic lymphocytic leukemia (CLL) |
| Myelogenous leukemia (also "myeloid" or "nonlymphocytic") | Acute myelogenous leukemia (AML) | Chronic myelogenous leukemia (CML) |

Symptoms of Leukemia

Damage to the bone marrow, by way of displacing the normal bone marrow cells with higher numbers of immature white blood cells, results in a lack of blood platelets, which are important in the blood clotting process. This means people with leukemia may become bruised, bleed excessively, or develop pinprick bleeds (petechiae).

White blood cells, which are involved in fighting pathogens, may be suppressed or dysfunctional. This could cause the patient's immune system to be unable to fight off a simple infection or to start attacking other body cells.

Finally, the red blood cell deficiency leads to anemia, which may cause dyspnea. All symptoms can be attributed to other diseases.

Some other related symptoms include: Fever, chills, night sweats and other flu-like symptoms, Weakness and fatigue, Swollen or bleeding gums, Neurological symptoms (headaches), Enlarged liver and spleen, Frequent infection, Bone pain, Joint pain, Dizziness, Nausea, Swollen tonsils, Diarrhea, Paleness, Malaise and Unintentional weight loss The word leukemia, which means 'white blood', is derived from the disease's namesake high white blood cell counts that most leukemia patients have before treatment. The high number of white blood cells are apparent when a blood sample is viewed under a microscope. Frequently, these extra white blood cells are immature or dysfunctional. The excessive number of cells can also interfere with the level of other cells, causing a harmful imbalance in the blood count.

Some leukemia patients do not have high white blood cell counts visible during a regular blood count. This less-common condition is called aleukemia. The bone marrow still contains cancerous white blood cells which disrupt the normal production of blood cells. However, the leukemic cells are staying in the marrow instead of entering the bloodstream, where they would be visible in a blood test. For an aleukemic patient, the white blood cell counts in the bloodstream can be normal or low. Aleukemia can occur in any of the four major types of leukemia, and is particularly common in hairy cell leukemia.

Diagnosis of Leukemia

Diagnosis requires blood tests to look for an abnormal number of white blood cells, and/or a bone marrow examination to look for abnormal numbers or forms of cells in the bone marrow.

Treatment of Leukemia by Type

1) Acute Lymphoblastic Leukemia (ALL)

Management of ALL focuses on control of bone marrow and systemic (whole-body) disease. Additionally, treatment must prevent leukemic cells from spreading to other sites, particularly the central nervous system (CNS). In general, ALL treatment is divided into several phases:

Induction chemotherapy to bring about bone marrow remission. For adults, standard induction plans include prednisone, vincristine, and an anthracycline drug; other drug plans may include L-asparaginase or cyclophosphamide. For children with low-risk ALL, standard therapy usually consists of three drugs (prednisone, L-asparaginase, and vincristine) for the first month of treatment.

Consolidation therapy to eliminate any remaining leukemia cells. This typically requires one to three months in adults and four to eight months in children. Patients with low- to average-risk ALL receive therapy with antimetabolite drugs such as methotrexate and 6-mercaptopurine (6-MP). High-risk patients receive higher drug doses of these drugs, plus additional drugs.

CNS prophylaxis (preventive therapy) to stop the cancer from spreading to the brain and nervous system. Standard prophylaxis may include radiation of the head and/or drugs delivered directly into the spine.

Maintenance treatments with chemotherapeutic drugs to prevent disease recurrence once remission has been achieved. Maintenance therapy usually involves lower drug doses, and may continue for two years.

Alternatively, allogeneic bone marrow transplantation may be appropriate for high-risk or relapsed patients.

2) Chronic Lymphocytic Leukemia (CLL)

Hematologists base CLL treatment upon both the stage and symptoms of the individual patient. A large group of CLL patients have low-grade disease, which does not benefit from treatment. Individuals with CLL-related complications or more advanced disease often benefit from treatment. In general, the indications for treatment are: a) falling hemoglobin or platelet count, b) progression to a later stage of disease, c) painful, disease-related overgrowth of lymph nodes or spleen and d) an increase in the rate of lymphocyte production.

CLL is probably incurable by present treatments. The primary chemotherapeutic plan is combination chemotherapy with chlorambucil or cyclophosphamide, plus a corticosteroid such as prednisone or prednisolone. The use of a corticosteroid has the additional benefit of suppressing some related autoimmune diseases, such as immunohemolytic anemia or immune-mediated thrombocytopenia. In resistant cases, single-agent treatments with nucleoside drugs such as fludarabine, pentostatin, or cladribine may be successful. Younger patients may consider allogeneic or autologous bone marrow transplantation.

3) Acute Myelogenous Leukemia (AML)

Many different anti-cancer drugs are effective for the treatment of AML. Treatments vary somewhat according to the age of the patient and according to the specific subtype of AML. Overall, the strategy is to control bone marrow and systemic (whole-body) disease, while offering specific treatment for the central nervous system (CNS), if involved.

In general, most oncologists rely on combinations of drugs for the initial, induction phase of chemotherapy. Such combination chemotherapy usually offers the benefits of early remission and a lower risk of disease resistance. Consolidation and maintenance treatments are intended to prevent disease recurrence. Consolidation treatment often entails a repetition of induction chemotherapy or the intensification chemotherapy with additional drugs. By contrast, maintenance treatment involves drug doses that are lower than those administered during the induction phase.

4) Chronic Myelogenous Leukemia (CML)

There are many possible treatments for CML, but the standard of care for newly diagnosed patients is imatinib (Gleevec) therapy. Compared to most anti-cancer drugs, it has relatively few side effects and can be taken orally at home. With this drug, more than 90% of patients will be able to keep the disease in check for at least five years, so that CML becomes a chronic, manageable condition.

In a more advanced, uncontrolled state, when the patient cannot tolerate imatinib, or if the patient wishes to attempt a permanent cure, then an allogeneic bone marrow transplantation may be performed. This procedure involves high-dose chemotherapy and radiation followed by infusion of bone marrow from a compatible donor. Approximately 30% of patients die from this procedure.

5) Hairy Cell Leukemia (HCL)

Patients with hairy cell leukemia who are symptom-free typically do not receive immediate treatment. Treatment is generally considered necessary when the patient shows signs and symptoms such as low blood cell counts (e.g., infection-fighting neutrophil count below 1.0 K/μL), frequent infections, unexplained bruises, anemia, or fatigue that is significant enough to disrupt the patient's everyday life.

Patients who need treatment usually receive either one week of cladribine, given daily by intravenous infusion or a simple injection under the skin, or six months of pentostatin, given every four weeks by intravenous infusion. In most cases, one round of treatment will produce a prolonged remission.

Other treatments include rituximab infusion or self-injection with Interferon-alpha. In limited cases, the patient may benefit from splenectomy (removal of the spleen). These treatments are not typically given as the first treatment because their success rates are lower than cladribine or pentostatin.

Liposarcoma

Liposarcoma is a malignant tumor that arises in fat cells in deep soft tissue, such as that inside the thigh or in the retroperitoneum.

They are typically large bulky tumors which tend to have multiple smaller satellites extending beyond the main confines of the tumor.

Because of their rarity, liposarcomas are best treated by a sarcoma center.

Symptoms

Patients usually note a deep seated mass in their soft tissue. Only when the tumor is very large do symptoms of pain or functional disturbances occur.

Retroperitoneal tumors may present themselves with signs of weight loss and emaciation and abdominal pain. These tumors may also compress the kidney or ureter leading to kidney failure.

Diagnosis

1) Lab Studies

Cytogenetics may be of value when diagnosing lipomatous tumors because different tumor types have different more or less specific chromosomal abnormalities.[6] The lipoblastoma, for example, often exhibits rearrangements of bands 8q11-13, and the gene PLAG1 has been implicated as the target of these chromosomal changes.

2) Imaging Studies

CT scanning is superior to MRI in detailing cortical bone erosion and tumor mineralization, whereas MRI is useful in providing views of the long axis of the limb and in depicting the fatty nature of the tumor.

Most liposarcomas have well-defined and mostly lobulated margins. The well-differentiated liposarcomas are composed of mainly fat with septa or nodules. These tumors are hyperintense on T2-weighted images, and they demonstrate faint enhancement or no enhancement after the intravenous administration of contrast material.

Myxoid liposarcomas are homogeneous or mildly heterogeneous, and a pseudocapsule can be present.

Pleomorphic types have a markedly heterogeneous internal structure.

Both myxoid and pleomorphic lesions have moderate or marked heterogeneous enhancement after the administration of contrast material.

Well-differentiated liposarcomas may be distinguished from the other types by their largely lipomatous appearance. The malignancy grade increases with the degree of tumor heterogeneity and contrast enhancement.

Angiography may demonstrate tumor malignancy on the basis of prominent vascularity; thus, angiography may be of value in planning surgical resection.

Chest radiography may be used as an initial screening for pulmonary metastases; however, the definitive test for detection of pulmonary metastases is chest CT.

An early-phase bone scan may show a marked increase of radioisotopic uptake.

Risk assessment in liposarcoma patients can be based on [(18)F]fluorodeoxyglucose (FDG) PET imaging.[7] Although tumor grade and subtype are considered standard parameters for risk assessment in patients with liposarcoma, pretherapy tumor standardized uptake values obtained by FDG PET imaging was found to be a more useful parameter for risk assessment in liposarcoma compared with tumor grade or subtype. A maximum standardized uptake value of more than 3.6 was associated with significantly reduced disease-free survival and identified patients at high risk for developing early local recurrences or metastatic disease.

3) Procedures

The diagnostic procedure of choice for liposarcoma is open biopsy.

With superficial, small, fatty tumors, excisional biopsy is recommended for diagnosis.

In large (>3 cm) and deep tumors, diagnosis and treatment may involve open incisional biopsy followed by definitive resection.

Fine needle aspiration or biopsy should be followed by histologic and immunohistochemical examination. Immunohistochemical examination aids in excluding other sarcomas. Lipid staining may be helpful, although Sudan black or oil red O stains are generally insufficient for diagnosis. Helpful stains include the following:

S-100—Positive results in fat cells and lipoblasts

Alpha-1-antitrypsin—Positive results in malignant fibrous histiocytomas

Desmin—Positive results in leiomyosarcomas

Myoglobin—Positive results in rhabdomyosarcomas

4) Histologic Findings

The recognition of lipoblasts is the key finding in the diagnosis of liposarcoma. A lipoblast has the ability to produce and accumulate non-membrane-bound lipid within its cytoplasm. The key morphologic features are well-demarcated cytoplasmic lipid that shifts, causes indentations in an irregular hyperchromatic nucleus, and creates a characteristic scalloping of the nuclear membrane.

The stage and further differentiation into 1 of the 4 major types affect the prognosis. Well-differentiated liposarcomas usually contain a predominance of mature fat cells with relatively few, widely scattered lipoblasts. A misdiagnosis of lipoma can result from inadequate sampling. In the sclerosing subtype of a well-differentiated liposarcoma, collagen fibrils that encircle fat cells and lipoblasts make up a prominent part of the matrix.

Myxoid liposarcoma, the most common type, is diagnosed by the observation of a delicate plexiform capillary network that is associated with both primitive mesenchyme-like cells and a variable number of lipoblasts. The stroma contains a large proportion of myxoid ground substance (ie, hyaluronic acid), in which numerous microcysts may form.

In the round-cell type, lipoblasts are interspersed among sheets of poorly differentiated round cells.

Poorly differentiated pleomorphic liposarcoma is recognized by a mixture of bizarre, often multivacuolated lipoblasts and atypical stromal cells, many of which contain highly abnormal mitotic figures. Hemorrhagic and necrotic areas are common. Lipoblasts are present.

5) Staging

The Enneking oncologic staging system defines the biologic behavior of primary tumors. This system has proven to be effective in planning surgery for limb lesions (eg, intralesional, marginal, wide, radical) and in evaluating its results.

The Enneking staging system divides benign tumors into 3 stages: S1, S2, and S3.

Localized malignant tumors are divided into 4 stages: IA, IB, IIA, and IIB.

Two other stages include metastatic high-grade intracompartmental tumors, or stage IIIA tumors, and extracompartmental malignant tumors, or stage IIIB tumors.

This classification scheme was formerly used to describe long-bone tumors.

This staging system is based on a complete preoperative workup that includes an assessment of the clinical features; the radiographic pattern and CT and MRI data regarding the extension of the tumor; the peculiar imaging features of the tumor and its relationship to the neighboring tissues; the findings from isotopic scanning, which provides information about local aggression and systemic diffusion; and the histologic findings obtained at biopsy.

Surgical staging is appropriate only after the diagnosis is established and the oncologic stage is determined.

Treatment

1) Medical Care

Liposarcoma has a number of different subtypes (ie, well differentiated, dedifferentiated, myxoid/round cell, pleomorphic), and their response to chemotherapy is not well documented. Thus, the response rates to chemotherapy of the different histological subtypes and overall and progression free survival were investigated; survival according to histological grade was also assessed. This retrospective analysis suggested that myxoid liposarcoma is relatively chemosensitive in comparison to a combination of other liposarcomas, in particular dedifferentiated and well-differentiated tumors.

In the case of well-differentiated liposarcoma, grade provides no incremental information over other histological subtypes in terms of response to therapy. In myxoid/round cell liposarcoma, the presence of a round cell component may be an adverse prognostic sign. Tumor site, a high proliferative fraction noted with MIB-1 labeling, and TP53 missense mutations are also adverse prognostic factors in myxoid/round cell tumors.

For liposarcomas, radiation therapy may be a valuable adjunct to surgery, especially in those of the myxoid variant.

The use of chemotherapy in liposarcomas remains experimental.

Although surgical resection is the mainstay of curative treatment, patients with large high-grade liposarcomas may benefit from multimodality treatment with chemotherapy and radiation.

2) Surgical Care

The rationale for wide surgical excision of atypical lipomatous tumors is the prevention of recurrence and dedifferentiation.

Wide and deep surgical excision, along with local radiation and/or chemotherapy, may be necessary for high-grade lesions.

Given the favorable outcome with wide surgical excision alone, regardless of the histologic type of the tumor, some authors believe that adjuvant radiation therapy is unjustified.

3) Consultations

Oncologist: When malignancy is strongly suspected or when previous incisional biopsy reveals liposarcoma, consultation with an oncologist prior to the definitive surgical procedure is recommended.

Radiation oncologist: Adjuvant therapy may be indicated in cases in which excision is incomplete. In such cases, consultation with a radiation oncologist is recommended.

Liver Cancer, Primary

Liver cancer is made by the presence of malignant hepatic tumors—tumors or growths on or in the liver. They may be discovered on medical imaging (even for a different reason than the cancer itself), or may be present in patients as an abdominal mass, hepatomegaly, abdominal pain, jaundice, or some other liver dysfunction.

Liver cancer (hepatocellular carcinoma) is a cancer arising from the liver. It is also known as primary liver cancer or hepatoma. The liver is made up of different cell types (for example, bile ducts, blood vessels, and fat-storing cells). However, liver cells (hepatocytes) make up 80% of the liver tissue. Thus, the majority of primary liver cancers (over 90 to 95%) arises from liver cells and is called hepatocellular cancer or carcinoma.

When patients or physicians speak of liver cancer, however, they are often referring to cancer that has spread to the liver, having originated in other organs (such as the colon, stomach, pancreas, breast, and lung). More specifically, this type of liver cancer is called metastatic liver disease (cancer) or secondary liver cancer. Thus, the term liver cancer actually can refer to either metastatic liver cancer or hepatocellular cancer.

Risk Factors for Liver Cancer

1) Hepatitis B Infection

The role of hepatitis B virus (HBV) infection in causing liver cancer is well established. Several lines of evidence point to this strong association. As noted earlier, the frequency of liver cancer relates to (correlates with) the frequency of chronic hepatitis B virus infection. In addition, the patients with hepatitis B virus who are at greatest risk for liver cancer are men with hepatitis B virus cirrhosis (scarring of the liver) and a family history of liver cancer. Perhaps the most convincing evidence, however, comes from a prospective (looking forward in time) study done in the 1970's in Taiwan involving male government employees over the age of 40. In this study, the investigators found that the risk of developing liver cancer was 200 times higher among employees who had chronic hepatitis B virus as compared to employees without chronic hepatitis B virus! Studies in animals also have provided evidence that hepatitis B virus can cause liver cancer. For example, we have learned that liver cancer develops in other mammals that are naturally infected with hepatitis B virus-related viruses. Finally, by infecting transgenic mice with certain parts of the hepatitis B virus, scientists caused liver cancer to develop in mice that do not usually develop liver cancer. (Transgenic mice are mice that have been injected with new or foreign genetic material.)

How does chronic hepatitis B virus cause liver cancer? In patients with both chronic hepatitis B virus and liver cancer, the genetic material of hepatitis B virus is frequently found to be part of the genetic material of the cancer cells. It is thought, therefore, that specific regions of the hepatitis B virus genome (genetic code) enter the genetic material of the liver cells. This hepatitis B virus genetic material may then disrupt the normal genetic material in the liver cells, thereby causing the liver cells to become cancerous.

The vast majority of liver cancer that is associated with chronic hepatitis B virus occurs in individuals who have been infected most of their lives. In areas where hepatitis B virus is not always present (endemic) in the community (for example, the U.S.), liver cancer is relatively uncommon. The reason for this is that most of the people with chronic hepatitis B virus in these areas acquired the infection as adults. However, liver cancer can develop in individuals who acquired chronic hepatitis B virus in adulthood if there are other risk factors, such as chronic alcohol use or co-infection with chronic hepatitis C virus infection.

2) Hepatitis C Infection

Hepatitis C virus (HCV) infection is also associated with the development of liver cancer. In fact, in Japan, hepatitis C virus is present in up to 75% of cases of liver cancer. As with hepatitis B virus, the majority of hepatitis C virus patients with liver cancer have associated cirrhosis (liver scarring). In several retrospective-prospective studies (looking backward and forward in time) of the natural history of hepatitis C, the average time to develop liver cancer after exposure to hepatitis C virus was about 28 years. The liver cancer occurred about eight to 10 years after the development of cirrhosis in these patients with hepatitis C. Several prospective European studies report that the annual incidence (occurrence over time) of liver cancer in cirrhotic hepatitis C virus patients ranges from 1.4 to 2.5% per year.

In hepatitis C virus patients, the risk factors for developing liver cancer include the presence of cirrhosis, older age, male gender, elevated baseline alpha-fetoprotein level (a blood tumor marker), alcohol use, and co-infection with hepatitis B virus. Some earlier studies suggested that hepatitis C virus genotype 1b (a common genotype in the U.S.) may be a risk factor, but more recent studies do not support this finding.

The way in which hepatitis C virus causes liver cancer is not well understood. Unlike hepatitis B virus, the genetic material of hepatitis C virus is not inserted directly into the genetic material of the liver cells. It is known, however, that cirrhosis from any cause is a risk factor for the development of liver cancer. It has been argued, therefore, that hepatitis C virus, which causes cirrhosis of the liver, is an indirect cause of liver cancer. On the other hand, there are some chronic hepatitis C virus infected individuals who have liver cancer without cirrhosis. So, it has been suggested that the core (central) protein of hepatitis C virus is the culprit in the development of liver cancer. The core protein itself (a part of the hepatitis C virus) is thought to impede the natural process of cell death or interfere with the function of a normal tumor suppressor (inhibitor) gene (the p53 gene).

The result of these actions is that the liver cells go on living and reproducing without the normal restraints, which is what happens in cancer.

3) Alcohol

Cirrhosis caused by chronic alcohol consumption is the most common association of liver cancer in the developed world. Actually, we now understand that many of these cases are also infected with chronic hepatitis C virus. The usual setting is an individual with alcoholic cirrhosis who has stopped drinking for ten years, and then develops liver cancer. It is somewhat unusual for an actively drinking alcoholic to develop liver cancer. What happens is that when the drinking is stopped, the liver cells try to heal by regenerating (reproducing). It is during this active regeneration that a cancer-producing genetic change (mutation) can occur, which explains the occurrence of liver cancer after the drinking has been stopped.

Patients who are actively drinking are more likely to die from non-cancer related complications of alcoholic liver disease (for example, liver failure). Indeed, patients with alcoholic cirrhosis who die of liver cancer are about 10 years older than patients who die of non-cancer causes. Finally, as noted above, alcohol adds to the risk of developing liver cancer in patients with chronic hepatitis C virus or hepatitis B virus infections.

4) Aflatoxin B1

Aflatoxin B1 is the most potent liver cancer-forming chemical known. It is a product of a mold called *Aspergillus flavus*, which is found in food that has been stored in a hot and humid environment. This mold is found in such foods as peanuts, rice, soybeans, corn, and wheat. Aflatoxin B1 has been implicated in the development of liver cancer in Southern China and Sub-Saharan Africa. It is thought to cause cancer by producing changes (mutations) in the p53 gene. These mutations work by interfering with the gene's important tumor suppressing (inhibiting) functions.

5) Drugs, Medications, and Chemicals

There are no medications that cause liver cancer, but female hormones (estrogens) and protein-building (anabolic) steroids are associated with the development of hepatic adenomas. These are benign liver tumors that may have the potential to become malignant (cancerous). Thus, in some individuals, hepatic adenoma can evolve into cancer.

Certain chemicals are associated with other types of cancers found in the liver. For example, thorotrast, a previously used contrast agent for imaging, caused a cancer of the blood vessels in the liver called hepatic angiosarcoma. Also, vinyl chloride, a compound used in the plastics industry, can cause hepatic angiosarcomas that appear many years after the exposure.

6) Hemochromatosis

Liver cancer will develop in up to 30% of patients with hereditary hemochromatosis. Patients at the greatest risk are those who develop cirrhosis with their hemochromatosis. Unfortunately, once cirrhosis is established, effective removal of excess iron (the treatment for hemochromatosis) will not reduce the risk of developing liver cancer.

7) Cirrhosis

Individuals with most types of cirrhosis of the liver are at an increased risk of developing liver cancer. In addition to the conditions described above (hepatitis B, hepatitis C, alcohol, and hemochromatosis), alpha 1 anti-trypsin deficiency, a hereditary condition that can cause emphysema and cirrhosis, may lead to liver cancer. Liver cancer is also strongly associated with hereditary tyrosinemia, a childhood biochemical abnormality that results in early cirrhosis.

Certain causes of cirrhosis are less frequently associated with liver cancer than are other causes. For example, liver cancer is rarely seen with the cirrhosis in Wilson's disease (abnormal copper metabolism) or primary sclerosing cholangitis (chronic scarring and narrowing of the bile ducts). It used to be thought that liver cancer is rarely found in primary biliary cirrhosis (PBC) as well. Recent studies, however, show that the frequency of liver cancer in PBC is comparable to that in other forms of cirrhosis.

Symptoms of Liver Cancer

The initial symptoms (the clinical presentations) of liver cancer are variable. In countries where liver cancer is very common, the cancer generally is discovered at a very advanced stage of disease for several reasons. For one thing, areas where there is a high frequency of liver cancer are generally developing countries where access to healthcare is limited. For another, screening examinations for patients at risk for developing liver cancer are not available in these areas. In addition, patients from these regions actually have more aggressive liver cancer disease. In other words, the tumor usually reaches an advanced stage and causes symptoms more rapidly. In contrast, patients in areas of low liver cancer frequency tend to have liver cancer tumors that progress more slowly and, therefore, remain without symptoms longer. Abdominal pain is the most common symptom of liver cancer and usually signifies a very large tumor or widespread involvement of the liver. Additionally, unexplained weight loss or unexplained fevers are warning signs of liver cancer in patients with cirrhosis. These symptoms are less common in individuals with liver cancer in the U.S. because these patients are usually diagnosed at an earlier stage. However, whenever the overall health of a patient with cirrhosis deteriorates, every effort should be made to look for liver cancer.

A very common initial presentation of liver cancer in a patient with compensated cirrhosis (no complications of liver disease) is the sudden onset of a complication. For example, the sudden appearance of ascites (abdominal fluid and swelling), jaundice (yellow color of the skin), or muscle wasting without causative (precipitating) factors (for example, alcohol consumption) suggests the possibility of liver cancer. What's more, the cancer can invade and block the portal vein (a large vein that brings blood to the liver from the intestine and spleen). When this happens, the blood will travel paths of less resistance, such as through esophageal veins. This causes increased pressure in these veins, which results in dilated (widened) veins called esophageal varices. The patient then is at risk for hemorrhage from the rupture of the varices into the gastrointestinal tract. Rarely, the cancer itself can rupture and bleed into the abdominal cavity, resulting in bloody ascites.

On physical examination, an enlarged, sometimes tender, liver is the most common finding. Liver cancers are very vascular (containing many blood vessels) tumors. Thus, increased amounts of blood feed into the hepatic artery (artery to the liver) and cause turbulent blood flow in the artery. The turbulence results in a distinct sound in the liver (hepatic bruit) that can be heard with a stethoscope in about one quarter to one half of patients with liver cancer. Any sign of advanced liver disease (for example, ascites, jaundice, or muscle wasting) means a poor prognosis. Rarely, a patient with liver cancer can become suddenly jaundiced when the tumor erodes into the bile duct. The jaundice occurs in this situation because both sloughing of the tumor into the duct and bleeding that clots in the duct can block the duct.

In advanced liver cancer, the tumor can spread locally to neighboring tissues or, through the blood vessels, to elsewhere in the body (distant metastasis). Locally, liver cancer can invade the veins that drain the liver (hepatic veins). The tumor can then block these veins, which results in congestion of the liver. The congestion occurs because the blocked veins cannot drain the blood out of the liver. (Normally, the blood in the hepatic veins leaving the liver flows through the inferior vena cava, which is the largest vein that drains into the heart.) In African patients, the tumor frequently blocks the inferior vena cava. Blockage of either the hepatic veins or the inferior vena cava results in a very swollen liver and massive formation of ascites. In some patients, as previously mentioned, the tumor can invade the portal vein and lead to the rupture of esophageal varices.

Regarding the distant metastases, liver cancer frequently spreads to the lungs, presumably by way of the blood stream. Usually, patients do not have symptoms from the lung metastases, which are diagnosed by radiologic (x-ray) studies. Rarely, in very advanced cases, liver cancer can spread to the bone or brain.

Diagnosis

1) Blood Tests

Liver cancer is not diagnosed by routine blood tests, including a standard panel of liver tests. This is why the diagnosis of liver cancer depends so much on the vigilance of the physician screening with a tumor marker (alpha-fetoprotein) in the blood and radiological imaging studies. Since most patients with liver cancer have associated liver disease (cirrhosis), their liver blood tests may not be normal to begin with. If these blood tests become abnormal or worsen due to liver cancer, this usually signifies extensive cancerous involvement of the liver. At that time, any medical or surgical treatment would be too late.

Sometimes, however, other abnormal blood tests can indicate the presence of liver cancer. Remember that each cell type in the body contains the full complement of genetic information. What differentiates one cell type from another is the particular set of genes that are turned on or off in that cell. When cells become cancerous, certain of the cell's genes that were turned off may become turned on. Thus, in liver cancer, the cancerous liver cells may take on the characteristics of other types of cells. For example, liver cancer cells sometimes can produce hormones that are ordinarily produced in other body systems. These hormones then can cause certain abnormal blood tests, such as a high red blood count (erythrocytosis), low blood sugar (hypoglycemia) and high blood calcium (hypercalcemia).

Another abnormal blood test, high serum cholesterol (hypercholesterolemia), is seen in up to 10% of patients from Africa with liver cancer. The high cholesterol occurs because the liver cancer cells are not able to turn off (inhibit) their production of cholesterol. (Normal cells are able to turn off their production of cholesterol.)

There is no reliable or accurate screening blood test for liver cancer. The most widely used biochemical blood test is alpha-fetoprotein (AFP), which is a protein normally made by the immature liver cells in the fetus. At birth, infants have relatively high levels of AFP, which fall to normal adult levels by the first year of life. Also, pregnant women carrying babies with neural tube defects may have high levels of AFP. (A neural tube defect is an abnormal fetal brain or spinal cord that is caused by folic acid deficiency during pregnancy.)

In adults, high blood levels (over 500 nanograms/milliliter) of AFP are seen in only three situations:

Liver cancer
Germ cell tumors (cancer of the testes and ovaries)
Metastatic cancer in the liver (originating in other organs)

Several assays (tests) for measuring AFP are available. Generally, normal levels of AFP are below 10 ng/ml. Moderate levels of AFP (up to 500 ng/ml) can be seen in patients with chronic hepatitis. Moreover, many patients with various types of acute and chronic liver diseases without documentable liver cancer can have mild or even moderate elevations of AFP.

The sensitivity of AFP for liver cancer is about 60%. In other words, an elevated AFP blood test is seen in about 60% of liver cancer patients. That leaves 40% of patients with liver cancer who have normal AFP levels. Therefore, a normal AFP does not exclude liver cancer. Also, as noted above, an abnormal AFP does not mean that a patient has liver cancer. It is important to note, however, that patients with cirrhosis and an abnormal AFP, despite having no documentable liver cancer, still are at very high risk of developing liver cancer. Thus, any patient with cirrhosis and an elevated AFP, particularly with steadily rising blood levels, will either most likely develop liver cancer or actually already have an undiscovered liver cancer.

An AFP greater than 500 ng/ml is very suggestive of liver cancer. In fact, the blood level of AFP loosely relates to (correlates with) the size of the liver cancer. Finally, in patients with liver cancer and abnormal AFP levels, the AFP may be used as a marker of response to treatment. For example, an elevated AFP is expected to fall to normal in a patient whose liver cancer is successfully removed surgically (resected).

There are a number of other liver cancer tumor markers that currently are research tools and not generally available. These include des-gamma-carboxyprothrombin (DCP), a variant of the gamma-glutamyltransferase enzymes, and variants of other enzymes (for example, alpha-L-fucosidase), which are produced by normal liver cells. (Enzymes are proteins that speed up biochemical reactions.) Potentially, these blood tests, used in conjunction with AFP, could be very helpful in diagnosing more cases of liver cancer than with AFP alone.

2) Imaging Studies

Imaging studies play a very important role in the diagnosis of liver cancer. A good study can provide information as to the size of the tumor, the number of tumors, and whether the tumor has involved major blood vessels locally or spread outside of the liver. There are several types of studies, each having its merits and disadvantages. In practice, several studies combined often complement each other. On the other hand, a plain X-ray is not very helpful, and therefore, is not routinely done in the diagnostic work-up of liver cancer. Further, there is no practical role for nuclear medicine scans of the liver and spleen in the work-up for liver cancer. Such scans are not very sensitive and they provide no additional information beyond that provided by the other (ultrasound, CT, and MRI) scans.

Ultrasound examination is usually the first study ordered if liver cancer is suspected in a patient. The accuracy of an ultrasound depends very much on the technician and radiologist who perform the study (operator dependent). Studies from Japan and Taiwan report that ultrasound is the most sensitive imaging study for diagnosing and characterizing liver cancer. But you should know that in these studies, highly experienced individuals performed the scans and spent up to one hour scanning each patient suspected of having liver cancer. An ultrasound has the advantages of not requiring intravenous contrast material and not involving radiation. Moreover, the price of an ultrasound is quite low as compared to the other types of scans.

Computerized axial tomography (CT scan) is a very common study used in the U.S. for the work-up of tumors in the liver. The ideal CT study is a multi-phase, spiral CT scan using oral and intravenous contrast material. Pictures are taken in three phases:
Without intravenous contrast
With intravenous contrast (enhanced imaging) that highlights the arterial system (arterial phase)
When the contrast is in the venous phase The pictures are taken at very frequent intervals (thin slices) as the body is moved through the CT scanner. Many radiologists use a specific protocol that determines how the contrast is infused in relation to how the pictures are taken. Therefore, CT is much less operator-dependent than is ultrasound. However, CT is considerably more expensive. Furthermore, CT requires the use of contrast material, which has the potential risks of an allergic reaction and adverse effects on kidney function.

There are several variations to CT scanning. For example, in a CT angiogram, which is a highly invasive (enters a part of the body) study, intravenous contrast is selectively infused through the hepatic artery (artery to the liver). The purpose is to highlight the vessels for better visualization of them by the CT scan. Also, in Japan, an oily contrast material called lipiodol, which is selectively taken up by liver cancer cells, has been used with CT. The purpose of this approach is to improve the sensitivity of the scan. That is to say, the goal is to increase the percentage of abnormal CT scans in patients who have liver cancer.

Magnetic resonance imaging (MRI) can provide very clear images of the body. Its advantage over CT is that MRI can provide sectional views of the body in different planes. The technology has evolved to the point that the newer MRIs can actually reconstruct images of the biliary tree (bile ducts and gallbladder) and of the arteries and veins of the liver. (The biliary tree transports bile from the liver to the duodenum, the first part of the intestine.) MRI studies can be made even more sensitive by using intravenous contrast material (for example, gadolinium).

MRI scans are very expensive and there is tremendous variability in the quality of the images. The quality depends on the age of the machine and the ability of the patients to hold their breath for up to 15 to 20 seconds at a time. Furthermore, many patients, because of claustrophobia, cannot tolerate being in the MRI scanner. However, the current open MRI scanners generally do not provide as high quality images as the closed scanners do.

Advances in ultrasound, CT, and MRI technology have almost eliminated the need for angiography. An angiography procedure involves inserting a catheter into the femoral artery (in the groin) through the aorta, and into the hepatic artery, the artery that supplies blood to the liver. Contrast material is then injected, and X-ray pictures of the arterial blood supply to the liver are taken. An angiogram of liver cancer shows a characteristic blush that is produced by newly formed abnormal small arteries that feed the tumor (neovascularization).

Liver Biopsy or Aspiration

In theory, a definitive diagnosis of liver cancer is always based on microscopic (histological) confirmation. However, some liver cancers are well differentiated, which means they are made up of nearly fully developed, mature liver cells (hepatocytes). Therefore, these cancers can look very similar to non-cancerous liver tissue under a microscope. Moreover, not all pathologists are trained to recognize the subtle differences between well-differentiated liver cancer and normal liver tissue. Also, some pathologists can mistake liver cancer for adenocarcinoma in the liver. An adenocarcinoma is a different type of cancer, and, as previously mentioned, it originates from outside of the liver. Most importantly, a metastatic adenocarcinoma would be treated differently from a primary liver cancer (liver cancer). Therefore, all of this considered, it is important that an expert liver pathologist review the tissue slides of liver tumors in questionable situations.

Tissue can be sampled with a very thin needle. This technique is called fine needle aspiration. When a larger needle is used to obtain a core of tissue, the technique is called a biopsy. Generally, radiologists, using ultrasound or CT scans to guide the placement of the needle, perform the biopsies or fine needle aspirations. The most common risk of the aspiration or biopsy is bleeding, especially because liver cancer is a tumor that is very vascular (contains many blood vessels). Rarely, new foci (small areas) of tumor can be seeded (planted) from the tumor by the needle into the liver along the needle track.

The aspiration procedure is safer than a biopsy with less risk for bleeding. However, interpretation of the specimen obtained by aspiration is more difficult because often only a cluster of cells is available for evaluation. Thus, a fine needle aspiration requires a highly skilled pathologist. Moreover, a core of tissue obtained with a biopsy needle is more ideal for a definitive diagnosis because the architecture of the tissue is preserved. The point is that sometimes a precise diagnosis can be important clinically. For example, some studies have shown that the degree of differentiation of the tumor may predict the patient's outcome (prognosis). That is to say, the more differentiated (resembling normal liver cells) the tumor is, the better the prognosis.

All of that said, in many instances, there is probably no need for a tissue diagnosis by biopsy or aspiration. If a patient has a risk factor for liver cancer (for example, cirrhosis, chronic hepatitis B, or chronic hepatitis C) and a significantly elevated alpha-fetoprotein blood level, the doctor can be almost certain that the patient has liver cancer without doing a biopsy. The patient and physician should always ask two questions before deciding on doing a liver biopsy:
1. Is this tumor most likely an liver cancer?
2. Will the biopsy findings change the management of the patient?

If the answer to both questions is yes, then the biopsy should be done. Finally, there are two other situations related to liver cancer in which a biopsy may be considered. The first is to characterize a liver abnormality (for example, a possible tumor) seen by imaging in the absence of risk factors for liver cancer or elevated alpha-fetoprotein. The second is to determine the extent of disease when there are multiple areas of abnormalities (possibly tumors) seen by imaging in the liver.

Overall, no blanket recommendation can be given regarding the need for liver biopsy or aspiration. The decision has to be made on an individual basis, depending on the treatment options and the expertise of the medical and surgical teams.

Treatment of Liver Cancer

The treatment options are dictated by the stage of liver cancer and the overall condition of the patient. The only proven cure for liver cancer is liver transplantation for a solitary, small (<3 cm) tumor. Now, many physicians may dispute this statement. They may argue that a small tumor can be surgically removed (partial hepatic resection) without the need for a liver transplantation. Moreover, they may claim that the one and three year survival rates for resection are perhaps comparable to those for liver transplantation.

However, most patients with liver cancer also have cirrhosis of the liver and would not tolerate liver resection surgery. But, they probably could tolerate the transplantation operation, which involves removal of the patient's entire diseased liver just prior to transplanting a donor liver. Furthermore, many patients who undergo hepatic resections will develop a recurrence of liver cancer elsewhere in the liver within several years. In fact, some experts believe that once a liver develops liver cancer, there is a tendency for that liver to develop other tumors at the same time (synchronous multicentric occurrence) or at a later time (metachronous multicentric occurrence). The results of the various medical treatments (chemotherapy, chemoembolization, ablation, and proton beam therapy) remain disappointing. Moreover, for reasons noted earlier (primarily the variability in natural history), there have been no systematic study comparisons of the different treatments. As a result, individual patients will find that the various treatment options available to them depend largely on the local expertise. How do we know if a particular treatment worked for a particular patient? Well, hopefully, the patient will feel better. However, a clinical response to treatment is usually defined more objectively. Thus, a response is defined as a decrease in the size of the tumor on imaging studies along with a reduction of the alpha-fetoprotein in the blood, if the level was elevated prior to treatment.

Chemotherapy

Systemic (Entire Body) Chemotherapy

The most commonly used systemic chemotherapeutic agents are doxorubicin (Adriamycin) and 5-fluorouracil (5 FU). These drugs are used together or in combination with new experimental agents. These drugs are quite toxic and results have been disappointing. A few studies suggest some benefit with tamoxifen (Nolvadex) but just as many studies show no advantage. Octreotide (Sandostatin) given as an injection was shown in one study to slow down the progression of large liver cancer tumors, but so far, no other studies have confirmed this benefit.

Hepatic Arterial Infusion of Chemotherapy

The normal liver gets its blood supply from two sources; the portal vein (about 70%) and the hepatic artery (30%). However, liver cancer gets its blood exclusively from the hepatic artery. Making use of this fact, investigators have delivered chemotherapy agents selectively through the hepatic artery directly to the tumor. The theoretical advantage is that higher concentrations of the agents can be delivered to the tumors without subjecting the patients to the systemic toxicity of the agents.

In reality, however, much of the chemotherapeutic agents does end up in the rest of the body. Therefore, selective intra-arterial chemotherapy can cause the usual systemic (body-wide) side effects. In addition, this treatment can result in some regional side effects, such as inflammation of the gallbladder (cholecystitis), intestinal and stomach ulcers, and inflammation of the pancreas (pancreatitis). Liver cancer patients with advanced cirrhosis may develop liver failure after this treatment. Well then, what is the benefit of intra-arterial chemotherapy? The bottom line is that fewer than 50% of patients will experience a reduction in tumor size.

An interventional radiologist (one who does therapeutic procedures) usually carries out this procedure. The radiologist must work closely with an oncologist (cancer specialist), who determines the amount of chemotherapy that the patient receives at each session. Some patients may undergo repeat sessions at 6 to 12 week intervals. This procedure is done with the help of fluoroscopy (type of x-ray) imaging. A catheter (long, narrow tube) is inserted into the femoral artery in the groin and is threaded into the aorta (the main artery of the body). From the aorta, the catheter is advanced into the hepatic artery. Once the branches of the hepatic artery that feed the liver cancer are identified, the chemotherapy is infused. The whole procedure takes one to two hours, and then the catheter is removed.

The patient generally stays in the hospital overnight for observation. A sandbag is placed over the groin to compress the area where the catheter was inserted into the femoral artery. The nurses periodically check for signs of bleeding from the femoral artery puncture. They also check for the pulse in the foot on the side of the catheter insertion to be sure that the femoral artery is not blocked as a result of the procedure. (Blockage would be signaled by the absence of a pulse.)

Generally, the liver tests increase (get worse) during the two to three days after the procedure. This worsening of the liver tests is actually due to death of the tumor (and some non-tumor) cells. The patient may experience some post-procedure abdominal pain and low-grade fever. However, severe abdominal pain and vomiting suggest that a more serious complication has developed. Imaging studies of the liver are repeated in six to 12 weeks to assess the size of the tumor in response to the treatment. For more, please read the Chemotherapy article.

Chemoembolization (Trans-arterial Chemoembolization or TACE)

This technique takes advantage of the fact that liver cancer is a very vascular (contains many blood vessels) tumor and gets its blood supply exclusively from the branches of the hepatic artery. This procedure is similar to intra-arterial infusion of chemotherapy. But in TACE, there is the additional step of blocking (embolizing) the small blood vessels with different types of compounds, such as gelfoam or even small metal coils. Thus, TACE has the advantages of exposing the tumor to high concentrations of chemotherapy and confining the agents locally since they are not carried away by the blood stream. At the same time, this technique deprives the tumor of its needed blood supply, which can result in the damage or death of the tumor cells.

The type and frequency of complications of TACE and intra-arterial chemotherapy are similar. The potential disadvantage of TACE is that blocking the feeding vessels to the tumor(s) may make future attempts at intra-arterial infusions impossible. Moreover, so far, there are no head-to-head studies directly comparing the effectiveness of intra-arterial infusion versus chemoembolization. In Japan, the chemotherapeutic agents are mixed with lipiodol. The idea is that since the tumor cells preferentially take up lipiodol, they would likewise take up the chemotherapy. This Japanese technique has not yet been validated in head-to-head comparisons with conventional TACE.

What are the benefits of TACE? In one large study involving several institutions in Italy, chemoembolization did not seem to be beneficial. Patients who did not undergo TACE lived as long as patients who received TACE, even though the tumors were more likely to shrink in size in patients who were treated.

Studies in Japan have shown that TACE can downstage liver cancer. In other words, the tumors shrank enough to lower (improve) the stage of the cancer. From the practical point of view, shrinking the tumor creates the option for surgery in some of these patients. Otherwise, these patients had tumors that were not operable (eligible for operation) because of the initial large size of their tumors. More importantly, these same studies showed an improvement in survival in patients whose tumors became considerably smaller. In the U.S., trials are underway to see whether doing TACE before liver transplantation increases patient survival as compared to liver transplantation without TACE.

It is safe to say that TACE or intra-arterial chemoinfusion are palliative treatment options for liver cancer. This means that these procedures can provide relief or make the disease less severe. However, they are not curative (do not result in a cure). Fewer than 50% of patients will have some shrinkage in tumor size. Further, they can be used only in patients with relatively preserved liver function. The reason for this is that these procedures, as mentioned previously, can lead to liver failure in individuals with poor liver function.

Ablation Techniques

Radiofrequency Ablation (RFA) Therapy

In the U.S., RFA therapy has become the ablation (tissue destruction) therapy of choice among surgeons. The surgeon can perform this procedure laparoscopically (through small holes in the abdomen) or during open exploration of the abdomen. In some instances, the procedure can be done without opening the abdomen by just using ultrasound for visual guidance.

In RFA, heat is generated locally by a high frequency, alternating current that flows from the electrodes. A probe is inserted into the center of the tumor and the non-insulated electrodes, which are shaped like prongs, are projected into the tumor. The local heat that is generated melts the tissue (coagulative necrosis) that is adjacent to the probe. The probe is left in place for about 10 to 15 minutes. The whole procedure is monitored visually by ultrasound scanning. The ideal size of an liver cancer tumor for RFA is less than 3 cm. Larger tumors may require more than one session. This treatment should be viewed as palliative (providing some relief), not curative.

Percutaneous Ethanol (Alcohol) Injection

In this technique, pure alcohol is injected into the tumor through a very thin needle with the help of ultrasound or CT visual guidance. Alcohol induces tumor destruction by drawing water out of tumor cells (dehydrating them) and thereby altering (denaturing) the structure of cellular proteins. It may take up to five or six sessions of injections to completely destroy the cancer. The ideal patient for alcohol injection has fewer than three liver cancer tumors, each of which is:

well defined (distinct margins)
less than 3 cm in diameter
surrounded by a shell consisting of scar tissue (fibrous encapsulation)
not near the surface of the liver Additionally, patients with liver cancer undergoing alcohol injection should have no signs of chronic liver failure, such as ascites or jaundice. (Patients with liver failure would not be able to tolerate the alcohol injections.)

The most common side effect of alcohol injection is leakage of alcohol onto the surface of the liver and into the abdominal cavity, thereby causing pain and fever. It is important that the location of the tumor relative to the adjacent blood vessels and bile ducts is clearly identified. The reason for needing to locate these structures is to avoid injuring them during the procedure and causing bleeding, bile duct inflammation, or bile leakage.

Proton Beam Therapy

This technique is able to deliver high doses of radiation to a defined local area. Proton beam therapy is used in the treatment of other solid tumors as well. There are not much data yet regarding the efficacy of this treatment in liver cancer. The ideal patient is one with only a small (<5 cm) solitary lesion. To have this procedure done, the patient actually is fitted with a body cast so that he or she can be placed in the identical position for each session. Therapy is conducted daily for 15 days. Preliminary data from the U.S. suggest similar effectiveness as seen with TACE or ablation therapy. It is not known, however, whether this type of radiation treatment prolongs the life of the patient.

How do these various medical treatment procedures compare to each other? We really don't know because there are no head-to-head studies comparing chemotherapy, chemoembolization, ablation techniques, and proton beam therapy to each other. Most reports deal with a heterogeneous group of patients who have undergone only one specific treatment procedure or another. Therefore, selection of a treatment option for a particular patient will depend primarily on the expertise of the doctors in the patient's area. Studies are also needed to evaluate combinations of these procedures (for example, proton beam and TACE). Now, what about surgery?

Surgery

Surgical options are limited to individuals whose tumors are less than 5 cm and confined to the liver, with no invasion of the blood vessels.

Liver Resection

The goal of liver resection is to completely remove the tumor and the appropriate surrounding liver tissue without leaving any tumor behind. This option is limited to patients with one or two small (3 cm or less) tumors and excellent liver function, ideally without associated cirrhosis. As a result of these strict guidelines, in practice, very few patients with liver cancer can undergo liver resection. The biggest concern about resection is that following the operation, the patient can develop liver failure. The liver failure can occur if the remaining portion of the liver is inadequate to provide the necessary support for life. Even in carefully selected patients, about 10% of them are expected to die shortly after surgery, usually as a result of liver failure.

When a portion of a normal liver is removed, the remaining liver can grow back (regenerate) to the original size within one to two weeks. A cirrhotic liver, however, cannot grow back. Therefore, before resection is performed for liver cancer, the non-tumor portion of the liver should be biopsied to determine whether there is associated cirrhosis.

For patients whose tumors are successfully resected, the five-year survival is about 30 to 40%. This means that 30 to 40% of patients who actually undergo liver resection for liver cancer are expected to live five years. Many of these patients, however, will have a recurrence of liver cancer elsewhere in the liver. Moreover, it should be noted that the survival rate of untreated patients with similar sized tumors and similar liver function is probably comparable. Some studies from Europe and Japan have shown that survival rates with alcohol injection or radiofrequency ablation procedures are comparable to the survival rates of those patients who underwent resection. But again, the reader should be cautioned that there are no head-to-head comparisons of these procedures versus resection.

Liver Transplantation

Liver transplantation has become an accepted treatment for patients with end-stage (advanced) liver disease of various types (for example, chronic hepatitis B and C, alcoholic cirrhosis, primary biliary cirrhosis, and sclerosing cholangitis). Survival rates for these patients without liver cancer are 90% at one year, 80% at three years, and 75% at five years. Moreover, liver transplantation is the best option for patients with tumors that are less than 5 cm in size who also have signs of liver failure. In fact, as one would expect, patients with small cancers (less than 3 cm) and no involvement of the blood vessels do very well. These patients have a less than 10% risk of recurrent liver cancer after transplant. On the other hand, there is a very high risk of recurrence in patients with tumors greater than 5 cm or with involvement of blood vessels. For these reasons, when patients are being evaluated for treatment of liver cancer, every effort should be made to characterize the tumor and look for signs of spread beyond the liver.

There is a severe shortage of organ donors in the U.S. Currently, there are about 18,000 patients on the waiting list for liver transplantation. About 4,000 donated cadaver livers (taken at the time of death) are available per year for patients with the highest priority. This priority goes to patients on the transplant waiting list who have the most severe liver failure. As a result, in many liver cancer patients, while they are on the waiting list, the tumor may become too large for the patient to benefit from liver transplantation. Doing palliative treatments, such as TACE, while the patient is on the waiting list for liver transplantation is currently being evaluated.

The use of a partial liver from a healthy, live donor may provide a few patients with liver cancer an opportunity to undergo liver transplantation before the tumor becomes too large. This innovation is a very exciting development in the field of liver transplantation. As a precaution, doing a biopsy or aspiration of liver cancer should probably be avoided in patients considering liver transplantation. The reason to avoid needling the liver is that there is about a 1-4% risk of seeding (planting) cancer cells from the tumor by the needle into the liver along the needle track. You see, after liver transplantation, patients take powerful anti-rejection medications to prevent the patient's immune system from rejecting the new liver. However, the suppressed immune system can allow new foci (small areas) of cancer cells to multiply rapidly. These new foci of cancer cells would normally be kept at bay by the immune cells of an intact immune system. In summary, liver resection should be reserved for patients with small tumors and normal liver function (no evidence of cirrhosis). Patients with multiple or large tumors should receive palliative therapy with intra-arterial chemotherapy or TACE, provided they do not have signs of severe liver failure. Patients with an early stage of cancer and signs of chronic liver disease should receive palliative treatment and undergo evaluation for liver transplantation.

Classification

There are several types of liver cancer:

Most cases are metastases from other tumors, frequently of the GI tract (like colon cancer, carcinoid tumors mainly of the appendix, etc.), but also from breast cancer, ovarian cancer, lung cancer, renal cancer, prostate cancer, etc.

The most frequent, malignant, primary liver cancer is hepatocellular carcinoma (also named hepatoma, which is a misnomer because adenomas are usually benign).

More rare primary forms of liver cancer include cholangiocarcinoma, mixed tumors, tumors of mesenchymal tissue, sarcoma and hepatoblastoma, a rare malignant tumor in children.

Liver Metastases

The liver provides a fertile soil in which metastases can become established, not only because of its rich, dual blood supply but also because of humoral factors that promote cell growth. The fenestrations in the sinusoidal endothelium allow a foothold into the space of Disse for tumor emboli arriving via the blood stream.

The liver is the second most commonly involved organ by metastatic disease, after the lymph nodes. In Europe and the United States, a focal liver lesion is more likely to represent a metastatic deposit than a primary malignancy. The liver may be the site of metastasis from virtually any primary malignant neoplasm, but the most common primary sites are the eye, colon, stomach, pancreas, breast, and lung. In children, the most common liver metastases are from a neuroblastoma, a Wilms tumor, or leukemia. Most liver metastases are multiple, involving both lobes in 77% patients, and only 10% are solitary. Multiple tumors often vary in size; this observation suggests that tumor seeding occurs in episodes. Growing metastases compress adjacent liver parenchyma, causing atrophy and forming a connective tissue rim. Large metastases often outgrow their blood supply, causing hypoxia and necrosis at the center of the lesion. Approximately 50% of the patients with liver metastases have clinical signs of hepatomegaly or ascites; liver function tests tend to be insensitive and nonspecific. Several factors influence the incidence and pattern of liver metastases. These include the patient's age and sex, the primary site, the histologic type, and the duration of the tumor. Few tumor types, such as colonic carcinoma, carcinoid, and hepatocellular carcinoma (HCC) may present with lesions confined to the liver. Most tumors that metastasize to the liver, such as breast and lung cancers, often spread to other sites at the same time.

Some focal lesions may be surgically resectable or treated by means of ablation techniques. Imaging plays a vital role in the diagnosis of liver metastases and in the assessment of the response to treatment. The recognition of a liver lesion as a metastatic focus may significantly influence the patient's treatment and prognosis.

Diagnosis of Liver Metastases

1) Physical Examination

Symptoms due to metastatic liver disease may be few, and the extent of liver involvement on images may be surprising, given the absence of clinical or laboratory evidence suggestive of hepatic functional insufficiency.

The only physical sign may be hepatomegaly, sometimes with nodularity of the free edge. About 30% of patients with liver metastases have a normal-sized liver, and more than 10% of the nodules have no surface involvement.[11] However, with large liver metastases or with tumors critically close to the bile ducts, signs of obstructive jaundice may be present, and results of liver function tests may be abnormal. The patient may have weight loss with malaise and abdominal enlargement secondary to hepatomegaly and/or ascites.

The presence of ascites usually indicates widespread tumors in the liver, and it is regarded as a grave prognostic sign. The spleen is often enlarged, without portal hypertension. Ascites and lower limb edema is indicative of invasion or occlusion of the IVC. With carcinoid tumors that cause pulmonary stenosis, liver metastases are invariably present.

2) Laboratory Examination

Laboratory examination reveals anemia, leukocytosis, minor elevation of bilirubin levels, and increased levels of alkaline phosphatase and transaminase. Various biochemical markers have been proposed to indicate liver metastases. Of these, 5'-nucleotidase is the most sensitive predictor compared with conventional markers and imaging findings. The diagnostic accuracy of tumor markers such alpha-fetoprotein (AFP), protein induced from the absence of vitamin K (PIVKA II), carcinoembryonic antigen (CEA), and CA19-9 for differentiating focal liver lesions has not yet been defined, but they are significantly linked to 3) Preferred Examination Plain chest radiographs are routinely obtained in patients who are suspected of having cancer, or they are used in the staging of cancer. A plain abdominal radiograph has a limited role in the investigation of liver metastases. Ultrasonography (US) is widely used in the investigation of suspected liver metastases.

Intraoperative US (IOUS) of the liver has the highest sensitivity for the detection of focal liver abnormalities, with 96% accuracy versus 84% for transabdominal US. Duplex and color flow image provide additional aids to the localization of lesions, the differentiation between ducts and blood vessels, the documentation of vascular invasion and/or occlusion, and the assessment of the presence of collateral circulation and the degree of vascularity of liver metastases. Late-phase pulse-inversion harmonic imaging is a useful technique for characterizing hepatic lesions and for demonstrating both greater numbers of liver metastases and smaller liver metastases. Contrast-enhanced US in the liver-specific phase of contrast enhancement improves the detection of hepatic metastases, relative to nonenhanced conventional US. MRI is usually reserved for problem solving because of the cost of the procedure. However, evidence supporting the use of MRI in the evaluation of liver metastases is accumulating because MRI allows the effective localization of hepatic and vascular invasion. However, CT remains the preferred option over both MRI and US. CT permits better evaluation of the involvement of extrahepatic tissues, including the bones, bowel, lymph nodes, and mesentery.

In their meta-analysis, Kinkel et al compared US, CT, MRI, and 2-[fluorine 18]-fluoro-2-deoxy-D-glucose (FDG) imaging in the detection of liver metastases from colorectal, gastric, and esophageal cancers.[12] The researchers concluded that, with an equivalent specificity, FDG positron emission tomography (PET) is the most sensitive noninvasive imaging modality for the diagnosis of liver metastases. Selective hepatic angiography can demonstrate hypervascular liver metastases by showing capillary blush in involved areas, highlighting the potential response of tumors to embolization. Angiography is an essential step when hepatic vascular intervention is planned.

Symptoms of Liver Metastases

In some cases, there are no symptoms. When symptoms occur, they may include Weight loss, Pain, usually in the right upper quadrant of the abdomen, Jaundice, Fevers, Sweats, Nausea and Anorexia.

Exams and Tests

Tests that may be done to diagnose liver metastases include:

Bilirubin blood test—may be high
Liver function tests—may be abnormal
CT scan or MRI—may show a mass in the liver
PET scan—may show a mass in the liver
Ultrasound of the liver—may show a mass in the liver Treatment Treatment depends on the primary cancer site, extent of spread to the liver (for example, only one tumor in the liver versus many tumors in the liver), whether it has spread to other organs, and the condition of the patient.

In situations where cancer has spread not only to the liver but to other organs as well, systemic chemotherapy (directed at treating the entire body) is usually used.

In situations in which spread is limited to the liver, systemic chemotherapy may be used, although other treatment methods may be effective. When the tumor is localized to only a few areas of the liver, the cancer may be removed surgically.

Use of radiofrequency waves or injection of toxic substances may also be used to kill tumors. When larger areas of the liver are involved, liver-directed chemotherapy (infusing chemotherapy directly into the liver), or embolization (blockage of blood flow to parts of the liver) may be used.

Lung Metastases

Lungs are the primary sites for most cancer metastasis. Many cancers can spread to this organ, such as Breast Cancer, Colon Cancer, Prostate Cancer, Stomach Cancer, Ovarian Cancer, Kidney Cancer, Malignant Melanoma, Esophageal Cancer, Head and Neck Cancers, Testis Cancer and Choriocarcinoma.

This is a partial list and almost any cancer can spread to the lungs. Symptoms associated with this condition vary, depending on the extent of lung involvement. Most patients are diagnosed with lung metastasis on routine work up of the cancer, when they have no symptoms at all. Others present with an advanced disease, where the case symptoms are Shortness of breath, Cough and Pain in the chest.

Regular x-ray, CT scan or MRI of the chest can establish the diagnosis. Once the diagnosis is established, treatment should be initiated promptly.

Symptoms of a Lung Metastasis

A lung metastasis produces symptoms similar to those of other serious lung or chest ailments. They include Shortness of breath, Chest or rib cage pain, Cough, Bloody sputum, Unintended weight loss and Weakness.

It is possible, however, for a lung metastasis to present no symptoms at all. Sometimes the cancerous growth is discovered by accident when the doctor takes a chest x-ray of the patient for other reasons.

Diagnosing a Lung Metastasis

There are numerous procedures at a doctor's disposal to develop a diagnosis. They include:
  listening to the sound of the patient's breathing with a stethoscope
  taking a chest x-ray to reveal the condition of and any growths in the lungs
  performing a CT (computed tomography) scan to obtain additional "internal" details
  obtaining for analysis lung cells or sputum by needle or a localized biopsy surgery Treating a Lung Metastasis In many cases, a lung metastasis indicates that the primary cancer has spread to the patient's bloodstream. Chances are cancer will be present in places not identified by x-rays or CT scans. That means removing visible lung metastases surgically offers no guarantee that the cancer has been fully or properly treated. As a result the treatment of choice usually is chemotherapy, along with its probability of cure.

Surgery, however, can be effective under the following group of circumstances:
  When the primary cancer has been controlled
  When there are only one or two clearly definable metastases
  When there is a high probability that the surgery will "get" all of the growths
  When the patient is strong enough to withstand a major invasive operation
  When there's no expectation that chemotherapy or radiation treatment would have a better chance of success Radiation, laser therapy, and even the placement of stents inside the patient's airway are sometimes selected as treatments. But they are much less common than chemotherapy and surgery.

Almost all patients are treated with chemotherapy. Radiation therapy may be used in selected patients, when tumor causes bleeding or obstruction of the airways. Surgery in selected patients to remove the tumor from the lungs—This is indicated when the primary site of the disease is under control.

Malignant Fibrous Histiocytoma

Malignant fibrous histiocytoma (MFH) is the most common soft-tissue sarcoma of late adult life.

Causes and Risk Factors

No one knows the exact cause or causes of malignant fibrous histiocytoma; however, research has shown that people with certain malignant fibrous histiocytoma risk factors are more likely than others to develop the condition. A risk factor is anything that increases a person's chances of developing a disease. Examples of risk factors for malignant fibrous histiocytoma include: 1) Having previously undergone radiation treatment for cancer; 2) Having a history of Paget's disease and 3) Having a history of sickle cell disease, non-Hodgkin's lymphoma, Hodgkin's lymphoma, or multiple myeloma.

Symptoms of Malignant Fibrous Histiocytoma

While an enlarging painless mass is a common symptom seen with the soft tissue type of malignant fibrous histiocytoma, a fracture can be the first symptom with malignant fibrous histiocytoma of bone. Symptoms of malignant fibrous histiocytoma may vary depending on the location and the size of the tumor. Examples of common malignant fibrous histiocytoma symptoms include: 1) Fever, 2) Weight loss ad 3) Low blood sugar.

Diagnosing Malignant Fibrous Histiocytoma

If a person has possible malignant fibrous histiocytoma symptoms, the doctor will likely need to perform a physical exam, ask about the patient's personal and family medical history, and recommend additional tests and procedures. Procedures and tests that healthcare providers may use to make a malignant fibrous histiocytoma diagnosis include: 1) X-rays, 2) Computed tomography (CT) scan, 3) Magnetic resonance imaging (MRI) scan, 4) Bone scan and 5) Biopsy.

Malignant Fibrous Histiocytoma Staging

Once healthcare providers diagnose malignant fibrous histiocytoma, they may order more tests to find out if cancer cells have spread to other parts of the body. This is called staging. Currently, there is no staging system for the different types of malignant fibrous histiocytoma. Instead, most patients are grouped depending on whether malignant fibrous histiocytoma is found in only one part of the body (localized malignant fibrous histiocytoma) or whether the malignant fibrous histiocytoma has spread from one part of the body to another (metastatic malignant fibrous histiocytoma). The doctor will need to determine where the cancer is located and how far the disease has spread in order to plan the best malignant fibrous histiocytoma treatment.

Pathophysiology

Uncertain histogenesis and numerous subtypes make MFH a rather controversial entity. Researchers have postulated both histiocytic and primitive mesenchymal cell theories of origin. In general, the tumor contains both fibroblast-like and histiocytelike cells in varying proportions, with spindled and rounded cells exhibiting a storiform arrangement. Five histologic subtypes have been described: (1) storiform/pleomorphic (most common), (2) myxoid, (3) giant cell, (4) inflammatory (usually retroperitoneal), and (5) angiomatoid (often located more superficially than other varieties).

Clinical Details

The most common clinical presentation is an enlarging painless soft-tissue mass in the thigh, typically 5-10 cm in diameter. Two thirds of tumors are intramuscular. Rare signs and symptoms include episodic hypoglycemia and rapid tumor enlargement during pregnancy. Additionally, MFH has been associated with hematopoietic diseases such as non-Hodgkin lymphoma, Hodgkin lymphoma, multiple myeloma, and malignant histiocytosis.

Retroperitoneal MFH usually presents with constitutional symptoms, including fever, malaise, and weight loss. The tumor is often larger than 10 cm in diameter at presentation and may cause displacement of the bowel, kidney, ureter, and/or bladder. MFH may also occur secondary to radiation exposure and shrapnel injury and may be seen adjacent to metallic fixation devices, including total joint prostheses.[7] Early and complete surgical removal using wide or radical resection is indicated because of the aggressive nature of the tumor.

Preferred Examination

As with other soft-tissue tumors, MRI is the imaging method of choice because of its ability to provide superior contrast between tumor and muscle, excellent definition of surrounding anatomy, and ease of imaging in multiple planes.

Axial CT may be obtained in lieu of MRI if the patient is claustrophobic or if metal implants (eg, pacemakers, aneurysm clips) render the patient unsuitable for MRI. CT is also useful for evaluation of calcifications.

Treatment for Malignant Fibrous Histiocytoma

Malignant fibrous histiocytoma is generally treated the same as osteosarcoma and appears to have a similar response to treatment.

Malignant fibrous histiocytoma treatment options vary based on factors such as: 1) Whether the malignant fibrous histiocytoma is localized or metastatic. 2) Where the tumor is found and 3) The patient's age and general health.

In general, treatment options for malignant fibrous histiocytoma include surgery and chemotherapy.

Treating Localized Malignant Fibrous Histiocytoma

Treatment of localized malignant fibrous histiocytoma may include chemotherapy followed by surgery to remove the tumor and surrounding tissue.

Metastatic Malignant Fibrous Histiocytoma Treatment

There is no standard treatment for cancer that cannot be removed with surgery or cancer cells that have spread (metastasized). In these situations, the malignant fibrous histiocytoma prognosis is poor.

Maxillary Sinus Carcinoma

Malignant tumors of the nasal cavity and paranasal sinuses are rare, with poorly differentiated squamous cell carcinoma of the maxillary sinus being the most common. Diagnosis can be achieved with an intra-oral biopsy, after the lesion had perforated the palate bone.

Medullary Thyroid Carcinoma

Medullary carcinoma of the thyroid (MTC) is a distinct thyroid carcinoma that originates in the parafollicular C cells of the thyroid gland. These C cells produce calcitonin. MTC has a genetic association with multiple endocrine neoplasia (MEN) type 2A and 2B syndromes, but it has an inheritable non-MEN mode of transmission.

Sporadic, or isolated, MTC occurs in 75% of patients, and familial MTC comprises the rest.

Outcome depends on extent of disease, nature of tumor biology, and overall efficacy of surgical treatment.

Advances in genetic testing in the past few years have revolutionized the management of this disease.

Diagnosis

Lab Studies

Obtain serum calcitonin levels to detect subclinical disease in the thyroid gland, cervical lymph nodes, or at distant sites.

Traditionally, the pentagastrin-induced rise in calcitonin secretion has been used to diagnose medullary thyroid carcinoma (MTC); however, DNA testing for ret has replaced this diagnostic method in familial cases.

Consider a 24-hour urinalysis for catecholamine metabolites (eg, vanillylmandelic acid [VMA], metanephrine) to rule out concomitant pheochromocytoma in patients diagnosed with MEN type 2A or 2B.

Obtain screening for the development of familial MTC in family members of patients with history of MTC or MEN 2A or 2B.

Screen all family members for missense mutation in ret in leukocytes.

Pentagastrin-stimulated calcitonin levels may indicate subclinical disease. If this occurs, conduct a thyroidectomy.

A positive ret in an asymptomatic family member should lead to discussion and pursuit of a prophylactic total thyroidectomy (see Treatment).

Imaging Studies

Preoperatively performing cervical ultrasonography can detect lymph node metastases.

CT scanning, MRI, and bone scanning can detect distant metastases to the liver, lung, bone, and brain.

Procedures

Fine-needle aspiration yields cytologic information, allowing diagnosis of MTC.

Histologic Findings

Grossly, MTC resembles a well-circumscribed off-white nodule with a rough texture. Microscopically, it contains nests of round or ovoid cells. A fibrovascular stroma is usually intercalated between cells. Sometimes, amyloid material, consisting of calcitonin prohormone, may occur in the MTC stroma. Perhaps most importantly, immunohistochemical diagnosis of MTC can be made by demonstrating calcitonin using radioactive calcitonin antiserum against MTC cells.

Medullary tumors are the third most common of all thyroid cancers (about 5 to 8 percent). Unlike papillary and follicular thyroid cancers which arise from thyroid hormone producing cells, medullary cancer of the thyroi originates from the parafollicular cells (also called C cells) of the thyroid. These C cells make a different hormone called calcitonin (thus their name) which has nothing to do with the control of metabolism the way thyroid hormone does. As you will see below, the production of this hormone can be measured after an operation to determine if the cancer is still present, and if it is growing. This cancer has a much lower cure rate than does the "well differentiated" thyroid cancers (papillary and follicular), but cure rates are higher than they are for anaplastic thyroid cancer. Overall 10 year survival rates are 90% when all the disease is confined to the thyroid gland, 70% with spread to cervical lymph nodes, and 20 when spread to distant sites is present.

Characteristics of Medullary Thyroid Cancer:

Occurs in 4 clinical settings (see below), can be associated with other endocrine tumors Females more common than males (except for inherited cancers)

Regional metastases (spread to neck lymph nodes) occurs early in the disease

Spread to distant organs (metastasis) occurs late and can be to the liver, bone, brain, and adrenal medulla
Not associated with radiation exposure
Usually originates in the upper central lobe of the thyroid
Poor prognostic factors include age >50, male, distant spread (metastases), and when seen in patients with other endocrine tumors due to MEN II-B syndrome.
Residual disease (following surgery) or recurrence can be detected by measuring calcitonin (a hormone that should be measured every 4 months for the first few years and then every 6 months for ever).

Medullary Thyroid Cancer Occurs in Four Clinical Settings:
1. Sporadic—Accounts for 80% of all cases of medullary thyroid cancer. They are typically unilateral and there are no associated endocrinopathies (not associated with disease in other endocrine glands. Peak onset 40-60. Females outnumber males by 3:2 ratio. One third will present with intractable diarrhea. Diarrhea is caused by increased gastrointestinal secretion and hypermotility due to the hormones secreted by the tumor (calcitonin, prostaglandins, serotonin, or VIP).
2. MEN II-A (Sipple Syndrome). Multiple Endocrine Neoplasia Syndromes (abbreviated as "MEN" and pronounced "M", "E", "N") are a group of endocrine disorders which occur together in the same patient and typically are found in families because they are inherited. "Syndromes" are medical conditions which occur in groups of three. Sipple syndrome has [1] bilateral medullary carcinoma or C cell C cel hyperplasia, [2] pheochromocytomand [3] hyperparathyroidism. This syndrome is inherited and is due to a defect of a gene (DNA) which helps control the normal growth of endocrine tissues. This inherited syndrome is passed on to all children who get the gene (inherited in an autosomal dominant fashion), which theoretically, would be 50% of all offspring of a person with this defective gene. Because of this, males and females are equally affected. Peak incidence of medullary carcinoma in these patients is in the 30's.
3. MEN II-B. This syndrome also has [1] medullary carcinoma and [2] pheochromocytoma, but only rarely will have hyperparathyroidism. Instead these patients have [3] an unusual appearance which is characterized by mucosal ganglioneuromas (tumors in the mouth) and a Marfanoid habitus. Inheritance is autosomal dominant as in MEN II-a, or it can occur sporadically (without being inherited). MEN II-B patients usually get medullary carcinoma in their 30's, and males and females are equally effected. As with MEN II-A, pheochromocytomas must be detected prior to any operation. The idea here is to remove the pheochromocytoma first to remove the risk of severe hypertensive episodes while the thyroid or parathyroid is being operated on.
4. Inherited medullary carcinoma without associated endocrinopathies. This form of medullary carcinoma is the least aggressive. Like other types of thyroid cancers, the peak incidence is between the ages of 40 and 50.

Management of Medullary Thyroid Cancer

In contrast to papillary and follicular cancers, little controversy exits when discussing the management of medullary thyroid cancer. After assessment and treatment of associated endocrine conditions (such as pheochromocytomas if present) by an endocrinologist, all patients should receive total thyroidectomy, a complete central neck dissection (removal of all lymph nodes and fatty tissues in the central area of the neck), and removal of all lymph nodes and surrounding fatty tissues within the side of the neck which harbored the tumor. A diagram of thyroid operations are covered in greater detail (with drawings) on another "surgical options" page.

Use of Radioactive Iodine Post-Operatively

Although thyroid cells have the cellular mechanism to absorb iodine, medullary thyroid cancer does not arise from this type of thyroid cell. Therefore, radioactive iodine therapy is not useful for the treatment of medullary thyroid cancer. Similarly, if medullary cancer spreads to distant sites, it cannot be found by iodine scanning the way that distant spread from papillary or follicular cancer can.

Long-Term Follow Up

In addition to the usual cancer follow up, patients should receive a yearly chest x-ray as well as calcitonin levels Serum calcitonin is very useful in follow up of medullary thyroid cancer because no other cells of the body make this hormone. A high serum calcitonin level that had previously been low following total thyroidectomy is indicative of recurrence. Under the best circumstances, surgery will remove all of the thyroid and all lymph nodes in the neck which harbor metastatic spread. In this case, post operative calcitonin levels will go to zero. This is often not the case, and calcitonin levels remain elevated, but less than preoperatively. These levels should still be checked every 6 months, and when they begin to rise, a more diligent examination is in order to find the source.

Melanoma

Melanoma is a malignant tumor of melanocytes which are found predominantly in skin but also in the bowel and the eye (uveal melanoma). It is one of the rarer types of skin cancer but causes the majority of skin cancer related deaths. Malignant melanoma is a serious type of skin cancer. It is due to uncontrolled growth of pigment cells, called melanocytes. Despite many years of intensive laboratory and clinical research, the sole effective cure is surgical resection of the primary tumor before it achieves a Breslow thickness greater than 1 mm.

On Jun. 23, 2008, Israeli scientists from the Oncology Institute of the Hadassa Medical Center in Jerusalem announced they developed a vaccine that prevents recurrences of the disease among previous sufferers and increases chances of survival for current ones.

Around 160,000 new cases of melanoma are diagnosed worldwide each year, and it is more frequent in males and caucasians. It is more common in caucasian populations living in sunny climates than other groups. According to the WHO Report about 48,000 melanoma related deaths occur worldwide per annum.

Malignant melanoma accounts for 75 percent of all deaths associated with skin cancer. The treatment includes surgical removal of the tumor; adjuvant treatment; chemo- and immunotherapy, or radiation therapy.

Genetics

Familial melanoma is genetically heterogeneous, and loci for familial melanoma have been identified on the chromosome arms 1p, 9p and 12q. Multiple genetic events have been related to the pathogenesis of melanoma. The multiple tumor suppressor 1 (CDKN2A/MTS1) gene encodes p16INK4a—a low-molecular weight protein inhibitor of cyclin-dependent protein kinases (CDKs)—which has been localised to the p21 region of human chromosome 9. Today, melanomas are diagnosed only after they become visible on the skin. In the future, however, physicians will hopefully be able detect melanomas based on a patient's genotype, not just his or her phenotype. Recent genetic advances promise to help doctors to identify people with high-risk genotypes and to determine which of a person's lesions have the greatest chance of becoming cancerous. A number of rare mutations, which often run in families, are known to greatly increase one's susceptibility to melanoma. One class of mutations affects the gene CDKN2A. An alternative reading frame mutation in this gene leads to the destabilization of p53, a transcription factor involved in apoptosis and in fifty percent of human cancers. Another mutation in the same gene results in a non-functional inhibitor of CDK4, a [cyclin-dependent kinase] that promotes cell division. Mutations that cause the skin condition Xeroderma Pigmentosum (XP) also seriously predispose one to melanoma. Scattered throughout the genome, these mutations reduce a cell's ability to repair DNA. Both CDKN2A and XP mutations are highly penetrant. Other mutations confer lower risk but are more prevalent in the population. People with mutations in the MC1R gene, for example, are two to four times more likely to develop melanoma than those with two wild-type copies of the gene. MC1R mutations are very common; in fact, all people with red hair have a mutated copy of the gene. Two-gene models of melanoma risk have already been created, and in the future, researchers hope to create genome-scale models that will allow them to predict a patient's risk of developing melanoma based on his or her genotype. In addition to identifying high-risk patients, researchers also want to identify high-risk lesions within a given patient. Many new technologies, such as optical coherence tomography (OCT), are being developed to accomplish this. OCT allows pathologists to view 3-D reconstructions of the skin and offers more resolution than past techniques could provide. In vivo confocal microscopy and fluorescently tagged antibodies are also proving to be valuable diagnostic tools.

Detection and Prevention

Minimizing exposure to sources of ultraviolet radiation (the sun and sunbeds), following sun protection measures and wearing sun protective clothing (long-sleeved shirts, long trousers, and broad-brimmed hats) can offer protection. In the past it was recommended to use sunscreens with an SPF rating of 30 or higher on exposed areas. However, there are severe doubts about the ability of sunscreen to prevent melanoma. To prevent or detect melanomas (and increase survival rates), it is recommended to learn what they look like (see "ABCDE" mnemonic below), to be aware of moles and check for changes (shape, size, color, itching or bleeding) and to show any suspicious moles to a doctor with an interest and skills in skin malignancy.

A popular method for remembering the signs and symptoms of melanoma is the mnemonic "ABODE":

Asymmetrical skin lesion.
Border of the lesion is irregular.
Color: melanomas usually have multiple colors.
Diameter: moles greater than 5 mm are more likely to be melanomas than smaller moles.
Evolution: The evolution (ie change) of a mole or lesion may be a hint that the lesion is becoming malignant—or—Elevation: The mole is raised or elevated above the skin.

The E is sometimes omitted, as in the ABCD guideline.

People with a personal or family history of skin cancer or of dysplastic nevus syndrome (multiple atypical moles) should see a dermatologist at least once a year to be sure they are not developing melanoma.

Diagnosis

Moles that are irregular in color or shape are suspicious of a malignant or a premalignant melanoma. Following a visual examination and a dermatoscopic exam (an instrument that illuminates a mole, revealing its underlying pigment and vascular network structure), or an examination using other in vivo diagnostic tools, such as a confocal microscope, the doctor may biopsy the suspicious mole. If it is malignant, the mole and an area around it needs excision.

The diagnosis of melanoma requires experience, as early stages may look identical to harmless moles or not have any color at all. A biopsy performed under local anesthesia is often required to assist in making or confirming the diagnosis and in defining the severity of the melanoma.

Excisional biopsy is the management of choice; this is where the suspect lesion is totally removed with an adequate ellipse of surrounding skin and tissue. The biopsy will include the epidermal, dermal, and subcutaneous layers of the skin, enabling the histopathologist to determine the depth of penetration of the melanoma by microscopic examination. This is described by Clark's level (involvement of skin structures) and Breslow's depth (measured in millimeters).

If an excisional biopsy is not possible in certain larger pigmented lesions, a punch biopsy may be performed using a surgical punch (an instrument similar to a tiny cookie cutter with a handle, with an opening ranging in size from 1 to 6 mm). The punch is used to remove a plug of skin (down to the subcutaneous layer) from a portion of a large suspicious lesion, for histopathological examination.

Lactate dehydrogenase (LDH) tests are often used to screen for metastases, although many patients with metastases (even end-stage) have a normal LDH; extraordinarily high LDH often indicates metastatic spread of the disease to the liver. It is common for patients diagnosed with melanoma to have chest X-rays and an LDH test, and in some cases CT, MRI, PET and/or PET/CT scans. Although controversial, sentinel lymph node biopsies and examination of the lymph nodes are also performed in patients to assess spread to the lymph nodes.

Sometimes the skin lesion may bleed, itch, or ulcerate, although this is a very late sign. A slow-healing lesion should be watched closely, as that may be a sign of melanoma. Be aware also that in circumstances that are still poorly understood, melanomas may "regress" or spontaneously become smaller or invisible—however the malignancy is still present. Amelanotic (colorless or flesh-colored) melanomas do not have pigment and may not even be visible. Lentigo maligna, a superficial melanoma confined to the topmost layers of the skin (found primarily in older patients) is often described as a "stain" on the skin. Some patients with metastatic melanoma do not have an obvious detectable primary tumor.

Types of Primary Melanoma

The most common types of Melanoma in the skin: 1) superficial spreading melanoma (SSM), 2) nodular melanoma, 3) acral lentiginous melanoma and 4) lentigo maligna (melanoma).

Any of the above types may produce melanin (and be dark in colour) or not (and be amelanotic—not dark). Similarly any subtype may show desmoplasia (dense fibrous reaction with neurotropism) which is a marker of aggressive behaviour and a tendency to local recurrence.

Elsewhere: 1) clear cell sarcoma (Melanoma of Soft Parts), 2) mucosal melanoma, 3) uveal melanoma.

Prognostic Factors

Features that affect prognosis are tumor thickness in millimeters (Breslow's depth), depth related to skin structures (Clark level), type of melanoma, presence of ulceration, presence of lymphatic/perineural invasion, presence of tumor infiltrating lymphocytes (if present, prognosis is better), location of lesion, presence of satellite lesions, and presence of regional or distant metastasis.

Certain types of melanoma have worse prognoses but this is explained by their thickness. Interestingly, less invasive melanomas even with lymph node metastases carry a better prognosis than deep melanomas without regional metastasis at time of staging. Local recurrences tend to behave similarly to a primary unless they are at the site of a wide local excision (as opposed to a staged excision or punch/shave excision) since these recurrences tend to indicate lymphatic invasion.

When melanomas have spread to the lymph nodes, one of the most important factors is the number of nodes with malignancy. Extent of malignancy within a node is also important; micrometastases in which malignancy is only microscopic have a more favorable prognosis than macrometastases. In some cases micrometastases may only be detected by special staining, and if malignancy is only detectable by a rarely-employed test known as the polymerase chain reaction (PCR), the prognosis is better. Macrometastases in which malignancy is clinically apparent (in some cases cancer completely replaces a node) have a far worse prognosis, and if nodes are matted or if there is extracapsular extension, the prognosis is still worse.

When there is distant metastasis, the cancer is generally considered incurable. The five year survival rate is less than 10%. The median survival is 6 to 12 months. Treatment is palliative, focusing on life-extension and quality of life. In some cases, patients may live many months or even years with metastatic melanoma (depending on the aggressiveness of the treatment). Metastases to skin and lungs have a better prognosis. Metastases to brain, bone and liver are associated with a worse prognosis. There is not enough definitive evidence to adequately stage, and thus give a prognosis for ocular melanoma and melanoma of soft parts, or mucosal melanoma (e.g. rectal melanoma), although these tend to metastasize more easily. Even though regression may increase survival, when a melanoma has regressed, it is impossible to know its original size and thus the original tumor is often worse than a pathology report might indicate.

Staging

Also of importance are the "Clark level" and "Breslow depth" which refer to the microscopic depth of tumor invasion.

Melanoma Stages:

Stage 0: Melanoma in Situ (Clark Level I), 100% Survival
Stage I/II: Invasive Melanoma, 85-95% Survival
 T1a: Less than 1.00 mm primary, w/o Ulceration, Clark Level II-III
 T1b: Less than 1.00 mm primary, w/Ulceration or Clark Level IV-V
 T2a: 1.00-2.00 mm primary, w/o Ulceration
Stage II: High Risk Melanoma, 40-85% Survival
 T2b: 1.00-2.00 mm primary, w/ Ulceration
 T3a: 2.00-4.00 mm primary, w/o Ulceration
 T3b: 2.00-4.00 mm primary, w/ Ulceration
 T4a: 4.00 mm or greater primary w/o Ulceration
 T4b: 4.00 mm or greater primary w/ Ulceration
Stage III: Regional Metastasis, 25-60% Survival
 N1: Single Positive Lymph Node
 N2: 2-3 Positive Lymph Nodes OR Regional Skin/In-Transit Metastasis
 N3: 4 Positive Lymph Nodes OR Lymph Node and Regional Skin/In Transit Metastases Stage IV: Distant Metastasis, 9-15% Survival
 M1 a: Distant Skin Metastasis, Normal LDH
 M1b: Lung Metastasis, Normal LDH
 M1 c: Other Distant Metastasis OR Any Distant Metastasis with Elevated LDH Treatment Surgery is the first choice therapy for localized cutaneous melanoma. Depending on the stage a sentinel lymph node biopsy is done as well, although controversy exists around trial evidence for this procedure. Treatment of advanced malignant melanoma is performed from a multidisciplinary approach.

1) Surgery

Diagnostic punch or excisional biopsies may appear to excise (and in some cases may indeed actually remove) the tumor, but further surgery is often necessary to reduce the risk of recurrence.

Complete surgical excision with adequate margins and assessment for the presence of detectable metastatic disease along with short- and long-term followup is standard. Often this is done by a "wide local excision" (WLE) with 1 to 2 cm margins. The wide excision aims to reduce the rate of tumour recurrence at the site of the original lesion. This is a common pattern of treatment failure in melanoma. Considerable research has aimed to elucidate appropriate margins for excision with a general trend toward less aggressive treatment during the last decades. There of 2 cm margins for even the thickest tumors.

Melanomas which spread usually do so to the lymph nodes in the region of the tumor before spreading elsewhere. Attempts to improve survival by removing lymph nodes surgically (lymphadenectomy) were associated with many complications but unfortunately no overall survival benefit. Recently the technique of sentinel lymph node biopsy has been developed to reduce the complications of lymph node surgery while allowing assessment of the involvement of nodes with tumor.

Although controversial and without prolonging survival, "sentinel lymph node" biopsy is often performed, especially for T1b/T2+ tumors, mucosal tumors, ocular melanoma and tumors of the limbs. A process called lymphoscintigraphy is performed in which a radioactive tracer is injected at the tumor site in order to localize the "sentinel node(s)". Further precision is provided using a blue tracer dye and surgery is performed to biopsy the node(s). Routine H&E staining, and immunoperoxidase staining will be adequate to rule out node involvement. PCR tests on nodes, usually performed to test for entry into clinical trials, now demonstrate that many patients with a negative SLN actually had a small number of positive cells in their nodes. Alternatively, a fine-needle aspiration may be performed and is often used to test masses.

If a lymph node is positive, depending on the extent of lymph node spread, a radical lymph node dissection will often be performed. If the disease is completely resected, the patient will be considered for adjuvant therapy.

2) Adjuvant Treatment

High risk melanomas may require adjuvant treatment. In the United States most patients in otherwise good health will begin up to a year of high-dose interferon treatment, which has severe side effects but may improve the patient's prognosis. This claim is not supported by all research at this time, and in Europe interferon is usually not used outside the scope of clinical trials.

Metastatic melanomas can be detected by X-rays, CT scans, MRIs, PET and PET/CTs, ultrasound, LDH testing and photoacoustic detection.

3) Chemotherapy and Immunotherapy

Various chemotherapy agents are used, including dacarbazine (also termed DTIC), immunotherapy (with interleukin-2 (IL-2) or interferon (IFN)) as well as local perfusion are used by different centers. They can occasionally show dramatic success, but the overall success in metastatic melanoma is quite limited. IL-2 (Proleukin) is the first new therapy approved for the treatment of metastatic melanoma in 20 years. Studies have demonstrated that IL-2 offers the possibility of a complete and long-lasting remission in this disease, although only in a small percentage of patients. A number of new agents and novel approaches are under evaluation and show promise.

4) Lentigo Maligna Treatment

Some superficial melanomas (lentigo maligna) have resolved with an experimental treatment, imiquimod (Aldara) topical cream, an immune enhancing agent. Application of this cream has been shown to decrease tumor size prior to surgery, reducing the invasiveness of the procedure. This treatment is used especially for smaller melanoma in situ lesions located in cosmetically sensitive regions. Several published studies demonstrate a 70% cure rate with this topical treatment. With lentigo maligna, surgical cure rates are no higher. Some dermasurgeons are combining the 2 methods: surgically excising the cancer and then treating the area with Aldara cream postoperatively for three months.

5) Radiation and Other Therapies

Radiation therapy is often used after surgical resection for patients with locally or regionally advanced melanoma or for patients with unresectable distant metastases. It may reduce the rate of local recurrence but does not prolong survival.

In research setting other therapies, such as gene therapy, may be tested. Radioimmunotherapy of metastatic melanoma is currently under investigation. Experimental treatment developed at the National Cancer Institute (NCI), part of the National Institutes of Health in the US was used in advanced (metastatic) melanoma with moderate success. The treatment, adoptive transfer of genetically altered autologous lymphocytes, depends on delivering genes that encode so called T cell receptors (TCRs), into patient's lymphocytes. After that manipulation lymphocytes recognize and bind to certain molecules found on the surface of melanoma cells and kill them.

Merkel Cell Carcinoma

Merkel cell cancer, also called Merkel cell carcinoma, trabecular cancer, Apudoma of skin, or Small cell neuroepithelial tumor of the skin, is a rare and highly aggressive cancer where malignant cancer cells develop on or just beneath the skin and in hair follicles. This cancer is a type of neuroendocrine tumor, like small cell lung cancer. Once it has metastasized to the lymph nodes, the 5-year survival rate for a patient is about 50 percent. A small tumor (less than 2 cm) that has not metastasized to the lymph nodes reported a 5-year survival rate of more than 90 percent; however, at the time of diagnosis of MCC the 5-year survival was 64 percent. Up to half of patients suffer a recurrence.

It occurs most often on the face, head, and neck. It usually appears as firm, painless, nodules, or tumors. These flesh-colored, red, or blue tumors vary in size from 5 mm (less than a quarter of an inch) to more than 5 cm (2 inches). The tumor grows rapidly. About half of all Merkel cell cancers occur on the sun-exposed areas of the head and neck, while one-third begin on the legs, and 15% occur on the arms. The cancer may also begin on other parts of the body, such as the trunk.

From initial onset, Merkel cell cancer metastasizes quickly and spreads to other parts of the body, tending towards the regional lymph nodes. The tumor tends to invade underlying subcutaneous fat, fascia, and muscle. It can also metastasize to the liver, lungs, brain or bones.

Cause

A newly discovered virus called Merkel cell polyomavirus (MCV) is suspected to contribute to the development of the majority of MCC. Approximately 80% of MCC tumors have this virus integrated in a monoclonal pattern, indicating that the infection was present in a precursor cell before it became cancerous. Polyomaviruses have been known to be cancer viruses in animals since the 1950s, but this is the first polyomavirus strongly suspected to cause tumors in humans. Like other tumor viruses, most people who are infected with MCV probably do not develop MCC; it is unknown what other steps are required for the development of MCC. Ultraviolet light (sun) exposure probably contributes to MCC development in a large number of cases. MCC also occurs more frequently than expected among immunosuppressed patients, such as transplant patients, AIDS patients and elderly persons, indicating that the tumor is under immune control. At least 20% of MCC tumors are not infected with MCV suggesting that MCC may have multiple causes.

Treatment

Because Merkel cell cancer is uncommon and is difficult to diagnose, patients may want a second opinion about the diagnosis and treatment plan before starting treatment. However, early diagnosis and treatment of Merkel cell cancer are important factors in decreasing the chance of its spreading, after which it is difficult to cure.

1) Surgery

Surgery is the usual treatment for Merkel cell cancer. The tumor is removed along with a border of healthy tissue surrounding it. Nearby, or regional, lymph nodes are often removed because they may contain cancer cells. Sometimes the doctor performs a sentinel lymph node biopsy. In this procedure, the doctor injects a dye or radioactive substance near the tumor. This material flows into the first lymph nodes where cancer is likely to spread (the sentinel nodes). These nodes are then removed and checked for cancer cells. This procedure has been demonstrated to be an important prognostic indicator. Results help dictate the use of appropriate adjuvant therapy, if necessary.

2) Radiation and Chemotherapy

Adjuvant radiotherapy has been shown to be effective in reducing recurrence and increasing five year survival of patients with Merkel Cell Carcinoma. Patients who present with no metastases and a negative sentinel lymph node biopsy have a good prognosis when treated with surgery and radiotherapy—approximately 90% survival at five years.

Merkel cell cancer that has metastasized may respond to treatment with chemotherapy and/or radiation. This therapy usually does not cure the disease, but can be effective in shrinking the tumor if the tumor is too large to be removed, or is located in a place where removal would be difficult or dangerous.

3) Sentinel Lymph Node Biopsy

Sentinel lymph node biopsy detects MCC spread in one third of patients whose tumors would have otherwise been clinically and radiologically understaged and who may not have received treatment to the involved node bed. There was a significant benefit of adjuvant nodal therapy, but only when the SLNB was positive. Thus, SLNB is important for both prognosis and therapy and should be performed routinely for patients with MCC. In contrast, computed tomographic scans have poor sensitivity in detecting nodal disease as well as poor specificity in detecting distant disease.

Mesothelioma

Mesothelioma is a form of cancer that is almost always caused by previous exposure to asbestos. In this disease, malignant cells develop in the mesothelium, a protective lining that covers most of the body's internal organs. Its most common site is the pleura (outer lining of the lungs and chest cavity), but it may also occur in the peritoneum (the lining of the abdominal cavity) or the pericardium (a sac that surrounds the heart). Most people who develop mesothelioma have worked on jobs where they inhaled asbestos particles, or they have been exposed to asbestos dust and fibre in other ways, such as by washing the clothes of a family member who worked with asbestos. Unlike lung cancer, there is no association between mesothelioma and smoking. Compensation via asbestos funds or lawsuits is an important issue in mesothelioma (see asbestos and the law).

The symptoms of mesothelioma include shortness of breath due to pleural effusion (fluid between the lung and the chest wall) or chest wall pain, and general symptoms such as weight loss. The diagnosis can be made with chest X-rays and a CT scan, and confirmed with a biopsy (tissue sample) and microscopic examination. A thoracoscopy (inserting a tube with a camera into the chest) can be used to take biopsies. It allows the introduction of substances such as talc to obliterate the pleural space (called pleurodesis), which prevents more fluid from accumulating and pressing on the lung. Despite treatment with chemotherapy, radiation therapy or sometimes surgery, the disease carries a poor prognosis. Research about screening tests for the early detection of mesothelioma is ongoing.

Signs and Symptoms

Symptoms of mesothelioma may not appear until 20 to 50 years after exposure to asbestos. Shortness of breath, cough, and pain in the chest due to an accumulation of fluid in the pleural space are often symptoms of pleural mesothelioma.

Symptoms of peritoneal mesothelioma include weight loss and cachexia, abdominal swelling and pain due to ascites (a buildup of fluid in the abdominal cavity). Other symptoms of peritoneal mesothelioma may include bowel obstruction, blood clotting abnormalities, anemia, and fever. If the cancer has spread beyond the mesothelium to other parts of the body, symptoms may include pain, trouble swallowing, or swelling of the neck or face.

These symptoms may be caused by mesothelioma or by other, less serious conditions. Mesothelioma that affects the pleura can cause these signs and symptoms: 1) chest wall pain, 2) pleural effusion, or fluid surrounding the lung, 3) shortness of breath, 4) fatigue or anemia, 5) wheezing, hoarseness, or cough and 6) blood in the sputum (fluid) coughed up (hemoptysis).

In severe cases, the person may have many tumor masses. The individual may develop a pneumothorax, or collapse of the lung. The disease may metastasize, or spread, to other parts of the body.

Tumors that affect the abdominal cavity often do not cause symptoms until they are at a late stage. Symptoms include: 1) abdominal pain, 2) ascites, or an abnormal buildup of fluid in the abdomen, 3) a mass in the abdomen, 4) problems with bowel function and 5) weight loss.

In severe cases of the disease, the following signs and symptoms may be present: 1) blood clots in the veins, which may cause thrombophlebitis, 2) disseminated intravascular coagulation, a disorder causing severe bleeding in many body organs, 3) jaundice, or yellowing of the eyes and skin, 4) low blood sugar level, 5) pleural effusion, 6) pulmonary emboli, or blood clots in the arteries of the lungs and 7) severe ascites. A mesothelioma does not usually spread to the bone, brain, or adrenal glands. Pleural tumors are usually found only on one side of the lungs.

Diagnosis

Diagnosing mesothelioma is often difficult, because the symptoms are similar to those of a number of other conditions. Diagnosis begins with a review of the patient's medical history. A history of exposure to asbestos may increase clinical suspicion for mesothelioma. A physical examination is performed, followed by chest X-ray and often lung function tests. The X-ray may reveal pleural thickening commonly seen after asbestos exposure and increases suspicion of mesothelioma. A CT (or CAT) scan or an MRI is usually performed. If a large amount of fluid is present, abnormal cells may be detected by cytology if this fluid is aspirated with a syringe. For pleural fluid this is done by a pleural tap or chest drain, in ascites with an paracentesis or ascitic drain and in a pericardial effusion with pericardiocentesis. While absence of malignant cells on cytology does not completely exclude mesothelioma, it makes it much more unlikely, especially if an alternative diagnosis can be made (e.g. tuberculosis, heart failure). If cytology is positive or a plaque is regarded as suspicious, a biopsy is needed to confirm a diagnosis of mesothelioma. A doctor removes a sample of tissue for examination under a microscope by a pathologist. A biopsy may be done in different ways, depending on where the abnormal area is located. If the cancer is in the chest, the doctor may perform a thoracoscopy. In this procedure, the doctor makes a small cut through the chest wall and puts a thin, lighted tube called a thoracoscope into the chest between two ribs. Thoracoscopy allows the doctor to look inside the chest and obtain tissue samples.

If the cancer is in the abdomen, the doctor may perform a laparoscopy. To obtain tissue for examination, the doctor makes a small opening in the abdomen and inserts a special instrument into the abdominal cavity. If these procedures do not yield enough tissue, more extensive diagnostic surgery may be necessary.

| Typical immunohistochemistry results | |
|---|---|
| Positive | Negative |
| EMA (epithelial membrane antigen) in a membranous distribution | CEA (carcinoembryonic antigen) |
| WT1 (Wilms' tumour 1) | B72.3 |
| Calretinin | MOC-3 1 |
| Mesothelin-1 | CD15 |
| Cytokeratin 5/6 | Ber-EP4 |
| HBME-1 (human mesothelial cell 1) | TTF-1 (thyroid transcription factor-1) |

Screening

There is no universally agreed protocol for screening people who have been exposed to asbestos. Screening tests might diagnose mesothelioma earlier than conventional methods thus improving the survival prospects for patients. The serum osteopontin level might be useful in screening asbestos-exposed people for mesothelioma. The level of soluble mesothelin-related protein is elevated in the serum of about 75% of patients at diagnosis and it has been suggested that it may be useful for screening. Doctors have begun testing the Mesomark assay which measures levels of soluble mesothelin-related proteins (SMRPs) released by diseased mesothelioma cells.

Staging

Mesothelioma is described as localized if the cancer is found only on the membrane surface where it originated. It is classified as advanced if it has spread beyond the original membrane surface to other parts of the body, such as the lymph nodes, lungs, chest wall, or abdominal organs.

Pathophysiology

The mesothelium consists of a single layer of flattened to cuboidal cells forming the epithelial lining of the serous cavities of the body including the peritoneal, pericardial and pleural cavities. Deposition of asbestos fibres in the parenchyma of the lung may result in the penetration of the visceral pleura from where the fibre can then be carried to the pleural surface, thus leading to the development of malignant mesothelial plaques. The processes leading to the development of peritoneal mesothelioma remain unresolved, although it has been proposed that asbestos fibres from the lung are transported to the abdomen and associated organs via the lymphatic system. Additionally, asbestos fibres may be deposited in the gut after ingestion of sputum contaminated with asbestos fibres.

Pleural contamination with asbestos or other mineral fibres has been shown to cause cancer. Long thin asbestos fibers (blue asbestos, amphibole fibers) are more potent carcinogens than "feathery fibers" (chrysotile or white asbestos fibers). However, there is now evidence that smaller particles may be more dangerous than the larger fibers. They remain suspended in the air where they can be inhaled, and may penetrate more easily and deeper into the lungs. Mesothelioma development in rats has been demonstrated following intra-pleural inoculation of phosphorylated chrysotile fibres. It has been suggested that in humans, transport of fibres to the pleura is critical to the pathogenesis of mesothelioma. This is supported by the observed recruitment of significant numbers of macrophages and other cells of the immune system to localised lesions of accumulated asbestos fibres in the pleural and peritoneal cavities of rats. These lesions continued to attract and accumulate macrophages as the disease progressed, and cellular changes within the lesion culminated in a morphologically malignant tumour.

Experimental evidence suggests that asbestos acts as a complete carcinogen with the development of mesothelioma occurring in sequential stages of initiation and promotion. The molecular mechanisms underlying the malignant transformation of normal mesothelial cells by asbestos fibres remain unclear despite the demonstration of its oncogenic capabilities. However, complete in vitro transformation of normal human mesothelial cells to malignant phenotype following exposure to asbestos fibres has not yet been achieved. In general, asbestos fibres are thought to act through direct physical interactions with the cells of the mesothelium in conjunction with indirect effects following interaction with inflammatory cells such as macrophages.

Analysis of the interactions between asbestos fibres and DNA has shown that phagocytosed fibres are able to make contact with chromosomes, often adhering to the chromatin fibres or becoming entangled within the chromosome. This contact between the asbestos fibre and the chromosomes or structural proteins of the spindle apparatus can induce complex abnormalities. The most common abnormality is monosomy of chromosome 22. Other frequent abnormalities include structural rearrangement of 1p, 3p, 9p and 6q chromosome arms.

Common gene abnormalities in mesothelioma cell lines include deletion of the tumor suppressor genes:

Neurofibromatosis type 2 at 22q12
$P16^{INK4A}$
$P14^{ARF}$

Asbestos has also been shown to mediate the entry of foreign DNA into target cells. Incorporation of this foreign DNA may lead to mutations and oncogenesis by several possible mechanisms:

Inactivation of tumor suppressor genes
Activation of oncogenes
Activation of proto-oncogenes due to incorporation of foreign DNA containing a promoter region
Activation of DNA repair enzymes, which may be prone to error
Activation of telomerase
Prevention of apoptosis Asbestos fibres have been shown to alter the function and secretory properties of macrophages, ultimately creating conditions which favour the development of mesothelioma. Following asbestos phagocytosis, macrophages generate increased amounts of hydroxyl radicals, which are normal by-products of cellular anaerobic metabolism. However, these free radicals are also known clastogenic and membrane-active agents thought to promote asbestos carcinogenicity. These oxidants can participate in the oncogenic process by directly and indirectly interacting with DNA, modifying membrane-associated cellular events, including oncogene activation and perturbation of cellular antioxidant defences.

Asbestos also may possess immunosuppressive properties. For example, chrysotile fibres have been shown to depress the in vitro proliferation of phytohemagglutinin-stimulated peripheral blood lymphocytes, suppress natural killer cell lysis and significantly reduce lymphokine-activated killer cell viability and recovery. Furthermore, genetic alterations in asbestos-activated macrophages may result in the release of potent mesothelial cell mitogens such as platelet-derived growth factor (PDGF) and transforming growth factor-β (TGF-β) which in turn, may induce the chronic stimulation and proliferation of mesothelial cells after injury by asbestos fibres.

Treatment

Treatment of malignant mesothelioma using conventional therapies has not proved successful and patients have a median survival time of 6-12 months after presentation. The clinical behaviour of the malignancy is affected by several factors including the continuous mesothelial surface of the pleural cavity which favours local metastasis via exfoliated cells, invasion to underlying tissue and other organs within the pleural cavity, and the extremely long latency period between asbestos exposure and development of the disease.

1) Surgery

Surgery, either by itself or used in combination with pre- and post-operative adjuvant therapies, has proved disappointing. A pleurectomy/decortication is the most common surgery, in which the lining of the chest is removed. Less common is an extrapleural pneumonectomy (EPP), in which the lung, lining of the inside of the chest, the hemi-diaphragm and the pericardium are removed. It is not possible to remove the entire mesothelium without killing the patient.

2) Radiation

For patients with localized disease, and who can tolerate a radical surgery, radiation is often given post-operatively as a consolidative treatment. The entire hemi-thorax is treated with radiation therapy, often given simultaneously with chemotherapy. This approach of using surgery followed by radiation with chemotherapy has been pioneered by the thoracic oncology team at Brigham & Women's Hospital in Boston. Delivering radiation and chemotherapy after a radical surgery has led to extended life expectancy in selected patient populations with some patients surviving more than 5 years. As part of a curative approach to mesothelioma, radiotherapy is also commonly applied to the sites of chest drain insertion, in order to prevent growth of the tumor along the track in the chest wall.

Although mesothelioma is generally resistant to curative treatment with radiotherapy alone, palliative treatment regimens are sometimes used to relieve symptoms arising from tumor growth, such as obstruction of a major blood vessel. Radiation therapy when given alone with curative intent has never been shown to improve survival from mesothelioma. The necessary radiation dose to treat mesothelioma that has not been surgically removed would be very toxic.

3) Chemotherapy

In February 2004, the United States Food and Drug Administration approved pemetrexed (brand name Alimta) for treatment of malignant pleural mesothelioma. Pemetrexed is given in combination with cisplatin. Folic acid is also used to reduce the side-effects of pemetrexed.

4) Immunotherapy

Treatment regimens involving immunotherapy have yielded variable results. For example, intrapleural inoculation of *Bacillus* Calmette-Guérin (BCG) in an attempt to boost the immune response, was found to be of no benefit to the patient (while it may benefit patients with bladder cancer). Mesothelioma cells proved susceptible to in vitro lysis by LAK cells following activation by interleukin-2 (IL-2), but patients undergoing this particular therapy experienced major side effects. Indeed, this trial was suspended in view of the unacceptably high levels of IL-2 toxicity and the severity of side effects such as fever and cachexia. Nonetheless, other trials involving interferon alpha have proved more encouraging with 20% of patients experiencing a greater than 50% reduction in tumor mass combined with minimal side effects.

5) Heated Intraoperative Intraperitoneal Chemotherapy

A procedure known as heated intraoperative intraperitoneal chemotherapy was developed by Paul Sugarbaker at the Washington Cancer Institute. The surgeon removes as much of the tumor as possible followed by the direct administration of a chemotherapy agent, heated to between 40 and 48° C., in the abdomen. The fluid is perfused for 60 to 120 minutes and then drained.

This technique permits the administration of high concentrations of selected drugs into the abdominal and pelvic surfaces. Heating the chemotherapy treatment increases the penetration of the drugs into tissues. Also, heating itself damages the malignant cells more than the normal cells.

Metastatic Neoplasm

Metastasis, sometimes abbreviated mets, is the spread of a disease from one organ or part to another non-adjacent organ or part. Only malignant tumor cells and infections have the capacity to metastasize. Metastatic disease is a synonym of metastasis. Cancer cells can "break away", "leak", or "spill" from a primary tumor, enter lymphatic and blood vessels, circulate through the bloodstream, and settle down to grow within normal tissues elsewhere in the body. Metastasis is one of three hallmarks of malignancy (contrast benign tumors). Most tumors and other neoplasms can metastasize, although in varying degrees (e.g., glioma and basal cell carcinoma rarely metastasize).

When tumor cells metastasize, the new tumor is called a secondary or metastatic tumor, and its cells are like those in the original tumor. This means, for example, that if breast cancer spreads (metastasizes) to the lung, the secondary tumor is made up of abnormal breast cells, not of abnormal lung cells. The tumor in the lung is then called metastatic breast cancer, not lung cancer.

Modes and Sites of Metastatic Dispersal

Metastatic tumors are very common in the late stages of cancer. The spread of metastases may occur via the blood or the lymphatics or through both routes. The most common places for the metastases to occur are the adrenals, liver, brain, and the bones. There is also a propensity for certain tumors to seed in particular organs. This was first discussed as the "seed and soil" theory by Stephen Paget over a century ago in 1889. For example, prostate cancer usually metastasizes to the bones. In a similar manner, colon cancer has a tendency to metastasize to the liver. Stomach cancer often metastasizes to the ovary in women, then it is called a Krukenberg tumor. It is difficult for cancer cells to survive outside their region of origin, so in order to metastasize they must find a location with similar characteristics.

For example, breast tumor cells, which gather calcium ions from breast milk, metastasize to bone tissue, where they can gather calcium ions from bone. Malignant melanoma spreads to the brain, presumably because neural tissue and melanocytes arise from the same cell line in the embryo.

Cancer cells may spread to lymph nodes (regional lymph nodes) near the primary tumor. This is called nodal involvement, positive nodes, or regional disease. Localized spread to regional lymph nodes near the primary tumor is not normally counted as metastasis, although this is a sign of worse prognosis. Transport through lymphatics is the most common pathway for the initial dissemination of carcinomas.

In addition to the above routes, metastasis may occur by direct seeding, e.g., in the peritoneal cavity or pleural cavity.

Factors Involved

Metastasis is a complex series of steps in which cancer cells leave the original tumor site and migrate to other parts of the body via the bloodstream or the lymphatic system. To do so, malignant cells break away from the primary tumor and attach to and degrade proteins that make up the surrounding extracellular matrix (ECM), which separates the tumor from adjoining tissue. By degrading these proteins, cancer cells are able to breach the ECM and escape. When oral cancers metastasize, they commonly travel through the lymph system to the lymph nodes in the neck. The body resists metastasis by a variety of mechanisms through the actions of a class of proteins known as metastasis suppressors, of which about a dozen are known.

Cancer researchers studying the conditions necessary for cancer metastasis have discovered that one of the critical events required is the growth of a new network of blood vessels, called tumor angiogenesis. It has been found that angiogenesis inhibitors would therefore prevent the growth of metastases.

Metastasis and Primary Cancer

It is theorized that metastasis always coincides with a primary cancer, and, as such, is a tumor that started from a cancer cell or cells in another part of the body. However, over 10% of patients presenting to oncology units will have metastases without a primary tumor found. In these cases, doctors refer to the primary tumor as "unknown" or "occult," and the patient is said to have cancer of unknown primary origin (CUP) or Unknown Primary Tumors (UPT). It is estimated that 3% of all cancers are of unknown primary origin. Studies have shown that, if simple questioning does not reveal the cancer's source (coughing up blood—'probably lung', urinating blood—'probably bladder'), complex imaging will not either. In some of these cases a primary may appear later.

The use of immunohistochemistry has permitted pathologists to give an identity to many of these metastases. However, imaging of the indicated area only occasionally reveals a primary. In rare cases (e.g., of melanoma), no primary tumor is found, even on autopsy. It is therefore thought that some primary tumors can regress completely, but leave their metastases behind.

Diagnosis of Primary and Secondary Tumors

The cells in a metastatic tumor resemble those in the primary tumor. Once the cancerous tissue is examined under a microscope to determine the cell type, a doctor can usually tell whether that type of cell is normally found in the part of the body from which the tissue sample was taken.

For instance, breast cancer cells look the same whether they are found in the breast or have spread to another part of the body. So, if a tissue sample taken from a tumor in the lung contains cells that look like breast cells, the doctor determines that the lung tumor is a secondary tumor. Still, the determination of the primary tumor can often be very difficult, and the pathologist may have to use several adjuvant techniques, such as immunohistochemistry, FISH (fluorescent in situ hybridization), and others. Despite the use of techniques, in some cases the primary tumor remains unidentified.

Metastatic cancers may be found at the same time as the primary tumor, or months or years later. When a second tumor is found in a patient that has been treated for cancer in the past, it is more often a metastasis than another primary tumor.

Treatments for Metastatic Cancer

Whether or not a cancer is local or has spread to other locations affects treatment and survival. If the cancer spreads to other tissues and organs, it may decrease a patient's likelihood of survival. However, there are some cancers (i.e., leukemia, brain) that can kill without spreading at all.

When cancer has metastasized, it may be treated with radiosurgery, chemotherapy, radiation therapy, biological therapy, hormone therapy, surgery or a combination of these. The choice of treatment generally depends on the type of primary cancer, the size and location of the metastasis, the patient's age and general health, and the types of treatments used previously. In patients diagnosed with CUP, it is still possible to treat the disease even when the primary tumor cannot be located.

The treatment options currently available are rarely able to cure metastatic cancer, though some tumors, such as testicular cancer, are usually still curable.

Microcystic Adnexal Carcinoma

Microcystic adnexal carcinoma (MAC) is a rare, malignant appendage tumor commonly classified as a low-grade sweat gland carcinoma that typically occurs on the head and neck, particularly the central face. It shows aggressive local invasion but has little metastatic potential.

Despite subsequent widespread recognition of MAC as a discrete clinicopathologic entity, its precise relationship to and histologic discrimination from other putative locally aggressive sweat gland carcinomas (reported under a variety of names, including sclerosing sweat duct carcinoma, syringoid eccrine carcinoma, syringomatous carcinoma, and eccrine epithelioma) remains unresolved and has provoked considerable nosologic and diagnostic confusion.

Diagnosis

1) Imaging Studies

CT scanning may be used to map out local invasion into nerves, muscle, cartilage, or bone, and it may also be used to help define metastatic disease, if suspected. MRI has also been used to assess tumor extent. However, imaging is not necessary in most cases.

2) Procedures

A deep incisional or excisional biopsy is required. Superficial biopsies lead to misdiagnosis because deep extension and perineural invasion are key features of the tumor.

3) Histologic Findings

MAC is a poorly circumscribed, deeply infiltrative, asymmetric tumor composed of variable proportions of keratocysts, squamoid or basaloid nests, infiltrating cords, and ductular structures set in a variably hyalinized but usually paucicellular desmoplastic stroma. The epithelial nests are tadpole shaped, creating a "paisley-tie" appearance. Lymphoid aggregates are common, particularly at the dermal-subcutaneous junction.

4) Hematoxylin and Eosin

In a minority of cases, MAC shows attachment to the epidermis or the follicles, but generally, a striking zonal separation is noted between the tumor and the epidermis. In the superficial aspects of the tumor, small-to-medium keratinizing cysts lined by squamous epithelium can be seen. Atypia and mitoses are sparse. Nests of small basaloid or squamoid cells, sometimes showing a whorled-appearing infiltrate between the cysts with depth, are present. These may be solid, show central keratinization, can rarely be calcified or demonstrate central lumen formation, and have a tadpole or paisley-tie appearance.

In deeper sections, variable numbers of small ducts lined by 1-2 layers of cuboidal cells are present throughout the tumor. Narrow cords of cuboidal cells usually characterize the deepest portion of the tumor. Some of the nests and ducts show tail-like cellular extensions reminiscent of syringoma. Glycogen-rich, clear-cell change, foci of decapitation secretion, and sebaceous cell or duct differentiation may be present. The nuclei of all the components are mainly small, slightly irregular, and hyperchromatic, but little pleomorphism or mitotic activity occurs. Perineural infiltration is common. With regard to histologic subtype, tumors displaying the architectural features of MAC but with increased nuclear pleomorphism, hyperchromasia, vascular invasion, and necrosis may be suggestive of a more aggressive subtype. Clinically, these have demonstrated rapid growth, carcinosarcomatous metaplastic transformation with relapse, and suspected metastases.

5) Toluidine Blue

Special staining with toluidine blue has been shown to highlight infiltrating tumor strands with a distinctive pink halo and perineural invasion with a maroon tint. This stain may be of benefit in Mohs micrographic surgery (MMS).

6) Immunohistochemistry

Pancytokeratin, AE1/AE3, and cytokeratin-1 positively highlight tumor cells. Reactivity to hard keratin subclasses AE 13 and AE 14 has been demonstrated and suggests pilar differentiation. Epithelial membrane antigen and carcinoembryonic antigen highlight ductal structures or intracytoplasmic lumen formation and suggest sudoriferous differentiation. Additionally, Leu-M1 is positive and S-100 is negative.

CD5, a lymphoid tumor marker, was recently found to stain MACs 71% of the time, particularly in deeper sections, which may help differentiate them from desmoplastic trichoepitheliomas and morpheaform basal cell carcinomas.

Cytokeratin-20 tumor staining was negative in one case report. Its utility was suggested to help differentiate MAC from other benign adnexal tumors that typically carry scattered Merkel cells throughout.

7) Histologic Differential Diagnosis

The important differentials histologically are syringoma and desmoplastic trichoepithelioma. With hematoxylin and eosin staining, attention to the infiltrative growth pattern, and, if present, perineural invasion, usually easily discriminates MAC from the others in suitable biopsy specimens. CD5 positivity in deeper sections would favor MAC over desmoplastic trichoepithelioma.

That being stated, rendering a definitive diagnosis from a shave or superficial punch biopsy specimen often is impossible. Duct formation, if present, would favor MAC over desmoplastic trichoepithelioma. Further, keratocysts with mild atypia and little mitosis would favor MAC over syringoma. Cytokeratin-20 testing for Merkel cell loss suggests MAC.

Distinction from a morpheaform basal cell carcinoma can be made by the demonstration of duct and intracytoplasmic lumen formation and with zonation of the tumor from the epidermis, which is typically seen with MAC. Ductal formation is rare in basal cell carcinoma. If seen, it is usually in nodular subtypes. CD5 positivity in deeper sections would also favor MAC over morpheaform basal cell carcinoma, whereas Ber-EP4 positivity favors basal cell carcinoma.

Desmoplastic squamous cell carcinoma generally lacks zonation from the epidermis, ductal structures, or intracytoplasmic lumen formation.

Desmoplastic melanoma also typically lacks zonation, ductal structures, and keratocyst formation, and it is reliably S-100 positive. Lymphoid aggregates are usually situated throughout the tumor, as opposed to the dermal-subcutaneous junction, as is seen in MAC.

Trichoadenomas tend to be more well-defined tumors with larger keratin cysts surrounded by a fibrovascular stroma. Typically, they lack deep invasion and do not show perineural invasion.

Metastatic adenocarcinomas (ie, breast and colon) demonstrate more pleomorphism and cytologic atypia, and they lack keratocyst formation.

Most authorities distinguish MAC from similar low-grade sweat gland carcinomas that have previously been termed syringomatous carcinoma, eccrine epithelioma, or group 2 sclerosing sweat duct carcinoma largely on the basis of the presence of keratocysts or other evidence of follicular differentiation. However, some have suggested that these tumors could be variations of the same entity.

Treatment

1) Medical Care

Surgery is the mainstay of treatment. Radiation therapy has also been used as a primary therapy or as an adjuvant to surgery. However, radiation alone often results in recurrence (It is also implicated as a cause of MAC.) and some tumors are radioresistant.

2) Surgical Care

MMS is the current treatment of choice. Clinical margins are difficult to define, and MMS offers an excellent way of following the infiltrating nature of the tumor and tracing perineural involvement. The discrepancy between clinical and histologic extent can be marked, in that the size of the defect after complete tumor removal following MMS can be as much as 4 to 6 times that of the clinically apparent size. Therefore, standardized, predictable, predetermined surgical margins cannot be used in the treatment of MAC.

3) MMS Versus Simple Excision

In the largest series to date (48 patients), little difference in the overall recurrence rate between tumors treated with MMS (2.4% per person-year) versus standard surgical excision (1.5% per person-year) at a mean follow-up of 3.2 years was found. However, MMS exhibited a clear benefit over simple excision in that 30% of tumors treated with simple excision required at least another office visit to clear the patient of histological tumor findings, with 1 patient still not tumor free after 4 simple excisions. This rate was compared with 0% if treated by MMS.

4) Staged Excision (Slow MMS)

Problems can also be encountered in interpreting frozen sections during MMS, when microscopic invasion can be elusive. Possibly, delayed-closure MMS using formalin-fixed, paraffin-embedded specimens improves the histologic assessment and decreases the risk of missing a strand of tumor. Some advocate the use of tangential frozen sections with MMS plus formalin-fixed paraffin sections for the final layer, and this is a workable compromise. Moreover, recent reports advocate the use of toluidine-blue staining on frozen sections to highlight MAC extension. Tumor stroma has a pink halo, owing to the presence of mucopolysaccharide and hyaluronic acid, and perineural involvement has a magenta hue, thereby augmenting visualization and clearance with MMS.

Heavy Chain Disease/Mu Chain Disease

Heavy chain disease is a form of paraproteinemia with a proliferation of heavy chains. This disease is characterized by an excessive production of immunoglobulin heavy chains that are short and truncated. The amino acid sequence on the amino terminal is completely normal, but there is a deletion in the protein structure that extends from the middle of the variable region, through the first domain of the constant region, and ending just before the position of the first disulfide bond between the two heavy chains. This deletion causes the heavy chains to lose the ability to form disulfide bonds with the light chains. The defect in the immunoglobulins arises during the faulty coupling of the variable and constant regions during somatic recombination.

Classification

There are three forms: 1) alpha chain disease, 2) gamma chain disease and 3) mu chain disease.

IgA/αHCD

The most common type of heavy chain disease is the IgA type, known as αHCD. This is because the most common immunoglobulin in the body is IgA. The most common type of αHCD is the digestive form, however it has also been reported in the respiratory tract, and other areas of the body.

IgG/γHCD

IgM and IgG heavy chain diseases, which are known as μHCD and γHCD respectively, are fairly common and are present in various tissues.

The γHCD can be divided into three categories based on the various clinical and pathological features. These categories are disseminated lymphoproliferative disease, localized proliferative disease and no apparent proliferative disease.

Disseminated lymphoproliferative disease is found in 57-66% of patients diagnosed with γHCD. Lymphadenopathy and constitutional symptoms are the usual features. Localized proliferative disease is found in approximately 25% of γHCD patients. This is characterized by a localization of the mutated heavy chains in extramedullary tissue, or solely in the bone marrow.

No apparent proliferative disease is seen in 9-17% of patients with γHCD, and there is almost always an underlying autoimmune disorder in these patients.

IgM/μHCD

The IgM type of heavy chain disease, μHCD, is often misdiagnosed as chronic lymphoid leukemia (CLL) because the two diseases are often associated with each other and show similar symptoms.

Mu Chain Disease/Heavy Chain Disease

Heavy chain diseases (HCDs) are rare B-cell proliferative disorders characterized by the synthesis and secretion of incomplete immunoglobulin heavy chains. These disorders initially were recognized as gammopathies due to the presence of monoclonal proteins in the patient's serum or urine. The disorders were defined in terms of the production of structurally aberrant immunoglobulin molecules. Normal immunoglobulin molecules are symmetrical and are composed of 2 pairs of polypeptide chains designated the light and heavy chains, which are interconnected by disulfide bonds. The heavy chains are the larger polypeptide subunits; they are specific and distinctive structures that distinguish the major classes of immunoglobulins. Reductive cleavage of the immunoglobulin molecule by papain yields 2 Fab fragments (consisting of a light chain and an Fd fragment) and one Fc fragment (consisting of portions of the 2 heavy chains). Plasma cell disorders characterized by an anomalous serum and urinary protein that is immunochemically related to the Fc fragment of the immunoglobulin molecule are known as HCDs. When the anomalous protein structurally resembles the heavy chain fragment of immunoglobulin M (IgM) molecule, it is designated as mu-HCD.

Diagnosis

1) Lab Studies

Laboratory studies should include complete blood cell count with differential, screening chemistries to ascertain renal function (eg, BUN and creatinine) and hepatic function (eg, total protein, albumin, aspartate aminotransferase, alanine aminotransferase, lactate dehydrogenase, alkaline phosphatase), calcium levels, and beta-2 microglobulin values.

2) Imaging Studies

No definitive guidelines are available regarding the extent of imaging studies that should be performed when diagnosing patients suggested to have mu-HCD.

Performing a chest radiograph is reasonable, and a skeletal survey is considered essential given the fact that 40% of patients present with osteolytic lesions.

Obtaining CT scans of the thorax and abdomen is appropriate because hepatosplenomegaly and lymphadenopathy are common. CT scan findings help to objectively quantify disease and are useful for assessing response to therapy.

3) Other Tests

Serum protein electrophoresis (SPEP) or urine protein electrophoresis (UPEP) and immunofixation are essential tests.

As a rule, the neoplastic cells do not produce large amounts of immunoglobulin, which may make detecting the abnormal immunoglobulin produced in a patient with HCD difficult. Performing a combination of electrophoretic, immunoelectrophoretic, and immunofixation techniques can help establish the diagnosis.

In a minority of cases, the proteins can initially be identified as a discrete homogenous band of mobility on SPEP or UPEP findings.

When developed with specific antiheavy and antilight sera, the immunoelectrophoretic pattern reveals a heavy chain—specific arc that does not react with either antikappa or antilambda antisera.

IgM M-proteins sometimes do not react with certain antilight sera. This is more common with immunoelectrophoresis than with immunofixation techniques. In these cases, separating the monoclonal proteins from the serum, treating them with reducing agents to cleave disulfide bonds, and subjecting them to gel electrophoresis to determine the size of the immunoglobulin heavy chain polypeptide may be necessary.

More commonly, the proteins are present in smaller amounts and give a heterogenous pattern on electrophoresis findings. A monoclonal spike was detected in 8 of 19 patients, and 3 of 28 patients had a biclonal gammopathy. Again, immunoelectrophoresis or immunofixation findings showing the development of patterns with a panel of antiheavy/antilight antibodies can strongly suggest the diagnosis. In specialized laboratories, more detailed structural analysis can be performed on the isolated, reduced, and alkylated heavy chain monomer to confirm the presence or absence of immunoglobulin light chains.

Urinary excretion of the mu fragment has been noted in only 2 patients; this presumably is because the polymers of the carboxy-terminal mu fragment are too large to be filtered by intact renal glomeruli. Monoclonal light chains have been found in the urine in two thirds of cases. Thus, Bence Jones proteinuria is a common occurrence in patients with this disorder. Nonetheless, renal complications are infrequent. Immunoglobulin light chains capable of producing amyloid are found in approximately 12% of cases, an incidence that is similar to that observed in patients with multiple myeloma.

Immunoglobulin gene rearrangement may be used to differentiate a B-cell lymphoproliferative process from a monoclonal or reactive proliferation of lymphocytes. This technique not only provides a specific marker for B cells, but it also is a true marker for monoclonality.

4) Procedures

Almost all patients should undergo bone marrow aspiration and biopsy. Certain histologic features, as outlined below, may aid in making the diagnosis of mu-HCD.

When mu-HCD is not considered based on the patient's presentation, as is commonly the case, biopsy of the appropriate involved area (eg, lymph node mass) is required to establish the diagnosis of a lymphoproliferative disorder.

5) Histologic Findings

Marrow involvement is characterized by infiltration with lymphocytes and plasma cells. Cells that often are described as lymphocytic plasmacytes or plasmacytoid lymphocytes are prominent. Although the marrow of almost all patients contains the multivacuolated plasma cells described in the index case, the vacuoles are not universally apparent. The identification of these vacuoles sometimes offers a clue to the diagnosis, which requires confirmation by appropriate electrophoretic and immunoelectrophoretic studies.

6) Staging

Given the rarity of mu-HCD, a clinical staging system has not been developed. Accompanying lymphoproliferative disorders such as CLL, non-Hodgkin lymphoma, and multiple myeloma should be appropriately staged.

Treatment

No specific treatment exists. In the absence of a demonstrated lymphoproliferative disorder, the condition is monitored as a monoclonal gammopathy of unknown significance. Once a lymphoproliferative disorder develops, chemotherapeutic agents are used as appropriate for the patient's disorder, stage, and clinical situation (eg, melphalan and prednisone or vincristine, doxorubicin, and dexamethasone for multiple myeloma; chlorambucil or fludarabine for CLL). Successful treatment with fludarabine phosphate has recently been reported.

Myeloma

Multiple myeloma (also known as MM, myeloma, plasma cell myeloma, or as Kahler's disease after Otto Kahler) is a type of cancer of plasma cells which are immune system cells in bone marrow that produce antibodies. Myeloma is regarded as incurable, but remissions may be induced with steroids, chemotherapy, thalidomide and stem cell transplants. Myeloma is part of the broad group of diseases called hematological malignancies.

Signs and Symptoms

Because many organs can be affected by myeloma, the symptoms and signs vary greatly. A mnemonic sometimes used to remember the common tetrad of multiple myeloma is CRAB—C=Calcium (elevated), R=Renal failure, A=Anemia, B=Bone lesions. Myeloma has many possible symptoms, and all symptoms may be due to other causes. They are presented here in decreasing order of incidence.

1) Bone Pain

Myeloma bone pain usually involves the spine and ribs, and worsens with activity.

Persistent localized pain may indicate a pathological bone fracture. Involvement of the vertebrae may lead to spinal cord compression. Myeloma bone disease is due to proliferation of tumor cells and release of IL-6, also known as osteoclast activating factor (OAF), which stimulates osteoclasts to break down bone. These bone lesions are lytic in nature and are best seen in plain radiographs, which may show "punched-out" resorptive lesions. The breakdown of bone also leads to release of calcium into the blood, leading to hypercalcemia and its associated symptoms.

2) Infection

The most common infections are pneumonias and pyelonephritis. Common pneumonia pathogens include S. pneumoniae, S. aureus, and K. pneumoniae, while common pathogens causing pyelonephritis include E. coli and other gram-negative organisms. The greatest risk period for the occurrence of infection is in the initial few months after the start of chemotherapy. The increased risk of infection is due to immune deficiency resulting from diffuse hypogammaglobulinemia, which is due to decreased production and increased destruction of normal antibodies. A selected group of patients may benefit from replacement immunoglobulin therapy to reduce the risk of infection.

3) Renal Failure

Renal failure may develop both acutely and chronically. It is commonly due to hypercalcemia (see above). It may also be due to tubular damage from excretion of light chains, also called Bence Jones proteins, which can manifest as the Fanconi syndrome (type II renal tubular acidosis). Other causes include glomerular deposition of amyloid, hyperuricemia, recurrent infections (pyelonephritis), and local infiltration of tumor cells.

4) Anemia

The anemia found in myeloma is usually normocytic and normochromic. It results from the replacement of normal bone marrow by infiltrating tumor cells and inhibition of normal red blood cell production (hematopoiesis) by cytokines.

5) Neurological Symptoms

Common problems are weakness, confusion and fatigue due to hypercalcemia. Headache, visual changes and retinopathy may be the result of hyperviscosity of the blood depending on the properties of the paraprotein. Finally, there may be radicular pain, loss of bowel or bladder control (due to involvement of spinal cord leading to cord compression) or carpal tunnel syndrome and other neuropathies (due to infiltration of peripheral nerves by amyloid). It may give rise to paraplegia in late presenting cases.

Diagnosis

1) Investigations

The presence of unexplained anemia, kidney dysfunction, a high erythrocyte sedimentation rate (ESR) and a high serum protein (especially raised immunoglobulin) may prompt further testing. A doctor will request protein electrophoresis of the blood and urine, which might show the presence of a paraprotein (monoclonal protein, or M protein) band, with or without reduction of the other (normal) immunoglobulins (known as immune paresis). One type of paraprotein is the Bence Jones protein which is a urinary paraprotein composed of free light chains (see below). Quantitative measurements of the paraprotein are necessary to establish a diagnosis and to monitor the disease. The paraprotein is an abnormal immunoglobulin produced by the tumor clone. Very rarely, the myeloma is nonsecretory (not producing immunoglobulins). In theory, multiple myeloma can produce all classes of immunoglobulin, but IgG paraproteins are most common, followed by IgA and IgM. IgD and IgE myeloma are very rare. In addition, light and or heavy chains (the building blocks of antibodies) may be secreted in isolation: κ- or λ-light chains or any of the five types of heavy chains (α-, γ-, δ-, ε- or μ-heavy chains).

Additional findings include: a raised calcium (when osteoclasts are breaking down bone, releasing calcium into the bloodstream), raised serum creatinine due to reduced renal function, which may be due to paraprotein deposition in the kidney.

2) Workup

The workup of suspected multiple myeloma includes a skeletal survey. This is a series of X-rays of the skull, axial skeleton and proximal long bones. Myeloma activity sometimes appear as "lytic lesions" (with local disappearance of normal bone due to resorption), and on the skull X-ray as "punched-out lesions" (pepper pot skull).

Magnetic resonance imaging (MRI) is more sensitive than simple X-ray in the detection of lytic lesions, and may supersede skeletal survey, especially when vertebral disease is suspected. Occasionally a CT scan is performed to measure the size of soft tissue plasmacytomas. Bone scans are typically not of any additional value in the workup of myeloma patients.

A bone marrow biopsy is usually performed to estimate the percentage of bone marrow occupied by plasma cells. This percentage is used in the diagnostic criteria for myeloma. Immunohistochemistry (staining particular cell types using antibodies against surface proteins) can detect plasma cells which express immunoglobulin in the cytoplasm but usually not on the surface; myeloma cells are typically CD56, CD38, CD138 positive and CD19 and CD45 negative. Cytogenetics may also be performed in myeloma for prognostic purposes.

Other useful laboratory tests include quantitative measurement of IgA, IgG, IgM (immunoglobulins) to look for immune paresis, and β2-microglobulin which provides prognostic information. On peripheral blood smear the rouleaux formation of red blood cells is commonly seen.

The recent introduction of a commercial immunoassay for measurement of free light chains potentially offers an improvement in monitoring disease progression and response to treatment, particularly where the paraprotein is difficult to measure accurately by electrophoresis (for example in light chain myeloma, or where the paraprotein level is very low). Initial research also suggests that measurement of free light chains may also be used, in conjunction with other markers, for assessment of the risk of progression from monoclonal gammopathy of undetermined significance (MGUS) to multiple myeloma.

3) Diagnostic Criteria

In 2003, the International Myeloma Working Group agreed on diagnostic criteria for symptomatic myeloma, asymptomatic myeloma and MGUS (monoclonal gammopathy of undetermined significance):

Symptomatic Myeloma:
1. Clonal plasma cells >10% on bone marrow biopsy or (in any quantity) in a biopsy from other tissues (plasmacytoma)
2. A monoclonal protein (paraprotein) in either serum or urine
3. Evidence of end-organ damage (related organ or tissue impairment, ROTI):
   Hypercalcemia (corrected calcium >2.75 mmol/L)
   Renal insufficiency attributable to myeloma
   Anemia (hemoglobin <10 g/dL)
   Bone lesions (lytic lesions or osteoporosis with compression fractures)
   Frequent severe infections (>2 a year)
   Amyloidosis of other organs
   Hyperviscosity syndrome Asymptomatic Myeloma:
1. Serum paraprotein >30 g/L AND/OR
2. Clonal plasma cells >10% on bone marrow biopsy AND
3. NO myeloma-related organ or tissue impairment Monoclonal Gammopathy of Undetermined Significance (MGUS):
1. Serum paraprotein <30 g/L AND
2. Clonal plasma cells <10% on bone marrow biopsy AND
3. NO myeloma-related organ or tissue impairment Related conditions include solitary plasmacytoma (a single tumor of plasma cells, typically treated with irradiation), plasma cell dyscrasia (where only the antibodies produce symptoms, e.g. AL amyloidosis), and POEMS syndrome (peripheral neuropathy, organomegaly, endocrinopathy, monoclonal plasma cell disorder, skin changes).

4) Staging

International Staging System

The International Staging System (ISS) for myeloma was published by the International Myeloma Working Group in 2005:

Stage I: $\beta_2$-microglobulin ($\beta 2M$)<3.5 mg/L, albumin>=3.5 g/dL
Stage II: $\beta 2M$<3.5 and albumin<3.5; or $\beta 2M$>=3.5 and <5.5
Stage III: $\beta 2M$>=5.5

Durie-Salmon Staging System

First published in 1975, the Durie-Salmon staging system is still in use, but has largely been superseded by the simpler ISS:

stage 1: all of
  Hb>10 g/dL
  normal calcium
  Skeletal survey: normal or single plasmacytoma or osteoporosis
  Serum paraprotein level <5 g/dL if IgG, <3 g/dL if IgA
  Urinary light chain excretion <4 g/24 h
stage 2: fulfilling the criteria of neither 1 nor 3
stage 3: one or more of
  Hb<8.5 g/dL
  high calcium >12 mg/dL
  Skeletal survey: 3 or more lytic bone lesions
  Serum paraprotein >7 g/dL if IgG, >5 g/dL if IgA
  Urinary light chain excretion >12 g/24 h Stages 1, 2 and 3 of the Durie-Salmon staging system can be divided into A or B depending on serum creatinine:
  A: serum creatinine <2 mg/dL (<177 umol/L)
  B: serum creatinine >2 mg/dL (>177 umol/L)

Pathophysiology

Multiple myeloma develops in post-germinal center B lymphocytes. A chromosomal translocation between the immunoglobulin heavy chain gene (on the fourteenth chromosome, locus 14q32) and an oncogene (often 11q13, 4p16.3, 6p21, 16q23 and 20q11) is frequently observed in patients with multiple myeloma. This mutation results in dysregulation of the oncogene which is thought to be an important initiating event in the pathogenesis of myeloma. The result is proliferation of a plasma cell clone and genomic instability that leads to further mutations and translocations. The chromosome 14 abnormality is observed in about 50% of all cases of myeloma. Deletion of (parts of) the thirteenth chromosome is also observed in about 50% of cases.

Production of cytokines (especially IL-6) by the plasma cells causes much of their localised damage, such as osteoporosis, and creates a microenvironment in which the malignant cells thrive. Angiogenesis (the attraction of new blood vessels) is increased. The produced antibodies are deposited in various organs, leading to renal failure, polyneuropathy and various other myeloma-associated symptoms.

Treatment

Treatment for multiple myeloma is focused on disease containment and suppression. If the disease is completely asymptomatic (i.e. there is a paraprotein and an abnormal bone marrow population but no end-organ damage), treatment may be deferred.

In addition to direct treatment of the plasma cell proliferation, bisphosphonates (e.g. pamidronate or zoledronic acid) are routinely administered to prevent fractures and erythropoietin to treat anemia.

1) Initial Therapy

Initial treatment is aimed at treating symptoms and reducing disease burden. Commonly used induction regimens include dexamethasone with or without thalidomide and cyclophosphamide, and VAD (vincristine, adriamycin, and dexamethasone). Low-dose therapy with melphalan combined with prednisone can be used to palliate symptoms in patients who cannot tolerate aggressive therapy. Plasmapheresis can be used to treat symptomatic protein proliferation (hyperviscosity syndrome).

In younger patients, therapy may include high-dose chemotherapy, melphalan, and autologous stem cell transplantation. This can be given in tandem fashion, i.e. an autologous transplant followed by a second transplant. Nonmyeloablative (or "mini") allogeneic stem cell transplantation is being investigated as an alternative to autologous stem cell transplant, or as part of a tandem transplant following an autologous transplant (also known as an "auto-mini" tandem transplant). Allogeneic stem cell transplant offers the possibility of a cure, but is not performed commonly. It is considered investigational given the high treatment-related mortality of 5-10% associated with the procedure.

A 2007 trial indicated that the addition of thalidomide to reduced-intensity chemotherapy (melphalan and prednisone, MP) in patients between 65-75 led to a marked prolongation (median 51 versus 33 months) in survival. Reduced intensity melphalan followed by a stem cell transplant was inferior to the MP-thalidomide regimen (median survival 38 months).

2) Relapse

The natural history of myeloma is of relapse following treatment. Depending on the patient's condition, the prior treatment modalities used and the duration of remission, options for relapsed disease include re-treatment with the original agent, use of other agents (such as melphalan, cyclophosphamide, thalidomide or dexamethasone, alone or in combination), and a second autologous stem cell transplant.

Later in the course of the disease, "treatment resistance" occurs. This may be a reversible effect, and some new treatment modalities may re-sensitize the tumor to standard therapy. For patients with relapsed disease, bortezomib (or Velcade) is a recent addition to the therapeutic arsenal, especially as second line therapy, since 2005. Bortezomib is a proteasome inhibitor. Finally, lenalidomide (or Revlimid), a less toxic thalidomide analog, is showing promise for treating myeloma.

Renal failure in multiple myeloma can be acute (reversible) or chronic (irreversible). Acute renal failure typically resolves when the calcium and paraprotein levels are brought under control. Treatment of chronic renal failure is dependent on the type of renal failure and may involve dialysis.

Nasal Type Natural Killer/T-cell Lymphoma

T-cell lymphoma describes several different types of Non-Hodgkin lymphoma which affect T cells.

T cells are involved in four classes of lymphoma. Together with lymphomas involving NK cells, these account for perhaps one in eight cases of NHL. The four classes are: 1) Extranodal T cell lymphoma, 2) Cutaneous T cell lymphomas: Sézary syndrome and Mycosis fungoides, 3) Anaplastic large cell lymphoma and 4) Angioimmunoblastic T cell lymphoma.

Nasopharyngeal Carcinoma

Nasopharyngeal carcinoma (NPC) is a cancer originating in the nasopharynx, the uppermost region of the pharynx or "throat", where the nasal passages and auditory tubes join the remainder of the upper respiratory tract. NPC differs significantly from other cancers of the head and neck in its occurrence, causes, clinical behavior, and treatment. It is vastly more common in certain regions of East Asia and Africa than elsewhere, with viral, dietary, and genetic factors implicated in its causation.

Classification

Nasopharyngeal carcinoma, commonly known as nasopharyngeal cancer, is classified as a malignant neoplasm, or cancer, arising from the mucosal epithelium of the nasopharynx, most often within the lateral nasopharyngeal recess or fossa of Rosenmüller. There are three microscopic subtypes of NPC: a well-differentiated keratinizing type, a moderately-differentiated nonkeratinizing type, and an undifferentiated type, which typically contains large numbers of non-cancerous lymphocytes (chronic inflammatory cells), thus giving rise to the name lymphoepithelioma. The undifferentiated form is most common, and is most strongly associated with Epstein-Barr virus infection of the cancerous cells.

Symptoms and Signs

Nasopharyngeal carcinoma produces few symptoms early in its course, with the result that most cases are quite advanced when detected. Once the tumor has expanded from its site of origin in the lateral wall of the nasopharynx, it may obstruct the nasal passages and cause nasal discharge or nosebleed. Obstruction of the auditory tubes may cause chronic ear infections, and patients may experience referred pain to the ear. Metastasis of cancer to the lymph nodes of the neck may also be the first noticeable sign of the disease.

Causes

Numerous studies have linked common subtypes of NPC to infection with the Epstein-Barr virus (EBV), which has also been implicated in the development of other cancers such as Hodgkin's disease, Burkitt's lymphoma, and HIV-associated lymphomas. There is some evidence that genetic factors, such as HLA type may play a role in the susceptibility of certain ethnic groups to NPC. Finally, dietary risk factors, such as the consumption of salt-cured fish high in nitrosamines, may play a role in the Asian endemic regions. Well-differentiated NPC, with a microscopic appearance most similar to other squamous cell cancers of the head and neck may be more closely associated with the standard risk factors for that disease, such as cigarette smoking.

Treatment

Because NPC occurs in an anatomical site which is poorly accessible to surgeons, and is often advanced at presentation, the most effective means of treatment is generally radiation therapy, either with or without concurrent chemotherapy. While the undifferentiated subtype of NPC is highly radiosensitive, this is less true of the more differentiated subtypes.

Nasopharyngeal Lymphoepithelioma

Lymphoepithelioma is a type of poorly differentiated nasopharyngeal carcinoma characterized by prominent infiltration of lymphocytes in the area involved by tumor. Lymphoepithelioma is also known as "class III nasopharyngeal carcinoma" in the WHO classification system. Most cases are associated with Epstein-Barr virus infection. Lymphoepithelioma may also be referred to as Schmincke-Regaud tumor, after the German pathologist Alexander Schminke and French radiologist Claude Regaud. Lymphoepithelioma-like carcinomas are carcinomas that arise outside of the nasopharynx, but resemble a lymphoepithelioma histologically. Lymphoepithelioma-like carcinomas may be found in almost any epithelial organ, including the lung, thymus, breast, colon, endometrium, prostate, and skin.

Nephroblastoma

Wilms' tumor or nephroblastoma is a tumor of the kidneys that typically occurs in children, rarely in adults.

Approximately 500 cases are diagnosed in the U.S. annually. The majority (75%) occur in otherwise normal children; a minority (25%) is associated with other developmental abnormalities. It is highly responsive to treatment, with about 90% of patients surviving at least five years.

Pathology

Pathologically, a triphasic nephroblastoma comprises three elements: 1) blastema, 2) mesenchyme and 3) epithelium Wilms' tumor is a malignant tumor containing metanephric blastema, stromal and epithelial derivatives. Characteristic is the presence of abortive tubules and glomeruli surrounded by a spindled cell stroma. The stroma may include striated muscle, cartilage, bone, fat tissue, fibrous tissue. The tumor is compressing the normal kidney parenchyma. Pathology images The mesenchymal component may include cells showing rhabdomyoid differentiation.

The rhabdomyoid component may itself show features of malignancy (rhabdomyosarcomatous Wilms).

Wilms tumor may be separated into 2 prognostic groups based on pathologic characteristics:

Favorable—Contains well developed components mentioned above

Anaplastic—Contains diffuse anaplasia (poorly developed cells)

Staging and Treatment

Staging is determined by combination of imaging studies, and pathologic findings if the tumor is operable (adapted from www.cancer.gov). Treatment strategy is determined by the stage:

Stage I (43% of Patients)

For stage I Wilms' tumor, 1 or more of the following criteria must be met:

Tumor is limited to the kidney and is completely excised.

The surface of the renal capsule is intact.

The tumor is not ruptured or biopsied (open or needle) prior to removal.

No involvement of renal sinus vessels.

No residual tumor apparent beyond the margins of excision.

Treatment: Nephrectomy+18 weeks of chemotherapy

Outcome: 98% 4-year survival; 85% 4-year survival if anaplastic

Stage II (23% of Patients)

For Stage II Wilms' tumor, 1 or more of the following criteria must be met:

Tumor extends beyond the kidney but is completely excised.

No residual tumor apparent at or beyond the margins of excision.

Any of the following conditions may also exist:

Tumor involvement of the blood vessels of the renal sinus and/or outside the renal parenchyma.

The tumor has been biopsied prior to removal or there is local spillage of tumor during surgery, confined to the flank.

Treatment: Nephrectomy+abdominal radiation+24 weeks of chemotherapy

Outcome: 96% 4-year survival; 70% 4-year survival if anaplastic

Stage III (23% of Patients)

For Stage III Wilms' tumor, 1 or more of the following criteria must be met:

Unresectable primary tumor.

Lymph node metastasis.

Positive surgical margins.

Tumor spillage involving peritoneal surfaces either before or during surgery, or transected tumor thrombus.

Treatment: Abdominal radiation+24 weeks of chemotherapy+nephrectomy after tumor shrinkage Outcome: 95% 4-year survival; 56% 4-year survival if anaplastic Stage IV (10% of Patients)

Stage IV Wilms' tumor is defined as the presence of hematogenous metastases (lung, liver, bone, or brain), or lymph node metastases outside the abdomenopelvic region.

Treatment: Nephrectomy+abdominal radiation+24 weeks of chemotherapy+radiation of metastatic site as appropriate Outcome: 90% 4-year survival; 17% 4-year survival if anaplastic Stage V (5% of Patients)

Stage V Wilms' tumor is defined as bilateral renal involvement at the time of initial diagnosis. Note: For patients with bilateral involvement, an attempt should be made to stage each side according to the above criteria (stage I to III) on the basis of extent of disease prior to biopsy. The 4-year survival was 94% for those patients whose most advanced lesion was stage I or stage II; 76% for those whose most advanced lesion was stage III.

Treatment: Individualized therapy based on tumor burden

Stage I-IV Anaplasia

Children with stage I anaplastic tumors have an excellent prognosis (80-90% five-year survival). They can be managed with the same regimen given to stage I favorable histology patients.

Children with stage II through stage IV diffuse anaplasia, however, represent a higher-risk group. These tumors are more resistant to the chemotherapy traditionally used in children with Wilms' tumor (favorable histology), and require more aggressive regimens.

Treatment

Once a kidney tumor is found, surgery can find out whether or not the tumor is cancer. A sample of tissue from the tumor is sent to a pathologist, who looks at it under a microscope to check for signs of cancer. If the tumor is only in the kidney, it can be removed along with the whole kidney (a process called nephrectomy). If there are tumors in both kidneys or if the tumor has spread outside the kidney, a piece of the tumor will be removed.

Neurogenic Sarcoma

A malignant tumor that arises from small cutaneous nerves, is locally aggressive, and has a potential for metastasis. Characteristic histopathologic features include proliferating atypical spindle cells with slender wavy and pointed nuclei, hypocellular areas, and areas featuring organized whorls of fibroblastic proliferation. The most common primary sites are the extremities, retroperitoneum, and trunk. These tumors tend to present in childhood, often in association with NEUROFIBROMATOSIS 1.

Non-Hodgkin Lymphoma

Non-Hodgkin lymphomas (NHL) are a diverse group of cancers which arise from lymphocytes, a type of white blood cell. NHL is distinct from Hodgkin lymphoma in its pathologic features, epidemiology, common sites of involvement, clinical behavior, and treatment. The broad category of non-Hodgkin lymphoma encompasses diseases with varying courses, treatments, and prognoses.

Non-Hodgkin lymphomas are medically classified as a hematological malignancy, meaning that they are cancers that arise from the blood. Non-Hodgkin lymphomas may develop in any organ associated with the lymphatic system, such as the spleen, lymph nodes, or tonsils. The diagnosis of a non-Hodgkin lymphoma requires a biopsy of involved tissue.

The numerous types of non-Hodgkin lymphoma are typically grouped into three distinct categories based on their aggressiveness. These categories are indolent (or low-grade), aggressive (or intermediate-grade), and highly aggressive (or high-grade). The treatment of indolent or low-grade lymphomas may initially involve a period of observation, while aggressive or highly aggressive non-Hodgkin lymphomas are typically treated with chemotherapy and/or radiation therapy. Some forms of non-Hodgkin lymphoma can be cured with chemotherapy, radiation, or hematopoietic stem cell transplantation.

Organ-specific Symptoms

Symptoms such as shortness of breath, chest pain, cough, abdominal pain and distention, or bone pain, may lead to the identification of specific sites of involvement. Careful evaluation for neurologic symptoms is necessary in order to rule out central nervous system (CNS) involvement, which may occur with aggressive histologies Such symptoms are non-specific and may be caused by other, less serious conditions.

Diagnosis

If a non-Hodgkin's lymphoma is suspected, the doctor asks about the person's medical history and performs a physical exam. The exam includes feeling to see if the lymph nodes in the neck, underarm, or groin are enlarged. In addition to checking general signs of health, the doctor may perform blood tests.

1) Biopsy: A biopsy is needed to make a diagnosis. A surgeon removes a sample of tissue, which a pathologist can examine under a microscope to check for cancer cells. A biopsy for a non-Hodgkin's lymphoma is usually taken from lymph nodes that are enlarged, but other tissues may be sampled as well. Biopsies in internal lymph nodes can also be taken as needle biopsies under the guidance of CT scans. Rarely, an operation called a laparotomy may be performed. During this operation, a surgeon cuts into the abdomen and removes samples of tissue to be checked under a microscope.

2) Common tests:

The laboratory workup for NHL includes a complete blood count (CBC) with differential. An examination of a peripheral smear is essential to assess bone marrow function and to investigate for the presence of abnormal circulating cells in the peripheral blood. Screening chemistries to ascertain renal and hepatic function, serum glucose, calcium, albumin, and lactate dehydrogenase (LDH) are also indicated, as they are frequently found to be abnormal. In fact, more than 50% of patients have elevated serum LDH levels. An elevated beta2-microglobulin level is associated with a poor prognosis. A serum protein electrophoresis should also be part of the workup.

The doctor may also order tests that produce pictures of the inside of the body. These may include:

X-rays: Pictures of areas inside the body created by high-energy radiation.

CT scan (computed tomography scan, also known as a "CAT scan"): A series of detailed pictures of areas inside the body. The pictures are created by a computer linked to an x-ray machine.

PET scan (positron emission tomography scan): This is an imaging test that detects uptake of a radioactive tracer by the tumor. More often, the PET scan can be combined with the CT scan.

MRI (magnetic resonance imaging): Detailed pictures of areas inside the body produced with a powerful magnet linked to a computer.

3) Less common tests: These tests are only used under certain circumstances.

Lymphangiogram: Pictures of the lymphatic system taken with x-rays after a special dye is injected to outline the lymph nodes and vessels. This test is not used as often because of the adoption of CT scan and the PET scan technologies.

Gallium scan: Gallium is a rare metal that behaves in the body in a fashion similar to iron, so that it concentrates in areas of inflammation or rapid cell-division, and hence is useful for imaging the entire lymphatic system for staging the lymphoma once the presence of the disease has been confirmed. PET scans have supplanted gallium scans for evaluation and follow up of NHL.

Types of Non-Hodgkin's Lymphomas

Over the years, doctors have used a variety of terms to classify the many different types of non-Hodgkin's lymphomas. Most often, they are grouped by how the cancer cells look under a microscope and how quickly they are likely to grow and spread. Current lymphoma classification is complex.

MeSH includes four different criteria for classifying NHL. (It is possible to be classified under more than one.)

High-grade vs. intermediate vs. low-grade: Aggressive lymphomas, also known as intermediate and high-grade lymphomas, tend to grow and spread quickly and cause severe symptoms. Indolent lymphomas, also referred to as low-grade lymphomas, tend to grow quite slowly and cause fewer symptoms. One of the paradoxes of the non-Hodgkin's lymphomas is that the indolent lymphomas generally cannot be permanently cured by chemotherapy, while in a significant number of cases aggressive lymphomas can be.

Diffuse vs. follicular. Follicular lymphomas tend to be indolent, and diffuse lymphomas tend to be aggressive.

T-cell Lymphomas Vs. B-cell Lymphomas

Gluten-sensitive enteropathy associated T-cell lymphoma or EATL

Large cell lymphomas (such as anaplastic large cell lymphoma) vs. Small cell lymphoma vs. Mixed cell lymphoma)

Details of the most popular classifications of lymphoma can be found in the lymphoma page.

Causes

The etiology, or cause, of most lymphomas is not known. Some types of lymphomas are associated with viruses. Burkitt's lymphoma, extranodal NK/T cell lymphoma, classical Hodgkin's disease and most AIDS-related lymphomas are associated with Epstein-Barr virus. Adult T-cell lymphoma/leukemia, which is endemic in parts of Japan and the Caribbean, is caused by the HTLV-1 virus. Lymphomas of the stomach (extranodal marginal zone B-cell lymphoma) are often caused by the *Helicobacter* bacteria.

The incidence of non-Hodgkin lymphomas has increased dramatically over the last couple of decades. This disease has gone from being relatively rare to being the fifth most common cancer in the United States. At this time, little is known about the reasons for this increase or about exactly what causes non-Hodgkin lymphomas. Doctors can seldom explain why one person gets a non-Hodgkin's lymphoma and another does not. It is clear, however, that cancer is not caused by an injury, and is not contagious; no one can "catch" a non-Hodgkin's lymphoma from another person. By studying patterns of cancer in the population, researchers have found certain risk factors that are more common in people who get non-Hodgkin's lymphomas than in those who do not. However, most people with these risk factors do not get non-Hodgkin lymphomas, and many who do get this disease have none of the known risk factors.

The following are some of the risk factors associated with this disease:

Age and sex. The likelihood of getting a non-Hodgkin's lymphoma increases with age and is more common in men than in women.

Weak immune system. Non-Hodgkin's lymphomas are more common among people with inherited immune deficiencies, autoimmune diseases, or HIV/AIDS, and among people taking immunosuppressant drugs following organ transplants. See post-transplant lymphoproliferative disorder and AIDS-related lymphomas.

Viruses. Human T-lymphotropic virus type I (HTLV-1) and Epstein-Barr virus are two infectious agents that increase the chance of developing a non-Hodgkin's lymphoma.

Environment. People who work extensively with or are otherwise exposed to certain chemicals, such as pesticides, solvents, or fertilizers, have a greater chance of developing a non-Hodgkin's lymphoma.

There is no clear connection between alcohol consumption and NHL. For further information, see the alcohol and cancer article.

Staging

If a non-Hodgkin's lymphoma is diagnosed, the doctor needs to learn the stage, or extent, of the disease. Staging is a careful attempt to find out whether the cancer has spread and, if so, what parts of the body are affected. Treatment decisions depend on these findings.

The doctor considers the following to determine the stage of non-Hodgkin's lymphomas:

The number and location of affected lymph nodes;

Whether the affected lymph nodes are above, below, or on both sides of the diaphragm (the thin muscle under the lungs and heart that separates the chest from the abdomen);

Whether the disease has spread to the bone marrow, spleen, or to organs outside the lymphatic system, such as the liver and the testes;

Whether B symptoms (systemic symptoms) such as fever, chills, night sweats, or weight loss are present.

In staging, the doctor may use some of the same tests used for the diagnosis of non-Hodgkin's lymphomas. Other staging procedures may include additional biopsies of lymph nodes, the liver, bone marrow, or other tissue. A bone marrow biopsy involves removing a sample of bone marrow through a needle inserted into the hip or another large bone. A pathologist examines the sample under a microscope to check for cancer cells.

1) Stages of NHL

The various stages of NHL (the Ann Arbor staging classification, developed for Hodgkin's lymphomas) are based on how far the cancer has spread throughout and beyond the lymphatic system, and whether constitutional symptoms (fever, night sweats, or weight loss) are present.

Stage I

"Stage I" indicates that the cancer is located in a single region, usually one lymph node and the surrounding area. Stage I often will not have outward symptoms.

Stage II

"Stage II" indicates that the cancer is located in two separate regions, an affected lymph node or organ within the lymphatic system and a second affected area, and that both affected areas are confined to one side of the diaphragm—that is, both are above the diaphragm, or both are below the diaphragm.

Stage III

"Stage III" indicates that the cancer has spread to both sides of the diaphragm, including one organ or area near the lymph nodes or the spleen.

Stage IV

"Stage IV" indicates that the cancer has spread beyond the lymphatic system and involves one or more major organs, possibly including the bone marrow or skin.

The absence of constitutional symptoms is denoted by adding an "A" to the stage; the presence is denoted by adding a "B" to the stage (hence the name B symptoms).

Staging in non-Hodgkin's lymphomas is far less significant in determining therapy than it is in Hodgkin's disease.

Treatment

The doctor develops a treatment plan to fit each patient's needs. Treatment for non-Hodgkin's lymphomas depends on the stage of the disease, the type of cells involved, whether they are indolent or aggressive, and the age and general health of the patient. Non-Hodgkin's lymphomas are often treated by a team of specialists that may include a hematologist, medical oncologist, and/or radiation oncologist. Non-Hodgkin's lymphomas are usually treated with chemotherapy and/or radiation therapy. In some cases, bone marrow transplantation, biological therapies, or surgery may be options. For indolent lymphomas, the doctor may decide to wait until the disease causes symptoms before starting treatment. Often, this approach is called "watchful waiting." Taking part in a clinical trial (research study) to evaluate promising new ways to treat non-Hodgkin's lymphomas is an important option for many people with this disease.

1) Chemotherapy and Radiation Therapy

Chemotherapy and radiation therapy are the most common treatments for non-Hodgkin's lymphomas, although bone marrow transplantation, biological therapies, or surgery are sometimes used. CHOP, with rituximab added in certain circumstances, is the most commonly used combination of chemotherapy.

Rituximab is an antibody-based therapy. Ibritumomab tiuxetan (commonly known as Zevalin) and Tositumomab (Bexxar) are FDA-approved options, requiring a Nuclear Medicine facility, but only two short infusions one week apart. There is mounting evidence that more patients have long-term remission if they use radioimmunotherapy first.

Radiation therapy (also called radiotherapy) is the use of high-energy rays to kill cancer cells. Treatment with radiation may be given alone or with chemotherapy. Radiation therapy is local treatment; it affects cancer cells only in the treated area. Radiation therapy for Non Hodgkin's lymphomas comes from a machine that aims the high-energy rays at a specific area of the body. There is no radioactivity in the body when the treatment is over.

Sometimes patients are given chemotherapy and/or radiation therapy to kill undetected cancer cells that may be present in the central nervous system (CNS). In this treatment, called central nervous system prophylaxis, the doctor injects anticancer drugs directly into the cerebrospinal fluid.

2) Hematopoietic Stem Cell Transplantation

Hematopoietic stem cell transplantation (HSCT), or Bone marrow transplantation (BMT) may also be a treatment option, especially for patients whose non-Hodgkin's lymphoma has recurred (come back). BMT provides the patient with healthy stem cells (very immature cells, found in the marrow, that produce blood cells), the function of which is to replace white blood cells that are damaged or destroyed by treatment with very high doses of chemotherapy and/or radiation therapy. The healthy bone marrow may come from a donor, or it may be "autologous" (marrow that was removed from the patient, stored, and then given back to the person following the high-dose treatment). Autologous transplants are preferred, as the recipient is less likely to reject the cells, the origins of which were the same entity. However, in order for an autologous transplant to be performed, certain physiological conditions must be optimal within the patient. If these conditions are not present, transplanted stem cells can come from other donors. Until the transplanted bone marrow begins to produce enough white blood cells, patients have to be carefully protected from infection due to the virtual elimination of the immune system resulting from the high-intensity treatment. Without the introduction of the stem cells following the high dose treatment, the patient will not survive as the body will be unable to produce infection-fighting white blood cells. Patients usually stay in the hospital for several weeks and will be monitored for transplant rejection and overall health.

3) Immunotherapy

Biological therapy (also called immunotherapy) is a form of treatment that uses the body's immune system, either directly or indirectly, to fight cancer or to lessen the side effects that can be caused by some cancer treatments. It uses materials made by the body or made in a laboratory to boost, direct, or restore the body's natural defenses against disease. This approach is under close investigation. Biological therapy is sometimes also called biological response modifier therapy.

4) Measuring Response to Treatment

After treatment for a non-Hodgkin's lymphoma, the response is classified as follows:

Complete Response (CR). This indicates the disappearance of all detectable disease.

Partial Response (PR). A reduction in the bulk of disease by at least 50%, but with some remaining disease.

Stable Disease. Less than a partial remission, but no progression of disease and no new sites of disease.

Progressive Disease. Growth in bulk of disease by >50%, or the appearance of new sites of disease.

If a complete remission is achieved, the patient is watched closely for any evidence of recurrent disease. Standard guidelines dictate that a patient be monitored for relapse every three months in the first year following a complete remission, every six months in the second year, and finally once annually in the third and later years. Diffuse large B-cell lymphoma is the most common type of lymphoma that is considered curable. Currently, if a patient maintains a complete remission for 3 years, the patient is considered cured. Generally most relapses of diffuse large B-cell lymphoma occur within the first year after a complete remission is obtained. Reoccurrences after 3 years are rare but they do occur. The effect of Rituximab on relapse rates for diffuse large B-cell lymphoma is still largely unknown, though initial relapse rates since 2003 have been much lower than expected.

Patients with follicular lymphomas are generally not considered cured. Instead, they are categorized as in ongoing complete remission. Relapses occur steadily over time. Relapse rates are estimated to be 33%, 66%, and 100% for follicular lymphomas in Grades I, II, and III respectively.

Research has indicated that relapse rates can be lowered on patients with follicular lymphomas by giving supplemental radiation therapy, however, it is known that this additional therapy increases the chances of a second malignancy of unknown type later in life.

If the response to treatment falls short of a complete response, more treatment may be administered (using a different chemotherapy regimen), or watchful waiting may be utilized, depending on the goals of treatment.

5) Nutrition During Treatment

Eating well during cancer treatment means getting enough food energy and protein to help prevent weight loss and regain strength. Good nutrition often helps people feel better and have more energy.

Some people with cancer find it hard to eat a balanced diet because they may lose their appetite. In addition, common side effects of treatment, such as nausea, vomiting, or mouth sores, can make eating difficult. Often, foods may taste or smell different. Also, people being treated for cancer may not feel like eating when they are uncomfortable or tired.

Doctors, nurses, and dietitians can offer advice on how to get enough food energy and protein during cancer treatment. Patients and their families also may want to read the National Cancer Institute (USA) booklet Eating Hints for Cancer Patients, which contains many useful suggestions.

Oesophageal Cancer

Esophageal cancer is malignancy of the esophagus. There are various subtypes. Esophageal tumors usually lead to dysphagia (difficulty swallowing), pain and other symptoms, and are diagnosed with biopsy. Small and localized tumors are treated surgically with curative intent. Larger tumors tend not to be operable and hence cannot be cured; their growth can still be delayed with chemotherapy, radiotherapy or a combination of the two. In some cases chemo- and radiotherapy can render these larger tumors operable. Prognosis depends on the extent of the disease and other medical problems, but is fairly poor.

Signs and Symptoms

Dysphagia (difficulty swallowing) is the first symptom in most patients. Odynophagia (painful swallowing) may be present. Fluids and soft foods are usually tolerated, while hard or bulky substances (such as bread or meat) cause much more difficulty. Substantial weight loss is characteristic as a result of poor nutrition and the active cancer. Pain, often of a burning nature, may be severe and worsened by swallowing, and can be spasmodic in character. An early sign may be an unusually husky or raspy voice.

The presence of the tumor may disrupt normal peristalsis (the organised swallowing reflex), leading to nausea and vomiting, regurgitation of food, coughing and an increased risk of aspiration pneumonia. The tumor surface may be fragile and bleed, causing hematemesis (vomiting up blood). Compression of local structures occurs in advanced disease, leading to such problems as superior vena cava syndrome. Fistulas may develop between the esophagus and the trachea, increasing the pneumonia risk; this symptom is usually heralded by cough, fever or aspiration.

If the disease has spread elsewhere, this may lead to symptoms related to this: liver metastasis could cause jaundice and ascites, lung metastasis could cause shortness of breath, pleural effusions, etc.

Causes and Risk Factors

1) Increased Risk

There are a number of risk factors for esophageal cancer. Some subtypes of cancer are linked to particular risk factors:

Age. Most patients are over 60, and the median in US patients is 67.

Gender. It is more common in men.

Heredity. It is more likely in people who have close relatives with cancer.

Tobacco smoking and heavy alcohol use increase the risk, and together appear to increase the risk more than these two individually.

Gastroesophageal reflux disease (GERD) and its resultant Barrett's esophagus increase esophageal cancer risk due to the chronic irritation of the mucosal lining (adenocarcinoma is more common in this condition, while all other risk factors predispose more for squamous cell carcinoma).

Human papillomavirus (HPV)

Swallowing lye or other caustic substances.

Particular dietary substances, such as nitrosamine.

A medical history of other head and neck cancers increases the chance of developing a second cancer in the head and neck area, including esophageal cancer.

Plummer-Vinson syndrome (anemia and esophageal webbing)

Tylosis and Howel-Evans syndrome (hereditary thickening of the skin of the palms and soles).

Radiation therapy for other conditions in the mediastinum.

Celiac disease predisposes towards squamous cell carcinoma.

Obesity increases the risk of adenocarcinoma fourfold. It is suspected that increased risk of reflux may be behind this association.

2) Decreased Risk

Risk appears to be less in patients using aspirin or related drugs (NSAIDs).

The role of *Helicobacter pylori* in progression to esophageal adenocarcinoma is still uncertain, but, on the basis of population data, it may carry a protective effect. It is postulated that *H. pylori* prevents chronic gastritis, which is a risk factor for reflux, which in turn is a risk factor for esophageal adenocarcinoma.

According to the National Cancer Institute, "diets high in cruciferous (cabbage, broccoli, cauliflower) and green and yellow vegetables and fruits are associated with a decreased risk of esophageal cancer.

Moderate coffee consumption is associated with a decreased risk.

According to one Italian study of "diet surveys completed by 5,500 Italians"—a study which has raised debates questioning its claims among cancer researchers cited in news reports about it—eating pizza more than once a week appears "to be a favorable indicator of risk for digestive tract neoplasms in this population.

Diagnosis

1) Clinical Evaluation

Although an occlusive tumor may be suspected on a barium swallow or barium meal, the diagnosis is best made with esophagogastroduodenoscopy (EGD, endoscopy); this involves the passing of a flexible tube down the esophagus and visualising the wall. Biopsies taken of suspicious lesions are then examined histologically for signs of malignancy.

Additional testing is usually performed to estimate the tumor stage. Computed tomography (CT) of the chest, abdomen and pelvis, can evaluate whether the cancer has spread to adjacent tissues or distant organs (especially liver and lymph nodes). The sensitivity of CT scan is limited by its ability to detect masses (e.g. enlarged lymph nodes or involved organs) generally larger than 1 cm. FDG-PET (positron emission tomography) scan is also being used to estimate whether enlarged masses are metabolically active, indicating faster-growing cells that might be expected in cancer. Esophageal endoscopic ultrasound (EUS) can provide staging information regarding the level of tumor invasion, and possible spread to regional lymph nodes.

The location of the tumor is generally measured by the distance from the teeth. The esophagus (25 cm or 10 inches long) is commonly divided into three parts for purposes of determining the location. Adenocarcinomas tend to occur distally and squamous cell carcinomas proximally, but the converse may also be the case.

2) Histopathology

Most tumors of the esophagus are malignant. A very small proportion (under 10%) is leiomyoma (smooth muscle tumor) or gastrointestinal stromal tumor (GIST). Malignant tumors are generally adenocarcinomas, squamous cell carcinomas, and occasionally small-cell carcinomas. The latter share many properties with small-cell lung cancer, and are relatively sensitive to chemotherapy compared to the other types.

Classification

Esophageal cancers are typically carcinomas which arise from the epithelium, or surface lining, of the esophagus. Most esophageal cancers fall into one of two classes: squamous cell carcinomas, which are similar to head and neck cancer in their appearance and association with tobacco and alcohol consumption, and adenocarcinomas, which are often associated with a history of gastroesophageal reflux disease and Barrett's esophagus.

Treatment

1) General Approaches

The treatment is determined by the cellular type of cancer (adenocarcinoma or squamous cell carcinoma vs other types), the stage of the disease, the general condition of the patient and other diseases present. On the whole, adequate nutrition needs to be assured, and adequate dental care is vital.

If the patient cannot swallow at all, a stent may be inserted to keep the esophagus patent; stents may also assist in occluding fistulas. A nasogastric tube may be necessary to continue feeding while treatment for the tumor is given, and some patients require a gastrostomy (feeding hole in the skin that gives direct access to the stomach). The latter two are especially important if the patient tends to aspirate food or saliva into the airways, predisposing for aspiration pneumonia.

2) Tumor Treatments

Surgery is possible if the disease is localised, which is the case in 20-30% of all patients. If the tumor is larger but localised, chemotherapy and/or radiotherapy may occasionally shrink the tumor to the extent that it becomes "operable"; however, this combination of treatments (referred to as neoadjuvant chemoradiation) is still somewhat controversial in most medical circles. Esophagectomy is the removal of a segment of the esophagus; as this shortens the distance between the throat and the stomach, some other segment of the digestive tract (typically the stomach or part of the colon) is placed in the chest cavity and interposed. If the tumor is metastatic, surgical resection is not considered worthwhile, but palliative surgery may offer some benefit. Laser therapy is the use of high-intensity light to destroy tumor cells; it affects only the treated area. This is typically done if the cancer cannot be removed by surgery. The relief of a blockage can help to reduce dysphagia and pain. Photodynamic therapy (PDT), a type of laser therapy, involves the use of drugs that are absorbed by cancer cells; when exposed to a special light, the drugs become active and destroy the cancer cells.

Chemotherapy depends on the tumor type, but tends to be cisplatin-based (or carboplatin or oxaliplatin) every three weeks with fluorouracil (5-FU) either continuously or every three weeks. In more recent studies, addition of epirubicin (ECF) was better than other comparable regimens in advanced nonresectable cancer. Chemotherapy may be given after surgery (adjuvant, i.e. to reduce risk of recurrence), before surgery (neoadjuvant) or if surgery is not possible; in this case, cisplatin and 5-FU are used. Ongoing trials compare various combinations of chemotherapy; the phase II/III REAL-2 trial—for example—compares four regimens containing epirubicin and either cisplatin or oxaliplatin and either continuously infused fluorouracil or capecitabine.

Radiotherapy is given before, during or after chemotherapy or surgery, and sometimes on its own to control symptoms. In patients with localised disease but contraindications to surgery, "radical radiotherapy" may be used with curative intent.

Oropharyngeal Cancer

Oropharyngeal cancer is a disease in which malignant (cancer) cells form in the tissues of the oropharynx. The oropharynx is the middle part of the pharynx (throat) behind the mouth, and includes the back one-third of the tongue, the soft palate, the side and back walls of the throat, and the tonsils. The pharynx is a hollow tube about 5 inches long that starts behind the nose and ends at the top of the trachea (windpipe) and esophagus (the tube that goes from the throat to the stomach). Air and food pass through the pharynx on the way to the trachea or the esophagus.

Most oropharyngeal cancers are squamous cell carcinomas. Squamous cells are the thin, flat cells that line the inside of the oropharynx.

Risk Factors

Use of tobacco products and drinking too much alcohol can increase the risk of developing oropharyngeal cancer.

Anything that increases your risk of getting a disease is called a risk factor. Risk factors include the following:

Smoking and chewing tobacco.
Heavy alcohol use.
A diet low in fruits and vegetables.
Drinking mate, a stimulant drink common in South America.
Chewing betel quid, a stimulant commonly used in parts of Asia.
Being infected with human papillomavirus (HPV).

Symptoms

Possible signs of oropharyngeal cancer include a sore throat and a lump in the neck. These and other symptoms may be caused by oropharyngeal cancer. Other conditions may cause the same symptoms. A doctor should be consulted if any of the following problems occur:

A sore throat that does not go away.
A dull pain behind the breastbone.
Cough.
Trouble swallowing.
Weight loss for no known reason.
Ear pain.
A lump in the back of the mouth, throat, or neck.
A change in voice.

Diagnosis

Tests that examine the mouth and throat are used to help detect (find), diagnose, and stage oropharyngeal cancer.

The following tests and procedures may be used:

Physical exam and history: An exam of the body to check general signs of health, including checking for signs of disease, such as swollen lymph nodes in the neck or anything else that seems unusual. The doctor does a complete exam of the mouth and neck and looks down the throat with a small, long-handled mirror to check for abnormal areas. A history of the patient's health habits and past illnesses and treatments will also be taken.

CT scan (CAT scan): A procedure that makes a series of detailed pictures of areas inside the body, taken from different angles. The pictures are made by a computer linked to an x-ray machine. A dye may be injected into a vein or swallowed to help the organs or tissues show up more clearly. This procedure is also called computed tomography, computerized tomography, or computerized axial tomography.

MRI (magnetic resonance imaging): A procedure that uses a magnet, radio waves, and a computer to make a series of detailed pictures of areas inside the body. This procedure is also called nuclear magnetic resonance imaging (NMRI).

X-rays: An x-ray of the organs and bones. An x-ray is a type of energy beam that can go through the body and onto film, making pictures of areas inside the body.

PET scan (positron emission tomography scan): A procedure to find malignant tumor cells in the body. A small amount of radionuclide glucose (sugar) is injected into a vein. The PET scanner rotates around the body and makes a picture of where glucose is being used in the body. Malignant tumor cells show up brighter in the picture because they are more active and take up more glucose than normal cells do.

Endoscopy: A procedure to look at organs and tissues inside the body to check for abnormal areas. An endoscope is inserted through the patient's nose or mouth to look at areas in the throat that cannot be seen during a physical exam of the throat. An endoscope is a thin, tube-like instrument with a light and a lens for viewing. It may also have a tool to remove tissue or lymph node samples, which are checked under a microscope for signs of disease.

Biopsy: The removal of cells or tissues so they can be viewed under a microscope by a pathologist to check for signs of cancer.

Stages of Oropharyngeal Cancer

Stage 0 (Carcinoma in Situ): In stage 0, abnormal cells are found in the lining of the oropharynx. These abnormal cells may become cancer and spread into nearby normal tissue. Stage 0 is also called carcinoma in situ.

Stage I: In stage I, cancer has formed and is 2 centimeters or smaller and has not spread outside the oropharynx.

Stage II: In stage II, the cancer is larger than 2 centimeters, but not larger than 4 centimeters, and has not spread outside the oropharynx.

Stage III: In stage III, the cancer is either:
larger than 4 centimeters and has not spread outside the oropharynx; or
any size and has spread to only one lymph node on the same side of the neck as the cancer. The lymph node with cancer is 3 centimeters or smaller.

Stage IVA: In stage IVA, the cancer either:
has spread to tissues near the oropharynx, including the voice box, roof of the mouth, lower jaw, muscle of the tongue, or central muscles of the jaw, and may have spread to one or more nearby lymph nodes, none larger than 6 centimeters; or
is any size and has spread to one lymph node that is larger than 3 centimeters but not larger than 6 centimeters on the same side of the neck as the cancer, or to more than one lymph node, none larger than 6 centimeters, on one of both sides of the neck.

Stage IVB: In stage IVB, the cancer either:
surrounds the main artery in the neck or has spread to bones in the jaw or skull, to muscle in the side of the jaw, or to the upper part of the throat behind the nose, and may have spread to nearby lymph nodes; or
has spread to a lymph node that is larger than 6 centimeters and may have spread to tissues around the oropharynx.

Stage IVC: In stage IVC, cancer has spread to other parts of the body; the tumor may be any size and may have spread to lymph nodes.

Treatment

Treatment options depend on the following:
The stage and grade of the cancer.

The location of the tumor.

The patient's general health.

Different types of treatment are available for patients with oropharyngeal cancer. Some treatments are standard (the currently used treatment), and some are being tested in clinical trials. A treatment clinical trial is a research study meant to help improve current treatments or obtain information on new treatments for patients with cancer. When clinical trials show that a new treatment is better than the standard treatment, the new treatment may become the standard treatment. Patients may want to think about taking part in a clinical trial. Some clinical trials are open only to patients who have not started treatment.

Two types of standard treatment are used:

1) Surgery

Surgery (removing the cancer in an operation) is a common treatment of all stages of oropharyngeal cancer. A doctor may remove the cancer and some of the healthy tissue around the cancer. Even if the doctor removes all the cancer that can be seen at the time of the surgery, some patients may be given chemotherapy or radiation therapy after surgery to kill any cancer cells that are left. Treatment given after the surgery, to increase the chances of a cure, is called adjuvant therapy.

2) Radiation Therapy

Radiation therapy is a cancer treatment that uses high-energy x-rays or other types of radiation to kill cancer cells or keep them from growing. There are two types of radiation therapy. External radiation therapy uses a machine outside the body to send radiation toward the cancer. Internal radiation therapy uses a radioactive substance sealed in needles, seeds, wires, or catheters that are placed directly into or near the cancer. The way the radiation therapy is given depends on the type and stage of the cancer being treated. Fractionated radiation therapy divides the total dose of radiation therapy into several smaller, equal doses given over several days.

Radiation therapy may be more effective in patients who have stopped smoking before beginning treatment.

Radiation therapy to the thyroid or pituitary gland increases the risk of hypothyroidism (too little thyroid hormone). Thyroid function tests should be done before and after treatment.

New types of treatment are being tested in clinical trials. This summary section describes treatments that are being studied in clinical trials. It may not mention every new treatment being studied. Information about clinical trials is available from the NCI Web site.

Chemotherapy

Chemotherapy is a cancer treatment that uses drugs to stop the growth of cancer cells, either by killing the cells or by stopping them from dividing. When chemotherapy is taken by mouth or injected into a vein or muscle, the drugs enter the bloodstream and can reach cancer cells throughout the body (systemic chemotherapy). When chemotherapy is placed directly into the spinal column, an organ, or a body cavity such as the abdomen, the drugs mainly affect cancer cells in those areas (regional chemotherapy). The way the chemotherapy is given depends on the type and stage of the cancer being treated.

Radiosensitizers

Radiosensitizers are drugs that make tumor cells more sensitive to radiation therapy. Combining radiation therapy with radiosensitizers may kill more tumor cells.

Hyperthermia Therapy

Hyperthermia therapy is a treatment in which body tissue is exposed to increased temperature to damage and kill cancer cells or to make cancer cells more sensitive to the effects of radiation and certain anticancer drugs.

Patients may want to think about taking part in a clinical trial.

Follow-up Tests May be Needed.

Some of the tests that were done to diagnose the cancer or to find out the stage of the cancer may be repeated. Some tests will be repeated in order to see how well the treatment is working. Decisions about whether to continue, change, or stop treatment may be based on the results of these tests. This is sometimes called re-staging. Some of the tests will continue to be done from time to time after treatment has ended. The results of these tests can show if your condition has changed or if the cancer has recurred (come back).

After treatment for oropharyngeal cancer, frequent and careful follow-up is important because of the risk of developing a second cancer in the head or neck.

Treatment Options by Stage

Stage I Oropharyngeal Cancer: Treatment of stage I oropharyngeal cancer may include the following:

Radiation therapy.

Surgery.

A clinical trial of fractionated radiation therapy.

Check for U.S. clinical trials from NCI's PDQ Cancer Clinical Trials Registry that are now accepting patients with stage I oropharyngeal cancer.

Stage II Oropharyngeal Cancer: Treatment of stage II oropharyngeal cancer may include the following:

Radiation therapy (external radiation therapy and/or internal radiation therapy).

Surgery.

Check for U.S. clinical trials from NCI's PDQ Cancer Clinical Trials Registry that are now accepting patients with stage II oropharyngeal cancer.

Stage III Oropharyngeal Cancer: Treatment of stage III oropharyngeal cancer may include the following:

Surgery followed by radiation therapy or by chemotherapy given at the same time as radiation therapy.

Radiation therapy (for patients with tongue or tonsil cancer).

Chemotherapy given at the same time as radiation therapy.

A clinical trial of chemotherapy followed by surgery or radiation therapy.

A clinical trial of chemotherapy given at the same time as radiation therapy.

A clinical trial of fractionated and/or internal radiation therapy.

Check for U.S. clinical trials from NCI's PDQ Cancer Clinical Trials Registry that are now accepting patients with stage III oropharyngeal cancer.

Stage IV Oropharyngeal Cancer: Treatment of stage IV oropharyngeal cancer that can be treated by surgery may include the following:

Surgery followed by radiation therapy and chemotherapy.

Radiation therapy (for tonsil cancer).

A clinical trial of chemotherapy given at the same time as radiation therapy.

A clinical trial of fractionated and/or internal radiation therapy.

Treatment of stage IV oropharyngeal cancer that cannot be treated by surgery may include the following:

Radiation therapy with or without chemotherapy.

A clinical trial of chemotherapy with radiation therapy and/or radiosensitization.

A clinical trial of fractionated and/or internal radiation therapy.

A clinical trial of radiation therapy with or without chemotherapy.

A clinical trial of hyperthermia therapy with radiation therapy.

Following treatment, it is important to have careful head and neck examinations to look for recurrence. Check-ups will be done monthly in the first year, every 2 months in the second year, every 3 months in the third year, and every 6 months thereafter. Check for U.S. clinical trials from NCI's PDQ Cancer Clinical Trials Registry that are now accepting patients with stage IV oropharyngeal cancer.

Treatment Options for Recurrent Oropharyngeal Cancer

Treatment of recurrent oropharyngeal cancer may include the following:

Surgery if radiation therapy did not remove all the cancer.
Radiation therapy (if not previously used) or additional surgery if the first surgery did not remove all the cancer.
A clinical trial of chemotherapy.
A clinical trial of hyperthermia therapy with radiation therapy.

Following treatment, it is important to have careful head and neck examinations to look for recurrence. Check-ups will be done monthly in the first year, every 2 months in the second year, every 3 months in the third year, and every 6 months thereafter.

Check for U.S. clinical trials from NCI's PDQ Cancer Clinical Trials Registry that are now accepting patients with recurrent oropharyngeal cancer.

Osteoclastoma/Giant Cell Tumor

Giant cell tumor of the bone (also called giant cell myeloma or osteoclastoma) is a relatively uncommon tumor. It is characterized by the presence of multinucleated giant cells (osteoclast-like cells). These tumors are generally benign. In most patients, the tumors are slow to develop, but may recur locally in as many as 50% of cases. Metastasis to the lungs may occur.

Diagnosis

The radiographic appearance of giant cell tumors is often characteristic.

Magnetic resonance imaging (MRI) is sensitive for the detection of soft-tissue changes, intra-articular extension, and marrow changes. MRI is the best method for assessing subchondral breakthrough and extension of tumor into an adjacent joint. Its diagnostic accuracy is high, especially when MRIs are interpreted in conjunction with plain radiographs.

Computed tomography (CT) scans and bone scans are usually less useful than other examinations.

Limitations of Techniques

On radiographs, typical giant cell tumors are usually easily distinguished from other bone tumors. Giant cell tumors are lytic, subarticular, and eccentric, and they are often lacking a sclerotic rim; however, unusual variants may make the radiographic diagnosis difficult.

The disadvantages of MRI are its relatively high cost and limited availability. In addition, some patients experience claustrophobia during the examination and may require sedation. MRI is also contraindicated in patients with cardiac pacemakers, orbital foreign bodies, and noncompatible aneurysmal clips.

Patients usually present with pain and limited range of motion caused by tumor's proximity to the joint space. There may be swelling as well, if the tumor has been growing for a long time. Some patients may be asymptomatic until they develop a pathologic fracture at the site of the tumor.

Patient may also experience nerve pain which feels like an electric shock. On x-ray, giant cell tumors (GCTs) have a metaepiphyseal location and grow to the articular surface of the involved bone. Radiologically the tumours show characteristic 'soap bubble' appearance. They are distinguishable from other bony tumors in that GCTs usually have a non-sclerotic and sharply defined border. Because giant cell tumors are known to metastasize, when the diagnosis of giant cell tumor is suspected, a chest x-ray or CT may be needed. MRI can be used to assess intramedullary and soft tissue extension.

Treatment

Surgery is the treatment of choice if the tumor is determined to be resectable. Curettage is a commonly used technique.

Patients with tumors that are not amenable to surgery are treated with radiation therapy. The situation is complicated in a patient with a pathological fracture. It may be best to immobilize the affected limb and wait for the fracture to heal before performing surgery.

Other Bone Tumors with Giant Cells

A number of tumors have giant cells, but are not true benign giant cell tumors. These include, aneurysmal bone cyst, chondroblastoma, simple bone cyst, osteoid osteoma, osteoblastoma, osteosarcoma, giant cell reparative granuloma, and brown tumor of hyperparathyroidism.

Osteosarcoma

Osteosarcoma is the most common type of malignant bone cancer, accounting for 35% of primary bone malignancies. There is a preference for the metaphyseal region of tubular long bones. 50% of cases occur around the knee. It is a malignant connective (soft) tissue tumor whose neoplastic cells present osteoblastic differentiation and form tumoral bone.

Causes

The causes of osteosarcoma are not known. Questions remain about whether radium, or fluoride, in drinking water can act as "environmental triggers" for increasing the incidence of the disease. A low selenium or Vitamin D3 level or a high level of inflammation, as measured by interleukin-6, interleukin-8, or Nf-kB, Tumor Necrosis Factor Alpha may have a significant role as tumor suppressors and tumor initiators respectively. Recent studies show that an increased level of c-Fos can lead to osteosarcoma. The study that showed this result was done on transgenic mice in which the Fluid Sheer Stress (FSS) was increased to increase the number of osteoblast. Since c-Fos is ubiquitous in its over expression it can not only increase the osteoblast resulting in the symptoms osteosarcoma. Therefore it is recently believed that a biological effect that may cause osteosarcoma is an error in the molecular pathway that controls c-Fos, causing an overexpression with no other counter stimuli to stop over production.

Symptoms

Many patients first complain of pain that may be worse at night, and may have been occurring for some time. If the tumor is large, it can appear as a swelling. The affected bone is not as strong as normal bones and may fracture with minor trauma (a pathological fracture).

Diagnosis

Family physicians and orthopedists rarely see a malignant bone tumor (most bone tumors are benign). Thus, many patients are initially misdiagnosed with cysts or muscle problems, and some are sent straight to physical therapy without an x-ray.

The route to osteosarcoma diagnosis usually begins with an x-ray, continues with a combination of scans (CT scan, PET scan, bone scan, MRI) and ends with a surgical biopsy. Films are suggestive, but bone biopsy is the only definitive method to determine whether a tumor is malignant or benign.

The biopsy of suspected osteosarcoma should be performed by a qualified orthopedic oncologist. The American Cancer Society states: "Probably in no other cancer is it as important to perform this procedure properly. An improperly performed biopsy may make it difficult to save the affected limb from amputation.

Treatment

Patients with osteosarcoma are best managed by a medical oncologist when possible (or amputation in some cases) and an orthopedic oncologist experienced in managing sarcomas. Current standard treatment is to use neoadjuvant chemotherapy (chemotherapy given before surgery) followed by surgical resection. The percentage of tumor cell necrosis (cell death) seen in the tumor after surgery gives an idea of the prognosis and also lets the oncologist know if the chemotherapy regime should be altered after surgery.

Standard therapy is a combination of limb-salvage orthopedic surgery when possible (or amputation in some cases) and a combination of high dose methotrexate with leucovorin rescue, intra-arterial cisplatin, adriamycin, ifosfamide with mesna, BCD, etoposide, muramyl tri-peptide (MTP). Rotationplasty is also another surgical technique that may be used.

Ifosfamide can be used as an adjuvant treatment if the necrosis rate is low.

3-year event free survival ranges from 50% to 75%. and 5-year survival ranges from 60% to 85+% in some studies. Overall, 60-65% treated 5-years ago will be alive today. These survival rates are overall averages and vary greatly depending on the individual necrosis rate.

Osteosarcoma has one of the lowest survival rates for pediatric cancer despite chemotherapy's success in osteosarcoma of 6 chemotherapies, interferon-alpha, interleukin-2, and being the prototype of solid tumors in cancer.

Fluids are given for hydration.

Drugs like Kytril and Zofran help with nausea and vomiting.

Neupogen, epogen, Neulasta help with white blood cell counts and neutrophil counts. Blood transfusion helps with anemia.

Ovarian Cancer

Ovarian cancer is a malignant tumor, of any histology, arising from an ovary.

Classification

Ovarian cancer is classified according to the histology of the tumor, obtained in a pathology report. Histology dictates many aspects of clinical treatment, management, and prognosis.

Surface epithelial-stromal tumour, also known as ovarian epithelial carcinoma, is the most common type of ovarian cancer. It includes serous tumour, endometrioid tumor and mucinous cystadenocarcinoma.

Sex cord-stromal tumor, including estrogen-producing granulosa cell tumor and virilizing Sertoli-Leydig cell tumor or arrhenoblastoma, accounts for 8% of ovarian cancers.

Germ cell tumor accounts for approximately 30% of ovarian tumors but only 5% of ovarian cancers. It tends to occur in young women and girls. The prognosis depends on the specific histology of germ cell tumor, but overall is favorable.

Mixed tumors contain elements of more than one of the above classes of tumor histology.

Ovarian cancer can also be a secondary cancer, the result of metastasis from a primary cancer elsewhere in the body. Common primary cancers are breast cancer and gastrointestinal cancer (in which case the ovarian cancer is a Krukenberg cancer). Surface epithelial-stromal tumor can originate in the peritoneum (the lining of the abdominal cavity), in which case the ovarian cancer is secondary to primary peritoneal cancer, but treatment is basically the same as for primary surface epithelial-stromal tumor involving the peritoneum.

Symptoms

Two case-control studies, both subject to results being inflated by spectrum bias, have been reported. The first found that women with ovarian cancer had symptoms of increased abdominal size, bloating, urge to pass urine and pelvic pain. The smaller, second study found that women with ovarian cancer had pelvic/abdominal pain, increased abdominal size/bloating, and difficulty eating/feeling full. The latter study created a symptom index that was considered positive if any of the six (6) symptoms "occurred >12 times per month but were present for <1 year". They reported a sensitivity of 57% for early-stage disease and specificity 87% to 90%.

Diagnosis

Ovarian cancer at its early stages (I/II) is difficult to diagnose until it spreads and advances to later stages (III/IV). This is due to the fact that most of the common symptoms are non-specific.

When an ovarian malignancy is included in the list of diagnostic possibilities, a limited number of laboratory tests are indicated. A complete blood count (CBC) and serum electrolyte test should be obtained in all patients.

The serum BHCG level should be measured in any female in whom pregnancy is a possibility. In addition, serum alpha-fetoprotein (AFP) and lactate dehydrogenase (LDH) should be measured in young girls and adolescents with suspected ovarian tumors because the younger the patient, the greater the likelihood of a malignant germ cell tumor.

A blood test called CA-125 is useful in differential diagnosis and in follow up of the disease, but it has not been shown to be an effective method to screen for early-stage ovarian cancer due to its unacceptable low sensitivity and specificity. However, this is the only available, widely-used marker currently.

Current research is looking at ways to combine tumor markers proteomics along with other indicators of disease (i.e. radiology and/or symptoms) to improve accuracy. The challenge in such an approach is that the very low population prevalence of ovarian cancer means that even testing with very high sensitivity and specificity will still lead to a number of false positive results (i.e. performing surgical procedures in which cancer is not found intra-operatively). However, the contributions of proteomics are still in the early stages and require further refining. Current studies on proteomics mark the beginning of a paradigm shift towards individually tailored therapy.

A pelvic examination and imaging including CT scan and trans-vaginal ultrasound are essential. Physical examination may reveal increased abdominal girth and/or ascites (fluid within the abdominal cavity). Pelvic examination may reveal an ovarian or abdominal mass. The pelvic examination can include a rectovaginal component for better palpation of the ovaries. For very young patients, magnetic resonance imaging may be preferred to rectal and vaginal examination.

Staging

Ovarian cancer staging is by the FIGO staging system and uses information obtained after surgery, which can include a total abdominal hysterectomy, removal of (usually) both ovaries and fallopian tubes, (usually) the omentum, and pelvic (peritoneal) washings for cytology. The AJCC stage is the same as the FIGO stage.

Stage I—limited to one or both ovaries
  IA—involves one ovary; capsule intact; no tumor on ovarian surface; no malignant cells in ascites or peritoneal washings
  IB—involves both ovaries; capsule intact; no tumor on ovarian surface; negative washings
  IC—tumor limited to ovaries with any of the following: capsule ruptured, tumor on ovarian surface, positive washings
Stage II—pelvic extension or implants
  IIA—extension or implants onto uterus or fallopian tube; negative washings
  IIB—extension or implants onto other pelvic structures; negative washings
  IIC—pelvic extension or implants with positive peritoneal washings
Stage III—microscopic peritoneal implants outside of the pelvis; or limited to the pelvis with extension to the small bowel or omentum
  IIIA—microscopic peritoneal metastases beyond pelvis
  IIIB—macroscopic peritoneal metastases beyond pelvis less than 2 cm in size
  IIIC—peritoneal metastases beyond pelvis >2 cm or lymph node metastases
Stage IV—distant metastases to the liver or outside the peritoneal cavity Para-aortic lymph node metastases are considered regional lymph nodes (Stage IIIC).

Treatment

Surgical treatment may be sufficient for malignant tumors that are well-differentiated and confined to the ovary. Addition of chemotherapy may be required for more aggressive tumors that are confined to the ovary. For patients with advanced disease a combination of surgical reduction with a combination chemotherapy regimen is standard. Borderline tumors, even following spread outside of the ovary, are managed well with surgery, and chemotherapy is not seen as useful.

Surgery is the preferred treatment and is frequently necessary to obtain a tissue specimen for differential diagnosis via its histology. Surgery performed by a specialist in gynecologic oncology usually results in an improved result. Improved survival is attributed to more accurate staging of the disease and a higher rate of aggressive surgical excision of tumor in the abdomen by gynecologic oncologists as opposed to general gynecologists and general surgeons.

The type of surgery depends upon how widespread the cancer is when diagnosed (the cancer stage), as well as the presumed type and grade of cancer. The surgeon may remove one (unilateral oophorectomy) or both ovaries (bilateral oophorectomy), the fallopian tubes (salpingectomy), and the uterus (hysterectomy). For some very early tumors (stage 1, low grade or low-risk disease), only the involved ovary and fallopian tube will be removed (called a "unilateral salpingo-oophorectomy," USO), especially in young females who wish to preserve their fertility.

In advanced malignancy, where complete resection is not feasible, as much tumor as possible is removed (debulking surgery). In cases where this type of surgery is successful (i.e. <1 cm in diameter of tumor is left behind ["optimal debulking"]), the prognosis is improved compared to patients where large tumor masses (>1 cm in diameter) are left behind. Minimally invasive surgical techniques may facilitate the safe removal of very large (greater than 10 cm) tumors with fewer complications of surgery.

Chemotherapy has been a general standard of care for ovarian cancer for decades, although with highly variable protocols. Chemotherapy is used after surgery to treat any residual disease, if appropriate. This depends on the histology of the tumor; some kinds of tumor (particularly teratoma) are not sensitive to chemotherapy. In some cases, there may be reason to perform chemotherapy first, followed by surgery. Currently for Stage IIIC ovarian adenocarcinomas after optimal debulking, median time for survival is statistically significantly longer for patient receiving intraperitoneal (IP) chemotherapy. Patients in this clinical trial did report less compliance with IP chemotherapy, and fewer than half of the patients received all six cycles of IP chemotherapy. Despite this high "drop-out" rate, the group as a whole (including the patients that didn't complete IP chemotherapy treatment) survived longer on average than patients who received intravenous chemotherapy alone.

Some specialists believe the toxicities and other complications of IP chemotherapy will be unnecessary with improved IV chemotherapy drugs currently being developed. Although IP chemotherapy has been recommended as a standard of care for the first-line treatment of ovarian cancer, the basis for this recommendation has been challenged.

Radiation therapy is not effective for advanced stages because when vital organs are in the radiation field, a high dose cannot be safely delivered.

Paget Disease of the Nipple

Paget disease of the nipple, also called Paget disease of the breast, is an uncommon type of cancer that forms in or around the nipple. More than 95 percent of people with Paget disease of the nipple also have underlying breast cancer; however, Paget disease of the nipple accounts for less than 5 percent of all breast cancers.

Most patients diagnosed with Paget disease of the nipple are over age 50, but rare cases have been diagnosed in patients in their 20s. The average age at diagnosis is 62 for women and 69 for men. The disease is rare among both women and men.

Causes of Paget Disease of the Nipple

Scientists do not know exactly what causes Paget disease of the nipple, but two major theories have been suggested for how it develops. One theory proposes that cancer cells, called Paget cells, break off from a tumor inside the breast and move through the milk ducts to the surface of the nipple, resulting in Paget disease of the nipple. This theory is supported by the fact that more than 97 percent of patients with Paget disease also have underlying invasive breast cancer or ductal carcinoma in situ (DCIS). DCIS, also called intraductal carcinoma, is a condition in which abnormal cells are present only in the lining of the milk ducts in the breast, and have not invaded surrounding tissue or spread to the lymph nodes. DCIS sometimes becomes invasive breast cancer. Invasive breast cancer is cancer that has spread outside the duct into the breast tissue, and possibly into the lymph nodes under the arm or into other parts of the body.

The other theory suggests that skin cells of the nipple spontaneously become Paget cells. This theory is supported by the rare cases of Paget disease in which there is no underlying breast cancer, and the cases in which the underlying breast cancer is found to be a separate tumor from the Paget disease.

Symptoms of Paget Disease of the Nipple

Symptoms of early Paget disease of the nipple include redness and mild scaling and flaking of the nipple skin. Early symptoms may cause only mild irritation and may not be enough to prompt a visit to the doctor. Improvement in the skin can occur spontaneously, but this should not be taken as a sign that the disease has disappeared. More advanced disease may show more serious destruction of the skin. At this stage, the symptoms may include tingling, itching, increased sensitivity, burning, and pain. There may also be discharge from the nipple, and the nipple can appear flattened against the breast.

In approximately half of patients with Paget disease of the nipple, a lump or mass in the breast can be felt during physical examination. In most cases, Paget disease of the nipple is initially confined to the nipple, later spreading to the areola or other regions of the breast. The areola is the circular area of darker skin that surrounds the nipple. Paget disease of the nipple can also be found only on the areola, where it may resemble eczema, a noncancerous itchy red rash. Although rare, Paget disease of the nipple can occur in both breasts.

Diagnosis of Paget Disease of the Nipple

If a health care provider suspects Paget disease of the nipple, a biopsy of the nipple skin is performed. In a biopsy, the doctor removes a small sample of tissue. A pathologist examines the tissue under a microscope to see if Paget cells are present. The pathologist may use immunohistochemistry (staining tissues to identify specific cells) to differentiate Paget cells from other cell types. A sample of nipple discharge may also be examined under a microscope for the presence of Paget cells.

Because most people with Paget disease of the nipple also have underlying breast cancer, physical examination and mammography (x-ray of the breast) are used to make a complete diagnosis.

Treatment of Paget Disease of the Nipple

Surgery is the most common treatment for Paget disease of the nipple. The specific treatment often depends on the characteristics of the underlying breast cancer. A modified radical mastectomy may be recommended when invasive cancer or extensive DCIS has been diagnosed. In this operation, the surgeon removes the breast, the lining over the chest muscles, and some of the lymph nodes under the arm. In cases where underlying breast cancer is not invasive, the surgeon may perform a simple mastectomy to remove only the breast and the lining over the chest muscles. Alternatively, patients whose disease is confined to the nipple and the surrounding area may undergo breast-conserving surgery or lumpectomy followed by radiation therapy. During breast-conserving surgery, the surgeon removes the nipple, areola, and the entire portion of the breast believed to contain the cancer. In most cases, radiation therapy is also used to help prevent recurrence (return of the cancer).

During surgery, particularly modified radical mastectomy, the doctor may perform an axillary node dissection to remove the lymph nodes under the arm. The lymph nodes are then examined to see if the cancer has spread to them. In some cases, a sentinel lymph node biopsy may be performed to remove only one or a few lymph nodes. Adjuvant treatment (treatment that is given in addition to surgery to prevent the cancer from coming back) may be part of the treatment plan, depending on the type of cancer and whether cancer cells have spread to the lymph nodes. Radiation treatment is a common adjuvant therapy for Paget disease of the nipple following breast-conserving surgery. Adjuvant treatment with anticancer drugs or hormone therapies may also be recommended, depending on the extent of the disease and prognostic factors (estimated chance of recovery from the disease or chance that the disease will recur).

Pancoast Syndrome

Pancoast syndrome is characterized by a malignant neoplasm of the superior sulcus of the lung with destructive lesions of the thoracic inlet and involvement of the brachial plexus and cervical sympathetic nerves (stellate ganglion). This is accompanied by (1) severe pain in the shoulder region radiating toward the axilla and scapula along the ulnar aspect of the muscles of the hand, (2) atrophy of hand and arm muscles, (3) Horner syndrome (ptosis, miosis, hemianhidrosis, enophthalmos), and (4) compression of the blood vessels with edema.

Diagnosis

Imaging Studies

Imaging and biopsy are the cornerstones of evaluation.

The apex of the lung can be difficult to investigate because it is bounded laterally by the first rib, posteriorly by the first rib and the vertebral bodies, and anteriorly by the costal cartilage of the first rib and the manubrium. Plain radiographs of the chest frequently show no change or an asymmetry or thickening of the apical cap. Apical lordotic films may be more revealing. CT scans and MRIs have become standard imaging techniques.

CT scans are less expensive than MRIs and much more available. CT scans can help assess bone destruction, and they are useful in the general imaging of the lung for the evaluation of mediastinal adenopathy, other pulmonary nodules, and liver involvement. MRIs may be more accurate in evaluating chest wall invasion, examining vascular structures, and assessing the brachial plexus for invasion.

Additional staging studies should be considered. Mediastinoscopy should be performed to evaluate mediastinal nodes. The presence of N2 mediastinal lymphadenopathy has a significant adverse effect on survival. A CT scan or MRI of the head to exclude occult metastasis should be performed if treatment with curative intent is planned. A CT scan of the chest can be extended to include the liver and adrenal glands.

Since positron-emission tomography (PET) scanning is US Food and Drug Administration-approved for staging of non-small cell lung cancer in general, it is also being used in the setting of Pancoast syndrome.

Procedures

Tissue diagnosis should be performed. However, if a patient presents with supraclavicular lymph node enlargement, then a fine-needle aspiration biopsy of enlarged supraclavicular lymph nodes or an ipsilateral supraclavicular fullness procedure is a fast, safe, and inexpensive means of confirming the diagnosis.

Sputum cytology results are positive in fewer than 15% of patients. Fiberoptic bronchoscopy findings are more often positive, but only in 20-30% of patients, because of the peripheral location of the tumor. Bronchoscopy, however, can be useful in excluding otherwise unsuspected concurrent endobronchial lesions.

Transthoracic needle biopsy by CT guidance has a high yield, up to 95% in some series. Some tumors may be evaluated only by thoracotomy, either open or video assisted.

Staging

The American Joint Committee on Cancer (AJCC) and the Union Internationale Contre le Cancer (UICC) have adopted the International System for Staging Lung Cancer (Mountain, 1997). This classification stages lung cancers by describing tumor characteristics and tumor distribution.

The T designation describes the size and invasiveness of the primary tumor. T3 indicates a tumor of any size that invades the chest wall (the parietal pleura). T4 is a tumor of any size that invades the vertebral body, neural or vascular structure, mediastinum, esophagus, or trachea.

The N designation describes the distribution of positive lymph nodes. N1 indicates metastasis to ipsilateral peribronchial or hilar nodes. N2 indicates the spread to ipsilateral mediastinal and/or subcarinal nodes. N3 indicates metastasis to nodes of the contralateral hilar and mediastinal areas or scalene or supraclavicular nodes, either ipsilateral or contralateral.

The M designation describes the extent of distant metastasis. M0 indicates no identifiable metastatic disease, and M1 designates the presence of distant metastasis (eg, brain, bone, liver). Any M1 findings indicate stage IV disease.

AJCC Stages for Pancoast Tumors

| Stage | T (tumor) | N (nodes) |
|-------|-----------|-----------|
| IIB   | T3        | N0        |
| IIIA  | T3        | N1        |
|       | T3        | N2        |
| IIIB  | Any T     | N3        |
|       | T4        | Any N     |

Attar and coworkers reviewed their experience with 105 patients treated during 1955-1997. They found that 30% of patients presented with T3 N0 disease (stage IIB), 26% with T4 N0 (stage IIIA), and 25% with metastatic disease (M1, stage IV). In their review of 124 patients, Ginsberg and colleagues found that 58% of patients had T3 N0 disease, 16% had T3 N2, and only 1% had T3 N1. In addition, 6% of patients had T3 N3 disease, 18% had T4 N0, and 1% had T4 N.

Treatment

1) Medical Care

Today, most centers use cisplatin-based chemotherapy with etoposide and concurrent radiotherapy as neoadjuvant treatment, followed by surgical resection, as the standard of care for this group of patients. One cautionary note is that this trial mandated a negative mediastinoscopy result. The preoperative radiotherapy dose was 4500 cGy in 25 fractions.

2) Surgical Care

Historically, these tumors have been difficult to treat. In the 1950s, they were considered inoperable.

In 1956, Chardack and MacCallum reported the first 5-year survival of a patient treated with resection and postoperative radiation therapy.

The combination of radiation and surgery was further evaluated, and in 1961, Shaw and Paulson published a report of 18 patients treated with preoperative radiation therapy and surgical resection. They found a significant increase in resectability and cure; thereafter, preoperative radiation followed by surgery became the standard of care.

In many centers, the current practice is to individualize a treatment plan for each patient. Frequently, treatment decisions are made by a multidisciplinary thoracic oncology group with attention to adverse prognostic factors.

The surgical treatment of choice is complete removal of the tumor by en bloc chest wall resection combined with lobectomy and node staging (Ginsberg, 1994).

Depending upon the extent of local invasion, surgical treatment may require resection of the paravertebral sympathetic chain, stellate ganglion, lower trunks of the brachial plexus, subclavian artery, or portions of the thoracic vertebrae.

Radiation and chemotherapy may benefit local and systemic control by addressing individual adverse findings.

In many centers, neoadjuvant or induction chemoradiotherapy is administered to patients with potentially resectable tumors. Important factors include T category, nodal status, presence of Horner syndrome, and completeness of resection. Surgery is generally undertaken 2-4 weeks after the completion of radiation therapy.

For tumors that invade the brachial plexus, the spine, or both, a combined thoracic-neurosurgical approach is warranted.

A lung intergroup trial (SWOG 0220) is studying induction therapy with cisplatin, etoposide, and radiotherapy with 45 Gy, followed by resection if possible, and postoperative docetaxel.

Pancreatic Cancer

Pancreatic cancer is a malignant tumor of the pancreas. Depending on the extent of the tumor at the time of diagnosis, the prognosis is generally regarded as poor, with <5% of those diagnosed still alive five years after diagnosis, and complete remission still extremely rare. About 95 percent of pancreatic tumors are adenocarcinomas (M8140/3). The remaining 5 percent include other tumors of the exocrine pancreas (e.g., serous cystadenomas), acinar cell cancers, and pancreatic neuroendocrine tumors (such as insulinomas, M8150/1, M8150/3). These tumors have a completely different diagnostic and therapeutic profile, and generally a more favorable prognosis.

Signs and Symptoms

Early diagnosis of pancreatic cancer is difficult because the symptoms are so non-specific and varied. Common symptoms include pain in the upper abdomen that typically radiates to the back and is relieved by leaning forward (seen in carcinoma of the body or tail of the pancreas), loss of appetite, significant weight loss and painless jaundice related to bile duct obstruction (carcinoma of the head of the pancreas). All of these symptoms can have multiple other causes. Therefore, pancreatic cancer is often not diagnosed until it is advanced.

Jaundice occurs when the tumor grows and obstructs the common bile duct, which runs partially through the head of the pancreas. Tumors of the head of the pancreas (approximately 60% of cases) are more likely to cause jaundice by this mechanism. Trousseau sign, in which blood clots form spontaneously in the portal blood vessels, the deep veins of the extremities, or the superficial veins anywhere on the body, is sometimes associated with pancreatic cancer.

Clinical depression has been reported in association with pancreatic cancer, sometimes presenting before the cancer is diagnosed. However, the mechanism for this association is not known.

Risk factors for pancreatic cancer include: Age, Male gender, African-American ethnicity, Smoking, Diets high in red meat, Obesity, Diabetes mellitus, Chronic pancreatitis has been linked, but is not known to be causal, *Helicobacter pylori* infection, Occupational exposure to certain pesticides, dyes, and chemicals related to gasoline and Gingivitis or periodontal disease.

Family history is another risk factor—5-10% of pancreatic cancer patients have a family history of pancreatic cancer. The genes responsible for most of this clustering in families have yet to be identified. Pancreatic cancer has been associated with the following syndromes; autosomal recessive ataxia-telangiectasia and autosomal dominantly inherited mutations in the BRCA2 gene, Peutz-Jeghers syndrome due to mutations in the STK11 tumor suppressor gene, hereditary non-polyposis colon cancer (Lynch syndrome), familial adenomatous polyposis, and the familial atypical multiple mole melanoma-pancreatic cancer syndrome (FAMMM-PC) due to mutations in the CDKN2A tumor suppressor gene.

Diagnosis

Most patients with pancreatic cancer experience pain, weight loss, or jaundice. Pain is present in 80 to 85 percent of patients with locally advanced or advanced metastic disease. The pain is usually felt in the upper abdomen as a dull ache that radiates straight through to the back. It may be intermittent and made worse by eating. Weight loss can be profound; it may be associated with anorexia, early satiety, diarrhea, or steatorrhea. Jaundice is often accompanied by pruritus and dark urine. Painful jaundice is present in approximately one-half of patients with locally unresectable disease, while painless jaundice is present in approximately one-half of patients with a potentially resectable and curable lesion. The initial presentation varies according to tumor location. Tumors in the pancreatic body or tail usually present with pain and weight loss, while those in the head of the gland typically present with steatorrhea, weight loss, and jaundice. The recent onset of atypical diabetes mellitus, a history of recent but unexplained thrombophlebitis (Trousseau's sign), or a previous attack of pancreatitis are sometimes noted. Courvoisier sign defines the presence of jaundice and a painlessly distended gallbladder as strongly indicative of pancreatic cancer, and may be used to distinguish pancreatic cancer from gallstones.

Pancreatic cancer is usually discovered during the course of the evaluation of aforementioned symptoms. Liver function tests may show a combination of results indicative of bile duct obstruction (raised conjugated bilirubin, γ-glutamyl transpeptidase and alkaline phosphatase levels). CA19-9 (carbohydrate antigen 19.9) is a tumor marker that is frequently elevated in pancreatic cancer. However, it lacks sensitivity and specificity. When a cutoff above 37 U/mL is used, this marker has a sensitivity of 77% and specificity of 87% in discerning benign from malignant disease. CA 19-9 may be normal early in the course, and may be elevated due to benign causes of biliary obstruction.

Imaging studies, such as ultrasound or abdominal CT may be used to identify tumors. Endoscopic ultrasound (EUS) is another procedure that can help visualize the tumor and obtain tissue to establish the diagnosis. Endoscopic retrograde cholangiopancreatography (ERCP) is also used.

Treatment

1) Surgery

Treatment of pancreatic cancer depends on the stage of the cancer. The Whipple procedure is the most common surgical treatment for cancers involving the head of the pancreas. It can only be performed if the patient is likely to survive major surgery, and if the tumor is localised without invading local structures or metastasizing. It can therefore only be performed in the minority of cases. Recent advances have made possible resection (surgical removal) of tumors that were previously unresectable due to blood vessel involvement. Tumors of the tail of the pancreas can be resected using a procedure known as a distal pancreatectomy, and recently localized tumors of the pancreas have been resected using minimally invasive (laproscopic) approaches. After surgery, adjuvant chemotherapy with gemcitabine may be offered to eliminate whatever tumor tissue may remain in the body. This has been shown to increase 5-year survival rates. Addition of radiation therapy is a hotly debated topic, with groups in the US often favoring the use of adjuvant radiation therapy, while groups in Europe do not.

Surgery may be performed for palliation, if the tumor is invading or compressing the duodenum or colon. In that case, bypass surgery may overcome the obstruction and improve quality of life, but it is not intended as a cure.

2) Chemotherapy

In patients not suitable for resection with curative intent, palliative chemotherapy may be used to improve quality of life and gain a modest survival benefit. Gemcitabine was approved by the US FDA in 1998 after a clinical trial reported improvements in quality of life in patients with advanced pancreatic cancer. This marked the first FDA approval of a chemotherapy drug for a non-survival clinical trial endpoint. Gemcitabine is administered intravenously on a weekly basis. Addition of oxaliplatin (Gem/Ox) conferred benefit in small trials, but is not yet standard therapy. Fluorouracil (5FU) may also be included.

On the basis of a Canadian led Phase III Randomised Controlled trial involving 569 patients with advanced pancreatic cancer, the US FDA has licensed the use of erlotinib (Tarceva) in combination with gemcitabine as a palliative regimen for pancreatic cancer. This trial compared the action of gemcitabine/erlotinib vs gemcitabine/placebo and demonstrated improved survival rates, improved tumor response and improved progression-free survival rates. The survival improvement with the combination is on the order of less than four weeks, leading some cancer experts to question the incremental value of adding erlotinib to gemcitabine treatment. New trials are now investigating the effect of the above combination in the adjuvant and neoadjuvant setting. A trial of anti-angiogenesis agent bevacizumab (Avastin) as an addition to chemotherapy has shown no improvement in survival of patients with advanced pancreatic cancer. It may cause higher rates of high blood pressure, bleeding in the stomach and intestine, and intestinal perforations.

Penis Carcinoma

Penile cancer is a malignant growth found on the skin or in the tissues of the penis. A Squamous cell carcinoma usually originating in the glans or foreskin is by far the most common type, occurring in 9 out of 10 cases. Penile cancer is very rare in Europe and North America, occurring in about one in 100,000 men in the latter. It accounts for 0.2% of cancers and 0.1% of deaths from cancer amongst males in the United States. However, in some parts of Africa and South America it accounts for up to 10% of cancers in men.

Symptoms

Redness, irritation, or a sore on the penis or a lump on the penis. Anyone with these symptoms should consult a doctor immediately.

Pathology

A. Precancerous Dermatologic Lesions

B. Carcinoma in Situ (Bowen Disease, Erythroplasia of Queyrat)

C. Invasive Carcinoma of the Penis

Staging

Like many malignancies, penile cancer can spread to other parts of the body. It is usually a primary malignancy, the initial place from which a cancer spreads in the body. Much less often it is a secondary malignancy, one in which the cancer has spread to the penis from elsewhere. Doctors use the extent of metastasis to estimate what stage the disease is in, to aid in treatment decisions and prognosis. The stages are assessed as follows:

Stage I—Cancer has only affected the glans and/or foreskin.
Stage II—Cancer has spread to the shaft of the penis.
Stage III—Cancer has affected the penis and surrounding lymph nodes.
Stage IV—Cancer has moved beyond the groin area to other parts of the body.
Recurrent—Cancer that has returned after treatment.

Prognosis can range considerably for patients, depending where on the scale they have been staged. Generally speaking, the earlier the cancer is diagnosed, the better the prognosis. The overall 5-year survival rate for all stages of penile cancer is about 50%.

Treatment

There are several treatment options for penile cancer, depending on staging. They include surgery, radiation therapy, chemotherapy, and biological therapy. The most common treatment is one of five types of surgery:

1) Wide local excision—The tumor and some surrounding healthy tissue are removed
2) Microsurgery—Surgery performed with a microscope is used to remove the tumor and as little healthy tissue as possible
3) Laser surgery—laser light is used to burn or cut away cancerous cells
4) Circumcision—cancerous foreskin is removed
5) Amputation (penectomy)—a partial or total removal of the penis, and possibly the associated lymph nodes. This is the most common and effective treatment.

Radiation therapy is usually used adjuvantly with surgery to reduce the risk of recurrence. With earlier stages of penile cancer, a combination of topical chemotherapy and less invasive surgery may be used. More advanced stages of penile cancer usually require a combination of surgery, radiation and chemotherapy.

Risk Factors

The exact cause of penile cancer is unknown. The American Cancer Society provides the following as risk factors for penile cancer: human papillomavirus (HPV) infection, smoking, smegma, phimosis, treatment of psoriasis, age, and AIDS. The other etiologic factor most commonly associated with penile carcinoma is poor hygiene. There is some evidence that lichen sclerosus (also known as balanitis xerotica obliterans) may also be a risk factor.

Vaccine

Infection with HPV is associated with some penile cancers. A quadri-valent vaccine (Gardasil) to prevent infection by some types of HPV has been developed, successfully tested and approved for women by the US Food and Drug Administration. Approval for men is expected in 2008. It is licensed and in production, and could substantially reduce the incidence of HPV infection in men, the incidence of genital warts and ano-genital cancers including penile cancer, and mortality.

Pineoblastoma

A pineoblastoma is an aggressive primary brain tumor that develops in the pineal body (sometimes called the epiphysis cerebri or pineal gland), which is a small cone-shaped organ located in the midbrain. The pineal body secretes melatonin, a hormone that regulates moods and the sleep-wake cycle in humans. Pineoblastomas are also known as pinealoblastomas.

Causes and Symptoms

The cause of pineoblastomas is unknown, as of early 2005, but may be associated with gene mutations. A group of British radiologists reported in 2004 that the chances of survival in children diagnosed with pineoblastoma who had inherited a mutation of the retinoblastoma (RB) gene are much lower than the chances of children who did not inherit the RB mutation. The researchers suggested that this mutation may cause pineoblastomas as well as reduce or inhibit their response to therapy.

The symptoms of a pineoblastoma result from blockage of the flow of cerebrospinal fluid and increased pressure on the brain. Depending on the size of the tumor, symptoms may include the following:
headache
double vision
nausea and vomiting
weakness or loss of sensation on one side of the body
seizures
developmental delays or failure to thrive (in younger children)
lowered energy level or unusual need for sleep
personality changes
unexplained changes in weight or appetite Parents should note, however, that these symptoms are not unique to pineoblastomas; they may be produced by other types of brain tumors, head trauma, meningitis, migraine headaches, or several other medical conditions. In any event, a child with these symptoms should be seen by a doctor at once.

Diagnosis

The diagnosis of a pineoblastoma begins with a review of the child's medical history and a thorough physical examination. The child may be given several vision tests if he or she is seeing double or having other visual disturbances. The child's doctor will then order both laboratory tests and imaging studies. The laboratory tests are done to rule out such diseases as meningitis and to see whether the child's liver and other organs are functioning normally. The imaging studies are performed to determine the extent of the cancer and to assign the child to a risk group.

Unless surgical removal of the tumor is considered too risky, a neurosurgeon will perform what is known as an open biopsy to confirm the diagnosis of pineoblastoma. He or she will remove a small piece of the tumor for examination by a pathologist.

Laboratory Tests

Standard laboratory tests for children with brain tumors include a complete blood count (CBC), electrolyte analysis, tests of kidney, liver, and thyroid function, and tests that determine whether the child has been recently exposed to certain viruses. In addition, a lumbar puncture will be performed to look for cancer cells in the child's spinal fluid.

Imaging Tests

Imaging tests for pineoblastomas include the following:
Magnetic resonance imaging (MRIs).
Computed tomography (CT) scan. Doctors usually order MRIs and CT scans that cover the full length of the spinal column as well as the brain, because pineoblastomas are more likely than other PNETs to spread into the cerebrospinal fluid.
Chest x ray.
Bone scan. This test is necessary to determine whether the tumor has spread beyond the central nervous system.

Staging

Pineoblastomas are not staged in the same way as cancers elsewhere in the body. Instead, children with these tumors are divided as of the early 2000s into two risk groups, average risk and poor risk. Assignment to these groups is based on the following factors:

child's age size and location of the tumor whether the tumor has spread to other parts of the central nervous system whether the tumor has spread beyond the CNS to other parts of the body Average-risk children are those older than three years, with most or all of the tumor removed by surgery and no evidence that the cancer has spread beyond the pineal body. Poor-risk children are those who are younger than three years, whose cancer was located near the center of the brain or could not be removed completely by surgery, and whose cancer has spread to or beyond other parts of the CNS. The risk of recurrence is higher for children in the poor risk group.

Treatments

Treatments for pineoblastoma depend on the child's age and his or her risk group. Children younger than three years are not usually given radiation therapy because it can affect growth and normal brain development; they are usually treated with surgery to remove as much of the tumor as possible, followed by chemotherapy if they are considered poor-risk patients. The drugs most commonly used to treat PNETs include lomustine, cisplatin, carboplatin, and vincristine.

In addition to removing the tumor, the surgeon may also place a shunt to reduce pressure on the child's brain if the tumor is blocking the flow of cerebrospinal fluid. The shunt is a plastic tube with one end placed within the third ventricle of the brain. The rest of the shunt is routed under the skin of the head, neck, and chest with the other end placed in the abdomen or near the heart. Shunts are used very conservatively in children with pineoblastomas, however, because there have been reports of these tumors spreading into the abdomen via the shunt.

Children three years and older are treated with surgery first, followed by radiation treatment of the entire brain and spinal cord. Those considered poor risks may also be given chemotherapy. Recurrent pineoblastomas are treated with further surgery and an additional course of chemotherapy.

Treatments for pineoblastoma that are considered experimental as of 2005 include the following:

Gamma knife surgery (GKS). One group of neurosurgeons in Florida has reported good results in treating children with tumors in the pineal body with GKS. The advantages of GKS include more complete tumor removal and quicker recovery for the patient.

Gene therapy.

High-dose chemotherapy.

Photodynamic therapy.

Stem cell and bone marrow transplantation.

Newer drugs: Irinotecan, tipifarnib, lapatinib, ixabepilone, cilengitide, and tariquidar.

Primary Effusion Lymphoma

Primary effusion lymphoma (PEL) is a malignancy of B cells that is caused by Kaposi's sarcoma-associated herpesvirus (KSHV), also known as human herpesvirus 8 (HHV-8). In about 80% of cases, the lymphoma cells are also infected with Epstein Barr virus (EBV). PEL is unusual in that the majority of cases arise in body cavities, such as the pleural space or the pericardium; another name for PEL is "body cavity lymphoma". It was recognized as a unique type of lymphoma only after the discovery of KSHV in 1994.

PEL most commonly arises in patients with underlying immunodeficiency, such as AIDS. It is generally resistant to cancer chemotherapy drugs that are active against other lymphomas, and carries a very poor prognosis.

Primitive Neuroectodermal Tumor

Primitive neuroectodermal tumor (PNET) is a rare tumor, usually occurring in children under 10 years old. It is classified into two types, based on location in the body: peripheral PNET and CNS PNET.

Primitive neuroectodermal tumors (PNET) are neoplasms of which medulloblastoma is the prototype. These are small cell, malignant embryonal tumors showing divergent differentiation of variable degree along neuronal, glial, or rarely mesenchymal lines. Only tumors of the CNS are discussed here. Peripheral primitive neuroectodermal tumors are regarded as distinct entities.

Diagnosis

Lab Studies

Lab tests are not helpful in the diagnosis of PNET.

Imaging Studies

Diagnosis of these clinical entities is confirmed or excluded by lumbar puncture and CT scan and/or MRI. Presence of a mass lesion on an imaging study precludes lumbar puncture because of the risk of herniation.

Clinical diagnosis of these tumors is not possible. Radiologic features unique to each type of tumor may be helpful, but the only possible absolute confirmation is by pathologic examination of the surgical specimen.

MRI

MRI is the imaging technique of choice. The typical tumor is a heterogeneous mass with ill-defined margins arising from the vermis, which fills the fourth ventricle.

Typical findings include moderate to intense enhancement of the tumor, which is not homogenous.

Accompanying hydrocephalus is common, and associated cystic changes can occur.

The entire neuraxis should be imaged to detect spinal metastases, which may occur via subarachnoid dissemination.

CT scan

In emergent situations, CT scan is preferred over MRI because of its easy accessibility. However, CT scan resolution is inferior to that of MRI. The mass is typically midline, relatively heterogeneous, and variably contrast enhancing.

CT myelogram may be employed to rule out spinal dissemination in cases in which MRI is contraindicated.

MR spectroscopy

As compared to the normal cerebellum, these tumors on MR spectroscopy reveal a heterogeneous picture with decreased N-acetyl-aspartate (NAA) and creatine peaks and increased choline peaks.

The technique is still considered experimental.

Procedures

Ventriculostomy is rarely done preoperatively because of the risk of upward herniation.

Preoperative lumbar puncture is avoided because of the risk of downward herniation.

Histologic Findings

Primitive cells are observed growing in sheets or cords of dense cellularity with increased mitotic index and increased nuclear-cytoplasmic ratio.

Formation of Horner-Wright rosettes (ie, neuroblastic rosettes consisting of tumor cell nuclei disposed in a circular fashion about tangled cytoplasmic processes) is typical but not always seen and is not essential for diagnosis. When present, it is frequently associated with marked nuclear pleomorphism and high mitotic activity.

Associated gross pathologic findings may include cystic changes, although the tumors are usually solid. They may vary from soft to firm in consistency. Geographic areas of necrosis, vascular proliferation, or calcification are less common, while hemorrhage is rare.

Immunohistochemical markers can confirm differentiation toward astrocytic or neuronal lineage.

Unusual variants include those with melanin deposition, rhabdomyoblastic differentiation, or desmoplastic features, among others.

Treatment

1) Medical Care

Preoperative administration of steroids can help to alleviate some of the signs and symptoms by reducing peritumoral edema.

Radiation therapy

Radiation therapy, usually given adjuvantly, should be performed under the direction of a radiation oncologist.

Many series report a clear, dose-dependent relationship between postoperative radiation and local tumor control.

Adjuvant radiotherapy alone, with posterior fossa doses of 5000 cGy and neuraxis doses of 3000 cGy, results in a 5-year event-free survival rate of 50-70%. Lower than standard doses of radiation therapy, at least without chemotherapy, are less effective.

Craniospinal axis radiation is employed for patients with spinal dissemination.

Newer methods, including stereotactic radiosurgery and high fractionation radiotherapy, are being evaluated. These methods limit the dose of radiation to the local sites and avoid potential adverse effects in children, including cognitive dysfunction or delay in growth, that are seen frequently with conventional radiotherapy.

Chemotherapy

Chemotherapy should be administered under the direction of a medical oncologist.

Varying combinations of drugs used in these tumors include, but are not limited to, lomustine (CCNU), vincristine, cisplatin, etoposide (VP-16), and cyclophosphamide. Several trials, including those from the Pediatric Oncology Group (POG) and Children's Cancer Group (CCG), are underway, evaluating varying combinations of chemotherapy with and without radiotherapy. The best results, so far, have come from the Children's Hospital of Pennsylvania study, reporting a 5-year event-free survival rate of 80% among 51 patients.

CCNU has been shown to be of limited benefit, particularly in high-risk cases.

High-dose chemotherapy with stem cell rescue is being tried to improve survival and outcome.

2) Surgical Care

The goals of surgery are to achieve radical tumor resection, when possible, and to restore normal CSF outflow.

For persistent lesions, second-look surgery is recommended to remove residual tumor.

Available studies have failed to show a significant advantage, in terms of event-free survival, of total resection as compared to near-total and less-aggressive resections.

Permanent CSF diversion in the form of ventriculoperitoneal shunt is required in as many as 30% of these cases.

3) Consultations

Neurosurgeon

Neurologist/pediatric neurologist

Radiation oncologist

Medical oncologist

Prostate Cancer

Prostate cancer is a disease in which cancer develops in the prostate, a gland in the male reproductive system. It occurs when cells of the prostate mutate and begin to multiply out of control. These cells may spread (metastasize) from the prostate to other parts of the body, especially the bones and lymph nodes. Prostate cancer may cause pain, difficulty in urinating, erectile dysfunction and other symptoms.

Rates of prostate cancer vary widely across the world. Although the rates vary widely between countries, it is least common in South and East Asia, more common in Europe, and most common in the United States. According to the American Cancer Society, prostate cancer is least common among Asian men and most common among black men, with figures for white men in-between. However, these high rates may be affected by increasing rates of detection.

Prostate cancer develops most frequently in men over fifty. This cancer can occur only in men, as the prostate is exclusively of the male reproductive tract. It is the most common type of cancer in men in the United States, where it is responsible for more male deaths than any other cancer, except lung cancer. In the UK it is also the second most common cause of cancer death after lung cancer. Around 35,000 men in the UK are diagnosed per year; where around 10,000 die of it. However, many men who develop prostate cancer never have symptoms, undergo no therapy, and eventually die of other causes. That is because malignant neoplasms of the prostate are, in most cases, slow-growing, and because most of those affected are over 60. Hence they often die of causes unrelated to the prostate cancer, such as heart/circulatory disease, pneumonia, other unconnected cancers or old age. Many factors, including genetics and diet, have been implicated in the development of prostate cancer. A 2008 study found that finasteride reduces the incidence of prostate cancer rate by 30%.

Prostate cancer is most often discovered by physical examination or by screening blood tests, such as the PSA (prostate specific antigen) test. There is some current concern about the accuracy of the PSA test and its usefulness. Suspected prostate cancer is typically confirmed by removing a piece of the prostate (biopsy) and examining it under a microscope. Further tests, such as X-rays and bone scans, may be performed to determine whether prostate cancer has spread.

Prostate cancer can be treated with surgery, radiation therapy, hormonal therapy, occasionally chemotherapy, proton therapy, cryosurgery, or some combination of these. The age and underlying health of the man as well as the extent of spread, appearance under the microscope, and response of the cancer to initial treatment are important in determining the outcome of the disease. Since prostate cancer is predominantly a disease of older men, many will die of other causes before a slowly advancing prostate cancer can spread or cause symptoms. This makes treatment selection difficult. The decision whether or not to treat localized prostate cancer (a tumor that is contained within the prostate) with curative intent is a patient trade-off between the expected beneficial and harmful effects in terms of patient survival and quality of life.

Symptoms

Early prostate cancer usually causes no symptoms. Often it is diagnosed during the workup for an elevated PSA noticed during a routine checkup. Sometimes, however, prostate cancer does cause symptoms, often similar to those of diseases such as benign prostatic hypertrophy. These include frequent urination, increased urination at night, difficulty starting and maintaining a steady stream of urine, blood in the urine, and painful urination. Prostate cancer is associated with urinary disfunction as the prostate gland surrounds the prostatic urethra. Changes within the gland therefore directly affect urinary function. Prostate cancer may also cause problems with sexual function, such as difficulty achieving erection or painful ejaculation. Because the vas deferens deposits seminal fluid into the prostatic urethra, and secretions from the prostate gland itself are included in semen content, prostate cancer can affect sexual performance and cause painful ejaculation.

Advanced prostate cancer can spread to other parts of the body and this may cause additional symptoms; the most common symptom being bone pain, often in vertebrae (bones of the spine), pelvis or ribs. Spread of Cancer into other bones such as the femur is usually to the proximal part of the bone. Prostate cancer in the spine can also compress the spinal cord, causing leg weakness and urinary and fecal incontinence.

Screening

Prostate cancer screening is an attempt to find unsuspected cancers. Screening tests may lead to more specific follow-up tests such as a biopsy, where small pieces of the prostate are removed for closer study. Prostate cancer screening options include the digital rectal exam and the prostate specific antigen (PSA) blood test. Screening for prostate cancer is controversial because it is not clear if the benefits of screening outweigh the risks of follow-up diagnostic tests and cancer treatments.

Prostate cancer is usually a slow-growing cancer, very common among older men. In fact, most prostate cancers never grow to the point where they cause symptoms, and most men with prostate cancer die of other causes before prostate cancer has an impact on their lives. The PSA screening test may detect these small cancers that would never become life threatening. Doing the PSA test in these men may lead to overdiagnosis, including additional testing and treatment. Follow-up tests, such as prostate biopsy, may cause pain, bleeding and infection. Prostate cancer treatments may cause urinary incontinence and erectile dysfunction. Therefore, it is essential that the risks and benefits of diagnostic procedures and treatment be carefully considered before PSA screening.

No major scientific or medical organizations currently support routine screening for prostate cancer.

In 2002, the U.S. Preventive Services Task Force (USPSTF) concluded that the evidence was insufficient to recommend for or against routine screening for prostate cancer using PSA testing or digital rectal examination (DRE). The previous 1995 USPSTF recommendation was against routine screening.

In 1997, American Cancer Society (ACS) guidelines began recommending that beginning at age 50 (age 45 for African-American men and men with a family history of prostate cancer, and since 2001, age 40 for men with a very strong family history of prostate cancer), PSA testing and DRE be offered annually to men who have a life-expectancy of 10 or more years (average life expectancy is 10 years or more for U.S. men under age 76) along with information on the risks and benefits of screening. The previous ACS recommendations since 1980 had been for routine screening for prostate cancer with DRE annually beginning at age 40, and since 1992 had been for routine screening with DRE and PSA testing annually beginning at age 50.

The 2007 National Comprehensive Cancer Network (NCCN) guideline recommends offering a baseline PSA test and DRE at ages 40 and 45 and annual PSA testing and DRE beginning at age 50 (with annual PSA testing and DRE beginning at age 40 for African-American men, men with a family history of prostate cancer, and men with a PSA≥0.6 ng/mL at age 40 or PSA>0.6 ng/mL at age 45) through age 80, along with information on the risks and benefits of screening. Biopsy is recommended if DRE is positive or PSA≥4 ng/mL, and biopsy considered if PSA≥2.5 ng/mL or PSA velocity 0.35 ng/mL/year when PSA≤2.5 ng/mL.

Some U.S. radiation oncologists and medical oncologists who specialize in treating prostate cancer recommend obtaining a baseline PSA in all men at age 35 or beginning annual PSA testing in high risk men at age 35.

Digital rectal examination (DRE) is a procedure where the examiner inserts a gloved, lubricated finger into the rectum to check the size, shape, and texture of the prostate. Areas which are irregular, hard or lumpy need further evaluation, since they may contain cancer. Although the DRE only evaluates the back of the prostate, 85% of prostate cancers arise in this part of the prostate. Prostate cancer which can be felt on DRE is generally more advanced. The use of DRE has never been shown to prevent prostate cancer deaths when used as the only screening test.

Prostate Specific Antigen

The PSA test measures the blood level of prostate-specific antigen, an enzyme produced by the prostate. Specifically, PSA is a serine protease similar to kallikrein. Its normal function is to liquify gelatinous semen after ejaculation, allowing spermatozoa to more easily navigate through the uterine cervix.

The risk of prostate cancer increases with increasing PSA levels. 4 ng/mL was chosen arbitrarily as a decision level for biopsies in the clinical trial upon which the FDA in 1994 based adding prostate cancer detection in men age 50 and over as an approved indication for the first commercially available PSA test. 4 ng/mL was used as the biopsy decision level in the PLCO trial, 3 ng/mL was used in the ERSPC and ProtecT trials, and 2.5 ng/mL is used in the 2007 NCCN guideline.

PSA levels can change for many reasons other than cancer. Two common causes of high PSA levels are enlargement of the prostate (benign prostatic hypertrophy (BPH)) and infection in the prostate (prostatitis). It can also be raised for 24 hours after ejaculation and several days after catheterization. PSA levels are lowered in men who use medications used to treat BPH or baldness. These medications, finasteride (marketed as Proscar or Propecia) and dutasteride (marketed as Avodart), may decrease the PSA levels by 50% or more.

Several other ways of evaluating the PSA have been developed to avoid the shortcomings of simple PSA screening. The use of age-specific reference ranges improves the sensitivity and specificity of the test. The rate of rise of the PSA over time, called the PSA velocity, has been used to evaluate men with PSA levels between 4 and 10 ng/ml, but it has not proven to be an effective screening test. Comparing the PSA level with the size of the prostate, as measured by ultrasound or magnetic resonance imaging, has also been studied. This comparison, called PSA density, is both costly and has not proven to be an effective screening test. PSA in the blood may either be free or bound to other proteins. Measuring the amount of PSA which is free or bound may provide additional screening information, but questions regarding the usefulness of these measurements limit their widespread use.

Diagnosis

When a man has symptoms of prostate cancer, or a screening test indicates an increased risk for cancer, more invasive evaluation is offered.

The only test which can fully confirm the diagnosis of prostate cancer is a biopsy, the removal of small pieces of the prostate for microscopic examination. However, prior to a biopsy, several other tools may be used to gather more information about the prostate and the urinary tract. Cystoscopy shows the urinary tract from inside the bladder, using a thin, flexible camera tube inserted down the urethra. Transrectal ultrasonography creates a picture of the prostate using sound waves from a probe in the rectum.

Biopsy: If cancer is suspected, a biopsy is offered. During a biopsy a urologist obtains tissue samples from the prostate via the rectum. A biopsy gun inserts and removes special hollow-core needles (usually three to six on each side of the prostate) in less than a second. Prostate biopsies are routinely done on an outpatient basis and rarely require hospitalization. Fifty-five percent of men report discomfort during prostate biopsy.

Gleason score: The tissue samples are then examined under a microscope to determine whether cancer cells are present, and to evaluate the microscopic features (or Gleason score) of any cancer found.

Tumor markers: Tissue samples can be stained for the presence of PSA and other tumor markers in order to determine the origin of malignant cells that have metastasized.

New tests being investigated: Currently, an active area of research involves non-invasive methods of prostate tumor detection. Adenoviruses modified to transfect tumor cells with harmless yet distinct genes (such as luciferase) have proven capable of early detection. So far, though, this area of research has only been tested in animal and LNCaP models.

PCA3: Another potential non-invasive method of early prostate tumor detection is through a molecular test that detects the presence of cell-associated PCA3 mRNA in urine. PCA3 mRNA is expressed almost exclusively by prostate cells and has been shown to be highly overexpressed in prostate cancer cells. PCA3 is not a replacement for PSA but an additional tool to help decide if, in men suspected of having prostate cancer, a biopsy is really needed. The higher the expression of PCA3 in urine, the greater the likelihood of a positive biopsy, i.e. the presence of cancer cells in the prostate. Company Diagnocure has an exclusive worldwide license for all diagnostic and therapeutic applications related to PCA3.

Early prostate cancer: It was reported in April 2007 that a new blood test for early prostate cancer antigen-2 (EPCA-2) is being researched that may alert men if they have prostate cancer and how aggressive it will be.

Prostasomes: Epithelial cells of the prostate secrete prostasomes as well as PSA. Prostasomes are membrane— surrounded, prostate-derived organelles that appear extracellularly and one of their physiological functions is to protect the sperm from attacks by the female immune system. Cancerous prostate cells continue to synthesize and secrete prostasomes and may be shielded against immunological attacks by these prostasomes. Research of several aspects of prostasomal involvement in prostate cancer has been performed.

Staging

An important part of evaluating prostate cancer is determining the stage, or how far the cancer has spread. Knowing the stage helps define prognosis and is useful when selecting therapies. The most common system is the four-stage TNM system (abbreviated from Tumor/Nodes/Metastases). Its components include the size of the tumor, the number of involved lymph nodes, and the presence of any other metastases.

The most important distinction made by any staging system is whether or not the cancer is still confined to the prostate. In the TNM system, clinical T1 and T2 cancers are found only in the prostate, while T3 and T4 cancers have spread elsewhere. Several tests can be used to look for evidence of spread. These include computed tomography to evaluate spread within the pelvis, bone scans to look for spread to the bones, and endorectal coil magnetic resonance imaging to closely evaluate the prostatic capsule and the seminal vesicles. Bone scans should reveal osteoblastic appearance due to increased bone density in the areas of bone metastisis—opposite to what is found in many other cancers that metastasize.

Computed tomography (CT) and magnetic resonance imaging (MRI) currently do not add any significant information in the assessment of possible lymph node metastases in patients with prostate cancer according to a meta-analysis. The sensitivity of CT was 42% and specificity of CT was 82%. The sensitivity of MRI was 39% and the specificity of MRI was 82%. For patients at similar risk to those in this study (17% had positive pelvic lymph nodes in the CT studies and 30% had positive pelvic lymph nodes in the MRI studies), this leads to a positive predictive value (PPV) of 32.3% with CT, 48.1% with MRI, and negative predictive value (NPV) of 87.3% with CT, 75.8% with MRI. After a prostate biopsy, a pathologist looks at the samples under a microscope. If cancer is present, the pathologist reports the grade of the tumor. The grade tells how much the tumor tissue differs from normal prostate tissue and suggests how fast the tumor is likely to grow. The Gleason system is used to grade prostate tumors from 2 to 10, where a Gleason score of 10 indicates the most abnormalities. The pathologist assigns a number from 1 to 5 for the most common pattern observed under the microscope, then does the same for the second most common pattern. The sum of these two numbers is the Gleason score. The Whitmore-Jewett stage is another method sometimes used. Proper grading of the tumor is critical, since the grade of the tumor is one of the major factors used to determine the treatment recommendation.

Treatment

Treatment for prostate cancer may involve watchful waiting, surgery, radiation therapy including brachytherapy and external beam radiation, High Intensity Focused Ultrasound (HIFU), chemotherapy, cryosurgery, hormonal therapy, or some combination. Which option is best depends on the stage of the disease, the Gleason score, and the PSA level. Other important factors are the man's age, his general health, and his feelings about potential treatments and their possible side effects. Because all treatments can have significant side effects, such as erectile dysfunction and urinary incontinence, treatment discussions often focus on balancing the goals of therapy with the risks of lifestyle alterations.

The selection of treatment options may be a complex decision involving many factors. For example, radical prostatectomy after primary radiation failure is a very technically challenging surgery and may not be an option. This may enter into the treatment decision.

If the cancer has spread beyond the prostate, treatment options significantly change, so most doctors who treat prostate cancer use a variety of nomograms to predict the probability of spread. Treatment by watchful waiting, HIFU, radiation therapy, cryosurgery, and surgery are generally offered to men whose cancer remains within the prostate. Hormonal therapy and chemotherapy are often reserved for disease which has spread beyond the prostate. However, there are exceptions: radiation therapy may be used for some advanced tumors, and hormonal therapy is used for some early stage tumors. Cryotherapy, hormonal therapy, and chemotherapy may also be offered if initial treatment fails and the cancer progresses.

1) Watchful Waiting and Active Surveillance:

Watchful waiting, also called "active surveillance," refers to observation and regular monitoring without invasive treatment. Watchful waiting is often used when an early stage, slow-growing prostate cancer is found in an older man. Watchful waiting may also be suggested when the risks of surgery, radiation therapy, or hormonal therapy outweigh the possible benefits. Other treatments can be started if symptoms develop, or if there are signs that the cancer growth is accelerating (e.g., rapidly rising PSA, increase in Gleason score on repeat biopsy, etc.). Most men who choose watchful waiting for early stage tumors eventually have signs of tumor progression, and they may need to begin treatment within three years. Although men who choose watchful waiting avoid the risks of surgery and radiation, the risk of metastasis (spread of the cancer) may be increased. For younger men, a trial of active surveillance may not mean avoiding treatment altogether, but may reasonably allow a delay of a few years or more, during which time the quality of life impact of active treatment can be avoided. Published data to date suggest that carefully selected men will not miss a window for cure with this approach. Additional health problems that develop with advancing age during the observation period can also make it harder to undergo surgery and radiation therapy.

Clinically insignificant prostate tumors are often found by accident when a doctor incorrectly orders a biopsy not following the recommended guidelines (abnormal DRE and elevated PSA). The urologist must check that the PSA is not elevated for other reasons, Prostatitis, etc. An annual biopsy is often recommended by a urologist for a patient who has selected watchful waiting when the tumor is clinically insignificant (no abnormal DRE or PSA). The tumors tiny size can be monitored this way and the patient can decide to have surgery only if the tumor enlarges which may take many years or never.

2) Surgery

Surgical removal of the prostate, or prostatectomy, is a common treatment either for early stage prostate cancer, or for cancer which has failed to respond to radiation therapy. The most common type is radical retropubic prostatectomy, when the surgeon removes the prostate through an abdominal incision. Another type is radical perineal prostatectomy, when the surgeon removes the prostate through an incision in the perineum, the skin between the scrotum and anus. Radical prostatectomy can also be performed laparoscopically, through a series of small (1 cm) incisions in the abdomen, with or without the assistance of a surgical robot.

Radical prostatectomy is effective for tumors which have not spread beyond the prostate; cure rates depend on risk factors such as PSA level and Gleason grade. However, it may cause nerve damage that significantly alters the quality of life of the prostate cancer survivor.

Radical prostatectomy has traditionally been used alone when the cancer is small. In the event of positive margins or locally advanced disease found on pathology, adjuvant radiation therapy may offer improved survival. Surgery may also be offered when a cancer is not responding to radiation therapy. However, because radiation therapy causes tissue changes, prostatectomy after radiation has a higher risk of complications.

Laparoscopic radical prostatectomy, LRP, is the more modern form of the historical open radical retropubic prostatectomy. Contrasted with the open surgical form of prostate cancer surgery, laparoscopic radical prostatectomy does not require a large incision. Relying on modern technology, such as miniaturization, fiber optics, and the like, laparoscopic radical prostatectomy is a minimally invasive prostate cancer treatment and a departure from what historically required the application of relatively primitive surgical techniques. Laparoscopic radical prostatectomy is not a new prostate cancer treatment. Rather, laparoscopic radical prostatectomy is a modern means of performing prostate cancer surgery, the oldest treatment for prostate cancer.

The LRP technical manual was published in 1999 by Drs. Bertrand Guillonneau, Amon Krongrad, and Guy Vallancien. LRP is laparoscopic prostate surgery, not laser prostate surgery.

In the hands of an experienced surgeon, robotic assisted laparoscopic prostatectomy (RALP) may reduce positive surgical margins when compared to radical retropubic prostatectomy (RRP) among patients with prostate cancer according to a retrospective study. The relative risk reduction was 57.7%. For patients at similar risk to those in this study (35.5% of patients had positive surgical margins following RRP), this leads to an absolute risk reduction of 20.5%. 4.9 patients must be treated for one to benefit (number needed to treat=4.9).

Transurethral resection of the prostate, commonly called a "TURP," is a surgical procedure performed when the tube from the bladder to the penis (urethra) is blocked by prostate enlargement. TURP is generally for benign disease and is not meant as definitive treatment for prostate cancer. During a TURP, a small tube (cystoscope) is placed into the penis and the blocking prostate is cut away.

In metastatic disease, where cancer has spread beyond the prostate, removal of the testicles (called orchiectomy) may be done to decrease testosterone levels and control cancer growth.

The most common serious complications of surgery are loss of urinary control and impotence. Reported rates of both complications vary widely depending on how they are assessed, by whom, and how long after surgery, as well as the setting (e.g., academic series vs. community-based or population-based data). Although penile sensation and the ability to achieve orgasm usually remain intact, erection and ejaculation are often impaired. Medications such as sildenafil (Viagra), tadalafil (Clalis), or vardenafil (Levitra) may restore some degree of potency. For most men with organ-confined disease, a more limited "nerve-sparing" technique may help reduce urinary incontinence and impotence.

3) Radiation Therapy

Radiation therapy, also known as radiotherapy, is often used to treat all stages of prostate cancer, or when surgery fails. Radiotherapy uses ionizing radiation to kill prostate cancer cells. When absorbed in tissue, Ionizing radiation such as Gamma and x-rays damage the DNA in cells, which increases the probability of apoptosis (cell death). Two different kinds of radiation therapy are used in prostate cancer treatment: external beam radiation therapy and brachytherapy.

External beam radiation therapy uses a linear accelerator to produce high-energy x-rays which are directed in a beam towards the prostate. A technique called Intensity Modulated Radiation Therapy (IMRT) may be used to adjust the radiation beam to conform with the shape of the tumor, allowing higher doses to be given to the prostate and seminal vesicles with less damage to the bladder and rectum. External beam radiation therapy is generally given over several weeks, with daily visits to a radiation therapy center. New types of radiation therapy may have fewer side effects than traditional treatment. One of these is Tomotherapy.

Permanent implant brachytherapy is a popular treatment choice for patients with low to intermediate risk features, can be performed on an outpatient basis, and is associated with good 10-year outcomes with relatively low morbidity. It involves the placement of about 100 small "seeds" containing radioactive material (such as iodine-125 or palladium-103) with a needle through the skin of the perineum directly into the tumor while under spinal or general anesthetic. These seeds emit lower-energy X-rays which are only able to travel a short distance. Although the seeds eventually become inert, they remain in the prostate permanently. The risk of exposure to others from men with implanted seeds is generally accepted to be insignificant.

Radiation therapy is commonly used in prostate cancer treatment. It may be used instead of surgery or after surgery in early stage prostate cancer. In advanced stages of prostate cancer radiation is used to treat painful bone metastases. Radiation treatments also can be combined with hormonal therapy for intermediate risk disease, when radiation therapy alone is less likely to cure the cancer. Some radiation oncologists combine external beam radiation and brachytherapy for intermediate to high risk situations. One study found that the combination of six months of androgen suppressive therapy combined with external beam radiation had improved survival compared to radiation alone in patients with localized prostate cancer. Others use a "triple modality" combination of external beam radiation therapy, brachytherapy, and hormonal therapy.

Radiation therapy uses high-energy rays or particles to kill cancer cells. When delivered in the correct dosage, radiation can reduce the risk of recurrence.

Less common applications for radiotherapy are when cancer is compressing the spinal cord, or sometimes after surgery, such as when cancer is found in the seminal vesicles, in the lymph nodes, outside the prostate capsule, or at the margins of the biopsy.

Radiation therapy is often offered to men whose medical problems make surgery more risky. Radiation therapy appears to cure small tumors that are confined to the prostate just about as well as surgery. However, some issues remain unresolved, such as whether radiation should be given to the rest of the pelvis, how much the absorbed dose should be, and whether hormonal therapy should be given at the same time. Side effects of radiation therapy might occur after a few weeks into treatment. Both types of radiation therapy may cause diarrhea and mild rectal bleeding due to radiation proctitis, as well as urinary incontinence and impotence. Symptoms tend to improve over time. Rates for impotence when comparing radiation to nerve-sparing surgery are similar. Radiation has lower rates of incontinence but higher rates of occasional mild rectal bleeding. Men who have undergone external beam radiation therapy may have a slightly higher risk of later developing colon cancer and bladder cancer.

4) Cryosurgery

Cryosurgery is another method of treating prostate cancer in which the prostate gland is exposed to freezing temperatures. It is less invasive than radical prostatectomy, and general anesthesia is less commonly used. Under ultrasound guidance, a method invented by Dr. Gary Onik, metal rods are inserted through the skin of the perineum into the prostate. Highly purified Argon gas is used to cool the rods, freezing the surrounding tissue at −196° C. (−320° F.). As the water within the prostate cells freeze, the cells die. The urethra is protected from freezing by a catheter filled with warm liquid. Cryosurgery generally causes fewer problems with urinary control than other treatments, but impotence occurs up to ninety percent of the time. When used as the initial treatment for prostate cancer and in the hands of an experienced cryosurgeon, cryosurgery has a 10 year biochemical disease free rate superior to all other treatments including radical prostatectomy and any form of radiation. Cryosurgery has also been demonstrated to be superior to radical prostatectomy for recurrent cancer following radiation therapy.

5) Hormonal Therapy

Hormonal therapy uses medications or surgery to block prostate cancer cells from getting dihydrotestosterone (DHT), a hormone produced in the prostate and required for the growth and spread of most prostate cancer cells. Blocking DHT often causes prostate cancer to stop growing and even shrink. However, hormonal therapy rarely cures prostate cancer because cancers which initially respond to hormonal therapy typically become resistant after one to two years. Hormonal therapy is therefore usually used when cancer has spread from the prostate. It may also be given to certain men undergoing radiation therapy or surgery to help prevent return of their cancer. Hormonal therapy for prostate cancer targets the pathways the body uses to produce DHT. A feedback loop involving the testicles, the hypothalamus, and the pituitary, adrenal, and prostate glands controls the blood levels of DHT. First, low blood levels of DHT stimulate the hypothalamus to produce gonadotropin releasing hormone (GnRH). GnRH then stimulates the pituitary gland to produce luteinizing hormone (LH), and LH stimulates the testicles to produce testosterone. Finally, testosterone from the testicles and dehydroepiandrosterone from the adrenal glands stimulate the prostate to produce more DHT. Hormonal therapy can decrease levels of DHT by interrupting this pathway at any point.

There are several forms of hormonal therapy:

Orchiectomy is surgery to remove the testicles. Because the testicles make most of the body's testosterone, after orchiectomy testosterone levels drop. Now the prostate not only lacks the testosterone stimulus to produce DHT, but also it does not have enough testosterone to transform into DHT.

Antiandrogens are medications such as flutamide, bicalutamide, nilutamide, and cyproterone acetate which directly block the actions of testosterone and DHT within prostate cancer cells.

Medications which block the production of adrenal androgens such as DHEA include ketoconazole and aminoglutethimide. Because the adrenal glands only make about 5% of the body's androgens, these medications are generally used only in combination with other methods that can block the 95% of androgens made by the testicles. These combined methods are called total androgen blockade (TAB). TAB can also be achieved using antiandrogens.

GnRH action can be interrupted in one of two ways. GnRH antagonists suppress the production of LH directly, while GnRH agonists suppress LH through the process of down regulation after an initial stimulation effect. Abarelix is an example of a GnRH antagonist, while the GnRH agonists include leuprolide, goserelin, triptorelin, and buserelin. Initially, GnRH agonists increase the production of LH. However, because the constant supply of the medication does not match the body's natural production rhythm, production of both LH and GnRH decreases after a few weeks.

The most successful hormonal treatments are orchiectomy and GnRH agonists. Despite their higher cost, GnRH agonists are often chosen over orchiectomy for cosmetic and emotional reasons. Eventually, total androgen blockade may prove to be better than orchiectomy or GnRH agonists used alone.

Each treatment has disadvantages which limit its use in certain circumstances. Although orchiectomy is a low-risk surgery, the psychological impact of removing the testicles can be significant. The loss of testosterone also causes hot flashes, weight gain, loss of libido, enlargement of the breasts (gynecomastia), impotence and osteoporosis. GnRH agonists eventually cause the same side effects as orchiectomy but may cause worse symptoms at the beginning of treatment. When GnRH agonists are first used, testosterone surges can lead to increased bone pain from metastatic cancer, so antiandrogens or abarelix are often added to blunt these side effects. Estrogens are not commonly used because they increase the risk for cardiovascular disease and blood clots. The antiandrogens do not generally cause impotence and usually cause less loss of bone and muscle mass. Ketoconazole can cause liver damage with prolonged use, and aminoglutethimide can cause skin rashes.

6) Palliative Care

Palliative care for advanced stage prostate cancer focuses on extending life and relieving the symptoms of metastatic disease. Chemotherapy may be offered to slow disease progression and postpone symptoms. The most commonly used regimen combines the chemotherapeutic drug docetaxel with a corticosteroid such as prednisone. Bisphosphonates such as zoledronic acid have been shown to delay skeletal complications such as fractures or the need for radiation therapy in patients with hormone-refractory metastatic prostate cancer.

Bone pain due to metastatic disease is treated with opioid pain relievers such as morphine and oxycodone. External beam radiation therapy directed at bone metastases may provide pain relief. Injections of certain radioisotopes, such as strontium-89, phosphorus-32, or samarium-153, also target bone metastases and may help relieve pain.

7) High Intensity Focused Ultrasound (HIFU)

HIFU for prostate cancer utilizes high intensity focused ultrasound (HIFU) to ablate/destroy the tissue of the prostate. During the HIFU procedure, sound waves are used to heat the prostate tissue thus destroying the cancerous cells. Essentially, ultrasonic waves are precisely focused on specific areas of the prostate to eliminate the prostate cancer with minimal risks of affecting other tissue or organs. Temperatures at the focal point of the sound waves can exceed 100° C. In lay terms, the HIFU technology is similar to using a magnifying glass to burn a piece of paper by focusing sunlight at a small precise point on the sheet. The ability to focus the ultrasonic waves leads to a relatively low occurrence of both incontinence and impotence. (0.6% and 0-20%, respectively) According to international studies, when compared to other procedures, HIFU has a high success rate with a reduced risk of side effects. Studies using the Sonablate 500 HIFU machine have shown that 94% of patients with a pretreatment PSA (Prostate Specific Antigen) of less than 10 g/ml were cancer-free after three years. However, many studies of HIFU were performed by manufacturers of HIFU devices, or members of manufacturers' advisory panels.

Renal Adenocarcinoma

Renal adenocarcinoma: an adenocarcinoma arising in the renal parenchyma, usually occurring in middle-aged or older people of either gender (although more common in men). SYN: clear cell carcinoma of kidney, renal cell carcinoma.

Renal cell carcinoma (RCC) is the most common form of kidney cancer arising from the renal tubule. It is the most common type of kidney cancer in adults. Initial treatment is surgery. It is resistant to radiation therapy and chemotherapy, although some cases respond to immunotherapy. Targeted cancer therapies such as sunitinib have improved the outlook for RCC, although they have not yet demonstrated improved survival.

Signs and Symptoms

The classic triad is hematuria (blood in the urine), flank pain and an abdominal mass. This is now known as the 'too late triad' because by the time patients present with symptoms, their disease is often advanced beyond a curative stage. Today, the majority of renal tumors are asymptomatic and are detected incidentally on imaging, usually for an unrelated cause.

Other signs may include:

Abnormal urine color (dark, rusty, or brown) due to blood in the urine

Weight loss, malnourished appearance

The presenting symptom may be due to metastatic disease, such as a pathologic fracture of the hip due to a metastasis to the bone Enlargement of one testicle known as varicocele (usually the left, due to blockage of the left gonadal vein by tumor invasion of the left renal vein—the right gonadal vein drains directly into the inferior vena cava)

Vision abnormalities

Pallor or plethora

Hirsutism—Excessive hair growth (females)

Constipation

High blood pressure

Elevated calcium levels (Hypercalcemia)

Causes

Renal cell carcinoma affects about three in 10,000 people, resulting in about 31,000 new cases in the US per year. Every year, about 12,000 people in the US die from renal cell carcinoma. It is more common in men than women, usually affecting men older than 55.

Kidney cancer both RCC & TCC currently is diagnosed in some 6,600 people in Britain/UK per annum and some 3,600 people who die are recorded as having died of kidney cancer in a given year. The morbidity rate recorded is thought to underestimate the percentage who die of kidney cancer. Often the cause of death recorded on the death certificate may not mention kidney cancer but the subsequent metastases. It is clear that well over 50% of those diagnosed with kidney cancer in Britain will die of the disease or as a result of the disease.

Why the cells become cancerous is not known. A history of smoking greatly increases the risk for developing renal cell carcinoma. Some people may also have inherited an increased risk to develop renal cell carcinoma, and a family history of kidney cancer increases the risk.

Increasingly there is a belief that inhalation of a diversity of chemicals may be causal and it is also noted that there is a steady increase in diagnosis in women. That a disproportionate percentage of those diagnosed with kidney cancer are obese is increasingly believed to be a significant factor.

People with von Hippel-Lindau disease, a hereditary disease that also affects the capillaries of the brain, commonly also develop renal cell carcinoma. Kidney disorders that require dialysis for treatment also increase the risk for developing renal cell carcinoma.

Radiology

The characteristic appearance of renal cell carcinoma (RCC) is a solid renal lesion which disturbs the renal contour. It will frequently have an irregular or lobulated margin. 85% of solid renal masses will be RCC. 10% of RCC will contain calcifications, and some contain macroscopic fat (likely due to invasion and encasement of the perirenal fat). Following intravenous contrast administration (computed tomography or magnetic resonance imaging), enhancement will be noted, and will increase the conspicuity of the tumor relative to normal renal parenchyma.

A list of solid renal lesions includes: 1) renal cell carcinoma, 2) metastasis from an extra-renal primary neoplasm, 3) renal lymphoma, 4) squamous cell carcinoma, 5) juxtaglomerular tumor (reninoma), 6) transitional cell carcinoma, 7) angiomyolipoma, 8) oncocytoma and 9) Wilm's tumor.

In particular, reliably distinguishing renal cell carcinoma from an oncocytoma (a benign lesion) is not possible using current medical imaging or percutaneous biopsy. Renal cell carcinoma may also be cystic. As there are several benign cystic renal lesions (simple renal cyst, hemorrhagic renal cyst, multilocular cystic nephroma, polycystic kidney disease), it may occasionally be difficult for the radiologist to differentiate a benign cystic lesion from a malignant one. A classification system for cystic renal lesions that classifies them based specific imaging features into groups that are benign and those that need surgical resection is available. At diagnosis, 30% of renal cell carcinoma has spread to that kidney's renal vein, and 5-10% has continued on into the inferior vena cava.

Percutaneous biopsy can be performed by a radiologist using ultrasound or computed tomography to guide sampling of the tumor for the purpose of diagnosis. However this is not routinely performed because when the typical imaging features of renal cell carcinoma are present, the possibility of an incorrectly negative result together with the risk of a medical complication to the patient makes it unfavorable from a risk-benefit perspective. This is not completely accurate, there are new experimental treatments.

Treatment

If it is only in the kidneys, which is about 40% of cases, it can be cured roughly 90% of the time with surgery. If it has spread outside of the kidneys, often into the lymph nodes or the main vein of the kidney, then it must be treated with adjunctive therapy, including cytoreductive surgery 1) Watchful Waiting Small renal tumors represent the majority of tumors that are treated today by way of partial nephrectomy. The average growth of these masses is about 4-5 mm per year, and a significant proportion (up to 40%) of tumors less than 4 cm in diameter are benign. More centers of excellence are incorporating needle biopsy to confirm the presence of malignant histology prior to recommending definitive surgical extirpation. In the elderly, patients with co-morbidities and in poor surgical candidates, small renal tumors may be monitored carefully with serial imaging. Most clinicians conservatively follow tumors up to a size threshold between 3-5 cm, beyond which the risk of distant spread (metastases) is about 5%.

2) Surgery

Surgical removal of all or part of the kidney (nephrectomy) is recommended. This may include removal of the adrenal gland, retroperitoneal lymph nodes, and possibly tissues involved by direct extension (invasion) of the tumor into the surrounding tissues. In cases where the tumor has spread into the renal vein, inferior vena cava, and possibly the right atrium (angioinvasion), this portion of the tumor can be surgically removed, as well. In case of metastases surgical resection of the kidney ("cytoreductive nephrectomy") may improve survival, as well as resection of a solitary metastatic lesion.

3) Percutaneous Therapies

Percutaneous, image-guided therapies, usually managed by radiologists, are being offered to patients with localized tumor, but who are not good candidates for a surgical procedure. This sort of procedure involves placing a probe through the skin and into the tumor using real-time imaging of both the probe tip and the tumor by computed tomography, ultrasound, or even magnetic resonance imaging guidance, and then destroying the tumor with heat (radiofrequency ablation) or cold (cryotherapy). These modalities are at a disadvantage compared to traditional surgery in that pathologic confirmation of complete tumor destruction is not possible.

4) Medications

RCC "elicits an immune response, which occasionally results in dramatic spontaneous remissions." This has encouraged a strategy of using immunomodulating therapies, such as cancer vaccines and interleukin-2 (IL-2), to reproduce this response. IL-2 has produced "durable remissions" in a small number of patients, but with substantial toxicity. Another strategy is to restore the function of the VHL gene, which is to destroy proteins that promote inappropriate vascularization. Bevacizumab, an antibody to VEGF, has significantly prolonged time to progression, but phase 3 trials have not been published. Sunitinib (Sutent), sorafenib (Nexavar), and temsirolimus, which are small-molecule inhibitors of proteins, have been approved by the U.S. F.D.A.

Sorafenib was FDA approved in December 2005 for treatment of advanced renal cell cancer, the first receptor tyrosine kinase (RTK) inhibitor indicated for this use.

A month later, Sunitinib was approved as well. Sunitinib—an oral, small-molecule, multi-targeted (RTK) inhibitor—and sorafenib both interfere with tumor growth by inhibiting angiogenesis as well as tumor cell proliferation. Sunitinib appears to offer greater potency against advanced RCC, perhaps because it inhibits more receptors than sorafenib. However, these agents have not been directly compared against one another in a single trial.

Temsirolimus (CCI-779) is an inhibitor of mTOR kinase (mammalian target of rapamycin) that was shown to prolong overall survival vs. interferon-α in patients with previously untreated metastatic renal cell carcinoma with three or more poor prognostic features. The results of this Phase III randomized study were presented at the 2006 annual meeting of the American Society of Clinical Oncology (www.ASCO.org).

5) Chemotherapy

Chemotherapy may be used in some cases, but cure is unlikely unless all the cancer can be removed with surgery.

The use of Tyrosine Kinase (TK) inhibitors, such as Sunitinib and Sorafenib, and Temsirolimus are described in a different section.

6) Vaccine

Cancer vaccines, such as TroVax, are in phase 3 trials for treatment of renal cell carcinoma.

7) Cryoablation

This involves destroying the kidney tumor without surgery, by freezing the tumor. The process can remove 95% of tumors in one treatment and can be tolerated by patients who are not good candidates for surgery (older or weak patients).

Renal Metastases

The spread of a cancer to the kidney. This may be from a primary kidney cancer involving the opposite kidney, or from a cancer at a distant site.

Retinoblastoma

Retinoblastoma is a cancer of the retina. Development of this tumor is initiated by mutations that inactivate both copies of the RB1 gene, which codes for the retinoblastoma protein.

Treatment

Until recently the only treatment was to remove the affected eyeball before the cancer spread. Chemotherapy is the treatment of choice for most unilateral cases. However with locally advanced disease external beam radiation may be needed and if both eyes are involved enucleation may be the only option. Affected children in developing countries present with advanced features and usually die of metastatic spread. In its initial stages, retinoblastoma is very similar to Coats disease, a non-cancerous retina disease. Coats' disease should be ruled out before enucleation is done. A misdiagnosis of retinoblastoma accounts for the greatest number of Coats' disease eyes being enucleated.

Many children with bilateral retinoblastoma can be treated with a preservation attempt. Tumor chemoreduction with carboplatin and other drugs may reduce the tumor volume making them amenable to local therapies.

Local Therapies Include:
1) Laser therapy (Uses infrared laser light to precisely destroy the blood vessels surrounding a tumor.)
2) Cryotherapy (use of a cold gas which is injected into the affected part of the retina to shrink the tumor.)
3) Thermotherapy (A relatively new technique used mainly in new testing. It uses the principle that if heat is applied to the affected area, a tumor will sustain more damage than healthy cells because healthy cells can cool themselves better using healthy surrounding blood vessels. If this technique is not immediately successful it may increase the efficacy of other treatments such as chemotherapy and focused radiation plaques.)
4) Radiotherapy (Generally used as a last resort, radiotherapy was previously the treatment of choice before the above mentioned treatments were developed. Radiotherapy destroys cancerous growths using gamma radiation but it carries with it many drawbacks, including:—
    Possibility of secondary cancerous growths which present themselves months or years later.
    Destruction of healthy cells in the area surrounding the treated tumor.
    Bone deformation due to the destruction of the growth plates mainly in the area of the temple.)

It is important that children with retinoblastoma are treated in specialist centers. It is considered to be one of the most common inherited cancer syndromes.

Brachytherapy with beta-emitting eye applicators have also been a successful major treatment. BEBIG (GmbH-Berlin-Germany) produces various kinds of ruthenium ophthalmic applicators for treating retinoblastoma.

Rhabdomyosarcoma

Rhabdomyosarcoma is a type of cancer, specifically a sarcoma (cancer of connective tissues), in which the cancer cells are thought to arise from skeletal muscle progenitors. It can also be found attached to muscle tissue, wrapped around intestines, or anywhere, to include the neck area. It is most common in children ages one to five, and is also found in teens aged 15 to 19, although this is more rare.

Rhabdomyosarcoma is a relatively rare form of cancer. Its two most common forms are embryonal rhabdomyosarcoma and alveolar rhabdomyosarcoma. In the former, which is more common in younger children, the cancer cells resemble those of a typical 6-to-8-week embryo. In the latter, which is more common in older children and teenagers, they resemble those of a typical 10-to-12-week embryo.

Diagnosis

When rhabdomyosarcoma is suspected, tests will be run for blood, muscle, and marrow.

Diagnosis of rhabdomyosarcoma depends on recognition of differentiation toward skeletal muscle cells. The protein myo D1 is a protein normally found in developing skeletal muscle cells which disappears after the muscle matures and becomes innervated by a nerve. Thus, myo D1 is not found in normal skeletal muscle and serves as a useful immunohistochemical marker of rhabdomyosarcoma. Early manifestation can be misdiagnosed as a pseudotumor that is non responsive to steroid treatment.

Treatment

Treatment for rhabdomyosarcoma consists of chemotherapy, radiation therapy and sometimes surgery. Surgery to remove the tumor is often difficult or impossible because the tumor is usually embedded deep within the tissue, leaving it difficult to reach. If a tumor presents itself in the extremities, amputation is often necessary to improve chances of survival.

If there is no evidence of metastasis, surgery combined with chemotherapy and radiation offer the best prognosis. Patients whose tumors have metastasized usually have a poor chance for long-term survival. In patients who began treatment before metastasis, the prognosis is better, although the disease is generally incurable because the tumors that cannot be surgically removed tend to spread.

Salivary Gland Cancer

Signs and Symptoms

Salivary gland cancer may involve two primary glands:
Parotid gland, the largest of the salivary glands in the upper portion of each cheek, close to the ear, with ducts that empty into the upper inside of the cheek
Submandibular glands, in the floor of the mouth with ducts that empty near the lower front teeth.

Most cancers of these glands occur as painless lumps, either in front of the ear or under the jaw. Parotid cancers are more common than submandibular cancers. Some lumps can enlarge rapidly or be painful. Other symptoms may include facial weakness, fixation of the lump, sensory loss, ulceration, difficulty opening the jaw and tongue numbness or weakness.

Diagnosis

Needle biopsy is effective for diagnosis and is commonly recommended. Imaging studies including computerized tomography (CT) scan or magnetic resonance imaging (MRI) help delineate the tumor extent and status of neck lymph nodes.

Treatment

Surgery: Surgery is the mainstay of treatment for salivary gland cancers. The extent of surgery depends upon tumor type, size and location. A neck dissection is performed for removal of neck lymph nodes if they harbor tumor spread.

Radiation Therapy Radiation therapy, also called radiotherapy, is the use of high-energy rays to damage cancer cells and stop them from growing. Like surgery, radiation therapy is local therapy. It affects only the cells in the treated area. The energy may come from a large machine, or external radiation. Patients with large tumors may need both surgery and radiation therapy. Radiation therapy is given after surgery for advanced or aggressive tumors.

Chemotherapy: Chemotherapy is the use of drugs to kill cancer cells. Researchers are looking for effective drugs or drug combinations to treat salivary gland cancer. They are also exploring ways to combine chemotherapy with other forms of cancer treatment to help destroy the tumor and prevent the disease from spreading. Chemotherapy is given at the time of radiation therapy in select tumors usually in the setting of a therapeutic clinical trial. Chemotherapy is sometimes recommended if the cancer has spread to other locations in the body.

Small Bowel Lymphoma
  Small bowel is second most frequent site of GI tract involvement by lymphoma.
    Ileum is most common site of occurrence
      Ileum has most lymphoid tissue
    Duodenum is least frequent
  Most cases of small bowel lymphoma are due to non-Hodgkin's lymphoma
    Mesenteric involvement by lymphoma may occur by
    Direct extension from bowel
    Indirectly by displacement due to mass effect
    Risk factors include
    Immunocompromised or immunosuppressed state
    Long-term celiac sprue
    Chronic lymphocytic leukemia
    Mediterranean abdominal lymphoma
    Associated with immuno-proliferative small intestinal disease
    Presents with malabsorption syndrome
    Consists of diffuse lymphomatous infiltration of mucosa and submucosa in long segments of small intestine
    Infection may be important in the development of this type of lymphoma
      Some are reversible if treated by antibiotics in the very early stages
    Definitive diagnosis is based on histopathological examination from biopsy of the lesion
Staging:
  1E: single bowel tumor without nodal involvement
  2E: GI tumor focus with nodal disease below the diaphragm; nodal disease divided into regional and extraregional
  3E: GI tumor focus with nodal disease above and below the diaphragm and or serosal involvement +/−other organs involved
  3ES: Splenic involvement
  4E: Extralymphatic i.e. bone, liver
Prognosis
  Poor prognosis is associated with:
    Stage greater than 2E (nodal disease above and below the diaphragm)
    Tumor size greater than 10 cm
    T cell type
    Immunoblastic histology
    Presence of aneuploidy
    Presentation as an acute abdomen
  Primary lymphoma criteria include
    Confinement of disease to a small bowel segment
    Only regional lymphadenopathy
    No hepatic or splenic involvement except by direct tumor extension
    No palpable or mediastinal lymphadenopathy
    Normal peripheral blood smear and bone marrow biopsy
  Patterns of small bowel lymphoma
    Circumferential infiltration of a small bowel segment
      Results in a variable length of thickening and effacement of folds
      Widening of the lumen rather than narrowing
        From infiltration of muscularis layer with destruction of the myenteric plexus leading to aneurysmal dilatation, often at the antimesentric segment
    Nodular lesions can be variable in size and irregularly distributed
    Polypoidal lesions are sometimes reported to cause intussusception
    Endoexoenteric lesions can cause fistulas
  Imaging findings
    CT appearance of lymphoma is variable
      Typical appearances can be classified as aneurysmal, constrictive, nodular, or ulcerative
    Small bowel series can show luminal narrowing of the involved segment with loss of mucosal pattern and thickening of the plica circulares and intraluminal filling defects possibly with dilatation of the involved segment.
    Ultrasound may demonstrate a hypoechoic lesion of the affected bowel and presence of abdominal lymphadenopathy.
    CT scan shows a sausage shaped loop of bowel that is of relatively homogenous tissue density
      Also asymmetric wall thickening of usually greater than 2 cm
      Aneurysmal dilatation
      Polypoidal mass
      Abdominal lymphadenopathy
  Differential diagnoses include
    Tuberculosis
    Inflammatory small bowel disease and carcinoma.
  Treatment
    Malignant lymphoma of the small bowel is treated with surgical resection, usually followed by chemotherapy to prevent perforation
    Radiation therapy may also be used
Soft Tissue Sarcoma
  A soft tissue sarcoma is a rare form of cancer that develops in mesenchymal tissue: the muscle, connective tissues, and bones of the body. It is one of the sarcomas.
Risk Factors
  Most soft tissue sarcomas are not associated with any known risk factors or identifiable etiology. There are some exceptions:
    Studies suggest that workers who are exposed to Phenoxy herbicide in herbicides and chlorophenols in wood preservatives may have an increased risk of developing soft tissue sarcomas. An unusual percentage of patients with a rare blood vessel tumor, angiosarcoma of the liver, have been exposed to vinyl chloride in their work. This substance is used in the manufacture of certain plastics, notably PVC.
    In the early 1900s, when scientists were just discovering the potential uses of radiation to treat disease, little was known about safe dosage levels and precise methods of delivery. At that time, radiation was used to treat a variety of noncancerous medical problems, including enlargement of the tonsils, adenoids, and thymus gland. Later, researchers found that high doses of radiation caused soft tissue sarcomas in some patients. Because of this risk, radiation treatment for cancer is now planned to ensure that the maximum dosage of radiation is delivered to diseased tissue while surrounding healthy tissue is protected as much as possible.

It is believed that a retrovirus plays an indirect role in the development of Kaposi's sarcoma, a rare cancer of the cells that line blood vessels in the skin and mucus membranes. Kaposi's sarcoma often occurs in patients with AIDS (acquired immune deficiency syndrome). AIDS-related Kaposi's sarcoma, however, has different characteristics to and is treated differently from typical soft tissue sarcomas.

In a very small fraction of cases, sarcoma may be related to a rare inherited genetic alteration of the p53 gene and is known as Li-Fraumeni syndrome. Certain other inherited diseases are associated with an increased risk of developing soft tissue sarcomas. For example, people with neurofibromatosis type I (also called von Recklinghausen's disease associated with alterations in the NF1 gene) are at an increased risk of developing soft tissue sarcomas known as malignant peripheral nerve sheath tumors. Patients with inherited retinoblastoma have alterations in the RB1 gene, a tumor suppressor gene, and are likely to develop soft tissue sarcomas as they mature into adulthood.

Symptoms

In their early stages, soft tissue sarcomas usually do not cause symptoms. Because soft tissue is relatively elastic, tumors can grow rather large, pushing aside normal tissue, before they are felt or cause any problems. The first noticeable symptom is usually a painless lump or swelling. As the tumor grows, it may cause other symptoms, such as pain or soreness, as it presses against nearby nerves and muscles. If in the abdomen it can cause abdominal pains commonly mistaken for menstrual cramps, indigestion, or cause constipation.

Diagnosis

The only reliable way to determine whether a soft tissue tumor is benign or malignant is through a biopsy. Therefore, all soft tissue lumps that persist or grow should be biopsied. A biopsy can be obtained via needle biopsy or with surgical biopsy. During this procedure, a doctor makes an incision or uses a special needle to remove a sample of tumor tissue. A pathologist examines the tissue under a microscope. If cancer is present, the pathologist can usually determine the type of cancer and its grade. The grade of the tumor is determined by how abnormal the cancer cells appear when examined under a microscope. The grade predicts the probable growth rate of the tumor and its tendency to spread. Low-grade sarcomas, although cancerous, are unlikely to metastasize. High-grade sarcomas are more likely to spread to other parts of the body. The most common site of spread is to the lungs.

Treatment

In general, treatment for soft tissue sarcomas depends on the stage of the cancer. The stage of the sarcoma is based on the size and grade of the tumor, and whether the cancer has spread to the lymph nodes or other parts of the body (metastasized). Treatment options for soft tissue sarcomas include surgery, radiation therapy, and chemotherapy.

Surgery is the most common treatment for soft tissue sarcomas. If possible, the doctor will remove the cancer and a safe margin of the healthy tissue around it. It is important to obtain a margin free of tumor to decrease the likelihood of local recurrence and give the best chance for eradication of the tumor. Depending on the size and location of the sarcoma, it may, rarely, be necessary to remove all or part of an arm or leg.

Radiation therapy may be used either before surgery to shrink tumors or after surgery to kill any cancer cells that may have been left behind. In some cases, it can be used to treat tumours that cannot be surgically removed. In multiple studies, radiation therapy has been found to improve the rate of local control, but has not had any influence on overall survival.

Chemotherapy may be used with radiation therapy either before or after surgery to try to shrink the tumor or kill any remaining cancer cells. The use of chemotherapy to prevent the spread of soft tissue sarcomas has not been proven to be effective. If the cancer has spread to other areas of the body, chemotherapy may be used to shrink tumors and reduce the pain and discomfort they cause, but is unlikely to eradicate the disease.

Squamous Cell Carcinoma

In medicine, squamous cell carcinoma (SCC) is a form of cancer of the carcinoma type that may occur in many different organs, including the skin, lips, mouth, esophagus, urinary bladder, prostate, lungs, vagina, and cervix. It is a malignant tumor of squamous epithelium (epithelium that shows squamous cell differentiation).

Sites

1) Skin:

Squamous cell carcinoma is the second most common cancer of the skin (after basal cell carcinoma but more common than melanoma). It usually occurs in areas exposed to the sun, and can generally be treated by excision only. Sunlight exposure and immunosuppression are risk factors for SCC of the skin. The risk of metastasis is larger than with basal cell carcinoma.

2) Head and Neck Cancer

Most cases of head and neck cancer (cancer of the mouth, nasal cavity, throat and associated structures) are due to squamous cell carcinoma. Symptoms may include a poorly healing mouth ulcer, a hoarse voice or other persistent problems in the area. Treatment is usually with surgery (which may be extensive) and radiotherapy. Risk factors include smoking and alcohol consumption.

3) Esophagus

Esophageal cancer may be due to either squamous cell carcinoma (ESCC) or adenocarcinoma (EAC). SCCs tend to occur closer to the mouth, while adenocarcinomas occur closer to the stomach. Dysphagia (difficulty swallowing, solids worse than liquids) and odynophagia are common initial symptoms. If the disease is localized, esophagectomy may offer the possibility of a cure. If the disease has spread, chemotherapy and radiotherapy are commonly used.

4) Lung

When associated with the lung, it often causes ectopic production of parathyroid hormone-related protein (PTHrP), resulting in hypercalcemia.

5) Prostate

When associated with the prostate, squamous cell carcinoma is very aggressive in nature. It is difficult to detect as there is no increase in prostate specific antigen levels seen; meaning that the cancer is often diagnosed at an advanced stage.

6) Vagina and Cervix

Vaginal squamous cell carcinoma spreads slowly and usually stays near the vagina, but may spread to the lungs and liver. This is the most common type of vaginal cancer.

Treatment

A skin biopsy for microscopic examination may be done to confirm the diagnosis. A variety of different treatment options can be used depending on the location of the tumor, size, microscopic characteristics, health of the patient, and other factors. Most therapies are relatively minor office-based procedures that require only local anesthesia. Surgical excision to remove the entire cancer is the most commonly used treatment. "Mohs" micrographic controlled surgery, a method which requires specialized training by dermatologic surgeons, can be used to remove the tumor while sparing as much normal skin as possible. Other dermatologic surgical procedures include laser surgery, cryosurgery (liquid nitrogen—the frozen method), radiation therapy, and electrodesiccation and curettage which involves alternately scraping and cauterizing (burning) the tumor with low levels of electricity Stomach Cancer Stomach or gastric cancer can develop in any part of the stomach and may spread throughout the stomach and to other organs; particularly the esophagus and the small intestine. Stomach cancer causes nearly one million deaths worldwide per year.

Symptoms

Stomach cancer is often asymptomatic or causes only nonspecific symptoms in its early stages. By the time symptoms occur, the cancer has generally metastasized to other parts of the body, one of the main reasons for its poor prognosis. Stomach cancer can cause the following signs and symptoms:

Early symptoms: Indigestion or a burning sensation (heartburn) and/or Loss of appetite, especially for meat.

Late symptoms: Abdominal pain or discomfort in the upper abdomen, Nausea and vomiting, Diarrhea or constipation, Bloating of the stomach after meals, Weight loss, Weakness and fatigue, Bleeding (vomiting blood or having blood in the stool), which can lead to anemia and/or Dysphagia; this feature suggests a tumor in the cardia or extension of the gastric tumor in to the Oesopagus.

These can be symptoms of other problems such as a stomach virus, gastric ulcer or tropical sprue and diagnosis should be done by a gastroenterologist or an oncologist.

Diagnosis

To find the cause of symptoms, the doctor asks about the patient's medical history, does a physical exam, and may order laboratory studies. The patient may also have one or all of the following exams:

Gastroscopic exam is the diagnostic method of choice. This involves insertion of a fibre optic camera into the stomach to visualize it.

Upper GI series (may be called barium roentgenogram)

Computed tomography or CT scanning of the abdomen may reveal gastric cancer, but is more useful to determine invasion into adjacent tissues, or the presence of spread to local lymph nodes.

Abnormal tissue seen in a gastroscope examination will be biopsied by the surgeon or gastroenterologist. This tissue is then sent to a pathologist for histological examination under a microscope to check for the presence of cancerous cells. A biopsy, with subsequent histological analysis, is the only sure way to confirm the presence of cancer cells.

Various gastroscopic modalities have been developed to increased yield of detection of areas of dysplasia in the stomach. Chromoendoscopy, which involves staining the gastric mucosa with a dye that accentuates the cell structure and can identify areas of dysplasia. Endocytoscopy involves ultra-high magnification to visualize cellular structure to better determine areas of dysplasia. Other gastroscopic modalities such as optical coherence tomography are also being tested investigationally for similar applications.

A number of cutaneous conditions are associated with gastric cancer. A condition of darkened hyperplasia of the skin, frequently of the axilla and groin, known as acanthosis nigricans, is associated with intra-abdominal cancers such as gastric cancer. Other cutaneous manifestations of gastric cancer include tripe palms (a similar darkening hyperplasia of the skin of the palms) and the sign of Leser-Trelat, which is the rapid development of skin lesions known as seborrheic keratoses.

Histopathology

Gastric adenocarcinoma is a malignant epithelial tumor, originating from glandular epithelium of the gastric mucosa. It invades the gastric wall, infiltrating the muscularis mucosae, the submucosa and thence the muscularis propria. Histologically, there are two major types of gastric cancer (Lauren classification): intestinal type and diffuse type.

Intestinal type adenocarcinoma: tumor cells describe irregular tubular structures, harboring pluristratification, multiple lumens, reduced stroma ("back to back" aspect). Often, it associates intestinal metaplasia in neighboring mucosa. Depending on glandular architecture, cellular pleomorphism and mucosecretion, adenocarcinoma may present 3 degrees of differentiation: well, moderate and poorly differentiate. Diffuse type adenocarcinoma (mucinous, colloid): Tumor cells are discohesive and secrete mucus which is delivered in the interstitium producing large pools of mucus/colloid (optically "empty" spaces). It is poorly differentiated. If the mucus remains inside the tumor cell, it pushes the nucleus at the periphery—"signet-ring cell".

Staging

If cancer cells are found in the tissue sample, the next step is to stage, or find out the extent of the disease. Various tests determine whether the cancer has spread and, if so, what parts of the body are affected. Because stomach cancer can spread to the liver, the pancreas, and other organs near the stomach as well as to the lungs, the doctor may order a CT scan, a PET scan, an endoscopic ultrasound exam, or other tests to check these areas. Blood tests for tumor markers, such as carcinoembryonic antigen (CEA) and carbohydrate antigen (CA) may be ordered, as their levels correlate to extent of metastasis, especially to the liver, and the cure rate.

Staging may not be complete until after surgery. The surgeon removes nearby lymph nodes and possibly samples of tissue from other areas in the abdomen for examination by a pathologist.

TNM staging is used.

Treatment

Like any cancer, treatment is adapted to fit each person's individual needs and depends on the size, location, and extent of the tumor, the stage of the disease, and general health. Cancer of the stomach is difficult to cure unless it is found in an early stage (before it has begun to spread). Unfortunately, because early stomach cancer causes few symptoms, the disease is usually advanced when the diagnosis is made. Treatment for stomach cancer may include surgery, chemotherapy, and/or radiation therapy. New treatment approaches such as biological therapy and improved ways of using current methods are being studied in clinical trials.

1) Surgery

Surgery is the most common treatment for stomach cancer. The surgeon removes part or all of the stomach, as well as some of the tissue around the stomach, with the basic goal of removing all cancer and a margin of normal tissue.

Depending on the extent of invasion and the location of the tumor, surgery may also include removal of part of the intestine or pancreas. Tumors in the lower parts of the stomach may call for a Billroth I or Billroth II procedure. Endoscopic mucosal resection is a treatment for early gastric cancer that has been pioneered in Japan, but is available in the United States at some centers. In this procedure, the tumor is removed from the wall of the stomach using an endoscope, with the advantage in that it is a smaller operation than removing the stomach. Surgical interventions are currently curative in less than 40% of cases, and, in cases of metastasis, may only be palliative.

2) Chemotherapy

The use of chemotherapy to treat stomach cancer has no established standard of care. Unfortunately, stomach cancer has not been especially sensitive to these drugs until recently, and historically served to palliatively reduce the size of the tumor and increase survival time. Some drugs used in stomach cancer treatment include: 5-FU (fluorouracil), BCNU (carmustine), methyl-CCNU (Semustine), and doxorubicin (Adriamycin), as well as Mitomycin C, and more recently cisplatin and taxotere in various combinations. The relative benefits of these drugs, alone and in combination, are unclear. Scientists are exploring the benefits of giving chemotherapy before surgery to shrink the tumor, or as adjuvant therapy after surgery to destroy remaining cancer cells. Combination treatment with chemotherapy and radiation therapy is also under study. Doctors are testing a treatment in which anticancer drugs are put directly into the abdomen (intraperitoneal hyperthermic chemoperfusion). Chemotherapy also is being studied as a treatment for cancer that has spread, and as a way to relieve symptoms of the disease. The side effects of chemotherapy depend mainly on the drugs the patient receives.

3) Radiation Therapy

Radiation therapy (also called radiotherapy) is the use of high-energy rays to damage cancer cells and stop them from growing. When used, it is generally in combination with surgery and chemotherapy, or used only with chemotherapy in cases where the individual is unable to undergo surgery. Radiation therapy may be used to relieve pain or blockage by shrinking the tumor for palliation of incurable disease.

4) Multimodality Therapy

While previous studies of multimodality therapy (combinations of surgery, chemotherapy and radiation therapy) gave mixed results, the Intergroup 0116 (SWOG 9008) study showed a survival benefit to the combination of chemotherapy and radiation therapy in patients with non-metastatic, completely resected gastric cancer. Patients were randomized after surgery to the standard group of observation alone, or the study arm of combination chemotherapy and radiation therapy. Those in the study arm receiving chemotherapy and radiation therapy survived on average 36 months, compared to 27 months with observation.

Synovial Sarcoma

A synovial sarcoma is a rare form of cancer which usually occurs near to the joints of the arm or leg. It is one of the soft tissue sarcomas.

Histopathology

Two cell types can be seen microscopically in synovial sarcoma. One fibrous type, known as a spindle or sarcomatous cell, is relatively small and uniform and found in sheets. The other is epithelial in appearance. Classical synovial sarcoma has a biphasic appearance with both types present. Synovial sarcoma can also appear to be poorly differentiated or to be monophasic fibrous, consisting only of sheets of spindle cells. Some authorities state that, extremely rarely, there can be a monophasic epithelial form which causes difficulty in differential diagnosis.

Like other soft tissue sarcomas, there is no universal grading system for reporting histopathology results. In Europe, the Trojani or French system is gaining in popularity while the NCI grading system is more common in the United States. The Trojani system scores the sample, depending on tumour differentiation, mitotic index, and tumour necrosis, between 0 and 6 and then converts this into a grade of between 1 and 3, with 1 representing a less aggressive tumour. The NCI system is also a three grade one but takes account of a number of other factors.

Molecular Biology

Most, and perhaps all, cases of synovial sarcoma are associated with a reciprocal translocation t(x;18)(p11.2; q11.2). There is some debate about whether the molecular observation itself is definitional of synovial sarcoma.

The diagnosis of synovial sarcoma is typically made based on histology and is confirmed by the presence of t(X;18). This translocation event between the SYT gene on chromosome 18 and one of 3 SSX genes (SSX1, SSX2 and SSX4) on chromosome X causes the presence of a SYT-SSX fusion gene. The resulting fusion protein brings together the transcriptional activating domain of SYT and the transcriptional repressor domains of SSX. SYT-SSX is thought to underlie synovial sarcoma pathogenesis through dysregulation of gene expression.

There is some association between the SYT-SSX1 or SYT-SSX2 fusion type and both tumour morphology and five-year survival.

Symptoms

Synovial sarcoma usually presents with an otherwise asymptomatic swelling or mass, although general symptoms related to malignancies can be reported such as fatigue.

Treatment

Treatment Usually Involves:

Surgery, to remove the tumor and a safety margin of healthy tissue. This is the mainstay of synovial sarcoma treatment and is curative in approximately 20-70% of patients, depending on the particular study being quoted.

Conventional chemotherapy, (for example, Doxorubicin hydrochloride and Ifosfamide), to reduce the number of remaining microscopic cancer cells. The benefit of chemotherapy in synovial sarcoma to overall survival remains unclear, although a recent study has shown that survival of patients with advanced, poorly differentiated disease marginally improves with doxorubicin/ifosfamide treatment.

Radiotherapy to reduce the chance of local recurrence. The benefit of radiotherapy in this disease is less clear than for chemotherapy.

Teratoma

A teratoma is a type of neoplasm. The word teratoma comes from Greek and means roughly "monstrous tumor". Definitive diagnosis of a teratoma is based on its histology: a teratoma is a tumor with tissue or organ components resembling normal derivatives of all three germ layers. Rarely, not all three germ layers are identifiable. The tissues of a teratoma, although normal in themselves, may be quite different from surrounding tissues, and may be highly inappropriate, even grotesque (hence the monstrous): teratomas have been reported to contain hair, teeth, bone and very rarely more complex organs such as eyeball, torso, and hand. Usually, however, a teratoma will contain no organs but rather one or more tissues normally found in organs such as the brain, thyroid, liver, and lung.

Teratomas are thought to be present at birth, but often they are not diagnosed until much later in life.

Location and Incidence

Teratomas derived from germ cells occur in the testes in males and ovaries in females. Teratomas derived from embryonal cells usually occur on the body midline: in the brain, elsewhere inside the skull, in the nose, in the tongue, under the tongue, and in the neck (cervical teratoma), mediastinum, retroperitoneum, and attached to the coccyx. However, teratomas may also occur elsewhere: very rarely in solid organs (most notably the heart and liver) and hollow organs (such as the stomach and bladder), and more commonly on the skull sutures. Embryonal teratomas most commonly occur in the sacrococcygeal region: sacrococcygeal teratoma is the single most common tumor found in newborn babies.

Of teratomas on the skull sutures, approximately 50% are found in or adjacent to the orbit. Limbal dermoid is a choristoma, not a teratoma.

Teratoma qualifies as a rare disease, but is not extremely rare. Sacrococcygeal teratoma alone is diagnosed at birth in 1 out of 40,000 babies. Given the current world population birth rate, this equals 5 per day or 1800 per year. Add to that number sacrococcygeal teratomas diagnosed later in life, and teratomas in other locations, and the incidence approaches 10,000 new diagnoses of teratoma per year.

Teratoma also occurs, rarely, in non-human animals.

Pathology Classification of Individual Teratomas

Regardless of location in the body, a teratoma is classified according to a cancer staging system. This indicates whether chemotherapy or radiation therapy may be needed in addition to surgery. Teratomas commonly are classified using the Gonzalez-Crussi grading system: 0 or mature (benign); 1 or immature, probably benign; 2 or immature, possibly malignant (cancerous); and 3 or frankly malignant. If frankly malignant, the tumor is a cancer for which additional cancer staging applies. Teratomas are also classified by their content: a solid teratoma contains only tissues (perhaps including more complex structures); a cystic teratoma contain only pockets of fluid or semi-fluid such as cerebrospinal fluid, sebum, or fat; a mixed teratoma contains both solid and cystic parts. Cystic teratomas usually are grade 0 and, conversely, grade 0 teratomas usually are cystic.

Grade 0, 1 and 2 pure teratomas have the potential to become malignant (grade 3), and malignant pure teratomas have the potential to metastasize. These rare forms of teratoma with malignant transformation may contain elements of somatic (non germ cell) malignancy such as leukemia, carcinoma or sarcoma. A teratoma may contain elements of other germ cell tumors, in which case it is not a pure teratoma but rather is a mixed germ cell tumor and is malignant. In infants and young children, these elements usually are endodermal sinus tumor, followed by choriocarcinoma. Finally, a teratoma can be pure and not malignant yet highly aggressive: this is exemplified by growing teratoma syndrome, in which chemotherapy eliminates the malignant elements of a mixed tumor, leaving pure teratoma which paradoxically begins to grow very rapidly.

"Benign" teratoma may prove to be malignant:

A "benign" grade 0 (mature) teratoma nonetheless has a risk of malignancy.

Recurrence with malignant endodermal sinus tumor has been reported in cases of formerly benign mature teratoma, even in fetiform teratoma and fetus in fetu. Squamous cell carcinoma has been found in a mature cystic teratoma at the time of initial surgery.

A grade 1 immature teratoma that appears to be benign (e.g., because AFP is not elevated) has a much higher risk of malignancy, and requires adequate follow-up. This grade of teratoma also may be difficult to diagnose correctly. It can be confused with other small round cell neoplasms such as neuroblastoma, small cell carcinoma of hypercalcemic type, primitive neuroectodermal tumor, Wilm's tumor, desmoplastic small round cell tumor, and non-Hodgkin lymphoma.

Teratoma with Malignant Transformation:

A teratoma with malignant transformation or TMT is a very rare form of teratoma that may contain elements of somatic (non germ cell) malignant tumors such as leukemia, carcinoma or sarcoma. Of 641 children with pure teratoma, 9 developed TMT: 5 carcinoma, 2 glioma, and 2 embryonal carcinoma (here, these last are classified among germ cell tumors).

Extraspinal Ependymoma:

Extraspinal ependymoma, usually considered to be a glioma (a type of non-germ cell tumor), may be an unusual form of mature teratoma.

Initial Diagnosis

Teratomas are thought to be present since birth, or even before birth, and therefore can be considered congenital tumors. However, many teratomas are not diagnosed until much later in childhood or in adulthood. Large tumors are more likely to be diagnosed early on. Sacrococcygeal and cervical teratomas are often detected by prenatal ultrasound. Additional diagnostic methods may include prenatal MRI. In rare circumstances, the tumor is so large that the fetus may be damaged or dies. In the case of large sacrococcygeal teratomas, a significant portion of the fetus' blood flow is redirected toward the teratoma (a phenomenon called steal syndrome), causing heart failure, or hydrops, of the fetus. In certain cases, fetal surgery may be indicated. Beyond the newborn period, symptoms of a teratoma depend on its location and organ of origin. Ovarian teratomas often present with abdominal or pelvic pain, caused by torsion of the ovary or irritation of its ligaments. Testicular teratomas present as a palpable mass in the testis; mediastinal teratomas often cause compression of the lungs or the airways and may present with chest pain and/or respiratory symptoms. Some teratomas contain yolk sac elements, which secrete alpha-fetoprotein (AFP). Detection of AFP may help to confirm the diagnosis and is often used as a marker for recurrence or treatment efficacy, but is rarely the method of initial diagnosis. (Maternal serum alpha-fetoprotein, or MSAFP, is a useful screening test for other fetal conditions, including Down syndrome, spina bifida and abdominal wall defects such as gastroschisis).

Treatment

1) Surgery

The treatment of choice is complete surgical removal (i.e., complete resection). Teratomas normally are well encapsulated and non-invasive of surrounding tissues, hence they are relatively easy to resect from surrounding tissues. Exceptions include teratomas in the brain, and very large, complex teratomas that have pushed into and become interlaced with adjacent muscles and other structures.

Prevention of recurrence does not require en bloc resection of surrounding tissues.

2) Chemotherapy

For malignant teratomas, usually, surgery is followed by chemotherapy.

Teratomas that are in surgically inaccessible locations, or are very complex, or are likely to be malignant (due to late discovery and/or treatment) sometimes are treated first with chemotherapy.

Testicular Cancer

Testicular cancer is cancer that develops in the testicles, a part of the male reproductive system.

In the United States, between 7,500 and 8,000 diagnoses of testicular cancer are made each year. Over his lifetime, a man's risk of testicular cancer is roughly 1 in 250 (four tenths of one percent, or 0.4%). It is most common among males aged 15-35 years, particularly those in their mid-twenties. Testicular cancer has one of the highest cure rates of all cancers: in excess of 90%; essentially 100% if it has not metastasized. Even for the relatively few cases in which malignant cancer has spread widely, chemotherapy offers a cure rate of at least 85% today. Not all lumps on the testicles are tumors, and not all tumors are malignant; there are many other conditions such as Epididymal cysts, Hydatid of Morgagni, and so on which may be painful but are non-cancerous. All unusual lumps or pain in the testicles should be checked by a physician.

Signs and Symptoms

Because testicular cancer is curable (stage I can have a success rate of >95%) when detected early, experts recommend regular monthly testicular self-examination after a hot shower or bath, when the scrotum is looser. Men should examine each testicle, feeling for pea-shaped lumps.

Symptoms may include one or more of the following:
a lump in one testis or a hardening of one of the testicles
The testicle should normally feel smooth to the touch. Ridges may be felt because of enlarged blood vessels or tumor growth. Additionally the entire testicle may feel hard and bumpy to the touch.
Abnormal sensitivity (either numbness or pain)
loss of sexual activity
sexual withdrawal
build-up of fluid in the scrotum
a dull ache in the lower abdomen or groin
an increase, or significant decrease, in the size of one testis
blood in semen
General weak and tired feeling
The testicle with a tumor may be severely enlarged, as much as 3 times the original size. Simultaneously the other testicle may be shrunken in size, due to the tumor taking up the majority of the blood supply to the scrotum.

The nature of any palpated lump in the scrotum is evaluated by scrotal ultrasound, which can determine exact location, size, and some characteristics of the lump, such as cystic vs solid, uniform vs heterogeneous, sharply circumscribed or poorly defined. The extent of the disease is evaluated by CT scans, which are used to locate metastases. Blood tests are also used to identify and measure tumor markers that are specific to testicular cancer. AFP alpha1 feto protein, Beta-HCG, and LDH are the typical markers used to identify testicular cancer. The diagnosis is made by performing an orchiectomy, surgical excision of the entire testis along with attached structures epididymis and spermatic cord; the resected specimen is evaluated by a pathologist. A biopsy should not be performed, as it raises the risk of migrating cancer cells into the scrotum. The reason why inguinal orchiectomy is the preferred method is that the lymphatic system of the scrotum links to the lower extremities and that of the testicle links to the retroperitoneum. A transscrotal biopsy or orchiectomy will potentially leave cancer cells in the scrotum and create two vectors for cancer spread, while in an inguinal orchiectomy only the retroperitoneal route exists.

Diagnosis

The cardinal diagnostic finding in the patient with testis cancer is a mass in the substance of the testis. Unilateral enlargement of the testis with or without pain in the adolescent or young adult male should raise concern for testis cancer.

An incorrect diagnosis is made at the initial examination in up to 25% of patients with testicular tumors and may result in delay in treatment or a suboptimal approach (scrotal incision) for exploration.
Epididymitis or epididymoorchitis
Hematocele
Varicocele The differential diagnosis of testicular cancer requires examining the histology of tissue obtained from an orchiectomy specimen. Orchiectomy, rather than transcrotal biopsy, is preferred to reduce the risk of spill and thus the risk of metastasis, in the event that the tumor is malignant. For orchiectomy, an inguinal surgical approach is preferred.

Classification

Although testicular cancer can be derived from any cell type found in the testicles, more than 95% of testicular cancers are germ cell tumors. Most of the remaining 5% derive from Leydig cells or Sertoli cells. Thus, the focus of diagnosis is on determining which germ cell tumor is present. Correct diagnosis is necessary to ensure the most effective and least harmful treatment. To some extent, this can be done via blood tests for tumor markers, but differential diagnosis requires examination of the histology of a specimen by a pathologist.

Staging

After removal, a testicular tumor is staged by a pathologist according to the TNM Classification of Malignant Tumors as published in the AJCC Cancer Staging Manual. Testicular cancer is categorized as being in one of three stages (which have subclassifications). The size of the tumor in the testis is irrelevant to staging. In broad terms, testicular cancer is staged as follows:

Stage I: the cancer remains localized to the testis.
Stage II: the cancer involves the testis and metastasis to retroperitoneal and/or Paraaortic lymph nodes (lymph nodes below the diaphragm).
Stage III: the cancer involves the testis and metastasis beyond the retroperitoneal and Paraaortic lymph nodes. Stage III is further subdivided into nonbulky stage III and bulky stage III.

Histology

After removal, a testicular tumor is classified by a pathologist according to its histology.
1) Germ Cell Tumors of the Testis, by Frequency
   It contained the following materials
      40% mixed (usually teratoma plus another)
      35% seminoma (germinoma of the testis)
      20% embryonal carcinoma
      5% teratoma (pure)
      <1% choriocarcinoma
      Gonadoblastoma
   Also: Intratubular germ cell neoplasms (the in-situ stage of germ cell tumors)
2) Non-Germ Cell Tumors of the Testis
   Sertoli-Leydig cell tumor (usually benign)
3) Secondary Tumors of the Testis
   Lymphoma
   Leukemic infiltration of the testis
   Metastatic tumors Treatment The three basic types of treatment are surgery, radiation therapy, and chemotherapy. Surgery is performed by urologists; radiation therapy is administered by radiation oncologists; and chemotherapy is the work of medical oncologists.

In most patients with testicular cancer, the disease is cured readily with minimal long-term morbidity.
1) Surgery
2) Orchiectomy While it may be possible, in some cases, to remove testicular cancer tumors from a testis while leaving the testis functional, this is almost never done, as more than 95% of testicular tumors are malignant. Since only one testis is typically required to maintain fertility, hormone production, and other male functions, the afflicted testis is almost always removed completely in a procedure called inguinal orchiectomy. (The testicle is almost never removed through the scrotum; an incision is made beneath the belt line in the inguinal area.) Most notably, since removing the tumor alone does not eliminate the precancerous cells that exist in the testis, it is usually better in the long run to remove the entire testis to prevent another tumor. A plausible exception could be in the case of the second testis later developing cancer as well.

3) Retroperitoneal Lymph Node Dissection (RPLND)

In the case of nonseminomas that appear to be stage I, surgery may be done on the retroperitoneal/Paraaortic lymph nodes (in a separate operation) to accurately determine whether the cancer is in stage I or stage II and to reduce the risk that malignant testicular cancer cells that may have metastasized to lymph nodes in the lower abdomen. This surgery is called Retroperitoneal Lymph Node Dissection (RPLND). However, this approach, while standard in many places, especially the United States, is falling out of favor due to costs and the high level of expertise required to perform the surgery. The urologist may take extra care in the case of males who have not fathered children, to preserve the nerves involved in ejaculation.

Many patients are instead choosing surveillance, where no further surgery is performed unless tests indicate that the cancer has returned. This approach maintains a high cure rate because of the growing accuracy of surveillance techniques.

Lymph node surgery may also be performed after chemotherapy to remove masses left behind, particularly in the cases of advanced initial cancer or large nonseminomas.

4) Radiation Therapy

Radiation may be used to treat stage II seminoma cancers, or as adjuvant (preventative) therapy in the case of stage I seminomas, to minimize the likelihood that tiny, non-detectable tumors exist and will spread (in the inguinal and para-aortic lymph nodes). Radiation is never used as a primary therapy for nonseminoma because a much higher dose is required and chemotherapy is far more effective in that setting.

5) Chemotherapy

As an adjuvant treatment, use of chemotherapy as an alternative to radiation therapy is increasing, because radiation therapy appears to have more significant long-term side effects (for example, internal scarring, increased risks of secondary malignancies, etc.). Two doses, or occasionally a single dose of carboplatin, typically delivered three weeks apart, is proving to be a successful adjuvant treatment, with recurrence rates in the same ranges as those of radiotherapy.

Chemotherapy is the standard treatment for non-seminoma when the cancer has spread to other parts of the body (that is, stage II or III). The standard chemotherapy protocol is three, or sometimes four, rounds of Bleomycin-Etoposide-Cisplatin (BEP). This treatment was developed by Dr. Lawrence Einhorn at Indiana University. An alternative, equally effective treatment involves the use of four cycles of Etoposide-Cisplatin (EP).

While treatment success depends on the stage, the average survival rate after five years is around 95%, and stage I cancers cases (if monitored properly) have essentially a 100% survival rate (which is why prompt action, when testicular cancer is a possibility, is extremely important).

Actions after Treatment

1) Surveillance

For stage I cancers that have not had any adjuvant (preventive) therapy, close monitoring for at least a year is important, and should include blood tests (in cases of nonseminomas) and CT-scans (in all cases), to ascertain whether the cancer has metastasized (spread to other parts of the body). For other stages, and for those cases in which radiation therapy or chemotherapy was administered, the extent of monitoring (tests) will vary on the basis of the circumstances, but normally should be done for five years (with decreasing intensity). For the first year blood tests for tumor markers should be done monthly, and decreasing to once every three months in the years after. CT scans should be performed once every three months in the first year and decreasing to once every six months thereafter. The high cost of CT scans and the relative danger of the radiation involved both being factors in the relative infrequence with which tests are performed.

2) Fertility

A man with one remaining testis can lead a normal life, because the remaining testis takes up the burden of testosterone production and will generally have adequate fertility. However, it is worth the (minor) expense of measuring hormone levels before removal of a testicle, and sperm banking may be appropriate for younger men who still plan to have children, since fertility may be lessened by removal of one testicle, and can be severely affected if extensive chemotherapy and/or radiotherapy is done. Less than five percent of those who have testicular cancer will have it again in the remaining testis. A man who loses both testicles will normally have to take hormone supplements (in particular, testosterone, which is created in the testicles), and will be infertile, but can lead an otherwise normal life.

Thyroid Carcinoma

Thyroid cancer refers to any of four kinds of malignant tumors of the thyroid gland: papillary, follicular, medullary or anaplastic. Papillary and follicular tumors are the most common. They grow slowly and may recur, but are generally not fatal in patients under 45 years of age. Medullary tumors have a good prognosis if restricted to the thyroid gland and a poorer prognosis if metastasis occurs. Anaplastic tumors are fast-growing and respond poorly to therapy.

Thyroid nodules are diagnosed by ultrasound guided fine needle aspiration (USG/FNA) or frequently by thyroidectomy (surgical removal and subsequent histological examination). As thyroid cancer can take up iodine, radioactive iodine is commonly used to treat thyroid carcinomas, followed by TSH suppression by thyroxine therapy.

Symptoms

Most often the first symptom of thyroid cancer is a nodule in the thyroid region of the neck. However, many adults have small nodules in their thyroids. But typically under 5% of these nodules are found to be malignant. Sometimes the first sign is an enlarged lymph node. Later symptoms that can be present are pain in the anterior region of the neck and changes in voice.

Thyroid cancer is usually found in a euthyroid patient, but hyperthyroidism may be a symptom of a large or metastatic well-differentiated tumor.

Nodules should be of particular concern when they are found in children or those under the age of 20. The presentation of benign nodules at this age is less likely, and thus the potential for malignancy is far greater.

Diagnosis

After a nodule is found during a physical examination, a referral to an endocrinologist, or a thyroidologist is the best approach. Most commonly an ultrasound is performed to confirm the presence of a nodule, and assess the status of the whole gland. Measurement of thyroid stimulating hormone and anti-thyroid antibodies will help decide if there is a functional thyroid disease such as Hashimoto's thyroiditis present, a known cause of a benign nodular goiter.

1) Fine Needle Biopsy

One approach used to determine whether the nodule is malignant is the fine needle biopsy (FNB), which some have described as the most cost-effective, sensitive and accurate test. FNB or ultrasound-guided FNA usually yields sufficient thyroid cells to assess the risk of malignancy, although in some cases, the suspected nodule may need to be removed surgically for pathological examination.

Rarely, a biopsy is done using a large cutting needle, so that the a piece of nodule capsule can be obtained.

2) Blood Tests

Blood or imaging tests may be done prior to or in lieu of a biopsy. The possibility of a nodule which secretes thyroid hormone (which is less likely to be cancer) or hypothyroidism is investigated by measuring thyroid stimulating hormone (TSH), and the thyroid hormones thyroxine (T4) and triiodothyronine (T3).

Tests for serum thyroid autoantibodies are sometimes done as these may indicate autoimmune thyroid disease (which can mimic nodular disease).

3) Imaging

The blood assays may be accompanied by ultrasound imaging of the nodule to determine the position, size and texture, and to assess whether the nodule may be cystic (fluid filled). Also suspicious findings in a nodule are hypoechoic, irregular borders, microcalcifications, or very high levels of blood flow within the nodule. Less suspicious findings in benign nodules include, hyperechoic, comet tail artifacts from colloid, no blood flow in the nodule and a halo, or smooth border.

Some clinicians will also request technetium (Tc) or radioactive iodine (I) imaging of the thyroid. An $^{123}$I scan showing a hot nodule, accompanied by a lower than normal TSH, is strong evidence that the nodule is not cancerous.

Classification

Thyroid cancers can be classified according to their pathological characteristics. The following variants can be distinguished (distribution over various subtypes may show regional variation):

Papillary thyroid cancer
Follicular thyroid cancer
Medullary thyroid cancer (up to 8%) Anaplastic thyroid cancer
Others
Lymphoma
Squamous cell carcinoma, sarcoma The follicular and papillary types together can be classified as "differentiated thyroid cancer". These types have a more favorable prognosis than the medullary and undifferentiated types.

Tongue Cancer

The most common type of cancer of the tongue is called Squamous Cell Carcinoma. There are other types of cancers of the tongue but they are statistically uncommon.

Squamous Cell Cancer of the Oral Tongue.

This tumor is usually located on the side, or what we call the lateral border, of the oral tongue. It is usually somewhat ulcerated and is grayish-pink to red in color. It will often bleed easily if bitten or touched. It is generally seen in the older age groups though we have had one 21 year old woman present with a small cancer, and just recently a 32 old lady from the Austin area come to us from the Internet for treatment of a significant squamous cell cancer of the tongue. Smoking and drinking are known to contribute to the formation of the cancers, although some folks have developed squamous cancer of the tongue with no known extra risk factors.

Most very small cancers of the oral tongue can be quickly and successfully treated by surgical removal leaving behind little cosmetic or functional change. Larger cancers may indeed have some effect on speech and on swallowing, but one must remember that not treating this problem would cause far more significant problems, up to, and including death. If one thinks about that for a moment; a few changes in speech or swallowing seem like a pretty good swap. There is a school of thought that small oral tongue cancers can be better managed by radiation therapy alone, and this is indeed true in some cases, especially where the patient has serious heart and/or lung disease that might make anesthesia risky. Fortunately, this is a rare occurrence.

The main reason for treating small squamous cancer of the oral tongue with surgery is that it is at least as curative as radiation, possibly better, it is over with quickly, oftentimes done as an out patient procedure instead of 5-6 weeks of daily therapy, it may be significantly less expensive, and finally, and most importantly, it means that if a patient were to later present with a 2nd or 3rd Squamous Cell Cancer of the mouth/throat/or voice box area, you would still have radiation therapy as a treatment option, perhaps then being able to avoid a significant and disfiguring operation. There is a limit as to how much radiation normal tissue can take before it dies.

Some cases of Oral Tongue Cancer can be treated with just removal of the primary tumor in the tongue. But as the size of the primary tumor increases the statistical possibility of some cancer cells spreading through lymphatic vessels to the lymph nodes of the neck increases. The site and pattern of the involved lymph nodes is pretty much constant—that is to say we know where in the neck to look for enlarged lymph nodes that might contain metastatic cancer cells from the oral tongue cancer. Exceptions to these rules are sometimes seen, but they are uncommon. When the presence of enlarged lymph nodes in the neck is detected or when the index of suspicion is high that there may be cancer cells present in lymph nodes, then an operation called a neck dissection is performed to remove these "secondary" deposits of cancer. Remember, the oral tongue cancer is the "primary" tumor from where the spreading cells originate.

There are many forms of neck dissections from radical to conservative and I can not really go into the differences and unique characteristics of each one. Suffice to say that this is an area of medical judgement and decision making that relies heavily on the experience of the surgeon. While many physicians may have had some exposure to neck dissections at some point in their career, there are very few Head and Neck Surgeons, usually found in large medical centers, who can truly say that their career has been dedicated to this type of disease and they have done hundreds or perhaps thousands of these procedures. At The Head and Neck Surgery Clinic of Houston, we will have been doing Head and Neck cancer surgery and neck dissections for half a century come 1999.

Finally, there may sometimes be the need to perform plastic surgery and/or reconstruction following removal of the tumor, and radiation treatments may have to be given after the surgery to try to minimize the possibility of recurrence of the disease and ultimate treatment failure. Yes, sometimes in spite of every effort, every bit of hard work, in spite of supportive care and even our prayers, some patients will be lost to this disease. It is a sad thing to have to watch and be a part of, but it is one of life's unpleasant realities. For now, we will have to content ourselves with the knowledge that most of our tongue cancer patients survive quite nicely and hope that new research and new discoveries in the future will allow us to help our patients even more.

Squamous Cell Cancer of the Base of Tongue

Like the oral tongue, the base of tongue (or posterior ⅓) can also grow several types of cancers, but again, squamous cell carcinoma is the most common and we will direct our comments with that in mind. Unlike oral tongue cancers, base of tongue squamous cell cancer is usually larger when diagnosed because in the early stages it can not be seen and it creates few, if any, symptoms. Later however, base of tongue cancer may create pain, a sense of fullness, changes in what the voice sounds like, and perhaps even some difficulty in swallowing. Also, because the diagnosis often comes a bit later, a greater number of patients with this disease will already have neck metastasis, that is, cancer cells in the lymph nodes of the neck, by the time they are seen by the Head and Neck Surgeon. While it may technically feasible to surgically remove some base of tongue cancers, it is our opinion that most can and should be treated by radiotherapy. These tumors are arguably more sensitive to radiation treatment than some other cancers. Certainly, there are exceptions to this. Radiation therapy can also be used to control the cancer in the neck nodes as long as it is not too advanced. Interestingly, in those cases, we will sometimes remove massive neck node disease before starting radiation therapy when we know that x-ray therapy alone would not be successful in controlling the neck disease. The prognosis after treatment of base of tongue cancer will vary from patient to patient as with any type of malignant disease. It has been our experience that the cure rate is good, but not quite as good as for early detected oral tongue cancer. The fact that base of tongue cancers are usually larger at the time of diagnosis probably is a significant contributing factor to this disparity. Very large base of tongue cancer may require a combination of surgery and radiation.

Tonsillar Cancer

Cancer of the tonsils occurs predominantly in men. It is strongly linked to smoking and alcohol consumption. This cancer often spreads to the lymph nodes in the neck. Cancer of the tonsils occurs most often in people between the ages of 50 and 70. A sore throat is often the first symptom. Pain usually radiates to the ear on the same side as the affected tonsil. Sometimes, however, a lump in the neck resulting from the cancer's spread to a lymph node (metastasis) may be noticed before any other symptoms. A doctor diagnoses the cancer by performing a biopsy of the tonsil, in which a sample of tissue is removed for examination under a microscope. Evaluation usually includes laryngoscopy (examination of the larynx), bronchoscopy (examination of the lungs), and esophagoscopy (examination of the esophagus). These areas are evaluated because of the high risk of additional cancers being present (up to 10%). Treatment typically includes radiation therapy and surgery. Certain types of chemotherapy are effective as well, when combined with radiation therapy. Surgery may involve removal of the tumor, lymph nodes in the neck, and part of the jaw. There have been notable advances in the reconstruction used after surgery to remove the cancer, resulting in significant improvements in function and appearance. About 50% of the people survive for at least 5 years after diagnosis, although the exact number depends on the stage of the cancer at the time of treatment.

Urethral Cancer

Urethral cancer is an extremely rare lesion, with only approximately 600 reported cases. Urethral cancer comprises less than 1% of the total incidence of malignancies. Because many medical centers see only a few cases over many years, not enough data are available from large series to dictate the best-accepted treatment.

As with most tumors, early detection affords the best chance of cure. Once invasive cancer is detected, radical surgery is indicated, although the prognosis usually is poor.

Pathophysiology

Chronic inflammation, infection, or irritation of the urethra usually precedes the development of urethral cancer. Rapid turnover of the urethral mucosal cells predisposes to the development of dysplasia and neoplasia. Inflammation, infection, and irritation may impede the natural DNA repair mechanisms of the urethral mucosal cells. The tumor develops and invades deeply in order to metastasize to adjacent structures. The tumor thus becomes elusive to definitive therapies such as surgery and radiation.

Clinical

The signs and symptoms of urethral cancer vary and are neither diagnostic nor pathognomonic. Generally, the onset is insidious, and symptoms usually are more attributable to benign stricture disease (ie, bladder outlet obstruction, overflow incontinence), rather than malignancy (ie, perineal pain, hematuria). In fact, in both sexes, the cancer may be completely asymptomatic.

The interval between the onset of symptoms and diagnosis may be as long as 3 years because of misdiagnoses and failure by the patient to seek medical consultation. Remember that these tumors have a propensity to be highly advanced locally at the time of diagnosis. A raised index of suspicion is advisable if an elderly man presents with stricture disease, particularly if symptoms are present that are more consistent with malignancy or local extension (ie, urethral fistulae, necrosis and abscess formation).

Early evaluation should include cytologic analysis, imaging, and endoscopic management with biopsy of the strictured area, particularly if it appears abnormal (ie, irregular borders, erythema, macular or papular appearance, surface ulceration and tissue sloughing). This is in contrast to benign urethral stricture disease (USD), which generally appears as smooth gray-white areas of spongiofibrosis.

Symptoms

- Diminished stream, straining to void, and other obstructive voiding symptoms (Although these often are the symptoms of benign stricture disease, a neoplasm may be concealed by the presentation of a routine stricture. Keep a high index of suspicion in patients with a history of USD, and keep a vigilant eye over the proceeding cytological analysis, radiographic imaging, and cystoscopy.)
- Frequency, nocturia, itching, dysuria, and other irritative voiding symptoms (These are reported notoriously in association with carcinoma in situ.)
- Incontinence (Generally, this is overflow incontinence from bladder outlet obstruction due to USD. However, severe urgency may progress to urge incontinence and distortion of the urethral anatomy in females and may lead to stress urinary incontinence.)

Urinary retention from progressive USD
Hematuria, urethral or vaginal spotting
May produce no symptoms except a hard nodular area in the perineum, labia, or along the course of the penis
Purulent, foul-smelling, or watery discharge
Hematospermia
Perineal, suprapubic, or urethral pain
Dyspareunia
Swelling
Tenesmus
Signs and physical examination findings
Urethral-cutaneous fistula
Urethral-vaginal fistula
Urethral diverticula
Periurethral abscess or areas of tissue necrosis
Recurrent urinary tract infection
Penile or vaginal lesions
Lymphadenopathy
Palpable mass along the course of the urethra Diagnosis 1) Lab Studies Useful serologic studies include basic chemistry and liver function tests, particularly alkaline phosphatase, that may reveal bone metastases. Other useful laboratory studies include complete blood count, urinalysis, and urine cytology. Unfortunately, none of these is a good diagnostic study, and all have a poor sensitivity. Recently, Dalbagni et al have proven that urine cytology, particularly, had a poor sensitivity in diagnosing urethral carcinoma. For proper and timely diagnosis, one must have a keen index of suspicion and access to a cystoscope.

Perform urine culture to rule out infection. Any and all local wound infections or drainages should be assessed via culture and cytology examination because local invasion of urethral cancer can create sinus tracts, fistulae, and abscesses.

2) Imaging Studies

Chest radiograph and CT scan of the abdomen, pelvis, and perineum are modalities used in staging urethral cancer.

Intravenous urography (IVU) primarily is useful in evaluating hematuria if this is the presenting symptom and the diagnosis has not yet been confirmed. However, if urethral cancer is strongly suspected, performing a CT scan would be preferable because it would help evaluate both the upper tracts regarding the hematuria and the adjacent pelvic structures for the extent of possible tumor invasion.

Magnetic resonance imaging (MRI) has evolved into a superior imaging modality for the evaluation of urologic malignancies. Despite its expensive cost, MRI has several advantages over other techniques, as follows:

Iodinated contrast is not needed. Blood flow into vascular spaces often can be visualized without enhancement, and, when contrast is required to detect enhancing lesions, gadolinium-diethylenetriamine pentaacetic acid has been used as an intravascular agent. Reactions to this agent are rare, and renal function is not as significant a factor as it is for iodinated contrast, which is used for IVU and CT scan.

MRI offers multiplanar imaging using 3 orthogonal planes, thus providing more anatomic detail, which is particularly helpful when imaging the pelvis.

This wide-field imaging and the use of special suprapubic and transrectal phased array coils make local staging more accurate.

Tissue contrast is superb with spin-echo T1-weighted and T2-weighted images.

The nodes can be evaluated simultaneously, and differentiation between nodes and vessels is easier with MRI compared to CT scan.

Hricak used MRI for diagnostic evaluation of the female urethra in a series of patients and found that primary or metastatic urethral neoplasms were detected in every patient who was clinically found to have disease. Furthermore, this study noted that local staging of primary or metastatic disease with MRI was correct in 8 of 11 patients (72%).

MRI is being used increasingly in determining the extent of local invasiveness of urethral neoplasms for accurate staging and preoperative planning.

MRI is not without its drawbacks, as follows:

In addition to its cost, it is a sophisticated imaging technique and requires specialized personal to provide the right imaging and to read it effectively.

As with other imaging modalities, it is unable to detect micrometastases and cannot definitively determine prognosis.

Despite these drawbacks, MRI is being used increasingly for the staging of urethral cancer and has shown to be promising.

Retrograde urethrography and voiding cystourethrography may be helpful for diagnosis in conjunction with cystoscopy. An irregularly shaped urethra raises the index of suspicion. Remember that the association between urethral strictures and urethral cancer is highly significant.

Bone scintigraphy (bone scans) may be useful in confirming suspected bone metastases with advanced local disease or elevated alkaline phosphatase levels.

Positron emission tomography (PET) has an increasing role in the management of urologic malignancies, most specifically, prostate, kidney, and testicular cancer. As with these other malignancies, PET scanning is most valuable in the evaluation for suspected metastases to distant sites after local treatment. It is also useful in evaluating treatment for systemic disease with chemotherapy. In fact, with its ability to quantify metabolic reactions in tissue noninvasively, thus enabling physicians to observe the direct moment-to-moment biochemical effect of a drug at the tissue level, PET may prove useful in the design and testing of new drugs for clinical trials. In theory, the ultimate response to chemotherapy could be predicted soon after initiation by measuring the percent decrease in tumor metabolism with PET.

3) Other Tests

Flexible cystoscopy is a minimally invasive office procedure that has proven to be an excellent diagnostic tool for urethral lesions. One can evaluate the extent of urethral involvement of strictures or tumors in preparation for tissue diagnosis. Biopsies probably are best reserved for the operating room, where anesthesia is available.

Be wary of any papillary mass, macular or papular areas, or mucosal ulceration at the time of cystoscopy. Also be aware of any particularly erythematous areas. Benign USD generally is represented by spongiofibrosis, which appears smooth, flat, regular, and nonerythematous. Any of the aforementioned sites should raise one's index of suspicion, and biopsy would be indicated.

The bladder also should be evaluated carefully with direct visual cystoscopy because urethral cancer, particularly transitional-cell carcinoma of the urethra, generally is not the primary site if the bladder also is involved. For instance, primary transitional-cell carcinoma of the prostatic urethra without bladder involvement is staged as urethral cancer, but, if a synchronous bladder tumor is present, the cancer is staged as a bladder tumor based on the depth of invasion of the bladder lesion. Some experts contend that this is a stage 4 bladder cancer regardless because of the extension into the prostate.

4) Diagnostic Procedures

Examination under anesthesia of the external genitalia and perineum and bimanual palpation aid in evaluating the local or extensive involvement of the tumor.

Transurethral biopsy is essential to confirm a cystoscopic finding of urethral cancer. Under direct vision, biopsy forceps or an electric loop with a cutting current is extended from the cystoscope to resect and obtain a satisfactory biopsy specimen. In very superficial tumors, this resection technique can be therapeutic and diagnostic.

Percutaneous aspiration of a local fluctuant mass can be studied for culture and cytology.

Needle-core biopsy may prove diagnostic on a palpable lesion deep to the skin.

5) Histologic Findings

Male Urethra

Tumors of the male urethra can be categorized according to the location and histology of the cells. Anatomic distinctions are helpful not only in predicting the histologic association of the neoplastic cells, but also in planning treatment. The male urethra is subclassified anatomically as follows:

Prostatic urethra: This is the urethra as it traverses from the bladder neck to the urogenital diaphragm (UGD).

Membranous urethra: This is the urethra traversing the UGD, including the external sphincter muscle.

Bulbar urethra: This is the portion of the urethra measuring from the UGD to the penoscrotal junction.

Penile or pendulous urethra: This is the remainder of the urethra as it extends from the penoscrotal junction to the urethral meatus. The terminal aspect of the penile urethra is referred to as the fossa navicularis.

The prostatic urethra is lined predominantly by transitional cells, while the bulbar, membranous, and penile urethras are lined by a stratified or pseudostratified columnar epithelium. Patches of stratified squamous epithelium are common in the bulbar and penile urethra and become predominant in the distal urethra. At the terminal fossa navicularis, stratified squamous epithelium occurs as a rule. Within the mucosa, occasional mucous goblet cells may be found throughout the length of the urethra. Histologically, 80% of male urethral cancers are squamous-cell carcinomas, 15% are transitional-cell carcinomas, and 5% are adenocarcinomas and undifferentiated tumors. These tumors occur predominantly in the bulbomembranous urethra (60%), followed by the penile urethra (30%), and then by the prostatic urethra (10%).

Female Urethra

The female urethra is 3-4 cm in length and is lined primarily by stratified squamous cells, although pseudostratified columnar epithelium can be found. The epithelium forms numerous invaginations, the outpocketings of which are lined by clear mucous cells.

Generally speaking, the proximal two thirds of the female urethra demonstrates high-grade locally advanced tumors, while the anterior third usually contains low-grade less extensive carcinomas. Squamous-cell tumors account for 60% of all tumors, followed by transitional-cell carcinoma (20%), adenocarcinoma (10%), undifferentiated tumors and sarcomas (8%), and melanomas (2%).

6) Staging

Once the diagnosis is confirmed by biopsy, clinical staging is important in establishing a therapeutic plan and in determining prognosis. Modalities used to clinically stage urethral cancers include physical examination, chest radiograph, and CT scans of the abdomen and pelvis.

Of all penile urethral tumors, 73% are staged at 0 or A. In contrast, only 32% of bulbourethral malignancies are staged at 0 or A. One hypothesis is that many of the proximal lesions, upon initial discovery, are dismissed as strictures. The literature cites that as many as 35% of patients have a history of treatment for stricture disease. Urethral cancer is staged according to the Tumor Node Metastasis (TMN) criteria outlined by the American Joint Committee on Cancer staging system, as follows:

Primary tumor (T) (men and women)
Tx—Primary tumor cannot be assessed
T0—No evidence of primary tumor
Ta—Noninvasive papillary, polypoid, or verrucous carcinoma
Tis—Carcinoma in situ
T1—Tumor invading subepithelial connective tissue
T2—Tumor invading any of the following: corpus spongiosum, prostate, periurethral muscle
T3—Tumor invading any of the following: corpus cavernosum, beyond prostate capsule, anterior vagina, bladder neck
T4—Tumor invades other adjacent organs Regional lymph nodes (N)
Nx—Regional nodes cannot be assessed
N0—No regional lymph node metastasis
N1—Metastasis in a single lymph node, 2 cm or less in greatest dimension
N2—Metastasis in a single lymph node, larger than 2 cm in greatest dimension, or in multiple lymph nodes Distant metastases (M)
Mx—Distant metastasis cannot be assessed
M0—No distant metastasis
M1—Distant metastasis Treatment 1) Medical Therapy Therapeutic management varies with the stage and location of the lesion. Because of the rarity of this pathology and the lack of statistical analysis on the data, no consensus has been reached on treatment modalities. Distal urethral tumors usually are discovered earlier, at a lower stage, whereas proximal urethral malignancies present at a more clinically advanced stage.

2) Radiation Therapy

Superficial tumors (stage 0 and A) can be managed with radiation alone or in combination with surgical excision.

Raghaviah et al treated 4 patients with urethral carcinoma with external beam radiation. Two patients with metastatic disease died within 9 months. Two patients with distal penile carcinoma survived beyond 4 years.

Bracken et al studied 6 patients with urethral malignancies. Three patients with anterior urethral lesions developed only local recurrence; the patients with posterior (proximal) lesions died of metastatic disease.

Dalbagni et al offered radiation treatment to 6 patients and none responded. This outcome may be the result of selection bias because all 6 patients had T3 or higher lesions. Radiation therapy alone may be acceptable for lower-stage distal tumors; however, it is not acceptable for higher-staged proximal malignancies.

Kaplan et al followed 46 patients who received either no therapy or palliation. In most of these patients, the cause of death was inadequate local disease control, with no evidence of pathology beyond local invasion or regional lymphatics.

Although tumor control by irradiation has been reported, radiation generally has been reserved for patients with early-stage lesions of the anterior urethra who refuse surgery or as an adjunct to definitive surgery in more advanced disease. Surgical excision remains the primary mode of therapy, the extent depending on the location and stage of the primary tumor. Both irradiation and chemotherapy have been used as adjuvant modalities.

3) Chemotherapy

Combination chemotherapy with methotrexate, vinblastine, doxorubicin, and cisplatin is used frequently in the treatment of transitional-cell bladder cancer. Scher et al studied the effects of this therapeutic regimen on extravesical urinary tract tumors. In the 4 patients with mixed or nontransitional cell type carcinoma, 1 patient had a partial remission and 3 had progression.

Similar to the treatment for squamous-cell cancer of the esophagus and anal canal, a combination of radiation therapy and chemotherapy is used as a therapeutic measure. Multimodality therapy appears to be the mainstay treatment to achieve the longest survival without evidence of disease. Eng et al, as well as others who have performed retrospective studies, have reported that the patients who survived the longest without disease received combination therapy that consisted of either chemotherapy with radiation therapy or neoadjuvant chemotherapy with radiation therapy prior to surgery.

4) Surgical Therapy

Surgical excision remains the criterion standard as a primary mode of treatment for urethral cancer for both male and female patients. The extent of surgery depends on the location of the tumor within the urethra and the clinical stage. The extent of local invasion must be accurately predicted to ensure en bloc resection of all involved structures.

The literature describes 4 modalities of surgical management in male urethral cancer: (1) conservative therapy or local excision, (2) partial penectomy, (3) radical penectomy, and (4) pelvic lymphadenectomy and en bloc resection including penectomy and cystoprostatectomy with removal of the anterior pubis.

5) Conservative Therapy or Local Excision

Lesions with a low grade and stage might be the types best managed by transurethral resection, fulguration, or excision. Endoscopic treatment is performed with either transurethral electroresection or fulguration or transurethral laser therapy. Commonly used lasers for this purpose include the neodymium:yttrium-aluminum-garnet (Nd:YAG) laser, the carbon dioxide laser and the holmium:YAG laser. The Nd:YAG and carbon dioxide lasers are used for vaporization and fulguration; therefore, these do not provide the surgeon with a tissue diagnosis. The holmium:YAG laser has been used to resect urothelial tumors in such a way that it provides a noncauterized tissue sample. The holmium:YAG laser has not been exclusively studied in the management of urethral cancer; however, it has been reported as useful for urethral strictures and superficial bladder cancer. Since it has a low depth of penetration, the holmium:YAG laser may be ideal for management of superficial urethral cancer with minimal morbidity to the urethra and surrounding tissues while providing quality tissue samples for diagnosis.

6) Partial Penectomy

Partial penectomy involves excision of the malignant lesion with 2-cm margins. This treatment modality can only be used for infiltrative, distally occurring lesions of the penile urethra. If the proximal half of the penile urethra is involved by infiltrating tumor, then a total penectomy is indicated. Ilioinguinal node dissection is performed only if the nodes are palpable. In contrast to penile cancer, no apparent benefit is associated with prophylactic groin dissection.

Zeidman et al described a series of 44 patients, in which 98% of patients with anterior urethral lesions had no local recurrences; 1 died of metastatic disease.

Dinney et al described 4 patients with urethral cancer in the fossa navicularis who were treated with partial penectomy or urethrectomy. All 4 patients survived without any local recurrences. In 6 patients with urethral cancer of the penile segment, 5 achieved remission and 1 died of recurrent disease 44 months later. Partial penectomy, similar to local excision and external beam radiation, is a viable option for low-stage malignancies of the distal urethra.

7) Total or Radical Penectomy

Total penectomy involves removal of the penis, urethra, and penile root. This surgery is used primarily for lesions that are not amenable to partial penectomy (ie, infiltrative proximal penile urethral carcinomas).

Zeidman et al reported on 52 patients who underwent radical penectomy; 12 of these patients eventually died from their disease.

Mandle and Pool achieved a 50% success rate in their 4 patients with bulbomembranous urethral cancer. This result is expected because proximal urethral lesions often are discovered at a much later stage.

8) En Bloc Resection

En bloc resection is reserved for patients with T2/Nx/M0 or higher tumors in the bulbomembranous or prostatic urethra. Although poor survival figures are associated with these lesions, radical en bloc excision offers the best chance for long-term disease control and prevention of disease recurrence. This surgery includes a pelvic lymphadenectomy with an en bloc total penectomy, cystoprostatectomy, and in-continuity resection of the pubic rami and urogenital diaphragm. Portions of the scrotal and perineal skin and soft tissues may require excision with bulky tumor involvement of these structures. Similarly, the pubic symphysis is resected if bulky disease involves the presymphyseal tissues. The testicles may be preserved in thigh pouches if extensive scrotal skin is excised. In females, removal of most if not the entire vagina is a necessity. In males and females alike, inguinal lymphadenectomy is performed only if palpable disease is present.

Primary melanoma of the urethra presents a unique challenge compared to other histologic types. Oliva et al found that, despite distal locations and urethral confinement at the time of surgery, 9 of 15 patients exhibited a survival rate of less than 5 years. Perhaps combination therapy, consisting of radical surgery and adjuvant chemotherapy and radiation therapy, may improve these rates by destroying cancer cells that evaded surgical treatment. Chemotherapy may have a particularly good effect on primary melanoma of the urethra, considering the brisk mitotic activity of this histologic subtype.

9) Preoperative Details

Attempts to accurately stage the tumor should be exhausted prior to performing definitive surgery, particularly if significant reconstruction is required. The patient should have already been to the operating room at least once for a transurethral biopsy and examination under anesthesia. Based on these findings, an imaging modality such as MRI or CT scan should be performed to predict the extent of local invasion. After accurate staging, a lengthy discussion with the patient regarding the extent and severity of disease should be used. The issues of reconstruction, urinary diversion, social and family support, and physical therapy are of paramount importance. Plastic surgery and orthopedic surgery consults should be requested prior to surgery, and their presence should be readily available in the operating room.

Mechanical and biochemical bowel preparation should be performed one day prior to major pelvic surgery, particularly if urinary diversion is to be used.

10) Intraoperative Details

General anesthesia generally is required for en bloc excision. For diagnostic cystoscopy and transurethral biopsy, spinal anesthesia or even intravenous sedation may be sufficient.

The patient should be placed in the low lithotomy position to allow perineal access. Excision of scrotal or perineal skin is necessary with bulky tumors. Viable testes may be preserved in thigh pouches.

11) Postoperative Details

General postoperative precautions that are paramount to reducing complications include hemodynamic support with intravenous fluids, both crystalloid and colloid; intravenous antibiotics; incentive spirometry and aggressive pulmonary toilet; and deep venous thrombosis prophylaxis. These precautions should be used.

Strict measurement of 24-hour input and output from all drains should be carefully and clearly recorded in order to manage fluid status appropriately and determine when and if spontaneous diuresis is progressing. Use of diuretic agents may be required based on these recordings.

Stoma nurse care and teaching is necessary, particularly for when the patient is discharged home, because they will likely need to record their output initially. Initial teaching of stomal appliance care and/or intermittent catheterization provides the patient with much needed autonomy and leads to the development of a positive and proactive self-image. Visiting nurse assistance may be necessary if the patient cannot initially meet the high demands these procedures require.

Physical therapy often is required, particularly if portions of the pubic rami have been resected.

Social interaction should be monitored because patients with this grave disease may require a psychiatric consultation liaison. Social support services may provide the patient with much needed empathy.

12) Follow-up

Carefully obtain a history, with particular attention paid to new symptoms such as hematuria; decreased urine output; voiding symptoms (if the urethra has been preserved); gastrointestinal symptoms; changes in bowel habits; weight loss and other constitutional symptoms; bone, back, or flank pain; and neurologic symptoms. Periodically examine the remaining urethra, pelvis, and inguinal regions. Perform urinalysis, urine cytology, and cystoscopy periodically. Significant hematuria, urinary tract infections, and malignant cells noted in the urine all should be addressed promptly and appropriately. If lesions are noted upon cystoscopy, they should be subsequently biopsied.

Imaging studies of the pelvis (ie, CT scan with intravenous contrast) should be performed from every 6 months to a year to check for local recurrence or hydronephrosis.

Perform periodic chest radiographs and comprehensive metabolic panel blood tests every 3 months initially for the first 2 years, then every 6 months for up to 5 years, and annually thereafter. Rising serum urea nitrogen and creatinine levels may suggest an obstructive process or some element of renal toxicity. A new lesion noted on a chest radiograph would require a CT scan to further characterize it and possibly obtain a CT-guided biopsy specimen. If metastatic disease is confirmed, systemic chemotherapy should be strongly considered.

Uterine Sarcoma

A uterine sarcoma is a malignant tumor that arises from the smooth muscle or connective tissue of the uterus. If the lesion originates from the stroma of the uterine lining it is an endometrial stromal sarcoma, and if the uterine muscle cell is the originator the tumor is a uterine leiomyosarcoma. A lesion that also contains malignant tumor cells of epithelial origin is termed uterine carcinosarcoma (formerly called malignant mixed mesodermal/mullerian tumor).

Signs and Symptoms

Unusual or postmenopausal bleeding may be a sign of a malignancy including uterine sarcoma and needs to be investigated. Other signs include pelvic pain, pressure, and unusual discharge. A nonpregnant uterus that enlarges quickly is suspicious. However, none of the signs are specific. Specific screening test have not been developed; a Pap smear is a screening test for cervical cancer and not designed to detect uterine sarcoma.

Diagnosis

Investigations by the physician include imaging (ultrasound, CAT scan, MRI) and, if possible, obtaining a tissue diagnosis by biopsy, hysteroscopy, or D&C. Ultimately the diagnosis is established by the histologic examination of the specimen. Typically malignant lesions have >10 mitosis per high power field. In contrast a uterine leiomyoma as a benign lesion would have <5 mitosis per high power field.

Staging

Uterine sarcoma is staged like endometrial carcinoma at time of surgery using the FIGO cancer staging system.

Stage IA: tumor is limited to the endometrium
Stage IB: invasion of less than half the myometrium
Stage IC: invasion of more than half the myometrium
Stage IIA: endocervical glandular involvement only
Stage IIB: cervical stromal invasion
Stage IIIA: tumor invades serosa or adnexa, or malignant peritoneal cytology
Stage IIIB: vaginal metastasis
Stage IIIC: metastasis to pelvic or para-aortic lymph nodes
Stage IVA: invasion of the bladder or bowel
Stage IVB: distant metastasis, including intraabdominal or inguinal lymph nodes Therapy Therapy is based on staging and patient condition and utilizes one or more of the following approaches. Surgery is the mainstay of therapy if feasible involving total abdominal hysterectomy with bilateral salpingo-oophorectomy. Other approaches include radiation therapy, chemotherapy, and hormonal therapy.

Vaginal Cancer

Cancer of the vagina is a rare kind of cancer in women. In vaginal cancer, cancer (malignant) cells are found in the tissues of the vagina. The vagina is the passageway through which fluid passes out of the body during menstrual periods and through which a woman has babies. The vagina is also called the "birth canal." The vagina connects the cervix (the opening of the womb or uterus) and the vulva (the folds of skin around the opening to the vagina).

There are many different types of cancer of the vagina: squamous cell cancer (squamous carcinoma), adenocarcinoma, malignant melanomas, and sarcomas. About 90% of vaginal cancers are squamous cell carcinomas that begin in the epithelial lining of the vagina. These kinds of cancers tend to occur in the upper area of the vagina near the cervix. Vaginal squamous cell carcinomas do not appear suddenly, they develop over a period of many years from precancerous changes called vaginal intraepithelial neoplasia (abbreviated as VAIN). Squamous carcinomas are usually found in women between the ages of 60 and 80.

About 5% of vaginal cancers are adenocarcinomas. The most common type of vaginal adenocarcinoma usually develops in women over age 50. Another type called clear cell adenocarcinoma usually occurs in young women who were exposed to Diethhystilbestrol while they were in their mother's womb. Diethylstilbestrol is a hormonal drug that was prescribed between 1940 to 1971 for some women thought to be at increased risk for miscarriages. Adenocarcinomas are often found in women between the ages of 12 and 30.

Malignant melanoma is a cancer that develops from pigment-producing cells called melanocytes. Malignant melanomas are usually found on sun-exposed areas of the skin but occasionally form on the vagina or other internal organs. They account for about 2% to 3% of all vaginal cancers. Malignant melanoma usually affects the lower or outer portion of the vagina.

About 2% to 3% of vaginal cancers are sarcomas. These cancers form deep in the wall of the vagina, not on its surface epithelium. There are several types of vaginal sarcomas. Some of the types are: leiomyosarcomas and rhabdomyosarcoma. Leiomyosarcomas resemble the involuntary muscle cells of the vaginal wall. Rhabdomyosarcoma is a childhood cancer, usually found before the age of 3. This type of cancer has cells that resemble voluntary muscle cells. Voluntary muscle tissue is not normally found in the vaginal wall.

Symptoms of Vaginal Cancer

Some of the symptoms of vaginal cancer are: bleeding or discharge not related to menstrual periods, difficult or painful urination and pain during intercourse or in the pelvic area.

Vaginal Cancer Statistics

Vaginal cancer accounts for about 3% of cancers of the female reproductive system. Cancers found in the vagina are less common than cancers that start in other organs and then spread vagina.

Risk Factors for Vaginal Cancer

Some of the risk factors for developing vaginal cancer are: age, prescription of diethylstilbestrol, and already being diagnosed with cervical cancer, and Age. Age is a risk factor for squamous cell carcinoma. Most of the women who are diagnosed with squamous cell carcinoma are diagnosed while the women are between the ages of 50 and 70.

Diethylstilbestrol is a hormonal drug that was prescribed between 1940 to 1971 for some women thought to be at increased risk for miscarriages.

A person who has cervical cancer has a high risk of developing vaginal squamous cell cancer. This is because cervical and vaginal cancer has similar risk factors.

Methods of Treatment

Surgery, radiation therapy and chemotherapy are the most common treatments. Surgery may be performed to remove part or all of the pancreas, and any surrounding tissue that has become cancerous. It is the primary method of treatment for vaginal cancer.

Surgery options include:
1. Laser surgery. A narrow beam of light is used to kill very early stage cancer cells
2. Wide local excision. The surgeon takes out the cancer and some of the surrounding tissue.
3. Vaginectomy. The surgeon removes the vagina and maybe lymph nodes from the pelvic area.
4. Radical hysterectomy. If cancer has spread outside of the vagina, the uterus, ovaries and fallopian tubes, as well as lymph nodes may be removed.

Radiation therapy (also called radiotherapy) is the use of high-energy rays to kill cancer cells.

Chemotherapy is the use of drugs to kill cancer cells.

Diagnosis of Vaginal Cancer

A variety of tools are used to diagnose vaginal cancer. The most often used tools are:
1. Pelvic Exam: The doctor feels the uterus, vagina, ovaries, fallopian tubes, bladder and rectum for any abnormalities.
2. Pap test: The doctor gently scrapes the outside of the cervix and vagina and takes sample cells for testing.
3. Colposcopy: The doctor inserts an instrument with binocular magnifying lenses into the vagina and checks the vaginal walls and cervix.
4. Biopsy: The doctor take out a small piece of vaginal tissue to send to the laboratory. At the laboratory, a pathologist will look at the tissue under a microscope to determine whether the cells are cancer.

Vulval Squamous Cell Carcinoma/Valvae Cancer

The main type of vulvae cancer is Squamous Cell Carcinoma of the Vulva.

The vulvae are the female external genitalia, consisting of the mons pubis, the labia majora and minora and the clitoris. The proximal two-thirds of the labia minora and all tissues internal to them are of endodermal origin. All tissue external to this point is ectodermal in origin and histology resembles that of skin. Between the labia minora is the vestibule—containing the external urethral meatus, the hymen and the clitoris.

Diagnosis of Valvae Cancer

General investigations may show no abnormalities even in advanced stages. If bleeding has been a prominent feature there may be anaemia and an abnormal liver function may be detected if there has been spread to the liver. A chest x-ray is a compulsory investigation in all patients with suspicion of vulvar cancer and metastases may be evident in advanced disease.

Treatment of Valvae Cancer Treated

Surgical excision is the treatment of choice in all patients with vulvar carcinoma—irrespective of the stage of the disease at diagnosis. The introduction of vulvectomy in the treatment of vulvar carcinoma halved the mortality rate from the disease. The nature of the surgery should be individualised to the patient, with different locations and degrees of spread of tumour dictating the surgical approach and the need for lymph node clearance. Radiotherapy is used in addition to surgical excision in an increasing number of cases.

Bleomycin and doxorubicin are also effective treatments.

Improvement in symptoms is an important measurement. Specific monitoring may be by ongoing clinical examination and further investigations as indicated. If the vulvar cancer has spread, the measurement of size of individual lumps on a CT Scan or x-ray may show the response to treatment. Recurrence, should it occur, can be classified as local, inguinal or distant. Distant recurrence is associated with a very poor prognosis. The symptoms that may require attention are neurogenic pain if nerve tissue is compressed and visceral pain from liver or lung metastases. Coughing and breathlessness from lung involvement may require specific treatment. Death from vulvar carcinoma is commonly a long and extremely unpleasant process. It often occurs due to sepsis or haemorrhage. Bilateral ureteric obstruction and uraemia often occur. For this reason surgical debulking is offered to almost all patients suffering from vulvar carcinoma—irrespective of the stage of their disease or current physical condition.

B) Infectious Diseases

In one preferred embodiment the present invention relates to diagnosis and/or treatment of infectious disease. The infection can be any type of infection including the types of infection mentioned elsewhere herein and those listed in Tables A to G. The treatment can be any kind of treatment including the treatments mentioned elsewhere herein or in the items, or any combination thereof. The treatment can be ameliorating, symptomatic, curative or prophylactic. The treatment can result in relief one or more symptoms of the infection including one or more of the symptoms mentioned herein below. The infection can be diagnosed by any method including the methods mentioned herein below.

An infectious disease is a clinically evident disease resulting from the presence of pathogenic microbial agents, including pathogenic viruses, pathogenic bacteria, fungi, protozoa, multicellular parasites, and aberrant proteins known as prions. These pathogens are able to cause disease in animals and/or plants.

Infectious pathologies are usually qualified as contagious diseases (also called communicable diseases) due to their potentiality of transmission from one person or species to another. Transmission of an infectious disease may occur through one or more of diverse pathways including physical contact with infected individuals. These infecting agents may also be transmitted through liquids, food, body fluids, contaminated objects, airborne inhalation, or through vector-borne spread.

The term infectivity describes the ability of an organism to enter, survive and multiply in the host, while the infectiousness of a disease indicates the comparative ease with which the disease is transmitted to other hosts. An infection is not synonymous with an infectious disease, as an infection may not cause important clinical symptoms or impair host function.

Virus

A virus (from the Latin virus meaning "toxin" or "poison"), is a sub-microscopic infectious agent that is unable to grow or reproduce outside a host cell. Each viral particle, or virion, consists of genetic material, DNA or RNA, within a protective protein coat called a capsid. The capsid shape varies from simple helical and icosahedral (polyhedral or near-spherical) forms, to more complex structures with tails or an envelope. Viruses infect all cellular life forms and are grouped into animal, plant and bacterial types, according to the type of host infected.

Viral life cycles vary in their precise details depending on the species of virus, but they all share a general pattern:
  Attachment to a host cell.
  Release of viral genes and possibly enzymes into the host cell.
  Replication of viral components using host-cell machinery.
  Assembly of viral components into complete viral particles.
  Release of viral particles to infect new host cells.

Antivirals have tried to attack viruses at every stage of their life cycles.

The Baltimore classification of viruses is based on the mechanism of mRNA production. Viruses must generate positive strand mRNAs from their genomes to produce proteins and replicate themselves, but different mechanisms are used to achieve this in each virus family. Viral genomes may be single-stranded (ss) or double-stranded (ds), RNA or DNA, and may or may not use reverse transcriptase (RT). Additionally, ssRNA viruses be either sense (+) or antisense (−). This classification places viruses into seven groups:
  I: dsDNA viruses (e.g. Adenoviruses, Herpesviruses, Poxviruses)
  II: ssDNA viruses (+)sense DNA (e.g. Parvoviruses)
  III: dsRNA viruses (e.g. Reoviruses)
  IV: (+)ssRNA viruses (+)sense RNA (e.g. Picornaviruses, Togaviruses)
  V: (−)ssRNA viruses (−)sense RNA (e.g. Orthomyxoviruses, Rhabdoviruses)
  VI: ssRNA-RT viruses (+)sense RNA with DNA intermediate in life-cycle (e.g. Retroviruses)
  VII: dsDNA-RT viruses (e.g. Hepadnaviruses)
  For examples of viruses, please refer to the items.

Cytomegalovirus

The present invention relates in one embodiment to diagnosis and/or treatment of one or more diseases caused by a Herpesvirus species such as one of the Herpesviridae species mentioned herein below or in the items, including cytomegalovirus.

In another preferred embodiment the present invention relates to diagnosis and/or treatment of a disease caused by a herpesvirus such as cytomegalovirus (CMV) using one or more MHC-peptide complexes comprising one or more peptides comprising one or more sequences from one or more Herpesvirus species such as cytomegalovirus including the ones mentioned below and in the items.

Cytomegalovirus (CMV) is a viral genus of the Herpesviruses group: in humans it is commonly known as HCMV or Human Herpesvirus 5 (HHV-5). CMV belongs to the Betaherpesvirinae subfamily of Herpesviridae, which also includes Roseolovirus. Other herpesviruses fall into the subfamilies of Alphaherpesvirinae (including HSV 1 and 2 and varicella) or Gammaherpesvirinae (including Epstein-Barr virus). All herpesviruses share a characteristic ability to remain latent within the body over long periods.

HCMV infections are frequently associated with salivary glands, though they may be found throughout the body. HCMV infection can also be life threatening for patients who are immunocompromised (e.g. patients with HIV, organ transplant recipients, or neonates). Other CMV viruses are found in several mammal species, but species isolated from animals differ from HCMV in terms of genomic structure, and have not been reported to cause human disease.

HCMV is found throughout all geographic locations and socioeconomic groups, and infects between 50% and 80% of adults in the United States as indicated by the presence of antibodies in much of the general population. Seroprevalence is age-dependent: 58.9% of individuals aged 6 and over are infected with CMV while 90.8% of individuals aged 80 and over are positive for HCMV. HCMV is also the virus most frequently transmitted to a developing child before birth. HCMV infection is more widespread in developing countries and in communities with lower socioeconomic status and represents the most significant viral cause of birth defects in industrialized countries.

Most healthy people who are infected by HCMV after birth have no symptoms. Some of them develop an infectious mononucleosis/glandular fever-like syndrome, with prolonged fever, and a mild hepatitis. A sore throat is common. After infection, the virus remains latent in the body for the rest of the person's life. Overt disease rarely occurs unless immunity is suppressed either by drugs, infection or old-age. Initial HCMV infection, which is often asymptomatic, is followed by a prolonged, inapparent infection during which the virus resides in cells without causing detectable damage or clinical illness.

Infectious CMV may be shed in the bodily fluids of any infected person, and can be found in urine, saliva, blood, tears, semen, and breast milk. The shedding of virus can occur intermittently, without any detectable signs or symptoms.

CMV infection can be demonstrated microscopically by the detection of intranuclear inclusion bodies. The inclusion bodies stain dark pink by H&E staining, and are called "Owl's Eye" inclusion bodies.

HCMV infection is important to certain high-risk groups. Major areas of risk of infection include pre-natal or post-partum infants and immunocompromised individuals, such as organ transplant recipients, persons with leukemia, or those infected with human immunodeficiency virus (HIV). HCMV is considered an AIDS-defining infection, indicating that the T-cell count has dropped to low levels.

Lytically replicating virus disrupts the cytoskeleton, causing massive cell enlargement, which is the source of the virus' name.

The most common types of infections by CMV can be group as follows:
  Fetus/Infant
  Congenital CMV infection
  Perinatal CMV infection
  Immunocompetent Patient
  CMV mononucleosis
  Post-transfusion CMV—similar to CMV mononucleosis
  Immunocompromised Patient
  CMV pneumonitis
  CMV GI disease
  CMV retinitis
Diagnosis Most infections with CMV are not diagnosed because the virus usually produces few, if any, symptoms and tends to reactivate intermittently without symptoms. However, persons who have been infected with CMV develop antibodies to the virus, and these antibodies persist in the body for the lifetime of that individual. A number of laboratory tests that detect these antibodies to CMV have been developed to determine if infection has occurred and are widely available from commercial laboratories. In addition, the virus can be cultured from specimens obtained from urine, throat swabs, bronchial lavages and tissue samples to detect active infection. Both qualitative and quantitative polymerase chain reaction (PCR) testing for CMV are available as well, allowing physicians to monitor the viral load of CMV-infected patients.

CMV pp 65 antigenemia test is a immunoflourescence based assay which utilizes an indirect immunofluorescence technique for identifying the pp 65 protein of cytomegalovirus in peripheral blood leukocytes. the CMV pp 65 assay is widely used for monitoring CMV infections and its response to antiviral treatment in patients who are under immunosuppressive therapy and have had renal transplantation surgery as the Antigenemia results are obtained ~5 days before the onset of symptomatic CMV disease. The advantage of this assay is the rapidity in providing results in a few hours and that the pp 65 antigen determination represents a useful parameter for the physician to initiate antiviral therapy. The major disadvantage of the pp 65 assay is that only limited number of samples can be processed per test batch.

CMV should be suspected if a patient has symptoms of infectious mononucleosis but has negative test results for mononucleosis and Epstein-Barr virus, or if they show signs of hepatitis, but has negative test results for hepatitis A, B, and C.

For best diagnostic results, laboratory tests for CMV antibody should be performed by using paired serum samples. One blood sample should be taken upon suspicion of CMV, and another one taken within 2 weeks. A virus culture can be performed at any time the patient is symptomatic. Laboratory testing for antibody to CMV can be performed to determine if a woman has already had CMV infection. However, routine testing of all pregnant women is costly and the need for testing should therefore be evaluated on a case-by-case basis.

Serologic Testing

The enzyme-linked immunosorbent assay (or ELISA) is the most commonly available serologic test for measuring antibody to CMV. The result can be used to determine if acute infection, prior infection, or passively acquired maternal antibody in an infant is present. Other tests include various fluorescence assays, indirect hemagglutination, (PCR) and latex agglutination.

An ELISA technique for CMV-specific IgM is available, but may give false-positive results unless steps are taken to remove rheumatoid factor or most of the IgG antibody before the serum sample is tested. Because CMV-specific IgM may be produced in low levels in reactivated CMV infection, its presence is not always indicative of primary infection. Only virus recovered from a target organ, such as the lung, provides unequivocal evidence that the current illness is caused by acquired CMV infection. If serologic tests detect a positive or high titer of IgG, this result should not automatically be interpreted to mean that active CMV infection is present. However, if antibody tests of paired serum samples show a fourfold rise in IgG antibody and a significant level of IgM antibody, meaning equal to at least 30% of the IgG value, or virus is cultured from a urine or throat specimen, the findings indicate that an active CMV infection is present.

Relevance to Blood Donors

Although the risks discussed above are generally low, CMV assays are part of the standard screening for non-directed blood donation (donations not specified for a particular patient) in the U.S. CMV-negative donations are then earmarked for transfusion to infants or immunocompromised patients. Some blood donation centers maintain lists of donors whose blood is CMV negative due to special demands.

Treatment

No treatment is generally necessary for CMV infection in the healthy individual since the majority of infections resolve on their own. Antiviral drug therapy is now being evaluated in infants.

Ganciclovir treatment is used for patients with depressed immunity that has either sight-related or life-threatening illnesses. Valganciclovir (marketed as Valcyte) is an antiviral drug that is also effective and is given orally. The therapeutic effectiveness is frequently compromised by the emergence of drug-resistant virus isolates. A variety of amino acid changes in the UL97 protein kinase and the viral DNA polymerase have been reported to cause drug resistance. Foscarnet or cidofovir can be given in patients with CMV resistant to ganciclovir, because foscarnet has bad nephrotoxicity, increased or decreased $Ca^{2+}$ or P, and decreased $Mg^{2+}$. Vaccines are still in the research and development stage.

Epstein-Barr Virus

The present invention relates in one embodiment to diagnosis and/or treatment of one or more diseases caused by a Herpesvirus species such as one of the Herpesviridae species mentioned herein below or in the items, including Epstein-Barr Virus.

In another preferred embodiment the present invention relates to diagnosis and/or treatment of a disease caused by a herpesvirus such Epstein-Barr Virus using one or more MHC-peptide complexes comprising one or more peptides comprising one or more sequences from one or more Herpesvirus species such as Epstein-Barr Virus including the ones mentioned below and in the items.

The Epstein-Barr Virus (EBV), also called Human herpesvirus 4 (HHV-4), is a virus of the herpes family (which includes Herpes simplex virus), and is one of the most common viruses in humans. Most people become infected with EBV, which is often asymptomatic but commonly causes infectious mononucleosis.

Epstein-Barr virus, frequently referred to as EBV, is a member of the herpesvirus family and one of the most common human viruses. The virus occurs worldwide, and most people become infected with EBV sometime during their lives. In the United States, as many as 95% of adults between 35 and 40 years of age have been infected. Infants become susceptible to EBV as soon as maternal antibody protection (present at birth) disappears. Many children become infected with EBV, and these infections usually cause no symptoms or are indistinguishable from the other mild, brief illnesses of childhood. In the United States and in other developed countries, many persons are not infected with EBV in their childhood years. When infection with EBV occurs during adolescence or young adulthood, it causes infectious mononucleosis 35% to 50% of the time.

Symptoms of infectious mononucleosis are fever, sore throat, and swollen lymph glands. Sometimes, a swollen spleen or liver involvement may develop. Heart problems or involvement of the central nervous system occurs only rarely, and infectious mononucleosis is almost never fatal. There are no known associations between active EBV infection and problems during pregnancy, such as miscarriages or birth defects. Although the symptoms of infectious mononucleosis usually resolve in 1 or 2 months, EBV remains dormant or latent in a few cells in the throat and blood for the rest of the person's life. Periodically, the virus can reactivate and is commonly found in the saliva of infected persons. This reactivation usually occurs without symptoms of illness.

EBV also establishes a lifelong dormant infection in some cells of the body's immune system. A late event in a very few carriers of this virus is the emergence of Burkitt's lymphoma and nasopharyngeal carcinoma, two rare cancers that are not normally found in the United States. EBV appears to play an important role in these malignancies, but is probably not the sole cause of disease.

Most individuals exposed to people with infectious mononucleosis have previously been infected with EBV and are not at risk for infectious mononucleosis. In addition, transmission of EBV requires intimate contact with the saliva (found in the mouth) of an infected person. Transmission of this virus through the air or blood does not normally occur. The incubation period, or the time from infection to appearance of symptoms, ranges from 4 to 6 weeks. Persons with infectious mononucleosis may be able to spread the infection to others for a period of weeks. However, no special precautions or isolation procedures are recommended, since the virus is also found frequently in the saliva of healthy people. In fact, many healthy people can carry and spread the virus intermittently for life. These people are usually the primary reservoir for person-to-person transmission. For this reason, transmission of the virus is almost impossible to prevent.

Diseases Associated with EBV:
  Infectious Mononucleosis
    Several Non-Hodgkin's lymphomas, (e.g. Burkitt's lymphoma, primary cerebral lymphoma)
  Hodgkin's disease
  Stevens-Johnson syndrome
  Hepatitis
  Herpes
  Alice in Wonderland syndrome (Todd's syndrome)
  Post-transplant lymphoproliferative disorder
  Herpangina
  Multiple Sclerosis (higher risk in patients infected as teenagers than as children)
  Hairy leukoplakia
  Common variable immunodeficiency (CVID)
  Kikuchi's disease
  Nasopharyngeal cancer
  Subepithelial Infiltrates
  smooth muscle tumors EBV-associated Malignancies The strongest evidence linking EBV and cancer formation is found in Burkitt's lymphoma and nasopharyngeal carcinoma. It has been postulated to be a trigger for a subset of chronic fatigue syndrome patients as well as multiple sclerosis and other autoimmune diseases.

Burkitt's lymphoma is a type of Non-Hodgkin's lymphoma and is most common in equatorial Africa and is co-existent with the presence of malaria. Malaria infection causes reduced immune surveillance of B cells immortalized by EBV, resulting in an excessive number of B cells and an increased likelihood of an unchecked mutation. Repeated mutations can lead to loss of cell-cycle control, causing excessive proliferation observed as Burkitt's lymphoma. Burkitt's lymphoma commonly affects the jaw bone, forming a huge tumor mass. It responds quickly to chemotherapy treatment, namely cyclophosphamide, but recurrence is common.

Other B cell lymphomas arise in immunocompromised patients such as those with AIDS or who have undergone organ transplantation with associated immunosuppression (Post-Transplant Lymphoproliferative Disorder (PTLPD)). Smooth muscle tumors are also associated with the virus in malignant patients.

Nasopharyngeal carcinoma is a cancer found in the upper respiratory tract, most commonly in the nasopharynx, and is linked to the EBV virus. It is found predominantly in Southern China and Africa, due to both genetic and environmental factors. It is much more common in people of Chinese ancestry (genetic), but is also linked to the Chinese diet of a high amount of smoked fish, which contain nitrosamines, well known carcinogens (environmental).

Diagnosis

The clinical diagnosis of infectious mononucleosis is suggested on the basis of the symptoms of fever, sore throat, swollen lymph glands, and the age of the patient. Usually, laboratory tests are needed for confirmation. Serologic results for persons with infectious mononucleosis include an elevated white blood cell count, an increased percentage of certain atypical white blood cells, and a positive reaction to a "mono spot" test.

Treatment

There is no specific treatment for infectious mononucleosis, other than treating the symptoms. No antiviral drugs or vaccines are available. Some physicians have prescribed a 5-day course of steroids to control the swelling of the throat and tonsils. The use of steroids has also been reported to decrease the overall length and severity of illness, but these reports have not been published.

It is important to note that symptoms related to infectious mononucleosis caused by EBV infection seldom last for more than 4 months. When such an illness lasts more than 6 months, it is frequently called chronic EBV infection. However, valid laboratory evidence for continued active EBV infection is seldom found in these patients. The illness should be investigated further to determine if it meets the criteria for chronic fatigue syndrome, or CFS. This process includes ruling out other causes of chronic illness or fatigue.

Bacteria

Bacteria are unicellular microorganisms. Typically a few micrometres in length, bacteria have a wide range of shapes, ranging from spheres to rods and spirals. Bacteria are ubiquitous in every habitat on Earth, growing in soil, acidic hot springs, radioactive waste, seawater, and deep in the Earth's crust. The study of bacteria is known as bacteriology, a branch of microbiology.

There are approximately ten times as many bacterial cells as human cells in the human body, with large numbers of bacteria on the skin and in the digestive tract. Although the vast majority of these bacteria are rendered harmless by the protective effects of the immune system, and a few are beneficial, some are pathogenic bacteria and cause infectious diseases, including tuberculosis, borreliosis (Lyme's disease), cholera, syphilis, anthrax, leprosy and bubonic plague. The most common fatal bacterial diseases are respiratory infections, with tuberculosis alone killing about 2 million people a year, mostly in sub-Saharan Africa. In developed countries, antibiotics are used to treat bacterial infections and in various agricultural processes, so antibiotic resistance is becoming common. In industry, bacteria are important in processes such as sewage treatment, the production of cheese and yoghurt, biotechnology, and the manufacture of antibiotics and other chemicals.

Bacteria are prokaryotes. Unlike cells of animals and other eukaryotes, bacterial cells do not contain a nucleus and rarely harbour membrane-bound organelles. Although the term bacteria traditionally included all prokaryotes, the scientific classification changed after the discovery in the 1990s that prokaryotic life consists of two very different groups of organisms that evolved independently from an ancient common ancestor. These evolutionary domains are called Bacteria and Archaea.

Bacterial phyla comprises: Acidobacteria, Actinobacteria, Aquificae, Bacteroidetes, Chlamydiae, Chlorobi, Chloroflexi, Chrysiogenetes, Cyanobacteria, Deferribacteres, Deinococcus-Thermus, Dictyoglomi, Fibrobacteres, Firmicutes, Fusobacteria, Gemmatimonadetes, Nitrospirae, Planctomycetes, Proteobacteria, Spirochaetes, Thermodesulfobacteria, Thermomicrobia, Thermotogae and Verrucomicrobia.

Bacteria are either Gram negative (Spirochetal, Chlamydiae, Proteobacteria α, β, γ) or Gram positive (Firmicutes, Actinobacteria (*Mycobacterium*, Actinomycetales).

For a list of examples of bacteria, please refer to the items.

In one embodiment, the present invention relates to diagnosis, monitoring and/or treatment of infectious diseases caused by bacteria belonging to any of Acidobacteria, Actinobacteria, Aquificae, Bacteroidetes, Chlamydiae, Chlorobi, Chloroflexi, Chrysiogenetes, Cyanobacteria, Deferribacteres, Deinococcus-Thermus, Dictyoglomi, Fibrobacteres, Firmicutes, Fusobacteria, Gemmatimonadetes, Nitrospirae, Planctomycetes, Proteobacteria, Spirochaetes, Thermodesulfobacteria, Thermomicrobia, Thermotogae and Verrucomicrobia bacterial phyla; these may be Gram negative (Spirochetal, Chlamydiae, Proteobacteria α, β, γ) or Gram positive (Firmicutes, Actinobacteria (Mycobacterium, Actinomycetales)).

*Borrelia*

*Borrelia* is a genus of bacteria of the spirochete class. It is a zoonotic, vector-borne disease transmitted primarily by ticks and some by lice, depending on the species. There are at least 37 known species of *Borrelia*. Different species of *Borrelia* results in different clinical symptoms. Of the 37 known species of *Borrelia*, 12 of these species are known to cause Lyme disease or borreliosis and are transmitted by ticks. The major *Borrelia* species causing Lyme disease are *Borrelia burgdorferi, Borrelia afzelii, Borrelia garini* and *Borrelia valaisiana*.

Other *Borrelia* species cause relapsing fever such as *Borrelia recurrentis*, caused by the human body louse. No animal reservoir of *B. recurrentis* exists. Lice that feed on infected humans acquire the *Borrelia* organisms that then multiply in the gut of the louse. When an infected louse feeds on an uninfected human, the organism gains access when the victim crushes the louse or scratches the area where the louse is feeding. *B. recurrentis* infects the person via mucous membranes and then invades the bloodstream.

Other tick-borne relapsing infections are acquired from other species, such as *Borrelia hermsii* or *Borrelia Parkeri*, which can be spread from rodents, and serve as a reservoir for the infection, via a tick vector. *Borrelia hermsii* and *Borrelia recurrentis* cause very similar diseases although the disease associated with *Borrelia* hermsii has more relapses and is responsible for more fatalities, while the disease caused by *B. recurrentis* has longer febrile and afebrile intervals and a longer incubation period.

The present invention relates in one embodiment to diagnosis and/or treatment of a disease caused by a *Borrelia* infection using one or more MHC-peptide complexes comprising one or more peptides comprising one or more sequences from one or more *Borrelia* species including the ones mentioned above.

In another preferred embodiment the present invention relates to diagnosis and/or treatment of one or more diseases caused by a *Borrelia* species such as one of the *Borrelia* species mentioned herein below.

*Borrelia burgdorfei*

In one preferred embodiment the invention relates to one or more MHC-peptide complexes comprising one or more peptides comprising one or more sequences from *Borrelia burgdorferi* such as *Borrelia burgdorferi* B31.

In another preferred embodiment the present invention relates to diagnosis and/or treatment of one or more diseases caused by *Borrelia burgdorferi* such as *Borrelia burgdorferi* B31.

*Borrelia burgdorferi* is species of bacteria of the spirochete class of the genus *Borrelia*. *B. burgdorferi* is predominant in North America, but also exists in Europe, and is the agent of Lyme disease. It is a zoonotic, vector-borne disease transmitted by ticks and is named after the researcher Willy Burgdorfer who first isolated the bacterium in 1982. *B.* burgdorferi is one of the few pathogenic bacteria that can survive without iron, having replaced all of its iron-sulphur cluster enzymes with enzymes that use manganese, thus avoiding the problem many pathogenic bacteria face in acquiring iron. *B. burgdorferi* infections have been linked to non-Hodgkin lymphomas. The *B. burgdorferi* genome (B31 strain) contains 910,725 base pairs and 853 genes.

*Borrelia afzelii*

In one preferred embodiment the invention relates to one or more MHC-peptide complexes comprising one or more peptides comprising one or more sequences from *Borrelia afzelii* such as borrelia afzelii PKo. In another preferred embodiment the present invention relates to diagnosis and/or treatment of one or more diseases caused by *Borrelia afzelii* such as borrelia afzelii PKo.

*Borrelia afzelii* is considered a new species of the Genus *Borrelia* and considered homologous to *Borrelia burgdorferi* with regard to phenotypic, genetic, and immunological characteristics. Diseases linked to this species of *Borrelia* are Lyme disease and Acrodermatitis chronica atrophicans (ACA). Better understanding of the structure and function of this pathogen will create better methods of treatment to people with the diseases it causes.

*Borrelia garini*

In one preferred embodiment the invention relates to one or more MHC-peptide complexes comprising one or more peptides comprising one or more sequences from *Borrelia garini* such as garini PBi. In another preferred embodiment the present invention relates to diagnosis and/or treatment of one or more diseases caused by *Borrelia garini* such as garini PBi. *Borrelia garini* is one of two major strains found in Europe. It usually causes Lyme Disease symptoms of the neurological kind—such as extreme back- and leg-pains, meningitis and partial facial paralysis, Lyme arthritis due to B garini may be associated in susceptible hosts with amoxicillin resistance or treatment resistance.

Other *Borrelia* Species

In one preferred embodiment the present invention relates to diagnosis and/or treatment of one or more diseases caused by the *Borrelia* species mentioned herein below. In another preferred embodiment the present invention relates to one or more MHC-peptide complexes, wherein the sequence of one or more peptides is selected from the group consisting of *Borrelia anserine*, *Borrelia barbouri*, *Borrelia burgdorferi* such as burgdorferi B31, *Borrelia afzelii* such as *Borrelia afzelii* ACA-1, *Borrelia afzelii* K78 and/or *Borrelia afzelii* PKo, *Borrelia andersonii*, *Borrelia bissettii*, *Borrelia burgdorferi* 118a, *Borrelia burgdorferi* 156a, *Borrelia burgdorferi* 29805, *Borrelia burgdorferi* 64b, *Borrelia burgdorferi* 72a, *Borrelia burgdorferi* 80a, *Borrelia burgdorferi* 94a, *Borrelia burgdorferi* B31, *Borrelia burgdorferi* Bol26, *Borrelia burgdorferi* CA-11.2a, *Borrelia burgdorferi* WI91-23, *Borrelia burgdorferi* ZS7, *Borrelia californiensis*, *Borrelia garini* such as garini PBi, garini PBr, *Borrelia genomosp.* 1, *Borrelia genomosp.* 2, *Borrelia japonica*, *Borrelia lusitaniae*, *Borrelia spielmanii*, *Borrelia spielmanii* A14S, *Borrelia tanukii*, *Borrelia turdi*, *Borrelia valaisiana*, *Borrelia valaisiana* VS116, *Candidatus Borrelia texasensis*, *Borrelia* sp. AA4Pool, *Borrelia* sp. AI-1, *Borrelia* sp. B31, *Borrelia* sp. BC-1, *Borrelia* sp. CA1133, *Borrelia* sp. CA1176, *Borrelia* sp. CA128, *Borrelia* sp. CA13, *Borrelia* sp. CA134, *Borrelia* sp. CA142, *Borrelia* sp. CA20, *Borrelia* sp. CA22, *Borrelia* sp. CA27, *Borrelia* sp. CA28, *Borrelia* sp. CA29, *Borrelia* sp. CA31, *Borrelia* sp. CA33, *Borrelia* sp. CA370, *Borrelia* sp. CA372, *Borrelia* sp. CA378, *Borrelia* sp. CA388, *Borrelia* sp. CA393, *Borrelia* sp. CA394, *Borrelia* sp. CA395, *Borrelia* sp. CA399, *Borrelia* sp. CA400, *Borrelia* sp. CA401, *Borrelia* sp. CA402, *Borrelia* sp. CA404, *Borrelia* sp. CA411, *Borrelia* sp. CA426, *Borrelia* sp. CA443, *Borrelia* sp. CA446, *Borrelia* sp. CA448, *Borrelia* sp. CA462, *Borrelia* sp. CA468, *Borrelia* sp. CA502, *Borrelia* sp. CA504, *Borrelia* sp. CA507, *Borrelia* sp. CA547, *Borrelia* sp. CA552, *Borrelia* sp. CA8, *Borrelia* sp. D22, *Borrelia* sp. D35, *Borrelia* sp. FD-1, *Borrelia* sp. FL18, *Borrelia* sp. FL27, *Borrelia* sp. FL35, *Borrelia* sp. FL42, *Borrelia* sp. HN6, *Borrelia* sp. HN7, *Borrelia* sp. HN8, *Borrelia* sp. HNM13, *Borrelia* sp. HNM14, *Borrelia* sp. HNM19, *Borrelia* sp. IA1, *Borrelia* sp. Ir-3519, *Borrelia* sp. Ir-4721, *Borrelia* sp. Ir-4812, *Borrelia* sp. Ir-5215, *Borrelia* sp. LV5, *Borrelia* sp. MI-2, *Borrelia* sp. MI-5, *Borrelia* sp. MI-6, *Borrelia* sp. MI-8, *Borrelia* sp. MI-9, *Borrelia* sp. MOD-1, *Borrelia* sp. MOD-5, *Borrelia* sp. MOK-3a, *Borrelia* sp. MOS-1b, *Borrelia* sp. NE49, *Borrelia* sp. NE581, *Borrelia* sp. PHaP, *Borrelia* sp. PSigII, *Borrelia* sp. SCGT-10, *Borrelia* sp. SCGT-8a, *Borrelia* sp. SCI-2, *Borrelia* sp. SCW-30h, *Borrelia* sp. SI-1, *Borrelia* sp. SI-10, *Borrelia* sp. SM-1, *Borrelia* sp. SV1, *Borrelia* sp. W97F51, *Borrelia* sp. Z41293, *Borrelia* sp. Z41493, *Borrelia coriaceae*, *Borrelia crocidurae*, *Borrelia duttonii*, *Borrelia duttonii* Ly, *Borrelia hermsii*, *Borrelia hermsii* DAH, *Borrelia hispanica*, *Borrelia lonestari*, *Borrelia miyamotoi*, *Borrelia parkeri*, *Borrelia persica*, *Borrelia recurrentis*, *Borrelia recurrentis* A1, *Borrelia sinica*, *Borrelia theileri*, *Borrelia turcica*, *Borrelia turicatae*, *Borrelia turicatae* 91E135, *Borrelia* sp., *Borrelia* sp. 'Lake Gaillard', *Borrelia* sp. 000133, *Borrelia* sp. 010298, *Borrelia* sp. 10MT, *Borrelia* sp. 5145, *Borrelia* sp. 57Nsk, *Borrelia* sp. 5MT, *Borrelia* sp. 6T04-2, *Borrelia* sp. BR, *Borrelia* sp. BR 2007, *Borrelia* sp. C5-N52, *Borrelia* sp. CB-A1, *Borrelia* sp. CB-A11, *Borrelia* sp. CB-A3, *Borrelia* sp. EFL-S0100110, *Borrelia* sp. IK/23, *Borrelia* sp. IM/16, *Borrelia* sp. IM/19, *Borrelia* sp. KR1, *Borrelia* sp. KR3, *Borrelia* sp. LB-2001, *Borrelia* sp. LB-M56, *Borrelia* sp. LB-W100, *Borrelia* sp. MK-N61, *Borrelia* sp. NR-N8, *Borrelia* sp. OkME1, *Borrelia* sp. PAnz, *Borrelia* sp. PJes, *Borrelia* sp. PMai, *Borrelia* sp. PMew, *Borrelia* sp. R57, *Borrelia* sp. strain Spain, *Borrelia* sp. TA1, *Borrelia* sp. TM, *Borrelia* sp. TM1 and *Borrelia* sp. TM2.

Lyme Disease (Borreliosis)

*Borrelia burgdorferi* is species of bacteria of the spirochete class of the genus *Borrelia*. *B. burgdorferi* is predominant in North America, but also exists in Europe, and is the agent of Lyme disease.

Lyme disease, or borreliosis, is an emerging infectious disease caused by at least three species of bacteria belonging to the genus *Borrelia*. *Borrelia burgdorferi* is the predominant cause of Lyme disease in the United States, whereas *Borrelia afzelii* and *Borrelia garinii* are implicated in most European cases.

Lyme disease is the most common tick-borne disease in the Northern Hemisphere. *Borrelia* is transmitted to humans by the bite of infected hard ticks belonging to several species of the genus *Ixodes*. Early manifestations of infection may include fever, headache, fatigue, and a characteristic skin rash called erythema migrans. Left untreated, late manifestations involving the joints, heart, and nervous system can occur. In a majority of cases, symptoms can be eliminated with antibiotics, especially if diagnosis and treatment occur early in the course of illness. Late, delayed, or inadequate treatment can lead to late manifestations of Lyme disease which can be disabling and difficult to treat.

Some groups have argued that "chronic" Lyme disease is responsible for a range of medically unexplained symptoms beyond the objectively recognized manifestations of late Lyme disease, and that long-term antibiotic treatment is warranted in such cases. However, a series of randomized controlled trials found no significant benefit from prolonged antibiotic treatment in such patients, and most expert groups including the Infectious Diseases Society of America and the American Academy of Neurology have found that existing scientific evidence does not support a role for *Borrelia* nor ongoing antibiotic treatment in such cases.

Symptoms of Lyme Disease

Lyme disease can affect multiple body systems, producing a range of potential symptoms. Not all patients with Lyme disease will have all symptoms, and many of the symptoms are not specific to Lyme disease but can occur in other diseases as well. The incubation period from infection to the onset of symptoms is usually 1-2 weeks, but can be much shorter (days), or much longer (months to years). Symptoms most often occur from May through September because the nymphal stage of the tick is responsible for most cases. Asymptomatic infection exists but is found in less than 7% of infected individuals in the United States. Asymptomatic infection may be much more common among those infected in Europe.

Stage 1—Early Localized Infection

The classic sign of early local infection is a circular, outwardly expanding rash called erythema chronicum migrans (also erythema migrans or EM), which occurs at the site of the tick bite 3 to 32 days after being bitten. The rash is red, and may be warm, but is generally painless. Classically, the innermost portion remains dark red and becomes indurated; the outer edge remains red; and the portion in between clears—giving the appearance of a bullseye. However, the partial clearing is uncommon, and thus a true bullseye occurs in as few as 9% of cases.

Erythema migrans is thought to occur in about 80% of infected patients. Patients can also experience flu-like symptoms such as headache, muscle soreness, fever, and malaise.

Lyme disease can progress to later stages even in patients who do not develop a rash.

Stage 2—Early Disseminated Infection

Within days to weeks after the onset of local infection, the *borrelia* bacteria may begin to spread through the bloodstream. Erythema migrans may develop at sites across the body that bear no relation to the original tick bite. Other discrete symptoms include loss of muscle tone on one or both sides of the face (called facial or Bell's palsy), severe headaches and neck stiffness, shooting pains that may interfere with sleep, heart palpitations and dizziness caused by changes in heartbeat, and migrating joint pains. Some of these symptoms may resolve, even without treatment.

Stage 3—Late Persistent Infection

After several months, untreated or inadequately treated patients may go on to develop severe and chronic symptoms affecting many organs of the body including the brain, nerves, eyes, joints and heart. Shooting pains, numbness or tingling in the hands or feet, problems with concentration and short term memory, severe weakness, vision problems, intolerance to sound and touch, Vertigo, back pain, heart block, psychiatric disorders, and swelling of joints are just some of the myriad disabling symptoms that can occur.

Other less common findings in acute Lyme disease include cardiac manifestations (up to 10% of patients may have cardiac manifestations including heart block and palpitations, and neurologic symptoms (neuroborreliosis may occur in up to 18%). In addition, simple altered mental status as the sole presenting symptom has been reported in early neuroborreliosis. Patients have been known to get Baker's cysts.

Chronic symptoms: Cases may progress to a chronic form most commonly characterized by meningoencephalitis, cardiac inflammation (myocarditis), frank arthritis, and fatigue. Chronic Lyme disease can have a multitude of symptoms affecting numerous physiological systems: the symptoms appear heterogeneous in the affected population, which may be caused by innate immunity or variations in *Borrelia* bacteria. Late symptoms of Lyme disease can appear months or years after initial infection and often progress in cumulative fashion over time. Neuropsychiatric symptoms often develop much later in the disease progression, much like tertiary neurosyphilis.

In addition to the acute symptoms, chronic Lyme disease can be manifested by a wide-range of neurological disorders, either central or peripheral, including encephalitis or encephalomyelitis, muscle twitching, heightened sensitivity to touch, sound and light, paralysis polyneuropathy or paresthesia, and vestibular symptoms or other otolaryngologic symptoms, among others. Neuropsychiatric disturbances can occur (possibly from a low-level encephalitis), which may lead to symptoms of memory loss, sleep disturbances, or changes in mood or affect. In rare cases, frank psychosis has been attributed to chronic Lyme disease effects, including mis-diagnoses of schizophrenia and bipolar disorder. Panic attack and anxiety can occur, also delusional behavior, including somatoform delusions, sometimes accompanied by a depersonalization or derealization syndrome similar to what was seen in the past in the prodromal or early stages of general paresis.

Cause of Lyme Disease

Lyme disease is caused by Gram-negative spirochetal bacteria from the genus *Borrelia*. At least 11 *Borrelia* species have been described, 3 of which are Lyme related. The *Borrelia* species known to cause Lyme disease are collectively known as *Borrelia burgdorferi* sensu lato, and have been found to have greater strain diversity than previously estimated.

Three closely-related species of spirochetes are well-established as causing Lyme disease and are probably responsible for the large majority of cases: *B. burgdorferi* sensu stricto (predominant in North America, but also in Europe), *B. afzelii*, and *B. garinii* (both predominant in Eurasia). Some studies have also proposed that *B. bissettii* and *B. valaisiana* may sometimes infect humans, but these species do not seem to be important causes of disease.

Diagnosis of Lyme Disease

Lyme disease is diagnosed clinically based on symptoms, objective physical findings (such as erythema migrans, facial palsy, or arthritis), a history of possible exposure to infected ticks, as well as serological tests.

When making a diagnosis of Lyme disease, health care providers should consider other diseases that may cause similar illness. Not all patients with Lyme disease will develop the characteristic bulls-eye rash, and many may not recall a tick bite. Laboratory testing is not recommended for persons who do not have symptoms of Lyme disease.

Because of the difficulty in culturing *Borrelia* bacteria in the laboratory, diagnosis of Lyme disease is typically based on the clinical exam findings and a history of exposure to endemic Lyme areas. The EM rash, which does not occur in all cases, is considered sufficient to establish a diagnosis of Lyme disease even when serologies are negative. Serological testing can be used to support a clinically suspected case but is not diagnostic. Clinicians who diagnose strictly based on the CDC Case Definition for Lyme may be in error, since the CDC explicitly states that this definition is intended for surveillance purposes only and is "not intended to be used in clinical diagnosis. Diagnosis of late-stage Lyme disease is often difficult because of the multi-faceted appearance which can mimic symptoms of many other diseases. For this reason, Lyme has often been called the new "great imitator". Lyme disease may be misdiagnosed as multiple sclerosis, rheumatoid arthritis, fibromyalgia, chronic fatigue syndrome (CFS), lupus, or other autoimmune and neurodegenerative diseases.

Laboratory Testing

Several forms of laboratory testing for Lyme disease are available, some of which have not been adequately validated. Most recommended tests are blood tests that measure antibodies made in response to the infection. These tests may be falsely negative in patients with early disease, but they are quite reliable for diagnosing later stages of disease.

The serological laboratory tests most widely available and employed are the Western blot and ELISA. A two-tiered protocol is recommended by the CDC: the more sensitive ELISA is performed first, if it is positive or equivocal, the more specific Western blot is run. The reliability of testing in diagnosis remains controversial, however studies show the Western blot IgM has a specificity of 94-96% for patients with clinical symptoms of early Lyme disease.

Erroneous test results have been widely reported in both early and late stages of the disease. These errors can be caused by several factors, including antibody cross-reactions from other infections including Epstein-Barr virus and cytomegalovirus, as well as herpes simplex virus.

Polymerase chain reaction (PCR) tests for Lyme disease have also been developed to detect the genetic material (DNA) of the Lyme disease spirochete. PCR tests are susceptible to false-positive results from poor laboratory technique. Even when properly performed, PCR often shows false-negative results with blood and CSF specimens. Hence PCR is not widely performed for diagnosis of Lyme disease. However PCR may have a role in diagnosis of Lyme arthritis because it is highly sensitive in detecting ospA DNA in synovial fluid. With the exception of PCR, there is no currently practical means for detection of the presence of the organism, as serologic studies only test for antibodies of *Borrelia*. High titers of either immunoglobulin G (IgG) or immunoglobulin M (IgM) antibodies to *Borrelia* antigens indicate disease, but lower titers can be misleading. The IgM antibodies may remain after the initial infection, and IgG antibodies may remain for years.

Western blot, ELISA and PCR can be performed by either blood test via venipuncture or cerebrospinal fluid (CSF) via lumbar puncture. Though lumbar puncture is more definitive of diagnosis, antigen capture in the CSF is much more elusive; reportedly CSF yields positive results in only 10-30% of patients cultured. The diagnosis of neurologic infection by *Borrelia* should not be excluded solely on the basis of normal routine CSF or negative CSF antibody analyses.

New techniques for clinical testing of *Borrelia* infection have been developed, such as LTT-MELISA, which is capable of identifying the active form of *Borrelia* infection (Lyme disease). Others, such as focus floating microscopy, are under investigation. New research indicates chemokine CXCL13 may also be a possible marker for neuroborreliosis.

Some laboratories offer Lyme disease testing using assays whose accuracy and clinical usefulness have not been adequately established. These tests include urine antigen tests, immunofluorescent staining for cell wall-deficient forms of *Borrelia burgdorferi*, and lymphocyte transformation tests. In general, CDC does not recommend these tests.

Imaging

Single photon emission computed tomography (SPECT) imaging has been used to look for cerebral hypoperfusion indicative of Lyme encephalitis in the patient. Although SPECT is not a diagnostic tool itself, it may be a useful method of determining brain function.

In Lyme disease patients, cerebral hypoperfusion of frontal subcortical and cortical structures has been reported. In about 70% of chronic Lyme disease patients with cognitive symptoms, brain SPECT scans typically reveal a pattern of global hypoperfusion in a heterogeneous distribution through the white matter. This pattern is not specific for Lyme disease, since it can also be seen in other central nervous system (CNS) syndromes such as HIV encephalopathy, viral encephalopathy, chronic cocaine use, and vasculitides. However, most of these syndromes can be ruled out easily through standard serologic testing and careful patient history taking.

The presence of global cerebral hypoperfusion deficits on SPECT in the presence of characteristic neuropsychiatric features should dramatically raise suspicion for Lyme encephalopathy among patients who inhabit or have traveled to endemic areas, regardless of patient recall of tick bites. Late disease can occur many years after initial infection. The average time from symptom onset to diagnosis in these patients is about 4 years. Because seronegative disease can occur, and because CSF testing is often normal, Lyme encephalopathy often becomes a diagnosis of exclusion: once all other possibilities are ruled out, Lyme encephalopathy becomes ruled in. Although the aberrant SPECT patterns are caused by cerebral vasculitis, a vasculitide, brain biopsy is not commonly performed for these cases as opposed to other types of cerebral vasculitis.

Abnormal magnetic resonance imaging (MRI) findings are often seen in both early and late Lyme disease. MRI scans of patients with neurologic Lyme disease may demonstrate punctuated white matter lesions on T2-weighted images, similar to those seen in demyelinating or inflammatory disorders such as multiple sclerosis, systemic lupus erythematosus (SLE), or cerebrovascular disease. Cerebral atrophy and brainstem neoplasm has been indicated with Lyme infection as well.

Diffuse white matter pathology can disrupt these ubiquitous gray matter connections and could account for deficits in attention, memory, visuospatial ability, complex cognition, and emotional status. White matter disease may have a greater potential for recovery than gray matter disease, perhaps because neuronal loss is less common.

Spontaneous remission can occur in multiple sclerosis, and resolution of MRI white matter hyper-intensities, after antibiotic treatment, has been observed in Lyme disease.

Lyme Vaccine

After a decade of research, and pressure from patient advocates and Congress, the FDA licensed the first vaccine for Lyme borreliosis on Dec. 21, 1998. The vaccine, called Lymerix, was derived from a recombinant version of the bacterium's OspA lipoprotein. Lymerix was intended for "at-risk" individuals between the ages of 15 and 70 years. Given in three separate injections, the vaccine appeared to be effective in preventing infections. However, on Feb. 26, 2002, GlaxoSmithKline, the maker of the Lyme vaccine "LYMErix", pulled the vaccine off the market.

Prevention of Lyme Disease

For prevention of Lyme disease after a recognized tick bite, routine use of antimicrobial prophylaxis or serologic testing is not recommended (E-III). A single dose of doxycycline may be offered to adult patients (200 mg dose) and to children years of age (4 mg/kg up to a maximum dose of 200 mg) (B-I) when all of the following circumstances exist: (a) the attached tick can be reliably identified as an adult or nymphal . scapularis tick that is estimated to have been attached for h on the basis of the degree of engorgement of the tick with blood or of certainty about the time of exposure to the tick; (b) prophylaxis can be started within 72 h of the time that the tick was removed; (c) ecologic information indicates that the local rate of infection of these ticks with *B. burgdorferi* is ≥20%; and (d) doxycycline treatment is not contraindicated. The time limit of 72 h is suggested because of the absence of data on the efficacy of chemoprophylaxis for tick bites following tick removal after longer time intervals.

Treatment of Lyme Disease

1) Erythema Migrans

Doxycycline (100 mg twice per day), amoxicillin (500 mg 3 times per day), or cefuroxime axetil (500 mg twice per day) for 14 days (range, 10-21 days for doxycycline and 14-21 days for amoxicillin or cefuroxime axetil) is recommended for the treatment of adult patients with early localized or early disseminated Lyme disease associated with erythema migrans, in the absence of specific neurologic manifestations (see Lyme meningitis, below) or advanced atrioventricular heart block (A-I). Each of these antimicrobial agents has been shown to be highly effective for the treatment of erythema migrans and associated symptoms in prospective studies. Doxycycline has the advantage of being effective for treatment of HGA (but not for babesiosis), which may occur simultaneously with early Lyme disease. Doxycycline is relatively contraindicated during pregnancy or lactation and in children <8 years of age. Antibiotics recommended for children are amoxicillin (50 mg/kg per day in 3 divided doses [maximum of 500 mg per dose]), cefuroxime axetil (30 mg/kg per day in 2 divided doses [maximum of 500 mg per dose]), or, if the patient is ≥8 years of age, doxycycline (4 mg/kg per day in 2 divided doses [maximum of 100 mg per dose]) (A-II). Macrolide antibiotics are not recommended as first-line therapy for early Lyme disease, because those macrolides that have been compared with other antimicrobials in clinical trials have been found to be less effective (E-I). When used, they should be reserved for patients who are intolerant of, or should not take, amoxicillin, doxycycline, and cefuroxime axetil. For adults with these limitations, recommended dosage regimens for macrolide antibiotics are as follows: azithromycin, 500 mg orally per day for 7-10 days; clarithromycin, 500 mg orally twice per day for 14-21 days (if the patient is not pregnant); or erythromycin, 500 mg orally 4 times per day for 14-21 days. The recommended dosages of these agents for children are as follows: azithromycin, 10 mg/kg per day (maximum of 500 mg per day); clarithromycin, 7.5 mg/kg twice per day (maximum of 500 mg per dose); or erythromycin, 12.5 mg/kg 4 times per day (maximum of 500 mg per dose). Patients treated with macrolides should be closely observed to ensure resolution of the clinical manifestations.

First-generation cephalosporins, such as cephalexin, are ineffective for treatment of Lyme disease and should not be used (E-II). When erythema migrans cannot be reliably distinguished from community-acquired bacterial cellulitis, a reasonable approach is to treat with either cefuroxime axetil or amoxicillin-clavulanic acid (dosage of amoxicillin-clavulanic acid for adults, 500 mg 3 times per day; dosage for children, 50 mg/kg per day in 3 divided doses [maximum of 500 mg per dose]), because these antimicrobials are generally effective against both types of infection (A-III).

Ceftriaxone, while effective, is not superior to oral agents and is more likely than the recommended orally administered antimicrobials to cause serious adverse effects. Therefore, ceftriaxone is not recommended for treatment of patients with early Lyme disease in the absence of neurologic involvement or advanced atrioventricular heart block (E-I).

2) Lyme Meningitis and Other Manifestations of Early Neurologic Lyme Disease.

The use of ceftriaxone (2 g once per day intravenously for 14 days; range, 10-28 days) in early Lyme disease is recommended for adult patients with acute neurologic disease manifested by meningitis or radiculopathy (B-I). Parenteral therapy with cefotaxime (2 g intravenously every 8 h) or penicillin G (18-24 million Upper day for patients with normal renal function, divided into doses given every 4 h), may be a satisfactory alternative (B-I). For patients who are intolerant of β-lactam antibiotics, increasing evidence indicates that doxycycline (200-400 mg per day in 2 divided doses orally for 10-28) days may be adequate (B-I). Doxycycline is well absorbed orally; thus, intravenous administration should only rarely be needed.

For children, ceftriaxone (50-75 mg/kg per day) in a single daily intravenous dose (maximum, 2 g) (B-I) is recommended. An alternative is cefotaxime (150-200 mg/kg per day) divided into 3 or 4 intravenous doses per day (maximum, 6 g per day) (B-II) or penicillin G (200,000-400,000 units/kg per day; maximum, 18-24 million Upper day) divided into doses given intravenously every 4 h for those with normal renal function (B-I). Children 8 years of age have also been successfully treated with oral doxycycline at a dosage of 4-8 mg/kg per day in 2 divided doses (maximum, 100-200 mg per dose) (B-II).

Although antibiotic treatment may not hasten the resolution of seventh cranial nerve palsy associated with *B. burgdorferi* infection, antibiotics should be given to prevent further sequelae (A-II). Cranial nerve palsies in patients with Lyme disease are often associated with a lymphocytic CSF pleocytosis, with or without symptoms of meningitis. Panel members differed in their approach to the neurologic evaluation of patients with Lyme disease-associated seventh cranial nerve palsy. Some perform a CSF examination on all such patients. Others do not because of the good clinical response with orally administered antibiotics (even in the presence of CSF pleocytosis) and the absence of evidence of recurrent CNS disease in these patients. There was agreement that lumbar puncture is indicated for those in whom there is strong clinical suspicion of CNS involvement (e.g., severe or prolonged headache or nuchal rigidity). Patients with normal CSF examination findings and those for whom CSF examination is deemed unnecessary because of lack of clinical signs of meningitis may be treated with a 14-day course (range, 14-21 days) of the same antibiotics used for patients with erythema migrans (see above) (B-III). Those with both clinical and laboratory evidence of CNS involvement should be treated with regimens effective for Lyme meningitis, as described above (B-III).

3) Lyme Carditis

Patients with atrioventricular heart block and/or myopericarditis associated with early Lyme disease may be treated with either oral or parenteral antibiotic therapy for 14 days (range, 14-21 days). Hospitalization and continuous monitoring are advisable for symptomatic patients, such as those with syncope, dyspnea, or chest pain. It is also recommended for patients with second- or third-degree atrioventricular block, as well as for those with first-degree heart block when the PR interval is prolonged to ≥30 milliseconds, because the degree of block may fluctuate and worsen very rapidly in such patients.

A parenteral antibiotic, such as ceftriaxone, is recommended as initial treatment of hospitalized patients (see recommendations for treatment of Lyme meningitis above) (B-III). For patients with advanced heart block, a temporary pacemaker may be required; expert consultation with a cardiologist is recommended. Use of the pacemaker may be discontinued when the advanced heart block has resolved. An oral antibiotic treatment regimen should be used for completion of therapy and for outpatients, as is used for patients with erythema migrans without carditis (see above) (B-III).

4) Borrelial Lymphocytoma.

Available data indicate that borrelial lymphocytoma may be treated with the same regimens used to treat patients with erythema migrans (see above) (B-II).

5) Lyme Arthritis.

Lyme arthritis can usually be treated successfully with antimicrobial agents administered orally. Doxycycline (100 mg twice per day) (B-I), amoxicillin (500 mg 3 times per day) (B-I), or cefuroxime axetil (500 mg twice per day) (B-III) for 28 days is recommended for adult patients without clinical evidence of neurologic disease. For children, amoxicillin (50 mg/kg per day in 3 divided doses [maximum of 500 mg per dose]) (B-I), cefuroxime axetil (30 mg/kg per day in 2 divided doses [maximum of 500 mg per dose]) (B-III), or, if the patient is ≥8 years of age, doxycycline (4 mg/kg per day in 2 divided doses [maximum of 100 mg per dose]) (B-I) is recommended. Oral antibiotics are easier to administer than intravenous antibiotics, are associated with fewer serious complications, and are considerably less expensive. However, it is important to recognize that a small number of patients treated with oral agents have subsequently manifested overt neuroborreliosis, which may require intravenous therapy with a β-lactam antibiotic (see the paragraph below) for successful resolution. Further controlled trials are needed to compare the safety and efficacy of oral versus intravenous therapy for Lyme arthritis.

Neurologic evaluation that may include lumbar puncture should be performed for patients in whom there is a clinical suspicion of neurologic involvement. Adult patients with arthritis and objective evidence of neurologic disease should receive parenteral therapy with ceftriaxone (A-II) for 2-4 weeks. Cefotaxime or penicillin G administered parenterally is an acceptable alternative (B-II). For children, intravenous ceftriaxone or intravenous cefotaxime is recommended (B-III); penicillin G administered intravenously is an alternative (B-III). See the recommendations above for treatment of patients with Lyme meningitis for suggested doses of each of these antimicrobials.

For patients who have persistent or recurrent joint swelling after a recommended course of oral antibiotic therapy, we recommend re-treatment with another 4-week course of oral antibiotics or with a 2-4-week course of ceftriaxone IV (B-III) (for dosages of oral agents, see the recommendations above for treatment of erythema migrans, and for dosages of parenteral agents, see the recommendations above for treatment of Lyme meningitis). A second 4-week course of oral antibiotic therapy is favored by panel members for the patient whose arthritis has substantively improved but has not yet completely resolved, reserving intravenous antibiotic therapy for those patients whose arthritis failed to improve at all or worsened. Clinicians should consider waiting several months before initiating re-treatment with antimicrobial agents because of the anticipated slow resolution of inflammation after treatment. If patients have no resolution of arthritis despite intravenous therapy and if PCR results for a sample of synovial fluid (and synovial tissue if available) are negative, symptomatic treatment is recommended (B-III). Symptomatic therapy might consist of nonsteroidal anti-inflammatory agents, intra-articular injections of corticosteroids, or disease-modifying antirheumatic drugs (DMARDs), such as hydroxychloroquine; expert consultation with a rheumatologist is recommended. If persistent synovitis is associated with significant pain or limitation of function, arthroscopic synovectomy may reduce the duration of joint inflammation (B-II).

6) Late Neurologic Lyme Disease.

Adult patients with late neurologic disease affecting the central or peripheral nervous system should be treated with intravenous ceftriaxone for 2 to 4 weeks (B-II).

Cefotaxime or penicillin G administered intravenously is an alternative (B-II). Response to treatment is usually slow and may be incomplete. Re-treatment is not recommended unless relapse is shown by reliable objective measures. Ceftriaxone is also recommended for children with late neurologic Lyme disease (B-II). Cefotaxime or penicillin G administered intravenously is an alternative (B-III). See the recommendations above on the treatment of Lyme meningitis for suggested doses of each of these antimicrobials.

7) Acrodermatitis Chronica Atrophicans.

Available data indicate that acrodermatitis chronica atrophicans may be treated with a 21-day course of the same antibiotics (doxycycline [B-II], amoxicillin [B-II], and cefuroxime axetil [B-III]) used to treat patients with erythema migrans (see above). A controlled study is warranted to compare oral with parenteral antibiotic therapy for the treatment of acrodermatitis chronica atrophicans.

8) Coinfection.

Coinfection with *B. microti* or *A. phagocytophilum* or both may occur in patients with early Lyme disease (usually in patients with erythema migrans) in geographic areas where these pathogens are endemic. Coinfection should be considered in patients who present with more-severe initial symptoms than are commonly observed with Lyme disease alone, especially in those who have high-grade fever for >48 h, despite receiving antibiotic therapy appropriate for Lyme disease, or who have unexplained leukopenia, thrombocytopenia, or anemia (A-III). Coinfection might also be considered in the situation in which there has been resolution of the erythema migrans skin lesion but either no improvement or worsening of viral infection-like symptoms (B-III).

Post-Lyme Disease Syndromes

There is no well-accepted definition of post-Lyme disease syndrome. This has contributed to confusion and controversy and to a lack of firm data on its incidence, prevalence, and pathogenesis. In an attempt to provide a framework for future research on this subject and to reduce diagnostic ambiguity in study populations, a definition for post-Lyme disease syndrome is proposed in these guidelines. Whatever definition is eventually adopted, having once had objective evidence of *B. burgdorferi* infection must be a condition sine qua non. Furthermore, when laboratory testing is done to support the original diagnosis of Lyme disease, it is essential that it be performed by well-qualified and reputable laboratories that use recommended and appropriately validated testing methods and interpretive criteria. Unvalidated test methods (such as urine antigen tests or blood microscopy for *Borrelia* species) should not be used. There is no convincing biologic evidence for the existence of symptomatic chronic *B. burgdorferi* infection among patients after receipt of recommended treatment regimens for Lyme disease. Antibiotic therapy has not proven to be useful and is not recommended for patients with chronic (≥6 months) subjective symptoms after recommended treatment regimens for Lyme disease (E-I).

Therapeutic modalities not recommended. Because of a lack of biologic plausibility, lack of efficacy, absence of supporting data, or the potential for harm to the patient, the following are not recommended for treatment of patients with any manifestation of Lyme disease: first-generation cephalosporins, fluoroquinolones, carbapenems, vancomycin, metronidazole, tinidazole, amantadine, ketolides, isoniazid, trimethoprim-sulfamethoxazole, fluconazole, benzathine penicillin G, combinations of antimicrobials, pulsed-dosing (i.e., dosing on some days but not others), long-term antibiotic therapy, anti-*Bartonella* therapies, hyperbaric oxygen, ozone, fever therapy, intravenous immunoglobulin, cholestyramine, intravenous hydrogen peroxide, specific nutritional supplements, and others (E-III).

Erythema Chronicum Migrans

Erythema chronicum migrans refers to the rash often (though not always) seen in the early stage of Lyme disease. It can appear anywhere from one day to one month after a tick bite. This rash does not represent an allergic reaction to the bite, but rather an actual skin infection with the Lyme bacteria, *Borrelia burgdorferi* sensu lato. It is a pathognomonic sign: a physician-identified rash warrants an instant diagnosis of Lyme disease and immediate treatment without further testing, even by the strict criteria of the Centers for Disease Control. These rashes are characteristic of *Borrelia* infections and no other pathogens are known that cause this form of rash.

It is also sometimes called erythema migrans (without the "chronicum") or "EM". However, this phrase is also used to describe geographic tongue.

Tuberculosis

Tuberculosis (abbreviated as TB for tubercle *bacillus* or Tuberculosis) is a common and deadly infectious disease caused by mycobacteria, mainly *Mycobacterium tuberculosis*. Tuberculosis most commonly attacks the lungs (as pulmonary TB) but can also affect the central nervous system, the lymphatic system, the circulatory system, the genitourinary system, bones, joints and even the skin. Other mycobacteria such as *Mycobacterium bovis, Mycobacterium africanum, Mycobacterium canetti*, and *Mycobacterium microti* can also cause tuberculosis, but these species do not usually infect healthy adults.

One third of the world's current population has been infected by TB. Not everyone infected develops the full-blown disease; asymptomatic, latent infection is most common. However, one in ten latent infections will progress to active disease, which, if left untreated, kills more than half of its victims.

The rise in HIV infections and the neglect of TB control programs have enabled a resurgence of tuberculosis. The emergence of drug-resistant strains has also contributed to this new epidemic with, from 2000 to 2004, 20% of TB cases being resistant to standard treatments and 2% resistant to second-line drugs. TB incidence varies widely, even in neighboring countries, apparently because of differences in health care systems.

The present invention relates in one embodiment to diagnosis and/or treatment of one or more diseases caused by a bacteria species such as one of the bacteria species mentioned herein below or in the items, including mycobacteria.

In another preferred embodiment the present invention relates to diagnosis and/or treatment of a disease caused by a bacteria species such as mycobacterium using one or more MHC-peptide complexes comprising one or more peptides comprising one or more sequences from one or more bacteria species such as mycobacterium, including the ones mentioned elsewhere and/or in the items.

Symptoms

When the disease becomes active, 75% of the cases are pulmonary TB. Symptoms include chest pain, coughing up blood, and a productive, prolonged cough for more than three weeks. Systemic symptoms include fever, chills, night sweats, appetite loss, weight loss, pallor, and often a tendency to fatigue very easily.

In the other 25% of active cases, the infection moves from the lungs, causing other kinds of TB more common in immunosuppressed persons and young children. Extrapulmonary infection sites include the pleura, the central nervous system in meningitis, the lymphatic system in scrofula of the neck, the genitourinary system in urogenital tuberculosis, and bones and joints in Pott's disease of the spine. An especially serious form is disseminated TB, more commonly known as miliary tuberculosis. Although extrapulmonary TB is not contagious, it may co-exist with pulmonary TB, which is contagious.

Bacterial Species

The primary cause of TB is *Mycobacterium tuberculosis* (MTB). Using histological stains on expectorate samples from phlegm (also called sputum), scientists can identify MTB under a regular microscope. Since MTB retains certain stains after being treated with acidic solution, it is classified as an acid-fast *bacillus* (AFB). The most common staining technique, the Ziehl-Neelsen stain, dyes AFBs a bright red that stands out clearly against a blue background. Other ways to visualize AFBs include an auramine-rhodamine stain and fluorescent microscopy. The *M. tuberculosis* complex includes three other TB-causing mycobacteria: *M. bovis, M. africanum* and *M. microti*. The first two only very rarely cause disease in immunocompetent people. On the other hand, although *M. microti* is not usually pathogenic, it is possible that the prevalence of *M. microti* infections has been underestimated.

Diagnosis

Tuberculosis can be a difficult disease to diagnose, mainly due to the difficulty in culturing this slow-growing organism in the laboratory (4-12 weeks for blood culture). A complete medical evaluation for TB must include a medical history, a chest X-ray, and a physical examination. Tuberculosis radiology is used in the diagnosis of TB. It may also include a tuberculin skin test, a serological test, microbiological smears and cultures. The interpretation of the tuberculin skin test depends upon the person's risk factors for infection and progression to TB disease, such as exposure to other cases of TB or immunosuppression.

Currently, latent infection is diagnosed in a non-immunized person by a tuberculin skin test, which yields a delayed hypersensitivity type response to an extract made from *M. tuberculosis*. Those immunized for TB or with past-cleared infection will respond with delayed hypersensitivity parallel to those currently in a state of infection, so the test must be used with caution, particularly with regard to persons from countries where TB immunization is common. New TB tests are being developed that offer the hope of cheap, fast and more accurate TB testing. These use polymerase chain reaction detection of bacterial DNA and antibody assays to detect the release of interferon gamma in response to mycobacteria. These tests are not affected by immunization, so generate fewer false positive results. Rapid and inexpensive diagnosis will be particularly valuable in the developing world.

Treatment

Treatment for TB uses antibiotics to kill the bacteria. The two antibiotics most commonly used are rifampin and isoniazid. However, instead of the short course of antibiotics typically used to cure other bacterial infections, TB requires much longer periods of treatment (around 6 to 12 months) to entirely eliminate mycobacteria from the body. Latent TB treatment usually uses a single antibiotic, while active TB disease is best treated with combinations of several antibiotics, to reduce the risk of the bacteria developing antibiotic resistance. People with latent infections are treated to prevent them from progressing to active TB disease later in life.

Drug resistant tuberculosis is transmitted in the same way as regular TB. Primary resistance occurs in persons who are infected with a resistant strain of TB. A patient with fully-susceptible TB develops secondary resistance (acquired resistance) during TB therapy because of inadequate treatment, not taking the prescribed regimen appropriately, or using low quality medication. Drug-resistant TB is a public health issue in many developing countries, as treatment is longer and requires more expensive drugs. Multi-drug resistant TB (MDR-TB) is defined as resistance to the two most effective first line TB drugs: rifampin and isoniazid. Extensively drug-resistant TB (XDR-TB) is also resistant to three or more of the six classes of second-line drugs.

One standard therapy for active TB consists of a 6-month regimen:
  2 months with Rifater (isoniazid, rifampin, and pyrazinamide)
  4 months of isoniazid and rifampin (Rifamate, Rimactane)

Ethambutol (Myambutol) or streptomycin added until your drug sensitivity is known Treatment takes that long because the disease organisms grow very slowly and, unfortunately, also die very slowly.

Recommended Treatment Regimens

There are four recommended regimens for treating patients with tuberculosis caused by drug-susceptible organisms. Although these regimens are broadly applicable, there are modifications that should be made under specified circumstances, described subsequently. Each regimen has an initial phase of 2 months followed by a choice of several options for the continuation phase of either 4 or 7 months.
  First line drug:
    Isoniazid, rifampin, rifabutin, rifapentine, pyrazinamide, ethambutol,
  Second line drug:
    Cycloserine, ethionamide, streptomycin, amikacin/kanamycin, capreomycin, p-aminosalicylic acid (PAS), levofloxacin, moxifloxacin, gatifloxacin Because of the relatively high proportion of adult patients with tuberculosis caused by organisms that are resistant to isoniazid, four drugs are necessary in the initial phase for the 6-month regimen to be maximally effective. Thus, in most circumstances, the treatment regimen for all adults with previously untreated tuberculosis should consist of a 2-month initial phase of isoniazid (INH), rifampin (RIF), pyrazinamide (PZA), rifapentine (RPT) and ethambutol (EMB). If (when) drug susceptibility test results are known and the organisms are fully susceptible, EMB need not be included. For children whose visual acuity cannot be monitored, EMB is usually not recommended except when there is an increased likelihood of the disease being caused by INH-resistant organisms or when the child has "adult-type" (upper lobe infiltration, cavity formation) tuberculosis. If PZA cannot be included in the initial phase of treatment, or if the isolate is resistant to PZA alone (an unusual circumstance), the initial phase should consist of INH, RIF, and EMB given daily for 2 months (Regimen 4). Examples of circumstances in which PZA may be withheld include severe liver disease, gout, and, perhaps, pregnancy. EMB should be included in the initial phase of Regimen 4 until drug susceptibility is determined.

The initial phase may be given daily throughout, daily for 2 weeks and then twice weekly for 6 weeks, or three times weekly throughout. For patients receiving daily therapy, EMB can be discontinued as soon as the results of drug susceptibility studies demonstrate that the isolate is susceptible to INH and RIF. When the patient is receiving less than daily drug administration, expert opinion suggests that EMB can be discontinued safely in less than 2 months (i.e., when susceptibility test results are known), but there is no evidence to support this approach.

Although clinical trials have shown that the efficacy of streptomycin (SM) is approximately equal to that of EMB in the initial phase of treatment, the increasing frequency of resistance to SM globally has made the drug less useful. Thus, SM is not recommended as being interchangeable with EMB unless the organism is known to be susceptible to the drug or the patient is from a population in which SM resistance is unlikely.

The continuation phase of treatment is given for either 4 or 7 months. The 4-month continuation phase should be used in the large majority of patients. The 7-month continuation phase is recommended only for three groups: patients with cavitary pulmonary tuberculosis caused by drug-susceptible organisms and whose sputum culture obtained at the time of completion of 2 months of treatment is positive; patients whose initial phase of treatment did not include PZA; and patients being treated with once weekly INH and RPT and whose sputum culture obtained at the time of completion of the initial phase is positive. The continuation phase may be given daily, two times weekly by DOT, or three times weekly by DOT. For human immunodeficiency virus (HIV)-seronegative patients with noncavitary pulmonary tuberculosis (as determined by standard chest radiography), and negative sputum smears at completion of 2 months of treatment, the continuation phase may consist of RPT and INH given once weekly for 4 months by DOT. If the culture at completion of the initial phase of treatment is positive, the once weekly INH and RPT continuation phase should be extended to 7 months. All of the 6-month regimens, except the INH-RPT once weekly continuation phase for persons with HIV infection (Rating EI), are rated as AI or AII, or BI or BII, in both HIV-infected and uninfected patients. The once-weekly continuation phase is contraindicated (Rating EI) in patients with HIV infection because of an unacceptable rate of failure/relapse, often with rifamycin-resistant organisms. For the same reason twice weekly treatment, either as part of the initial phase (Regimen 2) or continuation phase (Regimens 1b and 2a), is not recommended for HIV-infected patients with $CD4^+$ cell counts <100 cells/µl. These patients should receive either daily (initial phase) or three times weekly (continuation phase) treatment. Regimen 4 (and 4a/4b), a 9-month regimen, is rated CI for patients without HIV infection and CII for those with HIV infection.

Tuberculosis Vaccine

Known as BCG, the TB vaccine has been around since the early 1920s. It is made by weakening a strain of bacteria similar to tuberculosis that was first isolated in cows. This strain of bacteria, called *Mycobacterium bovis*, is similar enough to the human strain (*Mycobacterium tuberculosis*) that vaccination with the bovine strain protects against disease caused by the human strain. An inhaled TB vaccine has been developed. Tuberculosis can also be prevented by other TB vaccines.

C) Immunodeficiencies

In one preferred embodiment the present invention relates to diagnosis and/or treatment of immunodeficiencies. The immunodeficiency can be any type of immunodeficiency including the types of immunodeficiencies mentioned herein below and those listed in Table H. The treatment can be any kind of treatment including the treatments mentioned herein below or in table R, or any combination thereof. The treatment can be ameliorating, symptomatic, curative or prophylactic. The treatment can result in relief one or more symptoms of the immunodeficiency including one or more of the symptoms mentioned herein below. The immunodeficiency can be diagnosed by any method including the methods mentioned herein below.

TABLE R

| Immunotherapy for Specific Cancers |
|---|
| A) Immunotherapy for Specific Cancers |
| The FDA has approved several cancer immunotherapies, including Bacille Calmette-Guerin (BCG), interferon-alfa (IFN-alfa), interleukin-2 (IL-2), and the monoclonal antibodies listed above.<br>Many other immunotherapies have shown promising results and are moving through the testing process in clinical trials. The cancers listed here are being studied most intensively, but treatments for other cancers are also being looked at. |
| Melanoma |
| Melanoma is probably the most-studied cancer when it comes to immunotherapy. Part of this is because doctors think this cancer may be more vulnerable to immune system responses. In rare cases, these cancers have been seen to shrink or even disappear without treatment. It is thought that this may be because of an effective immune response by the body.<br>Another reason immunotherapy has been studied more in melanoma is because other treatments, like chemotherapy, aren't very effective against this cancer.<br>The cytokines IFN-alfa and IL-2 are approved to treat people with metastatic melanoma.<br>The non-specific immune stimulant BCG has not been shown to prolong life or delay relapse when used alone, but it is being tested along with melanoma vaccines and other immunotherapies.<br>Although no melanoma vaccines are FDA approved yet, recent studies have found that some autologous and allogeneic tumor cell vaccines, as well as antigen vaccines, have shrunk tumors and helped some patients live longer.<br>Dendritic cell vaccines have also been shown to shrink tumors in some patients.<br>A recent small study showed that treating patients with tumor-infiltrating lymphocytes (TILs), immune system cells found in tumors, could shrink melanoma tumors and possibly prolong life too. Another study found that T cells from the blood that had their genes altered in the lab could cause tumors to shrink in a small fraction of patients.<br>Very early study results have suggested that suppressing regulatory T cells with denileukin diftitox (Ontak) can allow the immune system to fight cancers better, making some tumors shrink.<br>Clinical trials are continuing for these and other melanoma immunotherapies. |
| Kidney cancer |
| Immunotherapy has been studied a great deal for advanced kidney cancer, least in part because other treatments like chemotherapy often aren't helpful.<br>Two cytokines, IL-2 and IFN-alfa, are treatment options for people with advanced kidney cancer.<br>Whole tumor cell vaccines given along with the adjuvant BCG have shrunk tumors in a small number of people with advanced kidney cancer.<br>Researchers are studying DNA vaccines that insert genes (segments of DNA) into cancer cells, causing the cells to make cytokines. These cytokines help the immune system recognize the cancer cells and also help activate immune system cells to attack those cells.<br>Tumor-infiltrating lymphocytes (TILs) are also being studied to fight kidney cancer. They can be removed from the body and stimulated in the lab by cytokines. When put back into the body, they become more effective than immune cells from the bloodstream.<br>Some studies have suggested that bevacizumab (Avastin), a monoclonal antibody that slows blood vessel growth in tumors, may be effective against kidney cancer. This is being studied further. |
| Leukemias, lymphomas, and myelomas |
| Several immunotherapies are now used to treat these blood cell cancers, and many more are being studied.<br>Interferon-alfa is often used to treat people with hairy cell leukemia, chronic myelogenous leukemia, follicular lymphoma, multiple myeloma, and cutaneous (skin) T cell lymphoma. In some cases, interferon is used along with chemotherapy.<br>Denileukin diftitox (Ontak), a combination of IL-2 and diphtheria toxin, is sometimes used to treat cutaneous T cell lymphoma. |

TABLE R-continued Immunotherapy for Specific Cancers Rituximab (Rituxan), a monoclonal antibody (MAb), is used to treat some
kinds of B cell non-Hodgkin lymphoma. Clinical trials are currently testing
rituximab against other lymphomas, leukemias, multiple myeloma, and other
diseases.
Ibritumomab tiuxetan (Zevalin) and tositumomab (Bexxar) are radiolabeled
monoclonal antibodies used to treat non-Hodgkin lymphoma, usually in
people who aren't helped by other treatments such as chemotherapy or
rituximab. They are now being tested to see if they might be helpful earlier in
the course of this disease.
Several other MAbs are being studied in clinical trials for people with
leukemia, lymphoma, and multiple myeloma. Anti-idiotype vaccines have
shown promising results in clinical trials against B-cell non-Hodgkin
lymphomas, but are not yet FDA approved.
Breast cancer In terms of immunotherapy, only monoclonal antibodies (MAbs) have been approved
for use against breast cancer so far. But many other forms of treatment are being
studied.
The MAb trastuzumab (Herceptin) is used in women with breast cancer
whose cancer cells have too many copies of the HER2/neu gene. These
genes make extra receptors for growth-stimulating factors on the cells, which
results in a more aggressive form of breast cancer. Trastuzumab attaches to
the receptors, blocking the access of the growth factors to the cancer cells
and slowing their growth. Other HER2/neu antibodies are now being studied
in clinical trials.
Bevacizumab (Avastin), a monoclonal antibody that slows blood vessel
growth in tumors, is being studied along with chemotherapy in some women
with advanced breast cancer.
Some interferons and interleukins have shown promise against breast
cancer, particularly when used along with tumor vaccines or immunotoxins.
Autologous vaccine therapy has lengthened remission and survival times of
some women with early breast cancer. This approach is being studied
further.
A HER2/neu peptide (a small part of the protein made by the HER2/neu
gene), used as the antigen in a vaccine, has been shown to cause an
increased immune response against the HER2/neu receptor on cancer cells;
it is under study.
Other specific antigen vaccines are also promising. These vaccines are
almost always used after primary therapy (lumpectomy and radiation therapy,
or mastectomy) and sometimes together with hormonal therapy or
chemotherapy, to try to keep the cancer from coming back.
Prostate cancer Immunotherapy is not routinely used in treating prostate cancer. Most prostate
cancer immunotherapies now being studied are vaccines. They are designed to
cause immune responses to antigens present only on prostate cells, such as
prostate-specific antigen (PSA) and prostate-specific membrane antigen (PSMA).
In one approach that has shown promise, researchers take dendritic cells
from a patient's bloodstream and treat them in the lab with prostate cancer
antigens. When put back in to the patient, the dendritic cells can show these
antigens to other immune system cells, which are then better able to
recognize and attack the cancer cells. One fairly small study showed that this
approach may help men with advanced prostate cancer live longer.
GVAX is an autologous whole cell vaccine. It is made by removing cancer
cells from the patient during surgery and modifying them in the lab to express
GM-CSF (to help stimulate the immune system). The cells are irradiated so
they can't grow any more. They are then injected back into the patient to
cause an immune response. Early studies of patients with advanced prostate
cancer that no longer responded to hormone therapy have shown some
promising results in terms of survival time. This vaccine is now being tested
against the current standard chemotherapy regimen for prostate cancer.
Researchers also are looking into using a part of the prostate-specific
antigen (called a peptide) as the basis of a vaccine.
DNA vaccines, monoclonal antibodies, and cytokines have also shown
promise and are being tested in clinical trials.
Colorectal cancer Several monoclonal antibodies are now used to treat colorectal cancer. Clinical trials
are also being done using vaccines and many other immunotherapies as adjuvants
to surgery, with and without chemotherapy.
Bevacizumab (Avastin) is a monoclonal antibody against vascular endothelial
growth factor (VEGF). By attacking VEGF, the antibody stops tumors from
being able to form new blood vessels. It is used along with chemotherapy
against advanced colorectal cancer.
Cetuximab (Erbitux) is a monoclonal antibody that attacks the epidermal
growth factor receptor (EGFR), which normally signals cancer cells to grow

TABLE R-continued

Immunotherapy for Specific Cancers and divide. It is used against advanced colorectal cancer, usually along with chemotherapy, in people whose cancer is no longer responding to other treatments.
Another monoclonal antibody, panitumumab (Vectibix), also targets EGFR. Unlike cetuximab, this MAb has no parts that come from a mouse, so it may be less likely to cause an allergic reaction when it is given. Panitumumab is used to treat advanced colorectal cancer.
A number of autologous and allogeneic tumor cell vaccines have shown early promise, but so far none have improved patient survival time.
Some carcinoembryonic antigen (CEA) vaccines have caused an improved immune response (measured by blood tests) in a large percentage of colorectal cancer patients, but the studies have not been going on long enough to see whether this improves remission or survival times.
Cervical cancer Infection with the human papilloma virus (HPV) plays an important role in causing cervical cancer. HPV vaccines are now approved for use to help prevent cervical cancer. Other vaccines that may help treat this cancer are now being tested in clinical trials.
Some HPV vaccines are like more traditional vaccines against infections. They are intended to make women immune to HPV, so that when they are exposed to these viruses they will not develop infections. By avoiding persistent HPV infection, most cervical cancers may be prevented. One of these vaccines (Gardasil) is highly effective in protecting against infections from the 2 types of HPV that cause 70% of cervical cancers. This vaccine is now approved for use in females aged 9 to 26. But it is still new. Although it has been shown to help prevent pre-cancerous lesions, it's not yet clear how well it will protect against cervical cancer. This and other preventive vaccines are being studied further.
Other vaccines are meant to help women who already have advanced cervical cancer. These vaccines attempt to cause an immune reaction to the parts of the virus that contribute to the growth of cervical cancer cells. This may kill the cancer cells or stop them from growing.
Interferons and interleukins are also being studied in women with metastatic cervical cancer.
Ovarian cancer Immunotherapy is not used routinely to treat ovarian cancer. Several types of immunotherapy, including cancer vaccines and MAbs, are now being studied. Injection of interleukin-2 (IL-2) directly into the peritoneal cavity (the body cavity that contains the ovaries, uterus, and digestive organs) of women with recurrent ovarian cancer is currently being studied. Early studies suggest the treatment may increase the length of remissions after surgery.
Placing tumor-infiltrating lymphocytes (TILS) along with interleukin-2 directly into the peritoneal cavity has also shown promise and is being studied.
Trastuzumab (Herceptin), a monoclonal antibody, is being studied to see if it may help the roughly 20% of women with ovarian cancer whose cells have too many copies of the HER2/neu gene.
A monoclonal antibody that attaches to certain antigens on ovarian cancer cells and to specific spots on T cells (a bispecific antibody) has shown promise when used with IL-2. The antibody causes T cells to bind to and attack the cancer cells.
Early studies have shown that radiolabeled MAbs against ovarian cancer may help more women live longer.
Several forms of antigen vaccines are being studied to treat ovarian cancer.
Lung cancer Better treatments are needed for lung cancer,, especially for advanced disease. Immunotherapy may help people live longer without the severe side effects sometimes seen with chemotherapy. Thus far, only monoclonal antibodies have been approved for use against lung cancer, although many other forms of immunotherapy are being studied.
The monoclonal antibody bevacizumab (Avastin) slows the growth of tumor blood vessels by targeting the VEGF protein. For patients with non-small cell lung cancer (NSCLC), it can be added to standard chemotherapy and it may help them live longer than chemotherapy alone.
GVAX is an autologous whole cell vaccine. It is made by removing cancer cells from the patient during surgery and modifying them in the lab to express GM-CSF (to help stimulate the immune system). The cells are irradiated so they can't multiply. They are then injected back into the patient to cause an immune response. Early studies of patients with advanced NSCLC have shown some responses to this vaccine, but further studies are needed.
BLP25 is a peptide (antigen) vaccine that is encased in a fat droplet (liposome) to make it more effective. A small study of patients with advanced NSCLC suggested it may improve survival time. Larger studies are needed to confirm this.

TABLE R-continued

Immunotherapy for Specific Cancers

B) Immunostimulant herbs

Immunostimulant herbs include American Ginseng, Ashwaghanda, *Astragalus*, Balsam of Peru, Bilberry, Cacao Seed Raw, Caigua, Camu Camu Berries, Canchalagua, Catuaba, Chanca Piedra, Chia Seed, Chlorella, Chuchuhuasi, Clavohuasca, Coconut Oil, *Codonopsis*, Copaiba, Cordyceps, Dan Shen, Elderberiies, Eleuthero Root, Ginkgo Leaves, Green Tea, Guayusa, *Hercampuri*, He-Shou-Wu, Honeybush Tea, Iporuru, Jujube Dates, Licorice Root, Longan Berries, Lycii Berries, Maca Root, Manayupa, Medicinal Mushrooms, Milk Thistle Seed, Neem, Nettle Leaf, Pau D'arco, Pro-EM1, Purple Corn, Red Ginseng, *Rhodiola* Root, Rooibos Tea, Sangre De Drago, Sacha Jergon, Schizandra Berries, Seabuckthorn Berry, Spirulina, Suma Root, Tahuari, Tibetan Rhodiola, Una De Gato, White Ginseng, White Tea, and Yacon, Yerba Mate.

In medicine, immunodeficiency is a state in which the immune system's ability to fight infectious disease is compromised or entirely absent. Immunodeficiency or immunosuppression can be Congenital (Primary) or Acquired (Secondary), and may be caused by conditions such as: Malnutrition, Recurrent infections, Immunosuppressing agents for organ transplant recipients, Chemotherapy for cancer, AIDS or HIV-infection, Genetic predisposition, Skin damage, Antibiotic treatment and Medical procedures. Transplant patients take medications to suppress their immune system as an anti-rejection measure. A person who has an immunodeficiency of any kind is said to be immunocompromised. An immunocompromised person may be particularly vulnerable to opportunistic infections, in addition to normal infections that could affect everyone.

Primary Immunodeficiencies

Primary immunodeficiencies are disorders in which part of the body's immune system is missing or does not function properly. To be considered a primary immunodeficiency, the cause of the immune deficiency must not be secondary in nature (i.e., caused by other disease, drug treatment, or environmental exposure to toxins). Most primary immunodeficiencies are genetic disorders; the majority are diagnosed in children under the age of one, although milder forms may not be recognised until adulthood. About 1 in 500 people is born with a primary immunodeficiency.

The kind of defect to the immune system determines the symptoms of immunodeficiency. Generally, the problems that lead to the diagnosis of an immunodeficiency include recurrent or persistent infections, or developmental delay as a result of infection. Particular organ problems (e.g. diseases involving the skin, heart, facial development and skeletal system) may be present in certain conditions. Others predispose to autoimmune disease, where the immune system attacks the body's own tissues, or tumours (sometimes specific forms of cancer, such as lymphoma). The nature of the infections, as well as the additional features, may provide clues as to the exact nature of the immune defect.

Diagnosis of Primary Immunodeficiencies

The basic tests performed when an immunodeficiency is suspected should include a full blood count (including accurate lymphocyte and granulocyte counts) and immunoglobulin levels (the three most important types of antibodies: IgG, IgA and IgM). Other tests including the ones described herein below are performed depending on the suspected disorder:

1) Quantification of the different types of mononuclear cells in the blood (i.e. lymphocytes and monocytes): different groups of T lymphocytes (dependent on their cell surface markers, e.g. CD4+, CD8+, CD3+, TCRαβ and TCRγδ), groups of B lymphocytes (CD19, CD20, CD21 and Immunoglobulin), natural killer cells and monocytes (CD15+), as well as activation markers (HLA-DR, CD25, CD80 (B cells).
2) Tests for T cell function: skin tests for delayed-type hypersensitivity, cell responses to mitogens and allogeneic cells, cytokine production by cells
3) Tests for B cell function: antibodies to routine immunisations and commonly acquired infections, quantification of IgG subclasses
4) Tests for phagocyte function: reduction of nitro blue tetrazolium chloride, assays of chemotaxis, bactericidal activity.

For instance, an antibody deficiency can be diagnosed in the presence of low immunoglobulins, recurrent infections and failure of the development of antibodies on exposure to antigens. The 1999 criteria distinguish between "definitive", "probable" and "possible" in the diagnosis of primary immunodeficiency. "Definitive" diagnosis is made when it is likely that in 20 years, the patient has a >98% chance of the same diagnosis being made; this level of diagnosis is achievable with the detection of a genetic mutation or very specific circumstantial abnormalities. "Probable" diagnosis is made when no genetic diagnosis can be made, but the patient has all other characteristics of a particular disease; the chance of the same diagnosis being made 20 years later is estimated to be 85-97%. Finally, a "possible" diagnosis is made when the patient has only some of the characteristics of a disease are present, but not all.

Classes of Primary Immunodeficiencies

The International Union of Immunological societies recognise eight classes of primary immunodeficiencies, totaling over 120 conditions. These may be (a) Antibody/humoral (Hypogammaglobulinemia/agammaglobulinemia (X-linked, Transient of infancy), Dysgammaglobulinemia (IgA, IgG, IgM), Hyper IgM syndrome, Common variable immunodeficiency, WHIM syndrome); (b) Cell-mediated (DiGeorge syndrome, Nezelof syndrome, Purine nucleoside phosphorylase deficiency, Ataxia telangiectasia); (c) Combined (Severe combined immunodeficiency (Adenosine deaminase deficiency, Omenn syndrome, X-SCID, ZAP70 deficiency), Bare lymphocyte syndrome, Wiskott-Aldrich syndrome); (d) Complement deficiency (Angioedema); (e) Phagocyte bactericidal dysfunction (PBD) (chemotaxis/degranulation: Leukocyte adhesion deficiency, Chédiak-Higashi syndrome, Hyper-IgE syndrome; or respiratory burst: Chronic granulomatous disease, Myeloperoxidase deficiency; or (f) Others (ICF syndrome: Immunodeficiency, centromere instability and facial anomalies syndrome)

The present invention relates in one embodiment to diagnosis and/or treatment of any type of primary immunodeficiencies including the types listed in Table H.

Treatment of Primary Immunodeficiencies

The treatment of primary immunodeficiencies depends foremost on the nature of the abnormality. This may range from immunoglobulin replacement therapy intravenous immunoglobulin (IVIG) or subcutaneous immunoglobulin (SCIG) in antibody deficiencies to hematopoietic stem cell transplantation (for SCID). Reduction of exposure to pathogens may be recommended, and in many situations prophylactic antibiotics may be advised.

Secondary Immunodeficiencies

Secondary immunodeficiencies can be caused by:
Chronic infections (e.g. AIDS)
Malnutrition
  Protein loss
  Increased catabolism
Ageing
Irradiation
Medications
  Chemotherapy
  Immunosuppressive drugs (treatment for organ transplantation)
  Disease-modifying antirheumatic drugs
Cancer (in particular lymphoma & leukemia)

Due to the eclectic list of causes, it is difficult if not impossible to obtain exact epidemiological data encompassing all secondary immunodeficiency. It is known that the two current epidemics of AIDS and tuberculosis have caused global increases in the condition per se. Secondary immunodeficiency is also common in people who are hospitalised for various diseases.

Lymphoreticular malignancy: Chronic lymphatic leukaemia and myeloma are both associated with hypogammaglobulinaemia. it also occurs in patients treated for leukaemia with bone marrow transplants.

Drugs: These particularly include cytotoxic drugs and immunosuppressants including steroids.

Viruses: HIV affects T-cells. Other viral diseases, such as congenital rubella infection and cytomegalovirus, can affect antibody production.

Nutritional: The commonest cause worldwide is protein-calorie malnutrition and deficiencies of vitamins and trace elements, particularly vitamin A, zinc and selenium.

Metabolic: Prolonged metabolic disorders associated with liver and kidney failure compromise immunity (this occurs in 10% of patients on continuous ambulatory peritoneal dialysis).

Trauma: some degree of immunodeficiency may be seen following major surgery or severe trauma.

Protein Loss: Loss of immunoglobulin can result from a number of conditions including nephrotic syndrome, protein-losing enteropathy and intestinal lymphangiectasia.

D) Transplantation

In one preferred embodiment the present invention relates to diagnosis and/or treatment of transplantation-related disorders. The disorder can be any type of disorder including the types of disorders mentioned elsewhere herein and those listed in Table H. The treatment can be any kind of treatment including the treatments mentioned elsewhere herein or Table P, Q, R or S, or in the items, or any combination thereof. The treatment can be ameliorating, symptomatic, curative or prophylactic. The treatment can result in relief one or more symptoms of the transplantation-related disorder including one or more of the symptoms mentioned herein below. The transplantation-related disorder can be diagnosed by any method including the methods mentioned herein below.

Transplantation of the present invention is a treatment where a defective part of the unit will be replaced with a new part thereby repairing the unit. The following sections will focus on transplantation of organs to and/or from human or animal bodies, but the principles behind the treatment can be applied in other settings as well.

An organ transplant is the moving of a whole or partial organ from one body to another (or from a donor site on the patient's own body), for the purpose of replacing the recipient's damaged or failing organ with a working one from the donor site. Organ donors can be living or deceased. Examples of human organs that can be transplanted include but are not limited toe heart, kidneys, liver, lungs, pancreas, penis, intestine and tissues like bones, tendons, cornea, heart valves, veins, and skin.

Different types of organ transplants exist and are listed below:

Autograft is a transplant of a pack of tissue to the same person. Sometimes this is done with surplus tissue, or tissue that can regenerate, or tissues more desperately needed elsewhere (examples include skin grafts, vein extraction etc.) Sometimes an autograft is done to remove the tissue and then treat it or the person, before returning it (examples include stem cell autograft and storing blood in advance of surgery).

Allograft is a transplanted organ or tissue from a genetically non-identical member of the same species. Most human tissue and organ transplants are allografts. This however will result in the receiver of organs to take immunosuppressive drugs to prevent their body's antibodies causing transplant rejection, destroying the new organ. This dramatically affects the entire immune system making the body vulnerable to pathogens.

Isograft is a subset of allografts in which organs or tissues are transplanted from a donor to a genetically identical recipient (such as an identical twin). Isografts are differentiated from other types of transplants because while they are anatomically identical to allografts, they are the same autografts in terms of the recipient's immune response.

Xenograft and Xenotransplantation is the transplant of organs or tissue from one species to another. Examples include porcine heart valve transplants, which are quite common and successful. However xenotransplantion is often an extremely dangerous type of transplant. For example a baboon-to-human heart transplant failed. Other xenotransplants attempted include piscine-primate (fish to non-human primate) islet (i.e. pancreatic or insular tissue) transplant. The latter research study was intended to pave the way for potential human use if successful. See: xenotransplantation.

Split transplants. Sometimes, a deceased-donor organ (specifically the liver) may be divided between two recipients, especially an adult and a child. This is not usually a preferred option, because the transplantation of a whole organ is more successful.

Domino transplants is a type of transplantation usually performed for cystic fibrosis as both lungs need to be replaced and it is a technically easier operation to replace the heart and lungs en bloc. As the recipient's native heart is usually healthy, this can then itself be transplanted into someone needing a heart transplant. That term is also used for a special form of liver transplant, in which the recipient suffers from familial amyloidotic polyneuropathy in which the liver (slowly) produces a protein that damages other organs; their liver can be transplanted into an older patient who is likely to die from other causes before a problem arises.

Transplantation can be categorized as follows:
Replacement of defective organ or cells
    Replacement of solid tissue
        Replacement of complete organ (heart, kidney, liver)
        Replacement of part of organ (skin)
    Replacement of cells in suspension (e.g. bone marrow, erythrocytes, full blood)
    Transfer of additional cells or tissue (e.g. immunotherapy with purified T cells)
Transplantation Related Disorders In allogeneic organ transplants, the use of immunosuppressive drugs is necessary to reduce the activity of the patient's immune system and so the risk of organ rejection. Such immuno-suppressants may be divided into five groups according to mechanism of action; (1) Glucocorticoids (e.g. cortisol, cortisone acetate, prednisone, prednisolone, methylprednisolone, dexamethasone, betamethasone, triamcinolone, beclometasone, fludrocortisone acetate, deoxycorticosterone acetate, aldosterone), (2) Cytostatics (e.g. Alkylating agents such as cyclophosphamide, nitrosoureas, platinum compounds; Antimetabolites such as folic acid analogues (e.g. methotrexate), purine analogues (e.g. azathioprine, mycophenolate, mercaptopurine), pyrimidine analogues, protein synthesis inhibitor; and Cytotoxic antibiotics such as dactinomycin, anthracyclines, mitomycin C, bleomycin, mithramycin), (3) Antibodies (polyclonal, monoclonal), (4) Drugs acting on immunophilins (e.g. Cyclosporin (a calcineurin inhibitor); Tacrolimus (a calcineurin inhibitor, macrolide); Sirolimus (a macrolide)), and (5) other drugs (e.g. Interferons; Opioids; TNF-binding proteins; Mycophenolate; Small biological agents (e.g. FTY720)).

Due to the concurrent medicine-induced immuno-suppression, a number of side-effects related to a suppressed immune system are common in allergenic transplanted patients. Of particular importance is opportunistic infections such as Viral infections (e.g. Epstein-Barr (EBV), Hepatitis C(HCV), Cytomegalovirus (CMV)); Bacterial infections (e.g. *Staphylococcus aureus, Streptococcus pyogenes, Pseudomonas aeruginosa, Acinetobacter baumannii*); Fungal infections (e.g. *Pneumocystis jirovecii, Candida albicans, Aspergillus* sp.); and Parasitic infections (*Toxoplasma gondii*). For a list of examples of viral pathogens, see items. Examples of bacterial pathogens can be found elsewhere and in the items.

Disorders related to a medicine-induced suppressed immune system includes: Transplant-related cancers including Immunodeficiency-related B-cell disorders or Post-transplant lymphoproliferative disorders (PTLD), Kaposi's Sarcoma, Solid tumors (e.g. of the skin, mouth and lungs) or any other secondary cancer related to transplantation or its concurrent medicinal treatment (for a list of examples of cancers, see items); Toxoplasmosis, *Pneumocystis* pneumonia, Candidiasis or 'thrush', Pneumonia, Meningitis, Osteomyelitis endocarditis, Toxic shock syndrome (TSS), Septicemia, Pharyngitis, Impetigo, Necrotizing fasciitis, Scarlet fever, Skin infections (such as pimples, boils, cellulitis folliculitis, furuncles, carbuncles, erysipelas, scalded skin syndrome and abscesses). For a list of examples of infectious diseases, see Table A to G.

In one embodiment, the present invention relates to diagnosis, monitoring and/or treatment of infectious diseases as listed below:

TABLE A

Diseases Caused by Bacteria to Human

| Disease | Casual Agent | Description of Agent |
| --- | --- | --- |
| Strep Throat, Scarlet Fever | *Streptococcus*, Pyogenes | Gm(+) capsualted *streptococcus* |
| Diphtheria | *Corynebacterium diphtheriae* | Gm(+) rod |
| Pertussis (Whooping Cough) | *bordetella pertussis* | Gm (−) rod |
| Meningococcal Meningitis | *Neisseria meningitidis* | Gm(−) diplococcus |
| Haemophilus meningitis | *Haemophilus influenzae* | Gm(−) capsulated rod |
| Flavobacterium meningitis | *Flavobacterium meningospecticum* | Gm(−) rod |
| Tuberculosis | *Mycobacterium tuberculosis* | Acid fast rod |
| Pneumococcal pneumonia | *Sterptococcus pneumoniae* | Gm(+) capsualted diplococci in chains |
| Primary Atypical Pneumonia | *Mycoplasma pneumoniae* | Mycoplasma (No Cell Wall) |
| *Klebsiella pneumonia* | *Klebsiella pneumoniae* | Gm(−) capsulated rod |
| Serratia pneumonia | *Serratia marcescens* | Gm(−) rod, Red pigement at 25 degree C |
| Q Fever | *coxiella burnetti* | Rickettsia, 0.45 micron Diameter |
| Psittacosis | *chlamydia psittaci* | Chlamydia, 0.25 micron diameter |
| Botulism | *Clostridium botulinum* | Gm(+) spore forming rods |
| Staphylococcal Food Poisoning | *Stephylococcus aureus* | Gm(+) Staphylococcus |
| Clostridial Food Poisoning | *clostridium perfringes* | Gm(+) Spore forming Rods |
| Typhoid Fever | *Salmonella typhi* | Gm(−) rod |
| Salmonellosis | *Salmonella* serotypes | Gm(−) rods |
| Shigellosis | *shigella* serotypes | Gm(−) rods |
| Cholera | *vibrio cholerae* | Gm(−) Curves rod |
| Brucellosis | *Brucella* Spp. | Gm(−) rod |
| Anthrax | *Bacillus anthracis* | Gm(+) Spore Forming Rod |
| Tetanus | *Clostridium tetani* | Gm(+) spore forming anaerobic rod |
| Gas Gangrene | *clostridium perfringes* | Gm(+) spore forming anaerobic rod |
| Bubonic Plague | *yersinia pestis* | Gm(−) bipolar rod |

TABLE A-continued

Diseases Caused by Bacteria to Human

| Disease | Casual Agent | Description of Agent |
|---|---|---|
| Relapsing Fever | *Borrelia recurrentis* | Spirochete |
| Rocky Mountain Spotted Fever | *Rickettsia rickettsiae* | Rickettsia |
| Epidemic Typhus (Typhus Fever) | *Rickettsia prowazekii* | Rickettsia |
| Endemic Typhus (Murine Typhus) | *Rickettsia typhi* | Rickettsia |
| Scrub Typhus | *Rickettsia tsutsugamushi* | Rickettsia |
| Rickettsialpox | *Rickettsia akari* | Rickettsia |
| Tickborne Fevers | *Rickettsia conorii* | Rickettsia |
| Syphilis | *Treponema pallidum* | Spirochete |
| Gonorrhea | *Neisseria gonorrhoeae* | Gm(−) diplococcus |
| Chlamydial urethritis | *chlamydia trachomatis* | chlamydia |
| Ureaplasmal urethritis | *Ureaplasma urealyticum* | Mycoplasma |
| Lymphogranuloma venereum | *Chlamydia trachomatis* | Chlamydia |
| Vaginitis | *Gardnerella vaginalis* | Gm(−) rod |
| Mycoplasmal urethritis | *Mycoplasma hominis* | Mycoplasma |
| Leprosy (hansen's Disease) | *Mycobacterium leprae* | Acid Fast Rod |
| Staphylococcal skin diseases | *Staphlococcus aureus* | Gm(+) staphylococcus |
| Trachoma | *chlamydia trachomatis* | Chlamydia |
| Bacterial Conjuctivitis | Haemophilus influenze type III | Gm(−) rod |

TABLE B

Diseases Caused by Virus to Human

| Disease | Causal Agent | Organs Affected | Transmission/Vector |
|---|---|---|---|
| Influenza | RNA | Respiratory Tract | Droplets |
| Adenovirus Infections | DNA | Lungs, Eyes | Droplets, Contact Droplets |
| Respiratory Syncytial Disease | RNA | Respiratory Tract | Droplets |
| Rhinovirus Infections | RNA | Upper Respiratory Tract | Droplets, Contact |
| Herpes Simplex | DNA | Skin, Pharynx, Genital organs | Contact |
| Chicken pox (Varicella) | DNA | Skin, Nervous System | Droplets, Contact |
| Measles (Rubeola) | RNA | Respiratory Tract, Skin | Droplets, Contact |
| German Measles (Rubella) | RNA | Skin | Droplets, Contact |
| Mumps (Epidemic Parotitis) | RNA | Salivary Glands, Blood | Droplets |
| Small Pox (Variola) | DNA | Skin, Blood | Contact, Droplets |
| Warts Kawasaki Disease | DNA | Skin | ? |
| Yellow Fever | RNA | Liver, Blood | Mosquito (*Aedes Aegypti*) |
| Dengue Fever | RNA | Blood, Muscles | Mosquito (*Aedes Aegypti*) |
| Hepatitis A | RNA | Liver | Food, Water, Contact |
| Hepatitis B | DNA | Liver | Contact with body Fluids |
| NANB Hepatitis | RNA | Liver | Contact with body Fluids |
| Viral Gastroenteritis | Many RNA Viruses | Intestine | Food, Water |
| Viral Fevers | Many RNA Viruses | Blood | Contact, arthropods |
| Cytomegalovirus Disease | DNA | Blood, Lungs | Contact, Congenital transfer |
| AIDS | Retrovirus (RNA) | T-lymphocytes | Contact with body Fluids |
| Rabies | RNA | Brain, Spinal cord | Conact with body Fluids |
| Polio | RNA | Intestine, Brain, Spinal Cord | Food, Water, Contact |

TABLE B-continued

Diseases Caused by Virus to Human

| Disease | Causal Agent | Organs Affected | Transmission/Vector |
| --- | --- | --- | --- |
| Slow Virus Disease | Prions | Brain | ? |
| Arboviral Enephalitis | Many RNA viruses | Brain | Anthropods |

TABLE C

Diseases Caused by Fungi to Human

| Disease | Casual Agent | Description of Agent |
| --- | --- | --- |
| Cryptococcosis | *Cryptococcus neoformans* | Lungs, Spinal Cord |
| Candidiasis, Vaginitis, Thrush, Onychia | *Candida albicans* | Intestine, Vagina, Skin, Mouth |
| tinea Pedis | *Trichophyton* Spp. | Skin |
| Tinea Captis | *Microsporum* Spp. | Skin |
| Tinea Corporis, Tinea Barhae | *Epidermophyton* spp. | Skin |
| Histoplasmosis | *Histoplasma capsulatum* | Lungs, Other Organs |
| Blastomycosis | *Blastomyces dermatitidis* | Lungs, Other Organs |
| Coccidiodomycosis | *Coccidiodes immitis* | Lungs, Ears |
| Aspergillosis Otomycosis | *Aspergillus* | Lungs, Ears |

TABLE D

Diseases Caused by Protozoa to Human

| Disease | Causal Agent | Organs Affected |
| --- | --- | --- |
| Amoebiasis | *Entamoeba histolytica* | Intestine, Liver |
| Primary Amoebic meningoencephalitis | *Naegleria fowleri* | Brain, Lungs |
| Giardiasis | *Giardia Lamblia* | Intestine |
| Trichomoniasis | *Trichomonas vaginalis* | Urogenital Organs |
| African Sleeping Sickness | *Trypanosoma brucei* | Blood, Brain |
| Leishmaniasis (Kala-azar) | *Leishmania donovani* | White Blood Cells, Skin, Intestine |
| Toxoplasmosis | *Toxoplasma gondii* | Blood, Eyes |
| Malaria | *Plasmodium* spp. | Liver, Red Blood Cells |
| Babesiosis | *Babesia microti* | Red Blood Cells |
| Pneumocytosis (PCP) | *Pneumocystis carinii* | Lungs |

TABLE E

Diseases Caused by Multicellular Parasites - Flatworms

| Disease | Causal Agent | Transmission/Vector |
| --- | --- | --- |
| Chinese Liver Fluke (Animal Host - Snail, fish) | *Clonorchis sinesis* | Fish Consumption |
| Intestinal Fluke (Animal Host - Snail) | *Fasciolopsis buski* | Consumption of Water Plants |

TABLE E-continued

Diseases Caused by Multicellular Parasites - Flatworms

| Disease | Causal Agent | Transmission/Vector |
| --- | --- | --- |
| Lung Fluke (Animal Host - Snail, Crab) | *paragonimus westermani* | Consumption of Crabs |
| Liver Fluke (Animal Host - Snail, Cattle) | *Fasciola hepatica* | Consumption of Water Plants |
| Beef Tapeworm (Animal Host - Cattle) | *Taenia saginata* | Beef Consumption |
| Pork Tapeworm (Animal Host - Pig) | *Taenia Solium* | Pork Consumption |
| Fish Tapeworm (Animal Host - Copepod, Fish) | *Diphyllobothrium latum* | Pork, Fish |
| Dwarf Tapeworm (Animal Host - None Significant) | *Hymenolepis nana* | Food, Contact |
| Dog Tapeworm (Animal Host - Dog, Other Canines) | *Echinococcus granulosus* | Contact |

TABLE F

Diseases Caused by Multicellular Parasites - Roundworms

| Disease | Causal Agent | Transmission/Vector |
| --- | --- | --- |
| Pinworm | *Enterobius vermicularis* | Food, Contact, Clothing |
| Whipworm | *Trichuris trichiura* | Food, Water |
| Roundworm | *Ascaris lumbricoides* | Food, Water, Contact |
| Trichinosis | *Trichinella spiralis* | Pork Consumption |
| Hookworm | *Ancylostoma duodenale, necator* | Contact with Moist Vegetation |
| Filariasis (Animal Host - Mosquito) | *Wuchereria bancrofti* | Mosquito |
| Guinea worm (Host - Copepod, fish) | *dracunculus medinensis* | Food, Water |
| Eyeworm (Animal Host - Insects) | Loa Loa | Deerflies, Horseflies |

TABLE G various infection diseases

Various infectious diseases

Bacteria and bacterial diseases (Specific kind of Infections), Fungus and fungal infections (Specific kind of Infections), Helminths and helminthic conditions (Specific kind of Infections), Prions and prion related diseases (Specific kind of Infections), Protozoa and protozoal infections (Specific kind of Infections), Viruses and viral disease (Specific kind of Infections), Abscess, Acariasis, actinomycetoma, TABLE G-continued various infection diseases
Various infectious diseases Adenitis, Adenoiditis, African trypanosomiasis, Alpers Syndrome, Alphos, Alveolar osteitis, Amebiasis, Anorectal abscess, Anthrax, Ascariasis, Aspergillosis, Athlete's foot, Atypical pneumonia, Babesiosis, Bejel, Blastocystis hominis, Blastomycosis, Bolivian hemorrhagic fever, Botulism, Botryomycosis, Borna disease, Borreliosis (Lyme disease), Bovine spongiform encephalopathy, Brazilian purpuric fever (BPF), Bronchiolitis, Brucellosis, Bubonic plague, Buruli ulcer, Candidiasis, Campylobacteriosis, Cat scratch fever, Cellulitis, Chagas disease, Chalazion, Chickenpox (Varicella), Chikungunya, Cholangitis, Cholecystitis, Cholera, Clonorchiasis, Coccidioidomycosis, Colorado Tick Fever (CTF), Common cold, Creutzfeldt-Jakob disease, Crimean-Congo hemorrhagic fever, Cryptococcosis, Cryptosporidiosis, Cutaneous abscess, Cysticercosis, Cystitis, infective, Dengue fever, Dermatophytosis, Diarrheal diseases, Diphteria, Diphyllobothriasis, Discitis, Donovanosis, Dracunculiasis, Dukes' disease, Dysentery, Ebola hemorrhagic fever, Echinococcosis, Encephalitis, Enterobiasis, Epidural abscess, Erysipelas, Eumycetoma, Fascioliasis, Fatal Familial Insomnia, Filariasis, Finger pulp abscess, Fitz-Hugh-Curtis syndrome, Foodborne trematodiases, Foot-and-mouth disease, Gallbladder empyema, Gas gangrene, Gastroenteritis, Giardiasis, Glanders, Gnathostomiasis, Gonorrhea, Gradenigo-Lannois syndrome, Grisel syndrome, Helminthiasis, Hepatitis, Herpes simplex, Herpes zoster, HPV, Histoplasmosis, HIV/AIDS, Hookworm, Hordeolum externum, Human African trypanosomiasis, Hymenolepiasis, Impetigo, Infectious mononucleosis, Influenza, Intertrigo, Intracranial abscess/granuloma, Intraspinal abscess/granuloma, Isosporiasis, IV catheter infection, Japanese Encephalitis, Kuru, Kyasanur forest disease, Labrea fever, La Crosse encephalitis, Lacrimal canaliculitis, Lady Windermere syndrome, Laryngeal papillomatosis, Laryngitis, Lassa fever, Legionellosis, Leishmaniasis, Lemierre's syndrome, Leptospirosis, Leprosy, Listeriosis, Liver abscess, Loa loa filariasis, lobomycosis, Lower respiratory tract infection, Ludwig angina, Lung abscess, Lymphangitis, Lymphatic filariasis, Malaria, Marburg haemorrhagic fever, Measles, Mediastinitis, Melioidosis, Meningitis, Metagonimiasis, Mumps, Murrain, Mycetoma, Mycosis, Myiasis, Necrotizing fasciitis, Neurocysticercosis, Nocardiosis, Omphalitis, Onchocerciasis, Ophthalmia neonatorum, Orbital cellulitis, Oropouche fever, Oroya fever, Osteomyelitis, Paragonimiasis, Paratyphoid fevers, Pediculosis, Periorbital cellulitis, Periodontis, Pertussis (Whooping Cough), Pharyngitis, Pharyngoconjunctival fever, Phlegmon, Pigbel (enteritis necroticans), Pinta, Pinworm Infection, Plantar wart, Pneumonia, Pneumonic plague, Pogosta disease, Poliomyelitis, Pott's disease, Prostatitis, Protothecosis, Psittacosis, Pyelonephritis acute, Pyelonephritis chronic, Pyomyositis, Q fever, Quinsy, Rabies, Rat-bite fever, Relapsing fever, Retropharyngeal abscess, Rheumatic Fever, Rhinosporidiosis, Rickettsialpox, Rift Valley fever, Ringworm, Rodentoleposis, Rocky Mountain Spotted Fever (RMSF), Roseola, Rubella, Salmonellosis, Scabies, Scarlet fever, Schistosomiasis, Septicemic plague, Septic arthropathy, Septic shock, Sepsis, Severe acute respiratory syndrome (SARS), Sexually transmissable disease, Shigellosis, Smallpox (Variola), Sodoku, Spondylodiskitis, Strongyloidiasis, Subdiaphragmatic abscess, Subdural empyema, Suppurative thyroiditis, Surra, Sweating sickness, Syphilis, Taeniasis, Tetanus, Trachoma, Tick-borne diseases, Tinea barbae, Tinea capitis, Tinea corporis, Tinea cruris, Tinea faciei, Tinea manuum, Tinea nigra, Tinea pedis, Tinea versicolor, Tonsillitis, Toxocariasis, Toxoplasmosis, Tracheolaryngobronchitis, Trachoma, Transmissible spongiform encephalopathy, Traveler's diarrhea, Trench fever, Treponematoses, Trichinellosis, Trichinosis, Trichomoniasis, Trichuriasis, Tropical diseases, Trypanosomiasis, Tuberculosis (TB), Tularemia, Typhoid fever, Typhus, Upper respiratory tract infection, Urethritis, Urinary tract infection, Venezuelan hemorrhagic fever (VHF), Verruca plana, viral hemorrhagic fevers (VHFs), Wart, West Nile disease, Wound infection, Yaws, Yellow fever, Yersiniosis and Zygomycosis.

Side-effects of medicinal treatment concurrent to transplantation includes: Serum sickness (a reaction to proteins in antiserum derived from an animal source, e.g. polyclonal antibodies—a type of hypersensitivity that typically develops up to ten days after exposure to the antiserum); Immune complex glomerulonephritis; Delayed hypersensitivity (tuberculin skin reaction); Infertility; Cataracts (clouding of the lens of the eye, which causes loss of vision); Hormone changes; Risk of bleeding (due to destruction of platelets).

The immune-system, if not adequately suppressed, is responsible for a number of conditions related to allogeniec transplantation. These include: Graft-versus-host disease (GVHD): a common complication of allogeneic bone marrow transplantation in which functional immune cells in the transplanted marrow recognize the recipient as "foreign" and mount an immunologic attack on certain organs, often skin, liver and gastrointestinal tract. This may be acute or chronic. Host-versus-graft (transplant or graft rejection): occurs when the recipient's immune system attacks the grafted organ or tissue. Rejection may be hyperacute, acute or chronic.

EXAMPLES

Example 1

HercepTest is an indirect, invasive diagnostic test using antibodies specific for HER 2 to detect HER2 overexpression in cells in breast cancer tissue sections using an IHC assay. HercepTest™ is a semi-quantitative immunohistochemical assay for determination of HER2 protein (c-erbB-2 oncoprotein) overexpression in breast cancer tissues routinely processed for histological evaluation. HercepTest™ specifically demonstrates overexpression of HER2 protein.

Positive or negative results aid in the classification of abnormal cells/tissues and provide a basis for Herceptin™ treatment selection. HercepTest™ is indicated as an aid in the assessment of patients for whom Herceptin™ (trastuzumab) treatment is being considered.

Decision regarding Herceptin™ treatment should be made within the context of the patient's clinical history.

Example 2

EGFR pharmDx kit is an example of an indirect, invasive diagnostic test using antibodies to detect EGFR overexpression in cancer cells. Epidermal growth factor receptor (EGFR) is a transmembrane receptor encoded by the human HER1 gene. EGFR is a member of the EGF/erbB receptor family of related growth factor receptors, which include HER2/erbB2 or neu, HER3/erbB3, and HER4/erbB4. The EGFR protein is expressed by a variety of normal cells and is thought to play an important role in the regulation of cell division and tumor growth. EGFR overexpression has been demonstrated in a variety of neoplasms. EGFR pharmDx™ Kit is indicated as an aid in identifying colorectal cancer patients eligible for treatment with Erbitux® (cetuximab) or Vectibix™ (panitumumab).

Example 3

This is an example of a diagnostic test based on an indirect, invasive assay using IHC and DNA probes and described the use of the HER2 FISH pharmDx™ Kit. The human HER2 gene with the generic name ERBB2 (also known as NEU) encodes the HER2 protein or $p185^{HER2}$. The HER2 protein is a membrane receptor tyrosine kinase with homology to the epidermal growth factor receptor (EGFR). The HER2 gene is a normal component present in two copies in all normal diploid cells.

In a fraction of patients (25-30%) with breast cancer, the HER2 gene is amplified as a part of the process of malignant transformation and tumor progression. HER2 gene amplification leads to overexpression of the HER2 protein on the surface of breast cancer cells. HER2 gene amplification and receptor prevalence correlates with poor breast cancer prognosis, including relapse-free and overall survival.

The recombinant, humanized monoclonal antibody Herceptin™ was rationally developed to specifically target HER2-positive breast cancers. Demonstration of high HER2 overexpression or gene amplification is essential for treatment with Herceptin™. Clinical studies have shown that patients whose tumors have high HER2 receptor overexpression and/or amplification benefit most from Herceptin™.

HercepTest™ was the first FDA-approved diagnostic kit designed to quickly and accurately identify patients eligible for Herceptin™ therapy.

HER2 FISH pharmDx™ Kit is the second Dako HER2 diagnostic kit indicated as an aid in the assessment of patients for whom Herceptin™ treatment is considered. HER2 FISH pharmDx™ Kit is a direct fluorescence in situ hybridization (FISH) assay designed to quantitatively determine HER2 gene amplification in formalin-fixed, paraffin-embedded breast cancer tissue specimens. Gene amplification is determined from the ratio between the number of signals from the hybridization of the HER2 gene probe (red signals) and the number of signals from the hybridization of the reference chromosome 17 probe (green signals).

HER2 FISH pharmDx™ Kit is indicated as an aid in the assessment of patients for whom Herceptin™ treatment is being considered.

Results from the HER2 FISH pharmDx™ Kit are intended for use as an adjunct to the information currently used for estimating prognosis in stage II, node-positive breast cancer patients.

Example 4

This is an example of a diagnostic test based on an indirect, invasive assay using IHC and DNA probes and described the use of the TOP2A FISH pharmDx Kit.

Type II topoisomerases are essential enzymes that play important roles in fundamental nuclear processes such as DNA replication and recombination. The TOP2A gene is approximately 30 kb in size and encodes a 170 kDa protein. The TOP2A protein has been recognized as a proliferation marker and is expressed in proliferating cells and in numerous human malignant tumors, including colon, gastric and breast cancer, lymphomas and others. Type II topoisomerases are the targets for anticancer drugs, such as the topoisomerase II inhibitor therapies like the anthracyclines Doxorubicin and Epirubicin.

The TOP2A gene is present in two copies within all normal diploid cells. The copy number of the TOP2A gene has been shown to influence the sensitivity of the tumor towards topoisomerase II inhibitor therapies.

TOP2A FISH pharmDx™ Kit is designed to detect amplifications and deletions (copy number changes) of the TOP2A gene using fluorescence in situ hybridization (FISH) technique on formalin-fixed, paraffin-embedded human breast cancer tissue specimens.

Deletions and amplifications of the TOP2A gene serve as markers for poor prognosis in high-risk breast cancer patients. TOP2A gene amplification detected by the TOP2A FISH pharmDx™ Kit is further indicated as an aid to predict recurrence-free and overall survival in high-risk breast cancer patients treated with adjuvant epirubicin-based chemotherapy. Results from the TOP2A FISH pharmDx™ Kit are intended for use as an adjunct to existing clinical and pathological information.

Topoisomerase IIα is a key enzyme involved in DNA replication and is the molecular target for topoisomerase II inhibitor therapies. Clinical research shows that the TOP2A gene can be used as a predictive indicator of susceptibility or resistance to anthracycline therapies.

Example 5

This is an example of a diagnostic test based on an indirect, invasive method where the sample is a blood sample analysed using binding assay with antibodies and flow cytometry.

Haematopoietic progenitor cells (HPCs) can be mobilized from the bone marrow into the peripheral blood (PB) by cytotoxic drugs, cytokines, or combinations of the two. This mobilization allows the collection of HPCs by apheresis in sufficient quantities for transplantation procedures. The use of PB stem cells (PBSCs) for transplant purposes has rapidly increased during the past decade, and for autologous transplantation PB is now preferred as a source of HPCs over bone marrow (BM). Traditionally, the absolute mononuclear cell count of BM harvests in relation to the body weight of the recipient has served as a useful predictor of engraftment potential. However, this approach is insufficient for mobilized PBSC collections owing to their variable HPC content.

By the late 1980s, it was established that virtually all of the CFC (colonyforming cell) activity and engraftment potential of marrow or peripheral blood samples were contained in the small population of cells bearing the CD34 antigen. CD34 is a cell surface antigen, which on haematopoietic cells is restricted to early progenitors of all lineages.

Thus, CD34+ HPCs can restore multilineage haematopoiesis in myelo-ablated patients. The number of CD34+ cells as determined by flow cytometry per kilogram of recipient body weight has been shown to be the most useful indicator of the haematopoietic reconstitutive capacity of peripheral blood stem cell (PBSC) transplants. Sutherland et al. developed a set of clinical guidelines for the "International Society for Hematotherapy and Graft Engineering" (ISHAGE) for simple and standardized CD34+ enumeration. These guidelines have been adopted in the CD34Count Kit that contains Anti-CD45/FITC and Anti-CD34/RPE, and thus allows the identification of leukocytes (CD45+) and the verification of "true" CD34+ cells as being dim for CD45 fluorescence and having low side scatter (CD45dim, SSClow). The addition of the CytoCount™ counting beads to the cell suspension yields the concentration of CD34+ cells per unit of original specimen volume (i.e. the absolute CD34+ cell count) from a single flow-cytometric assessment (single-platform technique). The single-platform technique has fewer sources of variability compared with the previously commonly used dual-platform technique, and multi-centre studies have shown that it provides a better coefficient of variation (CV), and that the risk of generating aberrant results is lower (4).

The optional addition of the DNA stain, 7-aminoactinomycin D (7-AAD), which is also included in the kit, makes it possible to exclude dead cells from analysis. 7-AAD is only able to diffuse into and stain dead cells, because the cell membrane in these cells is no longer intact.

Principle of the Procedure: CD34Count Kit has been designed to provide an optimal method for CD34+ cell enumeration, following the ISHAGE guidelines for single-platform. The test is performed in duplicate by staining the sample with a dual-colour reagent composed of Anti-Human CD45/FITC and Anti-Human CD34/RPE. After staining of the sample, red blood cells are lysed with an ammonium chloride-based lysing reagent, and 7-AAD is added (optional) to the sample if viability measurement is wanted. Fluorescent count control beads (CytoCount™) are added to the sample for use as an internal reference population. During analysis, the absolute concentration of CD34+ cells in the sample can be determined by dividing the number of CD34 events by the number of fluorescent bead events, and then multiplying by the bead concentration in CytoCount™. The principle of the ISHAGE guidelines is to use sequential Boolean gating strategy to define the real progenitor cells with regenerative potential. This is obtained by counter-staining CD34+ cells with Anti-CD45/FITC and thus allowing the elimination of debris and non-specifically stained events from the analysis. Importantly, this approach also allows the discrimination between HPCs, which express relatively low levels of CD45 on their surface, and lymphocytes and monocytes, which express high levels. Just as lymphocytes, monocytes, and granulocytes form discrete clusters on bivariate plots of CD45 versus side scatter (SSC), so do non-malignant CD34+ haematopoietic stem and precursor cells. The addition of a known concentration of reference beads makes it possible to calculate the absolute concentration of CD34+ cells in the original specimen, i.e. to determine the number of CD34+ cells per µL of specimen.

Example 6

This example describes how a *streptococcus* test can be used for diagnosis of throat infection.

A throat infection with *streptococcus* bacteria (called strep throat) needs to be treated with an antibiotic. A test is commonly used to find out whether *streptococcus* bacteria are present on your throat surface. The traditional test for a strep throat has been a throat culture, which takes two to three days to produce results. Several different types of rapid strep tests, however, can produce results within minutes to hours. A rapid strep test can only detect the presence of Group A strep, the one most likely to cause serious throat infections; it does not detect other kinds of strep or other bacteria. Rapid strep tests are enzyme immunoassays that detect Group A streptococcal antigens. These tests can be performed in a medical office or clinic and results can be available within 10 minutes, allowing for quicker diagnosis and treatment. Rapid strep tests are based upon the principle of double antibody sandwich immunoassay. The first step of a rapid strep test is the extraction of specific Group A streptococcal antigen from the swab. The swab is placed in a test tube containing the extracting reagents (usually dilute acid). The swab is rotated vigorously in the solution while pressing the tip against the sides of the test tube. After all fluid is pressed from the swab, it is discarded and the extract is applied to a nitrocellulose membrane containing both immobilized antibodies and nonimmobilized antibodies to different regions of the Group A strep antigen. The non-immobilized antibodies are conjugated to colored particles or colloidal gold. If Group A streptococcal carbohydrate antigen is present in the extract, the conjugated antibodies bind to it, forming antigen-antibody complexes. These migrate along the pad until they reach the reaction zone containing immobilized antibodies to the same Group A strep antigen. These antibodies capture the antigen-antibody complexes, forming a colored bar or line in the reaction zone area.

QuickVue® In-line Strep A test is an immunochromogen method. A throat swab specimen is collected and inserted into the Swab Chamber of the Test Cassette. The Extraction Solutions are mixed and added to extract the antigenic component of the bacteria. The extracted sample flows through a label pad containing rabbit polyclonal anti-strep A antibody and a blue control label. If the extracted solution contains strep A antigen, it will be seen as a pink-to-purple Test Line. A blue Control Line should always appear in a properly functioning Test Cassette. If strep A is not present or present at very low levels, only a blue Control Line will be visible. The result of the test should be read after 5 minutes at 15-30° C.

Once an infection with *streptococcus* bacteria is diagnosed using the above test the infection may be treated with antibiotics.

Example 7

This example descries a non-invasive diagnostic test based on cytology and describes the Pap smear test.

The Papanicolaou test, or Pap smear, is an examination of a sample of cells from the cervix (the entrance to the uterus, located at the inner end of the vagina) to check for cervical cancer. This cancer is caused by infection with a virus called human papillomavirus, or HPV. Pap tests examine the shape of the cells under the microscope, to identify any that are clearly cancerous or appear precancerous. Today's Pap smear may include testing to see if the patients are infected with HPV. Only a fraction of people infected with that virus get cancer, but infection does increase risk. All women who are 21 or older, and younger women who are sexually active, should have a Pap smear every one to three years, and more often if any abnormalities are found.

The test begins with a pelvic examination (see page 44). The doctor might use a cotton swab to clear extra mucus from the vagina and cervix. The doctor then takes a small rounded spatula and gently rubs a few cells from the outer surface of the cervix. The doctor also collects cells by inserting a small brush into the opening in the center of the cervix (the cervical os). The cell samples are either smeared across a glass slide or shaken loose into a bottle containing special fluid (a laboratory technician will transfer the samples to a slide later). Both a machine and a trained laboratory specialist examine the sample to check for abnormal cells.

Example 8

This is an example of how MHC multimers may be used for diagnosis of Lyme Disease in humans and this diagnosis leads to treatment with antibiotics.

Lyme disease is caused by infection by *Borrelia* bacteria. MHC multimers include MHC dextramers, MHC tetramer, MHC pentamers or any carrier whereto two or more MHC complexes are attached. MHC multimers carrying *borrelia* specific peptides may be used to detect the presence of *Borrelia* specific T cells in the blood or cerebrospinal fluid of patients infected with *Borrelia*. During acute infection *Borrelia* specific T cells will be present in increased amounts in an activated state compared to healthy individuals. The presences of an increased amount of activated *Borrelia* specific T cells may thereby act as a surrogate marker for infection with *Borrelia* bacterium. Detection of *Borrelia* specific T cells using MHC dextramers may be performed using flow cytometry following a protocol similar to that described for detection of CMV specific T cells elsewhere herein. The sensitivity of the diagnostic test may be enhanced by addition of labeled antibodies specific for activation markers expressed in or on the surface of the *Borrelia* specific T cells.

Once diagnosed Lyme Disease may be treated using antibiotics.

Example 9

This is an example of diagnosis and treatment of Lyme disease: The diagnostic test is a T cell based ELISPOT assay and the treatment is antibiotics.

Lyme disease is caused by infection by *Borrelia* bacteria. During acute infection *Borrelia* specific T cells will be present in increased amounts in an activated state compared to healthy individuals. The presences of an increased amount of activated *Borrelia* specific T cells may thereby act as a surrogate marker for infection with *Borrelia* bacterium. *Borrelia* specific T cells in the blood or cerebrospinal fluid of patients infected with *Borrelia* may be detected with a T cell based ELISPOT assay. The ELISPOT assay may be performed as described for detection of TB specific T cells elsewhere herein.

Once diagnosed, Lyme Disease may be treated using antibiotics.

Example 10

This example describes how an infection with *mycobacterium tuberculosis* may be detected and treated.

Latent and active infection with *mycobacterium tuberculosis* may be diagnosed using Quantiferon-TB Gold marketed by Cellestis. It is an indirect, in vitro test for TB infection that measures interferon-gamma release from a clinical blood sample in response to peptides simulating two TB antigens, ESAT-6 and CFP-10 (the latter is called MTSA-10 in some literature). IFN-gamma is detected by ELISA. Briefly, the procedure is as follows: Fill a heparin-containing blood collection tube with the blood sample, then incubate the blood with the antigens within 12 hours of collection. Measure out aliquots into the wells of the plate, add three drops of antigen to the appropriate wells. Mix on a shaker, incubate for a day-ish. Remove the supernatant plasma, transfer to microtubes, and get ready for the ELISA. Mix up your IFN-gamma standard dilutions for positive control, prepare and distribute the conjugate to he plates. Add plasma samples to the plates. Mix, incubate, wash six times. Add enzyme substrate solution, incubate, add enzyme stopping solution. Read the OD of each well. Analyze. The OD value may be correlated to the amount of INF-gamma in the sample which is a surrogate marker for the presence of activated TB specific T cells in the sample. The presence of activated TB specific T cells in the sample is a surrogate marker for infection with *mycobacterium tuberculosis*.

QuantiFERON®-TB Gold is approved by the US FDA, is approved for sale in Japan, and has CE Marking for use in Europe.

Once infection with mycobacterium tuberculosis is detected the infection may be treated with isoniazid, 1 pill every day for 6 months if the infection is latent. An active TB infection is treated with isoniazid, rifampicin, pyrazinamide, and ethambutol for two months, then isoniazid and rifampicin alone for a further four months.

Example 11

This example describes how an infection with *mycobacterium tuberculosis* may be detected and treated.

Latent and active infection with *mycobacterium tuberculosis* may be diagnosed using T-SPOT (TB test from Oxford Immunotec.).

T-SPOT is a technology that can directly detect individual activated effector T cells, via their secretion of cytokines, when presented with specific antigens. The test is based on a technology known as the ELISPOT (Enzyme Linked Immunosorbent Spot) assay, which is widely recognised as a sensitive technique to measure antigen-specific T cell function. T-SPOT. TB is designed for the detection of effector T cells that respond to stimulation by peptides from the TB antigens, ESAT-6 and CFP-10. T-SPOT. TB enumerates individual activated TB-specific T cells.

- A patient's blood sample is collected in Vacutainer® Cell Preparation Tubes™, which are spun to separate white blood cells, known as peripheral blood mononuclear cells (PBMCs)
- PBMCs are washed in culture media to remove any background interference, counted to correct for a patient's immune status, and added in even amounts to the wells of a 96-well microtiter plate. These plate wells are pre-coated with a monoclonal antibody to a specific cytokine released by effector T cells in response to contact with specific antigens A specific antigen is added to the appropriate wells to stimulate cytokine release (positive and nil controls are used as internal assay controls)

The assay plate is placed in a $CO_2$ incubator overnight to allow the effector T cells to encounter the antigen The plates are washed, removing both the T cells and the antigen from the wells and leaving any T cell secreted cytokine captured by the antibodies lining the wells An enzyme-conjugated secondary antibody that binds to another epitope on the captured cytokine is then added. Coloured spots are generated by the conjugated enzyme upon application of a colorimetric substrate. These spots reveal a footprint of the antigen-specific effector T cells in the sample A colorimetric substrate is added to the wells to reveal spots where the cytokine was secreted, revealing the footprint of an effector T cell that reacted to the antigen The spots are counted to determine the number of T cells in the sample that reacted to the antigen relative to the negative control, thereby identifying infection.

Once infection with mycobacterium tuberculosis is detected the infection may be treated with isoniazid, 1 pill every day for 6 months if the infection is latent. An active TB infection is treated with isoniazid, rifampicin, pyrazinamide, and ethambutol for two months, then isoniazid and rifampicin alone for a further four months.

Example 12

This example describes how an infection with *mycobacterium tuberculosis* may be detected and treated using MHC dextramers for diagnosis.

Latent and active infection with *mycobacterium tuberculosis* may be diagnosed using MHC dextramers, tetramers or any other MHC multimer for detection of TB specific T cells in the blood of infected individuals. Specific T cells may be detected with MHC dextramers, tetramers or any other MHC multimer as described for detection of CMV specific T cells elsewhere herein. In stead of using CMV specific peptide epitopes TB specific peptide epitopes are used in complex with HLA-A*0201, HLA-A*0101, HLA-A*0301, HLA-A*2402 or any other human HLA allele able to bind a TB specific epitope. The peptide epitopes may derive form the TB antigens, ESAT-6 and CFP-10 or any other TB specific antigen. Antibodies binding various T cell activation markers may be included in the assay to distinguish resting T cells from activated T cells. Once infection with mycobacterium tuberculosis is detected the infection may be treated with isoniazid, 1 pill every day for 6 months if the infection is latent. An active TB infection is treated with isoniazid, rifampicin, pyrazinamide, and ethambutol for two months, then isoniazid and rifampicin alone for a further four months.

Example 13

This is an example of how MHC tetramers may be used to monitor the immune status of a patient following transplantation, thereby guiding the immune suppressive treatment.

T lymphocytes (T cells) play a critical role in host immune defense to microbial infections. Specialized phagocytic cells, known as antigen-presenting cells (APCs), process foreign proteins resulting in peptide fragment expression on their cell surfaces. These peptides are complexed to MHC (major histocompatibility complex) molecules. When naïve T cells encounter APCs expressing foreign peptide-MHC molecules, the T cells are induced to differentiate and proliferate. The result is a cellular immune response consisting of T cells that are capable of recognizing and destroying infected cells expressing the specific peptide—MHC molecule. Long-term memory cells capable of rapidly responding to a repeat infection are also generated. These antigen-specific T cells can be detected using Beckman Coulter iTAg MHC Tetramers.

Within their lifetime, more than half of the world's population will become infected with human cytomegalovirus (CMV), a member of the ubiquitous herpes virus family.

Once an individual is infected, viral particles can escape total immunoclearance and remain dormant within the host's cells. CMV antigen-specific CD8+ cytotoxic T cells can control the latent CMV infection in healthy individuals.

The detection of CD8+ antigen-specific T cells requires cognate recognition of the T cell receptor (TCR) by a unique combination of a Class I major histocompatibility complex (MHC) molecule coupled with a specific antigen peptide. Antigen-specific TCR on the surface of CD8+ T cells is recognized by iTAg MHC Class I Tetramers. iTAg MHC Class I Tetramers are a complex of four peptide—MHC Class I molecules stably bound with streptavidin to which a fluorochrome (most often PE) is attached. MHC Class I Tetramers are used in combination with fluorescently conjugated CD3 and CD8 antibodies to determine the frequency of CD3+CD8+ T cells.

The following flow cytometric protocol describes a two-panel technique for the determination of the absolute count (cells/µL) of CMV antigen-specific CD8+ T cells in whole blood. A similar approach has been used by the European Working Group on Clinical Cell Analysis. Panel 1 consists of a single assay tube containing whole blood, anti-CD3, anti-CD4, anti-CD8 monoclonal antibody reagents, and Flow-Count Fluorospheres and is prepared using a lyse-no-wash method. Results from panel 1 provide a direct determination of the CD3+CD4+ and CD3+CD8+ T cell subset absolute counts. Panel 2 consists of a variable number of tubes dependent on the MHC or HLA (Human Leukocyte Antigen) phenotype of the individual being tested. Each tube in panel 2 contains whole blood, anti-CD3, anti-CD8, and specific CMV MHC Class I Tetramer and is prepared using a lyse-with-wash method. Results from panel 2 are used to determine the relative percentage of antigen-specific CD3+ CD8+ T cells present within a sample. Identification of the CD3+CD8+ population is common to both panels. Therefore, by applying the percentage of antigen-specific CD3+ CD8+ T cells determined in panel 2 to the absolute CD3+ CD8+ cell count determined in panel 1, the absolute number of antigen-specific CD3+ CD8+ T cells is determined per µL of whole blood. Both panels may be prepared concomitantly. IMMUNO-TROL Control Cells are prepared as described above for use in panel 1 only.

Detection and Enumeration of CMV Antigen-Specific CD8-Positive T Lymphocytes in Whole Blood by Flow Cytometry.

Reagent Preparation

1. Lyse/Fixative solution: Calculate the total volume of Lyse/Fixative solution required (panel 1—1 mL/tube, panel 2—2 mL/tube). Add 25 µL of iTAg™ MHC Tetramer Fixative Reagent to 1 mL of iTAg MHC Tetramer Lyse Reagent.
2. 0.1% formaldehyde in PBS: Calculate the total volume of 0.1% formaldehyde/PBS fixative solution required (panel 2 only—0.5 mL/tube). Add 12.5 µL iTAg MHC Tetramer Fixative Reagent to 1 mL of PBS.

3. Bring all monoclonal antibody reagents, IMMUNO-TROL™ Control Cells and iTAg MHC Tetramers to room temperature (RT) before pipetting. Vortex before use.
4. On the same day of data acquisition by flow cytometry, remove Flow-Count™ Fluorospheres from 4° C. storage. Bring to RT prior to use. Vortex for 10-12 seconds and avoid excessive mixing to minimize air bubble formation.

Panel 1. Determination of Absolute T Cell Counts—Lyse-No-Wash

1. Appropriately label tubes for each patient being tested.
2. Pipette 10 µL of anti-CD3, 10 µL of anti-CD4, and 10 µL of anti-CD8 into the bottom of each tube.
3. Pipette 100 µL of whole blood into the bottom of each tube.
4. Vortex gently to ensure complete mixing of whole blood sample with antibody reagents.
5. Incubate tubes at room temperature (18-25° C.) for 20-30 minutes, protected from light.
6. Add 1 mL of Lyse/Fixative solution to each tube and vortex immediately for one second after each addition.
7. Incubate at room temperature for at least 10 minutes, protected from light.
8. Store prepared samples at 4° C., protected from light, until the addition of Flow-Count Fluorospheres within 24 hours.
9. Pipette 100 µL of adequately mixed room-temperature Flow-Count Fluorospheres into each tube immediately prior to analysis by flow cytometry.
10. Vortex each tube for 5 seconds to ensure proper mixing and resuspension of cells and fluorospheres.
11. Samples must be analyzed within one hour. Repeat vortexing immediately prior to flow-cytometric acquisition.

Panel 2. Determination of Relative Percent of CMV Antigen-Specific CD8+ T Cells—Lyse-with-Wash 1. Appropriately label tubes for each patient being tested.
2. Add 10 µL of specific iTAg MHC Class I Tetramer or Negative Tetramer and 10 µL each of anti-CD3 and anti-CD8 monoclonal antibody reagents into each tube.
3. Add 200 µL of whole blood into each tube. Specimens with low leukocyte counts (<3.0×10³/µL) or low lymphocyte counts (<0.5×10³/µL) may require whole blood volumes up to 400 µL. Under these circumstances, up to 4 mL of Lyse/Fixative solution is required—all other reagent volumes remain as described.
4. Vortex gently.
5. Incubate at room temperature (18-25° C.) for 20-30 minutes, protected from light.
6. Add 2 mL of Lyse/Fixative solution to each tube and vortex immediately for one second after each addition.
7. Incubate at room temperature for at least 10 minutes, protected from light.
8. Centrifuge tubes at 150×g for 5 minutes.
9. Aspirate or decant the supernatant.
10. Add 3 mL of PBS.
11. Centrifuge tubes at 150×g for 5 minutes.
12. Aspirate or decant the supernatant.
13. Resuspend the cell pellet in 500 µL of PBS with 0.1% formaldehyde.
14. Vortex each tube for 5 seconds.
15. Store prepared samples at 4° C. protected from light for a minimum of 1 hour (maximum 24 hours) until analysis by flow cytometry.

Example 14

MHC dextramers may be used to monitor the immune status of a patient following transplantation, thereby guiding the immune suppressive treatment. The procedure for the use of MHC tetramers to monitor immune status of a patient following transplantation described elsewhere herein may be followed replacing MHC tetramers with MHC dextramers.

Example 15

Any MHC multimer may be used to monitor the immune status of a patient following transplantation, thereby guiding the immune suppressive treatment. The procedure for the use of MHC tetramers to monitor immune status of a patient following transplantation described elsewhere herein may be followed replacing MHC tetramers with MHC dextramers.

Example 16

This example describes how EBV or CMV specific T cells may be detected in the blood from human donors using MHC multimers and flow cytometry.

Purified MHC (peptide) molecules consisting of the allele HLA-A*0201, human beta2 microglobulin and peptide was generated by in vitro refolding, purified and biotinylated as described elsewhere herein. Biotinylated HLA-A*0201 (peptide) was mixed with APC-SA-conjugated 270 kDa dextran in an amount corresponding to a ratio of three biotinylated HLA-A*0201(peptide) molecules per SA molecule and incubated for 30 minutes in the dark at room temperature. The APC-SA-conjugated 270 kDa dextran contained 9 molecules APC and 3.7 molecules SA per dextran molecule. Following incubation the mixture was diluted into a buffer containing 0.05M Tris/HCl, 15 nM $NaN_3$ and 1% BSA to a final concentration of $3.8 \times 10^{-8}$ M dextran.

By this procedure the following MHC multimer constructs were made:
1) A construct comprising APC-SA-conjugated 270 kDa dextran and biotinylated HLA-A*0201 in complex with beta2 microglobulin and the peptide NLVPMVATV (SEQ ID NO 1) derived from pp 65 protein from human cytomegalovirus (HCMV).
2) A construct comprising APC-SA-conjugated 270 kDa dextran and biotinylated HLA-A*0201 in complex with beta2 microglobulin and the peptide GLCTLVAML (SEQ ID NO 8) derived from BMLF-1 protein from Epstein Barr virus (EBV).
3) A construct comprising APC-SA-conjugated 270 kDa dextran and biotinylated HLA-A*0201 in complex with beta2 microglobulin and the peptide ILKEPVHGV (SEQ ID NO 2) Reverse Transcriptase from Human Immunodeficiency Virus (HIV).

The binding of the HLA-A*0201(peptide)/APC dextran constructs to Human Peripheral Blood Mononuclear Cells (HPBMC) from various donors was analyzed by flow cytometry following a standard flow cytometry protocol. Briefly, HPBMC from the blood of 9 individual donors were isolated, by a standard protocol using Ficoll-Hypaque. $1 \times 10^6$ purified HPBMC at a concentration of $2 \times 10^7$ cells/ml were incubated with 10 µl of one of the HLA-A*0201 (peptide)/APC dextran constructs described above for 10 minutes in the dark at room temperature. 10 µl of each of the antibodies mouse-anti-human CD3/PE (clone UCHT1 from Dako) and mouse-anti-human CD8/PB (clone DK25 from Dako) were added and the incubation continued for another 20 minutes at 4° C. in the dark. The samples were then washed by adding 2 ml PBS; pH=7.2 followed by centrifugation for 5 minutes at 200×g and the supernatant removed.

The cells were then resuspended in 400-500 µl PBS; pH=7.2 and analyzed on a CYAN ADP flow cytometer.

Donor 1-5 were known to have detectable T cells specific for HLA-A*0201 (NLVPMVATV) (SEQ ID NO 1) and no detectable T cells specific for HLA-A*0201(ILKEPVHGV) (SEQ ID NO 2) while donor 6 were known not to have detectable specific T cells for either HLA-A*0201(NLVPMVATV) (SEQ ID NO 1) nor HLA-A*0201(ILKEPVHGV) (SEQ ID NO 2). Lymphocytes from these 6 donors were stained with MHC multimer construct 1 and 3. Donor 1-5 showed positive staining with MHC multimer construct 1 as expected while no staining was observed with MHC complex construct 3. An example showing the staining patterns for donor 2 is shown in FIG. 1. No specific staining was observed of lymphocytes from donor 6 with either of the MHC multimer constructs.

Donor 7-8 known to have detectable T cells specific for HLA-A*0201(GLCTLVAML) (SEQ ID NO 8) and no detectable T cells recognizing HLA-A*0201(ILKEPVHGV) (SEQ ID NO 2) and donor 9 having no detectable T cells specific for either HLA-A*0201(GLCTLVAML) (SEQ ID NO 8) nor HLA-A*0201(ILKEPVHGV) (SEQ ID NO 2) were all stained with MHC multimer construct 2 and 3. Donor 7 and 8 demonstrated efficient staining with MHC multimer construct 2 as expected while no staining was observed with the other MHC multimer construct tested. No staining was observed of lymphocytes from donor 9 with either of the MHC multimer constructs tested. In conclusion this experiment demonstrates that donors known to have specific T cells for either an EBV specific epitope GLCTLVAML (SEQ ID NO 8) or a CMV specific epiotpe NLVPMVATV (SEQ ID NO 1) both binding HLA-A*0201 also demonstrated positive staining with the corresponding MHC multimer constructs 2 and 1. None of the donors were infected with HIV and as expected did not appear to have T cells specific for HLA-A*0201 in complex with the HIV derived peptide ILKEPVHGV (SEQ ID No 2), and as expected none of these donors showed staining with MHC multimere construct 3.

This method may be used to diagnose CMV, EBV or other viral infections in the blood of human beings. To increase sensitivity of the assay many MHC multimers carrying different viral epitopes binding different MHC alleles may be analysed on the same blood sample.

Example 17

This example describes how to identify specific T cells in a blood sample with MHC multimers using flow cytometry analysis without lysis of red blood cells and without washing the cells after staining. MHC complexes in this example consisted of HLA-A*0201 heavy chain, human beta2 microglobulin and different peptides, and the MHC complexes were coupled to a 270 kDa dextran multimerization domain.

Purified MHC-peptide complexes consisting of human heavy chain, human beta2 microglobulin and peptide were generated by in vitro refolding, purified and biotinylated as described elsewhere herein. Biotinylated MHC-peptide complexes were then coupled to a 270 kDa dextran multimerization domain labelled with PE by interaction with streptavidin (SA) on the dextran multimerization domain. The SA-PE-dextran was made as described elsewhere herein. MHC-peptide complexes were added in an amount corresponding to a ratio of three MHC-peptide molecules per SA molecule and each molecule dextran contained 6.1 SA molecule and 3.9 molecules PE. The final concentration of dextran was 3.8×10e-8 M. The following constructs were made:

1. PE conjugated 270 kDa dextran coupled with HLA-A*0101 in complex with beta2 microglobulin and the peptide VTEHDTLLY (SEQ ID NO 3) derived from Human Cytomegalo Virus (HCMV).
2. PE conjugated 270 kDa dextran coupled with HLA-A*0101 in complex with beta2 microglobulin and the peptide IVDCLTEMY (SEQ ID NO 4) derived from ubiquitin specific peptidase 9 (USP9).
3. PE conjugated 270 kDa dextran coupled with HLA-A*0201 in complex with beta2 microglobulin and the peptide NLVPMVATV (SEQ ID NO 1) derived from Human Cytomegalo Virus (HCMV).
4. PE conjugated 270 kDa dextran coupled with HLA-A*0201 in complex with beta2 microglobulin and the peptide ILKEPVHGV (SEQ ID NO 2) derived from Human Immunodeficiency Virus (HIV).
5. PE/SA conjugated 270 kDa dextran coupled with HLA-B*0207 in complex with beta2 microglobulin and the peptide TPRVTGGGAM (SEQ ID NO 5) derived from Human Cytomegalo Virus (HCMV).
6. PE conjugated 270 kDa dextran coupled with HLA-B*0207 in complex with beta2 microglobulin and the peptide RPHERNGFTVL (SEQ ID NO 6) derived from Human Cytomegalo Virus (HCMV).
7. PE conjugated 270 kDa dextran coupled with HLA-B*0207 in complex with beta2 microglobulin and the peptide TPGPGVRYPL (SEQ ID NO 7) derived from Human Immunodeficiency Virus (HIV).

These seven MHC multimer constructs were used for detection of specific T cells in flow cytometry analysis using a no-lyse no-wash procedure. Blood samples from three individual donors were analyzed. The donors had previously been screened for the presence of specific T cells using a general staining procedure including lysis and wash of the cell sample, and donor one turned out to be positive for HLA*0201 in complex with the peptide NLVPMVATV (SEQ ID NO 1), donor two were positive for HLA*0101 in complex with the peptide VTEHDTLLY (SEQ ID NO 3) and donor three were positive for HLA-B*0207 in complex with the peptides TPRVTGGGAM (SEQ ID NO 5) and RPHERNGFTVL (SEQ ID NO 6). In this experiment blood from each donor were analyzed with the MHC multimer construct they were supposed to have specific T cells restricted for and with MHC multimers of same haplotype but carrying a negative control peptide. The negative control peptides were either derived from HIV or the self-protein USP 9. Self-protein here means a naturally occurring protein in normal cells of a human individual. Normal healthy donors not infected with HIV are not expected to have specific T cells recognizing HIV derived peptides or peptides derived from self-proteins in complex with any HLA molecule in an amount detectable with this analysis method.

The Blood was Stained as Follows:

100 µl EDTA stabilized blood were incubated with 5 µl MHC (peptide)/PE dextran for 5 minutes at room temperature. Anti-CD45/PB, anti-CD3/FITC and anti-CD8/APC antibody in an amount of 0.4-1.2 µg/sample was added to each tube and the incubation continued for another 15 minutes. 850 µl PBS; pH=7.2 was added and the sample analyzed on a CyAn ADP flow cytometry instrument with a speed of 150 µl/minute. A total of 20.000 CD8 positive cells were acquired. During analysis CD45/PB antibody was used to set a trigger discriminator to allow the flow cytometer to distinguish between red blood cells and stained white blood cells (see FIG. 2A). Furthermore CD3/FITC antibody was used to select CD3 positive cells in a second gating strategy (see FIG. 2B).

Blood from donor one showed specific staining with HLA-A*0201(NLVPMVATV) (SEQ ID NO 1) multimer (construct 3) while no staining of specific T cells was observed with the negative control HLA-A*0201(IL-KEPVHGV) multimer (SEQ ID NO 2) (construct 4). Donor two showed specific staining with HLA-A*0101(VTEH-DTLLY) multimer (SEQ ID No 3) (construct 1) and no staining was observed with the negative control HLA-A*0101(IVDCLTEMY) multimer (SEQ ID NO 4) (construct 2). In blood from donor three a population of T cells were stained with HLA-B*0207(TPRVTGGGAM) (SEQ ID NO 5) multimer (construct 5) and another population with HLA-B*0207(RPHERNGFTVL) multimer (SEQ ID NO 6) (construct 6) while no specific staining was observed with the negative control HLA-B*0207(TPGPGVRYPL) multimer (SEQ ID NO 7) (construct 7). The results are shown in FIG. 3.

We have shown that MHC multimers of three different haplotypes can be used to identify specific T cells in blood samples from three different donors using an approach without lysing red blood cells and without wash following staining with MHC multimer. This method is simple, fast and interfere as little as possible with cells in the blood sample.

Example 18

This example describes how to identify specific T cells in a blood sample with MHC multimers using flow cytometry analysis without lysis of red blood cells and without washing cells upon staining. The MHC complex is here any MHC I or MHC II molecule of human, rodent, bovine, monkey or any other origin loaded with any peptide able to bind the peptide-binding cleft of the MHC complex and where the MHC-peptide complexes are coupled to any multimerization domain.

Purified MHC-peptide complexes is generated as described elsewhere herein and coupled to any multimerization domain labelled with a fluorescent dye, preferable FITC, PE, APC, pacific blue, cascade yellow or any other flour chrome. These MHC multimers are used for detection of specific T cells by flow cytometry using the following procedure:

EDTA stabilized blood are incubated with MHC multimer at room temperature. The amount of blood analyzed is preferable 50-150 µl but could be any volume ranging from 1-1000 µl. The amount of MHC multimer depends on the multimer construct and the volume of blood and should be determined by titration prior to this type of experiment. The incubation time with MHC multimer is preferably 5-20 minutes but could be anything between 0 minutes and 1 hour. Then anti-CD45/CY, anti-CD3/APC and anti-CD8/PB antibody is added and the incubation continued. The incubation time is preferably 5-20 minutes but can be anything between 1 minute and 1 hour. The amount of antibody is preferable 0.4-1.2 µg/100 µl blood but these limits can be extended and should be determined by titration prior to this kind of experiments. The antibodies can be labelled with any fluorochrome as long as the fluorochrome is different from the fluorochrome on the MHC multimer. Next PBS; pH=7.0-8.0 is added and the sample analyzed by a flow cytometer. The amount of PBS added is preferable 500-1000 µl but may also be more than 1000 µl and less than 500 µl. During analysis anti-CD45 antibody is used to set a trigger discriminator to allow the flow cytometer to distinguish between red blood cells and stained white blood cells. Different gating strategies can then be applied to analyse data. Preferably cells are first gated on CD3 positive cells and then for CD8 positive cells, but can also be gated only for CD8 positive cells of only for CD3 positive cells. Alternatively "dump" gates can be applied excluding unwanted cells, e.g. B-cells, CD4-positive cells, NK-cells.

In the above example MHC multimers are added prior to antibodies but MHC multimers and antibodies can also be added simultaneously to the blood sample and incubated for preferably 5-30 minutes but the incubation time can be anything between 1 minute and 2 hours.

This method can be used to identify specific T cells in blood samples from different donors using an approach without lysing red blood cells and without wash following staining with MHC multimer. This method is simple, fast and interfere as little as possible with cells in the blood sample Example 19

This example illustrates how MHC multimers together with counting beads was used for exact numeration of MHC-peptide specific T cells in a flow cytometry analysis whit no lyses of red blood cells and no washing steps during or after staining. Counting beads in this example was CytoCount™, Count Control Beads from Dako that are polystyrene Fluorospheres with a diameter of 5.2 µm. The MHC multimer consisted of HLA-A*0101 heavy chain complexed with human beta2 microgloblin and a peptide and the MHC-peptide complexes were coupled to a 270 kDa dextran multimerization domain labelled with PE. MHC multimers were generated as described elsewhere herein and the following two constructs were made:

1) PE conjugated 270 kDa dextran coupled with HLA-A*0101 in complex with beta2 microglobulin and the peptide VTEHDTLLY (SEQ ID NO 3) derived from Human Cytomegalo Virus (HCMV).
2) PE conjugated 270 kDa dextran coupled with HLA-A*0101 in complex with beta2 microglobulin and the peptide IVDCLTEMY (SEQ ID NO 4) derived from ubiquitin specific peptidase 9 (USP9).

Construct 2 is a negative control for construct 1 in this example and both were used for detection of specific T cells by flow cytometry using a no-lyse no-wash procedure:

100 µl of EDTA stabilized blood from a donor positive for HLA*0101 in complex with the peptide VTEHDLLY (SEQ ID NO 3) were incubated with 5 µl MHC multimer for 5 minutes at room temperature. Anti-CD45/CY, anti-CD3/PB and anti-CD8/APC antibody in an amount of 0.4-1.2 µg/sample was added and the incubation continued for another 15 minutes. 850 µl PBS; pH=7.2 was added together with precise 50 µl CytoCount beads 1028 bead/µl and the sample analyzed on a CyAn ADP flow cytometry instrument with a speed of 150 µl/minute. A total of 20.000 CD8 positive cells were acquired. During analysis CD45/CY antibody was used to set a trigger discriminator to allow the flow cytometer to distinguish between red blood cells and stained white blood cells.

A dot plot was made for each sample showing MHC multimer vs CD8 positive events (se FIGS. 4A and B). Based on the negative control a gate containing events representing CD8 positive T cells specific for MHC multimer was defined. Similarly histogram plots for each sample were made showing FITC signal vs counts (FIGS. 4 C and D). In these histograms the amount of beads in the analyzed sample were identified since the beads in contrast to the cells emit light in the FITC channel. In principle the beads could be visualized in any fluorochrome channel because they emit light in all channels but it was important to visualize the beads in a channel where there was no interfering signal from labelled cells.

The concentration of T cells specific for HLA-A*0101 (VTEHDTLLY) (SEQ ID NO 3) multimer (construct 1) in the blood sample were determined using the counting beads as an internal standard. Events obtained from staining with the negative control MHC multimer, construct 2, were defined as background signals and subtracted from the result obtained from staining with construct 1.

Concentration of HLA-A*0101(VTEHDTLLY) (SEQ ID NO 3) specific T cells in the blood sample=((Count of MHC multimer+CD8+ positive cells, construct 1×concentration of beads×dilution factor of beads)/counted beads))−((Counted MHC multimer+CD8+ cells, construct 2×concentration of beads×dilution factor of beads)/counted beads)=992.6 cells/ml. For details see FIG. 4.

This experiment demonstrated how CytoCount™ counting beads together with MHC multimers could be used to determine the exact concentration of MHC-peptide specific T cells in a blood sample using a no-lyse no-wash method.

Example 20

This example describes an analysis of specific T cells in blood using MHC multimers where MHC multimers together with antibodies are pre-mixed and embedded in a matrix material to retain and immobilize the reagents prior to use. In this example the matrix was composed of Trehalose and Fructose and the MHC complex consisted of HLA-A*0101 heavy chain complexed with human beta2 microglobulin and peptide. The MHC-peptide complexes were coupled to a 270 kDa dextran multimerization domain.

Purified MHC-peptide complexes consisting of heavy chain, human beta2 microglobulin and peptide were generated by in vitro refolding, purified and biotinylated as described elsewhere herein. Biotinylated MHC (peptide) complexes were coupled to a 270 kDa dextran multimerization domain labelled with PE, thereby generating PE labelled MHC multimers. The following MHC multimer constructs were made:
1) PE conjugated 270 kDa dextran coupled with HLA-A*0101 in complex with beta2 microglobulin and the peptide VTEHDTLLY (SEQ ID NO 3) derived from Human Cytomegalo Virus (HCMV).
2) PE conjugated 270 kDa dextran coupled with HLA-A*0101 in complex with beta2 microglobulin and the negative control peptide IVDCLTEMY (SEQ ID NO 4) derived from ubiquitin specific peptidase 9 (USP9).

Tubes with a matrix material to retain and immobilize the above described MHC multimer constructs together with antibodies relevant for later flow cytometer analysis were made. The matrix material was made to retain MHC multimer and antibody in the container when dry but release them into the sample medium when a sample containing cells of interest was added to the tube.

Experimentally, solutions of 20% Fructose in water and 20% Trehalose in water were made and mixed in a 1:1 ratio. 15 µl of this mixture were transferred to two 5 ml Falcon tubes. A premix of antibodies were made consisting of 40 µl anti-CD8 Alexa700 labelled antibody in a concentration of 25 µg/ml+40 µl anti-CD3 Pacific Blue labelled antibody in a concentration of 100 µg/ml+160 µl anti-CD45 Cascade Yellow labelled antibody in a concentration of 200 µg/ml. 12 µl of this mixture were added to each Falcon tube together with 3 µl of either of the two MHC multimer constructs. 100 µl butylated hydroxytoluen (BHT) with a concentration of 99 mg/L were added. The mixtures were dried under vacuum a 2-8° C. over night. 100 µl EDTA stabilized blood from a donor with T cells specific for HLA-A*0101 complexed with the peptide VTEHDTLLY (SEQ ID NO 3) were added to each of the two tubes. As a control experiment 6 µl of the antibody premix described above were transferred to two empty 5 ml Falcon tubes together with 3 µl of either of the MHC multimer constructs and 100 µl blood from the same donor. All four tubes were incubated for 15 minutes at room temperature. Then 900 µl PBS; pH=7.2 was added and the sample analyzed on a CyAn ADP flow cytometer instrument.

A total of 20.000 CD8 positive cells were acquired for each sample. During analysis CD45/CY antibody was used to set a trigger discriminator to allow the flow cytometer to distinguish between red blood cells and stained white blood cells.

As expected and shown in FIG. 5, a population of CD8 positive and HLA-A*0101(VTEHDTLLY) (SEQ ID NO 3) multimer positive cells were observed in the two samples stained with construct 1. The amount of specific T cells detected in the matrix sample was comparable to the amount of specific T cells detected in the control sample without matrix material. No HLA-A*0101(IVDCLTEMY) (SEQ ID NO 4) multimer specific CD8 positive cells were observed in the two samples stained with the negative control MHC multimer construct 2.

This experiment demonstrates that the MHC multimer constructs used in this experiment can be embedded in a sugar matrix and later used for analysis of specific T cells in a blood sample and that this method gives results comparable to results obtained from a no-lyse no-wash staining procedure.

Example 21

This example describes an analysis of specific T cells in blood or other samples with cells in solution using MHC multimers where MHC multimers together with antibodies are pre-mixed and embedded in a matrix material to retain and immobilize the reagents prior to use. In this example the matrix is composed of Trehalose and Fructose and the MHC multimer is any MHC I, MHC II or MHC like molecule.

Tubes with a matrix material to retain and immobilize MHC multimer constructs together with antibodies relevant for later flow cytometer analysis are made. The matrix material is made to retain MHC multimer and antibody in the container when dry but release them into the sample medium when a sample containing cells of interest is added to the tube. The matrix is preferable water-soluble sugar mixtures but can be any contiguous mass releasing its components upon addition of aqueous solution. The matrix embedding medium may comprise one or more compounds including carbohydrates, polymers, small proteins etc. Examples of carbohydrates for use in the matrix include saccharose, arabinose, ribulose, fructose, sorbose, glucose, mannose, gulose, galactose, sucrose, lactose, maltose, trehalose, raffinose and melizitose. Examples of suitable polymers for use in matrix include polyvinyl alcohols, polyethylene glycols, polyethylene imines, polyacryl amides, polyaziridines, glycols, polyacrylic acids, esters or derivatives thereof. Examples of small proteins include BSA, other albumins or protein fragments.

The matrix-embedding medium is transferred to tubes preferable 5 ml tubes or other tubes usable in flow cytometry. Fluorochrome antibodies are added and here means any antibody useable for gating when analysing samples with T lymphocytes. Preferable antibodies are directed against CD8, CD4, CD3, CD45, CD27, CD28, CD45RA, CD45RO and CD62L. Then MHC multimer constructs are added but can also be added simultaneously with the antibodies or before the antibodies. Addition of MHC multimer is not restricted to one type of MHC multimer but several different MHC multimers can be added to the same tube and thereby embedded in the same matrix sample. Optionally scavengers for oxygen-derived radicals can be added. Examples of such radical scavengers are ascorbic acid, beta-carotene, bilirubin, butylated hydroxytoluene, butylated hydroxyanisol, tert-butylhydroquinone, d-alpha-tocopherol, trolox and hydroxyanisol. The matrix mixtures are then dried under vacuum a 2-8° C. over night.

Cell samples in solution are added to the dry or semidry matrix tubes. Cell samples here means any sample containing specific T cells. That is preferable whole blood, homogenized spleen, lymph nodes, tumors or similar or purified lymphocytes from any of the above. The samples are incubated at room temperature for 1 minute to 2 hours, preferable 10-30 minutes. They can also be incubated at 4° C. or 37° C. or any temperature in between those two. The samples are analyzed on a flow cytometry instrument.

As an alternative to the above described method MHC multimers can be added to the sample after addition of cell sample thereby only embedding antibodies and not MHC multimer in the matrix. Similarly only MHC multimer are embedded in the matrix and antibodies added after addition of cell sample.

For enumeration of specific T cells in the samples counting beads can be embedded in the matrix medium. The beads are then added before, together with or after adding antibodies and MHC multimer. Alternatively counting beads are added following incubation with cell sample. The exact amount of specific T cells is determined as described elsewhere herein.

Example 22

This is an example of a diagnostic test for cancer based on a blood sample and a membrane based immunoassay.

In men, prostate-specific antigen (PSA) levels in the blood may be used to screen for prostate cancer. The PSA Prostate Specific Antigen Rapid Test Device (Whole Blood/Serum/Plasma) is a semi-quantitative, membrane based immunoassay for the detection of PSA in whole blood, serum or plasma.

The membrane is pre-coated with PSA antibodies on the test line region. During testing, specimen reacts with the particle coated with anti-PSA antibody. The mixture migrates upward on the membrane chromatographically by capillary action to react with anti-PSA antibodies on the membrane and generate a colored line. The intensity of the test line (T) is weaker than reference line (R) indicating the PSA level in the specimen is between 4-10 ng/mL; The intensity of the test line (T) is close to reference line (R) indicating the PSA level in the specimen is approximately at 10 ng/mL. The intensity of the test line (T) is stronger than the reference line (R) indicating that the PSA level is above 10 ng/mL. To serve as a procedural control, a colored line will always appear in the control line region (C) indicating that proper volume of specimen has been added and membrane wicking has occurred.

Example 23

This is an example of a non-invasive diagnostic test for cancer.

A mammogram is an x-ray of the breast used either to screen for breast cancers that are too small to be felt or to help determine if a lump felt in the breast is caused by cancer or something else. Mammography detects 85%-90% of breast cancers, including tiny cancers that may measure less than a quarter-inch. Generally, a lump can't be felt until it's at least twice that size. Most authorities agree that women should have a mammogram every year starting at age 40; all agree it should be done annually after age 50.

Example 24

This is an example of how nuclear medicine test may be used for diagnosis and describes a Thyroid scan.

There are two types of thyroid nuclear medicine tests. Both assess the health of your thyroid, a gland in your neck that controls metabolism. A thyroid scan produces a picture of the gland to help evaluate any lumps or inflammation, or to investigate the cause of an overactive thyroid. A radioactive iodine uptake test is performed to see if your thyroid is functioning normally and to determine why thyroid hormone levels may be elevated. For both types of test, a small amount of a weakly radioactive substance, known as a radionuclide, is either injected into a vein or given to you as a pill A thyroid scan is usually ordered when a physical examination or laboratory finding suggests that the thyroid is enlarged. If laboratory tests show an overactive thyroid, a radioactive iodine uptake test may be ordered at the same time.

A radioactive iodine uptake test measures the amount of radioactivity in your thyroid after you've been given a relatively small dose of radioactive iodine in pill form. Your thyroid gland absorbs iodine and uses it to make hormones. Therefore, the amount of radioactive iodine detected in your thyroid gland corresponds with the amount of hormone your thyroid is producing.

Example 25

This example describes how Magnetic Resonance Imaging (MRI) may be used for diagnosis of abnormalities in the spine.

MRI is a noninvasive technique for visualizing many different body tissues. Unlike x-rays, MRI does not use any radiation. Instead, it uses radio waves, a large magnet, and a computer to create images. As with a CT scan (see page 23), which does use x-rays, each MRI picture shows a different "slice," or cross-section, of the area being viewed. Because these slices usually are spaced about a quarter-inch apart, your doctor can get a detailed representation of a particular area.

An MRI of the spine reveals any abnormalities in the vertebrae, vertebral discs, nerves, spinal cord, and muscles.

Example 26

Fluoresceine Angiography test for Diabetic retinopathy is an example of a non-invasive diagnostic test. By looking into the back of your eye (the retina), eye doctors can see changes in the blood vessels there that show whether you are at risk for losing vision from diabetes or other causes. The earliest changes can be seen only with a special test called fluorescein angiography. For this test, a chemical that temporarily makes the blood vessels fluorescent and shows very tiny leaks in them is injected into one of your arm or hand veins while you are having your eyes examined.

Example 27

Electromyography and Nerve Conduction Studies (EMG) are examples of non-invasive diagnostic tests diagnosing physical abnormalities.

Electromyography (EMG) tests analyze nerve and muscle electrical activity. Some types of electrical activity are normal, whereas some patterns of electrical activity suggest a disease of nerves or muscles. Nerve conduction studies are tests that are often used in combination with the EMG evaluation. For nerve conduction studies, the muscles and nerves are stimulated with small bursts of electricity to see whether the nerves and muscles respond in a normal way.

Example 28

This is an example of treatment of cancer patients with a cancer vaccine and where the effect of the cancer vaccine was followed by immune monitoring.

The disease treated is Melanoma.

The vaccine was a dendritic cell (DC) based vaccine and were administered with or without an adjuvant.

Two different immune monitoring methods used: 1) Indirect detection of T cells by measurement of proliferation (proliferation assay) and 2) Indirect detection of individual T cell by capture of secreted soluble factor on solid support (ELISPOT assays).

Vaccine Administration Protocol

Eligible patients were randomized to DC alone, DC followed by low dose IL-2, or DC followed by high dose IL-2.

Each patient underwent a pretreatment leukapheresis to obtain PBMC for DC vaccine preparation and also to obtain pretreatment lymphocytes for immunologic monitoring. Pretreatment each patient received DTH testing with irradiated autologous melanoma cells. Each cohort of patients received for each vaccination $10^7$ DC pulsed with KLH and autologous melanoma lysate by i.d. injection near an inguinal or axillary nodal region felt to be free of disease. A total of 3 vaccinations administered at the same site at 2 week intervals were planned (week 0, 2 and 4). Vaccination preceded IL-2 administration in those subjects receiving IL-2. For those patients randomized to low dose IL-2 the IL-2 was administered at a fixed dose of 3 million IU subcutaneously once a day for 4 days starting the day of the vaccination. For those patients randomized to high dose IL-2 the IL-2 was administered at 360,000 IU/kg by 15 minute IV infusion every 8 hours beginning the day of vaccination for a planned maximum of 9 doses of IL-2 after each vaccination. A scheduled dose of IL-2 was omitted for toxicity rather than dose reduced or delayed. Reasons for omitting IL-2 doses were; systolic blood pressure <90 mmHg refractory to fluid boluses or requiring doses of dopamine >5 mcg/kg/hour, respiratory distress requiring supplemental oxygen, mental confusion, tachydysrhythmia or cardiac ischemia (patients with these events received no further IL-2 during the study), or any other serious toxicity that in the judgment of the investigator (B.G.R.) warranted omitting IL-2 doses. At week 7 patients had a lymph node removed draining the vaccine site under conscious sedation. At week 9 patients were assessed for tumor response and underwent a repeat leukapheresis or large volume peripheral blood draw (100 ml) to obtain lymphocytes for immunologic monitoring. Also at week 9 patients underwent repeat DTH testing with irradiated autologous melanoma cells as well as DTH testing to KLH. Tumor response was determined by RECIST criteria. Patients who had a tumor response (at least a PR) were eligible for retreatment at week 11.

Leukapheresis and Cryopreservation of PBMCs

Patients underwent a 4-h leukapheresis on a COBE spectrum apheresis system to ensure adequate numbers of PBMCs for DC culture and for immune monitoring. PBMCs were obtained by taking the apheresis product, diluting it 4-fold in DPBS and overlaying it on Ficoll-Hypaque gradients. The cells were then centrifuged at 900×g for 30 min at room temperature.

The interface representing the PBMCs were then collected and washed in DPBS twice to reduce platelets. Aliquots of PBMCs were then cryopreserved in 70% human AB serum 20% X-VIVO 15 and 10% DMSO for future use in cryopreservation bags (Baxter Corp., Deerfield, Ill.) or cryovials.

Vaccination Preparation

DC cultures and antigen pulsing were performed in the Human Applications Laboratory of the General Clinical Research Center, which is a facility that operates under Good Manufacturing Procedures. Vaccines were prepared from cryopreserved PBMCs obtained from the pretreatment leukapheresis. PBMCs were resuspended in serum-free X-VIVO 15 medium (BioWhittaker, Walkerville, Md.) at $1\times10^7$ cells/ml for a total volume of 30 ml in 225-cm2 flasks. The cells were allowed to adhere for 2 h at 37° C. in 5% CO2, and the nonadherent cells were removed after gentle rocking of the flasks and aspiration of the medium. Immediate replacement of 30 ml of X-VIVO 15 medium containing GM-CSF (100 µg/ml; Schering-Plough, Kenilworth, N.J.) and IL-4 (50 ug/ml, Schering-Plough) was completed, and the cells were incubated for 6 days at 37° C., 5% CO2 before pulsing with tumor lysate and KLH. The adherent DCs were harvested from the flasks using 10 ml of EDTA (3 mM) for each flask and allowed to incubate for 10 min. The detached DCs were harvested, washed, and resuspended at $1\times10^6$ cells/ml in fresh X-VIVO 15 medium containing GM-CSF and IL-4.

Ten ml of the cell suspension were placed in 75-cm2 flasks ($10^7$ DCs/flask) for pulsing with tumor lysate and KLH. Single cell suspensions of tumor were snap freeze-thawed three times in rapid succession, irradiated at 10,000 cGy, and stored at −80° C. for later use. Tumor lysate suspension was added to DCs at 1:1 cell equivalent ratio. Specifically, a volume of tumor lysate equal to $10^7$ tumor cells was added to the flask and incubated for 18 h at 37° C., 5% CO2. A volume of 300 µl of KLH stock solution diluted in PBS (50 µg/ml; Calbiochem, San Diego, Calif.) was added to the flask and incubated for 18 h. After incubation, the tumor lysate-pulsed and KLH-pulsed DCs were harvested and counted. The DC suspension was adjusted to a total volume of 0.5 ml of PBS at $10^7$ DC for injection.

Immune Monitoring Using PBMCs

PBMCs were harvested pretreatment at the time of leukapheresis for DC generation and 1 month after the third vaccination when tumor response assessment was determined. All of the assays were done in batch on cryopreserved PBMCs. Cells were used soon after thawing. Cell viabilities ranged from 67 to 98% between patients, but for a given patient, viabilities between pre- and post treatment samples were within 15%. PBMC were thawed, washed with sterile PBS, and suspended in complete medium: X-VIVO-15 supplemented with 2% HEPES, 100 units/ml penicillin, 10 mg/ml streptomycin, 2 mM glutamine, 50 µM 2-mercaptoethanol, and 3% AB serum. Counts and viability were determined with trypan blue. All incubations were conducted at 37° C., 5% CO2. Antigens for assays were KLH (40 µg/ml, Calbiochem, San Diego, Calif.), tumor lysate (cell equivalence), *C. albicans* (1/100 dilution of cellular lysate, (Allermed, San Diego, Calif.). The following assays were performed by the Immunologic Monitoring Core of the University of Michigan Comprehensive Cancer Center.

Proliferation Assay—Cryopreserved PBMCs were thawed, washed, and suspended in complete medium. Viability was assessed by trypan blue exclusion, and cell concentrations were adjusted to $5 \times 10^6$/ml. Cells were added to 96-well, round-bottomed plates (Falcon-BD, Franklin Lakes, N.J.) in 100 µl volumes and incubated in a final volume of 200 µl with either medium alone, KLH (40 µg/ml), or tumor lysate (prepared to deliver lysate at tumor cell equivalence) for a total of 6 days at 37° C., 5% CO2. Phytohemagglutinin (10 ug/ml; Sigma Chemical Co.) was added to some of the wells as a positive control on day 3. The cultures were pulsed with 1 µCi-well of [3H]thymidine (ICN, Costa Mesa, Calif.) on day 5 and incubated overnight before harvest onto glass fiber filter plates (Millipore, Bedford, Mass.). Data were collected on a TopCount NXT scintillation counter (Meriden, Conn.). A stimulation index (SI) was calculated:

$$SI = \text{Avg. cpm of antigen-stimulated culture/Avg. cpm of unstimulated culture}$$

ELISPOT Assay—One day prior to assay, ELISPOT plates (Millipore, Bedford, Ma) were pre-wet with 70% ethanol, immediately washed with sterile PBS, then incubated overnight at 4° C. with 75 µl/well of anti-IFN-γ coating Ab (Pierce, Rockford, Ill.) suspended at 4 µg/ml in sterile 0.1 M carbonate buffer. The day of assay, the plates were washed with sterile PBS (Mediatech, Herndon, Va.) and then blocked for 1 hour with complete medium. PBMCs were prepared as above and adjusted to $1 \times 10^7$/ml. One hundred µl of PBMCs were added to each well and incubated with antigen as above. Negative controls for the assay were unstimulated PBMCs. Background counts for these samples were quite low and were subtracted from the counts generated from stimulated cultures. Positive controls were stimulated with phorbol myristate+ ionomycin. Cultures were incubated undisturbed at 37° C., 5% CO2 for 24 h. After 24 h, cells were removed, and the plates were washed two times with PBS and then two times with wash buffer (tris-buffered saline+0.05% Tween-20). Biotinylated secondary Ab suspended in assay buffer (TBS+0.2% casein) at 2 µg/ml was added and incubated for 2 hours. Plates were washed 5 times and incubated for 1 hour with streptavidin-alkaline phosphatise (Sigma). After 6 washes, plates were developed with NBT-BCIP substrate (Bio/FX, Owings Mills, Md.) for 20-40 minutes, and stopped in running water. Plates were allowed to dry at least 24 hours before analysis using an ImmunoSpot Series 1 analyzer (Cellular Technologies Ltd, Cleveland, Ohio). Background counts were generally low and subtracted from the responses in stimulated cultures for presentation. We defined a positive ELISPOT as a 3× increase over the pretreatment result or if the pretreatment was 0 spots then the post-vaccine result had to be >10 spots.

Lymph Node Assays—Harvested lymph nodes were teased apart and cells were washed and cryopreserved prior to assay. ELISPOT and proliferation assays were performed as above using pre-vaccine PBMC as antigen presenting cells. For both assays, LN cells and PBMC were added at 105/well. The proliferation assay was performed in 96 well plates and developed using a dye-conversion assay (Dojindo, Gaithersburg, Md.).

DTH Testing

In addition to in vitro immune monitoring, we assessed patients for in vivo immune reactivity to KLH and autologous tumor by DTH testing. For KLH reactivity, patients were given intradermal injections of 2, 20, and 100 µg of KLH in 0.2-ml volumes of PBS. Induration was measured 48 h later in two perpendicular diameters. For autologous tumor reactivity, patients were assessed before treatment and 1 month after treatment with irradiated (6,000 cGy) autologous tumor cells at 104, 105, and 106 doses i.d. Induration was measured in a similar fashion as KLH. Positive DTH reactions were scored if the average perpendicular measurements exceeded 5 mm.

Results

Patient Characteristics

A total of 24 subjects were registered and randomized. Overall the patients were relatively young (median age 44 years old) and the majority had not received any systemic therapy for Stage IV disease. Only 3 subjects had a diagnosis of non-cutaneous primary melanoma (1 ocular, 2 mucosal). Twenty two subjects received at least one vaccine. Two subjects were not treated due to problems with vaccine production. Eighteen subjects received all 3 vaccines with 3 receiving 2 and 1 receiving 1 vaccine. Of the 3 subjects who received 2 vaccines, 2 had symptomatic progression of disease and 1 had vaccine production problems. The subject receiving 1 vaccine was due to production difficulties. All vaccines were prepared in antibiotic free medium as required at that time by the FDA. Of the 18 subjects who received all 3 vaccines, 14 had post treatment PBL harvest and 13 had post treatment lymph node biopsy. The 14 subjects for which there was post treatment PBL were randomized to; 5 no IL-2, 4 low dose IL-2 and 5 high dose IL-2.

DTH Response

Fourteen subjects received all 3 vaccines and had pre and post DTH responses assessed. No subject had a pretreatment DTH response to autologous tumor. Three subjects converted to positive DTH response to autologous tumor, one in each of the treatment arms. Nine subjects had a post treatment DTH response to KLH (2/4 high dose IL-2, 3/4 low dose IL-2, 4/5 vaccine alone). All 3 subjects with response to autologous tumor also had a response to KLH.

Analysis of PBMC (Immune Monitoring)

Pre and post treatment PBMC were available from 14 subjects. Interferon-gamma ELISPOT to KLH and autologous tumor was determined (FIG. 6). Across all treatment arms the post treatment response to KLH was significantly increased compared to pretreatment (p=0.005).

A similar significant increase was seen between pre and post treatment interferon gamma response to autologous tumor (p=0.011). A similar pattern was seen (FIG. 7) with respect to the proliferative responses to KLH and autologous tumor across all treatment arms (p<0.001, p=0.005, respectively). The three treatment arms were not significantly different from one another in respect to interferon-gamma ELISPOT or proliferation. The table below summarizes the DTH and ELISPOT responses by patient.

DTH and ELISPOT Response

| Patient | Post Tx DTH | | Post Tx ELISPOT | |
|---|---|---|---|---|
| | KLH | Tumor | KLH | Tumor |
| 11 | − | − | + | + |
| 12 | + | ND | − | − |
| 13 | + | − | + | + |
| 14 | + | − | − | − |
| 15 | + | + | − | − |
| 16 | + | − | + | + |
| 21 | + | + | + | + |
| 22 | + | − | + | + |
| 23 | − | − | + | + |
| 24 | + | − | + | + |
| 31 | − | − | + | − |
| 32 | + | + | − | − |
| 33 | − | − | + | + |
| 34 | − | − | + | + |

ND—Not Done

Analysis of Vaccine Draining Lymph Nodes

Vaccine draining lymph nodes were harvested approximately 10 to 14 days after the third vaccination. Ten subjects had vaccine draining lymph nodes retrieved and were analyzed for reactivity to KLH and autologous tumor lysate by ELISPOT and proliferative assays (FIGS. 8 and 9). By IFNγ ELISPOT assay, 9 of 10 subjects demonstrated reactivity to KLH whereas 4 of 10 had responses to autologous tumor lysate. The greater reactivity to KLH compared to tumor lysate was borne out in the proliferation assay as well. A ratio of proliferation was calculated for each subject (net absorbance of presenters+KLH to presenters) yielding ratios >1. The mean ratio for KLH was 1.61 and for tumor lysate was 1.28; this difference was statistically significant (p=0.03 by paired t-test). These data indicate that KLH immune reactivity was reliably elicited in draining lymph nodes; and was significantly more prevalent than reactivity to autologous tumor lysate. Due to the small number of subjects, no differences between the randomized groups could be observed.

Clinical Response

There was no tumor response as defined by RECIST criteria in any subject. There were 2 minor responses (patients 32 and 33) both in subjects who received high dose IL-2 and vaccine. These patients had reduction in size of their metastatic lesions but not enough to meet RECIST criteria for a partial response. One of these minor responses occurred in a subject who had progressed on high dose IL-2 prior to participation in the DC vaccine trial.

This examples shows how Dendritic cells can be pulsed with autologous tumor lysate and used for vaccination of cancer patients with melanoma and how the immunologic response can be followed using immune monitoring methods.

In this example several patients showed an increased immunological response while no patients had a clinical anti-tumor response.

This example is modified from Redman et al. Phase 1 b trial assessing autologous, tumor-pulsed dendritic cells as a vaccine administered with or without IL-2 in patients with metastatic melanoma. J. Immunother. 2008; 31 (6): 591-598.

Example 29

This is an example of treatment of cancer patients with a cancer vaccine and where the effect of the cancer vaccine is followed by immune monitoring. The disease treated is Melanoma The vaccine is a dendritic cell (DC) based vaccine administered with an adjuvant (IL-2). The immune monitoring methods used is: Direct detection of individual T cells in fluid sample using flow cytometry.

Vaccine Administration Protocol

Patients with the HLA type HLA-A*0201 are treated with DC pulsed with autologous tumor lysates and IL-2. Each patient gets a pretreatment leukapheresis to obtain PBMC for DC vaccine preparation and also to obtain pretreatment lymphocytes for immunologic monitoring. Each patient receives for each vaccination 107 DC pulsed with KLH and autologous melanoma lysate by i.d. injection near an inguinal or axillary nodal region felt to be free of disease. A total of 3 vaccinations administered at the same site at 2 week intervals are planned (week 0, 2 and 4). Vaccination preceded IL-2 administration. The IL-2 was administered at 360,000 IU/kg by 15 minute IV infusion every 8 hours beginning the day of vaccination for a planned maximum of 9 doses of IL-2 after each vaccination. At week 7 patients have a lymph node removed draining the vaccine site under conscious sedation. At week 9 patients are assessed for tumor response and undergoes a repeat leukapheresis or large volume peripheral blood draw (100 ml) to obtain lymphocytes for immunologic monitoring. Clinical tumor response is determined by RECIST criteria. Patients who have a tumor response (at least a PR) are eligible for retreatment at week 11.

Leukapheresis and Cryopreservation of PBMCs

Patients undergoes a 4-h leukapheresis on a COBE spectrum apheresis system to ensure adequate numbers of PBMCs for DC culture and for immune monitoring. PBMCs are obtained by taking the apheresis product, diluting it 4-fold in DPBS and overlaying it on Ficoll-Hypaque gradients. The cells are then centrifuged at 900×g for 30 min at room temperature. The interface representing the PBMCs are then collected and washed in DPBS twice to reduce platelets. Aliquots of PBMCs are then cryopreserved in 70% human AB serum 20% X-VIVO 15 and 10% DMSO for future use in cryopreservation bags (Baxter Corp., Deerfield, Ill.) or cryovials.

Vaccination Preparation

Vaccines are prepared from cryopreserved PBMCs obtained from the pretreatment leukapheresis. PBMCs are resuspended in serum-free X-VIVO 15 medium (BioWhittaker, Walkerville, Md.) at 1×107 cells/ml for a total volume of 30 ml in 225-cm2 flasks. The cells are allowed to adhere for 2 h at 37° C. in 5% CO2, and the nonadherent cells are removed after gentle rocking of the flasks and aspiration of the medium. Immediate replacement of 30 ml of X-VIVO 15 medium containing GM-CSF (100 μg/ml; Schering-Plough, Kenilworth, N.J.) and IL-4 (50 ug/ml, Schering-Plough) is completed, and the cells are incubated for 6 days at 37° C., 5% CO2 before pulsing with tumor lysate and KLH.

The adherent DCs are harvested from the flasks using 10 ml of EDTA (3 mM) for each flask and allowed to incubate for 10 min. The detached DCs are harvested, washed, and resuspended at 1×106 cells/ml in fresh X-VIVO 15 medium containing GM-CSF and IL-4.

Ten ml of the cell suspension are placed in 75-cm2 flasks (107 DCs/flask) for pulsing with tumor lysate and KLH. Single cell suspensions of tumor are snap freeze-thawed three times in rapid succession, irradiated at 10,000 cGy, and stored at −80° C. for later use. Tumor lysate suspension are added to DCs at 1:1 cell equivalent ratio.

Specifically, a volume of tumor lysate equal to 107 tumor cells is added to the flask and incubated for 18 h at 37° C., 5% CO2. A volume of 300 µl of KLH stock solution diluted in PBS (50 µg/ml; Calbiochem, San Diego, Calif.) is added to the flask and incubated for 18 h.

After incubation, the tumor lysate-pulsed and KLH-pulsed DCs are harvested and counted. The DC suspension is adjusted to a total volume of 0.5 ml of PBS at 107 DC for injection.

Immune Monitoring

Fluorochrome labelled MHC multimers are used to stain PBMC obtained from patients before and after vaccine treatment and then the sample are analyzed by flow cytometry.

In this example the MHC multimer used are MHC complexes coupled to fluorophor-labelled dextran (Dextramers). The Dextramers are used for direct detection of TCR in flow Cytometry.

MHC multimers carrying melanoma specific peptides is in this example used to detect the presence of melanoma specific T cells in the blood from cancer patients. Purified MHC-peptide complexes consisting of HLA-A*0201 heavy chain, human beta2 microglobulin and peptides derived from the melanoma antigens gp100 and Mart-1 or a negative control peptide are generated by in vitro refolding, purified and biotinylated using standard procedures known by persons skilled in the art. Biotinylated MHC-peptide complexes are then coupled to a 270 kDa dextran multimerization domain labelled with APC by interaction with streptavidin (SA) on the dextran multimerization domain. MHC-peptide complexes are added in an amount corresponding to a ratio of three MHC-peptide molecules per SA molecule and each molecule dextran contains 3.7 SA molecule and 8.95 molecules APC. The final concentration of dextran is $3.8 \times 10e-8$ M. The following MHC (peptide)/APC dextran constructs are made:
1. APC-SA conjugated 270 kDa dextran coupled with HLA-A*0201 in complex with beta2 microglobulin and the peptide ITDQVPGSV (SEQ ID NO 186) derived from the melanoma antigen gp100.
2. APC-SA conjugated 270 kDa dextran coupled with HLA-A*0201 in complex with beta2 microglobulin and the peptide GILTVILGV (SEQ ID NO 187) derived from the melanoma antigen Mart-1
3. APC-SA conjugated 270 kDa dextran coupled with HLA-A*0201 in complex with beta2 microglobulin and a negative control peptide (non-sense peptide): GLAGDVSAV (SEQ ID NO 10).

The binding of the above described MHC (peptide)/APC dextran is used to determine the presence of Melanoma specific T cells in the blood from cancer patients by flow cytometry following a standard flow cytometry protocol.

Cryopreserved PBMC isolated from the patients and prepared as described are thawed and washed once in 10 RPMI medium with 5% FCS. PBMC's are then resuspended in PBS with 5% BSA in a concentration of $1-5 \times 10^7$ cells/ml and aliquoted into appropriate tubes with 100 ul in each tube. 10 µl of each of the MHC (peptide)/APC dextran constructs described above are added to separate tubes and incubated for 10 minutes in the dark at room temperature. 5 µl of each of each of the antibodies mouse-anti-human CD3/PB (clone UCHT1 from Dako), and mouse-anti-human CD8/PE (clone DK25 from Dako) are added and the incubation continues for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flow cytometer.

The presence of cells labeled with anti-CD3/PB, anti-CD8/PE and the MHC (peptide)/APC dextran construct 1 or 2 can then be determined and thereby the presence of Melanoma specific T cells in the blood of the patients. Blood analysed with MHC (peptide)/APC dextran construct 3 is the negative control and is used to determine the level of background signal.

In order to exactly enumerate the melanoma specific T cells counting beads may be added to the sample before analysis on the flow cytometer as described in example 19.

An increase in the number of melanoma specific T cells upon vaccination with the DC vaccine then indicates that the vaccine has elicited an tumor-specific immune response while no increase in the number of melanoma specific T cells upon vaccination indicates that the effect of the vaccine is limited.

The sensitivity of the above described test may be enhanced further by addition of labeled antibodies specific for activation markers expressed in or on the surface of the Melanoma specific T cells.

Example 30

This is an example of treatment of cancer patients with a cancer vaccine and where the effect of the cancer vaccine is followed by immune monitoring.

The disease treated is Melanoma

The vaccine is a dendritic cell (DC) based vaccine pulsed with autologous tumor-lysates and administered with an adjuvant (IL-2).

The immune monitoring methods used are: Direct detection of individual T cells in fluid sample using flow cytometry and Direct detection of individual T cells in solid sample using IHC.

Vaccine Administration Protocol

Patients with the HLA type HLA-A*0201 are treated with DC pulsed with autologous tumor lysates and IL-2. Each patient gets a pretreatment leukapheresis to obtain PBMC for DC vaccine preparation and also to obtain pretreatment lymphocytes for immunologic monitoring. Each patient receives for each vaccination 107 DC pulsed with KLH and autologous melanoma lysate by i.d. injection near an inguinal or axillary nodal region felt to be free of disease. A total of 3 vaccinations administered at the same site at 2 week intervals are planned (week 0, 2 and 4). Vaccination preceded IL-2 administration. The IL-2 was administered at 360,000 IU/kg by 15 minute IV infusion every 8 hours beginning the day of vaccination for a planned maximum of 9 doses of IL-2 after each vaccination. At week 7 patients have a lymph node removed draining the vaccine site under conscious sedation. At week 9 patients are assessed for tumor response and undergoes a repeat leukapheresis or large volume peripheral blood draw (100 ml) to obtain lymphocytes for immunologic monitoring. Clinical tumor response is determined by RECIST criteria. Patients who have a tumor response (at least a PR) are eligible for retreatment at week 11.

Leukapheresis and Cryopreservation of PBMCs

Patients undergoes a 4-h leukapheresis on a COBE spectrum apheresis system to ensure adequate numbers of PBMCs for DC culture and for immune monitoring. PBMCs are obtained by taking the apheresis product, diluting it 4-fold in DPBS and overlaying it on Ficoll-Hypaque gradients. The cells are then centrifuged at 900×g for 30 min at room temperature. The interface representing the PBMCs are then collected and washed in DPBS twice to reduce platelets. Aliquots of PBMCs are then cryopreserved in 70% human AB serum 20% X-VIVO 15 and 10% DMSO for future use in cryopreservation bags (Baxter Corp., Deerfield, Ill.) or cryovials.

Vaccination Preparation

Vaccines are prepared from cryopreserved PBMCs obtained from the pretreatment leukapheresis. PBMCs are resuspended in serum-free X-VIVO 15 medium (BioWhittaker, Walkerville, Md.) at 1×107 cells/ml for a total volume of 30 ml in 225-cm2 flasks. The cells are allowed to adhere for 2 h at 37° C. in 5% CO2, and the nonadherent cells are removed after gentle rocking of the flasks and aspiration of the medium. Immediate replacement of 30 ml of X-VIVO 15 medium containing GM-CSF (100 µg/ml; Schering-Plough, Kenilworth, N.J.) and IL-4 (50 ug/ml, Schering-Plough) is completed, and the cells are incubated for 6 days at 37° C., 5% CO2 before pulsing with tumor lysate and KLH.

The adherent DCs are harvested from the flasks using 10 ml of EDTA (3 mM) for each flask and allowed to incubate for 10 min. The detached DCs are harvested, washed, and resuspended at 1×106 cells/ml in fresh X-VIVO 15 medium containing GM-CSF and IL-4. Ten ml of the cell suspension are placed in 75-cm2 flasks (107 DCs/flask) for pulsing with tumor lysate and KLH. Single cell suspensions of tumor are snap freeze-thawed three times in rapid succession, irradiated at 10,000 cGy, and stored at −80° C. for later use. Tumor lysate suspension are added to DCs at 1:1 cell equivalent ratio. Specifically, a volume of tumor lysate equal to 107 tumor cells is added to the flask and incubated for 18 h at 37° C., 5% CO2. A volume of 300 µl of KLH stock solution diluted in PBS (50 µg/ml; Calbiochem, San Diego, Calif.) is added to the flask and incubated for 18 h After incubation, the tumor lysate-pulsed and KLH-pulsed DCs are harvested and counted.

The DC suspension is adjusted to a total volume of 0.5 ml of PBS at 107 DC for injection.

Immune Monitoring

Flow Cytometry Analysis:

Fluorochrome labelled MHC multimers are used to stain PBMC obtained from patients before and after vaccine treatment and then the sample are analyzed by flow cytometry.

In this example the MHC multimer used are MHC complexes coupled to fluorophor-labelled dextran (Dextramers). The Dextramers are used for direct detection of TCR in flow Cytometry.

MHC multimers carrying melanoma specific peptides is in this example used to detect the presence of melanoma specific T cells in the blood from cancer patients. Purified MHC-peptide complexes consisting of HLA-A*0201 heavy chain, human beta2 microglobulin and peptides derived from the melanoma antigens gp100 and Mart-1 or a negative control peptide are generated by in vitro refolding, purified and biotinylated using standard procedures known by persons skilled in the art. Biotinylated MHC-peptide complexes are then coupled to a 270 kDa dextran multimerization domain labelled with FITC by interaction with streptavidin (SA) on the dextran multimerization domain. MHC-peptide complexes are added in an amount corresponding to a ratio of three MHC-peptide molecules per SA molecule and each molecule dextran contains 14 SA molecule and 31 molecules FITCC. The final concentration of dextran is 3.8×10e-8 M. The following MHC (peptide)/FITC dextran constructs are made:

1. FITC-SA conjugated 270 kDa dextran coupled with HLA-A*0201 in complex with beta2 microglobulin and the peptide ITDQVPGSV (SEQ ID NO 186) derived from the melanoma antigen gp100.

2. FITC-SA conjugated 270 kDa dextran coupled with HLA-A*0201 in complex with beta2 microglobulin and the peptide GILTVILGV (SEQ ID NO 187) derived from the melanoma antigen Mart-1

3. FITC-SA conjugated 270 kDa dextran coupled with HLA-A*0201 in complex with beta2 microglobulin and a negative control peptide (non-sense peptide): GLAGDVSAV (SEQ ID NO 10).

The binding of the above described MHC (peptide)/FITC dextran is used to determine the presence of Melanoma specific T cells in the blood from cancer patients by flow cytometry following a standard flow cytometry protocol.

Cryopreserved PBMC isolated from the patients and prepared as described are thawed and washed once in 10 RPMI medium with 5% FCS. PBMC's are then resuspended in PBS with 5% BSA in a concentration of 1-5×10⁷ cells/ml and aliquoted into appropriate tubes with 100 ul in each tube. 10 µl of each of the MHC (peptide)/FITC dextran constructs described above are added to separate tubes and incubated for 10 minutes in the dark at room temperature. 5 µl of each of each of the antibodies mouse-anti-human CD3/PB (clone UCHT1 from Dako), and mouse-anti-human CD8/PE (clone DK25 from Dako) are added and the incubation continues for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flow cytometer.

The presence of cells labeled with anti-CD3/PB, anti-CD8/PE and the MHC (peptide)/FITC dextran construct 1 or 2 can then be determined and thereby the presence of Melanoma specific T cells in the blood of the patients. Blood analysed with MHC (peptide)/APC dextran construct 3 is the negative control and is used to determine the level of background signal.

In order to exactly enumerate the melanoma specific T cells counting beads may be added to the sample before analysis on the flow cytometer as described in example 19. An increase in the number of melanoma specific T cells upon vaccination with the DC vaccine then indicates that the vaccine has elicited an tumor-specific immune response while no increase in the number of melanoma specific T cells upon vaccination indicates that the effect of the vaccine is limited.

The sensitivity of the above described test may be enhanced further by addition of labeled antibodies specific for activation markers expressed in or on the surface of the Melanoma specific T cells.

IHC Analysis

Tumor specific T cells are detected in biopsies taken from tumor before vaccination and after the 3 vaccinations. MHC dextramers are then used to detect antigen-specific T cells on frozen tissue sections using enzymatic chromogenic precipitation detection. Biopsies from melanoma tumor are taken out, freezed and stored frozen until use.

Satining Procedure:

Equilibrate the cryosection tissue (e.g. section of spleen from transgenic mice) to −20° C. in the cryostate. Cut 5 µm sections and then dry sections on slides at room temperature. Store slides frozen until use at −20° C.

Equilibrate frozen sections to room temperature. Fix with acetone for 5 min. Immediately after fixation transfer slides to TBS buffer (50 mM Tris-HCL pH 7.6, 150 mM NaCl) for 10 min.

Incubate slides with FITC-conjugated MHC-dextramers 1, 2 or 3 described above at appropriate dilution (1:40-1:80)

and incubate for 30 min at room temperature. Other dilution ranges, as well as incubation time and temperature, may be desirable. Decant solution and gently tap slides against filter paper, submerge in TBS buffer.

Decant and wash for 10 min in TBS buffer.

Incubate with rabbit polyclonal anti-FITC antibody (Dako P5100) at 1:100 dilution in TBS at room temperature for 30 min.

Repeat step 5 and 6.

Incubate with Envision anti-Rabbit HRP (Dako K4003) at room temperature for 30 min.

Other visualization systems may be used.

Repeat step 5 and 6.

Develop with DAB+ (Dako K3468) in fume hood for 10 min. Other substrates may be used. Rinse slides in tap-water for 5 min. Counterstain with hematoxylin (Dako S3309) for 2 min. Repeat step 12, mount slides. The slides stained with MHC-Dextramers can now be evaluated by microscopy.

An increase in the number of melanoma specific T cells in the tissue sections upon vaccination with the DC vaccine then indicates that the vaccine has elicited a tumor-specific immune response while no increase in the number of melanoma specific T cells upon vaccination indicates that the effect of the vaccine is limited.

The sensitivity of the above described test may be enhanced further by addition of labeled antibodies specific for other molecule expressed on the surface of the Melanoma specific T cells.

The result of the flow cytometry and IHC analysis may be combined and used to determine the effect of the vaccinations and/or to determine whether further vaccinations should be performed.

Example 31

This is an example of how antigen specific T-cells can be detected using a direct detection method detecting T cell immobilized in solid tissue. In this example MHC dextramers are used to detect antigen specific T cells on frozen tissue sections using enzymatic chromogenic precipitation detection.

Equilibrate the cryosection tissue (e.g. section of spleen from transgenic mice) to −20° C. in the cryostate. Cut 5 μm sections and then dry sections on slides at room temperature. Store slides frozen until use at −20° C.

Equilibrate frozen sections to room temperature. Fix with acetone for 5 min.

Immediately after fixation transfer slides to TBS buffer (50 mM Tris-HCL pH 7.6, 150 mM NaCl) for 10 min.

Incubate slides with FITC-conjugated MHC-dextramers at appropriate dilution (1:40-1:80) and incubate for 30 min at room temperature. Other dilution ranges, as well as incubation time and temperature, may be desirable.

Decant solution and gently tap slides against filter paper, submerge in TBS buffer. Decant and wash for 10 min in TBS buffer.

Incubate with rabbit polyclonal anti-FITC antibody (Dako P5100) at 1:100 dilution in TBS at room temperature for 30 min.

Repeat step 5 and 6.

Incubate with Envision anti-Rabbit HRP (Dako K4003) at room temperature for 30 min. Other visualization systems may be used.

Repeat step 5 and 6.

Develop with DAB+ (Dako K3468) in fume hood for 10 min. Other substrates may be used. Rinse slides in tap-water for 5 min. Counterstain with hematoxylin (Dako S3309) for 2 min. Repeat step 12, mount slides. The slides stained with MHC-Dextramers can now be evaluated by microscopy.

Example 32

This is an example of how antigen specific T-cells can be detected using a direct detection method detecting T cell immobilized in solid tissue. In this example MHC dextramers are used to detect antigen specific T cells on paraffin embedded tissue sections using enzymatic chromogenic precipitation detection.

Formaldehyde fixed paraffin-embedded tissue are cut in section and mounted on the glass slice, for subsequent IHC staining with MHC-dextramers. Tissue fixed and prepared according to other protocols may be used as well. E.g. fresh tissue, lightly fixed tissue section (e.g. tissue fixed in 2% formaldehyde) or formalin-fixed, paraffin-embedded tissue section.

Optimal staining may require target retrieval treatment with enzymes as well as heating in a suitable buffer before incubation with antibodies and MHC-dextramer.

The sample is stained for DNA using DAPI stain, followed by incubated with an antigen specific MHCdex/FITC reagent, followed by addition of anti-FITC antibody labeled with HRP.

Then the substrate for HRP, "DAP" is added and the reaction allows to progress. The sample is analyzed by light microscopy for the present of a colored precipitate on the cells (DAPI stained nucleus) positive for the specific MHC/dex reagent.

A digital image of the stained sample is obtained, and this can be analyzed manually in the same way as by microscopy. However, a digital image may be used for automatic determination of where and how many cells that are positive, related to the total amount of cells, determined by the DAPI staining, or other criteria or stainings.

Example 33

This is an example of how MHC multimers may be used for detection of cancer specific T cells in blood samples from patients. This can be used for immune monitoring of cancer immunotherapies e.g. treatment with cancer vaccines.

In this example the MHC multimer used are MHC complexes coupled to fluorophor-labelled dextran (Dextramers). The dextramers are used for direct detection of TCR in flow Cytometry. The antigen origin is cancer, thus, immune monitoring of a cancer. MHC multimers carrying cancer specific peptides is in this example used to detect the presence of cancer specific T cells in the blood from cancer patients.

Purified MHC-peptide complexes consisting of HLA-A*1101 heavy chain, human beta2 microglobulin and peptide derived from a region in Survivin or a negative control peptide were generated by in vitro refolding, purified and biotinylated as described elsewhere herein. Biotinylated MHC-peptide complexes were then coupled to a 270 kDa dextran multimerization domain labelled with APC by interaction with streptavidin (SA) on the dextran multimerization domain. The dextran-APC-SA multimerization domain was generated as described elsewhere herein. MHC-peptide complexes were added in an amount corresponding to a ratio of three MHC-peptide molecules per SA molecule and each molecule dextran contains 3.7 SA molecule and 8.95 molecules APC. The final concentration of dextran was $3.8 \times 10^{-8}$ M. The following MHC (peptide)/APC dextran constructs were made:

1. APC-SA conjugated 270 kDa dextran coupled with HLA-A*1101 in complex with beta2 microglobulin and the peptide DLAQCFFCFK (SEQ ID NO 188) derived from Survivin.
2. APC-SA conjugated 270 kDa dextran coupled with HLA-A*1101 in complex with beta2 microglobulin and the non-sense peptide.

The binding of the above described MHC (peptide)/APC dextran was used to determine the presence of Survivin specific T cells in the blood from cancer patients by flow cytometry following a standard flow cytometry protocol.

Blood from a cancer patient is isolated and 100 ul of this blood is incubated with 10 µl of the MHC (peptide)/APC dextran constructs described above for 10 minutes in the dark at room temperature. 5 µl of each of each of the antibodies mouse-anti-human CD3/PB (clone UCHT1 from Dako), and mouse-anti-human CD8/PE (clone DK25 from Dako) are added and the incubation continues for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flow cytometer.

The presence of cells labeled with anti-CD3/PB, anti-CD8/PE and the MHC (peptide)/APC dextran construct 1 described above and thereby the presence of Survivin specific T cells in the blood. Blood analysed with MHC (peptide)/APC dextran construct 2 show no staining of CD3 and CD8 positive cells with this MHC (peptide)/APC dextran construct.

The sensitivity of the above described test may be enhanced by addition of labeled antibodies specific for activation markers expressed in or on the surface of the Survivin specific T cells.

We conclude that the MHC (peptide)/APC dextran constructs can be used to detect the presence of Survivin specific T cells in the blood of cancer and thereby used for immune monitoring in cancer patients Example 34

This is an example of indirect detection of a population of T cells, where cells in suspension are induced to produce cytokines. The cytokine production is detected by a chromogen assay using anti-cytokine antibodies. The antigenic peptide origin is Tuberculosis (TB), thus, immune monitoring of TB infection.

The ELISA method on whole blood is performed by the use of the QuantiFERON-CMI (QF-CMI, manufactured by Cellestis Limited. South Melbourne, Australia.) Step 2 is performed according to the protocol and with reagents provided by the manufacture. 0.5 ml of blood is used instead of 1 ml, and therefore a 48-well plate instead of a 24-well is used. The whole procedure of the test requires the use of the following materials and reagents: IFN-gamma QuantiFERON-CMI kit; 48-well plate and 7 tubes, each containing the different stimuli at the desired concentration. The ELISA technique, performed on whole blood, is composed of the following steps:

Step 1. Culture of Whole Blood
1. mix the tubes containing heparinised whole blood
2. distribute blood (500 µl/well) into sterile 48-well plates. For the children similar results can be obtained using 250µ/well of blood. Consequently the volume of the Reagents 1-7 to be added will be 50% of the volume indicated.
3. add control mitogen and specific antigens according to the table below.
4. mix well.
5. incubate plate at 37° C. for 24 hours
6. harvest plasma aliquots from each well

TABLE

| Reagent | Stimulus and working concentration (values in parentheses relate to concentration in µg/mL) | Concentration of stock solution for 0.5 ml of blood (mg/mL) | Volume to be added (µL) |
|---|---|---|---|
| 1 | CTR* or DMSO (8)**, or DMSO (60)** | ** | 50 |
| 2 | ESAT-6 protein (0.2) and CFP-10 protein (0.2) | 0.01 | 50 |
| 3 | ESAT-6 pooled peptides (50) | 0.5 | 50 |
| 4 | CFP-10 pooled peptides (8) | 0.08 | 50 |
| 5 | ESAT-6 and CFP-10 pooled peptides (58) | 0.6 | 50 |
| 6 | PHA (1) | 0.05 | 50 |
| 7 | PPD (5) | 0.05 | 50 |

*CTR: complete culture medium
**for DMSO: an identical solvent concentration will be added in reagent 1 corresponding to the amount of DMSO present in reagents 3-5.

Step 2. IFN-Gamma-Based ELISA
1. prepare "conjugated antibody" by dissolving it in the "green diluent" solution, and distribute in the ready-to-use ELISA plate.
2. add harvested plasma and "standard solution" to the corresponding wells containing "green diluent".
3. mix well.
4. cover the plate and incubate for 2 hours at room temperature.
5. wash with "wash buffer".
6. prepare the 100×"chromogen" by diluting it with the "enzyme substrate buffer" and distribute in the plate.
7. cover the plate and incubate for 30 minutes at room temperature in the dark.
8. add stop solution to block the reaction and immediately read optic density in each well, at 450/620 nm using an ELISA reader.

Evaluation of Test Results and Diagnostic Response

The optic density values of the plate are analysed, a standard curve and IFN-gamma values, expressed as International Units (I.U.)/mL, are calculated for each well by the use of special software provided by the manufacturer.

Example 35

This is an example of indirect detection of TCR, where cells in suspension are induced to procure cytokines. The cytokine production is detected by a chromogen assay using anti-cytokine antibodies. The antigenic peptide origin is *Borrelia*, thus, immune monitoring of *Borrelia*.

The experiment is performed as describe in the protocol in the example above. In this example the specific antigens added in step 1 is an optimal combination of *Borrelia* peptides and relevant controls.

We conclude, that the assay can be used to detection of *Borrelia* infection.

Example 36

This is an example of indirect detection of TCR, where cells in suspension are induced to procure cytokines. The cytokine production is detected by a chromogen assay using anti-cytokine antibodies. The antigenic peptide origin is Multiple sclerosis (MS), thus, immune monitoring of MS.

The experiment is performed as describe in the protocol in the example above. In this example the specific antigens added in step 1 is an optimal combination of MS peptides and relevant controls.

We conclude, that the assay can be used to detection of MS.

Example 37

This is an example of how MHC multimers may be used for the detection of antigen specific T-cells simultaneously with activation of T cells.

This example is a combination of i) direct detection of TCR, using MHC complexes coupled to any multimerisation as described elsewhere herein to stain antigen specific T cells, and ii) indirect detection of TCR, by detection of induced intracellular cytokine production by addition of fluorophor-labelled anti-cytokine antibodies by flow cytometry. Multicolor immunofluorescent staining with antibodies against intracellular cytokines and cell surface markers provides a high resolution method to identify the nature and frequency of cells which express a particular cytokine(s). In addition to enabling highly specific and sensitive measurements of several parameters for individual cells simultaneously, this method has the capacity for rapid analysis of large numbers of cells which are required for making statistically significant measurements.

Production of cytokines plays an important role in the immune response. Examples include the induction of many antiviral proteins by IFN-γ, the induction of T cell proliferation by IL-2 and the inhibition of viral gene expression and replication by TNF-α. Cytokines are not preformed factors; instead they are rapidly produced upon relevant stimulation. Intracellular cytokine staining relies upon the stimulation of T cells in the presence of an inhibitor of protein transport thus retaining the cytokines inside the cell.

Cellular activation to trigger cytokine production generally results in down-regulation of the T cell receptor. For this reason, MHC multimer staining is carried out prior to activation to ensure a good level of staining. The MHC multimers may be internalized with the T cell receptor during this period, but can still be detected in permeabilized cells. To analyze the effector function of antigen-specific T cells, the cells are first stained with MHC multimers, and then stimulated with antigen. This is followed by staining with antibodies specific for extracellular epitopes (such as CD8), then by membrane permeabilization and intracellular cytokine staining. The following protocol is an example of MHC multimer co-staining with anti-IFN-γ, TNF-α, MIP-1b, or IL-2.

Protocol applicable for intracellular staining of IFNg, TNFa, MIP-1b, or IL-2
1. Prepare peripheral blood cells in phosphate buffered saline (PBS) at a cell concentration of $2 \times 10^7$ cells/ml.
2. Transfer the cell suspension to individual tubes in 50 µl aliquots.
3. Add relevant titrated fluorescently-labeled MHC multimers to the desired tubes, and incubate for 10 min at 22° C. (nonstimulated single-color controls should not be stained at this stage). Add 10 µl PBS to remaining tubes.
4. Add 500 µl PBS to each tube. Centrifuge at 450×g for 5 minutes at 10° C.
5. Aspirate supernatant. Agitate to disrupt cell pellets and resuspend in 200 µl complete RPMI.
6. Dilute peptide/antigen stock 1:50 in complete RPMI. Add 2 µl of this (10 µg/ml (investigate the effect on cytokine response of titrating your peptide)) to each desired tube. If using Leukocyte Activation cocktail (LAC) as a control, rapidly thaw this at 37° C. in a water bath and add 0.33 µl of this to each desired tube.
7. Place the tubes at 37° C. in a humidified $CO_2$ incubator for 15 minutes to 1 hour.
8. Add Brefeldin A (10 µg/ml final) to the desired tubes (n.b. LAC contains Brefeldin A) and return to the incubator. Incubate for 15 hours (the optimal incubation time is variable and must be determined).
9. Remove tubes from the incubator. Centrifuge at 450×g for 5 minutes at 10° C.
10. Aspirate supernatant. Resuspend desired cell pellets in 50 µl PBS containing an optimally titrated amount of anti-CD8 antibody. Add 50 µl PBS to remaining tubes.
Note: Single-color controls should be stained at this stage. If additional phenotyping of samples is desired, antibodies to other cell surface receptors may also be added at this time.
11. Incubate for 20 minutes on ice.
12. Add 500 µl PBS to each tube. Centrifuge at 450×g for 5 minutes at 10° C.
13. Aspirate supernatant. Agitate to disrupt cell pellets.
14. Add 200 µl 4% paraformaldehyde to each sample tube. Vortex tubes. Incubate for 20 minutes on ice. This step will fix the cell morphology of the activated cells.
Note: The procedure can be stopped at this point. Repeat steps 12 and 13. Resuspend the cells in 100 µl/tube PBS. Cover and store the cells at 4° C. for up to 3 days. To proceed, repeat steps 12 and 13. Resuspend the cells in 100 µl/tube permeabilization buffer and proceed to step 16.
15. Add 200 µl permeabilization buffer to each tube.
16. Centrifuge at 450×g for 5 minutes at 10° C. Aspirate supernatant.
17. Add 100 µl permeabilization buffer to the sample tubes that are to be stained with anti-cytokine antibody. Add 100 µl PBS to the remaining tubes (i.e. Single-color controls).
18. Incubate for 5 minutes at room temperature.
19. Add an optimally titrated amount of conjugated anti-cytokine antibody to the desired sample tubes and mix.
20. Incubate for 20 minutes at room temperature.
21. Add 200 µl permeabilization buffer to each tube and centrifuge at 450×g for 5 minutes at 10° C. Aspirate supernatant and agitate tubes to disrupt the cell pellets.
22. Resuspend the cells in 200 µl fix solution. Vortex tubes. It is important to vortex well when adding this fixative so that cells do not clump.
23. The samples are now ready for data acquisition and analysis on a flow cytometer but may be stored overnight at 4° C. in the dark prior to analysis.

We conclude that the MHC multimer constructs can be used to detect the presence of specific T cells in the blood simultaneously with activation and intracellular staining of cytokines.

Example 38

This is an example of how MHC multimers may be used for the detection of antigen specific T-cells simultaneously with activation of T cells.

This example is a combination of i) direct detection of TCR, using MHC complexes coupled as pentamers to stain antigen specific T cells, and ii) indirect detection of TCR, by detection of induced intracellular cytokine production by addition of fluorophor-labelled anti-cytokine antibodies by flow cytometry. The antigenic origin is Epstein-Barr Virus (EBV), thus, immune monitoring of EBV infection PBMCs were incubated with either a negative control (non-specific) Pentamer (A*0201/EBV (GLCTLVAML))

(SEQ ID NO 8) or a Pentamer specific for the cells of interest (B*0801/EBV (RAKFKQLL)) (SEQ ID NO 9), then stimulated with LAC (non-specific activation) or B*0801/EBV peptide (specific peptide activation) for 15 hours in the presence of Brefeldin A. Fixation, permeabilization and staining for IFN-γ were carried out exactly as detailed in the protocol outlined in the example above (example 37).

The result is shown in FIG. 10.

Specific staining extracellular and intracellular are shown only when staining with specific Dextramer and only when the cells have been activated specifically or non-specifically. When cells have been activated specifically only pentamer specific cells produce IFN-γ, i.e. only pentamer specific T cells have been activated.

This method can be used for immune monitoring of diseases or treatments.

Example 39

This is an example of indirect detection of a population of T cells, where cells in suspension are induced to produce soluble factor. The soluble factor produced is a cytokine (IFN-γ) and is detected by a chromogen assay using anti-cytokine antibodies. The antigenic peptides origin is *Borrelia* bacteria.

Blood from patients suspected to have *Borrelia* infection are withdrawn and the presence of IFN-γ releasing T cells are detected as described in the following.

The procedure used in this example is a whole blood IFN-γ assay (QuantiFERON [QFT]; Cellestis, Carnegie, Australia) and involves two stages: (1) overnight incubation of whole blood with antigens and (2) measurement of IFN-γ production in harvested plasma samples by ELISA.

Briefly, the procedure is as follows:

Within 12 hours of collection, 1-ml aliquots of blood samples are dispensed into 24-well tissue culture plates and antigens are added to appropriate wells. Three drops of saline (nil control) or phytohemagglutinin (5 µg/ml; mitogen-positive control), and 100 µl of a peptide cocktail, are added to separate wells to give a final peptide concentration of 1 µg/ml. The peptide cocktail contain 10 antigenic peptides selected from the *Borrelia* antigen OspB. The 10 peptides are able to bind different HLA class 2 molecules and have the following sequences:

| | |
|---|---|
| KKYLLGFALVLALIA; | (SEQ ID NO 189) |
| DTVKLFNDTKIFISK; | (SEQ ID NO 190) |
| SKVFKKQGSLTEETE; | (SEQ ID NO 191) |
| TAVWSDTSNTLTVSA; | (SEQ ID NO 192) |
| ETYDSSNTKVASKVF; | (SEQ ID NO 193) |
| MKKYLLGFALVLALI; | (SEQ ID NO 194) |
| TKAVETLKNGIMLEG; | (SEQ ID NO 195) |
| KAVETLKNGIMLEGN; | (SEQ ID NO 196) |
| TLEYSDMTNDENATK and | (SEQ ID NO 197) |
| ITVQNYDTAGTKLAG. | (SEQ ID NO 198) |

Blood samples were incubated with antigens for 16 to 24 hours at 37° C. before harvesting about 300 µl of plasma from above the settled blood cells.

The concentration of IFN-γ produced in the four plasma samples from each subject, as a result of stimulation of specific T cells with antigen presenting cells displaying the above listed peptides, is determined by QuantiFERON-CMI ELISA or another IFN-γ measuring ELISA assay following the manufacturer's instructions.

Samples from up to 16 subjects are tested in each ELISA run, which also included a set of standards that are measured in duplicate. For an ELISA run to be valid, strict performance criteria (coefficient of variation less than 15% and correlation coefficient for the standard curve greater than 0.98) had to be met. ELISA data for the *Borrelia*-specific antigen OspB and the nil and mitogen controls are converted to international units per milliliter on the basis of the IFN-γ standard curve generated for each ELISA plate. For an individual's test to be deemed valid, their response to at least one antigen (OspB or mitogen) has to be at least 0.25 IU of IFN-γ per milliliter above that of their nil control (five times the limit of detection for the ELISA). Results for OspB are expressed as the concentration of IFN-γ detected minus the concentration of IFN-γ in the respective nil control plasma.

The presence of IFN-γ in blood of the tested individual indicates the presence of activated T cells specific for one or more of the investigated peptide epitopes from the *Borrelia* antigen OspB tested and can be regarded as a surrogate marker for infection with *Borrelia* bacteria.

Example 40

This is an example of indirect detection of a population of T cells, where cells in suspension are induced to produce soluble factor. The soluble factor produced is a cytokine (IFN-γ) and is detected by a chromogen assay using anti-cytokine antibodies. The antigenic peptides origin is *Borrelia* bacteria.

Blood from patients suspected to have *Borrelia* infection are withdrawn and the presence of IFN-γ releasing T cells are detected as described in the following.

The procedure used in this example is a whole blood assay (QuantiFERON [QFT]; Cellestis, Carnegie, Australia) and involves two stages: (1) overnight incubation of whole blood with antigens and (2) measurement of IFN-γ production in harvested plasma samples by ELISA.

Briefly, the procedure is as follows:

Within 12 hours of collection, 1-ml aliquots of blood samples are dispensed into 24-well tissue culture plates and antigens are added to appropriate wells. Three drops of saline (nil control) or phytohemagglutinin (5 µg/ml; mitogen-positive control), and 100 µl of a peptide cocktail, are added to separate wells to give a final peptide concentration of 1 µg/ml. The peptide cocktail contain 10-20 antigenic peptides selected from one or more *Borrelia* antigen(s). The 10-20 peptides are able to bind different HLA class 1 and/or 2 molecules and have sequences selected from the lists of *borrelia* derived antigenic peptide sequences enclosed in this application.

Blood samples were incubated with antigens for 16 to 24 hours at 37° C. before harvesting about 300 µl of plasma from above the settled blood cells.

The concentration of IFN-γ produced in the four plasma samples from each subject, as a result of stimulation of specific T cells with antigen presenting cells displaying the above listed peptides, is determined by QuantiFERON-CMI ELISA or another IFN-γ measuring ELISA assay following the manufacturer's instructions.

Samples from up to 16 subjects are tested in each ELISA run, which also included a set of standards that are measured in duplicate. For an ELISA run to be valid, strict performance criteria (coefficient of variation less than 15% and correlation coefficient for the standard curve greater than 0.98) had to be met. ELISA data for the *Borrelia*-specific antigen(s) and the nil and mitogen controls are converted to international units per milliliter on the basis of the IFN-γ standard curve generated for each ELISA plate. For an individual's test to be deemed valid, their response to at least one antigen (*Borrelia* antigen or mitogen) has to be at least 0.25 IU of IFN-γ per milliliter above that of their nil control (five times the limit of detection for the ELISA). Results for *Borrelia* antigen(s) are expressed as the concentration of detected minus the concentration of IFN-γ in the respective nil control plasma.

The presence of IFN-γ in blood of the tested individual indicates the presence of activated T cells specific for one or more of the investigated antigenic peptide epitopes from the *Borrelia* antigen(s) tested and can be regarded as a surrogate marker for infection with *Borrelia* bacteria.

Example 41

This is an example of indirect detection of a population of T cells, where cells in suspension are induced to produce soluble factor. The soluble factor produced is a cytokine (IFN-γ) and is detected by a chromogen assay using anti-cytokine antibodies. The antigenic peptides origin is *Borrelia* bacteria.

Blood from patients suspected to have *Borrelia* infection are withdrawn and the presence of IFN-γ releasing T cells are detected as described in the following.

The procedure used in this example is a whole blood IFN-γ assay (QuantiFERON [QFT]; Cellestis, Carnegie, Australia) and involves two stages: (1) overnight incubation of whole blood with antigens and (2) measurement of IFN-γ production in harvested plasma samples by ELISA.

Briefly, the procedure is as follows:

Within 12 hours of collection, 1-ml aliquots of blood samples are dispensed into 24-well tissue culture plates and antigens are added to appropriate wells. Three drops of saline (nil control) or phytohemagglutinin (5 µg/ml; mitogen-positive control), and 100 µl of a peptide cocktail, are added to separate wells to give a final peptide concentration of 1 µg/ml. The peptide cocktail contain 10-20 antigenic peptides selected from one or more *Borrelia* antigen(s). The 10-20 peptides comprises antigenic peptides able to bind different HLA class 1 and/or 2 molecules and these antigenic peptides have sequences selected from the lists of *borrelia* derived antigenic peptide sequences enclosed in this application.

Blood samples were incubated with antigens for 16 to 24 hours at 37° C. before harvesting about 300 µl of plasma from above the settled blood cells.

The concentration of IFN-γ produced in the four plasma samples from each subject, as a result of stimulation of specific T cells with antigen presenting cells displaying the above listed peptides, is determined by QuantiFERON-CMI ELISA or another IFN-γ measuring ELISA assay following the manufacturer's instructions.

Samples from up to 16 subjects are tested in each ELISA run, which also included a set of standards that are measured in duplicate. For an ELISA run to be valid, strict performance criteria (coefficient of variation less than 15% and correlation coefficient for the standard curve greater than 0.98) had to be met. ELISA data for the *Borrelia*-specific antigen(s) and the nil and mitogen controls are converted to international units per milliliter on the basis of the IFN-γ standard curve generated for each ELISA plate. For an individual's test to be deemed valid, their response to at least one antigen (*Borrelia* antigen or mitogen) has to be at least 0.25 IU of IFN-γ per milliliter above that of their nil control (five times the limit of detection for the ELISA). Results for *Borrelia* antigen(s) are expressed as the concentration of IFN-γ detected minus the concentration of IFN-γ in the respective nil control plasma.

The presence of IFN-γ in blood of the tested individual indicates the presence of activated T cells specific for one or more of the investigated antigenic peptides epitopes from the *Borrelia* antigen(s) tested and can be regarded as a surrogate marker for infection with *Borrelia* bacteria.

Example 42

This is an example of how *borrelia* derived antigenic peptides can be used for vaccination of Gerbils.

To ascertain whether cross-protection between different OspC families was possible, OspC proteins were purified from *B. burgdorferi* strain ZS7 (OspC family 1), *B. afzelii* strain PKO (OspC family 7) and *B. garinii* strain W (OspC family 10) and used as immunogens in the gerbil model of Lyme borreliosis against a challenge with *B. afzelii* strain Orth (OspC family 5). To test protection within a family, the OspC from strain H7 (OspC family 5) was used as an immunogen against strain Orth. The OspC from strain H7 belongs to the same serovar and RFLP-type as the OspC from strain Orth.

Gerbils were given either a single, subcutaneous immunization of purified OspC (20 .mu.g protein/200 .mu.l, adjuvanted with TiterMax #R-1 (CytRx), that is, were prepared as a water-in-oil (squalene) emulsion with a synthetic immunomodulator (copolymer CRL89-41) or two intraperitoneal injections of OspC (10 .mu.g protein/500 .mu.l) adjuvanted with aluminium hydroxide. The purified antigens were prepared from strains by methods described in U.S. patent application Ser. No. 07/903,580, the contents of which were previously incorporated above by reference. Three and a half weeks after the first immunization, blood samples were taken from the eye and plasma prepared so that the antibody response to the immunogen at the time of the challenge could be ascertained (unimmunized control animals were likewise treated). Four weeks after the first immunization, the animals were challenged intraperitoneally with 10.sup.4 cells (25-100 ID.sub.50) of strain Orth, as were a group of unimmunized control animals. The challenge suspension was also titrated in unimmunized gerbils to determine the dose required to infect 50% of the animals. After a further two weeks, the animals challenged with the 10.sup.4 dose were killed and the bladder, heart, kidneys and spleens cultured in BSK medium. Cultures were inspected for spirochetes at weekly intervals, from the second to the sixth week post-inoculation, by dark-field microscopy. Blood also was taken and the resultant plasma analyzed by western blotting for sero-conversion, i.e. the development of antibodies post-challenge to antigens from strain Orth other than the immunogen. There was good agreement between the cultural and serological tests used to ascertain which animals were infected. Only serological testing was used for the ID (50) determinations but in this instance the animals were bled three weeks post-challenge, the extra time being given to ensure that the antibody response in infected gerbils was sufficiently strong to be easily detected.

There were no signs of cross-protection between species i.e. OspC proteins from OspC families 1 (*B. burgdorferi*) and (*B. garinii*) were ineffective as immunogens against the challenge strain Orth (*B. afzelii*). Likewise there was no sign of cross-protection between different OspC families of the same species i.e. the OspC protein from an OspC family 7 isolate (*B. afzelii* strain PKO) was ineffective as an immunogen against a challenge with strain Orth which expresses an OspC protein from OspC family 5. By contrast, immunization with the OspC protein from strain H7 (OspC family 5) was effective against a challenge strain Orth (OspC family 5). These data indicate that cross-protection between the OspC families is unlikely and that protection within a family is possible. A multivalent vaccine comprising one or more types of OspC proteins from each of the OspC families should be sufficient to protect against most Lyme disease *Borrelia* strains.

This example is modified from patent WO94/25596.

The biological effect of the vaccination may be determined using immune monitoring assays as described elsewhere herein.

Example 43

This is an example of how a *borrelia* derived antigenic peptides can be used for vaccination of Gerbils.

In this example the antigenic peptides is the first 86 amino acids of the *Borrelia* Outer surface protein G (OspG). The amino acids sequences used is MNKKMKNLIICAVFV-LIISCKIDASSEDLKQNVKEKVEGFLDKELMQGD-DPNNSLFNPP PVLPASSHDNTPVLKAVQAKDG-GQQEG (SEQ ID NO 199) and is derived from *Borrelia burgdorferi* strain ZS7. Genes encoding the antigenic peptides with this sequence are synthesized e.g. using Gene Assembler™ gene synthesis platform (made by GeneArt) and cloned into a suitable expression vector. Then this plasmid is transformed into *E. coli*, expressed and purified using standard procedures known by persons skilled in the art.

This OspG(1-86) antigenic peptides are used as immunogens in the gerbil model of Lyme borreliosis against a challenge with *Borrelia burgdorferi*.

Gerbils were given either a single, subcutaneous immunization of purified OspG(1-86) (20 .mu.g protein/200 .mu.l, adjuvanted with TiterMax #R-1 (CytRx), that is, were prepared as a water-in-oil (squalene) emulsion with a synthetic immunomodulator (copolymer CRL89-41) or two intraperitoneal injections of OspG(1-86) (10 .mu.g protein/500 .mu.l) adjuvanted with aluminium hydroxide.

Three and a half weeks after the first immunization, blood samples are taken from the eye and plasma prepared so that the antibody response to the immunogen at the time of the challenge can be ascertained (unimmunized control animals were likewise treated). Four weeks after the first immunization, the animals are challenged intraperitoneally with 10.sup.4 cells (25-100 ID.sub.50) of a *Borreli burgdorferi* strain (e.g. ZS7 or B31). The challenge suspension is also titrated in unimmunized gerbils to determine the dose required to infect 50% of the animals. After a further two weeks, the animals challenged with the 10.sup.4 dose are killed and the bladder, heart, kidneys and spleens cultured in BSK medium. Cultures are inspected for spirochetes at weekly intervals, from the second to the sixth week post-inoculation, by dark-field microscopy. Only serological testing was used for the ID (50) determinations but in this instance the animals are bled three weeks post-challenge, the extra time being given to ensure that the antibody response in infected gerbils is sufficiently strong to be easily detected.

It is expected that vaccination with the OspG(1-86) protein is effective against a challenge strain ZS7 and may also be effective against challenge with other strains since these strains have homologous sequences of the first 86 amino acids of the OspG proteins.

The biological effect of the vaccination may be determined using immune monitoring assays as described elsewhere herein.

Example 44

This is an example of how several *borrelia* derived antigenic peptides can be used for vaccination of Gerbils.

In this example 10 different antigenic peptides with sequences derived from 1-10 different *borrelia* proteins are used to generate a vaccine against Lyme disease. Each sequence is selected to be homologous among many *Borrelia* species and strains. Genes encoding the antigenic peptides with these sequences are synthesized e.g. using Gene Assembler™ gene synthesis platform (made by GeneArt) and cloned into a suitable expression vectors. Then these plasmids are transformed into *E. coli*, expressed and purified using standard procedures known by persons skilled in the art. The antigenic peptides are used as immunogens in the gerbil model of Lyme borreliosis against a challenge with *Borrelia burgdorferi, Borrelia Garinii* and/or *Borrelia afzelii*.

Gerbils were given either a single, subcutaneous immunization of purified antigenic peptides (each 20 .mu.g protein/200 .mu.l, adjuvanted with TiterMax #R-1 (CytRx), that is, were prepared as a water-in-oil (squalene) emulsion with a synthetic immunomodulator (copolymer CRL89-41) or two intraperitoneal injections of antigenic peptides (each 10 .mu.g protein/500 .mu.l) adjuvanted with aluminium hydroxide. Three and a half weeks after the first immunization, blood samples are taken from the eye and plasma prepared so that the antibody response to the immunogen at the time of the challenge can be ascertained (unimmunized control animals were likewise treated). Four weeks after the first immunization, the animals are challenged intraperitoneally with 10.sup.4 cells (25-100 ID.sub.50) of a *Borreli burgdorferi, Borrelia Garinii* and/or *Borrelia afzelii* strain(s). The challenge suspension is also titrated in unimmunized gerbils to determine the dose required to infect 50% of the animals. After a further two weeks, the animals challenged with the 10.sup.4 dose are killed and the bladder, heart, kidneys and spleens cultured in BSK medium. Cultures are inspected for spirochetes at weekly intervals, from the second to the sixth week post-inoculation, by dark-field microscopy.

Only serological testing was used for the ID (50) determinations but in this instance the animals are bled three weeks post-challenge, the extra time being given to ensure that the antibody response in infected gerbils is sufficiently strong to be easily detected.

It is expected that vaccination with these antigenic peptides are effective against a challenge a wide range of *Borrelia* species and strain since these strains have homologous sequences of the amino acid sequence of the selected antigenic peptides.

A multivalent vaccine comprising one or more types of *Borrelia* derived proteins s should be sufficient to protect against most Lyme disease *Borrelia* strains. In general antigenic peptides comprising one/or more antigenic peptides sequence(s) as described herein can be used.

The biological effect of the vaccination may be determined using immune monitoring assays as described elsewhere herein.

Example 45

This is an example of how several *borrelia* derived antigenic peptides can be used for vaccination of humans against Lyme disease.

In this example 10-20 different antigenic peptides with sequences derived from 1-20 different *borrelia* proteins are used to generate a vaccine against Lyme disease. Each sequence is selected to be homologous among many *Borrelia* species and strains. Genes encoding the antigenic peptides with these sequences are synthesized, expressed and produced.

The antigenic peptides are used as vaccine components in humans

To protect against *Borrelia burgdorferi, Borrelia Garinii* and/or *Borrelia afzelii* strains.

The antigenic peptides are given in doses suitable for humans and together with an adjuvant useful in humans. The vaccine is given either as a single dose or as multiple doses.

It is expected that vaccination with these antigenic peptides are effective against a challenge a wide range of *Borrelia* species and strain since these strains have homologous sequences of the amino acid sequence of the selected antigenic peptides.

A multivalent vaccine comprising one or more types of *Borrelia* derived proteins s should be sufficient to protect humans against most Lyme disease *Borrelia* strains. In general antigenic peptides comprising one/or more *Borrelia* derived antigenic peptide sequences as described in the present application can be used.

The biological effect of the vaccination may be determined using immune monitoring assays as described elsewhere herein.

Example 46

This is an example of how several *borrelia* derived antigenic peptides can be used for vaccination of humans against Lyme disease.

In this example 10-20 different antigenic peptides with sequences derived from 1-20 different *borrelia* proteins are used to generate a vaccine against Lyme disease. Each sequence is selected to be homologous among many *Borrelia* species and strains. Genes encoding the antigenic peptides with these sequences are synthesized, expressed and produced.

The antigenic peptides are used as vaccine components in humans

To protect against *Borrelia burgdorferi, Borrelia Garinii* and/or *Borrelia afzelii* strains.

The antigenic peptides are given in doses suitable for humans and together with an adjuvant useful in humans. The vaccine is given either as a single dose or as multiple doses.

It is expected that vaccination with these antigenic peptides are effective against a challenge a wide range of *Borrelia* species and strain since these strains have homologous sequences of the amino acid sequence of the selected antigenic peptides. A multivalent vaccine comprising one or more types of *Borrelia* derived proteins s should be sufficient to protect humans against most Lyme disease *Borrelia* strains. In general any antigenic peptides comprising *Borrelia* derived amino acid sequences as described in the present application can be used.

The biological effect of the vaccination may be determined using immune monitoring assays as described elsewhere herein.

Example 47

This is an example of how MHC multimers can be used as a *borrelia* vaccine for monkeys.

The vaccine is composed of a Dextran (270 kDa) carrier that has been derivatized by attaching Strepavidin (on average 8.6 Strepavidin molecules/Dextran molecule). Attached to the carrier are human HLA class 1 and 2 molecules containing antigenic peptides derived from the *Borrelia* antigen Basic membrane protein A (BmpA). The attached HLA-peptide complexes are:

```
HLA-A*0201(YLAPDNVIT),          (SEQ ID NO 200)

HLA-A*0101(YSDEIDIIH),          (SEQ ID NO 201)

HLA-B*0702(APDNVITST),          (SEQ ID NO 202)

HLA-DRB1*0401(IELVLKESSSNSYLS), (SEQ ID NO 203)

HLA-BRB1*1501(MNKILLLILLESIVF)  (SEQ ID NO 204)
and

HLA-DRB1*1101(SDLIWLIGYRFSDVA). (SEQ ID NO 205)
```

A single full dose of the final vaccine corresponds to, 100 µg of each MHC class 1; 113.5 µg of HLA class 2; 3×25.8 µg HSP70 and 3×162.2 µg dextran (corresponding to a total of approx 300 µg MHC multimer/kg body weight for a monkey of 3.5 kg) and consist of a 1:1:1 mixture of the following three MHC multimers:

MHC Multimer 1:
HLA-A*0101(YSDEIDIIH) (SEQ ID NO 201)+HLA-DR*0401(IELVLKESSSNSYLS) (SEQ ID NO 203)+HSP70+Dextran carrier, in the molar ratio 10/10/4/1

MHC Multimer 2:
HLA-A*0201(YLAPDNVIT) (SEQ ID NO 200)+HLA-DR*1501(MNKILLLILLESIVF) (SEQ ID NO 204)+HSP70+Dextran carrier, in the molar ratio 10/10/4/1

MHC Multimer 2:
HLA-B*0702(APDNVITST) (SEQ ID NO 202)+HLA-DRB1*1101(SDLIWLIGYRFSDVA) (SEQ ID NO 205)+HSP70+Dextran carrier, in the molar ratio 10/10/4/1

Administration:

The MHC multimer mix is emulsified with the adjuvant Titermax Gold as specified by the manufacturer and administered as intramuscular injections at time points 0, 4, 8, and 16 weeks such that a full dose is given at 0 weeks and half-full dose at 4, 8, and 16 5 weeks. This vaccine may give protection against infection with *Borrelia* bacteria.

The biological effect of the vaccination may be determined using immune monitoring assays as described elsewhere herein.

Example 48

This is an example of how MHC multimers can be used as a *borrelia* vaccine for monkeys.

The vaccine is composed of an antigen presenting cell (APC) e.g. a Dendritic cell expressing the HLA class 1 molecules HLA-A*0101 and HLA-B*0702. The APC is loaded with antigenic peptides derived from the *Borrelia* protein Basic membrane protein A (BmpA) by incubation with the peptides for 2-5 hours at 37° C. The amino acid sequence of the peptides are YSDEIDIIH (SEQ ID NO 201) and APDNVITST (SEQ ID NO 202).

Administration: The peptide loaded APC are added the adjuvant Titermax Gold as specified by the manufacturer and administered as intramuscular injections at time points 0, 4, 8, and 16 weeks. This vaccine may give protection against infection with *Borrelia* bacteria. The biological effect of the vaccination may be determined using immune monitoring assays as described elsewhere herein.

Example 49

This is an example of how MHC multimers may be used for diagnosis of Lyme Disease in blood samples from humans infected with *Borrelia* bacteria.

In this example the MHC multimer used are MHC complexes coupled to fluorophor-labelled dextran (Dextramers). The dextramers are used for direct detection of TCR in flow Cytometry. The antigen origin is *Borrelia*, thus, immune monitoring of a *Borrelia* infection.

Lyme disease is caused by infection by *Borrelia* bacteria. During acute infection *Borrelia* specific activated T cells will be present in increased amounts in an activated state compared to healthy individuals. The presences of an increased amount of activated *Borrelia* specific T cells may thereby act as a surrogate marker for infection with *Borrelia* bacterium. MHC multimers carrying *borrelia* specific antigenic peptides is in this example used to detect the presence of *Borrelia* specific T cells in the blood of patients infected with *Borrelia*.

Purified MHC-peptide complexes consisting of HLA-A*0201 heavy chain, human beta2 microglobulin and peptide derived from regions in Outer surface protein A (Table B) or Flagellin B (Table C) conserved among the three species *Borrelia Burgdorferi*, *Borrelia Garinii* and *Borrelia Afzelii* or a negative control peptide are generated by in vitro refolding, purified and biotinylated as described elsewhere herein. Biotinylated MHC-peptide complexes are then coupled to a 270 kDa dextran multimerization domain labelled with APC by interaction with streptavidin (SA) on the dextran multimerization domain. The dextran-APC-SA multimerization domain is generated as described elsewhere herein. MHC-peptide complexes are added in an amount corresponding to a ratio of three MHC-peptide molecules per SA molecule and each molecule dextran contains 3.7 SA molecule and 8.95 molecules APC. The final concentration of dextran is 3.8×10e-8 M. The following MHC (peptide)/APC dextran constructs are made:

1. APC-SA conjugated 270 kDa dextran coupled with HLA-A*0201 in complex with beta2 microglobulin and the peptide ALIACKQNV (SEQ ID NO 206) derived from OspA.
2. APC-SA conjugated 270 kDa dextran coupled with HLA-A*0201 in complex with beta2 microglobulin and the peptide FTKEDTIT (SEQ ID NO 207) derived from OspA.
3. APC-SA conjugated 270 kDa dextran coupled with HLA-A*0201 in complex with beta2 microglobulin and the peptide SIQIEIEQL (SEQ ID NO 208) derived from Fla B
4. APC-SA conjugated 270 kDa dextran coupled with HLA-A*0201 in complex with beta2 microglobulin and the peptide NLNEVEKVL (SEQ ID NO 209) derived from Fla B
5. APC-SA conjugated 270 kDa dextran coupled with HLA-A*0201 in complex with beta2 microglobulin and the peptide SLAKIENAI (SEQ ID NO 210) derived from Fla B
6. APC-SA conjugated 270 kDa dextran coupled with HLA-A*0201 in complex with beta2 microglobulin and the non-sense peptide GLAGDVSAV (SEQ ID NO 10).

The binding of the above described MHC (peptide)/APC dextran is used to determine the presence of Osp A or Fla B specific T cells in the blood from *Borrelia* infected individuals by flow cytometry following a standard flow cytometry protocol. Blood from a patient with Lyme disease is isolated and 100 ul of this blood is incubated with 10 µl of each of the MHC (peptide)/APC dextran constructs described above for 10 minutes in the dark at room temperature. 5 µl of each of each of the antibodies mouse-anti-human CD3/PB (clone UCHT1 from Dako), mouse-anti-human CD4/FITC (clone MT310 from Dako) and mouse-anti-human CD8/PE (clone DK25 from Dako) are added and the incubation continues for another 20 minutes at 4° C. in the dark. The samples are then washed by adding 2 ml PBS; pH=7.2 followed by centrifugation for 5 minutes at 300×g and the supernatant removed. The washing step is repeated twice. The washed cells are resuspended in 400-500 µl PBS+1% BSA; pH=7.2 and analyzed on flow cytometer.

The presence of cells labeled with anti-CD3/PB, anti-CD8/PE and the MHC (peptide)/APC dextran constructs 1, 2, 3, 4 and 5 described above and thereby the presence of *Borrelia* specific T cells indicate that the patient are infected with *Borrelia* bacteria. Blood analysed with MHC (peptide)/APC dextran construct 6 show no staining of CD3 and CD8 positive cells with this MHC (peptide)/APC dextran construct. The result is shown in FIG. 11.

The sensitivity of the above described diagnostic test may be enhanced by addition of labeled antibodies specific for activation markers expressed in or on the surface of the *Borrelia* specific T cells.

We conclude that the MHC (peptide)/APC dextran constructs can be used to detect the presence of *Borrelia* specific T cells in the blood of patients infected with *Borrelia*.

Example 50

This is an Example of Therapy of Relapsed or Refractory Metastatic Prostate Cancer RhuMAb 2C4 is a full-length, humanized monoclonal antibody (produced in CHO cells) directed against ErbB2. RhuMab 2C4 blocks the associated of ErbB2 with other ErbB family members thereby inhibiting intracellular signaling through the ErbB pathway. In contrast to HERCEPTIN.RTM., rhuMAb 2C4 not only inhibits the growth of ErbB2 overexpressing tumors but also blocks growth of tumors that require ErbB ligand-dependent signaling.

RhuMAb 2C4 is indicated as a single agent for treatment of hormone-refractory (androgen independent) prostate cancer patients. Primary endpoints for efficacy include overall survival compared to best available care (Mitoxantrone/Prednisone), when used as a single agent, and safety. Secondary efficacy endpoints include: time to disease progression, response rate, quality of life, pain and/or duration of response. RhuMAb 2C4 is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration).

RhuMAb 2C4 is also indicated in combination with chemotherapy for treatment of hormone-refractory (androgen independent) prostate cancer patients. Primary endpoints for efficacy include overall survival compared to chemotherapy, and safety. Secondary efficacy endpoints include: time to disease progression, response rate, quality of life, pain and/or duration of response. RhuMAb 2C4 is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration).

Examples of drugs that can be combined with the anti-ErbB2 antibody (which blocks ligand activation of an ErbB2 receptor) to treat prostate cancer (e.g. androgen independent prostate cancer) include a farnesyl transferase inhibitor; an anti-angiogenic agent (e.g. an anti-VEGF antibody); an EGFR-targeted drug (e.g. C225 or ZD1839); another anti-ErbB2 antibody (e.g. a growth inhibitory anti-ErbB2 antibody such as HERCEPTIN.RTM., or an anti-ErbB2 antibody which induces apoptosis such as 7C2 or 7F3, including humanized and/or affinity matured variants thereof); a cytokine (e.g. IL-2, IL-12, G-CSF or GM-CSF); an anti-androgen (such as flutamide or cyproterone acetate); leuprolide; suramin; a chemotherapeutic agent such as vinblastine, estramustine, mitoxantrone, liarozole (a retinoic acid metabolism-blocking agent), cyclophosphamide, anthracycline antibiotics such as doxorubicin, a taxane (e.g. paclitaxel or docetaxel), or methotrexate, or any combination of the above, such as vinblastine/estramustine or cyclophosphamide/doxorubicin/methotrexate; prednisone; hydrocortizone; or combinations thereof. Standard doses for these various drugs can be administered, e.g. 40 mg/m.sup.2/wk docetaxel (TAXOTERE.RTM.); 6 (AUC) carboplatin; and 200 mg/m.sup.2 paclitaxel (TAXOL.RTM.).

Example 51

Therapy of Metastatic Breast Cancer

RhuMAb 2C4 is indicated as a single agent for treatment of metastatic breast cancer patients whose tumors do not overexpress ErbB2. Primary endpoints for efficacy include response rate and safety. Secondary efficacy endpoints include: overall survival, time to disease progression, quality of life, and/or duration of response. RhuMAb 2C4 is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration).

RhuMAb 2C4 is also indicated in combination with chemotherapy for treatment of metastatic breast cancer patients whose tumors do not overexpress ErbB2. Primary endpoints for efficacy include overall survival compared to chemotherapy alone, and safety. Secondary efficacy endpoints include: time to disease progression, response rate, quality of life, and/or duration of response. RhuMAb 2C4 is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration).

Examples of drugs that can be combined with the anti-ErbB2 antibody (which blocks ligand activation of an ErbB2 receptor) to treat breast cancer (e.g. metastatic breast cancer which is not characterized by ErbB2 overexpression) include chemotherapeutic agents such as anthracycline antibiotics (e.g. doxorubicin), cyclophosphamide, a taxane (e.g. paclitaxel or docetaxel), navelbine, xeloda, mitomycin C, a platinum compound, oxaliplatin, gemcitabine, or combinations of two or more of these such as doxorubicin/cyclophosphomide; another anti-ErbB2 antibody (e.g. a growth inhibitory anti-ErbB2 antibody such as HERCEPTIN.RTM., or an anti-ErbB2 antibody which induces apoptosis such as 7C2 or 7F3, including humanized or affinity matured variants thereof); an anti-estrogen (e.g. tamoxifen); a farnesyl transferase inhibitor; an anti-angiogenic agent (e.g. an anti-VEGF antibody); an EGFR-targeted drug (e.g. C225 or ZD1839); a cytokine (e.g. IL-2, IL-12, G-CSF or GM-CSF); or combinations of the above. Standard dosages for such additional drugs may be used.

RhuMAb 2C4 is additionally indicated in combination with HERCEPTIN.RTM. for treatment of metastatic breast cancer patients whose tumors overexpress ErbB2. Primary endpoints for efficacy include response rate, and safety. Secondary efficacy endpoints include: time to disease progression, overall survival compared to HERCEPTIN.RTM. alone, quality of life, and/or duration of response. RhuMAb 2C4 is administered intravenously (IV) weekly or every three weeks at 2 or 4 mg/kg, respectively, until disease progression. The antibody is supplied as a multi-dose liquid formulation (20 mL fill at a concentration of 20 mg/mL or higher concentration). HERCEPTIN.RTM. is administered IV as an initial loading dose of 4 mg/kg followed by a weekly maintenance dose of 2 mg/kg. HERCEPTIN.RTM. is supplied as a lyophilized powder. Each vial of HERCEPTIN.RTM. contains 440 mg HERCEPTIN.RTM., 9.9 mg L-histidine HCl, 6.4 mg L-histidine, 400 mg .alpha.-.alpha.-trehalose dihydrate, and 1.8 mg polysorbate 20. Reconstitution with 20 mL of Bacteriostatic Water for Injection (BWFI) containing 1.1% benzyl alcohol as a preservative, yields 21 mL of a multi-dose solution containing 21 mg/mL HERCEPTIN.RTM., at a pH of approximately 6.0.

Example 52

This is an example of analysis using direct detection of a defined structure in a solid sample. The defined structure is SCF and the marker molecule used is a polyclonal antibody.
Staining Procedure for SCF SCF staining is performed using a polyclonal antibody to SCF (Santa Cruz Biotechnology, Santa Cruz, Calif.). A biotinylated anti-rabbit secondary antibody (Jackson Research Labs, West Lake, Pa.). the "StreptABComplex-HRP" (Streptavidin/Biotin Complex with a Horseradish Peroxidase) label kit (DAKO Corporation, Carpinteria, Calif.), and the DAB chromagen (Dako) are used as the detection system for SCF. 10% Neutral Buffered Formalin fixed 4 micron paraffin sections of the sample are place onto coated slides. To prepare the sample for staining, the sample is first deparaffinized and hydrated to water. Antigen retrieval is performed enzymatically with Digest-All 1 (Zymed Labs), a Ficin digestion solution. 1-2 drops of the manufacture's ready-to-use solution was added to the sections and incubated for 20 minutes at 37.degree. C. The sections are then washed well with deionized water and rinsed with TBS. Endogenous peroxidase was blocked by incubating the sections with a 3% hydrogen peroxide/methanol solution for 10 minutes, followed by a deionized water wash. The sections are then blocked using 10% blocking goat serum in 0.1% BSA/0.1% Triton X for 10 minutes. The goat serum is then shaken off.

The sections are incubated with a 1:20 dilution of SCF primary antibody at 37.degree. C. for 45 minutes. The StreptABC label is prepared while the primary antibody was incubating with the sections by adding 4 .mu.ls of Streptavidin solution with 4 .mu.ls biotin solution in 1 ml of 50 mM Tris-HCL buffer, pH 7.6. After SCF primary antibody incubation, the sections are washed well with TBS and incubated with a 1:300 dilution of biotinylated Goat anti-rabbit IgG at 37.degree. C. for 20 minutes. The sections are washed well with TBS, followed by incubation with the StreptABC label at 37.degree. C. for 20 minutes. The sections are washed well with TBS, and DAB liquid chromagen was applied at room temperature for 5 minutes. The sections are then washed well with deionized water. The slides are counterstained with 4% ethyl green.

The expression of SCF can then be determined using a microscope.

Example 53

This is an example of analysis using direct detection of a defined structure in a solid sample. The defined structure is Phospho-AKT and the marker molecule used is a monoclonal antibody.
Staining Procedure for Phospho-AKT p-AKT staining is performed using a Dako Autostainer with the LSAB2 kit. 10% Neutral Buffered Formalin fixed 4 micron paraffin sections of the sample are place onto coated slides. To prepare the sample for staining, the sample is first deparaffinized and hydrated to water. Antigen retrieval is preformed with 0.1 M citrate retrieval buffer, pH 6.0 in a Decloaker Chamber (Biocare Medical, Walnut Grove, Calif.) following the manufacturer's instructions. The sections are allowed to cool for 15 minutes, and then washed well with deionized water. Endogenous peroxidase is blocked by incubating the sections with a 3% hydrogen peroxide/Methanol solution for 10 minutes, followed by a deionized water wash. The sections are then blocked using 10% blocking goat serum in 0.1% BSA/0.1% Triton X for 10 minutes. The goat serum is then shaken off.

The sections are then incubated with a 1:75 dilution of p-AKT primary antibody (Cell Signaling Technology, Beverly, Mass.) at 4.degree. C. overnight. The next morning, the sections are removed from the refrigerator and allowed to come to room temperature, about 30 minutes. The slides are washed well with TBS and loaded into the Dako Autostainer. The Autostainer is programmed to apply the biotinylated link for 30 minutes, the streptavidin-HRP reagent for 30 minutes, and the DAB chromagen for 5 minutes. The slides are rinsed with TBS/Tween by the autostainer between the linking antibody, labeling, and DAB chromagen applications. After DAB chromagen, the slides are removed from the autostainer and washed well with deionized water. The slides are counterstained with 4% ethyl green. The expression of p-AKT can then be determined using a microscope.

Example 54

This is an example of analysis using direct detection of a defined structure in a solid sample. The defined structure can be any defined structure and the marker molecule used is any marker molecule able to bind a defined structure.
Staining Procedure Staining is performed using a Dako Autostainer or another automated or manual staining equipment with a set of labeled marker molecules. 10% Neutral Buffered Formalin fixed 4 micron paraffin sections of the sample are place onto coated slides. To prepare the sample for staining, the sample is first deparaffinized and hydrated to water. Antigen retrieval is preformed with 0.1 M citrate retrieval buffer, pH 6.0 in a Decloaker Chamber (Biocare Medical, Walnut Grove, Calif.) following the manufacturer's instructions. The sections are allowed to cool for 15 minutes, and then washed well with deionized water. Endogenous peroxidase is blocked by incubating the sections with a 3% hydrogen peroxide/Methanol solution for 10 minutes, followed by a deionized water wash. The sections are then blocked using 10% blocking goat serum in 0.1% BSA/0.1% Triton X for 10 minutes. The goat serum is then shaken off.

The sections are then incubated with a 1:5-1:1000000 dilution of primary antibody at 4.degree. C. overnight. The next morning, the sections are removed from the refrigerator and allowed to come to room temperature, about 30 minutes. The slides are washed well with TBS and loaded into the automated staining instrument or stained manually in either case following the procedure: apply the biotinylated marker able to bind primary antibody for 30 minutes, then streptavidin-HRP reagent for 30 minutes, and then DAB chromagen for 5 minutes. The slides are rinsed with TBS/Tween between the each step. After DAB chromagen, the slides are removed from the autostainer and washed well with deionized water. The slides are counterstained with 4% ethyl green. The expression of the defined structure for which the primary antibody is specific can then be determined using a microscope.

ITEMS

The present invention is disclosed herein below with reference to a number of items the combination of which characterises preferred embodiments of the present invention.

In a first item the present invention is directed to:
1. A method for analysis and treatment of an undesired state of an individual in need thereof, comprising the steps of:
   (i) analysis of a predetermined parameter or state in said individual to evaluate said undesired state; the analysis is performed on said individual or on one or more sample(s) derived from said individual; and
   (ii) treatment of said undesired state in said individual.
2. The method according to item 1, wherein the treatment comprises one or more vaccine(s).
3. The method according to item 2, wherein the one or more vaccine(s) comprises one or more living virulent organism(s).
4. The method according to item 3, wherein the one or more living virulent organism(s) comprises one or more fully virulent organism(s).
5. The method according to item 3, wherein the one or more living virulent organism(s) comprises one or more partly virulent organism(s).
6. The method according to item 3, wherein the one or more living virulent organism(s) comprises one or more partly virulent organism(s) and one or more fully virulent organism(s).
7. The method according to item 5, wherein the one or more partly virulent organism(s) comprises one or more live attenuated microorganism(s).
8. The method according to item 7, wherein the one or more live attenuated microorganism(s) are modified by physical means.
9. The method according to item 8, wherein the physical means comprises heat.
10. The method according to item 7, wherein the one or more live attenuated microorganism(s) are modified by chemical means.
11. The method according to item 10, wherein the chemical means comprises one or more chemical(s).
12. The method according to item 7, wherein the one or more live attenuated microorganism(s) are modified by genetic manipulation.

13. The method according to item 12, wherein the genetic manipulation comprises generation of a recombinant bacteria missing virulence factors.
14. The method according to item 7, wherein the one or more live attenuated microorganism(s) are cultured under conditions that disable their virulent properties.
15. The method according to item 2, wherein the one or more vaccine(s) comprises one or more killed organism(s).
16. The method according to item 15, wherein the one or more killed organism(s) comprises one or more physically killed organism(s).
17. The method according to item 16, wherein the one or more physically killed organism(s) is killed by heat.
18. The method according to item 16, wherein the one or more physically killed organism(s) is killed by irradiation.
19. The method according to item 15, wherein the one or more killed organism(s) comprises one or more chemically killed organism(s).
20. The method according to item 19, wherein the one or more chemically killed organism(s) are killed by phenol.
21. The method according to item 19, wherein the one or more chemically killed organism(s) are killed by formaldehyde.
22. The method according to item 2, wherein the one or more vaccine(s) comprises one or more fragments of one or more microorganism(s).
23. The method according to item 22, wherein the one or more fragments of one or more microorganism(s) are isolated directly from the one or more microorganism(s).
24. The method according to item 2, wherein the one or more vaccine(s) comprises early HBV vaccine.
25. The method according to item 22, wherein the one or more fragments of one or more microorganism(s) are produced by recombinant DNA technology.
26. The method according to item 2, wherein the one or more vaccine(s) comprises HPV vaccine.
27. The method according to item 2, wherein the one or more vaccine(s) comprises one or more macromolecule(s).
28. The method according to item 27, wherein the one or more macromolecule(s) comprises one or more naturally occurring protein(s).
29. The method according to item 28, wherein the one or more naturally occurring protein(s) are isolated and used directly.
30. The method according to item 29, wherein the one or more naturally occurring protein(s) that are isolated and used directly comprises one or more cytokine(s).
31. The method according to item 29, wherein the one or more naturally occurring protein(s) that are isolated and used directly comprises one or more interleukine(s).
32. The method according to item 29, wherein the one or more naturally occurring protein(s) that are isolated and used directly comprises one or more interferone(s).
33. The method according to item 29, wherein the one or more naturally occurring protein(s) that are isolated and used directly comprises one or more antibodies(s).
34. The method according to item 33, wherein the one or more antibodies(s) comprises one or more monoclonal antibodies.
35. The method according to item 33, wherein the one or more antibodies(s) comprises one or more polyclonal antibodies.
36. The method according to item 28, wherein the one or more naturally occurring protein(s) are isolated and modified.
37. The method according to item 36, wherein the one or more naturally occurring protein(s) that are isolated and modified comprises one or more modified toxin(s).
38. The method according to item 37, wherein the one or more modified toxin(s) are chemically modified.
39. The method according to item 37, wherein the one or more modified toxin(s) are physically modified.
40. The method according to item 36, wherein the one or more naturally occurring protein(s) that are isolated and modified comprises one or more modified antibodies.
41. The method according to item 40, wherein the one or more modified antibodies are chemically modified.
42. The method according to item 40, wherein the one or more modified antibodies are digested into one or more fragment(s).
43. The method according to item 42, wherein the one or more fragment(s) comprises one or more Fab fragment(s).
44. The method according to item 27, wherein the one or more macromolecule(s) comprises one or more recombinant protein(s).
45. The method according to item 44, wherein the one or more recombinant protein(s) comprises one or more antibodies.
46. The method according to item 45, wherein the one or more antibodies comprises one or more full length antibodies.
47. The method according to item 45, wherein the one or more antibodies comprises one or more Fab fragments.
48. The method according to item 45, wherein the one or more antibodies comprises one or more scFv fragments.
49. The method according to item 45, wherein the one or more antibodies comprises one or more antibody-like scaffolds.
50. The method according to item 45-49, wherein the one or more antibodies are natural in sequence.
51. The method according to item 45-49, wherein the one or more antibodies are artificial in sequence.
52. The method according to item 51, wherein the one or more antibodies that are artificial in sequence have one or more amino acid substitutions in the binding site.
53. The method according to item 44, wherein the one or more recombinant protein(s) comprises one or more MHC molecule(s).
54. The method according to item 53, wherein the one or more MHC molecule(s) are one or more MHC I molecules.
55. The method according to item 54, wherein the one or more MHC I molecules consists of full length and/or truncated heavy chain, full length and/or truncated beta2m and peptide.
56. The method according to item 54, wherein the one or more MHC I molecules consists of full length and/or truncated heavy chain and full length and/or truncated beta2m.
57. The method according to item 54, wherein the one or more MHC I molecules consists of full length and/or truncated heavy chain and peptide.
58. The method according to item 54, wherein the one or more MHC I molecules consists of full length and/or truncated heavy chain.
59. The method according to item 53, wherein the one or more MHC molecule(s) are one or more MHC II molecules.
60. The method according to item 59, wherein the one or more MHC II molecules consists of full length and/or truncated alpha chain and full length and/or truncated beta chain and peptide.

61. The method according to item 59, wherein the one or more MHC II molecules consists of full length and/or truncated alpha chain and full length and/or truncated beta chain.
62. The method according to item 44, wherein the one or more recombinant protein(s) comprises one or more cytokine(s).
63. The method according to item 62, wherein the one or more cytokine(s) are full length.
64. The method according to item 62, wherein the one or more cytokine(s) are truncated.
65. The method according to item 44, wherein the one or more recombinant protein(s) comprises one or more interleukine(s).
66. The method according to item 65, wherein the one or more interleukine(s) are full length.
67. The method according to item 65, wherein the one or more interleukine(s) are truncated.
68. The method according to item 44, wherein the one or more recombinant protein(s) comprises one or more interferrone(s).
69. The method according to item 68, wherein the one or more interferrone(s) are full length.
70. The method according to item 68, wherein the one or more interferrone(s) are truncated.
71. The method according to item 27, wherein the one or more macromolecule(s) comprises one or more nucleic acid(s).
72. The method according to item 71, wherein the one or more nucleic acid(s) comprises DNA.
73. The method according to item 72, wherein the DNA encodes one or more protein(s).
74. The method according to item 72, wherein the DNA does not encode one or more protein(s).
75. The method according to item 71, wherein the one or more nucleic acid(s) comprises RNA.
76. The method according to item 75, wherein the RNA comprises one or more ribozyme(s).
77. The method according to item 75, wherein the RNA comprises antisense.
78. The method according to item 75, wherein the RNA comprises silencing RNA.
79. The method according to item 71, wherein the one or more nucleic acid(s) comprises LNA.
80. The method according to item 71, wherein the one or more nucleic acid(s) comprises PNA.
81. The method according to item 27, wherein the one or more macromolecule(s) comprises one or more carbohydrate(s).
82. The method according to item 81, wherein the one or more carbohydrate(s) comprises one or more pure carbohydrates.
83. The method according to item 81, wherein the one or more pure carbohydrates comprises one or more monosaccharides.
84. The method according to item 83, wherein the one or more monosaccharides are modified.
85. The method according to item 81, wherein the one or more pure carbohydrates comprises one or more disaccharides.
86. The method according to item 85, wherein the one or more disaccharides are modified.
87. The method according to item 81, wherein the one or more pure carbohydrates comprises one or more polysaccharides.
88. The method according to item 87, wherein the one or more polysaccharides are modified.
89. The method according to item 81, wherein the one or more carbohydrate(s) comprises one or more glycoprotein(s).
90. The method according to item 81, wherein the one or more carbohydrate(s) comprises one or more glycolipid(s).
91. The method according to item 27, wherein the one or more macromolecule(s) are not part of a complex.
92. The method according to item 27, wherein the one or more macromolecule(s) are part of one or more complex(es).
93. The method according to item 92, wherein the one or more complex(es) comprises one or more polymer backbone(s).
94. The method according to item 92, wherein the one or more complex(es) is attached to one or more solid support(s).
95. The method according to item 92, wherein the complex is attached to one or more bead(s).
96. The method according to item 2, wherein the one or more vaccine(s) are one or more cell-based vaccine(s).
97. The method according to item 96, wherein the one or more cell based vaccine(s) comprises one or more naturally occurring cell(s).
98. The method according to item 97, wherein the one or more naturally occurring cell(s) are isolated and amplified (by proliferation).
99. The method according to item 97, wherein the one or more naturally occurring cell(s) are isolated and modified.
100. The method according to item 99, wherein the one or more naturally occurring cell(s) that are isolated are modified to display one or more specific MHC complex(es).
101. The method according to item 100, wherein the one or more naturally occurring cell(s) that are isolated and modified to display one or more specific MHC complex(es) are incubated with one or more peptide(s).
102. The method according to item 100, wherein the one or more naturally occurring cell(s) that are isolated and modified to display one or more specific MHC complex(es) are fused to one or more other cells.
103. The method according to item 102, wherein the one or more other cells comprise one or more hybridoma cell(s).
104. The method according to item 100, wherein the one or more naturally occurring cell(s) that are isolated and modified to display one or more specific MHC complex(es) are obtained by one or more transfection(s).
105. The method according to item 104, wherein the one or more transfection(s) comprises supercoiled plasmid DNA.
106. The method according to item 104, wherein the one or more transfection(s) comprises siRNA.
107. The method according to item 104, wherein the one or more transfection(s) comprises protein.
108. The method according to item 100, wherein the one or more naturally occurring cell(s) that are isolated and modified by one or more chemical modification step(s).
109. The method according to item 96, wherein the one or more cell based vaccine(s) comprises one or more non-naturally occurring cell(s).
110. The method according to item 109, wherein the one or more cell based vaccine(s) comprises one or more non-naturally occurring cell(s) that are chemically modified.
111. The method according to item 109, wherein the one or more cell based vaccine(s) comprises one or more non-naturally occurring cell(s) that are genetically modified.

112. The method according to item 2, wherein the one or more vaccine(s) are one or more liposome/micelle-based vaccine(s).
113. The method according to item 2, wherein the one or more vaccine(s) are one or more nanocluster-based vaccine(s).
114. The method according to item 1, wherein the treatment comprises one or more drug(s).
115. The method according to item 114, wherein the one or more drug(s) comprises one or more macromolecules.
116. The method according to item 115, wherein the one or more macromolecules comprises one or more naturally occurring protein(s) and/or one or more recombinant protein(s).
117. The method according to item 116, wherein the one or more naturally occurring protein(s) and/or one or more recombinant protein(s) comprises one or more antibodies.
118. The method according to item 117, wherein the one or more antibodies comprises one or more full length antibodies.
119. The method according to item 117, wherein the one or more antibodies comprises one or more Fab fragment(s).
120. The method according to item 117, wherein the one or more antibodies comprises one or more scFv fragment(s).
121. The method according to item 117, wherein the one or more antibodies comprises one or more antibody-like scaffold(s).
122. The method according to item 117-121, wherein the one or more antibodies are natural in sequence.
123. The method according to item 117-121, wherein the one or more antibodies are artificial in sequence.
124. The method according to item 123, wherein the one or more antibodies that are artificial in sequence have one or more amino acid substitutions the binding site.
125. The method according to item 116, wherein the one or more naturally occurring protein(s) and/or one or more recombinant protein(s) comprises one or more L-Peptide(s).
126. The method according to item 116, wherein the one or more naturally occurring protein(s) and/or one or more recombinant protein(s) comprises one or more D-Peptide(s).
127. The method according to item 116, wherein the one or more naturally occurring protein(s) and/or one or more recombinant protein(s) comprises one or more MHC molecule(s).
128. The method according to item 127, wherein the one or more MHC molecule(s) are one or more MHC I molecule(s).
129. The method according to item 127, wherein the one or more MHC I molecule(s) consists of full length and/or truncated heavy chain, full length and/or truncated beta2m and peptide.
130. The method according to item 127, wherein the one or more MHC I molecule(s) consists of full length and/or truncated heavy chain and full length and/or truncated beta2m.
131. The method according to item 127, wherein the one or more MHC I molecule(s) consists of full length and/or truncated heavy chain and peptide.
132. The method according to item 127, wherein the one or more MHC I molecule(s) consists of full length and/or truncated heavy chain.
133. The method according to item 127, wherein the one or more MHC molecule(s) are one or more MHC II molecule(s).
134. The method according to item 133, wherein the one or more MHC II molecule(s) consists of full length and/or truncated alpha chain and full length and/or truncated beta chain and peptide.
135. The method according to item 133, wherein the one or more MHC II molecule(s) consists of full length and/or truncated alpha chain and full length and/or truncated beta chain.
136. The method according to item 116, wherein the one or more naturally occurring protein(s) and/or one or more recombinant protein(s) comprises one or more growth factor(s).
137. The method according to item 116, wherein the one or more naturally occurring protein(s) and/or one or more recombinant protein(s) comprises one or more growth hormone(s).
138. The method according to item 115, wherein the one or more macromolecules comprise one or more modified protein(s).
139. The method according to item 115, wherein the one or more modified protein(s) are pegylated.
140. The method according to item 115, wherein the one or more modified protein(s) are glycosylated.
141. The method according to item 115, wherein the one or more modified protein(s) are phosphorylated.
142. The method according to item 115, wherein the one or more macromolecules comprise one or more nucleic acid(s) and/or nucleic acid analogue(s).
143. The method according to item 142, wherein the one or more nucleic acid(s) and/or nucleic acid analogue(s) comprises DNA.
144. The method according to item 143, wherein the DNA encodes one or more protein(s).
145. The method according to item 143, wherein the DNA does not encode protein.
146. The method according to item 142, wherein the one or more nucleic acid(s) and/or nucleic acid analogue(s) comprises RNA.
147. The method according to item 146, wherein the RNA comprises one or more ribozyme(s).
148. The method according to item 146, wherein the RNA comprises antisense RNA.
149. The method according to item 146, wherein the RNA comprises silencing RNA.
150. The method according to item 142, wherein the one or more nucleic acid(s) and/or nucleic acid analogue(s) comprises LNA.
151. The method according to item 142, wherein the one or more nucleic acid(s) and/or nucleic acid analogue(s) comprises PNA.
152. The method according to item 115, wherein the one or more macromolecules comprise one or more carbohydrate(s).
153. The method according to item 152, wherein the one or more carbohydrate(s) one or more pure carbohydrate(s).
154. The method according to item 153, wherein the one or more pure carbohydrate(s) comprises one or more monosaccharide(s).
155. The method according to item 154, wherein the one or more monosaccharide(s) are modified.
156. The method according to item 153, wherein the one or more pure carbohydrate(s) comprises one or more disaccharide(s).
157. The method according to item 156, wherein the one or more disaccharide(s) are modified.

158. The method according to item 153, wherein the one or more pure carbohydrate(s) comprises one or more polysaccharide(s).
159. The method according to item 158, wherein the one or more polysaccharide(s) are modified.
160. The method according to item 152, wherein the one or more carbohydrate(s) one or more glycoprotein(s).
161. The method according to item 152, wherein the one or more carbohydrate(s) one or more glycolipid(s).
162. The method according to item 114, wherein the one or more drug(s) comprises one or more small molecule drug(s).
163. The method according to item 162, wherein the one or more small molecule drug(s) comprises one or more natural compound(s).
164. The method according to item 163, wherein the one or more natural compound(s) comprise one or more steroid(s).
165. The method according to item 163, wherein the one or more natural compound(s) comprise one or more salt(s).
166. The method according to item 165, wherein the one or more salt(s) comprises Ca2+.
167. The method according to item 165, wherein the one or more salt(s) comprises Mg2+.
168. The method according to item 162, wherein the one or more small molecule drug(s) comprises one or more synthetic chemical compound(s).
169. The method according to item 168, wherein the one or more synthetic chemical compound(s) comprise one or more Benzodiazepines.
170. The method according to item 168, wherein the one or more synthetic chemical compound(s) comprise one or more short peptide(s).
171. The method according to item 168, wherein the one or more synthetic chemical compound(s) comprise one or more Peptidommimetic(s).
172. The method according to item 114, wherein the one or more drug(s) can be selected from the group consisting of A-HYDROCORT (HYDROCORTISONE SODIUM SUCCINATE), A-METHAPRED (METHYLPREDNISOLONE SODIUM SUCCINATE), A-N STANNOUS AGGREGATED ALBUMIN (TECHNETIUM TC-99M ALBUMIN AGGREGATED KIT), A-POXIDE (CHLORDIAZEPOXIDE HYDROCHLORIDE), A.P.L. (GONADOTROPIN, CHORIONIC), A/T/S (ERYTHROMYCIN), ABACAVIR (ABACAVIR SULFATE), ABACAVIR SULFATE (ABACAVIR SULFATE), ABELCET (AMPHOTERICIN B), ABILIFY (ARIPIPRAZOLE), ABITREXATE (METHOTREXATE SODIUM), ABRAXANE (PACLITAXEL), ABREVA (DOCOSANOL), ACARBOSE (ACARBOSE), ACCOLATE (ZAFIRLUKAST), ACCRETROPIN (SOMATROPIN RECOMBINANT), ACCUNEB (ALBUTEROL SULFATE), ACCUPRIL (QUINAPRIL HYDROCHLORIDE), ACCURBRON (THEOPHYLLINE), ACCURETIC (HYDROCHLOROTHIAZIDE; QUINAPRIL HYDROCHLORIDE), ACCUTANE (ISOTRETINOIN), ACEBUTOLOL HYDROCHLORIDE (ACEBUTOLOL HYDROCHLORIDE), ACEON (PERINDOPRIL ERBUMINE), ACEPHEN (ACETAMINOPHEN), ACETADOTE (ACETYLCYSTEINE), ACETAMINOPHEN (ACETAMINOPHEN), ACETAMINOPHEN AND CODEINE PHOSPHATE (ACETAMINOPHEN; CODEINE PHOSPHATE), ACETAMINOPHEN AND CODEINE PHOSPHATE #2 (ACETAMINOPHEN; CODEINE PHOSPHATE), ACETAMINOPHEN AND CODEINE PHOSPHATE #3 (ACETAMINOPHEN; CODEINE PHOSPHATE), ACETAMINOPHEN AND CODEINE PHOSPHATE #4 (ACETAMINOPHEN; CODEINE PHOSPHATE), ACETAMINOPHEN AND CODEINE PHOSPHATE NO. 2 (ACETAMINOPHEN; CODEINE PHOSPHATE), ACETAMINOPHEN AND CODEINE PHOSPHATE NO. 3 (ACETAMINOPHEN; CODEINE PHOSPHATE), ACETAMINOPHEN AND CODEINE PHOSPHATE NO. 4 (ACETAMINOPHEN; CODEINE PHOSPHATE), ACETAMINOPHEN AND HYDROCODONE BITARTRATE (ACETAMINOPHEN; HYDROCODONE BITARTRATE), ACETAMINOPHEN AND PENTAZOCINE HYDROCHLORIDE (ACETAMINOPHEN; PENTAZOCINE HYDROCHLORIDE), ACETAMINOPHEN W/ CODEINE (ACETAMINOPHEN; CODEINE PHOSPHATE), ACETAMINOPHEN W/ CODEINE #2 (ACETAMINOPHEN; CODEINE PHOSPHATE), ACETAMINOPHEN W/ CODEINE #4 (ACETAMINOPHEN; CODEINE PHOSPHATE), ACETAMINOPHEN W/ CODEINE NO. 2 (ACETAMINOPHEN; CODEINE PHOSPHATE), ACETAMINOPHEN W/ CODEINE NO. 3 (ACETAMINOPHEN; CODEINE PHOSPHATE), ACETAMINOPHEN W/ CODEINE PHOSPHATE (ACETAMINOPHEN; CODEINE PHOSPHATE), ACETAMINOPHEN W/ CODEINE PHOSPHATE #3 (ACETAMINOPHEN; CODEINE PHOSPHATE), ACETAMINOPHEN, ASPIRIN AND CAFFEINE (ACETAMINOPHEN; ASPIRIN; CAFFEINE), ACETAMINOPHEN, ASPIRIN, AND CODEINE PHOSPHATE (ACETAMINOPHEN; ASPIRIN; CODEINE PHOSPHATE), ACETAMINOPHEN, BUTALBITAL AND CAFFEINE (ACETAMINOPHEN; BUTALBITAL; CAFFEINE), ACETAMINOPHEN, BUTALBITAL, AND CAFFEINE (ACETAMINOPHEN; BUTALBITAL; CAFFEINE), ACETAMINOPHEN, BUTALBITAL, CAFFEINE, AND CODEINE PHOSPHATE (ACETAMINOPHEN; BUTALBITAL; CAFFEINE; CODEINE PHOSPHATE), ACETAMINOPHEN, CAFFEINE, AND DIHYDROCODEINE BITARTRATE (ACETAMINOPHEN; CAFFEINE; DIHYDROCODEINE BITARTRATE), ACETASOL (ACETIC ACID, GLACIAL), ACETASOL HC (ACETIC ACID, GLACIAL; HYDROCORTISONE), ACETATED RINGER'S IN PLASTIC CONTAINER (CALCIUM CHLORIDE; POTASSIUM CHLORIDE; SODIUM ACETATE; SODIUM CHLORIDE), ACETAZOLAMIDE (ACETAZOLAMIDE), ACETAZOLAMIDE SODIUM (ACETAZOLAMIDE SODIUM), ACETIC ACID (ACETIC ACID, GLACIAL), ACETIC ACID 0.25% IN PLASTIC CONTAINER (ACETIC ACID, GLACIAL), ACETIC ACID 2% IN AQUEOUS ALUMINUM ACETATE (ACETIC ACID, GLACIAL; ALUMINUM ACETATE), ACETIC ACID W/ HYDROCORTISONE (ACETIC ACID, GLACIAL; HYDROCORTISONE), ACETOHEXAMIDE (ACETOHEXAMIDE), ACETYLCYSTEINE (ACETYLCYSTEINE), ACHES-N-PAIN (IBUPROFEN), ACHROMYCIN (HYDROCORTISONE; TETRACYCLINE HYDROCHLORIDE), ACHROMYCIN (PROCAINE HYDROCHLORIDE; TETRACYCLINE HYDROCHLORIDE), ACHROMYCIN (TETRACYCLINE HYDROCHLORIDE), ACHROMYCIN V (TETRACYCLINE HYDROCHLORIDE), ACILAC (LACTULOSE), ACIPHEX (RABEPRAZOLE SODIUM), ACLOVATE (ALCLOMETASONE DIPROPIONATE), ACTAHIST (PSEUDOEPHEDRINE HYDROCHLORIDE; TRIPROLIDINE HYDROCHLORIDE), ACTH (CORTICOTROPIN), ACTHAR (CORTICOTROPIN), ACTHAR GEL-SYNTHETIC (SERACTIDE ACETATE), ACTHREL (CORTICORELIN OVINE TRIFLUTATE), ACTICORT (HYDROCORTISONE), ACTIDIL (TRIPROLIDINE HYDROCHLORIDE), ACTIFED (PSEUDOEPHEDRINE HYDROCHLORIDE; TRIPROLIDINE HYDROCHLORIDE), ACTIFED W/ CODEINE (CODEINE PHOSPHATE; PSEUDOEPHEDRINE HYDROCHLORIDE; TRIPROLIDINE HYDROCHLORIDE), ACTIGALL (URSODIOL), ACTIMMUNE (INTERFERON GAMMA-1B), ACTIN-N (NITROFURAZONE), ACTINEX (MASOPROCOL), ACTIQ (FENTANYL CITRATE), ACTISITE (TETRACYCLINE HYDROCHLORIDE), ACTIVASE (ALTEPLASE), ACTIVELLA (ESTRADIOL; NORETHINDRONE ACETATE), ACTONEL (RISEDRONATE SODIUM), ACTONEL WITH CALCIUM (COPACKAGED) (CALCIUM CARBONATE; RISEDRONATE SODIUM), ACTOPLUS MET (METFORMIN HYDROCHLORIDE; PIOGLITAZONE HYDROCHLORIDE), ACTOS (PIOGLITAZONE HYDROCHLORIDE), ACTRON (KETOPROFEN), ACULAR (KETOROLAC TROMETHAMINE), ACULAR LS (KETOROLAC TROMETHAMINE), ACULAR PRESERVATIVE FREE (KETOROLAC TROMETHAMINE), ACUTECT (TECHNETIUM TC-99M APCITIDE), ACYCLOVIR (ACYCLOVIR), ACYCLOVIR (ACYCLOVIR SODIUM), ACYCLOVIR IN SODIUM CHLORIDE 0.9% PRESERVATIVE FREE (ACYCLOVIR SODIUM), ACYCLOVIR SODIUM (ACYCLOVIR SODIUM), ACYLANID (ACETYLDIGITOXIN), ACZONE (DAPSONE), ADAGEN (PEGADEMASE BOVINE), ADALAT (NIFEDIPINE), ADALAT CC (NIFEDIPINE), ADDERALL 10 (AMPHETAMINE ASPARTATE; AMPHETAMINE SULFATE; DEXTROAMPHETAMINE SACCHARATE; DEXTROAMPHETAMINE SULFATE), ADDERALL 12.5 (AMPHETAMINE ASPARTATE; AMPHETAMINE SULFATE; DEXTROAMPHETAMINE SACCHARATE; DEXTROAMPHETAMINE SULFATE), ADDERALL 15 (AMPHETAMINE ASPARTATE; AMPHETAMINE SULFATE; DEXTROAMPHETAMINE SACCHARATE; DEXTROAMPHETAMINE SULFATE), ADDERALL 20 (AMPHETAMINE ASPARTATE; AMPHETAMINE SULFATE; DEXTROAMPHETAMINE SACCHARATE; DEXTROAMPHETAMINE SULFATE), ADDERALL 30 (AMPHETAMINE ASPARTATE; AMPHETAMINE SULFATE; DEXTROAMPHETAMINE SACCHARATE; DEXTROAMPHETAMINE SULFATE), ADDERALL 5 (AMPHETAMINE ASPARTATE; AMPHETAMINE SULFATE; DEXTROAMPHETAMINE SACCHARATE; DEXTROAMPHETAMINE SULFATE), ADDERALL 7.5 (AMPHETAMINE ASPARTATE; AMPHETAMINE SULFATE; DEXTROAMPHETAMINE SACCHARATE; DEXTROAMPHETAMINE SULFATE), ADDERALL XR 10 (AMPHETAMINE ASPARTATE; AMPHETAMINE SULFATE; DEXTROAMPHETAMINE SACCHARATE; DEXTROAMPHETAMINE SULFATE), ADDERALL XR 15 (AMPHETAMINE ASPARTATE; AMPHETAMINE SULFATE; DEXTROAMPHETAMINE SACCHARATE; DEXTROAMPHETAMINE SULFATE), ADDERALL XR 20 (AMPHETAMINE ASPARTATE; AMPHETAMINE SULFATE; DEXTROAMPHETAMINE SACCHARATE; DEXTROAMPHETAMINE SULFATE), ADDERALL XR 25 (AMPHETAMINE ASPARTATE; AMPHETAMINE SULFATE; DEXTROAMPHETAMINE SACCHARATE; DEXTROAMPHETAMINE SULFATE), ADDERALL XR 30 (AMPHETAMINE ASPARTATE; AMPHETAMINE SULFATE; DEXTROAMPHETAMINE SACCHARATE; DEXTROAMPHETAMINE SULFATE), ADDERALL XR 5 (AMPHETAMINE ASPARTATE; AMPHETAMINE SULFATE; DEXTROAMPHETAMINE SACCHARATE; DEXTROAMPHETAMINE SULFATE), ADENOCARD (ADENOSINE), ADENOSCAN (ADENOSINE), ADENOSINE (ADENOSINE), ADIPEX-P (PHENTERMINE HYDROCHLORIDE), ADPHEN (PHENDIMETRAZINE TARTRATE), ADRIAMYCIN PFS (DOXORUBICIN HYDROCHLORIDE), ADRIAMYCIN RDF (DOXORUBICIN HYDROCHLORIDE), ADRUCIL (FLUOROURACIL), ADVAIR DISKUS 100/50 (FLUTICASONE PROPIONATE; SALMETEROL XINAFOATE), ADVAIR DISKUS 250/50 (FLUTICASONE PROPIONATE; SALMETEROL XINAFOATE), ADVAIR DISKUS 500/50 (FLUTICASONE PROPIONATE; SALMETEROL XINAFOATE), ADVAIR HFA (FLUTICASONE PROPIONATE; SALMETEROL XINAFOATE), ADVICOR (LOVASTATIN; NIACIN), ADVIL (IBUPROFEN), ADVIL ALLERGY SINUS (CHLORPHENIRAMINE MALEATE; IBUPROFEN; PSEUDOEPHEDRINE HYDROCHLORIDE), ADVIL COLD AND SINUS (IBUPROFEN; PSEUDOEPHEDRINE HYDROCHLORIDE), ADVIL LIQUI-GELS (IBUPROFEN), ADVIL MIGRAINE LIQUI-GELS (IBUPROFEN), ADVIL PM (DIPHENHYDRAMINE CITRATE; IBUPROFEN), ADVIL PM (DIPHENHYDRAMINE HYDROCHLORIDE; IBUPROFEN), AEROBID (FLUNISOLIDE), AEROLATE (THEOPHYLLINE), AEROLATE III (THEOPHYLLINE), AEROLATE JR (THEOPHYLLINE), AEROLATE SR (THEOPHYLLINE), AEROLONE (ISOPROTERENOL HYDROCHLORIDE), AEROSEB-DEX (DEXAMETHASONE), AEROSEB-HC (HYDROCORTISONE), AEROSPAN HFA (FLUNISOLIDE), AEROSPORIN (POLYMYXIN B SULFATE), AFAXIN (VITAMIN A PALMITATE), AFEDITAB CR (NIFEDIPINE), AFRINOL (PSEUDOEPHEDRINE SULFATE), AGENERASE (AMPRENAVIR), AGGRASTAT (TIROFIBAN HYDROCHLORIDE), AGGRENOX (ASPIRIN; DIPYRIDAMOLE), AGRYLIN (ANAGRELIDE HYDROCHLORIDE), AK-PENTOLATE (CYCLOPENTOLATE HYDROCHLORIDE), AKBETA (LEVOBUNOLOL HYDROCHLORIDE), AKINETON (BIPERIDEN HYDROCHLORIDE), AKINETON (BIPERIDEN LACTATE), AKNE-MYCIN (ERYTHROMYCIN), AKPENTOLATE (CYCLOPENTOLATE HYDROCHLORIDE), AKPRO (DIPIVEFRIN HYDROCHLORIDE), AKRINOL (ACRISORCIN), AKTOB (TOBRAMYCIN), ALA-CORT (HYDROCORTISONE), ALA-SCALP (HYDROCORTISONE), ALAMAST (PEMIROLAST POTASSIUM), ALAVERT (LORATADINE), ALAWAY (KETOTIFEN FUMARATE), ALBALON (NAPHAZOLINE HYDROCHLORIDE), ALBAMYCIN (NOVOBIOCIN SODIUM), ALBENZA (ALBENDAZOLE), ALBUTEROL (ALBUTEROL), ALBUTEROL SULFATE (ALBUTEROL SULFATE), ALBUTEROL SULFATE AND IPRATROPIUM BROMIDE (ALBUTEROL SULFATE; IPRATROPIUM BROMIDE), ALBUTEROL SULFATE; IPRATROPIUM BROMIDE (ALBUTEROL SULFATE; IPRATROPIUM BROMIDE), ALCAINE (PROPARACAINE HYDROCHLORIDE), ALCOMETASONE DIPROPIONATE (ALCLOMETASONE DIPROPIONATE), ALCOHOL 10% AND DEXTROSE 5% (ALCOHOL; DEXTROSE), ALCOHOL 5% AND DEXTROSE 5% (ALCOHOL; DEXTROSE), ALCOHOL 5% IN D5-W (ALCOHOL; DEXTROSE), ALCOHOL 5% IN DEXTROSE 5% (ALCOHOL), ALCOHOL 5% IN DEXTROSE 5% IN WATER (ALCOHOL; DEXTROSE), ALDACTAZIDE (HYDROCHLOROTHIAZIDE; SPIRONOLACTONE), ALDACTONE (SPIRONOLACTONE), ALDARA (IMIQUIMOD), ALDOCLOR-150 (CHLOROTHIAZIDE; METHYLDOPA), ALDOCLOR-250 (CHLOROTHIAZIDE; METHYLDOPA), ALDOMET (METHYLDOPA), ALDOMET (METHYLDOPATE HYDROCHLORIDE), ALDORIL 15 (HYDROCHLOROTHIAZIDE; METHYLDOPA), ALDORIL 25 (HYDROCHLOROTHIAZIDE; METHYLDOPA), ALDORIL D30 (HYDROCHLOROTHIAZIDE; METHYLDOPA), ALDORIL D50 (HYDROCHLOROTHIAZIDE; METHYLDOPA), ALDURAZYME (LARONIDASE), ALENDRONATE SODIUM (ALENDRONATE SODIUM), ALESSE (ETHINYL ESTRADIOL; LEVONORGESTREL), ALEVE (NAPROXEN SODIUM), ALEVE COLD AND SINUS (NAPROXEN SODIUM; PSEUDOEPHEDRINE HYDROCHLORIDE), ALFENTA (ALFENTANIL HYDROCHLORIDE), ALFENTANIL (ALFENTANIL HYDROCHLORIDE), ALFERON N INJECTION (INTERFERON ALFA-N3), ALIMTA (PEMETREXED), ALIMTA (PEMETREXED DISODIUM), ALINIA (NITAZOXANIDE), ALKERAN (MELPHALAN), ALKERAN (MELPHALAN HYDROCHLORIDE), ALKERGOT (ERGOLOID MESYLATES), ALLAY (ACETAMINOPHEN; HYDROCODONE BITARTRATE), ALLEGRA (FEXOFENADINE HYDROCHLORIDE), ALLEGRA D 24 HOUR (FEXOFENADINE HYDROCHLORIDE; PSEUDOEPHEDRINE HYDROCHLORIDE), ALLEGRA-D 12 HOUR (FEXOFENADINE HYDROCHLORIDE; PSEUDOEPHEDRINE HYDROCHLORIDE), ALLERFED (PSEUDOEPHEDRINE HYDROCHLORIDE; TRIPROLIDINE HYDROCHLORIDE), ALLI (ORLISTAT), ALLOPURINOL (ALLOPURINOL), ALLOPURINOL SODIUM (ALLOPURINOL SODIUM), ALMOTRIPTAN MALATE (ALMOTRIPTAN MALATE), ALOCRIL (NEDOCROMIL SODIUM), ALOMIDE (LODOXAMIDE TROMETHAMINE), ALOPRIM (ALLOPURINOL SODIUM), ALORA (ESTRADIOL), ALOXI (PALONOSETRON HYDROCHLORIDE), ALPHA CHYMAR (CHYMOTRYPSIN), ALPHACAINE (LIDOCAINE), ALPHACAINE HYDROCHLORIDE (LIDOCAINE HYDROCHLORIDE), ALPHACAINE HYDROCHLORIDE W/ EPINEPHRINE (EPINEPHRINE; LIDOCAINE HYDROCHLORIDE), ALPHADERM (HYDROCORTISONE; UREA), ALPHADROL (FLUPREDNISOLONE), ALPHAGAN (BRIMONIDINE TARTRATE), ALPHAGAN P (BRIMONIDINE TARTRATE), ALPHALIN (VITAMIN A PALMITATE), ALPHAREDISOL (HYDROXOCOBALAMIN), ALPHATREX (BETAMETHASONE DIPROPIONATE), ALPHAZINE (PHENDIMETRAZINE TARTRATE), ALPRAZOLAM (ALPRAZOLAM), ALPROSTADIL (ALPROSTADIL), ALREX (LOTEPREDNOL ETABONATE), ALTABAX (RETAPAMULIN), ALTACE (RAMIPRIL), ALTOPREV (LOVASTATIN), ALUMINUM HYDROXIDE AND MAGNESIUM TRISILICATE (ALUMINUM HYDROXIDE; MAGNESIUM TRISILICATE), ALUPENT (METAPROTERENOL SULFATE), ALVESCO (CICLESONIDE), AMANTADINE HYDROCHLORIDE (AMANTADINE HYDROCHLORIDE), AMARYL (GLIMEPIRIDE), AMBENYL (BROMODIPHENHYDRAMINE HYDROCHLORIDE; CODEINE PHOSPHATE), AMBIEN (ZOLPIDEM TARTRATE), AMBIEN CR (ZOLPIDEM TARTRATE), AMBISOME (AMPHOTERICIN B), AMBODRYL (BROMODIPHENHYDRAMINE HYDROCHLORIDE), AMCILL (AMPICILLIN/AMPICILLIN TRIHYDRATE), AMCINONIDE (AMCINONIDE), AMEN (MEDROXYPROGESTERONE ACETATE), AMERGE (NARATRIPTAN HYDROCHLORIDE), AMERSCAN MDP KIT (TECHNETIUM TC-99M MEDRONATE KIT), AMEVIVE (ALEFACEPT), AMICAR (AMINOCAPROIC ACID), AMIDATE (ETOMIDATE), AMIFOSTINE (AMIFOSTINE), AMIKACIN SULFATE (AMIKACIN SULFATE), AMIKACIN SULFATE IN SODIUM CHLORIDE 0.9% IN PLASTIC CONTAINER (AMIKACIN SULFATE), AMIKIN (AMIKACIN SULFATE), AMIKIN IN SODIUM CHLORIDE 0.9% IN PLASTIC CONTAINER (AMIKACIN SULFATE), AMILORIDE HYDROCHLORIDE (AMILORIDE HYDROCHLORIDE), AMILORIDE HYDROCHLORIDE AND HYDROCHLOROTHIAZIDE (AMILORIDE HYDROCHLORIDE; HYDROCHLOROTHIAZIDE), AMINESS 5.2% ESSENTIAL AMINO ACIDS W/ HISTADINE (AMINO ACIDS), AMINOACETIC ACID 1.5% IN PLASTIC CONTAINER (GLYCINE), AMINOCAPROIC (AMINOCAPROIC ACID), AMINOCAPROIC ACID (AMINOCAPROIC ACID), AMINOCAPROIC ACID IN PLASTIC CONTAINER (AMINOCAPROIC ACID), AMINOHIPPURATE SODIUM (AMINOHIPPURATE SODIUM), AMINOPHYLLIN (AMINOPHYLLINE), AMINOPHYLLINE (AMINOPHYLLINE), AMINOPHYLLINE DYE FREE (AMINOPHYLLINE), AMINOPHYLLINE IN SODIUM CHLORIDE 0.45% (AMINOPHYLLINE), AMINOPHYLLINE IN SODIUM CHLORIDE 0.45% IN PLASTIC CONTAINER (AMINOPHYLLINE), AMINOSOL 5% (PROTEIN HYDROLYSATE), AMINOSYN 10% (AMINO ACIDS), AMINOSYN 10% (PH6) (AMINO ACIDS), AMINOSYN 3.5% (AMINO ACIDS), AMINOSYN 3.5% IN PLASTIC CONTAINER (AMINO ACIDS), AMINOSYN 3.5% M (AMINO ACIDS; MAGNESIUM ACETATE; PHOSPHORIC ACID; POTASSIUM ACETATE; SODIUM CHLORIDE), AMINOSYN 3.5% M (AMINO ACIDS; MAGNESIUM ACETATE; POTASSIUM ACETATE; SODIUM CHLORIDE), AMINOSYN 3.5% M IN PLASTIC CONTAINER (AMINO ACIDS; MAGNESIUM ACETATE; PHOSPHORIC ACID; POTASSIUM ACETATE; SODIUM CHLORIDE), AMINOSYN 3.5% W/ DEXTROSE 25% IN PLASTIC CONTAINER (AMINO ACIDS; DEXTROSE), AMINOSYN 3.5% W/ DEXTROSE 5% IN PLASTIC CONTAINER (AMINO ACIDS; DEXTROSE), AMINOSYN 4.25% W/ DEXTROSE 25% IN PLASTIC CONTAINER (AMINO ACIDS; DEXTROSE), AMINOSYN 5% (AMINO ACIDS), AMINOSYN 7% (AMINO ACIDS), AMINOSYN 7% (PH6) (AMINO ACIDS), AMINOSYN 7% W/ ELECTROLYTES (AMINO ACIDS; MAGNESIUM CHLORIDE; POTASSIUM PHOSPHATE, DIBASIC; SODIUM CHLORIDE), AMINOSYN 8.5% (AMINO ACIDS), AMINOSYN 8.5% (PH6) (AMINO ACIDS), AMINOSYN 8.5% W/ ELECTROLYTES (AMINO ACIDS; MAGNESIUM CHLORIDE; POTASSIUM PHOSPHATE, DIBASIC; SODIUM CHLO- RIDE), AMINOSYN II 10% (AMINO ACIDS), AMINOSYN II 10% IN PLASTIC CONTAINER (AMINO ACIDS), AMINOSYN II 10% W/ ELECTROLYTES (AMINO ACIDS; MAGNESIUM CHLORIDE; POTASSIUM CHLORIDE; POTASSIUM PHOSPHATE, DIBASIC; SODIUM CHLORIDE), AMINOSYN II 15% IN PLASTIC CONTAINER (AMINO ACIDS), AMINOSYN II 3.5% (AMINO ACIDS), AMINOSYN II 3.5% IN DEXTROSE 25% IN PLASTIC CONTAINER (AMINO ACIDS; DEXTROSE), AMINOSYN II 3.5% IN DEXTROSE 5% IN PLASTIC CONTAINER (AMINO ACIDS; DEXTROSE), AMINOSYN II 3.5% IN PLASTIC CONTAINER (AMINO ACIDS), AMINOSYN II 3.5% M (AMINO ACIDS; MAGNESIUM CHLORIDE; POTASSIUM CHLORIDE; SODIUM CHLORIDE; SODIUM PHOSPHATE, DIBASIC, HEPTAHYDRATE), AMINOSYN II 3.5% M IN DEXTROSE 5% IN PLASTIC CONTAINER (AMINO ACIDS; DEXTROSE; MAGNESIUM CHLORIDE; POTASSIUM CHLORIDE; SODIUM CHLORIDE; SODIUM PHOSPHATE, DIBASIC, HEPTAHYDRATE), AMINOSYN II 3.5% M IN PLASTIC CONTAINER (AMINO ACIDS; MAGNESIUM ACETATE; POTASSIUM ACETATE; SODIUM CHLORIDE; SODIUM PHOSPHATE, DIBASIC, HEPTAHYDRATE), AMINOSYN II 3.5% W/ ELECTROLYTES IN DEXTROSE 25% IN PLASTIC CONTAINER (AMINO ACIDS; DEXTROSE; MAGNESIUM CHLORIDE; POTASSIUM CHLORIDE; POTASSIUM PHOSPHATE, DIBASIC; SODIUM CHLORIDE), AMINOSYN II 3.5% W/ ELECTROLYTES IN DEXTROSE 25% W/ CALCIUM IN PLASTIC CONTAINER (AMINO ACIDS; CALCIUM CHLORIDE; DEXTROSE; MAGNESIUM CHLORIDE; POTASSIUM CHLORIDE; POTASSIUM PHOSPHATE, DIBASIC; SODIUM CHLORIDE), AMINOSYN II 4.25% IN DEXTROSE 10% IN PLASTIC CONTAINER (AMINO ACIDS; DEXTROSE), AMINOSYN II 4.25% IN DEXTROSE 20% IN PLASTIC CONTAINER (AMINO ACIDS; DEXTROSE), AMINOSYN II 4.25% IN DEXTROSE 25% IN PLASTIC CONTAINER (AMINO ACIDS; DEXTROSE), AMINOSYN II 4.25% M IN DEXTROSE 10% IN PLASTIC CONTAINER (AMINO ACIDS; DEXTROSE; MAGNESIUM CHLORIDE; POTASSIUM CHLORIDE; SODIUM CHLORIDE; SODIUM PHOSPHATE, DIBASIC, HEPTAHYDRATE), AMINOSYN II 4.25% W/ ELECT AND ADJUSTED PHOSPHATE IN DEXTROSE 10% IN PLASTIC CONTAINER (AMINO ACIDS; DEXTROSE; MAGNESIUM CHLORIDE; POTASSIUM ACETATE; POTASSIUM CHLORIDE; POTASSIUM PHOSPHATE, DIBASIC; SODIUM CHLORIDE), AMINOSYN II 4.25% W/ ELECTROLYTES IN DEXTROSE 20% W/ CALCIUM IN PLASTIC CONTAINER (AMINO ACIDS; CALCIUM CHLORIDE; DEXTROSE; MAGNESIUM CHLORIDE; POTASSIUM CHLORIDE; POTASSIUM PHOSPHATE, DIBASIC; SODIUM CHLORIDE), AMINOSYN II 4.25% W/ ELECTROLYTES IN DEXTROSE 25% IN PLASTIC CONTAINER (AMINO ACIDS; DEXTROSE; MAGNESIUM CHLORIDE; POTASSIUM CHLORIDE; POTASSIUM PHOSPHATE, DIBASIC; SODIUM CHLORIDE), AMINOSYN II 4.25% W/ ELECTROLYTES IN DEXTROSE 25% W/ CALCIUM IN PLASTIC CONTAINER (AMINO ACIDS; CALCIUM CHLORIDE; DEXTROSE; MAGNESIUM CHLORIDE; POTASSIUM CHLORIDE; POTASSIUM PHOSPHATE, DIBASIC; SODIUM CHLORIDE), AMINOSYN II 5% (AMINO ACIDS), AMINOSYN II 5% IN DEXTROSE 25% IN PLASTIC CONTAINER (AMINO ACIDS; DEXTROSE), AMINOSYN II 5% W/ ELECTROLYTES IN DEXTROSE 25% W/ CALCIUM IN PLASTIC CONTAINER (AMINO ACIDS; CALCIUM CHLORIDE; DEXTROSE; MAGNESIUM CHLORIDE; POTASSIUM CHLORIDE; POTASSIUM PHOSPHATE, DIBASIC; SODIUM CHLORIDE), AMINOSYN II 7% (AMINO ACIDS), AMINOSYN II 7% W/ ELECTROLYTES (AMINO ACIDS; MAGNESIUM CHLORIDE; POTASSIUM CHLORIDE; POTASSIUM PHOSPHATE, DIBASIC; SODIUM CHLORIDE), AMINOSYN II 8.5% (AMINO ACIDS), AMINOSYN II 8.5% W/ ELECTROLYTES (AMINO ACIDS; MAGNESIUM CHLORIDE; POTASSIUM CHLORIDE; POTASSIUM PHOSPHATE, DIBASIC; SODIUM CHLORIDE), AMINOSYN-HBC 7% (AMINO ACIDS), AMINOSYN-HBC 7% IN PLASTIC CONTAINER (AMINO ACIDS), AMINOSYN-HF 8% (AMINO ACIDS), AMINOSYN-PF 10% (AMINO ACIDS), AMINOSYN-PF 7% (AMINO ACIDS), AMINOSYN-RF 5.2% (AMINO ACIDS), AMIODARONE HYDROCHLORIDE (AMIODARONE HYDROCHLORIDE), AMIPAQUE (METRIZAMIDE), AMITID (AMITRIPTYLINE HYDROCHLORIDE), AMITIZA (LUBIPROSTONE), AMITRIL (AMITRIPTYLINE HYDROCHLORIDE), AMITRIPTYLINE HYDROCHLORIDE (AMITRIPTYLINE HYDROCHLORIDE), AMLEXANOX (AMLEXANOX), AMLODIPINE BESYLATE (AMLODIPINE BESYLATE), AMLODIPINE BESYLATE AND BENAZEPRIL HYDROCHLORIDE (AMLODIPINE BESYLATE; BENAZEPRIL HYDROCHLORIDE), AMLODIPINE MALEATE; BENAZEPRIL HYDROCHLORIDE (AMLODIPINE MALEATE; BENAZEPRIL HYDROCHLORIDE), AMMONIA N 13 (AMMONIA, N-13), AMMONIUM CHLORIDE (AMMONIUM CHLORIDE), AMMONIUM CHLORIDE 0.9% IN NORMAL SALINE (AMMONIUM CHLORIDE), AMMONIUM CHLORIDE 2.14% (AMMONIUM CHLORIDE), AMMONIUM CHLORIDE IN PLASTIC CONTAINER (AMMONIUM CHLORIDE), AMMONIUM LACTATE (AMMONIUM LACTATE), AMMONUL (SODIUM BENZOATE; SODIUM PHENYLACETATE), AMNESTEEM (ISOTRETINOIN), AMNESTROGEN (ESTROGENS, ESTERIFIED), AMOSENE (MEPROBAMATE), AMOXAPINE (AMOXAPINE), AMOXICILLIN (AMOXICILLIN), AMOXICILLIN AND CLAVULANATE POTASSIUM (AMOXICILLIN; CLAVULANATE POTASSIUM), AMOXICILLIN PEDIATRIC (AMOXICILLIN), AMOXIL (AMOXICILLIN), AMPHADASE (HYALURONIDASE), AMPHETAMINE SULFATE (AMPHETAMINE SULFATE), AMPHICOL (CHLORAMPHENICOL), AMPHOTEC (AMPHOTERICIN B), AMPHOTERICIN B (AMPHOTERICIN B), AMPICILLIN (AMPICILLIN/AMPICILLIN TRIHYDRATE), AMPICILLIN AND SULBACTAM (AMPICILLIN SODIUM; SULBACTAM SODIUM), AMPICILLIN SODIUM (AMPICILLIN SODIUM), AMPICILLIN TRIHYDRATE (AMPICILLIN/AMPICILLIN TRIHYDRATE), AMRINONE (INAMRINONE LACTATE), AMRINONE LACTATE (INAMRINONE LACTATE), AMRIX (CYCLOBENZAPRINE HYDROCHLORIDE), AMVAZ (AMLODIPINE MALEATE), AN-DTPA (TECHNETIUM TC-99M PENTETATE KIT), AN-MAA (TECHNETIUM TC-99M ALBUMIN AGGREGATED KIT), AN-SULFUR COLLOID (TECHNETIUM TC-99M SULFUR COLLOID KIT), ANADROL-50 (OXYMETHOLONE), ANAFRANIL (CLOMIPRAMINE HYDROCHLORIDE), ANAGRELIDE HYDROCHLORIDE (ANAGRELIDE HYDROCHLORIDE), ANAPROX (NAPROXEN SODIUM), ANAPROX DS (NAPROXEN SODIUM), ANASTROZOLE (ANASTROZOLE), ANASTROZOLE (ANASTROZONE), ANCEF (CEFAZOLIN SODIUM), ANCEF IN DEXTROSE 5% IN PLASTIC CONTAINER (CEFAZOLIN SODIUM), ANCEF IN PLASTIC CONTAINER (CEFAZOLIN SODIUM), ANCEF IN SODIUM CHLORIDE 0.9% IN PLASTIC CONTAINER (CEFAZOLIN SODIUM), ANCOBON (FLUCYTOSINE), ANDRODERM (TESTOSTERONE), ANDROGEL (TESTOSTERONE), ANDROID 10 (METHYLTESTOSTERONE), ANDROID 25 (METHYLTESTOSTERONE), ANDROID 5 (METHYLTESTOSTERONE), ANDROID-F (FLUOXYMESTERONE), ANECTINE (SUCCINYLCHOLINE CHLORIDE), ANESTACON (LIDOCAINE HYDROCHLORIDE), ANEXSIA (ACETAMINOPHEN; HYDROCODONE BITARTRATE), ANEXSIA 5/325 (ACETAMINOPHEN; HYDROCODONE BITARTRATE), ANEXSIA 7.5/325 (ACETAMINOPHEN; HYDROCODONE BITARTRATE), ANEXSIA 7.5/650 (ACETAMINOPHEN; HYDROCODONE BITARTRATE), ANGELIQ (DROSPIRENONE; ESTRADIOL), ANGIO-CONRAY (IOTHALAMATE SODIUM), ANGIOMAX (BIVALIRUDIN), ANGIOVIST 282 (DIATRIZOATE MEGLUMINE), ANGIOVIST 292 (DIATRIZOATE MEGLUMINE; DIATRIZOATE SODIUM), ANGIOVIST 370 (DIATRIZOATE MEGLUMINE; DIATRIZOATE SODIUM), ANHYDRON (CYCLOTHIAZIDE), ANISOTROPINE METHYLBROMIDE (ANISOTROPINE METHYLBROMIDE), ANOQUAN (ACETAMINOPHEN; BUTALBITAL; CAFFEINE), ANSAID (FLURBIPROFEN), ANSOLYSEN (PENTOLINIUM TARTRATE), ANSPOR (CEPHRADINE), ANTABUSE (DISULFIRAM), ANTAGONATE (CHLORPHENIRAMINE MALEATE), ANTARA (MICRONIZED) (FENOFIBRATE), ANTEPAR (PIPERAZINE CITRATE), ANTHELIOS 20 (AVOBENZONE; ECAMSULE; OCTOCRYLENE; TITANIUM DIOXIDE), ANTHELIOS 40 (AVOBENZONE; ECAMSULE; OCTOCRYLENE; TITANIUM DIOXIDE), ANTHELIOS SX (AVOBENZONE; ECAMSULE; OCTOCRYLENE), ANTITUSSIVE (DIPHENHYDRAMINE HYDROCHLORIDE), ANTIVERT (MECLIZINE HYDROCHLORIDE), ANTIZOL (FOMEPIZOLE), ANTRENYL (OXYPHENONIUM BROMIDE), ANTURANE (SULFINPYRAZONE), ANUSOL HC (HYDROCORTISONE), ANZEMET (DOLASETRON MESYLATE), APAP W/ CODEINE PHOSPHATE (ACETAMINOPHEN; CODEINE PHOSPHATE), APHTHASOL (AMLEXANOX), APIDRA (INSULIN GLULISINE RECOMBINANT), APLENZIN (BUPROPION HYDROBROMIDE), APOGEN (GENTAMICIN SULFATE), APOKYN (APOMORPHINE HYDROCHLORIDE), APRESAZIDE (HYDRALAZINE HYDROCHLORIDE; HYDROCHLOROTHIAZIDE), APRESOLINE (HYDRALAZINE HYDROCHLORIDE), APRESOLINE-ESIDRIX (HYDRALAZINE HYDROCHLORIDE; HYDROCHLOROTHIAZIDE), APTIVUS (TIPRANAVIR), AQUAMEPHYTON (PHYTONADIONE), AQUAPHYLLIN (THEOPHYLLINE), AQUASOL A (VITAMIN A), AQUASOL A (VITAMIN A PALMITATE), AQUATAG (BENZTHIAZIDE), AQUATENSEN (METHYCLOTHIAZIDE), ARALEN (CHLOROQUINE PHOSPHATE), ARALEN HYDROCHLORIDE (CHLOROQUINE HYDROCHLORIDE), ARALEN PHOSPHATE W/ PRIMAQUINE PHOSPHATE (CHLOROQUINE PHOSPHATE; PRIMAQUINE PHOSPHATE), ARAMINE (METARAMINOL BITARTRATE), ARANELLE (ETHINYL ESTRADIOL; NORETHINDRONE), ARANELLE (NORETHINDRONE; ETHINYL ESTRADIOL), ARANESP (DARBEPOETIN ALFA), ARAVA (LEFLUNOMIDE), ARCALYST (RILONACEPT), ARDUAN (PIPECURONIUM BROMIDE), AREDIA (PAMIDRONATE DISODIUM), ARESTIN (MINOCYCLINE HYDROCHLORIDE), ARESTOCAINE HYDROCHLORIDE (MEPIVACAINE HYDROCHLORIDE), ARESTOCAINE HYDROCHLORIDE W/ LEVONORDEFRIN (LEVONORDEFRIN; MEPIVACAINE HYDROCHLORIDE), ARFONAD (TRIMETHAPHAN CAMSYLATE), ARGATROBAN (ARGATROBAN), ARICEPT (DONEPEZIL HYDROCHLORIDE), ARICEPT ODT (DONEPEZIL HYDROCHLORIDE), ARIMIDEX (ANASTROZOLE), ARISTOCORT (TRIAMCINOLONE), ARISTOCORT (TRIAMCINOLONE ACETONIDE), ARISTOCORT (TRIAMCINOLONE DIACETATE), ARISTOCORT A (TRIAMCINOLONE ACETONIDE), ARISTOGEL (TRIAMCINOLONE ACETONIDE), ARISTOSPAN (TRIAMCINOLONE HEXACETONIDE), ARIXTRA (FONDAPARINUX SODIUM), AROMASIN (EXEMESTANE), ARRANON (NELARABINE), ARTANE (TRIHEXYPHENIDYL HYDROCHLORIDE), ARTHROTEC (DICLOFENAC SODIUM; MISOPROSTOL), ASACOL (MESALAMINE), ASBRON (THEOPHYLLINE SODIUM GLYCINATE), ASELLACRIN 10 (SOMATROPIN), ASELLACRIN 2 (SOMATROPIN), ASENDIN (AMOXAPINE), ASMANEX TWISTHALER (MOMETASONE FUROATE), ASPIRIN AND CAFFEINE W/ BUTALBITAL (ASPIRIN; BUTALBITAL; CAFFEINE), ASTELIN (AZELASTINE HYDROCHLORIDE), ASTRAMORPH PF (MORPHINE SULFATE), ATACAND (CANDESARTAN CILEXETIL), ATACAND HCT (CANDESARTAN CILEXETIL; HYDROCHLOROTHIAZIDE), ATARAX (HYDROXYZINE HYDROCHLORIDE), ATAZANAVIR SULFATE (ATAZANAVIR SULFATE), ATENOLOL (ATENOLOL), ATENOLOL AND CHLORTHALIDONE (ATENOLOL; CHLORTHALIDONE), ATHROMBIN (WARFARIN SODIUM), ATHROMBIN-K (WARFARIN POTASSIUM), ATIVAN (LORAZEPAM), ATNAA (ATROPINE; PRALIDOXIME CHLORIDE), ATRACURIUM BESYLATE (ATRACURIUM BESYLATE), ATRACURIUM BESYLATE PRESERVATIVE FREE (ATRACURIUM BESYLATE), ATRALIN (TRETINOIN), ATRIDOX (DOXYCYCLINE HYCLATE), ATRIPLA (EFAVIRENZ; EMTRICITABINE; TENOFOVIR DISOPROXIL FUMARATE), ATROMID-S (CLOFIBRATE), ATROPEN (ATROPINE), ATROPINE (ATROPINE), ATROPINE AND DEMEROL (ATROPINE SULFATE; MEPERIDINE HYDROCHLORIDE), ATROPINE SULFATE (ATROPINE SULFATE), ATROPINE SULFATE ANSYR PLASTIC SYRINGE (ATROPINE SULFATE), ATROVENT (IPRATROPIUM BROMIDE), ATROVENT HFA (IPRATROPIUM BROMIDE), AUGMENTIN '125' (AMOXICILLIN; CLAVULANATE POTASSIUM), AUGMENTIN '200' (AMOXICILLIN; CLAVULANATE POTASSIUM), AUGMENTIN '250' (AMOXICILLIN; CLAVULANATE POTASSIUM), AUGMENTIN '400' (AMOXICILLIN; CLAVULANATE POTASSIUM), AUGMENTIN '500' (AMOXICILLIN; CLAVULANATE POTASSIUM), AUGMENTIN '875' (AMOXICILLIN; CLAVULANATE POTASSIUM), AUGMENTIN ES-600 (AMOXICILLIN; CLAVULANATE POTASSIUM), AUGMENTIN XR (AMOXICILLIN; CLAVULANATE POTASSIUM), AUREOMYCIN (CHLORTETRACYCLINE HYDROCHLORIDE), AVAGARD (ALCOHOL; CHLORHEXIDINE GLUCONATE), AVAGE (TAZAROTENE), AVALIDE (HYDROCHLOROTHIAZIDE; IRBESARTAN), AVANDAMET (METFORMIN HYDROCHLORIDE; ROSIGLITAZONE MALEATE), AVANDARYL (GLIMEPIRIDE; ROSIGLITAZONE MALEATE), AVANDIA (ROSIGLITAZONE MALEATE), AVAPRO (IRBESARTAN), AVASTIN (BEVACIZUMAB), AVC (SULFANILAMIDE), AVELOX (MOXIFLOXACIN HYDROCHLORIDE), AVELOX IN SODIUM CHLORIDE 0.8% IN PLASTIC CONTAINER (MOXIFLOXACIN HYDROCHLORIDE), AVENTYL HYDROCHLORIDE (NORTRIPTYLINE HYDROCHLORIDE), AVIANE-21 (ETHINYL ESTRADIOL; LEVONORGESTREL), AVIANE-28 (ETHINYL ESTRADIOL; LEVONORGESTREL), AVINZA (MORPHINE SULFATE), AVITA (TRETINOIN), AVODART (DUTASTERIDE), AVONEX (INTERFERON BETA 1A), AXERT (ALMOTRIPTAN MALATE), AXID (NIZATIDINE), AXID AR (NIZATIDINE), AXOTAL (ASPIRIN; BUTALBITAL), AYGESTIN (NORETHINDRONE ACETATE), AZACTAM (AZTREONAM), AZACTAM IN PLASTIC CONTAINER (AZTREONAM), AZASAN (AZATHIOPRINE), AZASITE (AZITHROMYCIN), AZATHIOPRINE (AZATHIOPRINE), AZATHIOPRINE (AZATHIOPRINE SODIUM), AZATHIOPRINE SODIUM (AZATHIOPRINE SODIUM), AZDONE (ASPIRIN; HYDROCODONE BITARTRATE), AZELASTINE HYDROCHLORIDE (AZELASTINE HYDROCHLORIDE), AZELEX (AZELAIC ACID), AZILECT (RASAGILINE MESYLATE), AZITHROMYCIN (AZITHROMYCIN), AZLIN (AZLOCILLIN SODIUM), AZMACORT (TRIAMCINOLONE ACETONIDE), AZO GANTANOL (PHENAZOPYRIDINE HYDROCHLORIDE; SULFAMETHOXAZOLE), AZO GANTRISIN (PHENAZOPYRIDINE HYDROCHLORIDE; SULFISOXAZOLE), AZOLID (PHENYLBUTAZONE), AZOPT (BRINZOLAMIDE), AZOR (AMLODIPINE BESYLATE; OLMESARTAN MEDOXOMIL), AZULFIDINE (SULFASALAZINE), AZULFIDINE EN-TABS (SULFASALAZINE), BACI-RX (BACITRACIN), BACIGUENT (BACITRACIN), BACIIM (BACITRACIN), BACITRACIN (BACITRACIN), BACITRACIN ZINC AND POLYMYXIN B SULFATE (BACITRACIN ZINC; POLYMYXIN B SULFATE), BACITRACIN ZINC-NEOMYCIN SULFATE-POLYMYXIN B SULFATE (BACITRACIN ZINC; NEOMYCIN SULFATE; POLYMYXIN B SULFATE), BACITRACIN ZINC-POLYMYXIN B SULFATE (BACITRACIN ZINC; POLYMYXIN B SULFATE), BACITRACIN-NEOMYCIN-POLYMYXIN (BACITRACIN ZINC; NEOMYCIN SULFATE; POLYMYXIN B SULFATE), BACITRACIN-NEOMYCIN-POLYMYXIN W/ HYDROCORTISONE ACETATE (BACITRACIN; HYDROCORTISONE ACETATE; NEOMYCIN SULFATE; POLYMYXIN B SULFATE), BACLOFEN (BACLOFEN), BACTERIOSTATIC SODIUM CHLORIDE 0.9% IN PLASTIC CONTAINER (SODIUM CHLORIDE), BACTERIOSTATIC WATER FOR INJECTION IN PLASTIC CONTAINER (WATER FOR INJECTION, STERILE), BACTOCILL (OXACILLIN SODIUM), BACTOCILL IN PLASTIC CONTAINER (OXACILLIN SODIUM), BACTRIM (SULFAMETHOXAZOLE; TRIMETHOPRIM), BACTRIM DS (SULFAMETHOXAZOLE; TRIMETHOPRIM), BACTRIM PEDIATRIC (SULFAMETHOXAZOLE; TRIMETHOPRIM), BACTROBAN (MUPIROCIN), BACTROBAN (MUPIROCIN CALCIUM), BAL (DIMERCAPROL), BALANCED SALT (CALCIUM CHLORIDE; MAGNESIUM CHLORIDE; POTASSIUM CHLORIDE; SODIUM ACETATE; SODIUM CHLORIDE; SODIUM CITRATE), BALNEOL-HC (HYDROCORTISONE), BALSALAZIDE DISODIUM (BALSALAZIDE DISODIUM), BALZIVA-21 (ETHINYL ESTRADIOL; NORETHINDRONE), BALZIVA-28 (ETHINYL ESTRADIOL; NORETHINDRONE), BAMATE (MEPROBAMATE), BANAN (CEFPODOXIME PROXETIL), BANCAP (ACETAMINOPHEN; BUTALBITAL), BANCAP HC (ACETAMINOPHEN; HYDROCODONE BITARTRATE), BANTHINE (METHANTHELINE BROMIDE), BARACLUDE (ENTECAVIR), BAROS (SODIUM BICARBONATE; TARTARIC ACID), BARSTATIN 100 (NYSTATIN), BAYCOL (CERIVASTATIN SODIUM), BAYER EXTRA STRENGTH ASPIRIN FOR MIGRAINE PAIN (ASPIRIN), BECLOVENT (BECLOMETHASONE DIPROPIONATE), BECONASE (BECLOMETHASONE DIPROPIONATE), BECONASE AQ (BECLOMETHASONE DIPROPIONATE MONOHYDRATE), BEEPEN-VK (PENICILLIN V POTASSIUM), BELDIN (DIPHENHYDRAMINE HYDROCHLORIDE), BELIX (DIPHENHYDRAMINE HYDROCHLORIDE), BENADRYL (DIPHENHYDRAMINE HYDROCHLORIDE), BENADRYL PRESERVATIVE FREE (DIPHENHYDRAMINE HYDROCHLORIDE), BENAZEPRIL HYDROCHLORIDE (BENAZEPRIL HYDROCHLORIDE), BENAZEPRIL HYDROCHLORIDE AND HYDROCHLOROTHIAZIDE (BENAZEPRIL HYDROCHLORIDE; HYDROCHLOROTHIAZIDE), BENDECTIN (DOXYLAMINE SUCCINATE; PYRIDOXINE HYDROCHLORIDE), BENDOPA (LEVODOPA), BENEMID (PROBENECID), BENICAR (OLMESARTAN MEDOXOMIL), BENICAR HCT (HYDROCHLOROTHIAZIDE; OLMESARTAN MEDOXOMIL), BENOQUIN (MONOBENZONE), BENOXINATE HYDROCHLORIDE (BENOXINATE HYDROCHLORIDE), BENSULFOID (SULFUR), BENTYL (DICYCLOMINE HYDROCHLORIDE), BENTYL PRESERVATIVE FREE (DICYCLOMINE HYDROCHLORIDE), BENYLIN (DIPHENHYDRAMINE HYDROCHLORIDE), BENYLIN (DIPHENHYDRAMINE HYDROCHLORIDE; PSEUDOEPHEDRINE HYDROCHLORIDE), BENZACLIN (BENZOYL PEROXIDE; CLINDAMYCIN PHOSPHATE), BENZAMYCIN (BENZOYL PEROXIDE; ERYTHROMYCIN), BENZAMYCIN PAK (BENZOYL PEROXIDE; ERYTHROMYCIN), BENZEDRINE (AMPHETAMINE SULFATE), BENZONATATE (BENZONATATE), BENZPHETAMINE HYDROCHLORIDE (BENZPHETAMINE HYDROCHLORIDE), BENZTHIAZIDE (BENZTHIAZIDE), BENZTROPINE MESYLATE (BENZTROPINE MESYLATE), BENZYL BENZOATE (BENZYL BENZOATE), BEPADIN (BEPRIDIL HYDROCHLORIDE), BEROCCA PN (ASCORBIC ACID; BIOTIN; CYANOCOBALAMIN; DEXPANTHENOL; ERGOCALCIFEROL; FOLIC ACID; NIACINAMIDE; PYRIDOXINE HYDROCHLORIDE; RIBOFLAVIN PHOSPHATE SODIUM; THIAMINE HYDROCHLORIDE; VITAMIN A PALMITATE; VITAMIN E), BERUBIGEN (CYANOCOBALAMIN), BETA-2 (ISOETHARINE HYDROCHLORIDE), BETA-HC (HYDROCORTISONE), BETA-VAL (BETAMETHASONE VALERATE), BETADERM (BETAMETHASONE VALERATE), BETADINE (POVIDONE-IODINE), BETAGAN (LEVOBUNOLOL HYDROCHLORIDE), BETALIN 12 (CYANOCOBALAMIN), BETALIN S (THIAMINE HYDROCHLORIDE), BETAMETHASONE DIPROPIONATE (BETAMETHASONE DIPROPIONATE), BETAMETHASONE SODIUM PHOSPHATE (BETAMETHASONE SODIUM PHOSPHATE), BETAMETHASONE VALERATE (BETAMETHASONE VALERATE), BETAPACE (SOTALOL HYDROCHLORIDE), BETAPACE AF (SOTALOL HYDROCHLORIDE), BETAPAR (MEPREDNISONE), BETAPEN-VK (PENICILLIN V POTASSIUM), BETAPRONE (PROPIOLACTONE), BETASERON (INTERFERON BETA-1B), BETATREX (BETAMETHASONE VALERATE), BETAXOLOL (BETAXOLOL HYDROCHLORIDE), BETAXOLOL HYDROCHLORIDE (BETAXOLOL HYDROCHLORIDE), BETAXON (LEVOBETAXOLOL HYDROCHLORIDE), BETHANECHOL CHLORIDE (BETHANECHOL CHLORIDE), BETIMOL (TIMOLOL), BETOPTIC (BETAXOLOL HYDROCHLORIDE), BETOPTIC PILO (BETAXOLOL HYDROCHLORIDE; PILOCARPINE HYDROCHLORIDE), BETOPTIC S (BETAXOLOL HYDROCHLORIDE), BEXTRA (VALDECOXIB), BEXXAR (TOSITUMOMAB; IODINE I 131 TOSITUMOMAB), BIAXIN (CLARITHROMYCIN), BIAXIN XL (CLARITHROMYCIN), BICALUTAMIDE (BICALUTAMIDE), BICILLIN (PENICILLIN G BENZATHINE), BICILLIN C-R (PENICILLIN G BENZATHINE; PENICILLIN G PROCAINE), BICILLIN C-R 900/300 (PENICILLIN G BENZATHINE; PENICILLIN G PROCAINE), BICILLIN L-A (PENICILLIN G BENZATHINE), BICNU (CARMUSTINE), BIDIL (HYDRALAZINE HYDROCHLORIDE; ISOSORBIDE DINITRATE), BILIVIST (IPODATE SODIUM), BILOPAQUE (TYROPANOATE SODIUM), BILTRICIDE (PRAZIQUANTEL), BIO-TROPIN (SOMATROPIN RECOMBINANT), BIOSCRUB (CHLORHEXIDINE GLUCONATE), BIPHETAMINE 12.5 (AMPHETAMINE RESIN COMPLEX; DEXTROAMPHETAMINE RESIN COMPLEX), BIPHETAMINE 20 (AMPHETAMINE RESIN COMPLEX; DEXTROAMPHETAMINE RESIN COMPLEX), BIPHETAMINE 7.5 (AMPHETAMINE RESIN COMPLEX; DEXTROAMPHETAMINE RESIN COMPLEX), BIPHETAP (BROMPHENIRAMINE MALEATE; PHENYLPROPANOLAMINE HYDROCHLORIDE), BISOPROLOL FUMARATE (BISOPROLOL FUMARATE), BISOPROLOL FUMARATE AND HYDROCHLOROTHIAZIDE (BISOPROLOL FUMARATE; HYDROCHLOROTHIAZIDE), BLENOXANE (BLEOMYCIN SULFATE), BLEOMYCIN SULFATE (BLEOMYCIN SULFATE), BLEPH-10 (SULFACETAMIDE SODIUM), BLEPH-30 (SULFACETAMIDE SODIUM), BLEPHAMIDE (PREDNISOLONE ACETATE; SULFACETAMIDE SODIUM), BLEPHAMIDE S.O.P. (PREDNISOLONE ACETATE; SULFACETAMIDE SODIUM), BLOCADREN (TIMOLOL MALEATE), BONIVA (IBANDRONATE SODIUM), BONTRIL (PHENDIMETRAZINE TARTRATE), BONTRIL PDM (PHENDIMETRAZINE TARTRATE), BOROFAIR (ACETIC ACID, GLACIAL; ALUMINUM ACETATE), BOTOX COSMETIC (BOTULINUM TOXIN TYPE A), BRANCHAMIN 4% (AMINO ACIDS), BRANCHAMIN 4% IN PLASTIC CONTAINER (AMINO ACIDS), BRAVELLE (UROFOLLITROPIN), BREATHTEK UBT FOR H-PYLORI (UREA, C-13), BRETHAIRE (TERBUTALINE SULFATE), BRETHINE (TERBUTALINE SULFATE), BRETYLIUM TOSYLATE (BRETYLIUM TOSYLATE), BRETYLIUM TOSYLATE IN DEXTROSE 5% (BRETYLIUM TOSYLATE), BRETYLIUM TOSYLATE IN DEXTROSE 5% IN PLASTIC CONTAINER (BRETYLIUM TOSYLATE), BRETYLIUM TOSYLATE IN PLASTIC CONTAINER (BRETYLIUM TOSYLATE), BRETYLOL (BRETYLIUM TOSYLATE), BREVIBLOC (ESMOLOL HYDROCHLORIDE), BREVIBLOC DOUBLE STRENGTH IN PLASTIC CONTAINER (ESMOLOL HYDROCHLORIDE), BREVIBLOC IN PLASTIC CONTAINER (ESMOLOL HYDROCHLORIDE), BREVICON 21-DAY (ETHINYL ESTRADIOL; NORETHINDRONE), BREVICON 28-DAY (ETHINYL ESTRADIOL; NORETHINDRONE), BREVITAL SODIUM (METHOHEXITAL SODIUM), BRIAN CARE (CHLORHEXIDINE GLUCONATE), BRICANYL (TERBUTALINE SULFATE), BRIMONIDINE TARTRATE (BRIMONIDINE TARTRATE), BRISTACYCLINE (TETRACYCLINE HYDROCHLORIDE), BRISTAGEN (GENTAMICIN SULFATE), BRISTAMYCIN (ERYTHROMYCIN STEARATE), BROMANATE (BROMPHENIRAMINE MALEATE; PHENYLPROPANOLAMINE HYDROCHLORIDE), BROMANATE DC (BROMPHENIRAMINE MALEATE; CODEINE PHOSPHATE; PHENYLPROPANOLAMINE HYDROCHLORIDE), BROMANATE DM (BROMPHENIRAMINE MALEATE; DEXTROMETHORPHAN HYDROBROMIDE; PSEUDOEPHEDRINE HYDROCHLORIDE), BROMANYL (BROMODIPHENHYDRAMINE HYDROCHLORIDE; CODEINE PHOSPHATE), BROMATAPP (BROMPHENIRAMINE MALEATE; PHENYLPROPANOLAMINE HYDROCHLORIDE), BROMFED-DM (BROMPHENIRAMINE MALEATE; DEXTROMETHORPHAN HYDROBROMIDE; PSEUDOEPHEDRINE HYDROCHLORIDE), BROMOCRIPTINE MESYLATE (BROMOCRIPTINE MESYLATE), BROMODIPHENHYDRAMINE HYDROCHLORIDE AND CODEINE PHOSPHATE (BROMODIPHENHYDRAMINE HYDROCHLORIDE; CODEINE PHOSPHATE), BROMPHENIRAMINE MALEATE (BROMPHENIRAMINE MALEATE), BROMPHERIL (DEXBROMPHENIRAMINE MALEATE; PSEUDOEPHEDRINE SULFATE), BRONCHO SALINE (SODIUM CHLORIDE), BRONITIN MIST (EPINEPHRINE BITARTRATE), BRONKAID MIST (EPINEPHRINE), BRONKODYL (THEOPHYLLINE), BRONKOMETER (ISOETHARINE MESYLATE), BRONKOSOL (ISOETHARINE HYDROCHLORIDE), BROVANA (ARFORMOTEROL TARTRATE), BRYREL (PIPERAZINE CITRATE), BSS (CALCIUM CHLORIDE; MAGNESIUM CHLORIDE; POTASSIUM CHLORIDE; SODIUM ACETATE; SODIUM CHLORIDE; SODIUM CITRATE), BSS PLUS (CALCIUM CHLORIDE; DEXTROSE; GLUTATHIONE DISULFIDE; MAGNESIUM CHLORIDE; POTASSIUM CHLORIDE; SODIUM BICARBONATE; SODIUM CHLORIDE; SODIUM PHOSPHATE), BUCET (ACETAMINOPHEN; BUTALBITAL), BUCLADIN-S (BUCLIZINE HYDROCHLORIDE), BUMETANIDE (BUMETANIDE), BUMEX (BUMETANIDE), BUPHENYL (SODIUM PHENYLBUTYRATE), BUPIVACAINE (BUPIVACAINE HYDROCHLORIDE), BUPIVACAINE HYDROCHLORIDE (BUPIVACAINE HYDROCHLORIDE), BUPIVACAINE HYDROCHLORIDE AND EPINEPHRINE (BUPIVACAINE HYDROCHLORIDE; EPINEPHRINE), BUPIVACAINE HYDROCHLORIDE AND EPINEPHRINE (BUPIVACAINE HYDROCHLORIDE; EPINEPHRINE BITARTRATE), BUPIVACAINE HYDROCHLORIDE KIT (BUPIVACAINE HYDROCHLORIDE), BUPIVACAINE HYDROCHLORIDE PRESERVATIVE FREE (BUPIVACAINE HYDROCHLORIDE), BUPIVACAINE HYDROCHLORIDE W/ EPINEPHRINE (BUPIVACAINE HYDROCHLORIDE; EPINEPHRINE BITARTRATE), BUPRENEX (BUPRENORPHINE HYDROCHLORIDE), BUPRENORPHINE HYDROCHLORIDE (BUPRENORPHINE HYDROCHLORIDE), BUPROPION HYDROCHLORIDE (BUPROPION HYDROCHLORIDE), BUSPAR (BUSPIRONE HYDROCHLORIDE), BUSPIRONE HCL (BUSPIRONE HYDROCHLORIDE), BUSPIRONE HYDROCHLORIDE (BUSPIRONE HYDROCHLORIDE), BUSULFEX (BUSULFAN), BUTABARB (BUTABARBITAL SODIUM), BUTABARBITAL (BUTABARBITAL SODIUM), BUTABARBITAL SODIUM (BUTABARBITAL SODIUM), BUTAL COMPOUND (ASPIRIN; BUTALBITAL; CAFFEINE), BUTALAN (BUTABARBITAL SODIUM), BUTALBITAL AND ACETAMINOPHEN (ACETAMINOPHEN; BUTALBITAL), BUTALBITAL ASPIRIN AND CAFFEINE (ASPIRIN; BUTALBITAL; CAFFEINE), BUTALBITAL COMPOUND (ASPIRIN; BUTALBITAL; CAFFEINE), BUTALBITAL W/ ASPIRIN & CAFFEINE (ASPIRIN; BUTALBITAL; CAFFEINE), BUTALBITAL, ACETAMINOPHEN AND CAFFEINE (ACETAMINOPHEN; BUTALBITAL; CAFFEINE), BUTALBITAL, ACETAMINOPHEN, AND CAFFEINE WITH CODEINE PHOSPHATE (ACETAMINOPHEN; BUTALBITAL; CAFFEINE; CODEINE PHOSPHATE), BUTALBITAL, ACETAMINOPHEN, CAFFEINE AND CODEINE PHOSPHATE (ACETAMINOPHEN; BUTALBITAL; CAFFEINE; CODEINE PHOSPHATE), BUTALBITAL, APAP, AND CAFFEINE (ACETAMINOPHEN; BUTALBITAL; CAFFEINE), BUTALBITAL, ASPIRIN AND CAFFEINE (ASPIRIN; BUTALBITAL; CAFFEINE), BUTALBITAL, ASPIRIN, AND CAFFEINE (ASPIRIN; BUTALBITAL; CAFFEINE), BUTALBITAL, ASPIRIN, CAFFEINE, AND CODEINE PHOSPHATE (ASPIRIN; BUTALBITAL; CAFFEINE; CODEINE PHOSPHATE), BUTALBITAL; ACETAMINOPHEN; CAFFEINE; CODEINE (BUTALBITAL; ACETAMINOPHEN; CAFFEINE; CODEINE PHOSPHATE), BUTAPAP (ACETAMINOPHEN; BUTALBITAL), BUTAZOLIDIN (PHENYLBUTAZONE), BUTICAPS (BUTABARBITAL SODIUM), BUTISOL SODIUM (BUTABARBITAL SODIUM), BUTORPHANOL TARTRATE (BUTORPHANOL TARTRATE), BUTORPHANOL TARTRATE PRESERVATIVE FREE (BUTORPHANOL TARTRATE), BYETTA (EXENATIDE SYNTHETIC), BYSTOLIC (NEBIVOLOL HYDROCHLORIDE), C-SOLVE-2 (ERYTHROMYCIN), CABERGOLINE (CABERGOLINE), CADUET (AMLODIPINE BESYLATE; ATORVASTATIN CALCIUM), CAFCIT (CAFFEINE CITRATE), CAFERGOT (CAFFEINE; ERGOTAMINE TARTRATE), CAFFEINE CITRATE (CAFFEINE CITRATE), CALAN (VERAPAMIL HYDROCHLORIDE), CALCIBIND (CELLULOSE SODIUM PHOSPHATE), CALCIJEX (CALCITRIOL), CALCIMAR (CALCITONIN, SALMON), CALCIPARINE (HEPARIN CALCIUM), CALCIPOTRIENE (CALCIPOTRIENE), CALCITONIN-SALMON (CALCITONIN, SALMON), CALCITRIOL (CALCITRIOL), CALCIUM ACETATE (CALCIUM ACETATE), CALCIUM CARBONATE, FAMOTIDINE AND MAGNESIUM HYDROXIDE (CALCIUM CARBONATE; FAMOTIDINE; MAGNESIUM HYDROXIDE), CALCIUM CHLORIDE 10% IN PLASTIC CONTAINER (CALCIUM CHLORIDE), CALCIUM DISODIUM VERSENATE (EDETATE CALCIUM DISODIUM), CALCIUM GLUCEPTATE (CALCIUM GLUCEPTATE), CALDEROL (CALCIFEDIOL), CALMURID HC (HYDROCORTISONE; UREA), CALOMIST (CYANOCOBALAMIN), CAM-AP-ES (HYDRALAZINE HYDROCHLORIDE; HYDROCHLOROTHIAZIDE; RESERPINE), CAMMETRAZINE (PHENDIMETRAZINE TARTRATE), CAMILA (NORETHINDRONE), CAMOQUIN HYDROCHLORIDE (AMODIAQUINE HYDROCHLORIDE), CAMPATH (ALEMTUZUMAB), CAMPRAL (ACAMPROSATE CALCIUM), CAMPTOSAR (IRINOTECAN HYDROCHLORIDE), CANASA (MESALAMINE), CANCIDAS (CASPOFUNGIN ACETATE), CANDESARTAN CILEXETIL (CANDESARTAN CILEXETIL), CANDEX (NYSTATIN), CANTIL (MEPENZOLATE BROMIDE), CAP-PROFEN (IBUPROFEN), CAPASTAT SULFATE (CAPREOMYCIN SULFATE), CAPITAL AND CODEINE (ACETAMINOPHEN; CODEINE PHOSPHATE), CAPITAL SOLEIL 15 (AVOBENZONE; ECAMSULE; OCTOCRYLENE), CAPITAL WITH CODEINE (ACETAMINOPHEN; CODEINE PHOSPHATE), CAPITROL (CHLOROXINE), CAPOTEN (CAPTOPRIL), CAPOZIDE 25/15 (CAPTOPRIL; HYDROCHLOROTHIAZIDE), CAPOZIDE 25/25 (CAPTOPRIL; HYDROCHLOROTHIAZIDE), CAPOZIDE 50/15 (CAPTOPRIL; HYDROCHLOROTHIAZIDE), CAPOZIDE 50/25 (CAPTOPRIL; HYDROCHLOROTHIAZIDE), CAPTOPRIL (CAPTOPRIL), CAPTOPRIL AND HYDROCHLOROTHIAZIDE (CAPTOPRIL; HYDROCHLOROTHIAZIDE), CARAC (FLUOROURACIL), CARAFATE (SUCRALFATE), CARBACHOL (CARBACHOL), CARBAMAZEPINE (CARBAMAZEPINE), CARBASTAT (CARBACHOL), CARBATROL (CARBAMAZEPINE), CARBIDOPA AND LEVODOPA (CARBIDOPA; LEVODOPA), CARBILEV (CARBIDOPA; LEVODOPA), CARBINOXAMINE MALEATE (CARBINOXAMINE MALEATE), CARBOCAINE (MEPIVACAINE HYDROCHLORIDE), CARBOCAINE W/ NEO-COBEFRIN (LEVONORDEFRIN; MEPIVACAINE HYDROCHLORIDE), CARBOPLATIN (CARBOPLATIN), CARDENE (NICARDIPINE HYDROCHLORIDE), CARDENE SR (NICARDIPINE HYDROCHLORIDE), CARDIOGEN-82 (RUBIDIUM CHLORIDE RB-82), CARDIOGRAFIN (DIATRIZOATE MEGLUMINE), CARDIOLITE (TECHNETIUM TC-99M SESTAMIBI KIT), CARDIOPLEGIC IN PLASTIC CONTAINER (CALCIUM CHLORIDE; MAGNESIUM CHLORIDE; POTASSIUM CHLORIDE; SODIUM CHLORIDE), CARDIOQUIN (QUINIDINE POLYGALACTURONATE), CARDIOTEC (TECHNETIUM TC-99M TEBOROXIME KIT), CARDIZEM (DILTIAZEM HYDROCHLORIDE), CARDIZEM CD (DILTIAZEM HYDROCHLORIDE), CARDIZEM LA (DILTIAZEM HYDROCHLORIDE), CARDIZEM SR (DILTIAZEM HYDROCHLORIDE), CARDRASE (ETHOXZOLAMIDE), CARDURA (DOXAZOSIN MESYLATE), CARDURA XL (DOXAZOSIN MESYLATE), CARISOPRODOL (CARISOPRODOL), CARISOPRODOL AND ASPIRIN (ASPIRIN; CARISOPRODOL), CARISOPRODOL COMPOUND (ASPIRIN; CARISOPRODOL), CARISOPRODOL, ASPIRIN AND CODEINE PHOSPHATE (ASPIRIN; CARISOPRODOL; CODEINE PHOSPHATE), CARMOL HC (HYDROCORTISONE ACETATE; UREA), CARNITOR (LEVOCARNITINE), CARNITOR SF (LEVOCARNITINE), CARTEOLOL HYDROCHLORIDE (CARTEOLOL HYDROCHLORIDE), CARTIA XT (DILTIAZEM HYDROCHLORIDE), CARTROL (CARTEOLOL HYDROCHLORIDE), CARVEDILOL (CARVEDILOL), CASODEX (BICALUTAMIDE), CATAFLAM (DICLOFENAC POTASSIUM), CATAPRES (CLONIDINE HYDROCHLORIDE), CATAPRES-TTS-1 (CLONIDINE), CATAPRES-TTS-2 (CLONIDINE), CATAPRES-TTS-3 (CLONIDINE), CATARASE (CHYMOTRYPSIN), CATHFLO ACTIVASE (ALTEPLASE), CAVERJECT (ALPROSTADIL), CAVERJECT IMPULSE (ALPROSTADIL), CEA-SCAN (ARCITUMOMAB), CECLOR (CEFACLOR), CECLOR CD (CEFACLOR), CEDAX (CEFTIBUTEN DIHYDRATE), CEDILANID-D (DESLANOSIDE), CEENU (LOMUSTINE), CEFACLOR (CEFACLOR), CEFADROXIL (CEFADROXIL/CEFADROXIL HEMIHYDRATE), CEFADYL (CEPHAPIRIN SODIUM), CEFAZOLIN (CEFAZOLIN SODIUM), CEFAZOLIN AND DEXTROSE (CEFAZOLIN SODIUM), CEFAZOLIN SODIUM (CEFAZOLIN SODIUM), CEFDINIR (CEFDINIR), CEFEPIME HYDROCHLORIDE (CEFEPIME HYDROCHLORIDE), CEFIZOX (CEFTIZOXIME SODIUM), CEFIZOX IN DEXTROSE 5% IN PLASTIC CONTAINER (CEFTIZOXIME SODIUM), CEFIZOX IN PLASTIC CONTAINER (CEFTIZOXIME SODIUM), CEFMAX (CEFMENOXIME HYDROCHLORIDE), CEFOBID (CEFOPERAZONE SODIUM), CEFOBID IN PLASTIC CONTAINER (CEFOPERAZONE SODIUM), CEFOTAN (CEFOTETAN DISODIUM), CEFOTAN IN PLASTIC CONTAINER (CEFOTETAN DISODIUM), CEFOTAXIME (CEFOTAXIME SODIUM), CEFOTAXIME AND DEXTROSE 2.4% IN PLASTIC CONTAINER (CEFOTAXIME SODIUM), CEFOTAXIME AND DEXTROSE 3.9% IN PLASTIC CONTAINER (CEFOTAXIME SODIUM), CEFOTAXIME SODIUM (CEFOTAXIME SODIUM), CEFOTETAN (CEFOTETAN DISODIUM), CEFOTETAN AND DEXTROSE IN DUPLEX CONTAINER (CEFOTETAN DISODIUM), CEFOXITIN (CEFOXITIN SODIUM), CEFOXITIN AND DEXTROSE IN DUPLEX CONTAINER (CEFOXITIN SODIUM), CEFPIRAMIDE SODIUM (CEFPIRAMIDE SODIUM), CEFPODOXIME PROXETIL (CEFPODOXIME PROXETIL), CEFPROZIL (CEFPROZIL), CEFTAZIDIME (CEFTAZIDIME), CEFTAZIDIME SODIUM IN PLASTIC CONTAINER (CEFTAZIDIME SODIUM), CEFTIN (CEFUROXIME AXETIL), CEFTRIAXONE (CEFTRIAXONE), CEFTRIAXONE (CEFTRIAXONE SODIUM), CEFTRIAXONE AND DEXTROSE IN DUPLEX CONTAINER (CEFTRIAXONE SODIUM), CEFTRIAXONE IN PLASTIC CONTAINER (CEFTRIAXONE SODIUM), CEFTRIAXONE SODIUM (CEFTRIAXONE SODIUM), CEFUROXIME (CEFUROXIME), CEFUROXIME (CEFUROXIME SODIUM), CEFUROXIME AND DEXTROSE IN DUPLEX CONTAINER (CEFUROXIME SODIUM), CEFUROXIME AXETIL (CEFUROXIME AXETIL), CEFUROXIME SODIUM (CEFUROXIME SODIUM), CEFZIL (CEFPROZIL), CELEBREX (CELECOXIB), CELESTONE (BETAMETHASONE), CELESTONE (BETAMETHASONE SODIUM PHOSPHATE), CELESTONE SOLUSPAN (BETAMETHASONE ACETATE; BETAMETHASONE SODIUM PHOSPHATE), CELEXA (CITALOPRAM HYDROBROMIDE), CELLCEPT (MYCOPHENOLATE MOFETIL), CELLCEPT (MYCOPHENOLATE MOFETIL HYDROCHLORIDE), CELONTIN (METHSUXIMIDE), CENESTIN (ESTROGENS, CONJUGATED SYNTHETIC A), CENTANY (MUPIROCIN), CENTRAX (PRAZEPAM), CEPHALEXIN (CEPHALEXIN), CEPHALOTHIN (CEPHALOTHIN SODIUM), CEPHALOTHIN SODIUM (CEPHALOTHIN SODIUM), CEPHALOTHIN SODIUM W/ DEXTROSE IN PLASTIC CONTAINER (CEPHALOTHIN SODIUM), CEPHALOTHIN SODIUM W/ SODIUM CHLORIDE IN PLASTIC CONTAINER (CEPHALOTHIN SODIUM), CEPHAPIRIN SODIUM (CEPHAPIRIN SODIUM), CEPHRADINE (CEPHRADINE), CEPHULAC (LACTULOSE), CEPTAZ (CEFTAZIDIME), CERADON (CEFOTIAM HYDROCHLORIDE), CEREBYX (FOSPHENYTOIN SODIUM), CEREDASE (ALGLUCERASE), CERETEC (TECHNETIUM TC-99M EXAMETAZIME KIT), CEREZYME (IMIGLUCERASE), CERNEVIT-12 (ALPHA-TOCOPHEROL; ASCORBIC ACID; BIOTIN; CHOLECALCIFEROL; CYANOCOBALAMIN; FOLIC ACID; NIACINAMIDE; PANTOTHENIC ACID; PYRIDOXINE; RIBOFLAVIN; THIAMINE; VITAMIN A), CERTIRIZINE HYDROCHLORIDE (CETIRIZINE HYDROCHLORIDE), CERUBIDINE (DAUNORUBICIN HYDROCHLORIDE), CERUMENEX (TROLAMINE POLYPEPTIDE OLEATE CONDENSATE), CERVIDIL (DINOPROSTONE), CESAMET (NABILONE), CETACORT (HYDROCORTISONE), CETAMIDE (SULFACETAMIDE SODIUM), CETAPRED (PREDNISOLONE ACETATE; SULFACETAMIDE SODIUM), CETIRIZINE HYDROCHLORIDE (CETIRIZINE HYDROCHLORIDE), CETIRIZINE HYDROCHLORIDE ALLERGY (CETIRIZINE HYDROCHLORIDE), CETIRIZINE HYDROCHLORIDE AND PSEUDOEPHEDRINE HYDROCHLORIDE (CETIRIZINE HYDROCHLORIDE; PSEUDOEPHEDRINE HYDROCHLORIDE), CETIRIZINE HYDROCHLORIDE HIVES (CETIRIZINE HYDROCHLORIDE), CETROTIDE (CETRORELIX), CHANTIX (VARENICLINE TARTRATE), CHEMET (SUCCIMER), CHENIX (CHENODIOL), CHG SCRUB (CHLORHEXIDINE GLUCONATE), CHIBROXIN (NORFLOXACIN), CHILDREN'S ADVIL (IBUPROFEN), CHILDREN'S ADVIL ALLERGY SINUS (CHLORPHENIRAMINE MALEATE; IBUPROFEN; PSEUDOEPHEDRINE HYDROCHLORIDE), CHILDREN'S ADVIL COLD (IBUPROFEN; PSEUDOEPHEDRINE HYDROCHLORIDE), CHILDREN'S ADVIL-FLAVORED (IBUPROFEN), CHILDREN'S CETIRIZINE HYDROCHLORIDE ALLERGY (CETIRIZINE HYDROCHLORIDE), CHILDREN'S CETIRIZINE HYDROCHLORIDE HIVES RELIEF (CETIRIZINE HYDROCHLORIDE), CHILDREN'S CLARITIN (LORATADINE), CHILDREN'S ELIXSURE (IBUPRO- FEN), CHILDREN'S IBUPROFEN (IBUPROFEN), CHILDREN'S MOTRIN (IBUPROFEN), CHILDREN'S MOTRIN COLD (IBUPROFEN; PSEUDOEPHEDRINE HYDROCHLORIDE), CHILDREN'S ZYRTEC ALLERGY (CETIRIZINE HYDROCHLORIDE), CHILDREN'S ZYRTEC HIVES RELIEF (CETIRIZINE HYDROCHLORIDE), CHIRHOSTIM (SECRETIN SYNTHETIC HUMAN), CHIROCAINE (LEVOBUPIVACAINE HYDROCHLORIDE), CHLOR-TRIMETON (CHLORPHENIRAMINE MALEATE), CHLOR-TRIMETON (CHLORPHENIRAMINE MALEATE; PSEUDOEPHEDRINE SULFATE), CHLORAMPHENICOL (CHLORAMPHENICOL), CHLORAMPHENICOL (CHLORAMPHENICOL SODIUM SUCCINATE), CHLORAMPHENICOL SODIUM SUCCINATE (CHLORAMPHENICOL SODIUM SUCCINATE), CHLORAPREP ONE-STEP (CHLORHEXIDINE GLUCONATE; ISOPROPYL ALCOHOL), CHLORAPREP ONE-STEP FREPP (CHLORHEXIDINE GLUCONATE; ISOPROPYL ALCOHOL), CHLORAPREP ONE-STEP SEPP (CHLORHEXIDINE GLUCONATE; ISOPROPYL ALCOHOL), CHLORAPREP SINGLE SWABSTICK (CHLORHEXIDINE GLUCONATE; ISOPROPYL ALCOHOL), CHLORAPREP WITH TINT (CHLORHEXIDINE GLUCONATE; ISOPROPYL ALCOHOL), CHLORASCRUB MAXI SWABSTICK (CHLORHEXIDINE GLUCONATE; ISOPROPYL ALCOHOL), CHLORASCRUB SWAB (CHLORHEXIDINE GLUCONATE; ISOPROPYL ALCOHOL), CHLORASCRUB SWABSTICK (CHLORHEXIDINE GLUCONATE; ISOPROPYL ALCOHOL), CHLORDIAZEPDXIDE (CHLORDIAZEPDXIDE HYDROCHLORIDE), CHLORDIAZEPDXIDE AND AMITRIPTYLINE HYDROCHLORIDE (AMITRIPTYLINE HYDROCHLORIDE; CHLORDIAZEPDXIDE), CHLORDIAZEPDXIDE HYDROCHLORIDE (CHLORDIAZEPDXIDE HYDROCHLORIDE), CHLORHEXIDINE GLUCONATE (CHLORHEXIDINE GLUCONATE), CHLORMERODRIN HG 197 (CHLORMERODRIN, HG-197), CHLOROFAIR (CHLORAMPHENICOL), CHLOROHENIRAMINE MALEATE AND PHENYLPROPANOLAMINE HYDROCHLORIDE (CHLORPHENIRAMINE MALEATE; PHENYLPROPANOLAMINE HYDROCHLORIDE), CHLOROMYCETIN (CHLORAMPHENICOL), CHLOROMYCETIN (CHLORAMPHENICOL SODIUM SUCCINATE), CHLOROMYCETIN HYDROCORTISONE (CHLORAMPHENICOL; HYDROCORTISONE ACETATE), CHLOROMYCETIN PALMITATE (CHLORAMPHENICOL PALMITATE), CHLOROMYXIN (CHLORAMPHENICOL; POLYMYXIN B SULFATE), CHLOROPROCAINE HYDROCHLORIDE (CHLOROPROCAINE HYDROCHLORIDE), CHLOROPTIC (CHLORAMPHENICOL), CHLOROPTIC S.O.P. (CHLORAMPHENICOL), CHLOROPTIC-P S.O.P. (CHLORAMPHENICOL; PREDNISOLONE), CHLOROQUINE PHOSPHATE (CHLOROQUINE PHOSPHATE), CHLOROTHIAZIDE (CHLOROTHIAZIDE), CHLOROTHIAZIDE AND RESERPINE (CHLOROTHIAZIDE; RESERPINE), CHLOROTHIAZIDE W/ RESERPINE (CHLOROTHIAZIDE; RESERPINE), CHLOROTHIAZIDE-RESERPINE (CHLOROTHIAZIDE; RESERPINE), CHLOROTRIANISENE (CHLOROTRIANISENE), CHLORPHENIRAMINE MALEATE (CHLORPHENIRAMINE MALEATE), CHLORPHENIRAMINE MALEATE AND PHENYLPROPANOLAMINE HYDROCHLORIDE (CHLORPHENIRAMINE MALEATE; PHENYLPROPANOLAMINE HYDROCHLORIDE), CHLORPROMAZINE HYDROCHLORIDE (CHLORPROMAZINE HYDROCHLORIDE), CHLORPROMAZINE HYDROCHLORIDE INTENSOL (CHLORPROMAZINE HYDROCHLORIDE), CHLORPROPAMIDE (CHLORPROPAMIDE), CHLORTHALIDONE (CHLORTHALIDONE), CHLORZOXAZONE (CHLORZOXAZONE), CHOLAC (LACTULOSE), CHOLEBRINE (IOCETAMIC ACID), CHOLEDYL (OXTRIPHYLLINE), CHOLEDYL SA (OXTRIPHYLLINE), CHOLESTYRAMINE (CHOLESTYRAMINE), CHOLESTYRAMINE LIGHT (CHOLESTYRAMINE), CHOLETEC (TECHNETIUM TC-99M MEBROFENIN KIT), CHOLOGRAFIN MEGLUMINE (IODIPAMIDE MEGLUMINE), CHOLOGRAFIN SODIUM (IODIPAMIDE SODIUM), CHOLOVUE (IODOXAMATE MEGLUMINE), CHOLOXIN (DEXTROTHYROXINE SODIUM), CHOLYBAR (CHOLESTYRAMINE), CHORIONIC GONADOTROPIN (GONADOTROPIN, CHORIONIC), CHROMALBIN (ALBUMIN CHROMATED CR-51 SERUM), CHROMIC CHLORIDE (CHROMIC CHLORIDE), CHROMIC CHLORIDE IN PLASTIC CONTAINER (CHROMIC CHLORIDE), CHROMITOPE SODIUM (SODIUM CHROMATE, CR-51), CHRONULAC (LACTULOSE), CHYMEX (BENTIROMIDE), CHYMODIACTIN (CHYMOPAPAIN), CIALIS (TADALAFIL), CIBACALCIN (CALCITONIN HUMAN), CICLOPIROX (CICLOPIROX), CIDA-STAT (CHLORHEXIDINE GLUCONATE), CILOSTAZOL (CILOSTAZOL), CILOXAN (CIPROFLOXACIN HYDROCHLORIDE), CIMETIDINE (CIMETIDINE), CIMETIDINE HYDROCHLORIDE (CIMETIDINE HYDROCHLORIDE), CIMETIDINE HYDROCHLORIDE IN SODIUM CHLORIDE 0.9% IN PLASTIC CONTAINER (CIMETIDINE HYDROCHLORIDE), CIMZIA (CERTOLIZUMAB PEGOL), CIN-QUIN (QUINIDINE SULFATE), CINNASIL (RESCINNAMINE), CINOBAC (CINOXACIN), CINOXACIN (CINOXACIN), CINTICHEM TECHNETIUM 99M HEDSPA (TECHNETIUM TC-99M ETIDRONATE KIT), CIPRO (CIPROFLOXACIN), CIPRO (CIPROFLOXACIN HYDROCHLORIDE), CIPRO HC (CIPROFLOXACIN HYDROCHLORIDE; HYDROCORTISONE), CIPRO IN DEXTROSE 5% IN PLASTIC CONTAINER (CIPROFLOXACIN), CIPRO IN SODIUM CHLORIDE 0.9% IN PLASTIC CONTAINER (CIPROFLOXACIN), CIPRO XR (CIPROFLOXACIN; CIPROFLOXACIN HYDROCHLORIDE), CIPRODEX (CIPROFLOXACIN; DEXAMETHASONE), CIPROFLOXACIN (CIPROFLOXACIN), CIPROFLOXACIN EXTENDED RELEASE (CIPROFLOXACIN; CIPROFLOXACIN HYDROCHLORIDE), CIPROFLOXACIN HYDROCHLORIDE (CIPROFLOXACIN HYDROCHLORIDE), CIPROFLOXACIN IN DEXTROSE 5% IN PLASTIC CONTAINER (CIPROFLOXACIN), CIRCANOL (ERGOLOID MESYLATES), CIS-MDP (TECHNETIUM TC-99M MEDRONATE KIT), CIS-PYRO (TECHNETIUM TC-99M PYROPHOSPHATE KIT), CISPLATIN (CISPLATIN), CITALOPRAM HYDROBROMIDE (CITALOPRAM HYDROBROMIDE), CITANEST (PRILOCAINE HYDROCHLORIDE), CITANEST FORTE (EPINEPHRINE BITARTRATE; PRILOCAINE HYDROCHLORIDE), CITANEST PLAIN (PRILOCAINE HYDROCHLORIDE), CLADRIBINE (CLADRIBINE), CLAFORAN (CEFO- TAXIME SODIUM), CLAFORAN IN DEXTROSE 5% IN PLASTIC CONTAINER (CEFOTAXIME SODIUM), CLAFORAN IN SODIUM CHLORIDE 0.9% IN PLASTIC CONTAINER (CEFOTAXIME SODIUM), CLARAVIS (ISOTRETINOIN), CLARINEX (DESLORATADINE), CLARINEX D 24 HOUR (DESLORATADINE; PSEUDOEPHEDRINE SULFATE), CLARINEX-D 12 HOUR (DESLORATADINE; PSEUDOEPHEDRINE SULFATE), CLARITHROMYCIN (CLARITHROMYCIN), CLARITHROMYCIN EXTENDED RELEASE (CLARITHROMYCIN), CLARITIN (LORATADINE), CLARITIN HIVES RELIEF (LORATADINE), CLARITIN HIVES RELIEF REDITAB (LORATADINE), CLARITIN REDITABS (LORATADINE), CLARITIN-D (LORATADINE; PSEUDOEPHEDRINE SULFATE), CLARITIN-D 24 HOUR (LORATADINE; PSEUDOEPHEDRINE SULFATE), CLEMASTINE FUMARATE (CLEMASTINE FUMARATE), CLEOCIN (CLINDAMYCIN HYDROCHLORIDE), CLEOCIN (CLINDAMYCIN PALMITATE HYDROCHLORIDE), CLEOCIN (CLINDAMYCIN PHOSPHATE), CLEOCIN HYDROCHLORIDE (CLINDAMYCIN HYDROCHLORIDE), CLEOCIN PHOSPHATE (CLINDAMYCIN PHOSPHATE), CLEOCIN PHOSPHATE IN DEXTROSE 5% IN PLASTIC CONTAINER (CLINDAMYCIN PHOSPHATE), CLEOCIN T (CLINDAMYCIN PHOSPHATE), CLIMARA (ESTRADIOL), CLIMARA PRO (ESTRADIOL; LEVONORGESTREL), CLINDA-DERM (CLINDAMYCIN PHOSPHATE), CLINDAGEL (CLINDAMYCIN PHOSPHATE), CLINDAMYCIN HYDROCHLORIDE (CLINDAMYCIN HYDROCHLORIDE), CLINDAMYCIN PHOSPHATE (CLINDAMYCIN PHOSPHATE), CLINDAMYCIN PHOSPHATE IN DEXTROSE 5% (CLINDAMYCIN PHOSPHATE), CLINDAMYCIN PHOSPHATE IN DEXTROSE 5% IN PLASTIC CONTAINER (CLINDAMYCIN PHOSPHATE), CLINDESSE (CLINDAMYCIN PHOSPHATE), CLINDETS (CLINDAMYCIN PHOSPHATE), CLINIMIX 2.75/10 SULFITE FREE IN DEXTROSE 10% IN PLASTIC CONTAINER (AMINO ACIDS; DEXTROSE), CLINIMIX 2.75/25 SULFITE FREE IN DEXTROSE 25% IN PLASTIC CONTAINER (AMINO ACIDS; DEXTROSE), CLINIMIX 2.75/5 SULFITE FREE IN DEXTROSE 5% IN PLASTIC CONTAINER (AMINO ACIDS; DEXTROSE), CLINIMIX 4.25/10 SULFITE FREE IN DEXTROSE 10% IN PLASTIC CONTAINER (AMINO ACIDS; DEXTROSE), CLINIMIX 4.25/20 SULFITE FREE IN DEXTROSE 20% IN PLASTIC CONTAINER (AMINO ACIDS; DEXTROSE), CLINIMIX 4.25/25 SULFITE FREE IN DEXTROSE 25% IN PLASTIC CONTAINER (AMINO ACIDS; DEXTROSE), CLINIMIX 4.25/5 SULFITE FREE IN DEXTROSE 5% IN PLASTIC CONTAINER (AMINO ACIDS; DEXTROSE), CLINIMIX 5/10 SULFITE FREE IN DEXTROSE 10% IN PLASTIC CONTAINER (AMINO ACIDS; DEXTROSE), CLINIMIX 5/15 SULFITE FREE IN DEXTROSE 15% IN PLASTIC CONTAINER (AMINO ACIDS; DEXTROSE), CLINIMIX 5/20 SULFITE FREE IN DEXTROSE 20% IN PLASTIC CONTAINER (AMINO ACIDS; DEXTROSE), CLINIMIX 5/25 SULFITE FREE IN DEXTROSE 25% IN PLASTIC CONTAINER (AMINO ACIDS; DEXTROSE), CLINIMIX 5/35 SULFITE FREE IN DEXTROSE 35% IN PLASTIC CONTAINER (AMINO ACIDS; DEXTROSE), CLINIMIX E 2.75/10 SULFITE-FREE W/ ELECT IN DEXTROSE 10% W/ CALCIUM IN PLASTIC CONTAINER (AMINO ACIDS; CALCIUM CHLORIDE; DEXTROSE; MAGNESIUM CHLORIDE; POTASSIUM PHOSPHATE, DIBASIC; SODIUM ACETATE; SODIUM CHLORIDE), CLINIMIX E 2.75/25 SULFITE-FREE W/ ELECT IN DEXTROSE 25% W/ CALCIUM IN PLASTIC CONTAINER (AMINO ACIDS; CALCIUM CHLORIDE; DEXTROSE; MAGNESIUM CHLORIDE; POTASSIUM PHOSPHATE, DIBASIC; SODIUM ACETATE; SODIUM CHLORIDE), CLINIMIX E 2.75/5 SULFITE-FREE W/ ELECT IN DEXTROSE 5% W/ CALCIUM IN PLASTIC CONTAINER (AMINO ACIDS; CALCIUM CHLORIDE; DEXTROSE; MAGNESIUM CHLORIDE; POTASSIUM PHOSPHATE, DIBASIC; SODIUM ACETATE; SODIUM CHLORIDE), CLINIMIX E 4.25/10 SULFITE-FREE W/ ELECT IN DEXTROSE 10% W/ CALCIUM IN PLASTIC CONTAINER (AMINO ACIDS; CALCIUM CHLORIDE; DEXTROSE; MAGNESIUM CHLORIDE; POTASSIUM PHOSPHATE, DIBASIC; SODIUM ACETATE; SODIUM CHLORIDE), CLINIMIX E 4.25/20 SULFITE-FREE W/ ELECT IN DEXTROSE 20% W/ CALCIUM IN PLASTIC CONTAINER (AMINO ACIDS; CALCIUM CHLORIDE; DEXTROSE; MAGNESIUM CHLORIDE; POTASSIUM PHOSPHATE, DIBASIC; SODIUM ACETATE; SODIUM CHLORIDE), CLINIMIX E 4.25/25 SULFITE-FREE W/ ELECT IN DEXTROSE 25% W/ CALCIUM IN PLASTIC CONTAINER (AMINO ACIDS; CALCIUM CHLORIDE; DEXTROSE; MAGNESIUM CHLORIDE; POTASSIUM PHOSPHATE, DIBASIC; SODIUM ACETATE; SODIUM CHLORIDE), CLINIMIX E 4.25/5 SULFITE-FREE W/ ELECT IN DEXTROSE 5% W/ CALCIUM IN PLASTIC CONTAINER (AMINO ACIDS; CALCIUM CHLORIDE; DEXTROSE; MAGNESIUM CHLORIDE; POTASSIUM PHOSPHATE, DIBASIC; SODIUM ACETATE; SODIUM CHLORIDE), CLINIMIX E 5/10 SULFITE-FREE W/ ELECT IN DEXTROSE 10% W/ CALCIUM IN PLASTIC CONTAINER (AMINO ACIDS; CALCIUM CHLORIDE; DEXTROSE; MAGNESIUM CHLORIDE; POTASSIUM PHOSPHATE, DIBASIC; SODIUM ACETATE; SODIUM CHLORIDE), CLINIMIX E 5/15 SULFITE-FREE W/ ELECT IN DEXTROSE 15% W/ CALCIUM IN PLASTIC CONTAINER (AMINO ACIDS; CALCIUM CHLORIDE; DEXTROSE; MAGNESIUM CHLORIDE; POTASSIUM PHOSPHATE, DIBASIC; SODIUM ACETATE; SODIUM CHLORIDE), CLINIMIX E 5/20 SULFITE-FREE W/ ELECT IN 20% DEXTROSE W/ CALCIUM IN PLASTIC CONTAINER (AMINO ACIDS; CALCIUM CHLORIDE; DEXTROSE; MAGNESIUM CHLORIDE; POTASSIUM PHOSPHATE, DIBASIC; SODIUM ACETATE; SODIUM CHLORIDE), CLINIMIX E 5/25 SULFITE-FREE W/ ELECT IN DEXTROSE 25% W/ CALCIUM IN PLASTIC CONTAINER (AMINO ACIDS; CALCIUM CHLORIDE; DEXTROSE; MAGNESIUM CHLORIDE; POTASSIUM PHOSPHATE, DIBASIC; SODIUM ACETATE; SODIUM CHLORIDE), CLINIMIX E 5/35 SULFITE-FREE W/ ELECT IN DEXTROSE 35% W/ CALCIUM IN PLASTIC CONTAINER (AMINO ACIDS; CALCIUM CHLORIDE; DEXTROSE; MAGNESIUM CHLORIDE; POTASSIUM PHOSPHATE, DIBASIC; SODIUM ACETATE; SODIUM CHLORIDE), CLINISOL 15% SULFITE FREE IN PLASTIC CONTAINER (AMINO ACIDS), CLINORIL (SULINDAC), CLISTIN (CARBINOXAMINE MALEATE), CLOBETASOL PROPIONATE (CLOBETASOL PROPIONATE), CLOBETASOL PROPIONATE (EMOLLIENT) (CLOBETASOL PROPIONATE), CLOBEX (CLOBETASOL PROPIONATE), CLODERM (CLOCORTOLONE PIVALATE), CLOFIBRATE (CLOFIBRATE), CLOLAR (CLOFARABINE), CLOMID (CLOMIPHENE CITRATE), CLOMIPHENE CITRATE (CLOMIPHENE CITRATE), CLOMIPRAMINE HYDROCHLORIDE (CLOMIPRAMINE HYDROCHLORIDE), CLONAZEPAM (CLONAZEPAM), CLONIDINE HYDROCHLORIDE (CLONIDINE HYDROCHLORIDE), CLONIDINE HYDROCHLORIDE AND CHLORTHALIDONE (CHLORTHALIDONE; CLONIDINE HYDROCHLORIDE), CLOPIDOGREL (CLOPIDOGREL), CLOPIDOGREL BISULFATE (CLOPIDOGREL BISULFATE), CLOPRA (METOCLOPRAMIDE HYDROCHLORIDE), CLOPRA-"YELLOW" (METOCLOPRAMIDE HYDROCHLORIDE), CLORAZEPATE DIPOTASSIUM (CLORAZEPATE DIPOTASSIUM), CLORPRES (CHLORTHALIDONE; CLONIDINE HYDROCHLORIDE), CLOTRIMAZOLE (CLOTRIMAZOLE), CLOTRIMAZOLE AND BETAMETHASONE DIPROPIONATE (BETAMETHASONE DIPROPIONATE; CLOTRIMAZOLE), CLOXACILLIN SODIUM (CLOXACILLIN SODIUM), CLOXAPEN (CLOXACILLIN SODIUM), CLOZAPINE (CLOZAPINE), CLOZARIL (CLOZAPINE), CO-GESIC (ACETAMINOPHEN; HYDROCODONE BITARTRATE), CO-LAV (POLYETHYLENE GLYCOL 3350; POTASSIUM CHLORIDE; SODIUM BICARBONATE; SODIUM CHLORIDE; SODIUM SULFATE, ANHYDROUS), COACTIN (AMDINOCILLIN), COBAVITE (CYANOCOBALAMIN), CODAMINE (HYDROCODONE BITARTRATE; PHENYLPROPANOLAMINE HYDROCHLORIDE), CODEINE PHOSPHATE AND ACETAMINOPHEN (ACETAMINOPHEN; CODEINE PHOSPHATE), CODEINE, ASPIRIN, APAP FORMULA NO. 2 (ACETAMINOPHEN; ASPIRIN; CODEINE PHOSPHATE), CODEINE, ASPIRIN, APAP FORMULA NO. 3 (ACETAMINOPHEN; ASPIRIN; CODEINE PHOSPHATE), CODEINE, ASPIRIN, APAP FORMULA NO. 4 (ACETAMINOPHEN; ASPIRIN; CODEINE PHOSPHATE), CODEPREX (CHLORPHENIRAMINE POLISTIREX; CODEINE POLISTIREX), CODIMAL-L.A. 12 (CHLORPHENIRAMINE MALEATE; PSEUDOEPHEDRINE HYDROCHLORIDE), CODOXY (ASPIRIN; OXYCODONE HYDROCHLORIDE; OXYCODONE TEREPHTHALATE), CODRIX (ACETAMINOPHEN; CODEINE PHOSPHATE), COGENTIN (BENZTROPINE MESYLATE), COGNEX (TACRINE HYDROCHLORIDE), COLPROBENECID (COLCHICINE; PROBENECID), COLAZAL (BALSALAZIDE DISODIUM), COLBENEMID (COLCHICINE; PROBENECID), COLD CAPSULE IV (CHLORPHENIRAMINE MALEATE; PHENYLPROPANOLAMINE HYDROCHLORIDE), COLD CAPSULE V (CHLORPHENIRAMINE MALEATE; PHENYLPROPANOLAMINE HYDROCHLORIDE), COLESTID (COLESTIPOL HYDROCHLORIDE), COLESTIPOL HYDROCHLORIDE (COLESTIPOL HYDROCHLORIDE), COLGATE TOTAL (SODIUM FLUORIDE; TRICLOSAN), COLISTIMETHATE (COLISTIMETHATE), COLISTIMETHATE (COLISTIMETHATE SODIUM), COLOCORT (HYDROCORTISONE), COLONAID (ATROPINE SULFATE; DIPHENOXYLATE HYDROCHLORIDE), COLOVAGE (POLYETHYLENE GLYCOL 3350; POTASSIUM CHLORIDE; SODIUM BICARBONATE; SODIUM CHLORIDE; SODIUM SULFATE, ANHYDROUS), COLY-MYCIN M (COLISTIMETHATE SODIUM), COLY-MYCIN S (COLISTIN SULFATE), COLY-MYCIN S (COLISTIN SULFATE; HYDROCORTISONE ACETATE; NEOMYCIN SULFATE; THONZONIUM BROMIDE), COLYTE (POLYETHYLENE GLYCOL 3350; POTASSIUM CHLORIDE; SODIUM BICARBONATE; SODIUM CHLORIDE; SODIUM SULFATE, ANHYDROUS), COLYTE WITH FLAVOR PACKS (POLYETHYLENE GLYCOL 3350; POTASSIUM CHLORIDE; SODIUM BICARBONATE; SODIUM CHLORIDE; SODIUM SULFATE, ANHYDROUS), COLYTE-FLAVORED (POLYETHYLENE GLYCOL 3350; POTASSIUM CHLORIDE; SODIUM BICARBONATE; SODIUM CHLORIDE; SODIUM SULFATE, ANHYDROUS), COMBIGAN (BRIMONIDINE TARTRATE; TIMOLOL MALEATE), COMBIPATCH (ESTRADIOL; NORETHINDRONE ACETATE), COMBIPRES (CHLORTHALIDONE; CLONIDINE HYDROCHLORIDE), COMBIVENT (ALBUTEROL SULFATE; IPRATROPIUM BROMIDE), COMBIVIR (LAMIVUDINE; ZIDOVUDINE), COMBUNOX (IBUPROFEN; OXYCODONE HYDROCHLORIDE), COMMIT (NICOTINE POLACRILEX), COMPAZINE (PROCHLORPERAZINE), COMPAZINE (PROCHLORPERAZINE EDISYLATE), COMPAZINE (PROCHLORPERAZINE MALEATE), COMPOUND 65 (ASPIRIN; CAFFEINE; PROPDXYPHENE HYDROCHLORIDE), COMPRO (PROCHLORPERAZINE), COMTAN (ENTACAPONE), CONCENTRAID (DESMOPRESSIN ACETATE), CONCERTA (METHYLPHENIDATE HYDROCHLORIDE), CONDYLOX (PODOFILOX), CONRAY (IOTHALAMATE MEGLUMINE), CONRAY 30 (IOTHALAMATE MEGLUMINE), CONRAY 325 (IOTHALAMATE SODIUM), CONRAY 400 (IOTHALAMATE SODIUM), CONRAY 43 (IOTHALAMATE MEGLUMINE), CONSTILAC (LACTULOSE), CONSTULOSE (LACTULOSE), CONTAC (CHLORPHENIRAMINE MALEATE; PHENYLPROPANOLAMINE HYDROCHLORIDE), CONTAC 12 HOUR (CHLORPHENIRAMINE MALEATE; PHENYLPROPANOLAMINE HYDROCHLORIDE), COPAXONE (GLATIRAMER ACETATE), COPEGUS (RIBAVIRIN), COR-OTICIN (HYDROCORTISONE ACETATE; NEOMYCIN SULFATE), CORDARONE (AMIODARONE HYDROCHLORIDE), CORDRAN (FLURANDRENOLIDE), CORDRAN SP (FLURANDRENOLIDE), CORDRAN-N (FLURANDRENOLIDE; NEOMYCIN SULFATE), COREG (CARVEDILOL), COREG CR (CARVEDILOL PHOSPHATE), CORGARD (NADOLOL), CORLOPAM (FENOLDOPAM MESYLATE), CORMAX (CLOBETASOL PROPIONATE), CORPHED (PSEUDOEPHEDRINE HYDROCHLORIDE; TRIPROLIDINE HYDROCHLORIDE), CORSYM (CHLORPHENIRAMINE POLISTIREX; PHENYLPROPANOLAMINE POLISTIREX), CORTDOME (HYDROCORTISONE), CORTALONE (PREDNISOLONE), CORTAN (PREDNISONE), CORTEF (HYDROCORTISONE), CORTEF (HYDROCORTISONE CYPIONATE), CORTEF ACETATE (HYDROCORTISONE ACETATE), CORTENEMA (HYDROCORTISONE), CORTICOTROPIN (CORTICOTROPIN), CORTIFOAM (HYDROCORTISONE ACETATE), CORTISONE ACETATE (CORTISONE ACETATE), CORTISPORIN (BACITRACIN ZINC; HYDROCORTISONE; NEOMYCIN SULFATE; POLYMYXIN B SULFATE), CORTISPORIN (HYDROCORTISONE ACETATE; NEOMYCIN SULFATE; POLYMYXIN B SULFATE), CORTISPORIN (HYDROCORTISONE; NEOMYCIN SULFATE; POLYMYXIN B SULFATE), CORTONE (CORTISONE ACETATE), CORTRIL (HYDROCORTISONE), CORTRIL (HYDROCORTISONE ACETATE), CORTROPHIN-ZINC (CORTICOTROPIN-ZINC HYDROXIDE), CORTROSYN (COSYNTROPIN), CORVERT (IBUTILIDE FUMARATE), CORZIDE (BENDROFLUMETHIAZIDE; NADOLOL), COSMEGEN (DACTINOMYCIN), COSOPT (DORZOLAMIDE HYDROCHLORIDE; TIMOLOL MALEATE), COSYNTROPIN (COSYNTROPIN), COTAZYM (PANCRELIPASE (AMYLASE; LIPASE; PROTEASE)), COTRIM (SULFAMETHOXAZOLE; TRIMETHOPRIM), COTRIM D.S. (SULFAMETHOXAZOLE; TRIMETHOPRIM), COUMADIN (WARFARIN SODIUM), COVERA-HS (VERAPAMIL HYDROCHLORIDE), COZAAR (LOSARTAN POTASSIUM), CRESCORMON (SOMATROPIN), CRESTOR (ROSUVASTATIN CALCIUM), CRINONE (PROGESTERONE), CRIXIVAN (INDINAVIR SULFATE), CROLOM (CROMOLYN SODIUM), CROMOLYN SODIUM (CROMOLYN SODIUM), CROMOPTIC (CROMOLYN SODIUM), CROTAN (CROTAMITON), CRYSELLE (ETHINYL ESTRADIOL; NORGESTREL), CRYSTODIGIN (DIGITOXIN), CU-7 (COPPER), CUBICIN (DAPTOMYCIN), CUPRIC CHLORIDE IN PLASTIC CONTAINER (CUPRIC CHLORIDE), CUPRIC SULFATE (CUPRIC SULFATE), CUPRIMINE (PENICILLAMINE), CUROSURF (PORACTANT ALFA), CURRETAB (MEDROXYPROGESTERONE ACETATE), CUTIVATE (FLUTICASONE PROPIONATE), CYANOCOBALAMIN (CYANOCOBALAMIN), CYANOCOBALAMIN CO 57 SCHILLING TEST KIT (CYANOCOBALAMIN; CYANOCOBALAMIN, CO-57; INTRINSIC FACTOR), CYANOKIT (HYDROXOCOBALAMIN), CYCLACILLIN (CYCLACILLIN), CYCLAINE (HEXYLCAINE HYDROCHLORIDE), CYCLAPEN-W (CYCLACILLIN), CYCLESSA (DESOGESTREL; ETHINYL ESTRADIOL), CYCLOBENZAPRINE HYDROCHLORIDE (CYCLOBENZAPRINE HYDROCHLORIDE), CYCLOCORT (AMCINONIDE), CYCLOGYL (CYCLOPENTOLATE HYDROCHLORIDE), CYCLOMYDRIL (CYCLOPENTOLATE HYDROCHLORIDE; PHENYLEPHRINE HYDROCHLORIDE), CYCLOPAR (TETRACYCLINE HYDROCHLORIDE), CYCLOPENTOLATE HYDROCHLORIDE (CYCLOPENTOLATE HYDROCHLORIDE), CYCLOPHOSPHAMIDE (CYCLOPHOSPHAMIDE), CYCLOSPORINE (CYCLOSPORINE), CYCRIN (MEDROXYPROGESTERONE ACETATE), CYKLOKAPRON (TRANEXAMIC ACID), CYLERT (PEMOLINE), CYMBALTA (DULOXETINE HYDROCHLORIDE), CYPROHEPTADINE HYDROCHLORIDE (CYPROHEPTADINE HYDROCHLORIDE), CYPROHEPTADINE HYDROCLORIDE (CYPROHEPTADINE HYDROCHLORIDE), CYSTADANE (BETAINE HYDROCHLORIDE), CYSTAGON (CYSTEAMINE BITARTRATE), CYSTEINE HYDROCHLORIDE (CYSTEINE HYDROCHLORIDE), CYSTO-CONRAY (IOTHALAMATE MEGLUMINE), CYSTO-CONRAY II (IOTHALAMATE MEGLUMINE), CYSTOGRAFIN (DIATRIZOATE MEGLUMINE), CYSTOGRAFIN DILUTE (DIATRIZOATE MEGLUMINE), CYTADREN (AMINOGLUTETHIMIDE), CYTARABINE (CYTARABINE), CYTOMEL (LIOTHYRONINE SODIUM), CYTOSAR-U (CYTARABINE), CYTOTEC (MISOPROSTOL), CYTOVENE (GANCICLOVIR), CYTOVENE IV (GANCICLOVIR SODIUM), CYTOXAN (CYCLOPHOSPHAMIDE), D.H.E. 45 (DIHYDROERGOTAMINE MESYLATE), DACARBAZINE (DACARBAZINE), DACOGEN (DECITABINE), DALGAN (DEZOCINE), DALMANE (FLURAZEPAM HYDROCHLORIDE), DANAZOL (DANAZOL), DANOCRINE (DANAZOL), DANTRIUM (DANTROLENE SODIUM), DANTROLENE SODIUM (DANTROLENE SODIUM), DAPSONE (DAPSONE), DARANIDE (DICHLORPHENAMIDE), DARAPRIM (PYRIMETHAMINE), DARBID (ISOPROPAMIDE IODIDE), DARICON (OXYPHENCYCLIMINE HYDROCHLORIDE), DARVOCET (ACETAMINOPHEN; PROPDXYPHENE HYDROCHLORIDE), DARVOCET A500 (ACETAMINOPHEN; PROPDXYPHENE NAPSYLATE), DARVOCET-N 100 (ACETAMINOPHEN; PROPDXYPHENE NAPSYLATE), DARVOCET-N 50 (ACETAMINOPHEN; PROPDXYPHENE NAPSYLATE), DARVON (PROPDXYPHENE HYDROCHLORIDE), DARVON COMPOUND (ASPIRIN; CAFFEINE; PROPDXYPHENE HYDROCHLORIDE), DARVON COMPOUND-65 (ASPIRIN; CAFFEINE; PROPDXYPHENE HYDROCHLORIDE), DARVON W/ ASA (ASPIRIN; PROPDXYPHENE HYDROCHLORIDE), DARVON-N (PROPDXYPHENE NAPSYLATE), DARVON-N W/ ASA (ASPIRIN; PROPDXYPHENE NAPSYLATE), DAUNORUBICIN HYDROCHLORIDE (DAUNORUBICIN HYDROCHLORIDE), DAUNOXOME (DAUNORUBICIN CITRATE), DAYPRO (OXAPROZIN), DAYPRO ALTA (OXAPROZIN POTASSIUM), DAYTRANA (METHYLPHENIDATE), DDAVP (DESMOPRESSIN ACETATE), DDAVP (NEEDS NO REFRIGERATION) (DESMOPRESSIN ACETATE), DEAPRIL-ST (ERGOLOID MESYLATES), DECA-DURABOLIN (NANDROLONE DECANOATE), DECABID (INDECAINIDE HYDROCHLORIDE), DECADERM (DEXAMETHASONE), DECADRON (DEXAMETHASONE), DECADRON (DEXAMETHASONE SODIUM PHOSPHATE), DECADRON W/ XYLOCAINE (DEXAMETHASONE SODIUM PHOSPHATE; LIDOCAINE HYDROCHLORIDE), DECADRON-LA (DEXAMETHASONE ACETATE), DECAPRYN (DOXYLAMINE SUCCINATE), DECASPRAY (DEXAMETHASONE), DECLOMYCIN (DEMECLOCYCLINE HYDROCHLORIDE), DEFEROXAMINE MESYLATE (DEFEROXAMINE MESYLATE), DEFINITY (PERFLUTREN), DEL-VI-A (VITAMIN A PALMITATE), DELALUTIN (HYDROXYPROGESTERONE CAPROATE), DELATESTRYL (TESTOSTERONE ENANTHATE), DELAXIN (METHOCARBAMOL), DELCOBESE (AMPHETAMINE ADIPATE; AMPHETAMINE SULFATE; DEXTROAMPHETAMINE ADIPATE; DEXTROAMPHETAMINE SULFATE), DELESTROGEN (ESTRADIOL VALERATE), DELFEN (NONOXYNOL-9), DELFLEX W/ DEXTROSE 1.5% IN PLASTIC CONTAINER (CALCIUM CHLORIDE; DEXTROSE; MAGNESIUM CHLORIDE; SODIUM CHLORIDE; SODIUM LACTATE), DELFLEX W/ DEXTROSE 1.5% LOW MAGNESIUM IN PLASTIC CONTAINER (CALCIUM CHLORIDE; DEXTROSE; MAGNESIUM CHLORIDE; SODIUM CHLORIDE; SODIUM LACTATE), DELFLEX W/ DEXTROSE 1.5%

LOW MAGNESIUM LOW CALCIUM IN PLASTIC CONTAINER (CALCIUM CHLORIDE; DEXTROSE; MAGNESIUM CHLORIDE; SODIUM CHLORIDE; SODIUM LACTATE), DELFLEX W/ DEXTROSE 2.5% IN PLASTIC CONTAINER (CALCIUM CHLORIDE; DEXTROSE; MAGNESIUM CHLORIDE; SODIUM CHLORIDE; SODIUM LACTATE), DELFLEX W/ DEXTROSE 2.5% LOW MAGNESIUM IN PLASTIC CONTAINER (CALCIUM CHLORIDE; DEXTROSE; MAGNESIUM CHLORIDE; SODIUM CHLORIDE; SODIUM LACTATE), DELFLEX W/ DEXTROSE 2.5% LOW MAGNESIUM LOW CALCIUM IN PLASTIC CONTAINER (CALCIUM CHLORIDE; DEXTROSE; MAGNESIUM CHLORIDE; SODIUM CHLORIDE; SODIUM LACTATE), DELFLEX W/ DEXTROSE 3.5% IN PLASTIC CONTAINER (CALCIUM CHLORIDE; DEXTROSE; MAGNESIUM CHLORIDE; SODIUM CHLORIDE; SODIUM LACTATE), DELFLEX W/ DEXTROSE 4.25% IN PLASTIC CONTAINER (CALCIUM CHLORIDE; DEXTROSE; MAGNESIUM CHLORIDE; SODIUM CHLORIDE; SODIUM LACTATE), DELFLEX W/ DEXTROSE 4.25% LOW MAGNESIUM IN PLASTIC CONTAINER (CALCIUM CHLORIDE; DEXTROSE; MAGNESIUM CHLORIDE; SODIUM CHLORIDE; SODIUM LACTATE), DELFLEX W/ DEXTROSE 4.25% LOW MAGNESIUM LOW CALCIUM IN PLASTIC CONTAINER (CALCIUM CHLORIDE; DEXTROSE; MAGNESIUM CHLORIDE; SODIUM CHLORIDE; SODIUM LACTATE), DELFLEX-LM W/ DEXTROSE 1.5% IN PLASTIC CONTAINER (CALCIUM CHLORIDE; DEXTROSE; MAGNESIUM CHLORIDE; SODIUM CHLORIDE; SODIUM LACTATE), DELFLEX-LM W/ DEXTROSE 2.5% IN PLASTIC CONTAINER (CALCIUM CHLORIDE; DEXTROSE; MAGNESIUM CHLORIDE; SODIUM CHLORIDE; SODIUM LACTATE), DELFLEX-LM W/ DEXTROSE 3.5% IN PLASTIC CONTAINER (CALCIUM CHLORIDE; DEXTROSE; MAGNESIUM CHLORIDE; SODIUM CHLORIDE; SODIUM LACTATE), DELFLEX-LM W/ DEXTROSE 4.25% IN PLASTIC CONTAINER (CALCIUM CHLORIDE; DEXTROSE; MAGNESIUM CHLORIDE; SODIUM CHLORIDE; SODIUM LACTATE), DELSYM (DEXTROMETHORPHAN POLISTIREX), DELTA-CORTEF (PREDNISOLONE), DELTA-DOME (PREDNISONE), DELTALIN (ERGOCALCIFEROL), DELTASONE (PREDNISONE), DEMADEX (TORSEMIDE), DEMAZIN (CHLORPHENIRAMINE MALEATE; PHENYLPROPANOLAMINE HYDROCHLORIDE), DEMECLOCYCLINE HYDROCHLORIDE (DEMECLOCYCLINE HYDROCHLORIDE), DEMEROL (MEPERIDINE HYDROCHLORIDE), DEMI-REGROTON (CHLORTHALIDONE; RESERPINE), DEMSER (METYROSINE), DEMULEN 1/35-21 (ETHINYL ESTRADIOL; ETHYNODIOL DIACETATE), DEMULEN 1/35-28 (ETHINYL ESTRADIOL; ETHYNODIOL DIACETATE), DEMULEN 1/50-21 (ETHINYL ESTRADIOL; ETHYNODIOL DIACETATE), DEMULEN 1/50-28 (ETHINYL ESTRADIOL; ETHYNODIOL DIACETATE), DENAVIR (PENCICLOVIR SODIUM), DENDRID (IDOXURIDINE), DENTIPATCH (LIDOCAINE), DEPACON (VALPROATE SODIUM), DEPAKENE (VALPROIC ACID), DEPAKOTE (DIVALPROEX SODIUM), DEPAKOTE CP (DIVALPROEX SODIUM), DEPAKOTE ER (DIVALPROEX SODIUM), DEPEN (PENICILLAMINE), DEPINAR (CYANOCOBALAMIN; TANNIC ACID; ZINC ACETATE), DEPO-ESTRADIOL (ESTRADIOL CYPIONATE), DEPO-MEDROL (METHYLPREDNISOLONE ACETATE), DEPO-PROVERA (MEDROXYPROGESTERONE ACETATE), DEPO-SUBQ PROVERA 104 (MEDROXYPROGESTERONE ACETATE), DEPO-TESTADIOL (ESTRADIOL CYPIONATE; TESTOSTERONE CYPIONATE), DEPO-TESTOSTERONE (TESTOSTERONE CYPIONATE), DEPOCYT (CYTARABINE), DEPODUR (MORPHINE SULFATE), DERMA-SMOOTHE/FS (FLUOCINOLONE ACETONIDE), DERMABET (BETAMETHASONE VALERATE), DERMACORT (HYDROCORTISONE), DERMATOP (PREDNICARBATE), DERMATOP E EMOLLIENT (PREDNICARBATE), DESFERAL (DEFEROXAMINE MESYLATE), DESIPRAMINE HYDROCHLORIDE (DESIPRAMINE HYDROCHLORIDE), DESMOPRESSIN ACETATE (DESMOPRESSIN ACETATE), DESMOPRESSIN ACETATE (NEEDS NO REFRIGERATION) (DESMOPRESSIN ACETATE), DESMOPRESSIN ACETATE PRESERVATIVE FREE (DESMOPRESSIN ACETATE), DESOGEN (DESOGESTREL; ETHINYL ESTRADIOL), DESOGESTREL AND ETHINYL ESTRADIOL (DESOGESTREL; ETHINYL ESTRADIOL), DESOGESTREL; ETHINYL (DESOGESTREL; ETHINYL ESTRADIOL), DESOGESTREL; ETHINYL ESTRADIOL (DESOGESTREL; ETHINYL ESTRADIOL), DESOGESTREL; ETHINYLESTRADIOL; ETHINYL ESTRADIOL (DESOGESTREL; ETHINYL ESTRADIOL; ETHINYL ESTRADIOL), DESONATE (DESONIDE), DESONIDE (DESONIDE), DESOWEN (DESONIDE), DESOXIMETASONE (DESOXIMETASONE), DESOXYN (METHAMPHETAMINE HYDROCHLORIDE), DESYREL (TRAZODONE HYDROCHLORIDE), DETROL (TOLTERODINE TARTRATE), DETROL LA (TOLTERODINE TARTRATE), DEXACEN-4 (DEXAMETHASONE SODIUM PHOSPHATE), DEXACIDIN (DEXAMETHASONE; NEOMYCIN SULFATE; POLYMYXIN B SULFATE), DEXACORT (DEXAMETHASONE SODIUM PHOSPHATE), DEXAIR (DEXAMETHASONE SODIUM PHOSPHATE), DEXAMETHASONE (DEXAMETHASONE), DEXAMETHASONE (DEXAMETHASONE SODIUM PHOSPHATE), DEXAMETHASONE ACETATE (DEXAMETHASONE ACETATE), DEXAMETHASONE INTENSOL (DEXAMETHASONE), DEXAMETHASONE SODIUM PHOSPHATE (DEXAMETHASONE SODIUM PHOSPHATE), DEXAMPEX (DEXTROAMPHETAMINE SULFATE), DEXASPORIN (DEXAMETHASONE; NEOMYCIN SULFATE; POLYMYXIN B SULFATE), DEXCHLORPHENIRAMINE MALEATE (DEXCHLORPHENIRAMINE MALEATE), DEXEDRINE (DEXTROAMPHETAMINE SULFATE), DEXFERRUM (IRON DEXTRAN), DEXMETHYLPHENIDATE HYDROCHLORIDE (DEXMETHYLPHENIDATE HYDROCHLORIDE), DEXONE 0.5 (DEXAMETHASONE), DEXONE 0.75 (DEXAMETHASONE), DEXONE 1.5 (DEXAMETHASONE), DEXONE 4 (DEXAMETHASONE), DEXRAZOXANE (DEXRAZOXANE HYDROCHLORIDE), DEXTROAMP SACCHARATE, AMP ASPARTATE, DEXTROAMP SULFATE AND AMP SULFATE (AMPHETAMINE ASPARTATE; AMPHETAMINE SULFATE; DEXTROAMPHETAMINE SACCHARATE; DEXTROAMPHETAMINE SULFATE), DEXTROAMPHETAMINE SULFATE (DEXTROAMPHETAMINE SULFATE), DEXTROSE 10% AND SODIUM CHLORIDE 0.11% IN PLASTIC CONTAINER (DEXTROSE; SODIUM CHLORIDE), DEXTROSE 10% AND SODIUM CHLORIDE 0.2% IN PLASTIC CONTAINER (DEXTROSE; SODIUM CHLORIDE), DEXTROSE 10% AND SODIUM CHLORIDE 0.33% IN PLASTIC CONTAINER (DEXTROSE; SODIUM CHLORIDE), DEXTROSE 10% AND SODIUM CHLORIDE 0.45% IN PLASTIC CONTAINER (DEXTROSE; SODIUM CHLORIDE), DEXTROSE 10% AND SODIUM CHLORIDE 0.9% IN PLASTIC CONTAINER (DEXTROSE; SODIUM CHLORIDE), DEXTROSE 10% IN PLASTIC CONTAINER (DEXTROSE), DEXTROSE 2.5% AND SODIUM CHLORIDE 0.11% IN PLASTIC CONTAINER (DEXTROSE; SODIUM CHLORIDE), DEXTROSE 2.5% AND SODIUM CHLORIDE 0.2% IN PLASTIC CONTAINER (DEXTROSE; SODIUM CHLORIDE), DEXTROSE 2.5% AND SODIUM CHLORIDE 0.33% IN PLASTIC CONTAINER (DEXTROSE; SODIUM CHLORIDE), DEXTROSE 2.5% AND SODIUM CHLORIDE 0.45% IN PLASTIC CONTAINER (DEXTROSE; SODIUM CHLORIDE), DEXTROSE 2.5% AND SODIUM CHLORIDE 0.9% IN PLASTIC CONTAINER (DEXTROSE; SODIUM CHLORIDE), DEXTROSE 2.5% IN HALF-STRENGTH LACTATED RINGER'S IN PLASTIC CONTAINER (CALCIUM CHLORIDE; DEXTROSE; POTASSIUM CHLORIDE; SODIUM CHLORIDE; SODIUM LACTATE), DEXTROSE 2.5% IN PLASTIC CONTAINER (DEXTROSE), DEXTROSE 20% IN PLASTIC CONTAINER (DEXTROSE), DEXTROSE 25% (DEXTROSE), DEXTROSE 3.3% AND SODIUM CHLORIDE 0.3% IN PLASTIC CONTAINER (DEXTROSE; SODIUM CHLORIDE), DEXTROSE 30% IN PLASTIC CONTAINER (DEXTROSE), DEXTROSE 38.5% IN PLASTIC CONTAINER (DEXTROSE), DEXTROSE 4% IN MODIFIED LACTATED RINGER'S IN PLASTIC CONTAINER (CALCIUM CHLORIDE; DEXTROSE; POTASSIUM CHLORIDE; SODIUM CHLORIDE; SODIUM LACTATE), DEXTROSE 40% IN PLASTIC CONTAINER (DEXTROSE), DEXTROSE 5% AND ELECTROLYTE NO 75 IN PLASTIC CONTAINER (DEXTROSE; POTASSIUM CHLORIDE; POTASSIUM PHOSPHATE, MONOBASIC; SODIUM CHLORIDE; SODIUM LACTATE), DEXTROSE 5% AND ELECTROLYTE NO. 48 IN PLASTIC CONTAINER (DEXTROSE; MAGNESIUM CHLORIDE; POTASSIUM CHLORIDE; POTASSIUM PHOSPHATE, MONOBASIC; SODIUM CHLORIDE; SODIUM LACTATE), DEXTROSE 5% AND LACTATED RINGER'S IN PLASTIC CONTAINER (CALCIUM CHLORIDE; DEXTROSE; POTASSIUM CHLORIDE; SODIUM CHLORIDE; SODIUM LACTATE), DEXTROSE 5% AND POTASSIUM CHLORIDE 0.075% IN PLASTIC CONTAINER (DEXTROSE; POTASSIUM CHLORIDE), DEXTROSE 5% AND POTASSIUM CHLORIDE 0.15% IN PLASTIC CONTAINER (DEXTROSE; POTASSIUM CHLORIDE), DEXTROSE 5% AND POTASSIUM CHLORIDE 0.224% IN PLASTIC CONTAINER (DEXTROSE; POTASSIUM CHLORIDE), DEXTROSE 5% AND POTASSIUM CHLORIDE 0.3% IN PLASTIC CONTAINER (DEXTROSE; POTASSIUM CHLORIDE), DEXTROSE 5% AND RINGER'S IN PLASTIC CONTAINER (CALCIUM CHLORIDE; DEXTROSE; POTASSIUM CHLORIDE; SODIUM CHLORIDE), DEXTROSE 5% AND SODIUM CHLORIDE 0.11% IN PLASTIC CONTAINER (DEXTROSE; SODIUM CHLORIDE), DEXTROSE 5% AND SODIUM CHLORIDE 0.2% IN PLASTIC CONTAINER (DEXTROSE; SODIUM CHLORIDE), DEXTROSE 5% AND SODIUM CHLORIDE 0.225% IN PLASTIC CONTAINER (DEXTROSE; SODIUM CHLORIDE), DEXTROSE 5% AND SODIUM CHLORIDE 0.3% IN PLASTIC CONTAINER (DEXTROSE; SODIUM CHLORIDE), DEXTROSE 5% AND SODIUM CHLORIDE 0.33% IN PLASTIC CONTAINER (DEXTROSE; SODIUM CHLORIDE), DEXTROSE 5% AND SODIUM CHLORIDE 0.45% IN PLASTIC CONTAINER (DEXTROSE; SODIUM CHLORIDE), DEXTROSE 5% AND SODIUM CHLORIDE 0.9% IN PLASTIC CONTAINER (DEXTROSE; SODIUM CHLORIDE), DEXTROSE 5% IN ACETATED RINGER'S IN PLASTIC CONTAINER (CALCIUM CHLORIDE; DEXTROSE; POTASSIUM CHLORIDE; SODIUM ACETATE; SODIUM CHLORIDE), DEXTROSE 5% IN LACTATED RINGER'S IN PLASTIC CONTAINER (CALCIUM CHLORIDE; DEXTROSE; POTASSIUM CHLORIDE; SODIUM CHLORIDE; SODIUM LACTATE), DEXTROSE 5% IN PLASTIC CONTAINER (DEXTROSE), DEXTROSE 5% IN RINGER'S IN PLASTIC CONTAINER (CALCIUM CHLORIDE; DEXTROSE; POTASSIUM CHLORIDE; SODIUM CHLORIDE), DEXTROSE 5% IN SODIUM CHLORIDE 0.2% IN PLASTIC CONTAINER (DEXTROSE; SODIUM CHLORIDE), DEXTROSE 5% IN SODIUM CHLORIDE 0.33% IN PLASTIC CONTAINER (DEXTROSE; SODIUM CHLORIDE), DEXTROSE 5% IN SODIUM CHLORIDE 0.45% IN PLASTIC CONTAINER (DEXTROSE; SODIUM CHLORIDE), DEXTROSE 5% IN SODIUM CHLORIDE 0.9% IN PLASTIC CONTAINER (DEXTROSE; SODIUM CHLORIDE), DEXTROSE 5%, SODIUM CHLORIDE 0.2% AND POTASSIUM CHLORIDE 0.075% (DEXTROSE; POTASSIUM CHLORIDE; SODIUM CHLORIDE), DEXTROSE 5%, SODIUM CHLORIDE 0.2% AND POTASSIUM CHLORIDE 0.15% IN PLASTIC CONTAINER (DEXTROSE; POTASSIUM CHLORIDE; SODIUM CHLORIDE), DEXTROSE 5%, SODIUM CHLORIDE 0.2% AND POTASSIUM CHLORIDE 0.224% IN PLASTIC CONTAINER (DEXTROSE; POTASSIUM CHLORIDE; SODIUM CHLORIDE), DEXTROSE 5%, SODIUM CHLORIDE 0.2% AND POTASSIUM CHLORIDE 0.3% IN PLASTIC CONTAINER (DEXTROSE; POTASSIUM CHLORIDE; SODIUM CHLORIDE), DEXTROSE 5%, SODIUM CHLORIDE 0.2% AND POTASSIUM CHLORIDE 10MEQ (DEXTROSE; POTASSIUM CHLORIDE; SODIUM CHLORIDE), DEXTROSE 5%, SODIUM CHLORIDE 0.2% AND POTASSIUM CHLORIDE 15MEQ (K) (DEXTROSE; POTASSIUM CHLORIDE; SODIUM CHLORIDE), DEXTROSE 5%, SODIUM CHLORIDE 0.2% AND POTASSIUM CHLORIDE 20MEQ (DEXTROSE; POTASSIUM CHLORIDE; SODIUM CHLORIDE), DEXTROSE 5%, SODIUM CHLORIDE 0.2% AND POTASSIUM CHLORIDE 20MEQ (K) (DEXTROSE; POTASSIUM CHLORIDE; SODIUM CHLORIDE), DEXTROSE 5%, SODIUM CHLORIDE 0.2% AND POTASSIUM CHLORIDE 30MEQ (DEXTROSE; POTASSIUM CHLORIDE; SODIUM CHLORIDE), DEXTROSE 5%, SODIUM CHLORIDE 0.2% AND POTASSIUM CHLORIDE 40MEQ (DEXTROSE; POTASSIUM CHLORIDE; SODIUM CHLORIDE), DEXTROSE 5%, SODIUM CHLORIDE 0.2% AND POTASSIUM CHLO-

RIDE 5MEQ (DEXTROSE; POTASSIUM CHLORIDE; SODIUM CHLORIDE), DEXTROSE 5%, SODIUM CHLORIDE 0.2% AND POTASSIUM CHLORIDE 5MEQ (K) (DEXTROSE; POTASSIUM CHLORIDE; SODIUM CHLORIDE), DEXTROSE 5%, SODIUM CHLORIDE 0.33% AND POTASSIUM CHLORIDE 0.075% IN PLASTIC CONTAINER (DEXTROSE; POTASSIUM CHLORIDE; SODIUM CHLORIDE), DEXTROSE 5%, SODIUM CHLORIDE 0.33% AND POTASSIUM CHLORIDE 0.15% IN PLASTIC CONTAINER (DEXTROSE; POTASSIUM CHLORIDE; SODIUM CHLORIDE), DEXTROSE 5%, SODIUM CHLORIDE 0.33% AND POTASSIUM CHLORIDE 0.22% IN PLASTIC CONTAINER (DEXTROSE; POTASSIUM CHLORIDE; SODIUM CHLORIDE), DEXTROSE 5%, SODIUM CHLORIDE 0.33% AND POTASSIUM CHLORIDE 0.30% IN PLASTIC CONTAINER (DEXTROSE; POTASSIUM CHLORIDE; SODIUM CHLORIDE), DEXTROSE 5%, SODIUM CHLORIDE 0.33% AND POTASSIUM CHLORIDE 10MEQ IN PLASTIC CONTAINER (DEXTROSE; POTASSIUM CHLORIDE; SODIUM CHLORIDE), DEXTROSE 5%, SODIUM CHLORIDE 0.33% AND POTASSIUM CHLORIDE 15MEQ IN PLASTIC CONTAINER (DEXTROSE; POTASSIUM CHLORIDE; SODIUM CHLORIDE), DEXTROSE 5%, SODIUM CHLORIDE 0.33% AND POTASSIUM CHLORIDE 20MEQ IN PLASTIC CONTAINER (DEXTROSE; POTASSIUM CHLORIDE; SODIUM CHLORIDE), DEXTROSE 5%, SODIUM CHLORIDE 0.33% AND POTASSIUM CHLORIDE 30MEQ IN PLASTIC CONTAINER (DEXTROSE; POTASSIUM CHLORIDE; SODIUM CHLORIDE), DEXTROSE 5%, SODIUM CHLORIDE 0.33% AND POTASSIUM CHLORIDE 40MEQ IN PLASTIC CONTAINER (DEXTROSE; POTASSIUM CHLORIDE; SODIUM CHLORIDE), DEXTROSE 5%, SODIUM CHLORIDE 0.33% AND POTASSIUM CHLORIDE 5MEQ IN PLASTIC CONTAINER (DEXTROSE; POTASSIUM CHLORIDE; SODIUM CHLORIDE), DEXTROSE 5%, SODIUM CHLORIDE 0.45% AND POTASSIUM CHLORIDE 0.075% (DEXTROSE; POTASSIUM CHLORIDE; SODIUM CHLORIDE), DEXTROSE 5%, SODIUM CHLORIDE 0.45% AND POTASSIUM CHLORIDE 0.15% IN PLASTIC CONTAINER (DEXTROSE; POTASSIUM CHLORIDE; SODIUM CHLORIDE), DEXTROSE 5%, SODIUM CHLORIDE 0.45% AND POTASSIUM CHLORIDE 0.22% IN PLASTIC CONTAINER (DEXTROSE; POTASSIUM CHLORIDE; SODIUM CHLORIDE), DEXTROSE 5%, SODIUM CHLORIDE 0.45% AND POTASSIUM CHLORIDE 0.3% IN PLASTIC CONTAINER (DEXTROSE; POTASSIUM CHLORIDE; SODIUM CHLORIDE), DEXTROSE 5%, SODIUM CHLORIDE 0.45% AND POTASSIUM CHLORIDE 15MEQ IN PLASTIC CONTAINER (DEXTROSE; POTASSIUM CHLORIDE; SODIUM CHLORIDE), DEXTROSE 5%, SODIUM CHLORIDE 0.45% AND POTASSIUM CHLORIDE 20MEQ (K) IN PLASTIC CONTAINER (DEXTROSE; POTASSIUM CHLORIDE; SODIUM CHLORIDE), DEXTROSE 5%, SODIUM CHLORIDE 0.45% AND POTASSIUM CHLORIDE 5MEQ IN PLASTIC CONTAINER (DEXTROSE; POTASSIUM CHLORIDE; SODIUM CHLORIDE), DEXTROSE 50% IN PLASTIC CONTAINER (DEXTROSE), DEXTROSE 60% (DEXTROSE), DEXTROSE 60% IN PLASTIC CONTAINER (DEXTROSE), DEXTROSE 7.7% IN PLASTIC CONTAINER (DEXTROSE), DEXTROSE 70% IN PLASTIC CONTAINER (DEXTROSE), DEXTROSTAT (DEXTROAMPHETAMINE SULFATE), DHC PLUS (ACETAMINOPHEN; CAFFEINE; DIHYDROCODEINE BITARTRATE), DI-ATRO (ATROPINE SULFATE; DIPHENOXYLATE HYDROCHLORIDE), DI-METREX (PHENDIMETRAZINE TARTRATE), DIABETA (GLYBURIDE), DIABINESE (CHLORPROPAMIDE), DIAL (HEXACHLOROPHENE), DIALYTE CONCENTRATE W/ DEXTROSE 30% IN PLASTIC CONTAINER (CALCIUM CHLORIDE; DEXTROSE; MAGNESIUM CHLORIDE; SODIUM ACETATE; SODIUM CHLORIDE), DIALYTE CONCENTRATE W/ DEXTROSE 50% IN PLASTIC CONTAINER (CALCIUM CHLORIDE; DEXTROSE; MAGNESIUM CHLORIDE; SODIUM ACETATE; SODIUM CHLORIDE), DIALYTE LM/DEXTROSE 1.5% IN PLASTIC CONTAINER (CALCIUM CHLORIDE; DEXTROSE; MAGNESIUM CHLORIDE; SODIUM CHLORIDE; SODIUM LACTATE), DIALYTE LM/DEXTROSE 2.5% IN PLASTIC CONTAINER (CALCIUM CHLORIDE; DEXTROSE; MAGNESIUM CHLORIDE; SODIUM ACETATE; SODIUM CHLORIDE), DIALYTE LM/DEXTROSE 2.5% IN PLASTIC CONTAINER (CALCIUM CHLORIDE; DEXTROSE; MAGNESIUM CHLORIDE; SODIUM CHLORIDE; SODIUM LACTATE), DIALYTE LM/DEXTROSE 4.25% IN PLASTIC CONTAINER (CALCIUM CHLORIDE; DEXTROSE; MAGNESIUM CHLORIDE; SODIUM CHLORIDE; SODIUM LACTATE), DIALYTE W/ DEXTROSE 1.5% IN PLASTIC CONTAINER (CALCIUM CHLORIDE; DEXTROSE; MAGNESIUM CHLORIDE; SODIUM ACETATE; SODIUM CHLORIDE), DIALYTE W/ DEXTROSE 4.25% IN PLASTIC CONTAINER (CALCIUM CHLORIDE; DEXTROSE; MAGNESIUM CHLORIDE; SODIUM ACETATE; SODIUM CHLORIDE), DIAMOX (ACETAZOLAMIDE), DIAMOX (ACETAZOLAMIDE SODIUM), DIANEAL 137 W/ DEXTROSE 1.5% IN PLASTIC CONTAINER (CALCIUM CHLORIDE; DEXTROSE; MAGNESIUM CHLORIDE; SODIUM CHLORIDE; SODIUM LACTATE), DIANEAL 137 W/ DEXTROSE 2.5% IN PLASTIC CONTAINER (CALCIUM CHLORIDE; DEXTROSE; MAGNESIUM CHLORIDE; SODIUM CHLORIDE; SODIUM LACTATE), DIANEAL 137 W/ DEXTROSE 4.25% IN PLASTIC CONTAINER (CALCIUM CHLORIDE; DEXTROSE; MAGNESIUM CHLORIDE; SODIUM CHLORIDE; SODIUM LACTATE), DIANEAL LOW CALCIUM W/ DEXTROSE 1.5% IN PLASTIC CONTAINER (CALCIUM CHLORIDE; DEXTROSE; MAGNESIUM CHLORIDE; SODIUM CHLORIDE; SODIUM LACTATE), DIANEAL LOW CALCIUM W/ DEXTROSE 2.5% IN PLASTIC CONTAINER (CALCIUM CHLORIDE; DEXTROSE; MAGNESIUM CHLORIDE; SODIUM CHLORIDE; SODIUM LACTATE), DIANEAL LOW CALCIUM W/ DEXTROSE 3.5% IN PLASTIC CONTAINER (CALCIUM CHLORIDE; DEXTROSE; MAGNESIUM CHLORIDE; SODIUM CHLORIDE; SODIUM LACTATE), DIANEAL LOW CALCIUM W/ DEXTROSE 4.25% IN PLASTIC CONTAINER (CALCIUM CHLORIDE; DEXTROSE; MAGNESIUM CHLORIDE; SODIUM CHLORIDE; SODIUM LACTATE), DIANEAL PD-1 W/ DEXTROSE 1.5% IN PLASTIC CONTAINER (CALCIUM CHLORIDE; DEXTROSE; MAGNESIUM CHLORIDE; SODIUM CHLORIDE; SODIUM LACTATE), DIANEAL PD-1 W/

DEXTROSE 2.5% IN PLASTIC CONTAINER (CALCIUM CHLORIDE; DEXTROSE; MAGNESIUM CHLORIDE; SODIUM CHLORIDE; SODIUM LACTATE), DIANEAL PD-1 W/ DEXTROSE 3.5% IN PLASTIC CONTAINER (CALCIUM CHLORIDE; DEXTROSE; MAGNESIUM CHLORIDE; SODIUM CHLORIDE; SODIUM LACTATE), DIANEAL PD-1 W/ DEXTROSE 4.25% IN PLASTIC CONTAINER (CALCIUM CHLORIDE; DEXTROSE; MAGNESIUM CHLORIDE; SODIUM CHLORIDE; SODIUM LACTATE), DIANEAL PD-2 W/ DEXTROSE 1.5% IN PLASTIC CONTAINER (CALCIUM CHLORIDE; DEXTROSE; MAGNESIUM CHLORIDE; SODIUM LACTATE), DIANEAL PD-2 W/ DEXTROSE 2.5% IN PLASTIC CONTAINER (CALCIUM CHLORIDE; DEXTROSE; MAGNESIUM CHLORIDE; SODIUM CHLORIDE; SODIUM LACTATE), DIANEAL PD-2 W/ DEXTROSE 3.5% IN PLASTIC CONTAINER (CALCIUM CHLORIDE; DEXTROSE; MAGNESIUM CHLORIDE; SODIUM CHLORIDE; SODIUM LACTATE), DIANEAL PD-2 W/ DEXTROSE 4.25% IN PLASTIC CONTAINER (CALCIUM CHLORIDE; DEXTROSE; MAGNESIUM CHLORIDE; SODIUM CHLORIDE; SODIUM LACTATE), DIAPID (LYPRESSIN), DIASONE SODIUM (SULFOXONE SODIUM), DIASTAT (DIAZEPAM), DIASTAT ACUDIAL (DIAZEPAM), DIATRIZOATE MEGLUMINE (DIATRIZOATE MEGLUMINE), DIATRIZOATE-60 (DIATRIZOATE MEGLUMINE; DIATRIZOATE SODIUM), DIAZEPAM (DIAZEPAM), DIAZEPAM INTENSOL (DIAZEPAM), DIAZOXIDE (DIAZOXIDE), DIBENIL (DIPHENHYDRAMINE HYDROCHLORIDE), DIBENZYLINE (PHENOXYBENZAMINE HYDROCHLORIDE), DICLOFENAC POTASSIUM (DICLOFENAC POTASSIUM), DICLOFENAC SODIUM (DICLOFENAC SODIUM), DICLOXACILLIN SODIUM (DICLOXACILLIN SODIUM), DICOPAC KIT (CYANOCOBALAMIN; CYANOCOBALAMIN, CO-57; CYANOCOBALAMIN, CO-58), DICUMAROL (DICUMAROL), DICURIN PROCAINE (PROCAINE MERETHOXYLLINE; THEOPHYLLINE), DICYCLOMINE HYDROCHLORIDE (DICYCLOMINE HYDROCHLORIDE), DICYCLOMINE HYDROCHLORIDE (PRESERVATIVE-FREE) (DICYCLOMINE HYDROCHLORIDE), DIDANOSINE (DIDANOSINE), DIDREX (BENZPHETAMINE HYDROCHLORIDE), DIDRONEL (ETIDRONATE DISODIUM), DIENESTROL (DIENESTROL), DIETHYLPROPION HYDROCHLORIDE (DIETHYLPROPION HYDROCHLORIDE), DIETHYLSTILBESTROL (DIETHYLSTILBESTROL), DIFFERIN (ADAPALENE), DIFLORASONE DIACETATE (DIFLORASONE DIACETATE), DIFLUCAN (FLUCONAZOLE), DIFLUCAN IN DEXTROSE 5% IN PLASTIC CONTAINER (FLUCONAZOLE), DIFLUCAN IN SODIUM CHLORIDE 0.9% (FLUCONAZOLE), DIFLUCAN IN SODIUM CHLORIDE 0.9% IN PLASTIC CONTAINER (FLUCONAZOLE), DIFLUNISAL (DIFLUNISAL), DIGOXIN (DIGOXIN), DIGOXIN PEDIATRIC (DIGOXIN), DIHYDROERGOTAMINE MESYLATE (DIHYDROERGOTAMINE MESYLATE), DILACOR XR (DILTIAZEM HYDROCHLORIDE), DILANTIN (PHENYTOIN), DILANTIN (PHENYTOIN SODIUM), DILANTIN-125 (PHENYTOIN), DILANTIN-30 (PHENYTOIN), DILATRATE-SR (ISOSORBIDE DINITRATE), DILAUDID (HYDROMORPHONE HYDROCHLORIDE), DILAUDID-HP (HYDROMORPHONE HYDROCHLORIDE), DILOR (DYPHYLLINE), DILOR-400 (DYPHYLLINE), DILT-CD (DILTIAZEM HYDROCHLORIDE), DILTIAZEM HYDROCHLORIDE (DILTIAZEM HYDROCHLORIDE), DILTZAC (DILTIAZEM HYDROCHLORIDE), DIMENHYDRINATE (DIMENHYDRINATE), DIMETANE (BROMPHENIRAMINE MALEATE), DIMETANE-DC (BROMPHENIRAMINE MALEATE; CODEINE PHOSPHATE; PHENYLPROPANOLAMINE HYDROCHLORIDE), DIMETANE-DX (BROMPHENIRAMINE MALEATE; DEXTROMETHORPHAN HYDROBROMIDE; PSEUDOEPHEDRINE HYDROCHLORIDE), DIMETANE-TEN (BROMPHENIRAMINE MALEATE), DIMETAPP (BROMPHENIRAMINE MALEATE; PHENYLPROPANOLAMINE HYDROCHLORIDE), DIMETHYL SULFOXIDE (DIMETHYL SULFOXIDE), DIONOSIL AQUEOUS (PROPYLIODONE), DIONOSIL OILY (PROPYLIODONE), DIOVAN (VALSARTAN), DIOVAN HCT (HYDROCHLOROTHIAZIDE; VALSARTAN), DIPENTUM (OLSALAZINE SODIUM), DIPHEN (DIPHENHYDRAMINE HYDROCHLORIDE), DIPHENHYDRAMINE HYDROCHLORIDE (DIPHENHYDRAMINE HYDROCHLORIDE), DIPHENHYDRAMINE HYDROCHLORIDE PRESERVATIVE FREE (DIPHENHYDRAMINE HYDROCHLORIDE), DIPHENOXYLATE HYDROCHLORIDE AND ATROPINE SULFATE (ATROPINE SULFATE; DIPHENOXYLATE HYDROCHLORIDE), DIPHENOXYLATE HYDROCHLORIDE W/ ATROPINE SULFATE (ATROPINE SULFATE; DIPHENOXYLATE HYDROCHLORIDE), DIPHENYLAN SODIUM (PHENYTOIN SODIUM), DIPIVEFRIN HYDROCHLORIDE (DIPIVEFRIN HYDROCHLORIDE), DIPRIVAN (PROPOFOL), DIPROLENE (BETAMETHASONE DIPROPIONATE), DIPROLENE AF (BETAMETHASONE DIPROPIONATE), DIPROSONE (BETAMETHASONE DIPROPIONATE), DIPYRIDAMOLE (DIPYRIDAMOLE), DISCASE (CHYMOPAPAIN), DISIPAL (ORPHENADRINE HYDROCHLORIDE), DISOBROM (DEXBROMPHENIRAMINE MALEATE; PSEUDOEPHEDRINE SULFATE), DISODIUM EDETATE (EDETATE DISODIUM), DISOMER (DEXBROMPHENIRAMINE MALEATE), DISOPHROL (DEXBROMPHENIRAMINE MALEATE; PSEUDOEPHEDRINE SULFATE), DISOPYRAMIDE PHOSPHATE (DISOPYRAMIDE PHOSPHATE), DISPERMOX (AMOXICILLIN), DISULFIRAM (DISULFIRAM), DITATE-DS (ESTRADIOL VALERATE; TESTOSTERONE ENANTHATE), DITROPAN (OXYBUTYNIN CHLORIDE), DITROPAN XL (OXYBUTYNIN CHLORIDE), DIUCARDIN (HYDROFLUMETHIAZIDE), DIULO (METOLAZONE), DIUPRES-250 (CHLOROTHIAZIDE; RESERPINE), DIUPRES-500 (CHLOROTHIAZIDE; RESERPINE), DIURIL (CHLOROTHIAZIDE), DIURIL (CHLOROTHIAZIDE SODIUM), DIUTENSEN-R (METHYCLOTHIAZIDE; RESERPINE), DIVALPROEX (DIVALPROEX SODIUM), DIVALPROEX SODIUM (DIVALPROEX SODIUM), DIVIGEL (ESTRADIOL), DIZAC (DIAZEPAM), DOBUTAMINE HYDROCHLORIDE (DOBUTAMINE HYDROCHLORIDE), DOBUTAMINE HYDROCHLORIDE IN DEXTROSE 5% (DOBUTAMINE HYDROCHLORIDE), DOBUTAMINE HYDROCHLORIDE IN DEXTROSE 5% IN PLASTIC CONTAINER (DOBUTAMINE HYDROCHLORIDE), DOBUTREX (DOBUTAMINE HYDROCHLORIDE),

DOCA (DESOXYCORTICOSTERONE ACETATE), DOLENE (PROPDXYPHENE HYDROCHLORIDE), DOLENE AP-65 (ACETAMINOPHEN; PROPDXYPHENE HYDROCHLORIDE), DOLOBID (DIFLUNISAL), DOLOPHINE HYDROCHLORIDE (METHADONE HYDROCHLORIDE), DOMEBORO (ACETIC ACID, GLACIAL; ALUMINUM ACETATE), DONEPEZIL (DONEPEZIL HYDROCHLORIDE), DONEPEZIL HYDROCHLORIDE (DONEPEZIL HYDROCHLORIDE), DOPAMINE HYDROCHLORIDE (DOPAMINE HYDROCHLORIDE), DOPAMINE HYDROCHLORIDE AND DEXTROSE 5% (DOPAMINE HYDROCHLORIDE), DOPAMINE HYDROCHLORIDE AND DEXTROSE 5% IN PLASTIC CONTAINER (DOPAMINE HYDROCHLORIDE), DOPAMINE HYDROCHLORIDE IN DEXTROSE 5% (DOPAMINE HYDROCHLORIDE), DOPAMINE HYDROCHLORIDE IN DEXTROSE 5% IN PLASTIC CONTAINER (DOPAMINE HYDROCHLORIDE), DOPAR (LEVODOPA), DOPRAM (DOXAPRAM HYDROCHLORIDE), DORAL (QUAZEPAM), DORIBAX (DORIPENEM), DORIDEN (GLUTETHIMIDE), DORMATE (MEBUTAMATE), DORYX (DOXYCYCLINE HYCLATE), DORZOLAMIDE HYDROCHLORIDE; TIMOLOL MALEATE (DORZOLAMIDE HYDROCHLORIDE; TIMOLOL MALEATE), DOSTINEX (CABERGOLINE), DOVONEX (CALCIPOTRIENE), DOW-ISONIAZID (ISONIAZID), DOXAPRAM HYDROCHLORIDE (DOXAPRAM HYDROCHLORIDE), DOXAZOSIN MESYLATE (DOXAZOSIN MESYLATE), DOXEPIN HYDROCHLORIDE (DOXEPIN HYDROCHLORIDE), DOXIL (DOXORUBICIN HYDROCHLORIDE), DOXORUBICIN HYDROCHLORIDE (DOXORUBICIN HYDROCHLORIDE), DOXY 100 (DOXYCYCLINE HYCLATE), DOXY 200 (DOXYCYCLINE HYCLATE), DOXY-LEMMON (DOXYCYCLINE HYCLATE), DOXY-SLEEP-AID (DOXYLAMINE SUCCINATE), DOXYCHEL (DOXYCYCLINE), DOXYCHEL HYCLATE (DOXYCYCLINE HYCLATE), DOXYCYCLINE (DOXYCYCLINE), DOXYCYCLINE (DOXYCYCLINE HYCLATE), DOXYCYCLINE HYCLATE (DOXYCYCLINE HYCLATE), DOXYLAMINE SUCCINATE (DOXYLAMINE SUCCINATE), DRALSERP (HYDRALAZINE HYDROCHLORIDE; RESERPINE), DRALZINE (HYDRALAZINE HYDROCHLORIDE), DRAXIMAGE MDP-10 (TECHNETIUM TC-99M MEDRONATE KIT), DRAXIMAGE MDP-25 (TECHNETIUM TC-99M MEDRONATE KIT), DRICORT (HYDROCORTISONE ACETATE), DRISDOL (ERGOCALCIFEROL), DRIXORAL (DEXBROMPHENIRAMINE MALEATE; PSEUDOEPHEDRINE SULFATE), DRIXORAL PLUS (ACETAMINOPHEN; DEXBROMPHENIRAMINE MALEATE; PSEUDOEPHEDRINE SULFATE), DRIZE (CHLORPHENIRAMINE MALEATE; PHENYLPROPANOLAMINE HYDROCHLORIDE), DROLBAN (DROMOSTANOLONE PROPIONATE), DRONABINOL (DRONABINOL), DROPERIDOL (DROPERIDOL), DROSPIRENONE AND ETHINYL ESTRADIOL (DROSPIRENONE; ETHINYL ESTRADIOL), DROXIA (HYDROXYUREA), DTIC-DOME (DACARBAZINE), DTPA (TECHNETIUM TC-99M PENTETATE KIT), DUAC (BENZOYL PEROXIDE; CLINDAMYCIN PHOSPHATE), DUETACT (GLIMEPIRIDE; PIOGLITAZONE HYDROCHLORIDE), DUO-MEDIHALER (ISOPROTERENOL HYDROCHLORIDE; PHENYLEPHRINE BITARTRATE), DUOCAINE (BUPIVACAINE HYDROCHLORIDE; LIDOCAINE HYDROCHLORIDE), DUODOTE (ATROPINE; PRALIDOXIME CHLORIDE), DUONEB (ALBUTEROL SULFATE; IPRATROPIUM BROMIDE), DUPHALAC (LACTULOSE), DURABOLIN (NANDROLONE PHENPROPIONATE), DURACILLIN A.S. (PENICILLIN G PROCAINE), DURACLON (CLONIDINE HYDROCHLORIDE), DURADYNE DHC (ACETAMINOPHEN; HYDROCODONE BITARTRATE), DURAGESIC-100 (FENTANYL), DURAGESIC-12 (FENTANYL), DURAGESIC-25 (FENTANYL), DURAGESIC-50 (FENTANYL), DURAGESIC-75 (FENTANYL), DURAMORPH PF (MORPHINE SULFATE), DURANEST (EPINEPHRINE BITARTRATE; ETIDOCAINE HYDROCHLORIDE), DURANEST (EPINEPHRINE; ETIDOCAINE HYDROCHLORIDE), DURANEST (ETIDOCAINE HYDROCHLORIDE), DURAPHYL (THEOPHYLLINE), DURAPREP (IODINE POVACRYLEX; ISOPROPYL ALCOHOL), DURAQUIN (QUINIDINE GLUCONATE), DUREZOL (DIFLUPREDNATE), DURICEF (CEFADROXIL/CEFADROXIL HEMIHYDRATE), DUTOPROL (HYDROCHLOROTHIAZIDE; METOPROLOL SUCCINATE), DUVOID (BETHANECHOL CHLORIDE), DV (DIENESTROL), DYAZIDE (HYDROCHLOROTHIAZIDE; TRIAMTERENE), DYCILL (DICLOXACILLIN SODIUM), DYCLONE (DYCLONINE HYDROCHLORIDE), DYMELOR (ACETOHEXAMIDE), DYNA-HEX (CHLORHEXIDINE GLUCONATE), DYNABAC (DIRITHROMYCIN), DYNACIN (MINOCYCLINE HYDROCHLORIDE), DYNACIRC (ISRADIPINE), DYNACIRC CR (ISRADIPINE), DYNAPEN (DICLOXACILLIN SODIUM), DYRENIUM (TRIAMTERENE), E-BASE (ERYTHROMYCIN), E-GLADES (ERYTHROMYCIN), E-MYCIN (ERYTHROMYCIN), E-MYCIN E (ERYTHROMYCIN ETHYLSUCCINATE), E-SOLVE 2 (ERYTHROMYCIN), E-Z PREP (POVIDONE-IODINE), E-Z PREP 220 (POVIDONE-IODINE), E-Z SCRUB (CHLORHEXIDINE GLUCONATE), E-Z SCRUB (HEXACHLOROPHENE), E-Z SCRUB 201 (POVIDONE-IODINE), E-Z SCRUB 241 (POVIDONE-IODINE), E-Z-EM PREP LYTE (POLYETHYLENE GLYCOL 3350; POTASSIUM CHLORIDE; SODIUM BICARBONATE; SODIUM CHLORIDE; SODIUM SULFATE, ANHYDROUS), E.E.S. (ERYTHROMYCIN ETHYLSUCCINATE), E.E.S. 200 (ERYTHROMYCIN ETHYLSUCCINATE), E.E.S. 400 (ERYTHROMYCIN ETHYLSUCCINATE), EC-NAPROSYN (NAPROXEN), ECONAZOLE NITRATE (ECONAZOLE NITRATE), ECONOCHLOR (CHLORAMPHENICOL), ECONOPRED (PREDNISOLONE ACETATE), EDECRIN (ETHACRYNATE SODIUM), EDECRIN (ETHACRYNIC ACID), EDETATE DISODIUM (EDETATE DISODIUM), EDEX (ALPROSTADIL), EDROPHONIUM CHLORIDE (EDROPHONIUM CHLORIDE), EDROPHONIUM CHLORIDE PRESERVATIVE FREE (EDROPHONIUM CHLORIDE), EFAVIRENZ (EFAVIRENZ), EFFEXOR (VENLAFAXINE HYDROCHLORIDE), EFFEXOR XR (VENLAFAXINE HYDROCHLORIDE), EFIDAC 24 CHLORPHENIRAMINE MALEATE (CHLORPHENIRAMINE MALEATE), EFIDAC 24 PSEUDOEPHEDRINE HYDROCHLORIDE/BROMPHENIRAMINE MALEATE (BROMPHENIRAMINE MALEATE; PSEUDOEPHEDRINE HYDROCHLORIDE), EFUDEX (FLUOROURACIL), ELAPRASE (IDURSULFASE), ELASE-CHLOROMYCETIN (CHLORAMPHENICOL; DESOXYRIBONUCLEASE; FIBRINOLYSIN), ELAVIL (AMITRIPTYLINE HYDROCHLORIDE), ELDECORT (HYDROCORTISONE), ELDEPRYL (SELEGILINE HYDROCHLORIDE), ELESTAT (EPINASTINE HYDROCHLORIDE), ELESTRIN (ESTRADIOL), ELIDEL (PIMECROLIMUS), ELIGARD (LEUPROLIDE ACETATE), ELIMITE (PERMETHRIN), ELITEK (RASBURICASE), ELIXICON (THEOPHYLLINE), ELIXOMIN (THEOPHYLLINE), ELIXOPHYLLIN (THEOPHYLLINE), ELIXOPHYLLIN SR (THEOPHYLLINE), ELLENCE (EPIRUBICIN HYDROCHLORIDE), ELLIOTTS B SOLUTION (CALCIUM CHLORIDE; DEXTROSE; MAGNESIUM SULFATE; POTASSIUM CHLORIDE; SODIUM BICARBONATE; SODIUM CHLORIDE; SODIUM PHOSPHATE, DIBASIC, HEPTAHYDRATE), ELMIRON (PENTOSAN POLYSULFATE SODIUM), ELOCON (MOMETASONE FUROATE), ELOXATIN (OXALIPLATIN), ELSPAR (ASPARAGINASE), EMADINE (EMEDASTINE DIFUMARATE), EMBELINE (CLOBETASOL PROPIONATE), EMBELINE E (CLOBETASOL PROPIONATE), EMBOLEX (DIHYDROERGOTAMINE MESYLATE; HEPARIN SODIUM; LIDOCAINE HYDROCHLORIDE), EMCYT (ESTRAMUSTINE PHOSPHATE SODIUM), EMEND (APREPITANT), EMEND (FOSAPREPITANT DIMEGLUMINE), EMETE-CON (BENZQUINAMIDE HYDROCHLORIDE), EMGEL (ERYTHROMYCIN), EMLA (LIDOCAINE; PRILOCAINE), EMPRACET W/ CODEINE PHOSPHATE #3 (ACETAMINOPHEN; CODEINE PHOSPHATE), EMPRACET W/ CODEINE PHOSPHATE #4 (ACETAMINOPHEN; CODEINE PHOSPHATE), EMSAM (SELEGILINE), EMTRICITABINE (EMTRICITABINE), EMTRIVA (EMTRICITABINE), ENABLEX (DARIFENACIN HYDROBROMIDE), ENALAPRIL MALEATE (ENALAPRIL MALEATE), ENALAPRIL MALEATE AND HYDROCHLOROTHIAZIDE (ENALAPRIL MALEATE; HYDROCHLOROTHIAZIDE), ENALAPRILAT (ENALAPRILAT), ENBREL (ETANERCEPT), ENDEP (AMITRIPTYLINE HYDROCHLORIDE), ENDOMETRIN (PROGESTERONE), ENDOSOL EXTRA (CALCIUM CHLORIDE; DEXTROSE; GLUTATHIONE DISULFIDE; MAGNESIUM CHLORIDE; POTASSIUM CHLORIDE; SODIUM BICARBONATE; SODIUM CHLORIDE; SODIUM PHOSPHATE), ENDRATE (EDETATE DISODIUM), ENDURON (METHYCLOTHIAZIDE), ENDURONYL (DESERPIDINE; METHYCLOTHIAZIDE), ENDURONYL FORTE (DESERPIDINE; METHYCLOTHIAZIDE), ENFLURANE (ENFLURANE), ENJUVIA (ESTROGENS, CONJUGATED SYNTHETIC B), ENLON (EDROPHONIUM CHLORIDE), ENLON-PLUS (ATROPINE SULFATE; EDROPHONIUM CHLORIDE), ENOVID (MESTRANOL; NORETHYNODREL), ENOVID-E (MESTRANOL; NORETHYNODREL), ENOVID-E 21 (MESTRANOL; NORETHYNODREL), ENPRESSE-21 (ETHINYL ESTRADIOL; LEVONORGESTREL), ENPRESSE-28 (ETHINYL ESTRADIOL; LEVONORGESTREL), ENTEREG (ALVIMOPAN), ENTOCORT EC (BUDESONIDE), ENULOSE (LACTULOSE), EOVIST (GADOXETATE DISODIUM), EPI E Z PEN JR (EPINEPHRINE), EPICORT (HYDROCORTISONE), EPIFOAM (HYDROCORTISONE ACETATE; PRAMOXINE HYDROCHLORIDE), EPINEPHRINE (EPINEPHRINE), EPIPEN (EPINEPHRINE), EPIPEN E Z PEN (EPINEPHRINE), EPIPEN JR. (EPINEPHRINE), EPIRUBICIN HYDROCHLORIDE (EPIRUBICIN HYDROCHLORIDE), EPITOL (CARBAMAZEPINE), EPIVIR (LAMIVUDINE), EPIVIR-HBV (LAMIVUDINE), EPOGEN/PROCRIT (EPOETIN ALFA), EPOPROSTENOL (EPOPROSTENOL), EPOPROSTENOL SODIUM (EPOPROSTENOL SODIUM), EPREX (EPOETIN ALFA), EPZICOM (ABACAVIR SULFATE; LAMIVUDINE), EQUAGESIC (ASPIRIN; MEPROBAMATE), EQUANIL (MEPROBAMATE), EQUETRO (CARBAMAZEPINE), EQUIPIN (HOMATROPINE METHYLBROMIDE), ERAXIS (ANIDULAFUNGIN), ERBITUX (CETUXIMAB), ERGAMISOL (LEVAMISOLE HYDROCHLORIDE), ERGOLOID MESYLATES (ERGOLOID MESYLATES), ERGOMAR (ERGOTAMINE TARTRATE), ERGOSTAT (ERGOTAMINE TARTRATE), ERGOTAMINE TARTRATE AND CAFFEINE (CAFFEINE; ERGOTAMINE TARTRATE), ERRIN (NORETHINDRONE), ERTACZO (SERTACONAZOLE NITRATE), ERY-TAB (ERYTHROMYCIN), ERYC (ERYTHROMYCIN), ERYC 125 (ERYTHROMYCIN), ERYC SPRINKLES (ERYTHROMYCIN), ERYCETTE (ERYTHROMYCIN), ERYDERM (ERYTHROMYCIN), ERYGEL (ERYTHROMYCIN), ERYMAX (ERYTHROMYCIN), ERYPAR (ERYTHROMYCIN STEARATE), ERYPED (ERYTHROMYCIN ETHYLSUCCINATE), ERYTHRA-DERM (ERYTHROMYCIN), ERYTHROSTATIN (ERYTHROMYCIN), ERYTHROCIN (ERYTHROMYCIN LACTOBIONATE), ERYTHROCIN STEARATE (ERYTHROMYCIN STEARATE), ERYTHROMYCIN (ERYTHROMYCIN), ERYTHROMYCIN (ERYTHROMYCIN LACTOBIONATE), ERYTHROMYCIN AND BENZOYL PEROXIDE (BENZOYL PEROXIDE; ERYTHROMYCIN), ERYTHROMYCIN ESTOLATE (ERYTHROMYCIN ESTOLATE), ERYTHROMYCIN ETHYLSUCCINATE (ERYTHROMYCIN ETHYLSUCCINATE), ERYTHROMYCIN ETHYLSUCCINATE AND SULFISOXAZOLE ACETYL (ERYTHROMYCIN ETHYLSUCCINATE; SULFISOXAZOLE ACETYL), ERYTHROMYCIN LACTOBIONATE (ERYTHROMYCIN LACTOBIONATE), ERYTHROMYCIN STEARATE (ERYTHROMYCIN STEARATE), ERYZOLE (ERYTHROMYCIN ETHYLSUCCINATE; SULFISOXAZOLE ACETYL), ESCITALOPRAM (ESCITALOPRAM OXALATE), ESCITALOPRAM OXALATE (ESCITALOPRAM OXALATE), ESCLIM (ESTRADIOL), ESGIC (ACETAMINOPHEN; BUTALBITAL; CAFFEINE), ESGIC-PLUS (ACETAMINOPHEN; BUTALBITAL; CAFFEINE), ESIDRIX (HYDROCHLOROTHIAZIDE), ESIMIL (GUANETHIDINE MONOSULFATE; HYDROCHLOROTHIAZIDE), ESKALITH (LITHIUM CARBONATE), ESKALITH CR (LITHIUM CARBONATE), ESMOLOL HYDROCHLORIDE (ESMOLOL HYDROCHLORIDE), ESOMEPRAZOLE MAGNESIUM (ESOMEPRAZOLE MAGNESIUM), ESTAZOLAM (ESTAZOLAM), ESTERIFIED ESTROGENS (ESTROGENS, ESTERIFIED), ESTINYL (ETHINYL ESTRADIOL), ESTRACE (ESTRADIOL), ESTRADERM (ESTRADIOL), ESTRADIOL (ESTRADIOL), ESTRADIOL AND NORETHINDRONE ACETATE (ESTRADIOL; NORETHINDRONE ACETATE), ESTRADIOL AND NORGESTIMATE (ESTRADIOL; NORGESTIMATE),

ESTRADIOL CYPIONATE (ESTRADIOL CYPIONATE), ESTRADIOL VALERATE (ESTRADIOL VALERATE), ESTRADURIN (POLYESTRADIOL PHOSPHATE), ESTRAGUARD (DIENESTROL), ESTRASORB (ESTRADIOL HEMIHYDRATE), ESTRATAB (ESTROGENS, ESTERIFIED), ESTRING (ESTRADIOL), ESTROGEL (ESTRADIOL), ESTROGENIC SUBSTANCE (ESTRONE), ESTRONE (ESTRONE), ESTROPIPATE (ESTROPIPATE), ESTROSTEP 21 (ETHINYL ESTRADIOL; NORETHINDRONE ACETATE), ESTROSTEP FE (ETHINYL ESTRADIOL; NORETHINDRONE ACETATE), ESTROVIS (QUINESTROL), ETHAMBUTOL HYDROCHLORIDE (ETHAMBUTOL HYDROCHLORIDE), ETHAMIDE (ETHOXZOLAMIDE), ETHAMOLIN (ETHANOLAMINE OLEATE), ETHCHLORVYNOL (ETHCHLORVYNOL), ETHIODOL (ETHIODIZED OIL), ETHMOZINE (MORICIZINE HYDROCHLORIDE), ETHOSUXIMIDE (ETHOSUXIMIDE), ETHRANE (ENFLURANE), ETHRIL 250 (ERYTHROMYCIN STEARATE), ETHRIL 500 (ERYTHROMYCIN STEARATE), ETHYOL (AMIFOSTINE), ETIDRONATE DISODIUM (ETIDRONATE DISODIUM), ETODOLAC (ETODOLAC), ETOMIDATE (ETOMIDATE), ETOPOPHOS PRESERVATIVE FREE (ETOPOSIDE PHOSPHATE), ETOPOSIDE (ETOPOSIDE), ETRAFON 2-10 (AMITRIPTYLINE HYDROCHLORIDE; PERPHENAZINE), ETRAFON 2-25 (AMITRIPTYLINE HYDROCHLORIDE; PERPHENAZINE), ETRAFON-A (AMITRIPTYLINE HYDROCHLORIDE; PERPHENAZINE), ETRAFON-FORTE (AMITRIPTYLINE HYDROCHLORIDE; PERPHENAZINE), EULEXIN (FLUTAMIDE), EURAX (CROTAMITON), EUTHROID-0.5 (LIOTRIX (T4; T3)), EUTHROID-1 (LIOTRIX (T4; T3)), EUTHROID-2 (LIOTRIX (T4; T3)), EUTHROID-3 (LIOTRIX (T4; T3)), EUTONYL (PARGYLINE HYDROCHLORIDE), EUTRON (METHYCLOTHIAZIDE; PARGYLINE HYDROCHLORIDE), EVALOSE (LACTULOSE), EVAMIST (ESTRADIOL), EVANS BLUE (EVANS BLUE), EVEX (ESTROGENS, ESTERIFIED), EVISTA (RALOXIFENE HYDROCHLORIDE), EVOCLIN (CLINDAMYCIN PHOSPHATE), EVOXAC (CEVIMELINE HYDROCHLORIDE), EXCEDRIN (MIGRAINE) (ACETAMINOPHEN; ASPIRIN; CAFFEINE), EXELDERM (SULCONAZOLE NITRATE), EXELON (RIVASTIGMINE), EXELON (RIVASTIGMINE TARTRATE), EXEMESTANE (EXEMESTANE), EXFORGE (AMLODIPINE BESYLATE; VALSARTAN), EXIDINE (CHLORHEXIDINE GLUCONATE), EXJADE (DEFERASIROX), EXNA (BENZTHIAZIDE), EXOSURF NEONATAL (CETYL ALCOHOL; COLFOSCERIL PALMITATE; TYLOXAPOL), EXSEL (SELENIUM SULFIDE), EXTENDED PHENYTOIN SODIUM (PHENYTOIN SODIUM), EXTENDED PHENYTOIN SODIUM (PHENYTOIN SODIUM, EXTENDED), EXTINA (KETOCONAZOLE), EXTRA-STRENGTH AIM (SODIUM MONOFLUOROPHOSPHATE), EXTRANEAL (ICODEXTRIN), EXUBERA (INSULIN RECOMBINANT HUMAN), FABRAZYME (AGALSIDASE BETA), FACTIVE (GEMIFLOXACIN MESYLATE), FACTREL (GONADORELIN HYDROCHLORIDE), FAMCICLOVIR (FAMCICLOVIR), FAMOTIDINE (FAMOTIDINE), FAMOTIDINE PRESERVATIVE FREE (FAMOTIDINE), FAMOTIDINE PRESERVATIVE FREE (PHARMACY BULK) (FAMOTIDINE), FAMOTIDINE PRESERVATIVE FREE IN PLASTIC CONTAINER (FAMOTIDINE), FAMVIR (FAMCICLOVIR), FANSIDAR (PYRIMETHAMINE; SULFADOXINE), FARESTON (TOREMIFENE CITRATE), FASLODEX (FULVESTRANT), FASTIN (PHENTERMINE HYDROCHLORIDE), FAZACLO ODT (CLOZAPINE), FELBATOL (FELBAMATE), FELDENE (PIROXICAM), FELODIPINE (FELODIPINE), FEMARA (LETROZOLE), FEMCET (ACETAMINOPHEN; BUTALBITAL; CAFFEINE), FEMCON FE (ETHINYL ESTRADIOL; NORETHINDRONE), FEMHRT (ETHINYL ESTRADIOL; NORETHINDRONE ACETATE), FEMINONE (ETHINYL ESTRADIOL), FEMOGEN (ESTROGENS, ESTERIFIED), FEMPATCH (ESTRADIOL), FEMRING (ESTRADIOL ACETATE), FEMSTAT (BUTOCONAZOLE NITRATE), FEMSTAT 3 (BUTOCONAZOLE NITRATE), FEMTRACE (ESTRADIOL ACETATE), FENOFIBRATE (FENOFIBRATE), FENOFIBRATE (MICRONIZED) (FENOFIBRATE), FENOLDOPAM MESYLATE (FENOLDOPAM MESYLATE), FENOPROFEN CALCIUM (FENOPROFEN CALCIUM), FENTANYL (FENTANYL CITRATE), FENTANYL CITRATE (FENTANYL CITRATE), FENTANYL CITRATE AND DROPERIDOL (DROPERIDOL; FENTANYL CITRATE), FENTANYL CITRATE PRESERVATIVE FREE (FENTANYL CITRATE), FENTANYL-100 (FENTANYL), FENTANYL-12 (FENTANYL), FENTANYL-25 (FENTANYL), FENTANYL-50 (FENTANYL), FENTANYL-75 (FENTANYL), FENTORA (FENTANYL CITRATE), FERIDEX I.V. (FERUMOXIDES), FERNDEX (DEXTROAMPHETAMINE SULFATE), FERNISOLONE-P (PREDNISOLONE), FERNISONE (PREDNISONE), FERRISELTZ (FERRIC AMMONIUM CITRATE), FERRLECIT (SODIUM FERRIC GLUCONATE COMPLEX), FERROUS CITRATE FE 59 (FERROUS CITRATE, FE-59), FERTINEX (UROFOLLITROPIN), FEXOFENADINE HCl; PSEUDOEPHEDRINE HCl (FEXOFENADINE HYDROCHLORIDE; PSEUDOEPHEDRINE HYDROCHLORIDE), FEXOFENADINE HCL; PSEUDOEPHEDRINE HCL (FEXOFENADINE HYDROCHLORIDE; PSEUDOEPHEDRINE HYDROCHLORIDE), FEXOFENADINE HYDROCHLORIDE (FEXOFENADINE HYDROCHLORIDE), FEXOFENADINE HYDROCHLORIDE AND PSEUDOEPHEDRINE HYDROCHLORIDE (FEXOFENADINE HYDROCHLORIDE; PSEUDOEPHEDRINE HYDROCHLORIDE), FINACEA (AZELAIC ACID), FINASTERIDE (FINASTERIDE), FIORICET (ACETAMINOPHEN; BUTALBITAL; CAFFEINE), FIORICET W/ CODEINE (ACETAMINOPHEN; BUTALBITAL; CAFFEINE; CODEINE PHOSPHATE), FIORINAL (ASPIRIN; BUTALBITAL; CAFFEINE), FIORINAL W/ CODEINE (ASPIRIN; BUTALBITAL; CAFFEINE; CODEINE PHOSPHATE), FLAGYL (METRONIDAZOLE), FLAGYL ER (METRONIDAZOLE), FLAGYL I.V. (METRONIDAZOLE HYDROCHLORIDE), FLAGYL I.V. RTU IN PLASTIC CONTAINER (METRONIDAZOLE), FLAREX (FLUOROMETHOLONE ACETATE), FLAVORED COLESTID (COLESTIPOL HYDROCHLORIDE), FLAVOXATE HYDROCHLORIDE (FLAVOXATE HYDROCHLORIDE), FLAXEDIL (GALLAMINE TRIETHIODIDE), FLECAINIDE ACETATE (FLECAINIDE ACETATE), FLECTOR (DICLOFENAC EPOLAMINE), FLEXERIL (CYCLOBENZAPRINE HYDROCHLO-

RIDE), FLEXICORT (HYDROCORTISONE), FLOPRED (PREDNISOLONE ACETATE), FLOLAN (EPOPROSTENOL SODIUM), FLOMAX (TAMSULOSIN HYDROCHLORIDE), FLONASE (FLUTICASONE PROPIONATE), FLORINEF (FLUDROCORTISONE ACETATE), FLORONE (DIFLORASONE DIACETATE), FLORONE E (DIFLORASONE DIACETATE), FLOROPRYL (ISOFLUROPHATE), FLOVENT (FLUTICASONE PROPIONATE), FLOVENT DISKUS 100 (FLUTICASONE PROPIONATE), FLOVENT DISKUS 250 (FLUTICASONE PROPIONATE), FLOVENT DISKUS 50 (FLUTICASONE PROPIONATE), FLOVENT HFA (FLUTICASONE PROPIONATE), FLOXIN (OFLOXACIN), FLOXIN IN DEXTROSE 5% (OFLOXACIN), FLOXIN IN DEXTROSE 5% IN PLASTIC CONTAINER (OFLOXACIN), FLOXIN OTIC (OFLOXACIN), FLOXURIDINE (FLOXURIDINE), FLUCONAZOLE (FLUCONAZOLE), FLUCONAZOLE IN DEXTROSE 5% IN PLASTIC CONTAINER (FLUCONAZOLE), FLUCONAZOLE IN SODIUM CHLORIDE 0.9% (FLUCONAZOLE), FLUCONAZOLE IN SODIUM CHLORIDE 0.9% IN PLASTIC CONTAINER (FLUCONAZOLE), FLUDARA (FLUDARABINE PHOSPHATE), FLUDARABINE PHOSPHATE (FLUDARABINE PHOSPHATE), FLUDEOXYGLUCOSE F 18 (FLUDEOXYGLUCOSE F-18), FLUDEOXYGLUCOSE F18 (FLUDEOXYGLUCOSE F-18), FLUDROCORTISONE ACETATE (FLUDROCORTISONE ACETATE), FLUIDIL (CYCLOTHIAZIDE), FLUMADINE (RIMANTADINE HYDROCHLORIDE), FLUMAZENIL (FLUMAZENIL), FLUNISOLIDE (FLUNISOLIDE), FLUOCET (FLUOCINOLONE ACETONIDE), FLUOCINOLONE ACETONIDE (FLUOCINOLONE ACETONIDE), FLUOCINONIDE (FLUOCINONIDE), FLUOCINONIDE EMULSIFIED BASE (FLUOCINONIDE), FLUONID (FLUOCINOLONE ACETONIDE), FLUOR-OP (FLUOROMETHOLONE), FLUORESCITE (FLUORESCEIN SODIUM), FLUORINE F-18 (SODIUM FLUORIDE, F-18), FLUOROPLEX (FLUOROURACIL), FLUOROURACIL (FLUOROURACIL), FLUOTHANE (HALOTHANE), FLUOTREX (FLUOCINOLONE ACETONIDE), FLUOXETINE (FLUOXETINE HYDROCHLORIDE), FLUOXETINE HYDROCHLORIDE (FLUOXETINE HYDROCHLORIDE), FLUOXYMESTERONE (FLUOXYMESTERONE), FLUPHENAZINE (FLUPHENAZINE DECANOATE), FLUPHENAZINE DECANOATE (FLUPHENAZINE DECANOATE), FLUPHENAZINE HCL (FLUPHENAZINE HYDROCHLORIDE), FLUPHENAZINE HYDROCHLORIDE (FLUPHENAZINE HYDROCHLORIDE), FLURANDRENOLIDE (FLURANDRENOLIDE), FLURAZEPAM HYDROCHLORIDE (FLURAZEPAM HYDROCHLORIDE), FLURBIPROFEN (FLURBIPROFEN), FLURBIPROFEN SODIUM (FLURBIPROFEN SODIUM), FLUTAMIDE (FLUTAMIDE), FLUTEX (TRIAMCINOLONE ACETONIDE), FLUTICASONE PROPIONATE (FLUTICASONE PROPIONATE), FLUVOXAMINE MALEATE (FLUVOXAMINE MALEATE), FLUXID (FAMOTIDINE), FML (FLUOROMETHOLONE), FML FORTE (FLUOROMETHOLONE), FML-S (FLUOROMETHOLONE; SULFACETAMIDE SODIUM), FOAMCOAT (ALUMINUM HYDROXIDE; MAGNESIUM TRISILICATE), FOAMICON (ALUMINUM HYDROXIDE; MAGNESIUM TRISILICATE), FOCALIN (DEXMETHYLPHENIDATE HYDROCHLORIDE), FOCALIN XR (DEXMETHYLPHENIDATE HYDROCHLORIDE), FOLEX (METHOTREXATE SODIUM), FOLEX PFS (METHOTREXATE SODIUM), FOLIC ACID (FOLIC ACID), FOLICET (FOLIC ACID), FOLLISTIM (FOLLITROPIN ALFA/BETA), FOLLISTIM AQ (FOLLITROPIN ALFA/BETA), FOLLUTEIN (GONADOTROPIN, CHORIONIC), FOLVITE (FOLIC ACID), FOLVRON (FERROUS SULFATE; FOLIC ACID), FOMEPIZOLE (FOMEPIZOLE), FORADIL (FORMOTEROL FUMARATE), FORADIL CERTIHALER (FORMOTEROL FUMARATE), FORANE (ISOFLURANE), FORBAXIN (METHOCARBAMOL), FORTAMET (METFORMIN HYDROCHLORIDE), FORTAZ (CEFTAZIDIME), FORTAZ IN PLASTIC CONTAINER (CEFTAZIDIME SODIUM), FORTEO (TERIPARATIDE RECOMBINANT HUMAN), FORTICAL (CALCITONIN SALMON RECOMBINANT), FORTOVASE (SAQUINAVIR), FOSAMAX (ALENDRONATE SODIUM), FOSAMAX PLUS D (ALENDRONATE SODIUM; CHOLECALCIFEROL), FOSCARNET SODIUM (FOSCARNET SODIUM), FOSCAVIR (FOSCARNET SODIUM), FOSINOPRIL SODIUM (FOSINOPRIL SODIUM), FOSINOPRIL SODIUM AND HYDROCHLOROTHIAZIDE (FOSINOPRIL SODIUM; HYDROCHLOROTHIAZIDE), FOSPHENYTOIN SODIUM (FOSPHENYTOIN SODIUM), FOSRENOL (LANTHANUM CARBONATE), FOVANE (BENZTHIAZIDE), FRAGMIN (DALTEPARIN SODIUM), FREAMINE 8.5% (AMINO ACIDS), FREAMINE HBC 6.9% (AMINO ACIDS), FREAMINE II 8.5% (AMINO ACIDS), FREAMINE III 10% (AMINO ACIDS), FREAMINE III 3% W/ ELECTROLYTES (AMINO ACIDS; MAGNESIUM ACETATE; PHOSPHORIC ACID; POTASSIUM CHLORIDE; SODIUM ACETATE; SODIUM CHLORIDE), FREAMINE III 8.5% (AMINO ACIDS), FREAMINE III 8.5% W/ ELECTROLYTES (AMINO ACIDS; MAGNESIUM ACETATE; PHOSPHORIC ACID; POTASSIUM ACETATE; POTASSIUM CHLORIDE; SODIUM ACETATE), FROVA (FROVATRIPTAN SUCCINATE), FS (FLUOCINOLONE ACETONIDE), FUDR (FLOXURIDINE), FULVICIN P/G (GRISEOFULVIN, ULTRAMICROCRYSTALLINE), FULVICIN P/G 165 (GRISEOFULVIN, ULTRAMICROCRYSTALLINE), FULVICIN P/G 330 (GRISEOFULVIN, ULTRAMICROCRYSTALLINE), FULVICIN-U/F (GRISEOFULVIN, MICROCRYSTALLINE), FUNDUSCEIN-25 (FLUORESCEIN SODIUM), FUNGIZONE (AMPHOTERICIN B), FURACIN (NITROFURAZONE), FURADANTIN (NITROFURANTOIN), FURALAN (NITROFURANTOIN), FUROSEMIDE (FUROSEMIDE), FUROXONE (FURAZOLIDONE), FUZEON (ENFUVIRTIDE), GABAPENTIN (GABAPENTIN), GABITRIL (TIAGABINE HYDROCHLORIDE), GALANTAMINE HYDROBROMIDE (GALANTAMINE HYDROBROMIDE), GALLIUM CITRATE GA 67 (GALLIUM CITRATE, GA-67), GALZIN (ZINC ACETATE), GAMENE (LINDANE), GAMOPHEN (HEXACHLOROPHENE), GANCICLOVIR (GANCICLOVIR), GANCICLOVIR SODIUM (GANCICLOVIR SODIUM), GANIRELIX ACETATE INJECTION (GANIRELIX ACETATE), GANITE (GALLIUM NITRATE), GANTANOL (SULFAMETHOXAZOLE), GANTANOL-DS (SULFAMETHOXAZOLE), GANTRISIN (SULFISOXAZOLE), GANTRISIN (SULFISOXAZOLE ACETYL), GANTRISIN (SULFISOXAZOLE DIOLAMINE), GANTRISIN

PEDIATRIC (SULFISOXAZOLE ACETYL), GARAMYCIN (GENTAMICIN SULFATE), GASTROCROM (CROMOLYN SODIUM), GASTROGRAFIN (DIATRIZOATE MEGLUMINE; DIATRIZOATE SODIUM), GASTROMARK (FERUMOXSIL), GASTROVIST (DIATRIZOATE MEGLUMINE; DIATRIZOATE SODIUM), GATIFLOXACIN (GATIFLOXACIN), GAVISCON (ALUMINUM HYDROXIDE; MAGNESIUM TRISILICATE), GEMCITABINE HYDROCHLORIDE (GEMCITABINE HYDROCHLORIDE), GEMFIBROZIL (GEMFIBROZIL), GEMONIL (METHARBITAL), GEMZAR (GEMCITABINE HYDROCHLORIDE), GEN-XENE (CLORAZEPATE DIPOTASSIUM), GENAPAX (GENTIAN VIOLET), GENCEPT 10/11-21 (ETHINYL ESTRADIOL; NORETHINDRONE), GENCEPT 10/11-28 (ETHINYL ESTRADIOL; NORETHINDRONE), GENERLAC (LACTULOSE), GENESA (ARBUTAMINE HYDROCHLORIDE), GENGRAF (CYCLOSPORINE), GENOPTIC (GENTAMICIN SULFATE), GENOTROPIN (SOMATROPIN RECOMBINANT), GENOTROPIN PRESERVATIVE FREE (SOMATROPIN RECOMBINANT), GENTACIDIN (GENTAMICIN SULFATE), GENTAFAIR (GENTAMICIN SULFATE), GENTAK (GENTAMICIN SULFATE), GENTAMICIN (GENTAMICIN SULFATE), GENTAMICIN SULFATE (GENTAMICIN SULFATE), GENTAMICIN SULFATE IN SODIUM CHLORIDE 0.9% IN PLASTIC CONTAINER (GENTAMICIN SULFATE), GEOCILLIN (CARBENICILLIN INDANYL SODIUM), GEODON (ZIPRASIDONE HYDROCHLORIDE), GEODON (ZIPRASIDONE MESYLATE), GEOPEN (CARBENICILLIN DISODIUM), GEREF (SERMORELIN ACETATE), GERIMAL (ERGOLOID MESYLATES), GERMAMEDICA (HEXACHLOROPHENE), GERMAMEDICA "MG" (HEXACHLOROPHENE), GLEEVEC (IMATINIB MESYLATE), GLIADEL (CARMUSTINE), GLIMEPIRIDE (GLIMEPIRIDE), GLIPIZIDE (GLIPIZIDE), GLIPIZIDE AND METFORMIN HYDROCHLORIDE (GLIPIZIDE; METFORMIN HYDROCHLORIDE), GLOFIL-125 (IOTHALAMATE SODIUM, I-125), GLUCAGEN (GLUCAGON HYDROCHLORIDE RECOMBINANT), GLUCAGON (GLUCAGON HYDROCHLORIDE), GLUCAGON (GLUCAGON RECOMBINANT), GLUCAMIDE (CHLORPROPAMIDE), GLUCOPHAGE (METFORMIN HYDROCHLORIDE), GLUCOPHAGE XR (METFORMIN HYDROCHLORIDE), GLUCOSCAN (TECHNETIUM TC-99M GLUCEPTATE KIT), GLUCOTROL (GLIPIZIDE), GLUCOTROL XL (GLIPIZIDE), GLUCOVANCE (GLYBURIDE; METFORMIN HYDROCHLORIDE), GLUMETZA (METFORMIN HYDROCHLORIDE), GLUTETHIMIDE (GLUTETHIMIDE), GLYBURIDE (GLYBURIDE), GLYBURIDE (MICRONIZED) (GLYBURIDE), GLYBURIDE AND METFORMIN HYDROCHLORIDE (GLYBURIDE; METFORMIN HYDROCHLORIDE), GLYCINE 1.5% IN PLASTIC CONTAINER (GLYCINE), GLYCOLAX (POLYETHYLENE GLYCOL 3350), GLYCOPREP (POLYETHYLENE GLYCOL 3350; POTASSIUM CHLORIDE; SODIUM BICARBONATE; SODIUM CHLORIDE; SODIUM SULFATE, ANHYDROUS), GLYCOPYRROLATE (GLYCOPYRROLATE), GLYCORT (HYDROCORTISONE), GLYNASE (GLYBURIDE), GLYSET (MIGLITOL), GO-EVAC (POLYETHYLENE GLYCOL 3350; POTASSIUM CHLORIDE; SODIUM BICARBONATE; SODIUM CHLORIDE; SODIUM SULFATE, ANHYDROUS), GOLYTELY (POLYETHYLENE GLYCOL 3350; POTASSIUM CHLORIDE; SODIUM BICARBONATE; SODIUM CHLORIDE; SODIUM SULFATE, ANHYDROUS), GONAL-F (FOLLITROPIN ALFA/BETA), GONAL-F RFF (FOLLITROPIN ALFA/BETA), GONAL-F RFF PEN (FOLLITROPIN ALFA/BETA), GRANISETRON HYDROCHLORIDE (GRANISETRON HYDROCHLORIDE), GRANISETRON HYDROCHLORIDE PRESERVATIVE FREE (GRANISETRON HYDROCHLORIDE), GRIFULVIN V (GRISEOFULVIN, MICROCRYSTALLINE), GRISPEG (GRISEOFULVIN, ULTRAMICROCRYSTALLINE), GRISACTIN (GRISEOFULVIN, MICROCRYSTALLINE), GRISACTIN ULTRA (GRISEOFULVIN, ULTRAMICROCRYSTALLINE), GRISEOFULVIN (GRISEOFULVIN), GRISEOFULVIN (GRISEOFULVIN, MICROCRYSTALLINE), GUANABENZ ACETATE (GUANABENZ ACETATE), GUANETHIDINE MONOSULFATE (GUANETHIDINE MONOSULFATE), GUANFACINE HYDROCHLORIDE (GUANFACINE HYDROCHLORIDE), GUANIDINE HYDROCHLORIDE (GUANIDINE HYDROCHLORIDE), GVS (GENTIAN VIOLET), GYNAZOLE-1 (BUTOCONAZOLE NITRATE), GYNE-LOTRIMIN (CLOTRIMAZOLE), GYNE-LOTRIMIN 3 (CLOTRIMAZOLE), GYNE-LOTRIMIN 3 COMBINATION PACK (CLOTRIMAZOLE), GYNE-LOTRIMIN COMBINATION PACK (CLOTRIMAZOLE), GYNE-SULF (TRIPLE SULFA (SULFABENZAMIDE; SULFACETAMIDE; SULFATHIAZOLE)), GYNIX (CLOTRIMAZOLE), GYNODIOL (ESTRADIOL), GYNOREST (DYDROGESTERONE), H-CORT (HYDROCORTISONE), H.P. ACTHAR GEL (CORTICOTROPIN), H.R.-50 (HYDROCHLOROTHIAZIDE; RESERPINE), HABITROL (NICOTINE), HALCION (TRIAZOLAM), HALDOL (HALOPERIDOL), HALDOL (HALOPERIDOL DECANOATE), HALDOL (HALOPERIDOL LACTATE), HALDOL SOLUTAB (HALOPERIDOL), HALDRONE (PARAMETHASONE ACETATE), HALFAN (HALOFANTRINE HYDROCHLORIDE), HALFLYTELY (BISACODYL; POLYETHYLENE GLYCOL 3350; POTASSIUM CHLORIDE; SODIUM BICARBONATE; SODIUM CHLORIDE), HALOBETASOL PROPIONATE (HALOBETASOL PROPIONATE), HALOG (HALCINONIDE), HALOG-E (HALCINONIDE), HALOPERIDOL (HALOPERIDOL), HALOPERIDOL (HALOPERIDOL LACTATE), HALOPERIDOL DECANOATE (HALOPERIDOL DECANOATE), HALOPERIDOL INTENSOL (HALOPERIDOL LACTATE), HALOPERIDOL LACTATE (HALOPERIDOL LACTATE), HALOTESTIN (FLUOXYMESTERONE), HALOTEX (HALOPROGIN), HALOTHANE (HALOTHANE), HARMONYL (DESERPIDINE), HC #1 (HYDROCORTISONE), HC #4 (HYDROCORTISONE), HC (HYDROCORTISONE) (HYDROCORTISONE), HEAD & SHOULDERS CONDITIONER (PYRITHIONE ZINC), HEAVY SOLUTION NUPERCAINE (DIBUCAINE HYDROCHLORIDE), HECTOROL (DOXERCALCIFEROL), HEDULIN (PHENINDIONE), HELICOSOL (UREA, C-13), HELIDAC (BISMUTH SUBSALICYLATE; METRONIDAZOLE; TETRACYCLINE HYDROCHLORIDE), HEMABATE (CARBOPROST TROMETHAMINE), HEMSOL-HC (HYDROCORTISONE ACETATE), HEP FLUSH KIT IN PLASTIC CONTAINER (HEPARIN SODIUM), HEP-LOCK (HEPARIN SODIUM), HEP-LOCK U/P (HEPARIN SODIUM), HEPARIN LOCK

FLUSH (HEPARIN SODIUM), HEPARIN LOCK FLUSH IN PLASTIC CONTAINER (HEPARIN SODIUM), HEPARIN LOCK FLUSH PRESERVATIVE FREE (HEPARIN SODIUM), HEPARIN LOCK FLUSH PRESERVATIVE FREE IN PLASTIC CONTAINER (HEPARIN SODIUM), HEPARIN SODIUM (HEPARIN SODIUM), HEPARIN SODIUM 1,000 UNITS AND SODIUM CHLORIDE 0.9% IN PLASTIC CONTAINER (HEPARIN SODIUM), HEPARIN SODIUM 1,000 UNITS IN DEXTROSE 5% IN PLASTIC CONTAINER (HEPARIN SODIUM), HEPARIN SODIUM 1,000 UNITS IN SODIUM CHLORIDE 0.9% IN PLASTIC CONTAINER (HEPARIN SODIUM), HEPARIN SODIUM 10,000 UNITS IN DEXTROSE 5% (HEPARIN SODIUM), HEPARIN SODIUM 10,000 UNITS IN DEXTROSE 5% IN PLASTIC CONTAINER (HEPARIN SODIUM), HEPARIN SODIUM 10,000 UNITS IN SODIUM CHLORIDE 0.45% (HEPARIN SODIUM), HEPARIN SODIUM 10,000 UNITS IN SODIUM CHLORIDE 0.9% (HEPARIN SODIUM), HEPARIN SODIUM 12,500 UNITS IN DEXTROSE 5% (HEPARIN SODIUM), HEPARIN SODIUM 12,500 UNITS IN DEXTROSE 5% IN PLASTIC CONTAINER (HEPARIN SODIUM), HEPARIN SODIUM 12,500 UNITS IN SODIUM CHLORIDE 0.45% IN PLASTIC CONTAINER (HEPARIN SODIUM), HEPARIN SODIUM 12,500 UNITS IN SODIUM CHLORIDE 0.9% (HEPARIN SODIUM), HEPARIN SODIUM 2,000 UNITS AND SODIUM CHLORIDE 0.9% IN PLASTIC CONTAINER (HEPARIN SODIUM), HEPARIN SODIUM 2,000 UNITS IN DEXTROSE 5% IN PLASTIC CONTAINER (HEPARIN SODIUM), HEPARIN SODIUM 2,000 UNITS IN SODIUM CHLORIDE 0.9% IN PLASTIC CONTAINER (HEPARIN SODIUM), HEPARIN SODIUM 20,000 UNITS AND DEXTROSE 5% IN PLASTIC CONTAINER (HEPARIN SODIUM), HEPARIN SODIUM 20,000 UNITS IN DEXTROSE 5% IN PLASTIC CONTAINER (HEPARIN SODIUM), HEPARIN SODIUM 25,000 UNITS AND DEXTROSE 5% IN PLASTIC CONTAINER (HEPARIN SODIUM), HEPARIN SODIUM 25,000 UNITS IN DEXTROSE 5% (HEPARIN SODIUM), HEPARIN SODIUM 25,000 UNITS IN DEXTROSE 5% IN PLASTIC CONTAINER (HEPARIN SODIUM), HEPARIN SODIUM 25,000 UNITS IN SODIUM CHLORIDE 0.45% IN PLASTIC CONTAINER (HEPARIN SODIUM), HEPARIN SODIUM 25,000 UNITS IN SODIUM CHLORIDE 0.9% (HEPARIN SODIUM), HEPARIN SODIUM 25,000 UNITS IN SODIUM CHLORIDE 0.9% IN PLASTIC CONTAINER (HEPARIN SODIUM), HEPARIN SODIUM 5,000 UNITS AND SODIUM CHLORIDE 0.9% IN PLASTIC CONTAINER (HEPARIN SODIUM), HEPARIN SODIUM 5,000 UNITS IN DEXTROSE 5% IN PLASTIC CONTAINER (HEPARIN SODIUM), HEPARIN SODIUM 5,000 UNITS IN SODIUM CHLORIDE 0.45% (HEPARIN SODIUM), HEPARIN SODIUM 5,000 UNITS IN SODIUM CHLORIDE 0.9% (HEPARIN SODIUM), HEPARIN SODIUM 5,000 UNITS IN SODIUM CHLORIDE 0.9% IN PLASTIC CONTAINER (HEPARIN SODIUM), HEPARIN SODIUM IN PLASTIC CONTAINER (HEPARIN SODIUM), HEPARIN SODIUM PRESERVATIVE FREE (HEPARIN SODIUM), HEPATAMINE 8% (AMINO ACIDS), HEPATASOL 8% (AMINO ACIDS), HEPATOLITE (TECHNETIUM TC-99M DISOFENIN KIT), HEPFLUSH-10 (HEPARIN SODIUM), HEPSERA (ADEFOVIR DIPIVOXIL), HEPTALAC (LACTULOSE), HERCEPTIN (TRASTUZUMAB), HERPLEX (IDOXURIDINE), HETRAZAN (DIETHYLCARBAMAZINE CITRATE), HEXA-BETALIN (PYRIDOXINE HYDROCHLORIDE), HEXA-GERM (HEXACHLOROPHENE), HEXABRIX (IOXAGLATE MEGLUMINE; IOXAGLATE SODIUM), HEXADROL (DEXAMETHASONE), HEXADROL (DEXAMETHASONE SODIUM PHOSPHATE), HEXALEN (ALTRETAMINE), HEXASCRUB (HEXACHLOROPHENE), HI-COR (HYDROCORTISONE), HIBICLENS (CHLORHEXIDINE GLUCONATE), HIBISTAT (CHLORHEXIDINE GLUCONATE), HICON (SODIUM IODIDE, I-131), HIPPURAN I 131 (IODOHIPPURATE SODIUM, I-131), HIPPUTOPE (IODOHIPPURATE SODIUM, I-131), HIPREX (METHENAMINE HIPPURATE), HISERPIA (RESERPINE), HISPRIL (DIPHENYLPYRALINE HYDROCHLORIDE), HISTAFED (PSEUDOEPHEDRINE HYDROCHLORIDE; TRIPROLIDINE HYDROCHLORIDE), HISTALOG (BETAZOLE HYDROCHLORIDE), HISTAMINE PHOSPHATE (HISTAMINE PHOSPHATE), HIVID (ZALCITABINE), HIWOLFIA (*RAUWOLFIA SERPENTINA*), HMS (MEDRYSONE), HOMAPIN-10 (HOMATROPINE METHYLBROMIDE), HOMAPIN-5 (HOMATROPINE METHYLBROMIDE), HOMATROPRINE METHYLBROMIDE AND HYDROCODONE BITARTRATE (HOMATROPINE METHYLBROMIDE; HYDROCODONE BITARTRATE), HUMALOG (INSULIN LISPRO RECOMBINANT), HUMALOG KWIKPEN (INSULIN LISPRO RECOMBINANT), HUMALOG MIX 50/50 (INSULIN LISPRO PROTAMINE RECOMBINANT; INSULIN LISPRO RECOMBINANT), HUMALOG MIX 50/50 KWIKPEN (INSULIN LISPRO PROTAMINE RECOMBINANT; INSULIN LISPRO RECOMBINANT), HUMALOG MIX 75/25 (INSULIN LISPRO PROTAMINE RECOMBINANT; INSULIN LISPRO RECOMBINANT), HUMALOG MIX 75/25 KWIKPEN (INSULIN LISPRO PROTAMINE RECOMBINANT; INSULIN LISPRO RECOMBINANT), HUMALOG PEN (INSULIN LISPRO RECOMBINANT), HUMATIN (PAROMOMYCIN SULFATE), HUMATROPE (SOMATROPIN RECOMBINANT), HUMEGON (MENOTROPINS (FSH; LH)), HUMIRA (ADALIMUMAB), HUMORSOL (DEMECARIUM BROMIDE), HUMULIN 50/50 (INSULIN RECOMBINANT HUMAN; INSULIN SUSP ISOPHANE RECOMBINANT HUMAN), HUMULIN 70/30 (INSULIN RECOMBINANT HUMAN; INSULIN SUSP ISOPHANE RECOMBINANT HUMAN), HUMULIN 70/30 PEN (INSULIN RECOMBINANT HUMAN; INSULIN SUSP ISOPHANE RECOMBINANT HUMAN), HUMULIN BR (INSULIN RECOMBINANT HUMAN), HUMULIN L (INSULIN ZINC SUSP RECOMBINANT HUMAN), HUMULIN N (INSULIN SUSP ISOPHANE RECOMBINANT HUMAN), HUMULIN R (INSULIN RECOMBINANT HUMAN), HUMULIN R PEN (INSULIN RECOMBINANT HUMAN), HUMULIN U (INSULIN ZINC SUSP EXTENDED RECOMBINANT HUMAN), HY-PAM "25" (HYDROXYZINE PAMOATE), HY-PHEN (ACETAMINOPHEN; HYDROCODONE BITARTRATE), HYCAMTIN (TOPOTECAN HYDROCHLORIDE), HYCODAN (HOMATROPINE METHYLBROMIDE; HYDROCODONE BITARTRATE), HYCOMINE (HYDROCODONE BITARTRATE; PHENYLPROPANOLAMINE HYDROCHLORIDE), HYCOMINE PEDIATRIC (HYDROCODONE BITAR-

TRATE; PHENYLPROPANOLAMINE HYDROCHLORIDE), HYDASE (HYALURONIDASE), HYDELTRA-TBA (PREDNISOLONE TEBUTATE), HYDELTRASOL (PREDNISOLONE SODIUM PHOSPHATE), HYDERGINE (ERGOLOID MESYLATES), HYDERGINE LC (ERGOLOID MESYLATES), HYDRA-ZIDE (HYDRALAZINE HYDROCHLORIDE; HYDROCHLOROTHIAZIDE), HYDRALAZINE AND HYDROCHLORTHIAZIDE (HYDRALAZINE HYDROCHLORIDE; HYDROCHLOROTHIAZIDE), HYDRALAZINE HYDROCHLORIDE (HYDRALAZINE HYDROCHLORIDE), HYDRALAZINE HYDROCHLORIDE AND HYDROCHLOROTHIAZIDE (HYDRALAZINE HYDROCHLORIDE; HYDROCHLOROTHIAZIDE), HYDRALAZINE HYDROCHLORIDE W/ HYDROCHLOROTHIAZIDE 100/50 (HYDRALAZINE HYDROCHLORIDE; HYDROCHLOROTHIAZIDE), HYDRALAZINE HYDROCHLORIDE W/ HYDROCHLOROTHIAZIDE 25/25 (HYDRALAZINE HYDROCHLORIDE; HYDROCHLOROTHIAZIDE), HYDRALAZINE HYDROCHLORIDE W/ HYDROCHLOROTHIAZIDE 50/50 (HYDRALAZINE HYDROCHLORIDE; HYDROCHLOROTHIAZIDE), HYDRALAZINE HYDROCHLORIDE, HYDROCHLOROTHIAZIDE AND RESERPINE (HYDRALAZINE HYDROCHLORIDE; HYDROCHLOROTHIAZIDE; RESERPINE), HYDRALAZINE HYDROCHLORIDE-HYDROCHLOROTHIAZIDE-RESERPINE (HYDRALAZINE HYDROCHLORIDE; HYDROCHLOROTHIAZIDE; RESERPINE), HYDRALAZINE, HYDROCHLOROTHIAZIDE W/ RESERPINE (HYDRALAZINE HYDROCHLORIDE; HYDROCHLOROTHIAZIDE; RESERPINE), HYDRAMINE (DIPHENHYDRAMINE HYDROCHLORIDE), HYDRAP-ES (HYDRALAZINE HYDROCHLORIDE; HYDROCHLOROTHIAZIDE; RESERPINE), HYDREA (HYDROXYUREA), HYDRO-D (HYDROCHLOROTHIAZIDE), HYDRO-RESERP (HYDROCHLOROTHIAZIDE; RESERPINE), HYDRO-RIDE (AMILORIDE HYDROCHLORIDE; HYDROCHLOROTHIAZIDE), HYDRO-RX (HYDROCORTISONE), HYDRO-SERP "25" (HYDROCHLOROTHIAZIDE; RESERPINE), HYDRO-SERP "50" (HYDROCHLOROTHIAZIDE; RESERPINE), HYDROCET (ACETAMINOPHEN; HYDROCODONE BITARTRATE), HYDROCHLOROTHIAZIDE (HYDROCHLOROTHIAZIDE), HYDROCHLOROTHIAZIDE INTENSOL (HYDROCHLOROTHIAZIDE), HYDROCHLOROTHIAZIDE W/ HYDRALAZINE (HYDRALAZINE HYDROCHLORIDE; HYDROCHLOROTHIAZIDE), HYDROCHLOROTHIAZIDE W/ RESERPINE (HYDROCHLOROTHIAZIDE; RESERPINE), HYDROCHLOROTHIAZIDE W/ RESERPINE AND HYDRALAZINE (HYDRALAZINE HYDROCHLORIDE; HYDROCHLOROTHIAZIDE; RESERPINE), HYDROCODONE BITARTRATE AND ACETAMINOPHEN (ACETAMINOPHEN; HYDROCODONE BITARTRATE), HYDROCODONE BITARTRATE AND HOMATROPINE METHYLBROMIDE (HOMATROPINE METHYLBROMIDE; HYDROCODONE BITARTRATE), HYDROCODONE BITARTRATE AND IBUPROFEN (HYDROCODONE BITARTRATE; IBUPROFEN), HYDROCODONE COMPOUND (HOMATROPINE METHYLBROMIDE; HYDROCODONE BITARTRATE), HYDROCORTISONE (HYDROCORTISONE), HYDROCORTISONE ACETATE (HYDROCORTISONE ACETATE), HYDROCORTISONE ACETATE 1% AND PRAMOXINE HYDROCHLORIDE 1% (HYDROCORTISONE ACETATE; PRAMOXINE HYDROCHLORIDE), HYDROCORTISONE AND ACETIC ACID (ACETIC ACID, GLACIAL; HYDROCORTISONE), HYDROCORTISONE BUTYRATE (HYDROCORTISONE BUTYRATE), HYDROCORTISONE IN ABSORBASE (HYDROCORTISONE), HYDROCORTISONE SODIUM PHOSPHATE (HYDROCORTISONE SODIUM PHOSPHATE), HYDROCORTISONE SODIUM SUCCINATE (HYDROCORTISONE SODIUM SUCCINATE), HYDROCORTISONE VALERATE (HYDROCORTISONE VALERATE), HYDROCORTONE (HYDROCORTISONE), HYDROCORTONE (HYDROCORTISONE ACETATE), HYDROCORTONE (HYDROCORTISONE SODIUM PHOSPHATE), HYDRODIURIL (HYDROCHLOROTHIAZIDE), HYDROFLUMETHIAZIDE (HYDROFLUMETHIAZIDE), HYDROFLUMETHIAZIDE AND RESERPINE (HYDROFLUMETHIAZIDE; RESERPINE), HYDROGENATED ERGOT ALKALOIDS (ERGOLOID MESYLATES), HYDROMORPHONE HYDROCHLORIDE (HYDROMORPHONE HYDROCHLORIDE), HYDROMOX (QUINETHAZONE), HYDROMOX R (QUINETHAZONE; RESERPINE), HYDROPANE (HOMATROPINE METHYLBROMIDE; HYDROCODONE BITARTRATE), HYDROPRES 25 (HYDROCHLOROTHIAZIDE; RESERPINE), HYDROPRES 50 (HYDROCHLOROTHIAZIDE; RESERPINE), HYDROSERPINE PLUS (R-H-H) (HYDRALAZINE HYDROCHLORIDE; HYDROCHLOROTHIAZIDE; RESERPINE), HYDROXOCOBALAMIN (HYDROXOCOBALAMIN), HYDROXOMIN (HYDROXOCOBALAMIN), HYDROXYCHLOROQUINE SULFATE (HYDROXYCHLOROQUINE SULFATE), HYDROXYPROGESTERONE CAPROATE (HYDROXYPROGESTERONE CAPROATE), HYDROXYSTILBAMIDINE ISETHIONATE (HYDROXYSTILBAMIDINE ISETHIONATE), HYDROXYUREA (HYDROXYUREA), HYDROXYZINE (HYDROXYZINE HYDROCHLORIDE), HYDROXYZINE HYDROCHLORIDE (HYDROXYZINE HYDROCHLORIDE), HYDROXYZINE PAMOATE (HYDROXYZINE PAMOATE), HYGROTON (CHLORTHALIDONE), HYLENEX RECOMBINANT (HYALURONIDASE RECOMBINANT HUMAN), HYLOREL (GUANADREL SULFATE), HYPAQUE (DIATRIZOATE MEGLUMINE), HYPAQUE (DIATRIZOATE SODIUM), HYPAQUE SODIUM 20% (DIATRIZOATE SODIUM), HYPAQUE-76 (DIATRIZOATE MEGLUMINE; DIATRIZOATE SODIUM), HYPAQUE-CYSTO (DIATRIZOATE MEGLUMINE), HYPAQUE-M, 75% (DIATRIZOATE MEGLUMINE; DIATRIZOATE SODIUM), HYPAQUE-M, 90% (DIATRIZOATE MEGLUMINE; DIATRIZOATE SODIUM), HYPERSTAT (DIAZOXIDE), HYPROTIGEN 5% (PROTEIN HYDROLYSATE), HYSERPIN (*RAUWOLFIA SERPENTINA*), HYTONE (HYDROCORTISONE), HYTRIN (TERAZOSIN HYDROCHLORIDE), HYZAAR (HYDROCHLOROTHIAZIDE; LOSARTAN POTASSIUM), HYZYD (ISONIAZID), IBRIN (FIBRINOGEN, I-125), IBU (IBUPROFEN), IBU-TAB (IBUPROFEN), IBU-TAB 200 (IBUPROFEN), IBUPRIN (IBUPROFEN), IBUPROFEN (IBUPROFEN), IBUPROFEN AND PSEUDOEPHEDRINE HYDROCHLORIDE (IBUPROFEN; PSEUDOEPHEDRINE HYDROCHLORIDE), IBU-

PROHM (IBUPROFEN), IBUPROHM COLD AND SINUS (IBUPROFEN; PSEUDOEPHEDRINE HYDROCHLORIDE), IC-GREEN (INDOCYANINE GREEN), IDAMYCIN (IDARUBICIN HYDROCHLORIDE), IDAMYCIN PFS (IDARUBICIN HYDROCHLORIDE), IDARUBICIN HYDROCHLORIDE (IDARUBICIN HYDROCHLORIDE), IDARUBICIN HYDROCHLORIDE PFS (IDARUBICIN HYDROCHLORIDE), IDKIT:HP (CITRIC ACID; UREA, C-13), IFEX (IFOSFAMIDE), IFEX/MESNEX KIT (IFOSFAMIDE; MESNA), IFOSFAMIDE (IFOSFAMIDE), IFOSFAMIDE/MESNA KIT (IFOSFAMIDE; MESNA), IFSOFAMIDE (IFOSFAMIDE), ILETIN I (INSULIN PORK), ILETIN II (INSULIN PURIFIED PORK), ILOSONE (ERYTHROMYCIN ESTOLATE), ILOSONE SULFA (ERYTHROMYCIN ESTOLATE; SULFISOXAZOLE ACETYL), ILOTYCIN (ERYTHROMYCIN), ILOTYCIN GLUCEPTATE (ERYTHROMYCIN GLUCEPTATE), IMAGENT (DIMYRISTOYL LECITHIN; PERFLEXANE), IMAGENT (PERFLUBRON), IMDUR (ISOSORBIDE MONONITRATE), IMIPRAMINE HYDROCHLORIDE (IMIPRAMINE HYDROCHLORIDE), IMITREX (SUMATRIPTAN), IMITREX (SUMATRIPTAN SUCCINATE), IMITREX STATDOSE (SUMATRIPTAN SUCCINATE), IMODIUM (LOPERAMIDE HYDROCHLORIDE), IMODIUM A-D (LOPERAMIDE HYDROCHLORIDE), IMODIUM A-D EZ CHEWS (LOPERAMIDE HYDROCHLORIDE), IMODIUM MULTI-SYMPTOM RELIEF (LOPERAMIDE HYDROCHLORIDE; SIMETHICONE), IMPLANON (ETONOGESTREL), IMURAN (AZATHIOPRINE), IMURAN (AZATHIOPRINE SODIUM), INAPSINE (DROPERIDOL), INCRELEX (MECASERMIN RECOMBINANT), INDAPAMIDE (INDAPAMIDE), INDERAL (PROPRANOLOL HYDROCHLORIDE), INDERAL LA (PROPRANOLOL HYDROCHLORIDE), INDERIDE LA 120/50 (HYDROCHLOROTHIAZIDE; PROPRANOLOL HYDROCHLORIDE), INDERIDE LA 160/50 (HYDROCHLOROTHIAZIDE; PROPRANOLOL HYDROCHLORIDE), INDERIDE LA 80/50 (HYDROCHLOROTHIAZIDE; PROPRANOLOL HYDROCHLORIDE), INDERIDE-40/25 (HYDROCHLOROTHIAZIDE; PROPRANOLOL HYDROCHLORIDE), INDERIDE-80/25 (HYDROCHLOROTHIAZIDE; PROPRANOLOL HYDROCHLORIDE), INDICLOR (INDIUM IN-111 CHLORIDE), INDICLOR (INDIUM IN-111 CHLORIDE-STERILE SOLUTION), INDIUM IN 111 CHLORIDE (INDIUM IN-111 CHLORIDE), INDIUM IN-111 OXYQUINOLINE (INDIUM IN-111 OXYQUINOLINE), INDO-LEMMON (INDOMETHACIN), INDOCIN (INDOMETHACIN), INDOCIN I.V. (INDOMETHACIN SODIUM), INDOCIN SR (INDOMETHACIN), INDOCYANINE GREEN (INDOCYANINE GREEN), INDOMETHACIN (INDOMETHACIN), INDOMETHACIN SODIUM (INDOMETHACIN SODIUM), INFANTS' FEVERALL (ACETAMINOPHEN), INFASURF PRESERVATIVE FREE (CALFACTANT), INFED (IRON DEXTRAN), Infergen (Interferon alfacon-1), INFLAMASE FORTE (PREDNISOLONE SODIUM PHOSPHATE), INFLAMASE MILD (PREDNISOLONE SODIUM PHOSPHATE), INFUMORPH (MORPHINE SULFATE), INFUVITE ADULT (ALPHA-TOCOPHEROL ACETATE; ASCORBIC ACID; BIOTIN; CHOLECALCIFEROL; CYANOCOBALAMIN; DEXPANTHENOL; FOLIC ACID; NIACINAMIDE; PYRIDOXINE HYDROCHLORIDE; RIBOFLAVIN PHOSPHATE SODIUM; THIAMINE HYDROCHLORIDE; VITAMIN A PALMITATE; VITAMIN K), INFUVITE PEDIATRIC (ASCORBIC ACID; BIOTIN; CHOLECALCIFEROL; CYANOCOBALAMIN; DEXPANTHENOL; FOLIC ACID; NIACINAMIDE; PYRIDOXINE; RIBOFLAVIN; THIAMINE; TOCOPHEROL ACETATE; VITAMIN A; VITAMIN K), INFUVITE PEDIATRIC (PHARMACY BULK PACKAGE) (ASCORBIC ACID; BIOTIN; CHOLECALCIFEROL; CYANOCOBALAMIN; DEXPANTHENOL; FOLIC ACID; NIACINAMIDE; PYRIDOXINE; RIBOFLAVIN; THIAMINE; TOCOPHEROL ACETATE; VITAMIN A; VITAMIN K), INH (ISONIAZID), INJECTAPAP (ACETAMINOPHEN), INNOFEM (ESTRADIOL), INNOHEP (TINZAPARIN SODIUM), INNOPRAN XL (PROPRANOLOL HYDROCHLORIDE), INNOVAR (DROPERIDOL; FENTANYL CITRATE), INOCOR (INAMRINONE LACTATE), INOMAX (NITRIC OXIDE), INPERSOL-LC/LM W/ DEXTROSE 1.5% IN PLASTIC CONTAINER (CALCIUM CHLORIDE; DEXTROSE; MAGNESIUM CHLORIDE; SODIUM CHLORIDE; SODIUM LACTATE), INPERSOL-LC/LM W/ DEXTROSE 2.5% IN PLASTIC CONTAINER (CALCIUM CHLORIDE; DEXTROSE; MAGNESIUM CHLORIDE; SODIUM CHLORIDE; SODIUM LACTATE), INPERSOL-LC/LM W/ DEXTROSE 3.5% IN PLASTIC CONTAINER (CALCIUM CHLORIDE; DEXTROSE; MAGNESIUM CHLORIDE; SODIUM CHLORIDE; SODIUM LACTATE), INPERSOL-LC/LM W/ DEXTROSE 4.25% IN PLASTIC CONTAINER (CALCIUM CHLORIDE; DEXTROSE; MAGNESIUM CHLORIDE; SODIUM CHLORIDE; SODIUM LACTATE), INPERSOL-ZM W/ DEXTROSE 1.5% IN PLASTIC CONTAINER (CALCIUM CHLORIDE; DEXTROSE; SODIUM CHLORIDE; SODIUM LACTATE), INPERSOL-ZM W/ DEXTROSE 2.5% IN PLASTIC CONTAINER (CALCIUM CHLORIDE; DEXTROSE; SODIUM CHLORIDE; SODIUM LACTATE), INPERSOL-ZM W/ DEXTROSE 4.25% IN PLASTIC CONTAINER (CALCIUM CHLORIDE; DEXTROSE; SODIUM CHLORIDE; SODIUM LACTATE), INSPRA (EPLERENONE), INSTANT MICROSPHERES (TECHNETIUM TC-99M ALBUMIN MICROSPHERES KIT), INSULATARD NPH HUMAN (INSULIN SUSP ISOPHANE SEMISYNTHETIC PURIFIED HUMAN), INSULIN (INSULIN PORK), INSULIN INSULATARD NPH NORDISK (INSULIN SUSP ISOPHANE PURIFIED PORK), INSULIN NORDISK MIXTARD (PORK) (INSULIN PURIFIED PORK; INSULIN SUSP ISOPHANE PURIFIED PORK), INTAL (CROMOLYN SODIUM), INTEGRILIN (EPTIFIBATIDE), INTELENCE (ETRAVIRINE), INTRALIPID 10% (SOYBEAN OIL), INTRALIPID 20% (SOYBEAN OIL), INTRALIPID 30% (SOYBEAN OIL), INTRON A (INTERFERON ALFA-2B), INTROPIN (DOPAMINE HYDROCHLORIDE), INULIN AND SODIUM CHLORIDE (INULIN), INVAGESIC (ASPIRIN; CAFFEINE; ORPHENADRINE CITRATE), INVAGESIC FORTE (ASPIRIN; CAFFEINE; ORPHENADRINE CITRATE), INVANZ (ERTAPENEM SODIUM), INVEGA (PALIPERIDONE), INVERSINE (MECAMYLAMINE HYDROCHLORIDE), INVIRASE (SAQUINAVIR MESYLATE), IOBENGUANE SULFATE I 131 (IOBENGUANE SULFATE I 131), IODOHIPPURATE SODIUM I 131 (IODOHIPPURATE SODIUM, I-131), IODOTOPE (SODIUM IODIDE, I-131), IONAMIN (PHENTERMINE RESIN COMPLEX), IONOSOL B AND DEXTROSE 5% IN PLASTIC CONTAINER (DEXTROSE; MAGNESIUM CHLORIDE; POTASSIUM CHLORIDE; POTASSIUM PHOSPHATE, DIBASIC; SODIUM CHLORIDE; SODIUM LACTATE; SODIUM PHOSPHATE, MONOBASIC, ANHYDROUS), IONOSOL MB AND DEXTROSE 5% IN PLASTIC CONTAINER (DEXTROSE; MAGNESIUM CHLORIDE; POTASSIUM CHLORIDE; POTASSIUM PHOSPHATE, MONOBASIC; SODIUM LACTATE; SODIUM PHOSPHATE, MONOBASIC, ANHYDROUS), IONOSOL T AND DEXTROSE 5% IN PLASTIC CONTAINER (DEXTROSE; POTASSIUM CHLORIDE; POTASSIUM LACTATE; SODIUM CHLORIDE; SODIUM PHOSPHATE, MONOBASIC, ANHYDROUS), IONSYS (FENTANYL HYDROCHLORIDE), IONTOCAINE (EPINEPHRINE; LIDOCAINE HYDROCHLORIDE), IOPAMIDOL (IOPAMIDOL), IOPAMIDOL-200 (IOPAMIDOL), IOPAMIDOL-200 IN PLASTIC CONTAINER (IOPAMIDOL), IOPAMIDOL-250 (IOPAMIDOL), IOPAMIDOL-250 IN PLASTIC CONTAINER (IOPAMIDOL), IOPAMIDOL-300 (IOPAMIDOL), IOPAMIDOL-300 IN PLASTIC CONTAINER (IOPAMIDOL), IOPAMIDOL-370 (IOPAMIDOL), IOPAMIDOL-370 IN PLASTIC CONTAINER (IOPAMIDOL), IOPIDINE (APRACLONIDINE HYDROCHLORIDE), IOSAT (POTASSIUM IODIDE), IPLEX (MECASERMIN RINFABATE RECOMBINANT), IPRATROPIUM BROMIDE (IPRATROPIUM BROMIDE), IPRIVASK (DESIRUDIN RECOMBINANT), IQUIX (LEVOFLOXACIN), IRBESARTAN (IRBESARTAN), IRBESARTAN AND HYDROCHLOROTHIAZIDE (IRBESARTAN; HYDROCHLOROTHIAZIDE), IRBESARTAN; HYDROCHLOROTHIAZIDE (IRBESARTAN; HYDROCHLOROTHIAZIDE), IRESSA (GEFITINIB), IRINOTECAN HYDROCHLORIDE (IRINOTECAN HYDROCHLORIDE), IRON DEXTRAN (IRON DEXTRAN), IRRIGATING SOLUTION G IN PLASTIC CONTAINER (CITRIC ACID; MAGNESIUM OXIDE; SODIUM CARBONATE), ISENTRESS (RALTEGRAVIR POTASSIUM), ISMELIN (GUANETHIDINE MONOSULFATE), ISMO (ISOSORBIDE MONONITRATE), ISMOTIC (ISOSORBIDE), ISOCAINE HYDROCHLORIDE (MEPIVACAINE HYDROCHLORIDE), ISOCAINE HYDROCHLORIDE W/ LEVONORDEFRIN (LEVONORDEFRIN; MEPIVACAINE HYDROCHLORIDE), ISOCLOR (CHLORPHENIRAMINE MALEATE; PSEUDOEPHEDRINE HYDROCHLORIDE), ISOETHARINE HYDROCHLORIDE (ISOETHARINE HYDROCHLORIDE), ISOETHARINE HYDROCHLORIDE S/F (ISOETHARINE HYDROCHLORIDE), ISOETHARINE MESYLATE (ISOETHARINE MESYLATE), ISOFLURANE (ISOFLURANE), ISOLYTE E IN DEXTROSE 5% IN PLASTIC CONTAINER (CALCIUM CHLORIDE; DEXTROSE; MAGNESIUM CHLORIDE; POTASSIUM CHLORIDE; SODIUM ACETATE; SODIUM CHLORIDE; SODIUM CITRATE), ISOLYTE E IN PLASTIC CONTAINER (CALCIUM CHLORIDE; MAGNESIUM CHLORIDE; POTASSIUM CHLORIDE; SODIUM ACETATE; SODIUM CHLORIDE; SODIUM CITRATE), ISOLYTE E W/ DEXTROSE 5% IN PLASTIC CONTAINER (CALCIUM CHLORIDE; DEXTROSE; MAGNESIUM CHLORIDE; POTASSIUM CHLORIDE; SODIUM ACETATE; SODIUM CHLORIDE; SODIUM CITRATE), ISOLYTE H IN DEXTROSE 5% IN PLASTIC CONTAINER (DEXTROSE; MAGNESIUM CHLORIDE; POTASSIUM CHLORIDE; SODIUM ACETATE; SODIUM CHLORIDE), ISOLYTE H W/ DEXTROSE 5% IN PLASTIC CONTAINER (DEXTROSE; MAGNESIUM CHLORIDE; POTASSIUM CHLORIDE; SODIUM ACETATE; SODIUM CHLORIDE), ISOLYTE M IN DEXTROSE 5% IN PLASTIC CONTAINER (DEXTROSE; POTASSIUM CHLORIDE; POTASSIUM PHOSPHATE, DIBASIC; SODIUM ACETATE; SODIUM CHLORIDE), ISOLYTE M W/ DEXTROSE 5% IN PLASTIC CONTAINER (DEXTROSE; POTASSIUM CHLORIDE; POTASSIUM PHOSPHATE, DIBASIC; SODIUM ACETATE; SODIUM CHLORIDE), ISOLYTE P IN DEXTROSE 5% IN PLASTIC CONTAINER (DEXTROSE; MAGNESIUM CHLORIDE; POTASSIUM CHLORIDE; POTASSIUM PHOSPHATE, DIBASIC; SODIUM ACETATE), ISOLYTE P W/ DEXTROSE 5% IN PLASTIC CONTAINER (DEXTROSE; MAGNESIUM CHLORIDE; POTASSIUM CHLORIDE; POTASSIUM PHOSPHATE, DIBASIC; SODIUM ACETATE), ISOLYTE R IN DEXTROSE 5% IN PLASTIC CONTAINER (CALCIUM CHLORIDE; DEXTROSE; MAGNESIUM CHLORIDE; POTASSIUM CHLORIDE; SODIUM ACETATE; SODIUM CHLORIDE), ISOLYTE R W/ DEXTROSE 5% IN PLASTIC CONTAINER (CALCIUM CHLORIDE; DEXTROSE; MAGNESIUM CHLORIDE; POTASSIUM CHLORIDE; SODIUM ACETATE; SODIUM CHLORIDE), ISOLYTE S IN DEXTROSE 5% IN PLASTIC CONTAINER (DEXTROSE; MAGNESIUM CHLORIDE; POTASSIUM CHLORIDE; SODIUM ACETATE; SODIUM CHLORIDE; SODIUM GLUCONATE), ISOLYTE S IN PLASTIC CONTAINER (MAGNESIUM CHLORIDE; POTASSIUM CHLORIDE; SODIUM ACETATE; SODIUM CHLORIDE; SODIUM GLUCONATE), ISOLYTE S PH 7.4 IN PLASTIC CONTAINER (MAGNESIUM CHLORIDE; POTASSIUM CHLORIDE; POTASSIUM PHOSPHATE, MONOBASIC; SODIUM ACETATE; SODIUM CHLORIDE; SODIUM GLUCONATE; SODIUM PHOSPHATE, DIBASIC, HEPTAHYDRATE), ISOLYTE S W/ DEXTROSE 5% IN PLASTIC CONTAINER (DEXTROSE; MAGNESIUM CHLORIDE; POTASSIUM CHLORIDE; SODIUM ACETATE; SODIUM CHLORIDE; SODIUM GLUCONATE), ISONIAZID (ISONIAZID), ISOPAQUE 280 (CALCIUM; MEGLUMINE; METRIZOIC ACID), ISOPAQUE 440 (CALCIUM METRIZOATE; MEGLUMINE METRIZOATE; METRIZOATE MAGNESIUM; METRIZOATE SODIUM), ISOPROTERENOL HYDROCHLORIDE (ISOPROTERENOL HYDROCHLORIDE), ISOPTIN (VERAPAMIL HYDROCHLORIDE), ISOPTIN SR (VERAPAMIL HYDROCHLORIDE), ISOPTO CETAMIDE (SULFACETAMIDE SODIUM), ISOPTO CETAPRED (PREDNISOLONE ACETATE; SULFACETAMIDE SODIUM), ISORDIL (ISOSORBIDE DINITRATE), ISOSORBIDE DINITRATE (ISOSORBIDE DINITRATE), ISOSORBIDE MONONITRATE (ISOSORBIDE MONONITRATE), ISOTONIC GENTAMICIN SULFATE IN PLASTIC CONTAINER (GENTAMICIN SULFATE), ISOVUE-128 (IOPAMIDOL), ISOVUE-200 (IOPAMIDOL), ISOVUE-250 (IOPAMIDOL), ISOVUE-300 (IOPAMIDOL), ISOVUE-370 (IOPAMIDOL), ISOVUE-M 200 (IOPAMIDOL), ISOVUE-M 300 (IOPAMIDOL), ISRADIPINE (ISRADIPINE), ISTALOL (TIMOLOL MALEATE), ISUPREL (ISOPROTERENOL HYDROCHLORIDE), ITRACONAZOLE (ITRACONAZOLE), IV PERSANTINE (DIPYRIDAMOLE), IVADANTIN (NITROFURANTOIN SODIUM), IVY BLOCK (BENTOQUATAM), IXEMPRA KIT (IXABEPILONE), JANIMINE (IMIPRAMINE HYDROCHLORIDE), JANTOVEN (WARFARIN SODIUM), JANUMET (METFORMIN HYDROCHLORIDE; SITAGLIPTIN PHOSPHATE), JANUVIA (SITAGLIPTIN PHOSPHATE), JEANATOPE (ALBUMIN IODINATED I-125 SERUM), JUNEL 1.5/30 (ETHINYL ESTRADIOL; NORETHINDRONE ACETATE), JUNEL 1/20 (ETHINYL ESTRADIOL; NORETHINDRONE ACETATE), JUNEL FE 1.5/30 (ETHINYL ESTRADIOL; NORETHINDRONE ACETATE), JUNEL FE 1/20 (ETHINYL ESTRADIOL; NORETHINDRONE ACETATE), JUNIOR STRENGTH ADVIL (IBUPROFEN), JUNIOR STRENGTH IBUPROFEN (IBUPROFEN), JUNIOR STRENGTH MOTRIN (IBUPROFEN), K+10 (POTASSIUM CHLORIDE), K+8 (POTASSIUM CHLORIDE), K-LEASE (POTASSIUM CHLORIDE), K-TAB (POTASSIUM CHLORIDE), KADIAN (MORPHINE SULFATE), KAFOCIN (CEPHALOGLYCIN), KAINAIR (PROPARACAINE HYDROCHLORIDE), KALETRA (LOPINAVIR; RITONAVIR), KANAMYCIN (KANAMYCIN SULFATE), KANAMYCIN SULFATE (KANAMYCIN SULFATE), KANTREX (KANAMYCIN SULFATE), KAON CL (POTASSIUM CHLORIDE), KAON CL-10 (POTASSIUM CHLORIDE), KAPPADIONE (MENADIOL SODIUM DIPHOSPHATE), KARIVA (DESOGESTREL; ETHINYL ESTRADIOL), KAYEXALATE (SODIUM POLYSTYRENE SULFONATE), KEFLET (CEPHALEXIN), KEFLEX (CEPHALEXIN), KEFLIN (CEPHALOTHIN SODIUM), KEFLIN IN PLASTIC CONTAINER (CEPHALOTHIN SODIUM), KEFTAB (CEPHALEXIN HYDROCHLORIDE), KEFUROX (CEFUROXIME SODIUM), KEFUROX IN PLASTIC CONTAINER (CEFUROXIME SODIUM), KEFZOL (CEFAZOLIN SODIUM), KELNOR (ETHINYL ESTRADIOL; ETHYNODIOL DIACETATE), KEMADRIN (PROCYCLIDINE HYDROCHLORIDE), KEMSTRO (BACLOFEN), KENACORT (TRIAMCINOLONE), KENACORT (TRIAMCINOLONE DIACETATE), KENALOG (TRIAMCINOLONE ACETONIDE), KENALOG IN ORABASE (TRIAMCINOLONE ACETONIDE), KENALOG-10 (TRIAMCINOLONE ACETONIDE), KENALOG-40 (TRIAMCINOLONE ACETONIDE), KENALOG-H (TRIAMCINOLONE ACETONIDE), KEPIVANCE (PALIFERMIN), KEPPRA (LEVETIRACETAM), KERLEDEX (BETAXOLOL HYDROCHLORIDE; CHLORTHALIDONE), KERLONE (BETAXOLOL HYDROCHLORIDE), KESSO-GESIC (PROPDXYPHENE HYDROCHLORIDE), KETALAR (KETAMINE HYDROCHLORIDE), KETAMINE HCL (KETAMINE HYDROCHLORIDE), KETAMINE HYDROCHLORIDE (KETAMINE HYDROCHLORIDE), KETEK (TELITHROMYCIN), KETOCONAZOLE (KETOCONAZOLE), KETOPROFEN (KETOPROFEN), KETOROLAC TROMETHAMINE (KETOROLAC TROMETHAMINE), KETOTIFEN (KETOTIFEN FUMARATE), KETOTIFEN FUMARATE (KETOTIFEN FUMARATE), KETOZOLE (KETOCONAZOLE), KINERET (ANAKINRA), KINEVAC (SINCALIDE), KINLYTIC (UROKINASE), KIONEX (SODIUM POLYSTYRENE SULFONATE), KLARON (SULFACETAMIDE SODIUM), KLEBCIL (KANAMYCIN SULFATE), KLONOPIN (CLONAZEPAM), KLONOPIN RAPIDLY DISINTEGRATING (CLONAZEPAM), KLOR-CON (POTASSIUM CHLORIDE), KLOR-CON M10 (POTASSIUM CHLORIDE), KLOR-CON M15 (POTASSIUM CHLORIDE), KLOR-CON M20 (POTASSIUM CHLORIDE), KLOROMIN (CHLORPHENIRAMINE MALEATE), KLOTRIX (POTASSIUM CHLORIDE), KOGLUCOID (*RAUWOLFIA SERPENTINA*), KONAKION (PHYTONADIONE), KOROSTATIN (NYSTATIN), KUVAN (SAPROPTERIN DIHYDROCHLORIDE), KWELL (LINDANE), KYTRIL (GRANISETRON HYDROCHLORIDE), LABETALOL HYDROCHLORIDE (LABETALOL HYDROCHLORIDE), LABID (THEOPHYLLINE), LAC-HYDRIN (AMMONIUM LACTATE), LACRISERT (HYDROXYPROPYL CELLULOSE), LACTATED RINGER'S AND DEXTROSE 5% IN PLASTIC CONTAINER (CALCIUM CHLORIDE; DEXTROSE; POTASSIUM CHLORIDE; SODIUM CHLORIDE; SODIUM LACTATE), LACTATED RINGER'S IN PLASTIC CONTAINER (CALCIUM CHLORIDE; POTASSIUM CHLORIDE; SODIUM CHLORIDE; SODIUM LACTATE), LACTULOSE (LACTULOSE), LAMICTAL (LAMOTRIGINE), LAMICTAL CD (LAMOTRIGINE), LAMISIL (TERBINAFINE), LAMISIL (TERBINAFINE HYDROCHLORIDE), LAMISIL AT (TERBINAFINE), LAMISIL AT (TERBINAFINE HYDROCHLORIDE), LAMIVUDINE (LAMIVUDINE), LAMIVUDINE (LAMIVUDINE; ZIDOVUDINE; NEVIRAPINE), LAMIVUDINE/ZIDOVUDINE TABLETS CO-PACKAGED WITH NEVIRAPINE TABLETS (LAMIVUDINE; ZIDOVUDINE; NEVIRAPINE), LAMIVUDINE; STAVUDINE (LAMIVUDINE; STAVUDINE), LAMIVUDINE; STAVUDINE; NEVIRAPINE (LAMIVUDINE; STAVUDINE; NEVIRAPINE), LAMIVUDINE; ZIDOVUDINE (LAMIVUDINE; ZIDOVUDINE), LAMIVUDINE; ZIDOVUDINE; ABACAVIR (LAMIVUDINE; ZIDOVUDINE; ABACAVIR), LAMIVUDINE; ZIDOVUDINE; EFAVIRENZ (LAMIVUDINE; ZIDOVUDINE; EFAVIRENZ), LAMIVUDINE; ZIDOVUDINE; NEVIRAPINE (LAMIVUDINE; ZIDOVUDINE; NEVIRAPINE), LAMOTRIGINE (LAMOTRIGINE), LAMPRENE (CLOFAZIMINE), LAMVUDINE; ZIDOVUDINE (LAMVUDINE; ZIDOVUDINE; EFAVIRENZ), LANABIOTIC (BACITRACIN ZINC; LIDOCAINE; NEOMYCIN SULFATE; POLYMYXIN B SULFATE), LANABIOTIC (BACITRACIN; POLYMYXIN B SULFATE), LANIAZID (ISONIAZID), LANOPHYLLIN (THEOPHYLLINE), LANORINAL (ASPIRIN; BUTALBITAL; CAFFEINE), LANOXICAPS (DIGOXIN), LANOXIN (DIGOXIN), LANOXIN PEDIATRIC (DIGOXIN), LANSOPRAZOLE (LANSOPRAZOLE), LANTRISUL (TRISULFAPYRIMIDINES (SULFADIAZINE; SULFAMERAZINE; SULFAMETHAZINE)), LANTUS (INSULIN GLARGINE RECOMBINANT), LARGON (PROPIOMAZINE HYDROCHLORIDE), LARIAM (MEFLOQUINE HYDROCHLORIDE), LARODOPA (LEVODOPA), LAROTID (AMOXICILLIN), LARYNG-O-JET KIT (LIDOCAINE HYDROCHLORIDE), LARYNGOTRACHEAL ANESTHESIA KIT (LIDOCAINE HYDROCHLORIDE), LASIX (FUROSEMIDE), LATANOPROST (LATANOPROST), LAXILOSE (LACTULOSE), LEDERCILLIN VK (PENICILLIN V POTASSIUM), LEFLUNOMIDE (LEFLUNOMIDE), LENTARD (INSULIN ZINC SUSP PURIFIED BEEF/PORK), LENTE (INSULIN ZINC SUSP PURIFIED PORK), LENTE ILETIN II (INSULIN ZINC SUSP PURIFIED BEEF), LENTE ILETIN II (PORK) (INSULIN ZINC SUSP PURIFIED PORK), LENTE INSULIN (INSULIN ZINC SUSP BEEF), LERITINE (ANILERIDINE HYDROCHLORIDE), LERITINE (ANILERIDINE PHOSPHATE), LESCOL (FLUVASTATIN SODIUM), LESCOL XL (FLUVASTATIN SODIUM), LESSINA-21 (ETHINYL ESTRADIOL; LEVONORGESTREL), LESSINA-28 (ETHINYL ESTRADIOL; LEVONORGESTREL), LETAIRIS (AMBRISENTAN), LETROZOLE (LETROZOLE), LEUCOVORIN CALCIUM (LEUCOVORIN CALCIUM), LEUCOVORIN CALCIUM PRESERVATIVE FREE (LEUCOVORIN CALCIUM), LEUKERAN (CHLORAMBUCIL), LEUKINE (SARGRAMOSTIM), LEUPROLIDE ACETATE (LEUPROLIDE ACETATE), LEUSTATIN (CLADRIBINE), LEVALBUTEROL HYDROCHLORIDE (LEVALBUTEROL HYDROCHLORIDE), LEVAQUIN (LEVOFLOXACIN), LEVAQUIN IN DEXTROSE 5% IN PLASTIC CONTAINER (LEVOFLOXACIN), LEVATOL (PENBUTOLOL SULFATE), LEVEMIR (INSULIN DETEMIR), LEVEMIR (INSULIN DETEMIR RECOMBINANT), LEVITRA (VARDENAFIL HYDROCHLORIDE), LEVLITE (ETHINYL ESTRADIOL; LEVONORGESTREL), LEVO-DROMORAN (LEVORPHANOL TARTRATE), LEVO-T (LEVOTHYROXINE SODIUM), LEVOBUNOLOL HYDROCHLORIDE (LEVOBUNOLOL HYDROCHLORIDE), LEVOCARNITINE (LEVOCARNITINE), LEVOFLOXACIN (LEVOFLOXACIN), LEVOFLOXACIN (LEVOFLOXACIN; SODIUM CHLORIDE), LEVOLET (LEVOTHYROXINE SODIUM), LEVOLEUCOVORIN (LEVOLEUCOVORIN CALCIUM), LEVONORGESTREL (LEVONORGESTREL), LEVONORGESTREL AND ETHINYL ESTRADIOL (ETHINYL ESTRADIOL; LEVONORGESTREL), LEVOPHED (NOREPINEPHRINE BITARTRATE), LEVOPROME (LEVOMEPROMAZINE), LEVORA 0.15/30-21 (ETHINYL ESTRADIOL; LEVONORGESTREL), LEVORA 0.15/30-28 (ETHINYL ESTRADIOL; LEVONORGESTREL), LEVORPHANOL TARTRATE (LEVORPHANOL TARTRATE), LEVOTHROID (LEVOTHYROXINE SODIUM), LEVOTHYROXINE SODIUM (LEVOTHYROXINE SODIUM), LEVOXYL (LEVOTHYROXINE SODIUM), LEVULAN (AMINOLEVULINIC ACID HYDROCHLORIDE), LEXAPRO (ESCITALOPRAM OXALATE), LEXISCAN (REGADENOSON), LEXIVA (FOSAMPRENAVIR CALCIUM), LEXXEL (ENALAPRIL MALEATE; FELODIPINE), LIALDA (MESALAMINE), LIBRE-LEASE (CHLORDIAZEPDXIDE), LIBRITABS (CHLORDIAZEPDXIDE), LIBRIUM (CHLORDIAZEPDXIDE HYDROCHLORIDE), LIDEX (FLUOCINONIDE), LIDEX-E (FLUOCINONIDE), LIDOCAINE (LIDOCAINE), LIDOCAINE AND PRILOCAINE (LIDOCAINE; PRILOCAINE), LIDOCAINE AND TETRACAINE (LIDOCAINE; TETRACAINE), LIDOCAINE HYDROCHLORIDE (LIDOCAINE HYDROCHLORIDE), LIDOCAINE HYDROCHLORIDE 0.1% AND DEXTROSE 5% IN PLASTIC CONTAINER (LIDOCAINE HYDROCHLORIDE), LIDOCAINE HYDROCHLORIDE 0.2% AND DEXTROSE 5% IN PLASTIC CONTAINER (LIDOCAINE HYDROCHLORIDE), LIDOCAINE HYDROCHLORIDE 0.2% IN DEXTROSE 5% (LIDOCAINE HYDROCHLORIDE), LIDOCAINE HYDROCHLORIDE 0.2% IN DEXTROSE 5% IN PLASTIC CONTAINER (LIDOCAINE HYDROCHLORIDE), LIDOCAINE HYDROCHLORIDE 0.4% AND DEXTROSE 5% IN PLASTIC CONTAINER (LIDOCAINE HYDROCHLORIDE), LIDOCAINE HYDROCHLORIDE 0.4% IN DEXTROSE 5% (LIDOCAINE HYDROCHLORIDE), LIDOCAINE HYDROCHLORIDE 0.4% IN DEXTROSE 5% IN PLASTIC CONTAINER (LIDOCAINE HYDROCHLORIDE), LIDOCAINE HYDROCHLORIDE 0.8% AND DEXTROSE 5% IN PLASTIC CONTAINER (LIDOCAINE HYDROCHLORIDE), LIDOCAINE HYDROCHLORIDE 0.8% IN DEXTROSE 5% IN PLASTIC CONTAINER (LIDOCAINE HYDROCHLORIDE), LIDOCAINE HYDROCHLORIDE 5% AND DEXTROSE 7.5% (LIDOCAINE HYDROCHLORIDE), LIDOCAINE HYDROCHLORIDE AND EPINEPHRINE (EPINEPHRINE; LIDOCAINE HYDROCHLORIDE), LIDOCAINE HYDROCHLORIDE IN PLASTIC CONTAINER (LIDOCAINE HYDROCHLORIDE), LIDOCAINE HYDROCHLORIDE PRESERVATIVE FREE (LIDOCAINE HYDROCHLORIDE), LIDOCAINE HYDROCHLORIDE PRESERVATIVE FREE IN PLASTIC CONTAINER (LIDOCAINE HYDROCHLORIDE), LIDOCAINE HYDROCHLORIDE VISCOUS (LIDOCAINE HYDROCHLORIDE), LIDOCAINE HYDROCHLORIDE W/ EPINEPHRINE (EPINEPHRINE; LIDOCAINE HYDROCHLORIDE), LIDOCAINE VISCOUS (LIDOCAINE HYDROCHLORIDE), LIDOCATON (EPINEPHRINE; LIDOCAINE HYDROCHLORIDE), LIDOCATON (LIDOCAINE HYDROCHLORIDE), LIDODERM (LIDOCAINE), LIDOPEN (LIDOCAINE HYDROCHLORIDE), LIDOSITE TOPICAL SYSTEM KIT (EPINEPHRINE; LIDOCAINE HYDROCHLORIDE), LIGNOSPAN FORTE (EPINEPHRINE BITARTRATE; LIDOCAINE HYDROCHLORIDE), LIGNOSPAN STANDARD (EPINEPHRINE BITARTRATE; LIDOCAINE HYDROCHLORIDE), LIMBITROL (AMITRIPTYLINE HYDROCHLORIDE; CHLORDIAZEPDXIDE), LIMBITROL DS (AMITRIPTYLINE HYDROCHLORIDE; CHLORDIAZEPDXIDE), LINCOCIN (LINCOMYCIN HYDROCHLORIDE), LINCOMYCINHCL (LINCOMYCIN HYDROCHLORIDE), LINCOMYCIN HYDROCHLORIDE (LINCOMYCIN HYDROCHLORIDE), LINDANE (LINDANE), LINEZOLID (LINEZOLID), LIORESAL (BACLOFEN), LIOTHYRONINE SODIUM (LIOTHYRONINE SODIUM), LIPIDIL (FENOFIBRATE), LIPITOR (ATORVASTATIN CALCIUM), LIPO GANTRISIN (SULFISOXAZOLE ACETYL), LIPO-HEPIN (HEPARIN SODIUM), LIPOFEN (FENOFIBRATE), LIPOSYN 10% (SAFFLOWER OIL), LIPOSYN 20% (SAFFLOWER OIL), LIPOSYN II 10% (SAFFLOWER OIL; SOYBEAN OIL), LIPOSYN II 20% (SAFFLOWER OIL; SOYBEAN OIL), LIPOSYN III 10% (SOYBEAN OIL), LIPOSYN III 20% (SOYBEAN OIL), LIPOSYN III 30% (SOYBEAN OIL), LIQUAEMIN LOCK FLUSH (HEPARIN SODIUM), LIQUAEMIN SODIUM (HEPARIN SODIUM), LIQUAEMIN SODIUM PRESERVATIVE FREE (HEPARIN SODIUM), LIQUAMAR (PHENPROCOUMON), LIQUID PRED (PREDNISONE), LISINOPRIL (LISINOPRIL), LISINOPRIL AND HYDROCHLOROTHIAZIDE (HYDROCHLOROTHIAZIDE; LISINOPRIL), LITHANE (LITHIUM CARBONATE), LITHIUM CARBONATE (LITHIUM CARBONATE), LITHIUM CITRATE (LITHIUM CITRATE), LITHOBID (LITHIUM CARBONATE), LITHONATE (LITHIUM CARBONATE), LITHONATE (LITHIUM CITRATE), LITHOSTAT (ACETOHY- DROXAMIC ACID), LITHOTABS (LITHIUM CARBONATE), LIVOSTIN (LEVOCABASTINE HYDROCHLORIDE), LO-TROL (ATROPINE SULFATE; DIPHENOXYLATE HYDROCHLORIDE), LO/OVRAL (ETHINYL ESTRADIOL; NORGESTREL), LO/OVRAL-28 (ETHINYL ESTRADIOL; NORGESTREL), LOCHOLEST (CHOLESTYRAMINE), LOCHOLEST LIGHT (CHOLESTYRAMINE), LOCOID (HYDROCORTISONE BUTYRATE), LOCOID LIPOCREAM (HYDROCORTISONE BUTYRATE), LOCORTEN (FLUMETHASONE PIVALATE), LODINE (ETODOLAC), LODINE XL (ETODOLAC), LODOSYN (CARBIDOPA), LOESTRIN 21 1.5/30 (ETHINYL ESTRADIOL; NORETHINDRONE ACETATE), LOESTRIN 21 1/20 (ETHINYL ESTRADIOL; NORETHINDRONE ACETATE), LOESTRIN 24 FE (ETHINYL ESTRADIOL; NORETHINDRONE ACETATE), LOESTRIN FE 1.5/30 (ETHINYL ESTRADIOL; NORETHINDRONE ACETATE), LOESTRIN FE 1/20 (ETHINYL ESTRADIOL; NORETHINDRONE ACETATE), LOGEN (ATROPINE SULFATE; DIPHENOXYLATE HYDROCHLORIDE), LOMANATE (ATROPINE SULFATE; DIPHENOXYLATE HYDROCHLORIDE), LOMOTIL (ATROPINE SULFATE; DIPHENOXYLATE HYDROCHLORIDE), LONITEN (MINOXIDIL), LONOX (ATROPINE SULFATE; DIPHENOXYLATE HYDROCHLORIDE), LOPERAMIDE HYDROCHLORIDE (LOPERAMIDE HYDROCHLORIDE), LOPERAMIDE HYDROCHLORIDE AND SIMETHICONE (LOPERAMIDE HYDROCHLORIDE; SIMETHICONE), LOPID (GEMFIBROZIL), LOPRESSIDONE (CHLORTHALIDONE; METOPROLOL TARTRATE), LOPRESSOR (METOPROLOL FUMARATE), LOPRESSOR (METOPROLOL TARTRATE), LOPRESSOR HCT (HYDROCHLOROTHIAZIDE; METOPROLOL TARTRATE), LOPROX (CICLOPIROX), LOPURIN (ALLOPURINOL), LORABID (LORACARBEF), LORATADINE (LORATADINE), LORATADINE AND PSEUDOEPHEDRINE SULFATE (LORATADINE; PSEUDOEPHEDRINE SULFATE), LORATADINE REDIDOSE (LORATADINE), LORAZ (LORAZEPAM), LORAZEPAM (LORAZEPAM), LORAZEPAM INTENSOL (LORAZEPAM), LORAZEPAM PRESERVATIVE FREE (LORAZEPAM), LORCET-HD (ACETAMINOPHEN; HYDROCODONE BITARTRATE), LORELCO (PROBUCOL), LORFAN (LEVALLORPHAN TARTRATE), LORTAB (ACETAMINOPHEN; HYDROCODONE BITARTRATE), LOSARTAN (LOSARTAN POTASSIUM), LOSARTAN (LOSARTAN POTASSIUM; HYDROCHLOROTHIAZIDE), LOSARTAN POTASSIUM (LOSARTAN POTASSIUM), LOSARTAN POTASSIUM; HYDROCHLOROTHIAZIDE (LOSARTAN POTASSIUM; HYDROCHLOROTHIAZIDE), LOTEMAX (LOTEPREDNOL ETABONATE), LOTENSIN (BENAZEPRIL HYDROCHLORIDE), LOTENSIN HCT (BENAZEPRIL HYDROCHLORIDE; HYDROCHLOROTHIAZIDE), LOTREL (AMLODIPINE BESYLATE; BENAZEPRIL HYDROCHLORIDE), LOTRIMIN (CLOTRIMAZOLE), LOTRIMIN AF (CLOTRIMAZOLE), LOTRIMIN ULTRA (BUTENAFINE HYDROCHLORIDE), LOTRISONE (BETAMETHASONE DIPROPIONATE; CLOTRIMAZOLE), LOTRONEX (ALOSETRON HYDROCHLORIDE), LOTUSATE (TALBUTAL), LOVASTATIN (LOVASTATIN), LOVAZA (OMEGA-3-ACID ETHYL ESTERS), LOVENOX (ENOXAPARIN SODIUM), LOVENOX (PRESERVATIVE FREE) (ENOXAPARIN SODIUM), LOW-OGESTREL-21 (ETHINYL ESTRADIOL; NORGESTREL), LOW-OGESTREL-28 (ETHINYL ESTRADIOL; NORGESTREL), LOW-QUEL (ATROPINE SULFATE; DIPHENOXYLATE HYDROCHLORIDE), LOXAPINE (LOXAPINE SUCCINATE), LOXAPINE SUCCINATE (LOXAPINE SUCCINATE), LOXITANE (LOXAPINE SUCCINATE), LOXITANE C (LOXAPINE HYDROCHLORIDE), LOXITANE IM (LOXAPINE HYDROCHLORIDE), LOZOL (INDAPAMIDE), LTA II KIT (LIDOCAINE HYDROCHLORIDE), LUCENTIS (RANIBIZUMAB), LUDIOMIL (MAPROTILINE HYDROCHLORIDE), LUFYLLIN (DYPHYLLINE), LUMENHANCE (MANGANESE CHLORIDE TETRAHYDRATE), LUMIGAN (BIMATOPROST), LUNELLE (ESTRADIOL CYPIONATE; MEDROXYPROGESTERONE ACETATE), LUNESTA (ESZOPICLONE), LUNGAGGREGATE REAGENT (TECHNETIUM TC-99M ALBUMIN AGGREGATED KIT), LUPRON (LEUPROLIDE ACETATE), LUPRON DEPOT (LEUPROLIDE ACETATE), LUPRON DEPOT-3 (LEUPROLIDE ACETATE), LUPRON DEPOT-4 (LEUPROLIDE ACETATE), LUPRON DEPOT-PED (LEUPROLIDE ACETATE), LUTREPULSE KIT (GONADORELIN ACETATE), LUVERIS (LUTROPIN ALFA), LUVOX (FLUVOXAMINE MALEATE), LUVOX CR (FLUVOXAMINE MALEATE), LUXIQ (BETAMETHASONE VALERATE), LYBREL (ETHINYL ESTRADIOL; LEVONORGESTREL), LYGEN (CHLORDIAZEPDXIDE HYDROCHLORIDE), LYMPHAZURIN (ISOSULFAN BLUE), LYNORAL (ETHINYL ESTRADIOL), LYOPHILIZED CYTOXAN (CYCLOPHOSPHAMIDE), LYRICA (PREGABALIN), LYSODREN (MITOTANE), M-PREDROL (METHYLPREDNISOLONE ACETATE), M-ZOLE 3 COMBINATION PACK (MICONAZOLE NITRATE), M-ZOLE 7 DUAL PACK (MICONAZOLE NITRATE), M.V.C. 9+3 (ASCORBIC ACID; BIOTIN; CYANOCOBALAMIN; DEXPANTHENOL; ERGOCALCIFEROL; FOLIC ACID; NIACINAMIDE; PYRIDOXINE HYDROCHLORIDE; RIBOFLAVIN PHOSPHATE SODIUM; THIAMINE HYDROCHLORIDE; VITAMIN A; VITAMIN E), M.V.I. ADULT (ASCORBIC ACID; BIOTIN; CYANOCOBALAMIN; DEXPANTHENOL; ERGOCALCIFEROL; FOLIC ACID; NIACINAMIDE; PYRIDOXINE HYDROCHLORIDE; RIBOFLAVIN PHOSPHATE SODIUM; THIAMINE HYDROCHLORIDE; VITAMIN A; VITAMIN E; VITAMIN K), M.V.I. ADULT (PHARMACY BULK PACKAGE) (ASCORBIC ACID; BIOTIN; CYANOCOBALAMIN; DEXPANTHENOL; ERGOCALCIFEROL; FOLIC ACID; NIACINAMIDE; PYRIDOXINE HYDROCHLORIDE; RIBOFLAVIN PHOSPHATE SODIUM; THIAMINE HYDROCHLORIDE; VITAMIN A; VITAMIN E; VITAMIN K), M.V.I. PEDIATRIC (ASCORBIC ACID; BIOTIN; CYANOCOBALAMIN; DEXPANTHENOL; ERGOCALCIFEROL; FOLIC ACID; NIACINAMIDE; PHYTONADIONE; PYRIDOXINE HYDROCHLORIDE; RIBOFLAVIN PHOSPHATE SODIUM; THIAMINE HYDROCHLORIDE; VITAMIN A; VITAMIN E), M.V.I.-12 (ASCORBIC ACID; BIOTIN; CYANOCOBALAMIN; DEXPANTHENOL; ERGOCALCIFEROL; FOLIC ACID; NIACINAMIDE; PYRIDOXINE HYDROCHLORIDE; RIBOFLAVIN PHOSPHATE SODIUM; THIAMINE HYDROCHLORIDE; VITAMIN A; VITAMIN E), M.V.I.-12 (ASCORBIC ACID; BIO- TIN; CYANOCOBALAMIN; DEXPANTHENOL; ERGOCALCIFEROL; FOLIC ACID; NIACINAMIDE; PYRIDOXINE HYDROCHLORIDE; RIBOFLAVIN; THIAMINE HYDROCHLORIDE; VITAMIN A; VITAMIN E), M.V.I.-12 (WITHOUT VITAMIN K) (ASCORBIC ACID; BIOTIN; CYANOCOBALAMIN; DEXPANTHENOL; ERGOCALCIFEROL; FOLIC ACID; NIACINAMIDE; PYRIDOXINE HYDROCHLORIDE; RIBOFLAVIN PHOSPHATE SODIUM; THIAMINE HYDROCHLORIDE; VITAMIN A; VITAMIN E), M.V.I.-12 LYOPHILIZED (ASCORBIC ACID; BIOTIN; CYANOCOBALAMIN; DEXPANTHENOL; ERGOCALCIFEROL; FOLIC ACID; NIACINAMIDE; PYRIDOXINE; RIBOFLAVIN PHOSPHATE SODIUM; THIAMINE; VITAMIN A; VITAMIN E), MACROBID (NITROFURANTOIN; NITROFURANTOIN, MACROCRYSTALLINE), MACRODANTIN (NITROFURANTOIN, MACROCRYSTALLINE), MACROTEC (TECHNETIUM TC-99M ALBUMIN AGGREGATED KIT), MACUGEN (PEGAPTANIB SODIUM), MAGNACORT (HYDROCORTAMATE HYDROCHLORIDE), MAGNESIUM SULFATE (MAGNESIUM SULFATE), MAGNESIUM SULFATE IN DEXTROSE 5% IN PLASTIC CONTAINER (MAGNESIUM SULFATE), MAGNESIUM SULFATE IN PLASTIC CONTAINER (MAGNESIUM SULFATE), MAGNEVIST (GADOPENTETATE DIMEGLUMINE), MALARONE (ATOVAQUONE; PROGUANIL HYDROCHLORIDE), MALARONE PEDIATRIC (ATOVAQUONE; PROGUANIL HYDROCHLORIDE), MANDOL (CEFAMANDOLE NAFATE), MANGANESE CHLORIDE IN PLASTIC CONTAINER (MANGANESE CHLORIDE), MANGANESE SULFATE (MANGANESE SULFATE), MANNITOL 10% (MANNITOL), MANNITOL 10% IN PLASTIC CONTAINER (MANNITOL), MANNITOL 10% W/ DEXTROSE 5% IN DISTILLED WATER (MANNITOL), MANNITOL 15% (MANNITOL), MANNITOL 15% IN PLASTIC CONTAINER (MANNITOL), MANNITOL 15% W/ DEXTROSE 5% IN SODIUM CHLORIDE 0.45% (MANNITOL), MANNITOL 20% (MANNITOL), MANNITOL 20% IN PLASTIC CONTAINER (MANNITOL), MANNITOL 25% (MANNITOL), MANNITOL 5% (MANNITOL), MANNITOL 5% IN PLASTIC CONTAINER (MANNITOL), MANNITOL 5% W/ DEXTROSE 5% IN SODIUM CHLORIDE 0.12% (MANNITOL), MAOLATE (CHLORPHENESIN CARBAMATE), MAPROTILINE HYDROCHLORIDE (MAPROTILINE HYDROCHLORIDE), MARCAINE (BUPIVACAINE HYDROCHLORIDE), MARCAINE HYDROCHLORIDE (BUPIVACAINE HYDROCHLORIDE), MARCAINE HYDROCHLORIDE PRESERVATIVE FREE (BUPIVACAINE HYDROCHLORIDE), MARCAINE HYDROCHLORIDE W/ EPINEPHRINE (BUPIVACAINE HYDROCHLORIDE; EPINEPHRINE BITARTRATE), MARCAINE HYDROCHLORIDE W/ EPINEPHRINE PRESERVATIVE FREE (BUPIVACAINE HYDROCHLORIDE; EPINEPHRINE BITARTRATE), MAREZINE (CYCLIZINE LACTATE), MARINOL (DRONABINOL), MARPLAN (ISOCARBOXAZID), MATULANE (PROCARBAZINE HYDROCHLORIDE), MAVIK (TRANDOLAPRIL), MAXAIR (PIRBUTEROL ACETATE), MAXALT (RIZATRIPTAN BENZOATE), MAXALT-MLT (RIZATRIPTAN BENZOATE), MAXAQUIN (LOMEFLOXACIN HYDROCHLORIDE), MAXIBOLIN (ETHYLESTRENOL), MAXIDEX (DEXAMETHASONE), MAXIDEX (DEXAMETHASONE SODIUM PHOSPHATE), MAXIPIME (CEFEPIME HYDROCHLORIDE), MAXITROL (DEXAMETHASONE; NEOMYCIN SULFATE; POLYMYXIN B SULFATE), MAXOLON (METOCLOPRAMIDE HYDROCHLORIDE), MAXZIDE (HYDROCHLOROTHIAZIDE; TRIAMTERENE), MAXZIDE-25 (HYDROCHLOROTHIAZIDE; TRIAMTERENE), MAZANOR (MAZINDOL), MD-50 (DIATRIZOATE SODIUM), MD-60 (DIATRIZOATE MEGLUMINE; DIATRIZOATE SODIUM), MD-76 (DIATRIZOATE MEGLUMINE; DIATRIZOATE SODIUM), MD-76R (DIATRIZOATE MEGLUMINE; DIATRIZOATE SODIUM), MD-GASTROVIEW (DIATRIZOATE MEGLUMINE; DIATRIZOATE SODIUM), MDP-BRACCO (TECHNETIUM TC-99M MEDRONATE KIT), MEASURIN (ASPIRIN), MEBENDAZOLE (MEBENDAZOLE), MECLAN (MECLOCYCLINE SULFOSALICYLATE), MECLIZINE HYDROCHLORIDE (MECLIZINE HYDROCHLORIDE), MECLODIUM (MECLOFENAMATE SODIUM), MECLOFENAMATE SODIUM (MECLOFENAMATE SODIUM), MECLOMEN (MECLOFENAMATE SODIUM), MEDIGESIC PLUS (ACETAMINOPHEN; BUTALBITAL; CAFFEINE), MEDIHALER ERGOTAMINE (ERGOTAMINE TARTRATE), MEDIHALER-EPI (EPINEPHRINE BITARTRATE), MEDIHALER-ISO (ISOPROTERENOL SULFATE), MEDIPREN (IBUPROFEN), MEDROL (METHYLPREDNISOLONE), MEDROL (METHYLPREDNISOLONE ACETATE), MEDROL ACETATE (METHYLPREDNISOLONE ACETATE), MEDROXYPROGESTERONE ACETATE (MEDROXYPROGESTERONE ACETATE), MEFLOQUINE (MEFLOQUINE HYDROCHLORIDE), MEFLOQUINE HYDROCHLORIDE (MEFLOQUINE HYDROCHLORIDE), MEFOXIN (CEFOXITIN SODIUM), MEFOXIN IN DEXTROSE 5% IN PLASTIC CONTAINER (CEFOXITIN SODIUM), MEFOXIN IN PLASTIC CONTAINER (CEFOXITIN SODIUM), MEFOXIN IN SODIUM CHLORIDE 0.9% IN PLASTIC CONTAINER (CEFOXITIN SODIUM), MEGACE (MEGESTROL ACETATE), MEGACE ES (MEGESTROL ACETATE), MEGATOPE (ALBUMIN IODINATED 1-131 SERUM), MEGESTROL ACETATE (MEGESTROL ACETATE), MELFIAT (PHENDIMETRAZINE TARTRATE), MELFIAT-105 (PHENDIMETRAZINE TARTRATE), MELLARIL (THIORIDAZINE HYDROCHLORIDE), MELLARIL-S (THIORIDAZINE), MELOXICAM (MELOXICAM), MEN'S ROGAINE (MINOXIDIL), MENADIONE (MENADIONE), MENEST (ESTROGENS, ESTERIFIED), MENOPUR (MENOTROPINS (FSH; LH)), MENOSTAR (ESTRADIOL), MENOTROPINS (MENOTROPINS (FSH; LH)), MENRIUM 10-4 (CHLORDIAZEPDXIDE; ESTROGENS, ESTERIFIED), MENRIUM 5-2 (CHLORDIAZEPDXIDE; ESTROGENS, ESTERIFIED), MENRIUM 5-4 (CHLORDIAZEPDXIDE; ESTROGENS, ESTERIFIED), MENTAX (BUTENAFINE HYDROCHLORIDE), MENTAX-TC (BUTENAFINE HYDROCHLORIDE), MEPERGAN (MEPERIDINE HYDROCHLORIDE; PROMETHAZINE HYDROCHLORIDE), MEPERIDINE AND ATROPINE SULFATE (ATROPINE SULFATE; MEPERIDINE HYDROCHLORIDE), MEPERIDINE HYDROCHLORIDE (MEPERIDINE HYDROCHLORIDE), MEPERIDINE HYDROCHLORIDE PRESERVATIVE FREE (MEPERIDINE HYDROCHLORIDE), MEPHYTON (PHY- TONADIONE), MEPIVACAINE HYDROCHLORIDE (MEPIVACAINE HYDROCHLORIDE), MEPIVACAINE HYDROCHLORIDE W/ LEVONORDEFRIN (LEVONORDEFRIN; MEPIVACAINE HYDROCHLORIDE), MEPRIAM (MEPROBAMATE), MEPRO-ASPIRIN (ASPIRIN; MEPROBAMATE), MEPROBAMATE (MEPROBAMATE), MEPROBAMATE AND ASPIRIN (ASPIRIN; MEPROBAMATE), MEPRON (ATOVAQUONE), MEPROSPAN (MEPROBAMATE), MERCAPTOPURINE (MERCAPTOPURINE), MERETEK UBT KIT (W/ PRANACTIN) (UREA, C-13), MERIDIA (SIBUTRAMINE HYDROCHLORIDE), MERREM I.V. (MEROPENEM), MERSALYL-THEOPHYLLINE (MERSALYL SODIUM; THEOPHYLLINE), MESALAMINE (MESALAMINE), MESANTOIN (MEPHENYTOIN), MESNA (MESNA), MESNEX (MESNA), MESTINON (PYRIDOSTIGMINE BROMIDE), METADATE CD (METHYLPHENIDATE HYDROCHLORIDE), METADATE ER (METHYLPHENIDATE HYDROCHLORIDE), METAGLIP (GLIPIZIDE; METFORMIN HYDROCHLORIDE), METAHYDRIN (TRICHLORMETHIAZIDE), METANDREN (METHYLTESTOSTERONE), METAPROTERENOL SULFATE (METAPROTERENOL SULFATE), METARAMINOL BITARTRATE (METARAMINOL BITARTRATE), METASTRON (STRONTIUM CHLORIDE, SR-89), METATENSIN #2 (RESERPINE; TRICHLORMETHIAZIDE), METATENSIN #4 (RESERPINE; TRICHLORMETHIAZIDE), METAXALONE (METAXALONE), METFORMIN HYDROCHLORIDE (METFORMIN HYDROCHLORIDE), METHADONE HYDROCHLORIDE (METHADONE HYDROCHLORIDE), METHADONE HYDROCHLORIDE INTENSOL (METHADONE HYDROCHLORIDE), METHADOSE (METHADONE HYDROCHLORIDE), METHAMPEX (METHAMPHETAMINE HYDROCHLORIDE), METHAMPHETAMINE HYDROCHLORIDE (METHAMPHETAMINE HYDROCHLORIDE), METHAZOLAMIDE (METHAZOLAMIDE), METHDILAZINE HYDROCHLORIDE (METHDILAZINE HYDROCHLORIDE), METHENAMINE HIPPURATE (METHENAMINE HIPPURATE), METHERGINE (METHYLERGONOVINE MALEATE), METHIMAZOLE (METHIMAZOLE), METHOCARBAMOL (METHOCARBAMOL), METHOCARBAMOL AND ASPIRIN (ASPIRIN; METHOCARBAMOL), METHOTREXATE LPF (METHOTREXATE SODIUM), METHOTREXATE PRESERVATIVE FREE (METHOTREXATE SODIUM), METHOTREXATE SODIUM (METHOTREXATE SODIUM), METHOTREXATE SODIUM PRESERVATIVE FREE (METHOTREXATE SODIUM), METHOXSALEN (METHOXSALEN), METHSCOPOLAMINE BROMIDE (METHSCOPOLAMINE BROMIDE), METHYCLOTHIAZIDE (METHYCLOTHIAZIDE), METHYCLOTHIAZIDE AND DESERPIDINE (DESERPIDINE; METHYCLOTHIAZIDE), METHYLDOPA (METHYLDOPA), METHYLDOPA AND CHLOROTHIAZIDE (CHLOROTHIAZIDE; METHYLDOPA), METHYLDOPA AND HYDROCHLOROTHIAZIDE (HYDROCHLOROTHIAZIDE; METHYLDOPA), METHYLDOPATE HCL (METHYLDOPATE HYDROCHLORIDE), METHYLDOPATE HYDROCHLORIDE (METHYLDOPATE HYDROCHLORIDE), METHYLIN (METHYLPHENIDATE HYDROCHLORIDE), METHYLIN ER (METHYLPHENIDATE HYDROCHLORIDE), METHYLPHENIDATE HYDROCHLORIDE (METHYLPHENIDATE HYDROCHLORIDE), METHYLPREDNISOLONE (METHYLPREDNISOLONE), METHYLPREDNISOLONE (METHYLPREDNISOLONE SODIUM SUCCINATE), METHYLPREDNISOLONE ACETATE (METHYLPREDNISOLONE ACETATE), METHYLPREDNISOLONE SODIUM SUCCINATE (METHYLPREDNISOLONE SODIUM SUCCINATE), METHYLTESTOSTERONE (METHYLTESTOSTERONE), METI-DERM (PREDNISOLONE), METICORTELONE (PREDNISOLONE ACETATE), METICORTEN (PREDNISONE), METIMYD (PREDNISOLONE ACETATE; SULFACETAMIDE SODIUM), METIPRANOLOL (METIPRANOLOL HYDROCHLORIDE), METOCLOPRAMIDE (METOCLOPRAMIDE HYDROCHLORIDE), METOCLOPRAMIDE HCL (METOCLOPRAMIDE HYDROCHLORIDE), METOCLOPRAMIDE HYDROCHLORIDE (METOCLOPRAMIDE HYDROCHLORIDE), METOCLOPRAMIDE INTENSOL (METOCLOPRAMIDE HYDROCHLORIDE), METOCURINE IODIDE (METOCURINE IODIDE), METOLAZONE (METOLAZONE), METOPIRONE (METYRAPONE), METOPROLOL SUCCINATE (METOPROLOL SUCCINATE), METOPROLOL TARTRATE (METOPROLOL TARTRATE), METOPROLOL TARTRATE AND HYDROCHLOROTHIAZIDE (HYDROCHLOROTHIAZIDE; METOPROLOL TARTRATE), METRA (PHENDIMETRAZINE TARTRATE), METRETON (PREDNISOLONE SODIUM PHOSPHATE), METRO I.V. (METRONIDAZOLE), METRO I.V. IN PLASTIC CONTAINER (METRONIDAZOLE), METROCREAM (METRONIDAZOLE), METRODIN (UROFOLLITROPIN), METROGEL (METRONIDAZOLE), METROGEL-VAGINAL (METRONIDAZOLE), METROLOTION (METRONIDAZOLE), METROMIDOL (METRONIDAZOLE), METRONIDAZOLE (METRONIDAZOLE), METRONIDAZOLE HYDROCHLORIDE (METRONIDAZOLE HYDROCHLORIDE), METRONIDAZOLE IN PLASTIC CONTAINER (METRONIDAZOLE), METUBINE IODIDE (METOCURINE IODIDE), METVIXIA (METHYL AMINOLEVULINATE HYDROCHLORIDE), MEVACOR (LOVASTATIN), MEXATE (METHOTREXATE SODIUM), MEXATE-AQ (METHOTREXATE SODIUM), MEXATE-AQ PRESERVED (METHOTREXATE SODIUM), MEXILETINE HYDROCHLORIDE (MEXILETINE HYDROCHLORIDE), MEXITIL (MEXILETINE HYDROCHLORIDE), MEZLIN (MEZLOCILLIN SODIUM MONOHYDRATE), MIACALCIN (CALCITONIN, SALMON), MICARDIS (TELMISARTAN), MICARDIS HCT (HYDROCHLOROTHIAZIDE; TELMISARTAN), MICONAZOLE 3 (MICONAZOLE NITRATE), MICONAZOLE 3 COMBINATION PACK (MICONAZOLE NITRATE), MICONAZOLE 7 (MICONAZOLE NITRATE), MICONAZOLE 7 COMBINATION PACK (MICONAZOLE NITRATE), MICONAZOLE NITRATE (MICONAZOLE NITRATE), MICONAZOLE NITRATE COMBINATION PACK (MICONAZOLE NITRATE), MICORT-HC (HYDROCORTISONE ACETATE), MICRAININ (ASPIRIN; MEPROBAMATE), MICRO-K (POTASSIUM CHLORIDE), MICRO-K 10 (POTASSIUM CHLORIDE), MICRO-K LS (POTASSIUM CHLORIDE), MICRODERM (CHLORHEXIDINE GLUCONATE), MICROGESTIN 1.5/30 (ETHINYL ESTRADIOL; NORETHINDRONE ACETATE), MICROGESTIN 1/20 (ETHINYL ESTRADIOL; NORETHINDRONE ACETATE), MICROGESTIN FE 1.5/30 (ETHINYL ESTRADIOL; NORETHINDRONE ACETATE), MICROGESTIN FE 1/20 (ETHINYL ESTRADIOL; NORETHINDRONE ACETATE), MICROLITE (TECHNETIUM TC-99M ALBUMIN COLLOID KIT), MICRONASE (GLYBURIDE), MICRONOR (NORETHINDRONE), MICROSUL (SULFAMETHIZOLE), MICROZIDE (HYDROCHLOROTHIAZIDE), MIDAMOR (AMILORIDE HYDROCHLORIDE), MIDAZOLAM HYDROCHLORIDE (MIDAZOLAM HYDROCHLORIDE), MIDAZOLAM HYDROCHLORIDE PRESERVATIVE FREE (MIDAZOLAM HYDROCHLORIDE), MIDODRINE HYDROCHLORIDE (MIDODRINE HYDROCHLORIDE), MIDOL (IBUPROFEN), MIFEPREX (MIFEPRISTONE), MIGERGOT (CAFFEINE; ERGOTAMINE TARTRATE), MIGRANAL (DIHYDROERGOTAMINE MESYLATE), MILONTIN (PHENSUXIMIDE), MILOPHENE (CLOMIPHENE CITRATE), MILPREM-200 (ESTROGENS, CONJUGATED; MEPROBAMATE), MILPREM-400 (ESTROGENS, CONJUGATED; MEPROBAMATE), MILRINONE LACTATE (MILRINONE LACTATE), MILRINONE LACTATE IN 5% DEXTROSE IN PLASTIC CONTAINER (MILRINONE LACTATE), MILRINONE LACTATE IN DEXTROSE 5% IN PLASTIC CONTAINER (MILRINONE LACTATE), MILRINONE LACTOSE IN 5% DEXTROSE (MILRINONE LACTATE), MILTOWN (MEPROBAMATE), MINIPRESS (PRAZOSIN HYDROCHLORIDE), MINIPRESS XL (PRAZOSIN HYDROCHLORIDE), MINIRIN (DESMOPRESSIN ACETATE), MINITEC (TECHNETIUM TC-99M SODIUM PERTECHNETATE GENERATOR), MINITRAN (NITROGLYCERIN), MINIZIDE (POLYTHIAZIDE; PRAZOSIN HYDROCHLORIDE), MINOCIN (MINOCYCLINE HYDROCHLORIDE), MINOCYCLINE HYDROCHLORIDE (MINOCYCLINE HYDROCHLORIDE), MINODYL (MINOXIDIL), MINOXIDIL (MINOXIDIL), MINOXIDIL (FOR MEN) (MINOXIDIL), MINOXIDIL (FOR WOMEN) (MINOXIDIL), MINOXIDIL EXTRA STRENGTH (FOR MEN) (MINOXIDIL), MINTEZOL (THIABENDAZOLE), MIOCHOL (ACETYLCHOLINE CHLORIDE), MIOCHOL-E (ACETYLCHOLINE CHLORIDE), MIOSTAT (CARBACHOL), MIRADON (ANISINDIONE), MIRALAX (POLYETHYLENE GLYCOL 3350), MIRALUMA (TECHNETIUM TC-99M SESTAMIBI KIT), MIRAPEX (PRAMIPEXOLE DIHYDROCHLORIDE), MIRCERA (METHOXY POLYETHYLENE GLYCOL-EPOETIN BETA), MIRCETTE (DESOGESTREL; ETHINYL ESTRADIOL), MIRENA (LEVONORGESTREL), MIRTAZAPINE (MIRTAZAPINE), MISOPROSTOL (MISOPROSTOL), MITHRACIN (PLICAMYCIN), MITOMYCIN (MITOMYCIN), MITOXANTRONE (MITOXANTRONE HYDROCHLORIDE), MITOXANTRONE HYDROCHLORIDE (MITOXANTRONE HYDROCHLORIDE), MITOZYTREX (MITOMYCIN), MIVACRON (MIVACURIUM CHLORIDE), MIVACRON IN DEXTROSE 5% IN PLASTIC CONTAINER (MIVACURIUM CHLORIDE), MIXTARD HUMAN 70/30 (INSULIN RECOMBINANT PURIFIED HUMAN; INSULIN SUSP ISOPHANE SEMISYNTHETIC PURIFIED HUMAN), MOBAN (MOLINDONE HYDROCHLORIDE), MOBIC (MELOXICAM), MOCTANIN (MONOCTANOIN), MODAFINIL (MODAFINIL), MODERIL (RESCINNAMINE), MODICON 21 (ETHINYL ESTRADIOL; NORETHINDRONE), MODICON 28 (ETHINYL ESTRADIOL; NORETHINDRONE), MODRASTANE (TRILOSTANE), MODURETIC 5-50 (AMILORIDE HYDROCHLORIDE; HYDROCHLOROTHIAZIDE), MOEXIPRIL HYDROCHLORIDE (MOEXIPRIL HYDROCHLORIDE), MOEXIPRIL HYDROCHLORIDE AND HYDROCHLOROTHIAZIDE (HYDROCHLOROTHIAZIDE; MOEXIPRIL HYDROCHLORIDE), MOMETASONE FUROATE (MOMETASONE FUROATE), MONISTAT (MICONAZOLE), MONISTAT 1 COMBINATION PACK (MICONAZOLE NITRATE), MONISTAT 3 (MICONAZOLE NITRATE), MONISTAT 3 COMBINATION PACK (MICONAZOLE NITRATE), MONISTAT 3 COMBINATION PACK (PREFILLED) (MICONAZOLE NITRATE), MONISTAT 5 (MICONAZOLE NITRATE), MONISTAT 7 (MICONAZOLE NITRATE), MONISTAT 7 COMBINATION PACK (MICONAZOLE NITRATE), MONISTAT DUAL-PAK (MICONAZOLE NITRATE), MONISTAT-3 COMBINATION PACK (MICONAZOLE NITRATE), MONISTAT-DERM (MICONAZOLE NITRATE), MONOCID (CEFONICID SODIUM), MONODOX (DOXYCYCLINE), MONOKET (ISOSORBIDE MONONITRATE), MONOPRIL (FOSINOPRIL SODIUM), MONOPRIL-HCT (FOSINOPRIL SODIUM; HYDROCHLOROTHIAZIDE), MONUROL (FOSFOMYCIN TROMETHAMINE), MORPHINE SULFATE (MORPHINE SULFATE), MOTOFEN (ATROPINE SULFATE; DIFENOXIN HYDROCHLORIDE), MOTOFEN HALF-STRENGTH (ATROPINE SULFATE; DIFENOXIN HYDROCHLORIDE), MOTRIN (IBUPROFEN), MOTRIN IB (IBUPROFEN), MOTRIN MIGRAINE PAIN (IBUPROFEN), MOVIPREP (ASCORBIC ACID; POLYETHYLENE GLYCOL 3350; POTASSIUM CHLORIDE; SODIUM ASCORBATE; SODIUM CHLORIDE; SODIUM SULFATE), MOXAM (MOXALACTAM DISODIUM), MOXATAG (AMOXICILLIN), MOXIFLOXACIN HYDROCHLORIDE (MOXIFLOXACIN HYDROCHLORIDE), MPI DMSA KIDNEY REAGENT (TECHNETIUM TC-99M SUCCIMER KIT), MPI DTPA KIT—CHELATE (TECHNETIUM TC-99M PENTETATE KIT), MPI INDIUM DTPA IN 111 (INDIUM IN-111 PENTETATE DISODIUM), MPI KRYPTON 81M GENERATOR (KRYPTON, KR-81M), MPI STANNOUS DIPHOSPHONATE (TECHNETIUM TC-99M ETIDRONATE KIT), MS CONTIN (MORPHINE SULFATE), MUCINEX (GUAIFENESIN), MUCINEX D (GUAIFENESIN; PSEUDOEPHEDRINE HYDROCHLORIDE), MUCINEX DM (DEXTROMETHORPHAN HYDROBROMIDE; GUAIFENESIN), MUCOMYST (ACETYLCYSTEINE), MUCOMYST W/ ISOPROTERENOL (ACETYLCYSTEINE; ISOPROTERENOL HYDROCHLORIDE), MUCOSIL-10 (ACETYLCYSTEINE), MUCOSIL-20 (ACETYLCYSTEINE), MULTIFUGE (PIPERAZINE CITRATE), MULTIHANCE (GADOBENATE DIMEGLUMINE), MULTIHANCE MULTIPACK (GADOBENATE DIMEGLUMINE), MUPIROCIN (MUPIROCIN), MUSE (ALPROSTADIL), MUSTARGEN (MECHLORETHAMINE HYDROCHLORIDE), MUTAMYCIN (MITOMYCIN), MVC PLUS (ASCORBIC ACID; BIOTIN; CYANOCOBALAMIN; DEXPANTHENOL; ERGOCALCIFEROL; FOLIC ACID; NIACINAMIDE; PYRIDOXINE HYDROCHLORIDE; RIBOFLAVIN PHOSPHATE SODIUM; THIAMINE HYDROCHLORIDE; VITAMIN A; VITAMIN E), MYAMBUTOL (ETHAMBUTOL HYDROCHLORIDE), MYCAMINE (MICAFUNGIN SODIUM), MYCELEX (CLOTRIMAZOLE), MYCELEX-7 (CLOTRIMAZOLE), MYCELEX-7 COMBINATION PACK (CLOTRIMAZOLE), MYCELEX-G (CLOTRIMAZOLE), MYCHEL (CHLORAMPHENICOL), MYCHEL-S (CHLORAMPHENICOL SODIUM SUCCINATE), MYCIFRADIN (NEOMYCIN SULFATE), MYCITRACIN (BACITRACIN; NEOMYCIN SULFATE; POLYMYXIN B SULFATE), MYCO-TRIACET II (NYSTATIN; TRIAMCINOLONE ACETONIDE), MYCOBUTIN (RIFABUTIN), MYCOLOG-II (NYSTATIN; TRIAMCINOLONE ACETONIDE), MYCOSTATIN (NYSTATIN), MYDRIACYL (TROPICAMIDE), MYDRIAFAIR (TROPICAMIDE), MYFED (PSEUDOEPHEDRINE HYDROCHLORIDE; TRIPROLIDINE HYDROCHLORIDE), MYFORTIC (MYCOPHENOLIC ACID), MYIDYL (TRIPROLIDINE HYDROCHLORIDE), MYKACET (NYSTATIN; TRIAMCINOLONE ACETONIDE), MYKINAC (NYSTATIN), MYKROX (METOLAZONE), MYLAXEN (HEXAFLUORENIUM BROMIDE), MYLERAN (BUSULFAN), MYLOTARG (GEMTUZUMAB OZOGAMICIN), MYMETHAZINE FORTIS (PROMETHAZINE HYDROCHLORIDE), MYOBLOC (BOTULINUM TOXIN TYPE B), MYOSCINT (IMCIROMAB PENTETATE), MYOTONACHOL (BETHANECHOL CHLORIDE), MYOVIEW (TECHNETIUM TC-99M TETROFOSMIN KIT), MYOVIEW 30ML (TECHNETIUM TC-99M TETROFOSMIN KIT), MYOZYME (ALGLUCOSIDASE ALFA), MYPHETANE DC (BROMPHENIRAMINE MALEATE; CODEINE PHOSPHATE; PHENYLPROPANOLAMINE HYDROCHLORIDE), MYPHETANE DX (BROMPHENIRAMINE MALEATE; DEXTROMETHORPHAN HYDROBROMIDE; PSEUDOEPHEDRINE HYDROCHLORIDE), MYSOLINE (PRIMIDONE), MYTELASE (AMBENONIUM CHLORIDE), MYTREX A (NEOMYCIN SULFATE; TRIAMCINOLONE ACETONIDE), MYTREX F (NYSTATIN; TRIAMCINOLONE ACETONIDE), N.E.E. 1/35 21 (ETHINYL ESTRADIOL; NORETHINDRONE), N.E.E. 1/35 28 (ETHINYL ESTRADIOL; NORETHINDRONE), NABUMETONE (NABUMETONE), NADOLOL (NADOLOL), NADOLOL AND BENDROFLUMETHAZIDE (BENDROFLUMETHIAZIDE; NADOLOL), NADOLOL AND BENDROFLUMETHIAZIDE (BENDROFLUMETHIAZIDE; NADOLOL), NAFAZAIR (NAPHAZOLINE HYDROCHLORIDE), NAFCILLIN SODIUM (NAFCILLIN SODIUM), NAFTIN (NAFTIFINE HYDROCHLORIDE), NAGLAZYME (GALSULFASE), NALBUPHINE (NALBUPHINE HYDROCHLORIDE), NALBUPHINE HYDROCHLORIDE (NALBUPHINE HYDROCHLORIDE), NALFON (FENOPROFEN CALCIUM), NALFON 200 (FENOPROFEN CALCIUM), NALIDIXIC ACID (NALIDIXIC ACID), NALLPEN (NAFCILLIN SODIUM), NALLPEN IN PLASTIC CONTAINER (NAFCILLIN SODIUM), NALOXONE (NALOXONE HYDROCHLORIDE), NALOXONE HCL (NALOXONE HYDROCHLORIDE), NALOXONE HYDROCHLORIDE (NALOXONE HYDROCHLORIDE), NALOXONE HYDROCHLORIDE AND PENTAZOCAINE (NALOXONE HYDROCHLORIDE; PENTAZOCINE HYDROCHLORIDE), NALTREXONE HYDROCHLORIDE (NALTREXONE HYDROCHLORIDE), NAMENDA (MEMANTINE HYDROCHLORIDE), NANDROLONE DECANOATE (NANDROLONE DECANOATE), NANDROLONE PHENPROPIONATE (NANDROLONE PHENPROPIONATE), NAPHAZOLINE HYDROCHLORIDE (NAPHAZOLINE HYDROCHLORIDE), NAPHCON FORTE (NAPHAZOLINE HYDROCHLORIDE), NAPHCON-A (NAPHAZOLINE HYDROCHLORIDE; PHENIRAMINE MALEATE), NAPRELAN (NAPROXEN SODIUM), NAPROSYN (NAPROXEN), NAPROXEN (NAPROXEN), NAPROXEN SODIUM (NAPROXEN SODIUM), NAPROXEN SODIUM AND PSEUDOEPHEDRINE HYDROCHLORIDE (NAPROXEN SODIUM; PSEUDOEPHEDRINE HYDROCHLORIDE), NAQUA (TRICHLORMETHIAZIDE), NAQUIVAL (RESERPINE; TRICHLORMETHIAZIDE), NARCAN (NALOXONE HYDROCHLORIDE), NARDIL (PHENELZINE SULFATE), NAROPIN (ROPIVACAINE HYDROCHLORIDE MONOHYDRATE), NASACORT (TRIAMCINOLONE ACETONIDE), NASACORT AQ (TRIAMCINOLONE ACETONIDE), NASACORT HFA (TRIAMCINOLONE ACETONIDE), NASALCROM (CROMOLYN SODIUM), NASALIDE (FLUNISOLIDE), NASAREL (FLUNISOLIDE), NASCOBAL (CYANOCOBALAMIN), NASONEX (MOMETASONE FUROATE MONOHYDRATE), NATACYN (NATAMYCIN), NATEGLINIDE (NATEGLINIDE), NATRECOR (NESIRITIDE RECOMBINANT), NATURAL ESTROGENIC SUBSTANCE-ESTRONE (ESTRONE), NATURETIN-10 (BENDROFLUMETHIAZIDE), NATURETIN-2.5 (BENDROFLUMETHIAZIDE), NATURETIN-5 (BENDROFLUMETHIAZIDE), NAVANE (THIOTHIXENE), NAVANE (THIOTHIXENE HYDROCHLORIDE), NAVELBINE (VINORELBINE TARTRATE), NEBCIN (TOBRAMYCIN SULFATE), NEBUPENT (PENTAMIDINE ISETHIONATE), NEFAZODONE HYDROCHLORIDE (NEFAZODONE HYDROCHLORIDE), NEGGRAM (NALIDIXIC ACID), NEMBUTAL (PENTOBARBITAL), NEMBUTAL (PENTOBARBITAL SODIUM), NEMBUTAL SODIUM (PENTOBARBITAL SODIUM), NEO TECT KIT (TECHNETIUM TC-99M DEPREOTIDE), NEO-CORT-DOME (ACETIC ACID, GLACIAL; HYDROCORTISONE; NEOMYCIN SULFATE), NEO-CORT-DOME (HYDROCORTISONE; NEOMYCIN SULFATE), NEO-CORTEF (HYDROCORTISONE ACETATE; NEOMYCIN SULFATE), NEO-DELTA-CORTEF (NEOMYCIN SULFATE; PREDNISOLONE ACETATE), NEO-FRADIN (NEOMYCIN SULFATE), NEO-HYDELTRASOL (NEOMYCIN SULFATE; PREDNISOLONE SODIUM PHOSPHATE), NEO-MEDROL (METHYLPREDNISOLONE; NEOMYCIN SULFATE), NEO-MEDROL ACETATE (METHYLPREDNISOLONE ACETATE; NEOMYCIN SULFATE), NEO-POLYCIN (BACITRACIN ZINC; NEOMYCIN SULFATE; POLYMYXIN B SULFATE), NEO-POLYCIN (GRAMICIDIN; NEOMYCIN SULFATE; POLYMYXIN B SULFATE), NEO-RX (NEOMYCIN SULFATE), NEO-SYNALAR (FLUOCINOLONE ACETONIDE; NEOMYCIN SULFATE), NEOBIOTIC (NEOMYCIN SULFATE), NEODECADRON (DEXAMETHASONE SODIUM PHOSPHATE; NEOMYCIN SULFATE), NEOMYCIN & POLYMYXIN B SULFATES & BACITRACIN ZINC & HYDROCORTISONE (BACITRACIN ZINC; HYDROCORTISONE; NEOMYCIN SULFATE; POLYMYXIN B SULFATE), NEOMYCIN AND POLYMYXIN B SULFATE (NEOMYCIN SULFATE; POLYMYXIN B SULFATE), NEOMYCIN AND POLYMYXIN B SULFATE AND BACITRACIN ZINC (BACITRACIN ZINC; NEOMYCIN SULFATE;

POLYMYXIN B SULFATE), NEOMYCIN AND POLYMYXIN B SULFATES AND BACITRACIN ZINC (BACITRACIN ZINC; NEOMYCIN SULFATE; POLYMYXIN B SULFATE), NEOMYCIN AND POLYMYXIN B SULFATES AND DEXAMETHASONE (DEXAMETHASONE; NEOMYCIN SULFATE; POLYMYXIN B SULFATE), NEOMYCIN AND POLYMYXIN B SULFATES AND GRAMICIDIN (GRAMICIDIN; NEOMYCIN SULFATE; POLYMYXIN B SULFATE), NEOMYCIN AND POLYMYXIN B SULFATES AND HYDROCORTISONE (HYDROCORTISONE; NEOMYCIN SULFATE; POLYMYXIN B SULFATE), NEOMYCIN AND POLYMYXIN B SULFATES, BACITRACIN ZINC AND HYDROCORTISONE (BACITRACIN ZINC; HYDROCORTISONE; NEOMYCIN SULFATE; POLYMYXIN B SULFATE), NEOMYCIN SULFATE (NEOMYCIN SULFATE), NEOMYCIN SULFATE AND DEXAMETHASONE SODIUM PHOSPHATE (DEXAMETHASONE SODIUM PHOSPHATE; NEOMYCIN SULFATE), NEOMYCIN SULFATE AND POLYMYXIN B SULFATE GRAMICIDIN (GRAMICIDIN; NEOMYCIN SULFATE; POLYMYXIN B SULFATE), NEOMYCIN SULFATE, POLYMYXIN B SULFATE & HYDROCORTISONE (HYDROCORTISONE; NEOMYCIN SULFATE; POLYMYXIN B SULFATE), NEOMYCIN SULFATE-DEXAMETHASONE SODIUM PHOSPHATE (DEXAMETHASONE SODIUM PHOSPHATE; NEOMYCIN SULFATE), NEOMYCIN SULFATE-POLYMYXIN B SULFATE-HYDROCORTISONE (HYDROCORTISONE; NEOMYCIN SULFATE; POLYMYXIN B SULFATE), NEOMYCIN SULFATE-TRIAMCINOLONE ACETONIDE (NEOMYCIN SULFATE; TRIAMCINOLONE ACETONIDE), NEOPAP (ACETAMINOPHEN), NEOPASALATE (AMINOSALICYLATE SODIUM; AMINOSALICYLIC ACID), NEOPHAM 6.4% (AMINO ACIDS), NEOPROFEN (IBUPROFEN LYSINE), NEORAL (CYCLOSPORINE), NEOSAR (CYCLOPHOSPHAMIDE), NEOSCAN (GALLIUM CITRATE, GA-67), NEOSPORIN (BACITRACIN ZINC; NEOMYCIN SULFATE; POLYMYXIN B SULFATE), NEOSPORIN (GRAMICIDIN; NEOMYCIN SULFATE; POLYMYXIN B SULFATE), NEOSPORIN (NEOMYCIN SULFATE; POLYMYXIN B SULFATE), NEOSPORIN G.U. IRRIGANT (NEOMYCIN SULFATE; POLYMYXIN B SULFATE), NEOTHYLLINE (DYPHYLLINE), NEOTRIZINE (TRISULFAPYRIMIDINES (SULFADIAZINE; SULFAMERAZINE; SULFAMETHAZINE)), NEPHRAMINE 5.4% (AMINO ACIDS), NEPHROFLOW (IODOHIPPURATE SODIUM, I-123), NEPTAZANE (METHAZOLAMIDE), NESACAINE (CHLOROPROCAINE HYDROCHLORIDE), NESACAINE-MPF (CHLOROPROCAINE HYDROCHLORIDE), NETROMYCIN (NETILMICIN SULFATE), NEULASTA (PEGFILGRASTIM), NEUMEGA (OPRELVEKIN), NEUPOGEN (FILGRASTIM), NEUPRO (ROTIGOTINE), NEURAMATE (MEPROBAMATE), NEUROLITE (TECHNETIUM TC-99M BICISATE KIT), NEURONTIN (GABAPENTIN), NEUTREXIN (TRIMETREXATE GLUCURONATE), NEVANAC (NEPAFENAC), NEVIRAPINE (NEVIRAPINE), NEVIS (NORETHINDRONE ACETATE; ETHINYL ESTRADIOL), NEXAVAR (SORAFENIB TOSYLATE), NEXIUM (ESOMEPRAZOLE MAGNESIUM), NEXIUM IV (ESOMEPRAZOLE SODIUM), NIACIN (NIACIN), NIACOR (NIACIN), NIASPAN (NIACIN), NIASPAN TITRATION STARTER PACK (NIACIN), NICARDIPINE HYDROCHLORIDE (NICARDIPINE HYDROCHLORIDE), NICLOCIDE (NICLOSAMIDE), NICODERM CQ (NICOTINE), NICOLAR (NIACIN), NICORETTE (NICOTINE POLACRILEX), NICORETTE (MINT) (NICOTINE POLACRILEX), NICOTINE (NICOTINE), NICOTINE POLACRILEX (NICOTINE POLACRILEX), NICOTROL (NICOTINE), NIFEDIPINE (NIFEDIPINE), NILANDRON (NILUTAMIDE), NILSTAT (NYSTATIN), NIMBEX (CISATRACURIUM BESYLATE), NIMBEX PRESERVATIVE FREE (CISATRACURIUM BESYLATE), NIMODIPINE (NIMODIPINE), NIMOTOP (NIMODIPINE), NIPENT (PENTOSTATIN), NIPRIDE (SODIUM NITROPRUSSIDE), NIRAVAM (ALPRAZOLAM), NITRO IV (NITROGLYCERIN), NITRO-BID (NITROGLYCERIN), NITRO-DUR (NITROGLYCERIN), NITROFURANTOIN (NITROFURANTOIN), NITROFURANTOIN (NITROFURANTOIN, MACROCRYSTALLINE), NITROFURANTOIN (MONOHYDRATE/MACROCRYSTALS) (NITROFURANTOIN; NITROFURANTOIN, MACROCRYSTALLINE), NITROFURANTOIN MACROCRYSTALLINE (NITROFURANTOIN, MACROCRYSTALLINE), NITROFURAZONE (NITROFURAZONE), NITROGLYCERIN (NITROGLYCERIN), NITROGLYCERIN IN DEXTROSE 5% (NITROGLYCERIN), NITROL (NITROGLYCERIN), NITROLINGUAL (NITROGLYCERIN), NITROLINGUAL PUMPSPRAY (NITROGLYCERIN), NITROMIST (NITROGLYCERIN), NITRONAL (NITROGLYCERIN), NITROPRESS (SODIUM NITROPRUSSIDE), NITROSTAT (NITROGLYCERIN), NIX (PERMETHRIN), NIZATIDINE (NIZATIDINE), NIZORAL (KETOCONAZOLE), NIZORAL A-D (KETOCONAZOLE), NOGENIC HC (HYDROCORTISONE), NOLUDAR (METHYPRYLON), NOLVADEX (TAMOXIFEN CITRATE), NOR-QD (NORETHINDRONE), NORCEPT-E 1/35 21 (ETHINYL ESTRADIOL; NORETHINDRONE), NORCEPT-E 1/35 28 (ETHINYL ESTRADIOL; NORETHINDRONE), NORCET (ACETAMINOPHEN; HYDROCODONE BITARTRATE), NORCO (ACETAMINOPHEN; HYDROCODONE BITARTRATE), NORCURON (VECURONIUM BROMIDE), NORDETTE-21 (ETHINYL ESTRADIOL; LEVONORGESTREL), NORDETTE-28 (ETHINYL ESTRADIOL; LEVONORGESTREL), NORDITROPIN (SOMATROPIN RECOMBINANT), NORDITROPIN NORDIFLEX (SOMATROPIN RECOMBINANT), NOREPINEPHRINE BITARTRATE (NOREPINEPHRINE BITARTRATE), NORETHIN 1/35E-21 (ETHINYL ESTRADIOL; NORETHINDRONE), NORETHIN 1/35E-28 (ETHINYL ESTRADIOL; NORETHINDRONE), NORETHIN 1/50M-21 (MESTRANOL; NORETHINDRONE), NORETHIN 1/50M-28 (MESTRANOL; NORETHINDRONE), NORETHINDRONE ACETATE (NORETHINDRONE ACETATE), NORETHINDRONE ACETATE AND ETHINYL ESTRADIOL AND FERROUS FUMARATE (ETHINYL ESTRADIOL; NORETHINDRONE ACETATE), NORETHINDRONE AND ETHINYL ESTRADIOL (ETHINYL ESTRADIOL; NORETHINDRONE), NORETHINDRONE AND ETHINYL ESTRADIOL (10/11) (ETHINYL ESTRADIOL; NORETHINDRONE), NORETHINDRONE AND ETHINYL ESTRADIOL (7/14) (ETHINYL ESTRADIOL; NORETHINDRONE), NORETHINDRONE AND MESTRANOL (MESTRANOL; NORE-

THINDRONE), NORFLEX (ORPHENADRINE CITRATE), NORFLOXACIN (NORFLOXACIN), NORGESIC (ASPIRIN; CAFFEINE; ORPHENADRINE CITRATE), NORGESIC FORTE (ASPIRIN; CAFFEINE; ORPHENADRINE CITRATE), NORGESTIMATE AND ETHINYL ESTRADIOL (ETHINYL ESTRADIOL; NORGESTIMATE), NORGESTIMATE; ETHINYL ESTRADIOL (NORGESTIMATE; ETHINYL ESTRADIOL), NORINYL (MESTRANOL; NORETHINDRONE), NORINYL 1+35 21-DAY (ETHINYL ESTRADIOL; NORETHINDRONE), NORINYL 1+35 28-DAY (ETHINYL ESTRADIOL; NORETHINDRONE), NORINYL 1+50 21-DAY (MESTRANOL; NORETHINDRONE), NORINYL 1+50 28-DAY (MESTRANOL; NORETHINDRONE), NORINYL 1+80 21-DAY (MESTRANOL; NORETHINDRONE), NORINYL 1+80 28-DAY (MESTRANOL; NORETHINDRONE), NORISODRINE (ISOPROTERENOL SULFATE), NORISODRINE AEROTROL (ISOPROTERENOL HYDROCHLORIDE), NORITATE (METRONIDAZOLE), NORLESTRIN 21 1/50 (ETHINYL ESTRADIOL; NORETHINDRONE ACETATE), NORLESTRIN 21 2.5/50 (ETHINYL ESTRADIOL; NORETHINDRONE ACETATE), NORLESTRIN 28 1/50 (ETHINYL ESTRADIOL; NORETHINDRONE ACETATE), NORLESTRIN FE 1/50 (ETHINYL ESTRADIOL; FERROUS FUMARATE; NORETHINDRONE ACETATE), NORLESTRIN FE 2.5/50 (ETHINYL ESTRADIOL; FERROUS FUMARATE; NORETHINDRONE ACETATE), NORLUTATE (NORETHINDRONE ACETATE), NORLUTIN (NORETHINDRONE), NORMIFLO (ARDEPARIN SODIUM), NORMOCARB HF 25 (MAGNESIUM CHLORIDE; SODIUM BICARBONATE; SODIUM CHLORIDE), NORMOCARB HF 35 (MAGNESIUM CHLORIDE; SODIUM BICARBONATE; SODIUM CHLORIDE), NORMODYNE (LABETALOL HYDROCHLORIDE), NORMOSOL-M AND DEXTROSE 5% IN PLASTIC CONTAINER (DEXTROSE; MAGNESIUM ACETATE; POTASSIUM ACETATE; SODIUM CHLORIDE), NORMOSOL-R AND DEXTROSE 5% IN PLASTIC CONTAINER (DEXTROSE; MAGNESIUM CHLORIDE; POTASSIUM CHLORIDE; SODIUM ACETATE; SODIUM CHLORIDE; SODIUM GLUCONATE), NORMOSOL-R IN PLASTIC CONTAINER (MAGNESIUM CHLORIDE; POTASSIUM CHLORIDE; SODIUM ACETATE; SODIUM CHLORIDE; SODIUM GLUCONATE), NORMOZIDE (HYDROCHLOROTHIAZIDE; LABETALOL HYDROCHLORIDE), NOROXIN (NORFLOXACIN), NORPACE (DISOPYRAMIDE PHOSPHATE), NORPACE CR (DISOPYRAMIDE PHOSPHATE), NORPLANT (LEVONORGESTREL), NORPLANT II (LEVONORGESTREL), NORPLANT SYSTEM IN PLASTIC CONTAINER (LEVONORGESTREL), NORPRAMIN (DESIPRAMINE HYDROCHLORIDE), NORQUEST FE (ETHINYL ESTRADIOL; FERROUS FUMARATE; NORETHINDRONE), NORTREL 0.5/35-21 (ETHINYL ESTRADIOL; NORETHINDRONE), NORTREL 0.5/35-28 (ETHINYL ESTRADIOL; NORETHINDRONE), NORTREL 1/35-21 (ETHINYL ESTRADIOL; NORETHINDRONE), NORTREL 1/35-28 (ETHINYL ESTRADIOL; NORETHINDRONE), NORTREL 7/7/7 (ETHINYL ESTRADIOL; NORETHINDRONE), NORTRIPTYLINE HYDROCHLORIDE (NORTRIPTYLINE HYDROCHLORIDE), NORVASC (AMLODIPINE BESYLATE), NORVIR (RITONAVIR), NOVAFED (PSEUDOEPHEDRINE HYDROCHLORIDE), NOVAMINE 11.4% (AMINO ACIDS), NOVAMINE 15% (AMINO ACIDS), NOVAMINE 15% SULFITE FREE IN PLASTIC CONTAINER (AMINO ACIDS), NOVAMINE 8.5% (AMINO ACIDS), NOVANTRONE (MITOXANTRONE HYDROCHLORIDE), NOVOCAIN (PROCAINE HYDROCHLORIDE), NOVOLIN 70/30 (INSULIN RECOMBINANT HUMAN; INSULIN SUSP ISOPHANE RECOMBINANT HUMAN), NOVOLIN 70/30 (INSULIN RECOMBINANT PURIFIED HUMAN; INSULIN SUSP ISOPHANE SEMISYNTHETIC PURIFIED HUMAN), NOVOLIN L (INSULIN ZINC SUSP RECOMBINANT HUMAN), NOVOLIN L (INSULIN ZINC SUSP SEMISYNTHETIC PURIFIED HUMAN), NOVOLIN N (INSULIN SUSP ISOPHANE RECOMBINANT HUMAN), NOVOLIN N (INSULIN SUSP ISOPHANE SEMISYNTHETIC PURIFIED HUMAN), NOVOLIN R (INSULIN RECOMBINANT HUMAN), NOVOLIN R (INSULIN RECOMBINANT PURIFIED HUMAN), NOVOLOG (INSULIN ASPART RECOMBINANT), NOVOLOG MIX 70/30 (INSULIN ASPART PROTAMINE RECOMBINANT; INSULIN ASPART RECOMBINANT), NOVOTHYROX (LEVOTHYROXINE SODIUM), NOVRAD (LEVOPROPDXYPHENE NAPSYLATE, ANHYDROUS), NOXAFIL (POSACONAZOLE), NPH ILETIN I (BEEF-PORK) (INSULIN SUSP ISOPHANE BEEF/PORK), NPH ILETIN II (INSULIN SUSP ISOPHANE PURIFIED BEEF), NPH ILETIN II (PORK) (INSULIN SUSP ISOPHANE PURIFIED PORK), NPH INSULIN (INSULIN SUSP ISOPHANE BEEF), NPH PURIFIED PORK ISOPHANE INSULIN (INSULIN SUSP ISOPHANE PURIFIED PORK), NUBAIN (NALBUPHINE HYDROCHLORIDE), NULYTELY (POLYETHYLENE GLYCOL 3350; POTASSIUM CHLORIDE; SODIUM BICARBONATE; SODIUM CHLORIDE), NULYTELY-FLAVORED (POLYETHYLENE GLYCOL 3350; POTASSIUM CHLORIDE; SODIUM BICARBONATE; SODIUM CHLORIDE), NUMORPHAN (OXYMORPHONE HYDROCHLORIDE), NUPRIN (IBUPROFEN), NUROMAX (DOXACURIUM CHLORIDE), NUTRACORT (HYDROCORTISONE), NUTRESTORE (GLUTAMINE), NUTRILIPID 10% (SOYBEAN OIL), NUTRILIPID 20% (SOYBEAN OIL), NUTROPIN (SOMATROPIN [rDNA origin]), NUTROPIN (SOMATROPIN RECOMBINANT), NUTROPIN AQ (SOMATROPIN RECOMBINANT), NUTROPIN AQ PEN (SOMATROPIN RECOMBINANT), NUTROPIN DEPOT (SOMATROPIN RECOMBINANT), NUVARING (ETHINYL ESTRADIOL; ETONOGESTREL), NUVIGIL (ARMODAFINIL), NYDRAZID (ISONIAZID), NYSERT (NYSTATIN), NYSTAFORM (CLIOQUINOL; NYSTATIN), NYSTATIN (NYSTATIN), NYSTATIN AND TRIAMCINOLONE ACETONIDE (NYSTATIN; TRIAMCINOLONE ACETONIDE), NYSTATIN-TRIAMCINOLONE ACETONIDE (NYSTATIN; TRIAMCINOLONE ACETONIDE), NYSTEX (NYSTATIN), NYSTOP (NYSTATIN), OBESTIN-30 (PHENTERMINE HYDROCHLORIDE), OBY-TRIM (PHENTERMINE HYDROCHLORIDE), OCL (POLYETHYLENE GLYCOL 3350; POTASSIUM CHLORIDE; SODIUM BICARBONATE; SODIUM CHLORIDE; SODIUM SULFATE), OCTOCAINE (EPINEPHRINE; LIDOCAINE HYDROCHLORIDE), OCTREOSCAN (INDIUM IN-111 PENTETREOTIDE KIT), OCTREOTIDE ACETATE (OCTREOTIDE ACETATE), OCTREOTIDE ACETATE (PRESERVA- TIVE FREE) (OCTREOTIDE ACETATE), OCUCLEAR (OXYMETAZOLINE HYDROCHLORIDE), OCUFEN (FLURBIPROFEN SODIUM), OCUFLOX (OFLOXACIN), OCUMYCIN (BACITRACIN ZINC; POLYMYXIN B SULFATE), OCUPRESS (CARTEOLOL HYDROCHLORIDE), OCUSERT PILO-20 (PILOCARPINE), OCUSERT PILO-40 (PILOCARPINE), OCUSULF-10 (SULFACETAMIDE SODIUM), OCUSULF-30 (SULFACETAMIDE SODIUM), OFLOXACIN (OFLOXACIN), OGEN (ESTROPIPATE), OGEN 0.625 (ESTROPIPATE), OGEN 1.25 (ESTROPIPATE), OGEN 2.5 (ESTROPIPATE), OGEN 5 (ESTROPIPATE), OGESTREL 0.5/50-21 (ETHINYL ESTRADIOL; NORGESTREL), OGESTREL 0.5/50-28 (ETHINYL ESTRADIOL; NORGESTREL), OLANZAPINE (OLANZAPINE), OLANZAPINE; FLUOXETINE HYDROCHLORIDE (OLANZAPINE; FLUOXETINE HYDROCHLORIDE), OLMESARTAN MEDOXOMIL (OLMESARTAN MEDOXOMIL), OLOPATADINE HYDROCHLORIDE (OLOPATADINE HYDROCHLORIDE), OLUX (CLOBETASOL PROPIONATE), OLUX E (CLOBETASOL PROPIONATE), OMACOR (OMEGA-3ACID ETHYL ESTERS), OMEPRAZOLE (OMEPRAZOLE), OMNARIS (CICLESONIDE), OMNICEF (CEFDINIR), OMNIPAQUE 140 (IOHEXOL), OMNIPAQUE 180 (IOHEXOL), OMNIPAQUE 210 (IOHEXOL), OMNIPAQUE 240 (IOHEXOL), OMNIPAQUE 300 (IOHEXOL), OMNIPAQUE 350 (IOHEXOL), OMNIPAQUE 70 (IOHEXOL), OMNIPEN (AMPICILLIN) (AMPICILLIN/ AMPICILLIN TRIHYDRATE), OMNIPEN-N (AMPICILLIN SODIUM), OMNIPRED (PREDNISOLONE ACETATE), OMNISCAN (GADODIAMIDE), OMNITROPE (SOMATROPIN RECOMBINANT), ONAMAST (PHENTERMINE HYDROCHLORIDE), ONCASPAR (PEGASPARGASE), ONCOVIN (VINCRISTINE SULFATE), ONDANSETRON (ONDANSETRON), ONDANSETRON (ONDANSETRON HYDROCHLORIDE), ONDANSETRON HYDROCHLORIDE (ONDANSETRON HYDROCHLORIDE), ONDANSETRON HYDROCHLORIDE AND DEXTROSE IN PLASTIC CONTAINER (ONDANSETRON HYDROCHLORIDE), ONDANSETRON HYDROCHLORIDE AND SODIUM CHLORIDE IN PLASTIC CONTAINER (ONDANSETRON HYDROCHLORIDE), ONDANSETRON HYDROCHLORIDE PRESERVATIVE FREE (ONDANSETRON HYDROCHLORIDE), ONTAK (DENILEUKIN DIFTITOX), OPANA (OXYMORPHONE HYDROCHLORIDE), OPANA ER (OXYMORPHONE HYDROCHLORIDE), OPCON (NAPHAZOLINE HYDROCHLORIDE), OPCON-A (NAPHAZOLINE HYDROCHLORIDE; PHENIRAMINE MALEATE), OPHTHAINE (PROPARACAINE HYDROCHLORIDE), OPHTHETIC (PROPARACAINE HYDROCHLORIDE), OPHTHOCHLOR (CHLORAMPHENICOL), OPHTHOCORT (CHLORAMPHENICOL; HYDROCORTISONE ACETATE; POLYMYXIN B SULFATE), OPTICROM (CROMOLYN SODIUM), OPTIMARK (GADOVERSETAMIDE), OPTIMARK IN PLASTIC CONTAINER (GADOVERSETAMIDE), OPTIMINE (AZATADINE MALEATE), OPTIPRANOLOL (METIPRANOLOL HYDROCHLORIDE), OPTIRAY 160 (IOVERSOL), OPTIRAY 240 (IOVERSOL), OPTIRAY 300 (IOVERSOL), OPTIRAY 320 (IOVERSOL), OPTIRAY 350 (IOVERSOL), OPTISON (ALBUMIN HUMAN), OPTIVAR (AZELASTINE HYDROCHLORIDE), OPTOMYCIN (CHLORAMPHENICOL), ORATESTRYL (FLUOXYMESTERONE), ORABASE HCA (HYDROCORTISONE ACETATE), ORACEA (DOXYCYCLINE), ORACORT (TRIAMCINOLONE ACETONIDE), ORAGRAFIN CALCIUM (IPODATE CALCIUM), ORAGRAFIN SODIUM (IPODATE SODIUM), ORALONE (TRIAMCINOLONE ACETONIDE), ORAMORPH SR (MORPHINE SULFATE), ORAP (PIMOZIDE), ORAPRED (PREDNISOLONE SODIUM PHOSPHATE), ORAPRED ODT (PREDNISOLONE SODIUM PHOSPHATE), ORAQIX (LIDOCAINE; PRILOCAINE), ORASONE (PREDNISONE), ORAVERSE (PHENTOLAMINE MESYLATE), ORENCIA (ABATACEPT), ORETIC (HYDROCHLOROTHIAZIDE), ORETICYL 25 (DESERPIDINE; HYDROCHLOROTHIAZIDE), ORETICYL 50 (DESERPIDINE; HYDROCHLOROTHIAZIDE), ORETICYL FORTE (DESERPIDINE; HYDROCHLOROTHIAZIDE), ORETON (METHYLTESTOSTERONE), ORETON METHYL (METHYLTESTOSTERONE), ORFADIN (NITISINONE), ORGARAN (DANAPAROID SODIUM), ORGATRAX (HYDROXYZINE HYDROCHLORIDE), ORINASE (TOLBUTAMIDE), ORINASE DIAGNOSTIC (TOLBUTAMIDE SODIUM), ORLAAM (LEVOMETHADYL ACETATE HYDROCHLORIDE), ORLEX (ACETIC ACID, GLACIAL), ORLEX HC (ACETIC ACID, GLACIAL; HYDROCORTISONE), ORNADE (CHLORPHENIRAMINE MALEATE; PHENYLPROPANOLAMINE HYDROCHLORIDE), ORNIDYL (EFLORNITHINE HYDROCHLORIDE), ORPHENADRINE CITRATE (ORPHENADRINE CITRATE), ORPHENADRINE CITRATE, ASPIRIN, AND CAFFEINE (ASPIRIN; CAFFEINE; ORPHENADRINE CITRATE), ORPHENGESIC (ASPIRIN; CAFFEINE; ORPHENADRINE CITRATE), ORPHENGESIC FORTE (ASPIRIN; CAFFEINE; ORPHENADRINE CITRATE), ORTHO CYCLEN-21 (ETHINYL ESTRADIOL; NORGESTIMATE), ORTHO CYCLEN-28 (ETHINYL ESTRADIOL; NORGESTIMATE), ORTHO EVRA (ETHINYL ESTRADIOL; NORELGESTROMIN), ORTHO TRI-CYCLEN (ETHINYL ESTRADIOL; NORGESTIMATE), ORTHO TRI-CYCLEN 21 (ETHINYL ESTRADIOL; NORGESTIMATE), ORTHO TRI-CYCLEN 28 (ETHINYL ESTRADIOL; NORGESTIMATE), ORTHO TRI-CYCLEN LO (ETHINYL ESTRADIOL; NORGESTIMATE), ORTHO-CEPT (DESOGESTREL; ETHINYL ESTRADIOL), ORTHO-EST (ESTROPIPATE), ORTHO-NOVUM 1/35-21 (ETHINYL ESTRADIOL; NORETHINDRONE), ORTHO-NOVUM 1/35-28 (ETHINYL ESTRADIOL; NORETHINDRONE, ORTHO-NOVUM 1/50 21 (MESTRANOL; NORETHINDRONE), ORTHO-NOVUM 1/50 28 (MESTRANOL; NORETHINDRONE), ORTHO-NOVUM 1/80 21 (MESTRANOL; NORETHINDRONE), ORTHO-NOVUM 1/80 28 (MESTRANOL; NORETHINDRONE), ORTHO-NOVUM 10-21 (MESTRANOL; NORETHINDRONE), ORTHO-NOVUM 10/11-21 (ETHINYL ESTRADIOL; NORETHINDRONE), ORTHO-NOVUM 10/11-28 (ETHINYL ESTRADIOL; NORETHINDRONE), ORTHO-NOVUM 2-21 (MESTRANOL; NORETHINDRONE), ORTHO-NOVUM 7/14-21 (ETHINYL ESTRADIOL; NORETHINDRONE), ORTHO-NOVUM 7/14-28 (ETHINYL ESTRADIOL; NORETHINDRONE), ORTHO-NOVUM 7/7/7-21 (ETHINYL ESTRADIOL; NORETHINDRONE), ORTHO-NOVUM 7/7/7-28 (ETHINYL ESTRADIOL; NORETHINDRONE), ORTHOCLONE OKT3 (MUROMONAB-CD3), ORUDIS (KETOPROFEN), ORUDIS KT (KETOPROFEN), ORUVAIL (KETOPROFEN), ORVATEN (MIDODRINE HYDROCHLORIDE), OSMITROL 10% IN WATER (MANNITOL), OSMITROL 10% IN WATER IN PLASTIC CONTAINER (MANNITOL), OSMITROL 15% IN WATER (MANNITOL), OSMITROL 15% IN WATER IN PLASTIC CONTAINER (MANNITOL), OSMITROL 20% IN WATER (MANNITOL), OSMITROL 20% IN WATER IN PLASTIC CONTAINER (MANNITOL), OSMITROL 5% IN WATER (MANNITOL), OSMITROL 5% IN WATER IN PLASTIC CONTAINER (MANNITOL), OSMOPREP (SODIUM PHOSPHATE, DIBASIC, ANHYDROUS; SODIUM PHOSPHATE, MONOBASIC, MONOHYDRATE), OSMOVIST 190 (IOTROLAN), OSMOVIST 240 (IOTROLAN), OSTEOLITE (TECHNETIUM TC-99M MEDRONATE KIT), OSTEOSCAN (TECHNETIUM TC-99M ETIDRONATE KIT), OTICAIR (HYDROCORTISONE; NEOMYCIN SULFATE; POLYMYXIN B SULFATE), OTOBIONE (HYDROCORTISONE; NEOMYCIN SULFATE; POLYMYXIN B SULFATE), OTOBIOTIC (HYDROCORTISONE; POLYMYXIN B SULFATE), OTOCORT (HYDROCORTISONE; NEOMYCIN SULFATE; POLYMYXIN B SULFATE), OVCON-35 (ETHINYL ESTRADIOL; NORETHINDRONE), OVCON-50 (ETHINYL ESTRADIOL; NORETHINDRONE), OVIDE (MALATHION), OVIDREL (CHORIOGONADOTROPIN ALFA), OVRAL (ETHINYL ESTRADIOL; NORGESTREL), OVRAL-28 (ETHINYL ESTRADIOL; NORGESTREL), OVRETTE (NORGESTREL), OVULEN (ETHYNODIOL DIACETATE; MESTRANOL), OVULEN-21 (ETHYNODIOL DIACETATE; MESTRANOL), OVULEN-28 (ETHYNODIOL DIACETATE; MESTRANOL), OXACILLIN SODIUM (OXACILLIN SODIUM), OXANDRIN (OXANDROLONE), OXANDROLONE (OXANDROLONE), OXAPROZIN (OXAPROZIN), OXAZEPAM (OXAZEPAM), OXCARBAZEPINE (OXCARBAZEPINE), OXILAN-300 (IOXILAN), OXILAN-350 (IOXILAN), OXISTAT (OXICONAZOLE NITRATE), OXSORALEN (METHOXSALEN), OXSORALEN-ULTRA (METHOXSALEN), OXTRIPHYLLINE (OXTRIPHYLLINE), OXTRIPHYLLINE PEDIATRIC (OXTRIPHYLLINE), OXY-KESSO-TETRA (OXYTETRACYCLINE HYDROCHLORIDE), OXYBUTYNIN CHLORIDE (OXYBUTYNIN CHLORIDE), OXYCET (ACETAMINOPHEN; OXYCODONE HYDROCHLORIDE), OXYCODONE 2.5/APAP 500 (ACETAMINOPHEN; OXYCODONE HYDROCHLORIDE), OXYCODONE 5/APAP 500 (ACETAMINOPHEN; OXYCODONE HYDROCHLORIDE), OXYCODONE AND ACETAMINOPHEN (ACETAMINOPHEN; OXYCODONE HYDROCHLORIDE), OXYCODONE AND ASPIRIN (ASPIRIN; OXYCODONE HYDROCHLORIDE; OXYCODONE TEREPHTHALATE), OXYCODONE AND ASPIRIN (HALF-STRENGTH) (ASPIRIN; OXYCODONE HYDROCHLORIDE; OXYCODONE TEREPHTHALATE), OXYCODONE HYDROCHLORIDE (OXYCODONE HYDROCHLORIDE), OXYCODONE HYDROCHLORIDE AND IBUPROFEN (IBUPROFEN; OXYCODONE HYDROCHLORIDE), OXYCONTIN (OXYCODONE HYDROCHLORIDE), OXYLONE (FLUOROMETHOLONE), OXYPHENBUTAZONE (OXYPHENBUTAZONE), OXYTETRACYCLINE HYDROCHLORIDE (OXYTETRACYCLINE HYDROCHLORIDE), OXYTOCIN (OXYTOCIN), OXYTOCIN 10 USP UNITS IN DEXTROSE 5% (OXYTOCIN), OXYTOCIN 20 USP UNITS IN DEXTROSE 5% (OXYTOCIN), OXYTOCIN 5 USP UNITS IN DEXTROSE 5% (OXYTOCIN), OXYTROL (OXYBUTYIN), OXYTROL (OXYBUTYNIN), P.A.S. SODIUM (AMINOSALICYLATE SODIUM), PACERONE (AMIODARONE HYDROCHLORIDE), PACLITAXEL (PACLITAXEL), PAGITANE (CYCRIMINE HYDROCHLORIDE), PALLADONE (HYDROMORPHONE HYDROCHLORIDE), PAMELOR (NORTRIPTYLINE HYDROCHLORIDE), PAMIDRONATE DISODIUM (PAMIDRONATE DISODIUM), PAMINE (METHSCOPOLAMINE BROMIDE), PAMINE FORTE (METHSCOPOLAMINE BROMIDE), PANCURONIUM (PANCURONIUM BROMIDE), PANCURONIUM BROMIDE (PANCURONIUM BROMIDE), PANDEL (HYDROCORTISONE PROBUTATE), PANHEPRIN (HEPARIN SODIUM), PANIXINE DISPERDOSE (CEPHALEXIN), PANMYCIN (TETRACYCLINE HYDROCHLORIDE), PANRETIN (ALITRETINOIN), PANTOPAQUE (IOPHENDYLATE), PANTOPRAZOLE (PANTOPRAZOLE SODIUM), PANTOPRAZOLE SODIUM (PANTOPRAZOLE SODIUM), PANWARFIN (WARFARIN SODIUM), PAPA-DEINE #3 (ACETAMINOPHEN; CODEINE PHOSPHATE), PAPA-DEINE #4 (ACETAMINOPHEN; CODEINE PHOSPHATE), PARACAINE (PROPARACAINE HYDROCHLORIDE), PARACORT (PREDNISONE), PARADIONE (PARAMETHADIONE), PARAFLEX (CHLORZOXAZONE), PARAFON FORTE DSC (CHLORZOXAZONE), PARAGARD T 380A (COPPER), PARAPLATIN (CARBOPLATIN), PARASAL (AMINOSALICYLIC ACID), PARASAL SODIUM (AMINOSALICYLATE SODIUM), PARATHAR (TERIPARATIDE ACETATE), PARCOPA (CARBIDOPA; LEVODOPA), PAREDRINE (HYDROXYAMPHETAMINE HYDROBROMIDE), PAREMYD (HYDROXYAMPHETAMINE HYDROBROMIDE; TROPICAMIDE), PARLODEL (BROMOCRIPTINE MESYLATE), PARNATE (TRANYLCYPROMINE SULFATE), PAROMOMYCIN SULFATE (PAROMOMYCIN SULFATE), PAROXETINE HYDROCHLORIDE (PAROXETINE HYDROCHLORIDE), PARSIDOL (ETHOPROPAZINE HYDROCHLORIDE), PASER (AMINOSALICYLIC ACID), PASKALIUM (POTASSIUM AMINOSALICYLATE), PATADAY (OLOPATADINE HYDROCHLORIDE), PATANASE (OLOPATADINE HYDROCHLORIDE), PATANOL (OLOPATADINE HYDROCHLORIDE), PATHILON (TRIDIHEXETHYL CHLORIDE), PATHOCIL (DICLOXACILLIN SODIUM), PAVULON (PANCURONIUM BROMIDE), PAXIL (PAROXETINE HYDROCHLORIDE), PAXIL CR (PAROXETINE HYDROCHLORIDE), PAXIPAM (HALAZEPAM), PBZ (TRIPELENNAMINE CITRATE), PBZ (TRIPELENNAMINE HYDROCHLORIDE), PBZ-SR (TRIPELENNAMINE HYDROCHLORIDE), PCE (ERYTHROMYCIN), PEDIAMYCIN (ERYTHROMYCIN ETHYLSUCCINATE), PEDIAMYCIN 400 (ERYTHROMYCIN ETHYLSUCCINATE), PEDIAPRED (PREDNISOLONE SODIUM PHOSPHATE), PEDIATRIC ADVIL (IBUPROFEN), PEDIATRIC LTA KIT (LIDOCAINE HYDROCHLORIDE), PEDIAZOLE (ERYTHROMYCIN ETHYLSUCCINATE; SULFISOXAZOLE ACETYL), PEDIOTIC (HYDROCORTISONE; NEOMYCIN SULFATE; POLYMYXIN B SULFATE), PEG-LYTE (POLYETHYLENE GLYCOL 3350; POTASSIUM CHLORIDE; SODIUM BICARBONATE; SODIUM CHLORIDE; SODIUM SULFATE, ANHYDROUS), PEGANONE (ETHOTOIN), PEGASYS (PEGINTERFERON ALFA 2A), PEGINTERFERON (PEGINTERFERON ALFA-2A; RIBAVIRIN), PEGINTRON (PEGINTERFERON ALFA-2B), PEGINTRON/REBETOL COMBO PACK (PEGINTERFERON ALFA-2B; RIBAVIRIN), PEMOLINE (PEMOLINE), PEN-VEE K (PENICILLIN V POTASSIUM), PENAPAR-VK (PENICILLIN V POTASSIUM), PENBRITIN (AMPICILLIN/AMPICILLIN TRIHYDRATE), PENBRITIN-S (AMPICILLIN SODIUM), PENECORT (HYDROCORTISONE), PENETREX (ENOXACIN), PENICILLIN (PENICILLIN G POTASSIUM), PENICILLIN G POTASSIUM (PENICILLIN G POTASSIUM), PENICILLIN G POTASSIUM IN PLASTIC CONTAINER (PENICILLIN G POTASSIUM), PENICILLIN G PROCAINE (PENICILLIN G PROCAINE), PENICILLIN G SODIUM (PENICILLIN G SODIUM), PENICILLIN V POTASSIUM (PENICILLIN V POTASSIUM), PENICILLIN-2 (PENICILLIN G POTASSIUM), PENICILLIN-VK (PENICILLIN V POTASSIUM), PENLAC (CICLOPIROX), PENNTUSS (CHLORPHENIRAMINE POLISTIREX; CODEINE POLISTIREX), PENTACARINAT (PENTAMIDINE ISETHIONATE), PENTACEF (CEFTAZIDIME), PENTAM (PENTAMIDINE ISETHIONATE), PENTAMIDINE ISETHIONATE (PENTAMIDINE ISETHIONATE), PENTASA (MESALAMINE), PENTAZOCINE AND NALOXONE HYDROCHLORIDES (NALOXONE HYDROCHLORIDE; PENTAZOCINE HYDROCHLORIDE), PENTAZOCINE HYDROCHLORIDE AND ACETAMINOPHEN (ACETAMINOPHEN; PENTAZOCINE HYDROCHLORIDE), PENTETATE CALCIUM TRISODIUM (PENTETATE CALCIUM TRISODIUM), PENTETATE ZINC TRISODIUM (PENTETATE ZINC TRISODIUM), PENTHRANE (METHOXYFLURANE), PENTIDS '200' (PENICILLIN G POTASSIUM), PENTIDS '250' (PENICILLIN G POTASSIUM), PENTIDS '400' (PENICILLIN G POTASSIUM), PENTIDS '800' (PENICILLIN G POTASSIUM), PENTOBARBITAL SODIUM (PENTOBARBITAL SODIUM), PENTOLAIR (CYCLOPENTOLATE HYDROCHLORIDE), PENTOSTATIN (PENTOSTATIN), PENTOTHAL (THIOPENTAL SODIUM), PENTOXIFYLLINE (PENTOXIFYLLINE), PENTOXIL (PENTOXIFYLLINE), PEPCID (FAMOTIDINE), PEPCID AC (FAMOTIDINE), PEPCID AC (GELTAB) (FAMOTIDINE), PEPCID COMPLETE (CALCIUM CARBONATE; FAMOTIDINE; MAGNESIUM HYDROXIDE), PEPCID PRESERVATIVE FREE (FAMOTIDINE), PEPCID PRESERVATIVE FREE IN PLASTIC CONTAINER (FAMOTIDINE), PEPCID RPD (FAMOTIDINE), PEPTAVLON (PENTAGASTRIN), PERCHLORACAP (POTASSIUM PERCHLORATE), PERCOCET (ACETAMINOPHEN; OXYCODONE HYDROCHLORIDE), PERCODAN (ASPIRIN; OXYCODONE HYDROCHLORIDE), PERCODAN (ASPIRIN; OXYCODONE HYDROCHLORIDE; OXYCODONE TEREPHTHALATE), PERCODAN-DEMI (ASPIRIN; OXYCODONE HYDROCHLORIDE; OXYCODONE TEREPHTHALATE), PERCORTEN (DESOXYCORTICOSTERONE ACETATE), PERCORTEN (DESOXYCORTICOSTERONE PIVALATE), PERFOROMIST (FORMOTEROL FUMARATE), PERGOLIDE MESYLATE (PERGOLIDE MESYLATE), PERGONAL (MENOTROPINS (FSH; LH)), PERIACTIN (CYPROHEPTADINE HYDROCHLORIDE), PERIDEX (CHLORHEXIDINE GLUCONATE), PERIOCHIP (CHLORHEXIDINE GLUCONATE), PERIOGARD (CHLORHEXIDINE GLUCONATE), PERIOSTAT (DOXYCYCLINE HYCLATE), PERMAPEN (PENICILLIN G BENZATHINE), PERMAX (PERGOLIDE MESYLATE), PERMETHRIN (PERMETHRIN), PERMITIL (FLUPHENAZINE HYDROCHLORIDE), PERPHENAZINE (PERPHENAZINE), PERPHENAZINE AND AMITRIPTYLINE HYDROCHLORIDE (AMITRIPTYLINE HYDROCHLORIDE; PERPHENAZINE), PERSANTINE (DIPYRIDAMOLE), PERTOFRANE (DESIPRAMINE HYDROCHLORIDE), PEXEVA (PAROXETINE MESYLATE), PFIZER-E (ERYTHROMYCIN STEARATE), PFIZERPEN (PENICILLIN G POTASSIUM), PFIZERPEN G (PENICILLIN G POTASSIUM), PFIZERPEN VK (PENICILLIN V POTASSIUM), PFIZERPEN-A (AMPICILLIN/AMPICILLIN TRIHYDRATE), PFIZERPEN-AS (PENICILLIN G PROCAINE), PHARMASEAL SCRUB CARE (CHLORHEXIDINE GLUCONATE), PHENAPHEN W/ CODEINE NO. 2 (ACETAMINOPHEN; CODEINE PHOSPHATE), PHENAPHEN W/ CODEINE NO. 3 (ACETAMINOPHEN; CODEINE PHOSPHATE), PHENAPHEN W/ CODEINE NO. 4 (ACETAMINOPHEN; CODEINE PHOSPHATE), PHENAPHEN-650 W/ CODEINE (ACETAMINOPHEN; CODEINE PHOSPHATE), PHENAZINE (PHENDIMETRAZINE TARTRATE), PHENAZINE-35 (PHENDIMETRAZINE TARTRATE), PHENDIMETRAZINE TARTRATE (PHENDIMETRAZINE TARTRATE), PHENERGAN (PROMETHAZINE HYDROCHLORIDE), PHENERGAN VC (PHENYLEPHRINE HYDROCHLORIDE; PROMETHAZINE HYDROCHLORIDE), PHENERGAN VC W/ CODEINE (CODEINE PHOSPHATE; PHENYLEPHRINE HYDROCHLORIDE; PROMETHAZINE HYDROCHLORIDE), PHENERGAN W/ CODEINE (CODEINE PHOSPHATE; PROMETHAZINE HYDROCHLORIDE), PHENETRON (CHLORPHENIRAMINE MALEATE), PHENTERMINE HYDROCHLORIDE (PHENTERMINE HYDROCHLORIDE), PHENTERMINE RESIN 30 (PHENTERMINE RESIN COMPLEX), PHENTOLAMINE MESYLATE (PHENTOLAMINE MESYLATE), PHENTYTOIN (PHENYTOIN), PHENURONE (PHENACEMIDE), PHENY-PAS-TEBAMIN (PHENYL AMINOSALICYLATE), PHENYLBUTAZONE (PHENYLBUTAZONE), PHENYLEPHRINE HYDROCHLORIDE AND PROMETHAZINE HYDROCHLORIDE (PHENYLEPHRINE HYDROCHLORIDE; PROMETHAZINE HYDROCHLORIDE), PHENYLPROPANOLAMINE HYDROCHLORIDE W/ CHLORPHENIRAMINE MALEATE (CHLORPHENIRAMINE MALEATE; PHENYLPROPANOLAMINE HYDROCHLORIDE), PHENYTEK (PHENYTOIN SODIUM), PHENYTEX (PHENYTOIN SODIUM), PHENYTOIN (PHENYTOIN), PHENYTOIN SODIUM (PHENYTOIN SODIUM), PHERAZINE DM (DEXTROMETHORPHAN HYDROBROMIDE; PROMETHAZINE HYDROCHLORIDE), PHERAZINE VC (PHENYLEPHRINE HYDROCHLORIDE; PROMETHAZINE HYDROCHLORIDE), PHERAZINE VC W/ CODEINE (CODEINE PHOSPHATE; PHENYLEPHRINE HYDROCHLORIDE; PROMETHAZINE HYDROCHLORIDE), PHERAZINE W/ CODEINE (CODEINE PHOSPHATE; PROMETHAZINE HYDRO- CHLORIDE), PHISO-SCRUB (HEXACHLOROPHENE), PHISOHEX (HEXACHLOROPHENE), PHOSLO (CALCIUM ACETATE), PHOSLO GELCAPS (CALCIUM ACETATE), PHOSPHOCOL P32 (CHROMIC PHOSPHATE, P-32), PHOSPHOLINE IODIDE (ECHOTHIOPHATE IODIDE), PHOSPHOTEC (TECHNETIUM TC-99M PYROPHOSPHATE KIT), PHOSPHOTOPE (SODIUM PHOSPHATE, P-32), PHOTOFRIN (PORFIMER SODIUM), PHRENILIN (ACETAMINOPHEN; BUTALBITAL), PHRENILIN FORTE (ACETAMINOPHEN; BUTALBITAL), PHRENILIN WITH CAFFEINE AND CODEINE (ACETAMINOPHEN; BUTALBITAL; CAFFEINE; CODEINE PHOSPHATE), PHYLLOCONTIN (AMINOPHYLLINE), PHYSIOLYTE IN PLASTIC CONTAINER (MAGNESIUM CHLORIDE; POTASSIUM CHLORIDE; SODIUM ACETATE; SODIUM CHLORIDE; SODIUM GLUCONATE), PHYSIOSOL IN PLASTIC CONTAINER (MAGNESIUM CHLORIDE; POTASSIUM CHLORIDE; SODIUM ACETATE; SODIUM CHLORIDE; SODIUM GLUCONATE), PHYSIOSOL PH 7.4 IN PLASTIC CONTAINER (MAGNESIUM CHLORIDE; POTASSIUM CHLORIDE; SODIUM ACETATE; SODIUM CHLORIDE; SODIUM GLUCONATE), PHYTONADIONE (PHYTONADIONE), PILOCARPINE HYDROCHLORIDE (PILOCARPINE HYDROCHLORIDE), PILOPINE HS (PILOCARPINE HYDROCHLORIDE), PINDAC (PINACIDIL), PINDOLOL (PINDOLOL), PIOGLITAZONE (PIOGLITAZONE HYDROCHLORIDE), PIPERACILLIN (PIPERACILLIN SODIUM), PIPERAZINE CITRATE (PIPERAZINE CITRATE), PIPRACIL (PIPERACILLIN SODIUM), PIROXICAM (PIROXICAM), PITOCIN (OXYTOCIN), PITRESSIN TANNATE (VASOPRESSIN TANNATE), PLACIDYL (ETHCHLORVYNOL), PLAN B (LEVONORGESTREL), PLAQUENIL (HYDROXYCHLOROQUINE SULFATE), PLASMA-LYTE 148 AND DEXTROSE 5% IN PLASTIC CONTAINER (DEXTROSE; MAGNESIUM CHLORIDE; POTASSIUM CHLORIDE; SODIUM ACETATE; SODIUM CHLORIDE; SODIUM GLUCONATE), PLASMA-LYTE 148 IN WATER IN PLASTIC CONTAINER (MAGNESIUM CHLORIDE; POTASSIUM CHLORIDE; SODIUM ACETATE; SODIUM CHLORIDE; SODIUM GLUCONATE), PLASMA-LYTE 56 AND DEXTROSE 5% IN PLASTIC CONTAINER (DEXTROSE; MAGNESIUM ACETATE TETRAHYDRATE; POTASSIUM ACETATE; SODIUM CHLORIDE), PLASMA-LYTE 56 IN PLASTIC CONTAINER (MAGNESIUM ACETATE TETRAHYDRATE; POTASSIUM ACETATE; SODIUM CHLORIDE), PLASMA-LYTE A IN PLASTIC CONTAINER (MAGNESIUM CHLORIDE; POTASSIUM CHLORIDE; SODIUM ACETATE; SODIUM CHLORIDE; SODIUM GLUCONATE), PLASMA-LYTE M AND DEXTROSE 5% IN PLASTIC CONTAINER (CALCIUM CHLORIDE; DEXTROSE; MAGNESIUM CHLORIDE; POTASSIUM CHLORIDE; SODIUM ACETATE; SODIUM CHLORIDE; SODIUM LACTATE), PLASMA-LYTE R IN PLASTIC CONTAINER (CALCIUM CHLORIDE; MAGNESIUM CHLORIDE; POTASSIUM CHLORIDE; SODIUM ACETATE; SODIUM CHLORIDE; SODIUM LACTATE), PLATINOL (CISPLATIN), PLATINOL-AQ (CISPLATIN), PLAVIX (CLOPIDOGREL BISULFATE), PLEGINE (PHENDIMETRAZINE TARTRATE), PLEGISOL IN PLASTIC CONTAINER (CALCIUM CHLORIDE; MAGNESIUM CHLORIDE; POTASSIUM CHLORIDE; SODIUM CHLORIDE), PLENAXIS (ABARELIX), PLENDIL (FELODIPINE), PLETAL (CILOSTAZOL), PMB 200 (ESTROGENS, CONJUGATED; MEPROBAMATE), PMB 400 (ESTROGENS, CONJUGATED; MEPROBAMATE), PODOFILOX (PODOFILOX), POLARAMINE (DEXCHLORPHENIRAMINE MALEATE), POLOCAINE (MEPIVACAINE HYDROCHLORIDE), POLOCAINE W/ LEVONORDEFRIN (LEVONORDEFRIN; MEPIVACAINE HYDROCHLORIDE), POLOCAINE-MPF (MEPIVACAINE HYDROCHLORIDE), POLY-PRED (NEOMYCIN SULFATE; POLYMYXIN B SULFATE; PREDNISOLONE ACETATE), POLY-RX (POLYMYXIN B SULFATE), POLYCILLIN (AMPICILLIN/AMPICILLIN TRIHYDRATE), POLYCILLIN-N (AMPICILLIN SODIUM), POLYCILLIN-PRB (AMPICILLIN/AMPICILLIN TRIHYDRATE; PROBENECID), POLYETHYLENE GLYCOL 3350 (POLYETHYLENE GLYCOL 3350), POLYMOX (AMOXICILLIN), POLYMXIN B SULFATE (POLYMYXIN B SULFATE), POLYMYXIN B SULFATE (POLYMYXIN B SULFATE), POLYSPORIN (BACITRACIN ZINC; POLYMYXIN B SULFATE), POLYTRIM (POLYMYXIN B SULFATE; TRIMETHOPRIM SULFATE), PONSTEL (MEFENAMIC ACID), PORTALAC (LACTULOSE), PORTIA-21 (ETHINYL ESTRADIOL; LEVONORGESTREL), PORTIA-28 (ETHINYL ESTRADIOL; LEVONORGESTREL), POTASSIUM ACETATE IN PLASTIC CONTAINER (POTASSIUM ACETATE), POTASSIUM AMINOSALICYLATE (POTASSIUM AMINOSALICYLATE), POTASSIUM CHLORIDE (POTASSIUM CHLORIDE), POTASSIUM CHLORIDE 0.037% IN DEXTROSE 10% AND SODIUM CHLORIDE 0.2% IN PLASTIC CONTAINER (DEXTROSE; POTASSIUM CHLORIDE; SODIUM CHLORIDE), POTASSIUM CHLORIDE 0.037% IN DEXTROSE 10% AND SODIUM CHLORIDE 0.45% IN PLASTIC CONTAINER (DEXTROSE; POTASSIUM CHLORIDE; SODIUM CHLORIDE), POTASSIUM CHLORIDE 0.037% IN DEXTROSE 10% AND SODIUM CHLORIDE 0.9% IN PLASTIC CONTAINER (DEXTROSE; POTASSIUM CHLORIDE; SODIUM CHLORIDE), POTASSIUM CHLORIDE 0.037% IN DEXTROSE 5% AND SODIUM CHLORIDE 0.11% IN PLASTIC CONTAINER (DEXTROSE; POTASSIUM CHLORIDE; SODIUM CHLORIDE), POTASSIUM CHLORIDE 0.037% IN DEXTROSE 5% AND SODIUM CHLORIDE 0.2% IN PLASTIC CONTAINER (DEXTROSE; POTASSIUM CHLORIDE; SODIUM CHLORIDE), POTASSIUM CHLORIDE 0.037% IN DEXTROSE 5% AND SODIUM CHLORIDE 0.33% IN PLASTIC CONTAINER (DEXTROSE; POTASSIUM CHLORIDE; SODIUM CHLORIDE), POTASSIUM CHLORIDE 0.037% IN DEXTROSE 5% AND SODIUM CHLORIDE 0.45% IN PLASTIC CONTAINER (DEXTROSE; POTASSIUM CHLORIDE; SODIUM CHLORIDE), POTASSIUM CHLORIDE 0.037% IN DEXTROSE 5% AND SODIUM CHLORIDE 0.9% IN PLASTIC CONTAINER (DEXTROSE; POTASSIUM CHLORIDE; SODIUM CHLORIDE), POTASSIUM CHLORIDE 0.037% IN DEXTROSE 5% IN PLASTIC CONTAINER (DEXTROSE; POTASSIUM CHLORIDE), POTASSIUM CHLORIDE 0.037% IN SODIUM CHLORIDE 0.9% IN PLASTIC CONTAINER (POTASSIUM CHLORIDE; SODIUM CHLORIDE), POTASSIUM CHLORIDE 0.075% IN DEXTROSE 10% AND SODIUM CHLORIDE 0.2% IN PLASTIC CONTAINER (DEXTROSE; POTASSIUM CHLORIDE; SODIUM CHLORIDE), POTASSIUM CHLORIDE 0.075% IN DEXTROSE 10% AND SODIUM CHLORIDE 0.45% IN PLASTIC CONTAINER (DEXTROSE; POTASSIUM CHLORIDE; SODIUM CHLORIDE), POTASSIUM CHLORIDE 0.075% IN DEXTROSE 10% AND SODIUM CHLORIDE 0.9% IN PLASTIC CONTAINER (DEXTROSE; POTASSIUM CHLORIDE; SODIUM CHLORIDE), POTASSIUM CHLORIDE 0.075% IN DEXTROSE 3.3% AND SODIUM CHLORIDE 0.3% IN PLASTIC CONTAINER (DEXTROSE; POTASSIUM CHLORIDE; SODIUM CHLORIDE), POTASSIUM CHLORIDE 0.075% IN DEXTROSE 5% AND SODIUM CHLORIDE 0.11% IN PLASTIC CONTAINER (DEXTROSE; POTASSIUM CHLORIDE; SODIUM CHLORIDE), POTASSIUM CHLORIDE 0.075% IN DEXTROSE 5% AND SODIUM CHLORIDE 0.2% IN PLASTIC CONTAINER (DEXTROSE; POTASSIUM CHLORIDE; SODIUM CHLORIDE), POTASSIUM CHLORIDE 0.075% IN DEXTROSE 5% AND SODIUM CHLORIDE 0.33% IN PLASTIC CONTAINER (DEXTROSE; POTASSIUM CHLORIDE; SODIUM CHLORIDE), POTASSIUM CHLORIDE 0.075% IN DEXTROSE 5% AND SODIUM CHLORIDE 0.45% IN PLASTIC CONTAINER (DEXTROSE; POTASSIUM CHLORIDE; SODIUM CHLORIDE), POTASSIUM CHLORIDE 0.075% IN DEXTROSE 5% AND SODIUM CHLORIDE 0.9% IN PLASTIC CONTAINER (DEXTROSE; POTASSIUM CHLORIDE; SODIUM CHLORIDE), POTASSIUM CHLORIDE 0.075% IN DEXTROSE 5% IN PLASTIC CONTAINER (DEXTROSE; POTASSIUM CHLORIDE), POTASSIUM CHLORIDE 0.075% IN SODIUM CHLORIDE 0.9% IN PLASTIC CONTAINER (POTASSIUM CHLORIDE; SODIUM CHLORIDE), POTASSIUM CHLORIDE 0.11% IN DEXTROSE 10% AND SODIUM CHLORIDE 0.2% IN PLASTIC CONTAINER (DEXTROSE; POTASSIUM CHLORIDE; SODIUM CHLORIDE), POTASSIUM CHLORIDE 0.11% IN DEXTROSE 10% AND SODIUM CHLORIDE 0.45% IN PLASTIC CONTAINER (DEXTROSE; POTASSIUM CHLORIDE; SODIUM CHLORIDE), POTASSIUM CHLORIDE 0.11% IN DEXTROSE 10% AND SODIUM CHLORIDE 0.9% IN PLASTIC CONTAINER (DEXTROSE; POTASSIUM CHLORIDE; SODIUM CHLORIDE), POTASSIUM CHLORIDE 0.11% IN DEXTROSE 3.3% AND SODIUM CHLORIDE 0.3% IN PLASTIC CONTAINER (DEXTROSE; POTASSIUM CHLORIDE; SODIUM CHLORIDE), POTASSIUM CHLORIDE 0.11% IN DEXTROSE 5% AND SODIUM CHLORIDE 0.11% IN PLASTIC CONTAINER (DEXTROSE; POTASSIUM CHLORIDE; SODIUM CHLORIDE), POTASSIUM CHLORIDE 0.11% IN DEXTROSE 5% AND SODIUM CHLORIDE 0.2% IN PLASTIC CONTAINER (DEXTROSE; POTASSIUM CHLORIDE; SODIUM CHLORIDE), POTASSIUM CHLORIDE 0.11% IN DEXTROSE 5% AND SODIUM CHLORIDE 0.33% IN PLASTIC CONTAINER (DEXTROSE; POTASSIUM CHLORIDE; SODIUM CHLORIDE), POTASSIUM CHLORIDE 0.11% IN DEXTROSE 5% AND SODIUM CHLORIDE 0.45% IN PLASTIC CONTAINER (DEXTROSE; POTASSIUM CHLORIDE; SODIUM CHLORIDE), POTASSIUM CHLORIDE 0.11% IN DEXTROSE 5% AND SODIUM CHLORIDE 0.9% IN PLASTIC CONTAINER (DEXTROSE; POTASSIUM CHLORIDE; SODIUM CHLORIDE), POTASSIUM CHLORIDE 0.11% IN DEXTROSE 5% IN PLASTIC CONTAINER (DEXTROSE; POTASSIUM CHLORIDE), POTASSIUM CHLORIDE 0.11% IN SODIUM CHLORIDE 0.9% IN PLASTIC CONTAINER (POTASSIUM CHLORIDE; SODIUM CHLORIDE), POTASSIUM CHLORIDE 0.15% IN DEXTROSE 10% AND SODIUM CHLORIDE 0.2% IN PLASTIC CONTAINER (DEXTROSE; POTASSIUM CHLORIDE; SODIUM CHLORIDE), POTASSIUM CHLORIDE 0.15% IN DEXTROSE 10% AND SODIUM CHLORIDE 0.45% IN PLASTIC CONTAINER (DEXTROSE; POTASSIUM CHLORIDE; SODIUM CHLORIDE), POTASSIUM CHLORIDE 0.15% IN DEXTROSE 10% AND SODIUM CHLORIDE 0.9% IN PLASTIC CONTAINER (DEXTROSE; POTASSIUM CHLORIDE; SODIUM CHLORIDE), POTASSIUM CHLORIDE 0.15% IN DEXTROSE 3.3% AND SODIUM CHLORIDE 0.3% IN PLASTIC CONTAINER (DEXTROSE; POTASSIUM CHLORIDE; SODIUM CHLORIDE), POTASSIUM CHLORIDE 0.15% IN DEXTROSE 5% AND SODIUM CHLORIDE 0.11% IN PLASTIC CONTAINER (DEXTROSE; POTASSIUM CHLORIDE; SODIUM CHLORIDE), POTASSIUM CHLORIDE 0.15% IN DEXTROSE 5% AND SODIUM CHLORIDE 0.2% IN PLASTIC CONTAINER (DEXTROSE; POTASSIUM CHLORIDE; SODIUM CHLORIDE), POTASSIUM CHLORIDE 0.15% IN DEXTROSE 5% AND SODIUM CHLORIDE 0.33% IN PLASTIC CONTAINER (DEXTROSE; POTASSIUM CHLORIDE; SODIUM CHLORIDE), POTASSIUM CHLORIDE 0.15% IN DEXTROSE 5% AND SODIUM CHLORIDE 0.45% IN PLASTIC CONTAINER (DEXTROSE; POTASSIUM CHLORIDE; SODIUM CHLORIDE), POTASSIUM CHLORIDE 0.15% IN DEXTROSE 5% AND SODIUM CHLORIDE 0.9% IN PLASTIC CONTAINER (DEXTROSE; POTASSIUM CHLORIDE; SODIUM CHLORIDE), POTASSIUM CHLORIDE 0.15% IN DEXTROSE 5% IN PLASTIC CONTAINER (DEXTROSE; POTASSIUM CHLORIDE), POTASSIUM CHLORIDE 0.15% IN SODIUM CHLORIDE 0.9% IN PLASTIC CONTAINER (POTASSIUM CHLORIDE; SODIUM CHLORIDE), POTASSIUM CHLORIDE 0.22% IN DEXTROSE 10% AND SODIUM CHLORIDE 0.2% IN PLASTIC CONTAINER (DEXTROSE; POTASSIUM CHLORIDE; SODIUM CHLORIDE), POTASSIUM CHLORIDE 0.22% IN DEXTROSE 10% AND SODIUM CHLORIDE 0.45% IN PLASTIC CONTAINER (DEXTROSE; POTASSIUM CHLORIDE; SODIUM CHLORIDE), POTASSIUM CHLORIDE 0.22% IN DEXTROSE 10% AND SODIUM CHLORIDE 0.9% IN PLASTIC CONTAINER (DEXTROSE; POTASSIUM CHLORIDE; SODIUM CHLORIDE), POTASSIUM CHLORIDE 0.22% IN DEXTROSE 3.3% AND SODIUM CHLORIDE 0.3% IN PLASTIC CONTAINER (DEXTROSE; POTASSIUM CHLORIDE; SODIUM CHLORIDE), POTASSIUM CHLORIDE 0.22% IN DEXTROSE 5% AND SODIUM CHLORIDE 0.11% IN PLASTIC CONTAINER (DEXTROSE; POTASSIUM CHLORIDE; SODIUM CHLORIDE), POTASSIUM CHLORIDE 0.22% IN DEXTROSE 5% AND SODIUM CHLORIDE 0.2% IN PLASTIC CONTAINER (DEXTROSE; POTASSIUM CHLORIDE; SODIUM CHLORIDE), POTASSIUM CHLORIDE 0.22% IN DEXTROSE 5% AND SODIUM CHLORIDE 0.33% IN PLASTIC CONTAINER (DEXTROSE; POTASSIUM CHLORIDE; SODIUM CHLORIDE), POTASSIUM CHLORIDE 0.22% IN DEXTROSE 5% AND SODIUM CHLORIDE 0.45% IN PLASTIC CONTAINER (DEX- TROSE; POTASSIUM CHLORIDE; SODIUM CHLORIDE), POTASSIUM CHLORIDE 0.22% IN DEXTROSE 5% AND SODIUM CHLORIDE 0.9% IN PLASTIC CONTAINER (DEXTROSE; POTASSIUM CHLORIDE; SODIUM CHLORIDE), POTASSIUM CHLORIDE 0.22% IN DEXTROSE 5% IN PLASTIC CONTAINER (DEXTROSE; POTASSIUM CHLORIDE), POTASSIUM CHLORIDE 0.22% IN SODIUM CHLORIDE 0.9% IN PLASTIC CONTAINER (POTASSIUM CHLORIDE; SODIUM CHLORIDE), POTASSIUM CHLORIDE 0.3% IN DEXTROSE 10% AND SODIUM CHLORIDE 0.2% IN PLASTIC CONTAINER (DEXTROSE; POTASSIUM CHLORIDE; SODIUM CHLORIDE), POTASSIUM CHLORIDE 0.3% IN DEXTROSE 10% AND SODIUM CHLORIDE 0.45% IN PLASTIC CONTAINER (DEXTROSE; POTASSIUM CHLORIDE; SODIUM CHLORIDE), POTASSIUM CHLORIDE 0.3% IN DEXTROSE 10% AND SODIUM CHLORIDE 0.9% IN PLASTIC CONTAINER (DEXTROSE; POTASSIUM CHLORIDE; SODIUM CHLORIDE), POTASSIUM CHLORIDE 0.3% IN DEXTROSE 3.3% AND SODIUM CHLORIDE 0.3% IN PLASTIC CONTAINER (DEXTROSE; POTASSIUM CHLORIDE; SODIUM CHLORIDE), POTASSIUM CHLORIDE 0.3% IN DEXTROSE 5% AND SODIUM CHLORIDE 0.11% IN PLASTIC CONTAINER (DEXTROSE; POTASSIUM CHLORIDE; SODIUM CHLORIDE), POTASSIUM CHLORIDE 0.3% IN DEXTROSE 5% AND SODIUM CHLORIDE 0.2% IN PLASTIC CONTAINER (DEXTROSE; POTASSIUM CHLORIDE; SODIUM CHLORIDE), POTASSIUM CHLORIDE 0.3% IN DEXTROSE 5% AND SODIUM CHLORIDE 0.33% IN PLASTIC CONTAINER (DEXTROSE; POTASSIUM CHLORIDE; SODIUM CHLORIDE), POTASSIUM CHLORIDE 0.3% IN DEXTROSE 5% AND SODIUM CHLORIDE 0.45% IN PLASTIC CONTAINER (DEXTROSE; POTASSIUM CHLORIDE; SODIUM CHLORIDE), POTASSIUM CHLORIDE 0.3% IN DEXTROSE 5% AND SODIUM CHLORIDE 0.9% IN PLASTIC CONTAINER (DEXTROSE; POTASSIUM CHLORIDE; SODIUM CHLORIDE), POTASSIUM CHLORIDE 0.3% IN DEXTROSE 5% IN PLASTIC CONTAINER (DEXTROSE; POTASSIUM CHLORIDE), POTASSIUM CHLORIDE 0.3% IN SODIUM CHLORIDE 0.9% IN PLASTIC CONTAINER (POTASSIUM CHLORIDE; SODIUM CHLORIDE), POTASSIUM CHLORIDE 10MEQ IN DEXTROSE 5% AND LACTATED RINGER'S IN PLASTIC CONTAINER (CALCIUM CHLORIDE; DEXTROSE; POTASSIUM CHLORIDE; SODIUM CHLORIDE; SODIUM LACTATE), POTASSIUM CHLORIDE 10MEQ IN DEXTROSE 5% AND SODIUM CHLORIDE 0.225% IN PLASTIC CONTAINER (DEXTROSE; POTASSIUM CHLORIDE; SODIUM CHLORIDE), POTASSIUM CHLORIDE 10MEQ IN DEXTROSE 5% AND SODIUM CHLORIDE 0.3% IN PLASTIC CONTAINER (DEXTROSE; POTASSIUM CHLORIDE; SODIUM CHLORIDE), POTASSIUM CHLORIDE 10MEQ IN DEXTROSE 5% AND SODIUM CHLORIDE 0.45% IN PLASTIC CONTAINER (DEXTROSE; POTASSIUM CHLORIDE; SODIUM CHLORIDE), POTASSIUM CHLORIDE 10MEQ IN DEXTROSE 5% AND SODIUM CHLORIDE 0.9% IN PLASTIC CONTAINER (DEXTROSE; POTASSIUM CHLORIDE; SODIUM CHLORIDE), POTASSIUM CHLORIDE 10MEQ IN PLASTIC CONTAINER (POTASSIUM CHLORIDE), POTASSIUM CHLORIDE 15MEQ IN DEXTROSE 5% AND LACTATED RINGER'S IN PLASTIC CONTAINER (CALCIUM CHLORIDE; DEXTROSE; POTASSIUM CHLORIDE; SODIUM CHLORIDE; SODIUM LACTATE), POTASSIUM CHLORIDE 15MEQ IN DEXTROSE 5% AND SODIUM CHLORIDE 0.225% IN PLASTIC CONTAINER (DEXTROSE; POTASSIUM CHLORIDE; SODIUM CHLORIDE), POTASSIUM CHLORIDE 15MEQ IN DEXTROSE 5% AND SODIUM CHLORIDE 0.3% IN PLASTIC CONTAINER (DEXTROSE; POTASSIUM CHLORIDE; SODIUM CHLORIDE), POTASSIUM CHLORIDE 15MEQ IN DEXTROSE 5% AND SODIUM CHLORIDE 0.45% IN PLASTIC CONTAINER (DEXTROSE; POTASSIUM CHLORIDE; SODIUM CHLORIDE), POTASSIUM CHLORIDE 15MEQ IN DEXTROSE 5% AND SODIUM CHLORIDE 0.9% IN PLASTIC CONTAINER (DEXTROSE; POTASSIUM CHLORIDE; SODIUM CHLORIDE), POTASSIUM CHLORIDE 20MEQ IN DEXTROSE 5% AND LACTATED RINGER'S IN PLASTIC CONTAINER (CALCIUM CHLORIDE; DEXTROSE; POTASSIUM CHLORIDE; SODIUM CHLORIDE; SODIUM LACTATE), POTASSIUM CHLORIDE 20MEQ IN DEXTROSE 5% AND SODIUM CHLORIDE 0.225% IN PLASTIC CONTAINER (DEXTROSE; POTASSIUM CHLORIDE; SODIUM CHLORIDE), POTASSIUM CHLORIDE 20MEQ IN DEXTROSE 5% AND SODIUM CHLORIDE 0.3% IN PLASTIC CONTAINER (DEXTROSE; POTASSIUM CHLORIDE; SODIUM CHLORIDE), POTASSIUM CHLORIDE 20MEQ IN DEXTROSE 5% AND SODIUM CHLORIDE 0.45% IN PLASTIC CONTAINER (DEXTROSE; POTASSIUM CHLORIDE; SODIUM CHLORIDE), POTASSIUM CHLORIDE 20MEQ IN DEXTROSE 5% AND SODIUM CHLORIDE 0.9% IN PLASTIC CONTAINER (DEXTROSE; POTASSIUM CHLORIDE; SODIUM CHLORIDE), POTASSIUM CHLORIDE 20MEQ IN DEXTROSE 5% IN PLASTIC CONTAINER (DEXTROSE; POTASSIUM CHLORIDE), POTASSIUM CHLORIDE 20MEQ IN DEXTROSE 5% IN SODIUM CHLORIDE 0.3% IN PLASTIC CONTAINER (DEXTROSE; POTASSIUM CHLORIDE; SODIUM CHLORIDE), POTASSIUM CHLORIDE 20MEQ IN PLASTIC CONTAINER (POTASSIUM CHLORIDE), POTASSIUM CHLORIDE 20MEQ IN SODIUM CHLORIDE 0.9% IN PLASTIC CONTAINER (POTASSIUM CHLORIDE; SODIUM CHLORIDE), POTASSIUM CHLORIDE 30MEQ IN DEXTROSE 5% AND LACTATED RINGER'S IN PLASTIC CONTAINER (CALCIUM CHLORIDE; DEXTROSE; POTASSIUM CHLORIDE; SODIUM CHLORIDE; SODIUM LACTATE), POTASSIUM CHLORIDE 30MEQ IN DEXTROSE 5% AND SODIUM CHLORIDE 0.225% IN PLASTIC CONTAINER (DEXTROSE; POTASSIUM CHLORIDE; SODIUM CHLORIDE), POTASSIUM CHLORIDE 30MEQ IN DEXTROSE 5% AND SODIUM CHLORIDE 0.3% IN PLASTIC CONTAINER (DEXTROSE; POTASSIUM CHLORIDE; SODIUM CHLORIDE), POTASSIUM CHLORIDE 30MEQ IN DEXTROSE 5% AND SODIUM CHLORIDE 0.45% IN PLASTIC CONTAINER (DEXTROSE; POTASSIUM CHLORIDE; SODIUM CHLORIDE), POTASSIUM CHLORIDE 30MEQ IN DEXTROSE 5% AND SODIUM CHLORIDE 0.9% IN PLASTIC CONTAINER (DEXTROSE; POTASSIUM CHLORIDE; SODIUM CHLORIDE), POTASSIUM CHLORIDE 30MEQ IN DEXTROSE 5%

IN PLASTIC CONTAINER (DEXTROSE; POTASSIUM CHLORIDE), POTASSIUM CHLORIDE 30MEQ IN PLASTIC CONTAINER (POTASSIUM CHLORIDE), POTASSIUM CHLORIDE 40MEQ IN DEXTROSE 5% AND LACTATED RINGER'S IN PLASTIC CONTAINER (CALCIUM CHLORIDE; DEXTROSE; POTASSIUM CHLORIDE; SODIUM CHLORIDE; SODIUM LACTATE), POTASSIUM CHLORIDE 40MEQ IN DEXTROSE 5% AND SODIUM CHLORIDE 0.225% IN PLASTIC CONTAINER (DEXTROSE; POTASSIUM CHLORIDE; SODIUM CHLORIDE), POTASSIUM CHLORIDE 40MEQ IN DEXTROSE 5% AND SODIUM CHLORIDE 0.3% IN PLASTIC CONTAINER (DEXTROSE; POTASSIUM CHLORIDE; SODIUM CHLORIDE), POTASSIUM CHLORIDE 40MEQ IN DEXTROSE 5% AND SODIUM CHLORIDE 0.45% IN PLASTIC CONTAINER (DEXTROSE; POTASSIUM CHLORIDE; SODIUM CHLORIDE), POTASSIUM CHLORIDE 40MEQ IN DEXTROSE 5% AND SODIUM CHLORIDE 0.9% IN PLASTIC CONTAINER (DEXTROSE; POTASSIUM CHLORIDE; SODIUM CHLORIDE), POTASSIUM CHLORIDE 40MEQ IN DEXTROSE 5% IN PLASTIC CONTAINER (DEXTROSE; POTASSIUM CHLORIDE), POTASSIUM CHLORIDE 40MEQ IN PLASTIC CONTAINER (POTASSIUM CHLORIDE), POTASSIUM CHLORIDE 40MEQ IN SODIUM CHLORIDE 0.9% IN PLASTIC CONTAINER (POTASSIUM CHLORIDE; SODIUM CHLORIDE), POTASSIUM CHLORIDE 5MEQ IN DEXTROSE 5% AND LACTATED RINGER'S IN PLASTIC CONTAINER (CALCIUM CHLORIDE; DEXTROSE; POTASSIUM CHLORIDE; SODIUM CHLORIDE; SODIUM LACTATE), POTASSIUM CHLORIDE 5MEQ IN DEXTROSE 5% AND SODIUM CHLORIDE 0.225% IN PLASTIC CONTAINER (DEXTROSE; POTASSIUM CHLORIDE; SODIUM CHLORIDE), POTASSIUM CHLORIDE 5MEQ IN DEXTROSE 5% AND SODIUM CHLORIDE 0.3% IN PLASTIC CONTAINER (DEXTROSE; POTASSIUM CHLORIDE; SODIUM CHLORIDE), POTASSIUM CHLORIDE 5MEQ IN DEXTROSE 5% AND SODIUM CHLORIDE 0.45% IN PLASTIC CONTAINER (DEXTROSE; POTASSIUM CHLORIDE; SODIUM CHLORIDE), POTASSIUM CHLORIDE 5MEQ IN DEXTROSE 5% AND SODIUM CHLORIDE 0.9% IN PLASTIC CONTAINER (DEXTROSE; POTASSIUM CHLORIDE; SODIUM CHLORIDE), POTASSIUM CHLORIDE IN PLASTIC CONTAINER (POTASSIUM CHLORIDE), POTASSIUM CITRATE (POTASSIUM CITRATE), POTASSIUM IODIDE (POTASSIUM IODIDE), POVAN (PYRVINIUM PAMOATE), POVIDONE IODINE (POVIDONE-IODINE), PRALIDOXIME CHLORIDE (PRALIDOXIME CHLORIDE), PRAMINE (IMIPRAMINE HYDROCHLORIDE), PRAMIPEXOLE DIHYDROCHLORIDE (PRAMIPEXOLE DIHYDROCHLORIDE), PRAMOSONE (HYDROCORTISONE ACETATE; PRAMOXINE HYDROCHLORIDE), PRANDIMET (REPAGLINIDE; METFORMIN HYDROCHLORIDE), PRANDIN (REPAGLINIDE), PRANTAL (DIPHEMANIL METHYLSULFATE), PRAVACHOL (PRAVASTATIN SODIUM), PRAVASTATIN SODIUM (PRAVASTATIN SODIUM), PRAVIGARD PAC (COPACKAGED) (ASPIRIN; PRAVASTATIN SODIUM), PRAZEPAM (PRAZEPAM), PRAZOSIN HYDROCHLORIDE (PRAZOSIN HYDROCHLORIDE), PRE-OP (HEXACHLOROPHENE), PRE-OP II (HEXACHLOROPHENE), PRE-PEN (BENZYL PENICILLOYL-POLYLYSINE), PRE-SATE (CHLORPHENTERMINE HYDROCHLORIDE), PRECEDEX (DEXMEDETOMIDINE), PRECEF (CEFORANIDE), PRECOSE (ACARBOSE), PRED FORTE (PREDNISOLONE ACETATE), PRED MILD (PREDNISOLONE ACETATE), PRED-G (GENTAMICIN SULFATE; PREDNISOLONE ACETATE), PREDAIR (PREDNISOLONE SODIUM PHOSPHATE), PREDAIR FORTE (PREDNISOLONE SODIUM PHOSPHATE), PREDAMIDE (PREDNISOLONE ACETATE; SULFACETAMIDE SODIUM), PREDNICARBATE (PREDNICARBATE), PREDNICEN-M (PREDNISONE), PREDNISOLONE (PREDNISOLONE), PREDNISOLONE ACETATE (PREDNISOLONE ACETATE), PREDNISOLONE SODIUM PHOSPHATE (PREDNISOLONE SODIUM PHOSPHATE), PREDNISOLONE TEBUTATE (PREDNISOLONE TEBUTATE), PREDNISONE (PREDNISONE), PREDNISONE INTENSOL (PREDNISONE), PREDSULFAIR (PREDNISOLONE ACETATE; SULFACETAMIDE SODIUM), PREDSULFAIR II (PREDNISOLONE ACETATE; SULFACETAMIDE SODIUM), PREFEST (ESTRADIOL; NORGESTIMATE), PREFRIN-A (PHENYLEPHRINE HYDROCHLORIDE; PYRILAMINE MALEATE), PREGNYL (GONADOTROPIN, CHORIONIC), PRELAY (TROGLITAZONE), PRELONE (PREDNISOLONE), PRELUDIN (PHENMETRAZINE HYDROCHLORIDE), PREMARIN (ESTROGENS, CONJUGATED), PREMASOL 10% IN PLASTIC CONTAINER (AMINO ACIDS), PREMASOL 6% IN PLASTIC CONTAINER (AMINO ACIDS), PREMPHASE (PREMARIN; CYCRIN 14/14) (ESTROGENS, CONJUGATED; MEDROXYPROGESTERONE ACETATE), PREMPHASE 14/14 (ESTROGENS, CONJUGATED; MEDROXYPROGESTERONE ACETATE), PREMPRO (ESTROGENS, CONJUGATED; MEDROXYPROGESTERONE ACETATE), PREMPRO (PREMARIN; CYCRIN) (ESTROGENS, CONJUGATED; MEDROXYPROGESTERONE ACETATE), PREMPRO/PREMPHASE (CONJUGATED ESTROGENS/MEDROXYPROGESTERONE ACETATE), PREPIDIL (DINOPROSTONE), PRESAMINE (IMIPRAMINE HYDROCHLORIDE), PREVACARE R (CHLORHEXIDINE GLUCONATE), PREVACID (LANSOPRAZOLE), PREVACID IV (LANSOPRAZOLE), PREVACID NAPRAPAC 250 (COPACKAGED) (LANSOPRAZOLE; NAPROXEN), PREVACID NAPRAPAC 375 (COPACKAGED) (LANSOPRAZOLE; NAPROXEN), PREVACID NAPRAPAC 500 (COPACKAGED) (LANSOPRAZOLE; NAPROXEN), PREVALITE (CHOLESTYRAMINE), PREVEN EMERGENCY CONTRACEPTIVE KIT (ETHINYL ESTRADIOL; LEVONORGESTREL), PREVIFEM (ETHINYL ESTRADIOL; NORGESTIMATE), PREVPAC (AMOXICILLIN; CLARITHROMYCIN; LANSOPRAZOLE), PREZISTA (DARUNAVIR ETHANOLATE), PRIALT (ZICONOTIDE), PRIFTIN (RIFAPENTINE), PRILOSEC (OMEPRAZOLE), PRILOSEC (OMEPRAZOLE MAGNESIUM), PRILOSEC OTC (OMEPRAZOLE MAGNESIUM), PRIMACOR (MILRINONE LACTATE), PRIMACOR IN DEXTROSE 5% IN PLASTIC CONTAINER (MILRINONE LACTATE), PRIMAQUINE (PRIMAQUINE PHOSPHATE), PRIMATENE MIST (EPINEPHRINE), PRIMAXIN (CILASTATIN SODIUM; IMIPENEM), PRIMIDONE (PRIMIDONE), PRIMSOL (TRIMETHOPRIM HYDROCHLORIDE),

PRINCIPEN (AMPICILLIN/AMPICILLIN TRIHYDRATE), PRINCIPEN '125' (AMPICILLIN/AMPICILLIN TRIHYDRATE), PRINCIPEN '250' (AMPICILLIN/AMPICILLIN TRIHYDRATE), PRINCIPEN '500' (AMPICILLIN/AMPICILLIN TRIHYDRATE), PRINCIPEN W/ PROBENECID (AMPICILLIN/AMPICILLIN TRIHYDRATE; PROBENECID), PRINIVIL (LISINOPRIL), PRINZIDE (HYDROCHLOROTHIAZIDE; LISINOPRIL), PRISCOLINE (TOLAZOLINE HYDROCHLORIDE), PRISMASOL BGK 0/2.5 IN PLASTIC CONTAINER (CALCIUM CHLORIDE; DEXTROSE; LACTIC ACID; MAGNESIUM CHLORIDE; POTASSIUM CHLORIDE; SODIUM BICARBONATE; SODIUM CHLORIDE), PRISMASOL BGK 2/0 IN PLASTIC CONTAINER (CALCIUM CHLORIDE; DEXTROSE; LACTIC ACID; MAGNESIUM CHLORIDE; POTASSIUM CHLORIDE; SODIUM BICARBONATE; SODIUM CHLORIDE), PRISMASOL BGK 2/3.5 IN PLASTIC CONTAINER (CALCIUM CHLORIDE; DEXTROSE; LACTIC ACID; MAGNESIUM CHLORIDE; POTASSIUM CHLORIDE; SODIUM BICARBONATE; SODIUM CHLORIDE), PRISMASOL BGK 4/0 IN PLASTIC CONTAINER (CALCIUM CHLORIDE; DEXTROSE; LACTIC ACID; MAGNESIUM CHLORIDE; POTASSIUM CHLORIDE; SODIUM BICARBONATE; SODIUM CHLORIDE), PRISMASOL BGK 4/2.5 IN PLASTIC CONTAINER (CALCIUM CHLORIDE; DEXTROSE; LACTIC ACID; MAGNESIUM CHLORIDE; POTASSIUM CHLORIDE; SODIUM BICARBONATE; SODIUM CHLORIDE), PRISMASOL BK 0/0 IN PLASTIC CONTAINER (CALCIUM CHLORIDE; DEXTROSE; LACTIC ACID; MAGNESIUM CHLORIDE; POTASSIUM CHLORIDE; SODIUM BICARBONATE; SODIUM CHLORIDE), PRISMASOL BK 0/3.5 IN PLASTIC CONTAINER (CALCIUM CHLORIDE; DEXTROSE; LACTIC ACID; MAGNESIUM CHLORIDE; POTASSIUM CHLORIDE; SODIUM BICARBONATE; SODIUM CHLORIDE), PRISTIQ (DESVENLAFAXINE SUCCINATE), PRO-BANTHINE (PROPANTHELINE BROMIDE), PROAIR HFA (ALBUTEROL SULFATE), PROAMATINE (MIDODRINE HYDROCHLORIDE), PROBALAN (PROBENECID), PROBAMPACIN (AMPICILLIN/AMPICILLIN TRIHYDRATE; PROBENECID), PROBEN-C (COLCHICINE; PROBENECID), PROBENECID (PROBENECID), PROBENECID AND COLCHICINE (COLCHICINE; PROBENECID), PROBENECID W/ COLCHICINE (COLCHICINE; PROBENECID), PROCAINAMIDE HCL (PROCAINAMIDE HYDROCHLORIDE), PROCAINAMIDE HYDROCHLORIDE (PROCAINAMIDE HYDROCHLORIDE), PROCAINE HYDROCHLORIDE (PROCAINE HYDROCHLORIDE), PROCAINE HYDROCHLORIDE W/ EPINEPHRINE (EPINEPHRINE; PROCAINE HYDROCHLORIDE), PROCALAMINE (AMINO ACIDS; CALCIUM ACETATE; GLYCERIN; MAGNESIUM ACETATE; PHOSPHORIC ACID; POTASSIUM CHLORIDE; SODIUM ACETATE; SODIUM CHLORIDE), PROCAN (PROCAINAMIDE HYDROCHLORIDE), PROCAN SR (PROCAINAMIDE HYDROCHLORIDE), PROCANBID (PROCAINAMIDE HYDROCHLORIDE), PROCAPAN (PROCAINAMIDE HYDROCHLORIDE), PROCARDIA (NIFEDIPINE), PROCARDIA XL (NIFEDIPINE), PROCHLORPERAZINE (PROCHLORPERAZINE), PROCHLORPERAZINE (PROCHLORPERAZINE EDISYLATE), PROCHLORPERAZINE (PROCHLORPERAZINE MALEATE), PROCHLORPERAZINE EDISYLATE (PROCHLORPERAZINE EDISYLATE), PROCHLORPERAZINE MALEATE (PROCHLORPERAZINE MALEATE), PROCTOCORT (HYDROCORTISONE), PROCTOFOAM HC (HYDROCORTISONE ACETATE; PRAMOXINE HYDROCHLORIDE), PROFEN (IBUPROFEN), PROFENAL (SUPROFEN), PROFERDEX (IRON DEXTRAN), PROGESTASERT (PROGESTERONE), PROGESTERONE (PROGESTERONE), PROGLYCEM (DIAZOXIDE), PROGRAF (TACROLIMUS), PROHANCE (GADOTERIDOL), PROHANCE MULTIPACK (GADOTERIDOL), PROKETAZINE (CARPHENAZINE MALEATE), PROKLAR (SULFAMETHIZOLE), PROLEUKIN (ALDESLEUKIN), PROLIXIN (FLUPHENAZINE HYDROCHLORIDE), PROLIXIN DECANOATE (FLUPHENAZINE DECANOATE), PROLIXIN ENANTHATE (FLUPHENAZINE ENANTHATE), PROLOID (THYROGLOBULIN), PROLOPRIM (TRIMETHOPRIM), PROMAPAR (CHLORPROMAZINE HYDROCHLORIDE), PROMAZINE HYDROCHLORIDE (PROMAZINE HYDROCHLORIDE), PROMETA (METAPROTERENOL SULFATE), PROMETH FORTIS (PROMETHAZINE HYDROCHLORIDE), PROMETH HYDROCHLORIDE, PHENYLEPHRINE HYDROCHLORIDE W/ CODEINE PHOSPHATE (CODEINE PHOSPHATE; PHENYLEPHRINE HYDROCHLORIDE; PROMETHAZINE HYDROCHLORIDE), PROMETH PLAIN (PROMETHAZINE HYDROCHLORIDE), PROMETH VC PLAIN (PHENYLEPHRINE HYDROCHLORIDE; PROMETHAZINE HYDROCHLORIDE), PROMETH VC W/ CODEINE (CODEINE PHOSPHATE; PHENYLEPHRINE HYDROCHLORIDE; PROMETHAZINE HYDROCHLORIDE), PROMETH W/ CODEINE (CODEINE PHOSPHATE; PROMETHAZINE HYDROCHLORIDE), PROMETH W/ DEXTROMETHORPHAN (DEXTROMETHORPHAN HYDROBROMIDE; PROMETHAZINE HYDROCHLORIDE), PROMETHACON (PROMETHAZINE HYDROCHLORIDE), PROMETHAZINE (PROMETHAZINE HYDROCHLORIDE), PROMETHAZINE DM (DEXTROMETHORPHAN HYDROBROMIDE; PROMETHAZINE HYDROCHLORIDE), PROMETHAZINE HYDROCHLORIDE (PROMETHAZINE HYDROCHLORIDE), PROMETHAZINE HYDROCHLORIDE AND CODEINE PHOSPHATE (CODEINE PHOSPHATE; PROMETHAZINE HYDROCHLORIDE), PROMETHAZINE HYDROCHLORIDE AND DESTROMETHORPHAN HYDROBROMIDE (DEXTROMETHORPHAN HYDROBROMIDE; PROMETHAZINE HYDROCHLORIDE), PROMETHAZINE HYDROCHLORIDE AND DEXTROMETHORPHAN HYDROBROMIDE (DEXTROMETHORPHAN HYDROBROMIDE; PROMETHAZINE HYDROCHLORIDE), PROMETHAZINE HYDROCHLORIDE PLAIN (PROMETHAZINE HYDROCHLORIDE), PROMETHAZINE PLAIN (PROMETHAZINE HYDROCHLORIDE), PROMETHAZINE VC PLAIN (PHENYLEPHRINE HYDROCHLORIDE; PROMETHAZINE HYDROCHLORIDE), PROMETHAZINE VC W/ CODEINE (CODEINE PHOSPHATE; PHENYLEPHRINE HYDROCHLORIDE; PROMETHAZINE HYDROCHLORIDE), PROMETHAZINE W/ CODEINE (CODEINE PHOSPHATE; PROMETHAZINE HYDROCHLORIDE), PROMETHAZINE W/

DEXTROMETHORPHAN (DEXTROMETHORPHAN HYDROBROMIDE; PROMETHAZINE HYDROCHLORIDE; PROMETHAZINE WITH CODEINE (CODEINE PHOSPHATE; PROMETHAZINE HYDROCHLORIDE), PROMETHEGAN (PROMETHAZINE HYDROCHLORIDE), PROMETRIUM (PROGESTERONE), PROMPT PHENYTOIN SODIUM (PHENYTOIN SODIUM), PRONESTYL (PROCAINAMIDE HYDROCHLORIDE), PRONESTYL-SR (PROCAINAMIDE HYDROCHLORIDE), PROPACET 100 (ACETAMINOPHEN; PROPDXYPHENE NAPSYLATE), PROPAFENONE HYDROCHLORIDE (PROPAFENONE HYDROCHLORIDE), PROPANTHELINE BROMIDE (PROPANTHELINE BROMIDE), PROPARACAINE HYDROCHLORIDE (PROPARACAINE HYDROCHLORIDE), PROPECIA (FINASTERIDE), PROPHENE 65 (PROPDXYPHENE HYDROCHLORIDE), PROPINE (DIPIVEFRIN HYDROCHLORIDE), PROPOFOL (PROPOFOL), PROPDXYPHENE COMPOUND 65 (ASPIRIN; CAFFEINE; PROPDXYPHENE HYDROCHLORIDE), PROPDXYPHENE COMPOUND-65 (ASPIRIN; CAFFEINE; PROPDXYPHENE HYDROCHLORIDE), PROPDXYPHENE HYDROCHLORIDE (PROPDXYPHENE HYDROCHLORIDE), PROPDXYPHENE HYDROCHLORIDE 65 (PROPDXYPHENE HYDROCHLORIDE), PROPDXYPHENE HYDROCHLORIDE AND ACETAMINOPHEN (ACETAMINOPHEN; PROPDXYPHENE HYDROCHLORIDE), PROPDXYPHENE HYDROCHLORIDE W/ ASPIRIN AND CAFFEINE (ASPIRIN; CAFFEINE; PROPDXYPHENE HYDROCHLORIDE), PROPDXYPHENE NAPSYLATE AND ACETAMINOPHEN (ACETAMINOPHEN; PROPDXYPHENE NAPSYLATE), PROPRANOLOL HYDROCHLORIDE (PROPRANOLOL HYDROCHLORIDE), PROPRANOLOL HYDROCHLORIDE & HYDROCHLOROTHIAZIDE (HYDROCHLOROTHIAZIDE; PROPRANOLOL HYDROCHLORIDE), PROPRANOLOL HYDROCHLORIDE AND HYDROCHLOROTHIAZIDE (HYDROCHLOROTHIAZIDE; PROPRANOLOL HYDROCHLORIDE), PROPRANOLOL HYDROCHLORIDE INTENSOL (PROPRANOLOL HYDROCHLORIDE), PROPULSID (CISAPRIDE MONOHYDRATE), PROPULSID QUICKSOLV (CISAPRIDE MONOHYDRATE), PROPYLTHIOURACIL (PROPYLTHIOURACIL), PROQUIN XR (CIPROFLOXACIN HYDROCHLORIDE), PROSCAR (FINASTERIDE), PROSOL 20% SULFITE FREE IN PLASTIC CONTAINER (AMINO ACIDS), PROSOM (ESTAZOLAM), PROSTAPHLIN (OXACILLIN SODIUM), PROSTASCINT (CAPROMAB PENDETIDE), PROSTEP (NICOTINE), PROSTIN E2 (DINOPROSTONE), PROSTIN F2 ALPHA (DINOPROST TROMETHAMINE), PROSTIN VR PEDIATRIC (ALPROSTADIL), PROTAMINE SULFATE (PROTAMINE SULFATE), PROTAMINE ZINC & ILETIN I (BEEF-PORK) (INSULIN SUSP PROTAMINE ZINC BEEF/PORK), PROTAMINE ZINC AND ILETIN II (INSULIN SUSP PROTAMINE ZINC PURIFIED BEEF), PROTAMINE ZINC AND ILETIN II (PORK) (INSULIN SUSP PROTAMINE ZINC PURIFIED PORK), PROTAMINE ZINC INSULIN (INSULIN SUSP PROTAMINE ZINC PURIFIED BEEF), PROTONIX (PANTOPRAZOLE SODIUM), PROTONIX IV (PANTOPRAZOLE SODIUM), PROTOPAM CHLORIDE (PRALIDOXIME CHLORIDE), PROTOPIC (TACROLIMUS), PROTOSTAT (METRONIDAZOLE), PROTROPIN (SOMATREM), PROVAL #3 (ACETAMINOPHEN; CODEINE PHOSPHATE), PROVENTIL (ALBUTEROL), PROVENTIL (ALBUTEROL SULFATE), PROVENTIL-HFA (ALBUTEROL SULFATE), PROVERA (MEDROXYPROGESTERONE ACETATE), PROVIGIL (MODAFINIL), PROVOCHOLINE (METHACHOLINE CHLORIDE), PROZAC (FLUOXETINE HYDROCHLORIDE), PROZAC WEEKLY (FLUOXETINE HYDROCHLORIDE), PSEUDO-12 (PSEUDOEPHEDRINE POLISTIREX), PSEUDOEPHEDRINE HYDROCHLORIDE (PSEUDOEPHEDRINE HYDROCHLORIDE), PSEUDOEPHEDRINE HYDROCHLORIDE AND CHLORPHENIRAMINE MALEATE (CHLORPHENIRAMINE MALEATE; PSEUDOEPHEDRINE HYDROCHLORIDE), PSEUDOEPHEDRINE HYDROCHLORIDE AND TRIPROLIDINE HYDROCHLORIDE (PSEUDOEPHEDRINE HYDROCHLORIDE; TRIPROLIDINE HYDROCHLORIDE), PSORCON (DIFLORASONE DIACETATE), PSORCON E (DIFLORASONE DIACETATE), PULMICORT (BUDESONIDE), PULMICORT FLEXHALER (BUDESONIDE), PULMICORT RESPULES (BUDESONIDE), PULMOLITE (TECHNETIUM TC-99M ALBUMIN AGGREGATED KIT), PULMOZYME (DORNASE ALFA), PURIFIED CORTROPHIN GEL (CORTICOTROPIN), PURINETHOL (MERCAPTOPURINE), PYLERA (BISMUTH SUBCITRATE POTASSIUM; METRONIDAZOLE; TETRACYCLINE), PYLORI-CHEK BREATH TEST (UREA, C-13), PYOCIDIN (HYDROCORTISONE; POLYMYXIN B SULFATE), PYOPEN (CARBENICILLIN DISODIUM), PYRAZINAMIDE (PYRAZINAMIDE), PYRIDAMAL 100 (CHLORPHENIRAMINE MALEATE), PYRIDOSTIGMINE BROMIDE (PYRIDOSTIGMINE BROMIDE), PYRIDOXINE HYDROCHLORIDE (PYRIDOXINE HYDROCHLORIDE), PYRILAMINE MALEATE (PYRILAMINE MALEATE), PYROLITE (TECHNETIUM TC-99M PYRO/TRIMETA PHOSPHATES KIT), PYTEST (UREA, C-14), PYTEST KIT (UREA, C-14), Q-GESIC (ASPIRIN; MEPROBAMATE), Q-PAM (DIAZEPAM), QUADRAMET (SAMARIUM SM 153 LEXIDRONAM PENTASODIUM), QUALAQUIN (QUININE SULFATE), QUARZAN (CLIDINIUM BROMIDE), QUASENSE (ETHINYL ESTRADIOL; LEVONORGESTREL), QUELICIN (SUCCINYLCHOLINE CHLORIDE), QUELICIN PRESERVATIVE FREE (SUCCINYLCHOLINE CHLORIDE), QUESTRAN (CHOLESTYRAMINE), QUESTRAN LIGHT (CHOLESTYRAMINE), QUIBRON-T (THEOPHYLLINE), QUIBRON-T/SR (THEOPHYLLINE), QUIDE (PIPERACETAZINE), QUINACT (QUINIDINE GLUCONATE), QUINAGLUTE (QUINIDINE GLUCONATE), QUINALAN (QUINIDINE GLUCONATE), QUINAPRIL (QUINAPRIL HYDROCHLORIDE), QUINAPRIL HYDROCHLORIDE (QUINAPRIL HYDROCHLORIDE), QUINAPRIL HYDROCHLORIDE AND HYDROCHLOROTHIAZIDE (HYDROCHLOROTHIAZIDE; QUINAPRIL HYDROCHLORIDE), QUINARETIC (HYDROCHLOROTHIAZIDE; QUINAPRIL HYDROCHLORIDE), QUINATIME (QUINIDINE GLUCONATE), QUINIDEX (QUINIDINE SULFATE), QUINIDINE GLUCONATE (QUINIDINE GLUCONATE), QUINIDINE SULFATE (QUINIDINE SULFATE), QUINORA (QUINIDINE SULFATE), QUIXIN (LEVOFLOXACIN), QVAR 40 (BECLOMETHASONE DIPROPIONATE), QVAR 80 (BECLOMETHASONE DIPROPIONATE), R-GENE 10 (ARGI-

NINE HYDROCHLORIDE), R-P MYCIN (ERYTHROMYCIN), RABEPRAZOLE (RABEPRAZOLE SODIUM), RABEPRAZOLE SODIUM (RABEPRAZOLE SODIUM), RADIO-IODINATED (I 125) SERUM ALBUMIN (HUMAN) (ALBUMIN IODINATED I-125 SERUM), RADIOGARDASE (PRUSSIAN BLUE) (FERRIC HEXACYANOFERRATE (II)), RADIOIODINATED SERUM ALBUMIN (HUMAN) IHSA I 125 (ALBUMIN IODINATED I-125 SERUM), RADIONUCLIDE-LABELED (125 I) FIBRINOGEN (HUMAN) SENSOR (FIBRINOGEN, I-125), RALOXIFENE HYDROCHLORIDE (RALOXIFENE HYDROCHLORIDE), RAMIPRIL (RAMIPRIL), RANEXA (RANOLAZINE), RANICLOR (CEFACLOR), RANITIDINE (RANITIDINE), RANITIDINE (RANITIDINE HYDROCHLORIDE), RANITIDINE HYDROCHLORIDE (RANITIDINE HYDROCHLORIDE), RAPAMUNE (SIROLIMUS), RAPLON (RAPACURONIUM BROMIDE), RAPTIVA (EFALIZUMAB), RAUSED (RESERPINE), RAUDIXIN (*RAUWOLFIA SERPENTINA*), RAUSERPIN (*RAUWOLFIA SERPENTINA*), RAUTENSIN (ALSEROXYLON), RAUVAL (*RAUWOLFIA SERPENTINA*), RAUWILOID (ALSEROXYLON), *RAUWOLFIA SERPENTINA* (*RAUWOLFIA SERPENTINA*), RAVOCAINE AND NOVOCAIN W/ LEVOPHED (NOREPINEPHRINE BITARTRATE; PROCAINE HYDROCHLORIDE; PROPDXYCAINE HYDROCHLORIDE), RAVOCAINE AND NOVOCAIN W/ NEO-COBEFRIN (LEVONORDEFRIN; PROCAINE HYDROCHLORIDE; PROPDXYCAINE HYDROCHLORIDE), RAXAR (GREPAFLOXACIN HYDROCHLORIDE), RAZADYNE (GALANTAMINE HYDROBROMIDE), RAZADYNE ER (GALANTAMINE HYDROBROMIDE), RBC-SCAN (TECHNETIUM TC-99M RED BLOOD CELL KIT), REBETOL (RIBAVIRIN), Rebif (Interferon beta-1a), RECLAST (ZOLEDRONIC ACID), REDISOL (CYANOCOBALAMIN), REFLUDAN (LEPIRUDIN RECOMBINANT), REGITINE (PHENTOLAMINE MESYLATE), REGLAN (METOCLOPRAMIDE HYDROCHLORIDE), REGLAN ODT (METOCLOPRAMIDE HYDROCHLORIDE), REGONOL (PYRIDOSTIGMINE BROMIDE), REGRANEX (BECAPLERMIN), REGROTON (CHLORTHALIDONE; RESERPINE), REGULAR ILETIN II (INSULIN PURIFIED BEEF), REGULAR ILETIN II (PORK) (INSULIN PURIFIED PORK), REGULAR INSULIN (INSULIN PORK), REGULAR PURIFIED PORK INSULIN (INSULIN PURIFIED PORK), RELA (CARISOPRODOL), RELAFEN (NABUMETONE), RELENZA (ZANAMIVIR), RELISTOR (METHYLNALTREXONE BROMIDE), RELPAX (ELETRIPTAN HYDROBROMIDE), REMERON (MIRTAZAPINE), REMERON SOLTAB (MIRTAZAPINE), REMICADE (INFLIXIMAB), REMODULIN (TREPROSTINIL SODIUM), REMSED (PROMETHAZINE HYDROCHLORIDE), RENACIDIN (CITRIC ACID; GLUCONOLACTONE; MAGNESIUM CARBONATE), RENAGEL (SEVELAMER HYDROCHLORIDE), RENAMIN W/O ELECTROLYTES (AMINO ACIDS), RENESE (POLYTHIAZIDE), RENESE-R (POLYTHIAZIDE; RESERPINE), RENO-30 (DIATRIZOATE MEGLUMINE), RENO-60 (DIATRIZOATE MEGLUMINE), RENO-DIP (DIATRIZOATE MEGLUMINE), RENOCAL-76 (DIATRIZOATE MEGLUMINE; DIATRIZOATE SODIUM), RENOGRAFIN-60 (DIATRIZOATE MEGLUMINE; DIATRIZOATE SODIUM), RENOGRAFIN-76 (DIATRIZOATE MEGLUMINE; DIATRIZOATE SODIUM), RENOQUID (SULFACYTINE), RENORMAX (SPIRAPRIL HYDROCHLORIDE), RENOTEC (TECHNETIUM TC-99M FERPENTETATE KIT), RENOVA (TRETINOIN), RENOVIST (DIATRIZOATE MEGLUMINE; DIATRIZOATE SODIUM), RENOVIST II (DIATRIZOATE MEGLUMINE; DIATRIZOATE SODIUM), RENOVUE-65 (IODAMIDE MEGLUMINE), RENOVUE-DIP (IODAMIDE MEGLUMINE), RENVELA (SEVELAMER CARBONATE), REOPRO (ABCIXIMAB), REPAGLINIDE (REPAGLINIDE), REPREXAIN (HYDROCODONE BITARTRATE; IBUPROFEN), REPRONEX (MENOTROPINS (FSH; LH)), REQUIP (ROPINIROLE HYDROCHLORIDE), REQUIP XL (ROPINIROLE), RESCRIPTOR (DELAVIRDINE MESYLATE), RESCULA (UNOPROSTONE ISOPROPYL), RESECTISOL (MANNITOL), RESECTISOL IN PLASTIC CONTAINER (MANNITOL), RESERPINE (RESERPINE), RESERPINE AND HYDROCHLOROTHIAZIDE (HYDROCHLOROTHIAZIDE; RESERPINE), RESERPINE AND HYDROCHLOROTHIAZIDE-50 (HYDROCHLOROTHIAZIDE; RESERPINE), RESERPINE AND HYDROFLUMETHIAZIDE (HYDROFLUMETHIAZIDE; RESERPINE), RESERPINE, HYDRALAZINE HYDROCHLORIDE AND HYDROCHLOROTHIAZIDE (HYDRALAZINE HYDROCHLORIDE; HYDROCHLOROTHIAZIDE; RESERPINE), RESERPINE, HYDROCHLOROTHIAZIDE, AND HYDRALAZINE HYDROCHLORIDE (HYDRALAZINE HYDROCHLORIDE; HYDROCHLOROTHIAZIDE; RESERPINE), RESPORAL (DEXBROMPHENIRAMINE MALEATE; PSEUDOEPHEDRINE SULFATE), RESTASIS (CYCLOSPORINE), RESTORIL (TEMAZEPAM), RETAVASE (RETEPLASE), RETET (TETRACYCLINE HYDROCHLORIDE), RETIN-A (TRETINOIN), RETIN-A MICRO (TRETINOIN), RETISERT (FLUOCINOLONE ACETONIDE), RETROVIR (ZIDOVUDINE), REV-EYES (DAPIPRAZOLE HYDROCHLORIDE), REVATIO (SILDENAFIL CITRATE), REVERSOL (EDROPHONIUM CHLORIDE), REVEX (NALMEFENE HYDROCHLORIDE), REVIA (NALTREXONE HYDROCHLORIDE), REVLIMID (LENALIDOMIDE), REYATAZ (ATAZANAVIR SULFATE), REZIPAS (AMINOSALICYLIC ACID RESIN COMPLEX), REZULIN (TROGLITAZONE), RHINOCORT (BUDESONIDE), RIBASPHERE (RIBAVIRIN), RIBAVIRIN (RIBAVIRIN), RID MOUSSE (PIPERONYL BUTOXIDE; PYRETHRINS), RIDAURA (AURANOFIN), RIFADIN (RIFAMPIN), RIFAMATE (ISONIAZID; RIFAMPIN), RIFAMPIN (RIFAMPIN), RIFAMPIN AND ISONIAZID (ISONIAZID; RIFAMPIN), RIFATER (ISONIAZID; PYRAZINAMIDE; RIFAMPIN), RILUTEK (RILUZOLE), RILUZOLE (RILUZOLE), RIMACTANE (RIFAMPIN), RIMADYL (CARPROFEN), RIMANTADINE HYDROCHLORIDE (RIMANTADINE HYDROCHLORIDE), RIMIFON (ISONIAZID), RIMSO-50 (DIMETHYL SULFOXIDE), RINGER'S IN PLASTIC CONTAINER (CALCIUM CHLORIDE; POTASSIUM CHLORIDE; SODIUM CHLORIDE), RIOMET (METFORMIN HYDROCHLORIDE), RISEDRONATE SODIUM (RISEDRONATE SODIUM), RISPERDAL (RISPERIDONE), RISPERDAL CONSTA (RISPERIDONE), RISPERIDONE (RISPERIDONE), RITALIN (METHYLPHENIDATE HYDROCHLORIDE), RITALIN LA (METHYLPHENIDATE HYDROCHLORIDE), RITALIN-SR (METHYL- PHENIDATE HYDROCHLORIDE), RITODRINE HCL (RITODRINE HYDROCHLORIDE), RITODRINE HYDROCHLORIDE (RITODRINE HYDROCHLORIDE), RITODRINE HYDROCHLORIDE IN DEXTROSE 5% IN PLASTIC CONTAINER (RITODRINE HYDROCHLORIDE), RITUXAN (RITUXIMAB), RIVASTIGMINE (RIVASTIGMINE TARTRATE), RIVASTIGMINE TARTRATE (RIVASTIGMINE TARTRATE), RIZATRIPTAN BENZOATE (RIZATRIPTAN BENZOATE), ROBAXIN (METHOCARBAMOL), ROBAXIN-750 (METHOCARBAMOL), ROBAXISAL (ASPIRIN; METHOCARBAMOL), ROBENGATOPE (ROSE BENGAL SODIUM, I-131), ROBIMYCIN (ERYTHROMYCIN), ROBINUL (GLYCOPYRROLATE), ROBINUL FORTE (GLYCOPYRROLATE), ROBITET (TETRACYCLINE HYDROCHLORIDE), ROCALTROL (CALCITRIOL), ROCEPHIN (CEFTRIAXONE SODIUM), ROCEPHIN KIT (CEFTRIAXONE SODIUM; LIDOCAINE), ROCEPHIN W/ DEXTROSE IN PLASTIC CONTAINER (CEFTRIAXONE SODIUM), ROFERON A (INTERFERON ALFA-2A), ROGAINE (FOR MEN) (MINOXIDIL), ROGAINE (FOR WOMEN) (MINOXIDIL), ROGAINE EXTRA STRENGTH (FOR MEN) (MINOXIDIL), ROMAZICON (FLUMAZENIL), RONDOMYCIN (METHACYCLINE HYDROCHLORIDE), ROPINIROLE HYDROCHLORIDE (ROPINIROLE HYDROCHLORIDE), ROSIGLITAZONE (ROSIGLITAZONE MALEATE), ROSIGLITAZONE MALEATE (ROSIGLITAZONE MALEATE), ROSIGLITAZONE MALEATE; METFORMIN HYDROCHLORIDE (ROSIGLITAZONE MALEATE; METFORMIN HYDROCHLORIDE), ROWASA (MESALAMINE), ROXICET (ACETAMINOPHEN; OXYCODONE HYDROCHLORIDE), ROXICET 5/500 (ACETAMINOPHEN; OXYCODONE HYDROCHLORIDE), ROXICODONE (OXYCODONE HYDROCHLORIDE), ROXILOX (ACETAMINOPHEN; OXYCODONE HYDROCHLORIDE), ROXIPRIN (ASPIRIN; OXYCODONE HYDROCHLORIDE; OXYCODONE TEREPHTHALATE), ROZEREM (RAMELTEON), RUBEX (DOXORUBICIN HYDROCHLORIDE), RUBIVITE (CYANOCOBALAMIN), RUBRAMIN PC (CYANOCOBALAMIN), RUBRATOPE-57 (CYANOCOBALAMIN, CO-57), RUBRATOPE-57 KIT (COBALT CHLORIDE, CO-57; CYANOCOBALAMIN; CYANOCOBALAMIN, CO-57; INTRINSIC FACTOR), RUBRATOPE-60 (CYANOCOBALAMIN, CO-60), RUBRATOPE-60 KIT (COBALT CHLORIDE, CO-60; CYANOCOBALAMIN; CYANOCOBALAMIN, CO-60; INTRINSIC FACTOR), RUFEN (IBUPROFEN), RUVITE (CYANOCOBALAMIN), RYTHMOL (PROPAFENONE HYDROCHLORIDE), RYTHMOL SR (PROPAFENONE HYDROCHLORIDE), S.A.S.-500 (SULFASALAZINE), SAIZEN (SOMATROPIN RECOMBINANT), SALAGEN (PILOCARPINE HYDROCHLORIDE), SALONPAS (MENTHOL; METHYL SALICYLATE), SALPIX (ACETRIZOATE SODIUM), SALURON (HYDROFLUMETHIAZIDE), SALUTENSIN (HYDROFLUMETHIAZIDE; RESERPINE), SALUTENSIN-DEMI (HYDROFLUMETHIAZIDE; RESERPINE), SANCTURA (TROSPIUM CHLORIDE), SANCTURA XR (TROSPIUM CHLORIDE), SANDIMMUNE (CYCLOSPORINE), SANDOSTATIN (OCTREOTIDE ACETATE), SANDOSTATIN LAR (OCTREOTIDE ACETATE), SANDRIL (RESERPINE), SANGCYA (CYCLOSPORINE), SANOREX (MAZINDOL), SANSAC (ERYTHROMYCIN), SANSERT (METHYSERGIDE MALEATE), SANTYL (COLLAGENASE), SARAFEM (FLUOXETINE HYDROCHLORIDE), SARENIN (SARALASIN ACETATE), SARISOL (BUTABARBITAL SODIUM), SARISOL NO. 1 (BUTABARBITAL SODIUM), SARISOL NO. 2 (BUTABARBITAL SODIUM), SATRIC (METRONIDAZOLE), SCABENE (LINDANE), SCANDONEST L (LEVONORDEFRIN; MEPIVACAINE HYDROCHLORIDE), SCANDONEST PLAIN (MEPIVACAINE HYDROCHLORIDE), SCLEROSOL (TALC), SCRUBTEAM SURGICAL SPONGEBRUSH (HEXACHLOROPHENE), SEASONALE (ETHINYL ESTRADIOL; LEVONORGESTREL), SEASONIQUE (ETHINYL ESTRADIOL; LEVONORGESTREL), SECOBARBITAL SODIUM (SECOBARBITAL SODIUM), SECONAL SODIUM (SECOBARBITAL SODIUM), SECREFLO (SECRETIN), SECREFLO (SECRETIN SYNTHETIC PORCINE), SECRETIN-FERRING (SECRETIN), SECTRAL (ACEBUTOLOL HYDROCHLORIDE), SEDAPAP (ACETAMINOPHEN; BUTALBITAL), SEFFIN (CEPHALOTHIN SODIUM), SELEGILINE HYDROCHLORIDE (SELEGILINE HYDROCHLORIDE), SELENIUM SULFIDE (SELENIUM SULFIDE), SELENOMETHIONINE SE 75 (SELENOMETHIONINE, SE-75), SELSUN (SELENIUM SULFIDE), SELZENTRY (MARAVIROC), SEMILENTE (INSULIN ZINC SUSP PROMPT PURIFIED PORK), SEMILENTE INSULIN (INSULIN ZINC SUSP PROMPT BEEF), SEMPREX-D (ACRIVASTINE; PSEUDOEPHEDRINE HYDROCHLORIDE), SENSIPAR (CINACALCET HYDROCHLORIDE), SENSORCAINE (BUPIVACAINE HYDROCHLORIDE), SENSORCAINE (BUPIVACAINE HYDROCHLORIDE; EPINEPHRINE BITARTRATE), SEPTI-SOFT (HEXACHLOROPHENE), SEPTISOL (HEXACHLOROPHENE), SEPTOCAINE (ARTICAINE HYDROCHLORIDE; EPINEPHRINE BITARTRATE), SEPTRA (SULFAMETHOXAZOLE; TRIMETHOPRIM), SEPTRA DS (SULFAMETHOXAZOLE; TRIMETHOPRIM), SEPTRA GRAPE (SULFAMETHOXAZOLE; TRIMETHOPRIM), SER-A-GEN (HYDRALAZINE HYDROCHLORIDE; HYDROCHLOROTHIAZIDE; RESERPINE), SER-AP-ES (HYDRALAZINE HYDROCHLORIDE; HYDROCHLOROTHIAZIDE; RESERPINE), SERAX (OXAZEPAM), SERENTIL (MESORIDAZINE BESYLATE), SEREVENT (SALMETEROL XINAFOATE), SEROMYCIN (CYCLOSERINE), SEROPHENE (CLOMIPHENE CITRATE), SEROQUEL (QUETIAPINE FUMARATE), SEROQUEL XR (QUETIAPINE FUMARATE), SEROSTIM (SOMATROPIN RECOMBINANT), SEROSTIM LQ (SOMATROPIN RECOMBINANT), SERPALAN (RESERPINE), SERPANRAY (RESERPINE), SERPASIL (RESERPINE), SERPASIL-APRESOLINE (HYDRALAZINE HYDROCHLORIDE; RESERPINE), SERPASIL-ESIDRIX #1 (HYDROCHLOROTHIAZIDE; RESERPINE), SERPASIL-ESIDRIX #2 (HYDROCHLOROTHIAZIDE; RESERPINE), SERPATE (RESERPINE), SERPIVITE (RESERPINE), SERTRALINE HYDROCHLORIDE (SERTRALINE HYDROCHLORIDE), SERVISONE (PREDNISONE), SERZONE (NEFAZODONE HYDROCHLORIDE), SETHOTOPE (SELENOMETHIONINE, SE-75), SEVOFLURANE (SEVOFLURANE), SHADE UVAGUARD (AVOBENZONE; OCTINOXATE; OXYBENZONE), SILDAFLO (SILVER SULFADIAZINE), SILDENAFIL CITRATE (SILDENAFIL CITRATE), SILPHEN (DIPHENHYDRAMINE HYDROCHLORIDE), SILVADENE (SILVER SULFADIAZINE), SIMCOR (NIACIN; SIMVASTATIN), SIMULECT (BASILIXIMAB), SIMVASTATIN (SIMVASTATIN), SINE-AID IB (IBUPROFEN; PSEUDOEPHEDRINE HYDROCHLORIDE), SINEMET (CARBIDOPA; LEVODOPA), SINEMET CR (CARBIDOPA; LEVODOPA), SINEQUAN (DOXEPIN HYDROCHLORIDE), SINGULAIR (MONTELUKAST SODIUM), SINOGRAFIN (DIATRIZOATE MEGLUMINE; IODIPAMIDE MEGLUMINE), SKELAXIN (METAXALONE), SKELID (TILUDRONATE DISODIUM), SKIN EXPOSURE REDUCTION PASTE AGAINST CHEMICAL WARFARE AGENTS (PERFLUOROPOLYMETHYLISOPROPYL ETHER; POLYTETRAFLUOROETHYLENE), SLO-BID (THEOPHYLLINE), SLO-PHYLLIN (THEOPHYLLINE), SLOW-K (POTASSIUM CHLORIDE), SODIUM ACETATE IN PLASTIC CONTAINER (SODIUM ACETATE, ANHYDROUS), SODIUM AMINOSALICYLATE (AMINOSALICYLATE SODIUM), SODIUM BICARBONATE (SODIUM BICARBONATE), SODIUM BICARBONATE IN PLASTIC CONTAINER (SODIUM BICARBONATE), SODIUM BUTABARBITAL (BUTABARBITAL SODIUM), SODIUM CHLORIDE (SODIUM CHLORIDE), SODIUM CHLORIDE 0.45% AND POTASSIUM CHLORIDE 0.15% IN PLASTIC CONTAINER (POTASSIUM CHLORIDE; SODIUM CHLORIDE), SODIUM CHLORIDE 0.45% IN PLASTIC CONTAINER (SODIUM CHLORIDE), SODIUM CHLORIDE 0.9% AND POTASSIUM CHLORIDE 0.075% IN PLASTIC CONTAINER (POTASSIUM CHLORIDE; SODIUM CHLORIDE), SODIUM CHLORIDE 0.9% AND POTASSIUM CHLORIDE 0.15% IN PLASTIC CONTAINER (POTASSIUM CHLORIDE; SODIUM CHLORIDE), SODIUM CHLORIDE 0.9% AND POTASSIUM CHLORIDE 0.22% IN PLASTIC CONTAINER (POTASSIUM CHLORIDE; SODIUM CHLORIDE), SODIUM CHLORIDE 0.9% AND POTASSIUM CHLORIDE 0.224% (POTASSIUM CHLORIDE; SODIUM CHLORIDE), SODIUM CHLORIDE 0.9% AND POTASSIUM CHLORIDE 0.3% IN PLASTIC CONTAINER (POTASSIUM CHLORIDE; SODIUM CHLORIDE), SODIUM CHLORIDE 0.9% IN PLASTIC CONTAINER (SODIUM CHLORIDE), SODIUM CHLORIDE 0.9% IN STERILE PLASTIC CONTAINER (SODIUM CHLORIDE), SODIUM CHLORIDE 23.4% IN PLASTIC CONTAINER (SODIUM CHLORIDE), SODIUM CHLORIDE 3% IN PLASTIC CONTAINER (SODIUM CHLORIDE), SODIUM CHLORIDE 5% IN PLASTIC CONTAINER (SODIUM CHLORIDE), SODIUM CHLORIDE IN PLASTIC CONTAINER (SODIUM CHLORIDE), SODIUM CHROMATE CR 51 (SODIUM CHROMATE, CR-51), SODIUM HEPARIN (HEPARIN SODIUM), SODIUM IODIDE I 123 (SODIUM IODIDE, I-123), SODIUM IODIDE I 131 (SODIUM IODIDE, I-131), SODIUM LACTATE 0.167 MOLAR IN PLASTIC CONTAINER (SODIUM LACTATE), SODIUM LACTATE 1/6 MOLAR IN PLASTIC CONTAINER (SODIUM LACTATE), SODIUM LACTATE IN PLASTIC CONTAINER (SODIUM LACTATE), SODIUM NITROPRUSSIDE (SODIUM NITROPRUSSIDE), SODIUM P.A.S. (AMINOSALICYLATE SODIUM), SODIUM PENTOBARBITAL (PENTOBARBITAL SODIUM), SODIUM PERTECHNETATE TC 99M (TECHNETIUM TC-99M SODIUM PERTECHNETATE), SODIUM PHOSPHATE P 32 (SODIUM PHOSPHATE, P-32), SODIUM PHOSPHATES IN PLASTIC CONTAINER (SODIUM PHOSPHATE, DIBASIC, HEPTAHYDRATE; SODIUM PHOSPHATE, MONOBASIC, ANHYDROUS), SODIUM POLYPHOSPHATE-TIN KIT (TECHNETIUM TC-99M POLYPHOSPHATE KIT), SODIUM POLYSTYRENE SULFONATE (SODIUM POLYSTYRENE SULFONATE), SODIUM ROSE BENGAL I 131 (ROSE BENGAL SODIUM, I-131), SODIUM SECOBARBITAL (SECOBARBITAL SODIUM), SODIUM SUCCINATE (SODIUM SUCCINATE), SODIUM SULAMYD (SULFACETAMIDE SODIUM), SODIUM SULFACETAMIDE (SULFACETAMIDE SODIUM), SODIUM THIOSULFATE (SODIUM THIOSULFATE), SODIUM VERSENATE (EDETATE DISODIUM), SOJOURN (SEVOFLURANE), SOLAGE (MEQUINOL; TRETINOIN), SOLARAZE (DICLOFENAC SODIUM), SOLATENE (BETACAROTENE), SOLIRIS (ECULIZUMAB), SOLODYN (MINOCYCLINE HYDROCHLORIDE), SOLTAMOX (TAMOXIFEN CITRATE), SOLU-CORTEF (HYDROCORTISONE SODIUM SUCCINATE), SOLU-MEDROL (METHYLPREDNISOLONE SODIUM SUCCINATE), SOMA (CARISOPRODOL), SOMA COMPOUND (ASPIRIN; CARISOPRODOL), SOMA COMPOUND W/ CODEINE (ASPIRIN; CARISOPRODOL; CODEINE PHOSPHATE), SOMATULINE DEPOT (LANREOTIDE ACETATE), SOMAVERT (PEGVISOMANT), SOMOPHYLLIN (AMINOPHYLLINE), SOMOPHYLLIN-CRT (THEOPHYLLINE), SOMOPHYLLIN-DF (AMINOPHYLLINE), SOMOPHYLLIN-T (THEOPHYLLINE), SONATA (ZALEPLON), SONAZINE (CHLORPROMAZINE HYDROCHLORIDE), SONORX (SIMETHICONE-CELLULOSE), SORBITOL 3% IN PLASTIC CONTAINER (SORBITOL), SORBITOL 3.3% IN PLASTIC CONTAINER (SORBITOL), SORBITOL-MANNITOL (MANNITOL; SORBITOL), SORBITOL-MANNITOL IN PLASTIC CONTAINER (MANNITOL; SORBITOL), SORBITRATE (ISOSORBIDE DINITRATE), SORIATANE (ACITRETIN), SORINE (SOTALOL HYDROCHLORIDE), SOSOL (SULFISOXAZOLE), SOTALOL HYDROCHLORIDE (SOTALOL HYDROCHLORIDE), SOTRADECOL (SODIUM TETRADECYL SULFATE), SOTRET (ISOTRETINOIN), SOXAZOLE (SULFISOXAZOLE), SOY-DOME (HEXACHLOROPHENE), SOYACAL 10% (SOYBEAN OIL), SOYACAL 20% (SOYBEAN OIL), SPARINE (PROMAZINE HYDROCHLORIDE), SPECTAMINE (IOFETAMINE HYDROCHLORIDE I-123), SPECTAZOLE (ECONAZOLE NITRATE), SPECTRACEF (CEFDITOREN PIVOXIL), SPECTROBID (BACAMPICILLIN HYDROCHLORIDE), SPIRIVA (TIOTROPIUM BROMIDE MONOHYDRATE), SPIRONOLACTONE (SPIRONOLACTONE), SPIRONOLACTONE AND HYDROCHLOROTHIAZIDE (HYDROCHLOROTHIAZIDE; SPIRONOLACTONE), SPIRONOLACTONE W/ HYDROCHLOROTHIAZIDE (HYDROCHLOROTHIAZIDE; SPIRONOLACTONE), SPORANOX (ITRACONAZOLE), SPRINTEC (ETHINYL ESTRADIOL; NORGESTIMATE), SPRX-105 (PHENDIMETRAZINE TARTRATE), SPRX-3 (PHENDIMETRAZINE TARTRATE), SPRYCEL (DASATINIB), SPS (SODIUM POLYSTYRENE SULFONATE), SSD (SILVER SULFADIAZINE), SSD AF (SILVER SULFADIAZINE), STADOL (BUTORPHANOL TARTRATE), STADOL PRESERVATIVE FREE (BUTORPHANOL TARTRATE), STALEVO 100 (CARBIDOPA; ENTACAPONE; LEVODOPA), STALEVO 150 (CARBIDOPA; ENTACAPONE; LEVODOPA), STALEVO 200 (CARBIDOPA; ENTACAPONE; LEVODOPA), STALEVO 50 (CARBIDOPA; ENTACAPONE; LEVODOPA), STANOZIDE (ISONIAZID), STAPHCILLIN (METHICILLIN SODIUM), STARLIX (NATEGLINIDE), STATICIN (ERYTHROMYCIN), STATOBEX (PHENDIMETRAZINE TARTRATE), STATOBEX-G (PHENDIMETRAZINE TARTRATE), STATROL (NEOMYCIN SULFATE; POLYMYXIN B SULFATE), STAVUDIINE; LAMIVUDINE W/NEVIRAPINE (STAVUDIINE; LAMIVUDINE W/NEVIRAPINE), STAVUDINE (STAVUDINE), STAVUDINE/LAMIVUDINE (STAVUDINE; LAMIVUDINE), STAVUDINE; LAMIVUDINE; EFAVIRENZ (STAVUDINE; LAMIVUDINE; EFAVIRENZ), STAVUDINE; LAMIVUDINE; NEVIRAPINE (STAVUDINE; LAMIVUDINE; NEVIRAPINE), STELAZINE (TRIFLUOPERAZINE HYDROCHLORIDE), STERANE (PREDNISOLONE), STERANE (PREDNISOLONE ACETATE), STERISTAT (CHLORHEXIDINE GLUCONATE), STERILE UREA (UREA), STERILE WATER (STERILE WATER), STERILE WATER (WATER FOR IRRIGATION, STERILE), STERILE WATER FOR INJECTION IN PLASTIC CONTAINER (WATER FOR INJECTION, STERILE), STERILE WATER IN PLASTIC CONTAINER (WATER FOR IRRIGATION, STERILE), STIE-CORT (HYDROCORTISONE), STILBESTROL (DIETHYLSTILBESTROL), STILBETIN (DIETHYLSTILBESTROL), STILPHOSTROL (DIETHYLSTILBESTROL DIPHOSPHATE), STIMATE (DESMOPRESSIN ACETATE), STOXIL (IDOXURIDINE), STRATTERA (ATOMOXETINE HYDROCHLORIDE), STREPTASE (STREPTOKINASE), STREPTOMYCIN SULFATE (STREPTOMYCIN SULFATE), STRIANT (TESTOSTERONE), STRIFON FORTE DSC (CHLORZOXAZONE), STROMECTOL (IVERMECTIN), STRONTIUM CHLORIDE SR-89 (STRONTIUM CHLORIDE, SR-89), SUBLIMAZE PRESERVATIVE FREE (FENTANYL CITRATE), SUBOXONE (BUPRENORPHINE HYDROCHLORIDE; NALOXONE HYDROCHLORIDE), SUBUTEX (BUPRENORPHINE HYDROCHLORIDE), SUCCINYLCHOLINE CHLORIDE (SUCCINYLCHOLINE CHLORIDE), SUCOSTRIN (SUCCINYLCHOLINE CHLORIDE), SUCRAID (SACROSIDASE), SUCRALFATE (SUCRALFATE), SUDAFED 12 HOUR (PSEUDOEPHEDRINE HYDROCHLORIDE), SUDAFED 24 HOUR (PSEUDOEPHEDRINE HYDROCHLORIDE), SUFENTA PRESERVATIVE FREE (SUFENTANIL CITRATE), SUFENTANIL CITRATE (SUFENTANIL CITRATE), SULAR (NISOLDIPINE), SULF-10 (SULFACETAMIDE SODIUM), SULF-15 (SULFACETAMIDE SODIUM), SULFA-TRIPLE #2 (TRISULFAPYRIMIDINES (SULFADIAZINE; SULFAMERAZINE; SULFAMETHAZINE)), SULFABID (SULFAPHENAZOLE), SULFACEL-15 (SULFACETAMIDE SODIUM), SULFACETAMIDE SODIUM (SULFACETAMIDE SODIUM), SULFACETAMIDE SODIUM AND PREDNISOLONE SODIUM PHOSPHATE (PREDNISOLONE SODIUM PHOSPHATE; SULFACETAMIDE SODIUM), SULFADIAZINE (SULFADIAZINE), SULFADIAZINE SODIUM (SULFADIAZINE SODIUM), SULFAIR 10 (SULFACETAMIDE SODIUM), SULFAIR FORTE (SULFACETAMIDE SODIUM), SULFAIR-15 (SULFACETAMIDE SODIUM), SULFALAR (SULFISOXAZOLE), SULFALOID (TRISULFAPYRIMIDINES (SULFADIAZINE; SULFAMERAZINE; SULFAMETHAZINE)), SULFAMETHOPRIM (SULFAMETHOXAZOLE; TRIMETHOPRIM), SULFAMETHOPRIM-DS (SULFAMETHOXAZOLE; TRIMETHOPRIM), SULFAMETHOXAZOLE (SULFAMETHOXAZOLE), SULFAMETHOXAZOLE AND TRIMETHOPRIM (SULFAMETHOXAZOLE; TRIMETHOPRIM), SULFAMETHOXAZOLE AND TRIMETHOPRIM AND PENAZOPYRIDINE HYDROCHLORIDE (PHENAZOPYRIDINE HYDROCHLORIDE; SULFAMETHOXAZOLE; TRIMETHOPRIM), SULFAMETHOXAZOLE AND TRIMETHOPRIM DOUBLE STRENGTH (SULFAMETHOXAZOLE; TRIMETHOPRIM), SULFAMETHOXAZOLE AND TRIMETHOPRIM SINGLE STRENGTH (SULFAMETHOXAZOLE; TRIMETHOPRIM), SULFAMYLON (MAFENIDE ACETATE), SULFANILAMIDE (SULFANILAMIDE), SULFAPYRIDINE (SULFAPYRIDINE), SULFASALAZINE (SULFASALAZINE), SULFATRIM (SULFAMETHOXAZOLE; TRIMETHOPRIM), SULFATRIM PEDIATRIC (SULFAMETHOXAZOLE; TRIMETHOPRIM), SULFATRIM-DS (SULFAMETHOXAZOLE; TRIMETHOPRIM), SULFATRIM-SS (SULFAMETHOXAZOLE; TRIMETHOPRIM), SULFINPYRAZONE (SULFINPYRAZONE), SULFISOXAZOLE (SULFISOXAZOLE), SULFISOXAZOLE DIOLAMINE (SULFISOXAZOLE DIOLAMINE), SULFONAMIDES DUPLEX (SULFADIAZINE; SULFAMERAZINE), SULFOSE (TRISULFAPYRIMIDINES (SULFADIAZINE; SULFAMERAZINE; SULFAMETHAZINE)), SULINDAC (SULINDAC), SULLA (SULFAMETER), SULMEPRIM (SULFAMETHOXAZOLE; TRIMETHOPRIM), SULMEPRIM PEDIATRIC (SULFAMETHOXAZOLE; TRIMETHOPRIM), SULPHRIN (PREDNISOLONE ACETATE; SULFACETAMIDE SODIUM), SULSOXIN (SULFISOXAZOLE), SULSTER (PREDNISOLONE SODIUM PHOSPHATE; SULFACETAMIDE SODIUM), SULTEN-10 (SULFACETAMIDE SODIUM), SULTRIN (TRIPLE SULFA (SULFABENZAMIDE; SULFACETAMIDE; SULFATHIAZOLE)), SUMATRIPTAN (SUMATRIPTAN SUCCINATE), SUMATRIPTAN SUCCINATE (SUMATRIPTAN SUCCINATE), SUMYCIN (TETRACYCLINE HYDROCHLORIDE), SUPPRELIN (HISTRELIN ACETATE), SUPPRELIN LA (HISTRELIN ACETATE), SUPRANE (DESFLURANE), SUPRAX (CEFIXIME), SURITAL (THIAMYLAL SODIUM), SURMONTIL (TRIMIPRAMINE MALEATE), SURVANTA (BERACTANT), SUS-PHRINE SULFITE-FREE (EPINEPHRINE), SUSTAIRE (THEOPHYLLINE), SUSTIVA (EFAVIRENZ), SUTENT (SUNITINIB MALATE), SYMADINE (AMANTADINE HYDROCHLORIDE), SYMBICORT (BUDESONIDE; FORMOTEROL FUMARATE DIHYDRATE), SYMBYAX (FLUOXETINE HYDROCHLORIDE; OLANZAPINE), SYMLIN (PRAMLINTIDE ACETATE), SYMMETREL (AMANTADINE HYDROCHLORIDE), SYNACORT (HYDROCORTISONE), SYNAGIS (PALIVIZUMAB), SYNALAR (FLUOCINOLONE ACETONIDE), SYNALAR-HP (FLUOCINOLONE ACETONIDE), SYNALGOS-DC (ASPIRIN; CAFFEINE; DIHYDROCODEINE BITARTRATE), SYNALGOS-DC-A (ACETAMINOPHEN; CAFFEINE; DIHYDROCODEINE BITARTRATE), SYNAREL (NAFARELIN ACETATE), SYNCURINE (DECAMETHO- NIUM BROMIDE), SYNERA (LIDOCAINE; TETRACAINE), SYNERCID (DALFOPRISTIN; QUINUPRISTIN), SYNERCID (QUINUPRISTIN; DALFOPRISTIN), SYNKAYVITE (MENADIOL SODIUM DIPHOSPHATE), SYNOPHYLATE (THEOPHYLLINE SODIUM GLYCINATE), SYNOVALYTE IN PLASTIC CONTAINER (MAGNESIUM CHLORIDE; POTASSIUM CHLORIDE; SODIUM ACETATE; SODIUM CHLORIDE; SODIUM GLUCONATE), SYNTHROID (LEVOTHYROXINE SODIUM), SYNTOCINON (OXYTOCIN), SYPRINE (TRIENTINE HYDROCHLORIDE), T-PHYL (THEOPHYLLINE), T-STAT (ERYTHROMYCIN), TAB-PROFEN (IBUPROFEN), TACARYL (METHDILAZINE), TACARYL (METHDILAZINE HYDROCHLORIDE), TACE (CHLOROTRIANISENE), TACLONEX (BETAMETHASONE DIPROPIONATE; CALCIPOTRIENE HYDRATE), TACLONEX SCALP (BETAMETHASONE DIPROPIONATE; CALCIPOTRIENE HYDRATE), TAGAMET (CIMETIDINE), TAGAMET (CIMETIDINE HYDROCHLORIDE), TAGAMET HB (CIMETIDINE), TAGAMET HB 200 (CIMETIDINE), TAGAMET HYDROCHLORIDE IN SODIUM CHLORIDE 0.9% IN PLASTIC CONTAINER (CIMETIDINE HYDROCHLORIDE), TALACEN (ACETAMINOPHEN; PENTAZOCINE HYDROCHLORIDE), TALC (TALC), TALWIN (PENTAZOCINE LACTATE), TALWIN 50 (PENTAZOCINE HYDROCHLORIDE), TALWIN COMPOUND (ASPIRIN; PENTAZOCINE HYDROCHLORIDE), TALWIN NX (NALOXONE HYDROCHLORIDE; PENTAZOCINE HYDROCHLORIDE), TAMBOCOR (FLECAINIDE ACETATE), TAMIFLU (OSELTAMIVIR PHOSPHATE), TAMOXIFEN CITRATE (TAMOXIFEN CITRATE), TAMSULOSIN (TAMSULOSIN), TAMSULOSIN HYDROCHLORIDE (TAMSULOSIN HYDROCHLORIDE), TANDEARIL (OXYPHENBUTAZONE), TAO (TROLEANDOMYCIN), TAPAZOLE (METHIMAZOLE), TARACTAN (CHLORPROTHIXENE), TARCEVA (ERLOTINIB HYDROCHLORIDE), TARGRETIN (BEXAROTENE), TARKA (TRANDOLAPRIL; VERAPAMIL HYDROCHLORIDE), TASIGNA (NILOTINIB HYDROCHLORIDE MONOHYDRATE), TASMAR (TOLCAPONE), TATUM-T (COPPER), TAVIST (CLEMASTINE FUMARATE), TAVIST ALLERGY/SINUS/HEADACHE (ACETAMINOPHEN; CLEMASTINE FUMARATE; PSEUDOEPHEDRINE HYDROCHLORIDE), TAVIST-1 (CLEMASTINE FUMARATE), TAVIST-D (CLEMASTINE FUMARATE; PHENYLPROPANOLAMINE HYDROCHLORIDE), TAXOL (PACLITAXEL), TAXOTERE (DOCETAXEL), TAZICEF (CEFTAZIDIME), TAZIDIME (CEFTAZIDIME), TAZIDIME IN PLASTIC CONTAINER (CEFTAZIDIME), TAZORAC (TAZAROTENE), TAZTIA XT (DILTIAZEM HYDROCHLORIDE), TC 99M-LUNGAGGREGATE (TECHNETIUM TC-99M ALBUMIN AGGREGATED), TECHNECOLL (TECHNETIUM TC-99M SULFUR COLLOID KIT), TECHNELITE (TECHNETIUM TC-99M SODIUM PERTECHNETATE GENERATOR), TECHNESCAN (TECHNETIUM TC-99M OXIDRONATE KIT), TECHNESCAN GLUCEPTATE (TECHNETIUM TC-99M GLUCEPTATE KIT), TECHNESCAN HIDA (TECHNETIUM TC-99M LIDOFENIN KIT), TECHNESCAN MAA (TECHNETIUM TC-99M ALBUMIN AGGREGATED KIT), TECHNESCAN MAG3 (TECHNETIUM TC-99M MERTIATIDE KIT), TECHNESCAN PYP KIT (TECHNETIUM TC-99M PYROPHOSPHATE KIT), TECHNETIUM (99m Tc) FANOLESOMAB; NEUTROSPEC (TECHNETIUM (99m Tc) FANOLESOMAB; NEUTROSPEC), TECHNETIUM TC 99M ALBUMIN AGGREGATED KIT (TECHNETIUM TC-99M ALBUMIN AGGREGATED KIT), TECHNETIUM TC 99M DIPHOSPHONATE-TIN KIT (TECHNETIUM TC-99M ETIDRONATE KIT), TECHNETIUM TC 99M GENERATOR (TECHNETIUM TC-99M SODIUM PERTECHNETATE GENERATOR), TECHNETIUM TC 99M HSA (TECHNETIUM TC-99M ALBUMIN KIT), TECHNETIUM TC 99M MAA (TECHNETIUM TC-99M ALBUMIN AGGREGATED KIT), TECHNETIUM TC 99M MPI MDP (TECHNETIUM TC-99M MEDRONATE KIT), TECHNETIUM TC 99M SULFUR COLLOID (TECHNETIUM TC-99M SULFUR COLLOID), TECHNETIUM TC 99M TSC (TECHNETIUM TC-99M SULFUR COLLOID KIT), TECHNETIUM TC-99M MEBROFENIN (TECHNETIUM TC-99M MEBROFENIN KIT), TECHNETIUM TC-99M PENTETATE KIT (TECHNETIUM TC-99M PENTETATE KIT), TECHNETIUM TC-99M SESTAMIBI (TECHNETIUM TC-99M SESTAMIBI), TECZEM (DILTIAZEM MALATE; ENALAPRIL MALEATE), TEEBACIN (AMINOSALICYLATE SODIUM), TEGISON (ETRETINATE), TEGOPEN (CLOXACILLIN SODIUM), TEGRETOL (CARBAMAZEPINE), TEGRETOL-XR (CARBAMAZEPINE), TEKTURNA (ALISKIREN HEMIFUMARATE), TEKTURNA HCT (ALISKIREN HEMIFUMARATE; HYDROCHLOROTHIAZIDE), TELDRIN (CHLORPHENIRAMINE MALEATE), TELEPAQUE (IOPANOIC ACID), TELMISARTAN (TELMISARTAN), TEMARIL (TRIMEPRAZINE TARTRATE), TEMAZ (TEMAZEPAM), TEMAZEPAM (TEMAZEPAM), TEMODAR (TEMOZOLOMIDE), TEMOVATE (CLOBETASOL PROPIONATE), TEMOVATE E (CLOBETASOL PROPIONATE), TEN-K (POTASSIUM CHLORIDE), TENATHAN (BETHANIDINE SULFATE), TENCON (ACETAMINOPHEN; BUTALBITAL), TENEX (GUANFACINE HYDROCHLORIDE), TENOFOVIR DISOPROXIL FUMARATE (TENOFOVIR DISOPROXIL FUMARATE), TENORETIC 100 (ATENOLOL; CHLORTHALIDONE), TENORETIC 50 (ATENOLOL; CHLORTHALIDONE), TENORMIN (ATENOLOL), TENSILON (EDROPHONIUM CHLORIDE), TENSILON PRESERVATIVE FREE (EDROPHONIUM CHLORIDE), TENUATE (DIETHYLPROPION HYDROCHLORIDE), TENUATE DOSPAN (DIETHYLPROPION HYDROCHLORIDE), TEPANIL (DIETHYLPROPION HYDROCHLORIDE), TEPANIL TEN-TAB (DIETHYLPROPION HYDROCHLORIDE), TEQUIN (GATIFLOXACIN), TEQUIN IN DEXTROSE 5% IN PLASTIC CONTAINER (GATIFLOXACIN), TERAZOL 3 (TERCONAZOLE), TERAZOL 7 (TERCONAZOLE), TERAZOSIN HYDROCHLORIDE (TERAZOSIN HYDROCHLORIDE), TERBINAFINE HYDROCHLORIDE (TERBINAFINE HYDROCHLORIDE), TERBUTALINE SULFATE (TERBUTALINE SULFATE), TERCONAZOLE (TERCONAZOLE), TERFONYL (TRISULFAPYRIMIDINES (SULFADIAZINE; SULFAMERAZINE; SULFAMETHAZINE)), TERIL (CARBAMAZEPINE), TERRA-CORTRIL (HYDROCORTISONE ACETATE; OXYTETRACYCLINE HYDROCHLORIDE), TERRAMYCIN (LIDOCAINE HYDROCHLORIDE; OXYTETRACYCLINE), TERRAMYCIN (OXYTETRACYCLINE), TERRAMYCIN (OXYTETRACYCLINE CALCIUM), TERRAMYCIN (OXYTETRACYCLINE HYDROCHLORIDE), TERRAMYCIN W/ POLYMYXIN (OXYTETRACYCLINE HYDROCHLORIDE; POLYMYXIN B SULFATE), TERRAMYCIN W/ POLYMYXIN B SULFATE (OXYTETRACYCLINE HYDROCHLORIDE; POLYMYXIN B SULFATE), TERRAMYCIN-POLYMYXIN (OXYTETRACYCLINE HYDROCHLORIDE; POLYMYXIN B SULFATE), TESLAC (TESTOLACTONE), TESLASCAN (MANGAFODIPIR TRISODIUM), TESSALON (BENZONATATE), TESTIM (TESTOSTERONE), TESTODERM (TESTOSTERONE), TESTODERM TTS (TESTOSTERONE), TESTOSTERONE (TESTOSTERONE), TESTOSTERONE CYPIONATE (TESTOSTERONE CYPIONATE), TESTOSTERONE CYPIONATE-ESTRADIOL CYPIONATE (ESTRADIOL CYPIONATE; TESTOSTERONE CYPIONATE), TESTOSTERONE ENANTHATE (TESTOSTERONE ENANTHATE), TESTOSTERONE ENANTHATE AND ESTRADIOL VALERATE (ESTRADIOL VALERATE; TESTOSTERONE ENANTHATE), TESTOSTERONE ETHANATE (TESTOSTERONE ENANTHATE), TESTOSTERONE PROPIONATE (TESTOSTERONE PROPIONATE), TESTRED (METHYLTESTOSTERONE), TESULOID (TECHNETIUM TC-99M SULFUR COLLOID KIT), TETRACHEL (TETRACYCLINE HYDROCHLORIDE), TETRACYCLINE HYDROCHLORIDE (TETRACYCLINE HYDROCHLORIDE), TETRACYN (PROCAINE HYDROCHLORIDE; TETRACYCLINE HYDROCHLORIDE), TETRACYN (TETRACYCLINE HYDROCHLORIDE), TETRAMED (TETRACYCLINE HYDROCHLORIDE), TETREX (TETRACYCLINE PHOSPHATE COMPLEX), TEV-TROPIN (SOMATROPIN RECOMBINANT), TEVETEN (EPROSARTAN MESYLATE), TEVETENHCT (EPROSARTAN MESYLATE; HYDROCHLOROTHIAZIDE), TEXACORT (HYDROCORTISONE), THALITONE (CHLORTHALIDONE), THALLOUS CHLORIDE TL 201 (THALLOUS CHLORIDE, TL-201), THALOMID (THALIDOMIDE), THAM (TROMETHAMINE), THAM-E (POTASSIUM CHLORIDE; SODIUM CHLORIDE; TROMETHAMINE), THEELIN (ESTRONE), THEO-24 (THEOPHYLLINE), THEO-DUR (THEOPHYLLINE), THEOBID (THEOPHYLLINE), THEOBID JR. (THEOPHYLLINE), THEOCHRON (THEOPHYLLINE), THEOCLEAR L.A.-130 (THEOPHYLLINE), THEOCLEAR L.A.-260 (THEOPHYLLINE), THEOCLEAR-100 (THEOPHYLLINE), THEOCLEAR-200 (THEOPHYLLINE), THEOCLEAR-80 (THEOPHYLLINE), THEOLAIR (THEOPHYLLINE), THEOLAIR-SR (THEOPHYLLINE), THEOLIXIR (THEOPHYLLINE), THEOPHYL (THEOPHYLLINE), THEOPHYL-225 (THEOPHYLLINE), THEOPHYL-SR (THEOPHYLLINE), THEOPHYLLINE (THEOPHYLLINE), THEOPHYLLINE 0.04% AND DEXTROSE 5% IN PLASTIC CONTAINER (THEOPHYLLINE), THEOPHYLLINE 0.08% AND DEXTROSE 5% IN PLASTIC CONTAINER (THEOPHYLLINE), THEOPHYLLINE 0.16% AND DEXTROSE 5% IN PLASTIC CONTAINER (THEOPHYLLINE), THEOPHYLLINE 0.2% AND DEXTROSE 5% IN PLASTIC CONTAINER (THEOPHYLLINE), THEOPHYLLINE 0.32% AND DEXTROSE 5% IN PLASTIC CONTAINER (THEOPHYLLINE), THEOPHYLLINE 0.4% AND DEXTROSE 5% IN PLASTIC CONTAINER (THEOPHYLLINE), THEOPHYLLINE AND DEXTROSE 5% IN PLASTIC CONTAINER (THEOPHYLLINE), THEOPHYLLINE IN DEXTROSE 5% IN PLASTIC CONTAINER (THEOPHYLLINE), THEOPHYLLINE-SR (THEOPHYLLINE), THEOVENT (THEOPHYLLINE), THERMAZENE (SILVER SULFADIAZINE), THEROXIDIL (MINOXIDIL), THIAMINE HYDROCHLORIDE (THIAMINE HYDROCHLORIDE), THIOGUANINE (THIOGUANINE), THIOPLEX (THIOTEPA), THIORIDAZINE HYDROCHLORIDE (THIORIDAZINE HYDROCHLORIDE), THIORIDAZINE HYDROCHLORIDE INTENSOL (THIORIDAZINE HYDROCHLORIDE), THIOSULFIL (SULFAMETHIZOLE), THIOTEPA (THIOTEPA), THIOTHIXENE (THIOTHIXENE), THIOTHIXENE HYDROCHLORIDE (THIOTHIXENE HYDROCHLORIDE), THIOTHIXENE HYDROCHLORIDE INTENSOL (THIOTHIXENE HYDROCHLORIDE), THORAZINE (CHLORPROMAZINE), THORAZINE (CHLORPROMAZINE HYDROCHLORIDE), THRIVE (NICOTINE POLACRILEX), THYPINONE (PROTIRELIN), THYREL TRH (PROTIRELIN), THYRO-BLOCK (POTASSIUM IODIDE), THYROGEN (THYROTROPIN ALFA), THYROGLOBULIN (THYROGLOBULIN), THYROLAR-0.25 (LIOTRIX (T4; T3)), THYROLAR-0.5 (LIOTRIX (T4; T3)), THYROLAR-1 (LIOTRIX (T4; T3)), THYROLAR-2 (LIOTRIX (T4; T3)), THYROLAR-3 (LIOTRIX (T4; T3)), THYROLAR-5 (LIOTRIX (T4; T3)), THYROSAFE (POTASSIUM IODIDE), THYROSHIELD (POTASSIUM IODIDE), THYTROPAR (THYROTROPIN), TIAGABINE HYDROCHLORIDE (TIAGABINE HYDROCHLORIDE), TIAMATE (DILTIAZEM MALATE), TIAZAC (DILTIAZEM HYDROCHLORIDE), TICAR (TICARCILLIN DISODIUM), TICLID (TICLOPIDINE HYDROCHLORIDE), TICLOPIDINE HYDROCHLORIDE (TICLOPIDINE HYDROCHLORIDE), TIGAN (TRIMETHOBENZAMIDE HYDROCHLORIDE), TIKOSYN (DOFETILIDE), TILADE (NEDOCROMIL SODIUM), TIMENTIN (CLAVULANATE POTASSIUM; TICARCILLIN DISODIUM), TIMENTIN IN PLASTIC CONTAINER (CLAVULANATE POTASSIUM; TICARCILLIN DISODIUM), TIMOLIDE 10-25 (HYDROCHLOROTHIAZIDE; TIMOLOL MALEATE), TIMOLOL MALEATE (TIMOLOL MALEATE), TIMOPTIC (TIMOLOL MALEATE), TIMOPTIC IN OCUDOSE (TIMOLOL MALEATE), TIMOPTIC-XE (TIMOLOL MALEATE), TINDAL (ACETOPHENAZINE MALEATE), TINDAMAX (TINIDAZOLE), TIOCONAZOLE (TIOCONAZOLE), TIOPRONIN (TIOPRONIN), TIROSINT (LEVOTHYROXINE SODIUM), TIS-U-SOL (MAGNESIUM SULFATE; POTASSIUM CHLORIDE; POTASSIUM PHOSPHATE, MONOBASIC; SODIUM CHLORIDE; SODIUM PHOSPHATE), TIS-U-SOL IN PLASTIC CONTAINER (MAGNESIUM SULFATE; POTASSIUM CHLORIDE; POTASSIUM PHOSPHATE, MONOBASIC; SODIUM CHLORIDE; SODIUM PHOSPHATE), TIZANIDINE HYDROCHLORIDE (TIZANIDINE HYDROCHLORIDE), TNKASE (TENECTEPLASE), TOBI (TOBRAMYCIN), TOBRADEX (DEXAMETHASONE; TOBRAMYCIN), TOBRAMYCIN (TOBRAMYCIN), TOBRAMYCIN AND DEXAMETHASONE (DEXAMETHASONE; TOBRAMYCIN), TOBRAMYCIN SULFATE (TOBRAMYCIN SULFATE), TOBRAMYCIN SULFATE (PHARMACY BULK) (TOBRAMYCIN SULFATE), TOBRAMYCIN SULFATE IN SODIUM CHLORIDE 0.9% IN PLASTIC CONTAINER (TOBRAMYCIN SULFATE), TOBRASONE (FLUOROMETHOLONE ACETATE; TOBRAMYCIN), TOBREX (TOBRAMYCIN), TODAY (NONOXYNOL-9), TOFRANIL (IMIPRAMINE HYDROCHLORIDE), TOFRANIL-PM (IMIPRAMINE PAMOATE), TOLAZAMIDE (TOLAZAMIDE), TOLBUTAMIDE (TOLBUTAMIDE), TOLECTIN (TOLMETIN SODIUM), TOLECTIN 600 (TOLMETIN SODIUM), TOLECTIN DS (TOLMETIN SODIUM), TOLINASE (TOLAZAMIDE), TOLMETIN SODIUM (TOLMETIN SODIUM), TOLTERODINE (TOLTERODINE TARTRATE), TONOCARD (TOCAINIDE HYDROCHLORIDE), TOPAMAX (TOPIRAMATE), TOPAMAX SPRINKLE (TOPIRAMATE), TOPICORT (DESOXIMETASONE), TOPICORT LP (DESOXIMETASONE), TOPICYCLINE (TETRACYCLINE HYDROCHLORIDE), TOPIRAMATE (TOPIRAMATE), TOPIRAMATE (TOPIRAMATE HYDROCHLORIDE), TOPOSAR (ETOPOSIDE), TOPROL-XL (METOPROLOL SUCCINATE), TORA (PHENTERMINE HYDROCHLORIDE), TORADOL (KETOROLAC TROMETHAMINE), TORECAN (THIETHYLPERAZINE MALATE), TORECAN (THIETHYLPERAZINE MALEATE), TORISEL (TEMSIROLIMUS), TORNALATE (BITOLTEROL MESYLATE), TORSEMIDE (TORSEMIDE), TOTACILLIN (AMPICILLIN/AMPICILLIN TRIHYDRATE), TOTACILLIN-N (AMPICILLIN SODIUM), TOTECT (DEXRAZOXANE HYDROCHLORIDE), TOVALT ODT (ZOLPIDEM TARTRATE), TPN (NIACINAMIDE; PYRIDOXINE HYDROCHLORIDE; TYROSINE), TPN ELECTROLYTES IN PLASTIC CONTAINER (CALCIUM CHLORIDE; MAGNESIUM CHLORIDE; POTASSIUM CHLORIDE; SODIUM ACETATE; SODIUM CHLORIDE), TRACLEER (BOSENTAN), TRACRIUM (ATRACURIUM BESYLATE), TRACRIUM PRESERVATIVE FREE (ATRACURIUM BESYLATE), TRAL (HEXOCYCLIUM METHYLSULFATE), TRAMADOL HYDROCHLORIDE (TRAMADOL HYDROCHLORIDE), TRAMADOL HYDROCHLORIDE AND ACETAMINOPHEN (ACETAMINOPHEN; TRAMADOL HYDROCHLORIDE), TRAMADOL HYDROCHLORIDE; ACETAMINOPHEN (TRAMADOL HYDROCHLORIDE; ACETAMINOPHEN), TRANCOPAL (CHLORMEZANONE), TRANDATE (LABETALOL HYDROCHLORIDE), TRANDATE HCT (HYDROCHLOROTHIAZIDE; LABETALOL HYDROCHLORIDE), TRANDOLAPRIL (TRANDOLAPRIL), TRANMEP (MEPROBAMATE), TRANSDERM SCOP (SCOPOLAMINE), TRANSDERM-NITRO (NITROGLYCERIN), TRANXENE (CLORAZEPATE DIPOTASSIUM), TRANXENE SD (CLORAZEPATE DIPOTASSIUM), TRANYLCYPROMINE SULFATE (TRANYLCYPROMINE SULFATE), TRASICOR (OXPRENOLOL HYDROCHLORIDE), TRASYLOL (APROTININ BOVINE), TRAVAMULSION 10% (SOYBEAN OIL), TRAVAMULSION 20% (SOYBEAN OIL), TRAVASE (SUTILAINS), TRAVASOL 10% IN PLASTIC CONTAINER (AMINO ACIDS), TRAVASOL 10% W/O ELECTROLYTES (AMINO ACIDS), TRAVASOL 2.75% IN DEXTROSE 10% IN PLASTIC CONTAINER (AMINO ACIDS; DEXTROSE), TRAVASOL 2.75% IN DEXTROSE 15% IN PLASTIC CONTAINER (AMINO ACIDS; DEXTROSE), TRAVASOL 2.75% IN DEXTROSE 20% IN PLASTIC CONTAINER (AMINO ACIDS; DEXTROSE), TRAVASOL 2.75% IN DEXTROSE 25% IN PLASTIC CONTAINER (AMINO ACIDS; DEXTROSE), TRAVASOL 2.75% IN DEXTROSE 5% IN PLASTIC CONTAINER (AMINO ACIDS; DEXTROSE), TRAVASOL 2.75% SULFITE FREE W/ ELECTROLYTES IN DEXTROSE 10% IN PLASTIC CONTAINER (AMINO ACIDS; DEXTROSE; MAGNESIUM CHLORIDE; POTASSIUM PHOSPHATE, DIBASIC; SODIUM ACETATE; SODIUM CHLORIDE), TRAVASOL 2.75% SULFITE FREE W/ ELECTROLYTES IN DEXTROSE 15% IN PLASTIC CONTAINER (AMINO ACIDS; DEXTROSE; MAGNESIUM CHLORIDE; POTASSIUM PHOSPHATE, DIBASIC; SODIUM ACETATE; SODIUM CHLORIDE), TRAVASOL 2.75% SULFITE FREE W/ ELECTROLYTES IN DEXTROSE 20% IN PLASTIC CONTAINER (AMINO ACIDS; DEXTROSE; MAGNESIUM CHLORIDE; POTASSIUM PHOSPHATE, DIBASIC; SODIUM ACETATE; SODIUM CHLORIDE), TRAVASOL 2.75% SULFITE FREE W/ ELECTROLYTES IN DEXTROSE 25% IN PLASTIC CONTAINER (AMINO ACIDS; DEXTROSE; MAGNESIUM CHLORIDE; POTASSIUM PHOSPHATE, DIBASIC; SODIUM ACETATE; SODIUM CHLORIDE), TRAVASOL 2.75% SULFITE FREE W/ ELECTROLYTES IN DEXTROSE 5% IN PLASTIC CONTAINER (AMINO ACIDS; DEXTROSE; MAGNESIUM CHLORIDE; POTASSIUM PHOSPHATE, DIBASIC; SODIUM ACETATE; SODIUM CHLORIDE), TRAVASOL 3.5% SULFITE FREE W/ ELECTROLYTES IN PLASTIC CONTAINER (AMINO ACIDS; MAGNESIUM CHLORIDE; POTASSIUM PHOSPHATE, DIBASIC; SODIUM ACETATE; SODIUM CHLORIDE), TRAVASOL 3.5% W/ ELECTROLYTES (AMINO ACIDS; MAGNESIUM CHLORIDE; POTASSIUM PHOSPHATE, DIBASIC; SODIUM ACETATE; SODIUM CHLORIDE), TRAVASOL 4.25% IN DEXTROSE 10% IN PLASTIC CONTAINER (AMINO ACIDS; DEXTROSE), TRAVASOL 4.25% IN DEXTROSE 15% IN PLASTIC CONTAINER (AMINO ACIDS; DEXTROSE), TRAVASOL 4.25% IN DEXTROSE 20% IN PLASTIC CONTAINER (AMINO ACIDS; DEXTROSE), TRAVASOL 4.25% IN DEXTROSE 25% IN PLASTIC CONTAINER (AMINO ACIDS; DEXTROSE), TRAVASOL 4.25% IN DEXTROSE 5% IN PLASTIC CONTAINER (AMINO ACIDS; DEXTROSE), TRAVASOL 4.25% SULFITE FREE W/ ELECTROLYTES IN DEXTROSE 10% IN PLASTIC CONTAINER (AMINO ACIDS; DEXTROSE; MAGNESIUM CHLORIDE; POTASSIUM PHOSPHATE, DIBASIC; SODIUM ACETATE; SODIUM CHLORIDE), TRAVASOL 4.25% SULFITE FREE W/ ELECTROLYTES IN DEXTROSE 15% IN PLASTIC CONTAINER (AMINO ACIDS; DEXTROSE; MAGNESIUM CHLORIDE; POTASSIUM PHOSPHATE, DIBASIC; SODIUM ACETATE; SODIUM CHLORIDE), TRAVASOL 4.25% SULFITE FREE W/ ELECTROLYTES IN DEXTROSE 20% IN PLASTIC CONTAINER (AMINO ACIDS; DEXTROSE; MAGNESIUM CHLORIDE; POTASSIUM PHOSPHATE, DIBASIC; SODIUM ACETATE; SODIUM CHLORIDE), TRAVASOL 4.25% SULFITE FREE W/ ELECTROLYTES IN DEXTROSE 25% IN PLASTIC CONTAINER (AMINO ACIDS; DEXTROSE; MAGNESIUM CHLORIDE; POTASSIUM PHOSPHATE, DIBASIC; SODIUM ACETATE; SODIUM CHLORIDE), TRAVASOL 4.25% SULFITE FREE W/ ELECTROLYTES IN DEXTROSE 5% IN PLASTIC CONTAINER (AMINO ACIDS; DEXTROSE; MAGNESIUM CHLORIDE; POTASSIUM PHOSPHATE, DIBASIC; SODIUM ACETATE; SODIUM CHLORIDE), TRAVASOL 5.5% IN PLASTIC CONTAINER (AMINO ACIDS), TRAVASOL 5.5% SULFITE FREE W/ ELECTROLYTES IN PLASTIC CONTAINER (AMINO ACIDS; MAGNESIUM CHLORIDE; POTASSIUM PHOSPHATE, DIBASIC; SODIUM ACETATE; SODIUM CHLORIDE), TRAVASOL 5.5% W/ ELECTROLYTES (AMINO ACIDS; MAGNESIUM CHLORIDE; POTASSIUM PHOSPHATE, DIBASIC; SODIUM ACETATE; SODIUM CHLORIDE), TRAVASOL 5.5% W/O ELECTROLYTES (AMINO ACIDS), TRAVASOL 8.5% IN PLASTIC CONTAINER (AMINO ACIDS), TRAVASOL 8.5% SULFITE FREE W/ ELECTROLYTES IN PLASTIC CONTAINER (AMINO ACIDS; MAGNESIUM CHLORIDE; POTASSIUM PHOSPHATE, DIBASIC; SODIUM ACETATE; SODIUM CHLORIDE), TRAVASOL 8.5% W/ ELECTROLYTES (AMINO ACIDS; MAGNESIUM CHLORIDE; POTASSIUM PHOSPHATE, DIBASIC; SODIUM ACETATE; SODIUM CHLORIDE), TRAVASOL 8.5% W/O ELECTROLYTES (AMINO ACIDS), TRAVATAN (TRAVOPROST), TRAVATAN Z (TRAVOPROST), TRAVERT 10% IN PLASTIC CONTAINER (INVERT SUGAR), TRAZODONE HYDROCHLORIDE (TRAZODONE HYDROCHLORIDE), TREANDA (BENDAMUSTINE HYDROCHLORIDE), TRECATOR (ETHIONAMIDE), TRELSTAR (TRIPTORELIN PAMOATE), TRELSTAR DEPOT (TRIPTORELIN PAMOATE), TREMIN (TRIHEXYPHENIDYL HYDROCHLORIDE), TRENTAL (PENTOXIFYLLINE), TREST (METHIXENE HYDROCHLORIDE), TRETINOIN (TRETINOIN), TREXALL (METHOTREXATE SODIUM), TREXIMET (NAPROXEN SODIUM; SUMATRIPTAN SUCCINATE), TRI-LEGEST 21 (ETHINYL ESTRADIOL; NORETHINDRONE ACETATE), TRI-LEGEST FE (ETHINYL ESTRADIOL; NORETHINDRONE ACETATE), TRI-LUMA (FLUOCINOLONE ACETONIDE; HYDROQUINONE; TRETINOIN), TRI-NASAL (TRIAMCINOLONE ACETONIDE), TRI-NORINYL 21-DAY (ETHINYL ESTRADIOL; NORETHINDRONE), TRI-NORINYL 28-DAY (ETHINYL ESTRADIOL; NORETHINDRONE), TRI-PREVIFEM (ETHINYL ESTRADIOL; NORGESTIMATE), TRI-SPRINTEC (ETHINYL ESTRADIOL; NORGESTIMATE), TRIACET (TRIAMCINOLONE ACETONIDE), TRIACIN-C (CODEINE PHOSPHATE; PSEUDOEPHEDRINE HYDROCHLORIDE; TRIPROLIDINE HYDROCHLORIDE), TRIACORT (TRIAMCINOLONE ACETONIDE), TRIAD (ACETAMINOPHEN; BUTALBITAL; CAFFEINE), TRIALODINE (TRAZODONE HYDROCHLORIDE), TRIAMCINOLONE (TRIAMCINOLONE), TRIAMCINOLONE ACETONIDE (TRIAMCINOLONE ACETONIDE), TRIAMCINOLONE ACETONIDE IN ABSORBASE (TRIAMCINOLONE ACETONIDE), TRIAMCINOLONE DIACETATE (TRIAMCINOLONE DIACETATE), TRIAMINIC-12 (CHLORPHENIRAMINE MALEATE; PHENYLPROPANOLAMINE HYDROCHLORIDE), TRIAMTERENE AND HYDROCHLOROTHIAZIDE (HYDROCHLOROTHIAZIDE; TRIAMTERENE), TRIAPRIN (ACETAMINOPHEN; BUTALBITAL), TRIATEX (TRIAMCINOLONE ACETONIDE), TRIAVIL 2-10 (AMITRIPTYLINE HYDROCHLORIDE; PERPHENAZINE), TRIAVIL 2-25 (AMITRIPTYLINE HYDROCHLORIDE; PERPHENAZINE), TRIAVIL 4-10 (AMITRIPTYLINE HYDROCHLORIDE; PERPHENAZINE), TRIAVIL 4-25 (AMITRIPTYLINE HYDROCHLORIDE; PERPHENAZINE), TRIAVIL 4-50 (AMITRIPTYLINE HYDROCHLORIDE; PERPHENAZINE), TRIAZOLAM (TRIAZOLAM), TRICHLOREX (TRICHLORMETHIAZIDE), TRICHLORMAS (TRICHLORMETHIAZIDE), TRICHLORMETHIAZIDE (TRICHLORMETHIAZIDE), TRICHLORMETHIAZIDE W/ RESERPINE (RESERPINE; TRICHLORMETHIAZIDE), TRICLOS (TRICLOFOS SODIUM), TRICOR (FENOFIBRATE), TRICOR (MICRONIZED) (FENOFIBRATE), TRIDERM (TRIAMCINOLONE ACETONIDE), TRIDESILON (ACETIC ACID, GLACIAL; DESONIDE), TRIDIL (NITROGLYCERIN), TRIDIONE (TRIMETHADIONE), TRIESENCE (TRIAMCINOLONE ACETONIDE), TRIFLUOPERAZINE HCL (TRIFLUOPERAZINE HYDROCHLORIDE), TRIFLUOPERAZINE HYDROCHLORIDE (TRIFLUOPERAZINE HYDROCHLORIDE), TRIFLURIDINE (TRIFLURIDINE), TRIGLIDE (FENOFIBRATE), TRIHEXYPHENIDYL HYDROCHLORIDE (TRIHEXYPHENIDYL HYDROCHLORIDE), TRILAFON (PERPHENAZINE), TRILEPTAL (OXCARBAZEPINE), TRILITRON (PSEUDOEPHEDRINE HYDROCHLORIDE; TRIPROLIDINE HYDROCHLORIDE), TRILYTE (POLYETHYLENE GLYCOL 3350; POTASSIUM CHLORIDE; SODIUM BICARBONATE; SODIUM CHLORIDE), TRIMEPRAZINE TARTRATE (TRIMEPRAZINE TARTRATE), TRIMETH/SULFA (SULFAMETHOXAZOLE; TRIMETHOPRIM), TRIMETHOBENZAMIDE HYDROCHLORIDE (TRIMETHOBENZAMIDE HYDROCHLORIDE), TRIMETHOPRIM (TRIMETHOPRIM), TRIMETHOPRIM SULFATE AND POLYMYXIN B SULFATE (POLYMYXIN B SULFATE; TRIMETHOPRIM), TRIMETHOPRIM SULFATE AND POLYMYXIN B SULFATE (POLYMYXIN B SULFATE; TRIMETHOPRIM SULFATE), TRIMIPRAMINE MALEATE (TRIMIPRAMINE MALEATE), TRIMOX (AMOXICILLIN), TRIMPEX (TRIMETHOPRIM), TRIMPEX 200 (TRIMETHOPRIM), TRINALIN (AZATADINE MALEATE; PSEUDOEPHEDRINE SULFATE), TRIOSTAT (LIOTHYRONINE SODIUM), TRIPELENNAMINE HYDROCHLORIDE (TRIPELENNAMINE HYDROCHLORIDE), TRIPHASIL-21 (ETHINYL ESTRADIOL; LEVONORGESTREL), TRIPHASIL-28 (ETHINYL ESTRADIOL; LEVONORGESTREL), TRIPHED (PSEUDOEPHEDRINE HYDROCHLORIDE; TRIPROLIDINE HYDROCHLORIDE), TRIPLE SULFA (TRIPLE SULFA (SULFABENZAMIDE; SULFACETAMIDE; SULFATHIAZOLE)), TRIPLE SULFA (TRISULFAPYRIMIDINES (SULFADIAZINE; SULFAMERAZINE; SULFAMETHAZINE)), TRIPLE SULFAS (TRISULFAPYRIMIDINES (SULFADIAZINE; SULFAMERAZINE; SULFAMETHAZINE)), TRIPLE SULFOID (TRISULFAPYRIMIDINES (SULFADIAZINE; SULFAMERAZINE; SULFAMETHAZINE)), TRIPROLIDINE AND PSEUDOEPHEDRINE (PSEUDOEPHEDRINE HYDROCHLORIDE; TRIPROLIDINE HYDROCHLORIDE), TRIPROLIDINE AND PSEUDOEPHEDRINE HYDROCHLORIDES (PSEUDOEPHEDRINE HYDROCHLORIDE; TRIPROLIDINE HYDROCHLORIDE), TRIPROLIDINE AND PSEUDOEPHEDRINE HYDROCHLORIDES W/ CODEINE (CODEINE PHOSPHATE; PSEUDOEPHEDRINE HYDROCHLORIDE; TRIPROLIDINE HYDROCHLORIDE), TRIPROLIDINE HCL, PSEUDOEPHEDRINE HCL AND CODEINE PHOS- PHATE (CODEINE PHOSPHATE; PSEUDOEPHEDRINE HYDROCHLORIDE; TRIPROLIDINE HYDROCHLORIDE), TRIPROLIDINE HYDROCHLORIDE (TRIPROLIDINE HYDROCHLORIDE), TRIPROLIDINE HYDROCHLORIDE AND PSEUDOEPHEDRINE HYDROCHLORIDE (PSEUDOEPHEDRINE HYDROCHLORIDE; TRIPROLIDINE HYDROCHLORIDE), TRISENOX (ARSENIC TRIOXIDE), TRISORALEN (TRIOXSALEN), TRITEC (RANITIDINE BISMUTH CITRATE), TRIVAGIZOLE 3 (CLOTRIMAZOLE), TRIVARIS (TRIAMCINOLONE ACETONIDE), TRIVORA-21 (ETHINYL ESTRADIOL; LEVONORGESTREL), TRIVORA-28 (ETHINYL ESTRADIOL; LEVONORGESTREL), TRIZIVIR (ABACAVIR SULFATE; LAMIVUDINE; ZIDOVUDINE), TROBICIN (SPECTINOMYCIN HYDROCHLORIDE), TROPHAMINE (AMINO ACIDS), TROPHAMINE 10% (AMINO ACIDS), TROPICACYL (TROPICAMIDE), TROPICAMIDE (TROPICAMIDE), TROVAN (TROVAFLOXACIN MESYLATE), TROVAN PRESERVATIVE FREE (ALATROFLOXACIN MESYLATE), TROVAN/ZITHROMAX COMPLIANCE PAK (AZITHROMYCIN DIHYDRATE; TROVAFLOXACIN MESYLATE), TRUPHYLLINE (AMINOPHYLLINE), TRUSOPT (DORZOLAMIDE HYDROCHLORIDE), TRUVADA (EMTRICITABINE; TENOFOVIR DISOPROXIL FUMARATE), TRYMEX (TRIAMCINOLONE ACETONIDE), TRYSUL (TRIPLE SULFA (SULFABENZAMIDE; SULFACETAMIDE; SULFATHIAZOLE)), TUBOCURARINE CHLORIDE (TUBOCURARINE CHLORIDE), TURGEX (HEXACHLOROPHENE), TUSSICAPS (CHLORPHENIRAMINE POLISTIREX; HYDROCODONE POLISTIREX), TUSSIGON (HOMATROPINE METHYLBROMIDE; HYDROCODONE BITARTRATE), TUSSIONEX PENNKINETIC (CHLORPHENIRAMINE POLISTIREX; HYDROCODONE POLISTIREX), TWINJECT 0.15 (EPINEPHRINE), TWINJECT 0.3 (EPINEPHRINE), TYCOLET (ACETAMINOPHEN; HYDROCODONE BITARTRATE), TYGACIL (TIGECYCLINE), TYKERB (LAPATINIB DITOSYLATE), TYLENOL (ACETAMINOPHEN), TYLENOL (CAPLET) (ACETAMINOPHEN), TYLENOL (GELTAB) (ACETAMINOPHEN), TYLENOL W/ CODEINE (ACETAMINOPHEN; CODEINE PHOSPHATE), TYLENOL W/ CODEINE NO. 1 (ACETAMINOPHEN; CODEINE PHOSPHATE), TYLENOL W/ CODEINE NO. 2 (ACETAMINOPHEN; CODEINE PHOSPHATE), TYLENOL W/ CODEINE NO. 3 (ACETAMINOPHEN; CODEINE PHOSPHATE), TYLENOL W/ CODEINE NO. 4 (ACETAMINOPHEN; CODEINE PHOSPHATE), TYLOX (ACETAMINOPHEN; OXYCODONE HYDROCHLORIDE), TYLOX (ACETAMINOPHEN; OXYCODONE HYDROCHLORIDE; OXYCODONE TEREPHTHALATE), TYLOX-325 (ACETAMINOPHEN; OXYCODONE HYDROCHLORIDE), TYMTRAN (CERULETIDE DIETHYLAMINE), TYSABRI (NATALIZUMAB), TYZEKA (TELBIVUDINE), TYZINE (TETRAHYDROZOLINE HYDROCHLORIDE), TZ-3 (TIOCONAZOLE), U-CORT (HYDROCORTISONE ACETATE; UREA), U-GENCIN (GENTAMICIN SULFATE), UCEPHAN (SODIUM BENZOATE; SODIUM PHENYLACETATE), ULO (CHLOPHEDIANOL HYDROCHLORIDE), ULTANE (SEVOFLURANE), ULTIVA (REMIFENTANIL HYDROCHLORIDE), ULTRA-TECHNEKOW FM (TECHNETIUM TC-99M SODIUM PERTECHNETATE GENERATOR), ULTRACEF (CEFADROXIL/CEFADROXIL HEMIHYDRATE), ULTRACET (ACETAMINOPHEN; TRAMADOL HYDROCHLORIDE), ULTRAGRIS-165 (GRISEOFULVIN, ULTRAMICROCRYSTALLINE), ULTRAGRIS-330 (GRISEOFULVIN, ULTRAMICROCRYSTALLINE), ULTRALENTE (INSULIN ZINC SUSP EXTENDED PURIFIED BEEF), ULTRALENTE INSULIN (INSULIN ZINC SUSP EXTENDED BEEF), ULTRAM (TRAMADOL HYDROCHLORIDE), ULTRAM ER (TRAMADOL HYDROCHLORIDE), ULTRATAG (TECHNETIUM TC-99M RED BLOOD CELL KIT), ULTRAVATE (HALOBETASOL PROPIONATE), ULTRAVIST (PHARMACY BULK) (IOPROMIDE), ULTRAVIST 150 (IOPROMIDE), ULTRAVIST 240 (IOPROMIDE), ULTRAVIST 300 (IOPROMIDE), ULTRAVIST 370 (IOPROMIDE), UNASYN (AMPICILLIN SODIUM; SULBACTAM SODIUM), UNIDUR (THEOPHYLLINE), UNIPEN (NAFCILLIN SODIUM), UNIPEN IN PLASTIC CONTAINER (NAFCILLIN SODIUM), UNIPHYL (THEOPHYLLINE), UNIPRES (HYDRALAZINE HYDROCHLORIDE; HYDROCHLOROTHIAZIDE; RESERPINE), UNIRETIC (HYDROCHLOROTHIAZIDE; MOEXIPRIL HYDROCHLORIDE), UNISOM (DOXYLAMINE SUCCINATE), UNITENSEN (CRYPTENAMINE ACETATES), UNITENSEN (CRYPTENAMINE TANNATES), UNITHROID (LEVOTHYROXINE SODIUM), UNIVASC (MOEXIPRIL HYDROCHLORIDE), URACIL MUSTARD (URACIL MUSTARD), UREAPHIL (UREA), URECHOLINE (BETHANECHOL CHLORIDE), URESE (BENZTHIAZIDE), UREX (METHENAMINE HIPPURATE), URISPAS (FLAVOXATE HYDROCHLORIDE), UROBAK (SULFAMETHOXAZOLE), UROCIT-K (POTASSIUM CITRATE), UROLOGIC G IN PLASTIC CONTAINER (CITRIC ACID; MAGNESIUM OXIDE; SODIUM CARBONATE), UROPLUS DS (SULFAMETHOXAZOLE; TRIMETHOPRIM), UROPLUS SS (SULFAMETHOXAZOLE; TRIMETHOPRIM), UROVIST CYSTO (DIATRIZOATE MEGLUMINE), UROVIST CYSTO PEDIATRIC (DIATRIZOATE MEGLUMINE), UROVIST MEGLUMINE DIU/CT (DIATRIZOATE MEGLUMINE), UROVIST SODIUM 300 (DIATRIZOATE SODIUM), UROXATRAL (ALFUZOSIN HYDROCHLORIDE), URSO 250 (URSODIOL), URSO FORTE (URSODIOL), URSODIOL (URSODIOL), UTICILLIN VK (PENICILLIN V POTASSIUM), UTICORT (BETAMETHASONE BENZOATE), UTIMOX (AMOXICILLIN), UVADEX (METHOXSALEN), V-CILLIN (PENICILLIN V), V-CILLIN K (PENICILLIN V POTASSIUM), VAGIFEM (ESTRADIOL), VAGILIA (TRIPLE SULFA (SULFABENZAMIDE; SULFACETAMIDE; SULFATHIAZOLE)), VAGISTAT-1 (TIOCONAZOLE), VALACYCLOVIR (VALACYCLOVIR HYDROCHLORIDE), VALACYCLOVIR HYDROCHLORIDE (VALACYCLOVIR HYDROCHLORIDE), VALCYTE (VALGANCICLOVIR HYDROCHLORIDE), VALGANCICLOVIR HYDROCHLORIDE (VALGANCICLOVIR HYDROCHLORIDE), VALISONE (BETAMETHASONE VALERATE), VALIUM (DIAZEPAM), VALMID (ETHINAMATE), VALNAC (BETAMETHASONE VALERATE), VALPIN 50 (ANISOTROPINE METHYLBROMIDE), VALPROATE SODIUM (VALPROATE SODIUM), VALPROIC ACID (VALPROIC ACID), VALRELEASE (DI- AZEPAM), VALSARTAN (VALSARTAN), VALSARTAN AND HYDROCHLOROTHIAZIDE (VALSARTAN; HYDROCHLOROTHIAZIDE), VALSTAR PRESERVATIVE FREE (VALRUBICIN), VALTREX (VALACYCLOVIR HYDROCHLORIDE), VALTROPIN (SOMATROPIN RECOMBINANT), VANCENASE (BECLOMETHASONE DIPROPIONATE), VANCENASE AQ (BECLOMETHASONE DIPROPIONATE MONOHYDRATE), VANCERIL (BECLOMETHASONE DIPROPIONATE), VANCERIL DOUBLE STRENGTH (BECLOMETHASONE DIPROPIONATE), VANCOCIN HYDROCHLORIDE (VANCOMYCIN HYDROCHLORIDE), VANCOCIN HYDROCHLORIDE IN PLASTIC CONTAINER (VANCOMYCIN HYDROCHLORIDE), VANCOLED (VANCOMYCIN HYDROCHLORIDE), VANCOMYCIN HCL (VANCOMYCIN HYDROCHLORIDE), VANCOMYCIN HYDROCHLORIDE (VANCOMYCIN HYDROCHLORIDE), VANCOR (VANCOMYCIN HYDROCHLORIDE), VANDAZOLE (METRONIDAZOLE), VANIQA (EFLORNITHINE HYDROCHLORIDE), VANOBID (CANDICIDIN), VANOS (FLUOCINONIDE), VANSIL (OXAMNIQUINE), VANTAS (HISTRELIN ACETATE), VANTIN (CEFPODOXIME PROXETIL), VAPO-ISO (ISOPROTERENOL HYDROCHLORIDE), VAPRISOL (CONIVAPTAN HYDROCHLORIDE), VASCOR (BEPRIDIL HYDROCHLORIDE), VASCORAY (IOTHALAMATE MEGLUMINE; IOTHALAMATE SODIUM), VASERETIC (ENALAPRIL MALEATE; HYDROCHLOROTHIAZIDE), VASOCIDIN (PREDNISOLONE ACETATE; SULFACETAMIDE SODIUM), VASOCIDIN (PREDNISOLONE SODIUM PHOSPHATE; SULFACETAMIDE SODIUM), VASOCON (NAPHAZOLINE HYDROCHLORIDE), VASOCON-A (ANTAZOLINE PHOSPHATE; NAPHAZOLINE HYDROCHLORIDE), VASOTEC (ENALAPRIL MALEATE), VASOTEC (ENALAPRILAT), VASOXYL (METHOXAMINE HYDROCHLORIDE), VECTIBIX (PANITUMUMAB), VECURONIUM BROMIDE (VECURONIUM BROMIDE), VEETIDS (PENICILLIN V POTASSIUM), VEETIDS '125' (PENICILLIN V POTASSIUM), VEETIDS '250' (PENICILLIN V POTASSIUM), VEETIDS '500' (PENICILLIN V POTASSIUM), VEINAMINE 8% (AMINO ACIDS; MAGNESIUM CHLORIDE; POTASSIUM ACETATE; POTASSIUM CHLORIDE; SODIUM ACETATE), VELBAN (VINBLASTINE SULFATE), VELCADE (BORTEZOMIB), VELIVET (DESOGESTREL; ETHINYL ESTRADIOL), VELOSEF (CEPHRADINE), VELOSEF '125' (CEPHRADINE), VELOSEF '250' (CEPHRADINE), VELOSEF '500' (CEPHRADINE), VELOSULIN (INSULIN PURIFIED PORK), VELOSULIN BR (INSULIN RECOMBINANT HUMAN), VELOSULIN BR HUMAN (INSULIN RECOMBINANT PURIFIED HUMAN), VELTANE (BROMPHENIRAMINE MALEATE), VENLAFAXINE HYDROCHLORIDE (VENLAFAXINE HYDROCHLORIDE), VENOFER (IRON SUCROSE), VENTAIRE (PROTOKYLOL HYDROCHLORIDE), VENTAVIS (ILOPROST), VENTOLIN (ALBUTEROL), VENTOLIN (ALBUTEROL SULFATE), VENTOLIN HFA (ALBUTEROL SULFATE), VENTOLIN ROTACAPS (ALBUTEROL SULFATE), VEPESID (ETOPOSIDE), VERAMYST (FLUTICASONE FUROATE), VERAPAMIL HCL (VERAPAMIL HYDROCHLORIDE), VERAPAMIL HYDROCHLORIDE (VERAPAMIL HYDROCHLORIDE), VERCYTE (PIPOBROMAN), VERDESO (DESONIDE), VEREGEN (SINECATECHINS), VERELAN (VERAPAMIL HYDROCHLORIDE), VERELAN PM (VERAPAMIL HYDROCHLORIDE), VERILOID (ALKAVERVIR), VERLUMA (NOFETUMOMAB), VERMIDOL (PIPERAZINE CITRATE), VERMOX (MEBENDAZOLE), VERSAPEN (HETACILLIN), VERSAPEN-K (HETACILLIN POTASSIUM), VERSED (MIDAZOLAM HYDROCHLORIDE), VERTAVIS (VERATRUM VIRIDE), VESANOID (TRETINOIN), VESICARE (SOLIFENACIN SUCCINATE), VESPRIN (TRIFLUPROMAZINE), VESPRIN (TRIFLUPROMAZINE HYDROCHLORIDE), VEXOL (RIMEXOLONE), VFEND (VORICONAZOLE), VI-DOM-A (VITAMIN A PALMITATE), VI-TWEL (CYANOCOBALAMIN), VIADUR (LEUPROLIDE ACETATE), VIAGRA (SILDENAFIL CITRATE), VIBISONE (CYANOCOBALAMIN), VIBRA-TABS (DOXYCYCLINE HYCLATE), VIBRAMYCIN (DOXYCYCLINE), VIBRAMYCIN (DOXYCYCLINE CALCIUM), VIBRAMYCIN (DOXYCYCLINE HYCLATE), VICKS FORMULA 44 (DIPHENHYDRAMINE HYDROCHLORIDE), VICODIN (ACETAMINOPHEN; HYDROCODONE BITARTRATE), VICODIN ES (ACETAMINOPHEN; HYDROCODONE BITARTRATE), VICODIN HP (ACETAMINOPHEN; HYDROCODONE BITARTRATE), VICOPRIN (ASPIRIN; HYDROCODONE BITARTRATE), VICOPROFEN (HYDROCODONE BITARTRATE; IBUPROFEN), VIDAZA (AZACITIDINE), VIDEX (DIDANOSINE), VIDEX EC (DIDANOSINE), VIGAMOX (MOXIFLOXACIN HYDROCHLORIDE), VINBLASTINE SULFATE (VINBLASTINE SULFATE), VINCASAR PFS (VINCRISTINE SULFATE), VINCREX (VINCRISTINE SULFATE), VINCRISTINE SULFATE (VINCRISTINE SULFATE), VINCRISTINE SULFATE PFS (VINCRISTINE SULFATE), VINORELBINE TARTRATE (VINORELBINE TARTRATE), VIOCIN SULFATE (VIOMYCIN SULFATE), VIOXX (ROFECOXIB), VIRA-A (VIDARABINE), VIRAC REX (UNDECOYLIUM CHLORIDE; UNDECOYLIUM CHLORIDE IODINE COMPLEX), VIRACEPT (NELFINAVIR MESYLATE), VIRAMUNE (NEVIRAPINE), VIRAZOLE (RIBAVIRIN), VIREAD (TENOFOVIR DISOPROXIL FUMARATE), VIRILON (METHYLTESTOSTERONE), VIROPTIC (TRIFLURIDINE), VISICOL (SODIUM PHOSPHATE, DIBASIC, ANHYDROUS; SODIUM PHOSPHATE, MONOBASIC, MONOHYDRATE), VISINE L.R. (OXYMETAZOLINE HYDROCHLORIDE), VISINE-A (NAPHAZOLINE HYDROCHLORIDE; PHENIRAMINE MALEATE), VISIONBLUE (TRYPAN BLUE), VISIPAQUE 270 (IODIXANOL), VISIPAQUE 320 (IODIXANOL), VISKAZIDE (HYDROCHLOROTHIAZIDE; PINDOLOL), VISKEN (PINDOLOL), VISTARIL (HYDROXYZINE HYDROCHLORIDE), VISTARIL (HYDROXYZINE PAMOATE), VISTIDE (CIDOFOVIR), VISUDYNE (VERTEPORFIN), VITAMIN A (VITAMIN A), VITAMIN A (VITAMIN A PALMITATE), VITAMIN A PALMITATE (VITAMIN A PALMITATE), VITAMIN A SOLUBILIZED (VITAMIN A PALMITATE), VITAMIN D (ERGOCALCIFEROL), VITAMIN K1 (PHYTONADIONE), VITAPED (ASCORBIC ACID; BIOTIN; CYANOCOBALAMIN; ERGOCALCIFEROL; FOLIC ACID; NIACINAMIDE; PANTOTHENIC ACID; PHYTONADIONE; PYRIDOXINE; RIBOFLAVIN; THIAMINE; VITAMIN A PALMITATE; VITAMIN E), VIT- RASE (HYALURONIDASE), VITRASERT (GANCICLOVIR), VITRAVENE PRESERVATIVE FREE (FOMIVIRSEN SODIUM), VIVACTIL (PROTRIPTYLINE HYDROCHLORIDE), VIVELLE (ESTRADIOL), VIVELLE-DOT (ESTRADIOL), VIVITROL (NALTREXONE), VOLMAX (ALBUTEROL SULFATE), VOLTAREN (DICLOFENAC SODIUM), VOLTAREN-XR (DICLOFENAC SODIUM), VONTROL (DIPHENIDOL HYDROCHLORIDE), VOSOL (ACETIC ACID, GLACIAL), VOSOL HC (ACETIC ACID, GLACIAL; HYDROCORTISONE), VOSPIRE ER (ALBUTEROL SULFATE), VUMON (TENIPOSIDE), VUSION (MICONAZOLE NITRATE; PETROLATUM, WHITE; ZINC OXIDE), VYTORIN (EZETIMIBE; SIMVASTATIN), VYVANSE (LISDEXAMFETAMINE DIMESYLATE), WAMPOCAP (NIACIN), WARFARIN SODIUM (WARFARIN SODIUM), WELCHOL (COLESEVELAM HYDROCHLORIDE), WELLBUTRIN (BUPROPION HYDROCHLORIDE), WELLBUTRIN SR (BUPROPION HYDROCHLORIDE), WELLBUTRIN XL (BUPROPION HYDROCHLORIDE), WELLCOVORIN (LEUCOVORIN CALCIUM), WESTADONE (METHADONE HYDROCHLORIDE), WESTCORT (HYDROCORTISONE VALERATE), WIGRAINE (CAFFEINE; ERGOTAMINE TARTRATE), WIGRETTES (ERGOTAMINE TARTRATE), WINSTROL (STANOZOLOL), WOLFINA (*RAUWOLFIA SERPENTINA*), WYAMINE SULFATE (MEPHENTERMINE SULFATE), WYAMYCIN E (ERYTHROMYCIN ETHYLSUCCINATE), WYAMYCIN S (ERYTHROMYCIN STEARATE), WYDASE (HYALURONIDASE), WYGESIC (ACETAMINOPHEN; PROPDXYPHENE HYDROCHLORIDE), WYMOX (AMOXICILLIN), WYTENSIN (GUANABENZ ACETATE), X-TROZINE (PHENDIMETRAZINE TARTRATE), X-TROZINE L.A. (PHENDIMETRAZINE TARTRATE), XALATAN (LATANOPROST), XANAX (ALPRAZOLAM), XANAX XR (ALPRAZOLAM), XELODA (CAPECITABINE), XENEISOL (XENON, XE-133), XENICAL (ORLISTAT), XENON XE 127 (XENON, XE-127), XENON XE 133 (XENON, XE-133), XENON XE 133-V.S.S. (XENON, XE-133), XIBROM (BROMFENAC SODIUM), XIFAXAN (RIFAXIMIN), XIGRIS (DROTRECOGIN ALFA (ACTIVATED)), XOLAIR (OMALIZUMAB), XOLEGEL (KETOCONAZOLE), XOPENEX (LEVALBUTEROL HYDROCHLORIDE), XOPENEX HFA (LEVALBUTEROL TARTRATE), XYLO-PFAN (XYLOSE), XYLOCAINE (LIDOCAINE), XYLOCAINE (LIDOCAINE HYDROCHLORIDE), XYLOCAINE 1.5% W/ DEXTROSE 7.5% (LIDOCAINE HYDROCHLORIDE), XYLOCAINE 4% PRESERVATIVE FREE (LIDOCAINE HYDROCHLORIDE), XYLOCAINE 5% W/ GLUCOSE 7.5% (LIDOCAINE HYDROCHLORIDE), XYLOCAINE PRESERVATIVE FREE (LIDOCAINE HYDROCHLORIDE), XYLOCAINE VISCOUS (LIDOCAINE HYDROCHLORIDE), XYLOCAINE W/ EPINEPHRINE (EPINEPHRINE; LIDOCAINE HYDROCHLORIDE), XYLOSE (XYLOSE), XYREM (SODIUM OXYBATE), XYZAL (LEVOCETIRIZINE DIHYDROCHLORIDE), YASMIN (DROSPIRENONE; ETHINYL ESTRADIOL), YAZ (DROSPIRENONE; ETHINYL ESTRADIOL), YTTERBIUM YB 169 DTPA (PENTETATE CALCIUM TRISODIUM YB-169), YUTOPAR (RITODRINE HYDROCHLORIDE), ZADITOR (KETOTIFEN FUMARATE), ZAGAM (SPARFLOXACIN), ZALEPLON (ZALEPLON), ZANAFLEX (TIZANIDINE HYDROCHLORIDE), ZANOSAR (STREPTOZOCIN), ZANTAC (RANITIDINE HYDROCHLORIDE), ZANTAC 150 (RANITIDINE HYDROCHLORIDE), ZANTAC 25 (RANITIDINE HYDROCHLORIDE), ZANTAC 300 (RANITIDINE HYDROCHLORIDE), ZANTAC 75 (RANITIDINE HYDROCHLORIDE), ZANTAC IN PLASTIC CONTAINER (RANITIDINE HYDROCHLORIDE), ZARONTIN (ETHOSUXIMIDE), ZAROXOLYN (METOLAZONE), ZAVESCA (MIGLUSTAT), ZAXOPAM (OXAZEPAM), ZEBETA (BISOPROLOL FUMARATE), ZEFAZONE (CEFMETAZOLE SODIUM), ZEFAZONE IN PLASTIC CONTAINER (CEFMETAZOLE SODIUM), ZEGERID (MAGNESIUM HYDROXIDE; OMEPRAZOLE; SODIUM BICARBONATE), ZEGERID (OMEPRAZOLE; SODIUM BICARBONATE), ZELAPAR (SELEGILINE HYDROCHLORIDE), ZELNORM (TEGASEROD MALEATE), ZEMPLAR (PARICALCITOL), ZEMURON (ROCURONIUM BROMIDE), ZENAPAX (DACLIZUMAB), ZERIT (STAVUDINE), ZERIT XR (STAVUDINE), ZESTORETIC (HYDROCHLOROTHIAZIDE; LISINOPRIL), ZESTRIL (LISINOPRIL), ZETIA (EZETIMIBE), ZEVALIN (IBRITUMOMAB TIUXETAN), ZIAC (BISOPROLOL FUMARATE; HYDROCHLOROTHIAZIDE), ZIAGEN (ABACAVIR SULFATE), ZIANA (CLINDAMYCIN PHOSPHATE; TRETINOIN), ZIBA-RX (BACITRACIN ZINC), ZIDE (HYDROCHLOROTHIAZIDE), ZIDOVUDINE (ZIDOVUDINE), ZINACEF (CEFUROXIME SODIUM), ZINACEF IN PLASTIC CONTAINER (CEFUROXIME SODIUM), ZINC BACITRACIN, NEOMYCIN SULFATE, POLYMYXIN B SULFATE & HYDROCORTISONE (BACITRACIN ZINC; HYDROCORTISONE; NEOMYCIN SULFATE; POLYMYXIN B SULFATE), ZINC CHLORIDE IN PLASTIC CONTAINER (ZINC CHLORIDE), ZINC SULFATE (ZINC SULFATE), ZINECARD (DEXRAZOXANE HYDROCHLORIDE), ZINGO (LIDOCAINE HYDROCHLORIDE), ZIPAN-25 (PROMETHAZINE HYDROCHLORIDE), ZIPAN-50 (PROMETHAZINE HYDROCHLORIDE), ZIPRASIDONE HYDROCHLORIDE (ZIPRASIDONE HYDROCHLORIDE), ZITHROMAX (AZITHROMYCIN), ZMAX (AZITHROMYCIN), ZOCOR (SIMVASTATIN), ZOFRAN (ONDANSETRON HYDROCHLORIDE), ZOFRAN AND DEXTROSE IN PLASTIC CONTAINER (ONDANSETRON HYDROCHLORIDE), ZOFRAN ODT (ONDANSETRON), ZOFRAN PRESERVATIVE FREE (ONDANSETRON HYDROCHLORIDE), ZOLADEX (GOSERELIN ACETATE), ZOLINZA (VORINOSTAT), ZOLOFT (SERTRALINE HYDROCHLORIDE), ZOLPIDEM (ZOLPIDEM TARTRATE), ZOLPIDEM TARTRATE (ZOLPIDEM TARTRATE), ZOLYSE (CHYMOTRYPSIN), ZOMETA (ZOLEDRONIC ACID), ZOMIG (ZOLMITRIPTAN), ZOMIG-ZMT (ZOLMITRIPTAN), ZONALON (DOXEPIN HYDROCHLORIDE), ZONEGRAN (ZONISAMIDE), ZONISAMIDE (ZONISAMIDE), ZORBTIVE (SOMATROPIN RECOMBINANT), ZOSYN (PIPERACILLIN SODIUM; TAZOBACTAM SODIUM), ZOSYN IN PLASTIC CONTAINER (PIPERACILLIN SODIUM; TAZOBACTAM SODIUM), ZOVIA 1/35E-21 (ETHINYL ESTRADIOL; ETHYNODIOL DIACETATE), ZOVIA 1/35E-28 (ETHINYL ESTRADIOL; ETHYNODIOL DIACETATE), ZOVIA 1/50E-21 (ETHINYL ESTRADIOL; ETHYNODIOL DIACETATE), ZOVIA 1/50E-28 (ETHINYL ESTRADIOL; ETHYNODIOL DIACETATE), ZOVIRAX (ACYCLOVIR), ZOVIRAX (ACYCLOVIR SODIUM), ZYBAN (BUPROPION HYDROCHLORIDE), ZYDONE (ACETAMINOPHEN; HYDROCODONE BITARTRATE), ZYFLO (ZILEUTON), ZYFLO CR (ZILEUTON), ZYLET (LOTEPREDNOL ETABONATE; TOBRAMYCIN), ZYLOPRIM (ALLOPURINOL), ZYMAR (GATIFLOXACIN), ZYPREXA (OLANZAPINE), ZYPREXA ZYDIS (OLANZAPINE), ZYRTEC (CETIRIZINE HYDROCHLORIDE), ZYRTEC ALLERGY (CETIRIZINE HYDROCHLORIDE), ZYRTEC HIVES RELIEF (CETIRIZINE HYDROCHLORIDE), ZYRTEC-D 12 HOUR (CETIRIZINE HYDROCHLORIDE; PSEUDOEPHEDRINE HYDROCHLORIDE), ZYVOX (LINEZOLID), 8-HOUR BAYER (ASPIRIN), and 8-MOP (METHOXSALEN).

173. The method according to item 114, wherein the one or more drug(s) comprises one or more antibiotics.

174. The method according to item 173, wherein the one or more antibiotics can be selected from the group consisting of Amikacin disulfate salt, Amikacin hydrate, Anisomycin from *Streptomyces griseolus*, Apramycin sulfate salt, Azithromycin, Blasticidine S hydrochloride, Brefeldin A, Brefeldin A from *Penicillium brefeldianum*, Butirosin sulfate salt, Butirosin A from *Bacillus vitellinus*, Chloramphenicol, Chloramphenicol base, Chloramphenicol succinate sodium salt, Chlortetracycline hydrochloride, Chlortetracycline hydrochloride from *Streptomyces aureofaciens*, Clindamycin 2-phosphate, Clindamycin hydrochloride, Clotrimazole, Cycloheximide from microbial, Demeclocycline hydrochloride, Dibekacin sulfate salt, Dihydrostreptomycin sesquisulfate, Dihydrostreptomycin solution, Doxycycline hyclate, Duramycin from *Streptoverticillium cinnamoneus*, Emetine dihydrochloride hydrate), Erythromycin, Erythromycin USP, Erythromycin powder, Erythromycin, Temephos, Erythromycin estolate, Erythromycin ethyl succinate, Erythromycin standard solution, Erythromycin stearate, Fusidic acid sodium salt, G 418 disulfate salt, G 418 disulfate salt powder, G 418 disulfate salt solution liquid, Gentamicin solution liquid, Gentamicin solution, Gentamicin sulfate *Micromonospora purpurea*, Gentamicin sulfate salt, Gentamicin sulfate salt powder USP, Gentamicin-Glutamine solution liquid, Helvolic acid from *Cephalosporium caerulens*, Hygromycin B *Streptomyces hygroscopicus*, Hygromycin B *Streptomyces hygroscopicus* powder, Hygromycin B solution *Streptomyces hygroscopicus*, Josamycin, Josamycin solution, Kanamycin B sulfate salt, Kanamycin disulfate salt from *Streptomyces kanamyceticus*, Kanamycin monosulfate from *Streptomyces kanamyceticus*, Kanamycin monosulfate from *Streptomyces kanamyceticus* powder USP, Kanamycin solution from *Streptomyces kanamyceticus*, Kirromycin from *Streptomyces collinus*, Lincomycin hydrochloride, Lincomycin standard solution, Meclocycline sulfosalicylate salt, Mepartricin, Midecamycin from *Streptomyces mycarofaciens*, Minocycline hydrochloride crystalline, Neomycin solution, Neomycin trisulfate salt hydrate, Neomycin trisulfate salt hydrate powder, Neomycin trisulfate salt hydrate USP powder, Netilmicin sulfate salt, Nitrofurantoin crystalline, Nourseothricin sulfate, Oleandomycin phosphate salt, Oleandomycin triacetate, Oxytetracycline dihydrate, Oxytetracycline hemicalcium salt, Oxytetracycline hydrochloride, Paromomycin sulfate salt, Puromycin dihydrochloride from *Streptomyces alboniger*, Rapamycin from *Streptomyces hygroscopicus*, Ribostamycin sulfate salt, Rifampicin, Rifamycin SV sodium salt, Rosamicin *Micromonospora rosaria*, Sisomicin sulfate salt, Spectinomycin dihydrochloride hydrate, Spectinomycin dihydrochloride hydrate powder, Spectinomycin dihydrochloride pentahydrate, Spiramycin, Spiramycin from *Streptomyces* sp., Spiramycin solution, Streptomycin solution, Streptomycin sulfate salt, Streptomycin sulfate salt powder, Tetracycline, Tetracycline hydrochloride, Tetracycline hydrochloride USP, Tetracycline hydrochloride powder, Thiamphenicol, Thiostrepton from *Streptomyces azureus*, Tobramycin, Tobramycin sulfate salt, Tunicamycin $A_1$ homolog, Tunicamycin $C_2$ homolog, Tunicamycin *Streptomyces* sp., Tylosin solution, Tylosin tartrate, Viomycin sulfate salt, Virginiamycin $M_1$, (S)-(+)-Camptothecin, 10-Deacetylbaccatin III from *Taxus baccata*, 5-Azacytidine, 7-Aminoactinomycin D, 8-Quinolinol crystalline, 8-Quinolinol hemisulfate salt crystalline, 9-Dihydro-13-acetylbaccatin III from *Taxus canadensis*, Aclarubicin, Aclarubicin hydrochloride, Actinomycin D from *Streptomyces* sp., Actinomycin I from *Streptomyces antibioticus*, Actinomycin V from *Streptomyces antibioticus*, Aphidicolin *Nigrospora sphaerica*, Bafilomycin A1 from *Streptomyces griseus*, Bleomycin sulfate from *Streptomyces verticillus*, Capreomycin sulfate from *Streptomyces capreolus*, Chromomycin $A_3$ *Streptomyces griseus*, Cinoxacin, Ciprofloxacin BioChemika, cis-Diammineplatinum(II) dichloride, Coumermycin A1, Cytochalasin B *Helminthosporium dematioideum*, Cytochalasin D *Zygosporium mansonii*, Dacarbazine, Daunorubicin hydrochloride, Daunorubicin hydrochloride USP, Distamycin A hydrochloride from *Streptomyces distallicus*, Doxorubicin hydrochloride, Echinomycin, Echinomycin BioChemika, Enrofloxacin BioChemika, Etoposide, Etoposide solid, Flumequine, Formycin, Fumagillin from *Aspergillus fumigatus*, Ganciclovir, Gliotoxin from *Gliocladium fimbriatum*, Lomefloxacin hydrochloride, Metronidazole purum, Mithramycin A from *Streptomyces plicatus*, Mitomycin C *Streptomyces caespitosus*, Nalidixic acid, Nalidixic acid sodium salt, Nalidixic acid sodium salt powder, Netropsin dihydrochloride hydrate, Nitrofurantoin, Nogalamycin from *Streptomyces nogalater*, Nonactin from *Streptomyces tsusimaensis*, Novobiocin sodium salt, Ofloxacin, Oxolinic acid, Paclitaxel from *Taxus yannanensis*, Paclitaxel from *Taxus brevifolia*, Phenazine methosulfate, Phleomycin *Streptomyces verticillus*, Pipemidic acid, Rebeccamycin from *Saccharothrix aerocolonigenes*, Sinefungin, Streptonigrin from *Streptomyces flocculus*, Streptozocin, Succinylsulfathiazole, Sulfadiazine, Sulfadimethoxine, Sulfaguanidine purum, Sulfamethazine, Sulfamonomethoxine, Sulfanilamide, Sulfaquinoxaline sodium salt, Sulfasalazine, Sulfathiazole sodium salt, Trimethoprim, Trimethoprim lactate salt, Tubercidin from *Streptomyces tubercidicus*, 5-Azacytidine, Cordycepin, Formycin A, (+)-6-Aminopenicillanic acid, 7-Aminodesacetoxycephalosporanic acid, Amoxicillin, Ampicillin, Ampicillin sodium salt, Ampicillin trihydrate, Ampicillin trihydrate USP, Azlocillin sodium salt, Bacitracin *Bacillus licheniformis*, Bacitracin zinc salt *Bacillus licheniformis*, Carbenicillin disodium salt, Cefaclor, Cefamandole lithium salt, Cefamandole nafate, Cefamandole sodium salt, Cefazolin sodium salt, Cefmetazole sodium salt, Cefoperazone sodium salt, Cefotaxime sodium salt, Cefsulodin sodium salt, Cefsulodin sodium salt hydrate, Ceftriaxone sodium salt, Cephalexin hydrate, Cephalosporin C zinc salt, Cephalothin sodium salt, Cephapirin sodium salt, Cephradine, Cloxacillin sodium salt, Cloxacillin sodium salt monohydrate, D-( )-Penicillamine hydrochloride, D-Cycloserine microbial, D-Cycloserine powder, Dicloxacillin sodium salt monohydrate, D-Penicillamine, Econazole nitrate salt, Ethambutol dihydrochloride, Lysostaphin from *Staphylococcus staphylolyticus*, Moxalactam sodium salt, Nafcillin sodium salt monohydrate, Nikkomycin, Nikkomycin Z *Streptomyces tendae*, Nitrofurantoin crystalline, Oxacillin sodium salt, Penicillic acid powder, Penicillin G potassium salt, Penicillin G potassium salt powder, Penicillin G potassium salt, Penicillin G sodium salt hydrate powder, Penicillin G sodium salt powder, Penicillin G sodium salt, Phenethicillin potassium salt, Phenoxymethylpenicillinic acid potassium salt, Phosphomycin disodium salt, Pipemidic acid, Piperacillin sodium salt, Ristomycin monosulfate, Vancomycin hydrochloride from *Streptomyces orientalis*, 2-Mercaptopyridine N-oxide sodium salt, 4-Bromocalcimycin A23187 BioChemika, Alamethicin *Trichoderma viride*, Amphotericin B *Streptomyces* sp., Amphotericin B preparation, Calcimycin A23187, Calcimycin A23187 hemi (calcium-magnesium) salt, Calcimycin A23187 hemicalcium salt, Calcimycin A23187 hemimagnesium salt, Chlorhexidine diacetate salt monohydrate, Chlorhexidine diacetate salt hydrate, Chlorhexidine digluconate, Clotrimazole, Colistin sodium methanesulfonate, Colistin sodium methanesulfonate from *Bacillus colistinus*, Colistin sulfate salt, Econazole nitrate salt, Hydrocortisone 21-acetate, Filipin complex *Streptomyces filipinensis*, Gliotoxin from *Gliocladium fimbriatum*, Gramicidin A from *Bacillus brevis*, Gramicidin C from *Bacillus brevis*, Gramicidin from *Bacillus aneurinolyticus* (*Bacillus brevis*), Ionomycin calcium salt *Streptomyces conglobatus*, Lasalocid A sodium salt, Lonomycin A sodium salt from *Streptomyces ribosidificus*, Monensin sodium salt, N-(6-Aminohexyl)-5-chloro-1-naphthalenesulfonamide hydrochloride, Narasin from *Streptomyces auriofaciens*, Nigericin sodium salt from *Streptomyces hygroscopicus*, Nisin from *Streptococcus lactis*, Nonactin from *Streptomyces* sp., Nystatin, Nystatin powder, Phenazine methosulfate, Pimaricin, Pimaricin from *Streptomyces chattanoogensis*, Polymyxin B solution, Polymyxin B sulfate salt, DL-Penicillamine acetone adduct hydrochloride monohydrate, Polymyxin B sulfate salt powder USP, Praziquantel, Salinomycin from *Streptomyces albus*, Salinomycin from *Streptomyces albus*, Surfactin from *Bacillus subtilis*, Valinomycin, (+)-Usnic acid from *Usnea dasypoga*, (±)-Miconazole nitrate salt, (S)-(+)-Camptothecin, 1-Deoxymannojirimycin hydrochloride, 1-Deoxynojirimycin hydrochloride, 2-Heptyl-4-hydroxyquinoline N-oxide, Cordycepin, 1,10-Phenanthroline hydrochloride monohydrate puriss., 6-Diazo-5-oxo-L-norleucine, 8-Quinolinol crystalline, 8-Quinolinol hemisulfate salt, Antimycin A from *Streptomyces* sp., Antimycin $A_1$, Antimycin $A_2$, Antimycin $A_3$, Antipain, Ascomycin, Azaserine, Bafilomycin A1 from *Streptomyces griseus*, Bafilomycin B1 from *Streptomyces* species, Cerulenin BioChemika, Chloroquine diphosphate salt, Cinoxacin, Ciprofloxacin, Mevastatin BioChemika, Concanamycin A, Concanamycin A *Streptomyces* sp, Concanamycin C from *Streptomyces* species, Coumermycin A1, Cyclosporin A from *Tolypocladium inflatum*, Cyclosporin A, Econazole nitrate salt, Enrofloxacin, Etoposide, Flumequine, Formycin A, Furazolidone, Fusaric acid from *Gibberella fujikuroi*, Geldanamycin from *Streptomyces hygroscopicus*, Gliotoxin from *Gliocladium fimbriatum*, Gramicidin A from *Bacillus brevis*, Gramicidin C from *Bacillus brevis*, Gramicidin from *Bacillus aneurinolyticus* (*Bacillus brevis*), Gramicidin from *Bacillus brevis*, Herbimycin A from *Streptomyces hygroscopicus*, Indomethacin, Irgasan, Lomefloxacin hydrochloride, Mycophenolic acid powder, Myxothiazol BioChemika, N-(6-Aminohexyl)-5-chloro-1-naphthalenesulfonamide hydrochloride, Nalidixic acid, Netropsin dihydrochloride hydrate, Niclosamide, Nikkomycin BioChemika, Nikkomycin Z *Streptomyces tendae*, N-Methyl-1-deoxynojirimycin, Nogalamycin from *Streptomyces nogalater*, Nonactin □80% from *Streptomyces tsusimaensis*, Nonactin from *Streptomyces* sp., Novobiocin sodium salt, Ofloxacin, Oleandomycin triacetate, Oligomycin *Streptomyces diastatochromogenes*, Oligomycin A, Oligomycin B, Oligomycin C, Oligomycin *Streptomyces diastatochromogenes*, Oxolinic acid, Piericidin A from *Streptomyces mobaraensis*, Pipemidic acid, Radicicol from *Diheterospora chlamydosporia* solid, Rapamycin from *Streptomyces hygroscopicus*, Rebeccamycin from *Saccharothrix aerocolonigenes*, Sinefungin, Staurosporine *Streptomyces* sp., Stigmatellin, Succinylsulfathiazole, Sulfadiazine, Sulfadimethoxine, Sulfaguanidine purum, Sulfamethazine, Sulfamonomethoxine, Sulfanilamide, Sulfaquinoxaline sodium salt, Sulfasalazine, Sulfathiazole sodium salt, Triacsin C from *Streptomyces* sp., Trimethoprim, Trimethoprim lactate salt, Vineomycin $A_1$ from *Streptomyces albogriseolus* subsp., □-*Tectorigenin*, and Paracelsin *Trichoderma reesei*.

175. The method according to item 173, wherein the one or more antibiotics comprises Aminoglycosides such as Amikacin, Gentamicin, Kanamycin, Neomycin, Netilmicin, Streptomycin, Tobramycin, and Paromomycin.

176. The method according to item 173, wherein the one or more antibiotics comprises Ansamycins such as Geldanamycin and Herbimycin.

177. The method according to item 173, wherein the one or more antibiotics comprises Carbacephem such as Loracarbef.

178. The method according to item 173, wherein the one or more antibiotics comprises Carbapenems such as Ertapenem, Doripenem, Imipenem/Cilastatin and Meropenem.

179. The method according to item 173, wherein the one or more antibiotics comprises Cephalosporins such as Cefadroxil, Cefazolin, Cefalotin or Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime and Ceftobiprole.

180. The method according to item 173, wherein the one or more antibiotics comprises Glycopeptides such as Teicoplanin and Vancomycin.

181. The method according to item 173, wherein the one or more antibiotics comprises Macrolides such as Azithromycin, Clarithromycin, Dirithromycin, Erythromycin, Roxithromycin, Troleandomycin, Telithromycin and Spectinomycin.

182. The method according to item 173, wherein the one or more antibiotics comprises Monobactams such as Aztreonam.

183. The method according to item 173, wherein the one or more antibiotics comprises Penicillins such as Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin and Ticarcillin.

184. The method according to item 173, wherein the one or more antibiotics comprises Polypeptides such as Bacitracin, Colistin and Polymyxin B.

185. The method according to item 173, wherein the one or more antibiotics comprises Quinolones such as Ciprofloxacin, Enoxacin, Gatifloxacin, Levofloxacin, Lomefloxacin, Moxifloxacin, Norfloxacin, Ofloxacin and Trovafloxacin.
186. The method according to item 173, wherein the one or more antibiotics comprises Sulfonamides such as Mafenide, Prontosil (archaic), Sulfacetamide, Sulfamethizole, Sulfanilimide (archaic), Sulfasalazine, Sulfisoxazole, Trimethoprim, and Trimethoprim-Sulfamethoxazole (Co-trimoxazole) (TMP-SMX).
187. The method according to item 173, wherein the one or more antibiotics comprises Tetracyclines such as Demeclocycline, Doxycycline, Minocycline, Oxytetracycline and Tetracycline.
188. The method according to item 173, wherein the one or more antibiotics comprises one or more antibiotics selected from the group consisting of Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampin or Rifampicin and Tinidazole.
189. The method according to item 114, wherein the one or more drug(s) comprises one or more antiviral drugs.
190. The method according to item 189, wherein the one or more antiviral drugs can be selected from the group consisting of Abacavir, Aciclovir, Acyclovir, Adefovir, Alferon LDO, Amantadine, Amdoxovir, Ampligen, Amprenavir, Aplaviroc, Apricitabine, Arbidol, Atazanavir, Ateviridine, Atripla, Bevirimat, BILN 2061, Brecanavir, Brivudine, Calanolide A, Capravirine, Cidofovir, Combivir, Condylox, Cyanovirin-N, Darunavir, Delavirdine, Dexelvucitabine, Diarylpyrimidines, Didanosine, Docosanol, Edoxudine, Efavirenz, Elvitegravir, Elvucitabine, Emivirine, Emtricitabine, Enfuvirtide, Entecavir, Epigallocatechin gallate, Etravirine, Famciclovir, Fialuridine, Fomivirsen, Fosamprenavir, Foscarnet, Fosfonet, Fusion inhibitor, Ganciclovir, Gardasil, Globoidnan A, Griffithsin, GS-9137, Ibacitabine, Ibalizumab, Immunovir, Idoxuridine, Imiquimod, Indinavir, Inosine, Interferon-gamma, Interferon type III, Interferon type II, Interferon type I, Interferon, Lamivudine, Lodenosine, Lopinavir, Loviride, MK-0518, Maraviroc, Miltefosine, Moroxydine, Nelfinavir, Nevirapine, Nexavir, Oragen, Oseltamivir, Penciclovir, Peramivir, Pleconaril, Podophyllotoxin, Portmanteau inhibitors, PRO 140, Quinotaline, Racivir, Raltegravir, Ribavirin, Rilpivirine, Rimantadine, Ritonavir, R-roscovitine, Saquinavir, SCH 503034, Stampidine, Stavudine, Taribavirin, Telbivudine, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Vivecon, VX 950/Telaprevir, Zalcitabine, Zanamivir, and Zidovudine (AZT).
191. The method according to item 114, wherein the one or more drug(s) comprises one or more antifungal drugs.
192. The method according to item 191, wherein the one or more antifungal drugs comprises polyene antimycotics such as Natamycin, Rimocidin, Filipin, Nystatin, Amphotericin B, and Candicin.
193. The method according to item 191, wherein the one or more antifungal drugs comprises imidazole and triazole antifungal drugs such as Imidazoles like Miconazole (Miconazole nitrate), Ketoconazole, Clotrimazole (marketed as Lotrimin, Canesten in the UK), Econazole, Bifonazole, Butoconazole, Fenticonazole, Isoconazole, Oxiconazole, Sertaconazole (marketed as Ertaczo), Sulconazole, Tioconazole, Fluconazole, Itraconazole, Isavuconazole, Ravuconazole, Posaconazole, Voriconazole, and Terconazole.
194. The method according to item 191, wherein the one or more antifungal drugs comprises Allylamines such as Terbinafine (marketed as Lamisil), Amorolfine, Naftifine (marketed as Naftin), and Butenafine (marketed as Lotrimin Ultra).
195. The method according to item 191, wherein the one or more antifungal drugs comprises Echinocandins such as Anidulafungin, Caspofungin, and Micafungin.
196. The method according to item 191, wherein the one or more antifungal drugs comprises one or more antifungal drugs selected from the group consisting of Benzoic acid in combination with a keratolytic agent (such as in Whitfield's Ointment), Ciclopirox olamine, Flucytosine, or 5-fluorocytosine, Griseofulvin, Gentian Violet Haloprogin Tolnaftate (marketed as Tinactin, Desenex, Aftate), Undecylenic acid, Tea tree oil, Citronella oil, lemon grass, orange oil, palmarosa oil, patchouli, lemon, myrtle, Neem Seed Oil, Coconut Oil (medium chain triglycerides in the oil have antifungal activities), Zinc dietary supplements or natural food sources, including pumpkin seeds and chick peas, Selenium dietary supplements or natural food sources, particularly Brazil nuts.
197. The method according to item 114, wherein the one or more drug(s) comprises one or more antiparasitic drugs.
198. The method according to item 197, wherein the one or more antiparasitic drugs comprises Antinematodes such as Mebendazole (for most nematode infections), Pyrantel pamoate (for most nematode infections), Thiabendazole (for roundworm infections), and Diethycarbazine (for treatment of Lymphatic filariasis).
199. The method according to item 197, wherein the one or more antiparasitic drugs comprises Anticestodes such as Niclosamide (for tapeworm infections), and Praziquantel (for tapeworm infections).
200. The method according to item 197, wherein the one or more antiparasitic drugs comprises Antitrematodes such as Praziquantel.
201. The method according to item 197, wherein the one or more antiparasitic drugs comprises Antiamoebics such as Rifampin, Amphotericin B, Clioquinol, Iodoquinol Metronidazole, Tinidazole, Ornidazole, Secnidazole Atovaquone, Emetine, Fumagillin, and Trimetrexate.
202. The method according to item 197, wherein the one or more antiparasitic drugs comprises Antiprotozoals such as Amphotericin, Antimony, Eflornithine, Furazolidone, Melarsoprol, Metronidazole, Miltefosine (Impavido), Ornidazole, Paromomycin sulfate, Pentamidine, Pyrimethamine, and Tinidazole.
203. The method according to item 114, wherein the one or more drug(s) comprises one or more drugs for treatment of cancer.
204. The method according to item 203, wherein one or more drugs for treatment of cancer can be selected from the group consisting of abarelix, aldesleukin, Aldesleukin, Alemtuzumab, alitretinoin, allopurinol, altretamine, amifostine, anakinra, anastrozole, arsenic trioxide, asparaginase, azacitidine, BCG Live, bevacizumab, bexarotene capsules, bexarotene gel, bleomycin, bortezombi, busulfan intravenous, busulfan oral, calusterone, capecitabine, carboplatin, carmustine, carmustine with Polifeprosan 20 Implant, celecoxib, cetuximab, chlorambucil, cisplatin, cladribine, clofarabine, cyclophosphamide, cytarabine, cytarabine liposomal, dacarbazine, dactinomycin, actinomycin D, dalteparin sodium, darbepoetin alfa, dasatinib, daunorubicin liposomal, daunorubicin, daunomycin, decitabine, denileukin, Denileukin diftitox, dexrazoxane, docetaxel, doxorubicin, doxorubicin liposomal, DROMOSTANOLONE PROPIONATE, eculizumab, Elliott's B Solution, epirubicin, epirubicin hcl, epoetin alfa, erlotinib, estramustine, etoposide phosphate, etoposide, VP-16, exemestane, fentanyl citrate, Filgrastim, floxuridine (intraarterial), fludarabine, fluorouracil, 5-FU, fulvestrant, gefitinib, gemcitabine, gemcitabine hcl, gemicitabine, gemtuzumab ozogamicin, goserelin acetate, histrelin acetate, hydroxyurea, Ibritumomab Tiuxetan, idarubicin, ifosfamide, imatinib mesylate, interferon alfa 2a, Interferon alfa-2b, irinotecan, lapatinib ditosylate, lenalidomide, letrozole, leucovorin, Leuprolide Acetate, levamisole, lomustine, CCNU, meclorethamine, nitrogen mustard, megestrol acetate, melphalan, L-PAM, mercaptopurine, 6-MP, mesna, methotrexate, methoxsalen, mitomycin C, mitotane, mitoxantrone, nandrolone phenpropionate, nelarabine, Nofetumomab, Oprelvekin, oxaliplatin, paclitaxel, paclitaxel protein-bound particles, palifermin, pamidronate, panitumumab, pegademase, pegaspargase, Pegfilgrastim, Peginterferon alfa-2b, pemetrexed disodium, pentostatin, pipobroman, plicamycin, mithramycin, porfimer sodium, procarbazine, quinacrine, Rasburicase, rituximab, Sargramostim, sorafenib, streptozocin, sunitinib, sunitinib maleate, talc, tamoxifen, temozolomide, teniposide, VM-26, testolactone, thalidomide, thioguanine, 6-TG, thiotepa, topotecan, topotecan hcl, toremifene, Tositumomab, Tositumomab/I-131 tositumomab, trastuzumab, tretinoin, ATRA, Uracil Mustard, valrubicin, vinblastine, vincristine, vinorelbine, vorinostat, zoledronate, and zoledronic acid.

205. he method according to item 203, wherein one or more drugs for treatment of cancer can be selected from the group consisting of Aldesleukin/Proleukin (Chiron Corp), Alemtuzumab/Campath (Millennium and ILEX Partners, LP), alitretinoin/Panretin (Ligand Pharmaceuticals), allopurinol/Zyloprim (GlaxoSmithKline), altretamine/Hexalen (US Bioscience), amifostine/Ethyol (US Bioscience), anastrozole/Arimidex (AstraZeneca), arsenic trioxide/Trisenox (Cell Therapeutic), Asparaginase/Elspar (Merck & Co, Inc), BCG Live/TICE BCG (Organon Teknika Corp), bexarotene capsules/Targretin (Ligand Pharmaceuticals), bleomycin/Blenoxane (Bristol-Myers Squibb), busulfan/Busulfex (GlaxoSmithKline), calusterone/Methosarb (Pharmacia & Upjohn Company), capecitabine/Xeloda (Roche), carboplatin/Paraplatin (Bristol-Myers Squibb), carmustine/BCNU, BiCNU (Bristol-Myers Squibb), carmustine with Polifeprosan 20 Implant/Gliadel Wafer (Guilford Pharmaceuticals Inc.), celecoxib/Celebrex (Searle), chlorambucil/Leukeran (GlaxoSmithKline), cisplatin/Platinol (Bristol-Myers Squibb), cladribine/Leustatin, 2-CdA (R.W. Johnson Pharmaceutical Research Institute), cyclophosphamide Cytoxan/Neosar (Bristol-Myers Squibb), cytarabine/Cytosar-U (Pharmacia & Upjohn Company), dacarbazine/DTIC-Dome (Bayer), dactinomycin/actinomycin D Cosmegen (Merck), Darbepoetin alfa/Aranesp (Amgen, Inc), daunorubicin/daunomycin/Daunorubicin (Bedford Labs), daunorubicin/daunomycin/Cerubidine (Wyeth Ayerst), Denileukin/diftitox/Ontak (Seragen, Inc), dexrazoxane/Zinecard (Pharmacia & Upjohn Company), docetaxel/Taxotere (Aventis Pharmaceutical), doxorubicin Adriamycin/Rubex (Pharmacia & Upjohn Company), DROMOSTANOLONE PROPIONATE/MASTERONE INJECTION (SYNTEX), Elliott's B Solution (Orphan Medical, Inc), epirubicin/Ellence (Pharmacia & Upjohn Company), etoposide phosphate (Bristol-Myers Squibb), etoposide/VP-16/Vepesid (Bristol-Myers Squibb), exemestane/Aromasin (Pharmacia & Upjohn Company), Filgrastim/Neupogen (Amgen, Inc), floxuridine/FUDR (Roche), fludarabine/Fludara (Berlex Laboratories Inc.), fluorouracil/5-FU/Adrucil (ICN Puerto Rico), fulvestrant/Faslodex (IPR), gemcitabine/Gemzar (Eli Lilly), gemtuzumab/ozogamicin/Mylotarg (Wyeth Ayerst), goserelin acetate/Zoladex Implant (AstraZeneca Pharmaceuticals), hydroxyurea/Hydrea (Bristol-Myers Squibb), Ibritumomab Tiuxetan/Zevalin (IDEC Pharmaceuticals Corp), idarubicin/Idamycin (Adria Laboratories), ifosfamide/IFEX (Bristol-Myers Squibb), imatinib mesylate/Gleevec (Novartis), Interferon alfa-2a/Roferon-A (Hoffmann-La Roche Inc), Interferon alfa-2b/Intron A (Schering Corp), irinotecan/Camptosar (Pharmacia & Upjohn Company), letrozole/Femara (Novartis), leucovorin Wellcovorin/Leucovorin (Immunex Corporation), levamisole/Ergamisol (Janssen Research Foundation), lomustine/CCNU/CeeBU (Bristol-Myers Squibb), meclorethamine/nitrogen mustard/Mustargen (Merck), megestrol acetate/Megace (Bristol-Myers Squibb), melphalan/L-PAM/Alkeran (GlaxoSmithKline), mercaptopurine/6-MP Purinethol (GlaxoSmithKline), mesna/Mesnex (Asta Medica), methotrexate (Lederle Laboratories), methoxsalen/Uvadex (Therakos), mitomycin C/Mutamycin (Bristol-Myers Squibb), mitomycin C/Mitozytrex (Supergen), mitotane/Lysodren (Bristol-Myers Squibb), mitoxantrone/Novantrone (Lederle Laboratories), nandrolone phenpropionate/Durabolin-50 (Organon), Nofetumomab/Verluma (Boehringer Ingelheim Pharma KG (formerly Dr. Karl Thomae GmbH)), Oprelvekin/Neumega (Genetics Institute), oxaliplatin/Eloxatin (Sanofi Synthelabo), paclitaxel/Taxol (Bristol-Myers Squibb), pamidronate/Aredia (Novartis), pegademase/Adagen (Pegademase Bovine) (Enzon), Pegaspargase/Oncaspar (Enzon, Inc), Pegfilgrastim/Neulasta (Amgen, Inc), pentostatin/Nipent (Parke-Davis Pharmaceutical Co.), pipobroman/Vercyte (Abbott Labs), plicamycin/mithramycin/Mithracin (Pfizer Labs), porfimer sodium/Photofrin (QLT Phototherapeutics Inc.), procarbazine/Matulane (Sigma Tau Pharms), quinacrine/Atabrine (Abbott Labs), Rasburicase/Elitek (Sanofi-Synthelabo, Inc), Rituximab/Rituxan (Genentech, Inc), Sargramostim/Prokine (Immunex Corp), streptozocin/Zanosar (Pharmacia & Upjohn Company), talc/Sclerosol (Bryan), tamoxifen/Nolvadex (AstraZeneca Pharmaceuticals), temozolomide/Temodar (Schering), teniposide/VM-26/Vumon (Bristol-Myers Squibb), testolactone/Teslac (Bristol-Myers Squibb), thioguanine/6-TG/Thioguanine (GlaxoSmithKline), thiotepa/Thioplex (Lederle Laboratories), topotecan/Hycamtin (GlaxoSmithKline), topotecan/Hycamtin (GlaxoSmithKline), toremifene/Fareston (Orion Corp), Tositumomab/Bexxar (Corixa Corporation), Trastuzumab/Herceptin (Genentech, Inc), tretinoin/ATRA/Vesanoid (Roche), Uracil Mustard (Roberts Labs), valrubicin/Valstar (Medeva), vinblastine/Velban (Eli Lilly), vincristine/Oncovin (Eli Lilly), vinorelbine/Navelbine (GlaxoSmithKline), and, zoledronate/Zometa (Novartis).

206. The method according to item 114, wherein the one or more drug(s) comprises one or more immunostimulants.

207. The method according to item 206, wherein one or more immunostimulants comprises granulocyte macrophage colony-stimulating factor.

208. The method according to item 206, wherein one or more immunostimulants comprises Leukine.

209. The method according to item 206, wherein one or more immunostimulants comprises Levamisole.
210. The method according to item 206, wherein one or more immunostimulants comprises Ampligen.
211. The method according to item 206, wherein one or more immunostimulants comprises Lentinan.
212. The method according to item 206, wherein one or more immunostimulants comprises Low dose naltrexone.
213. The method according to item 206, wherein one or more immunostimulants comprises Roquinimex.
214. The method according to item 206, wherein one or more immunostimulants comprises Thymopentin.
215. The method according to item 206, wherein one or more immunostimulants comprises one or more specific immunostimulators.
216. The method according to item 206, wherein one or more immunostimulants comprises one or more vaccines.
217. The method according to item 206, wherein one or more immunostimulants comprises one or more antigens.
218. The method according to item 206, wherein one or more immunostimulants comprises Non-specific immunostimulators.
219. The method according to item 206, wherein one or more immunostimulants comprises one or more adjuvants such as one or more oils, aluminum salts and/or virosomes.
220. The method according to item 206, wherein one or more immunostimulants comprises one or more Inorganic adjuvants such as Aluminium salts like aluminum phosphate and aluminum hydroxide.
221. The method according to item 206, wherein one or more immunostimulants comprises one or more Organic adjuvants such as Squalene.
222. The method according to item 206, wherein one or more immunostimulants comprises one or more Oil-based adjuvants.
223. The method according to item 206, wherein one or more immunostimulants comprises one or more virosomes.
224. The method according to item 206, wherein one or more immunostimulants comprises one or more phosphate adjuvants.
225. The method according to item 206, wherein one or more immunostimulants comprises QS21.
226. The method according to item 206, wherein one or more immunostimulants comprises Novartis' (formerly Chiron) MF59.
227. The method according to item 206, wherein one or more immunostimulants comprises one or more adjuvants that help in the translocation of antigens to the lymph nodes where they can be recognized by T cells.
228. The method according to item 206, wherein one or more immunostimulants comprises one or more adjuvants that lead to greater T cell activity.
229. The method according to item 206, wherein one or more immunostimulants comprises one or more adjuvants that increase the clearance of pathogen throughout the organism.
230. The method according to item 206, wherein one or more immunostimulants comprises one or more adjuvants that provide physical protection to antigens which grants the antigen a prolonged delivery.
231. The method according to item 206, wherein one or more immunostimulants comprises one or more adjuvants that make the immune system more robust by upregulating the production of B and T cells needed for greater immunological memory in the adaptive immune response.
232. The method according to item 206, wherein one or more immunostimulants comprises one or more adjuvants that help to increase the capacity to cause local reactions at the injection site (during vaccination), inducing greater release of danger signals by chemokine releasing cells such as helper T cells and mast cells.
233. The method according to item 206, wherein one or more immunostimulants comprises one or more adjuvants that induce the release of inflammatory cytokines which helps to not only recruit B and T cells at sites of infection but also to increase transcriptional events leading to a net increase of immune cells as a whole.
234. The method according to item 206, wherein one or more immunostimulants comprises one or more adjuvants that increase the innate immune response to antigen by interacting with pattern recognition receptors (PRRs), specifically Toll-like receptors (TLRs), on accessory cells.
235. The method according to item 206, wherein one or more immunostimulants comprises one or more hormones such as female sex hormones.
236. The method according to item 206, wherein one or more immunostimulants comprises prolactin.
237. The method according to item 206, wherein one or more immunostimulants comprises growth hormone.
238. The method according to item 206, wherein one or more immunostimulants comprises vitamin D.
239. The method according to item 206, wherein one or more immnostimulants comprises one or more of the immunostimulant herbs from the group consisting of American Ginseng, Ashwaghanda, *Astragalus*, Balsam of Peru, Bilberry, Cacao Seed Raw, Caigua, Camu Berries, Canchalagua, Catuaba, Chanca Piedra, Chia Seed, *Chlorella*, Chuchuhuasi, Clavohuasca, Coconut Oil, Codonopsis, Copaiba, Cordyceps, Dan Shen, Elderberries, Eleuthero Root, Ginkgo Leaves, Green Tea, Guayusa, Hercampuri, He-Shou-Wu, Honeybush Tea, Iporuru, Jujube Dates, Licorice Root, Longan Berries, Lycii Berries, Maca Root, Manayupa, Medicinal Mushrooms, Milk Thistle Seed, Neem, Nettle Leaf, Pau D'arco, Pro-EM1, Purple Corn, Red Ginseng, Rhodiola Root, Rooibos Tea, Sangre De Drago, Sacha Jergon, Schizandra Berries, Seabuckthorn Berry, Spirulina, Suma Root, Tahuari, Tibetan Rhodiola, Una De Gato, White Ginseng, White Tea, and Yacon, and Yerba Mate.
240. The method according to item 114, wherein the one or more drug(s) comprises one or more drugs for immunotherapy for treatment of cancer.
241. The method according to item 240, wherein the one or more drugs for immunotherapy for treatment of cancer comprises Bacille Calmette-Guérin (BCG).
242. The method according to item 240, wherein the one or more drugs for immunotherapy for treatment of cancer comprises interferon-alfa (IFN-alfa).
243. The method according to item 240, wherein the one or more drugs for immunotherapy for treatment of cancer comprises interleukin-2 (IL-2).
244. The method according to item 240, wherein the one or more drugs for immunotherapy for treatment of cancer comprises monoclonal antibodies.
245. The method according to item 240, wherein the one or more drugs for immunotherapy for treatment of cancer comprises drugs for treatment of Melanoma.
246. The method according to item 240, wherein the one or more drugs for immunotherapy for treatment of cancer comprises use of cytokines IFN-alfa and/or IL-2 for treatment of metastatic melanoma.

247. The method according to item 240, wherein the one or more drugs for immunotherapy for treatment of cancer comprises one or more melanoma vaccines.
248. The method according to item 240, wherein the one or more drugs for immunotherapy for treatment of cancer comprises treatment with tumor-infiltrating lymphocytes (TILs).
249. The method according to item 240, wherein the one or more drugs for immunotherapy for treatment of cancer comprises treatment with T cells from the blood that had their genes altered in the lab.
250. The method according to item 240, wherein the one or more drugs for immunotherapy for treatment of cancer comprises treatment with denileukin diftitox (Ontak).
251. The method according to item 240, wherein the one or more drugs for immunotherapy for treatment of cancer comprises one or more drugs for treatment of kidney cancer.
252. The method according to item 240, wherein the one or more drugs for immunotherapy for treatment of cancer comprises treatment of an individual with advanced kidney cancer with IL-2 and/or IFN-alfa.
253. The method according to item 240, wherein the one or more drugs for immunotherapy for treatment of cancer comprises one or more Whole tumor cell vaccines given along with the adjuvant BCG e.g. for treatment of advanced kidney cancer.
254. The method according to item 240, wherein the one or more drugs for immunotherapy for treatment of cancer comprises DNA vaccines that insert genes (segments of DNA) into cancer cells, causing the cells to make cytokines.
255. The method according to item 240, wherein the one or more drugs for immunotherapy for treatment of cancer comprises tumor-infiltrating lymphocytes (TILs) that have been removed from the body and stimulated in the lab by cytokines, and subsequently put back into the body e.g. for treatment of kidney cancer.
256. The method according to item 240, wherein the one or more drugs for immunotherapy for treatment of cancer comprises use of bevacizumab (Avastin) e.g. for treatment of kidney cancer.
257. The method according to item 240, wherein the one or more drugs for immunotherapy for treatment of cancer comprises one or more drugs for treatment of Leukemias, lymphomas, and/or myelomas.
258. The method according to item 240, wherein the one or more drugs for immunotherapy for treatment of cancer comprises Interferon-alfa e.g. for treatment of hairy cell leukemia, chronic myelogenous leukemia, follicular lymphoma, multiple myeloma, and cutaneous (skin) T cell lymphoma.
259. The method according to item 240, wherein the one or more drugs for immunotherapy for treatment of cancer comprises use of interferon in combination with chemotherapy.
260. The method according to item 240, wherein the one or more drugs for immunotherapy for treatment of cancer comprises use of Denileukin diftitox (Ontak), a combination of IL-2 and diphtheria toxin, e.g. for treatment of cutaneous T cell lymphoma.
261. The method according to item 240, wherein the one or more drugs for immunotherapy for treatment of cancer comprises Rituximab (Rituxan), a monoclonal antibody (MAb), e.g. for treatment of some kinds of B cell non-Hodgkin lymphoma.
262. The method according to item 240, wherein the one or more drugs for immunotherapy for treatment of cancer comprises rituximab e.g. for treatment of lymphomas, leukemias, and multiple myeloma.
263. The method according to item 240, wherein the one or more drugs for immunotherapy for treatment of cancer comprises Ibritumomab tiuxetan (Zevalin) and/or tositumomab (Bexxar) e.g. for treatment of non-Hodgkin lymphoma.
264. The method according to item 240, wherein the one or more drugs for immunotherapy for treatment of cancer comprises one or more MAbs e.g. for treatment of leukemia, lymphoma, and multiple myeloma.
265. The method according to item 240, wherein the one or more drugs for immunotherapy for treatment of cancer comprises one or more Anti-idiotype vaccines e.g. for treatment of B-cell non-Hodgkin lymphomasd.
266. The method according to item 240, wherein the one or more drugs for immunotherapy for treatment of cancer comprises one or more drugs for treatment of Breast cancer.
267. The method according to item 240, wherein the one or more drugs for immunotherapy for treatment of cancer comprises MAbs e.g. for treatment of breast cancer.
268. The method according to item 240, wherein the one or more drugs for immunotherapy for treatment of cancer comprises the MAb trastuzumab (Herceptin) e.g. for treatment of women with breast cancer whose cancer cells have too many copies of the HER2/neu gene.
269. The method according to item 240, wherein the one or more drugs for immunotherapy for treatment of cancer comprises one or more HER2/neu antibodies e.g. for treatment of breast cancer.
270. The method according to item 240, wherein the one or more drugs for immunotherapy for treatment of cancer comprises Bevacizumab (Avastin) e.g in combination with chemotherapy e.g. for treatment of women with advanced breast cancer.
271. The method according to item 240, wherein the one or more drugs for immunotherapy for treatment of cancer comprises one or more interferons and/or interleukins e.g. along with tumor vaccines and/or immunotoxins e.g. for treatment of breast cancer.
272. The method according to item 240, wherein the one or more drugs for immunotherapy for treatment of cancer comprises Autologous vaccine therapy e.g. for treatment of breast cancer.
273. The method according to item 240, wherein the one or more drugs for immunotherapy for treatment of cancer comprises one or more HER2/neu peptides e.g. for treatment of breast cancer.
274. The method according to item 240, wherein the one or more drugs for immunotherapy for treatment of cancer comprises one or more antigen vaccines e.g. used after primary therapy (like lumpectomy and radiation therapy, or mastectomy) and sometimes together with hormonal therapy or chemotherapy, e.g. to treat breast cancer.
275. The method according to item 240, wherein the one or more drugs for immunotherapy for treatment of cancer comprises one or more drugs for treatment of prostate cancer.
276. The method according to item 240, wherein the one or more drugs for immunotherapy for treatment of cancer comprises prostate cancer vaccines e.g designed to cause immune responses to antigens present only on prostate cells, such as prostate-specific antigen (PSA) and prostate-specific membrane antigen (PSMA).

277. The method according to item 240, wherein the one or more drugs for immunotherapy for treatment of cancer comprises to take dendritic cells from a patient's bloodstream and treat them in the lab with prostate cancer antigens and subsequently put the dendritic cells back in the patient.
278. The method according to item 240, wherein the one or more drugs for immunotherapy for treatment of cancer comprises GVAX, an autologous whole cell vaccine, e.g. for treatment of prostate cancer.
279. The method according to item 240, wherein the one or more drugs for immunotherapy for treatment of cancer comprises a vaccine based on a part of the prostate-specific antigen (a peptide) for treatment of prostate cancer.
280. The method according to item 240, wherein the one or more drugs for immunotherapy for treatment of cancer comprises DNA vaccines, monoclonal antibodies, and/or cytokines e.g for treatment of prostate cancer.
281. The method according to item 240, wherein the one or more drugs for immunotherapy for treatment of cancer comprises one or more drugs for treatment of Colorectal cancer.
282. The method according to item 240, wherein the one or more drugs for immunotherapy for treatment of cancer comprises one or more monoclonal antibodies for treatment of colorectal cancer.
283. The method according to item 240, wherein the one or more drugs for immunotherapy for treatment of cancer comprises Bevacizumab (Avastin) e.g. used along with chemotherapy e.g. against advanced colorectal cancer.
284. The method according to item 240, wherein the one or more drugs for immunotherapy for treatment of cancer comprises Cetuximab (Erbitux) e.g. along with chemotherapy, e.g. for treatment of colorectal cancer.
285. The method according to item 240, wherein the one or more drugs for immunotherapy for treatment of cancer comprises panitumumab (Vectibix) e.g. for treatment of advanced colorectal cancer.
286. The method according to item 240, wherein the one or more drugs for immunotherapy for treatment of cancer comprises one or more autologous and/or allogeneic tumor cell vaccines e.g. for treatment of colorectal cancer.
287. The method according to item 240, wherein the one or more drugs for immunotherapy for treatment of cancer comprises one or more carcinoembryonic antigen (CEA) vaccines e.g. for treatment of colorectal cancer.
288. The method according to item 240, wherein the one or more drugs for immunotherapy for treatment of cancer comprises one or more drugs for treatment of Cervical cancer.
289. The method according to item 240, wherein the one or more drugs for immunotherapy for treatment of cancer comprises one or more HPV vaccines e.g for prevention of cervical cancer.
290. The method according to item 240, wherein the one or more drugs for immunotherapy for treatment of cancer comprises vaccines for prevention of one or more cancers such as cervical cancer.
291. The method according to item 240, wherein the one or more drugs for immunotherapy for treatment of cancer comprises Gardasil for treatment of e.g. cervical cancer.
292. The method according to item 240, wherein the one or more drugs for immunotherapy for treatment of cancer comprises one or more Interferons and interleukins e.g. for treatment of metastatic cervical cancer.
293. The method according to item 240, wherein the one or more drugs for immunotherapy for treatment of cancer comprises one or more drugs for treatment of Ovarian cancer.
294. The method according to item 240, wherein the one or more drugs for immunotherapy for treatment of cancer comprises one or more cancer vaccines for treatment of ovarian cancer.
295. The method according to item 240, wherein the one or more drugs for immunotherapy for treatment of cancer comprises one or more MAbs e.g for treatment of ovarian cancer.
296. The method according to item 240, wherein the one or more drugs for immunotherapy for treatment of cancer comprises injection of interleukin-2 (IL-2) directly into the peritoneal cavity (the body cavity that contains the ovaries, uterus, and digestive organs) of women with recurrent ovarian cancer.
297. The method according to item 240, wherein the one or more drugs for immunotherapy for treatment of cancer comprises placing tumor-infiltrating lymphocytes (TILs) along with interleukin-2 directly into the peritoneal cavity.
298. The method according to item 240, wherein the one or more drugs for immunotherapy for treatment of cancer comprises Trastuzumab (Herceptin) e.g. for treatment for ovarian cancer.
299. The method according to item 240, wherein the one or more drugs for immunotherapy for treatment of cancer comprises a monoclonal antibody that attaches to certain antigens on ovarian cancer cells and to specific spots on T cells (a bispecific antibody) used along with IL-2 e.g. for treatment of ovarian cancer.
300. The method according to item 240, wherein the one or more drugs for immunotherapy for treatment of cancer comprises radiolabeled MAbs against ovarian cancer.
301. The method according to item 240, wherein the one or more drugs for immunotherapy for treatment of cancer comprises one or more drugs for treatment of Lung cancer.
302. The method according to item 240, wherein the one or more drugs for immunotherapy for treatment of cancer comprises one or more monoclonal antibodies e.g. for treatment of Lung cancer.
303. The method according to item 240, wherein the one or more drugs for immunotherapy for treatment of cancer comprises bevacizumab (Avastin) e.g. along with chemotherapy e.g. for treatment of non-small cell lung cancer (NSCLC).
304. The method according to item 240, wherein the one or more drugs for immunotherapy for treatment of cancer comprises GVAX e.g. for treatment of lung cancer.
305. The method according to item 240, wherein the one or more drugs for immunotherapy for treatment of cancer comprises BLP25 vaccine e.g. for treatment of NSCLC.
306. The method according to item 114, wherein the one or more drug(s) comprises one or more cancer vaccines e.g. selected from the cancer vaccines listed in Table S.
307. The method according to item 114, wherein the one or more drug(s) comprises one or more chemotherapy drugs.
308. The method according to item 307, wherein the one or more chemotherapy drugs comprises one or more Alkylating agents such as Cisplatin, carboplatin, oxaliplatin, mechlorethamine, cyclophosphamide, and chlorambucil.
309. The method according to item 307, wherein the one or more chemotherapy drugs comprises one or more Antimetabolites.

310. The method according to item 307, wherein the one or more chemotherapy drugs comprises one or more Plant alkaloids and/or terpenoids such as vinca alkaloids and taxanes.
311. The method according to item 307, wherein the one or more chemotherapy drugs comprises one or more Vinca alkaloids such as Vincristine, Vinblastine, Vinorelbine, and Vindesine.
312. The method according to item 307, wherein the one or more chemotherapy drugs comprises one or more Podophyllotoxin such as etoposide and teniposide.
313. The method according to item 307, wherein the one or more chemotherapy drugs comprises one or more Taxanes such as paclitaxel, originally known as Taxol.
314. The method according to item 307, wherein the one or more chemotherapy drugs comprises one or more Topoisomerase inhibitors.
315. The method according to item 307, wherein the one or more chemotherapy drugs comprises one or more type I topoisomerase inhibitors such as camptothecins like irinotecan and topotecan.
316. The method according to item 307, wherein the one or more chemotherapy drugs comprises one or more type II topoisomerase inhibitors such as amsacrine, etoposide, etoposide phosphate, and teniposide.
317. The method according to item 307, wherein the one or more chemotherapy drugs comprises one or more Antitumour antibiotics such as dactinomycin.
318. The method according to item 307, wherein the one or more chemotherapy drugs comprises one or more Monoclonal antibodies such as trastuzumab (Herceptin), cetuximab, rituximab (Rituxan or Mabthera) and Bevacizumab (Avastin).
319. The method according to item 307, wherein the one or more chemotherapy drugs comprises one or more types of Hormonal therapy such as administration of Steroids (often dexamethasone), finasteride, aromatase inhibitors, tamoxifen, Gonadotropin-releasing hormone agonists (GnRH), and/or goserelin.
320. The method according to item 1, wherein the treatment comprises immunotherapy.
321. The method according to item 320, wherein the immunotherapy comprises Cancer immunotherapy.
322. The method according to item 320, wherein the immunotherapy comprises Dendritic cell based immunotherapy.
323. The method according to item 320, wherein the immunotherapy comprises T cell based adoptive immunotherapy.
324. The method according to item 320, wherein the immunotherapy comprises one or more Vaccination.
325. The method according to item 320, wherein the immunotherapy comprises one or more monoclonal antibodies.
326. The method according to item 320, wherein the immunotherapy comprises non-specific immunotherapies and/or adjuvants.
327. The method according to item 1, wherein the treatment comprises one or more type of gene therapy.
328. The method according to item 1, wherein the treatment comprises one or more type of germ line gene therapy.
329. The method according to item 1, wherein the treatment comprises one or more type of somatic cell gene therapy.
330. The method according to item 1, wherein the treatment comprises one or more type of physical treatment.
331. The method according to item 330, wherein the physical treatment comprises surgery.
332. The method according to item 331, wherein the surgery comprises General surgery.
333. The method according to item 331, wherein the surgery comprises Trauma surgery.
334. The method according to item 331, wherein the surgery comprises Cardiovascular surgery.
335. The method according to item 331, wherein the surgery comprises Neurosurgery.
336. The method according to item 331, wherein the surgery comprises Maxillofacial surgery.
337. The method according to item 331, wherein the surgery comprises Orthopedic surgery.
338. The method according to item 331, wherein the surgery comprises Otolaryngology.
339. The method according to item 331, wherein the surgery comprises Plastic surgery.
340. The method according to item 331, wherein the surgery comprises Oncologic surgery.
341. The method according to item 331, wherein the surgery comprises Vascular surgery.
342. The method according to item 331, wherein the surgery comprises Pediatric surgery.
343. The method according to item 331, wherein the surgery comprises Diagnostic Surgery such as incisional biopsy, excisional biopsy, endoscopic biopsy, colposcopic biopsy, bone marrow biopsy, fine needle aspiration biopsy, stereotactic biopsy, and core biopsy.
344. The method according to item 331, wherein the surgery comprises preventive surgery.
345. The method according to item 331, wherein the surgery comprises curative surgery.
346. The method according to item 331, wherein the surgery comprises Palliative Surgery.
347. The method according to item 331, wherein the surgery comprises Reconstructive Surgery.
348. The method according to item 331, wherein the surgery comprises Major surgery.
349. The method according to item 331, wherein the surgery comprises Minor surgery.
350. The method according to item 331, wherein the surgery comprises Elective surgery.
351. The method according to item 331, wherein the surgery comprises Required surgery.
352. The method according to item 331, wherein the surgery comprises Urgent or emergency surgery.
353. The method according to item 330, wherein the physical treatment comprises radiotherapy/radiation therapy.
354. The method according to item 353, wherein the radiation therapy comprises External Beam Radiation Therapy.
355. The method according to item 353, wherein the radiation therapy comprises Internal Radiation Therapy.
356. The method according to item 353, wherein the radiation therapy comprises Internal systemic radiation therapy.
357. The method according to item 353, wherein the radiation therapy comprises Interstitial radiation therapy.
358. The method according to item 353, wherein the radiation therapy comprises Intracavitary radiation therapy.
359. The method according to item 353, wherein the radiation therapy comprises brachytherapy.
360. The method according to item 353, wherein the radiation therapy comprises prophylactic radiation therapy.
361. The method according to item 353, wherein the radiation therapy comprises Curative radiation therapy.
362. The method according to item 353, wherein the radiation therapy comprises Intraoperative radiation therapy (IORT).

363. The method according to item 353, wherein the radiation therapy comprises Prophylactic cranial irradiation.
364. The method according to item 353, wherein the radiation therapy comprises Intracavitary or intraluminal radiation therapy.
365. The method according to item 353, wherein the radiation therapy comprises radiation therapy using radioactive materials such as iodine 131 and/or strontium 89.
366. The method according to item 353, wherein the radiation therapy comprises Stereotactic (or stereotaxic) radiosurgery.
367. The method according to item 353, wherein the radiation therapy comprises Three-dimensional (3-D) conformal radiation therapy.
368. The method according to item 353, wherein the radiation therapy comprises Radiation therapy using a dose in the range of 5 to 200 Gy, such as from 5 to 10 Gy, for example from 10 to 20 Gy, such as from 20 to 30 Gy, for example from 30 to 40 Gy, such as from 40 to 50 Gy, for example from 50 to 60 Gy, such as from 60 to 70 Gy, for example from 70 to 80 Gy, such as from 80 to 90 Gy, for example from 90 to 100 Gy, such as from 100 to 120 Gy, for example from 120 to 140 Gy, such as from 140 to 160 Gy, for example from 160 to 180 Gy, such as from 180 to 200 Gy.
369. The method according to item 330, wherein the physical treatment comprises massage.
370. The method according to item 330, wherein the physical treatment comprises physiotherapy.
371. The method according to item 370, wherein the physiotherapy comprises Cardiovascular and pulmonary rehabilitation physiotherapy.
372. The method according to item 370, wherein the physiotherapy comprises Geriatric physiotherapy.
373. The method according to item 370, wherein the physiotherapy comprises Neurological physiotherapy.
374. The method according to item 370, wherein the physiotherapy comprises orthopaedic physiotherapy.
375. The method according to item 370, wherein the physiotherapy comprises Pediatric physiotherapy.
376. The method according to item 330, wherein the physical treatment comprises ergotherapy.
377. The method according to item 330, wherein the physical treatment comprises chiropractic treatment.
378. The method according to item 330, wherein the physical treatment comprises transplantation.
379. The method according to item 330, wherein the physical treatment comprises electric stimulation.
380. The method according to item 330, wherein the physical treatment comprises acupuncture.
381. The method according to item 1, wherein the treatment comprises one or more types of counseling.
382. The method according to item 1, wherein the treatment comprises one or more psychological treatment(s).
383. The method according to item 382, wherein the one or more psychological treatment(s) comprises psychotherapy.
384. The method according to item 383, wherein the psychotherapy comprises Psychoanalysis.
385. The method according to item 383, wherein the psychotherapy comprises Cognitive behavioral therapy.
386. The method according to item 383, wherein the psychotherapy comprises Psychodynamic therapy.
387. The method according to item 383, wherein the psychotherapy comprises Existential therapy.
388. The method according to item 331, wherein the psychotherapy comprises Humanistic therapy.
389. The method according to item 383, wherein the psychotherapy comprises Brief therapy.
390. The method according to item 383, wherein the psychotherapy comprises Systemic Therapy.
391. The method according to item 383, wherein the psychotherapy comprises Somatic Psychotherapy.
392. The method according to item 383, wherein the psychotherapy comprises Transpersonal Psychotherapy.
393. The method according to item 383, wherein the psychotherapy comprises Hypno-Psychotherapy.
394. The method according to item 383, wherein the psychotherapy comprises Psychodrama/Dramatherapy.
395. The method according to item 382, wherein the one or more psychological treatment(s) comprises meditation.
396. The method according to item 382, wherein the one or more psychological treatment(s) comprises hypnosis.
397. The method according to item 1, wherein the treatment comprises one or more types of pharmacotherapy.
398. The method according to item 397, wherein the one or more types of pharmacotherapy therapy comprises pharmacotherapy directed towards the gastrointestinal tract or digestive system.
399. The method according to item 397, wherein the one or more types of pharmacotherapy therapy comprises pharmacotherapy directed towards the Upper digestive tract (e.g. antacids, reflux suppressants, antiflatulents, antidopaminergics, proton pump inhibitors, H2-receptor antagonists, cytoprotectants, prostaglandin analogues).
400. The method according to item 397, wherein the one or more types of pharmacotherapy therapy comprises pharmacotherapy directed towards the Lower digestive tract (e.g. laxatives, antispasmodics, antidiarrhoeals, bile acid sequestrants, opioids).
401. The method according to item 397, wherein the one or more types of pharmacotherapy therapy comprises pharmacotherapy directed towards the cardiovascular system.
402. The method according to item 397, wherein the one or more types of pharmacotherapy therapy comprises pharmacotherapy directed towards the cardiovascular system such as the general cardiovascular system (e.g. beta-receptor blocker or beta blocker, calcium channel blockers, diuretics, cardiac glycosides, antiarrhythmics, nitrate, antianginals, vasoconstrictor, vasodilator, peripheral activator).
403. The method according to item 397, wherein the one or more types of pharmacotherapy therapy comprises pharmacotherapy directed towards the cardiovascular system Affecting Blood pressure (e.g. ACE inhibitors, angiotensin receptor blockers, alpha blocker).
404. The method according to item 397, wherein the one or more types of pharmacotherapy therapy comprises pharmacotherapy directed towards the cardiovascular system affecting Coagulation (anticoagulant, heparin, antiplatelet drug, fibrinolytic, anti-hemophilic factor, haemostatic drugs).
405. The method according to item 397, wherein the one or more types of pharmacotherapy therapy comprises pharmacotherapy directed towards the cardiovascular system such as administration of Atherosclerosis/cholesterol agents (e.g. hypolipidaemic agents, statins).
406. The method according to item 397, wherein the one or more types of pharmacotherapy therapy comprises pharmacotherapy directed towards the central nervous system e.g. comprising administration of hypnotic, anaesthetics, antipsychotic, antidepressant (including tricyclic antidepressants, monoamine oxidase inhibitor, lithium salt, selective serotonin reuptake inhibitor), anti-emetic, anticonvulsant and antiepileptic, anxiolytic, barbiturate, movement disorder drug, stimulant (including amphetamines), benzodiazepine, cyclopyrrolone, dopamine antagonist, antihistamine, cholinergic, anticholinergic, emetic, cannabinoids, and 5-HT antagonist.

407. The method according to item 397, wherein the one or more types of pharmacotherapy therapy comprises pharmacotherapy related to pain and consciousness (analgesic drugs) including NSAIDs, opioids and various orphans such as paracetamol, tricyclic antidepressants and anticonvulsants.

408. The method according to item 397, wherein the one or more types of pharmacotherapy therapy comprises pharmacotherapy directed towards musculo-skeletal disorders including administration of NSAIDs (such as COX-2 selective inhibitors), muscle relaxant, neuromuscular drug and/or anticholinesterase.

409. The method according to item 397, wherein the one or more types of pharmacotherapy therapy comprises pharmacotherapy directed towards the eye.

410. The method according to item 397, wherein the one or more types of pharmacotherapy therapy comprises pharmacotherapy directed towards the eye comprising administration of adrenergic neurone blocker, astringent, ocular lubricant, topical anesthetics, sympathomimetics, parasympatholytics, mydriatics, cycloplegics, Anti-bacterial agents, antibiotics, topical antibiotics, sulfa drugs, aminoglycosides, fluoroquinolones, Anti-viral agents, Anti-fungal agents, imidazoles, polyenes, Anti-inflammatory agents, NSAIDs, corticosteroids, Anti-allergy agents, mast cell inhibitors, Anti-glaucoma agents, adrenergic agonists, beta-blockers, carbonic anhydrase inhibitors/hyperosmotics, cholinergics, miotics, parasympathomimetics, prostaglandin agonists/prostaglandin inhibitors, and/or nitroglycerin.

411. The method according to item 397, wherein the one or more types of pharmacotherapy therapy comprises pharmacotherapy directed towards the ear, nose and/or oropharynx such as administration of sympathomimetic agents, antihistamine, anticholinergic, NSAIDs, steroid, antiseptic, local anesthetic, antifungal agents, and/or cerumenolyti.

412. The method according to item 397, wherein the one or more types of pharmacotherapy therapy comprises pharmacotherapy directed towards the respiratory system such as administration of bronchodilator, NSAIDs, anti-allergic, antitussive, mucolytic, decongestant, corticosteroid, beta-receptor antagonist, anticholinergic, and/or steroid.

413. The method according to item 397, wherein the one or more types of pharmacotherapy therapy comprises pharmacotherapy directed towards endocrine problems such as administration of androgen, antiandrogen, gonadotropin, corticosteroid, growth hormone, insulin, antidiabetic (sulfonylurea, biguanide/metformin, thiazolidinedione, insulin), thyroid hormones, antithyroid drugs, calcitonin, diphosphonate, and/or vasopressin analogues.

414. The method according to item 397, wherein the one or more types of pharmacotherapy therapy comprises pharmacotherapy directed towards the reproductive system and/or urinary system such as administration of antifungal agent, alkalising agent, quinolones, antibiotic, cholinergic, anticholinergic, anticholinesterase, antispasmodic, 5-alpha reductase inhibitor, selective alpha-1 blocker, sildenafil, and/or fertility medication.

415. The method according to item 397, wherein the one or more types of pharmacotherapy therapy comprises pharmacotherapy related to contraception including Hormonal contraception, Ormeloxifene, and/or Spermicide.

416. The method according to item 397, wherein the one or more types of pharmacotherapy therapy comprises pharmacotherapy related to obstetrics and gynecology including administration of NSAIDs, anticholinergic, haemostatic drug, antifibrinolytic, Hormone Replacement Therapy, bone regulator, beta-receptor agonist, follicle stimulating hormone, luteinising hormone, LHRH gamolenic acid, gonadotropin release inhibitor, progestogen, dopamine agonist, oestrogen, prostaglandin, gonadorelin, clomiphene, tamoxifen, and/or Diethylstilbestrol.

417. The method according to item 397, wherein the one or more types of pharmacotherapy therapy comprises pharmacotherapy directed towards the skin including administration of emollient, anti-pruritic, antifungal, disinfectant, scabicide, pediculicide, tar products, vitamin A derivatives, vitamin D analogue, keratolytic, abrasive, systemic antibiotic, topical antibiotic, hormones, desloughing agent, exudate absorbent, fibrinolytic, proteolytic, sunscreen, antiperspirant, and/or corticosteroid.

418. The method according to item 397, wherein the one or more types of pharmacotherapy therapy comprises pharmacotherapy related to infections and infestations including administration of antibiotic, antifungal, antileprotic, antituberculous drug, antimalarial, anthelmintic, amoebicide, antiviral, and/or antiprotozoal.

419. The method according to item 397, wherein the one or more types of pharmacotherapy therapy comprises pharmacotherapy related to immunology including administration of vaccine, immunoglobulin, immunosuppressant, interferon, monoclonal antibody.

420. The method according to item 397, wherein the one or more types of pharmacotherapy therapy comprises pharmacotherapy related to allergic disorders including administration of anti-allergic, antihistamine, and/or NSAIDs.

421. The method according to item 397, wherein the one or more types of pharmacotherapy therapy comprises pharmacotherapy related to nutrition including administration of tonic, iron preparation, electrolyte, parenteral nutritional supplement, vitamins, anti-obesity drug, anabolic drug, haematopoietic drug, and/or food product drug.

422. The method according to item 397, wherein the one or more types of pharmacotherapy therapy comprises pharmacotherapy directed towards neoplastic disorders including administration of cytotoxic drug, sex hormones, aromatase inhibitor, somatostatin inhibitor, recombinant interleukins, G-CSF, and/or erythropoietin.

423. The method according to item 397, wherein the one or more types of pharmacotherapy therapy comprises pharmacotherapy directed towards diagnostics including administration of contrast media.

424. The method according to item 397, wherein the one or more types of pharmacotherapy therapy comprises pharmacotherapy related to euthanasia including administration of an euthanaticum.

425. The method according to item 1, wherein the treatment comprises diet adjustment.

426. The method according to item 425, wherein the diet adjustment comprises a Gluten-free diet.

427. The method according to item 425, wherein the diet adjustment comprises a diet adjustment to obtain weight loss.

428. The method according to item 425, wherein the diet adjustment comprises a diet adjustment to obtain a weight gain.

429. The method according to item 425, wherein the diet adjustment comprises a diet comprising one or more Herbs and/or Nutritional Supplements such as Vitamin and/or mineral supplement.
430. The method according to item 1, wherein the treatment is therapeutic.
431. The method according to item 1, wherein the treatment is prophylactic.
432. The method according to item 1, wherein the treatment is ameliorating.
433. The method according to item 1, wherein the treatment results in complete recovery and/or elimination of said undesired state of said individual.
434. The method according to item 1, wherein the treatment results in improvement of said undesired state of said individual.
435. The method according to item 1, wherein the treatment results in relief from symptoms associated with said undesired state of said individual.
436. The method according to item 1, wherein the treatment comprises administration of one or more drug(s) and/or one or more vaccine(s) by oral administration.
437. The method according to item 1, wherein the treatment comprises administration of one or more drug(s) and/or one or more vaccine(s) by sublingual administration.
438. The method according to item 1, wherein the treatment comprises administration of one or more drug(s) and/or one or more vaccine(s) by nasal administration.
439. The method according to item 1, wherein the treatment comprises administration of one or more drug(s) and/or one or more vaccine(s) by inhalation.
440. The method according to item 1, wherein the treatment comprises administration of one or more drug(s) and/or one or more vaccine(s) by injection.
441. The method according to item 1, wherein the treatment comprises administration of one or more drug(s) and/or one or more vaccine(s) by intravenous administration.
442. The method according to item 1, wherein the treatment comprises administration of one or more drug(s) and/or one or more vaccine(s) by intramuscular administration.
443. The method according to item 1, wherein the treatment comprises administration of one or more drug(s) and/or one or more vaccine(s) by intrathecal administration.
444. The method according to item 1, wherein the treatment comprises administration of one or more drug(s) and/or one or more vaccine(s) by subcutan administration.
445. The method according to item 1, wherein the treatment comprises administration of one or more drug(s) and/or one or more vaccine(s) by implantation.
446. The method according to item 1, wherein the treatment comprises administration of one or more drug(s) and/or one or more vaccine(s) by rectal administration.
447. The method according to item 1, wherein the treatment comprises administration of one or more drug(s) and/or one or more vaccine(s) by vaginal administration.
448. The method according to item 1, wherein the treatment comprises administration of one or more drug(s) and/or one or more vaccine(s) by the ocular route.
449. The method according to item 1, wherein the treatment comprises administration of one or more drug(s) and/or one or more vaccine(s) by applying it to the skin (cutaneously) for a local (topical) effect.
450. The method according to item 1, wherein the treatment comprises administration of one or more drug(s) and/or one or more vaccine(s) by applying it to the skin (cutaneously) for bodywide (systemic) effect.
451. The method according to item 1, wherein the treatment comprises administration of one or more drug(s) and/or one or more vaccine(s) by delivering it through the skin (transdermally) for a systemic effect.
452. The method according to item 1, wherein the treatment comprises administration of one or more drug(s) and/or one or more vaccine(s) together with one or more adjuvants.
453. The method according to item 207, wherein the one or more drug(s) and/or one or more vaccine(s) and one or more adjuvants are administered simultaneously.
454. The method according to item 1, wherein the treatment comprises administration of one or more drug(s) and/or one or more vaccine(s) and one or more adjuvants are administered sequentially in any order.
455. The method according to any of items 1 to 454, wherein the analysis comprises one or more types of diagnosis.
456. The method according to any of items 1 to 454, wherein the analysis comprises one or more types of screening method(s).
457. The method according to any of items 1 to 454, wherein the analysis comprises one or more physical examination procedures.
458. The method according to item 457, wherein the one or more physical examination procedures comprises one or more types of inspection.
459. The method according to item 458, wherein the one or more types of inspection comprises one or more types of visual inspection.
460. The method according to item 459, wherein the one or more types of visual inspection comprises visual inspection of body features and/or symmetri appearance.
461. The method according to item 459, wherein the one or more types of visual inspection comprises visual inspection of nutritional state of said individual.
462. The method according to item 459, wherein the one or more types of visual inspection comprises visual inspection of the weight of said individual.
463. The method according to item 459, wherein the one or more types of visual inspection comprises visual inspection of the body-mass index (BMI) state of said individual.
464. The method according to item 459, wherein the one or more types of visual inspection comprises visual inspection of the height of said individual.
465. The method according to item 459, wherein the one or more types of visual inspection comprises visual inspection of the skin color of said individual.
466. The method according to item 459, wherein the one or more types of visual inspection comprises visual inspection of discoloration of said individual.
467. The method according to item 459, wherein the one or more types of visual inspection comprises visual inspection of the hair-distribution of said individual.
468. The method according to item 459, wherein the one or more types of visual inspection comprises visual inspection of the frequency and/or volume of breath of said individual.
469. The method according to item 459, wherein the one or more types of visual inspection comprises visual inspection of the lung capacity of said individual.
470. The method according to item 459, wherein the one or more types of visual inspection comprises visual inspection of the manner of speaking of said individual.
471. The method according to item 459, wherein the one or more types of visual inspection comprises visual inspection of the manner of movement of said individual.

472. The method according to item 459, wherein the one or more types of visual inspection comprises visual inspection of the muscle tone of said individual.
473. The method according to item 459, wherein the one or more types of visual inspection comprises visual inspection of one or more scars on said individual.
474. The method according to item 459, wherein the one or more types of visual inspection comprises visual inspection of visible masses on said individual.
475. The method according to item 459, wherein the one or more types of visual inspection comprises visual inspection of swelling of said individual.
476. The method according to item 459, wherein the one or more types of visual inspection comprises visual inspection of tremor of said individual.
477. The method according to item 459, wherein the one or more types of visual inspection comprises visual inspection of abnormal contour of said individual.
478. The method according to item 458, wherein the one or more types of inspection comprises listening to one or more sounds emanating from the patient.
479. The method according to item 458, wherein the one or more types of inspection comprises analysis of one or more odors from the patient.
480. The method according to item 457, wherein the one or more physical examination procedures comprises one or more types of palpation.
481. The method according to item 480, wherein the one or more types of palpation comprises palpation to determine the size of one or more abnormalities.
482. The method according to item 480, wherein the one or more types of palpation comprises palpation to determine the shape of one or more abnormalities.
483. The method according to item 480, wherein the one or more types of palpation comprises palpation to determine the firmness of one or more abnormalities.
484. The method according to item 480, wherein the one or more types of palpation comprises palpation to determine the localization of one or more abnormalities.
485. The method according to item 457, wherein the one or more physical examination procedures comprises one or more types of percussion (a method to monitor change in e.g. abdomen or thorax by tapping on the surface of abdomen or thorax to determine the underlying structure.
486. The method according to item 457, wherein the one or more physical examination procedures comprises one or more types of ascultation (listening to internal sounds of the body).
487. The method according to item 486, wherein the one or more types of ascultation comprises use of the naked ear.
488. The method according to item 486, wherein the one or more types of ascultation comprises use of a stethoscope or the like.
489. The method according to item 486, wherein the one or more types of ascultation comprises auscultation of the circulatory system of said individual.
490. The method according to item 486, wherein the one or more types of ascultation comprises auscultation of the respiratory system of said individual.
491. The method according to item 486, wherein the one or more types of ascultation comprises auscultation of the gastrointestinal system of said individual.
492. The method according to any of items 1 to 454, wherein the analysis comprises one or more test(s) of said individual.
493. The method according to item 492, wherein the one or more test(s) of said individual comprises one or more chemical test(s).
494. The method according to item 493, wherein the one or more chemical test(s) comprises measuring of binding.
495. The method according to item 494, wherein the measuring of binding comprises one or more ELISA or one or more ELISA-like assays.
496. The method according to item 494, wherein the measuring of binding comprises binding of one or more molecule(s) of interest to its one or more binding partner(s) on solid support, followed by labelling and determination of available binding sites.
497. The method according to item 494, wherein the measuring of binding comprises one or more ELISPOT or one or more ELISPOT-like assays.
498. The method according to item 494, wherein the measuring of binding comprises a method comprising the principle of ELISPOT analysis.
499. The method according to item 494, wherein the measuring of binding comprises measurement of induced cross-linking.
500. The method according to item 499, wherein the measurement of induced cross-linking is performed by one or more steps of turbidemetry.
501. The method according to item 494, wherein the measuring of binding comprises one or more steps of cytometry.
502. The method according to item 501, wherein the one or more steps of cytometry comprises use of one or more antibody-probe.
503. The method according to item 501, wherein the one or more steps of cytometry comprises use of one or more MHC molecule-probe(s).
504. The method according to item 501, wherein the one or more steps of cytometry comprises use of one or more protein-probe(s).
505. The method according to item 501, wherein the one or more steps of cytometry comprises use of one or more DNA-probes.
506. The method according to item 501, wherein the one or more steps of cytometry comprises use of one or more RNA-probes.
507. The method according to item 501, wherein the one or more steps of cytometry comprises use of one or more LNA-probes.
508. The method according to item 501, wherein the one or more steps of cytometry comprises use of one or more PNA-probes.
509. The method according to item 501, wherein the one or more steps of cytometry comprises one or more steps of flow cytometry.
510. The method according to item 501, wherein the one or more steps of cytometry comprises one or more steps of stationary cytometry.
511. The method according to item 510, wherein the one or more steps of stationary cytometry comprise on or more steps of immunehistochemistry (IHC).
512. The method according to item 510, wherein the one or more steps of stationary cytometry comprise on or more steps of fluorescence microscopy.
513. The method according to item 494, wherein the measuring of binding comprises one or more steps of PCR.
514. The method according to item 513, wherein the one or more steps of PCR comprises one or more allele specific PCR step(s).

515. The method according to item 514, wherein the one or more steps of allele specific PCR is used to identify single base differences in DNA.
516. The method according to item 513, wherein the one or more steps of PCR comprises one or more intersequence-specific PCR step(s) (ISSR).
517. The method according to item 513, wherein the one or more steps of PCR comprises one or more methylation-specific PCR step(s) (MSP).
518. The method according to item 513, wherein the one or more steps of PCR comprises one or more Helicase-dependent PCR step(s).
519. The method according to item 518, wherein the one or more Helicase-dependent PCR step(s) uses constant temperature.
520. The method according to item 513, wherein the one or more steps of PCR comprises one or more quantitative PCR step(s).
521. The method according to item 513, wherein the one or more steps of PCR comprises one or more reverse transcription (RT)-PCR step(s).
522. The method according to item 494, wherein the measuring of binding comprises one or more steps of gel electrophoresis.
523. The method according to item 522, wherein the one or more steps of gel electrophoresis comprises determination of polypeptide length.
524. The method according to item 522, wherein the one or more steps of gel electrophoresis comprises one or more steps of SDS-PAGE.
525. The method according to item 522, wherein the one or more steps of gel electrophoresis comprises one or more steps of denaturing gel electrophoresis.
526. The method according to item 522, wherein the one or more steps of gel electrophoresis comprises one or more steps of native gel electrophoresis.
527. The method according to item 522, wherein the one or more steps of gel electrophoresis comprises determination of one or more protein structure(s).
528. The method according to item 522, wherein the one or more steps of gel electrophoresis comprises determination of one or more protein interaction(s).
529. The method according to item 522, wherein the one or more steps of gel electrophoresis comprises determination of the size of one or more DNA fragment(s).
530. The method according to item 522, wherein the one or more steps of gel electrophoresis comprises determination of the size of one or more RNA fragment(s).
531. The method according to item 522, wherein the one or more steps of gel electrophoresis comprises one or more steps of agarose gel electrophoresis.
532. The method according to item 522, wherein the one or more steps of gel electrophoresis comprises separation of proteins according to mass and isoelectric point.
533. The method according to item 522, wherein the one or more steps of gel electrophoresis comprises one or more step(s) of two-dimensional gel electrophoresis.
534. The method according to item 494, wherein the measuring of binding comprises one or more steps of blotting.
535. The method according to item 534, wherein the one or more steps of blotting comprises western blotting.
536. The method according to item 534, wherein the one or more steps of blotting comprises northern blotting.
537. The method according to item 534, wherein the one or more steps of blotting comprises southern blotting.
538. The method according to item 494, wherein the measuring of binding comprises one or more steps of cytology.
539. The method according to item 494, wherein the one or more steps of cytology comprises use of one or more antibody-probe(s).
540. The method according to item 494, wherein the one or more steps of cytology comprises use of one or more MHC molecule-probe(s)
541. The method according to item 494, wherein the one or more steps of cytology comprises use of one or more protein-probe(s).
542. The method according to item 494, wherein the one or more steps of cytology comprises use of one or more DNA-probe(s).
543. The method according to item 494, wherein the one or more steps of cytology comprises use of one or more RNA-probe(s).
544. The method according to item 494, wherein the one or more steps of cytology comprises use of one or more LNA-probe(s).
545. The method according to item 494, wherein the one or more steps of cytology comprises use of one or more PNA-probe(s).
546. The method according to item 494, wherein the measuring of binding comprises one or more steps of chip technology.
547. The method according to item 546, wherein the one or more steps of chip technology comprises use of one or more antibody-probe(s).
548. The method according to item 546, wherein the one or more steps of chip technology comprises use of one or more MHC molecule-probe(s).
549. The method according to item 546, wherein the one or more steps of chip technology comprises use of one or more protein-probe(s).
550. The method according to item 546, wherein the one or more steps of chip technology comprises use of one or more DNA-probe(s).
551. The method according to item 546, wherein the one or more steps of chip technology comprises use of one or more RNA-probe(s).
552. The method according to item 546, wherein the one or more steps of chip technology comprises use of one or more LNA-probe(s).
553. The method according to item 546, wherein the one or more steps of chip technology comprises use of one or more PNA-probe(s).
554. The method according to item 494, wherein the measuring of binding comprises one or more steps of chromatography.
555. The method according to item 554, wherein the one or more steps of chromatography comprises one or more steps of column chromatography.
556. The method according to item 555, wherein the one or more steps of column chromatography comprises one or more steps of affinity chromatography.
557. The method according to item 555, wherein the one or more steps of column chromatography comprises one or more steps of ion-exchange chromatography.
558. The method according to item 557, wherein the one or more steps of ion-exchange chromatography comprises one or more steps of cat-ion exchange chromatography.
559. The method according to item 557, wherein the one or more steps of ion-exchange chromatography comprises one or more steps of an-ion exchange chromatography.

560. The method according to item 555, wherein the one or more steps of column chromatography comprises one or more steps of size exclusion chromatography.
561. The method according to item 555, wherein the one or more steps of column chromatography comprises one or more steps of liquid chromatography.
562. The method according to item 555, wherein the one or more steps of column chromatography comprises one or more steps of HPLC.
563. The method according to item 555, wherein the one or more steps of column chromatography comprises one or more steps of gas chromatography.
564. The method according to item 554, wherein the one or more steps of chromatography comprises one or more steps of planar chromatography.
565. The method according to item 564, wherein the one or more steps of planar chromatography comprises one or more steps of paper chromatography.
566. The method according to item 564, wherein the one or more steps of planar chromatography comprises one or more steps of thin layer chromatography.
567. The method according to item 494, wherein the measuring of binding comprises one or more steps of mass spectrometry analysis.
568. The method according to item 567, wherein the one or more steps of mass spectrometry analysis comprises one or more steps of time of flight mass spectrometry analysis.
569. The method according to item 567, wherein the one or more steps of mass spectrometry analysis comprises one or more steps of sector mass spectrometry analysis.
570. The method according to item 567, wherein the one or more steps of mass spectrometry analysis comprises one or more steps of quadropole mass spectrometry analysis.
571. The method according to item 567, wherein the one or more steps of mass spectrometry analysis comprises one or more steps of Orbitrap mass spectrometry analysis.
572. The method according to item 567, wherein the one or more steps of mass spectrometry analysis comprises one or more steps of ion-trap mass spectrometry analysis.
573. The method according to item 494, wherein the measuring of binding comprises measurement of binding of one or more protein(s).
574. The method according to item 494, wherein the measuring of binding comprises measurement of binding of one or more antibodies.
575. The method according to item 494, wherein the measuring of binding comprises measurement of binding of one or more antibody fragment(s).
576. The method according to item 494, wherein the measuring of binding comprises measurement of binding of one or more receptor(s).
577. The method according to item 494, wherein the measuring of binding comprises measurement of binding of one or more receptor fragment(s).
578. The method according to item 494, wherein the measuring of binding comprises measurement of binding of one or more MHC molecule(s).
579. The method according to item 494, wherein the measuring of binding comprises measurement of binding of one or more MHC molecule fragment(s).
580. The method according to item 494, wherein the measuring of binding comprises measurement of binding of one or more cytokine(s).
581. The method according to item 494, wherein the measuring of binding comprises measurement of binding of one or more interleukin(s).
582. The method according to item 494, wherein the measuring of binding comprises measurement of binding of one or more interferon(s).
583. The method according to item 494, wherein the measuring of binding comprises measurement of binding of one or more hormone(s).
584. The method according to item 494, wherein the measuring of binding comprises measurement of binding of one or more growth factor(s).
585. The method according to item 494, wherein the measuring of binding comprises measurement of binding of one or more DNA(s).
586. The method according to item 494, wherein the measuring of binding comprises measurement of binding of one or more RNA(s).
587. The method according to item 494, wherein the measuring of binding comprises measurement of binding of one or more protein(s).
588. The method according to item 494, wherein the measuring of binding comprises measurement of binding of one or more sugar(s).
589. The method according to item 494, wherein the measuring of binding comprises measurement of binding of one or more lipid(s).
590. The method according to item 494, wherein the measuring of binding comprises measurement of binding of one or more chemical bond(s).
591. The method according to item 494, wherein the measuring of binding comprises measurement of binding of one or more atom(s).
592. The method according to item 494, wherein the measuring of binding comprises measurement of binding of one or more ion(s).
593. The method according to item 493, wherein the one or more chemical test(s) comprises measurement of catalysis.
594. The method according to item 593, wherein the measurement of catalysis comprises measurement of enzymatic activity.
595. The method according to item 593, wherein the measurement of catalysis comprises measurement of induction of enzymatic activity.
596. The method according to item 593, wherein the measurement of catalysis comprises measurement of inhibition of enzymatic activity.
597. The method according to item 593, wherein the measurement of catalysis comprises measurement of one or more substrates for one or more enzymes in a sample.
598. The method according to item 493, wherein the one or more chemical test(s) comprises measurement of impact on growth.
599. The method according to item 493, wherein the one or more chemical test(s) comprises measurement of inhibition of growth.
600. The method according to item 493, wherein the one or more chemical test(s) comprises measurement of induction of growth.
601. The method according to item 492, wherein the one or more test(s) of said individual comprises one or more physical test(s).
602. The method according to item 492, wherein the one or more physical test(s) comprises measurement of one or more electric pulse(s).
603. The method according to item 602, wherein the measurement of one or more electric pulse(s) comprises one or more step(s) of electroencephalography (method for determination of electrical activity produced by the brain).

604. The method according to item 602, wherein the measurement of one or more electric pulse(s) comprises one or more step(s) of electrocorticography.

605. The method according to item 602, wherein the measurement of one or more electric pulse(s) comprises one or more step(s) of electromyography (technique for detection of electrical potential generated by muscle cells).

606. The method according to item 602, wherein the measurement of one or more electric pulse(s) comprises one or more step(s) of electrocardiography (measurement of electrical activity of the heart).

607. The method according to item 602, wherein the measurement of one or more electric pulse(s) comprises one or more step(s) of electrooculography (technique for measurement of resting potential in retina).

608. The method according to item 602, wherein the measurement of one or more electric pulse(s) comprises one or more step(s) of electroretinography (used for measurement of electrical responses of various cells in the retina).

609. The method according to item 602, wherein the measurement of one or more electric pulse(s) comprises one or more step(s) of EEG topography.

610. The method according to item 602, wherein the measurement of one or more electric pulse(s) comprises one or more step(s) of electroneuronography.

611. The method according to item 492, wherein the one or more physical test(s) comprises one or more steps of endoscopy.

612. The method according to item 611, wherein the one or more steps of endoscopy comprises one or more step(s) of colonscopy.

613. The method according to item 611, wherein the one or more steps of endoscopy comprises one or more step(s) of gastroscopy.

614. The method according to item 611, wherein the one or more steps of endoscopy comprises one or more step(s) of cytocopy.

615. The method according to item 611, wherein the one or more steps of endoscopy comprises one or more step(s) of sigmoidoscopy.

616. The method according to item 611, wherein the one or more steps of endoscopy comprises one or more step(s) of colposcopy.

617. The method according to item 611, wherein the one or more steps of endoscopy comprises one or more step(s) of otoscopy.

618. The method according to item 611, wherein the one or more steps of endoscopy comprises one or more step(s) of ophthalmoscopy.

619. The method according to item 611, wherein the one or more steps of endoscopy comprises one or more step(s) of videoendoscopy.

620. The method according to item 611, wherein the one or more steps of endoscopy comprises one or more step(s) of laparoscopy.

621. The method according to item 492, wherein the one or more physical test(s) comprises measurement of one or more pressure(s).

622. The method according to item 621, wherein the measurement of one or more pressure(s) comprises measurement of blood pressure.

623. The method according to item 621, wherein the measurement of one or more pressure(s) comprises measurement of esophageal motility study (EMS).

624. The method according to item 621, wherein the measurement of one or more pressure(s) comprises measurement of esophageal manometry.

625. The method according to item 621, wherein the measurement of one or more pressure(s) comprises measurement of muscle tonus.

626. The method according to item 621, wherein the measurement of one or more pressure(s) comprises measurement of muscle strength.

627. The method according to item 492, wherein the one or more physical test(s) comprises one or more medical imaging analysis.

628. The method according to item 627, wherein the one or more medical imaging analysis comprises one or more ultrasound analysis.

629. The method according to item 628, wherein the one or more ultrasound analysis comprises echocardiography analysis.

630. The method according to item 628, wherein the one or more ultrasound analysis comprises medical ultrasonography analysis.

631. The method according to item 628, wherein the one or more ultrasound analysis comprises contrast enhanced ultrasound analysis.

632. The method according to item 628, wherein the one or more ultrasound analysis comprises intravascular ultrasound analysis.

633. The method according to item 627, wherein the one or more medical imaging analysis comprises one or more X-ray analysis.

634. The method according to item 627, wherein the one or more medical imaging analysis comprises one or more magnetic resonance imaging (MRI) analysis.

635. The method according to item 627, wherein the one or more medical imaging analysis comprises one or more computed tomography (CT) analysis.

636. The method according to item 627, wherein the one or more medical imaging analysis comprises one or more radiography analysis.

637. The method according to item 627, wherein the one or more medical imaging analysis comprises one or more fluoroscopy analysis.

638. The method according to item 627, wherein the one or more medical imaging analysis comprises one or more positron emission tomography analysis.

639. The method according to item 627, wherein the one or more medical imaging analysis comprises one or more single positron emission computed tomography (SPECT) analysis.

640. The method according to item 627, wherein the one or more medical imaging analysis comprises one or more scintillography analysis.

641. The method according to item 627, wherein the one or more medical imaging analysis comprises one or more thermography analysis.

642. The method according to item 627, wherein the one or more medical imaging analysis comprises one or more electric impedance tomography analysis.

643. The method according to item 627, wherein the one or more medical imaging analysis comprises one or more corneal topography analysis.

644. The method according to item 492, wherein the one or more physical test(s) comprises measurement of one or more temperature(s).

645. The method according to item 492, wherein the one or more physical test(s) comprises measurement of one or more humidity.

646. The method according to item 492, wherein the one or more physical test(s) comprises measurement of torsional flexibility.
647. The method according to item 492, wherein the one or more physical test(s) comprises measurement of one or more emission(s).
648. The method according to item 247, wherein the one or more physical test(s) comprises measurement of one or more sound(s).
649. The method according to item 492, wherein the one or more physical test(s) comprises measurement of one or more weight(s).
650. The method according to item 492, wherein the one or more physical test(s) comprises measurement of one or more flow(s).
651. The method according to item 650, wherein the measurement of one or more flow(s) comprises measurement of blood flow.
652. The method according to item 650, wherein the measurement of one or more flow(s) comprises measurement of breath.
653. The method according to item 492, wherein the one or more physical test(s) comprises measurement of one or more volume.
654. The method according to item 492, wherein the one or more physical test(s) comprises measurement of one or more conductivity.
655. The method according to any of items 1 to 454, wherein the analysis comprises one or more Hematological tests such as RBC tests, analysis of erythrocyte sedimentation rate (ESR), hematocrit-values, hemoglobin level, WBC tests, white blood number and blood cell types, Blood sugar, Blood count, maternal serum screening, analysis of Erythrocyte sedimentation rate (ESR), Complete blood count (CBC), Comprehensive metabolic panel (CMP), Arterial blood gas (ABG).
656. The method according to any of items 1 to 454, wherein the analysis comprises one or more Urine testing.
657. The method according to any of items 1 to 454, wherein the analysis comprises one or more analysis comprising Histochemical staining of one or more tissue sections.
658. The method according to any of items 1 to 454, wherein the analysis comprises one or more analysis comprising Antibody-specific staining of tissue sections.
659. The method according to any of items 1 to 454, wherein the analysis comprises one or more Papanicolaou test (or Pap smear, cervical smear).
660. The method according to any of items 1 to 454, wherein the analysis comprises one or more analysis comprising DNA-based chip technologies (e.g. Affymax DNA arrays).
661. The method according to any of items 1 to 454, wherein the analysis comprises one or more Nucleic acid analogue-based chip technologies for measuring abundance of RNA transcripts.
662. The method according to any of items 1 to 454, wherein the analysis comprises one or more analysis comprising Arrays of aptamers on chips (e.g. RNA aptamers or antibodies located in array) for measurement of abundance of e.g. specific proteins.
663. The method according to any of items 1 to 454, wherein the analysis comprises one or more analysis comprising Hybridisation of antibody to antigen.
664. The method according to any of items 1 to 454, wherein the analysis comprises one or more analysis comprising Hybridization of nucleic acid or nucleic acid analogue to nucleic acid or nucleic acid analogue.
665. The method according to any of items 1 to 454, wherein the analysis comprises one or more analysis comprising ELISA, DELFIA, RIA, Immune electrophoresis, or ELISPOT.
666. The method according to any of items 1 to 454, wherein the analysis comprises one or more analysis comprising Measurement of induced crosslinking by e.g. turbidometry, PCR (polymerase chain reaction), SDS-PAGE, Western blotting, Northern blotting, Southern blotting, Cytology with DNA-, RNA-, LNA-, PNA-, protein-, antibody-, MHC-probes; Flow cytometry with DNA-, RNA-, LNA-, PNA-, protein-, antibody-, MHC-probes; Stationary cytometry with DNA-, RNA-, LNA-, PNA-, protein-, antibody-, MHC-probes; IHC (immunohistochemistry) with DNA-, RNA-, LNA-, PNA-, protein-, antibody-, or MHC-probes.
667. The method according to any of items 1 to 454, wherein the analysis comprises one or more analysis comprising Genetic testing (the analysis of RNA, DNA, proteins, and certain metabolites in order to detect heritable disease-related genotypes, mutations, phenotypes, or karyotypes for clinical purposes).
668. The method according to any of items 1 to 454, wherein the analysis comprises one or more analysis comprising Measurement of Temperature, Heart rate, Pulse, Blood pressure, Body weight, Height, Reflexes, Breath, Hearing, and/or Eyesight.
669. The method according to any of items 1 to 454, wherein the analysis comprises one or more analysis comprising Visual observation.
670. The method according to any of items 1 to 454, wherein the analysis comprises one or more analysis comprising Electromyography (EMG), Electroencephalography (EEG), Electrocardiography (ECG or EKG), Ballistocardiography or BCG, Electrogastrography (EGG), Electroretinography, and/or Exercise tests.
671. The method according to any of items 1 to 454, wherein the analysis comprises one or more analysis comprising Physical examination.
672. The method according to any of items 1 to 454, wherein the analysis comprises one or more analysis comprising Amniocentesis (also referred to as amniotic fluid test or AFT).
673. The method according to any of items 1 to 454, wherein the analysis comprises one or more analysis comprising Chorionic villus sampling (CVS).
674. The method according to any of items 1 to 454, wherein the analysis comprises one or more analysis comprising Percutaneous umbilical cord blood sampling.
675. The method according to any of items 1 to 454, wherein the analysis comprises one or more analysis comprising Pulse diagnosis or Chinese pulse diagnosis.
676. The method according to any of items 1 to 454, wherein the analysis comprises one or more analysis comprising Auscultation.
677. The method according to any of items 1 to 454, wherein the analysis comprises one or more analysis comprising medical imaging such as Electron microscopy, Fluoroscopy, CEA-scan using arcitumomab, a monoclonal ab, CT scan (computerized tomography, aka. CAT scan: computed axial tomography), Electron beam tomography (EBT), Helical (or spiral) cone beam computed tomography, MRI scan (magnetic resonance imaging, alias Nuclear magnetic resonance NMR), Functional MRI or functional Magnetic Resonance Imaging (fMRI), Contrast MR, Arterial spin labeling, Magnetic resonance spectroscopic imaging, Diffusion tensor imaging, In vivo magnetic resonance spectroscopy (MRS).

678. The method according to any of items 1 to 454, wherein the analysis comprises one or more analysis comprising Nuclear medicine such as radioactive-labelled substances or radionuclides are administered to patients by intravenous injection (e.g. Technetium-99m, Iodine-123 and 131, Thallium-201, Gallium-67, Fluorine-18 Fluorodeoxyglucose, Indium-111 Labeled Leukocytes), ingestion, inhalation (e.g. Xenon-133, Krypton-81m, Technetium-99m Technegas, Technetium-99m DTPA), and the radiation emitted is detected by e.g. gamma camera or positron emission tomography.

679. The method according to any of items 1 to 454, wherein the analysis comprises one or more analysis comprising medical imaging such as Gallium imaging, Indium leukocyte imaging, Technetium antigranulocyte antibodies, Scintigraphy, Leukocyte scintigraphy, Red blood cell scintigraphy, Radionuclide cisternogram, PET scan (positron emission tomography), Gamma camera analysis, Single photon emission computed tomography (SPECT), Ultrasound, including echocardiography, Medical sonography (ultrasonography), Nuchal scan (nuchal translucency (NT)), Ultrasonography, X-ray imaging (including Chest radiology, Abdominal & Pelvic radiology.

680. The method according to any of items 1 to 454, wherein the analysis comprises one or more analysis comprising medical imaging such as Interventional radiology, Vascular radiology, Neuroradiology, Interventional Neuroradiology, Musculoskeletal radiology, Pediatric radiology, Mammography, Emergency radiology, Nuclear Medicine, Barium enema, intravenous pyelography (IVP, intravenous urography or IVU), with or without the use of Radiocontrast agents (contrast agents, based on barium sulphate or iodine).

681. The method according to any of items 1 to 454, wherein the analysis comprises one or more analysis comprising medical imaging such as Angiography (arteriography; may be coronary, retinal or peripheral), Arthrography, Magnetic Resonance, Arthrography, Hysterosalpingography (HSG), Infrared scanning, Visual inspection.

682. The method according to any of items 1 to 454, wherein the analysis comprises one or more analysis comprising medical imaging such as Radiography of a certain distribution pattern obtained by the addition of a tracer molecule such as a radioactive antibody, e.g. with affinity for a tumor, to a cancer patient.

683. The method according to any of items 1 to 454, wherein the analysis comprises one or more analysis comprising medical imaging such as NMR, Thermographic scanning, Electrophysiologic study (EPS), Endoscopy (including gastroscopy, esophagogastroduodenoscopy, colonoscopy, sigmoidscopy, endoscopic retrograde cholangiopancreatography (ERCP), anoscopy, cystoscopy, bronchoscopy, laryngoscopy, esophagoscopy, proctosigmoidoscopy, rhinoscopy, colposcopy, hysteroscopy, Falloscopy, laparoscopy, arthroscopy, thoracoscopy, mediastinoscopy, amnioscopy, fetoscopy, Panendoscopy (or triple endoscopy), architectural endoscopy, borescope), Magnetic resonance, cholangiopancreatography (MRCP), Magnetic resonance neurography, Dual energy x-ray absorptiometry (DXA), Computed Quantitative Computer Tomography (QCT), Photoacoustic imaging, Projection radiography, Diffuse optical tomography, Elastography (using ultrasound or magnetic resonance elastography (MRE) or CT), Transient elastography, Electrical impedance tomography, Optoacoustic imaging, Ophthalmology (A-scan, B-scan, Corneal topography, Optical coherence tomography, Scanning laser ophthalmoscopy), Embroscopy, Fetoscopy, Video cystometrography or VCMG, MAG3 scan, MUGA scan (Multiple Uptake Gated Acquisition Scan), Positron emission tomography-computed tomography (PET-CT), FDG imaging (fluorodeoxyglucose, FDG), Perfusion scanning, Magnetoencephalography (MEG) and Imaging for infection/inflammation using Sulesomab, A monoclonal antibody.

684. The method according to any of the previous items, wherein the entire sample derived from said individual is used for the analysis.

685. The method according to any of the previous items, wherein part of the sample derived from said individual is used for the analysis.

686. The method according to any of the previous items, wherein the sample derived from said individual is modified.

687. The method according to any of the previous items, wherein the one or more sample(s) derived from said individual is sweat.

688. The method according to any of the previous items, wherein the one or more sample(s) derived from said individual is urine.

689. The method according to any of the previous items, wherein the one or more sample(s) derived from said individual is blood.

690. The method according to any of the previous items, wherein the one or more sample(s) derived from said individual is semen.

691. The method according to any of the previous items, wherein the one or more sample(s) derived from said individual is cerebrospinal fluid (CSF).

692. The method according to any of the previous items, wherein the one or more sample(s) derived from said individual is sputum.

693. The method according to any of the previous items, wherein the one or more sample(s) derived from said individual is vaginal fluid.

694. The method according to any of the previous items, wherein the one or more sample(s) derived from said individual is tears.

695. The method according to any of the previous items, wherein the one or more sample(s) derived from said individual is one or more body fluids.

696. The method according to any of the previous items, wherein the one or more sample(s) derived from said individual is one or more sub-structures of human or animal body.

697. The method according to any of the previous items, wherein the one or more sample(s) derived from said individual is one or more tissue sample(s).

698. The method according to any of the previous items, wherein the one or more sample(s) derived from said individual is one or more whole organ(s).

699. The method according to any of the previous items, wherein the one or more sample(s) derived from said individual is solid.

700. The method according to any of the previous items, wherein the one or more sample(s) derived from said individual is semi-solid.

701. The method according to any of the previous items, wherein the one or more sample(s) derived from said individual is a fluid.

702. The method according to any of the previous items, wherein the one or more sample(s) derived from said individual is obtained by invasive sampling.

703. The method according to item 702, wherein the invasive sampling comprises drawing of blood.
704. The method according to item 702, wherein the invasive sampling comprises resection of tissues.
705. The method according to item 702, wherein the invasive sampling comprises resection of one or more organs.
706. The method according to item 702, wherein the invasive sampling comprises resection of part of one or more organs.
707. The method according to item 702, wherein the invasive sampling comprises drawing of cerebrospinal fluid.
708. The method according to item 702, wherein the invasive sampling comprises drawing of cerebrospinal fluid by limbar puncture.
709. The method according to any of the previous items, wherein the one or more sample(s) derived from said individual is obtained by non-invasive sampling.
710. The method according to item 709, wherein the non-invasive sampling is collection of one or more externally secreted fluid(s).
711. The method according to item 709, wherein the non-invasive sampling is measurement/recording of physical impulses such as heartbeat, breath and nerve impulses).
712. The method according to item 709, wherein the non-invasive sampling is measurement and recording of muscle tonus.
713. The method according to item 709, wherein the non-invasive sampling is measurement and recording of one or more images.
714. The method according to item 709, wherein the non-invasive sampling is measurement and recording of one or more sounds.
715. The method according to any of the previous items, wherein the one or more sample(s) is derived from a live source.
716. The method according to any of the previous items, wherein the one or more sample(s) is derived from a non-live source.
717. The method according to any of the previous items, wherein the individual is a human being.
718. The method according to any of the previous items, wherein the individual is a man.
719. The method according to any of the previous items, wherein the individual is a woman.
720. The method according to any of the previous items, wherein the individual is a pregnant woman.
721. The method according to any of the previous items, wherein the individual is a lactating woman.
722. The method according to any of the previous items, wherein the individual is an infant.
723. The method according to any of the previous items, wherein the individual is a child.
724. The method according to any of the previous items, wherein the individual is an adult.
725. The method according to any of the previous items, wherein the individual is of any age such as from newborn to 120 years old, for example from 0 to 6 months, such as from 6 to 12 months, for example from 1 to 5 years, such as from 5 to 10 years, for example from 10 to 15 years, such as from 15 to 20 years, for example from 20 to 25 years, such as from 25 to 30 years, for example from 30 to 35 years, such as from 35 to 40 years, for example from 40 to 45 years, such as from 45 to 50 years, for example from 50 to 60 years, such as from 60 to 70 years, for example from 70 to 80 years, such as from 80 to 90 years, for example from 90 to 100 years, such as from 100 to 110 years, for example from 110 to 120 years.
726. The method according to any of the previous items, wherein the individual is of any race such as a Caucasian, a black person, an East Asian person, a person of Mongoloid race, a person of Ethiopian race, a person of Negroid race, a person of American Indian race, or a person of Malayan race.
727. The method according to any of the previous items, wherein the individual is healthy.
728. The method according to any of the previous items, wherein the individual is ill.
729. The method according to any of the previous items, wherein the individual is diagnosed with one or more diseases.
730. The method according to any of the previous items, wherein the individual has one or more symptoms of one or more diseases.
731. The method according to any of the previous items, wherein the individual is asymptomatic.
732. The method according to any of the previous items, wherein the individual is genetically disposed for one or more diseases.
733. The method according to any of the previous items, wherein the individual is an animal.
734. The method according to any of the previous items, wherein the individual is a bird.
735. The method according to any of the previous items, wherein the individual is an insect.
736. The method according to any of the previous items, wherein the individual is a plant.
737. The method according to any of the previous items, wherein the individual is an algae.
738. The method according to any of the previous items, wherein the individual is a fungi.
739. The method according to any of the previous items, wherein the individual is an yeast.
740. The method according to any of the previous items, wherein the individual is a virus.
741. The method according to any of the previous items, wherein the individual is a bacteria.
742. The method according to any of the previous items, wherein the individual is a phage.
743. The method according to any of the previous items, wherein the individual is a multi-cellular organism.
744. The method according to any of the previous items, wherein the individual is a mono-cellular organism.
745. The method according to any of items 1 and 455 to 716, wherein the analysis is repeated more than once, such as twice, for example three times, such as four times, for example five times, such as six times, for example seven times, such as eight times, for example nine times or such as ten times, for example more than 10 times, such as more than 25 times, for example more than 50 times, such as more than 75 times, for example more than 100 times, such more than 200 times, for example more than 300 times, such as more than 500 times, for example more than 1000 times, such as more than 2000 times, for example more than 5000 times.
746. The method according to any of items 1 to 454, wherein the treatment is repeated more than once, such as twice, for example three times, such as four times, for example five times, such as six times, for example seven times, such as eight times, for example nine times or such as ten times, for example more than 10 times, such as more than 25 times, for example more than 50 times, such as more than 75 times, for example more than 100 times, such more than 200 times, for example more than 300 times, such as more than 500 times, for example more than 1000 times, such as more than 2000 times, for example more than 5000 times.
747. The method according to item 1, wherein the treatment comprises one or more vaccine(s) and one or more vaccine adjuvant(s).
748. The method according to item 747, wherein the one or more vaccine adjuvant(s) increases or otherwise modifies the immune response to said vaccine.
749. The method according to item 747, wherein the one or more vaccine adjuvant(s) elicit an earlier and/or more potent immune response to said vaccine.
750. The method according to item 747, wherein the one or more vaccine adjuvant(s) elicit a prolonged and/or more potent immune response to said vaccine.
751. The method according to item 747, wherein the one or more vaccine adjuvant(s) results in increased humoral immunity to said vaccine.
752. The method according to item 747, wherein the one or more vaccine adjuvant(s) results in induction of the complement pathway.
753. The method according to item 747, wherein the one or more vaccine adjuvant(s) results in increased cell mediated immunity to said vaccine.
754. The method according to item 747, wherein the one or more vaccine adjuvant(s) comprises one or more antigenic determinant(s).
755. The method according to item 747, wherein the one or more vaccine adjuvant(s) comprises one or more haptenic determinant(s).
756. The method according to item 747, wherein the one or more vaccine adjuvant(s) comprises one or more mineral adjuvant(s).
757. The method according to item 756, wherein the one or more mineral adjuvant(s) comprises one or more aluminium compounds such as one or more aluminium salt(s).
758. The method according to item 756, wherein the one or more mineral adjuvant(s) comprises aluminium hydroxide.
759. The method according to item 747, wherein the one or more vaccine adjuvant(s) comprises one or more bacterial adjuvant(s).
760. The method according to item 759, wherein one or more bacterial adjuvant(s) are purified.
761. The method according to item 759, wherein one or more bacterial adjuvant(s) are chemically purified.
762. The method according to item 759, wherein one or more bacterial adjuvant(s) are synthesized.
763. The method according to item 759, wherein one or more bacterial adjuvant(s) comprises muramyl dipeptides.
764. The method according to item 759, wherein one or more bacterial adjuvant(s) comprises lipid A.
765. The method according to item 759, wherein one or more bacterial adjuvant(s) comprises Interleukin 1.
766. The method according to item 759, wherein one or more bacterial adjuvant(s) comprises Interleukin 2.
767. The method according to item 759, wherein one or more bacterial adjuvant(s) comprises one or more cloned host mediator(s).
768. The method according to item 759, wherein one or more bacterial adjuvant(s) comprises *Bordetella pertussis*.
769. The method according to item 759, wherein one or more bacterial adjuvant(s) comprises one or more lipopolysaccharide(s).
770. The method according to item 759, wherein one or more bacterial adjuvant(s) comprises Freund's Complete Adjuvant (FCA).
771. The method according to item 759, wherein one or more bacterial adjuvant(s) comprises Titermax.
772. The method according to item 759, wherein one or more bacterial adjuvant(s) comprises ISCOMS.
773. The method according to item 759, wherein one or more bacterial adjuvant(s) comprises Quil A.
774. The method according to item 759, wherein one or more bacterial adjuvant(s) comprises ALUN.
775. The method according to item 759, wherein one or more bacterial adjuvant(s) comprises one or more Lipid A derivatives.
776. The method according to item 759, wherein one or more bacterial adjuvant(s) comprises one or more choleratoxin derivatives.
777. The method according to item 759, wherein one or more bacterial adjuvant(s) comprises one or more HSP derivatives.
778. The method according to item 759, wherein one or more bacterial adjuvant(s) comprises one or more LPS derivatives.
779. The method according to item 759, wherein one or more bacterial adjuvant(s) comprises one or more synthetic peptide matrixes.
780. The method according to item 759, wherein one or more bacterial adjuvant(s) comprises GMDP.
781. The method according to item 759, wherein one or more bacterial adjuvant(s) comprises one or more lipopolysaccharide(s) and/or derivatives thereof.
782. The method according to item 759, wherein one or more bacterial adjuvant(s) comprises one or more lipopolysaccharide(s) and/or derivatives thereof in combination with one or more liposome(s).
783. The method according to item 759, wherein one or more bacterial adjuvant(s) comprises one or more lipopolysaccharide(s) and/or derivatives thereof in combination with one or more lipid emulsion(s).
784. The method according to item 747, wherein the one or more vaccine adjuvant(s) comprises one or more plant adjuvant(s).
785. The method according to item 784, wherein the one or more plant adjuvant(s) comprises saponin.
786. The method according to item 747, wherein the one or more vaccine adjuvant(s) comprises one or more animal products adjuvant(s).
787. The method according to item 786, wherein the one or more animal products adjuvant(s) comprises chitin.
788. The method according to item 747, wherein the one or more vaccine adjuvant(s) comprises one or more synthetic adjuvant(s).
789. The method according to item 747, wherein the one or more vaccine adjuvant(s) comprises one or more host adjuvant(s).
790. The method according to item 747, wherein the one or more vaccine adjuvant(s) comprises one or more antigens precipitated with aluminum salt(s).
791. The method according to item 747, wherein the one or more vaccine adjuvant(s) comprises one or more antigens mixed with or adsorbed to performed aluminum compounds.
792. The method according to item 747, wherein the one or more vaccine adjuvant(s) comprises one or more oil emulsion(s).

793. The method according to item 747, wherein the one or more vaccine adjuvant(s) comprises one or more liposome(s).

794. The method according to item 747, wherein the one or more vaccine adjuvant(s) comprises one or more synthetic polymer(s).

795. The method according to item 747, wherein the one or more vaccine adjuvant(s) act through antigen localization and delivery.

796. The method according to item 747, wherein the one or more vaccine adjuvant(s) act by direct effects on cells making up the immune system, such as macrophages and lymphocytes.

797. The method according to item 747, wherein the one or more vaccine adjuvant(s) act by creation of an antigen depot.

798. The method according to any of items 1 and 455 to 746, wherein the treatment comprises one or more administrations to said individual of Aldesleukin/Proleukin (Chiron Corp).

799. The method according to any of items 1 and 455 to 746, wherein the treatment comprises one or more administrations to said individual of Alemtuzumab/Campath (Millennium and ILEX Partners, LP).

800. The method according to any of items 1 and 455 to 746, wherein the treatment comprises one or more administrations to said individual of alitretinoin/Panretin (Ligand Pharmaceuticals).

801. The method according to any of items 1 and 455 to 746, wherein the treatment comprises one or more administrations to said individual of allopurinol/Zyloprim (GlaxoSmithKline).

802. The method according to any of items 1 and 455 to 746, wherein the treatment comprises one or more administrations to said individual of altretamine/Hexalen (US Bioscience).

803. The method according to any of items 1 and 455 to 746, wherein the treatment comprises one or more administrations to said individual of amifostine/Ethyol (US Bioscience).

804. The method according to any of items 1 and 455 to 746, wherein the treatment comprises one or more administrations to said individual of anastrozole/Arimidex (AstraZeneca).

805. The method according to any of items 1 and 455 to 746, wherein the treatment comprises one or more administrations to said individual of arsenic trioxide/Trisenox (Cell Therapeutic).

806. The method according to any of items 1 and 455 to 746, wherein the treatment comprises one or more administrations to said individual of Asparaginase/Elspar (Merck & Co, Inc).

807. The method according to any of items 1 and 455 to 746, wherein the treatment comprises one or more administrations to said individual of BCG Live/TICE BCG (Organon Teknika Corp).

808. The method according to any of items 1 and 455 to 746, wherein the treatment comprises one or more administrations to said individual of bexarotene capsules/Targretin (Ligand Pharmaceuticals).

809. The method according to any of items 1 and 455 to 746, wherein the treatment comprises one or more administrations to said individual of bleomycin/Blenoxane (Bristol-Myers Squibb) busulfan/Busulfex (GlaxoSmithKline).

810. The method according to any of items 1 and 455 to 746, wherein the treatment comprises one or more administrations to said individual of calusterone/Methosarb (Pharmacia & Upjohn Company).

811. The method according to any of items 1 and 455 to 746, wherein the treatment comprises one or more administrations to said individual of capecitabine/Xeloda (Roche).

812. The method according to any of items 1 and 455 to 746, wherein the treatment comprises one or more administrations to said individual of carboplatin/Paraplatin (Bristol-Myers Squibb).

813. The method according to any of items 1 and 455 to 746, wherein the treatment comprises one or more administrations to said individual of carmustine/BCNU, BiCNU (Bristol-Myers Squibb).

814. The method according to any of items 1 and 455 to 746, wherein the treatment comprises one or more administrations to said individual of carmustine with Polifeprosan 20 Implant/Gliadel Wafer (Guilford Pharmaceuticals Inc.).

815. The method according to any of items 1 and 455 to 746, wherein the treatment comprises one or more administrations to said individual of celecoxib/Celebrex (Searle).

816. The method according to any of items 1 and 455 to 746, wherein the treatment comprises one or more administrations to said individual of chlorambucil/Leukeran (GlaxoSmithKline).

817. The method according to any of items 1 and 455 to 746, wherein the treatment comprises one or more administrations to said individual of cisplatin/Platinol (Bristol-Myers Squibb).

818. The method according to any of items 1 and 455 to 746, wherein the treatment comprises one or more administrations to said individual of cladribine/Leustatin, 2-CdA (R.W. Johnson Pharmaceutical Research Institute).

819. The method according to any of items 1 and 455 to 746, wherein the treatment comprises one or more administrations to said individual of cyclophosphamide Cytoxan/Neosar (Bristol-Myers Squibb).

820. The method according to any of items 1 and 455 to 746, wherein the treatment comprises one or more administrations to said individual of cytarabine/Cytosar-U (Pharmacia & Upjohn Company).

821. The method according to any of items 1 and 455 to 746, wherein the treatment comprises one or more administrations to said individual of dacarbazine/DTIC-Dome (Bayer).

822. The method according to any of items 1 and 455 to 746, wherein the treatment comprises one or more administrations to said individual of dactinomycin/actinomycin D Cosmegen (Merck).

823. The method according to any of items 1 and 455 to 746, wherein the treatment comprises one or more administrations to said individual of Darbepoetin alfa/Aranesp (Amgen, Inc).

824. The method according to any of items 1 and 455 to 746, wherein the treatment comprises one or more administrations to said individual of daunorubicin/daunomycin/Daunorubicin (Bedford Labs).

825. The method according to any of items 1 and 455 to 746, wherein the treatment comprises one or more administrations to said individual of daunorubicin/daunomycin/Cerubidine (Wyeth Ayerst).

826. The method according to any of items 1 and 455 to 746, wherein the treatment comprises one or more administrations to said individual of Denileukin/diftitox/Ontak (Seragen, Inc).

827. The method according to any of items 1 and 455 to 746, wherein the treatment comprises one or more administra- 828. The method according to any of items 1 and 455 to 746, wherein the treatment comprises one or more administrations to said individual of docetaxel/Taxotere (Aventis Pharmaceutical).
829. The method according to any of items 1 and 455 to 746, wherein the treatment comprises one or more administrations to said individual of doxorubicin Adriamycin/Rubex (Pharmacia & Upjohn Company).
830. The method according to any of items 1 and 455 to 746, wherein the treatment comprises one or more administrations to said individual of DROMOSTANOLONE PROPIONATE/MASTERONE INJECTION (SYNTEX).
831. The method according to any of items 1 and 455 to 746, wherein the treatment comprises one or more administrations to said individual of Elliott's B Solution (Orphan Medical, Inc).
832. The method according to any of items 1 and 455 to 746, wherein the treatment comprises one or more administrations to said individual of epirubicin/Ellence (Pharmacia & Upjohn Company).
833. The method according to any of items 1 and 455 to 746, wherein the treatment comprises one or more administrations to said individual of etoposide phosphate (Bristol-Myers Squibb).
834. The method according to any of items 1 and 455 to 746, wherein the treatment comprises one or more administrations to said individual of etoposide/VP-16/Vepesid (Bristol-Myers Squibb).
835. The method according to any of items 1 and 455 to 746, wherein the treatment comprises one or more administrations to said individual of exemestane/Aromasin (Pharmacia & Upjohn Company).
836. The method according to any of items 1 and 455 to 746, wherein the treatment comprises one or more administrations to said individual of Filgrastim/Neupogen (Amgen, Inc).
837. The method according to any of items 1 and 455 to 746, wherein the treatment comprises one or more administrations to said individual of floxuridine/FUDR (Roche).
838. The method according to any of items 1 and 455 to 746, wherein the treatment comprises one or more administrations to said individual of fludarabine/Fludara (Berlex Laboratories Inc.).
839. The method according to any of items 1 and 455 to 746, wherein the treatment comprises one or more administrations to said individual of fluorouracil/5-FU/Adrucil (ICN Puerto Rico) fulvestrant/Faslodex (IPR).
840. The method according to any of items 1 and 455 to 746, wherein the treatment comprises one or more administrations to said individual of gemcitabine/Gemzar (Eli Lilly).
841. The method according to any of items 1 and 455 to 746, wherein the treatment comprises one or more administrations to said individual of gemtuzumab/ozogamicin/Mylotarg (Wyeth Ayerst).
842. The method according to any of items 1 and 455 to 746, wherein the treatment comprises one or more administrations to said individual of goserelin acetate/Zoladex Implant (AstraZeneca Pharmaceuticals).
843. The method according to any of items 1 and 455 to 746, wherein the treatment comprises one or more administrations to said individual of hydroxyurea/Hydrea (Bristol-Myers Squibb).
844. The method according to any of items 1 and 455 to 746, wherein the treatment comprises one or more administrations to said individual of Ibritumomab Tiuxetan/Zevalin (IDEC Pharmaceuticals Corp).
845. The method according to any of items 1 and 455 to 746, wherein the treatment comprises one or more administrations to said individual of idarubicin/Idamycin (Adria Laboratories).
846. The method according to any of items 1 and 455 to 746, wherein the treatment comprises one or more administrations to said individual of ifosfamide/IFEX (Bristol-Myers Squibb).
847. The method according to any of items 1 and 455 to 746, wherein the treatment comprises one or more administrations to said individual of imatinib mesylate/Gleevec (Novartis).
848. The method according to any of items 1 and 455 to 746, wherein the treatment comprises one or more administrations to said individual of Interferon alfa-2a/Roferon-A (Hoffmann-La Roche Inc).
849. The method according to any of items 1 and 455 to 746, wherein the treatment comprises one or more administrations to said individual of Interferon alfa-2b/Intron A (Schering Corp).
850. The method according to any of items 1 and 455 to 746, wherein the treatment comprises one or more administrations to said individual of irinotecan/Camptosar (Pharmacia & Upjohn Company).
851. The method according to any of items 1 and 455 to 746, wherein the treatment comprises one or more administrations to said individual of letrozole/Femara (Novartis).
852. The method according to any of items 1 and 455 to 746, wherein the treatment comprises one or more administrations to said individual of leucovorin Wellcovorin/Leucovorin (Immunex Corporation).
853. The method according to any of items 1 and 455 to 746, wherein the treatment comprises one or more administrations to said individual of levamisole/Ergamisol (Janssen Research Foundation).
854. The method according to any of items 1 and 455 to 746, wherein the treatment comprises one or more administrations to said individual of lomustine/CCNU/CeeBU (Bristol-Myers Squibb).
855. The method according to any of items 1 and 455 to 746, wherein the treatment comprises one or more administrations to said individual of meclorethamine/nitrogen mustard/Mustargen (Merck).
856. The method according to any of items 1 and 455 to 746, wherein the treatment comprises one or more administrations to said individual of megestrol acetate/Megace (Bristol-Myers Squibb).
857. The method according to any of items 1 and 455 to 746, wherein the treatment comprises one or more administrations to said individual of melphalan/L-PAM/Alkeran (GlaxoSmithKline).
858. The method according to any of items 1 and 455 to 746, wherein the treatment comprises one or more administrations to said individual of mercaptopurine/6-MP Purinethol (GlaxoSmithKline).
859. The method according to any of items 1 and 455 to 746, wherein the treatment comprises one or more administrations to said individual of mesna/Mesnex (Asta Medica).
860. The method according to any of items 1 and 455 to 746, wherein the treatment comprises one or more administrations to said individual of methotrexate (Lederle Laboratories).

861. The method according to any of items 1 and 455 to 746, wherein the treatment comprises one or more administrations to said individual of methoxsalen/Uvadex (Therakos).

862. The method according to any of items 1 and 455 to 746, wherein the treatment comprises one or more administrations to said individual of mitomycin C/Mutamycin (Bristol-Myers Squibb).

863. The method according to any of items 1 and 455 to 746, wherein the treatment comprises one or more administrations to said individual of mitomycin C/Mitozytrex (Supergen).

864. The method according to any of items 1 and 455 to 746, wherein the treatment comprises one or more administrations to said individual of mitotane/Lysodren (Bristol-Myers Squibb).

865. The method according to any of items 1 and 455 to 746, wherein the treatment comprises one or more administrations to said individual of mitoxantrone/Novantrone (Lederle Laboratories).

866. The method according to any of items 1 and 455 to 746, wherein the treatment comprises one or more administrations to said individual of nandrolone phenpropionate/Durabolin-50 (Organon).

867. The method according to any of items 1 and 455 to 746, wherein the treatment comprises one or more administrations to said individual of Nofetumomab/Verluma (Boehringer Ingelheim Pharma KG (formerly Dr. Karl Thomae GmbH)).

868. The method according to any of items 1 and 455 to 746, wherein the treatment comprises one or more administrations to said individual of Oprelvekin/Neumega (Genetics Institute).

869. The method according to any of items 1 and 455 to 746, wherein the treatment comprises one or more administrations to said individual of oxaliplatin/Eloxatin (Sanofi Synthelabo).

870. The method according to any of items 1 and 455 to 746, wherein the treatment comprises one or more administrations to said individual of paclitaxel/Taxol (Bristol-Myers Squibb).

871. The method according to any of items 1 and 455 to 746, wherein the treatment comprises one or more administrations to said individual of pamidronate/Aredia (Novartis).

872. The method according to any of items 1 and 455 to 746, wherein the treatment comprises one or more administrations to said individual of pegademase/Adagen (Pegademase Bovine) (Enzon).

873. The method according to any of items 1 and 455 to 746, wherein the treatment comprises one or more administrations to said individual of Pegaspargase/Oncaspar (Enzon, Inc).

874. The method according to any of items 1 and 455 to 746, wherein the treatment comprises one or more administrations to said individual of Pegfilgrastim/Neulasta (Amgen, Inc).

875. The method according to any of items 1 and 455 to 746, wherein the treatment comprises one or more administrations to said individual of pentostatin/Nipent (Parke-Davis Pharmaceutical Co.).

876. The method according to any of items 1 and 455 to 746, wherein the treatment comprises one or more administrations to said individual of pipobroman/Vercyte (Abbott Labs).

877. The method according to any of items 1 and 455 to 746, wherein the treatment comprises one or more administrations to said individual of plicamycin/mithramycin/Mithracin (Pfizer Labs).

878. The method according to any of items 1 and 455 to 746, wherein the treatment comprises one or more administrations to said individual of porfimer sodium/Photofrin (QLT Phototherapeutics Inc.).

879. The method according to any of items 1 and 455 to 746, wherein the treatment comprises one or more administrations to said individual of procarbazine/Matulane (Sigma Tau Pharms).

880. The method according to any of items 1 and 455 to 746, wherein the treatment comprises one or more administrations to said individual of quinacrine/Atabrine (Abbott Labs).

881. The method according to any of items 1 and 455 to 746, wherein the treatment comprises one or more administrations to said individual of Rasburicase/Elitek (Sanofi-Synthelabo, Inc).

882. The method according to any of items 1 and 455 to 746, wherein the treatment comprises one or more administrations to said individual of Rituximab/Rituxan (Genentech, Inc).

883. The method according to any of items 1 and 455 to 746, wherein the treatment comprises one or more administrations to said individual of Sargramostim/Prokine (Immunex Corp).

884. The method according to any of items 1 and 455 to 746, wherein the treatment comprises one or more administrations to said individual of streptozocin/Zanosar (Pharmacia & Upjohn Company).

885. The method according to any of items 1 and 455 to 746, wherein the treatment comprises one or more administrations to said individual of talc/Sclerosol (Bryan).

886. The method according to any of items 1 and 455 to 746, wherein the treatment comprises one or more administrations to said individual of tamoxifen/Nolvadex (AstraZeneca Pharmaceuticals).

887. The method according to any of items 1 and 455 to 746, wherein the treatment comprises one or more administrations to said individual of temozolomide/Temodar (Schering).

888. The method according to any of items 1 and 455 to 746, wherein the treatment comprises one or more administrations to said individual of teniposide/VM-26/Vumon (Bristol-Myers Squibb).

889. The method according to any of items 1 and 455 to 746, wherein the treatment comprises one or more administrations to said individual of testolactone/Teslac (Bristol-Myers Squibb).

890. The method according to any of items 1 and 455 to 746, wherein the treatment comprises one or more administrations to said individual of thioguanine/6-TG/Thioguanine (GlaxoSmithKline).

891. The method according to any of items 1 and 455 to 746, wherein the treatment comprises one or more administrations to said individual of thiotepa/Thioplex (Lederle Laboratories).

892. The method according to any of items 1 and 455 to 746, wherein the treatment comprises one or more administrations to said individual of topotecan/Hycamtin (GlaxoSmithKline).

893. The method according to any of items 1 and 455 to 746, wherein the treatment comprises one or more administrations to said individual of toremifene/Fareston (Orion Corp).

894. The method according to any of items 1 and 455 to 746, wherein the treatment comprises one or more administrations to said individual of Tositumomab/Bexxar (Corixa Corporation).
895. The method according to any of items 1 and 455 to 746, wherein the treatment comprises one or more administrations to said individual of Trastuzumab/Herceptin (Genentech, Inc).
896. The method according to any of items 1 and 455 to 746, wherein the treatment comprises one or more administrations to said individual of tretinoin/ATRA/Vesanoid (Roche).
897. The method according to any of items 1 and 455 to 746, wherein the treatment comprises one or more administrations to said individual of Uracil Mustard (Roberts Labs).
898. The method according to any of items 1 and 455 to 746, wherein the treatment comprises one or more administrations to said individual of valrubicin/Valstar (Medeva).
899. The method according to any of items 1 and 455 to 746, wherein the treatment comprises one or more administrations to said individual of vinblastine/Velban (Eli Lilly).
900. The method according to any of items 1 and 455 to 746, wherein the treatment comprises one or more administrations to said individual of vincristine/Oncovin (Eli Lilly).
901. The method according to any of items 1 and 455 to 746, wherein the treatment comprises one or more administrations to said individual of vinorelbine/Navelbine (GlaxoSmithKline).
902. The method according to any of items 1 and 455 to 746, wherein the treatment comprises one or more administrations to said individual of zoledronate/Zometa (Novartis).
903. The method according to any of items 1 and 455 to 746, wherein the treatment comprises one or more administrations to said individual of Alemtuzumab/Campath (Millennium and ILEX Partners, LP) for treatment or prophylaxis of B-cell chronic lymphocytic leukaemia (B-CLL).
904. The method according to any of items 1 and 455 to 746, wherein the treatment comprises one or more administrations to said individual of alitretinoin/Panretin (Ligand Pharmaceuticals) and/or one or more other drugs for treatment or prophylaxis of cutaneous lesions in sarcoma patients, such as in patients suffering from AIDS-related Kaposi's sarcoma.
905. The method according to any of items 1 and 455 to 746, wherein the treatment comprises one or more administrations to said individual of allopurinol/Zyloprim (GlaxoSmithKline) and/or one or more other drugs for treatment of patients with leukaemia and/or lymphoma and/or one or more solid tumor malignancies who are receiving cancer therapy which causes elevations of serum and urinary uric acid levels.
906. The method according to any of items 1 and 455 to 746, wherein the treatment comprises one or more administrations to said individual of altretamine/Hexalen (US Bioscience) and/or one or more other drugs for treatment or prophylaxis of ovarian cancer.
907. The method according to any of items 1 and 455 to 746, wherein the treatment comprises one or more administrations to said individual of amifostine/Ethyol (US Bioscience) and/or one or more other drugs for treatment or prophylaxis of post-radiation xerostomia for e.g. head and neck cancer and/or ovarian cancer (preferably advanced) and/or non-small cell lung cancer.
908. The method according to any of items 1 and 455 to 746, wherein the treatment comprises one or more administrations to said individual of anastrozole/Arimidex (AstraZeneca) and/or one or more other drugs for treatment of breast cancer, for example hormone receptor positive early breast cancer, advanced breast cancer, locally advanced or metastatic breast cancer.
909. The method according to any of items 1 and 455 to 746, wherein the treatment comprises one or more administrations to said individual of Asparaginase/Elspar (Merck & Co, Inc) and/or one or more other drugs for treatment of pediatric patients.
910. The method according to any of items 1 and 455 to 746, wherein the treatment comprises one or more administrations to said individual of bexarotene capsules/Targretin (Ligand Pharmaceuticals) and/or one or more other drugs for treatment of cutaneous manifestations of cutaneous T-cell lymphoma, preferably via oral administration.
911. The method according to any of items 1 and 455 to 746, wherein the treatment comprises one or more administrations to said individual of bleomycin/Blenoxane (Bristol-Myers Squibb) and/or one or more other drugs for treatment of malignant pleural effusion (MPE) and prevention of recurrent pleural effusions.
912. The method according to any of items 1 and 455 to 746, wherein the treatment comprises one or more administrations to said individual of busulfan/Busulfex (GlaxoSmithKline) and/or one or more other drugs prior to hematopoietic progenitor cell transplantation for chronic myelogenous leukemia, preferably via oral administration.
913. The method according to any of items 1 and 455 to 746, wherein the treatment comprises one or more administrations to said individual of capecitabine/Xeloda (Roche) and/or one or more other drugs for treatment of breast cancer, preferably metastatic breast cancer, or colorectal carcinoma, preferably metastatic colorectal carcinoma.
914. The method according to any of items 1 and 455 to 746, wherein the treatment comprises one or more administrations to said individual of Carboplatin/Paraplatin (Bristol-Myers Squibb) and/or one or more other drugs for treatment of ovarian carcinoma.
915. The method according to any of items 1 and 455 to 746, wherein the treatment comprises one or more administrations to said individual of carmustine with Polifeprosan 20 Implant/Gliadel Wafer (Guilford Pharmaceuticals Inc.) and/or one or more other drugs to prolong survival in patients with recurrent glioblastoma multiforme who qualify for surgery.
916. The method according to any of items 1 and 455 to 746, wherein the treatment comprises one or more administrations to said individual of celecoxib/Celebrex (Searle) and/or one or more other drugs for treatment of familial adenomatous polyposis.
917. The method according to any of items 1 and 455 to 746, wherein the treatment comprises one or more administrations to said individual of chlorambucil/Leukeran (GlaxoSmithKline) and/or one or more other drugs for treatment of chronic lymphocytic leukaemia.
918. The method according to any of items 1 and 455 to 746, wherein the treatment comprises one or more administrations to said individual of cisplatin/Platinol (Bristol-Myers Squibb) and/or one or more other drugs for treatment of ovarian tumour preferably metastatic ovarian tumour, testicular tumour, preferably testicular tumour, transitional cell bladder cancer.
919. The method according to any of items 1 and 455 to 746, wherein the treatment comprises one or more administrations to said individual of cladribine/Leustatin, 2-CdA (R.W. Johnson Pharmaceutical Research Institute) and/or one or more other drugs for treatment of active hairy cell leukaemia.
920. The method according to any of items 1 and 455 to 746, wherein the treatment comprises one or more administrations to said individual of Darbepoetin alfa/Aranesp (Amgen, Inc) and/or one or more other drugs for treatment of anemia associated with chemotherapeutic regimes.
921. The method according to any of items 1 and 455 to 746, wherein the treatment comprises one or more administrations to said individual of daunorubicin/daunomycin/Daunorubicin (Bedford Labs) e.g. in liposomal form and/or one or more other drugs for treatment of HIV-related Kaposi's sarcoma.
922. The method according to any of items 1 and 455 to 746, wherein the treatment comprises one or more administrations to said individual of daunorubicin/daunomycin/Cerubidine (Wyeth Ayerst) and/or one or more other drugs for treatment of leukaemia.
923. The method according to any of items 1 and 455 to 746, wherein the treatment comprises one or more administrations to said individual of Denileukin/diftitox/Ontak (Seragen, Inc) and/or one or more other drugs for treatment of T-cell lymphoma, preferably of individuals whose malignant cells express the CDC25 component of the IL-2 receptor.
924. The method according to any of items 1 and 455 to 746, wherein the treatment comprises one or more administrations to said individual of dexrazoxane/Zinecard (Pharmacia & Upjohn Company) and/or one or more other drugs to aid in reducing the severity of cardiomyopathy associated with doxorubicin administration in women with metastatic breast cancer.
925. The method according to any of items 1 and 455 to 746, wherein the treatment comprises one or more administrations to said individual of docetaxel/Taxotere (Aventis Pharmaceutical) and/or one or more other drugs for treatment of breast cancer, preferably locally advanced or metastatic breast cancer, or non-small cell lung cancer, preferably locally advanced or metastatic non-small cell lung cancer.
926. The method according to any of items 1 and 455 to 746, wherein the treatment comprises one or more administrations to said individual of doxorubicin/Adriamycin Rubex (Pharmacia & Upjohn Company) and/or one or more other drugs for treatment of AIDS-related Kaposi's sarcoma or metastatic carcinoma of the ovary.
927. The method according to any of items 1 and 455 to 746, wherein the treatment comprises one or more administrations to said individual of Elliott's B Solution (Orphan Medical, Inc) and/or one or more other drugs for treatment or prophylaxis of miningeal leukaemia or lymphocytic lymphoma.
928. The method according to any of items 1 and 455 to 746, wherein the treatment comprises one or more administrations to said individual of Epirubicin/Ellence (Pharmacia & Upjohn Company) and/or one or more other drugs for treatment or prophylaxis of breast cancer.
929. The method according to any of items 1 and 455 to 746, wherein the treatment comprises one or more administrations to said individual of etoposide phosphate (Bristol-Myers Squibb) and/or one or more other drugs for treatment or prophylaxis of refractory testicular tumours, small cell lung cancer.
930. The method according to any of items 1 and 455 to 746, wherein the treatment comprises one or more administrations to said individual of etoposide/VP-16/Vepesid (Bristol-Myers Squibb) and/or one or more other drugs for treatment or prophylaxis of refractory testicular tumours, small cell lung cancer.
931. The method according to any of items 1 and 455 to 746, wherein the treatment comprises one or more administrations to said individual of exemestane/Aromasin (Pharmacia & Upjohn Company) and/or one or more other drugs for treatment or prophylaxis of breast cancer, preferably for treatment of advanced breast cancer.
932. The method according to any of items 1 and 455 to 746, wherein the treatment comprises one or more administrations to said individual of Filgrastim/Neupogen (Amgen, Inc) and/or one or more other drugs for treatment of nonmyeloid malignancies undergoing myeloablative chemotherapy followed by marrow transplantation.
933. The method according to any of items 1 and 455 to 746, wherein the treatment comprises one or more administrations to said individual of fludarabine/Fludara (Berlex Laboratories Inc.) and/or one or more other drugs for treatment or prophylaxis of B-cell lymphocytic leukaemia.
934. The method according to any of items 1 and 455 to 746, wherein the treatment comprises one or more administrations to said individual of fluorouracil/5-FU/Adrucil (ICN Puerto Rico) and/or one or more other drugs to prolong survival of said individual.
935. The method according to any of items 1 and 455 to 746, wherein the treatment comprises one or more administrations to said individual of fulvestrant/Faslodex (IPR) and/or one or more other drugs for treatment or prophylaxis of breast cancer, preferably in post-menopausal women.
936. The method according to any of items 1 and 455 to 746, wherein the treatment comprises one or more administrations to said individual of gemcitabine/Gemzar (Eli Lilly) and/or one or more other drugs for treatment or prophylaxis of adenocarcinoma of the pancreas or non-small cell lung cancer, preferably locally advanced or metastatic adenocarcinoma of the pancreas or non-small cell lung cancer.
937. The method according to any of items 1 and 455 to 746, wherein the treatment comprises one or more administrations to said individual of is gemtuzumab/ozogamicin/Mylotarg (Wyeth Ayerst) and/or one or more other drugs for treatment or prophylaxis of CD33 positive acute myeloid leukaemia in patients who are preferably 60 years of age or older.
938. The method according to any of items 1 and 455 to 746, wherein the treatment comprises one or more administrations to said individual of goserelin acetate/Zoladex Implant (AstraZeneca Pharmaceuticals) and/or one or more other drugs for treatment or prophylaxis of breast cancer, preferably advanced stage breast cancer.
939. The method according to any of items 1 and 455 to 746, wherein the treatment comprises one or more administrations to said individual of Ibritumomab Tiuxetan/Zevalin (IDEC Pharmaceuticals Corp) and/or one or more other drugs for treatment or prophylaxis of non-Hodgkin's lymphoma, for example patients with Rituximab refractory follicular non-Hodgkin's lymphoma.
940. The method according to any of items 1 and 455 to 746, wherein the treatment comprises one or more administrations to said individual of idarubicin/Idamycin (Adria Laboratories) and/or one or more other drugs for treatment or prophylaxis of acute myeloid leukaemia, for example in adults.

941. The method according to any of items 1 and 455 to 746, wherein the treatment comprises one or more administrations to said individual of ifosfamide/IFEX (Bristol-Myers Squibb) and/or one or more other drugs for treatment of germ cell testicular cancer.
942. The method according to any of items 1 and 455 to 746, wherein the treatment comprises one or more administrations to said individual of imatinib mesylate/Gleevec (Novartis) and/or one or more other drugs for treatment of chronic myelogeneous leukaemia or gastrointestinal stromal tumours.
943. The method according to any of items 1 and 455 to 746, wherein the treatment comprises one or more administrations to said individual of Interferon alfa-2a/Roferon-A (Hoffmann-La Roche Inc) and/or one or more other drugs for treatment or prophylaxis of malignant melanoma, Non-Hodgkin's Lymphoma, condylomata acuminate, hairy cell leukaemia or AIDS-related Kaposi's sarcoma.
944. The method according to any of items 1 and 455 to 746, wherein the treatment comprises one or more administrations to said individual of irinotecan/Camptosar (Pharmacia & Upjohn Company) and/or one or more other drugs for treatment or prophylaxis of carcinoma of the colon or rectum, preferably metastatic carcinoma of the colon or rectum.
945. The method according to any of items 1 and 455 to 746, wherein the treatment comprises one or more administrations to said individual of letrozole/Femara (Novartis) and/or one or more other drugs for treatment of carcinoma of the colon or rectum, or treatment or prophylaxis of breast cancer, preferably in post-menopausal women.
946. The method according to any of items 1 and 455 to 746, wherein the treatment comprises one or more administrations to said individual of Leucovorin/Wellcovorin (Immunex Corporation) and/or one or more other drugs for treatment or prophylaxis of colorectal cancer, preferably advanced colorectal cancer.
947. The method according to any of items 1 and 455 to 746, wherein the treatment comprises one or more administrations to said individual of levamisole/Ergamisol (Janssen Research Foundation) and/or one or more other drugs for treatment or prophylaxis of colon cancer, preferably after surgical resection.
948. The method according to any of items 1 and 455 to 746, wherein the treatment comprises one or more administrations to said individual of melphalan/L-PAM/Alkeran (GlaxoSmithKline) and/or one or more other drugs for treatment or prophylaxis of multiple myeloma.
949. The method according to any of items 1 and 455 to 746, wherein the treatment comprises one or more administrations to said individual of mesna/Mesnex (Asta Medica) and/or one or more other drugs for treatment or prophylaxis of ifosfamide-induced hemorrhagic cystitis.
950. The method according to any of items 1 and 455 to 746, wherein the treatment comprises one or more administrations to said individual of methotrexate (Lederle Laboratories) and/or one or more other drugs for treatment or prophylaxis of osteosarcoma.
951. The method according to any of items 1 and 455 to 746, wherein the treatment comprises one or more administrations to said individual of methoxsalen/Uvadex (Therakos) and/or one or more other drugs for treatment or prophylaxis of skin manifestations of cutaneous T-cell lymphoma (CTCL).
952. The method according to any of items 1 and 455 to 746, wherein the treatment comprises one or more administrations to said individual of mitomycin C/Mitozytrex (Supergen) and/or one or more other drugs for treatment or prophylaxis of disseminated adenocarcinoma of the stomach or pancreas.
953. The method according to any of items 1 and 455 to 746, wherein the treatment comprises one or more administrations to said individual of mitoxantrone/Novantrone (Lederle Laboratories) and/or one or more other drugs for treatment or prophylaxis of prostrate cancer or acute nonlymphocytic leukaemia (ANLL) in adults.
954. The method according to any of items 1 and 455 to 746, wherein the treatment comprises one or more administrations to said individual of Oprelvekin/Neumega (Genetics Institute), preferably administered after myelosuppressive chemotherapy in patients with nonmyeloid malignancies.
955. The method according to any of items 1 and 455 to 746, wherein the treatment comprises one or more administrations to said individual of oxaliplatin/Eloxatin (Sanofi Synthelabo) and/or one or more other drugs for treatment or prophylaxis of carcinoma of the colon, preferably metastatic carcinoma of the colon.
956. The method according to any of items 1 and 455 to 746, wherein the treatment comprises one or more administrations to said individual of paclitaxel/Taxol/Paxene (Bristol-Myers Squibb) and/or one or more other drugs for treatment or prophylaxis of advanced AIDS-related Kaposi's sarcoma, breast cancer, metastatic breast cancer, carcinoma of the ovary, AIDS-related Kaposi's sarcoma, metastatic carcinoma of the ovary, non-small cell lung cancer or node-positive breast cancer.
957. The method according to any of items 1 and 455 to 746, wherein the treatment comprises one or more administrations to said individual of is pamidronate/Aredia (Novartis) and/or one or more other drugs for treatment or prophylaxis of osteolytic bone metastases of breast cancer.
958. The method according to any of items 1 and 455 to 746, wherein the treatment comprises one or more administrations to said individual of Pegfilgrastim/Neulasta (Amgen, Inc) and/or one or more other drugs for treatment or prophylaxis of non-myeloid malignancies.
959. The method according to any of items 1 and 455 to 746, wherein the treatment comprises one or more administrations to said individual of pentostatin/Nipent (Parke-Davis Pharmaceutical Co.) and/or one or more other drugs for treatment or prophylaxis of hairy cell leukaemia, for example alpha interferon refractory hairy cell leukaemia.
960. The method according to any of items 1 and 455 to 746, wherein the treatment comprises one or more administrations to said individual of porfimer sodium/Photofrin (QLT Phototherapeutics Inc.) and/or one or more other drugs for treatment or prophylaxis of partially obstructing or completely obstructing esophogeal cancer.
961. The method according to any of items 1 and 455 to 746, wherein the treatment comprises one or more administrations to said individual of is Rasburicase/Elitek (Sanofi-Synthelabo, Inc) and/or one or more other drugs for treatment or prophylaxis of patients suffering from leukaemia, lymphoma or solid tumor malignancies.
962. The method according to any of items 1 and 455 to 746, wherein the treatment comprises one or more administrations to said individual of talc/Sclerosol (Bryan) and/or one or more other drugs for treatment or prophylaxis of malignant pleural effusion in symptomatic patients.
963. The method according to any of items 1 and 455 to 746, wherein the treatment comprises one or more administrations to said individual of tamoxifen/Nolvadex (Astra- Zeneca Pharmaceuticals) and/or one or more other drugs for treatment or prophylaxis of breast cancer, for example following mastectomy and axillary dissection in post-menopausal women, or for metastatic breast cancer, for example in men.

964. The method according to any of items 1 and 455 to 746, wherein the treatment comprises one or more administrations to said individual of temozolomide/Temodar (Schering) and/or one or more other drugs for treatment or prophylaxis of refractory anaplastic astrocytma.

965. The method according to any of items 1 and 455 to 746, wherein the treatment comprises one or more administrations to said individual of teniposide/VM-26/Vumon (Bristol-Myers Squibb) and/or one or more other drugs for treatment or prophylaxis of refractory childhood acute lymphoblastic leukaemia.

966. The method according to any of items 1 and 455 to 746, wherein the treatment comprises one or more administrations to said individual of topotecan/Hycamtin (GlaxoSmithKline) and/or one or more other drugs for treatment or prophylaxis of metastatic carcinoma of the ovary, or small cell lung cancer.

967. The method according to any of items 1 and 455 to 746, wherein the treatment comprises one or more administrations to said individual of toremifene/Fareston (Orion Corp) and/or one or more other drugs for treatment or prophylaxis of advanced breast cancer in postmenopausal women.

968. The method according to any of items 1 and 455 to 746, wherein the treatment comprises one or more administrations to said individual of Tositumomab/Bexxar (Corixa Corporation) and/or one or more other drugs for treatment or prophylaxis of non-Hodgkin's lymphoma.

969. The method according to any of items 1 and 455 to 746, wherein the treatment comprises one or more administrations to said individual of Trastuzumab/Herceptin (Genentech, Inc) and/or one or more other drugs for treatment or prophylaxis of metastatic breast cancer.

970. The method according to any of items 1 and 455 to 746, wherein the treatment comprises one or more administrations to said individual of tretinoin/ATRA/Vesanoid (Roche) and/or one or more other drugs for treatment or prophylaxis of acute promyeocytic leukaemia.

971. The method according to any of items 1 and 455 to 746, wherein the treatment comprises one or more administrations to said individual of valrubicin/Valstar (Medeva) and/or one or more other drugs for treatment or prophylaxis of BCG-refractory carcinoma in situ (CIS) of the urinary bladder.

972. The method according to any of items 1 and 455 to 746, wherein the treatment comprises one or more administrations to said individual of vinorelbine/Navelbine (GlaxoSmithKline) and/or one or more other drugs for treatment or prophylaxis of non-small cell lung cancer, such as unresectable, advanced non-small cell lung cancer.

973. The method according to any of items 1 and 455 to 746, wherein the treatment comprises one or more administrations to said individual of zoledronate/Zometa (Novartis) and/or one or more other drugs for treatment or prophylaxis of multiple myeloma or patients with documented bone metastases from solid tumours.

974. The method according to any of items 1 and 455 to 746, wherein the treatment comprises one or more administrations to said individual of one or more hormone(s).

975. The method according to any of items 1 and 455 to 746, wherein the treatment comprises one or more administrations to said individual of one or more antibiotic(s).

976. The method according to any of items 1 and 455 to 746, wherein the treatment comprises one or more administrations to said individual of one or more anaesthetic(s).

977. The method according to any of items 1 and 455 to 746, wherein the treatment comprises one or more administrations to said individual of one or more analgesic(s).

978. The method according to any of items 1 and 455 to 746, wherein the treatment comprises one or more administrations to said individual of one or more anti-fungal compound(s).

979. The method according to any of items 1 and 455 to 746, wherein the treatment comprises one or more administrations to said individual of one or more bactericide(s).

980. The method according to any of items 1 and 455 to 746, wherein the treatment comprises one or more administrations to said individual of one or more bacteriostat(s).

981. The method according to any of items 1 and 455 to 746, wherein the treatment comprises one or more administrations to said individual of one or more anti-protozoan compound(s).

982. The method according to any of items 1 and 455 to 746, wherein the treatment comprises one or more administrations to said individual of one or more anti-viral compound(s).

983. The method according to any of items 1 and 455 to 746, wherein the treatment comprises one or more administrations to said individual of one or more antihistamines (e.g., dimenhydrinate, diphenhydramine, chlorpheniramine and dexchlorpheniramine maleate).

984. The method according to any of items 1 and 455 to 746, wherein the treatment comprises one or more administrations to said individual of one or more analgesics (e.g., aspirin, codeine, morphine, dihydromorphone, oxycodone, etc.).

985. The method according to any of items 1 and 455 to 746, wherein the treatment comprises one or more administrations to said individual of one or more anti-inflammatory agents (e.g., naproxyn, diclofenac, indomethacin, ibuprofen, acetaminophen, aspirin, sulindac).

986. The method according to any of items 1 and 455 to 746, wherein the treatment comprises one or more administrations to said individual of one or more gastro-intestinal(s).

987. The method according to any of items 1 and 455 to 746, wherein the treatment comprises one or more administrations to said individual of one or more anti-emetics (e.g., metoclopramide).

988. The method according to any of items 1 and 455 to 746, wherein the treatment comprises one or more administrations to said individual of one or more anti-epileptics (e.g., phenyloin, meprobamate and nitrazepam).

989. The method according to any of items 1 and 455 to 746, wherein the treatment comprises one or more administrations to said individual of one or more vasodilators (e.g., nifedipine, papaverine, diltiazem and nicardipine).

990. The method according to any of items 1 and 455 to 746, wherein the treatment comprises one or more administrations to said individual of one or more anti-tussive agent(s).

991. The method according to any of items 1 and 455 to 746, wherein the treatment comprises one or more administrations to said individual of one or more expectorant(s) (e.g., codeine phosphate)

992. The method according to any of items 1 and 455 to 746, wherein the treatment comprises one or more administrations to said individual of one or more anti-asthmatics (e.g. theophylline).

993. The method according to any of items 1 and 455 to 746, wherein the treatment comprises one or more administrations to said individual of one or more anti-spasmodics (e.g. atropine, scopolamine).

994. The method according to any of items 1 and 455 to 746, wherein the treatment comprises one or more administrations to said individual of one or more hormones (e.g., insulin, heparin).

995. The method according to any of items 1 and 455 to 746, wherein the treatment comprises one or more administrations to said individual of one or more diuretics (e.g., ethacrynic acid, bendroflumethiazide).

996. The method according to any of items 1 and 455 to 746, wherein the treatment comprises one or more administrations to said individual of one or more anti-hypotensives (e.g., propranolol, clonidine).

997. The method according to any of items 1 and 455 to 746, wherein the treatment comprises one or more administrations to said individual of one or more bronchodilators (e.g., albuterol).

998. The method according to any of items 1 and 455 to 746, wherein the treatment comprises one or more administrations to said individual of one or more anti-inflammatory steroids (e.g., hydrocortisone, triamcinolone, prednisone).

999. The method according to any of items 1 and 455 to 746, wherein the treatment comprises one or more administrations to said individual of one or more antibiotics (e.g., tetracycline).

1000. The method according to any of items 1 and 455 to 746, wherein the treatment comprises one or more administrations to said individual of one or more antihemorrhoidal(s).

1001. The method according to any of items 1 and 455 to 746, wherein the treatment comprises one or more administrations to said individual of one or more hypnotic(s).

1002. The method according to any of items 1 and 455 to 746, wherein the treatment comprises one or more administrations to said individual of one or more psychotropic(s).

1003. The method according to any of items 1 and 455 to 746, wherein the treatment comprises one or more administrations to said individual of one or more antidiarrheal(s).

1004. The method according to any of items 1 and 455 to 746, wherein the treatment comprises one or more administrations to said individual of one or more mucolytic(s).

1005. The method according to any of items 1 and 455 to 746, wherein the treatment comprises one or more administrations to said individual of one or more sedative(s).

1006. The method according to any of items 1 and 455 to 746, wherein the treatment comprises one or more administrations to said individual of one or more decongestant(s).

1007. The method according to any of items 1 and 455 to 746, wherein the treatment comprises one or more administrations to said individual of one or more laxative(s).

1008. The method according to any of items 1 and 455 to 746, wherein the treatment comprises one or more administrations to said individual of one or more antacid(s).

1009. The method according to any of items 1 and 455 to 746, wherein the treatment comprises one or more administrations to said individual of one or more vitamin(s).

1010. The method according to any of items 1 and 455 to 746, wherein the treatment comprises one or more administrations to said individual of one or more stimulant(s) (including appetite suppressants such as phenylpropanolamine).

1011. The method according to any of items 1 and 455 to 746, wherein the treatment comprises one or more administrations to said individual of flurazepam.

1012. The method according to any of items 1 and 455 to 746, wherein the treatment comprises one or more administrations to said individual of nimetazepam.

1013. The method according to any of items 1 and 455 to 746, wherein the treatment comprises one or more administrations to said individual of nitrazepam.

1014. The method according to any of items 1 and 455 to 746, wherein the treatment comprises one or more administrations to said individual of perlapine.

1015. The method according to any of items 1 and 455 to 746, wherein the treatment comprises one or more administrations to said individual of estazolam.

1016. The method according to any of items 1 and 455 to 746, wherein the treatment comprises one or more administrations to said individual of haloxazolam.

1017. The method according to any of items 1 and 455 to 746, wherein the treatment comprises one or more administrations to said individual of sodium valproate.

1018. The method according to any of items 1 and 455 to 746, wherein the treatment comprises one or more administrations to said individual of sodium cromoglycate.

1019. The method according to any of items 1 and 455 to 746, wherein the treatment comprises one or more administrations to said individual of primidone.

1020. The method according to any of items 1 and 455 to 746, wherein the treatment comprises one or more administrations to said individual of alclofenac.

1021. The method according to any of items 1 and 455 to 746, wherein the treatment comprises one or more administrations to said individual of perisoxal citrate.

1022. The method according to any of items 1 and 455 to 746, wherein the treatment comprises one or more administrations to said individual of clidanac.

1023. The method according to any of items 1 and 455 to 746, wherein the treatment comprises one or more administrations to said individual of indomethacin.

1024. The method according to any of items 1 and 455 to 746, wherein the treatment comprises one or more administrations to said individual of sulpyrine.

1025. The method according to any of items 1 and 455 to 746, wherein the treatment comprises one or more administrations to said individual of flufenamic acid.

1026. The method according to any of items 1 and 455 to 746, wherein the treatment comprises one or more administrations to said individual of ketoprofen.

1027. The method according to any of items 1 and 455 to 746, wherein the treatment comprises one or more administrations to said individual of sulindac.

1028. The method according to any of items 1 and 455 to 746, wherein the treatment comprises one or more administrations to said individual of metiazinic acid.

1029. The method according to any of items 1 and 455 to 746, wherein the treatment comprises one or more administrations to said individual of tolmetin sodium.

1030. The method according to any of items 1 and 455 to 746, wherein the treatment comprises one or more administrations to said individual of fentiazac.

1031. The method according to any of items 1 and 455 to 746, wherein the treatment comprises one or more administrations to said individual of naproxen.

1032. The method according to any of items 1 and 455 to 746, wherein the treatment comprises one or more administrations to said individual of fenbufen.

1033. The method according to any of items 1 and 455 to 746, wherein the treatment comprises one or more administrations to said individual of protizinic acid.
1034. The method according to any of items 1 and 455 to 746, wherein the treatment comprises one or more administrations to said individual of pranoprofen.
1035. The method according to any of items 1 and 455 to 746, wherein the treatment comprises one or more administrations to said individual of flurbiprofen.
1036. The method according to any of items 1 and 455 to 746, wherein the treatment comprises one or more administrations to said individual of diclofenac sodium.
1037. The method according to any of items 1 and 455 to 746, wherein the treatment comprises one or more administrations to said individual of mefenamic acid.
1038. The method according to any of items 1 and 455 to 746, wherein the treatment comprises one or more administrations to said individual of ibuprofen.
1039. The method according to any of items 1 and 455 to 746, wherein the treatment comprises one or more administrations to said individual of aspirin.
1040. The method according to any of items 1 and 455 to 746, wherein the treatment comprises one or more administrations to said individual of dextran sulfate.
1041. The method according to any of items 1 and 455 to 746, wherein the treatment comprises one or more administrations to said individual of carindacillin sodium.
1042. The method according to any of items 1 and 455 to 746, wherein the treatment comprises one or more administrations to said individual of a physiologically active polypeptide.
1043. The method according to any of items 1 and 455 to 746, wherein the treatment comprises one or more administrations to said individual of insulin.
1044. The method according to any of items 1 and 455 to 746, wherein the treatment comprises one or more administrations to said individual of somatostatin.
1045. The method according to any of items 1 and 455 to 746, wherein the treatment comprises one or more administrations to said individual of somatostatin derivatives.
1046. The method according to any of items 1 and 455 to 746, wherein the treatment comprises one or more administrations to said individual of growth hormone.
1047. The method according to any of items 1 and 455 to 746, wherein the treatment comprises one or more administrations to said individual of prolactin.
1048. The method according to any of items 1 and 455 to 746, wherein the treatment comprises one or more administrations to said individual of adrenocorticotrophic hormone.
1049. The method according to any of items 1 and 455 to 746, wherein the treatment comprises one or more administrations to said individual of melanocyte stimulating hormone.
1050. The method according to any of items 1 and 455 to 746, wherein the treatment comprises one or more administrations to said individual of thyrotropin releasing hormone, its salts or its derivatives.
1051. The method according to any of items 1 and 455 to 746, wherein the treatment comprises one or more administrations to said individual of thyroid stimulating hormone.
1052. The method according to any of items 1 and 455 to 746, wherein the treatment comprises one or more administrations to said individual of luteinizing hormone.
1053. The method according to any of items 1 and 455 to 746, wherein the treatment comprises one or more administrations to said individual of follicle stimulating hormone.
1054. The method according to any of items 1 and 455 to 746, wherein the treatment comprises one or more administrations to said individual of vasopressin.
1055. The method according to any of items 1 and 455 to 746, wherein the treatment comprises one or more administrations to said individual of vasopressin derivatives.
1056. The method according to any of items 1 and 455 to 746, wherein the treatment comprises one or more administrations to said individual of oxytocin.
1057. The method according to any of items 1 and 455 to 746, wherein the treatment comprises one or more administrations to said individual of carcitonin.
1058. The method according to any of items 1 and 455 to 746, wherein the treatment comprises one or more administrations to said individual of parathyroid hormone.
1059. The method according to any of items 1 and 455 to 746, wherein the treatment comprises one or more administrations to said individual of glucagon.
1060. The method according to any of items 1 and 455 to 746, wherein the treatment comprises one or more administrations to said individual of gastrin.
1061. The method according to any of items 1 and 455 to 746, wherein the treatment comprises one or more administrations to said individual of secretin.
1062. The method according to any of items 1 and 455 to 746, wherein the treatment comprises one or more administrations to said individual of pancreozymin.
1063. The method according to any of items 1 and 455 to 746, wherein the treatment comprises one or more administrations to said individual of cholecystokinin.
1064. The method according to any of items 1 and 455 to 746, wherein the treatment comprises one or more administrations to said individual of angiotensin.
1065. The method according to any of items 1 and 455 to 746, wherein the treatment comprises one or more administrations to said individual of human placental lactogen.
1066. The method according to any of items 1 and 455 to 746, wherein the treatment comprises one or more administrations to said individual of human chorionic gonadotropin.
1067. The method according to any of items 1 and 455 to 746, wherein the treatment comprises one or more administrations to said individual of enkephalin.
1068. The method according to any of items 1 and 455 to 746, wherein the treatment comprises one or more administrations to said individual of enkephalin derivatives.
1069. The method according to any of items 1 and 455 to 746, wherein the treatment comprises one or more administrations to said individual of endorphin.
1070. The method according to any of items 1 and 455 to 746, wherein the treatment comprises one or more administrations to said individual of interferon (in one or more of the forms alpha, beta, and gamma).
1071. The method according to any of items 1 and 455 to 746, wherein the treatment comprises one or more administrations to said individual of urokinase.
1072. The method according to any of items 1 and 455 to 746, wherein the treatment comprises one or more administrations to said individual of kallikrein.
1073. The method according to any of items 1 and 455 to 746, wherein the treatment comprises one or more administrations to said individual of thymopoietin.

1074. The method according to any of items 1 and 455 to 746, wherein the treatment comprises one or more administrations to said individual of thymosin.
1075. The method according to any of items 1 and 455 to 746, wherein the treatment comprises one or more administrations to said individual of motilin.
1076. The method according to any of items 1 and 455 to 746, wherein the treatment comprises one or more administrations to said individual of dynorphin.
1077. The method according to any of items 1 and 455 to 746, wherein the treatment comprises one or more administrations to said individual of bombesin.
1078. The method according to any of items 1 and 455 to 746, wherein the treatment comprises one or more administrations to said individual of neurotensin.
1079. The method according to any of items 1 and 455 to 746, wherein the treatment comprises one or more administrations to said individual of caerulein.
1080. The method according to any of items 1 and 455 to 746, wherein the treatment comprises one or more administrations to said individual of bradykinin.
1081. The method according to any of items 1 and 455 to 746, wherein the treatment comprises one or more administrations to said individual of substance P. kyotorophin.
1082. The method according to any of items 1 and 455 to 746, wherein the treatment comprises one or more administrations to said individual of nerve growth factor.
1083. The method according to any of items 1 and 455 to 746, wherein the treatment comprises one or more administrations to said individual of polymyxin B. colistin.
1084. The method according to any of items 1 and 455 to 746, wherein the treatment comprises one or more administrations to said individual of gramicidin.
1085. The method according to any of items 1 and 455 to 746, wherein the treatment comprises one or more administrations to said individual of bacitracin.
1086. The method according to any of items 1 and 455 to 746, wherein the treatment comprises one or more administrations to said individual of bleomycin.
1087. The method according to any of items 1 and 455 to 746, wherein the treatment comprises one or more administrations to said individual of neocarzinostatin.
1088. The method according to any of items 1 and 455 to 746, wherein the treatment comprises one or more administrations to said individual of one or more polysaccharide(s) such as heparin.
1089. The method according to any of items 1 and 455 to 746, wherein the treatment comprises one or more administrations to said individual of one or more antitumor agent(s) such as lentinan.
1090. The method according to any of items 1 and 455 to 746, wherein the treatment comprises one or more administrations to said individual of zymosan.
1091. The method according to any of items 1 and 455 to 746, wherein the treatment comprises one or more administrations to said individual of PS-K (krestin).
1092. The method according to any of items 1 and 455 to 746, wherein the treatment comprises one or more administrations to said individual of one or more aminoglycoside(s) such as e.g. gentamycin, streptomycin, kanamycin, dibekacin, paromomycin, kanendomycin, lipidomycin, tobramycin, amikacin, fradiomycin and sisomicin.
1093. The method according to any of items 1 and 455 to 746, wherein the treatment comprises one or more administrations to said individual of one or more beta-lactam antibiotic(s) such as e.g. a penicillin, such as e.g. sulbenicillin, mecillinam, carbenicillin, piperacillin and ticarcillin, thienamycin.
1094. The method according to any of items 1 and 455 to 746, wherein the treatment comprises one or more administrations to said individual of one or more cephalosporins such as cefotiam, cefsulodine, cefmenoxime, cefmetazole, cefazolin, cefotaxime, cefoperazone, ceftizoxime and moxalactam.
1095. The method according to any of items 1 and 455 to 746, wherein the treatment comprises one or more administrations to said individual of one or more nucleic acid drug(s) such as e.g. citicoline and similar antitumor agents, for example cytarabine and 5-FU (5-fluorouracil).
1096. The method according to any of items 1 and 455 to 746, wherein the treatment comprises one or more administrations to said individual of one or more medicament(s) suitable for vaginal administration such as contraceptives, hormones, antibiotics, anaesthetics, analgesics, contraction-preventers, anti-mycotica, bactericides, bacteriostats, anti-protozoan compounds, anti-viral compounds, and compositions for uterus contraction.
1097. The method according to any of items 1 and 455 to 746, wherein the treatment comprises one or more administrations to said individual of one or more dermatological medicaments such as antimycotica, antipruritic compositions, dermoprotective compositions.
1098. The method according to any of items 1 and 455 to 746, wherein the treatment comprises one or more administrations to said individual of one or more medicaments for administration in the ear (otogenic administration) such as antibiotics, corticosteroids, local anaesthetics, and analgesics.
1099. The method according to any of items 1 and 455 to 746, wherein the treatment comprises one or more administrations to said individual of one or more medicaments for nasal administration such as haemostatica, anti-allergenic compounds, antihistamines, anticholinergica, adrenergic (detumescent) compounds, and local analgesics.
1100. The method according to any of items 1 and 455 to 746, wherein the treatment comprises one or more administrations to said individual of one or more medicaments with local effects.
1101. The method according to any of items 1 and 455 to 746, wherein the treatment comprises one or more administrations to said individual of one or more medicaments with systemic effects.
1102. The method according to any of items 1 and 455 to 746, wherein the treatment comprises one or more administrations to said individual of at least one medicament that has a local effect and essentially does not have any systemic effects.
1103. The method according to any of items 1 and 455 to 746, wherein the treatment comprises one or more administrations to said individual of one or more medicament(s).
1104. The method according to item 1103, wherein the one or more medicament(s) are encapsulated.
1105. The method according to item 1103, wherein the one or more medicament(s) are encapsulated inside a microcapsule.
1106. The method according to item 1105, wherein the microcapsule comprises hydrophilic material.
1107. The method according to item 1105, wherein the microcapsule comprises hydrophobic material.

1108. The method according to item 1105, wherein the microcapsule comprises a coating material.
1109. The method according to item 1108, wherein the coating material prevents agglomeration or sticking of the microcapsules.
1110. The method according to item 1108, wherein the coating material prevents evaporation of the medicament and/or a solvent comprising the medicament inside the microcapsule.
1111. The method according to item 1108, wherein the coating material provide the microcapsule with an affinity for specific cells or tissues (an affinity-coating).
1112. The method according to item 1111, wherein the affinity-coating comprises one or more specific amino-acid sequences.
1113. The method according to item 1111, wherein the affinity-coating comprises one or more anti-bodies.
1114. The method according to item 1111, wherein the affinity-coating comprises one or more parts of antibodies having an affinity for specific proteins.
1115. The method according to item 1111, wherein the affinity-coating results in drug-delivery targeted to exactly those cells (e.g. cancer cells, metastases) to which the drug should be administered.
1116. The method according to any of items 1 and 455 to 746, wherein the analysis comprises one or more microcapsule(s) for diagnostic use.
1117. The method according to item 1116, wherein the one or more microcapsule(s) comprises one or more compound(s) suitable for labelling one or more target cell(s).
1118. The method according to item 1105 and 1116, wherein the one or more microcapsule(s) comprises one or more collloid(s).
1119. The method according to item 1105 and 1116, wherein the one or more microcapsule(s) comprises one or more hydrocolloid(s).
1120. The method according to item 1105 and 1116, wherein the one or more microcapsule(s) comprises gelatine.
1121. The method according to item 1105 and 1116, wherein the one or more microcapsule(s) comprises one or more exudates such as gum arabic, tragacanth, gum karya, gum ghatti.
1122. The method according to item 1105 and 1116, wherein the one or more microcapsule(s) comprises one or more extract(s) from seaweed such as agar, alginate, carrageenan and furcellaran.
1123. The method according to item 1105 and 1116, wherein the one or more microcapsule(s) comprises one or more extract(s) from plants such as pectin and arabinogalactan.
1124. The method according to item 1105 and 1116, wherein the one or more microcapsule(s) comprises one or more extract(s) from marine and terrestrial animals such as gelatines and other proteinaceous hydrocolloids.
1125. The method according to item 1105 and 1116, wherein the one or more microcapsule(s) comprises one or more flours from seeds such as guar, locust bean, soya bean.
1126. The method according to item 1105 and 1116, wherein the one or more microcapsule(s) comprises one or more protein(s) from seeds such as soya bean proteins.
1127. The method according to item 1105 and 1116, wherein the one or more microcapsule(s) comprises one or more flours from cereals such as starches and microcrystalline cellulose.
1128. The method according to item 1105 and 1116, wherein the one or more microcapsule(s) comprises one or more biosynthetic or fermentation derived hydrocolloids such as dextran, xanthan and curdlan.
1129. The method according to item 1105 and 1116, wherein the one or more microcapsule(s) comprises one or more chemically modified hydrocolloids such as cellulose derivatives, including methyl cellulose and other derivatives, including modified starches and low methoxyl pectin.
1130. The method according to item 1105 and 1116, wherein the one or more microcapsule(s) comprises one or more synthetic hydrocolloids such as polyvinylpyrrolidone and carboxyvinyl polymers.
1131. The method according to any of items 1 and 455 to 746, wherein the treatment comprises one or more administrations to said individual of one or more small molecule drug(s).
1132. The method according to item 1131, wherein the one or more small molecule drug(s) comprises one or more chemotherapeutic agent(s).
1133. The method according to item 1131, wherein the one or more small molecule drug(s) comprises one or more antiproliferative agent(s).
1134. The method according to item 1131, wherein the one or more small molecule drug(s) comprises one or more alkylating drugs (mechlorethamine, chlorambucil, Cyclophosphamide, Melphalan, Ifosfamide).
1135. The method according to item 1131, wherein the one or more small molecule drug(s) comprises one or more antimetabolites such as Methotrexate.
1136. The method according to item 1131, wherein the one or more small molecule drug(s) comprises one or more purine antagonists and pyrimidine antagonists (6-Mercaptopurine, 5-Fluorouracil, Cytarabile, Gemcitabine).
1137. The method according to item 1131, wherein the one or more small molecule drug(s) comprises one or more spindle poisons (Vinblastine, Vincristine, Vinorelbine, Paclitaxel).
1138. The method according to item 1131, wherein the one or more small molecule drug(s) comprises one or more podophyllotoxins (Etoposide, Irinotecan, Topotecan).
1139. The method according to item 1131, wherein the one or more small molecule drug(s) comprises one or more antibiotics (Doxorubicin, Bleomycin, Mitomycin).
1140. The method according to item 1131, wherein the one or more small molecule drug(s) comprises one or more nitrosoureas (Carmustine, Lomustine).
1141. The method according to item 1131, wherein the one or more small molecule drug(s) comprises one or more inorganic ions (Cisplatin, Carboplatin).
1142. The method according to item 1131, wherein the one or more small molecule drug(s) comprises one or more enzymes (Asparaginase).
1143. The method according to item 1131, wherein the one or more small molecule drug(s) comprises one or more angiogenesis inhibitors (Avastin).
1144. The method according to item 1131, wherein the one or more small molecule drug(s) comprises one or more hormones (Tamoxifen, Leuprolide, Flutamide, and Megestrol).
1145. The method according to item 1131, wherein the one or more small molecule drug(s) comprises Gleevec.
1146. The method according to item 1131, wherein the one or more small molecule drug(s) comprises dexamethasone.
1147. The method according to item 1131, wherein the one or more small molecule drug(s) comprises cyclophosphamide.
1148. The method according to item 1131, wherein the one or more small molecule drug(s) comprises one or more small molecule drug(s) for treatment of Alzheimer's Disease such as Aricept® and Excelon®.
1149. The method according to item 1131, wherein the one or more small molecule drug(s) comprises one or more small molecule drug(s) for treatment of Parkinson's Disease such as L-DOPA/carbidopa, entacapone, ropinrole, pramipexole, bromocriptine, pergolide, trihexephendyl, and amantadine.
1150. The method according to item 1131, wherein the one or more small molecule drug(s) comprises one or more small molecule drug(s) for treatment of Multiple Sclerosis (MS) such as beta interferon (e.g., Avonex® and Rebif®), Copaxone®, and mitoxantrone.
1151. The method according to item 1131, wherein the one or more small molecule drug(s) comprises one or more small molecule drug(s) for treatment of asthma such as albuterol and Singulair®.
1152. The method according to item 1131, wherein the one or more small molecule drug(s) comprises one or more small molecule drug(s) for treatment of schizophrenia such as zyprexa, risperdal, seroquel, and haloperidol.
1153. The method according to item 1131, wherein the one or more small molecule drug(s) comprises one or more small molecule drug(s) for treatment of inflammation such as corticosteroids, TNF blockers, IL-I RA, azathioprine, cyclophosphamide, and sulfasalazine.
1154. The method according to item 1131, wherein the one or more small molecule drug(s) comprises immunomodulatory and immunosuppressive agents such as cyclosporin, tacrolimus, rapamycin, mycophenolate mofetil, interferons, corticosteroids, cyclophosphamide, azathioprine, and sulfasalazine.
1155. The method according to item 1131, wherein the one or more small molecule drug(s) comprises one or more neurotrophic factors such as acetylcholinesterase inhibitors, MAO inhibitors, interferons, anti-convulsants, ion channel blockers, riluzole, and anti-Parkinsonian agents.
1156. The method according to item 1131, wherein the one or more small molecule drug(s) comprises one or more small molecule drug(s) for treatment of cardiovascular disease such as beta-blockers, ACE inhibitors, diuretics, nitrates, calcium channel blockers, and statins.
1157. The method according to item 1131, wherein the one or more small molecule drug(s) comprises one or more small molecule drug(s) for treatment of liver disease such as corticosteroids, cholestyramine, interferons, and anti-viral agents.
1158. The method according to item 1131, wherein the one or more small molecule drug(s) comprises one or more small molecule drug(s) for treatment of blood disorders such as corticosteroids.
1159. The method according to item 1131, wherein the one or more small molecule drug(s) comprises one or more anti-leukemic agents.
1160. The method according to item 1131, wherein the one or more small molecule drug(s) comprises one or more growth factors.
1161. The method according to item 1131, wherein the one or more small molecule drug(s) comprises one or more small molecule drug(s) for treating immunodeficiency disorders such as gamma globulin.
1162. The method according to item 114, wherein the one or more drug(s) can be selected from the list of FDA approved drugs at http://www.fda.gov/cder/cancer/druglistframe.htm.
1163. The method according to item 114, wherein the one or more drug(s) can be selected from the list of drugs included in The Merck Manual, Seventeenth Ed. 1999 (the entire contents of which are hereby incorporated by reference).
1164. The method according to any of items 1 and 455 to 746, wherein the treatment comprises organ and/or tissue transplantation.
1165. The method according to item 1164, wherein the organ transplantation comprises transplantation of heart.
1166. The method according to item 1164, wherein the organ transplantation comprises transplantation of kidney(s).
1167. The method according to item 1164, wherein the organ transplantation comprises transplantation of liver.
1168. The method according to item 1164, wherein the organ transplantation comprises transplantation of lung(s).
1169. The method according to item 1164, wherein the organ transplantation comprises transplantation of pancreas.
1170. The method according to item 1164, wherein the organ transplantation comprises transplantation of penis.
1171. The method according to item 1164, wherein the organ transplantation comprises transplantation of intestine.
1172. The method according to item 1164, wherein the tissue transplantation comprises transplantation of bones.
1173. The method according to item 1164, wherein the tissue transplantation comprises transplantation of tendons.
1174. The method according to item 1164, wherein the tissue transplantation comprises transplantation of cornea.
1175. The method according to item 1164, wherein the tissue transplantation comprises transplantation of heart valve(s).
1176. The method according to item 1164, wherein the tissue transplantation comprises transplantation of vein(s).
1177. The method according to item 1164, wherein the tissue transplantation comprises transplantation of skin.
1178. The method according to item 1164, wherein the organ and/or tissue transplantation comprises autograft transplantation.
1179. The method according to item 1164, wherein the organ and/or tissue transplantation comprises allograft transplantation.
1180. The method according to item 1164, wherein the organ and/or tissue transplantation comprises isograft transplantation.
1181. The method according to item 1164, wherein the organ and/or tissue transplantation comprises xenograft transplantation.
1182. The method according to item 1164, wherein the organ and/or tissue transplantation comprises split transplants.
1183. The method according to item 1164, wherein the organ and/or tissue transplantation comprises domino transplants.
1184. The method according to any of items 1 and 455 to 746, wherein the undesired state of said individual is one or more transplantation related disorders.
1185. The method according to item 1184, wherein the one or more transplantation related disorders comprises acute or chronic Graft-versus-host disease (GVHD).
1186. The method according to item 1184, wherein the one or more transplantation related disorders comprises opportunistic infections such as Viral infections (e.g. Epstein-Barr (EBV), Hepatitis C (HCV), Cytomegalovirus (CMV)).
1187. The method according to item 1184, wherein the one or more transplantation related disorders comprises infections such as Bacterial infections (e.g. *Staphylococcus aureus, Streptococcus pyogenes, Pseudomonas aeruginosa, Acinetobacter baumannii*).

1188. The method according to item 1184, wherein the one or more transplantation related disorders comprises infections such as Fungal infections (e.g. *Pneumocystis jirovecii, Candida albicans, Aspergillus* sp.).
1189. The method according to item 1184, wherein the one or more transplantation related disorders comprises opportunistic infections such as Parasitic infections such as *Toxoplasma gondii*.
1190. The method according to item 1184, wherein the one or more transplantation related disorders related to a medicine-induced suppressed immune system includes such as Transplant-related cancers including Immunodeficiency-related B-cell disorders or Post-transplant lymphoproliferative disorders (PTLD), Kaposi's Sarcoma, Solid tumors (e.g. of the skin, mouth and lungs) or any other secondary cancer related to transplantation or its concurrent medicinal treatment.
1191. The method according to item 1184, wherein the one or more transplantation related disorders related to a medicine-induced suppressed immune system includes Toxoplasmosis, *Pneumocystis* pneumonia, Candidiasis or 'thrush', Pneumonia, Meningitis, Osteomyelitis endocarditis, Toxic shock syndrome (TSS), Septicemia, Pharyngitis, Impetigo, Necrotizing fasciitis, Scarlet fever, Skin infections (such as pimples, boils, cellulitis folliculitis, furuncles, carbuncles, erysipelas, scalded skin syndrome and abscesses).
1192. The method according to item 1184, wherein the one or more transplantation related disorders related to a medicine-induced suppressed immune system includes Serum sickness (a reaction to proteins in antiserum derived from an animal source, e.g. polyclonal antibodies—a type of hypersensitivity that typically develops up to ten days after exposure to the antiserum).
1193. The method according to item 1184, wherein the one or more transplantation related disorders related to a medicine-induced suppressed immune system includes Immune complex glomerulonephritis.
1194. The method according to item 1184, wherein the one or more transplantation related disorders related to a medicine-induced suppressed immune system includes Delayed hypersensitivity (e.g. tuberculin skin reaction).
1195. The method according to item 1184, wherein the one or more transplantation related disorders related to a medicine-induced suppressed immune system includes Infertility.
1196. The method according to item 1184, wherein the one or more transplantation related disorders related to a medicine-induced suppressed immune system includes Cataracts (clouding of the lens of the eye, which causes loss of vision).
1197. The method according to item 1184, wherein the one or more transplantation related disorders related to a medicine-induced suppressed immune system includes Hormone changes.
1198. The method according to item 1184, wherein the one or more transplantation related disorders related to a medicine-induced suppressed immune system includes Risk of bleeding (due to destruction of platelets).
1199. The method according to any of items 1 and 455 to 746, wherein the treatment comprising treatment of one or more transplantation related disorders.
1200. The method according to any of items 1 and 455 to 746, wherein the treatment comprising treatment of one or more transplantation related disorders by one or more immunosuppressive drugs.
1201. The method according to item 1200, wherein the one or more immunosuppressive drugs comprises Glucocorticoids (e.g. cortisol, cortisone acetate, prednisone, prednisolone, methylprednisolone, dexamethasone, betamethasone, triamcinolone, beclometasone, fludrocortisone acetate, deoxycorticosterone acetate, aldosterone).
1202. The method according to item 1200, wherein the one or more immunosuppressive drugs comprises Cytostatics (e.g. Alkylating agents such as cyclophosphamide, nitrosoureas, platinum compounds; Antimetabolites such as folic acid analogues (e.g. methotrexate), purine analogues (e.g. azathioprine, mycophenolate, mercaptopurine), pyrimidine analogues, protein synthesis inhibitor; and Cytotoxic antibiotics such as dactinomycin, anthracyclines, mitomycin C, bleomycin, mithramycin).
1203. The method according to item 1200, wherein the one or more immunosuppressive drugs comprises Antibodies (polyclonal, monoclonal).
1204. The method according to item 1200, wherein the one or more immunosuppressive drugs comprises Drugs acting on immunophilins (e.g. Cyclosporin (a calcineurin inhibitor); Tacrolimus (a calcineurin inhibitor, macrolide); Sirolimus (a macrolide)).
1205. The method according to item 1200, wherein the one or more immunosuppressive drugs comprises drugs selected from the group consisting of Interferons; Opioids; TNF-binding proteins; Mycophenolate; Small biological agents (e.g. FTY720).
1206. The method according to any of the previous items, wherein the undesired state of said individual is a neoplastic disease.
1207. The method according to item 1206, wherein the neoplastic disease is characterized by one or more tumor antigens selected from the group consisting of alpha-actinin-4, ARTC1, BCR-ABL fusion protein (b3a2), B-RAF, CASP-5, CASP-8, beta-catenin, Cdc27, CDK4, CDKN2A, COA-1, dek-can fusion protein, EFTUD2, Elongation factor 2, ETV6-AML1 fusion protein, FLT3-ITD, FN1, GPNMB, LDLR-fucosyl transferase AS fusion protein, HLA-A2$^d$, HLA-A11$^d$, hsp70-2, KIAAO205, MART2, ME1, MUM-1$^f$, MUM-2, MUM-3, neo-PAP, Myosin class I, NFYC, OGT, OS-9, P53, pml-RARalpha fusion protein, PRDX5, PTPRK, K-ras, N-ras, RBAF600, SIRT2, SNRPD1, SYT-SSX1 or -SSX2 fusion protein, Triosephosphate Isomerase, BAGE-1, GAGE-1,2,8, GAGE-3,4,5,6,7, GnTV$^f$, HERV-K-MEL, KK-LC-1, KM-HN-1, LAGE-1, MAGE-A1, MAGE-A2, MAGE-A3, MAGE-A4, MAGE-A6, MAGE-A9, MAGE-A10, MAGE-A12, MAGE-C2, mucin$^k$, NA-88, NY-ESO-1/LAGE-2, SAGE, Sp17, SSX-2, SSX-4, TRAG-3, and TRP2-INT2$^g$.
1208. The method according to item 1206, wherein the neoplastic disease is characterized by one or more one or more mutations in one or more the genes or genes encoding the proteins in the group consisting of 101F6, ABR, ADPRTL3, ANP32C, ANP32D, APC2, APC, ARF, ARHGAP8, ARHI, AT1G14320, ATM, ATP8A2, AXUD1, BAP1, BECN1, BIN1, BRCA1, BRCA2, BTG1, BTG2, C1orf11, C5orf4, C5orf7, Cables, CACNA2D2, CAP-1, CARS, CAV1, CD81, CDC23, CDK2AP1, CDKN1A, CDKN1C, CDKN2A, CDKN2B, CDKN2X, Ciao1-pending, CLCA2, CREBL2, CTNNA1, CUL2, CW17R, DAB2, DAF-18, D-APC, DBC2, DCC, DDX26, DEC1, DLC1, DLEC1, DLEU1, DLEU2, DLG1, DLGH1, DLGH3, DMBT1, DNAJA3, DOC-1, DPC4, DPH2L, EGR1, FABP3, FAT, FGL1, FHIT, FLJ10506, FOXD1, FOXP1, FT, FUS1, FUS2, GAK, GAS1, GAS11, GLD-1, GLTSCR1, GLTSCR2, GRC5, GRLF1, HDAC3, HEMK, HIC1, HRG22, HSAL2, HTS1, HYAL1, HYAL2, IFGBP7, IGSF4, ING1, ING1L, ING4, I(2)tid, I(3)mbn, I(3)mbt, LAPSER1, LATS1, LATS2, LDOC1, LOH11CR2A, LRP1B, LUCA3, MAD, MAP2K4, MAPKAPK3, MCC, MDC, MEN1, ML-1, MLH1, MRVI1, MTAP, MXI1, NAPIL4, NBR2, NF1, NF2, NORE1, NPR2L, NtRb1, OVCA2, PDGFRL, PHEMX, pHyde, PIG8, PIK3CG, PINX1, PLAGL1, PRDM2, PTCH, PTEN, PTPNI3, PTPRG, RASSF1, RB1, RBBP7, RBX1, RBM6, RECK, RFP2, RIS1, RPL10, RPS29, RRM1, S100A2, SEMA3B, SF1, SFRP1, SLC22A1L, SLC26A3, SMARCA4, ST7, ST7L, ST13, ST14, STIM1, TCEB2, THW, TIMP3, TP53, TP63, TRIM8, TSC2, TSG101, TSSC1, TSSC3, TSSC4, VHL, Vhlh, WFDC1, WIT-1, WT1, and WWOX.

1209. The method according to item 1206, wherein the neoplastic disease is selected from the group consisting of Acute Lymphoblastic Leukemia, Acute Myeloid Leukemia, Adrenocortical Carcinoma, AIDS-Related Cancers, AIDS-Related Lymphoma, Anal Cancer, Astrocytoma (e.g. Childhood Cerebellar or Childhood Cerebral), Basal Cell Carcinoma, Extrahepatic Bile Duct Cancer, Bladder Cancer, Bone Cancer, Osteosarcoma/Malignant Fibrous Histiocytoma, Brain Stem Glioma, Brain Tumor, Breast Cancer, Male Breast Cancer, Bronchial Adenomas/Carcinoids, Burkitt's Lymphoma, Carcinoid Tumor, Carcinoma of Unknown Primary, Primary Central Nervous System Lymphoma, Cerebral Astrocytoma/Malignant Glioma, Cervical Cancer, Childhood Cancers, Chronic Lymphocytic Leukemia, Chronic Myelogenous Leukemia, Chronic Myeloproliferative Disorders, Colon Cancer, Cutaneous T-Cell Lymphoma, Endometrial Cancer, Ependymoma (such as Childhood Ependymoma), Esophageal Cancer, Ewing's Family of Tumors, Extracranial Germ Cell Tumor (such as Childhood Extracranial Germ Cell Tumor), Extragonadal Germ Cell Tumor, Eye Cancer (Intraocular Melanoma or Retinoblastoma), Gallbladder Cancer, Gastric (Stomach) Cancer, Gastrointestinal Carcinoid Tumor, Gestational Trophoblastic Tumor, Glioma, Hairy Cell Leukemia, Head and Neck Cancer, Hepatocellular (Liver) Cancer, Hodgkin's Lymphoma, Hypopharyngeal Cancer, Hypothalamic and Visual Pathway Glioma (such as Childhood Hypothalamic and Visual Pathway Glioma), Intraocular Melanoma, Islet Cell Carcinoma (Endocrine Pancreas), Kaposi's Sarcoma, Kidney (Renal Cell) Cancer, Laryngeal Cancer, Lip and Oral Cavity Cancer, Lung Cancer (Non-Small Cell or Small Cell), Lymphoma (such as AIDS-Related Lymphoma, Burkitt's Lymphoma, Cutaneous T-Cell Lymphoma, Non-Hodgkin's Lymphoma), Macroglobulinemia (such as Waldenstrom's Macroglobulinemia), Malignant Fibrous Histiocytoma of Bone/Osteosarcoma, Medulloblastoma (such as Childhood Medulloblastoma), Melanoma, Merkel Cell Carcinoma, Mesothelioma (such as Adult Malignant Mesothelioma or childhood Mesothelioma), Metastatic Squamous Neck Cancer with Occult Primary, Multiple Endocrine Neoplasia Syndrome (such as occurring in childhood), Multiple Myeloma/Plasma Cell Neoplasm, Mycosis Fungoides, Myelodysplastic Syndromes, Myelodysplastic/Myeloproliferative Diseases, Myeloma (such as Multiple Myeloma), Chronic myeloproliferative disorders, Nasal Cavity and Paranasal Sinus Cancer, Nasopharyngeal Cancer, Nasopharyngeal Cancer (such as Childhood Nasopharyngeal Cancer), Neuroblastoma, Oropharyngeal Cancer, Osteosarcoma/Malignant Fibrous Histiocytoma of Bone, Ovarian Cancer (such as Childhood Ovarian Cancer), Ovarian Epithelial Cancer, Ovarian Germ Cell Tumor, Ovarian Low Malignant Potential Tumor, Pancreatic Cancer, Pancreatic Cancer, Paranasal Sinus and Nasal Cavity Cancer, Parathyroid Cancer, Penile Cancer, Pheochromocytoma, Pineoblastoma and Supratentorial Primitive Neuroectodermal Tumors, Pituitary Tumor, Pleuropulmonary Blastoma, Prostate Cancer, Renal Pelvis and Ureter Transitional Cell Cancer, Retinoblastoma, Rhabdomyosarcoma (such as Childhood Rhabdomyosarcoma), Salivary Gland Cancer, Adult-onset soft tissue Sarcoma, Soft Tissue Sarcoma (such as Childhood Soft Tissue Sarcoma), uterine Sarcoma, Sezary Syndrome, Skin Cancer (such as non-Melanoma skin cancer), Merkel Cell Skin Carcinoma, Small Intestine Cancer, Supratentorial Primitive Neuroectodermal Tumors (such as occurring in Childhood), Cutaneous T-Cell Lymphoma, Testicular Cancer, Thymoma and Thymic Carcinoma, Thyroid Cancer, Transitional Cell Cancer of the Renal Pelvis and Ureter, Trophoblastic Tumor (such as Gestational Trophoblastic Tumor), Urethral Cancer, Endometrial uterine cancer, Uterine Sarcoma, Vaginal Cancer, Visual Pathway and Hypothalamic Glioma (such as Childhood Visual Pathway and Hypothalamic Glioma), Waldenstrom's Macroglobulinemia or Wilms' Tumor.

1210. The method according to item 1206, wherein the neoplastic disease is terminal cancer.

1211. The method according to any of the previous items, wherein the undesired state of said individual is selected from the group selected from A-alphalipoprotein Neuropathy, Tangier Disease, Abdominal Cramps, Colic, Abdominal Delivery, Cesarean Section, Abdominal Injuries, Abdominal Pain, Abortion Induced, Abortion Spontaneous, Abscess, Abscess Amebic, Amebiasis, Abscess Pulmonary, Lung Abscess, Abscess Retropharyngeal, Retropharyngeal Abscess, Acantholysis Bullosa, Epidermolysis Bullosa, Acariasis, Mite Infestations, Achalasia Esophageal, Esophageal Achalasia, Achondroplasia, Achromatopsia, Color Vision Defects, Acid-Base Imbalance, Acidosis Diabetic, Diabetic Ketoacidosis, Acne, Acne Vulgaris, Acne Vulgaris, Neuroma Acoustic, Acquired Childhood Aphasia with Convulsive Disorder, Landau-Kleffner Syndrome, Acquired Facial Neuropathy, Facial Nerve Diseases, Acquired Hyperostosis Syndrome, Acquired Immunodeficiency Syndrome, Acrocephalosyndactylia, Acrocephaly, Craniosynostoses, Acrodysplasia V, Langer-Giedion Syndrome, Acromegaly, Actinic Reticuloid Syndrome, Photosensitivity Disorders, *Actinomyces* Infections, Actinomycosis, Action Tremor, Tremor, Acute Autoimmune Neuropathy, Guillain-Barre Syndrome, Acute Confusional Migraine, Migraine Disorders, Acute Confusional Senile Dementia, Alzheimer Disease, Acute Inflammatory Demyelinating Polyradiculoneuropathy, Guillain-Barre Syndrome, Acute Inflammatory Polyneuropathy, Acute Zonal Occult Outer Retinopathy, Adam-Stokes Disease, Arrhythmia, Addison Disease, Addison's Anemia, Anemia, Pernicious, Adenitis, Lymphadenitis, Adenohypophyseal Diseases, Pituitary Diseases, Adenohypophyseal Hyposecretion, Hypopituitarism, Adenoma, Adenoma Basal Cell, Adenoma beta-Cell, Insulinoma, Adenoma Follicular, Adenoma Microcystic, Adenoma Monomorphic, Adenoma Papillary, Adenoma Trabecular, Adenomatous Polyposis Coli, Adenomyosis, Endometriosis, Adenomyosis, Adenoviridae Infections, Adenovirus Infections, Adenoviridae Infections, Adhesions Pelvic, Adhesive Capsulitis, Bursitis, Adiadochokinesis, Cerebellar Ataxia, Adie Syndrome, Adiposis Dolorosa, Adnexitis, Pelvic Inflammatory Disease, Adrenal Gland Diseases, Adrenal Hyperplasia Congenital, Adrenoleukodystrophy, Adrenoleukodystrophy Neonatal, Peroxisomal Disorders, Adrenomyeloneuropathy, Adrenoleukodystrophy, Affective Psychosis Bipolar, Bipolar Disorder, Afferent Pupillary Defect, Afibrinogenemia, African Lymphoma, Burkitt Lymphoma, African Sleeping Sickness, Trypanosomiasis, African, Agammaglobulinemia, Aganglionosis Colonic, Hirschsprung Disease, Age-Related Osteoporosis, Osteoporosis, Aggression, Agnogenic Myeloid Metaplasia, Myeloid Metaplasia, Agnosia, Agnosia for Faces, Prosopagnosia, Aicardi Syndrome, AIDP, AIDS, Acquired Immunodeficiency Syndrome, Airflow Obstruction Chronic, Pulmonary Disease, Chronic Obstructive, Airsickness, Motion Sickness, Airway Obstruction, Alagille Syndrome Alastrim, Smallpox, Albers-Schoenberg Disease, Osteopetrosis, Albinism, Albinism Ocular, Albright's Syndrome, Fibrous Dysplasia, Polyostotic, Aldosteronism, Hyperaldosteronism, Aldrich Syndrome, Wiskott-Aldrich Syndrome, Alexander Disease, Alexia, Dyslexia, Algodystrophy, Reflex Sympathetic Dystrophy, Type I Complex Regional Pain Syndrome, Alkalosis, Alkaptonuria, Allergic Angiitis, Churg-Strauss Syndrome, Allergic Granulomatosis, Allergic Granulomatous Angiitis, Allergic Granulomatosis, Allergic Purpura, Purpura, Schoenlein-Henoch, Allergy, Allergy Latex, Latex Hypersensitivity, Alobar Holoprosencephaly, Holoprosencephaly, Alopecia, Alopecia Androgenetic, Alpers Syndrome, Diffuse Cerebral Sclerosis of Schilder, alpha 1-Antitrypsin Deficiency, alpha-Mannosidosis, Alphavirus Infections, Alport's Syndrome, Nephritis, Hereditary Alport's Syndrome, ALS, Amyotrophic Lateral Sclerosis, Alstrom Syndrome, Altitude Sickness, Alveolitis Fibrosing, Pulmonary Fibrosis, Alzheimer Disease, Amaurosis, Blindness, Amaurosis Fugax, Amblyopia, Ambulation Disorders Neurologic, Gait Disorders Neurologic, Amebiasis, Ameboma, Amebiasis, Ametropia, Amino Acid Metabolism Inborn Errors, Amino Acid Transport Disorder Neutral, Hartnup Disease, Amino Acidopathies Congenital, Amnesia, Amniotic Band Syndrome, Amniotic Bands, Amniotic Band Syndrome, Amoebiasis, Amphibian Diseases, Amputation Intrauterine, Amniotic Band Syndrome, Amyloidosis, Amyoplasia Congenita, Arthrogryposis, Amyotonia Congenita, Neuromuscular Diseases, Amyotrophic Lateral Sclerosis, Amyotrophy Neuralgic, Brachial Plexus Neuritis, Parsonage-Turner Syndrome, Analgesia, Analphalipoproteinemia, Tangier Disease, Anaphylactic Reaction, Anaphylaxis, Anaphylactoid Purpura, Anaphylaxis, Anaplasmosis, Anderson-Fabry Disease, Fabry Disease, Androgen-Insensitivity Syndrome, Anemia, Anemia Addison's, Anemia Pernicious, Anemia Aplastic, Anemia Fanconi, Fanconi Anemia, Anemia Hemolytic, Anemia Hemolytic Anemia Hemolytic Congenital Nonspherocytic, Anemia Hypoplastic, Anemia Aplastic, Anemia Iron-Deficiency, Anemia Megaloblastic, Anemia Microangiopathic, Anemia Pernicious, Anemia Sickle Cell, Anencephaly, Anesthesia, Anesthesia and Analgesia, Aneurysm, Aneurysm Cerebral, Intracranial Aneurysm, Angelman Syndrome, Angiitis, Vasculitis, Angiitis Allergic Granulomatous, Churg-Strauss Syndrome, Allergic Granulomatosis, Angina Pectoris, Angina Pectoris with Normal Coronary Arteriogram, Microvascular Angina, Angina Microvascular, Microvascular Angina, Angioedema, Angioneurotic Edema, Angiofibroma, Angiofollicular Lymphoid Hyperplasia, Giant Lymph Node Hyperplasia, Angiohemophilia, von Willebrand Disease, Angiokeratoma Corporis Diffusum, Fabry Disease, Angiolymphoid Hyperplasia with Eosinophilia, Angioma, Hemangioma, Angiomyxoma, Myxoma, Angioneurotic Edema, Angor Pectoris, Angina Pectoris, Anguilluliasis, Strongyloidiasis, Anhidrosis, Hypohidrosis, Anhidrotic Ectodermal Dysplasia, Ectodermal Dysplasia, Animal Diseases, Aniridia, Anisakiasis, Anisocoria, Anisocoria Physiologic, Anisocoria, Anisometropic Amblyopia, Amblyopia, Ankyloglossia, Annular Grooves, Amniotic Band Syndrome, Anomia, Anophthalmos, Anosmia, Olfaction, Disorders, Anoxia, Anoxia Brain, Hypoxia, Brain, Anoxic Encephalopathy, Hypoxia, Brain, Anterior Horn Cell Disease, Motor Neuron Disease, Anterior Ischemic Optic Neuropathy, Optic Neuropathy, Ischemic, Anterior Pituitary Hyposecretion Syndrome, Hypopituitarism, Anthrax, Anthropology Forensic, Forensic Anthropology, Antibiotic-Associated Colitis, Enterocolitis, Pseudomembranous, Antibody Deficiency Syndrome, Immunologic deficiency syndromes, Anti-GBM Disease, Anti-Glomerular Basement Membrane Disease, Anti-Glomerular Basement Membrane Disease, Antiphospholipid Syndrome, Antithrombin III Deficiency, Anus Diseases, Anus Prolapse, Rectal Prolapse, Anxiety Disorders, Anxiety Neuroses, Anxiety States Neurotic, Aortic Arteritis Giant Cell, Temporal Arteritis, Aortic Stenosis, Aortic Valve Stenosis, Aortic Valve Stenosis, Aortitis Giant Cell, Temporal Arteritis, Aped Syndrome, Acrocephalosyndactylia, Aphakia, Aphasia, Aphasia Acquired, Aphasia, Aphasia Acquired Epileptic, Landau-Kleffner Syndrome, Aphasia Amnesic, Anomia, Aphasia Anomic, Aphasia Nominal, Aphthae, Stomatitis, Aphthous, Aplasia Cutis Congenita, Ectodermal Dysplasia, Apnea, Apnea Sleep Central, Apoplexy, Cerebrovascular Accident, Stroke, Appendicitis, Appetite Disorders, Apraxias, Aprosencephaly, Anencephaly, Aprosodia, Speech Disorders, Arachnodactyl), Marfan Syndrome, Arachnoid Cysts, Arachnoid Diverticula, Arachnoid Cysts, Arachnoidal Cerebellar Sarcoma Circumscribed, Medulloblastoma, Arachnoiditis, Arbovirus Infections, Argentaffinoma, Carcinoid Tumor, Arhinencephaly, Holoprosencephaly, Arm Injuries, Arnold-Chiari Malformation, Arrhythmia, Arrhythmogenic Right Ventricular Cardiomyopathy, Arrhythmogenic Right Ventricular Dysplasia, Arsenic Poisoning, Arson, Firesetting Behavior, Arteriohepatic Dysplasia, Alagille Syndrome, Arteriosclerosis, Arteriosclerotic Dementia, Dementia, Vascular, Arteriovenous Malformations, Arteritis Takayasu's, Takayasu's Arteritis, Arteritis Temporal, Temporal Arteritis, Arthritis, Arthritis Degenerative, Osteoarthritis, Arthritis Juvenile Chronic, Arthritis, Juvenile Rheumatoid, Arthritis Juvenile Idiopathic, Arthritis, Juvenile Rheumatoid, Arthritis Juvenile Rheumatoid, Arthritis Rheumatic Acute, Rheumatic Fever, Arthritis Rheumatoid, Arthrogryposis, Arthromyodysplasia Congenital, Arthrogryposis, Arthropathy Neurogenic, Arthropod Diseases, Arthropod-Borne Encephalitis, Encephalitis, Arbovirus, Arylsulfatase A Deficiency Disease, Leukodystrophy, Metachromatic, Asbestosis, Ascariasis, Ascites, Ascites Gelatinous, Pseudomyxoma Peritonei, Ascorbic Acid Deficiency, Aseptic Necrosis of Bone, Osteonecrosis, Asialia, Xerostomia, Asperger Syndrome, Aspergillosis, Asphyxia, Assaultive Behavior, Violence, Asthma, Asthma Bronchial, Asthma, Astigmatism, Astrocytoma, Astrocytoma Grade IV, Glioblastoma, Astrocytoma Subependymal Giant Cell, Astrocytoma, Asymmetric Septal Hypertrophy, Cardiomyopathy, Hypertrophic, Ataxia Telangiectasia, Ataxia Cerebellar, Cerebellar Ataxia, Atelectasis, Atheroembolism, Embolism, Cholesterol, Athlete's Foot, Dermatomycoses, Atopic Hypersensitivity, Hypersensitivity, Immediate, Atresia Biliary, Biliary Atresia, Atresia Esophageal, Esophageal Atresia, Atresia Pulmonary, Pulmonary Atresia, Atresia Tricuspid, Tricuspid Atresia, Atrial Fibrillation, Atrioventricular Block, Heart Block, Atrocities, Violence, Atrophy Muscular Peroneal, Charcot-Marie-Tooth Disease, HMSN I, II, Attention Deficit Disorder, Attention Deficit Disorder with Hyperactivity, Attention Deficit Disorder with Hyperactivity, Attention Deficit Hyperactivity Disorder, Attention Deficit Disorder with Hyperactivity, Attitude to Death, Auditory Agnosia, Agnosia, Auditory Hyperesthesia, Hyperacusis, Aura, Epilepsy, Auricular Cancer, Ear Neoplasms, Auricular Fibrillation, Atrial Fibrillation, Auricular Neoplasms, Ear Neoplasms, Auriculo-Ventricular Dissociation, Heart Block, Autism Infantile, Autistic Disorder, Autism-Dementia-Ataxia-Loss of Purposeful Hand Use Syndrome, Rett Syndrome, Autistic Disorder, Autoimmune Diseases, Autoimmune Polyendocrinopathy-Candidiasis-Ectodermal-Dystrophy, Polyendocrinopathies, Autoimmune, Autoimmune Syndrome Type I Polyglandular, Polyendocrinopathies, Autoimmune, Autoimmune Syndrome Type II Polyglandular, Polyendocrinopathies, Autoimmune, Autoimmune Thyroiditis, Thyroiditis, Autoimmune, Autonomic Failure Progressive, Shy-Drager Syndrome, Autonomic Nervous System Diseases, Autosomal Chromosome Disorders, Chromosome Disorders, Awakening Epilepsy, Epilepsy, Avascular Necrosis of Bone, Osteonecrosis, Avian Flu, Influenza in Birds, Avian Influenza, Influenza in Birds, Avitaminosis, Ayerza's Syndrome, Hypertension, Pulmonary, Azorean Disease, Machado-Joseph Disease, Babesiasis, Babesiosis, Babesiosis, Back Pain, Backache, Back Pain, Bacteremia, Bacterial Infections and Mycoses, Bacterial Infections and Mycoses, Bacterial Infections Gram-Negative, Bacterial Infections Gram-Positive, Bacterial Meningitis, Meningitis, Bacterial, Baker's Cyst, Popliteal Cyst, Balanitis Baldness, Alopecia, Balo Concentric Sclerosis, Diffuse Cerebral Sclerosis of Schilder, Bannayan-Zonana Syndrome, Bardet-Biedel Syndrome, Laurence-Moon Syndrome, Bare Lymphocyte Syndrome, Severe Combined Immunodeficiency, Barotrauma, Barre-Lieou Syndrome, Spinal Osteophytosis, Barrett Esophagus, Barrett Syndrome, Barrett Esophagus, Barth Syndrome, *Bartonella* Infections, Bartonellosis, *Bartonella* Infections, Basal Cell Nevus Syndrome, Basedow's Disease, Graves Disease, Batten Disease, Neuronal Ceroid-Lipofuscinoses, Beaver Fever, Giardiasis, Bechterew Disease, Spondylitis, Ankylosing, Beckwith-Wiedemann Syndrome, Bedsore, Pressure Ulcer, Behavior and Behavior Mechanisms, Behavior Assaultive, Violence, Behavioral Symptoms, Behcet Disease, Behcet Syndrome, Silk-Road Disease, Behcet Syndrome, Behcet Syndrome, Silk-Road Disease, Bell Palsy Bell's Palsy, Bell Palsy, Benign Essential Tremor, Essential Tremor, Benign Intracranial Hypertension, Pseudotumor Cerebri, Benign Meningioma, Meningioma, Berger's Disease, Glomerulonephritis, Beriberi, Beriberi Cerebral, Wernicke Encephalopathy, Bernard Syndrome, Horner Syndrome, Bernard-Soulier Syndrome, Berry Aneurysm, Intracranial Aneurysm, Bertielliasis, Cestode Infections, Berylliosis, Beryllium Disease, Berylliosis, Besnier-Boeck Disease, Sarcoidosis, Best Disease, Macular Degeneration, beta-Cell Tumor, Insulinoma, Bilharziasis, Schistosomiasis, Biliary Atresia, Biliary Tract Diseases, Bilirubin Encephalopathy, Kernicterus, Binswanger Disease, Dementia, Vascular, Biotimidase Deficiency, Bipolar Disorder, Bird Diseases, Birth Control, Contraception, Birth Defects, Birt-Hogg-Dube Syndrome, Bites and Stings, Blackwater Fever, Malaria, Bladder Cancer, Urinary Bladder Neoplasms, Bladder Diseases, Urinary Bladder Diseases, Bladder Exstrophy, Bladder Neoplasms, Urinary Bladder Neoplasms, Blastocystis hominis, infections Blepharitis Blepharoptosis, Blepharospasm, Blepharospasm-Oromandibular Dystonia, Meige Syndrome, Blindness, Blindness Legal, Blindness Monocular, Blindness Monocular Transient, Amaurosis Fugax, Blister, Bloch-Sulzberger Syndrome, Incontinentia Pigmenti, Blood Coagulation Disorders, Blood Diseases, Hematologic diseases, Blood Platelet Disorders, Blood Pressure High, Hypertension, Blood Pressure Low, Hypotension, Blood Transfusion, Bloom-Torre-Machacek Syndrome, Bloom Syndrome, Blount's Disease, Osteochondritis, Blue Rubber Bleb Nevus Syndrome, Body Dysmorphic Disorder, Boeck's Sarcoid, Sarcoidosis, Boils, Furunculosis, Bone Cancer, Bone Neoplasms, Bone Diseases, Bone Diseases Metabolic, Bone Fractures, Bone Hypertrophy, Hyperostosis, Bone Loss Age-Related, Osteoporosis, Bone Marrow Fibrosis, Myelofibrosis, Bone Neoplasms, Bonnevie-Ullrich Syndrome, Turner Syndrome, BOOP, Bronchiolitis Obliterans Organizing Pneumonia, BOR Syndrome, Branchio-Oto-Renal Syndrome, Borderline Personality Disorder, Borna Disease, Botulism, Botulism Infantile, Bouchard's Node, Osteoarthritis, Bourneville Disease, Tuberous Sclerosis, Bourneville's Disease, Bowen's Disease, Brachial Plexopathy, Brachial Plexus Neuropathies, Erb's Palsy, Brachial Plexus Neuritis, Brachial Plexus Neuropathies Brachmann-De Lange Syndrome, de Lange Syndrome, Bradyarrhythmia, Bradycardia, Brain Abscess, Brain Aneurysm, Intracranial Aneurysm, Brain Concussion, Brain Diseases, Brain Dysfunction Minimal, Attention Deficit Disorder with Hyperactivity, Brain Hemorrhage Cerebral, Cerebral Hemorrhage, Brain Hypoxia, Hypoxia, Brain, Brain Ischemia, Brain Pathology, BRAIN DISEASES, Brain Stem Ischemia Transient, Ischemic Attack, Transient, Brain Vascular Disorders, Cerebrovascular Disorders, Branched-Chain Ketoaciduria, Maple Syrup Urine Disease, Branchio-Oculo-Facial Syndrome, Branchio-Oto-Renal Syndrome, Branchio-Otorenal Dysplasia, Branchio-Oto-Renal Syndrome, Branchio-Oto-Renal Syndrome, Breast Cancer, Breast Neoplasms, Breast Cyst, Breast Diseases, Breast Dysplasia, Fibrocystic Breast Disease, Breast Neoplasms, Breast Neoplasms Male, Breast Tumors, Breast Neoplasms, Bright Disease, Glomerulonephritis, Brill's Disease, Typhus, Epidemic Louse-Borne, Brill-Zinsser Disease, Typhus, Epidemic Louse-Borne, Briquet Syndrome, Broad Thumb-Hallux Syndrome, Rubinstein-Taybi Syndrome, Bronchial Asthma, Asthma, Bronchial Diseases, Bronchiectasis, Bronchiolitis, Bronchiolitis Obliterans Organizing Pneumonia, Bronchitis, Bronchopulmonary Dysplasia, Brown Tendon Sheath Syndrome, Brown-Sequard Syndrome, Brown-Sequard Syndrome, Brucellosis Brueghel Syndrome, Meige Syndrome, Bruxism, Bubonic Plague, Plague, Budd-Chiari Syndrome, Hepatic Vein Thrombosis, Buerger's Disease, Thromboangiitis Obliterans, Bug Bite Bulbar Palsy Progressive, Bulbospinal Neuronopathy, Muscular Atrophy, Spinal, Bulla, Blister, Bullying, Social Behavior, Bunion, Hallux Valgus, Bunostomiasis, Hookworm Infections, Bunyavirus Infections, Bunyaviridae Infections, *Burkholderia* Infections, Burkitt Lymphoma, Burkitt Tumor, Burning Mouth Syndrome, Burns, Bursitis, Buruli Ulcer, *Mycobacterium* Infections, Butterfly Children, Epidermolysis Bullosa, Cadmium Poisoning, Cafe-au-Lait Spots, Caffey-De Toni-Silvermann Syndrome, Hyperostosis, Cortical, Congenital, Caliciviridae Infections, Calicivirus Infections, Caliciviridae Infections, 'Winter Vomiting Disease', *Campylobacter* Infections, Canavan Disease, Canavan-van Bogaert-Bertrand Disease, Canavan Disease, Cancer, Neoplasms, Cancer of Bladder, Urinary Bladder Neoplasms, Cancer of Bone, Bone Neoplasms, Cancer of Breast, Breast Neoplasms, Cancer of Digestive System, Digestive System Neoplasms, Cancer of Ear, Ear Neoplasms, Cancer of Endocrine Gland, Endocrine Gland Neoplasms, Cancer of Endocrine Gland, Endocrine Gland Neoplasms, Cancer of Endometrium, Endometrial Neoplasms, Cancer of Eye, Eye neoplasms, Cancer of Head and Neck, Head and Neck Neoplasms, Cancer of Intestines, Intestinal Neoplasms, Cancer of Larynx, Laryngeal Neoplasms, Cancer of Lung, Lung Neoplasms, Cancer of Mouth, Mouth Neoplasms, Cancer of Ovary, Ovarian Neoplasms, Cancer of Pancreas, Pancreatic Neoplasms, Cancer of Penis, Penile Neoplasms, Cancer of Prostate, Prostatic Neoplasms, Cancer of Rectum, Rectal Neoplasms, Cancer of Skin, Skin Neoplasms, Cancer of Thyroid, Thyroid Neoplasms, Cancer of Tonsil, Tonsillar Neoplasms, Cancer of Urinary Tract, Urologic Neoplasms, Cancer of Vulva, Vulvar Neoplasms, Candidiasis, Candidiasis Vulvovaginal, Canker Sore, Stomatitis, Aphthous, Cannulation, Catheterization, Capgras Syndrome, Capsulitis Adhesive, Bursitis, Carbohydrate-Deficient Glycoprotein Syndrome, Carboxylase Deficiency Multiple Late-Onset, Biotimidase Deficiency, Carcinoid, Carcinoid Tumor, Carcinoid Tumor, Carcinoid Goblet Cell, Carcinoid Tumor, Carcinoma, Carcinoma Anaplastic, Carcinoma Merkel Cell, Carcinoma Non-Small-Cell Lung, Carcinoma Oat Cell, Carcinoma, Small Cell, Carcinoma, Oat Cell, Carcinoma Reserve Cell, Carcinoma Small Cell, Carcinoma Round Cell, Carcinoma Small Cell Lung, Carcinoma, Small Cell, Carcinoma, Oat Cell, Carcinoma Spindle-Cell, Carcinoma, Carcinoma Thymic, Thymoma, Carcinoma Undifferentiated, Carcinoma, Carcinomatosis, Carcinoma, Cardiac Hypertrophy, Cardiomegaly, Cardiac Syndrome X, Microvascular Angina, Cardiac Tamponade, Cardiomyopathy Congestive, Cardiomyopathy, Dilated, Cardiomyopathy Dilated, Cardiomyopathy Hypertrophic, Cardiomyopathy Hypertrophic Obstructive, Cardiomyopathy, Hypertrophic, Cardiomyopathy Restrictive, Cardiospasm, Esophageal Achalasia, Cardiovascular Diseases, Cardiovascular Diseases, Carditis, Myocarditis, Caregiver Issues, Carnitine Disorders, Caroli Disease, Caroli's Disease, Carotid Artery Narrowing, Carotid Stenosis, Carotid Stenosis, Carotid Ulcer, Carotid Stenosis, Carpal Tunnel Syndrome, Carrion's Disease, *Bartonella* Infections, Carsickness, Motion Sickness, Cartilage Diseases, Castleman Disease, Giant Lymph Node Hyperplasia, Castleman's Tumor, Giant Lymph Node Hyperplasia, Cat Diseases, Cat Eye Syndrome, Cataract Membranous, Cataract, Catheterization, Catheterization Cardiac, Heart Catheterization, Cat-Scratch Disease, Cattle Diseases, Cauda Equina Syndrome, Polyradiculopathy, Causalgia, Cavernitis Fibrous, Penile Induration, Cavus Deformity, Celiac Disease, Celioscopy, Laparoscopy, Cellulitis, Cementoma, Central Autonomic Nervous System Diseases, Autonomic Nervous System Diseases, Central Cord Syndrome, Central Core Disease, Myopathies, Structural, Congenital, Central Nervous System Cysticercosis, Neurocysticercosis, Central Nervous System Diseases, Central Nervous System Infections, Central Pain Syndrome, Thalamic Diseases, Central Sleep Apnea, Sleep Apnea, Centronuclear Myopathy, Myopathies, Structural, Congenital, Cenuriasis, Cestode Infections, Cephalgia, Headache, Cerclage of Cervix, Cerclage, Cervical, Cerclage of Uterine Cervix, Cerclage, Cervical, Cerclage Cervical, Cerebellar Ataxia, Cerebellar Dysmetria, Cerebellar Ataxia, Cerebelloretinal Angiomatosis Familial, Hippel-Lindau Disease, Cerebral Aneurysm, Intracranial Aneurysm, Cerebral Anoxia, Hypoxia, Brain, Cerebral Concussion, Brain Concussion, Cerebral Gigantism, Cerebral Hemorrhage, Cerebral Ischemia, Brain Ischemia, Cerebral Ischemia Transient, Ischemic Attack, Transient, Cerebral Palsy, Cerebral Parenchymal Hemorrhage, Cerebral Hemorrhage, Cerebral Pseudosclerosis, Hepatolenticular Degeneration, Cerebral Sclerosis Diffuse, Diffuse Cerebral Sclerosis of Schilder, Cerebral Stroke, Cerebrovascular Accident, Stroke, Cerebral Vasospasm, Vasospasm, Intracranial, Cerebroatrophic Hyperammonemia, Rett Syndrome, Cerebrohepatorenal Syndrome, Zellweger Syndrome, Cerebrooculorenal Syndrome, Oculocerebrorenal Syndrome, Lowe Syndrome, Cerebroside Lipidosis Syndrome, Gaucher Disease, Cerebroside Sulphatase Deficiency Disease, Leukodystrophy, Metachromatic, Cerebrovascular Accident, Cerebrovascular Apoplexy, Cerebrovascular Accident, Stroke, Cerebrovascular Disorders, Cerebrovascular Moyamoya Disease, Moyamoya Disease, Ceroid-Lipofuscinosis Neuronal, Neuronal Ceroid-Lipofuscinoses, Cervical Dystonia, Torticollis, Cervical Pain, Neck Pain, Cervico-Brachial Neuralgia, Brachial Plexus Neuritis, Parsonage-Turner Syndrome, Cervix Dysplasia, Uterine Cervical Dysplasia, Cesarean Section, Cestode Infections, Chagas Disease, Chalazion, Chancroid, Charcot-Marie-Tooth Disease, Charcot's Joint, Arthropathy, Neurogenic, CHARGE Syndrome, Charles Bonnet Syndrome, Hallucinations, Chediak-Higashi Syndrome, Cheilitis Granulomatosa Facial Neuropathy Orofacial Edema, Melkersson-Rosenthal Syndrome, Cheilitis Granulomatosa, Cherry Red Spot Myoclonus Syndrome, Mucolipidoses, Cherubism, Chest Pain, Chiari's Syndrome, Hepatic Vein Thrombosis, Chickenpox, Chilblains, Child Behavior Disorders, Child Mental Disorders, Chiropractic Adjustment, Manipulation, Chiropractic, *Chlamydia* Infections, Chlamydophila Infections, Chloasma, Melanosis, Choked Disk, Papilledema, Choking, Airway Obstruction, Cholangitis, Cholecystitis, Choledochal Cyst, Choledochal Cyst Type I, Choledochal Cyst, Cholelithiasis, Cholera, Cholera Infantum, Gastrointestinal diseases, Cholesteatoma Middle Ear, Cholesterol Embolism, Embolism, Cholesterol, Chondritis Costal, Tietze's Syndrome, Chondroectodermal Dysplasia, Ellis-van Creveld Syndrome, Chondroma, Chondromalacia, Cartilage diseases, Chondrosarcoma, Chordoma, Chorea, Choreiform Movement, Chorea, Choreoathetosis Self-Mutilation Hyperuricemia Syndrome, Lesch-Nyhan Syndrome, Chorioangioma, Hemangioma, Chorioretinitis, Choroideremia, Christmas Disease, Hemophilia B, Factor IX Deficiency, Christmas Disease, Chromium Poisoning, Chromosome 16 Abnormalities, Chromosome 18 Abnormalities, Chromosome 20 Abnormalities, Chromosome 22 Abnormalities, Chromosome 5p-Syndrome, Cri-du-Chat Syndrome, Chromosome Abnormality Disorders, Chromosome Disorders, Chromosome Disorders, Chronic Airflow Obstruction, Pulmonary Disease, Chronic Obstructive, Chronic Disease, Chronic Fatigue Syndrome, Fatigue Syndrome, Chronic, Chronic Hepatitis, Hepatitis, Chronic, Chronic Illness, Chronic Disease, Chronic Obstructive Airway Disease, Chronic Obstructive Lung Disease, Pulmonary Disease, Churg-Strauss Syndrome, Chylopericardium, Pericardial Effusion, Ciliary Dyskinesia Primary, Kartagener Syndrome, Circulatory Collapse, Shock, Cirrhosis, Fibrosis, Cirrhosis Liver, Liver Cirrhosis, CJD Variant V-CJD, Creutzfeldt-Jakob Syndrome, Clasp-Knife Spasticity, Muscle Spasticity, Claustrophobia, Phobic Disorders, Cleft Lip, Cleidocranial Dysostosis, Cleidocranial Dysplasia, Cleidocranial Dysplasia, *Clostridium* Enterocolitis, Enterocolitis, Pseudomembranous, *Clostridium* Infections, Clouston's Syndrome, Ectodermal Dysplasia, Clubfoot, COAD, Pulmonary Disease, Chronic Obstructive, Coccidioidomycosis, Codependency, Psychology, Coenuriasis, Cestode Infections, Cold Sore, Herpes Labialis, Cold Common, Common Cold, Colic, Colitis Granulomatous, Crohn Disease, Colitis Mucous, Irritable Bowel Syndrome, Colitis Pseudomembranous, Enterocolitis, Pseudomembranous, Colitis Ulcerative, Coloboma, Colon Irritable, Irritable Bowel Syndrome, Colonic Aganglionosis, Hirschsprung Disease, Color Anomia, Anomia, Color Blindness, Color Vision Defects, Color Vision Defects Coma, Unconsciousness, Coma Hyperglycemic Hyperosmolar Nonketotic, Hyperglycemic Hyperosmolar Nonketotic Coma, Combat Disorders, Common Bile Duct Cyst, Choledochal Cyst, Common Cold, Common Variable Immunodeficiency, Communicating Hydrocephalus, Hydrocephalus, Communication Disorders, Compartment Syndromes, Complementary Medicine, Complementary Therapies, Complementary Therapies, Complex Regional Pain Syndrome Type II, Causalgia, Complex Regional Pain Syndrome Type I, Reflex Sympathetic Dystrophy, Type I Complex Regional Pain Syndrome, Compression Neuropathy Carpal Tunnel, Carpal Tunnel Syndrome, Condyloma Acuminata, Condylomata Acuminata, Warts, Confusion, Confusional State, Confusion, Congenital Central Hypoventilation Syndrome, Sleep Apnea, Central, Congenital Defects, abnormalities, Congenital Disorders, Congenital, Hereditary, and Neonatal Diseases and Abnormalities, Congenital Disorders, Congenital, Hereditary, and Neonatal Diseases and Abnormalities, Congenital Fiber Type Disproportion, Myopathies, Structural, Congenital, Congenital Hydrocephalus, Hydrocephalus, Congenital Hypothyroidism, Congenital Hereditary and Neonatal Diseases and Abnormalities, Congenital Hereditary and Neonatal Diseases and Abnormalities, Congestive Cardiomyopathy, Cardiomyopathy, Dilated, Conjunctival Diseases, Conjunctivitis, Connective Tissue Disease Mixed, Mixed Connective Tissue Disease, Connective Tissue Diseases, Consciousness Loss of, Unconsciousness, Constipation, Consumption Coagulopathy, Disseminated Intravascular Coagulation, Contagious Pustular Dermatitis, Ecthyma, Contagious, Orf, Contiguous Gene Syndrome Williams, Williams Syndrome, Contraception, Contractural Arachnodactyly Congenital, Beal's Syndrome Convergence Insufficiency, Convergence Nystagmus, Nystagmus, Pathologic, Convulsions, Seizures, Convulsive Seizures, Seizures, Cooley's Anemia, Thalassemia, COPD, Pulmonary Disease, Chronic Obstructive, Corneal Diseases, Corneal Dystrophies, Corneal Edema, Corneal Ulcer, Cornelia De Lange Syndrome, de Lange Syndrome, Coronaviridae Infections, Corpus Luteum Cyst, Ovarian Cysts, Cortical Hyperostosis Congenital, Hyperostosis, Cortical, Congenital, Corticobasal Ganglionic Degeneration CBGD Coryza Acute, Common Cold, Cosmetic Reconstructive Surgical Procedures, Reconstructive Surgical Procedures, Costal Chondritis, Tietze's Syndrome, Costello Syndrome, Costochondritis, Tietze's Syndrome, Costoclavicular Syndrome, Thoracic Outlet Syndrome, Cot Death, Sudden Infant Death, Cough, Cowden's Disease, Hamartoma Syndrome, Multiple, Cowden's Disease, Coxa Plana, Legg-Perthes Disease, Coxsackievirus Infections, Cramp, Muscle Cramp, Cranial Arteritis, Temporal Arteritis, Cranial Epidural Hematoma, Hematoma, Epidural, Cranial, Cranial Nerve Diseases, Cranial Nerve II Diseases, Cranial Nerve III Diseases, Oculomotor Nerve Diseases, Cranial Nerve IX Diseases, Glossopharyngeal Nerve Diseases, Cranial Nerve VII Diseases, Facial Nerve Diseases, Cranial Neuropathies, Cranial Nerve Diseases, Cranial Neuropathies Multiple, Cranial Nerve Diseases, Craniocerebral Trauma, Craniofacial Dysostosis, Craniopharyngioma, Craniopharyngioma Adamantinous, Craniopharyngioma, Craniopharyngioma Papillary, Craniopharyngioma, Craniosynostoses, Creeping Eruption, Larva Migrans, Crescendo Transient Ischemic Attacks, Ischemic Attack, Transient, Cretinism, Congenital Hypothyroidism, Creutzfeldt-Jakob Syndrome, Crib Death, Sudden Infant Death, Cri-du-Chat Syndrome, Crohn Disease, Cross Infection, Cross-Transfusion Intrauterine, Fetofetal Transfusion, Croup, Crouzon's Disease, Craniofacial Dysostosis, Crow-Fukase Syndrome, POEMS Syndrome, Cruveilhier-Baumgarten Syndrome, Hypertension, Portal, Cryoablation, Cryoglobulinemia, Cryptococcosis, Cryptogenic Chronic Hepatitis, Hepatitis, Chronic, Cryptogenic Infantile Spasms, Spasms, Infantile, Cryptorchidism, Cryptosporidiosis, Cuada Equina Syndrome, Polyradiculopathy, Cubital Tunnel Syndrome, Curling's Ulcer, Duodenal Ulcer, Currarino Syndrome, Cushing Syndrome, Cutaneous Larva Migrans, Larva Migrans, Cutis Elastica, Ehlers-Danlos Syndrome, Cutis Laxa, Cyanosis, Cyclosporiasis, Cyclothymic Disorder, Cyclothymic Personality, Cyclothymic Disorder, Cystathionine beta-Synthase Deficiency Disease, Homocystinuria, Cystic Fibrosis, Cysticercosis, Cysticercosis Brain, Neurocysticercosis, Cysticercosis Central Nervous System, Neurocysticercosis, Cystinosis, Cystinuria, Cystitis Chronic Interstitial, Cystitis, Interstitial, Cystitis Interstitial, Cysts, Cysts Hydatid, Echinococcosis, Cytomegalic Inclusion Disease, Cytomegalovirus Infections, Cytomegalovirus Infections, Dandy-Walker Malformation, Dandy-Walker Syndrome, Dandy-Walker Syndrome, Dangerous Substances Darier's Disease, Keratosis Follicularis, De Lange Syndrome, De Quervain Thyroiditis, Thyroiditis, Subacute, de Quervain's Tendinitis, Tenosynovitis, Deaf-Mutism, Deafness, Deafness, Deafness Sudden, Hearing Loss, Sudden, Death, Decubitus Ulcer, Pressure Ulcer, Deep Vein Thrombosis, Thrombosis, Deformities, ABNORMALITIES, Deglutition Disorders, Dehydration, Dejerine-Roussy Syndrome, Thalamic Diseases, Dejerine-Sottas Disease, Hereditary Motor and Sensory Neuropathies, Dejerine-Thomas Syndrome, Olivopontocerebellar Atrophies, Delivery Abdominal, Cesarean Section, Delusionary Parasitosis, Dementia, Dementia Praecox, Schizophrenia, Dementia Alzheimer Type, Alzheimer Disease, Dementia Lewy Body, Lewy Body Disease, Dementia Senile, Dementia Vascular, Dementias Transmissible, Prion Diseases, Demyelinating Diseases, Dengue, Dengue Fever, Dengue, 'Breakbone Fever', Dental Diseases, Stomatognathic Diseases, Dental Implantation, Dental Prosthesis Implantation, Dental Implantation, Dentigerous Cyst, Dentistry, Dependent Personality Disorder, Depression Bipolar, Bipolar Disorder, Depression Endogenous, Depressive Disorder, Depression Neurotic, Depressive Disorder, Depression Postpartum, Depression Unipolar, Depressive Disorder, Depressive Disorder, Depressive Syndrome, Dercum's Disease, Adiposis Dolorosa, Dermal Sinus, Spina Bifida Occulta, Dermatitis, Dermatitis Herpetiformis, Dermatitis Actinic, Photosensitivity Disorders, Dermatitis Contagious Pustular, Eethyma, Contagious, Orf, Dermatitis Eczematous, Eczema, Dermatitis Exfoliative, Dermatofibroma, Histiocytoma, Benign Fibrous, Dermatolysis, Cutis Laxa, Dermatomegaly, Cutis Laxa, Dermatomycoses, Dermatomyositis, Dermatophytoses, Dermatomycoses, Dermatoses, Skin diseases, Dermatosis Neutrophilic Febrile Acute, Sweet's Syndrome, Dermoid, Dermoid Cyst, Dermoid Cyst Desmoid, Fibromatosis, Aggressive, Devic Disease, Neuromyelitis Optica, Diabetes Insipidus, Diabetes Insipidus Nephrogenic, Diabetes Mellitus, Diabetes Mellitus Adult-Onset, Diabetes Mellitus Type 2, Diabetes Mellitus Brittle, Diabetes Mellitus Type 1, Diabetes Mellitus Gestational, Diabetes, Gestational, Diabetes Mellitus Insulin-Dependent, Diabetes Mellitus Type 1, Diabetes Mellitus Juvenile-Onset, Diabetes Mellitus Type 1, Diabetes Mellitus Ketosis-Prone, Diabetes Mellitus Type 1, Diabetes Mellitus Ketosis-Resistant, Diabetes Mellitus Type 2, Diabetes Mellitus Maturity-Onset, Diabetes Mellitus Type 2, Diabetes Mellitus Non-Insulin-Dependent, Diabetes Mellitus Type 2, Diabetes Mellitus Slow-Onset, Diabetes Mellitus Type 2, Diabetes Mellitus Stable, Diabetes Mellitus Type 2, Diabetes Mellitus Sudden-Onset, Diabetes Mellitus Type 1, Diabetes Mellitus Type 1 Diabetes Mellitus Type 2-Diabetes Autoimmune, Diabetes Mellitus Type 1, Diabetes Bronze, Hemochromatosis Diabetes Bronze, Diabetes Gestational, Diabetes Pregnancy-Induced, Diabetes Gestational, Diabetic Acidosis, Diabetic Ketoacidosis, Diabetic Amyotrophy, Diabetic Neuropathies, Diabetic Autonomic Neuropathy, Diabetic Neuropathies, Diabetic Ketoacidosis, Diabetic Ketosis, Diabetic Ketoacidosis, Diabetic Neuralgia, Diabetic Neuropathies, Diabetic Neuropathies, Diabetic Polyneuropathy, Diabetic Neuropathies, Diabetic Retinopathy, Diaper Rash, Dermatitis, Diaphragmatic Hernia, Hernia, Diaphragmatic, DIDMOAD, Wolfram Syndrome, Dientamoebiasis, Diffuse Cerebral Sclerosis of Schilder Diffuse Globoid Body Sclerosis, Leukodystrophy, Globoid Cell, Diffuse Lewy Body Disease, Lewy Body Disease, Diffuse Myofascial Pain Syndrome, Fibromyalgia, DiGeorge Syndrome, Digestive System Cancer, Digestive System Neoplasms, Digestive System Diseases, Digestive System Neoplasms, Dihydropteridine Reductase Deficiency Disease, Phenylketonurias, Dilated Cardiomyopathy, Cardiomyopathy, Dilated, Diphtheria, Diphyllobothriasis, Diplegic Infantile Cerebral Palsy, Cerebral Palsy, Diplopia, Dipylidiasis, Cestode Infections, Diseases of Camels and Camelids, Diseases of Insectivores, Diseases of Invertebrates, Diseases of Leporidae and Rodents, Diseases of Marine Mammals, Disk Herniated, Intervertebral Disk Displacement, Disorders of Environmental Origin, Disorders of the Autonomic Nervous System, Autonomic Nervous System Diseases, Disorders Usually Diagnosed in Infancy Childhood or Adolescence, Mental disorders diagnosed in childhood, Disseminated Intravascular Coagulation, Disseminated Intravascular Coagulation, Dissociation, Dissociative Disorders, Dissociative Identity Disorder, Multiple Personality Disorder, Distal Trisomy 10q, Distichiasis, Diverticulitis, Dizziness, DNA Virus Infections, Dog Diseases, Domestic Violence, Donovanosis, Granuloma Inguinale, Donovanosis, Double Vision, Diplopia, Down Syndrome, Dracunculiasis, Dracunculosis, Dracunculiasis, Dressing Apraxia, Apraxias, Drooling, Sialorrhea, propsy, Edema, Drug Abuse, Drug Addiction, Drug Dependence, Drug Habituation, Drug Toxicity, Drug Use Disorders, Substance Withdrawal Syndrome, Dry Eye Syndromes Dry Mouth, Xerostomia, Dual Personality, Multiple Personality Disorder, Duane Syndrome, Duane Retraction Syndrome, Dubin-Johnson Syndrome, Jaundice, Chronic Idiopathic, Duhring's Disease, Dermatitis Herpetiformis, Duncan's Syndrome, Lymphoproliferative disorders, Duodenal Ulcer, Dupuytren's Contracture, Dwarfism, Dwarfism Thanatophoric, Thanatophoric Dysplasia, Dysautonomia, Autonomic Nervous System Diseases, Dysautonomia Familial, Dyscalculia, Communication Disorders, Dysembryoma, Teratoma, Dysentery, Dyshidrosis, Eczema, Dyskinesia Syndromes, Dyslexia, Dyslexia Developmental, Dyslexia, Dyslipidemias, Dyslipoproteinemias, Dyslipidemias, Dysmetria, Cerebellar Ataxia, Dysmorphophobia, Dysmyelopoietic Syndromes, Myelodysplastic Syndromes, Dysnomia, Anomia, Dysostosis Cleidocranial, Cleidocranial Dysplasia, Dysostosis Craniofacial, Craniofacial Dysostosis, Dyspareunia, Dyspepsia, Dysphagia, Deglutition Disorders, Dysphasia, Aphasia, Dysphonia, Voice Disorders, Dysplasia Arteriohepatic, Alagille Syndrome, Dyspraxia, Apraxias, Dysthymic Disorder, Dystocia, Dystonia, Dystrophia Brevicollis Congenita, Klippel-Feil Syndrome, Ear Cancer, Ear Neoplasms, Ear Diseases, Ear Neoplasms, Eating Disorders, Eaton-Lambert Syndrome, Lambert-Eaton Myasthenic Syndrome, Ebola Virus Infections, Hemorrhagic Fevers, Viral, Ebstein's Anomaly, EBV Infections, Epstein-Barr Virus Infections, Ecchymosis, Echinococcosis, Eclampsia Eethyma Contagious Ectodermal Defect Congenital, Ectodermal Dysplasia, Ectodermal Dysplasia, Ectoparasitic Infestations, Ectopia Cordis, Heart Defects, Congenital, Ectopic Pregnancy, Pregnancy, Ectopic, Ectropion, Eczema, Edema, Efferent Pupillary Defect, Pupil disorders, Ehlers-Danlos Syndrome, Ehrlichiosis, Eisenmenger Complex, Eisenmenger Syndrome, Eisenmenger Complex, Ekbom Syndrome, Restless Legs Syndrome, Elaeophoriasis, Filariasis, Electric Injuries, Electrocution Accidental, Electric Injuries, Electron Transport Chain Deficiencies Mitochondrial, Mitochondrial Diseases, Electrosensitivity Elephant Man Disease, *Proteus* Syndrome, Elephantiasis, Filariasis, Elfin Facies Syndrome, Williams Syndrome, Ellis-Van Creveld Syndrome, Embolism Cholesterol, Embryopathies, Fetal diseases, Embryotomy, Abortion, Induced, Emesis, Vomiting, Emetophobia, Anxiety disorders, Pulmonary Emphysema, Empty Sella Syndrome, Empty Sella Syndrome Primary, Empty Sella Syndrome, Empty Sella Syndrome Secondary, Empyema Gallbladder, Cholecystitis, Empyema Pleural, Empyema Thoracic, Empyema, Pleural, Encephalitis, Encephalitis Periaxialis, Diffuse Cerebral Sclerosis of Schilder, Encephalitis Arbovirus, Encephalitis Epidemic, Encephalitis, Arbovirus, Encephalitis Herpes Simplex, Encephalitis Japanese, Encephalitis, Arbovirus, Encephalitis St. Louis, Encephalitis, Arbovirus, Encephalocele, Encephalomyelitis, Encephalomyelitis Myalgic, Fatigue Syndrome, Chronic, Encephalomyelitis Subacute Necrotizing, Leigh Disease, Subacute Necrotizing Encephalomyelopathy, Encephalopathy Binswanger, Dementia, Vascular, Encephalopathy Hypoxic, Hypoxia, Brain, Encephalopathy Subacute Necrotizing, Leigh Disease, Subacute Necrotizing Encephalomyelopathy, Encephalopathy Wernicke, Wernicke Encephalopathy, Enchondroma, Chondroma, Enchondroma Multiple, Enchondromatosis, Enchondromatosis, Enchondrosis Multiple, Enchondromatosis, Encopresis, Endocarditis Bacterial, Endocrine Cancer, Endocrine Gland Neoplasms, Endocrine Cancer, Endocrine Gland Neoplasms, Endocrine Diseases, Endocrine System Diseases, Endocrine Diseases, Endocrine System Diseases, Endocrine Gland Cancer, Endocrine Gland Neoplasms, Endocrine Gland Cancer, Endocrine Gland Neoplasms, Endocrine Gland Neoplasms, Endocrine Gland Neoplasms, Endocrine System Diseases, Endodontics, Endometrial Cancer, Endometrial Neoplasms, Endometrial Carcinoma, Endometrial Neoplasms, Endometrial Neoplasms, Endometrioma, Endometriosis, Adenomyosis, Endometriosis, Endoscopic Surgical Procedures, Endoscopy, Endoscopy End-Stage Renal Disease, Kidney Failure, Chronic, End Stage Renal Disease, Enlarged Heart, Cardiomegaly, Enteric Fever, Typhoid Fever, Enteritis Granulomatous, Crohn Disease, Enteritis Pseudomembranous, Enterocolitis, Pseudomembranous, Enteritis Regional, Crohn Disease, Enterocele, Hernia, Enterocolitis Pseudomembranous, Enthesopathy, Rheumatic diseases, Entomophthoramycosis, Zygomycosis, Entrapment Neuropathies, Nerve Compression Syndromes, Entrapment Neuropathy Carpal Tunnel, Carpal Tunnel Syndrome, Entropion Enuresis, Urination Disorders, Eosinophilia, Eosinophilia-Myalgia Syndrome, Ependymoma, Ependymoma Myxopapillary, Ependymoma, Ependymoma Papillary, Ependymoma, Eperythrozoonosis, *Mycoplasma* Infections, Epicondylitis Lateral Humeral, Tennis elbow, Epidemic Neurolabyrinthitis, Vestibular Neuronitis, Epidermal Cyst, Epidermoid Cyst, Epidermal Cyst, Epidermolysis Bullosa, Epidermophytosis, Tinea, Epididymitis, Epiglottitis, Epilepsy, Epileptic Seizures, Epilepsy, Epiloia, Tuberous Sclerosis, Bourneville's Disease, Epiphora, Lacrimal apparatus diseases, Episcleritis, Scleritis, Epistaxis, Epithelial Neoplasms Malignant, Carcinoma, Epithelioma, Carcinoma, Epstein-Barr Virus Infections, Equinovarus, Clubfoot, Erb Paralysis, Brachial Plexus Neuropathies, Erb's Palsy, Erdheim-Chester Disease, Erectile Dysfunction, Impotence, Ergot Poisoning, Ergotism, Ergotism, Erysipelas, Erythema, Erythema Infectiosum, Erythremia, Polycythemia Vera, Erythroblastosis Fetal, Erythroderma, Dermatitis, Exfoliative, Erythroderma, Erythroderma Maculopapular, Parapsoriasis, Erythroderma Sezary, Sezary Syndrome, Erythropoietic Porphyria, Porphyria, Erythropoietic, *Escherichia coli* Infections, Esophageal Achalasia, Esophageal Atresia, Esophageal Diseases, Esophageal Reflux, Gastroesophageal Reflux, Esophagitis, Esophagopharyngeal Diverticulum, Zenker Diverticulum, Esophagotracheal Fistula, Tracheoesophageal Fistula, Esophagus Barrett, Barrett Esophagus, Esophoria, Esotropia, Esotropia, ESRD, Kidney Failure, Chronic, End Stage Renal Disease, Essential Polyarteritis, Polyarteritis Nodosa, Essential Tremor, Etat Marbre, Movement disorders, Ethics, Ethnomedicine, Medicine, Traditional, Evans Syndrome Ewing's Tumor, Sarcoma, Ewing's, Exanthema Subitum, Exfoliation Syndrome, Exocrine Pancreatic Insufficiency, Exodontics, Exomphalos, Hernia, Umbilical, Omphalocele, Exomphalos-Macroglossia-Gigantism Syndrome, Beckwith-Wiedemann Syndrome, Exophoria, Exotropia, Exophthalmic Goiter, Graves Disease, Exostoses, Exotropia, Experimental Lung Inflammation, Pneumonia, Extracorporeal Dialysis, Renal Dialysis, Eye Abnormalities, Eye Cancer, Eye Diseases, Eye Hemorrhage, Eye Movement Disorders, Eye Neoplasms, Eye ENTEar-Nose-Throat and Respiratory System, Eye ENTEar-Nose-Throat and Respiratory System, Eyelid Diseases, Fabry Disease, Facial Asymmetry, Facial Hemiatrophy, Facial Myokymia, Facial Nerve Diseases, Facial Neuralgia, Facial Neuropathy, Facial Neuropathy Inflammatory Acute, Bell Palsy, Facial Pain Syndromes, Facial Neuralgia, Facial Palsy, Facial Paralysis, Facial Paralysis Facial Paralysis Idiopathic, Bell Palsy, Facial Recognition Agnosia, Prosopagnosia, Factor IX Deficiency, Hemophilia B, Factor IX Deficiency, Christmas Disease, Factor V Deficiency, Factor V Leiden, Blood Coagulation Disorders, Factor VII Deficiency, Factor VIII Deficiency, Hemophilia A, Factor VIII Deficiency, Factor X Deficiency, Factor XI Deficiency, Factor XII Deficiency, Fallot's Tetralogy, Tetralogy of Fallot, Familial Benign Chronic Pemphigus, Pemphigus, Benign Familial, Familial Juvenile Parkinsonism, Parkinsonian Disorders, Familial Mediterranean Fever, Familial Motor Neuron Disease, Motor Neuron Disease, Familial Tremor, Essential Tremor, Family Violence, Domestic Violence, Fanconi Anemia, Farsightedness, Hyperopia, Fasciculation, Fasciitis, Fasciitis Necrotizing, Fascioliasis Fatal Familial Insomnia, Insomnia, Fatal Familial, Fatigue, Fatigue Syndrome Chronic, Fatty Acid Oxidation Disorders, Fatty Liver, Fatty Tumor, Lipoma, Favism, Glucosephosphate Dehydrogenase Deficiency, Fazio-Londe Syndrome, Bulbar Palsy, Progressive, Fecal Incontinence, Felty Syndrome, Arthritis, Rheumatoid, Female Urogenital Diseases and Pregnancy Complications, Feminization, Ferret Diseases Fetal Alcohol Syndrome, Fetal Death, Fetal Diseases, Fetal Distress, Fetal Growth Retardation, Fetal Membranes Premature Rupture, Fetofetal Transfusion, Fever, Fever Blister, Herpes Labialis, Fibrinogen Deficiency, Afibrinogenemia, Factor I Deficiency, Fibrinogen Deficiency, Fibrocystic Breast Disease, Fibrocystic Mastopathy, Fibrocystic Breast Disease, Fibrodysplasia Ossificans Progressiva, Myositis Ossificans, Fibroid, Leiomyoma, Fibroid Tumor, Fibroid Tumor, Leiomyoma, Fibroid Tumor, Fibroid Uterus, Leiomyoma, Fibroid Tumor, Fibroids Uterine, Leiomyoma, Fibroid Tumor, Fibroma Shope, TUMOR VIRUS INFECTIONS, Fibroma Uterine, Leiomyoma, Fibroid Tumor, Fibromatosis Aggressive, Fibromatosis Juvenile Hyaline, Fibromuscular Dysplasia, Fibromyalgia, Fibromyoma, Leiomyoma, Fibroid Tumor, Fibrosis, Fibrosis Bone Marrow, Myelofibrosis, Fibrosis Liver, Liver Cirrhosis, Fibrositis, Fibromyalgia, Fibrous Dysplasia of Bone, Fibrous Dysplasia Polyostotic, Fifth Disease, Erythema Infectiosum, Filariasis, Filarioidea Infections, Filariasis, Finger Agnosia, Agnosia, Firesetting Behavior, Fish Diseases, Fisher Syndrome, Miller Fisher Syndrome, Fissure in Ano, Anus Diseases, Fistula, Flatfoot, Flatulence, Flatus, Flatulence, Floaters Floppy Mitral Valve, Mitral Valve Prolapse, Flushing, Follicle Stimulating Hormone Inappropriate Secretion, Hyperpituitarism, Food Poisoning, Foot and Mouth Disease, Foot Deformities, Forensic Anthropology, Forensic Medicine, Forensic Medicine, Forestier-Certonciny Syndrome, Polymyalgia Rheumatica, Foster-Kennedy Syndrome, Optic nerve diseases, Fournier Disease, Fournier Gangrene, Fournier Gangrene, Fournier's Gangrene, Fournier Gangrene, Fowl Plague, Influenza in Birds, Fractures Bone, Fragile X Syndrome, Fragilitas Ossium, Osteogenesis Imperfecta, Frambesia, Yaws, FRAXA Syndrome, Fragile X Syndrome, Martin-Bell syndrome, FRAXE Syndrome, Fragile X Syndrome, Martin-Bell syndrome, Freckle Melanotic, Hutchinson's Melanotic Freckle, Freckles, Melanosis, Freeman-Sheldon Syndrome, Freiberg's Disease Friedreich Ataxia, Friedreich Disease, Friedreich Ataxia, Frigidity, Sexual Dysfunctions, Psychological, Frontal Encephalocele, Encephalocele, Frontal Region Trauma, Craniocerebral Trauma, Frontotemporal Lobar Degeneration, Dementia, Frostbite Fucosidase Deficiency Disease, Fucosidosis, Fucosidosis Fugue, Dissociative disorders, Fumarylacetoacetase Deficiency Disease, Tyrosinemias, Fungus Diseases, Mycoses, Funnel Chest, Furunculosis, *Fusobacterium*, Infections G(M2Gangliosidosis Type I, Tay-Sachs Disease, G(M2Gangliosidosis Type II, Sandhoff Disease, Gait Disorders Neurologic, Galactokinase Deficiency Disease, Galactosemias, Galactorrhea, Lactation Disorders, Galactose-1-Phosphate Uridyl-Transferase Deficiency Disease, Galactosemias, Galactosemias, Galactosylceramidase Deficiency Disease, Leukodystrophy, Globoid Cell, Gallbladder Inflammation, Cholecystitis, Gammapathy Monoclonal, Paraproteinemias, Gammopathy Monoclonal, Paraproteinemias, Ganglioside Sialidase Deficiency Disease, Mucolipidoses, Gangliosidosis G(M2 Type I, Tay-Sachs Disease, Gangliosidosis G(M2 Type II, Sandhoff Disease, Gangliosidosis GM2 B Variant, Tay-Sachs Disease, Gangrene, Gardner Syndrome, Intestinal Polyps, Gas Gangrene, Gas Poisoning, Gasser's Syndrome, Hemolytic-Uremic Syndrome, Gastric Stasis, Gastroparesis, Gastritis Hypertrophic, Gastroduodenal Ulcer, Peptic Ulcer, Gastroenteritis, Gastroenterology, Gastroenterology, Gastroesophageal Reflux, Gastrointestinal Cancer, Gastrointestinal Neoplasms, Gastrointestinal Diseases, Gastrointestinal Hemorrhage, Gastrointestinal Neoplasms, Gastrointestinal Stromal Tumors, Gastroparesis, Gastroschisis, Gaucher Disease, Gelineau Syndrome, Narcolepsy, General Fibrosis Syndrome, Genetic Diseases Inborn, Geniculate Ganglionitis, Facial Nerve Diseases, Geniculate Herpes Zoster, Herpes Zoster Oticus, Genital Diseases Female, Genital Diseases Male, Genital Neoplasms Female, Genital Neoplasms Female, Genital Neoplasms Male, Geographic Tongue, Glossitis, Benign Migratory, Geriatrics and Gerontology, German Measles, Rubella, Germinoblastoma, Lymphoma, Gerstmann-Straussler Syndrome, Gerstmann-Straussler-Scheinker Disease, Gestational Diabetes, Giant Cell Arteritis, Temporal Arteritis, Giant Cell Glioblastoma, Glioblastoma, Giant Intracranial Aneurysm, Intracranial Aneurysm, Giant Lymph Node Hyperplasia, Giant Platelet Syndrome, Bernard-Soulier Syndrome, Giant Platelet Syndrome, Giardiasis Giedion-Langer Syndrome, Langer-Giedion Syndrome, Gigantism, Gilbert Disease, Gilles de la Tourette's Disease, Tourette Syndrome, Gingivitis, GIST, Digestive System Neoplasms, Glanders, *Burkholderia* Infections, Glandular Fever, Infectious Mononucleosis, Glanzmann Thrombasthenia, Thrombasthenia, Glaucoma, Glaucoma Capsulare, Exfoliation Syndrome, Glial Cell Tumors, Glioma, Glioblastoma, Glioblastoma Multiforme, Glioblastoma, Glioblastoma Retinal, Retinoblastoma, Glioma Astrocytic, Astrocytoma, Glioma Retinal, Retinoblastoma, GLNH, Giant Lymph Node Hyperplasia, Glomerulonephritis, Glossitis Areata Exfoliativa, Glossitis, Benign Migratory, Glossitis Benign Migratory, Glossopharyngeal Nerve Diseases, Glossopharyngeal Neuralgia, Glucocerebrosidase Deficiency Disease, Gaucher Disease, Glucosephosphate Dehydrogenase Deficiency, Glucosylceramide Beta-Glucosidase Deficiency Disease, Gaucher Disease, Glue Sniffing, Glutaric Acidemia Gluten Enteropathy, Celiac Disease, Glycogen Storage Disease, Glycogenosis, Glycoprotein Syndrome Carbohydrate-Deficient, Carbohydrate-Deficient Glycoprotein Syndrome, Goiter Exophthalmic, Graves Disease, Goldenhar Syndrome, Gonadal Disorders, Gonadal Dysgenesis 45X, Turner Syndrome, Gonadal Dysgenesis XO, Turner Syndrome, Gonorrhea, Goodpasture Syndrome, Anti-Glomerular Basement Membrane Disease, Gorlin Syndrome, Basal Cell Nevus Syndrome, Gorlin/Goltz Syndrome, Gout, Graft-Versus-Host Disease, Gram-Negative Bacterial Infections, Gram-Positive Bacterial Infections, Granuloma, Granuloma Annulare, Granuloma Inguinale, Granuloma Venereum, Granuloma Inguinale, Donovanosis, Granuloma Hodgkin, Hodgkin Disease, Granuloma Malignant, Hodgkin Disease, Granuloma Pseudopyogenic, Angiolymphoid Hyperplasia with Eosinophilia, Granulomatosis Lipid, Erdheim-Chester Disease, Granulomatosis Wegener's, Wegener Granulomatosis, Granulomatous Cheilitis, Melkersson-Rosenthal Syndrome, Cheilitis Granulomatosa, Granulomatous Disease Chronic, Graves Disease, Great Pox, Syphilis, Lues, Grippe, Influenza, Human, Gronblad-Strandberg Syndrome, Pseudoxanthoma Elasticum, Growth Retardation Intrauterine, Fetal Growth Retardation, Guerin-Stern Syndrome, Arthrogryposis, Guillain Barre Syndrome Miller Fisher Variant, Miller Fisher Syndrome, Guillain-Barre Syndrome, Guinea Worm Infection, Dracunculiasis, Gunther's Disease, Porphyria, Erythropoietic, Guyon Syndrome, Ulnar Nerve Compression Syndromes, Gynecologic Diseases, Genital diseases female, Gynecologic Neoplasms, Genital Neoplasms, Gynecologic Neoplasms, Gynecomastia, Gyrate Atrophy, Habilitation, Rehabilitation, Hageman Trait, Factor XII Deficiency, Hageman Factor Deficiency, Hailey-Hailey Disease, Pemphigus, Benign Familial, Hair Diseases, Hakim Syndrome, Hydrocephalus, Normal Pressure, Halitosis, Hallervorden-Spatz Syndrome, Hallucinations, Hallux Abductovalgus, Hallux Valgus, Hallux Valgus Hamartoma, Hamartoma Syndrome Multiple, Hamman-Rich Syndrome, Pulmonary Fibrosis, Hammertoes, Hand-Schuller-Christian Syndrome, Histiocytosis, Langerhans-Cell, Hansen's Disease, Leprosy, Hansen's Disease, Hantavirus Infections, Happy Puppet Syndrome, Angelman Syndrome, Harelip, Cleft Lip, Hartnup Disease, Head and Neck Cancer, Head and Neck Neoplasms, Head and Neck Neoplasms, Head Cancer, Head and Neck Neoplasms, Head Injuries, Craniocerebral Trauma, Head Lice, Lice Infestations, Head Trauma, Craniocerebral Trauma, Headache, Headache Migraine, Migraine Disorders, Hearing Disorders, Hearing Loss Sudden, Heart Abnormalities, Heart Defects, Congenital, Heart Block Heart Catheterization, Heart Decompensation, Heart Failure, Congestive, Heart Defects Congenital, Heart Disease Ischemic, Myocardial Ischemia, Heart Diseases, Heart Failure Congestive, Heart Hypertrophy, Cardiomegaly, Heart Septal Defects, Heart Valve Diseases, Heat Cramps, Heat Stress Disorders, Heat Stress Disorders, Heat Stress Syndromes, Heat Stress Disorders, Heberden's Node, Osteoarthritis, HELLP Syndrome, Eclampsia, Helminthiasis, Hemangioma, Hemangioma Histiocytoid, Hemangioma, Hemangioma Intramuscular, Hemangioma, Hemangioma Sclerosing, Histiocytoma, Benign Fibrous, Hematochezia, Gastrointestinal Hemorrhage, Hematologic Diseases, Hematology, Hematology, Hematoma Epidural Cranial, Hematoma Subdural, Hematospermia Hematuria, Hemeralopia, VISION DISORDERS, Hemianopsia, Hemianopsia Binasal, Hemianopsia, Hemianopsia Bitemporal, Hemianopsia Homonymous, Hemic and Lymphatic Diseases, Hemic and Lymphatic Diseases, Hemicrania, Headache, Hemifacial Atrophy, Facial Hemiatrophy, Romberg Disease, Hemifacial Microsomia, Facial Asymmetry, Hemifacial Paralysis, Facial Paralysis, Hemiplegia, Hemispinal Cord Syndrome, Brown-Sequard Syndrome, Hemochromatosis, Hemodialysis, Renal Dialysis, Hemoglobin S Disease, Anemia, Sickle Cell, Hemoglobinopathies, Hemoglobinuria Paroxysmal Hemolytic Disease of Newborn, Erythroblastosis, Fetal, Hemolytic-Uremic Syndrome, Hemopericardium, Pericardial Effusion, Hemophilia, Hemophilia A, Factor VIII Deficiency, Hemophilia AHemophilia BHemophilia C, Factor XI Deficiency, Rosenthal Syndrome, Hemophilia Vascular, von Willebrand Disease, Hemophthalmos, Hemoptysis, Hemorrhage Cerebral, Cerebral Hemorrhage, Hemorrhage Cranial Epidural, Hematoma, Epidural, Cranial, Hemorrhage Eye, Hemorrhage Gastrointestinal, Gastrointestinal Hemorrhage, Hemorrhage Postpartum, Postpartum Hemorrhage, Hemorrhage Subdural, Hematoma, Subdural, Hemorrhagic Disease of Newborn, Hemorrhagic Fevers Viral, Hemorrhagic Shock, Shock, Hemorrhagic, Hemorrhoids, Hemosiderosis, Hendra Virus Disease, Paramyxoviridae Infections, Henoch Purpura, Purpura, Schoenlein-Henoch, Henoch-Schoenlein Purpura, Purpura, Schoenlein-Henoch, Hepatic Cirrhosis, Liver Cirrhosis, Hepatic Vein Thrombosis, Hepatitis, Hepatitis Chronic, Hepatitis Chronic Cryptogenic, Hepatitis Viral Human, Hepatolenticular Degeneration, Hereditary Diseases, Genetic diseases, inborn, Hereditary Motor and Sensory Neuropathies, Hereditary Motor and Sensory-Neuropathy Type II, Charcot-Marie-Tooth Disease, HMSN I, II, Hereditary Motor and Sensory Neuropathy Type I, Charcot-Marie-Tooth Disease, HMSN I, II, Hereditary Optic Atrophy, Optic Atrophies, Hereditary, Hereditary Periodic Fever Syndromes, Familial Mediterranean Fever, Yerevanian Disease, Hereditary Sensory and Autonomic Neuropathies, Hereditary Spinal Sclerosis, Friedreich Ataxia, Hereditary Type III Motor and Sensory Neuropathy, Hereditary Motor and Sensory Neuropathies, Hereditary Type VII Motor and Sensory Neuropathy, Hereditary Motor and Sensory Neuropathies, Hereditary-Sensory and Autonomic Neuropathy Type III, Dysautonomia, Familial, Heredopathia Atactica Polyneuritiformis, Refsum Disease, Heredopathia Atactica Polyneuritiformis, Refsum Disease, Hermanski-Pudlak Syndrome, Hermaphroditism, Hernia Cerebral, Encephalocele, Hernia Diaphragmatic Hernia Esophageal, Hernia, Hiatal, Hernia Hiatal Hernia Paraesophageal, Hernia, Hiatal, Hernia Umbilical, Herpes Genitalis, Herpes Simplex, Herpes Labialis, Herpes Simplex, Herpes Simplex Encephalitis, Encephalitis, Herpes Simplex, Herpes Simplex Labial, Herpes Labialis, Herpes Zoste, rHerpes Zoster Oticus, Herpesviridae Infections, Herpesvirus Infections, Herpesviridae Infections, Herpetic Acute Necrotizing Encephalitis, Encephalitis, Herpes Simplex, Herpetic Facial Paralysis, Bell Palsy, Hexosaminidase A and B Deficiency Disease, Sandhoff Disease, Hexosaminidase A Deficiency Disease, Tay-Sachs Disease, Hiatal Hernia, Hernia, Hiatal, Hibernoma, Lipoma, Hiccup, Hidradenitis Suppurativa, Hidrotic Ectodermal Dysplasia, Ectodermal Dysplasia, Hip Dislocation Congenital, Hip Dysplasia Congenital, Hip Dislocation, Congenital, Hippel-Lindau Disease, Hirschsprung Disease, Hirsutism, Histidinemia Histiocytoma Benign Fibrous, Histiocytoma Cutaneous, Histiocytoma, Benign Fibrous, Histiocytoma Fibrous, Histiocytoma, Benign Fibrous, Histiocytoma Malignant Fibrous, Histiocytosis X, Histiocytosis, Langerhans-Cell, Histiocytosis Langerhans-Cell Histiocytosis Non-Langerhans-Cell, Histomoniasis, PROTOZOAN INFECTIONS, Histoplasmosis, HIV Infections, Hives, Urticaria, Hives, HMN Proximal Type I, Spinal Muscular Atrophies of Childhood, HMSN, Hereditary Motor and Sensory Neuropathies, HMSN Type I, Charcot-Marie-Tooth Disease, HMSN I, II, HMSN Type II, Charcot-Marie-Tooth Disease, HMSN I, II, HMSN Type III, Hereditary Motor and Sensory Neuropathies, HMSN Type IV, Refsum Disease, HMSN Type IV, Refsum Disease, HMSN Type VII, Hereditary Motor and Sensory Neuropathies, Hodgkin Disease, Holmes-Adie Syndrome, Adie Syndrome, Holoprosencephaly, Holt-Oram Syndrome, Heart Defects, Congenital, Home Remedies, Medicine, Traditional, Homocystinuria, Homologous Wasting Disease, Hookworm Infections, Hordeolum, Horizontal Nystagmus, Nystagmus, Pathologic, Horner Syndrome Horner's Syndrome, Horner Syndrome, Horse Diseases Horton Disease, Temporal Arteritis, Horton Giant Cell Arteritis, Temporal Arteritis, Hospital Infections, Cross Infection, Hospital-Addiction Syndrome, Munchausen Syndrome, HSAN, Hereditary Sensory and Autonomic Neuropathies, HSAN Type I, Hereditary Sensory and Autonomic Neuropathies, HSAN Type II, Hereditary Sensory and Autonomic Neuropathies, HSAN Type III, Dysautonomia, Familial, HSAN Type IV, Hereditary Sensory and Autonomic Neuropathies, HSAN Type V, Hereditary Sensory and Autonomic Neuropathies, HSN Type I, Hereditary Sensory and Autonomic Neuropathies, HSN Type II, Hereditary Sensory and Autonomic Neuropathies, HTLV-III Infections, HIV Infections, HTLV-III-LAV Infections, HIV Infections, Hughe's Syndrome, Antiphospholipid Syndrome, Human Flu, Influenza, Human, Human Identification, Forensic Anthropology, Human Influenza, Influenza, Human, Human Retrovirus, RNA virus infections, Huntington Chorea, Huntington Disease, Hurler's Syndrome, Mucopolysaccharidoses, Hutchinson-Gilford Syndrome, Progeria, Hutchinson's Melanotic Freckle, Hutchinson's Teeth, Syphilis, Congenital, Hydatid Cyst, Echinococcosis, Hydatidiform Mole, Hydatidosis, Echinococcosis, Hydramnios, Polyhydramnios, Hydrocephalus, Hydrocephalus Normal Pressure, Hydronephrosis, Hydrophobia, Rabies, Hydrops, Edema, Hydrosyringomyelia, Syringomyelia, Hyperacusis, Hyperaldosteronism, Hyperbilirubinemia Hereditary, Hyperbilirubinemic Encephalopathy, Kernicterus, Hypercalcemia, Hypercapnia, Hypercholesteremia, Hypercholesterolemia, Hypercholesterolemia, Hyperemesis Gravidarum, Hyperemia, Hyperglycemic Hyperosmolar Nonketotic Coma Hyperhidrosis, Hyperimmunoglobulin E-Recurrent Infection Syndrome, Job's Syndrome, Hyperinsulinism, Hyperkalemia, Hyperkinetic Syndrome, Attention Deficit Disorder with Hyperactivity, Hyperlipidemia Familial Combined, Hyperlipidemia Multiple Lipoprotein-Type, Hyperlipidemia, Familial Combined, Hypermetropia, Hyperopia, Hyperopia, Hyperostosis, Hyperostosis Cortical Congenital, Hyperoxaluria, Hyperphenylalaninemia Non-Phenylketonuric, Phenylketonurias, Hyperpipecolic Acidemia, Peroxisomal Disorders, Hyperpituitarism, Hyperplasia Giant Lymph Node, Giant Lymph Node Hyperplasia, Hyperpotassemia, Hyperkalemia, Hyperprolactinemia, Hyperpyrexia Malignant, Malignant Hyperthermia, Hypersalivation, Sialorrhea, Hypersensitivity, Hypersensitivity Atopic, Hypersensitivity, Immediate, Hypersensitivity Immediate, Hypersensitivity Latex, Latex Hypersensitivity, Hypersensitivity Respiratory, Hypersensitivity Type I, Hypersensitivity, Immediate, Hypersensitivity Type III, Immune Complex Diseases, Hypersomnia Periodic, Kleine-Levin Syndrome, Hypertension, Hypertension Portal, Hypertension Pulmonary, Hyperthermia, Fever, Hyperthermia Malignant, Malignant Hyperthermia, Hyperthyroidism, Hypertrophy Left Ventricular, Hypertrophy Right Ventricular, Hypertropia, Strabismus, Squint, Hyperventilation, Hypervitaminosis A, Hyphema, Hypocalcemia, Hypochondriasis, Hypocupremia Congenital, Menkes Kinky Hair Syndrome, Hypogalactia, Lactation Disorders, Hypogammaglobulinemia, Agammaglobulinemia, Hypoglycemia, Hypogonadism Hypohidrosis, Hypokalemia, Hypomenorrhea, Menstruation Disturbances, Hyponatremia, Hypophosphatasia, Hypophyseal Disorders, Pituitary Diseases, Hypopituitarism, Hypoplastic Left Heart Syndrome, Hypopotassemia, Hypokalemia, Hypoproconvertinemia, Factor VII Deficiency, Hyposalivation, Xerostomia, Hypospadias, Hypotension, Hypothermia, Hypothyroidism, Hypoventilation Central Alveolar, Sleep Apnea, Central, Hypovolemic Shock, Shock, Hypoxanthine-Phosphoribosyl-Transferase Deficiency Disease, Lesch-Nyhan Syndrome, Hypoxia, Anoxia, Hypoxia Brain, Hypoxic Encephalopathy, Hypoxia, Brain, Hypsarrhythmia, Spasms, Infantile, Hysteria Dissociative, Dissociative disorders, I-Cell Disease, Mucolipidoses, Ichthyosis Icterus, Jaundice, IDDM, Diabetes Mellitus, Type 1, Ideational Apraxia, Apraxias, Idiocy, Mental Retardation, Idiopathic Environmental Intolerances, Multiple Chemical Sensitivity, Idiopathic Hypertrophic Subaortic Stenosis, Cardiomyopathy, Hypertrophic, Idiopathic Hypertrophic Subvalvular Stenosis, Idiopathic Intracranial Hypertension, Pseudotumor Cerebri, Idiopathic Orofacial Dyskinesia, Meige Syndrome, Idiopathic Orthostatic Hypotension Shy-Drager Type, Shy-Drager Syndrome, Idiopathic Parkinson Disease, Parkinson Disease, IgA Deficiency IgA Neuropathy, Glomerulonephritis, IgE-Mediated Hypersensitivity, Hypersensitivity, Immediate, Ileitis Regional, Crohn Disease, Ileitis Terminal, Crohn Disease, Ileocolitis, Crohn Disease, Immune Complex Diseases Immune Disorders, Immune System Diseases, Immune Disorders, Immune System Diseases, Immune System Diseases, Immune System Diseases, Immunodeficiency Syndrome Acquired, Acquired Immunodeficiency Syndrome, Immunodeficiency Common Variable, Common Variable Immunodeficiency, Immunodeficiency Severe Combined, Severe Combined Immunodeficiency, Immunologic Deficiency Syndrome Acquired, Acquired Immunodeficiency Syndrome, Immunologic Deficiency Syndromes Immunologic Diseases, Immune System Diseases, Impetigo Contagiosa, Impetigo, Impotence Impulse Control Disorders, Inappropriate Follicle Stimulating Hormone Secretion, Hyperpituitarism, Inappropriate FSH Secretion Syndrome, Hyperpituitarism, Inappropriate Growth Hormone Secretion Syndrome, Acromegaly, Inappropriate LH Secretion Syndrome, Hyperpituitarism, Inappropriate Luteinizing Hormone Secretion, Hyperpituitarism, Inappropriate Thyroid Stimulating Hormone Secretion, Hyperpituitarism, Inappropriate TSH Secretion Syndrome, Hyperpituitarism, Inborn Errors of Metabolism, Metabolism, Inborn Errors, Inclusion Disease, Cytomegalovirus Infections, Incontinentia Pigmenti Incontinentia Pigmenti Achromians, Pigmentation Disorders, Indigestion, Dyspepsia, Infantile Cortical Hyperostosis, Hyperostosis, Cortical, Congenital, Infantile Paralysis, Poliomyelitis, Infantile Spasms, Spasms, Infantile, Infantile Spinal Muscular Atrophy, Spinal Muscular Atrophies of Childhood, Infectious and Parasitic Diseases, Infectious Mononucleosis, Infectious Mononucleosis-Like Syndrome Chronic, Fatigue Syndrome, Chronic, Infertility, Infertility Female, Infertility Male, Inflammation, Inflammation Brain, Encephalitis, Inflammatory Bowel Diseases, Inflammatory Myopathy, Myositis, Inflammatory Response Syndrome Systemic, Systemic Inflammatory Response Syndrome, Influenza in Birds Influenza in Humans, Influenza, Human, Influenza Avian, Influenza in Birds, Influenza Human Injuries, Injuries Poisonings and Occupational Diseases, Disorders of Environmental Origin, Inoculation Lymphoreticulosis, Cat-scratch Disease, Insensitivity to Pain with Anhidrosis Congenital, Hereditary Sensory and Autonomic Neuropathies, Insomnia Fatal Familial, Insulin Resistance, Insulin Resistance Syndrome X, Metabolic Syndrome X, Insulinoma, Insuloma, Insulinoma, Intention Tremor, Tremor, Intermittent Claudication, Intermittent Explosive Disorder, Internuclear Ophthalmoplegia, Intersexuality, Hermaphroditism, Interstitial Cystitis, Cystitis, Interstitial, Interstitial Lung Diseases, Lung Diseases, Interstitial, Intervertebral Disk Displacement, Intestinal Cancer, Intestinal Neoplasms, Intestinal Diseases, Intestinal Diseases Parasitic, Intestinal Neoplasms, Intestinal Neuronal Dysplasia, Intestinal Obstruction, Intestinal Polyps Intoxication, Poisoning, Intoxication, Poisoning, Intracerebral Hemorrhage, Cerebral Hemorrhage, Intracranial Aneurysm Intracranial Central Nervous System Disorders, Brain diseases, Intracranial Vascular Disorders, Cerebrovascular Disorders, Intracranial Vasospasm, Vasospasm, Intracranial, Intrauterine Cross-Transfusion, Fetofetal Transfusion, Intrauterine Growth Retardation, Fetal Growth Retardation, Iodamoebiasis, Amebiasis, Iodine Deficiency, Iritis, Iron Overload, Iron Poisoning, Iron-Deficiency Anemia, Anemia, Iron-Deficiency, Irritable Bowel Syndrome Isaac's Syndrome, Fasciculation, Ischemia Myocardial, Myocardial Ischemia, Ischemic Attack Transient Ischemic Encephalopathy, Brain Ischemia, Ischemic Heart Disease, Myocardial Ischemia, Ischemic Optic Neuropathy, Optic Neuropathy, Ischemic, Isoimmunization Rhesus, Rh Isoimmunization, Itai-Itai, Cadmium Poisoning, Itching, Pruritus, Ito Syndrome, Pigmentation Disorders, IUGR, Fetal Growth Retardation, Ivemark Syndrome, Jackknife Seizures, Spasms, Infantile, Jacksonian Seizure, Seizures, Jacobsen Syndrome, Jansky-Bielschowsky Disease, Neuronal Ceroid-Lipofuscinoses, Jaundice, Jaundice Chronic Idiopathic, Jaundice Hemolytic, Anemia, Hemolytic, Jaundice Neonatal, Jerk Nystagmus, Nystagmus, Pathologic, Job's Syndrome Jock Itch, Dermatomycoses, Joint Diseases, Joseph Disease, Machado-Joseph Disease, Juvenile Huntington Disease, Huntington Disease, Juvenile Spinal Muscular Atrophy, Spinal Muscular Atrophies of Childhood, Juvenile Temporal Arteritis, Temporal Arteritis, Kabuki Make-Up Syndrome, Kallmann Syndrome, Kanner's Syndrome, Autistic Disorder, Kaposi Disease, Xeroderma Pigmentosum, Kartagener Syndrome, Kartagener Triad, Kartagener Syndrome, Kawasaki Disease, Mucocutaneous Lymph Node Syndrome, Kearns Syndrome, Kearns-Sayer Syndrome, Kearns-Sayer Syndrome, Keloid, Kennedy Syndrome, Muscular Atrophy, Spinal, Keratitis, Keratitis Ulcerative, Corneal Ulcer, Keratoconus, Keratosis Follicularis, Keratosis Actinic, Keratosis Seborrheic, Kernicterus, Ketoacidosis Diabetic, Diabetic Ketoacidosis, Ketosis Diabetic, Diabetic Ketoacidosis, Kidney Calculi, Kidney Diseases, Kidney Failure Acute, Kidney Failure Chronic, Kidney Stones, Kidney Calculi, Kidney Tubular Necrosis Acute, Kienbock Disease, Osteonecrosis, Kimura Disease, Angiolymphoid Hyperplasia with Eosinophilia, Kinky Hair Syndrome, Menkes Kinky Hair Syndrome, Kissing Disease, Infectious Mononucleosis, *Klebsiella* Infections, Kleine-Levin Syndrome, Klein-Waardenburg Syndrome, Waardenburg's Syndrome, Kleptomania, Impulse control disorders, Klinefelter Syndrome, Klippel-Feil Syndrome, Klippel-Trenaunay Disease, Klippel-Trenaunay-Weber Syndrome, Klippel-Trenaunay-Weber Syndrome, Klumpke Paralysis, Brachial Plexus Neuropathies, Erb's Palsy, Kniest Dysplasia, Dwarfism, Koehler Disease, Osteochondritis, Konzo, Plant Poisoning, Krabbe Disease, Leukodystrophy, Globoid Cell, Krukenberg Tumor Kufs Disease, Neuronal Ceroid-Lipofuscinoses, Kugelberg-Welander Disease, Spinal Muscular Atrophies of Childhood, Kuru Encephalopathy, Kuru, Kussmaul Aphasia, Mutism, Kwashiorkor, Starvation, Labhart-Willi Syndrome, Prader-Willi Syndrome, Labyrinthitis, Lacrimal Apparatus Diseases, Lacrimal Duct Obstruction, Lactation Disorders, Lactose Intolerance, Lactose Malabsorption, Lactose Intolerance, Lambert-Eaton Myasthenic Syndrome, Lambliasis, Giardiasis, Landau-Kleffner Syndrome, Landry-Guillain-Barre Syndrome, Guillain-Barre Syndrome, Langer-Giedion Syndrome, Langerhans-Cell Granulomatosis, Histiocytosis, Langerhans-Cell, Larsen Syndrome, Larva Migrans, Larva Migrans Cutaneous, Larva Migrans, Larva Migrans Ocular, Larva Migrans, Laryngeal Cancer, Laryngeal Neoplasms, Laryngeal Diseases, Laryngeal Neoplasms, Laryngeal Nerve Palsy Recurrent, Vocal Cord Paralysis, Laryngeal Paralysis, Vocal Cord Paralysis, Laryngeal Perichondritis, Laryngeal diseases, Laryngeal Stenosis, Laryngostenosis, Laryngitis, Laryngomalacia, Laryngostenosis, Larynx Neoplasms, Laryngeal Neoplasms, Lassitude, Fatigue, Lateral Bulbar Syndrome, Lateral Medullary Syndrome, Wallenberg Syndrome, Lateral Medullary Syndrome, Lateral Sclerosis, Motor Neuron Disease, Latex Allergy, Latex Hypersensitivity, Latex Hypersensitivity, Laurence-Moon Syndrome, Laurence-Moon-Biedl Syndrome, Laurence-Moon Syndrome, Lazy Eye, Amblyopia, Lead Poisoning, Leber's Congenital Amaurosis, Blindness, Leeching, Left Heart Syndrome Hypoplastic, Hypoplastic Left Heart Syndrome, Left Ventricular Hypertrophy, Hypertrophy, Left Ventricular, Leg Ulcer, Legal Medicine, Forensic Medicine, Legal Medicine, Forensic Medicine, Legg-Perthes Disease, Legionellosis, Leigh Disease, Leiomyoma, Leiomyosarcoma, Leiomyosarcoma Epithelioid, Leiomyosarcoma, Leiomyosarcoma Myxoid, Leiomyosarcoma, Leishmaniasis, Lennox-Gastaut Syndrome, Epilepsy, Lens Diseases, Lens Opacities, Cataract, Lentiginosis, Lentigo, Lentiginosis Perioral, Peutz-Jeghers Syndrome, Lentigo, Lentigo Malignant, Hutchinson's Melanotic Freckle, Leprosy, Leptomeningeal Cysts, Arachnoid Cysts, Leptospirosis, Lesch-Nyhan Syndrome, Leucine Metabolism Disorders, Leukemia, Leukocytopenia, Leukopenia, Leukodystrophy Globoid Cell, Leukodystrophy Metachromatic, Leukodystrophy Spongiform, Canavan Disease, Leukoencephalitis Subacute Sclerosing, Subacute Sclerosing Panencephalitis, Leukoencephalopathy Subcortical, Dementia, Vascular, Leukopenia Lewy Body Disease Lewy Body Parkinson Disease, Parkinson Disease, Libman-Sacks Disease, Lupus Erythematosus, Systemic, Lice Infestations, Lichen Planus, Lichen Ruber Planus, Lichen Planus, Lichen Sclerosus, Lichen Sclerosus et Atrophicus, White Spot Disease, Lichen Sclerosus et Atrophicus, Lightheadedness, Dizziness, Limb Cramp, Muscle Cramp, Lindau Disease, Hippel-Lindau Disease, Lipodystrophy, Lipodystrophy Intestinal, Whipple Disease, Lipoma, Lipoma Pleomorphic, Lipoma, Lipomatosis, Lipomatosis, Lipomucopoly, saccharidosis, Mucolipidoses, Lissencephaly, *Listeria* Infections, Little Disease, Cerebral Palsy, Livedo Reticularis Systemic Involvement, Sneddon Syndrome, Liver Cirrhosis, Liver Diseases, Liver Fibrosis, Loaiasis, Loiasis, African Eye Worm, Lobar Holoprosencephaly, Holoprosencephaly, Lobstein Disease, Osteogenesis Imperfecta, Locked-In Syndrome, Quadriplegia, Lockjaw, Trismus, Loiasis Long QT Syndrome, Lordosis Lou Gehrig Disease, Amyotrophic Lateral Sclerosis, Loudness Recruitment, Hyperacusis, Louis-Bar Syndrome, Ataxia Telangiectasia, Louis-Bar Syndrome, Lowe Syndrome, Oculocerebrorenal Syndrome, Lowe Syndrome, Lower Nephron Nephrosis, Kidney Tubular Necrosis, Acute, Ludwig's Angina Lung Abscess Lung Cancer, Lung Neoplasms, Lung Diseases, Lung Diseases Interstitial, Lung Inflammation, Pneumonia, Lung Neoplasms, Lupus Erythematosus Disseminatus, Lupus Erythematosus, Systemic, Lupus Erythematosus Cutaneous, Lupus Erythematosus Cutaneous Subacute, Lupus Erythematosus Cutaneous, Lupus Erythematosus Systemic, Luteinizing Hormone Inappropriate Secretion, Hyperpituitarism, Lyme Borreliosis, Lyme Disease, Lyme Disease, Lymph Node Hyperplasia Giant, Giant Lymph Node Hyperplasia, Lymph Node Syndrome Mucocutaneous, Mucocutaneous Lymph Node Syndrome, Lymphadenitis, Lymphadenopathy, Lymphangioendothelioma, Lymphangioma, Lymphangioleiomyomatosis, Lymphangioma, Lymphangioma Cavernous, Lymphangioma, Lymphatic Diseases, Lymphatism, Lymphatic diseases, Lymphedema, Lymphogranuloma Inguinale, Lymphogranuloma Venereum, Lymphogranuloma Venereum, Lymphogranuloma Malignant, Hodgkin Disease, Lymphoma Burkitt, Burkitt Lymphoma, Lymphoma Malignant, LYMPHOMA, Lymphoma Non-Hodgkin, Lymphoproliferative Disorders, Lysosomal Enzyme Disorders, Lysosomal Storage Diseases, Lysosomal Storage Diseases, Machado-Joseph Disease, Macroglobulinemia, Waldenstrom Macroglobulinemia, Macroglossia, Macropsia Macular Degeneration, Maculopathy Age-Related, Macular Degeneration, Madura Foot, Maduromycosis, Mycetoma, Maduromycosis, Maffucci Syndrome, Enchondromatosis, Maggot Infestations, Myiasis, Magnesium Deficiency, Mal de Debarquement, Motion Sickness, Malaria, Male Breast Neoplasms, Breast Neoplasms, Male, Male Genital Diseases, Genital Diseases, Male, Male Genital Neoplasms, Genital Neoplasms, Male, Male Pattern Baldness, Alopecia, Male Urogenital Diseases, Male Urogenital Diseases, Malignant Hyperpyrexia, Malignant Hyperthermia, Malignant Hyperthermia, Malignant Melanoma, Melanoma, Malignant Meningioma, Meningioma, Malta Fever, Brucellosis, Mammary Dysplasia, Fibrocystic Breast Disease, Mandibulofacial Dysostosis, Manganese Poisoning, Mange, Mite Infestations, Mange Sarcoptic, Scabies, Manic Disorder, Bipolar Disorder, Manic-Depressive Psychosis, Bipolar Disorder, Manipulation Chiropractic, Mannosidosis alpha B Lysosomal, alpha-Mannosidosis, Maple Syrup Urine Disease, Marasmus, Starvation, Marble Bone Disease, Osteopetrosis, Marcus-Gunn Pupil, Pupil disorders, Marfan Syndrome, Marginal Ulcer, Peptic Ulcer, Marie-Struempell Disease, Spondylitis, Ankylosing, Marsh Fever, Malaria, Martin-Bell Syndrome, Fragile X Syndrome, Martin-Bell syndrome, Masseter Muscle Spasm, Trismus, Mastalgia, Breast Diseases, Mast-Cell Disease, Mastocytosis, Mastectomy, Mastocytosis, Mastoiditis, Maturity-Onset Diabetes Mellitus, Diabetes Mellitus, Type 2, Maxillofacial Procedures, Oral Surgical Procedures, McArdle Disease, Glycogen Storage Disease, McCune-Albright Syndrome, Fibrous Dysplasia, Polyostotic, MCLS, Mucocutaneous Lymph Node Syndrome, Measles, Measles Inclusion Body Encephalitis, Subacute Sclerosing Panencephalitis, Measles German, Rubella, Meckel Diverticulum, Meconium Aspiration Syndrome, Mediastinal Cyst, Medicine Indigenous, Mediterranean Fever Familial, Familial Mediterranean Fever, Yerevanian Disease, Medullary Sponge Kidney, Medulloblastoma, Medulloblastoma Desmoplastic, Medulloblastoma, Medullomyoblastoma, Medulloblastoma, Megacolon Congenital, Hirschsprung Disease, Megaesophagus, Esophageal Achalasia, Meibomian Cyst, Chalazion, Meige Syndrome Meigs Syndrome, Ovarian Neoplasms, Melancholia, Depressive Disorder, Melanism, Melanosis, Melanocytic Vestibular Schwannoma, Neuroma, Acoustic, Melanoma, Melanoma Amelanotic, Melanosis, Melanotic Freckle, Hutchinson's Melanotic Freckle, MELAS Syndrome, Melasma, Melanosis, Melena, Gastrointestinal Hemorrhage, Melioidosis, Melkersson-Rosenthal Syndrome, Melorheostosis, Memory Disorders, Memory Loss, Memory Disorders, Menetrier Disease, Gastritis, Hypertrophic, Meniere's Disease, Meniere's Syndrome, Meniere's Disease, Meningeal Plague, Plague, Meningioma, Meningiomas Multiple, Meningioma, Meningiomatosis, Meningioma, Meningitis Bacterial, Meningitis Viral, Meningoencephalitis Herpes Simplex Virus, Encephalitis, Herpes Simplex, Menkes Kinky Hair Syndrome, Menkes Syndrome, Menkes Kinky Hair Syndrome, Menstruation Disorders, Menstruation Disturbances, Menstruation Disturbances, Menstruation Retrograde, Menstruation Disturbances, Mental Disorders, Mental Disorders, Mental Disorders Diagnosed in Childhood, Mental Retardation, Mercury Poisoning, Merkel Cell Tumor, Carcinoma, Merkel Cell, Mesothelioma, Metabolic Diseases, Metabolic Syndrome X, Metabolism Inborn Errors, Metatarsal Deformity, Metatarsus Primus Varus, Hallux Valgus, Methemoglobinemia, Microbiology Infectious Diseases, Microcephaly, Microphthalmos, Micropsia, Vision disorders, Micropunctures, Punctures, Microvascular Angina, Middle Ear Cholesteatoma, Cholesteatoma, Middle Ear, Migraine Disorders, Miliaria, Sweat Gland Diseases, Milk-Alkali Syndrome, Hypercalcemia, Miller Fisher Syndrome, Milroy's Disease, Lymphedema, Minimally Invasive, Minimal Brain Dysfunction, Attention Deficit Disorder with Hyperactivity, Minimal Change Disease, Nephrosis, Minimal Residual Disease, Neoplasm, Residual, Miosis Innervational Defect, Horner Syndrome, Miscarriage, Abortion, Spontaneous, Mite Infestations, Mitochondrial Diseases, Mitochondrial Myopathies, Mitochondrial Myopathy Lactic Acidosis Stroke-Like Episode, Melas Syndrome, Mitral Click-Murmur Syndrome, Mitral Valve Prolapse, Mitral Valve Prolapse, Mixed Connective Tissue Disease, MODY, Diabetes Mellitus, Type 2, Moebius Syndrome, Paralysis, Moebius Syndrome, Moersch-Woltmann Syndrome, Stiff-Person Syndrome, Stiff Man Syndrome, Molar Pregnancy, Hydatidiform Mole, Mole Skin, Nevus, Molluscum Contagiosum, Mongolism, Down Syndrome, Moniliasis, Candidiasis, Moniliasis Vulvovaginal, Candidiasis, Vulvovaginal, Monochromatopsia, Color Vision Defects, Monoclonal Gammopathies, Paraproteinemias, Monocular Blindness Transient, Amaurosis Fugax, Monoplegia, Hemiplegia, Monoplegic Cerebral Palsy, Cerebral Palsy, Monosomy 9p-Morton's Neuroma Morvan Disease, Syringomyelia, Moschkowitz Disease, Purpura, Thrombotic Thrombocytopenic, Mosquito-Borne Encephalitis, Encephalitis, Arbovirus, Motion Sickness, Motor Neuron Disease, Motor Neuron Disease Amyotrophic Lateral Sclerosis, Amyotrophic Lateral Sclerosis, Motor Neuron Disease Lower, Motor Neuron Disease, Motor Neuron Disease Upper, Motor Neuron Disease, Mountain Sickness, Altitude Sickness, Mouth Cancer, Mouth Neoplasms, Mouth Dryness, Xerostomia, Mouth Neoplasms, Movement Disorders, Moyamoya Disease, MS Multiple Sclerosis, Mucocutaneous Lymph Node Syndrome, Mucolipidoses, Mucolipidosis, Mucolipidoses, Mucopolysaccharidoses, Mucoviscidosis, Cystic Fibrosis, Multicystic Dysplastic Kidney, Multiple Carboxylase Deficiency Late-Onset, Biotimidase Deficiency, Multiple Chemical Sensitivity, Multiple Hamartoma Syndrome, Hamartoma Syndrome, Multiple, Cowden's Disease, Multiple Myeloma, Multiple Personality Disorder, Multiple Sclerosis, Multiple Sclerosis Acute Fulminating, Multiple System Atrophy, Mumps, Munchausen Syndrome, Munchausen Syndrome by Proxy, Aggression, Muscle Cramp, Muscle Disorders, Muscle Dystonia, Dystonia, Muscle Spasm, Spasm, Muscle Spasticity, Muscular Atrophy Peroneal, Charcot-Marie-Tooth Disease, HMSN I, II, Muscular Atrophy Postpoliomyelitis, Postpoliomyelitis Syndrome, Muscular Atrophy Spinal, Muscular Atrophy Spinal Infantile, Spinal Muscular Atrophies of Childhood, Muscular Diseases, Muscular Dystrophies, Muscular Dystrophy, Muscular Dystrophies, Musculoskeletal Abnormalities, Musculoskeletal Abnormalities, Musculoskeletal Diseases, Musculoskeletal Diseases, Mutism, Myasthenia Gravis, Myasthenic Syndrome Lambert-Eaton, Lambert-Eaton Myasthenic Syndrome, Mycetoma, Maduromycosis, Mycetoma, *Mycobacterium* Infections, *Mycoplasma* Infections, Mycoses, Mycotic Aneurysm Intracranial, Intracranial Aneurysm, Myelinoclastic Diffuse Sclerosis, Diffuse Cerebral Sclerosis of Schilder, Myelitis, Myelodysplastic Syndromes, Myeloencephalitis, Encephalomyelitis, Myelofibrosis, Myeloid Metaplasia, Myeloma Plasma-Cell, Multiple Myeloma, Myelopathy, Spinal cord diseases, Myelopathy Inflammatory, Myelitis, Myelopathy Traumatic, Spinal Cord Injuries, Myeloproliferative Disorders, Myelosclerosis, Myelofibrosis, Myelosis Nonleukemic, Myeloid Metaplasia, Myiasis, Myocardial Infarction, Myocardial Ischemia, Myocarditis Myoclonus, Myoclonus Cherry Red Spot Syndrome, Mucolipidoses, Myoclonus Action, Myoclonus, Myoclonus Nocturnal, Myoclonus, Myoclonus Palatal, Myoclonus, Myodystrophia Fetalis Deformans, Arthrogryposis, Myofascial Pain Dysfunction Syndrome Temporomandibular Joint, Temporomandibular Joint Dysfunction Syndrome, Myoma, Myopathies Mitochondrial, Mitochondrial Myopathies, Myopathies Structural Congenital, Myopathy Myotubular, Myopathies, Structural, Congenital, Myopia, Myositis, Myositis Ossificans, Myositis Focal, Myositis, Myositis Infectious, Myositis, Myositis Multiple, Polymyositis, Myotonic Dystrophy, Muscular Dystrophies, Myotubular Myopathy, Myxedema Congenital, Congenital Hypothyroidism, Myxoma, Nagana, Trypanosomiasis, African, Nail Diseases Nail Fungus, Onychomycosis, Nail-Patella Syndrome, Nails Ingrown, Nanism, Dwarfism, Narcissistic Personality Disorder, Narcolepsy, Narcolepsy-Cataplexy Syndrome, Narcolepsy, Nasal Obstruction, Nasal Polyps, Nausea, Near-Death Experience, Death, Nearsightedness, Myopia, Neck Cancer, Head and Neck Neoplasms, Neck Neoplasms, Head and Neck Neoplasms, Neck Pain, Neckache, Necrobacillosis, *Fusobacterium* Infections, Necrosis Aseptic of Bone, Osteonecrosis, Necrosis Avascular of Bone, Osteonecrosis, Necrotizing Arteritis, Polyarteritis Nodosa, Necrotizing Pyelonephritis, Pyelonephritis, Necrotizing Scleritis, Scleritis, Nelson Syndrome, Nematomorpha Infections, Helminthiasis, Neonatal Diseases and Abnormalities, Congenital, Hereditary, and Neonatal Diseases and Abnormalities, Neonatal Diseases and Abnormalities, Congenital, Hereditary, and Neonatal Diseases and Abnormalities, Neoplasm Residual, Neoplasms, Neoplasms Breast Male, Neoplasms Connective and Soft Tissue Neoplasms Dental Tissue, Odontogenic Tumors, Neoplasms Nervous System, Neoplasms Upper Aerodigestive Tract, Head and Neck Neoplasms, Nephritis Familial, Nephritis, Hereditary, Alport's Syndrome, Nephritis Hereditary, Nephroblastoma, Wilms Tumor, Nephrosis, Nephrotic Syndrome, Nerve Compression Syndromes, Nerve Entrapments, Nerve Compression Syndromes, Nerve Pain, Neuralgia, Nervous System Diseases, Nervous System Diseases Autonomic, Nervous System Diseases Manganese-Induced, Manganese Poisoning, not on MeSH, Nervous System Diseases Parasympathetic, Autonomic Nervous System Diseases, Nervous System Diseases Sympathetic, Nervous System Neoplasms, Nervous System Poisoning Manganese, Manganese Poisoning, not on MeSH, Netherton Syndrome, Ichthyosis, Neuralgia, Neuralgia Amyotrophic, Brachial Plexus Neuritis, Parsonage-Turner Syndrome, Neuralgia Diabetic, Diabetic Neuropathies, Neuralgia Geniculate, Herpes Zoster Oticus, Neuralgia Sciatic, Sciatica, Neuralgic Amyotrophy, Brachial Plexus Neuritis, Parsonage-Turner Syndrome, Neurilemmoma, Neurilemmosarcoma, Neurilemmoma, Neurinoma, Neurinoma, Neurilemmoma, Neurinoma, Neuritis Brachial Plexus, Brachial Plexus Neuritis, Parsonage-Turner Syndrome, Neuritis Vestibular, Vestibular Neuronitis, Neuroblastoma, Neuroblastoma Retinal, Retinoblastoma, Neurocysticercosis, Neurocysticercosis, Neurodynia, Neuralgia, Neuroendocrine Tumors, Neurofibromatoses, Neurofibromatosis, Neurofibromatoses, Neurohepatic Degeneration, Hepatolenticular Degeneration, Neurohypophyseal Diseases, Pituitary Diseases, Neuroleptic Malignant Syndrome, Neuroleptic-Induced Neuroleptic Malignant Syndrome, Neuroleptic Malignant Syndrome, Neuroleptic-Malignant Syndrome Neuroleptic Induced, Neuroleptic Malignant Syndrome, Neurologic Disorders, Nervous System Diseases, Neuroma Acoustic, Neuroma Morton's, Neuromuscular Diseases, Neuromyelitis Optica, Neuronal Ceroid-Lipofuscinoses, Neuronitis Vestibular, Vestibular Neuronitis, Neuronopathic Gaucher Disease, Gaucher Disease, Neuropapillitis, Optic Neuritis, Neuropathies Cranial, Cranial Nerve Diseases, Neuropathies Hereditary Motor and Sensory, Hereditary Motor and Sensory Neuropathies, Neuropathies Hereditary Sensory and Autonomic, Hereditary Sensory and Autonomic Neuropathies, Neuropathy Hereditary and Autonomic Type III, Dysautonomia, Familial, Neuropathy Hereditary Motor and Sensory Type IV, Refsum Disease, Neuropathy Hereditary Motor and Sensory Type IV, Refsum Disease, Neuroretinoangiomatosis, Sturge-Weber Syndrome, Neuroses Anxiety, Anxiety disorders, Neuroses Phobic, Phobic Disorders, Neuroses Post-Traumatic, Stress Disorders, Post-Traumatic, Neuroses War, Combat Disorders, Neurosis Depressive, Depressive Disorder, Neurosis Hypochondriacal, Hypochondriasis, Neurosis Obsessive-Compulsive, Obsessive-Compulsive Disorder, Neurosurgical Procedures, Neurotoxicity Syndrome Manganese, Neurovascular Syndrome Thoracic Outlet, Thoracic Outlet Syndrome, Neutral Amino Acid Transport Disorder, Hartnup Disease, Neutropenia, Neutrophilic Dermatosis Acute Febrile, Sweet's Syndrome, New Variant Creutzfeldt-Jakob Disease, Creutzfeldt-Jakob Syndrome, Nevoid Basal Cell Carcinoma Syndrome, Basal Cell Nevus Syndrome, Gorlin/Goltz Syndrome, Nevus, Nevus Flammeus, Port-Wine Stain, Nevus Syndrome Basal Cell, Basal Cell Nevus Syndrome, Gorlin/Goltz Syndrome, Nickel Poisoning, NIDDM, Diabetes Mellitus Type 2, Niemann-Pick Diseases Night Terror, Sleep disorders, Ninth Cranial Nerve Diseases, Glossopharyngeal Nerve Diseases, Nipah Virus Encephalitis, Paramyxoviridae Infections, *Nocardia* Infections, Nocturia Nodding Spasm, Spasms, Infantile, Non-Hodgkin Lymphoma, Lymphoma, Non-Hodgkin, Nonreassuring Fetal Status, Fetal Distress, Non-Small-Cell Lung Carcinoma, Carcinoma, Non-Small-Cell Lung, Nonverbal Learning Disorder, Noonan Syndrome, Normal Pressure Hydrocephalus, Hydrocephalus, Normal Pressure, Normokalemic Periodic Paralysis, Paralyses, Familial Periodic, Nose Bleed, Epistaxis, Nose Diseases, Epistaxis, Nosocomial Infections, Cross Infection, Nutrition Disorders, Nutritional and Metabolic Diseases, Nycturia, Nocturia, Nystagmus Pathologic, Obesity, Obsessive-Compulsive Disorder, Obstructive Hydrocephalus, Hydrocephalus, Occipital Encephalocele, Encephalocele, Occipital Region Trauma, Craniocerebral Trauma, Occupational Diseases, Ochoa Syndrome, Urofacial Syndrome Hydronephrosis with Peculiar Facial Expression, Ocular Larva Migrans, Larva Migrans, Ocular Motility Disorders, Ocular Retraction Syndrome, Duane Retraction Syndrome, Ocular Torticollis, Oculoauriculovertebral Syndrome, Goldenhar Syndrome, Oculocerebrorenal Syndrome, Oculomotor Nerve Diseases, Oculomotor Paralysis, Ophthalmoplegia, Oculopharyngeal Spinal Muscular Atrophy, Muscular Atrophy, Spinal, Oculosympathetic Syndrome, Horner Syndrome, Odontogenic Tumors Olfaction Disorders, Oligoastrocytoma Mixed, Astrocytoma, Oliguria, Olivopontocerebellar Atrophies, Olivopontocerebellar Atrophy Idiopathic, Olivopontocerebellar Atrophies, Ollier's Disease, Enchondromatosis, Omphalocele, Hernia, Umbilical, Omphalocele, Onchocerciasis, Ondine Curse, Sleep Apnea, Central, Ondine Syndrome, Sleep Apnea, Central, Onychomycosis, Ophthalmoplegia, Ophthalmoplegia Ataxia and Areflexia Syndrome, Miller Fisher Syndrome, Ophthalmoplegia Progressive Supranuclear, Supranuclear Palsy, Progressive, Oppenheim Disease, Neuromuscular Diseases, Opsoclonus, Optic Atrophies Hereditary, Optic Disk Disorders, Optic Disk Edema, Papilledema, Optic Nerve Diseases, Optic Nerve Ischemia, Optic Neuropathy, Ischemic, Optic Neuritis, Optic Neuropathy, Optic Neuropathy Ischemic, Optic Papilla Edema, Papilledema, Oral Cancer, Mouth Neoplasms, Oral Neoplasms, Mouth Neoplasms, Orbital Cellulitis, Orf, Eethyma, Contagious, Orf, Organic Mental Disorders Substance-Induced, Substance-related disorders, Orgasmic Disorder, Sexual Dysfunctions, Psychological, Ormond Disease, Retroperitoneal Fibrosis, Ornithine Carbamoyltransferase Deficiency Disease, Ornithine Transcarbamylase Deficiency Disease, Ornithine Carbamoyltransferase Deficiency Disease, Ornithosis, Psittacosis, Oroya Fever, *Bartonella* Infections, Orthodontics, Orthostasis, Dizziness, Orthostatic Hypotension Dysautonomic, Shy-Drager Syndrome, Osgood-Schlatter Disease, Osteochondritis, Osler-Rendu Disease, Telangiectasia, Hereditary Hemorrhagic, Osler-Vaquez Disease, Polycythemia Vera, Osteitis Deformans, Osteitis Fibrosa Disseminata, Fibrous Dysplasia of Bone, Osteoarthritis, Osteoarthrosis, Osteoarthritis, Osteoarthrosis Deformans, Osteoarthritis, Osteochondritis, Osteochondrosis, Osteochondritis, Osteogenesis Imperfecta, Osteomalacia, Osteomyelitis, Osteonecrosis, Osteo-Onychodysplasia Hereditary, Nail-Patella Syndrome, Osteopenia, Bone Diseases, Metabolic, Osteopetrosis, Osteophytosis Spinal, Spinal Osteophytosis, Osteoporosis, Osteoporosis Age-Related, Osteoporosis, Osteoporosis Post-Traumatic, Osteoporosis, Osteoporosis Senile, Osteoporosis, Osteosarcoma, Osteosclerosis Fragilis, Osteopetrosis, Osterreicher Syndrome, Nail-Patella Syndrome, Ostomy, Otitis, Otitis Interna, Labyrinthitis, Otorhinolaryngologic Diseases, Otorhinolaryngologic Diseases, Otorhinolaryngologic Neoplasms, Otosclerosis, Otospongiosis, Otosclerosis, Ovarian Cancer, Ovarian Neoplasms, Ovarian Cysts, Ovarian Neoplasms, Ovarian Pregnancy, Pregnancy, Ectopic, Ovarian Torsion, Owren Disease, Factor V Deficiency, Owren's Disease, Parahemophilia, Oxaluria, Hyperoxaluria, Oxidative Phosphorylation Deficiencies, Mitochondrial Diseases, Oxycephaly, Craniosynostoses, Oxygen Deficiency, Anoxia, Paget's Disease of Bone, Osteitis Deformans, Paget's Disease, Paget's Disease of Breast, Paget's Disease, Mammary, Paget's Disease Mammary, Pain, Pain Disorder, Somatoform disorders, Pain Insensitivity with Anhidrosis Congenital, Hereditary Sensory and Autonomic Neuropathies, Pain Syndrome Type I Regional Complex, Reflex Sympathetic Dystrophy, Type I Complex Regional Pain Syndrome, Pallister-Killian Syndrome Palmoplantaris Pustulosis, Psoriasis, Palsy, Paralysis, Pancreatic Cancer, Pancreatic Neoplasms, Pancreatic Diseases, Pancreatic Insufficiency, Exocrine Pancreatic Insufficiency, Pancreatic Neoplasms, Pancreatitis, Panencephalitis Subacute Sclerosing, Subacute Sclerosing Panencephalitis, Panhypopituitarism, Hypopituitarism, Panniculitis, Panniculitis Subacute Nodular Migratory, Panniculitis, Papilledema, Papillitis Optic, Papilledema, Papilloma, Papilloma Shope, Tumor virus infections, Papilloma Squamous Cell, Papilloma, Papillomatosis, Papilloma, Pappataci Fever, Phlebotomus Fever, Sandfly Fever, Pappataci Fever, Paraganglioma, Paraganglioma Gangliocytic, Paraganglioma, Parahemophilia, Factor V Deficiency, Owren's Disease, Parahemophilia, Paraimmunoglobulinemias, Paraproteinemias, Parainfluenza, Paramyxoviridae Infections, Parainfluenza Virus Infections, Paramyxoviridae Infections, Parakeratosis Variegata, Parapsoriasis, Paralyses Familial Periodic, Paralysis, Paralysis Agitans, Parkinson Disease, Paralysis Bulbar, Bulbar Palsy, Progressive, Paramyxoviridae Infections, Paraneoplastic Autonomic Dysfunction, Paraneoplastic Syndromes, Nervous System, Paraneoplastic Encephalomyelitis, Paraneoplastic Syndromes, Nervous System, Paraneoplastic Syndromes Nervous System, Paraosmia, Olfaction Disorders, Paraphilias Paraplegia, Paralysis, Paraproteinemias, Parapsoriasis, Parapsoriasis en Plaques, Parapsoriasis, Parasitic Diseases, Parasitic Intestinal Diseases, Parasitic Skin Diseases, Parasuicide, Self-Injurious Behavior, Parasympathetic Nervous System Diseases, Autonomic Nervous System Diseases, Parathyroid Diseases, Parietal Region Trauma, Craniocerebral Trauma, Parinaud Syndrome, Parkinson Disease, Parkinsonian Disorders, Parkinsonian Syndrome, Parkinsonian Disorders, Parkinsonism, Parkinsonian Disorders, Parkinsonism Experimental, Parkinsonian Disorders, Parkinsonism Juvenile, Parkinsonian Disorders, Parodontosis, Periodontal Diseases, Paronychia Parotitis Epidemic, Mumps, Infectious Parotitis, Paroxysmal Cold Hemoglobinuria, Hemoglobinuria, Paroxysmal, Paroxysmal Nerve Pain, Neuralgia, Paroxysmal Nocturnal Hemoglobinuria, Hemoglobinuria, Paroxysmal, Paroxysmal Sleep, Narcolepsy, Parsonage-Turner Syndrome, Brachial Plexus Neuritis, Parsonage-Turner Syndrome, Passive-Dependent Personality, Dependent Personality Disorder, Pathological Conditions Signs and Symptoms Pearson's Syndrome, PANCREATIC DISEASES, Pectus Excavatum, Funnel Chest, Pediculosis, Lice Infestations, Pellagra, Pelvic Horn Syndrome, Nail-Patella Syndrome, Pelvic Inflammatory Disease, Pemphigoid, Pemphigoid, Bullous, Pemphigoid Bullous, Pemphigus Vulgaris, Pemphigus, Pemphigus Benign Familial, Pendular Nystagmus, Nystagmus, Pathologic, Penile Cancer, Penile Neoplasms, Penile Diseases, Penile Induration, Penile Neoplasms, Peptic Ulcer, Periadenitis Mucosa Necrotica Recurrens, Stomatitis, Aphthous, Perianeurysmal Fibrosis Inflammatory, Retroperitoneal Fibrosis, Periaortitis Chronic, Retroperitoneal Fibrosis, Periarteritis Nodosa, Polyarteritis Nodosa, Pericardial Cyst, Mediastinal Cyst, Pericardial Effusion, Pericarditis, Periodic Alternating Nystagmus, Nystagmus, Pathologic, Periodic Disease, Familial Mediterranean Fever, Yerevanian Disease, Periodic Paralysis Familial, Paralyses, Familial Periodic, Periodontal Diseases, Periodontics, Peripheral Angiopathies, Peripheral Vascular Diseases, Peripheral Autonomic Nervous System Diseases, Autonomic Nervous System Diseases, Peripheral Nerve Diseases, Peripheral Nervous System Diseases, Peripheral Nervous System Diseases, Peripheral Neuropathies, Peripheral Nervous System Diseases, Peripheral Vascular Diseases, Periphlebitis, Phlebitis, Peritoneoscopy, Laparoscopy, Pernicious Vomiting of Pregnancy, Hyperemesis Gravidarum, Peroneal Muscular Atrophy, Charcot-Marie-Tooth Disease, HMSN I, II, Peroxisomal Disorders, Personality Disorder Borderline, Borderline Personality Disorder, Personality Disorder Dependent, Dependent Personality Disorder, Perthes Disease, Legg-Perthes Disease, Pertussis, Whooping Cough, Pes Cavus, Pes Planus, Flatfoot, Petechiae, Purpura, Peter's Anomaly Peutz-Jeghers Syndrome, Peyronie's Disease, Penile Induration, Pfeiffer Syndrome, Acrocephalosyndactylia, Phakomatosis Bourneville, Tuberous Sclerosis, Bourneville's Disease, Phakomatosis Sturge-Weber, Sturge-Weber Syndrome, Phantom Limb, Pharyngeal Diseases, Pharyngeal Diverticulum, Zenker Diverticulum, Pharyngitis, Pharyngoesophageal Diverticulum, Zenker Diverticulum, Phenylalanine Hydroxylase Deficiency Disease, Phenylketonurias, Phenylketonurias, Pheochromocytoma, Pheochromocytoma Extra-Adrenal, Pheochromocytoma, Phimosis, Phlebitis, Phlebotomus Fever, Phlegmasia Alba Dolens, Thrombophlebitis, Phlegmon, Cellulitis, Phobia School, Phobic Disorders, Phobia Social, Phobic Disorders, Phobias, Phobic Disorders, Phobic Neuroses, Phobic Disorders, Phonation Disorders, Voice Disorders, Phorias, Strabismus, Squint, Photodermatitis, Photosensitivity Disorders, Photosensitivity Disorders, Phycomycosis, Zygomycosis, Phytanic Acid Storage Disease, Refsum Disease, Pica Syndrome, Eating disorders, Pick's Disease, Dementia, Pierre Robin Syndrome, Pigmentary Pallidal Degeneration, Hallervorden-Spatz Syndrome, Pigmentary Retinopathy, Retinitis Pigmentosa, Pigmentation Disorders, Pilar Cyst, Epidermal Cyst, Pilonidal Cyst, Pilonidal Sinus, Pilonidal Sinus Pin Worms, Parasitic intestinal diseases, Piriformin Syndrome, Nerve Compression Syndromes, Piroplasmosis, Babesiosis, Pituitary Diseases, Pityriasis, Pityriasis Versicolor, Tinea Versicolor, Placenta Diseases, Placental Insufficiency, Plague, Plant Poisoning, Plasma Cell Dyscrasias, Paraproteinemias, *Plasmodium* Infections, Malaria, Platelet Storage Pool Deficiency, Plegia, Paralysis, Pleural Diseases, Pleural Effusion, Pleurisy, Pneumococcal Infections, Pneumonia, Pneumonia Interstitial, Lung Diseases, Interstitial, Pneumonic Plague, Plague, Pneumonitis, Pneumonia, Pneumonitis Interstitial, Lung Diseases, Interstitial, Pneumothorax, POEMS Syndrome, Poikiloderma of Civatte, Poisoning, Poland Syndrome, Polio, Poliomyelitis, Poliodystrophia Cerebri, Diffuse Cerebral Sclerosis of Schilder, Poliomyelitis Nonpoliovirus, Poliomyelitis, Poliomyelitis Preparalytic, Poliomyelitis, Polyarteritis Nodosa, Polyarthritis, Arthritis, Polychondritis Chronic Atrophic, Polychondritis, Relapsing, Polychondritis Relapsing, Polycystic Ovary Syndrome, Polycythemia Vera, Polyendocrinopathies Autoimmune, Polyglandular Type I Autoimmune Syndrome, Polyendocrinopathies, Autoimmune, Polyglandular Type II Autoimmune Syndrome, Polyhydramnios, Polymenorrhea, Menstruation Disturbances, Polymyalgia Rheumatica, Polymyoclonus, Myoclonus, Polymyositis, Polymyositis-Dermatomyositis, Dermatomyositis, Polyneuropathies, Polyneuropathy Acquired, Polyneuropathies, Polyomavirus Infections, Polyopsia, Diplopia, Polyposis Coli Familial, Adenomatous Polyposis Coli, Polyposis Syndrome Familial, Adenomatous Polyposis Coli, Polyradiculitis, Polyradiculopathy, Polyradiculoneuropathy Acute Inflammatory, Guillain-Barre Syndrome, Polyradiculopathy, Polyradiculopathy Abdominal, Polyradiculopathy, Pompe's Disease, Glycogen Storage Disease, Popliteal Cyst, Porphyria Erythropoietic, Porphyria Erythropoietic Congenital, Porphyria, Erythropoietic, Porphyrias, Port-Wine Stain, Postcommissurotomy Syndrome, Postpericardiotomy Syndrome, Posterior Cervical Sympathetic Syndrome, Spinal Osteophytosis, Posterior Inferior Cerebellar Artery Syndrome, Lateral Medullary Syndrome, Wallenberg Syndrome, Posterior Ischemic Optic Neuropathy, Optic Neuropathy, Ischemic, Postnatal Depression, Depression, Postpartum, Postpartum Depression, Depression, Postpartum, Postpartum Hemorrhage, Postpericardiotomy Syndrome, Post-Polio Syndrome, Postpoliomyelitis Syndrome, Postpoliomyelitis Muscular Atrophy, Postpoliomyelitis Syndrome, Postpoliomyelitis Syndrome, Post-Poliomyelitis Syndrome, Postpoliomyelitis Syndrome, Post-Traumatic Hydrocephalus, Hydrocephalus, Post-Traumatic Stress Disorders, Stress Disorders, Post-Traumatic, Post-Traumatic Tic Disorder, Tic Disorders, Postural Orthostatic Tachycardia Syndrome, Tachycardia, Postviral Fatigue Syndrome, Fatigue Syndrome, Chronic, Pott Disease, Tuberculosis, Spinal, Prader-Willi Syndrome, Precancerous Conditions Pre-Eclampsia, Eclampsia, Pregnancy Complications, Pregnancy Ectopic Pregnancy Molar, Hydatidiform Mole, Premature Rupture of Membrane Pregnancy, Fetal Membranes, Premature Rupture, PROM, Preneoplastic Conditions, Precancerous Conditions, Presbycusis, Presbyopia, Presenile Alzheimer Dementia, Alzheimer Disease, Pressure Sore, Pressure Ulcer, Pressure Ulcer, Priapism, Primary Lateral Sclerosis, Motor Neuron Disease, Primary Parkinsonism, Parkinson Disease, Primate Diseases, Prion Diseases, Proctitis, Proctocolitis, Proctocolitis Hemorrhagic, Proctocolitis, Proctocolitis Ulcerative, Proctocolitis, Proctosigmoiditis, Proctocolitis, Progeria, Progeria Adult, Werner Syndrome, Prognathism, Progressive Intracranial Occlusive Arteropathy Moyamoya, Moyamoya Disease, Progressive Muscular Atrophy, Muscular Atrophy, Spinal, Progressive Supranuclear Ophthalmoplegia, Supranuclear Palsy, Progressive, Prolactin Hypersecretion Syndrome, Hyperprolactinemia, Prolactin Inappropriate Secretion, Hyperprolactinemia, Prolapsed Disk, Intervertebral Disk Displacement, Prosopagnosia Prostate Cancer, Prostatic Neoplasms, Prostatic Diseases Prostatic Neoplasms, Prosthesis Implantation, Prosthodontics, Protein C Deficiency, Protein S Deficiency, Proteinuria, *Proteus* Syndrome, Protozoan Infections, Prune Belly Syndrome, Pruritus, Pruritus Vulvae, Pseudoaphakia, Cataract, Pseudoexfoliation Syndrome, Exfoliation Syndrome, Pseudofolliculitis Barbae, Hair Diseases, Pseudo-Gaucher Disease, Pseudo-Hurler Polydystrophy, Mucolipidoses, Pseudomelia, Phantom Limb, *Pseudomonas* Infections, Pseudomyxoma Peritonei, Pseudopelade, Alopecia, Pseudopolyarthritis Rhizomelic, Polymyalgia Rheumatica, Pseudosclerosis, Hepatolenticular Degeneration, Pseudotumor Cerebri, Pseudoxanthoma Elasticum, Psittacosis, Psoriasis, Psudogout, Gout, Psychoses, Psychotic Disorders, Psychosexual Disorders, Sexual Dysfunctions, Psychological, Psychosexual Dysfunctions, Sexual Dysfunctions, Psychological, Psychosis Brief Reactive, Psychotic Disorders, Psychosis Manic-Depressive, Bipolar Disorder, Psychotic Disorders, PTA Deficiency, Factor XI Deficiency, Rosenthal Syndrome, Pterygium, Ptosis Eyelid, Blepharoptosis, PTSD, Stress Disorders, Post-Traumatic, Puberty Delayed, Puberty Precocious, Puerperal Disorders, Puerperal Infection, Pulmonary Alveolar Proteinosis, Pulmonary Atresia, Pulmonary Cancer, Lung Neoplasms, Pulmonary Disease, Chronic Obstructive, Pulmonary Diseases, lung diseases, Pulmonary Edema, Pulmonary Embolism, Pulmonary Emphysema, Pulmonary Fibrosis, Pulmonary Hypertension, Pulmonary Infarction, Pulmonary Embolism, Pulmonary Inflammation, Pneumonia, Pulmonary Neoplasms, Lung Neoplasms, Pulmonary Sarcoidosis, Sarcoidosis, Pulmonary, Pulmonary Thromboembolism, Pulmonary Embolism, Pulmonary Valve Atresia, Pulmonary Atresia, Pulmonic Plague, Plague, Pulsatile Tinnitus, Tinnitus, Pulseless Disease, Takayasu's Arteritis, Punctures, Pupil Disorders, Pupil Reaction Absent, Pupillary Functions Abnormal, Puppet Children, Angelman Syndrome, Purpura, Purpura Fulminans, Purpura, Schoenlein-Henoch, Purpura Hemorrhagica, Purpura, Schoenlein-Henoch, Purpura Nonthrombocytopenic, Purpura, Schoenlein-Henoch, Purpura Schoenlein-Henoch, Purpura Thrombocytopenic, Purpura Thrombopenic, Purpura, Thrombocytopenic, Purpura Thrombotic, Thrombocytopenic, Purpura Thrombotic, Thrombopenic, Purpura, Thrombotic Thrombocytopenic, Pustular Psoriasis of Palms and Soles, Psoriasis, Pustulosis of Palms and Soles, Psoriasis, Pustulosis Palmaris et Plantaris, Psoriasis, Pyelonephritis, Pyelonephritis Acute Necrotizing, Pyelonephritis, Pyoderma Gangrenosum, Pyorrhea Alveolaris, Periodontal Diseases, Pyothorax, Empyema, Pleural, Pyrexia, Fever, Pyromania, Firesetting Behavior, Q Fever, Quadrantanopsia, Hemianopsia, Quadriparesis, Quadriplegia, Quadriplegia, Quadriplegic Infantile, Cerebral Palsy, Quincke's Edema, Angioneurotic Edema, Rabies, Raccoon Diseases, Rachischisis, Spinal Dysraphism, Rachitis, Rickets, Raillietiniasis, Cestode Infections, Ramsay Hunt Auricular Syndrome, Herpes Zoster Oticus, Ramsay Hunt Paralysis Syndrome, Parkinsonian Disorders, Ranula, Rape, Rasmussen Syndrome, Encephalitis, Rat-Bite Fever, Rathke Pouch Tumor, Craniopharyngioma, Raynaud Disease, Reading Disability Developmental, Dyslexia, Reading Disorder, Dyslexia, Reading Disorder Developmental, Dyslexia, Reaven Syndrome X, Metabolic Syndrome X, Recruitment Loudness, Hyperacusis, Rectal Cancer, Rectal Neoplasms, Rectal Diseases, Rectal Neoplasms, Rectal Prolapse, Rectal Tumors, Rectal Neoplasms, Rectocolitis, Proctocolitis, Rectocolitis Hemorrhagic, Proctocolitis, Rectocolitis Ulcerative, Rectosigmoiditis, Proctocolitis, Refetoff Syndrome, Thyroid Hormone Resistance Syndrome, Reflex Sympathetic Dystrophy, Refractive Errors, Refsum Disease, Regurgitation Gastric, Gastroesophageal Reflux, Rehabilitation, Reinke's Edema, Voice Disorders, Reiter Syndrome, Reiter's Disease, Relapsing Fever, Remittent Fever, Malaria, Renal Artery Obstruction, Renal Artery Stenosis, Renal Artery Obstruction, Renal Calculi, Kidney Calculi, Renal Dialysis, Renal Disease End-Stage, Kidney Failure, Chronic, End Stage Renal Disease, Renal Failure Acute, Kidney Failure, Acute, Renal Failure Chronic, Kidney Failure, Chronic, Renal Failure End-Stage, Kidney Failure, Chronic, End Stage Renal Disease, Renal Osteodystrophy, Renal Rickets, Renal Osteodystrophy, Reptile Diseases, Residual Cancer, Neoplasm, Residual, Residual Tumor, Neoplasm, Residual, Respiratory Chain Deficiencies Mitochondrial, Respiratory Distress Syndrome Newborn, Respiratory Hypersensitivity, Respiratory Syncytial Virus Infections, Respiratory Syndrome Severe Acute, Severe Acute Respiratory Syndrome, Respiratory Tract Diseases, Respiratory Tract Infections, Respiratory Tract Neoplasms, Resting Tremor, Tremor, Restless Legs Syndrome, Retardation Mental, Mental Retardation, Reticulohistiocytoma, Histiocytosis, Non-Langerhans-Cell, Reticulolymphosarcoma, Lymphoma, Retinal Diseases, Retinal Pigment Epithelial Detachment, Retinal Detachment, Retinal Vein Occlusion, Retinitis Pigmentosa, Retinoblastoma, Retinopathy of Prematurity, Retinoschisis, Retinoschisis Degenerative, Retinoschisis, Retinoschisis Juvenile X-Linked, Retinoschisis, Retrobulbar Neuritis, Optic Neuritis, Retrolental Fibroplasia, Retinopathy of Prematurity, Retroperitoneal Fibrosis, Retropharyngeal Abscess, Rett Syndrome, Reye Syndrome, Rh Isoimmunization, Rhabdoid Tumor, Rhabdomyolysis, Rhabdomyosarcoma, Rheumatic Diseases, Rheumatic Fever, Rheumatism, Rheumatism Articular Acute, Rheumatic Fever, Rheumatism Muscular, Fibromyalgia, Rheumatism Peri-Extra-Articular, Polymyalgia Rheumatica, Rheumatoid Arthritis, Arthritis, Rheumatoid, Rheumatoid Purpura, Purpura, Schoenlein-Henoch, Rheumatoid Spondylitis, Spondylitis, Ankylosing, Rhinitis Rhinoscleroma, Rickets Renal, Renal Osteodystrophy, *Rickettsia* Infections, Rift Valley Fever, Right Ventricular Dysplasia Arrhythmogenic, Arrhythmogenic Right Ventricular Dysplasia, Right Ventricular Hypertrophy, Hypertrophy, Right Ventricular, Riley-Day Syndrome, Dysautonomia, Familial, Ring Constrictions Intrauterine, Amniotic Band Syndrome, Ringworm, Tinea, RNA Virus Infections Robinow Syndrome, Rochalimaea Infections, *Bartonella* Infections, Rocky Mountain Spotted Fever, Rod-Cone Dystrophy, Retinitis Pigmentosa, Romano-Ward Syndrome, Long QT Syndrome, Romberg Disease, Facial Hemiatrophy, Romberg Disease, Rosacea, Rosai-Dorfman Disease, Histiocytosis, Non-Langerhans-Cell, Rosenthal Syndrome, Factor XI Deficiency, Rosenthal Syndrome, Roseola Infantum, Exanthema Subitum, Roseola Infantum, Sixth Disease, Ross River Virus Infections, Alphavirus Infections, Rotary Nystagmus, Nystagmus, Pathologic, Rotor Syndrome, Hyperbilirubinemia, Hereditary, Roussy-Levy Syndrome, Charcot-Marie-Tooth Disease, HMSN I, II, Royer Syndrome, Prader-Willi Syndrome, RSH Syndrome, Smith-Lemli-Opitz Syndrome, Rubber Allergy, Latex Hypersensitivity, Rubella Rubeola, Measles, Rubinstein-Taybi Syndrome, Runt Disease, Russell Silver Syndrome Saccular Aneurysm, Intracranial Aneurysm, Saethre-Chotzen Syndrome, Acrocephalosyndactylia, Saint Anthonys Fire, Ergotism, Salaam Seizures, Spasms, Infantile, Salivary Gland Diseases, Salivary Gland Virus Disease, Cytomegalovirus Infections, *Salmonella* Infections, Salmonellosis, *Salmonella* Infections, Salpingitis, Samter's Syndrome, Sandfly Fever, Phlebotomus Fever, Sandfly Fever, Pappataci Fever, Sandhoff Disease, Sanfilippo Syndrome, Mucopolysaccharidoses, Santavuori-Haltia Disease, Neuronal Ceroid-Lipofuscinoses, Sao Paulo Typhus, Rocky Mountain Spotted Fever, SAPHO Syndrome, Acquired Hyperostosis Syndrome, SAPHO Syndrome, Sarcoidosis Pulmonary, Sarcoma, Sarcoma Cerebellar Circumscribed Arachnoidal, Medulloblastoma, Sarcoma Epithelioid, Sarcoma, Sarcoma Ewing's Sarcoma, Germinoblastic, Sarcoma Osteogenic, Osteosarcoma, Sarcoma Soft Tissue, Sarcoma, Sarcoma Spindle Cell, Sarcoma, SARS, Severe Acute Respiratory Syndrome, Scabies, Scalenus Anticus Syndrome, Thoracic Outlet Syndrome, Scapuloperoneal Form of Spinal Muscular Atrophy, Muscular Atrophy, Spinal, Scarlet Fever, Schamberg's Disease, Pigmentation Disorders, Schaumann's Disease, Sarcoidosis, Scheie Syndrome, Mucopolysaccharidoses, Scheuermann's Disease, Schilder Disease, Diffuse Cerebral Sclerosis of Schilder, Schilder-Addison Complex, Adrenoleukodystrophy, Schistosomiasis, Schizencephaly, Schizoaffective Disorder, Psychotic Disorders, Schizophrenia, Schizophrenic Disorders, Schizophreniform Disorders, Psychotic Disorders, Schmidt's Syndrome, Polyendocrinopathies, Autoimmune, Schoenlein-Henoch Purpura, Purpura, Schoenlein-Henoch, Schwannoma, Neurilemmoma, Neurinoma, Schwannoma Acoustic, Neuroma, Acoustic, Schwannomatosis Plexiform, Neurilemmoma, Neurinoma, Sciatic Neuralgia, Sciatica, Sciatica SCID, Severe Combined Immunodeficiency, Scimitar Syndrome, Scleritis, Scleroderma Systemic, Scleroma Nasal, Rhinoscleroma, Sclerosis Disseminated, Multiple Sclerosis, Sclerosis Hereditary Spinal, Friedreich Ataxia, Sclerosis Systemic, Scleroderma, Systemic, Scoliosis, Scotoma, Scotoma Arcuate, Scotoma, Scotoma Bjerrum, Scotoma, Scotoma Central, Scotoma, Scotoma Centrocecal, Scotoma, Scrub Typhus, Seasickness, Motion Sickness, Seasonal Affective Disorder, Seasonal Mood Disorder, Seasonal Affective Disorder, Sebaceous Cyst, Epidermal Cyst, Seborrheic Keratosis, Keratosis, Seborrheic, Second Cranial Nerve Diseases, Optic nerve diseases, -Saw Nystagmus, Nystagmus, Pathologic, Seizure Disorder, Epilepsy, Seizures, Seizures Convulsive, Seizures, Seizures Focal, Seizures, Seizures Generalized, Seizures, Seizures Motor, Seizures, Seizures Sensory, Seizures, Selective Mutism, Mutism, Self-Destructive Behavior, Self-Injurious Behavior, Self-Injurious Behavior, Semilobar Holoprosencephaly, Holoprosencephaly, Senile Dementia Alzheimer Type, Alzheimer Disease, Senile Osteoporosis, Osteoporosis, Senile Paranoid Dementia, Dementia, Senior Health Issues Sensory Agnosia, Agnosia, Sensory and Autonomic Neuropathies Hereditary, Sensory Neuropathy Hereditary, Hereditary Sensory and Autonomic Neuropathies, Sepsis, Sepsis Syndrome, Systemic Inflammatory Response Syndrome, Septic Shock, Septo-Optic Dysplasia, Serotonin Syndrome, Severe Acute Respiratory Syndrome, Severe Combined Immunodeficiency, Sever's Disease/Calceneal Apophysitis, Sex Chromosome Aberrations, Sex Chromosome Abnormalities, Sex Chromosome Aberrations, Sex Deviations, Paraphilias, Sexual and Gender Disorders, Sexual Arousal Disorder, Sexual Dysfunctions, Psychological, Sexual Aversion Disorder, Sexual Dysfunctions, Psychological, Sexual Dysfunctions Psychological, Sexually Transmitted Diseases Bacterial, Sezary Syndrome, Shaken Baby Syndrome, Sharp Syndrome, Mixed Connective Tissue Disease, Sheehan Syndrome, Hypopituitarism, Sheep and Goat Diseases Shingles, Herpes Zoster, Shingles, Shock, Shock Anaphylactic, Anaphylaxis, Shock Endotoxic, Shock, Septic, Shock Hemorrhagic, Shock Septic, Shock Toxic, Shock, Septic, Short Bowel Syndrome, Short Bowel Syndrome, Shoulder Injuries, Shoulder-Girdle Neuropathy, Brachial Plexus Neuritis, Parsonage-Turner Syndrome, Shoulder-Hand Syndrome, Reflex Sympathetic Dystrophy, Type I Complex Regional Pain Syndrome, Shy-Drager Syndrome, Sialidosis, Mucolipidoses, Sialorrhea, Siamese Twins, Twins, Conjoined, Sicca Syndrome, Sjogren's Syndrome, Sick Building Syndrome, SIDS, Sudden Infant Death, Silicosis, Simmonds Disease, Hypopituitarism, Sinusitis, Situs Inversus, Sixth Disease, Exanthema Subitum, Roseola Infantum, Sixth Disease, Sjogren's Syndrome, Skew Deviation, Skin and Connective Tissue Diseases, Skin and Connective Tissue Diseases, Skin Cancer, Skin Neoplasms, Skin Diseases, Skin Diseases Bacterial, Skin Diseases Fungal, Dermatomycoses, Skin Diseases Infectious, Skin Diseases Parasitic, Skin Mole, Nevus, Skin Neoplasms, Skin Ulcer, Sleep Apnea Central, Sleep Disorders, Sleep-Disordered Breathing Central, Sleep Apnea, Central, Slipped Disk, Intervertebral Disk Displacement, Slow Virus Diseases, Smallpox, Smell Disorders, Olfaction Disorders, Smith-Lemli-Opitz Syndrome, Smith-Magenis Syndrome, Smooth Pursuit Deficiency, Ocular motility disorder, Sneddon Syndrome, Sneddon-Champion Syndrome, Sneddon Syndrome, Snoring, Social Behavior, Sociology Sodoku, Rat-Bite Fever, Haverhill Fever, Somatization Disorder, Somatoform disorders, Somatoform Disorders, Somatotropin Hypersecretion Syndrome Acromegaly, Acromegaly, Sore Throat, Pharyngitis, Space Adaptation Syndrome, Space Motion Sickness, Space Motion Sickness, Spasm, Spasmodic Torticollis, Torticollis, Spasms Infantile, Spasmus Nutans, Spasms, Infantile, Spastic Diplegia, Cerebral Palsy, Spastic Dysphonia, Voice Disorders, Spastic Quadriplegia, Quadriplegia, Spastic Spinal Monoplegia Syndrome, Brown-Sequard Syndrome, Speech Disorders, Spermatic Cord Torsion, Sphaerophorus Infections, *Fusobacterium* Infections, Sphenopalatine Neuralgia, Facial Neuralgia, Spherocytosis Hereditary, Spider Veins, Telangiectasis, Spielmeyer-Vogt Disease, Neuronal Ceroid-Lipofuscinoses, Spina Bifida, Spinal Dysraphism, Spina Bifida Occulta Spinal Adjustment Chiropractic, Manipulation, Chiropractic, Spinal Bifida Closed, Spina Bifida Occulta, Spinal Cord Diseases, Spinal Cord Inflammation, Myelitis, Spinal Cord Injuries, Spinal Diseases, Spinal Dysraphism, Spinal Muscular Atrophies of Childhood, Spinal Muscular Atrophy, Muscular Atrophy, Spinal, Spinal Muscular Atrophy Infantile, Spinal Muscular Atrophies of Childhood, Spinal Muscular Atrophy Juvenile, Spinal Muscular Atrophies of Childhood, Spinal Osteophytosis, Spinal Stenosis, Spinocerebellar Ataxia Type 3, Machado-Joseph Disease, Splenic Diseases, Splenic Rupture, Spondylarthritis Ankylopoietica, Spondylitis, Ankylosing, Spondylitis Ankylosing, Spondylolisthesis, Spondylosis, Spinal Osteophytosis, Spondylosis Deformans, Spinal Osteophytosis, Spongiform Encephalopathies Transmissible, Prion Diseases, Spongiform Encephalopathy Subacute, Creutzfeldt-Jakob Syndrome, Spongy Disease of White Matter, Canavan Disease, Sprengel's Deformity Sprue Celiac, Celiac Disease, Sprue Nontropical, Celiac Disease, Squint, Strabismus, Squint, SSPE, Subacute Sclerosing Panencephalitis, St. Anthonys Fire, Ergotism, Staphylococcal Infections Stargardt Disease, Macular Degeneration, Starvation, Status Dysraphicus, Spinal Dysraphism, Status Lymphaticus, Lymphatic diesases, Status Marmoratus, Movement disorders, Status Migrainosus, Migraine Disorders, Steele-Richardson-Olszewski Syndrome, Supranuclear Palsy, Progressive, Steely Hair Syndrome, Menkes Kinky Hair Syndrome, Stein-Leventhal Syndrome, Polycystic Ovary Syndrome, Stenocardia, Angina Pectoris, Sterility, Infertility, Sterility, Infertility, Stevens-Johnson Syndrome, Stickler Syndrome, Stiff-Man Syndrome, Stiff-Person Syndrome, Stiff Man Syndrome, Stiff-Person Syndrome, Still's Disease Juvenile-Onset, Arthritis, Juvenile Rheumatoid, Stings, Bites and Stings, Stings, Bites and Stings, Stomatitis Aphthous, Stomatognathic Diseases, Storage Pool Deficiency, Platelet Storage Pool Deficiency, Strabismus, Strabismus Comitant, Strabismus, Squint, Strabismus Convergent, Esotropia, Strabismus Divergent, Exotropia, Strabismus Internal, Esotropia, Strabismus Noncomitant, Strabismus, Squint, Streeter Syndrome, Amniotic Band Syndrome, Streptococcal Infections, *Streptococcus pneumoniae* Infections, Pneumococcal Infections, Stress, Stress Disorders Post-Traumatic, Striatonigral Degeneration Autosomal Dominant, Machado-Joseph Disease, Stridor, Stroke, Cerebrovascular Accident, Stroke, Stroke, Cerebrovascular Accident, Stroke, Strongyloidiasis, Sturge-Weber Syndrome, Stuttering, Speech Disorders, Stye, Hordeolum, Subacute Sclerosing Panencephalitis, Subcortical Arteriosclerotic Encephalopathy, Dementia, Vascular, Subdural Hematoma, Hematoma, Subdural, Subglottic Stenosis, Laryngostenosis, Substance Abuse, Substance Dependence, Substance Use Disorders, Substance Withdrawal Syndrome, Substance-Related Disorders, Subvalvular Stenosis, Idiopathic Hypertrophic, Cardiomyopathy, Hypertrophic, Sudden Deafness, Hearing Loss, Sudden, Sudden Infant Death, Sudek Atrophy, Reflex Sympathetic Dystrophy, Type I Complex Regional Pain Syndrome, Suffering Physical, Pain, Suffocation, Asphyxia, Suicidal Behavior, Superior Vena Cava Obstruction, Superior Vena Cava Syndrome, Superior Vena Cava Syndrome, Superior Vena Cava Thrombosis, Superior Vena Cava Syndrome, Supraglottitis, Epiglottitis, Supranuclear Palsy Progressive, Surgery Maxillofacial, Swallowing Disorders, Deglutition Disorders, Sweat Gland Diseases, Sweet's Syndrome, Swimmer's Itch, Dermatitis, Swine Diseases, Sympathetic Nervous System Diseases, Autonomic Nervous System Diseases, Symptomatic Infantile Spasms, Spasms, Infantile, Symptoms and General Pathology, Pathological Conditions, Signs and Symptoms, Syncope, Unconsciousness, Syndrome X Angina, Microvascular Angina, Syndrome X Cardiac, Microvascular Angina, Synesthesia, Synovitis, Syphilis, Syphilis Congenital, Syringomyelia, Systemic Inflammatory Response Syndrome, Systolic Click-Murmur Syndrome, Mitral Valve Prolapse, Tachyarrhythmia, Tachycardia, Tachycardia Tactile Agnosia, Agnosia, *Taenia* Infections, Taeniasis, Taeniasis, Takatsuki's Syndrome, POEMS Syndrome, Takayasu Syndrome, Takayasu's Arteritis, Takayasu's Arteritis Talipes Cavus, foot deformities, Talipes Equinovarus, Clubfoot, Tangier Disease, Tangier Disease Neuropathy, Tangier Disease, Tapetoretinal Degeneration, Retinitis Pigmentosa, Tapeworm Infection, Cestode Infections, Tardive Dyskinesia, Taste Disorders, Taste Disorder Primary, Taste Disorder Secondary, Taste Disorders Taste Metallic, Taste Metallic, Tay-Sachs Disease, Tay-Sachs Disease B Variant, Tay-Sachs Disease, Teeth Grinding Disorder, Bruxism, Telangiectasia Hereditary Hemorrhagic Telangiectasis, Temporal Arteritis, Temporal Region Trauma, Craniocerebral Trauma, Temporomandibular Joint Disorders, Temporomandibular Joint Dysfunction Syndrome, Temporomandibular Joint Syndrome, Tendinitis, Tendinopathy, Tendinopathy Tendinosis, Tennis Elbow, Tenosynovitis, Teratoid Tumor, Teratoma, Teratoma Cystic, Teratoma Mature, Testicular Cancer, Testicular Diseases, Testicular Feminization, Androgen-Insensitivity Syndrome, Testicular Torsion, Spermatic Cord Torsion, Testis Undescended, Cryptorchidism, Tetanus Tethered Cord Syndrome, Spina Bifida Occulta, Tetrahydrobiopterin Deficiency, Tetralogy of Fallot Tetraplegia, Quadriplegia, Thalamic Diseases, Thalassemia Thallium Poisoning Thanatophoric Dwarfism, Thanatophoric Dysplasia, Thanatophoric Dysplasia The Aging Cell, The Visible Human Project, Thesaurismosis, Metabolic diseases, Thiamine Responsive Maple Syrup Urine Disease, Maple Syrup Urine Disease, Third-Nerve Palsy, Oculomotor Nerve Diseases, Thoracic Cyst, Mediastinal Cyst, Thoracic Outlet Nerve Compression Syndrome, Thoracic Outlet Syndrome, Thoracic Outlet Syndrome, Thrombasthenia, Thromboangiitis Obliterans, Thrombocytopathy, Blood Platelet Disorders, Thrombocytopenia, Thromboembolism Pulmonary, Pulmonary Embolism, Thrombopenia, Thrombocytopenia, Thrombophlebitis, Thrombosis, Thrombosis Retinal Vein, Retinal Vein Occlusion, Thrombus, Thrush, Candidiasis, Thygeson's Superficial Punctate Keratitis Thymic Cyst, Mediastinal Cyst, Thymoma Thyroid Cancer, Thyroid Neoplasms, Thyroid Diseases, Thyroid Hormone Resistance Syndrome, Thyroid Neoplasms, Thyroid Nodule, Thyroid Stimulating Hormone Inappropriate Secretion, Hyperpituitarism, Thyroiditis Autoimmune, Thyroiditis Lymphocytic, Thyroiditis, Autoimmune, Thyroiditis Lymphomatous, Thyroiditis, Autoimmune, Thyroiditis Subacute, Tic Disorder Chronic Motor or Vocal, Tic Disorders, Tic Disorder Combined Vocal and Multiple Motor, Tourette Syndrome, Tic Disorder Post-Traumatic, Tic Disorder Transient, Tic Disorders Vocal, Tic Douloureux, Trigeminal Neuralgia, Tick Paralysis, Tick-Borne Diseases, Tietze's Syndrome, Tinea Pedis, Dermatomycoses, Tinea Unguium, Onychomycosis, Tinea Versicolor, Tinnitus T-Lymphotropic Virus Type III Infections Human, HIV Infections, TMJ Disorders, Temporomandibular joint disorders, TMJ Syndrome, Temporomandibular Joint Dysfunction Syndrome, Tolosa-Hunt Syndrome, Ophthalmoplegia, Tongue Geographic, Glossitis, Benign Migratory, Tonsillar Cancer, Tonsillar Neoplasms, Tonsillar Neoplasms, Tonsillitis, Torticollis, Torture, Torulosis, Cryptococcosis, Tourette Syndrome, Toxic Shock Syndrome, Shock, Septic, Toxic Shock Syndrome, Shock, Septic, Toxocariasis, *Toxoplasma gondii* Infection, Toxoplasmosis, Tracheal Cyst, Mediastinal Cyst, Tracheal Stenosis, Tracheoesophageal Fistula Trachoma, Transient Ischemic Attack, Transmissible Dementias, Prion Diseases, Transport Disorder Neutral Amino Acid, Hartnup Disease, Trauma, Wounds and injuries, Treacher Collins Syndrome, Mandibulofacial Dysostosis, Tremor, Trench Foot, Immersion Foot, Trichinelliasis, Trichinosis, Trichinosis, Trichomonas Infections, Trichophytosis, Tinea, Trichorhinophalangeal Syndrome Type II, Langer-Giedion Syndrome, Trichothiodystrophy, Trichotillomania, Tricuspid Atresia, Tricuspid Valve Atresia, Tricuspid Atresia, Trigeminal Neuralgia, Trimethylaminuria, Fish Odor Syndrome; Triosephosphate Isomerase Deficiency, Anemia, Hemolytic, Congenital Nonspherocytic, Triple-Symptom Complex, Behcet Syndrome, Silk-Road Disease, Triple-X Females, Trismus, Trisomy 13, Patau Syndrome; Trisomy 21, Down Syndrome, Trisomy 9, Trophoblastic Cancer, Trophoblastic Neoplasms, Trophoblastic Tumor, Trypanosomiasis, Trypanosomiasis African Trypanosomiasis South American, Chagas Disease, Tsutsugamushi Disease, Scrub Typhus, Tuberculosis, Tuberculosis, Spinal Tuberous Sclerosis, Tubular Aggregate Myopathy, Myopathies, Structural, Congenital, Tularemia Tumor Virus Infections, Tumors, Turner Syndrome, Turner Syndrome Male, Noonan Syndrome, Turner-Kieser Syndrome, Nail-Patella Syndrome, Twin Transfusion, Fetofetal Transfusion, Twin Transfusion Syndrome, Twins Conjoined, Twins Siamese, Twins, Conjoined, Tympanic Membrane Perforation, Tympanic Membrane Rupture, Tympanic Membrane Perforation, Type I Hypersensitivity, Hypersensitivity, Immediate, Type III Hypersensitivity, Immune Complex Diseases, Typhoid Fever, Typhus, Epidemic Louse-Borne, Typhus Abdominal, Typhoid Fever, Typhus Epidemic Louse-Borne, Typhus Sao Paulo, Rocky Mountain Spotted Fever, Typhus Scrub, Scrub Typhus, Tyrosine Transaminase Deficiency Disease, Tyrosinemias, Tyrosinemias, UDP, glucose 4-Epimerase Deficiency Disease, Galactosemias, UDPglucose-Hexose-1-Phosphate Uridylyltransferase Deficiency, Galactosemias, Ulcer Aphthous, Stomatitis, Aphthous, Ulnar Nerve Compression Syndromes, Umbilical Hernia, Hernia, Umbilical, Omphalocele, Unconscious State, Unconsciousness, Unconsciousness, Undulant Fever, Brucellosis, Unipolar Depression, Depressive Disorder, Upper Aerodigestive Tract Neoplasms, Head and Neck Neoplasms, Upper Respiratory Infections, respiratory tract infections, Urea Cycle Disorders, Urethral Stenosis, Urethral Stricture, Urethral Stricture, Urethritis, Urinary Bladder Diseases, Urinary Bladder Neoplasms, Urinary Retention, Urinary Tract Cancer, Urologic Neoplasms, Urinary Tract Diseases, UROLOGIC DISEASES, Urinary Tract Infections, Urination Disorders, Urogenital, Urogenital, Urogenital, Urogenital, Urogenital Surgical Procedures, Urologic Cancer, Urologic Neoplasms, Urologic Diseases, Urologic Neoplasms, Urticaria, Urticaria Giant, Angioneurotic Edema, Usher Syndrome, Uterine Cervical Dysplasia, Uterine Cervical Neoplasms, Uterine Cervix Incompetence, Uterine Inversion, Uterine Prolapse, Uveitis, Uveomeningoencephalitic Syndrome, Uveomeningoencephalitis, Uveomeningoencephalitic Syndrome, Waardenburg's Syndrome Vaginal Diseases, Vaginal Prolapse, Uterine Prolapse, Vaginitis Monilial, Candidiasis, Vulvovaginal, Waldenstrom Macroglobulinemia, Wallenberg Syndrome, Lateral Medullary Syndrome, Valvular Heart Diseases, Van Bogaert's Leukoencephalitis, Subacute Sclerosing Panencephalitis, War Neuroses, Combat Disorders, Varicella, Chickenpox, Varices, Varicose Veins, Varicocele, Varicose Veins, Variola, Smallpox, Variola Minor, Smallpox, Warthin's Tumor, Salivary Gland Diseases, Warts, Vascular Accident Brain, Cerebrovascular Accident, Stroke, Vascular Dementia, Dementia, Vascular, Vascular Diseases, Vascular Diseases Intracranial, Cerebrovascular Disorders, Vascular Diseases Peripheral, Peripheral Vascular Diseases, Vasculitis, Vasculitis Churg-Strauss, Churg-Strauss Syndrome, Allergic Granulomatosis, Vasculitis Hemorrhagic, Purpura, Schoenlein-Henoch, Vasospasm Intracranial, Water Stress, Dehydration, Water-Electrolyte Imbalance, Weber-Christian Disease, Panniculitis, Wegener Granulomatosis, Velocardiofacial Syndrome, DiGeorge Syndrome, Thymic Dysplasia, Venereal Diseases Bacterial, Sexually Transmitted Diseases, Bacterial, Venereal Diseases Bacterial, Sexually Transmitted Diseases, Bacterial, Ventricular Dysplasia Right Arrhythmogenic, Arrhythmogenic Right Ventricular Dysplasia, Ventricular Fibrillation Ventricular Hypertrophy Left, Hypertrophy, Left Ventricular, Ventricular Hypertrophy Right, Hypertrophy, Right Ventricular, Werdnig-Hoffmann Disease, Spinal Muscular Atrophies of Childhood, Werner Syndrome, Wernicke Encephalopathy, Verruca, Warts, Verruga Peruana, *Bartonella* Infections, Vertical Nystagmus, Nystagmus, Pathologic, Vertigo Aural, Meniere's Disease, Vesication, Blister, Vesico-Ureteral Reflux, West Nile Fever, West Syndrome, Spasms, Infantile, Vestibular Neuronitis, Wet Lung, Pulmonary Edema, Whiplash Injuries, Whipple Disease, Whipple's Disease, Whipworm Infections, White Dot Syndrome, Whitmore's Disease, Melioidosis, Whooping Cough, *Vibrio* Infections, William-Beuren Syndrome, Williams Syndrome, Williams Syndrome, Wilms Tumor, Wilson Disease, Hepatolenticular Degeneration, Violence, Viral Meningitis, Virus Diseases, Vision Disorders, Wiskott-Aldrich Syndrome, Visual Agnosia, Agnosia, Vitamin A Deficiency, Vitamin B 12 Deficiency, Vitamin B Deficiency, Vitamin C Deficiency, Ascorbic Acid Deficiency, Vitamin Deficiency, Avitaminosis, Withdrawal Symptoms, Substance Withdrawal Syndrome, Vitiligo, Vocal Cord Paralysis, Vocal Tic Disorders, Tic Disorders, Vogt-Koyanagi-Harada Syndrome, Uveomeningoencephalitic Syndrome, Voice Disorders, Wolff Periodic Disease, Familial Mediterranean Fever, Yerevanian Disease, Wolff-Parkinson-White Syndrome, Wolf-Hirschhorn Syndrome, Wolfram Syndrome, Volkmann Contracture, Compartment Syndromes, Wolman Disease, Vomiting, von Hippel-Lindau Disease, Hippel-Lindau Disease, von Recklinghausen Disease, Neurofibromatoses, von Willebrand Disease, Wounds and Injuries, Wounds Penetrating & Nonpenetrating, WPW Syndrome, Wolff-Parkinson-White Syndrome, Wryneck, Torticollis, Vulvar Cancer, Vulvar Neoplasms, Vulvar Diseases, Vulvar Lichen Sclerosus, Vulvar Neoplasms, Waardenburg's Syndrome, Vaginal Diseases, Vaginal Prolapse, Uterine Prolapse, Vaginitis Monilial, Candidiasis, Vulvovaginal, Waldenstrom Macroglobulinemia, Wallenberg Syndrome, Lateral Medullary Syndrome, Wallenberg Syndrome, Valvular Heart Diseases, Heart Valve Diseases, Van Bogaert's Leukoencephalitis, Subacute Sclerosing Panencephalitis, War Neuroses, Combat Disorders, Varicella, Chickenpox, Varices, Varicose Veins, Varicocele, Varicose Veins, Variola, Smallpox, Variola Minor, Smallpox, Warthin's Tumor, Salivary Gland Diseases, Warts, Vascular Accident Brain, Cerebrovascular Accident, Stroke, Vascular Dementia, Dementia, Vascular, Vascular Diseases, Vascular Diseases Intracranial, Cerebrovascular Disorders, Vascular Diseases Peripheral, Peripheral Vascular Diseases, Vasculitis, Vasculitis Churg-Strauss, Churg-Strauss Syndrome, Allergic Granulomatosis, Vasculitis Hemorrhagic, Purpura, Schoenlein-Henoch, Vasospasm Intracranial, Water Stress, Dehydration, Water-Electrolyte Imbalance, Weber-Christian Disease, Panniculitis, Wegener Granulomatosis, Velocardiofacial Syndrome, DiGeorge Syndrome, Thymic Dysplasia, Venereal Diseases Bacterial, Sexually Transmitted Diseases, Bacterial, Venereal Diseases Bacterial, Sexually Transmitted Diseases, Bacterial, Ventricular Dysplasia Right Arrhythmogenic, Arrhythmogenic Right Ventricular Dysplasia, Ventricular Fibrillation Ventricular Hypertrophy Left, Ventricular Hypertrophy Right, Werdnig-Hoffmann Disease, Spinal Muscular Atrophies of Childhood, Werner Syndrome, Wernicke Encephalopathy, Verruca, Warts, Verruga Peruana, *Bartonella* Infections, Vertical Nystagmus, Nystagmus, Pathologic, Vertigo, Vertigo Aural, Meniere's Disease, Vesication, Blister, Vesico-Ureteral Reflux, West Nile Fever, West Syndrome, Spasms, Infantile, Vestibular Neuronitis, Wet Lung, Pulmonary Edema, Whiplash Injuries, Whipple Disease, Whipple's Disease, Whipworm Infections, White Dot Syndrome, Whitmore's Disease, Melioidosis, Whooping Cough, *Vibrio* Infections, William-Beuren Syndrome, Williams Syndrome, Wilms Tumor, Wilson Disease, Hepatolenticular Degeneration, Viral Meningitis, Virus Diseases, Vision Disorders, Wiskott-Aldrich Syndrome, Visual Agnosia, Agnosia, Vitamin A Deficiency, Vitamin B 12 Deficiency, Vitamin B Deficiency, Vitamin C Deficiency, Ascorbic Acid Deficiency, Vitamin Deficiency, Avitaminosis, Withdrawal Symptoms, Substance Withdrawal Syndrome, Vitiligo, Vitreous disorder, Vocal Cord Paralysis, Vocal Tic Disorders, Tic Disorders, Vogt-Koyanagi-Harada Syndrome, Uveomeningoencephalitic Syndrome, Voice Disorders, Wolff Periodic Disease, Familial Mediterranean Fever, Yerevanian Disease, Wolff-Parkinson-White Syndrome, Wolf-Hirschhorn Syndrome, Wolfram Syndrome, Volkmann Contracture, Compartment Syndromes, Wolman Disease, Vomitingvon Hippel-Lindau Disease, Hippel-Lindau Disease, von Recklinghausen Disease, Neurofibromatoses, von Willebrand Disease, Wounds and Injuries, Wounds Penetrating & Nonpenetrating, WPW Syndrome, Wolff-Parkinson-White Syndrome, Wryneck, Torticollis, Vulvar Cancer, Vulvar Neoplasms, Vulvar Diseases, Vulvar Lichen Sclerosus, Vulvar Neoplasms Xanthoma, Xanthomatosis, Xanthoma Disseminatum, Histiocytosis, Non-Langerhans-Cell, Xanthomatosis, Xanthomatosis Familial, Wolman Disease, Xanthomatosis Wolman's, Wolman Disease, Xeroderma, Ichthyosis, Xeroderma Pigmentosum, Xerostomia X-Linked Adrenoleukodystrophy, Adrenoleukodystrophy, X-Linked Lymphoproliferative Syndrome, Lymphoproliferative disorders, X-Linked Retinoschisis, Retinoschisis, XXY Males, Klinefelter Syndrome, XYY Karyotype, Yaws, Yellow Fever, *Yersinia* Infections Yersinosis, *Yersinia* Infections, Zellweger Syndrome, Zellweger-Like Syndrome, Zenker's Diverticulum, Zenker Diverticulum, Zollinger-Ellison Syndrome, Zona, Shingles, Zoonoses, Zoster, Herpes Zoster, Shingles, Zygomycosis.

1212. The method according to any of the previous items, wherein the undesired state of said individual is one or more Cardiovascular disease(s) such as heart disease, haemophilia, deep venous thrombosis, acute myocardial infarction and/or thrombocytopenia.

1213. The method according to any of the previous items, wherein the undesired state of said individual is Degeneration.

1214. The method according to any of the previous items, wherein the undesired state of said individual is one or more Dermatological disease(s).

1215. The method according to any of the previous items, wherein the undesired state of said individual is one or more ear, nose and/or throat disease(s).

1216. The method according to any of the previous items, wherein the undesired state of said individual is one or more endocrine disease(s).
1217. The method according to any of the previous items, wherein the undesired state of said individual is fatigue.
1218. The method according to any of the previous items, wherein the undesired state of said individual is one or more gastrointestinal disease(s).
1219. The method according to any of the previous items, wherein the undesired state of said individual is one or more genetic disorder(s).
1220. The method according to any of the previous items, wherein the undesired state of said individual is one or more genitourinary disease(s).
1221. The method according to any of the previous items, wherein the undesired state of said individual is one or more growth disorder(s).
1222. The method according to any of the previous items, wherein the undesired state of said individual is one or more andrology related disease(s).
1223. The method according to any of the previous items, wherein the undesired state of said individual is one or more gynaecology and obstetrics related disease(s).
1224. The method according to any of the previous items, wherein the undesired state of said individual is one or more haematological disease(s).
1225. The method according to any of the previous items, wherein the undesired state of said individual is one or more immune disorder(s).
1226. The method according to any of the previous items, wherein the undesired state of said individual is a primary immunodeficiency.
1227. The method according to item 1226, wherein the primary immunodeficiency is diagnosed by a method comprising a full blood count e.g. including accurate lymphocyte and granulocyte counts.
1228. The method according to item 1226, wherein the primary immunodeficiency is diagnosed by a method comprising determination of immunoglobulin levels e.g. of IgG, IgA and IgM.
1229. The method according to item 1226, wherein the primary immunodeficiency is diagnosed by a method comprising Quantification of the different types of mononuclear cells in the blood (i.e. lymphocytes and monocytes).
1230. The method according to item 1226, wherein the primary immunodeficiency is diagnosed by a method comprising Quantification of different groups of T lymphocytes (dependent on their cell surface markers, e.g. CD4+, CD8+, CD3+, TCRαβ and TCRγδ).
1231. The method according to item 1226, wherein the primary immunodeficiency is diagnosed by a method comprising Quantification of groups of B lymphocytes (e.g. CD19, CD20, CD21 and Immunoglobulin).
1232. The method according to item 1226, wherein the primary immunodeficiency is diagnosed by a method comprising Quantification of natural killer cells.
1233. The method according to item 1226, wherein the primary immunodeficiency is diagnosed by a method comprising Quantification of monocytes (e.g. CD15+).
1234. The method according to item 1226, wherein the primary immunodeficiency is diagnosed by a method comprising Quantification of activation markers (e.g. HLA-DR, CD25, CD80).
1235. The method according to item 1226, wherein the primary immunodeficiency is diagnosed by a method comprising Tests for T cell function such as skin tests for delayed-type hypersensitivity, cell responses to mitogens and allogeneic cells, and cytokine production by cells.
1236. The method according to item 1226, wherein the primary immunodeficiency is diagnosed by a method comprising Tests for B cell function such as antibodies to routine immunisations and commonly acquired infections, quantification of IgG subclasses.
1237. The method according to item 1226, wherein the primary immunodeficiency is diagnosed by a method comprising tests for phagocyte function e.g. reduction of nitro blue tetrazolium chloride, assays of chemotaxis, bactericidal activity.
1238. The method according to item 1226, wherein the primary immunodeficiency is treated with immunoglobulin replacement therapy intravenous immunoglobulin (IVIG) or subcutaneous immunoglobulin (SCIG) in antibody deficiencies or hematopoietic stem cell transplantation (for SCID).
1239. The method according to item 1226, wherein the primary immunodeficiency is of the Antibody/humoral type (Hypogammaglobulinemia/agammaglobulinemia (X-linked, Transient of infancy), Dysgammaglobulinemia (IgA, IgG, IgM), Hyper IgM syndrome, Common variable immunodeficiency, WHIM syndrome).
1240. The method according to item 1226, wherein the primary immunodeficiency is of the Cell-mediated type (DiGeorge syndrome, Nezelof syndrome, Purine nucleoside phosphorylase deficiency, Ataxia telangiectasia).
1241. The method according to item 1226, wherein the primary immunodeficiency is of the Combined type (Severe combined immunodeficiency (Adenosine deaminase deficiency, Omenn syndrome, X-SCID, ZAP70 deficiency), Bare lymphocyte syndrome, Wiskott-Aldrich syndrome).
1242. The method according to item 1226, wherein the primary immunodeficiency is of the Complement deficiency type (Angioedema).
1243. The method according to item 1226, wherein the primary immunodeficiency is of the Phagocyte bactericidal dysfunction (PBD) type (chemotaxis/degranulation: Leukocyte adhesion deficiency, Chediak-Higashi syndrome, Hyper-IgE syndrome; or respiratory burst: Chronic granulomatous disease, Myeloperoxidase deficiency)
1244. The method according to item 1226, wherein the primary immunodeficiency is comprises ICF syndrome characterized by Immunodeficiency, centromere instability and/or facial anomalies syndrome).
1245. The method according to any of the previous items, wherein the undesired state of said individual is a Combined T- and B-cell immunodeficiency.
1246. The method according to any of the previous items, wherein the undesired state of said individual is a Combined T- and B-cell immunodeficiency called T−/B+ SCID (T cells predominantly absent) characterized by γc deficiency, JAK3 deficiency, interleukin 7 receptor chain a deficiency, CD45 deficiency, and/or CD3δ/CD3ε deficiency.
1247. The method according to any of the previous items, wherein the undesired state of said individual is a Combined T- and B-cell immunodeficiency called T−/B− SCID (both T and B cells absent) characterized by RAG 1/2 deficiency, DCLRE1C deficiency, adenosine deaminase (ADA) deficiency, and/or reticular dysgenesis.

1248. The method according to any of the previous items, wherein the undesired state of said individual is a Combined T- and B-cell immunodeficiency called Omenn syndrome.
1249. The method according to any of the previous items, wherein the undesired state of said individual is a Combined T- and B-cell immunodeficiency called DNA ligase type IV deficiency.
1250. The method according to any of the previous items, wherein the undesired state of said individual is a Combined T- and B-cell immunodeficiency called CD40 ligand deficiency.
1251. The method according to any of the previous items, wherein the undesired state of said individual is a Combined T- and B-cell immunodeficiency called CD40 deficiency.
1252. The method according to any of the previous items, wherein the undesired state of said individual is a Combined T- and B-cell immunodeficiency called Purine nucleoside phosphorylase (PNP) deficiency.
1253. The method according to any of the previous items, wherein the undesired state of said individual is a Combined T- and B-cell immunodeficiency called MHC class II deficiency.
1254. The method according to any of the previous items, wherein the undesired state of said individual is a Combined T- and B-cell immunodeficiency called CD3γ deficiency.
1255. The method according to any of the previous items, wherein the undesired state of said individual is a Combined T- and B-cell immunodeficiency called CD8 deficiency.
1256. The method according to any of the previous items, wherein the undesired state of said individual is a Combined T- and B-cell immunodeficiency called ZAP-70 deficiency.
1257. The method according to any of the previous items, wherein the undesired state of said individual is a Combined T- and B-cell immunodeficiency called TAP-1/2 deficiency.
1258. The method according to any of the previous items, wherein the undesired state of said individual is a Combined T- and B-cell immunodeficiency called Winged helix deficiency.
1259. The method according to any of the previous items, wherein the undesired state of said individual is a Combined T- and B-cell immunodeficiency called X-SCID (X-linked SCID, absence of NK- and T-cells).
1260. The method according to any of the previous items, wherein the undesired state of said individual is an immunodeficiency characterised by antibody deficiency.
1261. The method according to item 1260, wherein the antibody deficiency is related to absense of B cells with a resultant severe reduction of all types of antibody characterized by X-linked agammaglobulinemia (btk deficiency), μ-Heavy chain deficiency, 15 deficiency, Igα deficiency, BLNK deficiency, and/or thymoma with immunodeficiency.
1262. The method according to item 1260, wherein antibody deficiency is related to reduction in 2 or more isotypes (usually IgG & IgA, sometimes IgM) resulting in variable immunodeficiency (LVID), ICOS deficiency, CD19 deficiency, TACI (TNFRSF13B) deficiency, and/or BAFF receptor deficiency.
1263. The method according to item 1260, wherein antibody deficiency is related to Normal numbers of B cells with decreased IgG and IgA and increased IgM e.g. resulting in AID deficiency, and/or UNG deficiency.
1264. The method according to item 1260, wherein antibody deficiency is related to Normal numbers of B cells with isotype or light chain deficiencies e.g. resulting in heavy chain deletions, kappa chain deficiency, isolated IgG subclass deficiency, IgA with IgG subclass deficiency, and/or selective immunoglobulin A deficiency.
1265. The method according to item 1260, wherein antibody deficiency is related to Specific antibody deficiency to specific antigens with normal B cell and normal Ig concentrations.
1266. The method according to item 1260, wherein antibody deficiency is related to Transient hypogammaglobulinemia of infancy (THI).
1267. The method according to any of the previous items, wherein the undesired state of said individual is an immunodeficiency termed Wiskott-Aldrich syndrome.
1268. The method according to any of the previous items, wherein the undesired state of said individual is an immunodeficiency characterized by DNA repair defects not causing isolated SCID including ataxia telangiectasia, ataxia-like syndrome, Nijmegen breakage syndrome, and/or Bloom syndrome.
1269. The method according to any of the previous items, wherein the undesired state of said individual is an immunodeficiency termed DiGeorge syndrome (when associated with thymic defects).
1270. The method according to any of the previous items, wherein the undesired state of said individual is an immunodeficiency Various immuno-osseous dysplasias (abnormal development of the skeleton with immune problems) including cartilage-hair hypoplasia, and/or Schimke syndrome.
1271. The method according to any of the previous items, wherein the undesired state of said individual is an immunodeficiency termed Hermansky-Pudlak syndrome type 2.
1272. The method according to any of the previous items, wherein the undesired state of said individual is an immunodeficiency Hyper-IgE syndrome.
1273. The method according to any of the previous items, wherein the undesired state of said individual is an immunodeficiency termed Chronic mucocutaneous candidiasis.
1274. The method according to any of the previous items, wherein the undesired state of said individual is an immunodeficiency termed Nezelof syndrome.
1275. The method according to any of the previous items, wherein the undesired state of said individual is an immunodeficiency termed Bare lymphocyte syndrome.
1276. The method according to any of the previous items, wherein the undesired state of said individual is an immunodeficiency termed Immune dysregulation diseases.
1277. The method according to any of the previous items, wherein the undesired state of said individual is an immunodeficiency with hypopigmentation or albinism including Chediak-Higashi syndrome, and/or Griscelli syndrome type 2.
1278. The method according to any of the previous items, wherein the undesired state of said individual is an immunodeficiency termed familial hemophagocytic lymphohistiocytosis characterized by perforin deficiency, MUNC13D deficiency, and/or syntaxin 11 deficiency.

1279. The method according to any of the previous items, wherein the undesired state of said individual is an immunodeficiency termed X-linked lymphoproliferative syndrome.
1280. The method according to any of the previous items, wherein the undesired state of said individual is an immunodeficiency comprising Syndromes with autoimmunity.
1281. The method according to any of the previous items, wherein the undesired state of said individual is an immunodeficiency comprising Syndromes with autoimmunity such as Autoimmune lymphoproliferative syndrome comprising type 1a (CD95 defects), type 1b (Fas ligand defects), type 2a (CASP10 defects), and/or type 2b (CASP8 defects).
1282. The method according to any of the previous items, wherein the undesired state of said individual is an immunodeficiency comprising APECED (autoimmune polyendocrinopathy with candidiasis and ectodermal dystrophy).
1283. The method according to any of the previous items, wherein the undesired state of said individual is an immunodeficiency comprising IPEX (immunodysregulation polyendocrinopathy enteropathy X-linked syndrome).
1284. The method according to any of the previous items, wherein the undesired state of said individual is an immunodeficiency comprising one or more Phagocyte disorders.
1285. The method according to any of the previous items, wherein the undesired state of said individual is an immunodeficiency comprising Phagocyte disorders such as severe congenital neutropenia due to ELA2 deficiency (with myelodysplasia), GFI1 deficiency (with T/B lymphopenia) and/or G-CSFR deficiency (G-CSF-unresponsive).
1286. The method according to any of the previous items, wherein the undesired state of said individual is an immunodeficiency comprising Kostmann syndrome.
1287. The method according to any of the previous items, wherein the undesired state of said individual is an immunodeficiency comprising Cyclic neutropenia.
1288. The method according to any of the previous items, wherein the undesired state of said individual is an immunodeficiency comprising X-linked neutropenia/myelodysplasia.
1289. The method according to any of the previous items, wherein the undesired state of said individual is an immunodeficiency comprising Leukocyte adhesion deficiency types 1, 2 and 3.
1290. The method according to any of the previous items, wherein the undesired state of said individual is an immunodeficiency comprising RAC2 deficiency.
1291. The method according to any of the previous items, wherein the undesired state of said individual is an immunodeficiency comprising Beta-actin deficiency.
1292. The method according to any of the previous items, wherein the undesired state of said individual is an immunodeficiency comprising Localized juvenile periodontitis.
1293. The method according to any of the previous items, wherein the undesired state of said individual is an immunodeficiency comprising Papillon-Lefèvre syndrome.
1294. The method according to any of the previous items, wherein the undesired state of said individual is an immunodeficiency comprising Specific granule deficiency.
1295. The method according to any of the previous items, wherein the undesired state of said individual is an immunodeficiency comprising Shwachman-Diamond syndrome.
1296. The method according to any of the previous items, wherein the undesired state of said individual is an immunodeficiency comprising Chronic granulomatous disease such as X-linked and/or autosomal forms.
1297. The method according to any of the previous items, wherein the undesired state of said individual is an immunodeficiency comprising Neutrophil glucose-6-phosphate dehydrogenase deficiency.
1298. The method according to any of the previous items, wherein the undesired state of said individual is an immunodeficiency comprising IL-12 and IL-23 β1 chain deficiency.
1299. The method according to any of the previous items, wherein the undesired state of said individual is an immunodeficiency comprising IL-12p40 deficiency.
1300. The method according to any of the previous items, wherein the undesired state of said individual is an immunodeficiency comprising Interferon γ receptor 1 deficiency.
1301. The method according to any of the previous items, wherein the undesired state of said individual is an immunodeficiency comprising Interferon γ receptor 2 deficiency.
1302. The method according to any of the previous items, wherein the undesired state of said individual is an immunodeficiency comprising STAT1 deficiency.
1303. The method according to any of the previous items, wherein the undesired state of said individual is an immunodeficiency comprising Innate immunity deficiencies.
1304. The method according to any of the previous items, wherein the undesired state of said individual is an immunodeficiency comprising Innate immunity deficiencies comprising Hypohidrotic ectodermal dysplasia.
1305. The method according to any of the previous items, wherein the undesired state of said individual is an immunodeficiency comprising Innate immunity deficiencies comprising NEMO deficiency.
1306. The method according to any of the previous items, wherein the undesired state of said individual is an immunodeficiency comprising Innate immunity deficiencies comprising IKBA deficiency.
1307. The method according to any of the previous items, wherein the undesired state of said individual is an immunodeficiency comprising Innate immunity deficiencies comprising IRAK-4 deficiency.
1308. The method according to any of the previous items, wherein the undesired state of said individual is an immunodeficiency comprising Innate immunity deficiencies comprising WHIM syndrome.
1309. The method according to any of the previous items, wherein the undesired state of said individual is an immunodeficiency comprising Innate immunity deficiencies comprising Epidermodysplasia verruciformis.
1310. The method according to any of the previous items, wherein the undesired state of said individual is an immunodeficiency comprising autoinflammatory disorders.

1311. The method according to any of the previous items, wherein the undesired state of said individual is an immunodeficiency comprising autoinflammatory disorders such as Familial Mediterranean fever.

1312. The method according to any of the previous items, wherein the undesired state of said individual is an immunodeficiency comprising autoinflammatory disorders such as TNF receptor associated periodic syndrome (TRAPS).

1313. The method according to any of the previous items, wherein the undesired state of said individual is an immunodeficiency comprising autoinflammatory disorders such as Hyper-IgD syndrome (HIDS).

1314. The method according to any of the previous items, wherein the undesired state of said individual is an immunodeficiency comprising autoinflammatory disorders such as CIAS1-related diseases including Muckle-Wells syndrome, Familial cold autoinflammatory syndrome and Neonatal onset multisystem inflammatory disease.

1315. The method according to any of the previous items, wherein the undesired state of said individual is an immunodeficiency comprising autoinflammatory disorders such as PAPA syndrome (pyogenic sterile arthritis, pyoderma gangrenosum, acne).

1316. The method according to any of the previous items, wherein the undesired state of said individual is an immunodeficiency comprising autoinflammatory disorders such as Blau syndrome.

1317. The method according to any of the previous items, wherein the undesired state of said individual is an immunodeficiency comprising Complement deficiencies.

1318. The method according to any of the previous items, wherein the undesired state of said individual is an immunodeficiency comprising Complement deficiencies comprising C1q deficiency (lupus-like syndrome, rheumatoid disease, infections).

1319. The method according to any of the previous items, wherein the undesired state of said individual is an immunodeficiency comprising Complement deficiencies comprising C1r deficiency (idem).

1320. The method according to any of the previous items, wherein the undesired state of said individual is an immunodeficiency comprising Complement deficiencies comprising C4 deficiency (idem).

1321. The method according to any of the previous items, wherein the undesired state of said individual is an immunodeficiency comprising Complement deficiencies comprising C2 deficiency (lupus-like syndrome, vasculitis, polymyositis, pyogenic infections).

1322. The method according to any of the previous items, wherein the undesired state of said individual is an immunodeficiency comprising Complement deficiencies comprising C3 deficiency (recurrent pyogenic infections).

1323. The method according to any of the previous items, wherein the undesired state of said individual is an immunodeficiency comprising Complement deficiencies comprising C5 deficiency (Neisserial infections, SLE).

1324. The method according to any of the previous items, wherein the undesired state of said individual is an immunodeficiency comprising Complement deficiencies comprising C6 deficiency (idem).

1325. The method according to any of the previous items, wherein the undesired state of said individual is an immunodeficiency comprising Complement deficiencies comprising C7 deficiency (idem, vasculitis).

1326. The method according to any of the previous items, wherein the undesired state of said individual is an immunodeficiency comprising Complement deficiencies comprising C8a and C8b deficiency (idem).

1327. The method according to any of the previous items, wherein the undesired state of said individual is an immunodeficiency comprising Complement deficiencies comprising C9 deficiency (Neisserial infections).

1328. The method according to any of the previous items, wherein the undesired state of said individual is an immunodeficiency comprising Complement deficiencies comprising C1-inhibitor deficiency (hereditary angioedema).

1329. The method according to any of the previous items, wherein the undesired state of said individual is an immunodeficiency comprising Complement deficiencies comprising Factor I deficiency (pyogenic infections).

1330. The method according to any of the previous items, wherein the undesired state of said individual is an immunodeficiency comprising Complement deficiencies comprising Factor H deficiency (haemolytic-uraemic syndrome, membranoproliferative glomerulonephritis).

1331. The method according to any of the previous items, wherein the undesired state of said individual is an immunodeficiency comprising Complement deficiencies comprising Factor D deficiency (Neisserial infections).

1332. The method according to any of the previous items, wherein the undesired state of said individual is an immunodeficiency comprising Complement deficiencies comprising Properdin deficiency (Neisserial infections).

1333. The method according to any of the previous items, wherein the undesired state of said individual is an immunodeficiency comprising Complement deficiencies comprising MBP deficiency (pyogenic infections).

1334. The method according to any of the previous items, wherein the undesired state of said individual is an immunodeficiency comprising Complement deficiencies comprising MASP2 deficiency.

1335. The method according to any of the previous items, wherein the undesired state of said individual is an immunodeficiency comprising secondary immunodeficiencies.

1336. The method according to any of the previous items, wherein the undesired state of said individual is an immunodeficiency comprising secondary immunodeficiencies caused by Chronic infection(s).

1337. The method according to any of the previous items, wherein the undesired state of said individual is an immunodeficiency comprising secondary immunodeficiencies caused by Malnutrition.

1338. The method according to any of the previous items, wherein the undesired state of said individual is an immunodeficiency comprising secondary immunodeficiencies caused by Ageing.

1339. The method according to any of the previous items, wherein the undesired state of said individual is an immunodeficiency comprising secondary immunodeficiencies caused by irradiation.

1340. The method according to any of the previous items, wherein the undesired state of said individual is an immunodeficiency comprising secondary immunodeficiencies caused by Medications such as chemotherapy, immunosuppressiva, and disease-modifying antirheumatic drugs.

1341. The method according to any of the previous items, wherein the undesired state of said individual is an immunodeficiency comprising secondary immunodeficiencies caused by Cancer.

1342. The method according to any of the previous items, wherein the undesired state of said individual is an immunodeficiency comprising secondary immunodeficiencies related to a transplant-related medicine-induced immunodeficiency.

1343. The method according to any of the previous items, wherein the undesired state of said individual is one or more infectious diseases.

1344. The method according to any of the previous items, wherein the undesired state of said individual is one or more infectious diseases can be selected from the group consisting of Bacteria and bacterial diseases (Specific kind of Infections), Fungus and fungal infections (Specific kind of Infections), Helminths and helminthic conditions (Specific kind of Infections), Prions and prion related diseases (Specific kind of Infections), Protozoa and protozoal infections (Specific kind of Infections), Viruses and viral disease (Specific kind of Infections), Abscess, Acariasis, actinomycetoma, Adenitis, Adenoiditis, African trypanosomiasis, Alpers Syndrome, Alphos, Alveolar osteitis, Amebiasis, Anorectal abscess, Anthrax, Ascariasis, Aspergillosis, Athlete's foot, Atypical pneumonia, Babesiosis, Bejel, Blastocystis hominis, Blastomycosis, Bolivian hemorrhagic fever, Botulism, Botryomycosis, Borna disease, Borreliosis (Lyme disease), Bovine spongiform encephalopathy, Brazilian purpuric fever (BPF), Bronchiolitis, Brucellosis, Bubonic plague, Buruli ulcer, Candidiasis, Campylobacteriosis, Cat scratch fever, Cellulitis, Chagas disease, Chalazion, Chickenpox (Varicella), Chikungunya, Cholangitis, Cholecystitis, Cholera, Clonorchiasis, Coccidioidomycosis, Colorado Tick Fever (CTF), Common cold, Creutzfeldt-Jakob disease, Crimean-Congo hemorrhagic fever, Cryptococcosis, Cryptosporidiosis, Cutaneous abscess, Cysticercosis, Cystitis, infective, Dengue fever, Dermatophytosis, Diarrheal diseases, Diphteria, Diphyllobothriasis, Discitis, Donovanosis, Dracunculiasis, Dukes' disease, Dysentery, Ebola hemorrhagic fever, Echinococcosis, Encephalitis, Enterobiasis, Epidural abscess, Erysipelas, Eumycetoma, Fascioliasis, Fatal Familial Insomnia, Filariasis, Finger pulp abscess, Fitz-Hugh-Curtis syndrome, Foodborne trematodiases, Foot-and-mouth disease, Gallbladder empyema, Gas gangrene, Gastroenteritis, Giardiasis, Glanders, Gnathostomiasis, Gonorrhea, Gradenigo-Lannois syndrome, Grisel syndrome, Helminthiasis, Hepatitis, Herpes simplex, Herpes zoster, HPV, Histoplasmosis, HIV/AIDS, Hookworm, Hordeolum externum, Human African trypanosomiasis, Hymenolepiasis, Impetigo, Infectious mononucleosis, Influenza, Intertrigo, Intracranial abscess/granuloma, Intraspinal abscess/granuloma, Isosporiasis, IV catheter infection, Japanese Encephalitis, Kuru, Kyasanur forest disease, Lábrea fever, La Crosse encephalitis, Lacrimal canaliculitis, Lady Windermere syndrome, Laryngeal papillomatosis, Laryngitis, Lassa fever, Legionellosis, Leishmaniasis, Lemierre's syndrome, Leptospirosis, Leprosy, Listeriosis, Liver abscess, Loa filariasis, lobomycosis, Lower respiratory tract infection, Ludwig angina, Lung abscess, Lymphangitis, Lymphatic filariasis, Malaria, Marburg haemorrhagic fever, Measles, Mediastinitis, Melioidosis, Meningitis, Metagonimiasis, Mumps, Murrain, Mycetoma, Mycosis, Myiasis, Necrotizing fasciitis, Neurocysticercosis, Nocardiosis, Omphalitis, Onchocerciasis, Ophthalmia neonatorum, Orbital cellulitis, Oropouche fever, Oroya fever, Osteomyelitis, Paragonimiasis, Paratyphoid fevers, Pediculosis, Periorbital cellulitis, Periodontis, Pertussis (Whooping Cough), Pharyngitis, Pharyngoconjunctival fever, Phlegmon, Pigbel (enteritis necroticans), Pinta, Pinworm Infection, Plantar wart, Pneumonia, Pneumonic plague, Pogosta disease, Poliomyelitis, Pott's disease, Prostatitis, Protothecosis, Psittacosis, Pyelonephritis acute, Pyelonephritis chronic, Pyomyositis, Q fever, Quinsy, Rabies, Rat-bite fever, Relapsing fever, Retropharyngeal abscess, Rheumatic Fever, Rhinosporidiosis, Rickettsialpox, Rift Valley fever, Ringworm, Rodentolepsis, Rocky Mountain Spotted Fever (RMSF), Roseola, Rubella, Salmonellosis, Scabies, Scarlet fever, Schistosomiasis, Septicemic plague, Septic arthropathy, Septic shock, Sepsis, Severe acute respiratory syndrome (SARS), Sexually transmissible disease, Shigellosis, Smallpox (Variola), Sodoku, Spondylodiskitis, Strongyloidiasis, Subdiaphragmatic abscess, Subdural empyema, Suppurative thyroiditis, Surra, Sweating sickness, Syphilis, Taeniasis, Tetanus, Trachoma, Tick-borne diseases, Tinea barbae, Tinea capitis, Tinea corporis, Tinea cruris, Tinea faciei, Tinea manuum, Tinea nigra, Tinea pedis, Tinea versicolor, Tonsillitis, Toxocariasis, Toxoplasmosis, Tracheolaryngobronchitis, Trachoma, Transmissible spongiform encephalopathy, Traveler's diarrhea, Trench fever, Treponematoses, Trichinellosis, Trichinosis, Trichomoniasis, Trichuriasis, Tropical diseases, Trypanosomiasis, Tuberculosis (TB), Tularemia, Typhoid fever, Typhus, Upper respiratory tract infection, Urethritis, Urinary tract infection, Venezuelan hemorrhagic fever (VHF), Verruca plana, viral hemorrhagic fevers (VHFs), Wart, West Nile disease, Wound infection, Yaws, Yellow fever, Yersiniosis, and Zygomycosis.

1345. The method according to any of the previous items, wherein the undesired state of said individual is Strep Throat, Scarlet Fever caused by *Streptococcus, Pyogenes*.

1346. The method according to any of the previous items, wherein the undesired state of said individual is Diphtheria caused by *Corynebacterium diphtheriae*.

1347. The method according to any of the previous items, wherein the undesired state of said individual is Pertussis (Whooping Cough) caused by *bordetella pertussis*.

1348. The method according to any of the previous items, wherein the undesired state of said individual is Meningococcal Meningitis caused by *Neisseria meningitides*.

1349. The method according to any of the previous items, wherein the undesired state of said individual is *Haemophilus* meningitis caused by *Haemophilus influenzae*.

1350. The method according to any of the previous items, wherein the undesired state of said individual is *Flavobacterium* meningitis caused by *Flavobacterium*.

1351. The method according to any of the previous items, wherein the undesired state of said individual is meningospecticum Tuberculosis caused by *Mycobacterium*.

1352. The method according to any of the previous items, wherein the undesired state of said individual is tuberculosis Pneumococcal pneumonia caused by *Sterptococcus pneumoniae*.

1353. The method according to any of the previous items, wherein the undesired state of said individual is Primary Atypical Pneumonia caused by *Mycoplasma pneumoniae*.

1354. The method according to any of the previous items, wherein the undesired state of said individual is *Klebsiella* pneumonia caused by *Klebsiella pneumoniae*.

1355. The method according to any of the previous items, wherein the undesired state of said individual is *Serratia* pneumonia caused by *Serratia marcescens*.
1356. The method according to any of the previous items, wherein the undesired state of said individual is Q Fever caused by *coxiella burnetti*.
1357. The method according to any of the previous items, wherein the undesired state of said individual is Psittacosis caused by *chlamydia psittaci*.
1358. The method according to any of the previous items, wherein the undesired state of said individual is Botulism caused by *Clostridium botulinum*.
1359. The method according to any of the previous items, wherein the undesired state of said individual is Staphylococcal Food Poisoning caused by *Stephylococcus aureus*.
1360. The method according to any of the previous items, wherein the undesired state of said individual is Clostridial Food Poisoning caused by *clostridium perfringes*.
1361. The method according to any of the previous items, wherein the undesired state of said individual is Typhoid Fever caused by *Salmonella typhi*.
1362. The method according to any of the previous items, wherein the undesired state of said individual is Salmonellosis caused by *Salmonella* serotypes.
1363. The method according to any of the previous items, wherein the undesired state of said individual is Shigellosis caused by *shigella* serotypes.
1364. The method according to any of the previous items, wherein the undesired state of said individual is Cholera caused by *vibrio cholerae*.
1365. The method according to any of the previous items, wherein the undesired state of said individual is Brucellosis caused by *Brucella* Spp.
1366. The method according to any of the previous items, wherein the undesired state of said individual is Anthrax caused by *Bacillus anthracis*.
1367. The method according to any of the previous items, wherein the undesired state of said individual is Tetanus caused by *Clostridium tetani*.
1368. The method according to any of the previous items, wherein the undesired state of said individual is Gas Gangrene caused by *clostridium perfringes*.
1369. The method according to any of the previous items, wherein the undesired state of said individual is Bubonic Plague caused by *yersinia pestis*.
1370. The method according to any of the previous items, wherein the undesired state of said individual is Relapsing Fever caused by *Borrelia recurrentis*.
1371. The method according to any of the previous items, wherein the undesired state of said individual is Rocky Mountain Spotted Fever caused by *Rickettsia rickettsiae*.
1372. The method according to any of the previous items, wherein the undesired state of said individual is Epidemic Typhus (Typhus Fever) caused by *Rickettsia prowazekii*.
1373. The method according to any of the previous items, wherein the undesired state of said individual is Endemic Typhus (Murine Typhus) caused by *Rickettsia typhi*.
1374. The method according to any of the previous items, wherein the undesired state of said individual is Scrub Typhus caused by *Rickettsia tsutsugamushi*.
1375. The method according to any of the previous items, wherein the undesired state of said individual is Rickettsialpox caused by *Rickettsia akari*.
1376. The method according to any of the previous items, wherein the undesired state of said individual is Tickborne Fevers caused by *Rickettsia conorii*.
1377. The method according to any of the previous items, wherein the undesired state of said individual is syphilis caused by *Treponema pallidum*.
1378. The method according to any of the previous items, wherein the undesired state of said individual is Gonorrhea caused by *Neisseria gonorrhoeae*.
1379. The method according to any of the previous items, wherein the undesired state of said individual is Chlamydial urethritis caused by *chlamydia trachomatis*.
1380. The method according to any of the previous items, wherein the undesired state of said individual is Ureaplasmal urethritis caused by *Ureaplasma urealyticum*.
1381. The method according to any of the previous items, wherein the undesired state of said individual is Lymphogranuloma venereum caused by *Chlamydia trachomatis*.
1382. The method according to any of the previous items, wherein the undesired state of said individual is Vaginitis caused by *Gardnerella vaginalis*.
1383. The method according to any of the previous items, wherein the undesired state of said individual is Mycoplasmal urethritis caused by *Mycoplasma hominis*.
1384. The method according to any of the previous items, wherein the undesired state of said individual is Leprosy (hansen's Disease) caused by *Mycobacterium leprae*.
1385. The method according to any of the previous items, wherein the undesired state of said individual is Staphylococcal skin diseases caused by *Staphlococcus aureus*.
1386. The method according to any of the previous items, wherein the undesired state of said individual is Trachoma caused by *chlamydia trachomatis*.
1387. The method according to any of the previous items, wherein the undesired state of said individual is Bacterial Conjuctivitis caused by *Haemophilus influenze* type III.
1388. The method according to any of the previous items, wherein the undesired state of said individual is Influenza.
1389. The method according to any of the previous items, wherein the undesired state of said individual is Adenovirus Infections.
1390. The method according to any of the previous items, wherein the undesired state of said individual is Respiratory Syncytial Disease.
1391. The method according to any of the previous items, wherein the undesired state of said individual is Rhinovirus Infections.
1392. The method according to any of the previous items, wherein the undesired state of said individual is Herpes Simplex.
1393. The method according to any of the previous items, wherein the undesired state of said individual is Chicken pox (Varicella).
1394. The method according to any of the previous items, wherein the undesired state of said individual is Measles (Rubeola).
1395. The method according to any of the previous items, wherein the undesired state of said individual is German Measles (Rubella).
1396. The method according to any of the previous items, wherein the undesired state of said individual is Mumps (Epidemic Parotitis).
1397. The method according to any of the previous items, wherein the undesired state of said individual is Small Pox (Variola).

1398. The method according to any of the previous items, wherein the undesired state of said individual is Warts Kawasaki Disease.

1399. The method according to any of the previous items, wherein the undesired state of said individual is Yellow Fever.

1400. The method according to any of the previous items, wherein the undesired state of said individual is Dengue Fever.

1401. The method according to any of the previous items, wherein the undesired state of said individual is Hepatitis A.

1402. The method according to any of the previous items, wherein the undesired state of said individual is Hepatitis B.

1403. The method according to any of the previous items, wherein the undesired state of said individual is NANB Hepatitis.

1404. The method according to any of the previous items, wherein the undesired state of said individual is Viral Gastroenteritis.

1405. The method according to any of the previous items, wherein the undesired state of said individual is Viral Fevers.

1406. The method according to any of the previous items, wherein the undesired state of said individual is Cytomegalovirus Disease.

1407. The method according to any of the previous items, wherein the undesired state of said individual is AIDS.

1408. The method according to any of the previous items, wherein the undesired state of said individual is Rabies.

1409. The method according to any of the previous items, wherein the undesired state of said individual is Polio.

1410. The method according to any of the previous items, wherein the undesired state of said individual is Slow Virus Disease.

1411. The method according to any of the previous items, wherein the undesired state of said individual is Arboviral Enephalitis.

1412. The method according to any of the previous items, wherein the undesired state of said individual is Cryptococcosis caused by *Cryptococcus neoformans.*

1413. The method according to any of the previous items, wherein the undesired state of said individual is Candidiasis, Vaginitis, Thrush, Onychia caused by *Candida albicans.*

1414. The method according to any of the previous items, wherein the undesired state of said individual is tinea Pedis caused by *Trichophyton* Spp.

1415. The method according to any of the previous items, wherein the undesired state of said individual is Tinea Captis caused by *Microsporum* Spp.

1416. The method according to any of the previous items, wherein the undesired state of said individual is Tinea Corporis, Tinea Barhae caused by *Epidermophyton* spp.

1417. The method according to any of the previous items, wherein the undesired state of said individual is Histoplasmosis caused by *Histoplasma capsulatum.*

1418. The method according to any of the previous items, wherein the undesired state of said individual is Blastomycosis caused by *Blastomyces dermatitidis.*

1419. The method according to any of the previous items, wherein the undesired state of said individual is Coccidiodomycosis caused by *Coccidiodes immitis.*

1420. The method according to any of the previous items, wherein the undesired state of said individual is Aspergillosis Otomycosis caused by *Aspergillus.*

1421. The method according to any of the previous items, wherein the undesired state of said individual is Amoebiasis caused by *Entamoeba histolytica.*

1422. The method according to any of the previous items, wherein the undesired state of said individual is Primary Amoebic meningoencephalitis caused by *Naegleria fowleri.*

1423. The method according to any of the previous items, wherein the undesired state of said individual is Giardiasis caused by *Giardia Lamblia.*

1424. The method according to any of the previous items, wherein the undesired state of said individual is Trichomoniasis caused by *Trichomonas vaginalis.*

1425. The method according to any of the previous items, wherein the undesired state of said individual is African Sleeping Sickness caused by *Trypanosoma brucei.*

1426. The method according to any of the previous items, wherein the undesired state of said individual is Leishmaniasis (Kala—azar) caused by *Leishmania donovani.*

1427. The method according to any of the previous items, wherein the undesired state of said individual is Toxoplasmosis caused by *Toxoplasma gondii.*

1428. The method according to any of the previous items, wherein the undesired state of said individual is Malaria caused by *Plasmodium* spp.

1429. The method according to any of the previous items, wherein the undesired state of said individual is Babesiosis caused by *Babesia microti.*

1430. The method according to any of the previous items, wherein the undesired state of said individual is Pneumocytosis (PCP) caused by *Pneumocystis carinii.*

1431. The method according to any of the previous items, wherein the undesired state of said individual is one or more infection(s).

1432. The method according to item 1431, wherein the one or more infection(s) comprises one or more bacterial infection(s).

1433. The method according to item 1432, wherein the one or more bacterial infection(s) causes one or more infectious diseases.

1434. The method according to item 1432, wherein the one or more bacterial infection(s) causes tuberculosis.

1435. The method according to item 1432, wherein the one or more bacterial infection(s) causes borreliosis (Lyme's disease).

1436. The method according to item 1432, wherein the one or more bacterial infection(s) causes cholera.

1437. The method according to item 1432, wherein the one or more bacterial infection(s) causes syphilis.

1438. The method according to item 1432, wherein the one or more bacterial infection(s) causes anthrax.

1439. The method according to item 1432, wherein the one or more bacterial infection(s) causes leprosy.

1440. The method according to item 1432, wherein the one or more bacterial infection(s) causes bubonic plague.

1441. The method according to item 1432, wherein the one or more bacterial infection(s) causes a fatal bacterial disease.

1442. The method according to item 1432, wherein the one or more bacterial infection(s) causes a respiratory infections 1443. The method according to item 1432, wherein the one or more bacterial infection(s) are caused by one or more bacteria that are resistant to one or more antibiotics.

1444. The method according to item 1432, wherein the one or more bacterial infection(s) are caused by one or more Acidobacteria.

1445. The method according to item 1432, wherein the one or more bacterial infection(s) are caused by one or more Actinobacteria.

1446. The method according to item 1432, wherein the one or more bacterial infection(s) are caused by one or more Aquificae.

1447. The method according to item 1432, wherein the one or more bacterial infection(s) are caused by one or more Bacteroidetes.

1448. The method according to item 1432, wherein the one or more bacterial infection(s) are caused by one or more Chlamydiae.

1449. The method according to item 1432, wherein the one or more bacterial infection(s) are caused by one or more Chlorobi.

1450. The method according to item 1432, wherein the one or more bacterial infection(s) are caused by one or more Chloroflexi.

1451. The method according to item 1432, wherein the one or more bacterial infection(s) are caused by one or more Chrysiogenetes.

1452. The method according to item 1432, wherein the one or more bacterial infection(s) are caused by one or more Cyanobacteria.

1453. The method according to item 1432, wherein the one or more bacterial infection(s) are caused by one or more Deferribacteres.

1454. The method according to item 1432, wherein the one or more bacterial infection(s) are caused by one or more Deinococcus-Thermus.

1455. The method according to item 1432, wherein the one or more bacterial infection(s) are caused by one or more Dictyoglomi.

1456. The method according to item 1432, wherein the one or more bacterial infection(s) are caused by one or more Fibrobacteres.

1457. The method according to item 894, wherein the one or more bacterial infection(s) are caused by one or more Firmicutes.

1458. The method according to item 1432, wherein the one or more bacterial infection(s) are caused by one or more Fusobacteria.

1459. The method according to item 1432, wherein the one or more bacterial infection(s) are caused by one or more Gemmatimonadetes.

1460. The method according to item 1432, wherein the one or more bacterial infection(s) are caused by one or more Nitrospirae.

1461. The method according to item 1432, wherein the one or more bacterial infection(s) are caused by one or more Planctomycetes.

1462. The method according to item 1432, wherein the one or more bacterial infection(s) are caused by one or more Proteobacteria.

1463. The method according to item 1432, wherein the one or more bacterial infection(s) are caused by one or more Spirochaetes.

1464. The method according to item 1432, wherein the one or more bacterial infection(s) are caused by one or more Thermodesulfobacteria.

1465. The method according to item 1432, wherein the one or more bacterial infection(s) are caused by one or more Thermomicrobia.

1466. The method according to item 1432, wherein the one or more bacterial infection(s) are caused by one or more Thermotogae.

1467. The method according to item 1432, wherein the one or more bacterial infection(s) are caused by one or more Verrucomicrobia.

1468. The method according to item 1432, wherein the one or more bacterial infection(s) are caused by one or more Gram negative bacteria.

1469. The method according to item 1432, wherein the one or more bacterial infection(s) are caused by one or more Gram positive bacteria.

1470. The method according to item 1432, wherein the one or more bacterial infection(s) are caused by one or more Gram positive bacteria and one and more Gram negative bacteria.

1471. The method according to item 1432, wherein the one or more bacterial infection(s) are caused by one or more of the bacteria selected from the group consisting of *Acetobacter aurantius, Acinetobacter* species: *Acinetobacter baumannii, Acinetobacter calcoaceticus, Acinetobacter johnsonii, Acinetobacter junii, Acinetobacter lwoffii, Acinetobacter radioresistens, Acinetobacter septicus, Acinetobacter schindleri, Acinetobacter ursingii; Actinomyces* species: *Actinomyces bovis, Actinomyces bowdenii, Actinomyces canis, Actinomyces cardiffensis, Actinomyces catuli, Actinomyces coleocanis, Actinomyces dentalis, Actinomyces denticolens, Actinomyces europaeus, Actinomyces funkei, Actinomyces georgiae, Actinomyces gerencseriae, Actinomyces graevenitzii, Actinomyces hongkongensis, Actinomyces hordeovulneris, Actinomyces howellii, Actinomyces humiferus, Actinomyces hyovaginalis, Actinomyces israelii, Actinomyces marimammalium, Actinomyces meyeri, Actinomyces naeslundii, Actinomyces nasicola, Actinomyces neuii, Actinomyces odontolyticus, Actinomyces oricola, Actinomyces radicidentis, Actinomyces radingae, Actinomyces slackii, Actinomyces streptomycini, Actinomyces suimastitidis, Actinomyces suis, Actinomyces turicensis, Actinomyces urogenitalis, Actinomyces vaccimaxillae, Actinomyces viscosus; Actinobacillus* species: *Actinobacillus actinomycetemcomitans, Actinobacillus arthritidis, Actinobacillus capsulatus, Actinobacillus delphinicola, Actinobacillus equuli, Actinobacillus hominis, Actinobacillus indolicus, Actinobacillus lignieresii, Actinobacillus minor, Actinobacillus muris, Actinobacillus pleuropneumoniae, Actinobacillus porcinus, Actinobacillus rossii, Actinobacillus scotiae, Actinobacillus seminis, Actinobacillus succinogenes, Actinobacillus suis, Actinobacillus ureae; Aeromonas* species: *Aeromonas allosaccharophila, Aeromonas bestiarum, Aeromonas bivalvium, Aeromonas encheleia, Aeromonas enteropelogenes, Aeromonas euchrenophila, Aeromonas hydrophila, Aeromonas ichthiosmia, Aeromonas jandaei, Aeromonas media, Aeromonas molluscorum, Aeromonas popoffii, Aeromonas punctata, Aeromonas salmonicida, Aeromonas schubertii, Aeromonas sharmana, Aeromonas simiae, Aeromonas sobria, Aeromonas veronii; Afipia felis, Agrobacterium* species: *Agrobacterium radiobacter, Agrobacterium rhizogenes, Agrobacterium rubi, Agrobacterium tumefaciens; Agromonas* species, *Alcaligenes* species: *Alcaligenes aquatilis, Alcaligenes eutrophus, Alcaligenes faecalis, Alcaligenes latus, Alcaligenes xylosoxidans; Alishewanella* species, *Alterococcus* species, *Anaplasma phagocytophilum, Anaplasma marginale, Aquamonas* species, *Arcanobacterium haemolyticum, Aranicola* species, *Arsenophonus* species, *Azotivirga* species, *Azotobacter vinelandii, Azotobacter chroococcum, Bacillary dysentery* (Shigellosis), *Bacillus* species: *Bacillus abortus* (*Brucella melitensis* biovar *abortus*), *Bacillus* anthracis (Anthrax), *Bacillus brevis, Bacillus cereus, Bacillus coagulans, Bacillus fusiformis, Bacillus globigii, Bacillus licheniformis, Bacillus megaterium, Bacillus mycoides, Bacillus natto, Bacillus stearothermophilus, Bacillus subtilis, Bacillus sphaericus, Bacillus thuringiensis; Bacteroides* species: *Bacteroides forsythus* (*Tannerella forsythensis*), *Bacteroides acidifaciens, Bacteroides distasonis* (reclassified as *Parabacteroides distasonis*), *Bacteroides gingivalis, Bacteroides gracilis, Bacteroides fragilis, Bacteroides oris, Bacteroides ovatus, Bacteroides putredinis, Bacteroides pyogenes, Bacteroides stercoris, Bacteroides suis, Bacteroides tectus, Bacteroides thetaiotaomicron, Bacteroides vulgatus; Bartonella* species: *Bartonella alsatica, Bartonella bacilliformis, Bartonella birtlesii, Bartonella bovis, Bartonella capreoli, Bartonella clarridgeiae, Bartonella doshiae, Bartonella elizabethae, Bartonella grahamii, Bartonella henselae* (cat scratch fever), *Bartonella koehlerae, Bartonella muris, Bartonella peromysci, Bartonella quintana, Bartonella rochalimae, Bartonella schoenbuchii, Bartonella talpae, Bartonella taylorii, Bartonella tribocorum, Bartonella vinsonii* spp. *Arupensis, Bartonella vinsonii* spp. *Berkhoffii, Bartonella vinsonii* spp. *Vinsonii, Bartonella washoensis*; BCG (Bacille Calmette-Guerin), *Bergeyella zoohelcum* (*Weeksella zoohelcum*), *Bifidobacterium bifidum, Blastobacter* species, *Blochmannia* species, *Bordetella* species: '*Bordetella ansorpii*', *Bordetella avium, Bordetella bronchiseptica, Bordetella hinzii, Bordetella holmesii, Bordetella parapertussis, Bordetella pertussis* (Whooping cough), *Bordetella petrii, Bordetella trematum; Borrelia* species: *Borrelia burgdorferi, Borrelia afzelii, Borrelia anserina, Borrelia garinii, Borrelia valaisiana, Borrelia hermsii, Borrelia Parkeri, Borrelia recurrentis; Bosea* species, *Bradyrhizobium* species, *Brenneria* species, *Brucella* species: *Brucella abortus, Brucella canis, Brucella melitensis, Brucella neotomae, Brucella ovis, Brucella suis, Brucella pinnipediae; Buchnera* species, *Budvicia* species, *Burkholderia* species: *Burkholderia cepacia* (*Pseudomonas cepacia*), *Burkholderia mallei* (*Pseudomonas mallei/Actinobacillus mallei*), *Burkholderia pseudomallei* (*Pseudomonas pseudomallei*); *Buttiauxella* species, *Calymmatobacterium granulomatis, Campylobacter* species: *Campylobacter coli, Campylobacter concisus, Campylobacter curvus, Campylobacter fetus, Campylobacter gracilis, Campylobacter helveticus, Campylobacter hominis, Campylobacter hyointestinalis, Campylobacter insulaenigrae, Campylobacter jejuni, Campylobacter lanienae, Campylobacter lari, Campylobacter mucosalis, Campylobacter rectus, Campylobacter showae, Campylobacter sputorum, Campylobacter upsaliensis; Capnocytophaga canimorsus* (Dysgonic fermenter type 2), *Corynebacterium* species, *Cardiobacterium hominis, Cedecea* species, *Chlamydia* species: *Chlamydia trachomatis* (Lymphogranuloma venereum), *Chlamydia muridarum, Chlamydia suis; Chlamydophila* species: *Chlamydophila pneumoniae, Chlamydophila psittaci* (Psittacosis), *Chlamydophila pecorum, Chlamydophila abortus, Chlamydophila felis, Chlamydophila caviae; Citrobacter* species: *Citrobacter amalonaticus, Citrobacter braakii, Citrobacter farmeri, Citrobacter freundii, Citrobacter gillenii, Citrobacter intermedius, Citrobacter koseri* aka *Citrobacter diversus, Citrobacter murliniae, Citrobacter rodentium, Citrobacter sedlakii, Citrobacter werkmanii, Citrobacter youngae; Clostridium* species: *Clostridium botulinum, Clostridium difficile, Clostridium novyi, Clostridium septicum, Clostridium tetani* (Tetanus), *Clostridium welchii* (*Clostridium perfringens*); *Corynebacterium* species: *Corynebacterium diphtheriae* (Diphtheria), *Corynebacterium amycolatum, Corynebacterium aquaticum, Corynebacterium bovis, Corynebacterium equi, Corynebacterium flavescens, Corynebacterium glutamicum, Corynebacterium haemolyticum, Corynebacterium jeikeiun* (corynebacteria of group JK), *Corynebacterium minutissimum* (Erythrasma), *Corynebacterium parvum* (also called *Propionibacterium acnes*), *Corynebacterium pseudodiptheriticum* (also called *Corynebacterium hofmannii*), *Corynebacterium pseudotuberculosis* (also called *Corynebacterium ovis*), *Corynebacterium pyogenes, Corynebacterium urealyticum* (corynebacteria of group D2), *Corynebacterium renale, Corynebacterium striatum, Corynebacterium tenuis* (Trichomycosis palmellina, Trichomycosis axillaris), *Corynebacterium ulcerans, Corynebacterium xerosis; Coxiella burnetii* (Q fever), *Cronobacter* species: *Cronobacter sakazakii, Cronobacter malonaticus, Cronobacter turicensis, Cronobacter muytjensii, Cronobacter dublinensis; Delftia acidovorans* (*Comamonas acidovorans*), *Dickeya* species, *Edwardsiella* species, *Eikenella corrodens, Enterobacter* species: *Enterobacter aerogenes, Enterobacter cloacae, Enterobacter sakazakii; Enterococcus* species: *Enterococcus avium, Enterococcus durans, Enterococcus faecalis* (*Streptococcus faecalis/Streptococcus* Group D), *Enterococcus faecium, Enterococcus solitarius, Enterococcus galllinarum, Enterococcus maloratus; Ehrlichia chaffeensis, Erysipelothrix rhusiopathiae, Erwinia* species, *Escherichia* species: *Escherichia adecarboxylata, Escherichia albertii, Escherichia blattae, Escherichia coli, Escherichia fergusonii, Escherichia hermannii, Escherichia vulneris; Ewingella* species, *Flavobacterium* species: *Flavobacterium aquatile, Flavobacterium branchiophilum, Flavobacterium columnare, Flavobacterium flevense, Flavobacterium gondwanense, Flavobacterium hydatis, Flavobacterium johnsoniae, Flavobacterium pectinovorum, Flavobacterium psychrophilum, Flavobacterium saccharophilum, Flavobacterium salegens, Flavobacterium scophthalmum, Flavobacterium succinans; Francisella tularensis* (Tularaemia), *Francisella novicida, Francisella philomiragia, Fusobacterium* species: *Fusobacterium necrophorum* (Lemierre syndrome/Sphaerophorus necrophorus), *Fusobacterium nucleatum, Fusobacterium polymorphum, Fusobacterium novum, Fusobacterium mortiferum, Fusobacterium varium; Gardnerella vaginalis, Gemella haemolysans, Gemella morbillorum* (*Streptococcus morbillorum*), *Grimontella* species, *Haemophilus* species: *Haemophilus aegyptius* (Koch-Weeks *bacillus*), *Haemophilus aphrophilus, Haemophilus avium, Haemophilus ducreyi* (Chancroid), *Haemophilus felis, Haemophilus haemolyticus, Haemophilus influenzae* (Pfeiffer *bacillus*), *Haemophilus paracuniculus, Haemophilus parahaemolyticus, Haemophilus parainfluenzae, Haemophilus paraphrophilus* (Aggregatibacter aphrophilus), *Haemophilus pertussis, Haemophilus pittmaniae, Haemophilus somnus, Haemophilus vaginalis; Hafnia* species, *Hafnia alvei, Helicobacter* species: *Helicobacter acinonychis, Helicobacter anseris, Helicobacter aurati, Helicobacter bilis, Helicobacter bizzozeronii, Helicobacter brantae, Helicobacter Canadensis, Helicobacter canis, Helicobacter cholecystus, Helicobacter cinaedi, Helicobacter cynogastricus, Helicobacter felis, Helicobacter fennelliae, Helicobacter ganmani, Helicobacter heilmannii* (*Gastrospirillum hominis*), *Helicobacter hepaticus, Helicobacter mesocricetorum, Helicobacter marmotae, Helicobacter muridarum, Helico-*

*bacter mustelae, Helicobacter pametensis, Helicobacter pullorum, Helicobacter pylori* (stomach ulcer), *Helicobacter rappini, Helicobacter rodentium, Helicobacter salomonis, Helicobacter trogontum, Helicobacter typhlonius, Helicobacter winghamensis*; Human granulocytic ehrlichiosis (*Anaplasma phagocytophilum/Ehrlichia phagocytophila*), Human monocytotropic ehrlichiosis (Monocytic ehrlichiosis/*Ehrlichia chaffeensis*), *Klebsiella* species: *Klebsiella granulomatis* (*Calymmatobacterium granulomatis*), *Klebsiella mobilis, Klebsiella ornithinolytica, Klebsiella oxytoca, Klebsiella ozaenae, Klebsiella planticola, Klebsiella pneumoniae, Klebsiella rhinoscleromatis, Klebsiella singaporensis, Klebsiella terrigena, Klebsiella trevisanii, Klebsiella variicola; Kingella kingae, Kluyvera* species, *Lactobacillus* species: *Lactobacillus acetotolerans, Lactobacillus acidifarinae, Lactobacillus acidipiscis, Lactobacillus acidophilus* (Doderlein bacillus), *Lactobacillus agilis, Lactobacillus algidus, Lactobacillus alimentarius, Lactobacillus amylolyticus, Lactobacillus amylophilus, Lactobacillus amylotrophicus, Lactobacillus amylovorus, Lactobacillus animalis, Lactobacillus antri, Lactobacillus apodemi, Lactobacillus aviarius, Lactobacillus bifermentans, Lactobacillus brevis, Lactobacillus buchneri, Lactobacillus camelliae, Lactobacillus casei, Lactobacillus catenaformis, Lactobacillus ceti, Lactobacillus coleohominis, Lactobacillus collinoides, Lactobacillus composti, Lactobacillus concavus, Lactobacillus coryniformis, Lactobacillus crispatus, Lactobacillus crustorum, Lactobacillus curvatus, Lactobacillus delbrueckii, Lactobacillus delbrueckii* subsp. *Bulgaricus, Lactobacillus delbrueckii* subsp. *Lactis, Lactobacillus diolivorans, Lactobacillus equi, Lactobacillus equigenerosi, Lactobacillus farraginis, Lactobacillus farciminis, Lactobacillus fermentum, Lactobacillus fornicalis, Lactobacillus fructivorans, Lactobacillus frumenti, Lactobacillus fuchuensis, Lactobacillus gallinarum, Lactobacillus gasseri, Lactobacillus gastricus, Lactobacillus ghanensis, Lactobacillus graminis, Lactobacillus hammesii, Lactobacillus hamsteri, Lactobacillus harbinensis, Lactobacillus hayakitensis, Lactobacillus helveticus, Lactobacillus hilgardii, Lactobacillus homohiochii, Lactobacillus iners, Lactobacillus ingluviei, Lactobacillus intestinalis, Lactobacillus jensenii, Lactobacillus johnsonii, Lactobacillus kalixensis, Lactobacillus kefuranofaciens, Lactobacillus kefiri, Lactobacillus kimchii, Lactobacillus kitasatonis, Lactobacillus kunkeei, Lactobacillus leichmannii, Lactobacillus lindneri, Lactobacillus malefermentans, Lactobacillus mali, Lactobacillus manihotivorans, Lactobacillus mindensis, Lactobacillus mucosae, Lactobacillus murinus, Lactobacillus nagelii, Lactobacillus namurensis, Lactobacillus nantensis, Lactobacillus oligofermentans, Lactobacillus oris, Lactobacillus panis, Lactobacillus pantheris, Lactobacillus parabrevis, Lactobacillus parabuchneri, Lactobacillus paracollinoides, Lactobacillus parafarraginis, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus psittaci, Lactobacillus rennini, Lactobacillus reuteri, Lactobacillus rhamnosus, Lactobacillus rimae, Lactobacillus rogosae, Lactobacillus rossiae, Lactobacillus ruminis, Lactobacillus saerimneri, Lactobacillus sakei, Lactobacillus salivarius, Lactobacillus sanfranciscensis, Lactobacillus satsumensis, Lactobacillus secaliphilus, Lactobacillus sharpeae, Lactobacillus siliginis, Lactobacillus spicheri, Lactobacillus suebicus, Lactobacillus thailandensis, Lactobacillus ultunensis, Lactobacillus vaccinostercus, Lactobacillus vaginalis, Lactobacillus versmoldensis, Lactobacillus vini, Lactobacillus vitulinus, Lactobacillus zeae, Lactobacillus zymae; Leclercia* species, *Legionella* species: *Legionella adelaidensis, Legionella anisa, Legionella beliardensis, Legionella birminghamensis, Legionella bozemanii, Legionella brunensis, Legionella busanensis, Legionella cherrii, Legionella cincinnatiensis, Legionella donaldsonii, Legionella drancourtii, Legionella drozanskii, Legionella erythra, Legionella fairfieldensis, Legionella fallonii, Legionella feeleii, Legionella geestiana, Legionella* genomospecies, *Legionella gratiana, Legionella gresilensis, Legionella hackeliae, Legionella impletisoli, Legionella israelensis, Legionella jamestowniensis,* 'Candidatus *Legionella jeonii*', *Legionella jordanis, Legionella lansingensis, Legionella londiniensis, Legionella longbeachae, Legionella lytica, Legionella maceachernii, Legionella micdadei, Legionella moravica, Legionella nautarum, Legionella oakridgensis, Legionella parisiensis, Legionella pneumophila, Legionella quateirensis, Legionella quinlivanii, Legionella rowbothamii, Legionella rubrilucens, Legionella sainthelensi, Legionella santicrucis, Legionella shakespearei, Legionella spiritensis, Legionella steigerwaltii, Legionella taurinensis, Legionella tucsonensis, Legionella wadsworthii, Legionella waltersii, Legionella worsleiensis, Legionella yabuuchiae; Leminorella* species, *Leptospira* species: *Leptospira interrogans, Leptospira kirschneri, Leptospira noguchii, Leptospira alexanderi, Leptospira weilii, Leptospira* genomospecies 1, *Leptospira borgpetersenii, Leptospira santarosai, Leptospira inadai, Leptospira fainei, Leptospira broomii, Leptospira licerasiae, Leptospira biflexa, Leptospira meyeri, Leptospira wolbachii, Leptospira* genomospecies 3, *Leptospira* genomospecies 4, *Leptospira* genomospecies 5; Lepromatous leprosy (Danielssen-Boeck disease), *Leptospira canicola, Leptospira hebdomadis,* Leptospirosis (Weil disease/*Leptospira icterohaemorrhagiae/Leptospira interrogans* serovar icterohaemorrhagiae), *Leptotrichia, Leuconostoc* species: *Leuconostoc carnosum, Leuconostoc citreum, Leuconostoc durionis, Leuconostoc fallax, Leuconostoc ficulneum, Leuconostoc fructosum, Leuconostoc garlicum, Leuconostoc gasicomitatum, Leuconostoc gelidum, Leuconostoc inhae, Leuconostoc kimchii, Leuconostoc lactis, Leuconostoc mesenteroides, Leuconostoc pseudoficulneum, Leuconostoc pseudomesenteroides; Listeria* species: *Listeria grayi, Listeria innocua, Listeria ivanovii, Listeria monocytogenes* (Listeriosis), *Listeria seeligeri, Listeria welshimeri; Methanobacterium extroquens, Microbacterium multiforme, Micrococcus* species: *Micrococcus antarcticus, Micrococcus flavus, Micrococcus luteus, Micrococcus lylae, Micrococcus mucilaginosis, Micrococcus roseus, Micrococcus sedentarius; Mobiluncus, Moellerella* species, *Morganella* species, *Moraxella* species: *Moraxella atlantae, Moraxella boevrei, Moraxella bovis, Moraxella canis, Moraxella caprae, Moraxella catarrhalis* (*Branhamella catarrhalis*), *Moraxella caviae, Moraxella cuniculi, Moraxella equi, Moraxella lacunata, Moraxella lincolnii, Moraxella nonliquefaciens, Moraxella oblonga, Moraxella osloensis, Moraxella saccharolytica; Morganella morganii, Mycobacterium* species: *Mycobacterium abscessus, Mycobacterium africanum, Mycobacterium agri, Mycobacterium aichiense, Mycobacterium alvei, Mycobacterium arupense, Mycobacterium asiaticum, Mycobacterium aubagnense, Mycobacterium aurum, Mycobacterium austroafricanum,*

*Mycobacterium avium* (Battey disease/Lady Windermere syndrome), *Mycobacterium avium paratuberculosis* (implicated in Crohn's disease in humans and Johne's disease in sheep), *Mycobacterium avium silvaticum, Mycobacterium avium* "hominissuis", *Mycobacterium colombiense, Mycobacterium boenickei, Mycobacterium bohemicum, Mycobacterium bolletii, Mycobacterium botniense, Mycobacterium bovis* (Bovine tuberculosis), *Mycobacterium branderi, Mycobacterium brisbanense, Mycobacterium brumae, Mycobacterium canariasense, Mycobacterium caprae, Mycobacterium celatum, Mycobacterium chelonae, Mycobacterium chimaera, Mycobacterium chitae, Mycobacterium chlorophenolicum, Mycobacterium chubuense, Mycobacterium conceptionense, Mycobacterium confluentis, Mycobacterium conspicuum, Mycobacterium cookii, Mycobacterium cosmeticum, Mycobacterium diernhoferi, Mycobacterium doricum, Mycobacterium duvalii, Mycobacterium elephantis, Mycobacterium fallax, Mycobacterium farcinogenes, Mycobacterium flavescens, Mycobacterium florentinum, Mycobacterium fluoroanthenivorans, Mycobacterium fortuitum, Mycobacterium fortuitum* subsp. *Acetamidolyticum, Mycobacterium frederiksbergense, Mycobacterium gadium, Mycobacterium gastri, Mycobacterium genavense, Mycobacterium gilvum, Mycobacterium goodii, Mycobacterium gordonae* (*Mycobacterium aquae*), *Mycobacterium haemophilum, Mycobacterium hassiacum, Mycobacterium heckeshornense, Mycobacterium heidelbergense, Mycobacterium hiberniae, Mycobacterium hodleri, Mycobacterium holsaticum, Mycobacterium houstonense, Mycobacterium immunogenum, Mycobacterium interjectum, Mycobacterium intermedium, Mycobacterium intracellulare, Mycobacterium kansasii, Mycobacterium komossense, Mycobacterium kubicae, Mycobacterium kumamotonense, Mycobacterium lacus, Mycobacterium lentiflavum, Mycobacterium leprae* (causes leprosy or Hansen disease/Hanseniasis), *Mycobacterium lepraemurium, Mycobacterium madagascariense, Mycobacterium mageritense, Mycobacterium malmoense, Mycobacterium marinum* (Fish tank granuloma), *Mycobacterium massiliense, Mycobacterium microti, Mycobacterium monacense, Mycobacterium montefiorense, Mycobacterium moriokaense, Mycobacterium mucogenicum, Mycobacterium murale, Mycobacterium nebraskense, Mycobacterium neoaurum, Mycobacterium neworleansense, Mycobacterium nonchromogenicum, Mycobacterium novocastrense, Mycobacterium obuense, Mycobacterium palustre, Mycobacterium parafortuitum, Mycobacterium parascrofulaceum, Mycobacterium parmense, Mycobacterium peregrinum, Mycobacterium phlei, Mycobacterium phocaicum, Mycobacterium pinnipedii, Mycobacterium porcinum, Mycobacterium poriferae, Mycobacterium pseudoshottsii, Mycobacterium pulveris, Mycobacterium psychrotolerans, Mycobacterium pyrenivorans, Mycobacterium rhodesiae, Mycobacterium saskatchewanense, Mycobacterium scrofulaceum, Mycobacterium senegalense, Mycobacterium seoulense, Mycobacterium septicum, Mycobacterium shimoidei, Mycobacterium shottsii, Mycobacterium simiae, Mycobacterium smegmatis, Mycobacterium sphagni, Mycobacterium szulgai, Mycobacterium terrae, Mycobacterium thermoresistibile, Mycobacterium tokaiense, Mycobacterium triplex, Mycobacterium triviale, Mycobacterium tuberculosis* (major cause of human tuberculosis), *Mycobacterium bovis, Mycobacterium africanum, Mycobacterium canetti, Mycobacterium caprae, Mycobacterium pinnipedii', Mycobacterium tusciae, Mycobacterium ulcerans* (causes Bairnsdale ulcer/Buruli ulcer), *Mycobacterium vaccae, Mycobacterium vanbaalenii, Mycobacterium wolinskyi, Mycobacterium xenopi; Mycoplasma* species: *Mycoplasma fermentans, Mycoplasma genitalium, Mycoplasma hominis, Mycoplasma penetrans, Mycoplasma phocacerebrale, Mycoplasma pneumoniae, Nanukayami* (Seven-day fever/Gikiyami), *Neisseria* species: *Neisseria gonorrhoea* (Gonococcus/Gonorrhea), *Neisseria meningiditis* (Meningococcus), *Neisseria sicca, Neisseria cinerea, Neisseria elongata, Neisseria flavescens, Neisseria lactamica, Neisseria mucosa, Neisseria polysaccharea, Neisseria subflava; Nitrobacter* species, *Nocardia* species: *Nocardia asteroides, Nocardia brasiliensis, Nocardia caviae; Noma* (cancrum oris/gangrenous stomatitis), *Obesumbacterium, Oligotropha* species, *Orientia tsutsugamushi* (Scrub typhus), *Oxalobacter formigenes, Pantoea* species: *Pantoea agglomerans, Pantoea ananatis, Pantoea citrea, Pantoea dispersa, Pantoea punctata, Pantoea stewartii, Pantoea terrea; Pasteurella* species: *Pasteurella aerogenes, Pasteurella anatis, Pasteurella avium, Pasteurella bettyae, Pasteurella caballi, Pasteurella canis, Pasteurella dagmatis, Pasteurella gallicida, Pasteurella gallinarum, Pasteurella granulomatis, Pasteurella langaaensis, Pasteurella lymphangitidis, Pasteurella mairii, Pasteurella multocida, Pasteurella pneumotropica, Pasteurella skyensis, Pasteurella stomatis, Pasteurella testudinis, Pasteurella trehalosi, Pasteurella tularensis, Pasteurella ureae, Pasteurella volantium; Pediococcus* species: *Pediococcus acidilactici, Pediococcus cellicola, Pediococcus claussenii, Pediococcus damnosus, Pediococcus dextrinicus, Pediococcus ethanolidurans, Pediococcus inopinatus, Pediococcus parvulus, Pediococcus pentosaceus, Pediococcus stilesii; Peptostreptococcus* species: *Peptostreptococcus anaerobius, Peptostreptococcus asaccharolyticus, Peptostreptococcus harei, Peptostreptococcus hydrogenalis, Peptostreptococcus indoliticus, Peptostreptococcus ivorii, Peptostreptococcus lacrimalis, Peptostreptococcus lactolyticus, Peptostreptococcus magnus, Peptostreptococcus micros, Peptostreptococcus octavius, Peptostreptococcus prevotii, Peptostreptococcus tetradius, Peptostreptococcus vaginalis; Photorhabdus* species, *Photorhizobium* species, *Plesiomonas shigelloides, Porphyromonas gingivalis, Pragia* species, *Prevotella, Propionibacterium* species: *Propionibacterium acnes, Propionibacterium propionicus; Proteus* species: *Proteus mirabilis, Proteus morganii, Proteus penneri, Proteus rettgeri, Proteus vulgaris; Providencia* species: *Providencia friedericiana, Providencia stuartii; Pseudomonas* species: *Pseudomonas aeruginosa, Pseudomonas alcaligenes, Pseudomonas anguilliseptica, Pseudomonas argentinensis, Pseudomonas borbori, Pseudomonas citronellolis, Pseudomonas flavescens, Pseudomonas mendocina, Pseudomonas nitroreducens, Pseudomonas oleovorans, Pseudomonas pseudoalcaligenes, Pseudomonas resinovorans, Pseudomonas straminea, Pseudomonas aurantiaca, Pseudomonas aureofaciens, Pseudomonas chlororaphis, Pseudomonas fragi, Pseudomonas lundensis, Pseudomonas taetrolens, Pseudomonas Antarctica, Pseudomonas azotoformans, Pseudomonas brassicacearum, Pseudomonas brenneri, Pseudomonas cedrina, Pseudomonas corrugate, Pseudomonas fluorescens, Pseudomonas gessardii, Pseudomonas libanensis, Pseudomonas mandelii, Pseudomonas marginalis, Pseudomonas mediterranea, Pseudomonas meridiana, Pseudomonas migulae, Pseudomonas mucidolens, Pseudomonas orientalis,*

*Pseudomonas panacis, Pseudomonas proteolytica, Pseudomonas rhodesiae, Pseudomonas synxantha, Pseudomonas thivervalensis, Pseudomonas tolaasii, Pseudomonas veronii, Pseudomonas denitrificans, Pseudomonas pertucinogena, Pseudomonas cremoricolorata, Pseudomonas fulva, Pseudomonas monteilii, Pseudomonas mosselii, Pseudomonas oryzihabitans, Pseudomonas parafulva, Pseudomonas plecoglossicida, Pseudomonas putida, Pseudomonas balearica, Pseudomonas luteola, Pseudomonas stutzeri, Pseudomonas amygdale, Pseudomonas avellanae, Pseudomonas caricapapayae, Pseudomonas cichorii, Pseudomonas coronafaciens, Pseudomonas ficuserectae, Pseudomonas meliae, Pseudomonas savastanoi, Pseudomonas syringae, Pseudomonas viridiflava, Pseudomonas abietaniphila, Pseudomonas acidophila, Pseudomonas agarici, Pseudomonas alcaliphila, Pseudomonas alkanolytica, Pseudomonas amyloderamosa, Pseudomonas asplenii, Pseudomonas azotifigens, Pseudomonas cannabina, Pseudomonas coenobios, Pseudomonas congelans, Pseudomonas costantinii, Pseudomonas cruciviae, Pseudomonas delhiensis, Pseudomonas excibis, Pseudomonas extremorientalis, Pseudomonas frederiksbergensis, Pseudomonas fuscovaginae, Pseudomonas gelidicola, Pseudomonas grimontii, Pseudomonas indica, Pseudomonas jessenii, Pseudomonas jinjuensis, Pseudomonas kilonensis, Pseudomonas knackmussii, Pseudomonas koreensis, Pseudomonas lini, Pseudomonas lutea, Pseudomonas moraviensis, Pseudomonas otitidis, Pseudomonas pachastrellae, Pseudomonas palleroniana, Pseudomonas papaveris, Pseudomonas peli, Pseudomonas perolens, Pseudomonas poae, Pseudomonas pohangensis, Pseudomonas psychrophila, Pseudomonas psychrotolerans, Pseudomonas rathonis, Pseudomonas reptilivora, Pseudomonas resiniphila, Pseudomonas rhizosphaerae, Pseudomonas rubescens, Pseudomonas salomonii, Pseudomonas segitis, Pseudomonas septica, Pseudomonas simiae, Pseudomonas suis, Pseudomonas thermotolerans, Pseudomonas tremae, Pseudomonas trivialis, Pseudomonas turbinellae, Pseudomonas tuticorinensis, Pseudomonas umsongensis, Pseudomonas vancouverensis, Pseudomonas vranovensis, Pseudomonas xanthomarina; Rahnella species, Ralstonia species: Ralstonia basilensis, Ralstonia campinensis, Ralstonia eutropha, Ralstonia gilardii, Ralstonia insidiosa, Ralstonia mannitolilytica, Ralstonia metallidurans, Ralstonia paucula, Ralstonia pickettii, Ralstonia respiraculi, Ralstonia solanacearum, Ralstonia syzygii, Ralstonia taiwanensis; Raoultella species, Rhodoblastus species, Rhodopseudomonas species, Rhinoscleroma, Rhizobium radiobacter, Rhodococcus equi, Rickettsia species: Rickettsia africae, Rickettsia akari, Rickettsia australis, Rickettsia conorii, Rickettsia felis, Rickettsia japonica, Rickettsia mooseri, Rickettsia prowazekii* (Typhus fever), *Rickettsia rickettsii, Rickettsia siberica, Rickettsia typhi, Rickettsia conorii, Rickettsia africae, Rickettsia psittaci, Rickettsia quintana, Rickettsia rickettsii, Rickettsia trachomae; Rothia dentocariosa, Salmonella* species: *Salmonella arizonae, Salmonella Bongori, Salmonella enterica, Salmonella enteriditis, Salmonella paratyphi, Salmonella typhi* (Typhoid fever), *Salmonella typhimurium, Salmonella salamae, Salmonella arizonae, Salmonella diarizonae, Salmonella houtenae, Salmonella indica; Samsonia* species, *Serratia* species: *Serratia entomophila, Serratia ficaria, Serratia fonticola, Serratia grimesii, Serratia liquefaciens, Serratia marcescens, Serratia odoriferae, Serratia plymuthica, Serratia proteamaculans, Serratia quinivorans, Serratia rubidaea, Serratia ureilytica; Shewanella putrefaciens, Shigella boydii, Shigella dysenteriae, Shigella flexneri, Shigella sonnei, Sodalis* species, *Spirillum* species: *Spirillum minus* rat bite fever, *Staphylococcus* species: *Staphylococcus aureus, Staphylococcus auricularis, Staphylococcus capitis, Staphylococcus caprae, Staphylococcus cohnii, Staphylococcus epidermidis, Staphylococcus felis, Staphylococcus haemolyticus, Staphylococcus hominis, Staphylococcus intermedius, Staphylococcus lugdunensis, Staphylococcus pettenkoferi, Staphylococcus saprophyticus, Staphylococcus schleiferi, Staphylococcus simulans, Staphylococcus vitulus, Staphylococcus warneri, Staphylococcus xylosus; Stenotrophomonas* species: *Stenotrophomonas acidaminiphila, Stenotrophomonas dokdonensis, Stenotrophomonas koreensis, Stenotrophomonas maltophilia, Stenotrophomonas nitritireducens, Stenotrophomonas rhizophila; Streptobacillus* species: *Streptobacillus moniliformis* (Streptobacillary rat bite fever); *Streptococcus* species: *Streptococcus* Group A, *Streptococcus* Group B, *Streptococcus agalactiae, Streptococcus aginosus, Streptococcus avium, Streptococcus bovis, Streptococcus canis, Streptococcus cricetus, Streptococcus faceium, Streptococcus faecalis, Streptococcus ferus, Streptococcus gallinarum, Streptococcus lactis, Streptococcus milleri, Streptococcus mitior, Streptococcus mitis, Streptococcus mutans, Streptococcus oralis, Streptococcus peroris, Streptococcus pneumoniae, Streptococcus pyogenes, Streptococcus ratti, Streptococcus salivarius, Streptococcus sanguinis, Streptococcus sobrinus, Streptococcus parasanguinis, Streptococcus suis, Streptococcus thermophilus, Streptococcus vestibularis, Streptococcus viridans, Streptococcus uberis, Streptococcus zooepidemicus; Tatumella* species, *Trabulsiella* species, *Treponema* species: *Treponema carateum* (Pinta), *Treponema denticola, Treponema endemicum* (Bejel), *Treponema pallidum* (Syphilis), *Treponema pertenue* (Yaws); *Tropheryma whipplei* (Whipple disease), Tuberculoid leprosy, *Ureaplasma urealyticum, Veillonella, Vibrio* species: *Vibrio aerogenes, Vibrio aestuarianus, Vibrio agarivorans, Vibrio albensis, Vibrio alginolyticus, Vibrio brasiliensis, Vibrio calviensis, Vibrio campbellii, Vibrio chagasii, Vibrio cholerae* (Cholera), *Vibrio cincinnatiensis, Vibrio Comma, Vibrio coralliilyticus, Vibrio crassostreae, Vibrio cyclitrophicus, Vibrio diabolicus, Vibrio diazotrophicus, Vibrio ezurae, Vibrio fischeri, Vibrio fluvialis, Vibrio fortis, Vibrio furnissii, Vibrio gallicus, Vibrio gazogenes, Vibrio gigantis, Vibrio haliotocoli, Vibrio harveyi, Vibrio hepatarius, Vibrio hispanicus, Vibrio ichthyoenteri, Vibrio kanaloae, Vibrio lentus, Vibrio litoralis, Vibrio logei, Vibrio mediterranei, Vibrio metschnikovii, Vibrio mimicus, Vibrio mytili, Vibrio natriegens, Vibrio navarrensis, Vibrio neonatus, Vibrio neptunius, Vibrio nereis, Vibrio nigripulchritudo, Vibrio ordalii, Vibrio orientalis, Vibrio pacinii, Vibrio parahaemolyticus, Vibrio pectenicida, Vibrio penaeicida, Vibrio pomeroyi, Vibrio ponticus, Vibrio proteolyticus, Vibrio rotiferianus, Vibrio ruber, Vibrio rumoiensis, Vibrio salmonicida, Vibrio scophthalmi, Vibrio splendidus, Vibrio superstes, Vibrio tapetis, Vibrio tasmaniensis, Vibrio tubiashii, Vibrio vulnificus, Vibrio wodanis, Vibrio xuii; Vogesella indigofera, Wigglesworthia* species, *Wolbachia* secies, *Xenorhabdus* species, *Yersinia enterocolitica, Yersinia pestis, Yersinia pseudotuberculosis,* and *Yokenella* species.

1472. The method according to item 1431, wherein the one or more infection(s) comprises one or more HIV infection(s).

1473. The method according to item 1431, wherein the one or more infection(s) comprises one or more fungal infection(s).

1474. The method according to item 1431, wherein the one or more infection(s) comprises one or more viral infection(s).

1475. The method according to item 1474, wherein the one or more viral infection(s) are caused by one or more animal vira.

1476. The method according to item 1474, wherein the one or more viral infection(s) are caused by one or more plant vira.

1477. The method according to item 1474, wherein the one or more viral infection(s) are caused by one or more bacterial vira.

1478. The method according to item 1474, wherein the one or more viral infection(s) are caused by one or more dsDNA viruses such as Adenoviruses, Herpesviruses, and Poxviruses.

1479. The method according to item 1474, wherein the one or more viral infection(s) are caused by one or more ssDNA viruses (+) sense DNA such as Parvoviruses.

1480. The method according to item 1474, wherein the one or more viral infection(s) are caused by one or more dsRNA viruses such as Reoviruses.

1481. The method according to item 1474, wherein the one or more viral infection(s) are caused by one or more (+)ssRNA viruses (+)sense RNA such as Picornaviruses, Togaviruses.

1482. The method according to item 1474, wherein the one or more viral infection(s) are caused by one or more (−)ssRNA viruses (−)sense RNA such as Orthomyxoviruses, and Rhabdoviruses.

1483. The method according to item 1474, wherein the one or more viral infection(s) are caused by one or more ssRNA-RT viruses (+)sense RNA with DNA intermediate in life-cycle such as Retroviruses.

1484. The method according to item 1474, wherein the one or more viral infection(s) are caused by one or more dsDNA-RT viruses such as Hepadnaviruses.

1485. The method according to item 1474, wherein the one or more viral infection(s) are caused by one or more vira from the Order Caudovirales.

1486. The method according to item 1474, wherein the one or more viral infection(s) are caused by one or more vira from the Family Myoviridae such as Enterobacteria phage T4.

1487. The method according to item 1474, wherein the one or more viral infection(s) are caused by one or more vira from the Family Podoviridae.

1488. The method according to item 1474, wherein the one or more viral infection(s) are caused by one or more vira from the Family Siphoviridae such as Enterobacteria phage λ.

1489. The method according to item 1474, wherein the one or more viral infection(s) are caused by one or more vira from the Order Herpesviridae.

1490. The method according to item 1474, wherein the one or more viral infection(s) are caused by one or more vira from the Family Alloherpesviridae.

1491. The method according to item 1474, wherein the one or more viral infection(s) are caused by one or more vira from the Family Herpesviridae such as human herpesviruses, Varicella Zoster virus, HSV1 (oral herpes), HSV2 (genital herpes), VZV (chickenpox), EBV (Epstein-Barr virus), and CMV (Cytomegalovirus).

1492. The method according to item 1474, wherein the one or more viral infection(s) are caused by one or more vira from the Family Malacoherpesviridae.

1493. The method according to item 1474, wherein the one or more viral infection(s) are caused by one or more vira from the Unassigned families.

1494. The method according to item 1474, wherein the one or more viral infection(s) are caused by one or more vira from the Family Ascoviridae such as Ascovirus.

1495. The method according to item 1474, wherein the one or more viral infection(s) are caused by one or more vira from the Family Adenoviridae.

1496. The method according to item 1474, wherein the one or more viral infection(s) are caused by one or more vira from the Family Asfarviridae such as African swine fever virus, and Asfivirus.

1497. The method according to item 1474, wherein the one or more viral infection(s) are caused by one or more vira from the Family Baculoviridae.

1498. The method according to item 1474, wherein the one or more viral infection(s) are caused by one or more vira from the Family Coccolithoviridae.

1499. The method according to item 1474, wherein the one or more viral infection(s) are caused by one or more vira from the Family Corticoviridae.

1500. The method according to item 1474, wherein the one or more viral infection(s) are caused by one or more vira from the Family Fuselloviridae.

1501. The method according to item 1474, wherein the one or more viral infection(s) are caused by one or more vira from the Family Guttaviridae.

1502. The method according to item 1474, wherein the one or more viral infection(s) are caused by one or more vira from the Family Iridoviridae.

1503. The method according to item 1474, wherein the one or more viral infection(s) are caused by one or more vira from the Family Lipothrixviridae.

1504. The method according to item 1474, wherein the one or more viral infection(s) are caused by one or more vira from the Family Nimaviridae.

1505. The method according to item 1474, wherein the one or more viral infection(s) are caused by one or more vira from the Family Papillomaviridae.

1506. The method according to item 1474, wherein the one or more viral infection(s) are caused by one or more vira from the Family Phycodnaviridae.

1507. The method according to item 1474, wherein the one or more viral infection(s) are caused by one or more vira from the Family Plasmaviridae.

1508. The method according to item 1474, wherein the one or more viral infection(s) are caused by one or more vira from the Family Polyomaviridae such as Simian virus 40, and JC virus.

1509. The method according to item 1474, wherein the one or more viral infection(s) are caused by one or more vira from the Family Poxyiridae such as Cowpox virus, and smallpox.

1510. The method according to item 1474, wherein the one or more viral infection(s) are caused by one or more vira from the Family Rudiviridae.

1511. The method according to item 1474, wherein the one or more viral infection(s) are caused by one or more vira from the Family Tectiviridae.

1512. The method according to item 1474, wherein the one or more viral infection(s) are caused by one or more vira from the Mimivirus.
1513. The method according to item 1474, wherein the one or more viral infection(s) are caused by one or more vira from the Unassigned bacteriophage families.
1514. The method according to item 1474, wherein the one or more viral infection(s) are caused by one or more vira from the Family Inoviridae.
1515. The method according to item 1474, wherein the one or more viral infection(s) are caused by one or more vira from the Family Microviridae.
1516. The method according to item 1474, wherein the one or more viral infection(s) are caused by one or more vira from the Family Geminiviridae.
1517. The method according to item 1474, wherein the one or more viral infection(s) are caused by one or more vira from the Family Circoviridae.
1518. The method according to item 1474, wherein the one or more viral infection(s) are caused by one or more vira from the Family Nanoviridae.
1519. The method according to item 1474, wherein the one or more viral infection(s) are caused by one or more vira from the Family Parvoviridae such as Parvovirus B19.
1520. The method according to item 1474, wherein the one or more viral infection(s) are caused by one or more vira from the Anellovirus.
1521. The method according to item 1474, wherein the one or more viral infection(s) are caused by one or more vira from the Family Birnaviridae.
1522. The method according to item 1474, wherein the one or more viral infection(s) are caused by one or more vira from the Family Chrysoviridae.
1523. The method according to item 1474, wherein the one or more viral infection(s) are caused by one or more vira from the Family Cystoviridae.
1524. The method according to item 1474, wherein the one or more viral infection(s) are caused by one or more vira from the Family Hypoviridae.
1525. The method according to item 1474, wherein the one or more viral infection(s) are caused by one or more vira from the Family Partitiviridae.
1526. The method according to item 1474, wherein the one or more viral infection(s) are caused by one or more vira from the Family Reoviridae such as Rotavirus.
1527. The method according to item 1474, wherein the one or more viral infection(s) are caused by one or more vira from the Family Totiviridae.
1528. The method according to item 1474, wherein the one or more viral infection(s) are caused by one or more vira from the Endornavirus.
1529. The method according to item 1474, wherein the one or more viral infection(s) are caused by one or more vira from the Order Nidovirales.
1530. The method according to item 1474, wherein the one or more viral infection(s) are caused by one or more vira from the Family Arteriviridae.
1531. The method according to item 1474, wherein the one or more viral infection(s) are caused by one or more vira from the Family Coronaviridae such as Coronavirus, and SARS.
1532. The method according to item 1474, wherein the one or more viral infection(s) are caused by one or more vira from the Family Roniviridae.
1533. The method according to item 1474, wherein the one or more viral infection(s) are caused by one or more vira from the Family Astroviridae.
1534. The method according to item 1474, wherein the one or more viral infection(s) are caused by one or more vira from the Family Barnaviridae.
1535. The method according to item 1474, wherein the one or more viral infection(s) are caused by one or more vira from the Family Bromoviridae.
1536. The method according to item 1474, wherein the one or more viral infection(s) are caused by one or more vira from the Family Caliciviridae such as Norwalk virus.
1537. The method according to item 1474, wherein the one or more viral infection(s) are caused by one or more vira from the Family Closteroviridae.
1538. The method according to item 1474, wherein the one or more viral infection(s) are caused by one or more vira from the Family Comoviridae.
1539. The method according to item 1474, wherein the one or more viral infection(s) are caused by one or more vira from the Family Dicistroviridae.
1540. The method according to item 1474, wherein the one or more viral infection(s) are caused by one or more vira from the Family Flaviviridae such as Yellow fever virus, West Nile virus, Hepatitis C virus, and Dengue fever virus.
1541. The method according to item 1474, wherein the one or more viral infection(s) are caused by one or more vira from the Family Flexiviridae.
1542. The method according to item 1474, wherein the one or more viral infection(s) are caused by one or more vira from the Family Leviviridae.
1543. The method according to item 1474, wherein the one or more viral infection(s) are caused by one or more vira from the Family Luteoviridae such as Barley yellow dwarf virus.
1544. The method according to item 1474, wherein the one or more viral infection(s) are caused by one or more vira from the Family Marnaviridae.
1545. The method according to item 1474, wherein the one or more viral infection(s) are caused by one or more vira from the Family Narnaviridae.
1546. The method according to item 1474, wherein the one or more viral infection(s) are caused by one or more vira from the Family Nodaviridae.
1547. The method according to item 1474, wherein the one or more viral infection(s) are caused by one or more vira from the Family Picornaviridae such as Poliovirus, the common cold virus, Hepatitis A virus, enteroviruses, rhinoviruses, and foot-and-mouth virus.
1548. The method according to item 1474, wherein the one or more viral infection(s) are caused by one or more vira from the Family Potyviridae.
1549. The method according to item 1474, wherein the one or more viral infection(s) are caused by one or more vira from the Family Sequiviridae.
1550. The method according to item 1474, wherein the one or more viral infection(s) are caused by one or more vira from the Family Tetraviridae.
1551. The method according to item 1474, wherein the one or more viral infection(s) are caused by one or more vira from the Family Togaviridae such as Rubella virus, Ross River virus, Sindbis virus, and Chikungunya virus.
1552. The method according to item 1474, wherein the one or more viral infection(s) are caused by one or more vira from the Family Tombusviridae.
1553. The method according to item 1474, wherein the one or more viral infection(s) are caused by one or more vira from the Family Tymoviridae.

1554. The method according to item 1474, wherein the one or more viral infection(s) are caused by one or more vira from the Genus *Benyvirus*.

1555. The method according to item 1474, wherein the one or more viral infection(s) are caused by one or more vira from the Genus *Cheravirus*.

1556. The method according to item 1474, wherein the one or more viral infection(s) are caused by one or more vira from the Genus *Furovirus*.

1557. The method according to item 1474, wherein the one or more viral infection(s) are caused by one or more vira from the Genus Hepevirus such as Hepatitis E virus.

1558. The method according to item 1474, wherein the one or more viral infection(s) are caused by one or more vira from the Genus *Hordeivirus*.

1559. The method according to item 1474, wherein the one or more viral infection(s) are caused by one or more vira from the Genus *Idaeovirus*.

1560. The method according to item 1474, wherein the one or more viral infection(s) are caused by one or more vira from the Genus *Ourmiavirus*.

1561. The method according to item 1474, wherein the one or more viral infection(s) are caused by one or more vira from the Genus *Pecluvirus*.

1562. The method according to item 1474, wherein the one or more viral infection(s) are caused by one or more vira from the Genus *Pomovirus*.

1563. The method according to item 1474, wherein the one or more viral infection(s) are caused by one or more vira from the Genus *Sadwavirus*.

1564. The method according to item 1474, wherein the one or more viral infection(s) are caused by one or more vira from the Genus *Sobemovirus*.

1565. The method according to item 1474, wherein the one or more viral infection(s) are caused by one or more vira from the Genus *Tobamovirus* such as tobacco mosaic virus.

1566. The method according to item 1474, wherein the one or more viral infection(s) are caused by one or more vira from the Genus *Tobravirus*.

1567. The method according to item 1474, wherein the one or more viral infection(s) are caused by one or more vira from the Genus *Umbravirus*.

1568. The method according to item 1474, wherein the one or more viral infection(s) are caused by one or more vira from the Order Mononegavirales.

1569. The method according to item 1474, wherein the one or more viral infection(s) are caused by one or more vira from the Family Bornaviridae such as Borna disease virus.

1570. The method according to item 1474, wherein the one or more viral infection(s) are caused by one or more vira from the Family Filoviridae such as Ebola virus, and Marburg virus.

1571. The method according to item 1474, wherein the one or more viral infection(s) are caused by one or more vira from the Family Paramyxoviridae such as Measles, Mumps, Nipah and Hendra virus.

1572. The method according to item 1474, wherein the one or more viral infection(s) are caused by one or more vira from the Family Rhabdoviridae such as Rabies virus.

1573. The method according to item 1474, wherein the one or more viral infection(s) are caused by one or more vira from the Family Arenaviridae such as Lassa virus.

1574. The method according to item 1474, wherein the one or more viral infection(s) are caused by one or more vira from the Family Bunyaviridae such as Hantavirus.

1575. The method according to item 1474, wherein the one or more viral infection(s) are caused by one or more vira from the Family Orthomyxoviridae such as Influenza viruses.

1576. The method according to item 1474, wherein the one or more viral infection(s) are caused by one or more vira from the Genus *Deltavirus*.

1577. The method according to item 1474, wherein the one or more viral infection(s) are caused by one or more vira from the Genus *Ophiovirus*.

1578. The method according to item 1474, wherein the one or more viral infection(s) are caused by one or more vira from the Genus *Tenuivirus*.

1579. The method according to item 1474, wherein the one or more viral infection(s) are caused by one or more vira from the Genus *Varicosavirus*.

1580. The method according to item 1474, wherein the one or more viral infection(s) are caused by one or more vira from the Family Metaviridae.

1581. The method according to item 1474, wherein the one or more viral infection(s) are caused by one or more vira from the Family Pseudoviridae.

1582. The method according to item 1474, wherein the one or more viral infection(s) are caused by one or more vira from the Family Retroviridae such as Retroviruses, e.g. like HIV.

1583. The method according to item 1474, wherein the one or more viral infection(s) are caused by one or more vira from the Family Hepadnaviridae such as Hepatitis B virus.

1584. The method according to item 1474, wherein the one or more viral infection(s) are caused by one or more vira from the Family Caulimoviridae such as Cauliflower mosaic virus.

1585. The method according to item 1474, wherein the one or more viral infection(s) are caused by one or more vira from the group consisting of Abelson murine leukemia virus (Ab-MLV, A-MuLV), acute laryngotracheobronchitis virus (or HPIV), Adelaide River virus, Adeno-associated virus group (Dependevirus), Adenovirus, African horse sickness virus, African swine fever virus, AIDS virus, Aleutian mink disease, parvovirus, alfalfa mosaic virus, Alphaherpesvirinae (including HSV 1 and 2 and varicella), Alpharetrovirus (Avian leukosis virus, Rous sarcoma virus), Alphavirus, alkhurma virus, ALV related virus, Amapari virus, Andean potato mottle virus, Aphthovirus, Aquareovirus, arbovirus, arbovirus C, arbovirus group A, arbovirus group B, Arenavirus group, Argentine hemorrhagic fever virus, Argentinian hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, Avian leukosis virus (ALV), avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus (Cercopithecine herpesvirus 1), B19 virus (Parvovirus B19), Babanki virus, baboon herpesvirus, bacterial virus, baculovirus, barley yellow dwarf virus, Barmah Forest virus, bean pod mottle virus, bean rugose mosaic virus, Bebaru virus, Berrimah virus, Betaherpesvirinae, betaretrovirus, Bird flu, Birnavirus, Bittner virus, BK virus, Black Creek Canal virus, bluetongue virus, Bolivian hemorrhagic fever virus, Boma disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, bracovirus, broad bean mottle virus, broad bean stain virus, brome mosaic virus, Bromovirus, Buggy Creek virus, bullet shaped virus group, Bunyamwera virus, Bunyavirus, Burkitt's lymphoma virus, Bwamba Fever, Bwattany hetero virus, CA virus (Croup-associated virus/parainfluenza virus type 2), Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, Capillovirus, caprine arthritis virus, caprine encephalitis virus, Caprine Herpes Virus, Capripox virus, Cardiovirus, Carlavirus, Carmovirus, carrot mottle virus, *Cassia* yellow blotch virus, Caulimovirus, Cauliflower mosaic virus, caviid herpesvirus 1, Cercopithecine herpesvirus 1, Cercopithecine herpesvirus 2, cereal yellow dwarf virus, Chandipura virus, Changuinola virus, channel catfish virus, Charleville virus, chickenpox virus, Chikungunya virus, chimpanzee herpesvirus, Chordopoxyirinae, chub reovirus, chum salmon virus, Closterovirus, Cocal virus, Coho salmon reovirus, coital exanthema virus, Colorado tick fever virus, Coltivirus Columbia SK virus, Commelina yellow mottle virus, Common cold virus, Comovirus, Condylomata accuminata, congenital cytomegalovirus, contagious ecthyma virus, contagious pustular dermatitis virus, Coronavirus, Corriparta virus, coryza virus, cowpea chlorotic mottle virus, cowpea mosaic virus, cowpea virus, cowpox virus, coxsackie virus, CPV (cytoplasmic polyhedrosis virus), cricket paralysis virus, Crimean-Congo hemorrhagic fever virus, croup associated virus, Crypotovirus, Cucumovirus, Cypovirus, Cytomegalovirus (HCMV or Human Herpesvirus 5 HHV-5), cytoplasmic polyhedrosis virus, Cytorhabdovirus, deer papillomavirus, Deltaretrovirus (Human T-lymphotropic virus), Deformed wing virus DWV, Dengue, Densovirus, Dependovirus, Dhori virus, Dianthovirus, diploma virus, DNA virus, Dobrava-Belgrade Virus, Dog Flu, *Drosophila* C virus, duck hepatitis B virus, duck hepatitis virus 1, duck hepatitis virus 2, duovirus, Duvenhage virus, eastern equine encephalitis virus, eastern equine encephalomyelitis virus, Ebola virus, Ebola-like virus, Echovirus, echovirus 10, echovirus 28, echovirus 9, ectromelia virus, EEE virus (Eastern equine encephalitis virus), EIA virus (equine infectious anemia), EMC virus (Encephalomyocarditis), Emiliania huxleyi virus 86, encephalitis virus, encephalomyocarditis virus, Endogenous retrovirus, Enterovirus, Entomopoxyirinae, Entomopoxvirus A, Entomopoxvirus B, Entomopoxvirus C, enzyme elevating virus, epidemic hemorrhagic fever virus, epizootic hemorrhagic disease virus, Epsilonretrovirus, Epstein-Barr virus (EBV; Human herpesvirus 4 HHV-4), equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, Fabavirus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Fijivirus, Filovirus, Flanders virus, Flavivirus, foot and mouth disease virus, Fort Morgan virus, Four Corners hantavirus, fowl adenovirus 1, Fowlpox virus, Friend virus, Furovirus, Gammaherpesvirinae, gammaretrovirus, GB virus C (GBV-C; formerly Hepatitis G virus), Geminivirus, German measles virus, Getah virus, gibbon ape leukemia virus, green monkey virus (mullburg), glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantavirus, hard clam reovirus, hare fibroma virus, HCMV (human cytomegalovirus), helper virus, hemadsorption virus 2, hemagglutinating virus of Japan, hemorrhagic fever virus, Hendra virus, Henipaviruses, Hepadnavirus, hepatitis A virus, hepatitis B virus, hepatitis C virus, hepatitis D (delta) virus, hepatitis E virus, hepatitis F virus, hepatitis G virus, hepatitis nonA nonB virus, hepatoencephalomyelitis reovirus 3, Hepatovirus, heron hepatitis B virus, herpes B virus, Herpes simplex virus, herpes simplex virus 1, herpes simplex virus 2, Herpesvirus, Herpes zoster, Herpes virus 6, Herpes virus 7, Herpes virus 8, Herpesvirus ateles, Herpesvirus hominis, Herpesvirus saimiri, Herpesvirus suis, Herpesvirus varicellae, Highlands J virus, Hirame rhabdovirus, HIV-1, hog cholera virus, Hordeivirus, Horse Flu, HTLV-1, HTLV-2, human adenovirus 2, human alphaherpesvirus 1, human alphaherpesvirus 2, human alphaherpesvirus 3, human B lymphotropic virus, human betaherpesvirus 5, human coronavirus, Human enterovirus A, Human enterovirus B, Human Flu, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus (HIV), human immunodeficiency virus 1, human immunodeficiency virus 2, Human metapneumovirus, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, ichnovirus, Ilarvirus, infantile gastroenteritis virus, infectious bovine rhinotracheitis virus, infectious haematopoietic necrosis virus, infectious pancreatic necrosis virus, influenza virus, influenzavirus A, influenzavirus B, influenzavirus C, influenzavirus D, influenzavirus pr8, insect iridescent virus, insect virus, interfering virus, iridovirus, Isavirus, Japanese B virus, Japanese encephalitis virus, JC virus, Junin virus, Johnson grass mosaic virus, Kaposi's sarcoma-associated herpesvirus, Kemerovo virus, Kilham's rat virus, Klamath virus, Kolongo virus, Korean hemorrhagic fever virus, kumba virus, Kumlinge virus, Kunjin virus, Kyasanur forest disease, Kyzylagach virus, La Crosse virus, lactic dehydrogenase elevating virus, Lagos bat virus, Lambda phage, langat virus, Langur virus, lapine parvovirus, Lassa fever virus, Lassa virus, latent rat virus, LCM virus, Leaky virus, Lentivirus, Leporipoxvirus, leukemia virus, leukovirus, louping ill virus, lumpy skin disease virus, Luteovirus, lymphadenopathy associated virus, Lymphocytic choriomeningitis virus (LCMV), Lymphocryptovirus, lymphocytic choriomeningitis virus, lymphoproliferative virus group, Lyssavirus, Machupo virus, mad itch virus, maize chlorotic dwarf virus, maize rough dwarf virus, mammalian type B oncovirus group, mammalian type B retroviruses, mammalian type C retrovirus group, mammalian type D retroviruses, mammary tumor virus, Mapuera virus, Marafivirus, Marburg virus, Marburg-like virus, Mason Pfizer monkey virus, Mastadenovirus, Mayaro virus, ME virus, Measles virus, Melandrium yellow fleck virus, Menangle virus, Mengo virus, Mengovirus, Merkel cell polyomavirus, Middelburg virus, milkers nodule virus, mink enteritis virus, minute virus of mice, MLV related virus, MM virus, Mokola virus, Molluscipoxvirus, Molluscum contagiosum virus, Moloney murine leukemia virus (M-MuLV), monkey B virus, Monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, Mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Necrovirus, Neethling virus, Nelson Bay virus, Nemtick Virus, Nepovirus, neurotropic virus, New World Arenavirus, newborn pneumonitis virus, Newcastle disease virus, Nipah virus, noncytopathogenic virus, Norovirus, Norwalk virus, nuclear polyhedrosis virus (NPV), nipple neck virus, O'nyong'nyong virus, oat sterile dwarf virus, Ockelbo virus, Omsk hemorrhagic fever virus, oncogenic virus, oncogenic viruslike particle, oncornavirus, Orbivirus, On virus, Oropouche virus, Orthohepadnavirus, orthomyxovirus, Orthopoxvirus, *Orthoreovirus*, Orungo, ovine papillomavirus, ovine catarrhal fever virus, owl monkey herpesvirus, Palyam virus, Papillomavirus, Papillomavirus sylvilagi, Papovavirus, Parainfluenza virus human (HPIV), parainfluenza virus type 1 human (HPIV-1), parainfluenza virus type 2 human (HPIV-2), parainfluenza virus type 3 human (HPIV-3), parainfluenza virus type 4 human (HPIV-4), Paramyxovirus, Parapoxvirus, paravaccinia virus, parsnip yellow fleck virus, Parvovirus, Parvovirus B19, pea enation mosaic virus, Pestivirus, Phlebovirus, phocine distemper virus, Phytoreovirus, Picodnavirus, Picornavirus, pig cytomegalovirus, pigeonpox virus, Piry virus, Pixuna virus, plant rhabdovirus group, plant virus, pneumonia virus of mice, Pneumovirus, Poliomyelitis virus, Poliovirus, Polydnavirus, polyhedral virus, Polyoma virus, Polyomavirus, Polyomavirus bovis, Polyomavirus cercopitheci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, Potato leaf roll virus, Potato mop top virus, Potato virus Y, Potexvirus, Potyvirus, Powassan encephalitis virus, Poxvirus, poxvirus variolae, Prospect Hill virus, provirus, pseudocowpox virus, pseudorabies virus, psittacinepox virus, Puumala virus, Qalyub virus, Quail pea mosaic virus, quailpox virus, Queensland fruitfly virus, Quokkapox virus, rabbit fibroma virus, rabbit kidney vaculolating virus, rabbit papillomavirus, Rabies virus, raccoon parvovirus, raccoonpox virus, radish mosaic virus, Ranikhet virus, rat cytomegalovirus, rat parvovirus, rat virus, Rauscher's virus, recombinant vaccinia virus, recombinant virus, Red Clover Necrotic Mosaic Virus, reovirus, reovirus 1, reovirus 2, reovirus 3, reptilian type C virus, Respiratory syncytial virus, respiratory virus, reticuloendotheliosis virus, Retrovirus, Rhabdovirus, Rhabdovirus carpia, Rhadinovirus, Rhinovirus, Rhizidiovirus, rice dwarf virus, rice gall dwarf virus, rice hoja blanca virus, rice ragged stunt virus, Rift Valley fever virus, Riley's virus, rinderpest virus, RNA tumor virus, RNA virus, Roseolovirus, Ross River virus, Rotavirus, rougeole virus, Rous sarcoma virus, Rubella virus, rubeola virus, Rubivirus, Russian autumn encephalitis virus, S6-14-03 virus, SA 11 simian virus, SA 15, SA2 virus, SA6 virus, SA8 virus, Sabia virus, Sabio virus, Sabo virus, Saboya virus, *Sabulodes caberata* GV, Sacbrood virus, *Saccharomyces cerevisiae* virus L-A, *Saccharomyces cerevisiae* virus La, *Saccharomyces cerevisiae* virus LBC, Sagiyama virus, Saguaro cactus virus, Saimirline herpesvirus 1, Saimirline herpesvirus 2, Sainpaulia leaf necrosis virus, SaintAbb's Head virus, Saint-Floris virus, Sakhalin virus, Sal Vieja virus, Salanga virus, Salangapox virus, Salehabad virus, salivary gland virus, Salmonid herpesvirus 1, Salmonid herpesvirus 2, Salmonis virus, *Sambucus* vein clearing virus, *Samia cynthia* NPV, *Samia pryeri* NPV, *Samia ricini* NPV, Sammons' Opuntia virus, SanAngelo virus, San Juan virus, San Miguel sealion virus, San Perlita virus, Sand rat nuclear inclusion agents, Sandfly fever Naples virus, Sandfly fever Sicilian virus, Sandjimba virus, Sango virus, Santa Rosa virus, Santarem virus, Santosai temperate virus, Sapphire II virus, Sapporo-like virus, Saraca virus, *Sarracenia purpurea* virus, SARS virus, satellite virus, Sathuperi virus, Satsuma dwarf virus, *Saturnia pavonia* virus, *Saturnia pyri* NPV, Saumarez Reef virus, Sawgrass virus, *Sceliodes cordalis* NPV, Schefflera ringspot virus, Sciaphila duplex GV, *Scirpophaga incertulas* NPV, Sciurid herpesvirus, Sciurid herpesvirus 2, *Scoliopteryx libatFix* NPV, *Scopelodes contracta* NPV, *Scopelodes venosa* NPV, *Scopula subpunctaria* NPV, *Scotogramma trifolii* GV, *Scotogramma trifolu* NPV, Scrophularia mottle virus, SDAV (sialodacryoadenitis virus), sealpox virus, *Selenephera lunigera* NPV, *Selepa celtis* GV, Seletar virus, *Selidosema suavis* NPV, *Semidonta biloba* NPV, *Semiothisa sexmaculata* GV, Semliki Forest Virus, Sena Madureira virus, Sendai virus, SENV-D, SENV-H, Seoul virus, Sepik virus, Serra do Navio virus, Serrano golden mosaic virus, Sesame yellow mosaic virus, *Sesamia calamistis* NPV, *Sesamia cretica* GV, *Sesamia inferens* NPV, *Sesamia nonagrioides* GV, Setora nitens virus, Shallot latent virus, Shamonda virus, Shark River virus, Sheep associated malignant catarrhal fever, Sheep papillomavirus, Sheep pulmonary adenomatosis associated herpesvirus, sheeppox virus, Shiant Islands virus, Shokwe virus, Shope fibroma virus, Shope papilloma virus, Shuni virus, Siamese cobra herpesvirus, *Sibine fusca* densovirus, *Sida* golden mosaic virus (SiGMV), *Sida* golden yellow vein virus (SiGYVV), Sigma virus, Sikte water-borne virus, Silverwater virus, Simbu virus, Simian adenoviruses 1 to 27, Simian agent virus 12, Simian enterovirus 1 to 18, simian foamy virus, Simian hemorrhagic fever virus, simian hepatitis A virus, simian human immunodeficiency virus, simian immunodeficiency virus, simian parainfluenza virus, Simian rotavirus SA11, Simian sarcoma virus, simian T cell lymphotrophic virus, Simian type D virus 1, Simian vancella herpesvirus, simian virus, simian virus 40, Simplexvirus, *Simulium vittatum* densovirus, Sin Nombre virus, Sindbis virus, Sint1em's onion latent virus, Sixgun city virus, Skunkpox virus, Smallpox virus, Smelt reovirus, *Smerinthus ocellata* NPV, Smithiantha virus, Snakehead rhabdovirus, Snowshoe hare virus, Snyder-Theilen feline sarcoma virus, Sobemovirus, Sofyn virus, Soil-borne wheat mosaic virus, Sokoluk virus, *Solanum apical* leaf curl virus, *Solanum nodiflorum* mottle virus, Solanurn yellows virus, Soldado virus, Somerville virus 4, Sonchus mottle virus, Sonchus virus, Sonchus yellow net virus, *Sorghum* chlorotic spot virus, *Sorghum* mosaic virus, *Sorghum* virus, Sororoca virus, Soursop yellow blotch virus, South African passiflora virus, South American hemorrhagic fever viruses, South African passiflora virus, South River virus, Southern bean mosaic virus, Southern potato latent virus, Sowbane mosaic virus, Sowthistle yellow vein virus, Soybean chlorotic mottle virus, Soybean crinkle leaf virus, Soybean dwarf virus, Soybean mosaic virus, SPAr-2317 virus, *Sparganothis pettitana* NPV, sparrowpox virus, Spartina mottle virus, Spectacled caimanpox virus, SPH 114202 virus, Sphenicid herpesvirus 1, *Sphinx ligustri* NPV, Spider monkey herpesvirus, *Spilarctia subcarnea* NPV, *Spilonota ocellana* NPV, *Spilosoma lubricipeda* NPV, Spinach latent virus, Spinach temperate virus, Spiroplasma phage 1, Spiroplasma phage 4, Spiroplasma phage aa, Spiroplasma phage C1/TS2, *Spodoptera exempta* cypovirus, *Spodoptera exigua* virus, *Spodoptera frugiperda* virus, *Spodoptera latifascia* virus, *Spodoptera littoralis, Spodoptera mauritia* virus, *Spodoptera ornithogalli* virus, Spondweni virus, spring beauty latent virus, Spring viremia of carp virus, Spumavirus (SFV, HFV), Squash leaf curl virus, squash mosaic virus, squirrel fibroma virus, Squirrel monkey herpesvirus, squirrel monkey retrovirus, SR-11 virus, Sri Lankan passionfruit mottle virus, Sripur virus, SSV 1 virus group, StAbbs Head virus, St. Louis encephalitis virus, *Staphylococcus* phage 107, *Staphylococcus* phage 187, *Staphylococcus* phage 2848A, *Staphylococcus* phage 3A, *Staphylococcus* phage 44A HJD, *Staphylococcus* phage 77, *Staphylococcus* phage B11-M15, *Staphylococcus* phage Twort, Starlingpox virus, Statice virus Y, P, STLV (simian T lymphotropic virus) type I, STLV (simian T lymphotropic virus) type II, STLV (simian T lymphotropic virus) type III, stomatitis papulosa virus, Stratford virus, Strawberry crinkle virus, Strawberry latent ringspot virus, Strawberry mild yellow edge virus, Strawberry vein banding virus, *Streptococcus* phage 182, *Streptococcus* phage 2BV, *Streptococcus* phage A25, *Streptococcus* phage 24, *Streptococcus* phage PEI, *Streptococcus* phage VD13, *Streptococcus* phage fD8, *Streptococcus* phage CP-1, *Streptococcus* phage Cvir, *Streptococcus* phage H39, Strigid herpesvirus 1, Striped bass reovirus, Striped Jack nervous, necrosis virus, Stumptailed macaque virus, submaxillary virus, Subterranean clover mottle virus, Subterranean clover mottle virus satellite, Subterranean clover red leaf virus, Subterranean clover stunt virus, Sugarcane bacilliform virus, Sugarcane mild mosaic virus, Sugarcane mosaic virus, Sugarcane streak virus, suid alphaherpesvirus 1, suid herpesvirus 2, Suipoxvirus, *Sulfolobus* virus 1, Sunday Canyon virus, Sunflower crinkle virus, Sunflower mosaic virus, Sunflower rugose mosaic virus, Sunflower yellow blotch virus, Sunflower yellow ringspot virus, Sun-hemp mosaic virus, swamp fever virus, Sweet clover necrotic mosaic virus, Sweet potato A virus, Sweet potato chlorotic leafspot virus, Sweet potato feathery mottle virus, Sweet potato internal cork virus, Sweet potato latent virus, Sweet potato mild mottle virus, Sweet potato russet crack virus, Sweet potato vein mosaic virus, Sweet potato yellow dwarf virus, Sweetwater Branch virus, Swine cytomegalovirus, Swine Flu, Swine infertility and respiratory syndrome virus, swinepox virus, Swiss mouse leukemia virus, Sword bean distortion mosaic virus, *Synaxis jubararia* NPV, *Synaxis pallulata* NPV, *Synetaeris tenuifemur* virus, *Syngrapha selecta* NPV, T4 phage, T7 phage, TAC virus, Tacaiuma virus, Tacaribe complex virus, Tacaribe virus, Tadpole edema virus LT 1-4, Taggert virus, Tahyna virus, Tai virus, Taiassui virus, Tamana bat virus, Tamarillo mosaic virus, Tamdy virus, [[Tamiami virus, Tanapox virus, Tanga virus, Tanjong Rabok virus, Taro bacilliform virus, Badnavirus Tataguine virus, Taterapox virus, Taterapox virus, Teasel mosaic virus, Tehran virus, Telfairia mosaic virus, Telok Forest virus, Tembe virus, Tembusu virus, Tench reovirus, Tensaw virus, Tenvivirus, Tephrosia symptomless virus, Termeil virus, Tete virus, *Tetralopha scortealis* NPV, *Tetropium cinnamoptemm* NPV, Texas pepper virus, Thailand virus, *Thaumetopoea pityocampa* virus, Theiler's encephalomyelitis virus, Theiler's virus, *Theophila mandarina* NPV, *Theretra japonica* NPV, Thermoproteus virus 1, Thermoproteus virus 2, Thermoproteus virus 3, Thermoproteus virus 4, Thiafora virus, Thimiri virus, Thistle mottle virus, Thogoto virus, Thormodseyjarklettur virus, *Thosea asigna* virus, *Thosea baibarana* NPV, *Thosea sinensis* GV, Thottapalayam virus, *Thylidolpteryx ephemeraeformis* NPV, *Thymelicus lineola* NPV, Tibrogargan virus, *Ticera castanea* NPV, Tick borne encephalitis virus (TBEV)—European and Far Eastern subtypes, Tillamook virus, Tilligerry virus, Timbo virus, Tilmboteua virus, Tilmaroo virus, Tindholmur virus, *Tinea pellionella* NPV, *Tineola hisselliella* NPV, *Tinpula paludosa* NPV, *Tinracola plagiata* NPV, Tioman virus, Tlacotalpan virus, Tobacco bushy top virus, Tobacco etch virus, Tobacco leaf curl virus, Tobacco mild green mosaic virus, tobacco mosaic virus, Tobacco mosaic virus satellite, Tobacco mottle virus, Tobacco necrosis virus, Tobacco necrosis virus satellite, Tobacco necrosis virus small satellite, Tobacco necrotic dwarf virus, tobacco rattle virus, Tobacco ringspot virus, Tobacco streak virus, Tobacco stunt virus, Tobacco vein banding mosaic virus, Tobacco vein distorting virus Tobacco vein mottling virus, Tobacco wilt virus, Tobacco yellow dwarf virus, Tobacco yellow net virus, Tobacco yellow vein virus, *Tobamovirus* Tobravirus, Togavirus, Tomato apical stunt viroid, Tomato aspermy virus, Tomato black ring virus, Tomato black ring virus satellite, Tomato bunchy top viroid, tomato bushy stunt virus, Tomato bushy stunt virus satellite, Tomato golden mosaic virus, Tomato leaf crumple virus, Tomato leaf curl virus, Tomato leafroll virus, Tomato mosaic virus, Tomato mottle virus, Tomato pale chlorosis virus, Tomato planta macho viroid, Tomato pseudo-curly top virus, Tomato ringspot virus, Tomato spotted wilt virus, Tomato top necrosis virus, Tomato vein yellowing virus, Tomato yellow dwarf virus, Tomato yellow leaf curl virus, Tomato yellow mosaic virus, Tomato yellow top virus, Tombusvirus, Tongan vanilla virus, Torovirus, Torque teno virus, *Tortrix loeflingiana* NPV, *Tortrix viridana* NPV, Toscana virus, Tospovirus, *Toxorhynchites brevipalpis* NPV, *Trabala vishnou* NPV, Tradescantia/Zebrina virus, Trager duck spleen necrosis virus, *Tra-* nosema sp. Virus, transforming virus, Tree shrew adenovirus 1, Tree shrew herpesvims, Triatoma virus, Tribec virus, *Trichiocampus irregularis* NPV, *Trichiocampus viminalis* NPV, *Trichomonas vaginalis* virus, *Trichoplusia ni* cypovirus 5, *Trichoplusia ni* granulovirus, *Trichoplusia ni* MNPV, *Trichoplusia ni* Single SNPV, *Trichoplusia ni* virus, Trichosanthes mottle virus, *Triticum aestivum* chlorotic spot virus, Trivittatus virus, Trombetas virus, Tropaeolum virus 1, Tropaeolum virus 2, Trubanarnan virus, Tsuruse virus, Tucunduba virus, Tulare apple mosaic virus, Tulip band breaking virus, Tulip breaking virus, Tulip chlorotic blotch virus, Tulip top breaking virus, Tulip virus X, tumor virus, Tupaia virus, Tupaiid herpesvirus 1, Turbot herpesvirus, Turbot reovirus, Turkey adenoviruses 1 to 3, Turkey coronavirus, Turkey herpesvirus 1, turkey rhinotracheitis virus, turkeypox virus, Turlock virus, Turnip crinkle virus, Turnip crinkle virus satellite, Turnip mild yellows virus, Turnip mosaic virus, Turnip rosette virus, turnip yellow mosaic virus, Turuna virus, Tymovirus, Tyuleniy virus, type C retroviruses, type D oncovirus, type D retrovirus group, Uasin Gishu disease virus, Uganda S virus, *Ugymyia sericariae* NPV, ulcerative disease rhabdovirus, Ullucus mild mottle virus, Ullucus mosaic virus, Ullucus virus C, Umatilla virus, Umbre virus, Una virus, Upolu virus, UR2 sarcoma virus, *Uranotaenia sapphirina* NPV, *Urbanus proteus* NPV, Urucuri virus, *Ustilago maydis* virus 1, *Ustilago maydis* virus 4, *Ustilago maydis* virus 6, Usutu virus, Utinga virus, Utive virus, Uukuniemi virus group, Vaccinia virus, Vaeroy virus, Vallota mosaic virus, *Vanessa atalanta* NPV, *Vanessa cardui* NPV, *Vanessa prorsa* NPV, Vanilla mosaic virus, Vanilla necrosis virus, Varicella zoster virus, Varicellovirus, Varicola virus, variola major virus, variola virus, Vasin Gishu disease virus, Vellore virus, Velvet tobacco mottle virus, Velvet tobacco mottle virus satellite, Venezuelan equine encephalitis virus, Venezuelan equine encephalomyelitis virus, Venezuelan hemorrhagic fever virus, Vesicular stomatitis virus, Vesiculovirus, *Vibrio* phage 06N-22P, *Vibrio* phage 06N-58P, *Vibrio* phage 4996, *Vibrio* phage a3a, *Vibrio* phage I, *Vibrio* phage II, *Vibrio* phage m, *Vibrio* phage IV, *Vibrio* phage kappa, *Vibrio* phage nt-1, *Vibrio* phage OXN-52P, *Vibrio* phage OXN-IOOP, *Vibrio* phage v6, *Vibrio* phage Vfl2, *Vibrio* phage Vf33, *Vibrio* phage VP11, *Vibrio* phage VP11, *Vibrio* phage VP3, *Vibrio* phage VP5, *Vibrio* phage X29, *Vicia* cryptic virus, *Vigna sinensis* mosaic virus, Vilyuisk virus, Vinces virus, Viola mottle virus, viper retrovirus, viral haemorrhagic septicemia virus, virus-like particle, Visna Maedi virus, Visna virus, Voandzeia mosaic virus, Voandzeia necrotic mosaic virus, volepox virus, Wad Medani virus, Wallal virus, Walleye epidermal hyperplasia, Walrus calicivirus, Wanowrie virus, Warrego virus, Watermelon chlorotic stunt virus, Watermelon curly mottle virus, Watermelon mosaic virus 1, Watermelon mosaic virus 2, Weddel water-borne virus, Weldona virus, Wesselsbron virus, West Nile virus, western equine encephalitis virus, western equine encephalomyelitis virus, Wexford virus, Whataroa virus, Wheat American striate mosaic virus, Wheat chlorotic streak virus, Wheat dwarf virus, Wheat rosette stunt virus, Wheat streak mosaic virus, Wheat yellow leaf virus, Wheat yellow mosaic virus, White bryony virus, White clover cryptic virus 1, White clover cryptic virus 2, White clover cryptic virus 3, White clover mosaic virus, White lupinrnosaic virus, Wild cucumber mosaic virus, Wild potato mosaic virus, Wildbeest herpesvirus, Wineberry latent virus, Winter wheat mosaic virus, Winter wheat Russian mosaic virus, *Wiseana cervinata* virus, *Wiseana signata* virus, *Wiseana umbraculata* virus, Wissadula mosaic virus, Wisteria vein mosaic virus, Witwatersrand virus, Wongal virus, Wongorr virus, Winter Vomiting Virus, woodchuck hepatitis B virus, Woodchuck herpesvirus marmota 1, woolly monkey sarcoma virus, wound tumor virus, WRSV virus, WVU virus 2937, WW virus 71 to 212, *Wyeomyia smithii* NPV, *Wyeomyia* virus, *Xanthomonas* phage Cf, *Xanthomonas* phage Cflt, *Xanthomonas* phage RR66, *Xanthomonas* phage Xf, *Xanthomonas* phage Xf2, *Xanthomonas* phage XP5, *Xenopus* virus T21, Xiburema virus, Xingu virus, *Xylena curvimacula* NPV, Y73 sarcoma virus, Yaba monkey tumor virus, Yaba-1 virus, Yaba-7 virus, Yacaaba virus, Yam mosaic virus, Yaounde virus, Yaquina Head virus, Yatapoxvirus, Yellow fever virus, Yogue virus, Yokapox virus, Yokase virus, *Yponomeuta cognatella* NPV, *Yponomeuta evonymella* NPV, *Yponomeuta malinellus* NPV, *Yponomeuta padella* NPV, Yucca baciliform virus, Yug Bogdanovac virus, Zaliv Terpeniya virus, *Zea mays* virus, Zegla virus, *Zeiraphera diniana* virus, *Zeiraphera pseudotsugana* NPV, Zika virus, Zirqa virus, Zoysia mosaic virus, Zucchini yellow fleck virus, Zucchini yellow mosaic virus, and Zygocactus virus.

1586. The method according to item 1474, wherein the one or more viral infection(s) are treated with one or more anti-viral drugs.

1587. The method according to item 1474, wherein the one or more viral infection(s) are treated with one or more anti-viral drugs that affects the attachment of the one or more vira to the host cell.

1588. The method according to item 1474, wherein the one or more viral infection(s) are treated with one or more anti-viral drugs that affect the release of viral genes and/or viral enzymes into the host cell.

1589. The method according to item 1474, wherein the one or more viral infection(s) are treated with one or more anti-viral drugs that affect the replication of viral components using host-cell machinery.

1590. The method according to item 1474, wherein the one or more viral infection(s) are treated with one or more anti-viral drugs that affect the assembly of viral components into complete viral particles.

1591. The method according to item 1474, wherein the one or more viral infection(s) are treated with one or more anti-viral drugs that affect the release of viral particles to infect new host cells.

1592. The method according to item 1431, wherein the one or more infection(s) comprises one or more cancer(s).

1593. The method according to item 1431, wherein the one or more infection(s) comprises one or more hepatitis C virus infection(s).

1594. The method according to item 1431, wherein the one or more infection(s) comprises one or more hepatitis B virus infection(s).

1595. The method according to item 1431, wherein the one or more infection(s) comprises one or more HIV-1 infection(s).

1596. The method according to item 1431, wherein the one or more infection(s) comprises one or more influenza virus infection(s).

1597. The method according to item 1431, wherein the one or more infection(s) comprises one or more herpes simplex virus infection(s).

1598. The method according to item 1431, wherein the one or more infection(s) comprises one or more *Mycobacterium* infection(s).

1599. The method according to item 1598, wherein the one or more *Mycobacterium* infection(s) comprises one or more *Mycobacterium tuberculosis* infection(s).

1600. The method according to item 1598, wherein the one or more *Mycobacterium* infection(s) comprises one or more *Mycobacterium bovis* infection(s).

1601. The method according to item 1598, wherein the one or more *Mycobacterium* infection(s) comprises one or more *Mycobacterium africanum* infection(s).

1602. The method according to item 1598, wherein the one or more *Mycobacterium* infection(s) comprises one or more *Mycobacterium canetti* infection(s).

1603. The method according to item 1598, wherein the one or more *Mycobacterium* infection(s) comprises one or more *Mycobacterium microti* infection(s).

1604. The method according to item 1598, wherein the one or more *Mycobacterium* infection(s) causes Tuberculosis.

1605. The method according to item 1604, wherein the Tuberculosis attacks the lungs (pulmonary TB).

1606. The method according to item 1604, wherein the Tuberculosis affects the central nervous system.

1607. The method according to item 1604, wherein the Tuberculosis affects the lymphatic system.

1608. The method according to item 1604, wherein the Tuberculosis affects the circulatory system.

1609. The method according to item 1604, wherein the Tuberculosis affects the genitourinary system.

1610. The method according to item 1604, wherein the Tuberculosis affects the bones.

1611. The method according to item 1604, wherein the Tuberculosis affects the joints.

1612. The method according to item 1604, wherein the Tuberculosis affects the skin.

1613. The method according to item 1604, wherein the Tuberculosis is asymptomatic.

1614. The method according to item 1604, wherein the Tuberculosis is symptomatic.

1615. The method according to item 1604, wherein the Tuberculosis comprises one or more of the symptoms selected from the group consisting of chest pain, coughing up blood, and a productive, prolonged cough for more than three weeks.

1616. The method according to item 1604, wherein the Tuberculosis comprises one or more of the systemic symptoms selected from the group consisting of fever, chills, night sweats, appetite loss, weight loss, pallor, and often a tendency to fatigue very easily.

1617. The method according to item 1604, wherein the Tuberculosis comprises one or more extrapulmonary infection sites selected from the group consisting of the pleura, the central nervous system in meningitis, the lymphatic system in scrofula of the neck, the genitourinary system in urogenital tuberculosis, and bones and joints in Pott's disease of the spine.

1618. The method according to item 1604, wherein the Tuberculosis comprises disseminated TB (miliary tuberculosis).

1619. The method according to item 1604, wherein the Tuberculosis is contagious.

1620. The method according to item 1604, wherein the Tuberculosis is not contagious.

1621. The method according to item 1604, wherein the Tuberculosis is diagnosed by detection of *Mycobacterium tuberculosis* in sputum e.g. by microscopy.

1622. The method according to item 1604, wherein the Tuberculosis is diagnosed by detection of *Mycobacterium tuberculosis* in sputum by Ziehl-Neelsen staining followed by microscopy.

1623. The method according to item 1604, wherein the Tuberculosis is diagnosed by detection of *Mycobacterium tuberculosis* in sputum by auramine-rhodamine staining followed by microscopy.

1624. The method according to item 1604, wherein the Tuberculosis is diagnosed by detection of *Mycobacterium tuberculosis* in sputum by fluorescent microscopy.

1625. The method according to item 1604, wherein the Tuberculosis is diagnosed by a method comprising the medical history of the individual.

1626. The method according to item 1604, wherein the Tuberculosis is diagnosed by a method comprising a chest X-ray.

1627. The method according to item 1604, wherein the Tuberculosis is diagnosed by a method comprising a physical examination.

1628. The method according to item 1604, wherein the Tuberculosis is diagnosed by a method comprising Tuberculosis radiology.

1629. The method according to item 1604, wherein the Tuberculosis is diagnosed by a method comprising a tuberculin skin test.

1630. The method according to item 1604, wherein the Tuberculosis is diagnosed by a method comprising a serological test.

1631. The method according to item 1604, wherein the Tuberculosis is diagnosed by a method comprising analysis of microbiological smears and cultures.

1632. The method according to item 1604, wherein the Tuberculosis is diagnosed by a method comprising use of polymerase chain reaction for detection of bacterial DNA.

1633. The method according to item 1604, wherein the Tuberculosis is diagnosed by a method comprising use of one or more antibody assays to detect the release of interferon gamma in response to mycobacteria.

1634. The method according to item 1604, wherein the Tuberculosis is treated with one or more antibiotics.

1635. The method according to item 1604, wherein the Tuberculosis is treated with one or more antibiotics for 6 to 12 months.

1636. The method according to item 1604, wherein the Tuberculosis is treated with Rifater.

1637. The method according to item 1604, wherein the Tuberculosis is treated with rifampin.

1638. The method according to item 1604, wherein the Tuberculosis is treated with isoniazid.

1639. The method according to item 1604, wherein the Tuberculosis is treated with pyrazinamide.

1640. The method according to item 1604, wherein the Tuberculosis is treated with isoniazid and pyrazinamide.

1641. The method according to item 1604, wherein the Tuberculosis is treated with rifamate.

1642. The method according to item 1604, wherein the Tuberculosis is treated with rimactane.

1643. The method according to item 1604, wherein the Tuberculosis is treated with Ethambutol (Myambutol) and/or streptomycin.

1644. The method according to item 1604, wherein the Tuberculosis is treated with one or more Tuberculosis vaccines.

1645. The method according to item 1604, wherein the Tuberculosis is treated with the Tuberculosis vaccine BCG.

1646. The method according to item 1604, wherein the Tuberculosis is treated with one or more injectable Tuberculosis vaccines.
1647. The method according to item 1604, wherein the Tuberculosis is treated with one or more inhalable Tuberculosis vaccines.
1648. The method according to item 1226, wherein the one or more infection(s) comprises one or more *Borrelia* infection(s).
1649. The method according to item 1648, wherein the one or more *Borrelia* infection(s) causes Lyme disease.
1650. The method according to item 1649, wherein the Lyme disease is an asymptomatic infection.
1651. The method according to item 1649, wherein the Lyme disease is a symptomatic infection.
1652. The method according to item 1649, wherein the Lyme disease is stage 1 Lyme disease.
1653. The method according to item 1649, wherein the Lyme disease is stage 2 Lyme disease.
1654. The method according to item 1649, wherein the Lyme disease is stage 3 Lyme disease.
1655. The method according to item 1649, wherein the Lyme disease is diagnosed by observation of one or more symptoms of Lyme disease.
1656. The method according to item 1649, wherein the Lyme disease is diagnosed by observation of one or more objective physical finding such as erythema migrans, facial palsy, and/or arthritis.
1657. The method according to item 1649, wherein the Lyme disease is diagnosed by a history of possible exposure to infected ticks.
1658. The method according to item 1649, wherein the Lyme disease is diagnosed by one or more serological tests.
1659. The method according to item 1649, wherein the Lyme disease is diagnosed by one or more blood test that measure one or more ontibodies made in response to the infection.
1660. The method according to item 1649, wherein the Lyme disease is diagnosed by a method comprising ELISA.
1661. The method according to item 1649, wherein the Lyme disease is diagnosed by a method comprising western blotting.
1662. The method according to item 1649, wherein the Lyme disease is diagnosed by a method comprising PCR.
1663. The method according to any of the items 1660 to 1662, wherein the method comprises a blood test via a venipuncture.
1664. The method according to any of the items 1660 to 1662, wherein the method comprises analysis of cerebrospinal fluid via lumbar puncture.
1665. The method according to item 1649, wherein the Lyme disease is diagnosed by a method comprising LTT-MELISA.
1666. The method according to item 1649, wherein the Lyme disease is diagnosed by a method comprising focus floating microscopy.
1667. The method according to item 1649, wherein the Lyme disease is diagnosed by a method comprising detection of CXCL13.
1668. The method according to item 1649, wherein the Lyme disease is diagnosed by a method comprising one or more urine antigen tests.
1669. The method according to item 1649, wherein the Lyme disease is diagnosed by a method comprising immunofluorescent staining for cell wall-deficient forms of *Borrelia burgdorferi.*
1670. The method according to item 1649, wherein the Lyme disease is diagnosed by a method comprising lymphocyte transformation tests.
1671. The method according to item 1649, wherein the Lyme disease is diagnosed by a method comprising SPECT.
1672. The method according to item 1649, wherein the Lyme disease is diagnosed by a method comprising MRI.
1673. The method according to item 1648, wherein the one or more *Borrelia* infection(s) causes relapsing fever.
1674. The method according to item 1648, wherein the one or more *Borrelia* infection(s) comprises one or more tick-borne relapsing infections.
1675. The method according to item 1648, wherein the one or more *Borrelia* infection(s) are caused by *Borrelia burgdorferi.*
1676. The method according to item 1648, wherein the one or more *Borrelia* infection(s) are caused by *Borrelia afzelii.*
1677. The method according to item 1648, wherein the one or more *Borrelia* infection(s) are caused by *Borrelia burgdorferi* sensu lato.
1678. The method according to item 1648, wherein the one or more *Borrelia* infection(s) are caused by *Borrelia garini.*
1679. The method according to item 1648, wherein the one or more *Borrelia* infection(s) are caused by *Borrelia valaisiana.*
1680. The method according to item 1648, wherein the one or more *Borrelia* infection(s) are caused by *Borrelia recurrentis.*
1681. The method according to item 1648, wherein the one or more *Borrelia* infection(s) are caused by *Borrelia hermsii.*
1682. The method according to item 1648, wherein the one or more *Borrelia* infection(s) are caused by *Borrelia Parkeri.*
1683. The method according to item 1648, wherein the one or more *Borrelia* infection(s) are caused by *Borrelia anserina.*
1684. The method according to item 1648, wherein the one or more *Borrelia* infection(s) are caused by *Borrelia barbouri.*
1685. The method according to item 1648, wherein the one or more *Borrelia* infection(s) are caused by the *Borrelia burgdorferi* group such as burgdorferi B31.
1686. The method according to item 1648, wherein the one or more *Borrelia* infection(s) are caused by *Borrelia afzelii* such as *Borrelia afzelii* ACA-1, *Borrelia* afzelii K78 and/or *Borrelia afzelii* PKo.
1687. The method according to item 1648, wherein the one or more *Borrelia* infection(s) are caused by *afzelii* PKo.
1688. The method according to item 1648, wherein the one or more *Borrelia* infection(s) are caused by *Borrelia andersonii.*
1689. The method according to item 1648, wherein the one or more *Borrelia* infection(s) are caused by *Borrelia bissettii.*
1690. The method according to item 1648, wherein the one or more *Borrelia* infection(s) are caused by *Borrelia burgdorferi* 118a.

1691. The method according to item 1648, wherein the one or more *Borrelia* infection(s) are caused by *Borrelia burgdorferi* 156a.
1692. The method according to item 1648, wherein the one or more *Borrelia* infection(s) are caused by *Borrelia burgdorferi* 29805.
1693. The method according to item 1648, wherein the one or more *Borrelia* infection(s) are caused by *Borrelia burgdorferi* 64b.
1694. The method according to item 1648, wherein the one or more *Borrelia* infection(s) are caused by *Borrelia burgdorferi* 72a.
1695. The method according to item 1648, wherein the one or more *Borrelia* infection(s) are caused by *Borrelia burgdorferi* 80a.
1696. The method according to item 1648, wherein the one or more *Borrelia* infection(s) are caused by *Borrelia burgdorferi* 94a.
1697. The method according to item 1648, wherein the one or more *Borrelia* infection(s) are caused by *Borrelia burgdorferi* B31.
1698. The method according to item 1648, wherein the one or more *Borrelia* infection(s) are caused by *Borrelia burgdorferi* Bol26.
1699. The method according to item 1648, wherein the one or more *Borrelia* infection(s) are caused by *Borrelia burgdorferi* CA-11.2a.
1700. The method according to item 1648, wherein the one or more *Borrelia* infection(s) are caused by *Borrelia burgdorferi* WI91-23.
1701. The method according to item 1648, wherein the one or more *Borrelia* infection(s) are caused by *Borrelia burgdorferi* ZS7.
1702. The method according to item 1648, wherein the one or more *Borrelia* infection(s) are caused by *Borrelia californiensis*.
1703. The method according to item 1648, wherein the one or more *Borrelia* infection(s) are caused by *Borrelia garini* such as *garini* PBi.
1704. The method according to item 1648, wherein the one or more *Borrelia* infection(s) are caused by *Borrelia garini* PBr.
1705. The method according to item 1648, wherein the one or more *Borrelia* infection(s) are caused by *Borrelia* genomosp. 1.
1706. The method according to item 1648, wherein the one or more *Borrelia* infection(s) are caused by *Borrelia* genomosp. 2.
1707. The method according to item 1648, wherein the one or more *Borrelia* infection(s) are caused by *Borrelia japonica*.
1708. The method according to item 1648, wherein the one or more *Borrelia* infection(s) are caused by *Borrelia lusitaniae*.
1709. The method according to item 1648, wherein the one or more *Borrelia* infection(s) are caused by *Borrelia spielmanii*.
1710. The method according to item 1648, wherein the one or more *Borrelia* infection(s) are caused by *Borrelia spielmanii* A14S.
1711. The method according to item 1648, wherein the one or more *Borrelia* infection(s) are caused by *Borrelia tanukii*.
1712. The method according to item 1648, wherein the one or more *Borrelia* infection(s) are caused by *Borrelia turdi*.
1713. The method according to item 1648, wherein the one or more *Borrelia* infection(s) are caused by *Borrelia valaisiana*.
1714. The method according to item 1648, wherein the one or more *Borrelia* infection(s) are caused by *Borrelia valaisiana* VS116.
1715. The method according to item 1648, wherein the one or more *Borrelia* infection(s) are caused by Candidatus *Borrelia texasensis*.
1716. The method according to item 1648, wherein the one or more *Borrelia* infection(s) are caused by *Borrelia* sp. AA4Pool.
1717. The method according to item 1648, wherein the one or more *Borrelia* infection(s) are caused by *Borrelia* sp. A1-1.
1718. The method according to item 1648, wherein the one or more *Borrelia* infection(s) are caused by *Borrelia* sp. B31.
1719. The method according to item 1648, wherein the one or more *Borrelia* infection(s) are caused by *Borrelia* sp. BC-1.
1720. The method according to item 1648, wherein the one or more *Borrelia* infection(s) are caused by *Borrelia* sp. CA1133.
1721. The method according to item 1648, wherein the one or more *Borrelia* infection(s) are caused by *Borrelia* sp. CA1176.
1722. The method according to item 1648, wherein the one or more *Borrelia* infection(s) are caused by *Borrelia* sp. CA128.
1723. The method according to item 1648, wherein the one or more *Borrelia* infection(s) are caused by *Borrelia* sp. CA13.
1724. The method according to item 1648, wherein the one or more *Borrelia* infection(s) are caused by *Borrelia* sp. CA134.
1725. The method according to item 1648, wherein the one or more *Borrelia* infection(s) are caused by *Borrelia* sp. CA142.
1726. The method according to item 1648, wherein the one or more *Borrelia* infection(s) are caused by *Borrelia* sp. CA20.
1727. The method according to item 1648, wherein the one or more *Borrelia* infection(s) are caused by *Borrelia* sp. CA22.
1728. The method according to item 1648, wherein the one or more *Borrelia* infection(s) are caused by *Borrelia* sp. CA27.
1729. The method according to item 1648, wherein the one or more *Borrelia* infection(s) are caused by *Borrelia* sp. CA28.
1730. The method according to item 1648, wherein the one or more *Borrelia* infection(s) are caused by *Borrelia* sp. CA29.
1731. The method according to item 1648, wherein the one or more *Borrelia* infection(s) are caused by *Borrelia* sp. CA31.
1732. The method according to item 1648, wherein the one or more *Borrelia* infection(s) are caused by *Borrelia* sp. CA33.
1733. The method according to item 1648, wherein the one or more *Borrelia* infection(s) are caused by *Borrelia* sp. CA370.
1734. The method according to item 1648, wherein the one or more *Borrelia* infection(s) are caused by *Borrelia* sp. CA372.

1735. The method according to item 1648, wherein the one or more *Borrelia* infection(s) are caused by *Borrelia* sp. CA378.
1736. The method according to item 1648, wherein the one or more *Borrelia* infection(s) are caused by *Borrelia* sp. CA388.
1737. The method according to item 1648, wherein the one or more *Borrelia* infection(s) are caused by *Borrelia* sp. CA393.
1738. The method according to item 1648, wherein the one or more *Borrelia* infection(s) are caused by *Borrelia* sp. CA394.
1739. The method according to item 1648, wherein the one or more *Borrelia* infection(s) are caused by *Borrelia* sp. CA395.
1740. The method according to item 1648, wherein the one or more *Borrelia* infection(s) are caused by *Borrelia* sp. CA399.
1741. The method according to item 1648, wherein the one or more *Borrelia* infection(s) are caused by *Borrelia* sp. CA400.
1742. The method according to item 1648, wherein the one or more *Borrelia* infection(s) are caused by *Borrelia* sp. CA401.
1743. The method according to item 1648, wherein the one or more *Borrelia* infection(s) are caused by *Borrelia* sp. CA402.
1744. The method according to item 1648, wherein the one or more *Borrelia* infection(s) are caused by *Borrelia* sp. CA404.
1745. The method according to item 1648, wherein the one or more *Borrelia* infection(s) are caused by *Borrelia* sp. CA411.
1746. The method according to item 1648, wherein the one or more *Borrelia* infection(s) are caused by *Borrelia* sp. CA426.
1747. The method according to item 1648, wherein the one or more *Borrelia* infection(s) are caused by *Borrelia* sp. CA443.
1748. The method according to item 1648, wherein the one or more *Borrelia* infection(s) are caused by *Borrelia* sp. CA446.
1749. The method according to item 1648, wherein the one or more *Borrelia* infection(s) are caused by *Borrelia* sp. CA448.
1750. The method according to item 1648, wherein the one or more *Borrelia* infection(s) are caused by *Borrelia* sp. CA462.
1751. The method according to item 1648, wherein the one or more *Borrelia* infection(s) are caused by *Borrelia* sp. CA468.
1752. The method according to item 1648, wherein the one or more *Borrelia* infection(s) are caused by *Borrelia* sp. CA502.
1753. The method according to item 1648, wherein the one or more *Borrelia* infection(s) are caused by *Borrelia* sp. CA504.
1754. The method according to item 1648, wherein the one or more *Borrelia* infection(s) are caused by *Borrelia* sp. CA507.
1755. The method according to item 1648, wherein the one or more *Borrelia* infection(s) are caused by *Borrelia* sp. CA547.
1756. The method according to item 1648, wherein the one or more *Borrelia* infection(s) are caused by *Borrelia* sp. CA552.
1757. The method according to item 1648, wherein the one or more *Borrelia* infection(s) are caused by *Borrelia* sp. CA8.
1758. The method according to item 1648, wherein the one or more *Borrelia* infection(s) are caused by *Borrelia* sp. D22.
1759. The method according to item 1648, wherein the one or more *Borrelia* infection(s) are caused by *Borrelia* sp. D35.
1760. The method according to item 1648, wherein the one or more *Borrelia* infection(s) are caused by *Borrelia* sp. FD-1.
1761. The method according to item 1648, wherein the one or more *Borrelia* infection(s) are caused by *Borrelia* sp. FL18.
1762. The method according to item 1648, wherein the one or more *Borrelia* infection(s) are caused by *Borrelia* sp. FL27.
1763. The method according to item 1648, wherein the one or more *Borrelia* infection(s) are caused by *Borrelia* sp. FL35.
1764. The method according to item 1648, wherein the one or more *Borrelia* infection(s) are caused by *Borrelia* sp. FL42.
1765. The method according to item 1648, wherein the one or more *Borrelia* infection(s) are caused by *Borrelia* sp. HN6.
1766. The method according to item 1648, wherein the one or more *Borrelia* infection(s) are caused by *Borrelia* sp. HN7.
1767. The method according to item 1648, wherein the one or more *Borrelia* infection(s) are caused by *Borrelia* sp. HN8.
1768. The method according to item 1648, wherein the one or more *Borrelia* infection(s) are caused by *Borrelia* sp. HNM13.
1769. The method according to item 1648, wherein the one or more *Borrelia* infection(s) are caused by *Borrelia* sp. HNM14.
1770. The method according to item 1648, wherein the one or more *Borrelia* infection(s) are caused by *Borrelia* sp. HNM19.
1771. The method according to item 1648, wherein the one or more *Borrelia* infection(s) are caused by *Borrelia* sp. IA1.
1772. The method according to item 1648, wherein the one or more *Borrelia* infection(s) are caused by *Borrelia* sp. Ir-3519.
1773. The method according to item 1648, wherein the one or more *Borrelia* infection(s) are caused by *Borrelia* sp. Ir-4721.
1774. The method according to item 1648, wherein the one or more *Borrelia* infection(s) are caused by *Borrelia* sp. Ir-4812.
1775. The method according to item 1648, wherein the one or more *Borrelia* infection(s) are caused by *Borrelia* sp. Ir-5215.
1776. The method according to item 1648, wherein the one or more *Borrelia* infection(s) are caused by *Borrelia* sp. LV5.
1777. The method according to item 1648, wherein the one or more *Borrelia* infection(s) are caused by *Borrelia* sp. MI-2.
1778. The method according to item 1648, wherein the one or more *Borrelia* infection(s) are caused by *Borrelia* sp. MI-5.

1779. The method according to item 1648, wherein the one or more *Borrelia* infection(s) are caused by *Borrelia* sp. MI-6.
1780. The method according to item 1648, wherein the one or more *Borrelia* infection(s) are caused by *Borrelia* sp. MI-8.
1781. The method according to item 1648, wherein the one or more *Borrelia* infection(s) are caused by *Borrelia* sp. MI-9.
1782. The method according to item 1648, wherein the one or more *Borrelia* infection(s) are caused by *Borrelia* sp. MOD-1.
1783. The method according to item 1648, wherein the one or more *Borrelia* infection(s) are caused by *Borrelia* sp. MOD-5.
1784. The method according to item 1648, wherein the one or more *Borrelia* infection(s) are caused by *Borrelia* sp. MOK-3a.
1785. The method according to item 1648, wherein the one or more *Borrelia* infection(s) are caused by *Borrelia* sp. MOS-1b.
1786. The method according to item 1648, wherein the one or more *Borrelia* infection(s) are caused by *Borrelia* sp. NE49.
1787. The method according to item 1648, wherein the one or more *Borrelia* infection(s) are caused by *Borrelia* sp. NE581.
1788. The method according to item 1648, wherein the one or more *Borrelia* infection(s) are caused by *Borrelia* sp. PHaP.
1789. The method according to item 1648, wherein the one or more *Borrelia* infection(s) are caused by *Borrelia* sp. PSigII.
1790. The method according to item 1648, wherein the one or more *Borrelia* infection(s) are caused by *Borrelia* sp. SCGT-10.
1791. The method according to item 1648, wherein the one or more *Borrelia* infection(s) are caused by *Borrelia* sp. SCGT-8a.
1792. The method according to item 1648, wherein the one or more *Borrelia* infection(s) are caused by *Borrelia* sp. SCI-2.
1793. The method according to item 1648, wherein the one or more *Borrelia* infection(s) are caused by *Borrelia* sp. SCW-30h.
1794. The method according to item 1648, wherein the one or more *Borrelia* infection(s) are caused by *Borrelia* sp. SI-1.
1795. The method according to item 1648, wherein the one or more *Borrelia* infection(s) are caused by *Borrelia* sp. SI-10.
1796. The method according to item 1648, wherein the one or more *Borrelia* infection(s) are caused by *Borrelia* sp. SM-1.
1797. The method according to item 1648, wherein the one or more *Borrelia* infection(s) are caused by *Borrelia* sp. SV1.
1798. The method according to item 1648, wherein the one or more *Borrelia* infection(s) are caused by *Borrelia* sp. W97F51.
1799. The method according to item 1648, wherein the one or more *Borrelia* infection(s) are caused by *Borrelia* sp. Z41293.
1800. The method according to item 1648, wherein the one or more *Borrelia* infection(s) are caused by *Borrelia* sp. Z41493.
1801. The method according to item 1648, wherein the one or more *Borrelia* infection(s) are caused by *Borrelia coriaceae*.
1802. The method according to item 1648, wherein the one or more *Borrelia* infection(s) are caused by *Borrelia crocidurae*.
1803. The method according to item 1648, wherein the one or more *Borrelia* infection(s) are caused by *Borrelia duttonii*.
1804. The method according to item 1648, wherein the one or more *Borrelia* infection(s) are caused by *Borrelia duttonii* Ly.
1805. The method according to item 1648, wherein the one or more *Borrelia* infection(s) are caused by *Borrelia hermsii*.
1806. The method according to item 1648, wherein the one or more *Borrelia* infection(s) are caused by *Borrelia hermsii* DAH.
1807. The method according to item 1648, wherein the one or more *Borrelia* infection(s) are caused by *Borrelia hispanica*.
1808. The method according to item 1648, wherein the one or more *Borrelia* infection(s) are caused by *Borrelia lonestari*.
1809. The method according to item 1648, wherein the one or more *Borrelia* infection(s) are caused by *Borrelia miyamotoi*.
1810. The method according to item 1648, wherein the one or more *Borrelia* infection(s) are caused by *Borrelia parkeri*.
1811. The method according to item 1648, wherein the one or more *Borrelia* infection(s) are caused by *Borrelia persica*.
1812. The method according to item 1648, wherein the one or more *Borrelia* infection(s) are caused by *Borrelia recurrentis*.
1813. The method according to item 1648, wherein the one or more *Borrelia* infection(s) are caused by *Borrelia recurrentis* A1.
1814. The method according to item 1648, wherein the one or more *Borrelia* infection(s) are caused by *Borrelia sinica*.
1815. The method according to item 1648, wherein the one or more *Borrelia* infection(s) are caused by *Borrelia theileri*.
1816. The method according to item 1648, wherein the one or more *Borrelia* infection(s) are caused by *Borrelia turcica*.
1817. The method according to item 1648, wherein the one or more *Borrelia* infection(s) are caused by *Borrelia turicatae*.
1818. The method according to item 1648, wherein the one or more *Borrelia* infection(s) are caused by *Borrelia turicatae* 91E135.
1819. The method according to item 1648, wherein the one or more *Borrelia* infection(s) are caused by *Borrelia sp.*
1820. The method according to item 1648, wherein the one or more *Borrelia* infection(s) are caused by *Borrelia* sp. 'Lake Gaillard'.
1821. The method according to item 1648, wherein the one or more *Borrelia* infection(s) are caused by *Borrelia* sp. 000133.
1822. The method according to item 1648, wherein the one or more *Borrelia* infection(s) are caused by *Borrelia* sp. 010298.

1823. The method according to item 1648, wherein the one or more *Borrelia* infection(s) are caused by *Borrelia* sp. 10MT.
1824. The method according to item 1648, wherein the one or more *Borrelia* infection(s) are caused by *Borrelia* sp. 5145.
1825. The method according to item 1648, wherein the one or more *Borrelia* infection(s) are caused by *Borrelia* sp. 57Nsk.
1826. The method according to item 1648, wherein the one or more *Borrelia* infection(s) are caused by *Borrelia* sp. 5MT.
1827. The method according to item 1648, wherein the one or more *Borrelia* infection(s) are caused by *Borrelia* sp. 6T04-2.
1828. The method according to item 1648, wherein the one or more *Borrelia* infection(s) are caused by *Borrelia* sp. BR.
1829. The method according to item 1648, wherein the one or more *Borrelia* infection(s) are caused by *Borrelia* sp. BR 2007.
1830. The method according to item 1648, wherein the one or more *Borrelia* infection(s) are caused by *Borrelia* sp. C5-N52.
1831. The method according to item 1648, wherein the one or more *Borrelia* infection(s) are caused by *Borrelia* sp. CB-A1.
1832. The method according to item 1648, wherein the one or more *Borrelia* infection(s) are caused by *Borrelia* sp. CB-A11.
1833. The method according to item 1648, wherein the one or more *Borrelia* infection(s) are caused by *Borrelia* sp. CB-A3.
1834. The method according to item 1648, wherein the one or more *Borrelia* infection(s) are caused by *Borrelia* sp. EFL-S0100110.
1835. The method according to item 1648, wherein the one or more *Borrelia* infection(s) are caused by *Borrelia* sp. IK/23.
1836. The method according to item 1648, wherein the one or more *Borrelia* infection(s) are caused by *Borrelia* sp. IM/16.
1837. The method according to item 1648, wherein the one or more *Borrelia* infection(s) are caused by *Borrelia* sp. IM/19.
1838. The method according to item 1648, wherein the one or more *Borrelia* infection(s) are caused by *Borrelia* sp. KR1.
1839. The method according to item 1648, wherein the one or more *Borrelia* infection(s) are caused by *Borrelia* sp. KR3.
1840. The method according to item 1648, wherein the one or more *Borrelia* infection(s) are caused by *Borrelia* sp. LB-2001.
1841. The method according to item 1648, wherein the one or more *Borrelia* infection(s) are caused by *Borrelia* sp. LB-M56.
1842. The method according to item 1648, wherein the one or more *Borrelia* infection(s) are caused by *Borrelia* sp. LB-W100.
1843. The method according to item 1648, wherein the one or more *Borrelia* infection(s) are caused by *Borrelia* sp. MK-N61.
1844. The method according to item 1648, wherein the one or more *Borrelia* infection(s) are caused by *Borrelia* sp. NR-N8.
1845. The method according to item 1648, wherein the one or more *Borrelia* infection(s) are caused by *Borrelia* sp. OkME1.
1846. The method according to item 1648, wherein the one or more *Borrelia* infection(s) are caused by *Borrelia* sp. PAnz.
1847. The method according to item 1648, wherein the one or more *Borrelia* infection(s) are caused by *Borrelia* sp. PJes.
1848. The method according to item 1648, wherein the one or more *Borrelia* infection(s) are caused by *Borrelia* sp. PMai.
1849. The method according to item 1648, wherein the one or more *Borrelia* infection(s) are caused by *Borrelia* sp. PMew.
1850. The method according to item 1648, wherein the one or more *Borrelia* infection(s) are caused by *Borrelia* sp. R57.
1851. The method according to item 1648, wherein the one or more *Borrelia* infection(s) are caused by *Borrelia* sp. strain Spain.
1852. The method according to item 1648, wherein the one or more *Borrelia* infection(s) are caused by *Borrelia* sp. TA1.
1853. The method according to item 1648, wherein the one or more *Borrelia* infection(s) are caused by *Borrelia* sp. TM.
1854. The method according to item 1648, wherein the one or more *Borrelia* infection(s) are caused by *Borrelia* sp. TM1.
1855. The method according to item 1648, wherein the one or more *Borrelia* infection(s) are caused by *Borrelia* sp. TM2.
1856. The method according to item 1648, wherein the one or more *Borrelia* infection(s) are treated with one or more antibiotics.
1857. The method according to item 1648, wherein the one or more *Borrelia* infection(s) are treated with one or more Lyme vaccines.
1858. The method according to item 1857, wherein the one or more Lyme vaccines comprises Lymerix.
1859. The method according to item 1648, wherein the one or more *Borrelia* infection(s) are treated with Doxycycline.
1860. The method according to item 1648, wherein the one or more *Borrelia* infection(s) are treated with amoxicillin.
1861. The method according to item 1648, wherein the one or more *Borrelia* infection(s) are treated with cefuroxime axetil.
1862. The method according to item 1648, wherein the one or more *Borrelia* infection(s) are treated with Doxycycline (100 mg twice per day), amoxicillin (500 mg 3 times per day), and/or cefuroxime axetil (500 mg twice per day) for 14 days (range, 10-21 days for doxycycline and 14-21 days for amoxicillin or cefuroxime axetil).
1863. The method according to item 1648, wherein the one or more *Borrelia* infection(s) are treated with one or more Macrolide antibiotics.
1864. The method according to item 1648, wherein the one or more *Borrelia* infection(s) are treated with azithromycin e.g. with 500 mg orally per day for 7-10 days.
1865. The method according to item 1648, wherein the one or more *Borrelia* infection(s) are treated with clarithromycin e.g. with 500 mg orally twice per day for 14-21 days.

1866. The method according to item 1648, wherein the one or more *Borrelia* infection(s) are treated with erythromycin e.g. 500 mg orally 4 times per day for 14-21 days.
1867. The method according to item 1648, wherein the one or more *Borrelia* infection(s) are treated with one or more cephalosporins, such as cephalexin.
1868. The method according to item 1648, wherein the one or more *Borrelia* infection(s) are treated with Ceftriaxone.
1869. The method according to item 1648, wherein the one or more *Borrelia* infection(s) are treated with ceftriaxone (e.g. 2 g once per day intravenously for 14 days; range, 10-28 days).
1870. The method according to item 1648, wherein the one or more *Borrelia* infection(s) are treated with parenteral therapy with cefotaxime (e.g. 2 g intravenously every 8 h).
1871. The method according to item 1648, wherein the one or more *Borrelia* infection(s) are treated with penicillin G (e.g. 18-24 million Upper day for patients with normal renal function, divided into doses given every 4 h).
1872. The method according to item 1648, wherein the one or more *Borrelia* infection(s) are treated with one or more β-lactam antibiotics.
1873. The method according to item 1648, wherein the one or more *Borrelia* infection(s) are treated with one or more compounds for treatment of Erythema migrans.
1874. The method according to item 1648, wherein the one or more *Borrelia* infection(s) are treated with one or more compounds for treatment of Lyme meningitis and/or other manifestations of early neurologic Lyme disease.
1875. The method according to item 1648, wherein the one or more *Borrelia* infection(s) are treated with one or more compounds for treatment of Lyme carditis.
1876. The method according to item 1648, wherein the one or more *Borrelia* infection(s) are treated with one or more compounds for treatment of Borrelial lymphocytoma.
1877. The method according to item 1648, wherein the one or more *Borrelia* infection(s) are treated with one or more compounds for treatment of Lyme arthritis.
1878. The method according to item 1648, wherein the one or more *Borrelia* infection(s) are treated with one or more compounds for treatment of Late neurologic Lyme disease.
1879. The method according to item 1648, wherein the one or more *Borrelia* infection(s) are treated with one or more compounds for treatment of Acrodermatitis chronica atrophicans.
1880. The method according to item 1648, wherein the one or more *Borrelia* infection(s) are treated with one or more compounds for treatment of on or more coinfections.
1881. The method according to item 1648, wherein the one or more *Borrelia* infection(s) are treated with one or more compounds for treatment of post-Lyme Disease Syndromes.
1882. The method according to item 1431, wherein the one or more infection(s) comprises one or more Human papillomavirus (HPV) infection(s).
1883. The method according to item 1431, wherein the one or more infection(s) comprises one or more Cytomegalovirus (CMV) infection(s).
1884. The method according to item 1431, wherein the one or more Cytomegalovirus (CMV) infection(s) comprises a HCMV/Human Herpesvirus 5 (HHV-5) infection.
1885. The method according to 1184, wherein the HCMV infection is associated with the salivary gland.
1886. The method according to 1184, wherein the HCMV infection is not associated with the salivary gland.
1887. The method according to 1184, wherein the HCMV infection is life threatening for the individual because said individual has HIV.
1888. The method according to 1184, wherein the HCMV infection is life threatening for the individual because said individual has leukemia.
1889. The method according to 1184, wherein the HCMV infection is life threatening for the individual because said individual is immunocompromised.
1890. The method according to 1184, wherein the HCMV infection is life threatening for the individual because said individual is an organ transplant recipient.
1891. The method according to 1184, wherein the HCMV infection is life threatening for the individual because said individual a neonatal.
1892. The method according to item 1431, wherein the one or more Cytomegalovirus (CMV) infection(s) comprises a herpes virus infection.
1893. The method according to item 1431, wherein the one or more Cytomegalovirus (CMV) infection(s) comprises an Alphaherpesvirinae infection.
1894. The method according to item 1431, wherein the one or more Cytomegalovirus (CMV) infection(s) comprises a HSV 1 infection.
1895. The method according to item 1431, wherein the one or more Cytomegalovirus (CMV) infection(s) comprises a HSV 2 infection.
1896. The method according to item 1431, wherein the one or more Cytomegalovirus (CMV) infection(s) comprises a varicella infection.
1897. The method according to item 1431, wherein the one or more Cytomegalovirus (CMV) infection(s) comprises a Gammaherpesvirinae infection.
1898. The method according to item 1431, wherein the one or more Cytomegalovirus (CMV) infection(s) comprises a Epstein-Barr virus infection.
1899. The method according to item 1431, wherein the one or more Cytomegalovirus (CMV) infection(s) comprises a latent herpesvirus infection.
1900. The method according to item 1431, wherein the one or more Cytomegalovirus (CMV) infection(s) comprises fetus/infant congenital CMV infection.
1901. The method according to item 1431, wherein the one or more Cytomegalovirus (CMV) infection(s) comprises fetus/infant perinatal CMV infection.
1902. The method according to item 1431, wherein the one or more Cytomegalovirus (CMV) infection(s) comprises CMV mononucleosis of immunocompetent patients.
1903. The method according to item 1431, wherein the one or more Cytomegalovirus (CMV) infection(s) comprises post-transfusion CMV of immunocompetent patients.
1904. The method according to item 1431, wherein the one or more Cytomegalovirus (CMV) infection(s) comprises CMV pneumonitis of immunocompromised patients.
1905. The method according to item 1431, wherein the one or more Cytomegalovirus (CMV) infection(s) comprises CMV GI disease of immunocompromised patients.
1906. The method according to item 1431, wherein the one or more Cytomegalovirus (CMV) infection(s) comprises CMV retinitis of immunocompromised patients.
1907. The method according to item 1431, wherein the one or more Cytomegalovirus (CMV) infection(s) are diagnosed by detection of one or more antibodies to CMV.
1908. The method according to item 1431, wherein the one or more Cytomegalovirus (CMV) infection(s) are diagnosed by a method comprising cultivation of CMV from specimens obtained e.g. from urine, throat swabs, bronchial lavages and tissue samples to detect active infection.
1909. The method according to item 1431, wherein the one or more Cytomegalovirus (CMV) infection(s) are diagnosed by a method comprising qualitative PCR analysis.
1910. The method according to item 1431, wherein the one or more Cytomegalovirus (CMV) infection(s) are diagnosed by a method comprising qualitative PCR analysis.
1911. The method according to item 1431, wherein the one or more Cytomegalovirus (CMV) infection(s) are diagnosed by a method comprising use of a CMV pp 65 antigenemia test.
1912. The method according to item 1431, wherein the one or more Cytomegalovirus (CMV) infection(s) are diagnosed by a method comprising use of ELISA for measurement of antibody to CMV.
1913. The method according to item 1431, wherein the one or more Cytomegalovirus (CMV) infection(s) are diagnosed by a method comprising use of one or more fluorescence assays.
1914. The method according to item 1431, wherein the one or more Cytomegalovirus (CMV) infection(s) are diagnosed by a method comprising use of indirect hemagglutination analysis.
1915. The method according to item 1431, wherein the one or more Cytomegalovirus (CMV) infection(s) are diagnosed by a method comprising use of latex agglutination analysis.
1916. The method according to item 1431, wherein the one or more Cytomegalovirus (CMV) infection(s) are treated with one or more antiviral drugs.
1917. The method according to item 1431, wherein the one or more Cytomegalovirus (CMV) infection(s) are treated with one or more CMV vaccines.
1918. The method according to item 1431, wherein the one or more Cytomegalovirus (CMV) infection(s) are treated with Ganciclovir.
1919. The method according to item 1431, wherein the one or more Cytomegalovirus (CMV) infection(s) are treated with Valganciclovir.
1920. The method according to item 1431, wherein the one or more Cytomegalovirus (CMV) infection(s) are treated with Foscarnet.
1921. The method according to item 1431, wherein the one or more Cytomegalovirus (CMV) infection(s) are treated with cidofovir.
1922. The method according to item 1431, wherein the one or more Cytomegalovirus (CMV) infection(s) are diagnosed by detection of CMV in one or more body fluids of the individual.
1923. The method according to item 1431, wherein the one or more Cytomegalovirus (CMV) infection(s) are diagnosed by detection of CMV in the urine of the individual.
1924. The method according to item 1431, wherein the one or more Cytomegalovirus (CMV) infection(s) are diagnosed by detection of CMV in the saliva of the individual.
1925. The method according to item 1431, wherein the one or more Cytomegalovirus (CMV) infection(s) are diagnosed by detection of CMV in the blood of the individual.
1926. The method according to item 1431, wherein the one or more Cytomegalovirus (CMV) infection(s) are diagnosed by detection of CMV in the tears of the individual.
1927. The method according to item 1431, wherein the one or more Cytomegalovirus (CMV) infection(s) are diagnosed by detection of CMV in the semen of the individual.
1928. The method according to item 1431, wherein the one or more Cytomegalovirus (CMV) infection(s) are diagnosed by detection of CMV in the breast milk of the individual.
1929. The method according to item 1431, wherein the one or more Cytomegalovirus (CMV) infection(s) are diagnosed by microscopic detection of intranuclear inclusion bodies.
1930. The method according to item 1431, wherein the one or more Cytomegalovirus (CMV) infection(s) are diagnosed by H&E staining of intranucear inclusion bodies followed by microscopic detection of intranuclear inclusion bodies.
1931. The method according to item 1431, wherein the one or more infection(s) comprises one or more Epstein-Barr Virus (EBV) infection(s).
1932. The method according to item 1931, wherein the one or more Epstein-Barr Virus (EBV) infection(s) comprises a Herpes simplex virus.
1933. The method according to item 1931, wherein the one or more Epstein-Barr Virus (EBV) infection(s) are symptomatic.
1934. The method according to item 1931, wherein the one or more Epstein-Barr Virus (EBV) infection(s) are asymptomatic.
1935. The method according to item 1931, wherein the one or more Epstein-Barr Virus (EBV) infection(s) gives one or more symptoms selected from the group consisting of fever, sore throat, and swollen lymph glands, a swollen spleen or liver, and heart problems.
1936. The method according to item 1931, wherein the one or more Epstein-Barr Virus (EBV) infection(s) causes infectious mononucleosis.
1937. The method according to item 1931, wherein the one or more Epstein-Barr Virus (EBV) infection(s) causes Burkitt's lymphoma.
1938. The method according to item 1931, wherein the one or more Epstein-Barr Virus (EBV) infection(s) causes nasopharyngeal carcinoma.
1939. The method according to item 1931, wherein the one or more Epstein-Barr Virus (EBV) infection(s) are associated with Infectious mononucleosis.
1940. The method according to item 1931, wherein the one or more Epstein-Barr Virus (EBV) infection(s) are associated with one or more Non-Hodgkin's lymphomas (e.g. Burkitt's lymphoma, primary cerebral lymphoma).
1941. The method according to item 1931, wherein the one or more Epstein-Barr Virus (EBV) infection(s) are associated with Hodgkin's disease.
1942. The method according to item 1931, wherein the one or more Epstein-Barr Virus (EBV) infection(s) are associated with Stevens-Johnson syndrome.
1943. The method according to item 1931, wherein the one or more Epstein-Barr Virus (EBV) infection(s) are associated with Hepatitis.
1944. The method according to item 1931, wherein the one or more Epstein-Barr Virus (EBV) infection(s) are associated with Herpes.
1945. The method according to item 1931, wherein the one or more Epstein-Barr Virus (EBV) infection(s) are associated with Alice in Wonderland syndrome (Todd's syndrome).
1946. The method according to item 1931, wherein the one or more Epstein-Barr Virus (EBV) infection(s) are associated with Post-transplant lymphoproliferative disorder.

1947. The method according to item 1931, wherein the one or more Epstein-Barr Virus (EBV) infection(s) are associated with Herpangina.
1948. The method according to item 1931, wherein the one or more Epstein-Barr Virus (EBV) infection(s) are associated with Multiple Sclerosis.
1949. The method according to item 1931, wherein the one or more Epstein-Barr Virus (EBV) infection(s) are associated with Hairy leukoplakia.
1950. The method according to item 1931, wherein the one or more Epstein-Barr Virus (EBV) infection(s) are associated with Common variable immunodeficiency (CVID).
1951. The method according to item 1931, wherein the one or more Epstein-Barr Virus (EBV) infection(s) are associated with Kikuchi's disease.
1952. The method according to item 1931, wherein the one or more Epstein-Barr Virus (EBV) infection(s) are associated with Nasopharyngeal cancer.
1953. The method according to item 1931, wherein the one or more Epstein-Barr Virus (EBV) infection(s) are associated with Subepithelial Infiltrates.
1954. The method according to item 1931, wherein the one or more Epstein-Barr Virus (EBV) infection(s) are associated with smooth muscle tumors.
1955. The method according to item 1931, wherein the one or more Epstein-Barr Virus (EBV) infection(s) are associated with one or more cancers.
1956. The method according to item 1931, wherein the one or more Epstein-Barr Virus (EBV) infection(s) are associated with one or more B cell lymphomas.
1957. The method according to item 1931, wherein the one or more Epstein-Barr Virus (EBV) infection(s) comprises one or more dormant infection.
1958. The method according to item 1931, wherein the one or more Epstein-Barr Virus (EBV) infection(s) are diagnosed by observation of symptoms of infectious mononucleosis including fever, sore throat and swollen lymph glands.
1959. The method according to item 1931, wherein the one or more Epstein-Barr Virus (EBV) infection(s) are diagnosed by one or more serologic tests.
1960. The method according to item 1959, wherein the one or more serologic tests demonstrates an elevated white blood cell count.
1961. The method according to item 1959, wherein the one or more serologic tests demonstrates an increased percentage of certain atypical white blood cells.
1962. The method according to item 1959, wherein the one or more serologic tests demonstrates a positive reaction to a "mono spot" test.
1963. The method according to item 1931, wherein the one or more Epstein-Barr Virus (EBV) infection(s) are treated with one or more drugs that ameliorate or remove the symptoms of infectious mononucleosis.
1964. The method according to item 1931, wherein the one or more Epstein-Barr Virus (EBV) infection(s) are treated with one or more antiviral agents.
1965. The method according to item 1931, wherein the one or more Epstein-Barr Virus (EBV) infection(s) are treated with one or more EBV vaccines.
1966. The method according to item 1931, wherein the one or more Epstein-Barr Virus (EBV) infection(s) are treated with one or more steroids.
1967. The method according to item 1431, wherein the one or more infection(s) comprises one or more BK virus infection(s).
1968. The method according to any of the previous items, wherein the undesired state of said individual is one or more inflammation disease(s).
1969. The method according to any of the previous items, wherein the undesired state of said individual is one or more injuries.
1970. The method according to any of the previous items, wherein the undesired state of said individual is one or more metabolic disorder such as diabetes.
1971. The method according to any of the previous items, wherein the undesired state of said individual is one or more mouth disease(s).
1972. The method according to any of the previous items, wherein the undesired state of said individual is one or more musculoskeletal disease(s).
1973. The method according to any of the previous items, wherein the undesired state of said individual is one or more Neoplasm(s) such as ovarian carcinoma, colonic and rectal carcinoma and/or cutaneous melanoma.
1974. The method according to any of the previous items, wherein the undesired state of said individual is one or more neurological disease(s).
1975. The method according to any of the previous items, wherein the undesired state of said individual is one or more nutritional disorder(s).
1976. The method according to any of the previous items, wherein the undesired state of said individual is one or more ocular disease(s), and/or one or more other eye-related disorder(s).
1977. The method according to any of the previous items, wherein the undesired state of said individual is one or more psychiatric disorder(s).
1978. The method according to any of the previous items, wherein the undesired state of said individual is one or more respiratory disease(s).
1979. The method according to any of the previous items, wherein the undesired state of said individual is one or more temperature disorder(s).
1980. The method according to any of the previous items, wherein the undesired state of said individual is one or more toxicity & intoxication related disorder(s).
1981. The method according to any of the previous items, wherein the undesired state of said individual is one or more ulcer(s).
1982. The method according to any of the previous items, wherein the undesired state of said individual is one or more digestive disorder(s).
1983. The method according to any of the previous items, wherein the undesired state of said individual is infertility.
1984. The method according to any of the previous items, wherein the undesired state of said individual is one or more autoimmune disease(s).
1985. The method according to any of the previous items, wherein the undesired state of said individual is one or more genetic disorder(s).
1986. The method according to any of the previous items, wherein the undesired state of said individual is one or more neurologic disorder(s).
1987. The method according to any of the previous items, wherein the undesired state of said individual is one or more respiratory disease(s).
1988. The method according to any of the previous items, wherein the undesired state of said individual is one or more skin disorder(s).
1989. The method according to any of the previous items, wherein the undesired state of said individual is one or more transplantation-related disorder(s).

1990. The method according to any of the previous items, wherein the undesired state of said individual is multiple sclerosis.
1991. The method according to any of the previous items, wherein the undesired state of said individual is diphtheria.
1992. The method according to any of the previous items, wherein the undesired state of said individual is tetanus.
1993. The method according to any of the previous items, wherein the undesired state of said individual is pertussis.
1994. The method according to any of the previous items, wherein the undesired state of said individual is osteomyelitis.
1995. The method according to any of the previous items, wherein the undesired state of said individual is anemia.
1996. The method according to any of the previous items, wherein the undesired state of said individual is Gaucher's disease.
1997. The method according to any of the previous items, wherein the undesired state of said individual is tuberculosis (TB).
1998. The method according to any of the previous items, wherein the undesired state of said individual is Borreliosis/Lyme disease.
1999. The method according to any of the previous items, wherein a method for combinatorial use of one or more analysis method(s) such as one or more diagnostic method(s), and one or more treatment(s), are employed.
2000. The method according to any of the previous items, wherein said analysis and/or treatment is performed once.
2001. The method according to any of the previous items, wherein said analysis and/or treatment is performed multiple times such as 2, for example 3, such as 4, for example 5, such as 6, for example 7, such as 8, for example 9, such as 10, for example 11, such as 12, for example 13, such as 14, for example 15, such as 16, for example 17, such as 18, for example 19, such as 20, for example 25, such as 30, for example 40, such as 50, for example 100, such as 200, for example 300, such as 400, for example 500, such as 750, for example 1,000, for example 5,000, such as 10,000, for example 10,000, such as 50,000, for example 50,000, such as 100,000, for example 100,000, such as 1,000,000, such as ∞ (infinity). Therefore, the number of diagnoses may be 1 to 2, such as 2 to 4, for example 4 to 6, such as 6 to 8, for example 8 to 10, such as 10 to 15, for example 15 to 20, such as 20 to 30, for example 30 to 40, such as 40 to 50, for example 50 to 75, such as 75 to 100, for example 100 to 200, such as 200 to 300, for example 300 to 400, such as 400 to 500, for example 500 to 750, such as 750 to 1,000, for example 1,000 to 5,000, such as 5,000 to 10,000, for example 10,000 to 50,000, such as 50,000 to 100,000, for example 100,000 to 1,000,000, such as 1,000,000 to ∞ (infinity) times.
2002. The method according to any of the previous items, wherein the combination of analysis and treatment may be 1:1 i.e. the individual or a sample there of is analysed as many times as the individual is treated.
2003. The method according to any of the previous items, wherein the individual or a sample thereof is analysed more times than the individual is treated, i.e. the ratio of analysis to treatment (analysis:treatment) may be equal to or more than 2:1, 3:1, 4:1, 5:1, 6:1, 7:1, 8:1, 9:1, 10:1, 11:1, 12:1, 13:1, 14:1, 15:1, 20:1, 25:1, 50:1, 100:1, 250:1, 500:1, 750:1, 1,000:1, 5,000:1, 10,000:1, 50,000:1, 100,000:1, 500,000:1 or 1,000,000:1.
2004. The method according to any of the previous items, wherein the individual or a sample thereof is analysed less times than the individual is treated, i.e. the ratio of treatment to analysis (treatment:analysis) may be equal to or more than 2:1, 3:1, 4:1, 5:1, 6:1, 7:1, 8:1, 9:1, 10:1, 11:1, 12:1, 13:1, 14:1, 15:1, 20:1, 25:1, 50:1, 100:1, 250:1, 500:1, 750:1, 1,000:1, 5,000:1, 10,000:1, 50,000:1, 100,000:1, 500,000:1 or 1,000,000:1.
2005. The method according to any of the previous items, wherein the individual or a sample thereof is analysed and treated multiple times to treat the undesired state.
2006. The method according to any of the previous items, wherein the individual is treated once daily.
2007. The method according to any of the previous items, wherein the individual is treated multiple times daily.
2008. The method according to any of the previous items, wherein the individual is treated weekly.
2009. The method according to any of the previous items, wherein the individual is treated monthly.
2010. The method according to any of the previous items, wherein the individual is treated yearly.
2011. The method according to any of the previous items, wherein the individual is treated for the entire lifespan of the individual.
2012. The method according to any of the previous items, wherein the individual is treated until the undesired state of the individual is eliminated and/or removed.
2013. The method according to any of the previous items, wherein the individual does not have the undesired state that was treated and/or the individual does not have any symptoms of the undesired state that was treated and/or until another treatment has been developed to treat said undesired state.
2014. The method according to any of the previous items, wherein treatment comprises administration of a medicament, a composition or a drug to the individual in a total dosage of from about 0.01 milligram per kg body weight per dose to about 1000 milligram per kg body weight per dose, such as from about 0.01 milligram per kg body weight per dose to about 0.025 milligram per kg body weight per dose, for example from about 0.025 milligram per kg body weight per dose to about 0.05 milligram per kg body weight per dose, such as from about 0.05 milligram per kg body weight per dose to about 0.075 milligram per kg body weight per dose, for example from about 0.075 milligram per kg body weight per dose to about 0.1 milligram per kg body weight per dose, such as from about 0.1 milligram per kg body weight per dose to about 0.25 milligram per kg body weight per dose, such as from about 0.25 milligram per kg body weight per dose to about 0.5 milligram per kg body weight per dose, for example from about 0.5 milligram per kg body weight per dose to about 0.75 milligram per kg body weight per dose, such as from about 0.75 milligram per kg body weight per dose to about 1.0 milligram per kg body weight per dose, for example from about 1.0 milligram per kg body weight per dose to about 2.5 milligram per kg body weight per dose, such as from about 2.5 milligram per kg body weight per dose to about 5 milligram per kg body weight per dose, for example from about 5 milligram per kg body weight per dose to about 7.5 milligram per kg body weight per dose, such as from about 7.5 milligram per kg body weight per dose to about 10 milligram per kg body weight per dose, for example from about 10 milligram per kg body weight per dose to about 25 milligram per kg body weight per dose, such as from about 25 milligram per kg body weight per dose to about 50 milligram per kg body weight per dose, such as from about 50 milligram per kg body weight per dose to about 75 milligram per kg body weight per dose, for example from about 75 milligram per kg body weight per dose to about 100 milligram per kg body weight per dose, such as from about 100 milligram per kg body weight per dose to about 250 milligram per kg body weight per dose, for example from about 250 milligram per kg body weight per dose to about 500 milligram per kg body weight per dose, such as from about 500 milligram per kg body weight per dose to about 750 milligram per kg body weight per dose, for example from about 750 milligram per kg body weight per dose to about 1000 milligram per kg body weight per dose.

2015. The method according to any of the previous items, wherein treatment comprises administration of a medicament, a composition or a drug to the individual in a total dosage of from about 0.01 milligram per kg body weight per dose to about 20 milligram per kg body weight per dose, such as from about 0.02 milligram per kg body weight per dose to about 18 milligram per kg body weight per dose, for example from about 0.04 milligram per kg body weight per dose to about 16 milligram per kg body weight per dose, such as from about 0.06 milligram per kg body weight per dose to about 14 milligram per kg body weight per dose, for example from about 0.08 milligram per kg body weight per dose to about 12 milligram per kg body weight per dose, such as from about 0.1 milligram per kg body weight per dose to about 10 milligram per kg body weight per dose, such as from about 0.2 milligram per kg body weight per dose to about 10 milligram per kg body weight per dose, for example from about 0.3 milligram per kg body weight per dose to about 10 milligram per kg body weight per dose, such as from about 0.4 milligram per kg body weight per dose to about 10 milligram per kg body weight per dose, for example from about 0.5 milligram per kg body weight per dose to about 10 milligram per kg body weight per dose, such as from about 0.6 milligram per kg body weight per dose to about 10 milligram per kg body weight per dose, for example from about 0.7 milligram per kg body weight per dose to about 10 milligram per kg body weight per dose, such as from about 0.8 milligram per kg body weight per dose to about 10 milligram per kg body weight per dose, for example from about 0.9 milligram per kg body weight per dose to about 10 milligram per kg body weight per dose, such as from about 1.0 milligram per kg body weight per dose to about 10 milligram per kg body weight per dose, for example from about 1.2 milligram per kg body weight per dose to about 10 milligram per kg body weight per dose, such as from about 1.4 milligram per kg body weight per dose to about 10 milligram per kg body weight per dose, for example from about 1.6 milligram per kg body weight per dose to about 10 milligram per kg body weight per dose, such as from about 1.8 milligram per kg body weight per dose to about 10 milligram per kg body weight per dose, for example from about 2.0 milligram per kg body weight per dose to about 10 milligram per kg body weight per dose, such as from about 2.2 milligram per kg body weight per dose to about 10 milligram per kg body weight per dose, for example from about 2.4 milligram per kg body weight per dose to about 10 milligram per kg body weight per dose, such as from about 2.6 milligram per kg body weight per dose to about 10 milligram per kg body weight per dose, for example from about 2.8 milligram per kg body weight per dose to about 10 milligram per kg body weight per dose, such as from about 3.0 milligram per kg body weight per dose to about 10 milligram per kg body weight per dose, for example from about 3.2 milligram per kg body weight per dose to about 10 milligram per kg body weight per dose, such as from about 3.4 milligram per kg body weight per dose to about 10 milligram per kg body weight per dose, for example from about 3.6 milligram per kg body weight per dose to about 10 milligram per kg body weight per dose, such as from about 3.8 milligram per kg body weight per dose to about 10 milligram per kg body weight per dose, for example from about 4.0 milligram per kg body weight per dose to about 10 milligram per kg body weight per dose, such as from about 4.2 milligram per kg body weight per dose to about 10 milligram per kg body weight per dose, for example from about 4.4 milligram per kg body weight per dose to about 10 milligram per kg body weight per dose, such as from about 4.6 milligram per kg body weight per dose to about 10 milligram per kg body weight per dose, for example from about 4.8 milligram per kg body weight per dose to about 10 milligram per kg body weight per dose, such as from about 5.0 milligram per kg body weight per dose to about 10 milligram per kg body weight per dose, for example from about 5.2 milligram per kg body weight per dose to about 10 milligram per kg body weight per dose, such as from about 5.4 milligram per kg body weight per dose to about 10 milligram per kg body weight per dose, for example from about 5.6 milligram per kg body weight per dose to about 10 milligram per kg body weight per dose, such as from about 5.8 milligram per kg body weight per dose to about 10 milligram per kg body weight per dose, for example from about 6.0 milligram per kg body weight per dose to about 10 milligram per kg body weight per dose, such as from about 6.2 milligram per kg body weight per dose to about 10 milligram per kg body weight per dose, for example from about 6.4 milligram per kg body weight per dose to about 10 milligram per kg body weight per dose, such as from about 6.6 milligram per kg body weight per dose to about 10 milligram per kg body weight per dose, for example from about 6.8 milligram per kg body weight per dose to about 10 milligram per kg body weight per dose, such as from about 7.0 milligram per kg body weight per dose to about 10 milligram per kg body weight per dose, for example from about 7.2 milligram per kg body weight per dose to about 10 milligram per kg body weight per dose, such as from about 7.4 milligram per kg body weight per dose to about 10 milligram per kg body weight per dose, for example from about 7.6 milligram per kg body weight per dose to about 10 milligram per kg body weight per dose, such as from about 7.8 milligram per kg body weight per dose to about 10 milligram per kg body weight per dose, for example from about 8.0 milligram per kg body weight per dose to about 10 milligram per kg body weight per dose, such as from about 0.2 milligram per kg body weight per dose to about 8 milligram per kg body weight per dose, for example from about 0.3 milligram per kg body weight per dose to about 8 milligram per kg body weight per dose, such as from about 0.4 milligram per kg body weight per dose to about 8 milligram per kg body weight per dose, for example from about 0.5 milligram per kg body weight per dose to about 8 milligram per kg body weight per dose, such as from about 0.6 milligram per kg body weight per dose to about 8 milligram per kg body weight per dose, for example from about 0.7 milligram per kg body weight per dose to about 8 milligram per kg body weight per dose, such as from about 0.8 milligram per kg body weight per dose to about 8 milligram per kg body weight per dose, for example from about 0.9 milligram per kg body weight per dose to about 8 milligram per kg body weight per dose, such as from about 1.0 milligram per kg body weight per dose to about 8 milligram per kg body weight per dose, for example from about 1.2 milligram per kg body weight per dose to about 8 milligram per kg body weight per dose, such as from about 1.4 milligram per kg body weight per dose to about 8 milligram per kg body weight per dose, for example from about 1.6 milligram per kg body weight per dose to about 8 milligram per kg body weight per dose, such as from about 1.8 milligram per kg body weight per dose to about 8 milligram per kg body weight per dose, for example from about 2.0 milligram per kg body weight per dose to about 8 milligram per kg body weight per dose, such as from about 2.2 milligram per kg body weight per dose to about 8 milligram per kg body weight per dose, for example from about 2.4 milligram per kg body weight per dose to about 8 milligram per kg body weight per dose, such as from about 2.6 milligram per kg body weight per dose to about 8 milligram per kg body weight per dose, for example from about 2.8 milligram per kg body weight per dose to about 8 milligram per kg body weight per dose, such as from about 3.0 milligram per kg body weight per dose to about 8 milligram per kg body weight per dose, for example from about 3.2 milligram per kg body weight per dose to about 8 milligram per kg body weight per dose, such as from about 3.4 milligram per kg body weight per dose to about 8 milligram per kg body weight per dose, for example from about 3.6 milligram per kg body weight per dose to about 8 milligram per kg body weight per dose, such as from about 3.8 milligram per kg body weight per dose to about 8 milligram per kg body weight per dose, for example from about 4.0 milligram per kg body weight per dose to about 8 milligram per kg body weight per dose, such as from about 4.2 milligram per kg body weight per dose to about 8 milligram per kg body weight per dose, for example from about 4.4 milligram per kg body weight per dose to about 8 milligram per kg body weight per dose, such as from about 4.6 milligram per kg body weight per dose to about 8 milligram per kg body weight per dose, for example from about 4.8 milligram per kg body weight per dose to about 8 milligram per kg body weight per dose, such as from about 5.0 milligram per kg body weight per dose to about 8 milligram per kg body weight per dose, for example from about 5.2 milligram per kg body weight per dose to about 8 milligram per kg body weight per dose, such as from about 5.4 milligram per kg body weight per dose to about 8 milligram per kg body weight per dose, for example from about 5.6 milligram per kg body weight per dose to about 8 milligram per kg body weight per dose, such as from about 5.8 milligram per kg body weight per dose to about 8 milligram per kg body weight per dose, for example from about 6.0 milligram per kg body weight per dose to about 8 milligram per kg body weight per dose, such as from about 0.2 milligram per kg body weight per dose to about 6 milligram per kg body weight per dose, for example from about 0.3 milligram per kg body weight per dose to about 6 milligram per kg body weight per dose, such as from about 0.4 milligram per kg body weight per dose to about 6 milligram per kg body weight per dose, for example from about 0.5 milligram per kg body weight per dose to about 6 milligram per kg body weight per dose, such as from about 0.6 milligram per kg body weight per dose to about 6 milligram per kg body weight per dose, for example from about 0.7 milligram per kg body weight per dose to about 6 milligram per kg body weight per dose, such as from about 0.8 milligram per kg body weight per dose to about 6 milligram per kg body weight per dose, for example from about 0.9 milligram per kg body weight per dose to about 6 milligram per kg body weight per dose, such as from about 1.0 milligram per kg body weight per dose to about 6 milligram per kg body weight per dose, for example from about 1.2 milligram per kg body weight per dose to about 6 milligram per kg body weight per dose, such as from about 1.4 milligram per kg body weight per dose to about 6 milligram per kg body weight per dose, for example from about 1.6 milligram per kg body weight per dose to about 6 milligram per kg body weight per dose, such as from about 1.8 milligram per kg body weight per dose to about 6 milligram per kg body weight per dose, for example from about 2.0 milligram per kg body weight per dose to about 6 milligram per kg body weight per dose, such as from about 2.2 milligram per kg body weight per dose to about 6 milligram per kg body weight per dose, for example from about 2.4 milligram per kg body weight per dose to about 6 milligram per kg body weight per dose, such as from about 2.6 milligram per kg body weight per dose to about 6 milligram per kg body weight per dose, for example from about 2.8 milligram per kg body weight per dose to about 6 milligram per kg body weight per dose, such as from about 3.0 milligram per kg body weight per dose to about 6 milligram per kg body weight per dose, for example from about 3.2 milligram per kg body weight per dose to about 6 milligram per kg body weight per dose, such as from about 3.4 milligram per kg body weight per dose to about 6 milligram per kg body weight per dose, for example from about 3.6 milligram per kg body weight per dose to about 6 milligram per kg body weight per dose, such as from about 3.8 milligram per kg body weight per dose to about 6 milligram per kg body weight per dose, for example from about 4.0 milligram per kg body weight per dose to about 6 milligram per kg body weight per dose, such as from about 4.2 milligram per kg body weight per dose to about 6 milligram per kg body weight per dose, for example from about 4.4 milligram per kg body weight per dose to about 6 milligram per kg body weight per dose, such as from about 4.6 milligram per kg body weight per dose to about 6 milligram per kg body weight per dose, for example from about 4.8 milligram per kg body weight per dose to about 6 milligram per kg body weight per dose, such as from about 5.0 milligram per kg body weight per dose to about 6 milligram per kg body weight per dose.

2016. The method according to item 2014 and 2015, wherein the dose or dosage is given as a single dose or in divided doses.

2017. The method according to item 2014 and 2015, wherein the dose or dosage is divided into multiple doses and given recurrently, such as twice (two times), for example three times, such as four times, for example five times, such as six times, for example seven times, such as eight times, for example nine times, such as ten divided doses.

2018. The method according to item 2014 and 2015, wherein the dose or dosage is given repeatedly, i.e. more than once, such as twice (two times), for example three times, such as four times, for example five times, such as six times, for example seven times, such as eight times, for example nine times, such as ten times a day.

2019. The method according to any of the previous items, wherein treatment comprises administration of a medicament, a composition or a drug to the individual once or more daily.

2020. The method according to any of the previous items, wherein treatment comprises administration of a medicament, a composition or a drug to the individual with intervals of 1 day, such as 2 days, for example 3 days, such as 4 days, such as 5 days, for example 6 days, such as 7 days (1 week), for example 8 days, such as 9 days, such as 10 days, for example 11 days, such as 12 days, for example 13 days, such as 14 days (2 weeks), such as 3 weeks, for example 4 weeks, such as 5 weeks, for example 6 weeks, such as 7 weeks, such as 8 weeks, for example 12 weeks.
2021. The method according to any of the previous items, wherein treatment comprises administration of a medicament, a composition or a drug to the individual by a continuous infusion.
2022. The method according to any of the previous items, wherein treatment comprises administration of a medicament, a composition or a drug to the individual by a continuous infusion, wherein the medicament, composition or drug is infused over 15 minutes to 24 hours, such as 15 to 30 minutes, for example 30 to 60 minutes, such as 60 to 90 minutes, for example 90 to 120 minutes, such as 2 hour to 3 hours, for example 3 hour to 4 hours, such as 4 hour to 5 hours, for example 5 hours to 6 hours, such as 6 hours to 7 hours, for example 7 hours to 8 hours, such as 8 hours to 9 hours, for example 9 hours to 10 hours, such as 10 hours to 11 hours, for example 11 hours to 12 hours, such as 12 hours to 14 hours, for example 14 hours to 16 hours, such as 16 hours to 18 hours, for example 18 hours to 20 hours, such as 20 hours to 22 hours, for example 22 hours to 24 hours.
2023. The method according to any of the previous items, wherein treatment comprises administration of more than one drug such as at least 2 drugs, such as 3 drugs, for example 4 drugs, such as 5 drugs, for example 6 drugs, such as 7 drugs, for example 8 drugs, such as 9 drugs, for example 10 drugs, such as 11 drugs, for example 12 drugs, such as 13 drugs, for example 14 drugs, such as 15 drugs, for example 16 drugs, such as 17 drugs, for example 18 drugs, such as 19 drugs, for example 20 drugs, such as 25 drugs, for example 30 drugs each at the doses and intervals cited in item 2014 to 2022.
2024. The method according to any of the previous items, wherein the analysis comprises a method for immune monitoring one or more diseases comprising the following steps
i) providing a MHC monomer or MHC multimer
ii) providing a population of T cells, and
iii) measuring the number, activity or state of T cells specific for said MHC monomer or MHC multimer, thereby immune monitoring said one or more diseases.
2025. The method according to any of the previous items, wherein the analysis comprises a method for diagnosing one or more diseases comprising the following steps:
i) providing a MHC monomer or MHC multimer,
ii) providing a population T cells, and
iii) measuring the number, activity or state T cells specific for said MHC monomer or MHC multimer, thereby diagnosing said one or more diseases.
2026. The method according to any of the previous items, wherein the analysis comprises a method for isolation of one or more antigen-specific T cells, said method comprising the steps of
i) providing the MHC monomer or MHC multimer
ii) providing a population of T cells, and
iii) isolating T cells specific for said MHC monomer or MHC multimer.
2027. The method according to any of the items 2024 to 2026, wherein the measurement of T cells comprises the step of counting of T cells specific for the MHC monomer or MHC multimer.
2028. The method according to any of the items 2024 to 2026, wherein the measurement of T cells comprises the step of sorting of T cells specific for said MHC monomer or MHC multimer.
2029. The method according to any of the items 2024 to 2026, wherein the measurement of T cells comprises the step of isolation of T cells specific for the peptide, polypeptide, MHC monomer or MHC multimer.
2030. The method according to any of the items 2024 to 2026, wherein the number of T cells specific for said MHC monomer or MHC multimer is determined from the number of T cells that are bound by more than a given threshold number of MHC multimers.
2031. The method according to item 2030, wherein the number of MHC multimers bound to an individual T cell is measured by flow cytometry.
2032. The method according to item 2030, wherein the number of MHC multimers bound to an individual T cell is measured by microscopy.
2033. The method according to item 2030, wherein the number of MHC multimers bound to an individual T cell is measured by capture on solid support, optionally followed by elution of T cells.
2034. The method according to item 2030, wherein the number of MHC multimers bound to a population of T cells is determined by the total number of MHC multimers bound to the population of T cells.
2035. The method according to any of the items 2024 to 2026, wherein the T cells of step (ii) are immobilized.
2036. The method of item 2035, wherein the MHC multimers are labelled, and the number of individual T cells specific for said MHC multimer is determined using microscopy.
2037. The method of item 2035, wherein the MHC multimers are labelled, and the number of T cells specific for said MHC multimer is determined from the total signal of the population of T cells.
2038. The method of items 2035 to 2037, wherein the immobilized T cells are part of a solid tissue.
2039. The method of item 2038, wherein the solid tissue is part of a living animal and the detection of T cells specific for the MHC multimer is performed in vivo.
2040. The method of item 2039, wherein the detection of T cells involves magnetic resonance imaging or electron spin resonance scanning.
2041. The method according to any of the items 2024 to 2026, wherein the number, activity or state of the T cells specific for said MHC multimer or MHC monomer, are determined from the result of the interaction of said MHC with said T cells.
2042. The method of item 2041, wherein the result of the interaction of said MHC multimer or MHC monomer with said T cells is an up- or down-regulation, such as an increased or decreased production, of the amount of a specific factor.
2043. The method of item 2042, wherein the specific factor is a secreted soluble factor.
2044. The method of item 2042, wherein the specific factor is an intracellular factor.
2045. The method of item 2042, wherein the specific factor is a mRNA.
2046. The method of item 2042, wherein the specific factor is a cytokine.

2047. The method of item 2042, wherein the specific factor is a surface receptor of T cells.
2048. The method of item 2042, wherein the specific factor is a secreted soluble factor that is captured on solid support.
2049. The method of item 2042, wherein the specific factor is interferon-gamma (INF-gamma).
2050. The method of any of the items 2024 to 2049, wherein individual T cells are measured.
2051. The method of any of the items 2024 to 2049, wherein populations of T cells are measured.
2052. The method of any of the items 2041 to 2049, wherein the specific factor is immobilized on solid support before measurement of its amount.
2053. The method of any of the items 2041 to 2049, wherein the specific factor is in solution when its amount is measured.
2054. The method of item 2041, wherein the result of the interaction of said MHC multimer with the T cell is T cell apoptosis.
2055. The method of item 2041, wherein the result of the interaction of said MHC multimer with the T cell is T cell differentiation.
2056. The method of item 2041, wherein the result of the interaction of said MHC multimer with the T cell is T cell inactivation.
2057. The method of item 2041, wherein the measurement of T cells specific for said MHC multimer with the T cell involves flow cytometry.
2058. The method according to any of the items 2024 to 2026, wherein the measurement of antigen-specific T cells comprises flow cytometry.
2059. The method according to any of the items 2024 to 2026, wherein the measurement of antigen-specific T cells comprises indirect measurement of individual T cells.
2060. The method according to any of the items 2024 to 2026, wherein the measurement of antigen-specific T cells comprises indirect measurement of populations of T cells.
2061. The method according to any of the items 2024 to 2026, wherein the measurement of antigen-specific T cells involves immunohistochemistry (IHC).
2062. The method according to any of the items 2024 to 2026, wherein the measurement of antigen-specific T cells involves limited dilution assay (LDA).
2063. The method according to any of the items 2024 to 2026, wherein the measurement of antigen-specific T cells involves microscopy.
2064. The method according to any of the items 2024 to 2026, wherein the method comprises the step of detecting one or more marker molecules associated with the MHC monomer or MHC multimer.
2065. The method of item 2064, wherein the one or more marker molecules comprises one or more antibodies and/or antibody fragments.
2066. The method of item 2064, wherein the one or more marker molecules comprises one or more aptamers.
2067. The method of item 2064, wherein the one or more marker molecules comprises one or more proteins.
2068. The method of item 2064, wherein the one or more marker molecules comprises one or more peptides.
2069. The method of item 2064, wherein the one or more marker molecules comprises one or more small organic molecules.
2070. The method of item 2064, wherein the one or more marker molecules comprises one or more natural compounds such as one or more steroids.
2071. The method of item 2064, wherein the one or more marker molecules comprises one or more non-peptide polymers.
2072. The method of any of the items 2024 to 2026, wherein the method comprises the further step of providing one or more labelling molecules.
2073. The method of item 2072, wherein the one or more labelling molecules comprises one or more labelling molecules that results in directly detectable T cells.
2074. The method of item 2072, wherein the one or more labelling molecules comprises one or more labelling molecules that results in indirectly detectable T cells.
2075. The method of item 2072, wherein the one or more labelling molecules are attached via one or more linkers.
2076. The method of item 2072, wherein the one or more labelling molecules comprises one or more fluorescent labels.
2077. The method of item 2076, wherein the one or more fluorescent labels can be selected from the group consisting of 5-(and 6)-carboxyfluorescein, 5- or 6-carboxyfluorescein, 6-(fluorescein)-5-(and 6)-carboxamido hexanoic acid, fluorescein isothiocyanate (FITC), rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeston Red, Green fluorescent protein (GFP) and analogues thereof, and conjugates of R-phycoerythrin or allophycoerythrin and e.g. Cy5 or Texas Red, and inorganic fluorescent labels based on semiconductor nanocrystals (like quantum dot and Qdot™ nanocrystals), and time-resolved fluorescent labels based on lanthanides like Eu3+ and Sm3+.
2078. The method of item 2072, wherein the one or more labelling molecules comprises one or more enzyme labels.
2079. The method of item 2078, wherein the one or more enzyme labels can be selected from the group consisting of horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, and firefly luciferase and glucose oxidase (GO).
2080. The method of item 2072, wherein the one or more labelling molecules comprises one or more radioisotopes.
2081. The method of item 2080, wherein the one or more radioisotopes can be selected from the group consisting of isotopes of iodide, cobalt, selenium, tritium, and/or phosphor.
2082. The method of item 2072, wherein the one or more labelling molecules comprises one or more chemiluminescent labels.
2083. The method of item 2072, wherein the one or more labelling molecules comprises one or more luminescent labels.
2084. The method of item 2083, wherein the one or more luminescent labels can be selected from the group consisting of luminol, isoluminol, acridinium esters, 1,2-dioxetanes and pyridopyridazines.
2085. The method of item 2072, wherein the one or more labelling molecules comprises one or more polymers.
2086. The method of item 2072, wherein the one or more labelling molecules comprises one or more metal particles.
2087. The method of item 2072, wherein the one or more labelling molecules comprises one or more haptens.

2088. The method of item 2087, wherein the one or more haptens can be selected from the group consisting of DNP, biotin, and digoxiginin.

2089. The method of item 2072, wherein the one or more labelling molecules comprises one or more antibodies.

2090. The method of item 2072, wherein the one or more labelling molecules comprises one or more dyes.

2091. The method of any of the items 2024 to 2026, wherein the method comprises a detection step based on flow cytometry or flow cytometry-like analysis.

2092. The method of any of the items 2024 to 2026, wherein the method comprises direct detection of TCRs attached to a lipid bilayer.

2093. The method of any of the items 2024 to 2026, wherein the method comprises direct detection of one or more individual T cells e.g. in a fluid sample.

2094. The method of any of the items 2024 to 2026, wherein the method comprises direct detection of one or more populations of T cells e.g. in a fluid sample.

2095. The method of item 2094, where in the direct detection of one or more individual T cells in a fluid sample comprises flow cytometry.

2096. The method of item 2094, where in the direct detection of one or more populations of T cells in a fluid sample comprises flow cytometry.

2097. The method of item 2094, where in the direct detection of one or more individual T cells in a fluid sample comprises microscopy.

2098. The method of item 2094, where in the direct detection of one or more populations of T cells in a fluid sample comprises microscopy.

2099. The method of item 2094, where in the direct detection of one or more individual T cells in a fluid sample comprises capture of T cells on a solid support followed by elution of said T cells.

2100. The method of item 2094, where in the direct detection of one or more populations of T cells in a fluid sample comprises capture of T cells on a solid support followed by elution of said T cells.

2101. The method of any of the items 2024 to 2026, wherein the method comprises direct detection of one or more individual immobilized T cells.

2102. The method of any of the items 2024 to 2026, wherein the method comprises direct detection of one or more populations of immobilized T cells.

2103. The method of item 2101, wherein one or more individual T cells are immobilized on a solid support such as particles, beads, biodegradable particles, sheets, gels, filters, membranes, nylon membranes, fibres, capillaries, needles, microtitre strips, tubes, plates, wells, combs, pipette tips, micro arrays, chips and slides.

2104. The method of item 2102, wherein one or more populations of T cells are immobilized on a solid support such as particles, beads, biodegradable particles, sheets, gels, filters, membranes, nylon membranes, fibres, capillaries, needles, microtitre strips, tubes, plates, wells, combs, pipette tips, micro arrays, chips and slides.

2105. The method of item 2101, wherein the immobilization of one or more individual T cells are directly immobilized on the solid support.

2106. The method of item 2102, wherein the immobilization of one or more populations of T cells are directly immobilized on the solid support.

2107. The method of item 2101, wherein the immobilization of one or more individual T cells are directly immobilized through a linker on the solid support.

2108. The method of item 2102, wherein the immobilization of one or more individual T cells are directly immobilized through a linker on the solid support.

2109. The method of any of the items 2024 to 2026 comprising a step wherein direct detection of one or more individual immobilized T cells comprises phenotyping a T cell sample using MHC multimer beads.

2110. The method of any of the items 2024 to 2026 comprising a step wherein direct detection of one or more populations of immobilized T cells comprises phenotyping a T cell sample using MHC multimer beads.

2111. The method of any of the items 2024 to 2026 comprising a step wherein direct detection of one or more individual immobilized T cells comprises detection of T cells immobilized to solid support in a defined pattern.

2112. The method of any of the items 2024 to 2026 comprising a step wherein direct detection of one or more populations of immobilized T cells comprises detection of T cells immobilized to solid support in a defined pattern.

2113. The method of any of items 2109 to 2112, wherein the direct detection of one or more individual immobilized T cells is followed by sorting of said T cells.

2114. The method of any of items 2009 to 2112, wherein the direct detection one or more populations of immobilized T cells is followed by sorting of said T cells.

2115. The method of any of the items 2024 to 2026, wherein the method comprises direct detection of one or more individual T cells in a solid tissue either in vitro or in vivo.

2116. The method of any of the items 2024 to 2026, wherein the method comprises direct detection of one or more populations of T cells in a solid tissue either in vitro or in vivo.

2117. The method of any of the items 2024 to 2026, wherein the method comprises indirect detection of one or more populations of T cells in a sample.

2118. The method of any of the items 2024 to 2026, wherein the method comprises indirect detection of one or more individual T cells in a sample.

2119. The method of any of the items 2024 to 2026, wherein the method comprises indirect detection of one or more individual T cells in a sample by measurement of activation.

2120. The method of any of the items 2024 to 2026, wherein the method comprises indirect detection of one or more populations of T cells in a sample by measurement of activation.

2121. The method of item 2119, wherein the indirect detection of one or more individual T cells in a sample comprises measurement of secretion of soluble factors.

2122. The method of 2120, wherein the indirect detection of one or more populations of T cells in a sample comprises measurement of secretion of soluble factors.

2123. The method of items 2121 and 2122, wherein the measurement of secretion of soluble factors comprises measurement of extracellular secreted soluble factors.

2124. The method of item 2123, wherein the measurement of extracellular secreted soluble factors comprises analysis of a fluid sample.

2125. The method of item 2123, wherein the measurement of extracellular secreted soluble factors comprises detection of T cells by capture of extracellular secreted soluble factor on a solid support.

2126. The method of item 2123, wherein the measurement of extracellular secreted soluble factors comprises detection of T cells immobilized to solid support in a defined pattern.

2127. The method of item 2123, wherein the measurement of extracellular secreted soluble factors comprises detection of T cells by measurement of effect of extracellular secreted soluble factor.

2128. The method of items 2121 and 2122, wherein the measurement of secretion of soluble factors comprises measurement of intracellular secreted soluble factors.

2129. The method of items 2121 and 2122, wherein the indirect detection of individual or populations of T cells in a sample comprises measurement of expression of one or more receptors.

2130. The method of item 2121 and 2122, wherein the indirect detection of individual or populations of T cells in a sample comprises measurement of T cell effector function.

2131. The method of any of the items 2024 to 2026, wherein the method comprises indirect detection of individual or populations of T cells in a sample by measurement of T cell proliferation.

2132. The method of any of the items 2024 to 2026, wherein the method comprises indirect detection of individual or populations of T cells in a sample by measurement of T cell inactivation such as measurement of blockage of TCR and/or measurement of induction of apoptosis.

2133. The method of any of the items 2024 to 2026, wherein the method comprises immunohistochemistry or immunohistochemistry-like analysis.

2134. The method according to any of the items 2024 to 2026, wherein the method comprises a measuring step involving an ELISA or ELISA-like analysis.

2135. The method of any of the items 2024 to 2026, wherein the antigen-specific T cells are isolated using MHC multimers immobilized on a solid phase.

2136. The method of item 2125, wherein the solid phase is a bead.

2137. The method of item 2125, wherein the solid phase is immunotubes.

2138. The method of item 2125, wherein the solid phase is microtiter plates.

2139. The method of item 2125, wherein the solid phase is microchips.

2140. The method of item 2125, wherein the solid phase is microarrays.

2141. The method of item 2125, wherein the solid phase is test strips.

2142. The method of any of the items 2024 to 2026, wherein the method comprises blocking of the sample with a protein solution such as BSA or skim milk.

2143. The method of any of the items 2024 to 2026, wherein the method comprises blocking of the MHC multimer with a protein solution such as BSA or skim milk.

2144. The method of any of the items 2024 to 2026, wherein the method comprises mixing of MHC multimer coated beads with the cell sample.

2145. The method of any of the items 2024 to 2026, wherein the method comprises incubation of MHC multimer coated beads with the cell sample.

2146. The method of any of the items 2024 to 2026, wherein the method comprises a washing step after incubation of MHC multimer coated beads with the cell sample.

2147. The method of any of the items 2024 to 2026, wherein the method comprises release of the immobilized T cells from the beads.

2148. The method of item 2147, wherein the T cells are released by cleavage of the linker.

2149. The method of item 2147, wherein the T cells are released by changing the pH.

2150. The method of item 2147, wherein the T cells are released by changing the salt concentration.

2151. The method of item 2147, wherein the T cells are released by addition of one or more competitive binders.

2152. The method of item 2147, wherein the T cells are released by a method that does not disrupts the integrity of the cells.

2153. The method of any of the items 2024 to 2026, wherein the method comprises manipulation of the T cells after release from the beads.

2154. The method of item 2153, wherein the manipulation is induction of apoptosis.

2155. The method of item 2153, wherein the manipulation is induction of proliferation.

2156. The method of item 2153, wherein the manipulation is induction of differentiation.

2157. The method of any of items 2024 to 2026, wherein said MHC monomer comprises a-b-P, or wherein said MHC multimer comprises $(a\text{-}b\text{-}P)_n$, wherein $n>1$,
wherein the polypeptides a and b together form a functional MHC protein capable of binding the peptide P,
wherein (a-b-P) is the MHC-peptide complex formed when the peptide P binds to the functional MHC protein,
wherein each MHC peptide complex of a MHC multimer is associated with one or more multimerization domains.

2158. The method according to item 2157, wherein the association is a covalent linkage so that one or more of the n MHC-peptide complexes is covalently linked to the one or more multimerization domains.

2159. The method according to item 2157, wherein the association is a non-covalent association so that one or more of the n MHC-peptide complexes is non-covalently associated with the one or more multimerization domains.

2160. The method according to item 2157, wherein the one or more multimerization domains comprises one or more scaffolds.

2161. The method according to item 2157, wherein the one or more multimerization domains comprises one or more carriers.

2162. The method according to item 2157, wherein the one or more multimerization domains comprises at least one scaffold and at least one carrier.

2163. The method according to item 2157, wherein the one or more multimerization domains comprise one or more optionally substituted organic molecules.

2164. The method according to item 2163, wherein the optionally substituted organic molecule comprises one or more functionalized cyclic structures.

2165. The method according to item 2164, wherein the one or more functionalized cyclic structures comprises one or more benzene rings.

2166. The method according to item 2163, wherein the optionally substituted organic molecule comprises a scaffold molecule comprising at least three reactive groups, or at least three sites suitable for non-covalent attachment.

2167. The method according to item 2157, wherein the one or more multimerization domains comprises one or more biological cells and/or cell-like structures, such as antigen presenting cells or dendritic cells.

2168. The method according to item 2157, wherein the one or more multimerization domains comprises one or more membranes.

2169. The method according to item 2168, wherein the one or more membranes comprises liposomes or micelles.

2170. The method according to item 2157, wherein the one or more multimerization domains comprises one or more polymers such as one or more synthetic polymers.
2171. The method according to item 2170, wherein the one or more polymers are selected from the group consisting of polysaccharides.
2172. The method according to item 2171, wherein the polysaccharide comprises one or more dextran moieties.
2173. The method according to item 2172, wherein the one or more dextran moieties are covalently attached to one or more MHC peptide complexes.
2174. The method according to item 2172, wherein the one or more dextran moieties are non-covalently attached to one or more MHC peptide complexes.
2175. The method according to item 2172, wherein the one or more dextran moieties are modified.
2176. The method according to item 2172, wherein the one or more dextran moieties comprises one or more Aminodextrans.
2177. The method according to item 2172, wherein the one or more dextran moieties comprises one or more Aminodextrans modified with divinyl sulfone.
2178. The method according to item 2172, wherein the one or more dextran moieties comprises one or more dextrans with a molecular weight of from 1,000 to 50,000, such as from 1,000 to 5,000, for example 5,000 to 10,000, such as from 10,000 to 15,000, for example 15,000 to 20,000, such as from 20,000 to 25,000, for example 25,000 to 30,000, such as from 30,000 to 35,000, for example 35,000 to 40,000, such as from 40,000 to 45,000, for example 45,000 to 50,000, including any consecutive combination of the afore-mentioned ranges.
2179. The method according to item 2172, wherein the one or more dextran moieties comprises one or more dextrans with a molecular weight of from 50,000 to 150,000, such as from 50,000 to 60,000, for example 60,000 to 70,000, such as from 70,000 to 80,000, for example 80,000 to 90,000, such as from 90,000 to 100,000, for example 100,000 to 110,000, such as from 110,000 to 120,000, for example 120,000 to 130,000, such as from 130,000 to 140,000, for example 140,000 to 150,000, including any consecutive combination of the afore-mentioned ranges.
2180. The method according to item 2172, wherein the one or more dextran moieties comprises one or more dextrans with a molecular weight of from 150,000-270,000 such as from 150,000 to 160,000, for example 160,000 to 170,000, such as from 170,000 to 180,000, for example 180,000 to 190,000, such as from 190,000 to 200,000, for example 200,000 to 210,000, such as from 210,000 to 220,000, for example 220,000 to 230,000, such as from 230,000 to 240,000, for example 240,000 to 250,000, such as from 250,000 to 260,000, for example 260,000 to 270,000, such as from 270,000 to 280,000, for example 280,000 to 290,000, such as from 290,000 to 300,000, for example 300,000 to 310,000 such as from 310,000 to 320,000, for example 320,000 to 330,000 such as from 330,000 to 340,000, for example 340,000 to 350,000 such as from 350,000 to 360,000, for example 360,000 to 370,000 such as from 370,000 to 380,000, for example 380,000 to 390,000, such as from 390,000 to 400,000, including any consecutive combination of the afore-mentioned ranges.
2181. The method according to item 2172, wherein the one or more dextran moieties are linear.
2182. The method according to item 2172, wherein the one or more dextran moieties are branched.
2183. The method according to item 2170, wherein the one or more synthetic polymers are selected from the group consisting of PNA, polyimide and PEG.
2184. The method according to item 2157, wherein the one or more multimerization domains comprises one or more entities selected from the group consisting of an IgG domain, a coiled-coil polypeptide structure, a DNA duplex, a nucleic acid duplex, PNA-PNA, PNA-DNA, DNA-RNA.
2185. The method according to item 2157, wherein the one or more multimerization domains comprises one or more avidins, such as one or more streptavidins.
2186. The method according to item 2185, wherein the one or more streptavidins comprises one or more tetrameric streptavidin variants.
2187. The method according to item 2185, wherein the one or more streptavidins comprises one or more monomeric streptavidin variants.
2188. The method according to item 2157, wherein the one or more multimerization domains comprises an antibody.
2189. The method according to item 2188, wherein the antibody is selected from the group consisting of polyclonal antibody, monoclonal antibody, IgA, IgG, IgM, IgD, IgE, IgG1, IgG2, IgG3, IgG4, IgA1, IgA2, IgM1, IgM2, humanized antibody, humanized monoclonal antibody, chimeric antibody, mouse antibody, rat antibody, rabbit antibody, human antibody, camel antibody, sheep antibody, engineered human antibody, epitope-focused antibody, agonist antibody, antagonist antibody, neutralizing antibody, naturally-occurring antibody, isolated antibody, monovalent antibody, bispecific antibody, trispecific antibody, multispecific antibody, heteroconjugate antibody, immunoconjugates, immunoliposomes, labeled antibody, antibody fragment, domain antibody, nanobody, minibody, maxibody, diabody, fusion antibody.
2190. The method according to item 2157, wherein the MHC multimer comprises one or more small organic scaffold molecules.
2191. The method according to item 2157, wherein the MHC multimer comprises one or more small organic molecules.
2192. The method according to item 2191, wherein the one or more small organic molecules comprises one or more steroids.
2193. The method according to item 2191, wherein the one or more small organic molecules comprises one or more peptides.
2194. The method according to item 2191, wherein the one or more small organic molecules comprises one or more aromatic organic molecules.
2195. The method according to item 2194, wherein the one or more aromatic organic molecules comprises one or more monocyclic structures.
2196. The method according to item 2195, wherein the one or more monocyclic structures comprises one or more optionally functionalized or substituted benzene rings.
2197. The method according to item 2194, wherein the one or more aromatic organic molecules comprises one or more dicyclic structures.
2198. The method according to item 2194, wherein the one or more aromatic organic molecules comprises one or more polycyclic structures.
2199. The method according to item 2194, wherein the one or more small organic molecules comprises one or more aliphatic molecules.

2200. The method according to item 2199, wherein the one or more aliphatic molecules comprises one or more monocyclic molecules.

2201. The method according to item 2199, wherein the one or more aliphatic molecules comprises one or more dicyclic molecules.

2202. The method according to item 2199, wherein the one or more aliphatic molecules comprises one or more polycyclic molecules.

2203. The method according to item 2157, wherein the MHC multimer comprises one or more monomeric molecules able to polymerize.

2204. The method according to item 2157, wherein the MHC multimer comprises one or more biological polymers such as one or more proteins.

2205. The method according to item 2157, wherein the MHC multimer comprises one or more small molecule scaffolds.

2206. The method according to item 2157, wherein the MHC multimer comprises one or more supramolecular structure(s) such as one or more nanoclusters.

2207. The method according to item 2157, wherein the MHC multimer comprises one or more further polypeptides in addition to a and b.

2208. The method according to item 2157, wherein the MHC multimer comprises one or more protein complexes.

2209. The method according to item 2157, wherein the MHC multimer comprises one or more beads.

2210. The method according to item 2209, wherein the one or more beads can be selected from the groups consisting of beads that carry electrophilic groups e.g. divinyl sulfone activated polysaccharide, polystyrene beads that have been functionalized with tosyl-activated esters, magnetic polystyrene beads functionalized with tosyl-activated esters, and beads where MHC complexes have been covalently immobilized to these by reaction of nucleophiles comprised within the MHC complex with the electrophiles of the beads.

2211. The method according to item 2209, wherein the one or more beads can be selected from the groups consisting of sepharose beads, sephacryl beads, polystyrene beads, agarose beads, polysaccharide beads, polycarbamate beads and any other kind of beads that can be suspended in an aqueous buffer.

2212. The method according to item 2157, wherein the multimerization domain comprises one or more compounds selected from the group consisting of agarose, sepharose, resin beads, glass beads, pore-glass beads, glass particles coated with a hydrophobic polymer, chitosan-coated beads, SH beads, latex beads, spherical latex beads, allele-type beads, SPA bead, PEG-based resins, PEG-coated bead, PEG-encapsulated bead, polystyrene beads, magnetic polystyrene beads, glutathione agarose beads, magnetic bead, paramagnetic beads, protein A and/or protein G sepharose beads, activated carboxylic acid bead, macroscopic beads, microscopic beads, insoluble resin beads, silica-based resins, cellulosic resins, cross-linked agarose beads, polystyrene beads, cross-linked polyacrylamide resins, beads with iron cores, metal beads, dynabeads, Polymethylmethacrylate beads activated with NHS, streptavidin-agarose beads, polypropylene, polyethylene, dextran, nylon, amylases, natural and modified celluloses, nitrocellulose, polyacrylamides, gabbros, magnetite, polymers, oligomers, non-repeating moieties, polyethylene glycol (PEG), monomethoxy-PEG, mono-($C_1$-$C_{10}$)alkoxy-PEG, aryloxy-PEG, poly-(N-vinyl pyrrolidone)PEG, tresyl monomethoxy PEG, PEG propionaldehyde, bis-succinimidyl carbonate PEG, polystyrene bead crosslinked with divinylbenzene, propylene glycol homopolymers, a polypropylene oxide/ethylene oxide co-polymer, polyoxyethylated polyols (e.g., glycerol), polyvinyl alcohol, dextran, aminodextran, carbohydrate-based polymers, cross-linked dextran beads, polysaccharide beads, polycarbamate beads, divinyl sulfone activated polysaccharide, polystyrene beads that have been functionalized with tosyl-activated esters, magnetic polystyrene beads functionalized with tosyl-activated esters, streptavidin beads, streptaivdin-monomer coated beads, streptaivdin-tetramer coated beads, Streptavidin Coated Compel Magnetic beads, avidin coated beads, dextramer coated beads, divinyl sulfone-activated dextran, Carboxylate-modified bead, amine-modified beads, antibody coated beads, cellulose beads, grafted co-poly beads, poly-acrylamide beads, dimethylacrylamide beads optionally crosslinked with N—N'-bis-acryloylethylenediamine, hollow fiber membranes, fluorescent beads, collagen-agarose beads, gelatin beads, collagen-gelatin beads, collagen-fibronectin-gelatin beads, collagen beads, chitosan beads, collagen-chitosan beads, protein-based beads, hydrogel beads, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin and chitosan.

2213. The method according to item 2157, wherein the one or more multimerization domains comprises a dimerization domain.

2214. The method according to item 2157, wherein the one or more multimerization domains comprises a trimerization domain.

2215. The method according to item 2157, wherein the one or more multimerization domains comprises a tetramerization domain.

2216. The method according to item 2157, wherein the one or more multimerization domains comprises a pentamerization domain.

2217. The method according to item 2216, wherein the pentamerization domain comprises a coiled-coil polypeptide structure.

2218. The method according to item 2157, wherein the one or more multimerization domains comprises a hexamerization domain.

2219. The method according to item 2218, wherein the hexamerization domain comprises three IgG domains.

2220. The method according to item 2157, wherein the one or more multimerization domains comprises a polymer structure to which is attached one or more scaffolds.

2221. The method according to item 2220, wherein the polymer structure comprises a polysaccharide.

2222. The method according to item 2221, wherein the polysaccharide comprises one or more dextran moieties.

2223. The method according to item 2157, wherein the one or more multimerization domains comprises a polyamide and/or a polyethylene glycol and/or a polysaccharide and/or a sepharose.

2224. The method according to item 2157, wherein the one or more multimerization domains comprises a carboxy methyl dextran and/or a dextran polyaldehyde and/or a carboxymethyl dextran lactone and/or a cyclodextrin.

2225. The method according to item 2157, wherein the one or more multimerization domains have a molecular weight of less than 1,000 Da.

2226. The method according to item 2157, wherein the one or more multimerization domains have a molecular weight of from 1,000 Da to preferably less than 10,000 Da.

2227. The method according to item 2157, wherein the one or more multimerization domains have a molecular weight of from 10,000 Da to preferably less than 100,000 Da.

2228. The method according to item 2157, wherein the one or more multimerization domains have a molecular weight of from 100,000 Da to preferably less than 1,000,000 Da.

2229. The method according to item 2157, wherein the one or more multimerization domains have a molecular weight of more than 1,000,000 Da.

2230. The method according to item 2157, wherein the one or more multimerization domains have a molecular weight of from 50,000 Da to preferably less than 1,000,000 Da, such as from 50,000 Da to 980,000; for example from 50,000 Da to 960,000; such as from 50,000 Da to 940,000; for example from 50,000 Da to 920,000; such as from 50,000 Da to 900,000; for example from 50,000 Da to 880,000; such as from 50,000 Da to 860,000; for example from 50,000 Da to 840,000; such as from 50,000 Da to 820,000; for example from 50,000 Da to 800,000; such as from 50,000 Da to 780,000; for example from 50,000 Da to 760,000; such as from 50,000 Da to 740,000; for example from 50,000 Da to 720,000; such as from 50,000 Da to 700,000; for example from 50,000 Da to 680,000; such as from 50,000 Da to 660,000; for example from 50,000 Da to 640,000; such as from 50,000 Da to 620,000; for example from 50,000 Da to 600,000; such as from 50,000 Da to 580,000; for example from 50,000 Da to 560,000; such as from 50,000 Da to 540,000; for example from 50,000 Da to 520,000; such as from 50,000 Da to 500,000; for example from 50,000 Da to 480,000; such as from 50,000 Da to 460,000; for example from 50,000 Da to 440,000; such as from 50,000 Da to 420,000; for example from 50,000 Da to 400,000; such as from 50,000 Da to 380,000; for example from 50,000 Da to 360,000; such as from 50,000 Da to 340,000; for example from 50,000 Da to 320,000; such as from 50,000 Da to 300,000; for example from 50,000 Da to 280,000; such as from 50,000 Da to 260,000; for example from 50,000 Da to 240,000; such as from 50,000 Da to 220,000; for example from 50,000 Da to 200,000; such as from 50,000 Da to 180,000; for example from 50,000 Da to 160,000; such as from 50,000 Da to 140,000; for example from 50,000 Da to 120,000; such as from 50,000 Da to 100,000; for example from 50,000 Da to 80,000; such as from 50,000 Da to 60,000; for example from 100,000 Da to 1,000,000; such as from 100,000 Da to 980,000; for example from 100,000 Da to 960,000; such as from 100,000 Da to 940,000; for example from 100,000 Da to 920,000; such as from 100,000 Da to 900,000; for example from 100,000 Da to 880,000; such as from 100,000 Da to 860,000; for example from 100,000 Da to 840,000; such as from 100,000 Da to 820,000; for example from 100,000 Da to 800,000; such as from 100,000 Da to 780,000; for example from 100,000 Da to 760,000; such as from 100,000 Da to 740,000; for example from 100,000 Da to 720,000; such as from 100,000 Da to 700,000; for example from 100,000 Da to 680,000; such as from 100,000 Da to 660,000; for example from 100,000 Da to 640,000; such as from 100,000 Da to 620,000; for example from 100,000 Da to 600,000; such as from 100,000 Da to 580,000; for example from 100,000 Da to 560,000; such as from 100,000 Da to 540,000; for example from 100,000 Da to 520,000; such as from 100,000 Da to 500,000; for example from 100,000 Da to 480,000; such as from 100,000 Da to 460,000; for example from 100,000 Da to 440,000; such as from 100,000 Da to 420,000; for example from 100,000 Da to 400,000; such as from 100,000 Da to 380,000; for example from 100,000 Da to 360,000; such as from 100,000 Da to 340,000; for example from 100,000 Da to 320,000; such as from 100,000 Da to 300,000; for example from 100,000 Da to 280,000; such as from 100,000 Da to 260,000; for example from 100,000 Da to 240,000; such as from 100,000 Da to 220,000; for example from 100,000 Da to 200,000; such as from 100,000 Da to 180,000; for example from 100,000 Da to 160,000; such as from 100,000 Da to 140,000; for example from 100,000 Da to 120,000; such as from 150,000 Da to 1,000,000; for example from 150,000 Da to 960,000; such as from 150,000 Da to 940,000; for example from 150,000 Da to 920,000; such as from 150,000 Da to 900,000; for example from 150,000 Da to 880,000; such as from 150,000 Da to 860,000; for example from 150,000 Da to 840,000; such as from 150,000 Da to 820,000; for example from 150,000 Da to 800,000; such as from 150,000 Da to 780,000; for example from 150,000 Da to 760,000; such as from 150,000 Da to 740,000; for example from 150,000 Da to 720,000; such as from 150,000 Da to 700,000; for example from 150,000 Da to 680,000; such as from 150,000 Da to 660,000; for example from 150,000 Da to 640,000; such as from 150,000 Da to 620,000; for example from 150,000 Da to 600,000; such as from 150,000 Da to 580,000; for example from 150,000 Da to 560,000; such as from 150,000 Da to 540,000; for example from 150,000 Da to 520,000; such as from 150,000 Da to 500,000; for example from 150,000 Da to 480,000; such as from 150,000 Da to 460,000; for example from 150,000 Da to 440,000; such as from 150,000 Da to 420,000; for example from 150,000 Da to 400,000; such as from 150,000 Da to 380,000; for example from 150,000 Da to 360,000; such as from 150,000 Da to 340,000; for example from 150,000 Da to 320,000; such as from 150,000 Da to 300,000; for example from 150,000 Da to 280,000; such as from 150,000 Da to 260,000; for example from 150,000 Da to 240,000; such as from 150,000 Da to 220,000; for example from 150,000 Da to 200,000; such as from 150,000 Da to 180,000; for example from 150,000 Da to 160,000.

2231. The method according to item 2157 further comprising one or more scaffolds, carriers and/or linkers selected from the group consisting of streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-tranferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia*

*ensiformis*) or WGA (wheat germ agglutinin) and tetranectin or Protein A or G (antibody affinity).

2232. The method according to item 2157, wherein n is 2.
2233. The method according to item 2157, wherein n is 3.
2234. The method according to item 2157, wherein n is 4.
2235. The method according to item 2157, wherein n is 5.
2236. The method according to item 2157, wherein n is 6.
2237. The method according to item 2157, wherein n is 7.
2238. The method according to item 2157, wherein n is 8.
2239. The method according to item 2157, wherein n is 9.
2240. The method according to item 2157, wherein n is 10.
2241. The method according to item 2157, wherein n is 11.
2242. The method according to item 2157, wherein n is 12.
2243. The method according to item 2157, wherein n≥13.
2244. The method according to item 2157, wherein 1<n≥100.
2245. The method according to item 2157, wherein 1<n≥1000.
2246. The method according to item 2157, wherein n≥1,000,000,000.
2247. The method according to item 2157, wherein n≥1,000,000,000,000,000,000 (one trillion).
2248. The method according to item 2157, wherein n is selected from the group of integers consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 50, 55, 60, 65, 70, 75, 80, 85, 90, 95, 100, 110, 120, 130, 140, 150, 160, 170, 180, 190, 200, 250, 300, 350, 400, 450, 500, 550, 600, 650, 700, 750, 800, 850, 900 and 1000.
2249. The method according to item 2157, wherein n has a value of from 1 to 1000, for example from 1 to 10, such as from 10 to 20, for example from 20 to 30, such as from 30 to 40, for example from 40 to 50, such as from 50 to 60, for example from 60 to 70, such as from 70 to 80, for example from 80 to 90, such as from 90 to 100, for example from 100 to 120, such as from 120 to 140, for example from 140 to 160, such as from 160 to 180, for example from 180 to 200, such as from 200 to 250, for example from 250 to 300, such as from 300 to 350, for example from 350 to 400, such as from 400 to 450, for example from 450 to 500, such as from 500 to 550, for example from 550 to 600, such as from 600 to 650, for example from 650 to 700, such as from 700 to 750, for example from 750 to 800, such as from 800 to 900, for example from 900 to 950, such as from 950 to 1000, including any consecutive combinations of the aforementioned ranges.
2250. The method according to item 2157, wherein a and/or b and/or P is of human origin.
2251. The method according to item 2157, wherein a and/or b and/or P is of mouse origin.
2252. The method according to item 2157, wherein a and/or b and/or P is of primate origin.
2253. The method according to item 2157, wherein a and/or b and/or P is of chimpanzee origin.
2254. The method according to item 2157, wherein a and/or b and/or P is of gorilla origin.
2255. The method according to item 2157, wherein a and/or b and/or P is of orangutan origin.
2256. The method according to item 2157, wherein a and/or b and/or P is of monkey origin.
2257. The method according to item 2157, wherein a and/or b and/or P is of Macaque origin.
2258. The method according to item 2157, wherein a and/or b and/or P is of porcine (swine/pig) origin.
2259. The method according to item 2157, wherein a and/or b and/or P is of bovine (cattle/antelopes) origin.
2260. The method according to item 2157, wherein a and/or b and/or P is of equine (horse) origin.
2261. The method according to item 2157, wherein a and/or b and/or P is of Camelides (camels) origin.
2262. The method according to item 2157, wherein a and/or b and/or P is of ruminant origin.
2263. The method according to item 2157, wherein a and/or b and/or P is of Canine (Dog) origin.
2264. The method according to item 2157, wherein a and/or b and/or P is of Feline (Cat) origin.
2265. The method according to item 2157, wherein a and/or b and/or P is of Bird origin.
2266. The method according to item 2157, wherein a and/or b and/or P is of Chicken origin.
2267. The method according to item 2157, wherein a and/or b and/or P is of Turkey origin.
2268. The method according to item 2157, wherein a and/or b and/or P is of Fish origin.
2269. The method according to item 2157, wherein a and/or b and/or P is of Reptile origin.
2270. The method according to item 2157, wherein a and/or b and/or P is of Amphibian origin.
2271. The method according to item 2157, wherein (a-b-P) is a class 1 MHC-peptide complex.
2272. The method according any of the items 2157 to 2271, wherein (a-b-P) is a class 2 MHC-peptide complex.
2273. The method according any of the items 2157 to 2272, wherein the MHC protein is the same or different MHC proteins selected from the group of HLA classes consisting of
A*01010101B*070201Cw*010201E*01010101F*01010101G*01010101, A*01010102NB*070202Cw*010202E*01010102F*01010102G*01010102, A*010102B*070203Cw*010203E*01010103F*01010103G*01010103, A*010103B*070204Cw*010204E*01030101F*01010104G*01010104, A*010104B*0703Cw*0103E*01030102F*01010105G*01010105, A*0102B*0704Cw*0104E*010302F*01010106G*01010201, A*0103B*070501Cw*0105E*010303F*01010107G*01010202, A*0104NB*070502Cw*0106E*010304F*01010108G*010103, A*0106B*070503Cw*0107E*0104F*01010201G*010104, A*0107B*0706Cw*0108F*01010202G*010105, A*0108B*0707Cw*0109F*01010203G*010106, A*0109B*0708Cw*0110F*01010204G*010107, A*0110B*0709Cw*0111F*01010205G*010108, A*0111NB*0710Cw*0112F*01010301G*010109, A*0112B*0711Cw*0113F*01010302G*010110, A*0113B*0712Cw*020201F*01010303G*0102, A*0114B*0713Cw*020202F*01010304G*0103, A*0115NB*0714Cw*020203F*0102G*010401, A*0116NB*0715Cw*020205F*01030101G*010402, A*0117B*0716Cw*0203F*01030102G*010403, A*0118NB*0717Cw*0204F*0104G*0105N, A*0119B*0718Cw*0205G*0106, A*0120B*0719Cw*0206G*0107, A*02010101B*07200w*0207, A*02010102LB*0721Cw*0208, A*020102B*0722Cw*0209, A*020103B*0723Cw*0210, A*020104B*0724Cw*0211, A*020105B*0725Cw*0212, A*020106B*0726Cw*0213, A*020107B*0727Cw*0214, A*020108B*0728Cw*0215, A*020109B*0729Cw*0216, A*020110B*07300w*0217, A*020111B*0731Cw*030201, A*020112B*0732Cw*030202, A*0202B*0733Cw*030301,
A*020301B*0734Cw*030302,
A*020302B*0735Cw*030303,
A*0204B*0736Cw*030304,
A*0205B*0737Cw*030305,
A*020601B*0738Cw*030401,
A*020602B*0739Cw*030402,
A*020603B*07400w*030403,
A*0207B*0741Cw*030404,
A*0208B*0742Cw*030405, A*0209B*0743Cw*0305,
A*0210B*0744Cw*0306, A*0211B*0745Cw*0307,
A*0212B*0746Cw*0308, A*0213B*0747Cw*0309,
A*0214B*0748Cw*0310,
A*0215NB*0749NCw*031101,
A*0216B*07500w*031102, A*021701B*0751Cw*0312,
A*021702B*080101Cw*0313,
A*0218B*080102Cw*0314,
A*0219B*080103Cw*0315,
A*022001B*0802Cw*0316,
A*022002B*0803Cw*0317, A*0221B*0804Cw*0318,
A*0222B*0805Cw*0319, A*0224B*0806Cw*0320N,
A*0225B*0807Cw*0321, A*0226B*0808NCw*0322Q,
A*0227B*0809Cw*0323, A*0228B*0810Cw*0324,
A*0229B*0811Cw*0325, A*0230B*0812Cw*0326,
A*0231B*0813Cw*0327, A*0232NB*0814Cw*0328,
A*0233B*0815Cw*0329, A*0234B*0816Cw*0330,
A*023501B*0817Cw*0331,
A*023502B*0818Cw*0332, A*0236B*0819NCw*0333,
A*0237B*08200w*0334, A*0238B*0821Cw*0335,
A*0239B*0822Cw*04010101,
A*0240B*0823Cw*04010102,
A*0241B*0824Cw*040102,
A*0242B*0825Cw*040103,
A*0243NB*0826Cw*040104, A*0244B*0827Cw*0403,
A*0245B*0828Cw*040401,
A*0246B*0829Cw*040402, A*0247B*0830NCw*0405,
A*0248B*0831Cw*0406, A*0249B*1301Cw*0407,
A*0250B*130201Cw*0408,
A*0251B*130202Cw*0409N,
A*0252B*130203Cw*0410, A*0253NB*1303Cw*0411,
A*0254B*1304Cw*0412, A*0255B*1306Cw*0413,
A*0256B*1307NCw*0414, A*0257B*1308Cw*0415,
A*0258B*1309Cw*0416, A*0259B*1310Cw*0417,
A*0260B*1311Cw*0418, A*0261B*1312Cw*0419,
A*0262B*1313Cw*0420, A*0263B*1314Cw*0421,
A*0264B*1315Cw*0423, A*0265B*1316Cw*0424,
A*0266B*1317Cw*050101,
A*0267B*1401Cw*050102,
A*0268B*140201Cw*050103,
A*0269B*140202Cw*0502, A*0270B*1403Cw*0503,
A*0271B*1404Cw*0504, A*0272B*1405Cw*0505,
A*0273B*140601Cw*0506,
A*027401B*140602Cw*0507N,
A*027402B*1407NCw*0508,
A*0275B*15010101Cw*0509,
A*0276B*15010102NCw*0510,
A*0277B*150102Cw*0511,
A*0278B*150103Cw*0512,
A*0279B*150104Cw*0513, A*0280B*1502Cw*0514,
A*0281B*1503Cw*0515,
A*0282NB*1504Cw*06020101,
A*0283NB*1505Cw*06020102,
A*0284B*1506Cw*060202, A*0285B*1507Cw*0603,
A*0286B*1508Cw*0604, A*0287B*1509Cw*0605,
A*0288NB*1510Cw*0606, A*0289B*151101Cw*0607,
A*0290B*151102Cw*0608,
A*0291B*151103Cw*0609, A*0292B*1512Cw*0610,
A*0293B*1513Cw*0611, A*0294NB*1514Cw*0612,
A*0295B*1515Cw*0613, A*0296B*1516Cw*0614,
A*0297B*15170101Cw*070101,
A*0299B*15170102Cw*070102,
A*03010101B*151702Cw*070103,
A*03010102NB*1518Cw*070104,
A*03010103B*1519Cw*070105,
A*030102B*15200w*070106,
A*030103B*1521Cw*070107,
A*030104B*1523Cw*07020101,
A*030105B*1524Cw*07020102,
A*0302B*1525Cw*07020103,
A*0303NB*1526NCw*0703,
A*0304B*1527Cw*070401,
A*0305B*1528Cw*070402, A*0306B*1529Cw*0705,
A*0307B*15300w*0706, A*0308B*1531Cw*0707,
A*0309B*1532Cw*0708, A*0310B*1533Cw*0709,
A*0311NB*1534Cw*0710, A*0312B*1535Cw*0711,
A*0313B*1536Cw*0712, A*0314B*1537Cw*0713,
A*0315B*1538Cw*0714, A*0316B*1539Cw*0715,
A*0317B*15400w*0716, A*0318B*1542Cw*0717,
A*0319B*1543Cw*0718, A*0320B*1544Cw*0719,
A*0321NB*1545Cw*0720, A*0322B*1546Cw*0721,
A*0323B*1547Cw*0722, A*0324B*1548Cw*0723,
A*0325B*1549Cw*0724, A*0326B*15500w*0725,
A*110101B*1551Cw*0726,
A*110102B*1552Cw*0727,
A*110103B*1553Cw*0728,
A*110104B*1554Cw*0729,
A*110105B*1555Cw*0730,
A*110106B*1556Cw*0731,
A*110201B*1557Cw*0732N,
A*110202B*1558Cw*0733N, A*1103B*15600w*0734,
A*1104B*1561Cw*0735, A*1105B*1562Cw*0736,
A*1106B*1563Cw*0737, A*1107B*1564Cw*0738,
A*1108B*1565Cw*0739, A*1109B*1566Cw*0740,
A*1110B*1567Cw*0741, A*1111B*1568Cw*0742,
A*1112B*1569Cw*0743, A*1113B*15700w*0744,
A*1114B*1571Cw*0745, A*1115B*1572Cw*080101,
A*1116B*1573Cw*080102, A*1117B*1574Cw*0802,
A*1118B*1575Cw*0803, A*1301B*1576Cw*0804,
A*1120B*1577Cw*0805, A*1121NB*1578Cw*0806,
A*1122B*1579NCw*0807, A*1123B*15800w*0808,
A*1124B*1581Cw*0809, A*1125B*1582Cw*0810,
A*1126B*1583Cw*0811, A*1127B*1584Cw*0812,
A*1128B*1585Cw*0813, A*1129B*1586Cw*0814,
A*2301B*1587Cw*120201,
A*2302B*1588Cw*120202,
A*2303B*1589Cw*120203,
A*2304B*15900w*12030101,
A*2305B*1591Cw*12030102,
A*2306B*1592Cw*120302,
A*2307NB*1593Cw*120303,
A*2308NB*1594NCw*120304,
A*2309B*1595Cw*120401,
A*2310B*1596Cw*120402, A*2311NB*1597Cw*1205,
A*2312B*1598Cw*1206, A*2313B*1599Cw*1207,
A*2314B*9501Cw*1208,
A*24020101B*9502Cw*1209,
A*24020102LB*9503Cw*1210,
A*240202B*9504Cw*1211,
A*240203B*9505Cw*1212,
A*240204B*9506Cw*1213,
A*240205B*9507Cw*1214,
A*240206B*9508Cw*1215,
A*240207B*9509Cw*1216,
A*240208B*95100w*1217, A*240209B*9511NCw*1218,
A*240210B*9512Cw*1219,
A*240211B*9513Cw*140201,
A*240212B*9514Cw*140202,
A*240213B*9515Cw*140203,
A*240301B*9516Cw*140204,
A*240302B*9517Cw*1403, A*2404B*9518Cw*1404,
A*2405B*9519Cw*1405, A*2406B*95200w*1406,
A*2407B*9521Cw*1407N, A*2408B*9522Cw*1408,
A*2409NB*180101Cw*150201,
A*2410B*180102Cw*150202,
A*2411NB*180103Cw*150203,
A*2413B*1802Cw*1503, A*2414B*1803Cw*1504,
A*2415B*1804Cw*150501,
A*2417B*1805Cw*150502,
A*2418B*1806Cw*150503,
A*2419B*1807Cw*150504, A*2420B*1808Cw*1506,
A*2421B*1809Cw*1507, A*2422B*1810Cw*1508,
A*2423B*1811Cw*1509, A*2424B*1812Cw*1510,
A*2425B*1813Cw*1511, A*2426B*1814Cw*1512,
A*2427B*1815Cw*1513, A*2428B*1817NCw*1514,
A*2429B*1818Cw*1515, A*2430B*1819Cw*1516,
A*2431B*18200w*1517, A*2432B*1821Cw*160101,
A*2433B*1822Cw*160102, A*2434B*1823NCw*1602,
A*2435B*1824Cw*160401, A*2436NB*2701Cw*1606,
A*2437B*2702Cw*1607, A*2438B*2703Cw*1608,
A*2439B*270401Cw*1609,
A*2440NB*270402Cw*1701,
A*2441B*270502Cw*1702,
A*2442B*270503Cw*1703,
A*2443B*270504Cw*1704,
A*2444B*270505Cw*1801,
A*2445NB*270506Cw*1802, A*2446B*270507,
A*2447B*270508, A*2448NB*270509, A*2449B*2706,
A*2450B*2707, A*2451B*2708, A*2452B*2709,
A*2453B*2710, A*2454B*2711, A*2455B*2712,
A*2456B*2713, A*2457B*2714, A*2458B*2715,
A*2459B*2716, A*2460NB*2717, A*2461B*2718,
A*2462B*2719, A*2463B*2720, A*2464B*2721,
A*2465B*2723, A*2466B*2724, A*2467B*2725,
A*2468B*2726, A*250101B*2727, A*250102B*2728,
A*2502B*2729, A*2503B*2730, A*2504B*2731,
A*2505B*2732, A*2506B*2733, A*260101B*2734,
A*260102B*2735, A*260103B*2736,
A*260104B*350101, A*2602B*350102,
A*2603B*350103, A*2604B*350104,
A*2605B*350105, A*2606B*350106,
A*260701B*350201, A*260702B*350202,
A*2608B*3503, A*2609B*350401, A*2610B*350402,
A*2611NB*3505, A*2612B*3506, A*2613B*3507,
A*2614B*350801, A*2615B*350802,
A*2616B*350901, A*2617B*350902, A*2618B*3510,
A*2619B*3511, A*2620B*3512, A*2621B*3513,
A*2622B*351401, A*2623B*351402, A*2624B*3515,
A*2625NB*3516, A*2626B*3517, A*2627B*3518,
A*2628B*3519, A*2629B*3520, A*2630B*3521,
A*2631B*3522, A*2632B*3523, A*2633B*3524,
A*2634B*3525, A*29010101B*3526,
A*29010102NB*3527, A*290201B*3528,
A*290202B*3529, A*290203B*3530, A*2903B*3531,
A*2904B*3532, A*2905B*3533, A*2906B*3534,
A*2907B*3535, A*2908NB*3536, A*2909B*3537,
A*2910B*3538, A*2911B*3539, A*2912B*3540N,
A*2913B*3541, A*2914B*3542, A*2915B*3543,
A*2916B*3544, A*300101B*3545, A*300102B*3546,
A*300201B*3547, A*300202B*3548,
A*300203B*3549, A*3003B*3550, A*3004B*3551,
A*3006B*3552, A*3007B*3553N, A*3008B*3554,
A*3009B*3555, A*3010B*3556, A*3011B*3557,
A*3012B*3558, A*3013B*3559, A*3014LB*3560,
A*3015B*3561, A*3016B*3562, A*3017B*3563,
A*3018B*3564, A*3019B*3565Q, A*310102B*3566,
A*3102B*3567, A*3103B*3568, A*3104B*3569,
A*3105B*3570, A*3106B*3571, A*3107B*3572,
A*3108B*370101, A*3109B*370102,
A*3110B*370103, A*3111B*370104, A*3112B*3702,
A*3113B*3703N, A*3114NB*3704, A*3115B*3705,
A*3201B*3706, A*3202B*3707, A*3203B*3708,
A*3204B*3709, A*3205B*3710, A*3206B*3711,
A*3207B*3712, A*3208B*380101, A*3209B*380102,
A*3210B*380201, A*3211QB*380202, A*3212B*3803,
A*3213B*3804, A*3214B*3805, A*3301B*3806,
A*330301B*3807, A*330302B*3808, A*3304B*3809,
A*3305B*3810, A*3306B*3811, A*3307B*3812,
A*3308B*3813, A*3309B*3814, A*3401B*3815,
A*3402B*39010101, A*3403B*39010102L,
A*3404B*390103, A*3405B*390104,
A*3406B*390201, A*3407B*390202, A*3408B*3903,
A*3601B*3904, A*3602B*3905, A*3603B*390601,
A*3604B*390602, A*4301B*3907, A*6601B*3908,
A*6602B*3909, A*6603B*3910, A*6604B*3911,
A*6605B*3912, A*6606B*391301,
A*680101B*391302, A*680102B*3914,
A*680103B*3915, A*680104B*3916,
A*680105B*3917, A*68020101B*3918,
A*68020102B*3919, A*680301B*3920,
A*680302B*3922, A*6804B*3923, A*6805B*3924,
A*6806B*3925N, A*6807B*3926, A*6808B*3927,
A*6809B*3928, A*6810B*3929, A*6811NB*3930,
A*6812B*3931, A*6813B*3932, A*6814B*3933,
A*6815B*3934, A*6816B*3935, A*6817B*3936,
A*6818NB*3937, A*6819B*3938Q, A*6820B*3939,
A*6821B*3940N, A*6822B*3941, A*6823B*400101,
A*6824B*400102, A*6825B*400103,
A*6826B*400104, A*6827B*400105,
A*6828B*400201, A*6829B*400202,
A*6830B*400203, A*6831B*4003, A*6832B*4004,
A*6833B*4005, A*6834B*40060101,
A*6835B*40060102, A*6836B*400602,
A*6901B*4007, A*7401B*4008, A*7402B*4009,
A*7403B*4010, A*7404B*4011, A*7405B*4012,
A*7406B*4013, A*7407B*401401, A*7408B*401402,
A*7409B*401403, A*7410B*4015, A*7411B*4016,
A*7412NB*4018, A*8001B*4019, A*9201B*4020,
A*9202B*4021, A*9203B*4022N, A*9204B*4023,
A*9205B*4024, A*9206B*4025, A*9207B*4026,
A*9208B*4027, A*9209B*4028, B*4029, B*4030,
B*4031, B*4032, B*4033, B*4034, B*4035, B*4036,
B*4037, B*4038, B*4039, B*4040, B*4042, B*4043,
B*4044, B*4045, B*4046, B*4047, B*4048, B*4049,
B*4050, B*4051, B*4052, B*4053, B*4054, B*4055,
B*4056, B*4057, B*4058, B*4059, B*4060, B*4061,
B*4062, B*4063, B*4064, B*4065, B*4066, B*4067,
B*4068, B*4069, B*4070, B*4101, B*4102, B*4103,
B*4104, B*4105, B*4106, B*4107, B*4108, B*4201,
B*4202, B*4204, B*420501, B*420502, B*4206,
B*4207, B*4208, B*4209, B*44020101, B*44020102S,
B*440202, B*440203, B*440204, B*440301, B*440302,
B*4404, B*4405, B*4406, B*4407, B*4408, B*4409,
B*4410, B*4411, B*4412, B*4413, B*4414, B*4415,
B*4416, B*4417, B*4418, B*4419N, B*4420, B*4421,
B*4422, B*4423N, B*4424, B*4425, B*4426, B*4427,
B*4428, B*4429, B*4430, B*4431, B*4432, B*4433,
B*4434, B*4435, B*4436, B*4437, B*4438, B*4439, B*4440, B*4441, B*4442, B*4443, B*4444, B*4445, B*4446, B*4447, B*4448, B*4449, B*4450, B*4451, B*4501, B*4502, B*4503, B*4504, B*4505, B*4506, B*4507, B*460101, B*460102, B*4602, B*4603, B*4604, B*4605, B*4606, B*4607N, B*4608, B*4609, B*47010101, B*47010102, B*4702, B*4703, B*4704, B*4705, B*4801, B*4802, B*480301, B*480302, B*4804, B*4805, B*4806, B*4807, B*4808, B*4809, B*4810, B*4811, B*4812, B*4813, B*4814, B*4815, B*4816, B*4901, B*4902, B*4903, B*4904, B*4905, B*5001, B*5002, B*5004, B*510101, B*510102, B*510103, B*510104, B*510105, B*510106, B*510107, B*510201, B*510202, B*5103, B*5104, B*5105, B*5106, B*5107, B*5108, B*5109, B*5110, B*5111N, B*5112, B*511301, B*511302, B*5114, B*5115, B*5116, B*5117, B*5118, B*5119, B*5120, B*5121, B*5122, B*5123, B*5124, B*5126, B*5127N, B*5128, B*5129, B*5130, B*5131, B*5132, B*5133, B*5134, B*5135, B*5136, B*5137, B*5138, B*5139, B*5140, B*5141N, B*5142, B*5143, B*5144N, B*5145, B*5146, B*520101, B*520102, B*520103, B*520104, B*5202, B*5203, B*5204, B*5205, B*5206, B*5207, B*5208, B*5209, B*5210, B*530101, B*530102, B*530103, B*530104, B*5302, B*5303, B*5304, B*5305, B*5306, B*5307, B*5308, B*5309, B*5310, B*5311, B*5312, B*5401, B*5402, B*5403, B*5404, B*5405N, B*5406, B*5407, B*5408N, B*5409, B*5410, B*5411, B*5412, B*550101, B*550102, B*550103, B*550104, B*550201, B*550202, B*5503, B*5504, B*5505, B*5507, B*5508, B*5509, B*5510, B*5511, B*5512, B*5513, B*5514, B*5515, B*5516, B*5517, B*5518, B*5519, B*5520, B*5521, B*5522, B*5523, B*5524, B*5601, B*5602, B*5603, B*5604, B*560501, B*560502, B*5606, B*5607, B*5608, B*5609, B*5610, B*5611, B*5612, B*5613, B*5614, B*5615, B*5616, B*5617, B*5618, B*5619N, B*570101, B*570102, B*570103, B*5702, B*570301, B*570302, B*5704, B*5705, B*5706, B*5707, B*5708, B*5709, B*5710, B*5711, B*5801, B*5802, B*5804, B*5805, B*5806, B*5807, B*5808, B*5809, B*5810N, B*5811, B*5812, B*5813, B*5814, B*5901, B*5902, B*670101, B*670102, B*6702, B*7301, B*7801, B*780201, B*780202, B*7803, B*7804, B*7805, B*8101, B*8102, B*8201, B*8202, B*8301, H*01010101J*01010101K*01010101L*01010101P*01010101, H*01010102J*01010102K*01010102L*01010102P*01010102, H*01010103J*01010103K*01010103L*01010103P*02010101, H*0102J*01010104K*01010104L*010102P*02010102, H*02010101J*01010105K*0102L*0102, H*02010102J*01010106K*0103, H*0202J*01010107, H*0203J*01010108, H*0204J*0201, H*0205, H*0206 and H*0301.

2274. The method according any of the items 2157 to 2273, wherein the MHC protein is the same or different MHC proteins selected from the group of HLA classes consisting of A*0201, C*0701, A*0101, A*0301, C*0702, C*0401, B*4402, B*0702, B*0801, C*0501, C*0304, C*0602, A*1101, B*4001, A*2402, B*3501, C*0303, B*5101, C*1203, B*1501, A*2902, A*2601, A*3201, C*0802, A*2501, B*5701, B*1402, C*0202, B*1801, B*4403, C*0401, C*0701, C*0602, A*0201, A*2301, C*0202, A*0301, C*0702, B*5301, B*0702, C*1601, B*1503, B*5801, A*6802, C*1701, B*4501, B*4201, A*3001, B*3501, A*0101, C*0304, A*3002, B*0801, A*3402, A*7401, A*3303, C*1801, A*2902, B*4403, B*4901, A*0201, C*0401, A*2402, C*0702, C*0701, C*0304, A*0301, B*0702, B*3501, C*0602, C*0501, A*0101, A*1101, B*5101, C*1601, B*4403, C*0102, A*2902, C*0802, B*1801, A*3101, B*5201, B*1402, C*0202, C*1203, A*2601, A*6801, B*0801, A*3002, B*4402, A*1101, A*2402, C*0702, C*0102, A*3303, C*0801, C*0304, A*0201, B*4001, C*0401, B*5801, B*4601, B*5101, C*0302, B*3802, A*0207, B*1501, A*0206, C*0303, B*1502, A*0203, B*4403, C*1402, B*3501, C*0602, B*5401, B*1301, B*4002, B*5502, A*2601.

2275. The method according any of the items 2157 to 2271, wherein the MHC multimer comprises one or more covalently attached labels.

2276. The method according any of the items 2157 to 2271, wherein the MHC multimer comprises one or more non-covalently attached labels.

2277. The method according to item 2275, wherein the one or more labels is covalently attached to the polypeptide a.

2278. The method according to item 2275, wherein the one or more labels is covalently attached to the polypeptide b.

2279. The method according to item 2275, wherein the one or more labels is covalently attached to the peptide P.

2280. The method according to item 2275, wherein the one or more labels is covalently attached to the one or more multimerization domains.

2281. The method according to item 2275, wherein the one or more labels is covalently attached to $(a-b-P)_n$.

2282. The method according to item 2276, wherein the one or more labels is non-covalently attached to the polypeptide a.

2283. The method according to item 2276, wherein the one or more labels is non-covalently attached to the polypeptide b.

2284. The method according to item 2276, wherein the one or more labels is non-covalently attached to P.

2285. The method according to item 2276, wherein the one or more labels is non-covalently attached to the one or more multimerization domains.

2286. The method according to item 2276, wherein the one or more labels is non-covalently attached to $(a-b-P)_n$.

2287. The method according to item 2276, wherein the one or more labels is non-covalently attached to the antibody in the multimerization domain.

2288. The method according to item 2275, wherein the one or more labels is covalently attached to an antibody in the multimerization domain.

2289. The method according to item 2276, wherein the one or more labels is non-covalently attached to an aptamer in the multimerization domain.

2290. The method according to item 2275, wherein the one or more labels is covalently attached to an aptamer in the multimerization domain.

2291. The method according to item 2276, wherein the one or more labels is non-covalently attached to a molecule in the multimerization domain.

2292. The method according to item 2275, wherein the one or more labels is covalently attached to a molecule in the multimerization domain.

2293. The method according to item 2276, wherein the one or more labels is non-covalently attached to a protein in the multimerization domain.

2294. The method according to item 2275, wherein the one or more labels is covalently attached to a protein in the multimerization domain.

2295. The method according to item 2276, wherein the one or more labels is non-covalently attached to a sugar residue in the multimerization domain.

2296. The method according to item 2275, wherein the one or more labels is covalently attached to a sugar residue in the multimerization domain.

2297. The method according to item 2276, wherein the one or more labels is non-covalently attached to a DNA in the multimerization domain.

2298. The method according to item 2275, wherein the one or more labels is covalently attached to a DNA in the multimerization domain.

2299. The method according to any of the items 2275 to 2298, wherein the attachment is directly between reactive groups in the labelling molecule and reactive groups in the marker molecule.

2300. The method according to any of the items 2275 to 2298, wherein the attachment is through a linker connecting labelling molecule and marker.

2301. The method according to any of the items 2275 to 2300, wherein one label is used.

2302. The method according to any of the items 2275 to 2300, wherein more than one label is used.

2303. The method according to item 2302, wherein the more than one label are all identical.

2304. The method according to item 2302, wherein at least two labels are different.

2305. The method according to any of the items 2275 to 2304, wherein the one or more labels is attached to $(a-b-P)_n$ via a streptavidin-biotin linkage.

2306. The method according to any of the items 2275 to 2304, wherein the one or more labels is a fluorophore label.

2307. The method according to item 2306, wherein the one or more fluorophore label are selected from the group of fluorescein isothiocyanate, rhodamine, phycoerythrin, phycocyanin, allophycocyanin, o-phthaldehyde and fluorescamine.

2308. The method according to item 2306, wherein the one or more fluorophore label are selected from the group consisting of 2-(4'-maleimidylanilino)naphthalene-6-sulfonic acid, sodium salt.

2309. The method according to item 2306, wherein the one or more fluorophore label are selected from the group consisting of 5-((((2-iodoacetyl)amino)ethyl)amino) naphthalene-1-sulfonic acid.

2310. The method according to item 2306, wherein the one or more fluorophore label are selected from the group consisting of Pyrene-1-butanoic acid.

2311. The method according to item 2306, wherein the one or more fluorophore label are selected from the group consisting of AlexaFluor 350 (7-amino-6-sulfonic acid-4-methyl coumarin-3-acetic acid.

2312. The method according to item 2306, wherein the one or more fluorophore label are selected from the group consisting of AMCA (7-amino-4-methyl coumarin-3-acetic acid.

2313. The method according to item 2306, wherein the one or more fluorophore label are selected from the group consisting of 7-hydroxy-4-methyl coumarin-3-acetic acid.

2314. The method according to item 2306, wherein the one or more fluorophore label are selected from the group consisting of Marina Blue (6,8-difluoro-7-hydroxy-4-methyl coumarin-3-acetic acid.

2315. The method according to item 2306, wherein the one or more fluorophore label are selected from the group consisting of 7-dimethylamino-coumarin-4-acetic acid.

2316. The method according to item 2306, wherein the one or more fluorophore label are selected from the group consisting of Fluorescamin-N-butyl amine adduct.

2317. The method according to item 2306, wherein the one or more fluorophore label are selected from the group consisting of 7-hydroxy-coumarine-3-carboxylic acid.

2318. The method according to item 2306, wherein the one or more fluorophore label are selected from the group consisting of Cascade Blue (pyrene-trisulphonic acid acetyl azide.

2319. The method according to item 2306, wherein the one or more fluorophore label are selected from the group consisting of Cascade Yellow.

2320. The method according to item 2306, wherein the one or more fluorophore label are selected from the group consisting of Pacific Blue (6,8 difluoro-7-hydroxy coumarin-3-carboxylic acid.

2321. The method according to item 2306, wherein the one or more fluorophore label are selected from the group consisting of 7-diethylamino-coumarin-3-carboxylic acid.

2322. The method according to item 2306, wherein the one or more fluorophore label are selected from the group consisting of N-(((4-azidobenzoyl)amino)ethyl)-4-amino-3,6-disulfo-1,8-naphthalimide, dipotassium salt.

2323. The method according to item 2306, wherein the one or more fluorophore label are selected from the group consisting of Alexa Fluor 430.

2324. The method according to item 2306, wherein the one or more fluorophore label are selected from the group consisting of 3-perylenedodecanoic acid.

2325. The method according to item 2306, wherein the one or more fluorophore label are selected from the group consisting of 8-hydroxypyrene-1,3,6-trisulfonic acid, trisodium salt.

2326. The method according to item 2306, wherein the one or more fluorophore label are selected from the group consisting of 12-(N-(7-nitrobenz-2-oxa-1,3-diazol-4-yl) amino)dodecanoic acid.

2327. The method according to item 2306, wherein the one or more fluorophore label are selected from the group consisting of N,N'-dimethyl-N-(iodoacetyl)-N'-(7-nitrobenz-2-oxa-1,3-diazol-4-yl)ethylenediamine.

2328. The method according to item 2306, wherein the one or more fluorophore label are selected from the group consisting of Oregon Green 488 (difluoro carboxy fluorescein).

2329. The method according to item 2306, wherein the one or more fluorophore label are selected from the group consisting of 5-iodoacetamidofluorescein.

2330. The method according to item 2306, wherein the one or more fluorophore label are selected from the group consisting of propidium iodide-DNA adduct.

2331. The method according to item 2306, wherein the one or more fluorophore label are selected from the group consisting of Carboxy fluorescein.

2332. The method according to any of items 2275-2305, wherein the one or more labels is a fluorescent label.

2333. The method according to item 2332, wherein the one or more fluorescent label is a simple fluorescent label.

2334. The method according to item 2333, wherein the one or more simple fluorescent label is selected from the group Fluor dyes, Pacific Blue™, Pacific Orange™, Cascade Yellow™.

2335. The method according to item 2333, wherein the one or more simple fluorescent label is selected from the group AlexaFluor® (AF), AF405, AF488, AF500, AF514, AF532, AF546, AF555, AF568, AF594, AF610, AF633, AF635, AF647, AF680, AF700, AF710, AF750, AF800.

2336. The method according to item 2333, wherein the one or more simple fluorescent label is selected from the group Quantum Dot based dyes, QDot® Nanocrystals (Invitrogen, MolecularProbs), Qdot®525, Qdot®565, Qdot®585, Qdot®605, Qdot®655, Qdot®705, Qdot®800.

2337. The method according to item 2333, wherein the one or more simple fluorescent label is selected from the group DyLight™ Dyes (Pierce) (DL); DL549, DL649, DL680, DL800.

2338. The method according to item 2333, wherein the one or more simple fluorescent label is selected from the group Fluorescein (Flu) or any derivate of that, such as FITC.

2339. The method according to item 2333, wherein the one or more simple fluorescent label is selected from the group Cy-Dyes, Cy2, Cy3, Cy3.5, Cy5, Cy5.5, Cy7.

2340. The method according to item 2333, wherein the one or more simple fluorescent label is selected from the group Fluorescent Proteins, RPE, PerCp, APC, Green fluorescent proteins; GFP and GFP derivated mutant proteins; BFP, CFP, YFP, DsRed, T1, Dimer2, mRFP1, MBanana, mOrange, dTomato, tdTomato, mTangerine, mStrawberry, mCherry.

2341. The method according to item 2333, wherein the one or more simple fluorescent label is selected from the group Tandem dyes, RPE-Cy5, RPE-Cy5.5, RPE-Cy7, RPE-AlexaFluor® tandem conjugates; RPE-Alexa610, RPE-TxRed, APC-Aleca600, APC-Alexa610, APC-Alexa750, APC-Cy5, APC-Cy5.5.

2342. The method according to item 2333, wherein the one or more simple fluorescent label is selected from the group multi fluorochrome assemblies, Multiple fluorochromes attached to a polymer molecule, such as a peptide/protein, Dextrane, polysaccharide, any combination of the fluorescent dyes involving in generation of FRET (Fluorescence resonance energy transfer) based techniques.

2343. The method according to item 2333, wherein the one or more simple fluorescent label is selected from the group ionophors; ion chelating fluorescent props, props that change wavelength when binding a specific ion, such as Calcium, props that change intensity when binding to a specific ion, such as Calcium.

2344. The method according to any of items 2275 to 2305, wherein the one or more labels is capable of absorption of light.

2345. The method according to item 2344, wherein the one or more labels capable of absorption of light is a chromophore.

2346. The method according to item 2344, wherein the one or more labels capable of absorption of light is a dye.

2347. The method according to any of items 2275 to 2305, wherein the one or more labels is capable of emission of light after excitation.

2348. The method according to item 2347, wherein the one or more labels capable of emission of light is one or more fluorochromes.

2349. The method according to item 2348, wherein the one or more fluorochrome is selected from the AlexaFluor® (AF) family, which include AF®350, AF405, AF430, AF488, AF500, AF514, AF532, AF546, AF555, AF568, AF594, AF610, AF633, AF635, AF647, AF680, AF700, AF710, AF750 and AF800.

2350. The method according to item 2348, wherein the one or more fluorochrome is selected from the Quantum Dot (Qdot®) based dye family, which include Qdot®525, Qdot®565, Qdot®585, Qdot®605, Qdot®655, Qdot®705, Qdot®800.

2351. The method according to item 2348, wherein the one or more fluorochrome is selected from the DyLight™ Dyes (DL) family, which include DL549, DL649, DL680, DL800.

2352. The method according to item 2348, wherein the one or more fluorochrome is selected from the family of Small fluorescing dyes, which include FITC, Pacific Blue™, Pacific Orange™, Cascade Yellow™, Marina Blue™, DSred, DSred-2,7-AAD, TO-Pro-3.

2353. The method according to item 2348, wherein the one or more fluorochrome is selected from the family of Cy-Dyes, which include Cy2, Cy3, Cy3.5, Cy5, Cy5.5, Cy7.

2354. The method according to item 2348, wherein the one or more fluorochrome is selected from the family of Phycobili Proteins, which include R-Phycoerythrin (RPE), PerCP, Allophycocyanin (APC), B-Phycoerythrin, C-Phycocyanin.

2355. The method according to item 2348, wherein the one or more fluorochrome is selected from the family of Fluorescent Proteins, which include (E)GFP and GFP ((enhanced) green fluorescent protein) derived mutant proteins; BFP, CFP, YFP, DsRed, T1, Dimer2, mRFP1, MBanana, mOrange, dTomato, tdTomato, mTangerine.

2356. The method according to item 2348, wherein the one or more fluorochrome is selected from the family of Tandem dyes with RPE, which include RPE-Cy5, RPE-Cy5.5, RPE-Cy7, RPE-AlexaFluor® tandem conjugates; RPE-Alexa610, RPE-TxRed.

2357. The method according to item 2348, wherein the one or more fluorochrome is selected from the family of Tandem dyes with APC, which include APC-Aleca600, APC-Alexa610, APC-Alexa750, APC-Cy5, APC-Cy5.5.

2358. The method according to item 2348, wherein the one or more fluorochrome is selected from the family of Calcium dyes, which include Indo-1-$Ca^{2+}$ Indo-2-$Ca^{2+}$.

2359. The method according to any of items 2275 to 2305, wherein the one or more labels is capable of reflection of light.

2360. The method according to item 2359, wherein the one or more labels capable of reflection of light comprises gold.

2361. The method according to item 2359, wherein the one or more labels capable of reflection of light comprises plastic.

2362. The method according to item 2359, wherein the one or more labels capable of reflection of light comprises glass.

2363. The method according to item 2359, wherein the one or more labels capable of reflection of light comprises polystyrene.

2364. The method according to item 2359, wherein the one or more labels capable of reflection of light comprises pollen.

2365. The method according to any of items 2275 to 2305, wherein the one or more labels is a chemiluminescent label.

2366. The method according to item 2365, wherein the chemiluminescent labels is selected from the group luminol, isoluminol, theromatic acridinium ester, imidazole, acridinium salt and oxalate ester.

2367. The method according to any of items 2275 to 2305, wherein the one or more labels is a bioluminescent label.

2368. The method according to item 2367, wherein the bioluminescent labels is selected from the group luciferin, luciferase and aequorin.
2369. The method according to any of items 2275 to 2305, wherein the one or more labels is a radioactive label.
2370. The method according to item 2369, wherein the one or more radioactive labels is a radionuclide.
2371. The method according to item 2369 wherein the one or more radioactive labels is an isotope.
2372. The method according to item 2369, wherein the one or more radioactive labels comprises α rays.
2373. The method according to item 2369, wherein the one or more radioactive labels comprises β rays.
2374. The method according to item 2369, wherein the one or more radioactive labels comprises γ rays.
2375. The method according to any of items 2275 to 2305, wherein the one or more labels is detectable by NMR (nuclear magnetic resonance form paramagnetic molecules).
2376. The method according to any of items 2275 to 2305, wherein the one or more labels is an enzyme label.
2377. The method according to item 2376, wherein the enzyme catalyze a reaction between chemicals in the near environment of the labeling molecules, producing a light signal (chemi-luminescence).
2378. The method according to item 2376, wherein the enzyme catalyze a reaction between chemicals in the near environment of the labeling molecules, resulting in precipitation of chromophor dyes.
2379. The method according to item 2376, wherein the enzyme catalyze a reaction between chemicals in the near environment of the labeling molecules, resulting in precipitates that can be detected by an additional layer of detection molecules.
2380. The method according to item 2376, wherein the enzyme label is selected from the group peroxidases, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.
2381. The method according to item 2376, wherein the enzyme label is horseradish peroxidase.
2382. The method according to item 2376, wherein the enzyme label is horseradish peroxidase and the substrate is diaminobenzidine (DAB).
2383. The method according to item 2376, wherein the enzyme label is horseradish peroxidase and the substrate is 3-amino-9-ethyl-carbazole (AEC+).
2384. The method according to item 2376, wherein the enzyme label is horseradish peroxidase and the substrate is biotinyl tyramide.
2385. The method according to item 2376, wherein the enzyme label is horseradish peroxidase and the substrate is fluorescein tyramide.
2386. The method according to item 2376, wherein the enzyme label is alkaline phosphatase.
2387. The method according to item 2376, wherein the enzyme label is alkaline phosphatase and the substrate is Fast red dye.
2388. The method according to any of items 2275 to 2305, wherein the one or more labels is a ionophore or chelating chemical compound binding to specific ions such as $Ca^{2+}$.
2389. The method according to any of items 2275 to 2305, wherein the one or more labels is a lanthanide.
2390. The method according to item 2389, wherein the lanthanide comprises fluorescence.
2391. The method according to item 2389, wherein the lanthanide comprises Phosphorescence.
2392. The method according to item 2389, wherein the lanthanide is paramagnetic.
2393. The method according to any of items 2275 to 2305, wherein the one or more labels is a DNA fluorescing stain.
2394. The method according to item 2393, wherein the DNA fluorescing stain is Propidium iodide.
2395. The method according to item 2393, wherein the DNA fluorescing stain is Hoechst stain.
2396. The method according to item 2393, wherein the DNA fluorescing stain is DAPI.
2397. The method according to item 2393, wherein the DNA fluorescing stain is AMC.
2398. The method according to item 2393, wherein the DNA fluorescing stain is DraQ5™
2399. The method according to item 2393, wherein the DNA fluorescing stain is Acridine orange.
2400. The method according to item 2157, wherein the MHC-peptide complex (a-b-P) is attached to a multimerization domain comprising an avidin or streptavidin via a linkage comprising a biotin moiety.
2401. The method according to any of items 2157 to 2400, wherein P is chemically modified.
2402. The method according to any of items 2157 to 2400, wherein P is pegylated.
2403. The method according to any of items 2157 to 2400, wherein P is phosphorylated.
2404. The method according to any of items 2157 to 2400, wherein P is glycosylated.
2405. The method according to any of items 2157 to 2400, wherein one of the amino acid residues of the peptide P is substituted with another amino acid.
2406. The method according to any of items 2157 to 2400, wherein a and b are both full-length peptides.
2407. The method according to any of items 2157 to 2400, wherein a is a full-length peptide.
2408. The method according to any of items 2157 to 2400, wherein b is a full-length peptide.
2409. The method according to any of items 2157 to 2400, wherein a is truncated.
2410. The method according to any of items 2157 to 2400, wherein b is truncated.
2411. The method according to any of items 2157 to 2400, wherein a and b are both truncated.
2412. The method according to any of items 2157 to 2400, wherein a is covalently linked to b.
2413. The method according to any of items 2157 to 2400, wherein a is covalently linked to P.
2414. The method according to any of items 2157 to 2400, wherein b is covalently linked to P.
2415. The method according to any of items 2157 to 2400, wherein a, b and P are all covalently linked.
2416. The method according to any of items 2157 to 2400, wherein a is non-covalently linked to b.
2417. The method according to any of items 2157 to 2400, wherein a is non-covalently linked to P.
2418. The method according to any of items 2157 to 2400, wherein b is non-covalently linked to P.
2419. The method according to any of items 2157 to 2400, wherein a, b and P are all non-covalently linked.
2420. The method according to any of items 2157 to 2400, wherein a is not included in the (a-b-P) complex.
2421. The method according to any of items 2157 to 2400, wherein b is not included in the (a-b-P) complex.

2422. The method according to any of items 2157 to 2400, wherein P is not included in the (a-b-P) complex.
2423. The method according to any of items 2157 to 2400, wherein P consists of 8, 9, 10, 11, 12, 13, 14, 15, 16, 17, 18, 19, 20, 21, 22, 23, 24, 25, 26, 27, 28, 29, or 30 amino acids.
2424. The method according to any of items 2157 to 2400, wherein P consist of more than 30 amino acids such as/or more than 35, 40, 45, 50, 55, 60, 65, 70, 75, 80, 85, 90, 95 or 100 amino acids.
2425. The method according to any of items 2157 to 2400, wherein the MHC-peptide complex is linked to at least one of the one or more multimerization domains by a linker moiety.
2426. The method according to item 2425, wherein the MHC-peptide complex is linked to at least one of the one or more multimerization domains by a covalent linker moiety.
2427. The method according to items 2425 and 2426, wherein the linkage of at least one of the one or more multimerization domains and at least one MHC-peptide complexes is formed by a binding entity X attached to, or being part of, at least one of the one or more multimerization domains, and a binding entity Y attached to, or being part of at least one of the MHC-peptide complexes.
2428. The method according to item 2425 and 2426, wherein the linker moiety linking at least one of the one or more multimerization domains and the MHC-peptide complex comprises the linker moiety XY, wherein the linker moiety XY results from a reaction of the moiety X comprising one or more reactive groups and the moiety Y comprising one or more reactive groups, wherein at least some of said reactive groups are capable of reacting with each other.
2429. The method according to any of items 2427 and 2428, wherein the moiety X comprises a nucleophilic group.
2430. The method according to item 2429, wherein the nucleophilic group is selected from the group consisting of —NH$_2$, —OH, —SH, —NH—NH$_2$.
2431. The method according to item 2428, wherein the moiety Y comprises an electrophilic group.
2432. The method according to item 2431, wherein the electrophilic group is selected from the group consisting of CHO, COOH and CO.
2433. The method according to items 2425 and 2426, wherein at least one of the reactive groups on one of the moieties X and Y comprises a radical capable of reacting with a reactive group forming part of the other moiety.
2434. The method according to items 2425 and 2426, wherein X and Y comprises reactive groups natively associated with the one or more multimerization domains and/or the MHC-peptide complexes.
2435. The method according to items 2425 and 2426, wherein X and Y comprises reactive groups not natively associated with the one or more multimerization domains and/or the MHC-peptide complex.
2436. The method according to items 2425 and 2426, wherein the linker moiety forms a covalent link between at least one of the one or more multimerization domains and at least one of the MHC-peptide complexes.
2437. The method according to items 2425 and 2426, wherein the reactive groups of MHC-peptide complexes include amino acid side chains selected from the group —NH$_2$, —OH, —SH, and —NH—
2438. The method according to items 2434 and 2435, wherein the reactive groups of multimerization domains include hydroxyls of polysaccharides such as dextrans.
2439. The method according to items 2434 and 2435, wherein the reactive groups of multimerization domains are selected from the group amino acid side chains comprising —NH$_2$, —OH, —SH, and —NH— of polypeptides.
2440. The method according to items 2425 and 2426, wherein one of the polypeptides of the MHC-peptide complex is linked by a protein fusion to the multimerization domain.
2441. The method according to items 2425 and 2426, wherein one of the polypeptides of the MHC-peptide complex is linked by a protein fusion to the multimerization domain, wherein an acyl group and an amino group react to form an amide bond.
2442. The method according to item 2157, wherein one of the polypeptides of the MHC-peptide complex is a β2M polypeptide.
2443. The method according to item 2157, wherein one of the polypeptides of the MHC-peptide complex is a heavy chain polypeptide.
2444. The method according to item 2157, wherein the peptides P of the MHC-peptide complex is an antigenic peptide.
2445. The method according to item 2157, wherein one of the polypeptides of the MHC-peptide complex is linked by non-native reactive groups to the multimerization domain.
2446. The method according to item 2445, wherein the non-native reactive groups include reactive groups that are attached to the multimerization domain through association of a linker molecule comprising the reactive group.
2447. The method according to item 2445, wherein the non-native reactive groups include reactive groups that are attached to the MHC-peptide complex through association of a linker molecule comprising the reactive group.
2448. The method according to item 2157, wherein the multimerization domain comprises one or more nucleophilic groups.
2449. The method according to item 2448, wherein the nucleophilic group is selected from the group consisting of —NH$_2$, —OH, —SH, —CN, —NH—NH$_2$.
2450. The method according to item 2157, wherein the multimerization domain is selected from the group polysaccharides, polypeptides comprising e.g. lysine, serine, and cysteine.
2451. The method according to item 2157, wherein the multimerization domain comprises one or more electrophilic groups.
2452. The method according to item 2451, wherein the electrophilic group is selected from the group —COOH, —CHO, —CO, NHS-ester, tosyl-activated ester, and other activated esters, acid-anhydrides.
2453. The method according to item 2157, wherein reactive groups involved in forming an association between the multimerization domain and the MHC peptide complex are located on glutamate or aspartate residues, or on a vinyl sulfone activated dextran.
2454. The method according to item 2157, wherein the multimerization domain is associated with the MHC peptide complex by a radical reaction.
2455. The method according to item 2157, wherein the multimerization domain comprises one or more conjugated double bonds.

2456. The method according to item 2157, wherein the MHC-peptide complex comprises one or more nucleophilic groups.

2457. The method according to item 2456, wherein the nucleophilic group is selected from the group consisting of —NH$_2$, —OH, —SH, —CN, —NH—NH$_2$.

2458. The method according to item 2157, wherein the MHC-peptide complex comprises one or more electrophilic groups.

2459. The method according to item 2458, wherein the electrophilic group is selected from the group consisting of —COOH, —CHO, —CO, NHS-ester, tosyl-activated ester, and other activated esters, acid-anhydrides.

2460. The method according to item 2157, wherein the MHC-peptide complex comprises one or more radicals.

2461. The method according to item 2157, wherein the MHC-peptide complex comprises one or more conjugated double bonds.

2462. The method according to item 2209, wherein the multimerization domain comprising one or more beads further comprises a linker moiety.

2463. The method according to item 2462, wherein the linker is a flexible linker.

2464. The method according to item 2462, wherein the linker is a rigid linker.

2465. The method according to item 2462, wherein the linker is a water-soluble linker.

2466. The method according to item 2462, wherein the linker is a cleavable linker.

2467. The method according to item 2466, wherein the cleavable linker is cleavable at physiological conditions.

2468. The method according to item 2157, wherein the MHC-peptide complex is linked to at least one of the one or more multimerization domains by a non-covalent linker moiety.

2469. The method according to item 2468, wherein the non-covalent linkage comprises natural dimerization.

2470. The method according to item 2468, wherein the non-covalent linkage comprises protein-protein interactions.

2471. The method according to item 2470, wherein the protein-protein interactions comprises one or more Fos/Jun interactions.

2472. The method according to item 2470, wherein the protein-protein interactions comprises one or more Acid/Base coiled coil structure based interactions.

2473. The method according to item 2470, wherein the protein-protein interactions comprises one or more antibody/antigen interactions.

2474. The method according to item 2468, wherein the non-covalent linkage comprises polynucleotide-polynucleotide interactions.

2475. The method according to item 2468, wherein the non-covalent linkage comprises protein-small molecule interactions.

2476. The method according to item 2468, wherein the non-covalent linkage comprises combinations of non-covalent linker molecules.

2477. The method according to item 2468, wherein the non-covalent linkage comprises synthetic molecule-synthetic molecule interactions.

2478. The method according to item 2469, wherein the natural dimerization comprises antigen-antibody pairs.

2479. The method according to item 2469, wherein the natural dimerization comprises DNA-DNA interactions.

2480. The method according to item 2468, wherein the non-covalent linkage comprises natural interactions.

2481. The method according to item 2480, wherein the natural interaction comprises biotin and streptavidin.

2482. The method according to item 2209, wherein the bead is coated with streptavidin monomers, which in turn are associated with biotinylated MHC peptide complexes.

2483. The method according to item 2209, wherein the bead is coated with streptavidin tetramers each of which being independently associated with 0, 1, 2, 3, or 4 biotinylated MHC complexes.

2484. The method according to item 2209, wherein the bead is coated with polysaccharide, such as a polysaccharide comprising dextran moieties.

2485. The method according to item 2480, wherein the natural interaction comprises the interaction of MHC complexes (comprising full-length polypeptide chains, including the transmembrane portion) with the cell membrane of for example dendritic cells.

2486. The method according to item 2468, wherein the non-covalent linkage comprises artificial interactions.

2487. The method according to item 2486, wherein the artificial interaction comprises His$_6$ tag interacting with Ni-NTA.

2488. The method according to item 2486, wherein the artificial interaction comprises PNA-PNA.

2489. The method according to item 2468, wherein the non-covalent linkage comprises non-specific adsorption.

2490. The method according to item 2489, wherein the non-specific adsorption comprises adsorption of proteins onto surfaces.

2491. The method according to item 2468, wherein the non-covalent linkage comprises the pentamer structure.

2492. The method according to item 2468, wherein the non-covalent linkage comprises interactions selected from the group streptavidin/biotin, avidin/biotin, antibody/antigen, DNA/DNA, DNA/PNA, DNA/RNA, PNA/PNA, LNA/DNA, leucine zipper e.g. Fos/Jun, IgG dimeric protein, IgM multivalent protein, acid/base coiled-coil helices, chelate/metal ion-bound chelate, streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-transferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity).

2493. The method according to any of items 2157 to 2492 further comprising one or more molecules with adjuvant effect.

2494. The method according to any of items 2157 to 2492 further comprising one or more immune targets.

2495. The method according to any of item 2494, wherein the one or more immune targets is an antigen.

2496. The method according to any of items 2157 to 2494 further comprising one or more molecules with biological activity.

2497. The method according to item 2496, wherein the one or more molecules with biological activity comprises proteins such as MHC Class I-like proteins like MIC A, MIC B, CD1d, HLA E, HLA F, HLA G, HLA H, ULBP-1, ULBP-2, and ULBP-3.
2498. The method according to item 2496, wherein the one or more molecules with biological activity comprises co-stimulatory molecules such as CD2, CD3, CD4, CD5, CD8, CD9, CD27, CD28, CD30, CD69, CD134 (0X40), CD137 (4-1BB), CD147, CDw150 (SLAM), CD152 (CTLA-4), CD153 (CD30L), CD40L (CD154), NKG2D, ICOS, HVEM, HLA Class II, PD-1, Fas (CD95), FasL expressed on T and/or NK cells, CD40, CD48, CD58, CD70, CD72, B7.1 (CD80), B7.2 (CD86), B7RP-1, B7-H3, PD-L1, PD-L2, CD134L, CD137L, ICOSL, LIGHT expressed on APC and/or tumour cells.
2499. The method according to item 2496, wherein the one or more molecules with biological activity comprises cell modulating molecules such as CD16, NKp30, NKp44, NKp46, NKp80, 2B4, KIR, LIR, CD94/NKG2A, CD94/NKG2C expressed on NK cells, IFN-alpha, IFN-beta, IFN-gamma, IL-1, IL-2, IL-3, IL-4, IL-6, IL-7, IL-8, IL-10, IL-11, IL-12, IL-15, CSFs (colony-stimulating factors), vitamin D3, IL-2 toxins, cyclosporin, FK-506, rapamycin, TGF-beta, clotrimazole, nitrendipine, and charybdotoxin.
2500. The method according to item 2496, wherein the one or more molecules with biological activity comprises accessory molecules such as LFA-1, CD11a/18, CD54 (ICAM-1), CD106 (VCAM), and CD49a,b,c,d,e,f/CD29 (VLA-4).
2501. The method according to item 2496, wherein the one or more molecules with biological activity comprises one or more non-classical MHC complexes and other MHC-like molecules such as protein products of MHC Ib and MHC IIb genes, β2m-associated cell-surface molecules, HLA-E, HLA-G, HLA-F, HLA-H, MIC A, MIC B, ULBP-1, ULBP-2, ULBP-3, H2-M, H2-Q, H2-T, Rae, Non-classical MHC II molecules, protein products of MHC IIb genes, HLA-DM, HLA-DO, H2-DM, H2-DO, and/or CD1.
2502. The method according to item 2496, wherein the one or more molecules with biological activity comprises one or more artificial molecules capable of binding specific TCRs such as antibodies that bind TCRs including full length antibodies of isotype IgG, IgM, IgE, IgA and truncated versions of these, antibody fragments like Fab fragments and scFv as well as antibodies of antibody fragments displayed on various supramolecular structures or solid supports, including filamentous phages, yeast, mammalian cells, fungi, artificial cells or micelles, and beads with various surface chemistries.
2503. The method according to item 2496, wherein the one or more molecules with biological activity comprises one or more peptides that bind TCRs including one or more peptides composed of natural, non-natural and/or chemically modified amino acids with a length of 8-20 amino acid.
2504. The method according to item 2496, wherein the one or more molecules with biological activity comprises one or more aptamers such as natural nucleic acids (e.g. RNA and DNA) or unnatural nucleic acids (e.g. PNA, LNA, morpholinos) capable of binding TCR, said aptamer molecules consist of natural or modified nucleotides in various lengths.
2505. The method according to item 2496, wherein the one or more molecules with biological activity comprises one or more ankyrin repeat proteins or other repeat proteins.
2506. The method according to item 2496, wherein the one or more molecules with biological activity comprises one or more Avimers.
2507. The method according to item 2496, wherein the one or more molecules with biological activity comprises one or more small chemical molecules capable of binding TCR with a dissociation constant smaller than $10^{-3}$ M.
2508. The method according to item 2496, wherein the one or more molecules with biological activity comprises adhesion molecules such as ICAM-1, ICAM-2, GlyCAM-1, CD34, anti-LFA-1, anti-CD44, anti-beta7, chemokines, CXCR4, CCR5, anti-selectin L, anti-selectin E, and anti-selectin P.
2509. The method according to item 2496, wherein the one or more molecules with biological activity comprises toxic molecules selected from toxins, enzymes, antibodies, radioisotopes, chemiluminescent substances, bioluminescent substances, polymers, metal particles, and haptens, such as cyclophosphamide, methrotrexate, Azathioprine, mizoribine, 15-deoxuspergualin, neomycin, staurosporine, genestein, herbimycin A, *Pseudomonas* exotoxin A, saporin, Rituxan, Ricin, gemtuzumab ozogamicin, Shiga toxin, heavy metals like inorganic and organic mercurials, and FN18-CRM9, radioisotopes such as incorporated isotopes of iodide, cobalt, selenium, tritium, and phosphor, and haptens such as DNP, and digoxiginin.
2510. The method according to item 2496, wherein the one or more molecules with biological activity comprises antibodies such as monoclonal antibodies, polyclonal antibodies, recombinant antibodies, antibody derivatives or fragments thereof.
2511. The method according to any of items 2157 to 2510, wherein the MHC multimer further comprises one or more molecules with a cytotoxic effect.
2512. The method according to any of items 2157 to 2511, wherein the MHC multimer further comprises one or more molecules selected from the group consisting of enzymes, regulators of receptor activity, receptor ligands, immune potentiators, drugs, toxins, co-receptors, proteins, peptides, sugar moieties, lipid groups, nucleic acids including siRNA, nano particles, and small molecules.
2513. The method according to any of items 2157 to 2511, wherein the MHC multimer further comprises one or more molecules selected from the group consisting of HIV gp120, HIV-GAG gp 27, HSP70, and MHC class II proteins or peptides or combinations thereof.
2514. The method according to any of items 2157 to 2513, wherein the MHC multimer comprises a plurality of identical or different multimerization domains linked by a multimerization domain linking moiety,
wherein at least one of said multimerization domains is associated with (a-b-P)$_n$, wherein n>1,
wherein a and b together form a functional MHC protein capable of binding the peptide P,
wherein (a-b-P) is the MHC-peptide complex formed when the peptide P binds to the functional MHC protein.
2515. The method according to item 2514, wherein the plurality of identical or different multimerization domains is in the range of from 2 to 100, such as 2 to 5, 5 to 10, 10 to 20, 20 to 30, 30 to 40, 40 to 50, 50 to 60, 60 to 70, 70 to 80, 80 to 90, 90 to 100.
2516. The method according to item 2514, wherein the MHC multimer comprises a first multimerization domain linked to a second multimerization domain.
2517. The method according to item 2516, wherein the first multimerization domain and the second multimerization domain is independently selected from the group consisting of multimerization domains cited in any of items 2157 to 328.
2518. The method according to item 2516, wherein the association is a covalent linkage so that one or more of the n MHC-peptide complexes is covalently linked to the first multimerization domains.
2519. The method according to item 2516, wherein the association is a non-covalent association so that one or more of the n MHC-peptide complexes is non-covalently associated with the first multimerization domain.
2520. The method according to item 2516, wherein the first multimerization domain comprises one or more scaffolds.
2521. The method according to item 2516, wherein the first multimerization domain comprises one or more carriers.
2522. The method according to item 2516, wherein the first multimerization domain comprises at least one scaffold and at least one carrier.
2523. The method according to item 2516, wherein the first multimerization domain comprises one or more optionally substituted organic molecules.
2524. The method according to item 2523, wherein the optionally substituted organic molecule comprises one or more functionalized cyclic structures.
2525. The method according to item 2524, wherein the one or more functionalized cyclic structures comprises one or more optionally substituted benzene rings.
2526. The method according to item 2523, wherein the optionally substituted organic molecule comprises a scaffold molecule comprising at least three reactive groups, or at least three sites suitable for non-covalent attachment.
2527. The method according to item 2516, wherein the first multimerization domain comprises one or more biological cells, such as antigen presenting cells or dendritic cells.
2528. The method according to item 2527, wherein the one or more biological cells are alive and mitotic active.
2529. The method according to item 2527, wherein the one or more biological cells are alive and mitotic inactive e.g. as a result of irradiation and/or chemically treatment.
2530. The method according to item 2527, wherein the one or more biological cells are dead.
2531. The method according to item 2527, wherein the one or more biological cells have a natural expression of MHC (i.e. not stimulated).
2532. The method according to item 2527, wherein the one or more biological cells have to be induced/stimulated by e.g. Inf-γ to express MHC.
2533. The method according to item 2527, wherein the one or more biological cells are macrophages.
2534. The method according to item 2527, wherein the one or more biological cells are Kupfer cells.
2535. The method according to item 2527, wherein the one or more biological cells are Langerhans cells.
2536. The method according to item 2527, wherein the one or more biological cells are B-cells.
2537. The method according to item 2527, wherein the one or more biological cells are MHC expressing cells.
2538. The method according to item 2527, wherein the one or more biological cells are one or more transfected cells expressing MHC.
2539. The method according to item 2527, wherein the one or more biological cells are one or more hybridoma cells expressing MHC.
2540. The method according to item 2516, wherein the first multimerization domain comprises one or more cell-like structures.
2541. The method according to item 2540, wherein the one or more cell-like structures comprises one or more membrane-based structures carrying MHC-peptide complexes in their membranes such as micelles, liposomes, and other structures of membranes, and phages such as filamentous phages.
2542. The method according to item 2516, wherein the first multimerization domain comprises one or more membranes.
2543. The method according to item 2542, wherein the one or more membranes comprises liposomes or micelles.
2544. The method according to item 2516, wherein the first multimerization domain comprises one or more polymers.
2545. The method according to item 2544, wherein the one or more polymers are selected from the group consisting of the group consisting of polysaccharides.
2546. The method according to item 2545, wherein the polysaccharide comprises one or more dextran moieties.
2547. The method according to item 2516, wherein the first multimerization domain comprises one or more entities selected from the group consisting of an IgG domain, a coiled-coil polypeptide structure, a DNA duplex, a nucleic acid duplex, PNA-PNA, PNA-DNA, DNA-RNA.
2548. The method according to item 2516, wherein the first multimerization domain comprises an avidin, such as streptavidin.
2549. The method according to item 2516, wherein the first multimerization domain comprises an antibody.
2550. The method according to item 2549, wherein the antibody is selected from the group consisting of polyclonal antibody, monoclonal antibody, IgA, IgG, IgM, IgD, IgE, IgG1, IgG2, IgG3, IgG4, IgA1, IgA2, IgM1, IgM2, humanized antibody, humanized monoclonal antibody, chimeric antibody, mouse antibody, rat antibody, rabbit antibody, human antibody, camel antibody, sheep antibody, engineered human antibody, epitope-focused antibody, agonist antibody, antagonist antibody, neutralizing antibody, naturally-occurring antibody, isolated antibody, monovalent antibody, bispecific antibody, trispecific antibody, multispecific antibody, heteroconjugate antibody, immunoconjugates, immunoliposomes, labeled antibody, antibody fragment, domain antibody, nanobody, minibody, maxibody, diabody, fusion antibody.
2551. The method according to item 2516, wherein the first multimerization domain comprises one or more small organic scaffold molecules.
2552. The method according to item 2516, wherein the first multimerization comprises one or more further polypeptides in addition to a and b.
2553. The method according to item 2516, wherein the first multimerization comprises one or more protein complexes.
2554. The method according to item 2516, wherein the first multimerization comprises one or more beads.
2555. The method according to item 2516, wherein the first multimerization domain comprises one or more compounds selected from the group consisting of agarose, sepharose, resin beads, glass beads, pore-glass beads, glass particles coated with a hydrophobic polymer, chitosan-coated beads, SH beads, latex beads, spherical latex beads, allele-type beads, SPA bead, PEG-based resins, PEG-coated bead, PEG-encapsulated bead, polystyrene beads, magnetic polystyrene beads, glutathione agarose beads, magnetic bead, paramagnetic beads, protein A and/or protein G sepharose beads, activated carboxylic acid bead, macroscopic beads, microscopic beads, insoluble resin beads, silica-based resins, cellulosic resins, cross-linked agarose beads, polystyrene beads, cross-linked polyacrylamide resins, beads with iron cores, metal beads, dynabeads, Polymethylmethacrylate beads activated with NHS, streptavidin-agarose beads, polypropylene, polyethylene, dextran, nylon, amylases, natural and modified celluloses, nitrocellulose, polyacrylamides, gabbros, magnetite, polymers, oligomers, non-repeating moieties, polyethylene glycol (PEG), monomethoxy-PEG, mono-($C_1$-$C_{10}$)alkoxy-PEG, aryloxy-PEG, poly-(N-vinyl pyrrolidone)PEG, tresyl monomethoxy PEG, PEG propionaldehyde, bis-succinimidyl carbonate PEG, polystyrene bead crosslinked with divinylbenzene, propylene glycol homopolymers, a polypropylene oxide/ethylene oxide co-polymer, polyoxyethylated polyols (e.g., glycerol), polyvinyl alcohol, dextran, aminodextran, carbohydrate-based polymers, cross-linked dextran beads, polysaccharide beads, polycarbamate beads, divinyl sulfone activated polysaccharide, polystyrene beads that have been functionalized with tosyl-activated esters, magnetic polystyrene beads functionalized with tosyl-activated esters, streptavidin beads, streptaivdin-monomer coated beads, streptaivdin-tetramer coated beads, Streptavidin Coated Compel Magnetic beads, avidin coated beads, dextramer coated beads, divinyl sulfone-activated dextran, Carboxylate-modified bead, amine-modified beads, antibody coated beads, cellulose beads, grafted co-poly beads, poly-acrylamide beads, dimethylacrylamide beads optionally crosslinked with N—N'-bis-acryloylethylenediamine, hollow fiber membranes, fluorescent beads, collagen-agarose beads, gelatin beads, collagen-gelatin beads, collagen-fibronectin-gelatin beads, collagen beads, chitosan beads, collagen-chitosan beads, protein-based beads, hydrogel beads, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin and chitosan.

2556. The method according to item 2516, wherein the first multimerization domain comprises a dimerization domain.

2557. The method according to item 2516, wherein the first multimerization domain comprises a trimerization domain.

2558. The method according to item 2516, wherein the first multimerization domain comprises a tetramerization domain.

2559. The method according to item 2516, wherein the first multimerization domain comprises a pentamerization domain.

2560. The method according to item 2559, wherein the pentamerization domain comprises a coiled-coil polypeptide structure.

2561. The method according to item 2516, wherein the first multimerization domain comprises a hexamerization domain.

2562. The method according to item 2561, wherein the hexamerization domain comprises three IgG domains.

2563. The method according to item 2516, wherein the first multimerization domain comprises a polymer structure to which is attached one or more scaffolds.

2564. The method according to item 2563, wherein the polymer structure comprises a polysaccharide.

2565. The method according to item 2564, wherein the polysaccharide comprises one or more dextran moieties.

2566. The method according to item 2516, wherein the first multimerization domain comprises a polyamide and/or a polyethylene glycol and/or a polysaccharide and/or a sepharose.

2567. The method according to item 2516, wherein the first multimerization domain comprises a carboxy methyl dextran and/or a dextran polyaldehyde and/or a carboxymethyl dextran lactone and/or or a cyclodextrin.

2568. The method according to item 2516, wherein one or more labels is covalently attached to the first multimerization domain.

2569. The method according to item 2516, wherein one or more labels is non-covalently attached to the first multimerization domain.

2570. The method according to item 2569, wherein the one or more labels is non-covalently attached to an antibody in the first multimerization domain.

2571. The method according item 2568, wherein the one or more labels is covalently attached to an antibody in the first multimerization domain.

2572. The method according to item 2569, wherein the one or more labels is non-covalently attached to an aptamer in the first multimerization domain.

2573. The method according to item 2568, wherein the one or more labels is covalently attached to an aptamer in the first multimerization domain.

2574. The method according to item 2569, wherein the one or more labels is non-covalently attached to a molecule in the first multimerization domain.

2575. The method according to item 2568, wherein the one or more labels is covalently attached to a molecule in the first multimerization domain.

2576. The method according to item 2569, wherein the one or more labels is non-covalently attached to a protein in the first multimerization domain.

2577. The method according to item 2568, wherein the one or more labels is covalently attached to a protein in the first multimerization domain.

2578. The method according to item 2569, wherein the one or more labels is non-covalently attached to a sugar residue in the first multimerization domain.

2579. The method according to item 2568, wherein the one or more labels is covalently attached to a sugar residue in the first multimerization domain.

2580. The method according to item 2569, wherein the one or more labels is non-covalently attached to a DNA in the first multimerization domain.

2581. The method according to item 2568, wherein the one or more labels is covalently attached to a DNA in the first multimerization domain.

2582. The method according to any of the items 2568 to 2581, wherein the attachment is directly between reactive groups in the labelling molecule and reactive groups in the marker molecule.

2583. The method according to any of the items 2568 to 2581, wherein the attachment is through a linker connecting labelling molecule and marker.

2584. The method according to any of the items 2568 to 2583, wherein one label is used.

2585. The method according to any of the items 2568 to 2583, wherein more than one label is used.

2586. The method according to item 2585, wherein the more than one labels are all identical.

2587. The method according to item 2585, wherein at least two labels are different.

2588. The method according to any of items 2568 to 2587, wherein the one or more labels is a fluorophore.

2589. The method according to item 2588, wherein the one or more fluorophore label are selected from the group consisting of selected from the group fluorescein isothiocyanate, rhodamine, phycoerythrin, phycocyanin, allophycocyanin, o-phthaldehyde and fluorescamine.

2590. The method according to item 2588, wherein the one or more fluorophore label are selected from the group consisting of 2-(4'-maleimidylanilino)naphthalene-6-sulfonic acid, sodium salt 2591. The method according to item 2588, wherein the one or more fluorophore label are selected from the group consisting of 5-((((2-iodoacetyl)amino)ethyl)amino) naphthalene-1-sulfonic acid 2592. The method according to item 2588, wherein the one or more fluorophore label are selected from the group consisting of Pyrene-1-butanoic acid 2593. The method according to item 2588, wherein the one or more fluorophore label are selected from the group consisting of AlexaFluor 350 (7-amino-6-sulfonic acid-4-methyl coumarin-3-acetic acid 2594. The method according to item 2588, wherein the one or more fluorophore label are selected from the group consisting of AMCA (7-amino-4-methyl coumarin-3-acetic acid 2595. The method according to item 2588, wherein the one or more fluorophore label are selected from the group consisting of 7-hydroxy-4-methyl coumarin-3-acetic acid.

2596. The method according to item 2588, wherein the one or more fluorophore label are selected from the group consisting of Marina Blue (6,8-difluoro-7-hydroxy-4-methyl coumarin-3-acetic acid.

2597. The method according to item 2588, wherein the one or more fluorophore label are selected from the group consisting of 7-dimethylamino-coumarin-4-acetic acid.

2598. The method according to item 2588, wherein the one or more fluorophore label are selected from the group consisting of Fluorescamin-N-butyl amine adduct.

2599. The method according to item 2588, wherein the one or more fluorophore label are selected from the group consisting of 7-hydroxy-coumarine-3-carboxylic acid.

2600. The method according to item 2588, wherein the one or more fluorophore label are selected from the group consisting of Cascade Blue (pyrene-trisulphonic acid acetyl azide.

2601. The method according to item 2588, wherein the one or more fluorophore label are selected from the group consisting of Cascade Yellow.

2602. The method according to item 2588, wherein the one or more fluorophore label are selected from the group consisting of Pacific Blue (6,8 difluoro-7-hydroxy coumarin-3-carboxylic acid.

2603. The method according to item 2588, wherein the one or more fluorophore label are selected from the group consisting of 7-diethylamino-coumarin-3-carboxylic acid.

2604. The method according to item 2588, wherein the one or more fluorophore label are selected from the group consisting of N-(((4-azidobenzoyl)amino)ethyl)-4-amino-3,6-disulfo-1,8-naphthalimide, dipotassium salt.

2605. The method according to item 2588, wherein the one or more fluorophore label are selected from the group consisting of Alexa Fluor 430.

2606. The method according to item 2588, wherein the one or more fluorophore label are selected from the group consisting of 3-perylenedodecanoic acid.

2607. The method according to item 2588, wherein the one or more fluorophore label are selected from the group consisting of 8-hydroxypyrene-1,3,6-trisulfonic acid, trisodium salt.

2608. The method according to item 2588, wherein the one or more fluorophore label are selected from the group consisting of 12-(N-(7-nitrobenz-2-oxa-1,3-diazol-4-yl) amino)dodecanoic acid.

2609. The method according to item 2588, wherein the one or more fluorophore label are selected from the group consisting of N,N'-dimethyl-N-(iodoacetyl)-N'-(7-nitrobenz-2-oxa-1,3-diazol-4-yl)ethylenediamine.

2610. The method according to item 2588, wherein the one or more fluorophore label are selected from the group consisting of Oregon Green 488 (difluoro carboxy fluorescein).

2611. The method according to item 2588, wherein the one or more fluorophore label are selected from the group consisting of 5-iodoacetamidofluorescein.

2612. The method according to item 2588, wherein the one or more fluorophore label are selected from the group consisting of propidium iodide-DNA adduct.

2613. The method according to item 2588, wherein the one or more fluorophore label are selected from the group consisting of Carboxy fluorescein.

2614. The method according to any of items 2568 to 2587, wherein the one or more labels is a fluorescent label.

2615. The method according to item 2614, wherein the one or more fluorescent label is a simple fluorescent label.

2616. The method according to item 2615, wherein the one or more simple fluorescent label is selected from the group Fluor dyes, Pacific Blue™, Pacific Orange™, Cascade Yellow™.

2617. The method according to item 2615, wherein the one or more simple fluorescent label is selected from the group AlexaFluor® (AF), AF405, AF488, AF500, AF514, AF532, AF546, AF555, AF568, AF594, AF610, AF633, AF635, AF647, AF680, AF700, AF710, AF750, AF800.

2618. The method according to item 2615, wherein the one or more simple fluorescent label is selected from the group Quantum Dot based dyes, QDot® Nanocrystals (Invitrogen, MolecularProbs), Qdot®525, Qdot®565, Qdot®585, Qdot®605, Qdot®655, Qdot®705, Qdot®800.

2619. The method according to item 2615, wherein the one or more simple fluorescent label is selected from the group DyLight™ Dyes (Pierce) (DL); DL549, DL649, DL680, DL800.

2620. The method according to item 2615, wherein the one or more simple fluorescent label is selected from the group Fluorescein (Flu) or any derivate of that, such as FITC.

2621. The method according to item 2615, wherein the one or more simple fluorescent label is selected from the group Cy-Dyes, Cy2, Cy3, Cy3.5, Cy5, Cy5.5, Cy7.

2622. The method according to item 2615, wherein the one or more simple fluorescent label is selected from the group Fluorescent Proteins, RPE, PerCp, APC, Green fluorescent proteins; GFP and GFP derivated mutant proteins; BFP, CFP, YFP, DsRed, T1, Dimer2, mRFP1, MBanana, mOrange, dTomato, tdTomato, mTangerine, mStrawberry, mCherry.

2623. The method according to item 2615, wherein the one or more simple fluorescent label is selected from the group Tandem dyes, RPE-Cy5, RPE-Cy5.5, RPE-Cy7, RPE-AlexaFluor® tandem conjugates; RPE-Alexa610, RPE-TxRed, APC-Aleca600, APC-Alexa610, APC-Alexa750, APC-Cy5, APC-Cy5.5.

2624. The method according to item 2615, wherein the one or more simple fluorescent label is selected from the group multi fluorochrome assemblies, Multiple fluorochromes attached to a polymer molecule, such as a peptide/protein, Dextrane, polysaccharide, any combination of the fluorescent dyes involving in generation of FRET (Fluorescence resonance energy transfer) based techniques.

2625. The method according to item 2615, wherein the one or more simple fluorescent label is selected from the group ionophors; ion chelating fluorescent props, props that change wavelength when binding a specific ion, such as Calcium, props that change intensity when binding to a specific ion, such as Calcium.

2626. The method according to any of items 2568 to 2587, wherein the one or more labels is capable of absorption of light 2627. The method according to item 2626, wherein the one or more labels capable of absorption of light is a chromophore.

2628. The method according to item 2626, wherein the one or more labels capable of absorption of light is a dye.

2629. The method according to any of items 2568 to 2587, wherein the one or more labels is capable of emission of light after excitation 2630. The method according to item 2629, wherein the one or more labels capable of emission of light is one or more fluorochromes.

2631. The method according to item 2630, wherein the one or more fluorochrome is selected from the AlexaFluor® (AF) family, which include AF®350, AF405, AF430, AF488, AF500, AF514, AF532, AF546, AF555, AF568, AF594, AF610, AF633, AF635, AF647, AF680, AF700, AF710, AF750 and AF800

2632. The method according to item 2630, wherein the one or more fluorochrome is selected from the Quantum Dot (Qdot®) based dye family, which include Qdot®525, Qdot®565, Qdot®585, Qdot®605, Qdot®655, Qdot®705, Qdot®800

2633. The method according to item 2630, wherein the one or more fluorochrome is selected from the DyLight™ Dyes (DL) family, which include DL549, DL649, DL680, DL800

2634. The method according to item 2630, wherein the one or more fluorochrome is selected from the family of Small fluorescing dyes, which include FITC, Pacific Blue™, Pacific Orange™, Cascade Yellow™, Marina Blue™, DSred, DSred-2,7-AAD, TO-Pro-3.

2635. The method according to item 2630, wherein the one or more fluorochrome is selected from the family of Cy-Dyes, which include Cy2, Cy3, Cy3.5, Cy5, Cy5.5, Cy7

2636. The method according to item 2630, wherein the one or more fluorochrome is selected from the family of Phycobili Proteins, which include R-Phycoerythrin (RPE), PerCP, Allophycocyanin (APC), B-Phycoerythrin, C-Phycocyanin.

2637. The method according to item 2630, wherein the one or more fluorochrome is selected from the family of Fluorescent Proteins, which include (E)GFP and GFP ((enhanced) green fluorescent protein) derived mutant proteins; BFP, CFP, YFP, DsRed, T1, Dimer2, mRFP1, MBanana, mOrange, dTomato, tdTomato, mTangerine.

2638. The method according to item 2630, wherein the one or more fluorochrome is selected from the family of Tandem dyes with RPE, which include RPE-Cy5, RPE-Cy5.5, RPE-Cy7, RPE-AlexaFluor® tandem conjugates; RPE-Alexa610, RPE-TxRed.

2639. The method according to item 2630, wherein the one or more fluorochrome is selected from the family of Tandem dyes with APC, which include APC-Aleca600, APC-Alexa610, APC-Alexa750, APC-Cy5, APC-Cy5.5.

2640. The method according to item 2630, wherein the one or more fluorochrome is selected from the family of Calcium dyes, which include Indo-1-$Ca^{2+}$ Indo-2-$Ca^{2+}$.

2641. The method according to any of items 2568 to 2587, wherein the one or more labels is capable of reflection of light.

2642. The method according to item 2641, wherein the one or more labels capable of reflection of light comprises gold.

2643. The MHC multimer according to item 2641, wherein the one or more labels capable of reflection of light comprises plastic 2644. The MHC multimer according to item 2641, wherein the one or more labels capable of reflection of light comprises glass 2645. The MHC multimer according to item 2641, wherein the one or more labels capable of reflection of light comprises polystyrene 2646. The MHC multimer according to item 2641, wherein the one or more labels capable of reflection of light comprises pollen 2647. The method according to any of items 2568 to 2587, wherein the one or more labels is a chemiluminescent label.

2648. The method according to item 2647, wherein the chemiluminescent labels is selected from the group luminol, isoluminol, theromatic acridinium ester, imidazole, acridinium salt and oxalate ester.

2649. The method according to any of items 2568 to 2587, wherein the one or more labels is a bioluminescent label.

2650. The method according to item 2649, wherein the bioluminescent labels is selected from the group luciferin, luciferase and aequorin.

2651. The method according to any of items 2568 to 2587, wherein the one or more labels is a radioactive label.

2652. The method according to item 2651, wherein the one or more radioactive labels is a radionuclide.

2653. The method according to item 2651, wherein the one or more radioactive labels is an isotope.

2654. The method according to item 2651, wherein the one or more radioactive labels comprises α rays.

2655. The method according to item 2651, wherein the one or more radioactive labels comprises β rays.

2656. The method according to item 2651, wherein the one or more radioactive labels comprises γ rays.

2657. The method according to any of items 2568 to 2587, wherein the one or more labels is detectable by NMR (nuclear magnetic resonance form paramagnetic molecules)

2658. The method according to any of items 2568 to 2587, wherein the one or more labels is an enzyme label.

2659. The method according to item 2658, wherein the enzyme catalyzes a reaction between chemicals in the near environment of the labeling molecules, producing a light signal (chemi-luminescence).

2660. The method according to item 2658, wherein the enzyme catalyzes a reaction between chemicals in the near environment of the labeling molecules, resulting in precipitation of chromophor dyes.

2661. The method according to item 2658, wherein the enzyme catalyzes a reaction between chemicals in the near environment of the labeling molecules, resulting in precipitates that can be detected by an additional layer of detection molecules.

2662. The method according to item 2658, wherein the enzyme label is selected from the group peroxidases, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

2663. The method according to item 2658, wherein the enzyme label is horseradish peroxidase.

2664. The method according to item 2658, wherein the enzyme label is horseradish peroxidase and the substrate is diaminobenzidine (DAB).

2665. The method according to item 2658, wherein the enzyme label is horseradish peroxidase and the substrate is 3-amino-9-ethyl-carbazole (AEC+).

2666. The method according to item 2658, wherein the enzyme label is horseradish peroxidase and the substrate is biotinyl tyramide.

2667. The method according to item 2658, wherein the enzyme label is horseradish peroxidase and the substrate is fluorescein tyramide.

2668. The method according to item 2658, wherein the enzyme label is alkaline phosphatase.

2669. The method according to item 2658, wherein the enzyme label is alkaline phosphatase and the substrate is Fast red dye.

2670. The method according to any of items 2568 to 2587, wherein the one or more labels is a ionophore or chelating chemical compound binding to specific ions such as $Ca^{2+}$ 2671. The method according to any of items 2568 to 2587, wherein the one or more labels is a lanthanide.

2672. The method according to item 2671, wherein the lanthanide comprises fluorescence.

2673. The method according to item 2671, wherein the lanthanide comprises Phosphorescence.

2674. The method according to item 2671, wherein the lanthanide is paramagnetic.

2675. The method according to any of items 2568 to 2587, wherein the one or more labels is a DNA fluorescing stain.

2676. The method according to item 2675, wherein the DNA fluorescing stain is Propidium iodide.

2677. The method according to item 2675, wherein the DNA fluorescing stain is Hoechst stain.

2678. The method according to item 2675, wherein the DNA fluorescing stain is DAPI.

2679. The method according to item 2675, wherein the DNA fluorescing stain is AMC.

2680. The method according to item 2675, wherein the DNA fluorescing stain is DraQ5™

2681. The method according to item 2675, wherein the DNA fluorescing stain is Acridine orange.

2682. The method according to item 2514, wherein the MHC-peptide complex (a-b-P) is attached to the first multimerization domain comprising an avidin or streptavidin via a linkage comprising a biotin moiety.

2683. The method according to any of items 2514 to 2682, wherein the MHC-peptide complex is linked to the first multimerization domain by a first linker moiety.

2684. The method according to item 2683, wherein the MHC-peptide complex is linked to the first multimerization domain by a covalent linker moiety.

2685. The method according to items 2683 and 2684, wherein the association of the first multimerization domain and at least one MHC-peptide complexes is formed by a binding entity X attached to, or being part of, the first multimerization domain, and a binding entity Y attached to, or being part of at least one of the MHC-peptide complexes.

2686. The method according to items 2683 and 2684, wherein the linker moiety linking the first multimerization domain and the MHC-peptide complex comprises the linker moiety XY, wherein the linker moiety XY results from a reaction of the moiety X comprising one or more reactive groups and the moiety Y comprising one or more reactive groups, wherein at least some of said reactive groups are capable of reacting with each other.

2687. The method according to any of items 2685 and 2686, wherein the moiety X comprises a nucleophilic group.

2688. The method according to item 2687, wherein the nucleophilic group is selected from the group consisting of —$NH_2$, —OH, —SH, —NH—$NH_2$.

2689. The method according to any of items 2685 and 2686, wherein the moiety Y comprises an electrophilic group.

2690. The method according to item 2689, wherein the electrophilic group is selected from the group consisting of CHO, COOH and CO.

2691. The method according to items 2685 and 2686, wherein at least one reactive group on one of the moieties X and Y comprises a radical capable of reacting with a reactive group forming part of the other moiety.

2692. The method according to items 2685 and 2686, wherein X and Y comprises reactive groups natively associated with the first multimerization domain and/or the MHC-peptide complexes.

2693. The method according to items 2685 and 2686, wherein X and Y comprises reactive groups not natively associated with the first multimerization domain and/or the MHC-peptide complex.

2694. The method according to items 2683 and 2684, wherein the linker moiety forms a covalent link between the first multimerization domain and at least one of the MHC-peptide complexes.

2695. The method according to items 2685 and 2686, wherein the reactive groups of MHC-peptide complexes include amino acid side chains selected from the group consisting of —$NH_2$, —OH, —SH, and —NH—

2696. The method according to items 2685 and 2686, wherein the reactive groups of the first multimerization domain include hydroxyls of polysaccharides such as dextrans 2697. The method according to items 2685 and 2686, wherein the reactive groups of the first multimerization domain selected from the group consisting of amino acid side chains comprising —$NH_2$, —OH, —SH, and —NH— of polypeptides 2698. The method according to items 2683 and 2684, wherein one of the polypeptides of the MHC-peptide complex is linked by a protein fusion to the first multimerization domain 2699. The method according to items 2683 and 2684, wherein one of the polypeptides of the MHC-peptide complex is linked by a protein fusion to the first multimerization domain, wherein an acyl group and an amino group react to form an amide bond 2700. The method according to item 2514, wherein one of the polypeptides of the MHC-peptide complex is linked by non-native reactive groups to the first multimerization domain.

2701. The method according to item 2514, wherein the reactive groups include reactive groups that are attached to the first multimerization domain through association of a linker molecule comprising the reactive group.

2702. The method according to item 2514, wherein the reactive groups include reactive groups that are attached to the MHC-peptide complex through association of a linker molecule comprising the reactive group.

2703. The method according to item 2516, wherein the first multimerization domain comprises one or more nucleophilic groups 2704. The method according to item 2703, wherein the nucleophilic group is selected from the group consisting of —$NH_2$, —OH, —SH, —CN, —NH—$NH_2$ 2705. The method according to item 2516, wherein the first multimerization domain is selected from the group consisting of polysaccharides, polypeptides comprising e.g. lysine, serine, and cysteine.

2706. The method according to item 2516, wherein the first multimerization domain comprises one or more electrophilic groups.

2707. The method according to item 2706, wherein the electrophilic group is selected from the group consisting of —COOH, —CHO, —CO, NHS-ester, tosyl-activated ester, and other activated esters, acid-anhydrides.

2708. The method according to item 2516, wherein the first multimerization domain is selected from the group consisting of polypeptides comprising e.g. glutamate and aspartate, or vinyl sulfone activated dextran.

2709. The method according to item 2516, wherein the first multimerization domain comprises one or more radicals.

2710. The method according to item 2516, wherein the first multimerization domain comprises one or more conjugated double bonds.

2711. The method according to item 2516, wherein the first multimerization domain comprises one or more beads, further comprising a linker moiety 2712. The method according to any of the items 2683 to 2711, wherein the linker is a flexible linker.

2713. The method according to any of the items 2683 to 2711, wherein the linker is a rigid linker.

2714. The method according to any of the items 2683 to 2711, wherein the linker is a water-soluble linker.

2715. The method according to any of the items 2683 to 2711, wherein the linker is a cleavable linker.

2716. The method according to item 2715, wherein the cleavable linker is cleavable at physiological conditions.

2717. The method according to items 2683 or 2684, wherein the MHC-peptide complex is linked to the first multimerization domain by a non-covalent linker moiety.

2718. The method according to item 2717, wherein the non-covalent linkage comprises natural dimerization 2719. The method according to item 2718, wherein the natural dimerization comprises antigen-antibody pairs 2720. The method according to item 2718, wherein the natural dimerization comprises DNA-DNA interactions 2721. The method according to item 2717, wherein the non-covalent linkage comprises natural interactions 2722. The method according to item 2721, wherein the natural interaction comprises biotin and streptavidin 2723. The method according to item 2722, wherein the bead is coated with streptavidin monomers, which in turn are associated with biotinylated MHC complexes 2724. The method according to item 2554, wherein the bead is coated with streptavidin tetramers, each of which being independently associated with 0, 1, 2, 3, or 4 biotinylated MHC complexes 2725. The method according to item 2554, wherein the bead is coated with a polysaccharide, such as a polysaccharide comprising dextran moieties.

2726. The method according to item 2721, wherein the natural interaction comprises the interaction of MHC complexes (comprising full-length polypeptide chains, including the transmembrane portion) with the cell membrane of for example dendritic cells 2727. The method according to item 2717, wherein the non-covalent linkage comprises artificial interactions 2728. The method according to item 2727, wherein the artificial interaction comprises $His_6$ tag interacting with Ni-NTA 2729. The method according to item 2727, wherein the artificial interaction comprises PNA-PNA 2730. The method according to item 2717, wherein the non-covalent linkage comprises non-specific adsorption 2731. The method according to item 2730, wherein the non-specific adsorption comprises adsorption of proteins onto surfaces 2732. The method according to item 2717, wherein the non-covalent linkage comprises the pentamer structure 2733. The method according to item 2717, wherein the non-covalent linkage comprises interactions selected from the group streptavidin/biotin, avidin/biotin, antibody/antigen, DNA/DNA, DNA/PNA, DNA/RNA, PNA/PNA, LNA/DNA, leucine zipper e.g. Fos/Jun, IgG dimeric protein, IgM multivalent protein, acid/base coiled-coil helices, chelate/metal ion-bound chelate, streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-transferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity).

2734. The method according to item 2518, wherein the association is a covalent linkage so that one or more of the n MHC-peptide complexes is covalently linked to the second multimerization domains.

2735. The method according to item 2518, wherein the association is a non-covalent association so that one or more of the n MHC-peptide complexes is non-covalently associated with the second multimerization domain.

2736. The method according to item 2516, wherein the second multimerization domain comprises one or more scaffolds.

2737. The method according to item 2516, wherein the second multimerization domain comprises one or more carriers.

2738. The method according to item 2516, wherein the second multimerization domain comprises at least one scaffold and at least one carrier.

2739. The method according to item 2516, wherein the second multimerization domain comprises one or more optionally substituted organic molecules.

2740. The method according to item 2739, wherein the optionally substituted organic molecule comprises one or more functionalized cyclic structures.

2741. The method according to item 2740, wherein the one or more functionalized cyclic structures comprises one or more benzene rings.

2742. The method according to item 2739, wherein the optionally substituted organic molecule comprises a scaffold molecule comprising at least three reactive groups, or at least three sites suitable for non-covalent attachment.

2743. The method according to item 2516, wherein the second multimerization domain comprises one or more biological cells, such as antigen presenting cells or dendritic cells.

2744. The method according to item 2516, wherein the second multimerization domain comprises one or more membranes.

2745. The method according to item 2744, wherein the one or more membranes comprises liposomes or micelles.

2746. The method according to item 2516, wherein the second multimerization domain comprises one or more polymers.

2747. The method according to item 2746 wherein the one or more polymers are selected from the group consisting of the group consisting of polysaccharides.

2748. The method according to item 2747, wherein the polysaccharide comprises one or more dextran moieties.

2749. The method according to item 2516, wherein the second multimerization domain comprises one or more entities selected from the group consisting of an IgG domain, a coiled-coil polypeptide structure, a DNA duplex, a nucleic acid duplex, PNA-PNA, PNA-DNA, DNA-RNA.

2750. The method according to item 2516, wherein the second multimerization domain comprises an avidin, such as streptavidin.

2751. The method according to item 2516, wherein the second multimerization domain comprises an antibody.

2752. The method according to item 2751, wherein the antibody is selected from the group consisting of polyclonal antibody, monoclonal antibody, IgA, IgG, IgM, IgD, IgE, IgG1, IgG2, IgG3, IgG4, IgA1, IgA2, IgM1, IgM2, humanized antibody, humanized monoclonal antibody, chimeric antibody, mouse antibody, rat antibody, rabbit antibody, human antibody, camel antibody, sheep antibody, engineered human antibody, epitope-focused antibody, agonist antibody, antagonist antibody, neutralizing antibody, naturally-occurring antibody, isolated antibody, monovalent antibody, bispecific antibody, trispecific antibody, multispecific antibody, heteroconjugate antibody, immunoconjugates, immunoliposomes, labeled antibody, antibody fragment, domain antibody, nanobody, minibody, maxibody, diabody, fusion antibody.

2753. The method according to item 2516, wherein the second multimerization domain comprises one or more small organic scaffold molecules.

2754. The method according to item 2516, wherein the second multimerization comprises one or more further polypeptides in addition to a and b.

2755. The method according to item 2516, wherein the second multimerization comprises one or more protein complexes.

2756. The method according to item 2516, wherein the second multimerization domain comprises one or more beads 2757. The method according to item 2516, wherein the second multimerization domain comprises one or more compounds selected from the group consisting of agarose, sepharose, resin beads, glass beads, pore-glass beads, glass particles coated with a hydrophobic polymer, chitosan-coated beads, SH beads, latex beads, spherical latex beads, allele-type beads, SPA bead, PEG-based resins, PEG-coated bead, PEG-encapsulated bead, polystyrene beads, magnetic polystyrene beads, glutathione agarose beads, magnetic bead, paramagnetic beads, protein A and/or protein G sepharose beads, activated carboxylic acid bead, macroscopic beads, microscopic beads, insoluble resin beads, silica-based resins, cellulosic resins, cross-linked agarose beads, polystyrene beads, cross-linked polyacrylamide resins, beads with iron cores, metal beads, dynabeads, Polymethylmethacrylate beads activated with NHS, streptavidin-agarose beads, polypropylene, polyethylene, dextran, nylon, amylases, natural and modified celluloses, nitrocellulose, polyacrylamides, gabbros, magnetite, polymers, oligomers, non-repeating moieties, polyethylene glycol (PEG), monomethoxy-PEG, mono-($C_1$-$C_{10}$)alkoxy-PEG, aryloxy-PEG, poly-(N-vinyl pyrrolidone)PEG, tresyl monomethoxy PEG, PEG propionaldehyde, bis-succinimidyl carbonate PEG, polystyrene bead crosslinked with divinylbenzene, propylene glycol homopolymers, a polypropylene oxide/ethylene oxide co-polymer, polyoxyethylated polyols (e.g., glycerol), polyvinyl alcohol, dextran, aminodextran, carbohydrate-based polymers, cross-linked dextran beads, polysaccharide beads, polycarbamate beads, divinyl sulfone activated polysaccharide, polystyrene beads that have been functionalized with tosyl-activated esters, magnetic polystyrene beads functionalized with tosyl-activated esters, streptavidin beads, streptaivdin-monomer coated beads, streptaivdin-tetramer coated beads, Streptavidin Coated Compel Magnetic beads, avidin coated beads, dextramer coated beads, divinyl sulfone-activated dextran, Carboxylate-modified bead, amine-modified beads, antibody coated beads, cellulose beads, grafted co-poly beads, poly-acrylamide beads, dimethylacrylamide beads optionally crosslinked with N—N'-bis-acryloylethylenediamine, hollow fiber membranes, fluorescent beads, collagen-agarose beads, gelatin beads, collagen-gelatin beads, collagen-fibronectin-gelatin beads, collagen beads, chitosan beads, collagen-chitosan beads, protein-based beads, hydrogel beads, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin and chitosan.

2758. The method according to item 2516, wherein the second multimerization domain comprises a dimerization domain.

2759. The method according to item 2516, wherein the second multimerization domain comprises a trimerization domain.

2760. The method according to item 2516, wherein the second multimerization domain comprises a tetramerization domain.

2761. The method according to item 2516, wherein the second multimerization domain comprises a pentamerization domain.

2762. The method according to item 2761, wherein the pentamerization domain comprises a coiled-coil polypeptide structure.

2763. The method according to item 2516, wherein the second multimerization domain comprises a hexamerization domain.
2764. The method according to item 2763, wherein the hexamerization domain comprises three IgG domains.
2765. The method according to item 2516, wherein the second multimerization domain comprises a polymer structure to which is attached one or more scaffolds.
2766. The method according to item 2765, wherein the polymer structure comprises a polysaccharide.
2767. The method according to item 2766, wherein the polysaccharide comprises one or more dextran moieties.
2768. The method according to item 2516, wherein the second multimerization domain comprises a polyamide and/or a polyethylene glycol and/or a polysaccharide and/or a sepharose.
2769. The method according to item 2516, wherein the second multimerization domain comprises a carboxy methyl dextran and/or a dextran polyaldehyde and/or a carboxymethyl dextran lactone and/or a cyclodextrin.
2770. The method according to item 2516, wherein one or more labels is covalently attached to the second multimerization domain.
2771. The method according to item 2516, wherein one or more labels is non-covalently attached to the second multimerization domain.
2772. The method according to item 2771, wherein the one or more labels is non-covalently attached to an antibody in the second multimerization domain.
2773. The method according to item 2770, wherein the one or more labels is covalently attached to an antibody in the second multimerization domain.
2774. The method according to item 2771, wherein the one or more labels is non-covalently attached to an aptamer in the second multimerization domain.
2775. The method according to item 2770, wherein the one or more labels is covalently attached to an aptamer in the second multimerization domain.
2776. The method according to item 2771, wherein the one or more labels is non-covalently attached to a molecule in the second multimerization domain.
2777. The method according to item 2770, wherein the one or more labels is covalently attached to a molecule in the second multimerization domain.
2778. The method according to item 2771, wherein the one or more labels is non-covalently attached to a protein in the second multimerization domain.
2779. The method according to item 2770, wherein the one or more labels is covalently attached to a protein in the second multimerization domain.
2780. The method according to item 2771, wherein the one or more labels is non-covalently attached to a sugar residue in the second multimerization domain.
2781. The method according to item 2770, wherein the one or more labels is covalently attached to a sugar residue in the second multimerization domain.
2782. The method according to item 2771, wherein the one or more labels is non-covalently attached to a DNA in the second multimerization domain.
2783. The method according to item 2770, wherein the one or more labels is covalently attached to a DNA in the second multimerization domain.
2784. The method according to any of the items 2770 to 2783, wherein the attachment is directly between reactive groups in the labelling molecule and reactive groups in the marker molecule.
2785. The method according to any of the items 2770 to 2784, wherein the attachment is through a linker connecting labelling molecule and marker.
2786. The method according to any of the items 2770 to 2785, wherein one label is used.
2787. The method according to any of the items 2770 to 2785, wherein more than one label is used.
2788. The method according to item 2787, wherein the more than one label are all identical.
2789. The method according to item 2787, wherein at least two labels are different.
2790. The method according to any of items 2770 to 2789, wherein the one or more labels is a fluorophore.
2791. The method according to item 2790, wherein the one or more fluorophore label are selected from the group consisting of selected from the group fluorescein isothiocyanate, rhodamine, phycoerythrin, phycocyanin, allophycocyanin, o-phthaldehyde and fluorescamine.
2792. The method according to item 2790, wherein the one or more fluorophore label are selected from the group consisting of 2-(4'-maleimidylanilino)naphthalene-6-sulfonic acid, sodium salt
2793. The method according to item 2790, wherein the one or more fluorophore label are selected from the group consisting of 5-((((2-iodoacetyl)amino)ethyl)amino) naphthalene-1-sulfonic acid
2794. The method according to item 2790, wherein the one or more fluorophore label are selected from the group consisting of Pyrene-1-butanoic acid
2795. The method according to item 2790, wherein the one or more fluorophore label are selected from the group consisting of AlexaFluor 350 (7-amino-6-sulfonic acid-4-methyl coumarin-3-acetic acid
2796. The method according to item 2790, wherein the one or more fluorophore label are selected from the group consisting of AMCA (7-amino-4-methyl coumarin-3-acetic acid
2797. The method according to item 2790, wherein the one or more fluorophore label are selected from the group consisting of 7-hydroxy-4-methyl coumarin-3-acetic acid
2798. The method according to item 2790, wherein the one or more fluorophore label are selected from the group consisting of Marina Blue (6,8-difluoro-7-hydroxy-4-methyl coumarin-3-acetic acid
2799. The method according to item 2790, wherein the one or more fluorophore label are selected from the group consisting of 7-dimethylamino-coumarin-4-acetic acid
2800. The method according to item 2790, wherein the one or more fluorophore label are selected from the group consisting of Fluorescamin-N-butyl amine adduct
2801. The method according to item 2790, wherein the one or more fluorophore label are selected from the group consisting of 7-hydroxy-coumarine-3-carboxylic acid
2802. The method according to item 2790, wherein the one or more fluorophore label are selected from the group consisting of Cascade Blue (pyrene-trisulphonic acid acetyl azide
2803. The method according to item 2790, wherein the one or more fluorophore label are selected from the group consisting of Cascade Yellow
2804. The method according to item 2790, wherein the one or more fluorophore label are selected from the group consisting of Pacific Blue (6,8 difluoro-7-hydroxy coumarin-3-carboxylic acid
2805. The method according to item 2790, wherein the one or more fluorophore label are selected from the group consisting of 7-diethylamino-coumarin-3-carboxylic acid 2806. The method according to item 2790, wherein the one or more fluorophore label are selected from the group consisting of N-(((4-azidobenzoyl)amino)ethyl)-4-amino-3,6-disulfo-1,8-naphthalimide, dipotassium salt 2807. The method according to item 2790, wherein the one or more fluorophore label are selected from the group consisting of Alexa Fluor 430

2808. The method according to item 2790, wherein the one or more fluorophore label are selected from the group consisting of 3-perylenedodecanoic acid 2809. The method according to item 2790, wherein the one or more fluorophore label are selected from the group consisting of 8-hydroxypyrene-1,3,6-trisulfonic acid, trisodium salt 2810. The method according to item 2790, wherein the one or more fluorophore label are selected from the group consisting of 12-(N-(7-nitrobenz-2-oxa-1,3-diazol-4-yl)amino)dodecanoic acid 2811. The method according to item 2790, wherein the one or more fluorophore label are selected from the group consisting of N,N'-dimethyl-N-(iodoacetyl)-N'-(7-nitrobenz-2-oxa-1,3-diazol-4-yl)ethylenediamine 2812. The method according to item 2790, wherein the one or more fluorophore label are selected from the group consisting of Oregon Green 488 (difluoro carboxy fluorescein)

2813. The method according to item 2790, wherein the one or more fluorophore label are selected from the group consisting of 5-iodoacetamidofluorescein 2814. The method according to item 2790, wherein the one or more fluorophore label are selected from the group consisting of propidium iodide-DNA adduct 2815. The method according to item 2790, wherein the one or more fluorophore label are selected from the group consisting of Carboxy fluorescein 2816. The method according to any of items 2770 to 2789, wherein the one or more labels is a fluorescent label.

2817. The method according to item 2816, wherein the one or more fluorescent label is a simple fluorescent label 2818. The method according to item 2817, wherein the one or more simple fluorescent label is selected from the group Fluor dyes, Pacific Blue™, Pacific Orange™, Cascade Yellow™

2819. The method according to item 2817, wherein the one or more simple fluorescent label is selected from the group AlexaFluor® (AF), AF405, AF488, AF500, AF514, AF532, AF546, AF555, AF568, AF594, AF610, AF633, AF635, AF647, AF680, AF700, AF710, AF750, AF800.

2820. The method according to item 2817, wherein the one or more simple fluorescent label is selected from the group Quantum Dot based dyes, QDot®Nanocrystals (Invitrogen, MolecularProbs), Qdot®525, Qdot®565, Qdot®585, Qdot®605, Qdot®655, Qdot®705, Qdot®800.

2821. The method according to item 2817, wherein the one or more simple fluorescent label is selected from the group DyLight™ Dyes (Pierce) (DL); DL549, DL649, DL680, DL800.

2822. The method according to item 2817, wherein the one or more simple fluorescent label is selected from the group Fluorescein (Flu) or any derivate of that, such as FITC 2823. The method according to item 2817, wherein the one or more simple fluorescent label is selected from the group Cy-Dyes, Cy2, Cy3, Cy3.5, Cy5, Cy5.5, Cy7.

2824. The method according to item 2817, wherein the one or more simple fluorescent label is selected from the group Fluorescent Proteins, RPE, PerCp, APC, Green fluorescent proteins; GFP and GFP derivated mutant proteins; BFP, CFP, YFP, DsRed, T1, Dimer2, mRFP1, MBanana, mOrange, dTomato, tdTomato, mTangerine, mStrawberry, mCherry.

2825. The method according to item 2817, wherein the one or more simple fluorescent label is selected from the group Tandem dyes, RPE-Cy5, RPE-Cy5.5, RPE-Cy7, RPE-AlexaFluor® tandem conjugates; RPE-Alexa610, RPE-TxRed, APC-Aleca600, APC-Alexa610, APC-Alexa750, APC-Cy5, APC-Cy5.5.

2826. The method according to item 2817, wherein the one or more simple fluorescent label is selected from the group multi fluorochrome assemblies, Multiple fluorochromes attached to a polymer molecule, such as a peptide/protein, Dextrane, polysaccharide, any combination of the fluorescent dyes involving in generation of FRET (Fluorescence resonance energy transfer) based techniques.

2827. The method according to item 2817, wherein the one or more simple fluorescent label is selected from the group ionophors; ion chelating fluorescent props, props that change wavelength when binding a specific ion, such as Calcium, props that change intensity when binding to a specific ion, such as Calcium.

2828. The method according to any of items 2770 to 2789, wherein the one or more labels is capable of absorption of light 2829. The method according to item 2828, wherein the one or more labels capable of absorption of light is a chromophore.

2830. The method according to item 2828, wherein the one or more labels capable of absorption of light is a dye.

2831. The method according to any of items 2770 to 2789, wherein the one or more labels is capable of emission of light after excitation 2832. The method according to item 2831, wherein the one or more labels capable of emission of light is one or more fluorochromes.

2833. The method according to item 2832, wherein the one or more fluorochrome is selected from the AlexaFluor® (AF) family, which include AF®350, AF405, AF430, AF488, AF500, AF514, AF532, AF546, AF555, AF568, AF594, AF610, AF633, AF635, AF647, AF680, AF700, AF710, AF750 and AF800

2834. The method according to item 2832, wherein the one or more fluorochrome is selected from the Quantum Dot (Qdot®) based dye family, which include Qdot®525, Qdot®565, Qdot®585, Qdot®605, Qdot®655, Qdot®705, Qdot®800

2835. The method according to item 2832, wherein the one or more fluorochrome is selected from the DyLight™ Dyes (DL) family, which include DL549, DL649, DL680, DL800

2836. The method according to item 2832, wherein the one or more fluorochrome is selected from the family of Small fluorescing dyes, which include FITC, Pacific Blue™, Pacific Orange™, Cascade Yellow™, Marina Blue™, DSred, DSred-2,7-AAD, TO-Pro-3.

2837. The method according to item 2832, wherein the one or more fluorochrome is selected from the family of Cy-Dyes, which include Cy2, Cy3, Cy3.5, Cy5, Cy5.5, Cy7

2838. The method according to item 2832, wherein the one or more fluorochrome is selected from the family of Phycobili Proteins, which include R-Phycoerythrin (RPE), PerCP, Allophycocyanin (APC), B-Phycoerythrin, C-Phycocyanin.

2839. The method according to item 2832, wherein the one or more fluorochrome is selected from the family of Fluorescent Proteins, which include (E)GFP and GFP ((enhanced) green fluorescent protein) derived mutant proteins; BFP, CFP, YFP, DsRed, T1, Dimer2, mRFP1, MBanana, mOrange, dTomato, tdTomato, mTangerine.

2840. The method according to item 2832, wherein the one or more fluorochrome is selected from the family of Tandem dyes with RPE, which include RPE-Cy5, RPE-Cy5.5, RPE-Cy7, RPE-AlexaFluor® tandem conjugates; RPE-Alexa610, RPE-TxRed.

2841. The method according to item 2832, wherein the one or more fluorochrome is selected from the family of Tandem dyes with APC, which include APC-Aleca600, APC-Alexa610, APC-Alexa750, APC-Cy5, APC-Cy5.5.

2842. The method according to item 2832, wherein the one or more fluorochrome is selected from the family of Calcium dyes, which include Indo-1-$Ca^{2+}$ Indo-2-$Ca^{2+}$.

2843. The method according to any of items 2770 to 2789, wherein the one or more labels is capable of reflection of light 2844. The MHC multimer according to item 2843, wherein the one or more labels capable of reflection of light comprises gold 2845. The MHC multimer according to item 2843, wherein the one or more labels capable of reflection of light comprises plastic 2846. The MHC multimer according to item 2843, wherein the one or more labels capable of reflection of light comprises glass 2847. The MHC multimer according to item 2843, wherein the one or more labels capable of reflection of light comprises polystyrene 2848. The MHC multimer according to item 2843, wherein the one or more labels capable of reflection of light comprises pollen 2849. The method according to any of items 2770 to 2789, wherein the one or more labels is a chemiluminescent label.

2850. The method according to item 2849, wherein the chemiluminescent labels is selected from the group luminol, isoluminol, theromatic acridinium ester, imidazole, acridinium salt and oxalate ester.

2851. The method according to any of items 2770 to 2789, wherein the one or more labels is a bioluminescent label.

2852. The method according to item 2851, wherein the bioluminescent labels is selected from the group consisting of luciferin, luciferase and aequorin.

2853. The method according to any of items 2770 to 2789, wherein the one or more labels is a radioactive label.

2854. The method according to item 2853, wherein the one or more radioactive labels is a radionuclide.

2855. The method according to item 2853, wherein the one or more radioactive labels is an isotope.

2856. The method according to item 2853, wherein the one or more radioactive labels comprises α rays.

2857. The method according to item 2853, wherein the one or more radioactive labels comprises β rays.

2858. The method according to item 2853, wherein the one or more radioactive labels comprises γ rays.

2859. The method according to any of items 2770 to 2789, wherein the one or more labels is detectable by NMR (nuclear magnetic resonance form paramagnetic molecules)

2860. The method according to any of items 2770 to 2789, wherein the one or more labels is an enzyme label.

2861. The method according to item 2860, wherein the enzyme catalyze a reaction between chemicals in the near environment of the labeling molecules, producing a light signal (chemi-luminescence)

2862. The method according to item 2860, wherein the enzyme catalyze a reaction between chemicals in the near environment of the labeling molecules, resulting in precipitation of chromophor dyes 2863. The method according to item 2860, wherein the enzyme catalyze a reaction between chemicals in the near environment of the labeling molecules, resulting in precipitates that can be detected by an additional layer of detection molecules 2864. The method according to item 2860, wherein the enzyme label is selected from the group peroxidases, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

2865. The method according to item 2860, wherein the enzyme label is horseradish peroxidase.

2866. The method according to item 2860, wherein the enzyme label is horseradish peroxidase and the substrate is diaminobenzidine (DAB).

2867. The method according to item 2860, wherein the enzyme label is horseradish peroxidase and the substrate is 3-amino-9-ethyl-carbazole (AEC+).

2868. The method according to item 2860, wherein the enzyme label is horseradish peroxidase and the substrate is biotinyl tyramide.

2869. The method according to item 2860, wherein the enzyme label is horseradish peroxidase and the substrate is fluorescein tyramide.

2870. The method according to item 2860, wherein the enzyme label is alkaline phosphatase.

2871. The method according to item 2860, wherein the enzyme label is alkaline phosphatase and the substrate is Fast red dye 2872. The method according to any of items 2770 to 2789, wherein the one or more labels is a ionophore or chelating chemical compound binding to specific ions such as $Ca^{2+}$ 2873. The method according to any of items 2770 to 2789, wherein the one or more labels is a lanthanide.

2874. The method according to item 2873, wherein the lanthanide comprises fluorescence.

2875. The method according to item 2873, wherein the lanthanide comprises Phosphorescence.

2876. The method according to item 2873, wherein the lanthanide is paramagnetic

2877. The method according to any of items 2770 to 2789, wherein the one or more labels is a DNA fluorescing stain 2878. The method according to item 2877, wherein the DNA fluorescing stain is Propidium iodide 2879. The method according to item 2877, wherein the DNA fluorescing stain is Hoechst stain 2880. The method according to item 2877, wherein the DNA fluorescing stain is DAPI 2881. The method according to item 2877, wherein the DNA fluorescing stain is AMC 2882. The method according to item 2877, wherein the DNA fluorescing stain is DraQ5™

2883. The method according to item 2877, wherein the DNA fluorescing stain is Acridine orange
2884. The method according to item 2514, wherein the MHC-peptide complex (a-b-P) is attached to the second multimerization domain comprising an avidin or streptavidin via a linkage comprising a biotin moiety.
2885. The method according to any of items 2734 to 2884, wherein the MHC-peptide complex is linked to the second multimerization domain by a second linker moiety.
2886. The method according to item 2885, wherein the MHC-peptide complex is linked to the second multimerization domain by a covalent linker moiety.
2887. The method according to items 2885 and 2886, wherein the linkage of the second multimerization domain and at least one MHC-peptide complexes is formed by a binding entity X attached to, or being part of, the second multimerization domain, and a binding entity Y attached to, or being part of at least one of the MHC-peptide complexes.
2888. The method according to items 2885 and 2886, wherein the linker moiety linking the second multimerization domain and the MHC-peptide complex comprises the linker moiety XY, wherein the linker moiety XY results from a reaction of the moiety X comprising one or more reactive groups and the moiety Y comprising one or more reactive groups, wherein at least some of said reactive groups are capable of reacting with each other.
2889. The method according to item 2888, wherein the moiety X comprises a nucleophilic group.
2890. The method according to item 2889, wherein the nucleophilic group is selected from the group consisting of —NH$_2$, —OH, —SH, —NH—NH$_2$.
2891. The method according to item 2888, wherein the moiety Y comprises an electrophilic group.
2892. The method according to item 2891, wherein the electrophilic group is selected from the group consisting of CHO, COOH and CO.
2893. The method according to items 2885 and 2886, wherein at least one of the reactive groups on one of the moieties X and Y comprises a radical capable of reacting with a reactive group forming part of the other moiety.
2894. The method according to items 2885 and 2886, wherein X and Y comprises reactive groups natively associated with the second multimerization domain and/or the MHC-peptide complexes.
2895. The method according to items 2885 and 2886, wherein X and Y comprises reactive groups not natively associated with the second multimerization domain and/or the MHC-peptide complex.
2896. The method according to items 2885 and 2886, wherein the linker moiety forms a covalent link between the second multimerization domain and at least one of the MHC-peptide complexes.
2897. The method according to items 2885 and 2886, wherein the reactive groups of MHC-peptide complexes include amino acid side chains selected from the group consisting of —NH$_2$, —OH, —SH, and —NH—
2898. The method according to items 2885 and 2886, wherein the reactive groups of the second multimerization domain include hydroxyls of polysaccharides such as dextrans
2899. The method according to items 2885 and 2886, wherein the reactive groups of the second multimerization domain selected from the group consisting of amino acid side chains comprising —NH$_2$, —OH, —SH, and —NH— of polypeptides
2900. The method according to items 2885 and 2886, wherein one of the polypeptides of the MHC-peptide complex is linked by a protein fusion to the second multimerization domain
2901. The method according to items 2885 and 2886, wherein one of the polypeptides of the MHC-peptide complex is linked by a protein fusion to the second multimerization domain, wherein an acyl group and an amino group react to form an amide bond
2902. The method according to item 2516, wherein one of the polypeptides of the MHC-peptide complex is linked by non-native reactive groups to the second multimerization domain.
2903. The method according to item 2516, wherein the reactive groups include reactive groups that are attached to the second multimerization domain through association of a linker molecule comprising the reactive group.
2904. The method according to item 2516, wherein the reactive groups include reactive groups that are attached to the MHC-peptide complex through association of a linker molecule comprising the reactive group.
2905. The method according to item 2516, wherein the second multimerization domain comprises one or more nucleophilic groups
2906. The method according to item 2905, wherein the nucleophilic group is selected from the group consisting of —NH$_2$, —OH, —SH, —CN, —NH—NH$_2$
2907. The method according to item 2516, wherein the second multimerization domain is selected from the group consisting of polysaccharides, polypeptides comprising e.g. lysine, serine, and cysteine.
2908. The method according to item 2516, wherein the second multimerization domain comprises one or more electrophilic groups.
2909. The method according to item 2908, wherein the electrophilic group is selected from the group consisting of —COOH, —CHO, —CO, NHS-ester, tosyl-activated ester, and other activated esters, acid-anhydrides.
2910. The method according to item 2516, wherein the second multimerization domain is selected from the group consisting of polypeptides comprising e.g. glutamate and aspartate, or vinyl sulfone activated dextran.
2911. The method according to item 2516, wherein the second multimerization domain comprises one or more radicals.
2912. The method according to item 2516, wherein the second multimerization domain comprises one or more conjugated double bonds.
2913. The method according to item 2516, wherein the second multimerization domain comprises one or more beads, further comprising a linker moiety
2914. The method according to any of the items 2885 to 2913, wherein the linker is a flexible linker.
2915. The method according to any of the items 2885 to 2913, wherein the linker is a rigid linker.
2916. The method according to any of the items 2885 to 2913, wherein the linker is a water-soluble linker.
2917. The method according to any of the items 2885 to 2913, wherein the linker is a cleavable linker.
2918. The method according to item 2917, wherein the cleavable linker is cleavable at physiological conditions
2919. The method according to items 2885 and 2918, wherein the MHC-peptide complex is linked to the second multimerization domain by a non-covalent linker moiety.
2920. The method according to item 2919, wherein the non-covalent linkage comprises natural dimerization 2921. The method according to item 2920, wherein the natural dimerization comprises antigen-antibody pairs.
2922. The method according to item 2920, wherein the natural dimerization comprises DNA-DNA interactions
2923. The method according to item 2919, wherein the non-covalent linkage comprises natural interactions
2924. The method according to item 2923, wherein the natural interaction comprises biotin and streptavidin.
2925. The method according to item 2756, wherein the bead is coated with streptavidin monomers, which in turn are associated with biotinylated MHC complexes.
2926. The method according to item 2756, wherein the bead is coated with streptavidin tetramers, which in turn are associated with 0, 1, 2, 3, or 4 biotinylated MHC complexes.
2927. The method according to item 2756, wherein the bead is coated with a polysaccharide, such as a polysaccharide comprising a dextran moiety.
2928. The method according to item 2923, wherein the natural interaction comprises the interaction of MHC complexes (comprising full-length polypeptide chains, including the transmembrane portion) with the cell membrane of for example dendritic cells.
2929. The method according to item 2919, wherein the non-covalent linkage comprises artificial interactions.
2930. The method according to item 2929, wherein the artificial interaction comprises $His_6$ tag interacting with Ni-NTA.
2931. The method according to item 2929, wherein the artificial interaction comprises PNA-PNA
2932. The method according to item 2919, wherein the non-covalent linkage comprises non-specific adsorption.
2933. The method according to item 2932, wherein the non-specific adsorption comprises adsorption of proteins onto surfaces.
2934. The method according to item 2919 wherein the non-covalent linkage comprises the pentamer structure.
2935. The method according to item 2919, wherein the non-covalent linkage comprises interactions selected from the group streptavidin/biotin, avidin/biotin, antibody/antigen, DNA/DNA, DNA/PNA, DNA/RNA, PNA/PNA, LNA/DNA, leucine zipper e.g. Fos/Jun, IgG dimeric protein, IgM multivalent protein, acid/base coiled-coil helices, chelate/metal ion-bound chelate, streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-transferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity).
2936. The method of any of the previous items, wherein the analysis comprises use of one or more chemical assays.
2937. The method of item 2936, wherein the one or more chemical assays are used as a diagnostic test.
2938. The method of item 2936, wherein the one or more chemical assays comprises measurement of binding of one or more binding molecules/marker molecules to one or more target structures in a sample.
2939. The method of item 2938, wherein the one or more binding molecules/marker molecules specifically associates with the one or more target structures belonging to or associated with an entity in the sample.
2940. The method of item 2938, wherein the one or more binding molecules/marker molecules specifically associates covalently with a target structure belonging to or associated with an entity in the sample.
2941. The method of item 2938, wherein the one or more binding molecules/marker molecules specifically associates non-covalently with a target structure belonging to or associated with an entity in the sample.
2942. The method of any of items 2938 to 2941, wherein the one or more binding molecules/marker molecules comprises one or more proteins.
2943. The method of any of items 2938 to 2942, wherein the one or more binding molecules/marker molecules comprises one or more antibodies (monoclonal and/or polyclonal, derived from any species e.g. man, mouse, rat, rabbit, pig or camel, monkey or may be recombinant antibodies).
2944. The method of any of items 2938 to 2943, wherein the one or more binding molecules/marker molecules comprises one or more antibody fragments.
2945. The method of any of items 2938 to 2944, wherein the one or more binding molecules/marker molecules comprises one or more MHC multimers (including but not limited to MHC dextramers, MHC tetramers, MHC Pentamers, cells expressing MHC molecules, MHC-peptide molecules covalently or non-covalently attached to beads, streptactin or other molecule structures).
2946. The method of any of items 2938 to 2945, wherein the one or more binding molecules/marker molecules comprises one or more scaffold molecules.
2947. The method of any of items 2938 to 2946, wherein the one or more binding molecules/marker molecules comprises one or more small organic molecules.
2948. The method of any of items 2938 to 2947, wherein the one or more binding molecules/marker molecules comprises one or more nucleic acids (e.g. DNA, RNA, PNA).
2949. The method of any of items 2938 to 2948, wherein the one or more binding molecules/marker molecules comprises one or more polysaccharides.
2950. The method of any of items 2938 to 2949, wherein the one or more binding molecules/marker molecules comprises one or more polymers other than polysaccharides.
2951. The method of any of items 2938 to 2950, wherein the one or more binding molecules/marker molecules comprises one or more Aptamers.
2952. The method of any of items 2938 to 2951, wherein the one or more binding molecules/marker molecules comprises one or more beads.
2953. The method of any of items 2938 to 2952, wherein the one or more binding molecules/marker molecules comprises one or more cells.
2954. The method of any of items 2938 to 2953, wherein the one or more binding molecules/marker molecules comprises one or more living cells.
2955. The method of any of items 2938 to 2954, wherein the one or more binding molecules/marker molecules comprises one or more dead cells.
2956. The method of any of items 2938 to 2955, wherein the one or more binding molecules/marker molecules comprises one or more naturally occurring cells.

2957. The method of any of items 2938 to 2956, wherein the one or more binding molecules/marker molecules comprises one or more genetic modified cells.

2958. The method of any of items 2938 to 2957, wherein the one or more binding molecules/marker molecules comprises one or more hybridoma cells.

2959. The method of any of items 2938 to 2958, wherein the one or more binding molecules/marker molecules comprises one or more gene transfected cells.

2960. The method of any of items 2938 to 2959, wherein the one or more binding molecules/marker molecules comprises one or more cell like structures (e.g. liposomes, micelles).

2961. The method of any of items 2938 to 2960, wherein the one or more binding molecules/marker molecules comprises one or more molecules able to bind defined target structure in sample.

2962. The method of any of items 2938 to 2961, wherein the one or more binding molecules/marker molecules comprises one or more cells able to bind defined target structure in sample.

2963. The method of any of items 2938 to 2962, wherein the one or more binding molecules/marker molecules comprises one or more substances able to bind defined target structure in sample.

2964. The method of any of the items 2938 to 2963, wherein the one or more binding molecules/marker molecules have an affinity for the one or more target structures in the sample of from $K_D=10^{-12}$ to $K_D=10^{-2}$ M, such as in the range of from $K_D=10^{-12}$ to $K_D=10^{-11}$ M, for example in the range of from $K_D=10^{-11}$ to $K_D=10^{-10}$ M, such as in the range of from $K_D=10^{-10}$ to $K_D=10^{-9}$ M, for example in the range of from $K_D=10^{-9}$ to $K_D=10^{-8}$ M, such as in the range of from $K_D=10^{-8}$ to $K_D=10^{-7}$ M, for example in the range of from $K_D=10^{-7}$ to $K_D=10^{-6}$ M, such as in the range of from $K_D=10^{-6}$ to $K_D=10^{-5}$ M, for example in the range of from $K_D=10^{-5}$ to $K_D=10^{-4}$ M, such as in the range of from $K_D=10^{-4}$ to $K_D=10^{-3}$ M, for example in the range of from $K_D=10^{-3}$ to $K_D=10^{-2}$ M, or any combination thereof.

2965. The method of any of the items 2938 to 2964, wherein the one or more binding molecules/marker molecules have an affinity for the one or more target structures in the sample that is higher than the binding affinity of the molecules/marker molecules other structures in the sample.

2966. The method of any of the items 2938 to 2965, wherein the binding affinity of the one or more binding molecules/marker molecules for the one or more target structures in the sample compared to the binding affinity of the one or more binding molecules/marker molecules for other structures in the sample (expressed as a ratio—i.e. marker molecules affinity for target structure: marker molecules affinity for other structures in the sample) is in the range of from 1:1 to $10^8$:1, such as from 1:1 to $10^1$:1, for example from $10^1$:1 to $10^2$:1, such as from $10^2$:1 to $10^3$:1, for example from $10^3$:1 to $10^4$:1, such as from $10^4$:1 to $10^5$:1, for example from $10^5$:1 to $10^6$:1, such as from $10^6$:1 to $10^7$:1, for example from $10^7$:1 to $10^8$:1, or any combination thereof.

2967. The method of any of the items 2938 to 2966, wherein one or more binding molecules/marker molecules are labelled with one or more labelling molecules.

2968. The method of item 2967, wherein one or more binding molecules/marker molecules labelled with one or more labelling molecules results in specific signal (i.e. a signal from binding of the one or more binding molecules/marker molecules to the one or more target structures in the sample) and in a background signal (i.e. a signal from binding of the one or more binding molecules/marker molecules to the one or more structures in the sample other than the one or more target structures).

2969. The method of item 2968, wherein the difference between the background signal and the specific signal is in the range (fold difference; i.e. the ratio specific signal: background signal) from 1:1 to $10^8$:1, such as from 1:1 to $10^1$:1, for example from $10^1$:1 to $10^2$:1, such as from $10^2$:1 to $10^3$:1, for example from $10^3$:1 to $10^4$:1, such as from $10^4$:1 to $10^5$:1, for example from $10^5$:1 to $10^6$:1, such as from $10^6$:1 to $10^7$:1, for example from $10^7$:1 to $10^8$:1, or any combination thereof.

2970. The method of any of the items 2938 to 2969, wherein one type of target structure is measured in the same sample.

2971. The method of any of the items 2938 to 2969, wherein more than one type of target structure is measured in the same sample.

2972. The method of any of the items 2938 to 2969, wherein more than one type of target structure is measured in the same sample such as from 2 to 50 different target structures, such as 2 to 3, for example 3 to 4, such as 4 to 5, for example 5 to 6, such as 6 to 7, for example 7 to 8, such as 8 to 9, for example 9 to 10, such as 10 to 11, for example 11 to 12, such as 12 to 13, for example 13 to 14, such as 14 to 15, for example 15 to 16, such as 16 to 17, for example 17 to 18, such as 18 to 19, for example 19 to 20, such as 20 to 21, for example 21 to 22, such as 22 to 23, for example 23 to 24, such as 24 to 25, for example 25 to 26, such as 26 to 27, for example 27 to 28, such as 28 to 29, for example 29 to 30, such as 30 to 31, for example 31 to 32, such as 32 to 33, for example 33 to 34, such as 34 to 35, for example 35 to 36, such as 36 to 37, for example 37 to 38, such as 38 to 39, for example 39 to 40, such as 40 to 41, for example 41 to 42, such as 42 to 43, for example 43 to 44, such as 44 to 45, for example 45 to 46, such as 46 to 47, for example 47 to 48, such as 48 to 49, for example 49 to 50, or any combination thereof.

2973. The method of any of the items 2938 to 2969, wherein one type of target structure is measured in different samples.

2974. The method of any of the items 2938 to 2969, wherein more than one type of target structure is measured in different samples.

2975. The method of any of the items 2938 to 2969, wherein more than one type of target structure is measured in different samples such as from 2 to 50 different target structures, such as 2 to 3, for example 3 to 4, such as 4 to 5, for example 5 to 6, such as 6 to 7, for example 7 to 8, such as 8 to 9, for example 9 to 10, such as 10 to 11, for example 11 to 12, such as 12 to 13, for example 13 to 14, such as 14 to 15, for example 15 to 16, such as 16 to 17, for example 17 to 18, such as 18 to 19, for example 19 to 20, such as 20 to 21, for example 21 to 22, such as 22 to 23, for example 23 to 24, such as 24 to 25, for example 25 to 26, such as 26 to 27, for example 27 to 28, such as 28 to 29, for example 29 to 30, such as 30 to 31, for example 31 to 32, such as 32 to 33, for example 33 to 34, such as 34 to 35, for example 35 to 36, such as 36 to 37, for example 37 to 38, such as 38 to 39, for example 39 to 40, such as 40 to 41, for example 41 to 42, such as 42 to 43, for example 43 to 44, such as 44 to 45, for example 45 to 46, such as 46 to 47, for example 47 to 48, such as 48 to 49, for example 49 to 50, or any combination thereof.

2976. The method of any of items 2973 to 2975, wherein the different samples are derived from the same individual such as the same human being.

2977. The method of any of items 2973 to 2975, wherein the different samples are derived from the different individuals such as different human beings.

2978. The method of any of items 2973 to 2975, wherein the expression level of the one or more target structures is graded according to the specific signal intensity from binding of one or more labelled marker molecules to the one or more target structures and then this grading is correlated to a certain diagnosis.

2979. The method of item 2978, wherein overexpression of one or more target structures is measured by binding of one or more marker molecules to the one or more target structure.

2980. The method of item 2979, wherein the measurement is performed by Immunohistochemistry (IHC) analysis.

2981. The method of items 2978 to 2980, wherein the specific signal intensity is graded as 0, 1+, 2+ or 3+ where 0 is signal corresponding to background signal, 1+ is signal intensity a little over background 2+ is signal intensity clearly different from background and 3+ is maximum signal.

2982. The method of any of the items 2938 to 2981, wherein the one or more target structures comprises one or more surface receptors on cells (e.g. TCR, CD molecules, growth receptors, MHC complexes, mannose binding receptor, transporter proteins).

2983. The method of any of the items 2938 to 2982, wherein the one or more target structures comprises one or more other structures on the surface of cells than surface receptors (e.g. lipids, sugars, proteins).

2984. The method of any of the items 2938 to 2983, wherein the one or more target structures comprises one or more intracellular substances in cells (e.g. DNA, RNA, ribosomes, cytokines, transcription factors, cytoskeleton components, intracellular proteins, sugars).

2985. The method of any of the items 2938 to 2984, wherein the one or more target structures comprises one or more components in fluidics (e.g. antibodies, blood plates, serum proteins, sugars, cytokines and/or interferones).

2986. The method of any of the items 2938 to 2985, wherein the one or more target structures comprises one or more structures in interstitial space in one or more tissues.

2987. The method of any of the items 2938 to 2986, wherein the one or more chemical assays results in quantitation of the one or more target structures.

2988. The method of any of the items 2938 to 2986, wherein the one or more chemical assays results in absolute quantitation of the one or more target structures.

2989. The method of any of the items 2938 to 2986, wherein the one or more chemical assays results in relative quantitation of the one or more target structures.

2990. The method of any of the items 2938 to 2989, wherein the method comprises detection of in the range of 1 to $1 \times 10^8$ copies of the one or more target structures in the sample, such as from 1 to 10 defined structures, for example from 10 to $10^2$ defined structures, such as from $10^2$ to $10^3$ defined structures, for example from $10^3$ to $10^4$ defined structures, such as from $10^4$ to $10^5$ defined structures, for example from $10^5$ to $10^6$ defined structures, such as from $10^6$ to $10^7$ defined structures, for example from $10^7$ to $10^8$ defined structures, or any combination thereof.

2991. The method of any of the items 2938 to 2989, wherein the method comprises detection of more than $1 \times 10^8$ copies of the one or more target structures in the sample.

2992. The method of any of the items 2938 to 2989, wherein the method comprises detection of more than one copy of the one or more target structures in the sample.

2993. The method of any of the items 2938 to 2992, wherein in more than one target structure is detected in the same sample or in different sample.

2994. The method of any of the items 2938 to 2992, wherein in more than one target structure is detected in the same sample or in different sample in one analysis.

2995. The method of any of the items 2938 to 2992, wherein in more than one target structure is detected in the same sample or in different sample in more than one analyses such as 2, 3, 4, 5, 6, 7, 8, 9, 10 or more than 10 analyses.

2996. The method of item 2993, wherein the more than one target structures are localized on the same entity such as on the same cell or in the same compartment of the sample (e.g. in the serum of a blood sample).

2997. The method of item 2993, wherein the more than one target structures are localized on different entities such as on different cells or in different compartments of the sample.

2998. The method of any of the previous items, wherein the analysis comprises immuno monitoring of one or more T cell response.

2999. The method of item 2998, wherein the monitoring of one or more T cell responses is used for diagnosing one or more diseases.

3000. The method of item 2998, wherein the monitoring of one or more T cell responses is used for monitoring one or more diseases.

3001. The method of item 2998, wherein the monitoring of one or more T cell responses is used in relation to treatment and/or development of treatment of one or more diseases including vaccination, transplantation and some treatments with drugs.

3002. The method of any of items 2999 to 3001, wherein the one or more diseases comprises a disease where changes in the immune system have an impact on the disease development, progression and/or cure of the disease.

3003. The method of item 2998, wherein the monitoring of one or more T cell responses is used in relation to development or/and use of one or more vaccines such as one or more cancer vaccines.

3004. The method of item 2998, wherein the method is used to determine whether the one or more vaccines are effective.

3005. The method of item 2998, wherein the method is used to fine-tuning a cancer vaccine treatment by determining whether the dose of the administered vaccine, the number of administrations of vaccine doses or the intervals between administrations of doses should be changed.

3006. The method of item 2998, wherein the method is used to determine if the content of a vaccine should be changed.

3007. The method of item 2998, wherein the method is used to determine whether a vaccination protocol should continue.

3008. The method of item 2998, wherein the method is used to determine the duration of a given vaccination protocol.

3009. The method of item 2998, wherein the method is used for selection of responsive patients and de-selection of non-responsive patients.

3010. The method of any of the items 2998 to 3009, wherein the immune monitoring of antigen-specific T-cell response comprises identification of antigen specific T cells.

3011. The method of any of the items 2998 to 3010, wherein the immune monitoring of antigen-specific T-cell response comprises enumeration of antigen specific T cells.

3012. The method of any of the items 2998 to 3011, wherein the immune monitoring of antigen-specific T-cell response comprises isolation of antigen specific T cells.

3013. The method of any of the items 2998 to 3012, wherein the immune monitoring of antigen-specific T-cell response comprises identification and/or enumeration and/or isolation of antigen specific T cells.

3014. The method of any of the items 2998 to 3013, wherein the amount of antigen-specific T-cells measured in fluidic samples is in the range of $10^{-4}$-$10^{6}$ antigen-specific T-cells pr. µl sample, such as from of $10^{-4}$ to $10^{-3}$ antigen-specific T-cells pr. µl sample, for example from $10^{-3}$ to $10^{-2}$ antigen-specific T-cells pr. µl sample, such as from of $10^{-2}$ to $10^{-1}$ antigen-specific T-cells pr. µl sample, for example from $10^{-1}$ to 10 antigen-specific T-cells pr. µl sample, such as from of 10 to $10^{2}$ antigen-specific T-cells pr. µl sample, for example from $10^{2}$ to $10^{3}$ antigen-specific T-cells pr. µl sample, such as from of $10^{3}$ to $10^{4}$ antigen-specific T-cells pr. µl sample, for example from $10^{4}$ to $10^{5}$ antigen-specific T-cells pr. µl sample, such as from of $10^{5}$ to $10^{6}$ antigen-specific T-cells pr. µl sample, or any combination thereof.

3015. The method of any of the items 2998 to 3013, wherein the amount of antigen-specific T-cells measured in solid samples is in the range of $10^{-4}$-$10^{6}$ antigen-specific T-cells pr. mm$^{2}$ sample analyzed, such as from of $10^{-4}$ to $10^{-3}$ antigen-specific T-cells pr. mm$^{2}$ sample, for example from $10^{-3}$ to $10^{-2}$ antigen-specific T-cells pr. mm$^{2}$ sample, such as from of $10^{-2}$ to $10^{-1}$ antigen-specific T-cells pr. mm$^{2}$ sample, for example from $10^{-1}$ to 10 antigen-specific T-cells pr. mm$^{2}$ sample, such as from of 10 to $10^{2}$ antigen-specific T-cells pr. mm$^{2}$ sample, for example from $10^{2}$ to $10^{3}$ antigen-specific T-cells pr. mm$^{2}$ sample, such as from of $10^{3}$ to $10^{4}$ antigen-specific T-cells pr. mm$^{2}$ sample, for example from $10^{4}$ to $10^{5}$ antigen-specific T-cells pr. mm$^{2}$ sample, such as from of $10^{5}$ to $10^{6}$ antigen-specific T-cells pr. mm$^{2}$ sample, or any combination thereof.

3016. The method of any of the items 2998 to 3015, wherein the method comprises use of one or more MHC multimers such as MHC Dextramers, MHC tetramers, MHC Pentamers, cells expressing MHC-peptide molecules, streptactin with MHC-peptide complexes covalently or non-covalently attached, beads with MHC-peptide complexes covalently or non-covalently attached or any other molecule with two or more MHC-peptide complexes covalently or non-covalently attached.

3017. The method of item 3016, wherein the one or more MHC multimers are marker molecules.

3018. The method of item 3016, wherein the one or more MHC multimers are labeled marker molecules.

INCORPORATION OF SUBJECT MATTER BY REFERENCE

This patent application is a non-provisional patent application and claims the benefit of U.S. 61/082,980 as filed on Jul. 23, 2008, which is hereby incorporated by reference in its entirety.

All patent and non-patent references cited in U.S. 61/082,980, as well as in the present application, are also incorporated herein by reference in their entirety.

Additionally, the following international patent applications designating the United States are hereby incorporated by reference in their entirety:

PCT/DK2008/050167 filed on Jul. 3, 2008 and published as WO2009/003492 on Jan. 8, 2009;

PCT/DK/2008/050168 filed on Jul. 3, 2008 and published as WO2009/003493 on Jan. 8, 2009; and PCT/DK2008/000451 filed on Dec. 30, 2008 and not yet published.

All patent and non-patent references cited in any of PCT/DK2008/050167; PCT/DK/2008/050168 and PCT/DK2008/000451 are also incorporated herein by reference in their entirety.

The invention claimed is:

1. A method for diagnosing and repairing leukemia and/or lymphoma in an individual in need thereof, by
   (i) determining the amount or relative amount of, and/or the activity of, and/or the state of antigen-specific T-cells of said individual, by measuring the amount, activity, and/or state of said antigen-specific T-cells of said individual, wherein said antigen is WT-1, and
   (ii) changing the amount or relative amount of, and/or the activity of, and/or the state of, antigen-specific T-cells of said individual, by addition of an amount of, or activation of, said antigen-specific T-cells from said individual, or by addition of an effector that mediates a decrease or increase in the amount and/or activity of said antigen-specific T-cells in said individual, wherein changing the amount and/or activity of said antigen-specific T-cells comprises one or more steps of administering a peptide cancer vaccine and one or more steps of administering at least one other treatment, wherein the one or more steps of administering a peptide cancer vaccine and the one or more steps of administering at least one other treatment do not include administering an adjuvant.

2. The method according to claim 1, wherein said determining the amount or activity of antigen-specific T-cells comprises one or more steps of identification or detection of said antigen-specific T-cells and one or more steps of measuring the amount of said antigen-specific T-cells.

3. The method according to claim 2 wherein said detection of said antigen-specific T-cells comprises indirect detection and direct detection.

4. The method according to claim 1, wherein said changing the amount or activity of antigen-specific T-cells comprises one or more steps of treatment of said individual to mediate an increase in said antigen-specific T-cells.

5. The method according to claim 1, wherein said changing the amount or relative amount of antigen-specific T-cells comprises one or more steps of treatment of said individual to mediate an increase in said antigen-specific T-cells, and comprises one or more steps of measuring said increase in said antigen-specific T-cells.

6. The method according to claim 1, wherein said method of diagnosing leukemia and/or lymphoma in an individual in need thereof comprises the following steps:
   providing an MHC monomer or MHC multimer,
   (ii) providing a population T-cells, and
   (iii) measuring the number, activity or state of T-cells specific for said MHC monomer or MHC multimer, thereby diagnosing said leukemia and/or lymphoma.

7. The method according to claim 1, wherein said at least one other treatment comprises T cell based adoptive immunotherapy.

8. The method according to claim 1, wherein said at least one other treatment comprises antibody-based immunotherapy.

9. The method according to claim 1, wherein said at least one other treatment comprises radiation therapy.

* * * * *

SEQUENCE LISTING

```
<160> NUMBER OF SEQ ID NOS: 210

<210> SEQ ID NO 1
<211> LENGTH: 9
<212> TYPE: PRT
<213> ORGANISM: Human cytomegalo virus

<400> SEQUENCE: 1

Asn Leu Val Pro Met Val Ala Thr Val
1               5

<210> SEQ ID NO 2
<211> LENGTH: 9
<212> TYPE: PRT
<213> ORGANISM: Human immunodeficiency virus

<400> SEQUENCE: 2

Ile Leu Lys Glu Pro Val His Gly Val
1               5

<210> SEQ ID NO 3
```

```
<211> LENGTH: 9
<212> TYPE: PRT
<213> ORGANISM: Human Cytomegalo Virus

<400> SEQUENCE: 3

Val Thr Glu His Asp Thr Leu Leu Tyr
1               5

<210> SEQ ID NO 4
<211> LENGTH: 9
<212> TYPE: PRT
<213> ORGANISM: Homo sapiens

<400> SEQUENCE: 4

Ile Val Asp Cys Leu Thr Glu Met Tyr
1               5

<210> SEQ ID NO 5
<211> LENGTH: 10
<212> TYPE: PRT
<213> ORGANISM: Human Cytomegalo Virus

<400> SEQUENCE: 5

Thr Pro Arg Val Thr Gly Gly Gly Ala Met
1               5                   10

<210> SEQ ID NO 6
<211> LENGTH: 11
<212> TYPE: PRT
<213> ORGANISM: Human Cytomegalo Virus

<400> SEQUENCE: 6

Arg Pro His Glu Arg Asn Gly Phe Thr Val Leu
1               5                   10

<210> SEQ ID NO 7
<211> LENGTH: 10
<212> TYPE: PRT
<213> ORGANISM: Human Immunodeficiency Virus

<400> SEQUENCE: 7

Thr Pro Gly Pro Gly Val Arg Tyr Pro Leu
1               5                   10

<210> SEQ ID NO 8
<211> LENGTH: 9
<212> TYPE: PRT
<213> ORGANISM: Epstein barr virus
<220> FEATURE:
<223> OTHER INFORMATION: Unknow organism - random sequence used as
      negative control

<400> SEQUENCE: 8

Gly Leu Cys Thr Leu Val Ala Met Leu
1               5

<210> SEQ ID NO 9
<211> LENGTH: 8
<212> TYPE: PRT
<213> ORGANISM: Epstein Barr virus

<400> SEQUENCE: 9

Arg Ala Lys Phe Lys Gln Leu Leu
1               5
```

-continued

```
<210> SEQ ID NO 10
<211> LENGTH: 9
<212> TYPE: PRT
<213> ORGANISM: Borrelia

<400> SEQUENCE: 10

Gly Leu Ala Gly Asp Val Ser Ala Val
1               5

<210> SEQ ID NO 11
<211> LENGTH: 10
<212> TYPE: PRT
<213> ORGANISM: Homo sapiens

<400> SEQUENCE: 11

Phe Ile Ala Ser Asn Gly Val Lys Leu Val
1               5                   10

<210> SEQ ID NO 12
<211> LENGTH: 15
<212> TYPE: PRT
<213> ORGANISM: Homo sapiens

<400> SEQUENCE: 12

Tyr Ser Val Tyr Phe Asn Leu Pro Ala Asp Thr Ile Tyr Thr Asn
1               5                   10                  15

<210> SEQ ID NO 13
<211> LENGTH: 9
<212> TYPE: PRT
<213> ORGANISM: Homo sapiens

<400> SEQUENCE: 13

Ser Ser Lys Ala Leu Gln Arg Pro Val
1               5

<210> SEQ ID NO 14
<211> LENGTH: 9
<212> TYPE: PRT
<213> ORGANISM: Homo sapiens

<400> SEQUENCE: 14

Gly Phe Lys Gln Ser Ser Lys Ala Leu
1               5

<210> SEQ ID NO 15
<211> LENGTH: 17
<212> TYPE: PRT
<213> ORGANISM: Homo sapiens

<400> SEQUENCE: 15

Ala Thr Gly Phe Lys Gln Ser Ser Lys Ala Leu Gln Arg Pro Val Ala
1               5                   10                  15

Ser

<210> SEQ ID NO 16
<211> LENGTH: 17
<212> TYPE: PRT
<213> ORGANISM: Homo sapiens

<400> SEQUENCE: 16

Ala Thr Gly Phe Lys Gln Ser Ser Lys Ala Leu Gln Arg Pro Val Ala
1               5                   10                  15

Ser
```

-continued

<210> SEQ ID NO 17
<211> LENGTH: 29
<212> TYPE: PRT
<213> ORGANISM: Homo sapiens

<400> SEQUENCE: 17

Glu Asp Leu Thr Val Lys Ile Gly Asp Phe Gly Leu Ala Thr Glu Lys
1               5                   10                  15

Ser Arg Trp Ser Gly Ser His Gln Phe Glu Gln Leu Ser
            20                  25

<210> SEQ ID NO 18
<211> LENGTH: 9
<212> TYPE: PRT
<213> ORGANISM: Homo sapiens

<400> SEQUENCE: 18

Phe Leu Ile Ile Trp Gln Asn Thr Met
1               5

<210> SEQ ID NO 19
<211> LENGTH: 9
<212> TYPE: PRT
<213> ORGANISM: Homo sapiens

<400> SEQUENCE: 19

Phe Pro Ser Asp Ser Trp Cys Tyr Phe
1               5

<210> SEQ ID NO 20
<211> LENGTH: 9
<212> TYPE: PRT
<213> ORGANISM: Homo sapiens

<400> SEQUENCE: 20

Ser Tyr Leu Asp Ser Gly Ile His Phe
1               5

<210> SEQ ID NO 21
<211> LENGTH: 12
<212> TYPE: PRT
<213> ORGANISM: Homo sapiens

<400> SEQUENCE: 21

Phe Ser Trp Ala Met Asp Leu Asp Pro Lys Gly Ala
1               5                   10

<210> SEQ ID NO 22
<211> LENGTH: 10
<212> TYPE: PRT
<213> ORGANISM: Homo sapiens

<400> SEQUENCE: 22

Ala Cys Asp Pro His Ser Gly His Phe Val
1               5                   10

<210> SEQ ID NO 23
<211> LENGTH: 9
<212> TYPE: PRT
<213> ORGANISM: Homo sapiens

<400> SEQUENCE: 23

Ala Val Cys Pro Trp Thr Trp Leu Arg

-continued

<210> SEQ ID NO 24
<211> LENGTH: 14
<212> TYPE: PRT
<213> ORGANISM: Homo sapiens

<400> SEQUENCE: 24

Thr Leu Tyr Gln Asp Asp Thr Leu Thr Leu Gln Ala Ala Gly
1               5                   10

<210> SEQ ID NO 25
<211> LENGTH: 14
<212> TYPE: PRT
<213> ORGANISM: Homo sapiens

<400> SEQUENCE: 25

Thr Leu Tyr Gln Asp Asp Thr Leu Thr Leu Gln Ala Ala Gly
1               5                   10

<210> SEQ ID NO 26
<211> LENGTH: 16
<212> TYPE: PRT
<213> ORGANISM: Homo sapiens

<400> SEQUENCE: 26

Thr Met Lys Gln Ile Cys Lys Lys Glu Ile Arg Arg Leu His Gln Tyr
1               5                   10                  15

<210> SEQ ID NO 27
<211> LENGTH: 10
<212> TYPE: PRT
<213> ORGANISM: Homo sapiens

<400> SEQUENCE: 27

Lys Ile Leu Asp Ala Val Val Ala Gln Lys
1               5                   10

<210> SEQ ID NO 28
<211> LENGTH: 9
<212> TYPE: PRT
<213> ORGANISM: Homo sapiens

<400> SEQUENCE: 28

Glu Thr Val Ser Glu Gln Ser Asn Val
1               5

<210> SEQ ID NO 29
<211> LENGTH: 9
<212> TYPE: PRT
<213> ORGANISM: Homo sapiens

<400> SEQUENCE: 29

Arg Ile Ala Glu Cys Ile Leu Gly Met
1               5

<210> SEQ ID NO 30
<211> LENGTH: 15
<212> TYPE: PRT
<213> ORGANISM: Homo sapiens

<400> SEQUENCE: 30

Ile Gly Arg Ile Ala Glu Cys Ile Leu Gly Met Asn Pro Ser Arg
1               5                   10                  15

<210> SEQ ID NO 31
<211> LENGTH: 15
<212> TYPE: PRT
<213> ORGANISM: Homo sapiens

<400> SEQUENCE: 31

Ile Gly Arg Ile Ala Glu Cys Ile Leu Gly Met Asn Pro Ser Arg
1               5                   10                  15

<210> SEQ ID NO 32
<211> LENGTH: 10
<212> TYPE: PRT
<213> ORGANISM: Homo sapiens

<400> SEQUENCE: 32

Tyr Val Asp Phe Arg Glu Tyr Glu Tyr Tyr
1               5                   10

<210> SEQ ID NO 33
<211> LENGTH: 14
<212> TYPE: PRT
<213> ORGANISM: Homo sapiens

<400> SEQUENCE: 33

Met Ile Phe Glu Lys His Gly Phe Arg Arg Thr Thr Pro Pro
1               5                   10

<210> SEQ ID NO 34
<211> LENGTH: 10
<212> TYPE: PRT
<213> ORGANISM: Homo sapiens

<400> SEQUENCE: 34

Thr Leu Asp Trp Leu Leu Gln Thr Pro Lys
1               5                   10

<210> SEQ ID NO 35
<211> LENGTH: 9
<212> TYPE: PRT
<213> ORGANISM: Homo sapiens

<400> SEQUENCE: 35

Trp Arg Arg Ala Pro Ala Pro Gly Ala
1               5

<210> SEQ ID NO 36
<211> LENGTH: 9
<212> TYPE: PRT
<213> ORGANISM: Homo sapiens

<400> SEQUENCE: 36

Pro Val Thr Trp Arg Arg Ala Pro Ala
1               5

<210> SEQ ID NO 37
<211> LENGTH: 10
<212> TYPE: PRT
<213> ORGANISM: Homo sapiens

<400> SEQUENCE: 37

Ser Leu Phe Glu Gly Ile Asp Ile Tyr Thr
1               5                   10

<210> SEQ ID NO 38

```
<211> LENGTH: 9
<212> TYPE: PRT
<213> ORGANISM: Homo sapiens

<400> SEQUENCE: 38

Ala Glu Pro Ile Asn Ile Gln Thr Trp
1               5

<210> SEQ ID NO 39
<211> LENGTH: 11
<212> TYPE: PRT
<213> ORGANISM: Homo sapiens

<400> SEQUENCE: 39

Phe Leu Glu Gly Asn Glu Val Gly Lys Thr Tyr
1               5                   10

<210> SEQ ID NO 40
<211> LENGTH: 9
<212> TYPE: PRT
<213> ORGANISM: Homo sapiens

<400> SEQUENCE: 40

Phe Leu Asp Glu Phe Met Glu Gly Val
1               5

<210> SEQ ID NO 41
<211> LENGTH: 9
<212> TYPE: PRT
<213> ORGANISM: Homo sapiens

<400> SEQUENCE: 41

Glu Glu Lys Leu Ile Val Val Leu Phe
1               5

<210> SEQ ID NO 42
<211> LENGTH: 11
<212> TYPE: PRT
<213> ORGANISM: Homo sapiens

<400> SEQUENCE: 42

Ser Glu Leu Phe Arg Ser Gly Leu Asp Ser Tyr
1               5                   10

<210> SEQ ID NO 43
<211> LENGTH: 9
<212> TYPE: PRT
<213> ORGANISM: Homo sapiens

<400> SEQUENCE: 43

Phe Arg Ser Gly Leu Asp Ser Tyr Val
1               5

<210> SEQ ID NO 44
<211> LENGTH: 9
<212> TYPE: PRT
<213> ORGANISM: Homo sapiens

<400> SEQUENCE: 44

Glu Ala Phe Ile Gln Pro Ile Thr Arg
1               5

<210> SEQ ID NO 45
<211> LENGTH: 11
<212> TYPE: PRT
```

<213> ORGANISM: Homo sapiens

<400> SEQUENCE: 45

Arg Val Ile Lys Asn Ser Ile Arg Leu Thr Leu
1               5                   10

<210> SEQ ID NO 46
<211> LENGTH: 9
<212> TYPE: PRT
<213> ORGANISM: Homo sapiens

<400> SEQUENCE: 46

Lys Ile Asn Lys Asn Pro Lys Tyr Lys
1               5

<210> SEQ ID NO 47
<211> LENGTH: 8
<212> TYPE: PRT
<213> ORGANISM: Homo sapiens

<400> SEQUENCE: 47

Gln Gln Ile Thr Lys Thr Glu Val
1               5

<210> SEQ ID NO 48
<211> LENGTH: 10
<212> TYPE: PRT
<213> ORGANISM: Homo sapiens

<400> SEQUENCE: 48

Ser Leu Tyr Lys Phe Ser Pro Phe Pro Leu
1               5                   10

<210> SEQ ID NO 49
<211> LENGTH: 9
<212> TYPE: PRT
<213> ORGANISM: Homo sapiens

<400> SEQUENCE: 49

Lys Glu Leu Glu Gly Ile Leu Leu Leu
1               5

<210> SEQ ID NO 50
<211> LENGTH: 9
<212> TYPE: PRT
<213> ORGANISM: Homo sapiens

<400> SEQUENCE: 50

Val Val Pro Cys Glu Pro Pro Glu Val
1               5

<210> SEQ ID NO 51
<211> LENGTH: 25
<212> TYPE: PRT
<213> ORGANISM: Homo sapiens

<400> SEQUENCE: 51

Asn Ser Asn His Val Ala Ser Gly Ala Gly Glu Ala Ala Ile Glu Thr
1               5                   10                  15

Gln Ser Ser Ser Ser Glu Glu Ile Val
            20                  25

<210> SEQ ID NO 52
<211> LENGTH: 10

```
<212> TYPE: PRT
<213> ORGANISM: Homo sapiens

<400> SEQUENCE: 52

Leu Leu Leu Asp Asp Leu Leu Val Ser Ile
1               5                   10

<210> SEQ ID NO 53
<211> LENGTH: 16
<212> TYPE: PRT
<213> ORGANISM: Homo sapiens

<400> SEQUENCE: 53

Pro Tyr Tyr Phe Ala Ala Glu Leu Pro Pro Arg Asn Leu Pro Glu Pro
1               5                   10                  15

<210> SEQ ID NO 54
<211> LENGTH: 9
<212> TYPE: PRT
<213> ORGANISM: Homo sapiens

<400> SEQUENCE: 54

Val Val Val Gly Ala Val Gly Val Gly
1               5

<210> SEQ ID NO 55
<211> LENGTH: 10
<212> TYPE: PRT
<213> ORGANISM: Homo sapiens

<400> SEQUENCE: 55

Ile Leu Asp Thr Ala Gly Arg Glu Glu Tyr
1               5                   10

<210> SEQ ID NO 56
<211> LENGTH: 9
<212> TYPE: PRT
<213> ORGANISM: Homo sapiens

<400> SEQUENCE: 56

Arg Pro His Val Pro Glu Ser Ala Phe
1               5

<210> SEQ ID NO 57
<211> LENGTH: 9
<212> TYPE: PRT
<213> ORGANISM: Homo sapiens

<400> SEQUENCE: 57

Lys Ile Phe Ser Glu Val Thr Leu Lys
1               5

<210> SEQ ID NO 58
<211> LENGTH: 9
<212> TYPE: PRT
<213> ORGANISM: Homo sapiens

<400> SEQUENCE: 58

Ser His Glu Thr Val Ile Ile Glu Leu
1               5

<210> SEQ ID NO 59
<211> LENGTH: 10
<212> TYPE: PRT
<213> ORGANISM: Homo sapiens
```

<400> SEQUENCE: 59

Gln Arg Pro Tyr Gly Tyr Asp Gln Ile Met
1               5                   10

<210> SEQ ID NO 60
<211> LENGTH: 15
<212> TYPE: PRT
<213> ORGANISM: Homo sapiens

<400> SEQUENCE: 60

Gly Glu Leu Ile Gly Ile Leu Asn Ala Ala Lys Val Pro Ala Asp
1               5                   10                  15

<210> SEQ ID NO 61
<211> LENGTH: 9
<212> TYPE: PRT
<213> ORGANISM: Homo sapiens

<400> SEQUENCE: 61

Ala Ala Arg Ala Val Phe Leu Ala Leu
1               5

<210> SEQ ID NO 62
<211> LENGTH: 8
<212> TYPE: PRT
<213> ORGANISM: Homo sapiens

<400> SEQUENCE: 62

Tyr Arg Pro Arg Pro Arg Arg Tyr
1               5

<210> SEQ ID NO 63
<211> LENGTH: 9
<212> TYPE: PRT
<213> ORGANISM: Homo sapiens

<400> SEQUENCE: 63

Tyr Tyr Trp Pro Arg Pro Arg Arg Tyr
1               5

<210> SEQ ID NO 64
<211> LENGTH: 10
<212> TYPE: PRT
<213> ORGANISM: Homo sapiens

<400> SEQUENCE: 64

Val Leu Pro Asp Val Phe Ile Arg Cys Val
1               5                   10

<210> SEQ ID NO 65
<211> LENGTH: 9
<212> TYPE: PRT
<213> ORGANISM: Homo sapiens

<400> SEQUENCE: 65

Met Leu Ala Val Ile Ser Cys Ala Val
1               5

<210> SEQ ID NO 66
<211> LENGTH: 9
<212> TYPE: PRT
<213> ORGANISM: Homo sapiens

<400> SEQUENCE: 66

Arg Gln Lys Arg Ile Leu Val Asn Leu
1               5

<210> SEQ ID NO 67
<211> LENGTH: 9
<212> TYPE: PRT
<213> ORGANISM: Homo sapiens

<400> SEQUENCE: 67

Asn Tyr Asn Asn Phe Tyr Arg Phe Leu
1               5

<210> SEQ ID NO 68
<211> LENGTH: 10
<212> TYPE: PRT
<213> ORGANISM: Homo sapiens

<400> SEQUENCE: 68

Glu Tyr Ser Lys Glu Cys Leu Lys Glu Phe
1               5                   10

<210> SEQ ID NO 69
<211> LENGTH: 9
<212> TYPE: PRT
<213> ORGANISM: Homo sapiens

<400> SEQUENCE: 69

Glu Tyr Leu Ser Leu Ser Asp Lys Ile
1               5

<210> SEQ ID NO 70
<211> LENGTH: 11
<212> TYPE: PRT
<213> ORGANISM: Homo sapiens

<400> SEQUENCE: 70

Met Leu Met Ala Gln Glu Ala Leu Ala Phe Leu
1               5                   10

<210> SEQ ID NO 71
<211> LENGTH: 9
<212> TYPE: PRT
<213> ORGANISM: Homo sapiens

<400> SEQUENCE: 71

Ser Leu Leu Met Trp Ile Thr Gln Cys
1               5

<210> SEQ ID NO 72
<211> LENGTH: 10
<212> TYPE: PRT
<213> ORGANISM: Homo sapiens

<400> SEQUENCE: 72

Leu Ala Ala Gln Glu Arg Arg Val Pro Arg
1               5                   10

<210> SEQ ID NO 73
<211> LENGTH: 9
<212> TYPE: PRT
<213> ORGANISM: Homo sapiens

<400> SEQUENCE: 73

Glu Leu Val Arg Arg Ile Leu Ser Arg

<210> SEQ ID NO 74
<211> LENGTH: 9
<212> TYPE: PRT
<213> ORGANISM: Homo sapiens

<400> SEQUENCE: 74

Ala Pro Arg Gly Val Arg Met Ala Val
1               5

<210> SEQ ID NO 75
<211> LENGTH: 14
<212> TYPE: PRT
<213> ORGANISM: Homo sapiens

<400> SEQUENCE: 75

Ser Leu Leu Met Trp Ile Thr Gln Cys Phe Leu Pro Val Phe
1               5                   10

<210> SEQ ID NO 76
<211> LENGTH: 20
<212> TYPE: PRT
<213> ORGANISM: Homo sapiens

<400> SEQUENCE: 76

Gln Gly Ala Met Leu Ala Ala Gln Glu Arg Arg Val Pro Arg Ala Ala
1               5                   10                  15

Glu Val Pro Arg
            20

<210> SEQ ID NO 77
<211> LENGTH: 18
<212> TYPE: PRT
<213> ORGANISM: Homo sapiens

<400> SEQUENCE: 77

Ala Ala Asp His Arg Gln Leu Gln Leu Ser Ile Ser Ser Cys Leu Gln
1               5                   10                  15

Gln Leu

<210> SEQ ID NO 78
<211> LENGTH: 22
<212> TYPE: PRT
<213> ORGANISM: Homo sapiens

<400> SEQUENCE: 78

Cys Leu Ser Arg Arg Pro Trp Lys Arg Ser Trp Ser Ala Gly Ser Cys
1               5                   10                  15

Pro Gly Met Pro His Leu
            20

<210> SEQ ID NO 79
<211> LENGTH: 22
<212> TYPE: PRT
<213> ORGANISM: Homo sapiens

<400> SEQUENCE: 79

Cys Leu Ser Arg Arg Pro Trp Lys Arg Ser Trp Ser Ala Gly Ser Cys
1               5                   10                  15

Pro Gly Met Pro His Leu
            20

```
<210> SEQ ID NO 80
<211> LENGTH: 13
<212> TYPE: PRT
<213> ORGANISM: Homo sapiens

<400> SEQUENCE: 80

Ile Leu Ser Arg Asp Ala Ala Pro Leu Pro Arg Pro Gly
1               5                   10

<210> SEQ ID NO 81
<211> LENGTH: 14
<212> TYPE: PRT
<213> ORGANISM: Homo sapiens

<400> SEQUENCE: 81

Ala Gly Ala Thr Gly Gly Arg Gly Pro Arg Gly Ala Gly Ala
1               5                   10

<210> SEQ ID NO 82
<211> LENGTH: 9
<212> TYPE: PRT
<213> ORGANISM: Homo sapiens

<400> SEQUENCE: 82

Glu Ala Asp Pro Thr Gly His Ser Tyr
1               5

<210> SEQ ID NO 83
<211> LENGTH: 9
<212> TYPE: PRT
<213> ORGANISM: Homo sapiens

<400> SEQUENCE: 83

Lys Val Leu Glu Tyr Val Ile Lys Val
1               5

<210> SEQ ID NO 84
<211> LENGTH: 9
<212> TYPE: PRT
<213> ORGANISM: Homo sapiens

<400> SEQUENCE: 84

Ser Leu Phe Arg Ala Val Ile Thr Lys
1               5

<210> SEQ ID NO 85
<211> LENGTH: 10
<212> TYPE: PRT
<213> ORGANISM: Homo sapiens

<400> SEQUENCE: 85

Glu Val Tyr Asp Gly Arg Glu His Ser Ala
1               5                   10

<210> SEQ ID NO 86
<211> LENGTH: 9
<212> TYPE: PRT
<213> ORGANISM: Homo sapiens

<400> SEQUENCE: 86

Arg Val Arg Phe Phe Phe Pro Ser Leu
1               5

<210> SEQ ID NO 87
```

```
<211> LENGTH: 9
<212> TYPE: PRT
<213> ORGANISM: Homo sapiens

<400> SEQUENCE: 87

Glu Ala Asp Pro Thr Gly His Ser Tyr
1               5

<210> SEQ ID NO 88
<211> LENGTH: 10
<212> TYPE: PRT
<213> ORGANISM: Homo sapiens

<400> SEQUENCE: 88

Arg Glu Pro Val Thr Lys Ala Glu Met Leu
1               5                   10

<210> SEQ ID NO 89
<211> LENGTH: 9
<212> TYPE: PRT
<213> ORGANISM: Homo sapiens

<400> SEQUENCE: 89

Asp Pro Ala Arg Tyr Glu Phe Leu Trp
1               5

<210> SEQ ID NO 90
<211> LENGTH: 11
<212> TYPE: PRT
<213> ORGANISM: Homo sapiens

<400> SEQUENCE: 90

Ile Thr Lys Lys Val Ala Asp Leu Val Gly Phe
1               5                   10

<210> SEQ ID NO 91
<211> LENGTH: 9
<212> TYPE: PRT
<213> ORGANISM: Homo sapiens

<400> SEQUENCE: 91

Ser Ala Phe Pro Thr Thr Ile Asn Phe
1               5

<210> SEQ ID NO 92
<211> LENGTH: 9
<212> TYPE: PRT
<213> ORGANISM: Homo sapiens

<400> SEQUENCE: 92

Ser Ala Tyr Gly Glu Pro Arg Lys Leu
1               5

<210> SEQ ID NO 93
<211> LENGTH: 9
<212> TYPE: PRT
<213> ORGANISM: Homo sapiens

<400> SEQUENCE: 93

Ser Ala Tyr Gly Glu Pro Arg Lys Leu
1               5

<210> SEQ ID NO 94
<211> LENGTH: 15
<212> TYPE: PRT
```

```
<213> ORGANISM: Homo sapiens

<400> SEQUENCE: 94

Thr Ser Cys Ile Leu Glu Ser Leu Phe Arg Ala Val Ile Thr Lys
1               5                   10                  15

<210> SEQ ID NO 95
<211> LENGTH: 15
<212> TYPE: PRT
<213> ORGANISM: Homo sapiens

<400> SEQUENCE: 95

Pro Arg Ala Leu Ala Glu Thr Ser Tyr Val Lys Val Leu Glu Tyr
1               5                   10                  15

<210> SEQ ID NO 96
<211> LENGTH: 14
<212> TYPE: PRT
<213> ORGANISM: Homo sapiens

<400> SEQUENCE: 96

Leu Leu Lys Tyr Arg Ala Arg Glu Pro Val Thr Lys Ala Glu
1               5                   10

<210> SEQ ID NO 97
<211> LENGTH: 12
<212> TYPE: PRT
<213> ORGANISM: Homo sapiens

<400> SEQUENCE: 97

Glu Tyr Val Ile Lys Val Ser Ala Arg Val Arg Phe
1               5                   10

<210> SEQ ID NO 98
<211> LENGTH: 10
<212> TYPE: PRT
<213> ORGANISM: Homo sapiens

<400> SEQUENCE: 98

Tyr Leu Gln Leu Val Phe Gly Ile Glu Val
1               5                   10

<210> SEQ ID NO 99
<211> LENGTH: 9
<212> TYPE: PRT
<213> ORGANISM: Homo sapiens

<400> SEQUENCE: 99

Glu Tyr Leu Gln Leu Val Phe Gly Ile
1               5

<210> SEQ ID NO 100
<211> LENGTH: 10
<212> TYPE: PRT
<213> ORGANISM: Homo sapiens

<400> SEQUENCE: 100

Arg Glu Pro Val Thr Lys Ala Glu Met Leu
1               5                   10

<210> SEQ ID NO 101
<211> LENGTH: 9
<212> TYPE: PRT
<213> ORGANISM: Homo sapiens
```

```
<400> SEQUENCE: 101

Glu Gly Asp Cys Ala Pro Glu Glu Lys
1               5

<210> SEQ ID NO 102
<211> LENGTH: 14
<212> TYPE: PRT
<213> ORGANISM: Homo sapiens

<400> SEQUENCE: 102

Leu Leu Lys Tyr Arg Ala Arg Glu Pro Val Thr Lys Ala Glu
1               5                   10

<210> SEQ ID NO 103
<211> LENGTH: 9
<212> TYPE: PRT
<213> ORGANISM: Homo sapiens

<400> SEQUENCE: 103

Glu Val Asp Pro Ile Gly His Leu Tyr
1               5

<210> SEQ ID NO 104
<211> LENGTH: 9
<212> TYPE: PRT
<213> ORGANISM: Homo sapiens

<400> SEQUENCE: 104

Phe Leu Trp Gly Pro Arg Ala Leu Val
1               5

<210> SEQ ID NO 105
<211> LENGTH: 9
<212> TYPE: PRT
<213> ORGANISM: Homo sapiens

<400> SEQUENCE: 105

Lys Val Ala Glu Leu Val His Phe Leu
1               5

<210> SEQ ID NO 106
<211> LENGTH: 9
<212> TYPE: PRT
<213> ORGANISM: Homo sapiens

<400> SEQUENCE: 106

Thr Phe Pro Asp Leu Glu Ser Glu Phe
1               5

<210> SEQ ID NO 107
<211> LENGTH: 9
<212> TYPE: PRT
<213> ORGANISM: Homo sapiens

<400> SEQUENCE: 107

Val Ala Glu Leu Val His Phe Leu Leu
1               5

<210> SEQ ID NO 108
<211> LENGTH: 10
<212> TYPE: PRT
<213> ORGANISM: Homo sapiens

<400> SEQUENCE: 108
```

Met Glu Val Asp Pro Ile Gly His Leu Tyr
1               5                   10

<210> SEQ ID NO 109
<211> LENGTH: 9
<212> TYPE: PRT
<213> ORGANISM: Homo sapiens

<400> SEQUENCE: 109

Glu Val Asp Pro Ile Gly His Leu Tyr
1               5

<210> SEQ ID NO 110
<211> LENGTH: 10
<212> TYPE: PRT
<213> ORGANISM: Homo sapiens

<400> SEQUENCE: 110

Arg Glu Pro Val Thr Lys Ala Glu Met Leu
1               5                   10

<210> SEQ ID NO 111
<211> LENGTH: 9
<212> TYPE: PRT
<213> ORGANISM: Homo sapiens

<400> SEQUENCE: 111

Ala Glu Leu Val His Phe Leu Leu Leu
1               5

<210> SEQ ID NO 112
<211> LENGTH: 10
<212> TYPE: PRT
<213> ORGANISM: Homo sapiens

<400> SEQUENCE: 112

Met Glu Val Asp Pro Ile Gly His Leu Tyr
1               5                   10

<210> SEQ ID NO 113
<211> LENGTH: 9
<212> TYPE: PRT
<213> ORGANISM: Homo sapiens

<400> SEQUENCE: 113

Trp Gln Tyr Phe Phe Pro Val Ile Phe
1               5

<210> SEQ ID NO 114
<211> LENGTH: 9
<212> TYPE: PRT
<213> ORGANISM: Homo sapiens

<400> SEQUENCE: 114

Glu Gly Asp Cys Ala Pro Glu Glu Lys
1               5

<210> SEQ ID NO 115
<211> LENGTH: 16
<212> TYPE: PRT
<213> ORGANISM: Homo sapiens

<400> SEQUENCE: 115

Lys Lys Leu Leu Thr Gln His Phe Val Gln Glu Asn Tyr Leu Glu Tyr
1               5                   10                  15

```
<210> SEQ ID NO 116
<211> LENGTH: 16
<212> TYPE: PRT
<213> ORGANISM: Homo sapiens

<400> SEQUENCE: 116

Lys Lys Leu Leu Thr Gln His Phe Val Gln Glu Asn Tyr Leu Glu Tyr
1               5                   10                  15

<210> SEQ ID NO 117
<211> LENGTH: 16
<212> TYPE: PRT
<213> ORGANISM: Homo sapiens

<400> SEQUENCE: 117

Ala Cys Tyr Glu Phe Leu Trp Gly Pro Arg Ala Leu Val Glu Thr Ser
1               5                   10                  15

<210> SEQ ID NO 118
<211> LENGTH: 12
<212> TYPE: PRT
<213> ORGANISM: Homo sapiens

<400> SEQUENCE: 118

Val Ile Phe Ser Lys Ala Ser Ser Ser Leu Gln Leu
1               5                   10

<210> SEQ ID NO 119
<211> LENGTH: 12
<212> TYPE: PRT
<213> ORGANISM: Homo sapiens

<400> SEQUENCE: 119

Val Ile Phe Ser Lys Ala Ser Ser Leu Gln Leu
1               5                   10

<210> SEQ ID NO 120
<211> LENGTH: 15
<212> TYPE: PRT
<213> ORGANISM: Homo sapiens

<400> SEQUENCE: 120

Gly Asp Asn Gln Ile Met Pro Lys Ala Gly Leu Leu Ile Ile Val
1               5                   10                  15

<210> SEQ ID NO 121
<211> LENGTH: 15
<212> TYPE: PRT
<213> ORGANISM: Homo sapiens

<400> SEQUENCE: 121

Thr Ser Tyr Val Lys Val Leu His His Met Val Lys Ile Ser Gly
1               5                   10                  15

<210> SEQ ID NO 122
<211> LENGTH: 14
<212> TYPE: PRT
<213> ORGANISM: Homo sapiens

<400> SEQUENCE: 122

Ala Glu Leu Val His Phe Leu Leu Leu Lys Tyr Arg Ala Arg
1               5                   10
```

-continued

<210> SEQ ID NO 123
<211> LENGTH: 14
<212> TYPE: PRT
<213> ORGANISM: Homo sapiens

<400> SEQUENCE: 123

Leu Leu Lys Tyr Arg Ala Arg Glu Pro Val Thr Lys Ala Glu
1               5                   10

<210> SEQ ID NO 124
<211> LENGTH: 9
<212> TYPE: PRT
<213> ORGANISM: Homo sapiens

<400> SEQUENCE: 124

Glu Val Asp Pro Ala Ser Asn Thr Tyr
1               5

<210> SEQ ID NO 125
<211> LENGTH: 10
<212> TYPE: PRT
<213> ORGANISM: Homo sapiens

<400> SEQUENCE: 125

Gly Val Tyr Asp Gly Arg Glu His Thr Val
1               5                   10

<210> SEQ ID NO 126
<211> LENGTH: 9
<212> TYPE: PRT
<213> ORGANISM: Homo sapiens

<400> SEQUENCE: 126

Asn Tyr Lys Arg Cys Phe Pro Val Ile
1               5

<210> SEQ ID NO 127
<211> LENGTH: 8
<212> TYPE: PRT
<213> ORGANISM: Homo sapiens

<400> SEQUENCE: 127

Ser Glu Ser Leu Lys Met Ile Phe
1               5

<210> SEQ ID NO 128
<211> LENGTH: 9
<212> TYPE: PRT
<213> ORGANISM: Homo sapiens

<400> SEQUENCE: 128

Met Val Lys Ile Ser Gly Gly Pro Arg
1               5

<210> SEQ ID NO 129
<211> LENGTH: 9
<212> TYPE: PRT
<213> ORGANISM: Homo sapiens

<400> SEQUENCE: 129

Glu Val Asp Pro Ile Gly His Val Tyr
1               5

<210> SEQ ID NO 130
<211> LENGTH: 10

```
<212> TYPE: PRT
<213> ORGANISM: Homo sapiens

<400> SEQUENCE: 130

Arg Glu Pro Val Thr Lys Ala Glu Met Leu
1               5                   10

<210> SEQ ID NO 131
<211> LENGTH: 9
<212> TYPE: PRT
<213> ORGANISM: Homo sapiens

<400> SEQUENCE: 131

Glu Gly Asp Cys Ala Pro Glu Glu Lys
1               5

<210> SEQ ID NO 132
<211> LENGTH: 9
<212> TYPE: PRT
<213> ORGANISM: Homo sapiens

<400> SEQUENCE: 132

Ile Ser Gly Gly Pro Arg Ile Ser Tyr
1               5

<210> SEQ ID NO 133
<211> LENGTH: 14
<212> TYPE: PRT
<213> ORGANISM: Homo sapiens

<400> SEQUENCE: 133

Leu Leu Lys Tyr Arg Ala Arg Glu Pro Val Thr Lys Ala Glu
1               5                   10

<210> SEQ ID NO 134
<211> LENGTH: 9
<212> TYPE: PRT
<213> ORGANISM: Homo sapiens

<400> SEQUENCE: 134

Ala Leu Ser Val Met Gly Val Tyr Val
1               5

<210> SEQ ID NO 135
<211> LENGTH: 9
<212> TYPE: PRT
<213> ORGANISM: Homo sapiens

<400> SEQUENCE: 135

Gly Leu Tyr Asp Gly Met Glu His Leu
1               5

<210> SEQ ID NO 136
<211> LENGTH: 9
<212> TYPE: PRT
<213> ORGANISM: Homo sapiens

<400> SEQUENCE: 136

Asp Pro Ala Arg Tyr Glu Phe Leu Trp
1               5

<210> SEQ ID NO 137
<211> LENGTH: 9
<212> TYPE: PRT
<213> ORGANISM: Homo sapiens
```

<400> SEQUENCE: 137

Phe Leu Trp Gly Pro Arg Ala Leu Val
1               5

<210> SEQ ID NO 138
<211> LENGTH: 9
<212> TYPE: PRT
<213> ORGANISM: Homo sapiens

<400> SEQUENCE: 138

Val Arg Ile Gly His Leu Tyr Ile Leu
1               5

<210> SEQ ID NO 139
<211> LENGTH: 9
<212> TYPE: PRT
<213> ORGANISM: Homo sapiens

<400> SEQUENCE: 139

Glu Gly Asp Cys Ala Pro Glu Glu Lys
1               5

<210> SEQ ID NO 140
<211> LENGTH: 15
<212> TYPE: PRT
<213> ORGANISM: Homo sapiens

<400> SEQUENCE: 140

Arg Glu Pro Phe Thr Lys Ala Glu Met Leu Gly Ser Val Ile Arg
1               5                   10                  15

<210> SEQ ID NO 141
<211> LENGTH: 14
<212> TYPE: PRT
<213> ORGANISM: Homo sapiens

<400> SEQUENCE: 141

Ala Glu Leu Val His Phe Leu Leu Leu Lys Tyr Arg Ala Arg
1               5                   10

<210> SEQ ID NO 142
<211> LENGTH: 10
<212> TYPE: PRT
<213> ORGANISM: Homo sapiens

<400> SEQUENCE: 142

Leu Leu Phe Gly Leu Ala Leu Ile Glu Val
1               5                   10

<210> SEQ ID NO 143
<211> LENGTH: 9
<212> TYPE: PRT
<213> ORGANISM: Homo sapiens

<400> SEQUENCE: 143

Ala Leu Lys Asp Val Glu Glu Arg Val
1               5

<210> SEQ ID NO 144
<211> LENGTH: 9
<212> TYPE: PRT
<213> ORGANISM: Homo sapiens

<400> SEQUENCE: 144

Ser Glu Ser Ile Lys Lys Lys Val Leu
1               5

<210> SEQ ID NO 145
<211> LENGTH: 20
<212> TYPE: PRT
<213> ORGANISM: Homo sapiens

<400> SEQUENCE: 145

Pro Asp Thr Arg Pro Ala Pro Gly Ser Thr Ala Pro Pro Ala His Gly
1               5                   10                  15

Val Thr Ser Ala
            20

<210> SEQ ID NO 146
<211> LENGTH: 9
<212> TYPE: PRT
<213> ORGANISM: Homo sapiens

<400> SEQUENCE: 146

Gln Gly Gln His Phe Leu Gln Lys Val
1               5

<210> SEQ ID NO 147
<211> LENGTH: 9
<212> TYPE: PRT
<213> ORGANISM: Homo sapiens

<400> SEQUENCE: 147

Ser Leu Leu Met Trp Ile Thr Gln Cys
1               5

<210> SEQ ID NO 148
<211> LENGTH: 11
<212> TYPE: PRT
<213> ORGANISM: Homo sapiens

<400> SEQUENCE: 148

Met Leu Met Ala Gln Glu Ala Leu Ala Phe Leu
1               5                   10

<210> SEQ ID NO 149
<211> LENGTH: 10
<212> TYPE: PRT
<213> ORGANISM: Homo sapiens

<400> SEQUENCE: 149

Ala Ser Gly Pro Gly Gly Gly Ala Pro Arg
1               5                   10

<210> SEQ ID NO 150
<211> LENGTH: 10
<212> TYPE: PRT
<213> ORGANISM: Homo sapiens

<400> SEQUENCE: 150

Leu Ala Ala Gln Glu Arg Arg Val Pro Arg
1               5                   10

<210> SEQ ID NO 151
<211> LENGTH: 9
<212> TYPE: PRT
<213> ORGANISM: Homo sapiens

<400> SEQUENCE: 151

Met Pro Phe Ala Thr Pro Met Glu Ala
1               5

<210> SEQ ID NO 152
<211> LENGTH: 9
<212> TYPE: PRT
<213> ORGANISM: Homo sapiens

<400> SEQUENCE: 152

Met Pro Phe Ala Thr Pro Met Glu Ala
1               5

<210> SEQ ID NO 153
<211> LENGTH: 9
<212> TYPE: PRT
<213> ORGANISM: Homo sapiens

<400> SEQUENCE: 153

Leu Ala Met Pro Phe Ala Thr Pro Met
1               5

<210> SEQ ID NO 154
<211> LENGTH: 9
<212> TYPE: PRT
<213> ORGANISM: Homo sapiens

<400> SEQUENCE: 154

Ala Arg Gly Pro Glu Ser Arg Leu Leu
1               5

<210> SEQ ID NO 155
<211> LENGTH: 14
<212> TYPE: PRT
<213> ORGANISM: Homo sapiens

<400> SEQUENCE: 155

Ser Leu Leu Met Trp Ile Thr Gln Cys Phe Leu Pro Val Phe
1               5                   10

<210> SEQ ID NO 156
<211> LENGTH: 25
<212> TYPE: PRT
<213> ORGANISM: Homo sapiens

<400> SEQUENCE: 156

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 157
<211> LENGTH: 25
<212> TYPE: PRT
<213> ORGANISM: Homo sapiens

<400> SEQUENCE: 157

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 158

```
<211> LENGTH: 12
<212> TYPE: PRT
<213> ORGANISM: Homo sapiens

<400> SEQUENCE: 158

Glu Phe Tyr Leu Ala Met Pro Phe Ala Thr Pro Met
1               5                   10

<210> SEQ ID NO 159
<211> LENGTH: 12
<212> TYPE: PRT
<213> ORGANISM: Homo sapiens

<400> SEQUENCE: 159

Arg Leu Leu Glu Phe Tyr Leu Ala Met Pro Phe Ala
1               5                   10

<210> SEQ ID NO 160
<211> LENGTH: 20
<212> TYPE: PRT
<213> ORGANISM: Homo sapiens

<400> SEQUENCE: 160

Gln Gly Ala Met Leu Ala Ala Gln Glu Arg Arg Val Pro Arg Ala Ala
1               5                   10                  15

Glu Val Pro Arg
            20

<210> SEQ ID NO 161
<211> LENGTH: 20
<212> TYPE: PRT
<213> ORGANISM: Homo sapiens

<400> SEQUENCE: 161

Pro Gly Val Leu Leu Lys Glu Phe Thr Val Ser Gly Asn Ile Leu Thr
1               5                   10                  15

Ile Arg Leu Thr
            20

<210> SEQ ID NO 162
<211> LENGTH: 10
<212> TYPE: PRT
<213> ORGANISM: Homo sapiens

<400> SEQUENCE: 162

Val Leu Leu Lys Glu Phe Thr Val Ser Gly
1               5                   10

<210> SEQ ID NO 163
<211> LENGTH: 18
<212> TYPE: PRT
<213> ORGANISM: Homo sapiens

<400> SEQUENCE: 163

Ala Ala Asp His Arg Gln Leu Gln Leu Ser Ile Ser Ser Cys Leu Gln
1               5                   10                  15

Gln Leu

<210> SEQ ID NO 164
<211> LENGTH: 25
<212> TYPE: PRT
<213> ORGANISM: Homo sapiens

<400> SEQUENCE: 164
```

```
Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 165
<211> LENGTH: 25
<212> TYPE: PRT
<213> ORGANISM: Homo sapiens

<400> SEQUENCE: 165

Pro Gly Val Leu Leu Lys Glu Phe Thr Val Ser Gly Asn Ile Leu Thr
1               5                   10                  15

Ile Arg Leu Thr Ala Ala Asp His Arg
            20                  25

<210> SEQ ID NO 166
<211> LENGTH: 25
<212> TYPE: PRT
<213> ORGANISM: Homo sapiens

<400> SEQUENCE: 166

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 167
<211> LENGTH: 14
<212> TYPE: PRT
<213> ORGANISM: Homo sapiens

<400> SEQUENCE: 167

Ala Gly Ala Thr Gly Gly Arg Gly Pro Arg Gly Ala Gly Ala
1               5                   10

<210> SEQ ID NO 168
<211> LENGTH: 9
<212> TYPE: PRT
<213> ORGANISM: Homo sapiens

<400> SEQUENCE: 168

Leu Tyr Ala Thr Val Ile His Asp Ile
1               5

<210> SEQ ID NO 169
<211> LENGTH: 9
<212> TYPE: PRT
<213> ORGANISM: Homo sapiens

<400> SEQUENCE: 169

Ile Leu Asp Ser Ser Glu Glu Asp Lys
1               5

<210> SEQ ID NO 170
<211> LENGTH: 9
<212> TYPE: PRT
<213> ORGANISM: Homo sapiens

<400> SEQUENCE: 170

Lys Ala Ser Glu Lys Ile Phe Tyr Val
1               5
```

```
<210> SEQ ID NO 171
<211> LENGTH: 16
<212> TYPE: PRT
<213> ORGANISM: Homo sapiens

<400> SEQUENCE: 171

Glu Lys Ile Gln Lys Ala Phe Asp Asp Ile Ala Lys Tyr Phe Ser Lys
1               5                   10                  15

<210> SEQ ID NO 172
<211> LENGTH: 18
<212> TYPE: PRT
<213> ORGANISM: Homo sapiens

<400> SEQUENCE: 172

Trp Glu Lys Met Lys Ala Ser Glu Lys Ile Phe Tyr Val Tyr Met Lys
1               5                   10                  15

Arg Lys

<210> SEQ ID NO 173
<211> LENGTH: 15
<212> TYPE: PRT
<213> ORGANISM: Homo sapiens

<400> SEQUENCE: 173

Lys Ile Phe Tyr Val Tyr Met Lys Arg Lys Tyr Glu Ala Met Thr
1               5                   10                  15

<210> SEQ ID NO 174
<211> LENGTH: 14
<212> TYPE: PRT
<213> ORGANISM: Homo sapiens

<400> SEQUENCE: 174

Lys Ile Phe Tyr Val Tyr Met Lys Arg Lys Tyr Glu Ala Met
1               5                   10

<210> SEQ ID NO 175
<211> LENGTH: 20
<212> TYPE: PRT
<213> ORGANISM: Homo sapiens

<400> SEQUENCE: 175

Ile Asn Lys Thr Ser Gly Pro Lys Arg Gly Lys His Ala Trp Thr His
1               5                   10                  15

Arg Leu Arg Glu
            20

<210> SEQ ID NO 176
<211> LENGTH: 20
<212> TYPE: PRT
<213> ORGANISM: Homo sapiens

<400> SEQUENCE: 176

Tyr Phe Ser Lys Lys Glu Trp Glu Lys Met Lys Ser Ser Glu Lys Ile
1               5                   10                  15

Val Tyr Val Tyr
            20

<210> SEQ ID NO 177
<211> LENGTH: 20
<212> TYPE: PRT
<213> ORGANISM: Homo sapiens
```

```
<400> SEQUENCE: 177

Met Lys Leu Asn Tyr Glu Val Met Thr Lys Leu Gly Phe Lys Val Thr
1               5                   10                  15

Leu Pro Pro Phe
            20

<210> SEQ ID NO 178
<211> LENGTH: 20
<212> TYPE: PRT
<213> ORGANISM: Homo sapiens

<400> SEQUENCE: 178

Lys His Ala Trp Thr His Arg Leu Arg Glu Arg Lys Gln Leu Val Val
1               5                   10                  15

Tyr Glu Glu Ile
            20

<210> SEQ ID NO 179
<211> LENGTH: 20
<212> TYPE: PRT
<213> ORGANISM: Homo sapiens

<400> SEQUENCE: 179

Leu Gly Phe Lys Val Thr Leu Pro Pro Phe Met Arg Ser Lys Arg Ala
1               5                   10                  15

Ala Asp Phe His
            20

<210> SEQ ID NO 180
<211> LENGTH: 20
<212> TYPE: PRT
<213> ORGANISM: Homo sapiens

<400> SEQUENCE: 180

Lys Ser Ser Glu Lys Ile Val Tyr Val Tyr Met Lys Leu Asn Tyr Glu
1               5                   10                  15

Val Met Thr Lys
            20

<210> SEQ ID NO 181
<211> LENGTH: 20
<212> TYPE: PRT
<213> ORGANISM: Homo sapiens

<400> SEQUENCE: 181

Lys His Ala Trp Thr His Arg Leu Arg Glu Arg Lys Gln Leu Val Val
1               5                   10                  15

Tyr Glu Glu Ile
            20

<210> SEQ ID NO 182
<211> LENGTH: 15
<212> TYPE: PRT
<213> ORGANISM: Homo sapiens

<400> SEQUENCE: 182

Cys Glu Phe His Ala Cys Trp Pro Ala Phe Thr Val Leu Gly Glu
1               5                   10                  15

<210> SEQ ID NO 183
<211> LENGTH: 15
```

```
<212> TYPE: PRT
<213> ORGANISM: Homo sapiens

<400> SEQUENCE: 183

Cys Glu Phe His Ala Cys Trp Pro Ala Phe Thr Val Leu Gly Glu
1               5                   10                  15

<210> SEQ ID NO 184
<211> LENGTH: 15
<212> TYPE: PRT
<213> ORGANISM: Homo sapiens

<400> SEQUENCE: 184

Cys Glu Phe His Ala Cys Trp Pro Ala Phe Thr Val Leu Gly Glu
1               5                   10                  15

<210> SEQ ID NO 185
<211> LENGTH: 10
<212> TYPE: PRT
<213> ORGANISM: Homo sapiens

<400> SEQUENCE: 185

Glu Val Ile Ser Cys Lys Leu Ile Lys Arg
1               5                   10

<210> SEQ ID NO 186
<211> LENGTH: 9
<212> TYPE: PRT
<213> ORGANISM: Homo sapiens

<400> SEQUENCE: 186

Ile Thr Asp Gln Val Pro Gly Ser Val
1               5

<210> SEQ ID NO 187
<211> LENGTH: 9
<212> TYPE: PRT
<213> ORGANISM: Homo sapiens

<400> SEQUENCE: 187

Gly Ile Leu Thr Val Ile Leu Gly Val
1               5

<210> SEQ ID NO 188
<211> LENGTH: 10
<212> TYPE: PRT
<213> ORGANISM: Homo sapiens

<400> SEQUENCE: 188

Asp Leu Ala Gln Cys Phe Phe Cys Phe Lys
1               5                   10

<210> SEQ ID NO 189
<211> LENGTH: 15
<212> TYPE: PRT
<213> ORGANISM: Borrelia

<400> SEQUENCE: 189

Lys Lys Tyr Leu Leu Gly Phe Ala Leu Val Leu Ala Leu Ile Ala
1               5                   10                  15

<210> SEQ ID NO 190
<211> LENGTH: 15
<212> TYPE: PRT
<213> ORGANISM: Borrelia
```

<400> SEQUENCE: 190

```
Asp Thr Val Lys Leu Phe Asn Asp Thr Lys Ile Phe Ile Ser Lys
1               5                  10                  15
```

<210> SEQ ID NO 191
<211> LENGTH: 15
<212> TYPE: PRT
<213> ORGANISM: Borrelia

<400> SEQUENCE: 191

```
Ser Lys Val Phe Lys Lys Gln Gly Ser Leu Thr Glu Glu Thr Glu
1               5                  10                  15
```

<210> SEQ ID NO 192
<211> LENGTH: 15
<212> TYPE: PRT
<213> ORGANISM: Borrelia

<400> SEQUENCE: 192

```
Thr Ala Val Trp Ser Asp Thr Ser Asn Thr Leu Thr Val Ser Ala
1               5                  10                  15
```

<210> SEQ ID NO 193
<211> LENGTH: 15
<212> TYPE: PRT
<213> ORGANISM: Borrelia

<400> SEQUENCE: 193

```
Glu Thr Tyr Asp Ser Ser Asn Thr Lys Val Ala Ser Lys Val Phe
1               5                  10                  15
```

<210> SEQ ID NO 194
<211> LENGTH: 15
<212> TYPE: PRT
<213> ORGANISM: Borrelia

<400> SEQUENCE: 194

```
Met Lys Lys Tyr Leu Leu Gly Phe Ala Leu Val Leu Ala Leu Ile
1               5                  10                  15
```

<210> SEQ ID NO 195
<211> LENGTH: 15
<212> TYPE: PRT
<213> ORGANISM: Borrelia

<400> SEQUENCE: 195

```
Thr Lys Ala Val Glu Thr Leu Lys Asn Gly Ile Met Leu Glu Gly
1               5                  10                  15
```

<210> SEQ ID NO 196
<211> LENGTH: 15
<212> TYPE: PRT
<213> ORGANISM: Borrelia

<400> SEQUENCE: 196

```
Lys Ala Val Glu Thr Leu Lys Asn Gly Ile Met Leu Glu Gly Asn
1               5                  10                  15
```

<210> SEQ ID NO 197
<211> LENGTH: 15
<212> TYPE: PRT
<213> ORGANISM: Borrelia

<400> SEQUENCE: 197

```
Thr Leu Glu Tyr Ser Asp Met Thr Asn Asp Glu Asn Ala Thr Lys
1               5                   10                  15

<210> SEQ ID NO 198
<211> LENGTH: 15
<212> TYPE: PRT
<213> ORGANISM: Borrelia

<400> SEQUENCE: 198

Ile Thr Val Gln Asn Tyr Asp Thr Ala Gly Thr Lys Leu Ala Gly
1               5                   10                  15

<210> SEQ ID NO 199
<211> LENGTH: 86
<212> TYPE: PRT
<213> ORGANISM: Borrelia burgdorferi

<400> SEQUENCE: 199

Met Asn Lys Lys Met Lys Asn Leu Ile Ile Cys Ala Val Phe Val Leu
1               5                   10                  15

Ile Ile Ser Cys Lys Ile Asp Ala Ser Ser Glu Asp Leu Lys Gln Asn
            20                  25                  30

Val Lys Glu Lys Val Glu Gly Phe Leu Asp Lys Glu Leu Met Gln Gly
        35                  40                  45

Asp Asp Pro Asn Asn Ser Leu Phe Asn Pro Pro Val Leu Pro Ala
    50                  55                  60

Ser Ser His Asp Asn Thr Pro Val Leu Lys Ala Val Gln Ala Lys Asp
65                  70                  75                  80

Gly Gly Gln Gln Glu Gly
                85

<210> SEQ ID NO 200
<211> LENGTH: 9
<212> TYPE: PRT
<213> ORGANISM: Borrelia

<400> SEQUENCE: 200

Tyr Leu Ala Pro Asp Asn Val Ile Thr
1               5

<210> SEQ ID NO 201
<211> LENGTH: 9
<212> TYPE: PRT
<213> ORGANISM: Borrelia

<400> SEQUENCE: 201

Tyr Ser Asp Glu Ile Asp Ile Ile His
1               5

<210> SEQ ID NO 202
<211> LENGTH: 9
<212> TYPE: PRT
<213> ORGANISM: Borrelia

<400> SEQUENCE: 202

Ala Pro Asp Asn Val Ile Thr Ser Thr
1               5

<210> SEQ ID NO 203
<211> LENGTH: 15
<212> TYPE: PRT
<213> ORGANISM: Borrelia
```

<400> SEQUENCE: 203

Ile Glu Leu Val Leu Lys Glu Ser Ser Asn Ser Tyr Leu Ser
1               5                   10                  15

<210> SEQ ID NO 204
<211> LENGTH: 15
<212> TYPE: PRT
<213> ORGANISM: Borrelia

<400> SEQUENCE: 204

Met Asn Lys Ile Leu Leu Ile Leu Leu Glu Ser Ile Val Phe
1               5                   10                  15

<210> SEQ ID NO 205
<211> LENGTH: 15
<212> TYPE: PRT
<213> ORGANISM: Borrelia

<400> SEQUENCE: 205

Ser Asp Leu Ile Trp Leu Ile Gly Tyr Arg Phe Ser Asp Val Ala
1               5                   10                  15

<210> SEQ ID NO 206
<211> LENGTH: 9
<212> TYPE: PRT
<213> ORGANISM: Borrelia

<400> SEQUENCE: 206

Ala Leu Ile Ala Cys Lys Gln Asn Val
1               5

<210> SEQ ID NO 207
<211> LENGTH: 8
<212> TYPE: PRT
<213> ORGANISM: Borrelia

<400> SEQUENCE: 207

Phe Thr Lys Glu Asp Thr Ile Thr
1               5

<210> SEQ ID NO 208
<211> LENGTH: 9
<212> TYPE: PRT
<213> ORGANISM: Borrelia

<400> SEQUENCE: 208

Ser Ile Gln Ile Glu Ile Glu Gln Leu
1               5

<210> SEQ ID NO 209
<211> LENGTH: 9
<212> TYPE: PRT
<213> ORGANISM: Borrelia

<400> SEQUENCE: 209

Asn Leu Asn Glu Val Glu Lys Val Leu
1               5

<210> SEQ ID NO 210
<211> LENGTH: 9
<212> TYPE: PRT

```
<213> ORGANISM: Borrelia

<400> SEQUENCE: 210

Ser Leu Ala Lys Ile Glu Asn Ala Ile
1               5
```